United States Patent
Beck et al.

(10) Patent No.: US 9,365,522 B2
(45) Date of Patent: Jun. 14, 2016

(54) PYRAZOLE AMIDE DERIVATIVE

(71) Applicants: AMGEN INC., Thousand Oaks, CA (US); TEIJIN PHARMA LIMITED, Tokyo (JP)

(72) Inventors: Hilary Plake Beck, Redwood City, CA (US); Shon Keith Booker, Sherman Oaks, CA (US); Howard Bregman, Melrose, MA (US); Victor J. Cee, Thousand Oaks, CA (US); Nagasree Chakka, Lexington, MA (US); Timothy D. Cushing, Pacifica, CA (US); Oleg Epstein, Belmont, MA (US); Brian M. Fox, Brisbane, CA (US); Stephanie Geuns-Meyer, Medford, MA (US); Xiaolin Hao, Foster City, CA (US); Kenta Hibiya, Tokyo (JP); Jun Hirata, Tokyo (JP); Zihao Hua, Andover, MA (US); Jason Human, Boston, MA (US); Shinji Kakuda, Tokyo (JP); Patricia Lopez, Woodland Hills, CA (US); Ryota Nakajima, Tokyo (JP); Kazuhisa Okada, Tokyo (JP); Steven H. Olson, Millbrae, CA (US); Hiroyuki Oono, Tokyo (JP); Lewis D. Pennington, Arlington, MA (US); Kosuke Sasaki, Tokyo (JP); Keiko Shimada, Tokyo (JP); Youngsook Shin, Thousand Oaks, CA (US); Ryan D. White, Somerville, MA (US); Ryan P. Wurz, Newbury Park, CA (US); Shuyan Yi, Malden, MA (US); Xiao Mei Zheng, Natick, MA (US)

(73) Assignees: AMGEN INC., Thousand Oaks, CA (US); TEIJIN PHARMA LIMITED, Tokyo (JP)

( * ) Notice: Subject to any disclaimer, the term of this patent is extended or adjusted under 35 U.S.C. 154(b) by 0 days.

(21) Appl. No.: 14/633,936

(22) Filed: Feb. 27, 2015

(65) Prior Publication Data

US 2015/0266824 A1    Sep. 24, 2015

(51) Int. Cl.
| | |
|---|---|
| *C07D 231/14* | (2006.01) |
| *C07D 403/12* | (2006.01) |
| *C07D 401/14* | (2006.01) |
| *C07D 405/14* | (2006.01) |
| *C07D 401/12* | (2006.01) |
| *C07D 405/12* | (2006.01) |
| *C07D 409/12* | (2006.01) |
| *C07D 417/14* | (2006.01) |
| *C07D 493/08* | (2006.01) |
| *C07D 413/12* | (2006.01) |
| *A61K 31/4155* | (2006.01) |
| *A61K 31/44* | (2006.01) |
| *A61K 31/4427* | (2006.01) |
| *A61K 31/422* | (2006.01) |

(52) U.S. Cl.
CPC ............ *C07D 231/14* (2013.01); *C07D 401/12* (2013.01); *C07D 401/14* (2013.01); *C07D 403/12* (2013.01); *C07D 405/12* (2013.01); *C07D 405/14* (2013.01); *C07D 409/12* (2013.01); *C07D 413/12* (2013.01); *C07D 417/14* (2013.01); *C07D 493/08* (2013.01)

(58) Field of Classification Search
None
See application file for complete search history.

(56) References Cited

U.S. PATENT DOCUMENTS 9,156,837 B2    10/2015    Yamamoto et al.

FOREIGN PATENT DOCUMENTS

| WO | WO-2013/018695 A1 | 2/2013 |
| WO | WO-2013/079223 A1 | 6/2013 |
| WO | WO-2014/023367 A1 | 2/2014 |

OTHER PUBLICATIONS

Waser et al., Hydrazines and azides via the metal-catalyzed hydrohydrazation and hydroazidation of olefins. *J. Am. Chem. Soc.* 128(35): 11693-712 (2006).

*Primary Examiner* — Samantha Shterengarts
(74) *Attorney, Agent, or Firm* — Marshall, Gerstein & Borun LLP

(57) ABSTRACT

The present invention relates to a novel compound having a function of inhibiting RORγ activity. The present invention also relates to pharmaceutical composition comprising the compound, a use of the compound in treating or preventing autoimmune diseases, inflammatory diseases, metabolic diseases, or cancer diseases.

14 Claims, No Drawings

PYRAZOLE AMIDE DERIVATIVE

This application claims the benefit of Japanese Application No. 2014-039880, filed Feb. 28, 2014, which is hereby incorporated by reference.

TECHNICAL FIELD

The present invention relates to novel compounds that modulate RORγ activity, pharmaceutical composition, and use in treatment or prevention of autoimmune diseases, inflammatory diseases, metabolic diseases, or cancer diseases.

BACKGROUND ART

Retinoid-related orphan receptor gamma (RORγ) is a nuclear receptor that binds to DNA and regulates transcription (NPL 1). Two isoforms of RORγ that differ only in the N-terminus are generated from the RORC gene; RORγ1 and RORγt (also referred to as RORγ2) (NPL 2). RORγ is used as a term to describe both isoforms of RORγ1 and RORγt.

RORγ1 is expressed in a variety of tissues including muscle, kidney, liver, and lung and is known to regulate adipogenesis (NPL 3). Loss of the RORC gene in mice accelerates preadipocyte differentiation to small adipocytes and protects against high fat diet induced insulin resistance. Consequently, by inhibiting the function of RORγ1, insulin resistance could be improved.

RORγt is expressed exclusively in cells of the immune system (NPLs 4 and 5) and is a master regulator of a Th17 cell-related transcriptional network associated with autoimmune pathology. Th17 cells are a subset of CD4+ helper T cells implicated as key drivers of the inflammatory process in autoimmunity and characterized by production of the pro-inflammatory cytokine IL-17A. Th17 cells also express $CCR^6$, which mediates migration to sites of inflammation, are maintained and expanded by IL-23, through the IL-23 receptor (IL23R), and express other pro-inflammatory cytokines and chemokines, including IL-17F, IL-21, IL-22, CCL20 and GM-CSF, which together promote recruitment of other inflammatory cell types, especially neutrophils, to mediate pathology at the target tissue. RORγt is required for the differentiation of Th17 cells and directly and indirectly regulates expression of many of these pro-inflammatory mediators (NPL 6). RORγ-deficient mice have significantly reduced numbers of Th17 cells in vivo, lack the ability to produce IL-17A and other Th17-related cytokines ex vivo, and show resistance to induction of various disease models such as EAE, dermatitis, enteritis and nephritis (NPLs 6, and 12 to 14). Therefore, by inhibiting the function of RORγ, development of various autoimmune diseases and inflammatory diseases, in which the Th17 cell-related cytokines are involved, could be suppressed. Furthermore, expression of RORγt and the consequent expression of the Th17 cell-related transcriptional network has been observed in other immune cell types that may also be important in disease pathogenesis, namely CD8+ T cells, so called Tc17s, γδ T cells, natural killer T cells, innate lymphoid cells, natural killer cells, and mast cells (NPLs 7 and 8).

Th17 cell-related cytokines and chemokines have been implicated in the pathogenesis of various human autoimmune and inflammatory diseases including multiple sclerosis, rheumatoid arthritis, psoriasis, psoriatic arthritis, ankylosing spondylitis, cystic fibrosis, asthma, chronic obstructive pulmonary disease, emphysema, lung fibrosis, systemic erythematodes, vasculitis, Wegener granuloma, polymyalgia rheumatica, giant cell arteritis, arteriosclerosis, autoimmune myositis, uveitis, dry eye, inflammatory bowel disease, alcohol-induced hepatitis, non-alcoholic steatohepatitis, primary biliary cirrhosis, viral hepatitis and type 1 diabetes. (NPLs 9 to 11).

RORγt is known to possess an inhibitory effect on the anti-tumorigenic activity of Th9 cells, a subtype of helper T cells (NPL 15). In the RORγ-deficient mice, production of IL-9 from Th9 cells is enhanced and tumor formation is delayed in mice injected with melanoma cells. Therefore, it is thought that, by inhibiting the function of RORγ, the function of Th9 cells is activated and formation of melanoma and other malignant tumors can be suppressed.

From the evidence described above, a RORγ modulator can be expected to show therapeutic or preventive benefit in treatment of; metabolic diseases such as diabetes; for autoimmune diseases or inflammatory diseases and; for melanoma and other cancer diseases.

CITATION LIST

Non Patent Literature

NPL 1: Gigure, Endocrine. Reviews. 20: 689-725, 1999
NPL 2: Jetten, Nucl. Recept. Signal. 7: e003, 2009
NPL 3: Meissburger et al., EMBO Mol. Med. 3: 637-651, 2011
NPL 4: Hirose et al., Biochem. Biophys. Res. Commun. 30: 1976-1983, 1994
NPL 5: Eberl and Littman., Science. 9: 248-251, 2004
NPL 6: Ivanov et al., Cell 126: 1121-1133, 2006
NPL 7: Sutton et al., Eur. J. Immunol. 42: 2221-2231, 2012
NPL 8: Hueber et al., J. Immunol., 184: 3336-3340, 2010
NPL 9: Miossec et al., Nature Reviews Drug Discovery 11: 763-776, 2012
NPL 10: Hammerich et al., Clin. Dev. Immunol. 2011: Article ID 345803, 2011
NPL 11: Ferraro et al., Diabetes 60: 2903-2913, 2011
NPL 12: Pantelyushin et al., J Clin Invest. 122: 2252-2256, 2012
NPL 13: Buonocore et al., Nature 464: 1371-1375, 2010
NPL 14: Steinmetz et al., J. Am. Soc. Nephrol. 22: 472-483, 2011
NPL 15: Purwar et al., Nat. Med. 18: 1248-1254, 2012

SUMMARY OF INVENTION

Technical Problem

The object of the present invention is to provide a compound having a function of inhibiting RORγ activity.

Solution to Problem

The present inventors conducted diligent research in order to achieve the above-described object and, as a result, found a novel compound represented by formula (I) or a pharmaceutically acceptable salt thereof, the compound or a pharmaceutically acceptable salt thereof having a function of inhibiting RORγ activity. That is, the present invention is as follows.

(1) A compound represented by formula (I) or a pharmaceutically acceptable salt thereof:

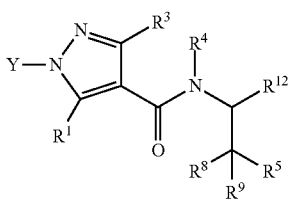

(I)

wherein:

$R^1$ is selected from F, Cl, Br, a $C_1$ to $C_6$ alkyl group substituted by 0, 1, 2 or 3 $R^a$ groups and a $C_3$ to $C_8$ cycloalkyl group substituted by 0, 1, 2 or 3 $R^a$ groups;

Y is selected from a $C_4$ to $C_6$ cycloalkyl group, a $C_6$ to $C_9$ bicycloalkyl group and a $C_6$ to $C_9$ spiroalkyl group, all of which are substituted by a $R^2$ group, 0 or 1 $R^6$ group and 0, 1, 2 or 3 $R^7$ groups;

$R^2$ is selected from —OH, —$CO_2H$, —$SO_3H$, —$CONH_2$, —$SO_2NH_2$, a ($C_1$ to $C_6$ alkoxy)carbonyl group substituted by 0, 1, 2 or 3 $R^c$ groups, a ($C_1$ to $C_6$ alkyl)aminocarbonyl group substituted by 0, 1, 2 or 3 $R^c$ groups, a $C_1$ to $C_6$ alkylsulfonyl group substituted by 0, 1, 2 or 3 $R^c$ groups, a $C_1$ to $C_6$ alkylaminosulfonyl group substituted by 0, 1, 2 or 3 $R^c$ groups, a (hydroxycarbonyl)($C_1$ to $C_3$ alkyl) group substituted by 0, 1, 2 or 3 $R^c$ groups, a ($C_1$ to $C_6$ alkoxy)carbonyl($C_1$ to $C_3$ alkyl) group substituted by 0, 1, 2 or 3 $R^c$ groups, a ($C_1$ to $C_6$ alkyl)sulfonyl($C_1$ to $C_3$ alkyl) group substituted by 0, 1, 2 or $3R^c$ groups and a (C2 to C6 alkenyl)(C1 to C3 alkyl) group substituted by 0, 1, 2 or 3 $R^c$ groups;

$R^6$ and $R^7$ are independently selected from H, F, —OH, —$NH_2$, —CN, a $C_1$ to $C_6$ alkyl group substituted by 0, 1, 2 or 3 $R^b$ groups and a $C_1$ to $C_6$ alkoxy group substituted by 0, 1, 2 or 3 $R^b$ groups;

$R^3$ is selected from H, F, Cl, —$CH_3$ and —$CF_3$;

$R^4$ is selected from a $C_1$ to $C_6$ alkyl group substituted by 0, 1, 2, 3, 4 or 5 $R^e$ groups, a ($C_2$ to $C_6$ alkenyl)($C_1$ to $C_3$ alkyl) group substituted by 0, 1, 2, 3, 4 or $5R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or 5 $R^g$ groups and a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_6$ to $C_9$ spiroheteroalkyl group substituted by 0, 1, 2, 3, 4 or 5 $R^g$ groups, a $C_5$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups, a $C_6$ to $C_9$ heterobicycloalkyl group substituted by 0, 1, 2, 3, 4 or 5 $R^g$ groups, and a ($C_6$ to $C_9$ heterobicycloalkyl)($C_1$ to $C_3$ alkyl) group substituted by 0, 1, 2, 3, 4 or 5 $R^g$ groups;

$R^5$ is selected from a $C_6$ to $C_{10}$ aryl group substituted by 0, 1, 2, 3, 4 or 5 $R^f$ groups, a 5- to 10-membered heteroaryl group substituted by 0, 1, 2, 3, or 4 $R^i$ groups, a $C_3$ to $C_8$ cycloalkyl group substituted by 0, 1, 2, 3, 4 or 5 $R^j$ groups, a $C_3$ to $C_8$ cycloalkenyl group substituted by 0, 1, 2, 3, 4 or 5 $R^j$ groups and a 3- to 8-membered heterocycloalkyl group substituted by 0, 1, 2, 3, 4 or 5 $R^j$ groups; $R^8$ and $R^9$ are independently selected from H, F, —OH, —$NH_2$, a $C_1$ to $C_3$ alkyl group substituted by 0, 1, 2 or 3 $R^h$ groups, and a $C_1$ to $C_6$ alkoxy group substituted by 0, 1, 2 or 3 $R^h$ groups; or $R^8$ and $R^9$ together form an oxo group or a thioxo group;

$R^{12}$ is H; or $R^4$ and $R^{12}$ together are —$CR^mR^m$—$CR^{13}R^{14}$—$CR^mR^m$— or —$CR^{13}R^{14}CR^mR^m$—$CR^mR^m$— to form a pyrrolidine ring;

$R^{13}$ is selected from H, a $C_1$ to $C_6$ alkyl group substituted by 0, 1, 2, 3, 4 or 5 $R^e$ groups, a $C_6$ to $C_{10}$ aryl group substituted by 0, 1, 2, 3, 4 or 5 $R^f$ groups, a $C_6$ to $C_{10}$ aryloxy group substituted by 0, 1, 2, 3, 4 or 5 $R^f$ groups, a ($C_2$ to $C_6$ alkenyl)($C_1$ to $C_3$ alkyl) group substituted by 0, 1, 2, 3, 4 or 5 $R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or $5R^g$ groups and a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or $5 R^g$ groups, a $C_6$ to $C_9$ spiroheteroalkyl group substituted by 0, 1, 2, 3, 4 or 5 $R^g$ groups, a $C_6$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups, a $C_6$ to $C_9$ heterobicycloalkyl group substituted by 0, 1, 2, 3, 4 or 5 $R^g$ groups, and a ($C_6$ to $C_9$ heterobicycloalkyl)($C_1$ to $C_3$ alkyl) group substituted by 0, 1, 2, 3, 4 or 5 $R^g$ groups;

$R^{14}$ is independently selected from H and a $C_1$ to $C_6$ alkyl group substituted by 0, 1, 2, 3, 4 or 5 $R^e$ groups; or $R^{13}$ and $R^{14}$ together form a $C_3$ to $C_8$ cycloalkane ring substituted by 0, 1, 2, 3, 4 or 5 $R^g$ groups, $C_3$ to $C_8$ cycloalkene ring substituted by 0, 1, 2, 3, 4 or 5 $R^g$ groups, or a 3- to 8-membered heterocycloalkane ring substituted by 0, 1, 2, 3, 4 or 5 $R^g$ groups;

$R^m$ is independently selected from H, F, Cl, —$CH_3$ and —$CF_3$;

$R^g$ and $R^j$ are, independently selected from F, Cl, a $C_1$ to $C_6$ alkyl group, —OH, —CN, —$NH_2$, —$NO_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$, a $C_1$ to $C_6$ alkylene group substituted by 0, 1, 2 or 3 $R^i$ groups, a $C_2$ to $C_6$ alkenylene group substituted by 0, 1, 2 or 3 $R^i$ groups and an oxo group; $R^f$ and $R^i$ are independently selected from F, Cl, Br, —OH, —CN, —$NO_2$, —$CO_2H$, a $C_1$ to $C_6$ alkyl group substituted by 0, 1, 2 or 3 $R^k$ groups, a $C_2$ to $C_6$ alkenyl group substituted by 0, 1, 2 or 3 $R^k$ groups, a $C_2$ to $C_6$ alkynyl group substituted by 0, 1, 2 or 3 $R^k$ groups, a $C_3$ to $C_8$ cycloalkyl group substituted by 0, 1, 2 or 3 $R^k$ groups, a $C_1$ to $C_6$ alkoxy group substituted by 0, 1, 2 or 3 $R^k$ groups, a $C_3$ to $C_8$ cycloalkyloxy group substituted by 0, 1, 2 or 3 $R^k$ groups, —SH, a $C_1$ to $C_6$ alkylthio group substituted by 0, 1, 2 or 3 $R^k$ groups, a $C_3$ to $C_8$ cycloalkylthio group substituted by 0, 1, 2 or 3 $R^k$ groups, a ($C_1$ to $C_6$ alkyl)carbonyl group substituted by 0, 1, 2 or 3 $R^k$ groups, a ($C_1$ to $C_6$ alkoxy)carbonyl group substituted by 0, 1, 2 or 3 $R^k$ groups, a ($C_1$ to $C_6$ alkyl)aminocarbonyl group substituted by 0, 1, 2 or 3 $R^k$ groups, a 3- to 8-membered heterocycloalkyl group substituted by 0, 1, 2 or 3 $R^k$ groups, a $C_1$ to $C_6$ alkylsulfonyl group substituted by 0, 1, 2 or 3 $R^k$ groups, —$NH_2$, a mono($C_1$ to $C_6$ alkyl)amino group substituted by 0, 1, 2 or 3 $R^k$ groups and a di($C_1$ to $C_6$ alkyl)amino group substituted by 0, 1, 2 or 3 $R^k$ groups; and $R^a$, $R^b$, $R^c$, $R^e$, $R^h$, $R^k$ and $R^i$ are independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group.

(2) The compound according to section 1 or pharmaceutically acceptable salt thereof, wherein Y is selected from formula (II-a), formula (II-b), formula (II-c) and formula (II-d):

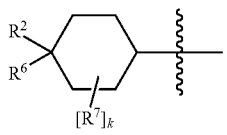

(II-a)

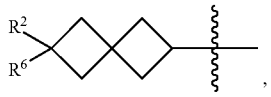

(II-b)

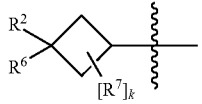

(II-c)

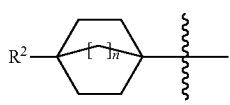

(II-d)

wherein:
k is 0, 1 or 2;
and n is 1, 2 or 3.

(3) The compound according to section 2 or pharmaceutically acceptable salt thereof, wherein Y is a group represented by formula (II-a):

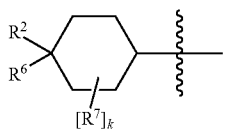

(II-a)

(4) The compound according to section 2 or pharmaceutically acceptable salt thereof, wherein Y is a group represented by formula (II-d):

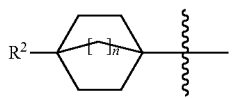

(II-d)

and n is 2.

(5) The compound according to any one of sections 1 to 4 or pharmaceutically acceptable salt thereof, wherein $R^3$ is H.

(6) The compound according to any one of sections 1 to 5 or pharmaceutically acceptable salt thereof, wherein $R^2$ is —$CO_2H$ or a hydroxycarbonylmethyl group substituted by 0, 1 or 2 $R^c$ groups.

(7) The compound according to any one of sections 1 to 6 or pharmaceutically acceptable salt thereof, wherein $R^{12}$ is H.

(8) The compound according to any one of sections 1 to 7 or pharmaceutically acceptable salt thereof, wherein $R^8$ and $R^9$ together form an oxo group or both $R^8$ and $R^9$ are H.

(9) The compound according to any one of sections 1 to 8 or pharmaceutically acceptable salt thereof, wherein $R^1$ is —$CF_3$, —$CF_2H$ or Cl.

(10) The compound according to any one of sections 1 to 9 or pharmaceutically acceptable salt thereof, wherein $R^5$ is a $C_6$ to $C_{10}$ aryl group substituted by 0, 1, 2, 3, 4 or 5 $R^i$ groups or a 5- to 10-membered heteroaryl group substituted by 0, 1, 2, 3, or 4 $R^i$ groups.

(11) The compound according to any one of sections 1 to 10 or pharmaceutically acceptable salt thereof, wherein $R^4$ is a $C_1$ to $C_6$ alkyl group substituted by 0, 1, 2 or 3 $R^e$ groups, a ($C_6$ to $C_{10}$ aryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_5$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups or a ($C_6$ to $C_9$ heterobicycloalkyl)($C_1$ to $C_3$ alkyl) group substituted by 0, 1, 2, 3, 4 or 5 $R^g$ groups.

(12) The method of treating or preventing a disease using a compound according to any one of sections 1 to 11 or pharmaceutically acceptable salt thereof, wherein the disease is multiple sclerosis, chronic rheumatoid arthritis, ankylosing spondylitis, systemic erythematodes, psoriasis, psoriatic arthritis, inflammatory bowel disease or asthma.

(13) A pharmaceutical composition comprising a compound according to any one of sections 1 to 11 or pharmaceutically acceptable salt thereof Advantageous Effects of Invention The present invention provides a novel compound having excellent activity of inhibiting RORγ and a method for producing the same. Further, the compound of the present invention or a pharmaceutically acceptable salt thereof is useful as a therapeutic agent or a preventive agent for autoimmune diseases, inflammatory diseases (for example, multiple sclerosis, chronic rheumatoid arthritis, ankylosing spondylitis, systemic erythematodes, psoriasis, psoriatic arthritis, inflammatory bowel disease, and asthma), metabolic diseases (especially diabetes), cancer diseases (especially malignant melanoma), or the like.

DESCRIPTION OF EMBODIMENTS

In the following, terms used either independently or in combination in the present description will be explained. Unless particularly described, explanation of each substituent shall be common to each position. In addition, when any variable substituent (for example, $R^j$ and the like) is present in respective arbitrary constituent elements (for example, $R^f$, $R^i$, and the like), its definition is independent in the respective constituent elements. Further, combination of substituents and variable substituents is allowed only when such combination provides a chemically stable compound. When a substituent itself is substituted by two or more groups, these plural groups can exist on the same carbon or different carbons as long as a stable structure is formed.

Each group of the compounds represented by formula (I) of the present invention is defined as described below. The writing order in each group indicates the order of the bonds in formula (I). For example, "a ($C_3$ to $C_8$ cycloalkyl)($C_1$ to $C_3$ alkyl) group" in $R^4$ is represented by group wherein "a $C_1$ to $C_3$ alkyl group" is bonded to nitrogen in formula (I) and "a $C_3$ to $C_8$ cycloalkyl group" and "a $C_1$ to $C_3$ alkyl group" are bonded.

Additionally, the number situated to the right of carbon indicates the number of the carbon. For example, "$C_1$ to $C_6$" means a group having "1 to 6 carbons". It is a matter of course that, in the present invention, different number of carbons means a group having that number of carbons. For example, "a $C_1$ to $C_4$ alkyl group" means alkyl groups having 1 to 4 carbon among those defined by "$C_1$ to $C_4$ alkyl group". Treatment of the number of carbons in other groups is the same.

In the present invention, "a $C_1$ to $C_6$ alkyl group" means a saturated linear or branched aliphatic hydrocarbon group having 1 to 6 carbons. For example, there may be mentioned a methyl group, an ethyl group, a n-propyl group, a n-butyl group, a n-pentyl group, a n-hexyl group, an isopropyl group, an isobutyl group, a sec-butyl group, a tert-butyl group, an isopentyl group, a 2-methylbutyl group, a 3-methylbutyl group, an 1-ethylpropyl group, an 1,1-dimethypropyl group, an 1,2-dimethylpropyl group, a neopentyl group, a 4-methylpentyl group, a 3-methylpentyl group, a 2-methylpentyl group, an 1-methylpentyl group, a 3,3-dimethylbutyl group, a 2,2-dimethylbutyl group, an 1,1-dimethylbutyl group, an 1,2-dimethylbutyl group, an 1,3-dimethylbutyl group, a 2,3-dimethylbutyl group, an 1-ethylbutyl group, a 2-ethylbutyl group, and the like.

In the present invention, "a $C_1$ to $C_4$ alkyl group" means a saturated linear or branched aliphatic hydrocarbon group having 1 to 4 carbons. For example, there may be mentioned a methyl group, an ethyl group, a n-propyl group, an isopropyl group a n-butyl group, an isobutyl group, a sec-butyl group, a tert-butyl group and the like.

In the present invention, "a $C_2$ to $C_4$ alkyl group" means a saturated linear or branched aliphatic hydrocarbon group having 2 to 4 carbons. For example, there may be mentioned an ethyl group, a n-propyl group, an isopropyl group, a n-butyl group, an isobutyl group, a sec-butyl group, a tert-butyl group and the like.

In the present invention, "a $C_1$ to $C_3$ alkyl group" means a saturated linear or branched aliphatic hydrocarbon group having 1 to 3 carbons. For example, there may be mentioned a methyl group, an ethyl group, a n-propyl group, an isopropyl group, and the like.

In the present invention, "a $C_2$ to $C_6$ alkenyl group" means a linear or branched aliphatic hydrocarbon group having 2 to 6 carbons with an unsaturated double bond. For example, there may be mentioned a vinyl group, an 1-propenyl group, a 2-propenyl group, a 2-methyl-1-propenyl group, a 2-methyl-2-propenyl group, a 2-buten-1-yl group, a 3-buten-1-yl group, a 2-penten-1-yl group, a 3-penten-1-yl group, a 4-penten-1-yl group, a 5-hexen-1-yl group, a 4-hexen-1-yl group, a 3-hexen-1-yl group, a 2-hexen-1-yl group, a 3-methyl-2-buten-1-yl group, a 3-methyl-3-penten-1-yl group, a 3-methyl-2-penten-1-yl group, a 4-methyl-3-penten-1-yl group, a 4-methyl-2-penten-1-yl group, a 2-methyl-2-penten-1-yl group, and the like.

In the present invention, "a $C_2$ to $C_6$ alkynyl group" means a linear or branched aliphatic hydrocarbon group having 2 to 6 carbons with an unsaturated triple bond. For example, there may be mentioned an ethynyl group, an 1-propyn-1-yl group, a 2-propyn-1-yl group, a 2-butyn-1-yl group, a 3-butyn-1-yl group, a 2-pentyn-1-yl group, a 3-pentyn-1-yl group, a 4-pentyn-1-yl group, a 5-hexyn-1-yl group, a 4-hexyn-1-yl group, a 3-hexyn-1-yl group, a 2-hexyn-1-yl group, and the like.

In the present invention, "a $C_1$ to $C_6$ alkylene group" means a bivalent group formed by removing hydrogen from "a $C_1$ to $C_6$ alkyl group". For example, there may be mentioned methylene, ethylene, propylene, butylene, pentylene, hexylene, and the like. The $C_1$ to $C_6$ alkylene group can be bonded to one carbon atom or two different carbon atoms to form a ring.

In the present invention, "a $C_2$ to $C_6$ alkenylene group" means a bivalent group having a double bond at arbitrary position of "a $C_2$ to $C_6$ alkylene group". There may be mentioned vinylene, propenylene, 1-butenylene, 2-butenylene, 1-pentenyene, 2-pentenyene, 1-hexenyene, 2-hexenyene, 3-hexenyene, and the like.

In the present invention, "a $C_3$ to $C_8$ cycloalkyl group" means a cyclic alkyl group having 3 to 8 carbons. For example, there may be mentioned a cyclopropyl group, a cyclobutyl group, a cyclopentyl group, a cyclohexyl group, a cycloheptyl group, a cyclooctyl group, and the like.

In the present invention, "a $C_4$ to $C_6$ cycloalkyl group" means a cyclic alkyl group having 4 to 6 carbons. For example, there may be mentioned a cyclobutyl group, a cyclopentyl group, a cyclohexyl group, and the like.

In the present invention, "a $C_6$ to $C_9$ bicycloalkyl group" means a bicyclic alkyl group having 6 to 9 carbons. For example, there may be mentioned a bicyclo[3.1.0]hexanyl group, a bicyclo[2.2.0]hexanyl group, a bicyclo[2.1.1]hexanyl group, bicyclo[3.2.0]heptanyl group, a bicyclo[2.2.1]heptanyl group, a bicyclo[3.1.1]heptanyl group, a bicyclo[4.1.0]heptanyl group, an octahydropentalenyl group, a bicyclo[2.2.2]octanyl group, a bicyclo[3.2.1]octanyl group, a bicyclo[4.2.0]octanyl group, a bicyclo[4.1.1]octanyl group, a bicyclo[5.1.0]octanyl group, an octahydro-1H-indenyl group, a bicyclo[3.2.2]nonanyl group, a bicyclo[3.3.1]nonanyl group, a bicyclo[4.2.1]nonanyl group, a bicyclo[5.2.0]nonanyl group, and the like.

In the present invention, "a $C_5$ to $C_9$ bicycloalkyl group" means a bicyclic alkyl group having 5 to 9 carbons. For example, there may be mentioned a bicyclo[1.1.1]pentanyl group, bicyclo[3.1.0]hexanyl group, a bicyclo[2.2.0]hexanyl group, a bicyclo[2.1.1]hexanyl group, bicyclo[3.2.0]heptanyl group, a bicyclo[2.2.1]heptanyl group, a bicyclo[3.1.1]heptanyl group, a bicyclo[4.1.0]heptanyl group, an octahydropentalenyl group, a bicyclo[2.2.2]octanyl group, a bicyclo[3.2.1]octanyl group, a bicyclo[4.2.0]octanyl group, a bicyclo[4.1.1]octanyl group, a bicyclo[5.1.0]octanyl group, an octahydro-1H-indenyl group, a bicyclo[3.2.2]nonanyl group, a bicyclo[3.3.1]nonanyl group, a bicyclo[4.2.1]nonanyl group, a bicyclo[5.2.0]nonanyl group, and the like.

In the present invention, "spiroalkyl group" means a group consisting of two cycloalkyl moieties that have exactly one atom in common. "A $C_6$ to $C_9$ spiroalkyl group" means a spiroalkyl group having 6 to 9 carbons. For example, there may be mentioned a spiro[2.3]hexanyl group, a spiro[2.4]heptanyl group, a spiro[3.3]heptanyl group, a spiro[2.5]octanyl group, a spiro[3.4]octanyl group, a spiro[2.6]nonanyl group, a spiro[3.5]nonanyl group, a spiro[4.4]nonanyl group, and the like.

In the present invention, "a ($C_6$ to $C_9$ spiroalkyl)($C_1$ to $C_3$ alkyl) group" means a group obtained by substituting "a $C_1$ to $C_3$ alkyl group" with "a ($C_6$ to $C_9$ spiroalkyl) group" at arbitrary position. For example, there may be mentioned a spiro[2.3]hexanyl methyl group, a spiro[2.4]heptanyl methyl group, a spiro[3.3]heptanyl methyl group, a spiro[2.5]octanyl methyl group, a spiro[3.4]octanyl methyl group, a spiro[2.6]nonanyl methyl group, a spiro[3.5]nonanyl methyl group, a spiro[4.4]nonanyl methyl group, and the like.

In the present invention, "a $C_3$ to $C_8$ cycloalkenyl group" means a group having a double bond at arbitrary position of "a $C_3$ to $C_8$ cycloalkyl group" having 3 to 8 carbons. For example, there may be mentioned a cyclopropenyl group, a cyclobutenyl group, a cyclopentenyl group, a cyclohexenyl group, a cycloheptenyl group, a cyclooctenyl group, and the like.

In the present invention, "a ($C_3$ to $C_8$ cycloalkyl)($C_1$ to $C_3$ alkyl) group" means a group obtained by substituting "a $C_1$ to $C_3$ alkyl group" with "a $C_3$ to $C_8$ cycloalkyl group" at arbitrary position. For example, there may be mentioned a cyclopropylmethyl group, a cyclopropylethyl group, a cyclopropylpropyl group, a cyclobutylmethyl group, a cyclobutylethyl group, a cyclopentylmethyl group, a cyclopentylethyl group, a cyclohexylmethyl group, a cyclohexylethyl group, a cycloheptylmethyl group, a cycloheptylethyl group, a cyclooctylmethyl group, and the like.

In the present invention, "a ($C_3$ to $C_8$ cycloalkenyl)($C_1$ to $C_3$ alkyl) group" means a group obtained by substituting "a $C_1$ to $C_3$ alkyl group" with "a $C_3$ to $C_8$ cycloalkenyl group" at arbitrary position. For example, there may be mentioned a cyclopropenylmethyl group, a cyclopropenylethyl group, a cyc lopropenylpropyl group, a cyclobutenylmethyl group, a cyclobutenylethyl group, a cyclopentenylmethyl group, a cyclopentenylethyl group, a cyclohexenylmethyl group, a cyclohexenylethyl group, a cycloheptenylmethyl group, a cycloheptenylethyl group, a cyclooctenylmethyl group, and the like.

In the present invention, "a ($C_2$ to $C_6$ alkenyl)($C_1$ to $C_3$ alkyl) group" means a group obtained by substituting "a $C_1$ to $C_3$ alkyl group" with "a $C_2$ to $C_6$ alkenyl group" at arbitrary position. For example, there may be mentioned a 2-propenyl group, an 1-methyl-2-propenyl group, a 2-methyl-2-propenyl group, a 2-buten-1-yl group, a 3-buten-1-yl group, a 2-penten-1-yl group, a 3-penten-1-yl group, a 4-penyten-1-yl group, a 5-hexen-1-yl group, a 4-hexen-1-yl group, a 3-hexen-1-yl group, a 2-hexen-1-yl group, an 1-methyl-2-buten-1-yl group, an 1-ethyl-2-buten-1-yl group, a 2-methyl-2-buten-1-yl group, a 3-methyl-2-buten-1-yl group, a 3-methyl-3-penten-1-yl group, a 3-methyl-2-penten-1-yl group, a 3-ethyl-2-penten-1-yl group, a 4-methyl-3-penten-1-yl group, a 4-methyl-2-penten-1-yl group, a 2-methyl-2-penten-1-yl group, and the like.

In the present invention, "a ($C_2$ to $C_6$ alkynyl)($C_1$ to $C_3$ alkyl) group" means a group obtained by substituting "a $C_1$ to $C_3$ alkyl group" with "a $C_2$ to $C_6$ alkynyl group" at arbitrary position. For example, there may be mentioned a 2-propyn-1-yl group, an 1-methyl-2-propyn-1-yl group, an 1-ethyl-2-propyn-1-yl group, a 2-butyn-1-yl group, an 1-methyl-2-butyn-1-yl group, an 1-ethyl-2-butyn-1-yl group, a 3-butyn-1-yl group, an 1-methyl-3-butyn-1-yl group, an 1-ethyl-3-butyn-1-yl group, a 2-pentyn-1-yl group, an 1-methyl-2-pentyn-1-yl group, a 3-pentyn-1-yl group, an 1-methyl-3-pentyn-1-yl group, a 4-pentyn-1-yl group, a 5-hexyn-1-yl group, a 4-hexyn-1-yl group, a 3-hexyn-1-yl group, a 2-hexyn-1-yl group, and the like.

In the present invention, "a $C_1$ to $C_6$ alkoxy group" means a group obtained by substituting an oxy group with "a $C_1$ to $C_6$ alkyl group". For example, there may be mentioned a methoxy group, an ethoxy group, a n-propoxy group, an isopropoxy group, a n-butoxy group, a sec-butoxy group, a 2-methylpropoxy group, a n-pentyloxy group, an isopentyloxy group, a 2-methylbutoxy group, an 1-ethylpropoxy group, a 2,2-dimethylpropoxy group, a n-hexyloxy group, a 4-methylpentoxy group, a 3-methylpentoxy group, a 2-methylpentoxy group, a 3,3-dimethylbutoxy group, a 2,2-dimethylbutoxy group, an 1,1-dimethylbutoxy group, a tert-butoxy group, and the like.

In the present invention, "a ($C_1$ to $C_6$ alkoxy)($C_2$ to $C_4$ alkyl)" means a group obtained by substituting "a $C_2$ to $C_4$ alkyl group" with "a $C_1$ to $C_6$ alkoxy group" or, in other words, a group obtained by replacing one carbon of a $C_4$ to $C_{11}$ alkyl group with one oxygen at arbitrary chemically possible position. For example, there may be mentioned a methoxyethyl group, an ethoxyethyl group, a propyloxyethyl group, an isopropyloxyethyl group, a butyloxyethyl group, an isobutyloxyethyl group, a sec-butyloxyethyl group, a tert-butyloxyethyl group, an isopentyloxyethyl group, a 2-methylbutyloxyethyl group, a 3-methylbutyloxyethyl group, an 1-ethylpropyloxyethyl group, an 1,1-dimethylpropyloxyethyl group, an 1,2-dimethylpropyloxyethyl group, a neopentyloxyethyl group, a hexyloxyethyl group, a 4-methylpentyloxyethyl group, a 3-methylpentyloxyethyl group, a 2-methylpentyloxyethyl group, an 1-methylpentyloxyethyl group, a 3,3-dimethylbutyloxyethyl group, a 2,2-dimethylbutyloxyethyl group, an 1,1-dimethylbutyloxyethyl group, an 1,2-dimethylbutyloxyethyl group, an 1,3-dimethylbutyloxyethyl group, a 2,3-dimethylbutyloxyethyl group, an 1-ethylbutyloxyethyl group, a 2-ethylbutyloxyethyl group, a methoxypropyl group, an ethoxypropyl group, a propyloxypropyl group, an isopropyloxypropyl group, a butyloxypropyl group, an isobutyloxypropyl group, a sec-butyloxypropyl group, a tert-butyloxypropyl group, an isopentyloxypropyl group, a 2-methylbutyloxypropyl group, a 3-methylbutyloxypropyl group, an 1-ethylpropyloxypropyl group, an 1,1-dimethylpropyloxypropyl group, an 1,2-dimethylpropyloxypropyl group, a neopentyloxypropyl group, a hexyloxypropyl group, a 4-methylpentyloxypropyl group, a 3-methylpentyloxypropyl group, a 2-methylpentyloxypropyl group, an 1-methylpentyloxypropyl group, a 3,3-dimethylbutyloxypropyl group, a 2,2-dimethylbutyloxypropyl group, an 1,1-dimethylbutyloxypropyl group, an 1,2-dimethylbutyloxypropyl group, an 1,3-dimethylbutyloxypropyl group, a 2,3-dimethylbutyloxypropyl group, an 1-ethylbutyloxypropyl group, a 2-ethylbutyloxypropyl group, a methoxybutyl group, an ethoxybutyl group, a propyloxybutyl group, an isopropyloxybutyl group, a butyloxybutyl group, an isobutyloxybutyl group, a sec-butyloxybutyl group, a tert-butyloxybutyl group, an isopentyloxybutyl group, a 2-methylbutyloxybutyl group, a 3-methylbutyloxybutyl group, an 1-ethylpropyloxybutyl group, an 1,1-dimethylpropyloxybutyl group, an 1,2-dimethylpropyloxybutyl group, a neopentyloxybutyl group, a hexyloxybutyl group, a 4-methylpentyloxybutyl group, a 3-methylpentyloxybutyl group, a 2-methylpentyloxybutyl group, an 1-methylpentyloxybutyl group, a 3,3-dimethylbutyloxybutyl group, a 2,2-dimethylbutyloxybutyl group, an 1,1-dimethylbutyloxybutyl group, an 1,2-dimethylbutyloxybutyl group, an 1,3-dimethylbutyloxybutyl group, a 2,3-dimethylbutyloxybutyl group, an 1-ethylbutyloxybutyl group, a 2-ethylbutyloxybutyl group, and the like.

In the present invention, "a $C_1$ to $C_6$ alkylthio group" means a group obtained by substituting a thio group with "a $C_1$ to $C_6$ alkyl group". For example, there may be mentioned a methylthio group, an ethylthio group, a propylthio group, an isopropylthio group, a butylthio group, an isobutylthio group, a sec-butylthio group, a tert-butylthio group, a pentylthio group, a neopentylthio group, a tert-pentylthio group, a 2-methylbutylthio group, a hexylthio group, an isohexylthio group, and the like.

In the present invention, "a $C_3$ to $C_8$ cycloalkylthio group" means a group obtained by substituting a thio group with "a $C_3$ to $C_8$ cycloalkyl group". For example, there may be mentioned a cyclopropylthio group, a cyclobutylthio group, a cyclopentylthio group, a cyclohexylthio group, a cycloheptylthio group, a cyclooctylthio group, and the like.

In the present invention, "a ($C_1$ to $C_6$ alkyl)carbonyl group" means a group obtained by substituting a carbonyl group with "a $C_1$ to $C_6$ alkyl group". For example, there may be mentioned an acetyl group, a propionyl group, a butyryl group, an isobutyryl group, a n-pentylcarbonyl group, a sec-butylcarbonyl group, a tert-butylcarbonyl group, an isopentylcarbonyl group, a 2-methylbutylcarbonyl group, a 3-methylbutylcarbonyl group, an 1-ethylpropylcarbonyl group, an 1,1-dimethylpropylcarbonyl group, an 1,2-dimethylpropylcarbonyl group, a neopentylcarbonyl group, a 4-methylpentylcarbonyl group, a 3-methylpentylcarbonyl, a 2-methylpentylcarbonyl group, an 1-methylpentylcarbonyl group, a 3,3-dimethylbutylcarbonyl group, a 2,2-dimethylbutylcarbonyl group, an 1,1-dimethylbutylcarbonyl group, an 1,2-dimethylbutylcarbonyl group, an 1,3-dimethylbutylcarbonyl group, a 2,3-dimethylbutylcarbonyl group, an 1-ethylbutylcarbonyl group, a 2-ethylbutylcarbonyl group, a n-hexylcarbonyl group, and the like.

In the present invention, "a ($C_1$ to $C_6$ alkoxy)carbonyl group" means a group obtained by substituting a carbonyl group with "a $C_1$ to $C_6$ alkoxy group". For example, there may be mentioned a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentoxycarbonyl group, an isopentoxycarbonyl group, a 2-methylbutoxycarbonyl group, a 3-methylbutoxycarbonyl group, an 1-ethylpropoxycarbonyl group, an 1,1-dimethylpropoxycarbonyl group, an 1,2-dimethylpropoxycarbonyl group, a neopentoxycarbonyl group, a 4-methylpentoxycarbonyl group, a 3-methylpentoxycarbonyl, a 2-methylpentoxycarbonyl group, an 1-methylpentoxycarbonyl group, a 3,3-dimethylbutoxycarbonyl group, a 2,2-dimethylbutoxycarbonyl group, an 1,1-dimethylbutoxycarbonyl group, an 1,2-dimethylbutoxycarbonyl group, an 1,3-dimethylbutoxycarbonyl group, a 2,3-dimethylbutoxycarbonyl group, an 1-ethylbutoxycarbonyl group, a 2-ethylbutoxycarbonyl group, a n-hexoxycarbonyl group, and the like.

In the present invention, "a $C_3$ to $C_8$ cycloalkyloxy group" means a group obtained by substituting an oxy group with "a $C_3$ to $C_8$ cycloalkyl group". For example, there may be mentioned a cyclopropyloxy group, a cyclobutyloxy group, a cyclopentyloxy group, a cyclohexyloxy group, a cycloheptyloxy group, a cyclooctyloxy group, and the like.

In the present invention, "a mono($C_1$ to $C_6$ alkyl)amino group" means a group obtained by substituting an amino group with "a $C_1$ to $C_6$ alkyl group". For example, there may be mentioned a methylamino group, an ethylamino group, a propylamino group, an isopropylamino group, a butylamino group, an isobutylamino group, a sec-butylamino group, a tert-butylamino group, a pentylamino group, a hexylamino group, and the like.

In the present invention, "a di($C_1$ to $C_6$ alkyl)amino group" means a group obtained by substituting an amino group with two of the same or different "a $C_1$ to $C_6$ alkyl group". For example, there may be mentioned a dimethylamino group, a diethylamino group, a dipropylamino group, a diisopropylamino group, a dibutylamino group, a diisobutylamino group, a di(sec-butyl)amino group, a di(tert-butyl)amino group, a dipentylamino group, a dihexylamino group, and the like.

In the present invention, "a ($C_1$ to $C_6$ alkyl)aminocarbonyl group" means a group obtained by substituting a carbonyl group with "a ($C_1$ to $C_6$ alkyl)amino group". For example, there may be mentioned a methylaminocarbonyl group, an ethylaminocarbonyl group, a propylaminocarbonyl group, an isopropylaminocarbonyl group, a butylaminocarbonyl group, an isobutylaminocarbonyl group, a sec-butylaminocarbonyl group, a tert-butylaminocarbonyl group, a pentylaminocarbonyl group, a hexylaminocarbonyl group, and the like.

In the present invention, "a $C_1$ to $C_6$ alkylsulfonyl group" means a group obtained by substituting a sulfonyl group with "a $C_1$ to $C_6$ alkyl group". For example, there may be mentioned a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, a hexylsulfonyl group, and the like.

In the present invention, "a $C_1$ to $C_6$ alkylaminosulfonyl group" means a group obtained by substituting a sulfonyl group with "a mono($C_1$ to $C_6$ alkyl)amino group". For example, there may be mentioned a methylaminosulfonyl group, an ethylaminosulfonyl group, a propylaminosulfonyl group, an isopropylaminosulfonyl group, a butylaminosulfonyl group, an isobutylaminosulfonyl group, a sec-butylaminosulfonyl group, a tert-butylaminosulfonyl group, a pentylaminosulfonyl group, a hexylaminosulfonyl group, and the like.

In the present invention, "a (hydroxycarbonyl)($C_1$ to $C_3$ alkyl) group" means a group obtained by substituting "a $C_1$ to $C_3$ alkyl group" with "a (hydroxycarbonyl) group" at arbitrary position. For example, there may be mentioned a hydroxycarbonylmethyl group, a (1-hydroxycarbonyl)ethyl group, a (2-hydroxycarbonyl)ethyl group, a (3-hydroxycarbonyl)propyl group, an a (2-hydroxycarbonyl)propyl group, a (1-hydroxycarbonyl)propyl group, a (1-hydroxycarbonyl)(1-methyl)ethyl group, and the like.

In the present invention, "a ($C_1$ to $C_6$ alkoxy)carbonyl($C_1$ to $C_3$ alkyl) group" means a group obtained by substituting "a $C_1$ to $C_3$ alkyl group" with "a ($C_1$ to $C_6$ alkoxy)carbonyl group" at arbitrary position. For example, there may be mentioned a methoxycarbonylmethyl group, a methoxycarbonylethyl group, a (3-methoxycarbonyl)propyl group, a (2-methoxycarbonyl)propyl group, a (1-methoxycarbonyl)propyl group, a (1-methoxycarbonyl)(1-methyl)ethyl group, an ethoxycarbonylmethyl group, an ethoxycarbonylethyl group, an (3-ethoxycarbonyl)propyl group, an (2-ethoxycarbonyl)propyl group, an (1-ethoxycarbonyl)propyl group, an (1-ethoxycarbonyl)(1-methyl)ethyl group, and the like.

In the present invention, "a ($C_1$ to $C_6$ alkyl)sulfonyl($C_1$ to $C_3$ alkyl) group" means a group obtained by substituting "a $C_1$ to $C_3$ alkyl group" with "a ($C_1$ to $C_6$ alkyl)sulfonyl group" at arbitrary position. For example, there may be mentioned a methylsulfonyl methyl group, a methylsulfonylethyl group, a (3-methylsulfonyl)propyl group, a (2-methylsulfonyl)propyl group, a (1-methylsulfonyl)propyl group, a (1-methylsulfonyl)(1-methyl)ethyl group, an ethylsulfonylmethyl group, an ethylsulfonylethyl group, an (3-ethylsulfonyl)propyl group, an (2-ethylsulfonyl)propyl group, an (1-ethylsulfonyl)propyl group, an (1-ethylsulfonyl)(1-methyl)ethyl group, and the like.

In the present invention, "a $C_6$ to $C_{10}$ aryl group" means an aromatic hydrocarbon group having 6 to 10 carbons. For example, there may be mentioned a phenyl group, a naphthyl group, an indenyl group, a tetrahydronaphthyl group, an indanyl group, an azulenyl group, and the like. In the present invention, "a $C_6$ to $C_{10}$ aryloxy group" means a group obtained by substituting an oxy group with "a $C_6$ to $C_{10}$ aryl group". For example, there may be mentioned a phenyloxy group, a naphthyloxy group, an indenyloxy group, a tetrahydronaphthyloxy group, an indanyloxy group, an azulenyloxy group, and the like.

In the present invention, "a ($C_6$ to $C_{10}$ aryl)($C_1$ to $C_3$ alkyl) group" means a group obtained by substituting "a $C_1$ to $C_3$ alkyl group" with "a $C_6$ to $C_{10}$ aryl group". For example, there may be mentioned a benzyl group, a phenethyl group, a phenylpropyl group, a naphthylmethyl group, and the like.

In the present invention, "a 5- to 10-membered heteroaryl group" means a 5- to 10-membered monocyclic or bicyclic heterocyclic group having aromaticity, wherein the heterocyclic group contains 1 to 5 heteroatoms selected from oxygen, sulfur and nitrogen. Further, in the case of a bicyclic aromatic heterocyclic group, if one ring is aromatic ring or aromatic heterocyclic ring, the other ring may be non-aromatic ring. In such aromatic heterocyclic group, the number of respective heteroatoms and combinations thereof are not particularly limited as long as ring having prescribed number of members can be formed and can exist chemically stably. As such "a 5- to 10-membered heteroaryl group", for example, there may be mentioned a pyridyl group, a pyrazyl group, a pyrimidyl group, a pyridazinyl group, a furyl group, a thienyl group, a pyrrole group, a pyrazolyl group, an 1,3-dioxaindanyl group, an isoxazolyl group, an isothiazolyl group, a benzofuranyl group, an isobenzofuryl group, a benzothienyl group, an indolyl group, an isoindolyl group, a chromanyl group, a benzothiazolyl group, a benzoimidazolyl group, a benzoxazolyl group, a pyranyl group, an imidazolyl group, an oxazolyl group, a thiazolyl group, a triazinyl group, a triazolyl group, a furazanyl group, a thiadiazolyl, a dihydrobenzofuryl group, a dihydroisobenzofuryl group, a dihydroquinolyl group, a dihydroisoquinolyl group, a dihydrobenzoxazolyl group, a dihydropteridinyl group, a benzoxazolyl group, a benzisoxazolyl group, a benzodioxazolyl group, a quinolyl group, an isoquinolyl group, a benzotriazolyl group, a pteridinyl group, a purinyl group, a quinoxalinyl group, a quinazolinyl group, a cinnolinyl group, a tetrazolyl group, and the like.

In the present invention, "a (5- to 10-membered heteroaryl)($C_1$ to $C_3$ alkyl) group" means a group obtained by substituting "a $C_1$ to $C_3$ alkyl group" with "a 5- to 10-membered heteroaryl group". For example, there may be mentioned a pyridylmethyl group, a thienylmethyl group, a thiazolylmethyl group, a benzothiazolylmethyl group, a benzothiophenylmethyl group, and the like.

In the present invention, "a 3- to 8-membered heterocycloalkyl group" means a 3- to 8-membered aliphatic heterocyclic group which may be saturated or partially unsaturated, wherein the ring contains 1 to 4 heteroatoms selected from oxygen, sulfur and nitrogen. For example, there may be mentioned a piperidyl group, a tetrahydrofuranyl group, a tetrahydropyranyl group, a tetrahydrothienyl group, a morpholyl group, and the like.

In the present invention, "a (3- to 8-membered heterocycloalkyl)($C_1$ to $C_3$ alkyl) group" means a group obtained by substituting "a $C_1$ to $C_3$ alkyl group" with "a 3- to 8-membered heterocycloalkyl group". For example, there may be mentioned a piperidylmethyl group, a tetrahydrofuranylmethyl group, a tetrahydropyranylmethyl group, a tetrahydrothienylmethyl group, a morpholinoethyl group, a oxetan-3-ylmethyl group, and the like.

In the present invention, "spiroheteroalkyl group" means a spiroalkyl group in which 1 to 4 carbon atoms replaced with 1 to 4 heteroatoms selected from oxygen, sulfur and nitrogen. "A $C_6$ to $C_9$ spiroheteroalkyl group" means a spiroalkyl group having 6 to 9 carbons. For example, there may be mentioned a 4-oxaspiro[2.4]heptanyl group, a 4-oxaspiro[2.5]octaneyl group, and the like.

In the present invention, "a ($C_5$ to $C_9$ bicycloalkyl)($C_1$ to $C_3$ alkyl) group" means a group obtained by substituting "a $C_1$ to $C_3$ alkyl group" with "a $C_5$ to $C_9$ bicycloalkyl group" at arbitrary position. For example, there may be mentioned a bicyclo[1.1.1]pentanyl methyl group, a bicyclo[3.1.0]hexanyl methyl group, a bicyclo[3.1.0]hexanyl ethyl group, a bicyclo[2.2.0]hexanyl methyl group, a bicyclo[2.2.0]hexanyl ethyl group, a bicyclo[2.1.1]hexanyl methyl group, a bicyclo[2.1.1]hexanyl ethyl group, a bicyclo[3.2.0]heptanyl methyl group, a bicyclo[3.2.0]heptanyl ethyl group, a bicyclo[2.2.1]heptanyl methyl group, a bicyclo[2.2.1]heptanyl ethyl group, a bicyclo[3.1.1]heptanyl methyl group, a bicyclo[4.1.0]heptanyl methyl group, an octahydropentalenyl methyl group, a bicyclo[2.2.2]octanyl methyl group, a bicyclo[3.2.1]octanyl methyl group, a bicyclo[4.2.0]octanyl methyl group, a bicyclo[4.1.1]octanyl methyl group, a bicyclo[5.1.0]octanyl methyl group, an octahydro-1H-indenyl methyl group, a bicyclo[3.2.2]nonanyl methyl group, a bicyclo[3.3.1]nonanyl methyl group, a bicyclo[4.2.1]nonanyl methyl group, a bicyclo[5.2.0]nonanyl methyl group, and the like.

In the present invention, "heterobicycloalkyl group" means a bicycloalkyl group in which 1 to 4 carbon atoms replaced with 1 to 4 heteroatoms selected from oxygen, sulfur and nitrogen. "A $C_6$ to $C_9$ heterobicycloalkyl group" means a heterobicycloalkyl group having 6 to 9 carbons. For example, there may be mentioned a 7-oxabicyclo[2.2.1]heptanyl group and the like.

In the present invention, "a ($C_6$ to $C_9$ heterobicycloalkyl)($C_1$ to $C_3$ alkyl) group" means a group obtained by substituting "a $C_1$ to $C_3$ alkyl group" with "a $C_6$ to $C_9$ heterobicycloalkyl group" at arbitrary position. For example, there may be mentioned a 7-oxabicyclo[2.2.1]heptanyl methyl group, a 7-oxabicyclo[2.2.1]heptanyl ethyl group, and the like.

In the present invention, in "a $C_1$ to $C_6$ alkyl group substituted by 0, 1, 2 or 3 $R^a$ groups", when the $C_1$ to $C_6$ alkyl group is substituted by a plurality of $R^a$ groups, each $R^a$ group can be selected independently and the $C_1$ to $C_6$ alkyl group can be substituted by the same $R^a$ groups or by different $R^a$ groups. In addition, meaning of other expressions such as "a $C_1$ to $C_6$ alkyl group substituted by 0, 1, 2 or 3 $R^b$ groups" and the like mean similar situations.

The present invention relates to a compound represented by formula (I) or a pharmaceutically acceptable salt thereof:

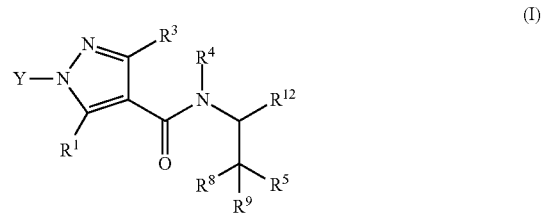

In the formula (I), $R^1$ is selected from F, Cl, Br, a $C_1$ to $C_6$ alkyl group substituted by 0, 1, 2 or 3 $R^a$ groups and a $C_3$ to $C_8$ cycloalkyl group substituted by 0, 1, 2 or 3 $R^a$ groups;
wherein $R^a$ is, independently selected from F, $C_1$ to $C_4$ alkyl group, —OH, —CN, —NO$_2$, —NH$_2$, —CO$_2$H, a $C_1$ to $C_6$ alkoxy group, a mono($C_1$ to $C_6$ alkyl)amino group, a di($C_1$ to $C_6$ alkyl)amino group, —CF$_3$ and an oxo group.

The "a $C_1$ to $C_6$ alkyl group substituted by 0, 1, 2 or 3 $R^a$ groups" in $R^1$ is preferably $C_1$ to $C_3$ alkyl group substituted by 0, 1, 2 or 3 $R^a$ groups, and more preferable is a trifluoromethyl group or a difluoromethyl group.

The "a $C_3$ to $C_8$ cycloalkyl group substituted by 0, 1, 2 or 3 $R^a$ groups" in $R^1$ is preferably $C_3$ to $C_4$ cycloalkyl group substituted by 0, 1, 2 or 3 $R^a$ groups, more preferable is a cyclopropyl group substituted by 0, 1, 2 or 3 $R^a$ groups.

On the whole, $R^1$ is preferably Cl, a $C_1$ to $C_4$ alkyl group substituted by 0, 1, 2 or 3 $R^a$ groups or a cyclopropyl group substituted by 0, 1, 2 or 3 $R^a$ groups, and more preferable is a trifluoromethyl group, a difluoromethyl group or Cl.

In the formula (I), Y is a $C_4$ to $C_6$ cycloalkyl group, a $C_6$ to $C_9$ bicycloalkyl group or a $C_6$ to $C_9$ spiroalkyl group, all of which are substituted by a $R^2$ group, 0 or 1 $R^6$ group and 0, 1, 2 or 3 $R^7$ groups;
wherein $R^2$ is selected from —OH, —$CO_2H$, —$SO_3H$, —$CONH_2$, —$SO_2NH_2$, a ($C_1$ to $C_6$ alkoxy)carbonyl group substituted by 0, 1, 2 or 3 $R^c$ groups, a ($C_1$ to $C_6$ alkyl)aminocarbonyl group substituted by 0, 1, 2 or 3 $R^c$ groups, a $C_1$ to $C_6$ alkylsulfonyl group substituted by 0, 1, 2 or 3 $R^c$ groups, a $C_1$ to $C_6$ alkylaminosulfonyl group substituted by 0, 1, 2 or 3 $R^c$ groups, a (hydroxycarbonyl)($C_1$ to $C_3$ alkyl) group substituted by 0, 1, 2 or 3 $R^c$ groups, a ($C_1$ to $C_6$ alkoxy)carbonyl($C_1$ to $C_3$ alkyl) group substituted by 0, 1, 2 or 3 $R^c$ groups, a ($C_1$ to $C_6$ alkyl)sulfonyl($C_1$ to $C_3$ alkyl) group substituted by 0, 1, 2 or 3 $R^c$ groups and a ($C_2$ to $C_6$ alkenyl)($C_1$ to $C_3$ alkyl) group substituted by 0, 1, 2 or 3 $R^c$ groups;
$R^6$ and $R^7$ are independently selected from H, F, —OH, —$NH_2$, —CN, a $C_1$ to $C_6$ alkyl group substituted by 0, 1, 2 or 3 $R^b$ groups and a $C_1$ to $C_6$ alkoxy group substituted by 0, 1, 2 or 3 $R^b$ groups;
wherein $R^b$ and $R^c$ are, independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group;

The "a $C_4$ to $C_6$ cycloalkyl group, a $C_6$ to $C_9$ bicycloalkyl group or a $C_6$ to $C_9$ spiroalkyl group, all of which are substituted by a $R^2$ group, 0 or 1 $R^6$ group and 0, 1, 2 or 3 $R^7$ groups" in Y is preferably a group represented by formula (II-a), formula (II-b), formula (II-c) or formula (II-d):

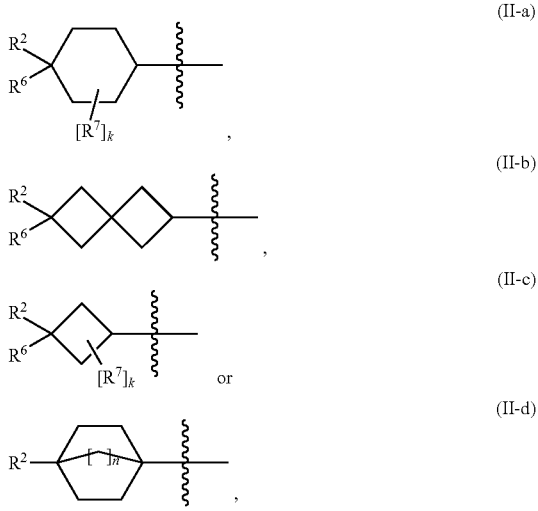

wherein:
k is 0, 1 or 2;
and n is 1, 2 or 3.

In the case of the group represented by formula (II-a), formula (II-b), formula (II-c) or formula (II-d), Y is preferably a group represented by formula (II-a), formula (II-c) or formula (II-d); and more preferably a group represented by formula (II-a) or formula (II-d).

The variable, n, is preferably 2 in a group represented by formula (II-d).

$R^2$ in Y is preferably —$CO_2H$, —$SO_3H$, —$CONH_2$, —$SO_2NH_2$, a ($C_1$ to $C_2$ alkyl)aminocarbonyl group substituted by 0 or 1 $R^c$ groups, a $C_1$ to $C_2$ alkylsulfonyl group substituted by 0 or 1 $R^c$ groups, a $C_1$ to $C_2$ alkylaminosulfonyl group substituted by 0 or 1 $R^c$ groups or a (hydroxycarbonyl)($C_1$ to $C_3$ alkyl) group substituted by 0, 1, 2 or 3 $R^c$ groups, and more preferable is —$CO_2H$ or a hydroxycarbonylmethyl group substituted by 0, 1 or 2 $R^c$ groups.

$R^6$ in Y is preferably H or a $C_1$ to $C_4$ alkyl group without $R^b$ group, and more preferable is H, a methyl group or an ethyl group.

$R^7$ in Y is preferably H or a $C_1$ to $C_2$ alkyl group without $R^b$ group, and more preferable is H or a methyl group.

In the formula (I), $R^3$ is selected from H, F, Cl, —$CH_3$ and —$CF_3$. $R^3$ is preferably H.

In the formula (I), $R^4$ is selected from a $C_1$ to $C_6$ alkyl group substituted by 0, 1, 2, 3, 4 or 5 $R^e$ groups, a ($C_2$ to $C_6$ alkenyl)($C_1$ to $C_3$ alkyl) group substituted by 0, 1, 2, 3, 4 or 5 $R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or 5 $R^g$ groups, a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_6$ to $C_9$ spiroheteroalkyl group substituted by 0, 1, 2, 3, 4 or 5 $R^g$ groups, a $C_5$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups, a $C_6$ to $C_9$ heterobicycloalkyl group substituted by 0, 1, 2, 3, 4 or 5 $R^g$ groups and a ($C_6$ to $C_9$ heterobicycloalkyl)($C_1$ to $C_3$ alkyl) group substituted by 0, 1, 2, 3, 4 or 5 $R^g$ groups;
wherein $R^e$ is independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group;
$R^f$ is independently selected from F, Cl, Br, —OH, —CN, —$NO_2$, —$CO_2H$, a $C_1$ to $C_6$ alkyl group substituted by 0, 1, 2 or 3 $R^k$ groups, a $C_2$ to $C_6$ alkenyl group substituted by 0, 1, 2 or 3 $R^k$ groups, a $C_2$ to $C_6$ alkynyl group substituted by 0, 1, 2 or 3 $R^k$ groups, a $C_3$ to $C_8$ cycloalkyl group substituted by 0, 1, 2 or 3 $R^k$ groups, a $C_1$ to $C_6$ alkoxy group substituted by 0, 1, 2 or 3 $R^k$ groups, a $C_3$ to $C_8$ cycloalkyloxy group substituted by 0, 1, 2 or 3 $R^k$ groups, —SH, a $C_1$ to $C_6$ alkylthio group substituted by 0, 1, 2 or 3 $R^k$ groups, a $C_3$ to $C_8$ cycloalkylthio group substituted by 0, 1, 2 or 3 $R^k$ groups, a ($C_1$ to $C_6$ alkyl)carbonyl group substituted by 0, 1, 2 or 3 $R^k$ groups, a ($C_1$ to $C_6$ alkoxy)carbonyl group substituted by 0, 1, 2 or 3 $R^k$ groups, a ($C_1$ to $C_6$ alkyl)aminocarbonyl group substituted by 0, 1, 2 or 3 $R^k$ groups, a 3- to 8-membered heterocycloalkyl group substituted by 0, 1, 2 or 3 $R^k$ groups, a $C_1$ to $C_6$ alkylsulfonyl group substituted by 0, 1, 2 or 3 $R^k$ groups, —$NH_2$, a mono($C_1$ to $C_6$ alkyl)amino group substituted by 0, 1, 2 or 3 $R^k$ groups and a di($C_1$ to $C_6$ alkyl)amino group substituted by 0, 1, 2 or 3 $R^k$ groups; wherein, $R^k$ is independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group;

$R^g$ is independently selected from F, Cl, a $C_1$ to $C_6$ alkyl group, —OH, —CN, —$NH_2$, —$NO_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$, a $C_1$ to $C_6$ alkylene group substituted by 0, 1, 2 or 3 $R^k$ groups, a $C_2$ to $C_6$ alkenylene group substituted by 0, 1, 2 or 3 $R^k$ groups and an oxo group; wherein $R^l$ is independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group.

The "a $C_1$ to $C_6$ alkyl group substituted by 0, 1, 2, 3, 4 or 5 $R^e$ groups" in $R^4$ is preferably $C_2$ to $C_6$ alkyl group substituted by 0, 1, 2, 3, 4 or 5 $R^e$ and more preferably a tert-butylmethyl group or a 3,3,3-trifluoro-2,2-dimethylpropyl group.

The "a ($C_2$ to $C_6$ alkenyl)($C_1$ to $C_3$ alkyl) group substituted by 0, 1, 2, 3, 4 or 5 $R^e$ groups" in $R^4$ is preferably one having 3 to 6 carbons in ($C_2$ to $C_6$ alkenyl)($C_1$ to $C_3$ alkyl) and more preferably a 3-methyl-2-buten-1-yl group.

The "a ($C_2$ to $C_6$ alkynyl)($C_1$ to $C_3$ alkyl) group substituted by 0, 1, 2, 3, 4 or 5 $R^e$ groups" in $R^4$ is preferably one having 4 to 8 carbons in ($C_2$ to $C_6$ alkynyl)($C_1$ to $C_3$ alkyl) and more preferably a 4,4-dimethyl-2-pentyn-1-yl group.

The "a ($C_1$ to $C_6$ alkoxy)($C_2$ to $C_4$ alkyl) group substituted by 0, 1, 2, 3, 4 or 5 $R^e$ groups" in $R^4$ is preferably one having 3 to 7 carbons in ($C_1$ to $C_6$ alkoxy)($C_2$ to $C_4$ alkyl), more preferably a $C_1$ to $C_4$ alkoxyethyl group substituted by 0, 1, 2 or 3 alkyl groups, and even more preferably a 2,2-dimethyl-2-methoxyethyl group or a 2-(tert-butoxy)ethyl group.

The "a ($C_6$ to $C_{10}$ aryl)($C_1$ to $C_3$ alkyl) group substituted by 0, 1, 2, 3, 4 or 5 $R^f$ groups" in $R^4$ is preferably a benzyl group substituted by 0, 1, 2, 3, 4 or 5 $R^f$'s; more preferably a benzyl group substituted by 1, 2 or 3 groups selected from F and Cl, or a unsubstituted benzyl group; and even more preferable is a 4-fluorobenzyl group, a 3,5-difluorobenzyl group or a 4-(trifluoromethyl)benzyl group.

The "a (5- to 10-membered heteroaryl)($C_1$ to $C_3$ alkyl) group substituted by 0, 1, 2, 3, 4 or 5 $R^f$ groups" in $R^4$ is preferably a pyridylmethyl group, a thienylmethyl group, a thiazolylmethyl group or a furanylmethyl group.

The "a $C_3$ to $C_8$ cycloalkyl group substituted by 0, 1, 2, 3, 4 or 5 $R^g$ groups" in $R^4$ is preferably $C_3$ to $C_6$ cycloalkyl group substituted by 0, 1, 2, 3, 4 or 5 $R^g$ groups and more preferably a 2,2-dimethylcyclobutyl group or a 4,4-dimethylcyclohexyl group.

The "a ($C_3$ to $C_8$ cycloalkyl)($C_1$ to $C_3$ alkyl) group substituted by 0, 1, 2, 3, 4 or 5 $R^g$ groups" in $R^4$ is preferably a $C_3$ to $C_6$ cycloalkyl methyl group substituted by 0, 1, 2, 3 or 4 $R^g$ groups; and more preferable is a (1-fluorocyclopentyl)methyl group, a (3,3-dimethylcyclobutyl)methyl group, a (1-methylcyclobutyl)methyl group, a (1-(trifluoromethyl)cyclobutyl) methyl group, a (1-(trifluoromethyl)cyclopropyl)methyl group or a (1-methylcyclopropyl)methyl group.

The "a 3- to 8-membered heterocycloalkyl group substituted by 0, 1, 2, 3, 4 or 5 $R^g$ groups" in $R^4$ is preferably a 3- to 6-membered heterocycloalkyl group substituted by 0, 1, 2, 3, 4 or 5 $R^g$ groups.

The "a (3- to 8-membered heterocycloalkyl)($C_1$ to $C_3$ alkyl) group substituted by 0, 1, 2, 3, 4 or 5 $R^g$ groups" in $R^4$ is preferably a 3- to 6-membered heterocycloalkyl methyl group substituted by 0, 1, 2, 3, 4 or 5 $R^g$ groups; more preferably a tetrahydrofuranylmethyl group substituted by 1, 2 or 3 groups selected from F, a $C_1$ to $C_4$ alkyl group and a $C_1$ to $C_6$ alkylene group substituted by 0, 1, 2 or 3 $R^l$ groups.

The "a $C_6$ to $C_9$ spiroalkyl group substituted by 0, 1, 2, 3, 4 or 5 $R^g$ groups" in $R^4$ is preferably a $C_7$ to $C_8$ spiroalkyl ring substituted by 0, 1, 2, 3, 4 or 5 $R^g$ groups; more preferably a spiro[2.5]octan-1-yl group, a spiro[3.5]nonan-1-yl group, a spiro[3.3]heptan-1-yl group or a spiro[3.3]heptan-2-yl group.

The "a ($C_6$ to $C_9$ spiroalkyl)($C_1$ to $C_3$ alkyl) group substituted by 0, 1, 2, 3, 4 or 5 $R^g$ groups" in $R^4$ is preferably a $C_6$ to $C_8$ spiroalkyl methyl group substituted by 0, 1, 2, 3, 4 or 5 $R^g$ groups; more preferably a spiro[2.5]octan-6-ylmethyl group substituted by 0, 1, 2 or 3 $R^g$ groups or a spiro[2.3]hexan-5-ylmethyl group substituted by 0, 1, 2 or 3 $R^g$ groups; and even more preferable is a spiro[2.5]octan-6-ylmethyl group, (5-fluoro-spiro[2.3]hexan)-5-ylmethyl group or spiro[2.3]hexan-5-ylmethyl group.

The "a $C_6$ to $C_9$ spiroheteroalkyl group substituted by 0, 1, 2, 3, 4 or 5 $R^g$ groups" in $R^4$ is preferably a $C_7$ to $C_8$ spiroheteroalkyl ring substituted by 0, 1, 2, 3, 4 or 5 $R^g$ groups.

The "a $C_5$ to $C_9$ bicycloalkyl group substituted by 0, 1, 2, 3, 4 or 5 $R^g$ groups" in $R^4$ is preferably a $C_6$ to $C_8$ bicycloalkyl ring substituted by 0, 1, 2, 3, 4 or 5 $R^g$ groups; more preferably a bicyclo[3.1.0]hexan-3-yl group substituted by 0, 1, 2 or 3 $R^g$ groups; and even more preferable is a 6,6-dimethylbicyclo[3.1.0]hexan-3-yl group.

The "a ($C_5$ to $C_9$ bicycloalkyl)($C_1$ to $C_3$ alkyl) group substituted by 0, 1, 2, 3, 4 or 5 $R^g$ groups" in $R^4$ is preferably a $C_5$ to $C_7$ bicycloalkyl methyl group substituted by 0, 1, 2, 3, 4 or 5 $R^g$ groups; more preferably a (bicyclo[1.1.1]pentan-1-yl) methyl group substituted by 0, 1, 2 or 3 $R^g$ groups or a (bicyclo[2.2.1]heptan-1-yl)methyl group substituted by 0, 1, 2 or 3 $R^g$ groups; and even more preferable is a (4-methylbicyclo[2.2.1]heptan-1-yl)methyl group or (bicyclo[1.1.1]pentan-1-yl)methyl group.

The "a ($C_6$ to $C_9$ heterobicycloalkyl)($C_1$ to $C_3$ alkyl) group substituted by 0, 1, 2, 3, 4 or 5 $R^g$ groups" in $R^4$ is preferably a $C_6$ to $C_7$ heterobicycloalkyl methyl group substituted by 0, 1, 2, 3, 4 or 5 $R^g$ groups; more preferably (7-oxabicyclo[2.2.1] heptan-1-yl)methyl group substituted by 0, 1, 2 or 3 $R^g$ groups; and, even more preferable is (4-methyl-7-oxabicyclo[2.2.1]heptan-1-yl)methyl group or (7-oxabicyclo[2.2.1]heptan-1-yl)methyl group.

In the formula (I), $R^5$ is selected from a $C_6$ to $C_{10}$ aryl group substituted by 0, 1, 2, 3, 4 or 5 $R^i$ groups, a 5- to 10-membered heteroaryl group substituted by 0, 1, 2, 3, or 4 $R^i$ groups, a $C_3$ to $C_8$ cycloalkyl group substituted by 0, 1, 2, 3, 4 or 5 $R^j$ groups, a $C_3$ to $C_8$ cycloalkenyl group substituted by 0, 1, 2, 3, 4 or 5 $R^j$ groups and a 3- to 8-membered heterocycloalkyl group substituted by 0, 1, 2, 3, 4 or 5 $R^j$ groups;

wherein $R^i$ is independently selected from F, Cl, Br, —OH, —CN, —$NO_2$, —$CO_2H$, a $C_1$ to $C_6$ alkyl group substituted by 0, 1, 2 or 3 $R^k$ groups, a $C_2$ to $C_6$ alkenyl group substituted by 0, 1, 2 or 3 $R^k$ groups, a $C_2$ to $C_6$ alkynyl group substituted by 0, 1, 2 or 3 $R^k$ groups, a $C_3$ to $C_8$ cycloalkyl group substituted by 0, 1, 2 or 3 $R^k$ groups, a $C_1$ to $C_6$ alkoxy group substituted by 0, 1, 2 or 3 $R^k$ groups, a $C_3$ to $C_8$ cycloalkyloxy group substituted by 0, 1, 2 or 3 $R^k$ groups, —SH, a $C_1$ to $C_6$ alkylthio group substituted by 0, 1, 2 or 3 $R^k$ groups, a $C_3$ to $C_8$ cycloalkylthio group substituted by 0, 1, 2 or 3 $R^k$ groups, a ($C_1$ to $C_6$ alkyl)carbonyl group substituted by 0, 1, 2 or 3 $R^k$ groups, a ($C_1$ to $C_6$ alkoxy)carbonyl group substituted by 0, 1, 2 or 3 $R^k$ groups, a ($C_1$ to $C_6$ alkyl)aminocarbonyl group substituted by 0, 1, 2 or 3 $R^k$ groups, a 3- to 8-membered heterocycloalkyl group substituted by 0, 1, 2 or 3 $R^k$ groups, a $C_1$ to $C_6$ alkylsulfonyl group substituted by 0, 1, 2 or 3 $R^k$ groups, —$NH_2$, a mono($C_1$ to $C_6$ alkyl)amino group substituted by 0, 1, 2 or 3 $R^k$ groups and a di($C_1$ to $C_6$ alkyl)amino group substituted by 0, 1, 2 or 3 $R^k$ groups;

$R^j$ is independently selected from F, Cl, a $C_1$ to $C_6$ alkyl group, —OH, —CN, —$NH_2$, —$NO_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$, a $C_1$ to $C_6$ alkylene group substituted by 0, 1, 2 or 3 $R^l$ groups, a $C_2$ to $C_6$ alkenylene group substituted by 0, 1, 2 or 3 $R^l$ groups and an oxo group;

wherein, when $R^j$ is a divalent group of a $C_1$ to $C_6$ alkylene group or a $C_2$ to $C_6$ alkenylene group, it is meant that each group forms bonds with atoms in $R^5$; in this case, two bonds of each of these divalent groups are formed with the same atom or two different atoms in $R^5$;

wherein $R^k$ and $R^l$ are independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group.

The "a $C_6$ to $C_{10}$ aryl group substituted by 0, 1, 2, 3, or 4 $R^i$ groups" in $R^5$ is preferably a phenyl group substituted by 2 to 4 groups selected from —OH, —$NH_2$, Cl, F, —CN, —$CF_3$, —$OCF_3$, —$OCF_2H$, a methyl group, a cyclopropyl group and a methoxy group; and more preferable is a 2,6-dichlorophenyl group, a 2,6-dichloro-4-fluorophenyl group, a 2,6-dichloro-4-methylphenyl group, a 2,4,6-trichlorophenyl group, a 2-chloro-6-fluorophenyl group or a 2,6-dichloro-3-fluorophenyl group.

The "a 5- to 10-membered heteroaryl group substituted by 0, 1, 2, 3, or 4 $R^i$ groups" in $R^5$ is preferably a pyridyl group substituted by 2 to 3 groups selected from —OH, —$NH_2$, Cl, F, —CN, —$CF_3$, a methyl group, and a methoxy group; and more preferable is a 3,5-dichloropyridin-4-yl group, a 3-chloro-5-methoxypyridin-4-yl group, a 3-chloro-5-fluoropyridin-4-yl group or a 2,4-dichloro-6-methylpyridin-3-yl group.

On the whole, $R^5$ is preferably a phenyl group optionally substituted by 2, 3 or 4 $R^i$ groups or a 6-membered heteroaryl group optionally substituted by 2 or 3 $R^i$ groups.

In the formula (I), $R^8$ and $R^9$ are independently selected from H, F, —OH, —$NH_2$, a $C_1$ to $C_3$ alkyl group substituted by 0, 1, 2 or 3 $R^h$ groups, and a $C_1$ to $C_6$ alkoxy group substituted by 0, 1, 2 or 3 $R^h$ groups; or $R^8$ and $R^9$ together form an oxo group or a thioxo group;

wherein $R^h$ is, independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group.

The "a $C_1$ to $C_3$ alkyl group substituted by 0, 1, 2 or 3 $R^h$ groups" in $R^8$ and $R^9$ is preferably methyl group substituted by 0, 1, 2 or 3 $R^h$ groups.

The "a $C_1$ to $C_6$ alkoxy group substituted by 0, 1, 2 or 3 $R^h$ groups" in $R^8$ and $R^9$ is preferably methoxy group substituted by 0, 1, 2 or 3 $R^h$ groups.

On the whole, $R^8$ and $R^9$ are preferably H, F, —OH or an oxo group, and more preferable are H or an oxo group.

In the formula (I), $R^{12}$ is H; or $R^4$ and $R^{12}$ together are —$CR^mR^m$—$CR^{13}R^{14}CR^mR^m$— or —$CR^{13}R^{14}CR^mR^m$—$CR^mR^m$— to form a pyrrolidine ring.

$R^{13}$ is selected from H, a $C_1$ to $C_6$ alkyl group substituted by 0, 1, 2, 3, 4 or 5 $R^e$ groups, a $C_6$ to $C_{10}$ aryl group substituted by 0, 1, 2, 3, 4 or 5 $R^f$ groups, a $C_6$ to $C_{10}$ aryloxy group substituted by 0, 1, 2, 3, 4 or 5 $R^f$ groups, a ($C_2$ to $C_6$ alkenyl)($C_1$ to $C_3$ alkyl) group substituted by 0, 1, 2, 3, 4 or 5 $R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or 5 $R^g$ groups and a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_6$ to $C_9$ spiroheteroalkyl group substituted by 0, 1, 2, 3, 4 or 5 $R^g$ groups, a $C_6$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups, ($C_6$ to $C_9$ heterobicycloalkyl) group substituted by 0, 1, 2, 3, 4 or 5 $R^g$ groups, and a ($C_6$ to $C_9$ heterobicycloalkyl)($C_1$ to $C_3$ alkyl) group substituted by 0, 1, 2, 3, 4 or 5 $R^g$ groups;

$R^{14}$ is selected from H and a $C_1$ to $C_6$ alkyl group substituted by 0, 1, 2, 3, 4 or 5 $R^e$ groups; or $R^{13}$ and $R^{14}$ together form a $C_3$ to $C_8$ cycloalkane ring substituted by 0, 1, 2, 3, 4 or 5 $R^g$ groups, $C_3$ to $C_8$ cycloalkene ring substituted by 0, 1, 2, 3, 4 or 5 $R^g$ groups, or a 3- to 8-membered heterocycloalkane ring substituted by 0, 1, 2, 3, 4 or 5 $R^g$ groups;

$R^m$ is independently selected from H, F, Cl, —$CH_3$ and —$CF_3$;

wherein $R^g$ is selected from F, Cl, a $C_1$ to $C_6$ alkyl group, —OH, —CN, —$NH_2$, —$NO_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$, a $C_1$ to $C_6$ alkylene group substituted by 0, 1, 2 or 3 $R^l$ groups, a $C_2$ to $C_6$ alkenylene group substituted by 0, 1, 2 or 3 $R^l$ groups and an oxo group;

$R^f$ is independently selected from F, Cl, Br, —OH, —CN, —$NO_2$, —$CO_2H$, a $C_1$ to $C_6$ alkyl group substituted by 0, 1, 2 or 3 $R^k$ groups, a $C_2$ to $C_6$ alkenyl group substituted by 0, 1, 2 or 3 $R^k$ groups, a $C_2$ to $C_6$ alkynyl group substituted by 0, 1, 2 or 3 $R^k$ groups, a $C_3$ to $C_8$ cycloalkyl group substituted by 0, 1, 2 or 3 $R^k$ groups, a $C_1$ to $C_6$ alkoxy group substituted by 0, 1, 2 or 3 $R^k$ groups, a $C_3$ to $C_8$ cycloalkyloxy group substituted by 0, 1, 2 or 3 $R^k$ groups, —SH, a $C_1$ to $C_6$ alkylthio group substituted by 0, 1, 2 or 3 $R^k$ groups, a $C_3$ to $C_8$ cycloalkylthio group substituted by 0, 1, 2 or 3 $R^k$ groups, a ($C_1$ to $C_6$ alkyl)carbonyl group substituted by 0, 1, 2 or 3 $R^k$ groups, a ($C_1$ to $C_6$ alkoxy)carbonyl group substituted by 0, 1, 2 or 3 $R^k$ groups, a ($C_1$ to $C_6$ alkyl)aminocarbonyl group substituted by 0, 1, 2 or 3 $R^k$ groups, a 3- to 8-membered heterocycloalkyl group substituted by 0, 1, 2 or 3 $R^k$ groups, a $C_1$ to $C_6$ alkylsulfonyl group substituted by 0, 1, 2 or 3 $R^k$ groups, —$NH_2$, a mono($C_1$ to $C_6$ alkyl)amino group substituted by 0, 1, 2 or 3 $R^k$ groups and a di($C_1$ to $C_6$ alkyl)amino group substituted by 0, 1, 2 or 3 $R^k$ groups;

and $R^e$ and $R^k$ are, independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group.

Preferably $R^{12}$ is H; or $R^4$ and $R^{12}$ together are —$CH_2$—$CR^{13}R^{14}$—$CH_2$ to form a pyrrolidine ring, more preferably $R^{12}$ is H.

$R^{13}$ is preferably a $C_1$ to $C_6$ alkyl group, a $C_6$ to $C_{10}$ aryl group, a $C_6$ to $C_{10}$ aryloxy group, a (C6 to C10 aryl)(C1 to C3 alkyl) group, or a $C_3$ to $C_8$ cycloalkenyl group.

$R^{14}$ is preferably H or $CH_3$; or $R^{13}$ and $R^{14}$ together form a $C_3$ to $C_8$ cycloalkane ring or a $C_3$ to $C_8$ cycloalkene ring. In the formula (I), a combination of $R^1$, $R^2$, $R^3$, $R^4$, $R^5$, $R^6$, $R^7$, $R^8$, $R^9$, $R^{12}$, $R^{13}$, $R^{14}$ Y, n, k, $R^a$, $R^b$, $R^c$, $R^e$, $R^f$, $R^g$, $R^h$, $R^i$, $R^j$, $R^k$, $R^l$, $R^m$ is preferably one where respective preferable components described above are combined; and more preferably one where components described above as more preferable are combined.

In another embodiment, in conjunction with any above or below embodiments, $R^1$ is a $C_1$ to $C_6$ alkyl group substituted by 0, 1, 2 or 3 $R^a$ groups.

In another embodiment, in conjunction with any above or below embodiments, $R^1$ is a $C_1$ alkyl group substituted by 0, 1, 2 or 3 $R^a$ groups. In another embodiment, in conjunction with any above or below embodiments, $R^1$ is $CF_3$.

In another embodiment, in conjunction with any above or below embodiments, $R^2$ is $CO_2H$.

In another embodiment, in conjunction with any above or below embodiments, Y is selected from formula (II-a), formula (II-b), formula (II-c) and formula (II-d):

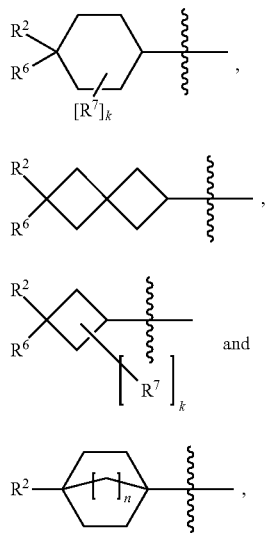

wherein, k is 0, 1 or 2; and n is 1, 2 or 3.

In another embodiment, in conjunction with any above or below embodiments, Y is selected from formula (II-a) and formula (II-d);

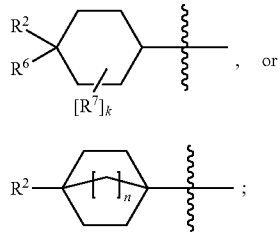

wherein in k is 0, 1 or 2; and n is 1, 2 or 3.

In another embodiment, in conjunction with any above or below embodiments, Y is selected from formula (II-a) and formula (II-d);

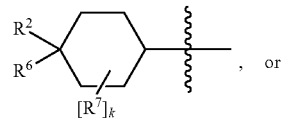

wherein in k is 0; and n 2.

In another embodiment, in conjunction with any above or below embodiments, Y is

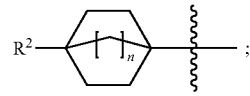

In another embodiment, in conjunction with any above or below embodiments, Y is

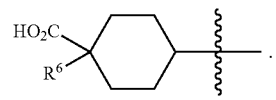

In another embodiment, in conjunction with any above or below embodiments, $R^6$ is selected from F, —OH, —$NH_2$, —CN, a $C_1$ to $C_6$ alkyl group substituted by 0, 1, 2 or 3 $R^b$ groups and a $C_1$ to $C_6$ alkoxy group substituted by 0, 1, 2 or 3 $R^b$ groups.

In another embodiment, in conjunction with any above or below embodiments, $R^6$ is a $C_1$ to $C_6$ alkyl group substituted by 0, 1, 2 or 3 $R^b$.

In another embodiment, in conjunction with any above or below embodiments, $R^6$ is $CH_3$.

In another embodiment, in conjunction with any above or below embodiments, $R^7$ is independently selected from H, F and a $C_1$ to $C_6$ alkyl group substituted by 0, 1, 2 or 3 $R^b$ groups.

In another embodiment, in conjunction with any above or below embodiments, $R^7$ is H.

In another embodiment, in conjunction with any above or below embodiments, $R^2$ is selected from —OH, —$CO_2H$, —$SO_3H$, —$CONH_2$ and —$SO_2NH_2$.

In another embodiment, in conjunction with any above or below embodiments, $R^3$ is H.

In another embodiment, in conjunction with any above or below embodiments, $R^4$ is selected from a $C_1$ to $C_6$ alkyl group substituted by 0, 1, 2 or 3 $R^e$ groups, a ($C_6$ to $C_{10}$ aryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_5$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups or a ($C_6$ to $C_9$ heterobicycloalkyl)($C_1$ to $C_3$ alkyl) group substituted by 0, 1, 2, 3, 4 or 5 $R^g$ groups.

In another embodiment, in conjunction with any above or below embodiments,
$R^4$ is a $C_1$ to $C_6$ alkyl group substituted by 0, 1, 2, 3, 4 or 5 $R^e$ groups.

In another embodiment, in conjunction with any above or below embodiments,
$R^4$ is a ($C_6$ to $C_{10}$ aryl)($C_1$ to $C_3$ alkyl) group substituted by 0, 1, 2, 3, 4 or 5 $R^f$ groups.

In another embodiment, in conjunction with any above or below embodiments,
$R^4$ is a $C_3$ to $C_8$ cycloalkyl group substituted by 0, 1, 2 or 3 $R^g$ groups.

In another embodiment, in conjunction with any above or below embodiments,
$R^4$ is a ($C_5$ to $C_9$ bicycloalkyl) group substituted by 0, 1, 2, 3, 4 or 5 $R^g$ groups.

In another embodiment, in conjunction with any above or below embodiments,
$R^4$ is a ($C_3$ to $C_8$ cycloalkyl)($C_1$ to $C_3$ alkyl) group substituted by 0, 1, 2, 3, 4 or 5 $R^g$ groups.

In another embodiment, in conjunction with any above or below embodiments,
$R^4$ is a $C_6$ to $C_9$ spiroalkyl group substituted by 0, 1, 2, 3, 4 or 5 $R^g$ groups.

In another embodiment, in conjunction with any above or below embodiments,
$R^4$ is a ($C_6$ to $C_9$ spiroalkyl)($C_1$ to $C_3$ alkyl) group substituted by 0, 1, 2, 3, 4 or 5 $R^g$ groups.

In another embodiment, in conjunction with any above or below embodiments,
$R^4$ is a ($C_5$ to $C_9$ bicycloalkyl)($C_1$ to $C_3$ alkyl) group substituted by 0, 1, 2, 3, 4 or 5 $R^g$ groups.

In another embodiment, in conjunction with any above or below embodiments,
$R^4$ is a ($C_6$ to $C_9$ heterobicycloalkyl)($C_1$ to $C_3$ alkyl) group substituted by 0, 1, 2, 3, 4 or 5 $R^g$ groups.

In another embodiment, in conjunction with any above or below embodiments, $R^8$ and $R^9$ are independently selected from H and F.

In another embodiment, in conjunction with any above or below embodiments, $R^8$ and $R^9$ together form an oxo group.

In another embodiment, in conjunction with any above or below embodiments, $R^5$ is a $C_6$ to $C_{10}$ aryl group substituted by 0, 1, 2, 3, 4 or 5 $R^i$ groups.

In another embodiment, in conjunction with any above or below embodiments, $R^5$ is a phenyl group substituted by 0, 1, 2, 3, 4 or 5 $R^i$ groups.

In another embodiment, in conjunction with any above or below embodiments, $R^5$ is a 5- to 10-membered heteroaryl group substituted by 0, 1, 2, 3, or 4 $R^i$ groups.

In another embodiment, in conjunction with any above or below embodiments, $R^5$ is a 6-membered heteroaryl group substituted by 0, 1, 2, 3, or 4 $R^i$ groups.

In another embodiment, in conjunction with any above or below embodiments, $R^5$ is pyridyl substituted by 0, 1, 2, 3, or 4 $R^i$ groups.

In another embodiment, in conjunction with any above or below embodiments, $R^{12}$ is H.

In another embodiment, in conjunction with any above or below embodiments, $R^4$ and $R^{12}$ together are —$CH_2$—$CR^{13}R^{14}CH_2$— to form a pyrrolidine ring.

In another embodiment, in conjunction with any above or below embodiments, $R^{14}$ is selected from H and $CH_3$. In another embodiment, in conjunction with any above or below embodiments, $R^{13}$ and $R^{14}$ together form a $C_3$ to $C_8$ cycloalkane ring substituted by 0, 1, 2, 3, 4 or 5 $R^g$ groups, $C_3$ to $C_8$ cycloalkene ring substituted by 0, 1, 2, 3, 4 or 5 $R^g$ groups, or a 3- to 8-membered heterocycloalkane ring substituted by 0, 1, 2, 3, 4 or 5 $R^g$ groups.

In another embodiment, in conjunction with any above or below embodiments, $R^{13}$ is selected from a $C_1$ to $C_6$ alkyl group substituted by 0, 1, 2, 3, 4 or 5 $R^e$ groups, a $C_6$ to $C_{10}$ aryl group substituted by 0, 1, 2, 3, 4 or 5 $R^f$ groups, a $C_6$ to $C_{10}$ aryloxy group substituted by 0, 1, 2, 3, 4 or 5 $R^f$ groups, a ($C_2$ to $C_6$ alkenyl)($C_1$ to $C_3$ alkyl) group substituted by 0, 1, 2, 3, 4 or 5 $R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or 5 $R^g$ groups and a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_6$ to $C_9$ spiroheteroalkyl group substituted by 0, 1, 2, 3, 4 or 5 $R^g$ groups, a $C_6$ to $C_9$ bicycloalkyl group substituted by 0, 1, 2, 3, 4 or 5 $R^g$ groups, a ($C_8$ to $C_9$ bicycloalkyl)($C_1$ to $C_3$ alkyl) group substituted by 0, 1, 2, 3, 4 or 5 $R^g$ groups, a $C_6$ to $C_9$ heterobicycloalkyl group substituted by 0, 1, 2, 3, 4 or 5 $R^g$ groups, and a ($C_6$ to $C_9$ heterobicycloalkyl)($C_1$ to $C_3$ alkyl) group substituted by 0, 1, 2, 3, 4 or 5 $R^g$ groups;

In another embodiment, in conjunction with any above or below embodiments, $R^m$ is H;

The present invention also relates to a pharmaceutically acceptable salt of a compound represented by formula (I). For example, in the present invention, there are cases where a compound represented by formula (I) forms acid addition salts. Further, depending on the kind of substituent, there are cases where the pyrazole amide derivative forms salts with bases. These salts are not particularly limited as long as they are pharmaceutically acceptable ones. Specifically, the acid addition salts include mineral acid salts such as a hydrofluoride, a hydrochloride, a hydrobromide, a hydroiodide, a phosphate, a nitrate, a sulfate, and the like; organic sulfonate such as a methanesulfonate, an ethanesulfonate, a 2-hydroxyethanesulfonate, a p-toluenesulfonate, a benzenesulfonate, an ethane-1,2-disulfonate ion, a 1,5-naphthalenedisulfonate ion, a naphthalene-2-sulfonate ion, and the like; and organic carboxylate such as an acetate, a trifluoroacetate, a propionate, an oxalate, a fumarate, a phthalate, a malonate, a succinate, a glutarate, an adipate, a tartrate, a maleate, a malate, a mandelate, a 1-hydroxy-2-naphthoate, and the like. As the salts with bases, there are mentioned salts with inorganic bases such as a sodium salt, a potassium salt, a magnesium salt, a calcium salt, an aluminum salt, and the like; and salts with organic bases such as a methylamine salt, an ethylamine salt, a lysine salt, an ornithine salt, and the like.

The various pharmaceutically acceptable salts of a compound represented by formula (I) can be produced suitably based on common knowledge in the present technical field.

A compound represented by formula (I) of the present invention contains isomers in some cases. Such isomers are included in a compound represented by formula (I) of the present invention. For example, there may be mentioned isomers in the ring and condensed ring systems (E-, Z-, cis-, and trans-forms), isomers due to the presence of chiral carbons (R- and S-forms, a- and β-configurations, enantiomers, and diastereomers), optically active substances with optical rotation (D-, L-, d-, and l-forms), tautomers, polar compounds obtained by chromatographic separation (a highly-polar compound and a lowly-polar compound), equilibrium compounds, rotamers, mixtures of these compounds in an arbitrary ratio, racemic mixtures, and the like.

The present invention also includes various deuterated forms of the compounds represented by formula (I). Each hydrogen atom attached to a carbon atom may be independently replaced with a deuterium atom.

Although the present invention has been described with respect to specific aspects or embodiments thereof, the invention can be understood by existing technology in the relevant field, and various modifications and substitutions of equivalents are possible without deviation from the true spirit and scope of the invention. Further, to the extent allowed by patent laws and rules, all publications, patents, and patent applications cited in the present description are herein incorporated by reference in their entirety to the same extent as if each individual document were individually indicated to be incorporated herein by reference in its entirety.

General Synthesis Method

The compound represented by formula (I) in the present invention can be produced by applying publicly known various synthesis methods with the use of characteristics based on types of basic structures or substituents. In this case, it may be effective in terms of manufacturing technology that the functional group may be protected with an appropriate protecting group or a group that can be easily converted to a functional group in the process of using a raw material and an intermediate depending on functional groups. Such a functional group includes, for example, an amino group, a hydroxyl group, a carboxyl group, and the like. The protecting groups thereof include, for example, protecting groups described in the "Protecting Groups in Organic Synthesis (the third edition, 1999)" written by T. W. Greene and P. G. M. Wuts. They may be suitably chosen and used depending on the reaction conditions. In these methods, the reaction is carried out by introducing the protecting group followed by eliminating the protecting group as necessary, or converting to an intended group to obtain an intended compound.

Among compound represented by formula (I) in the present invention, a compound (I-1) can be prepared, for example, by the following method:

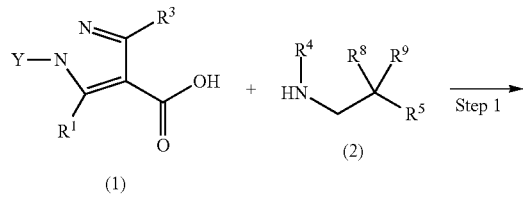

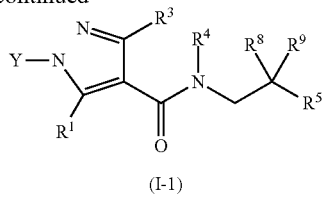

(I-1)

(wherein, $R^8$ and $R^9$ are independently H; F; a hydroxyl group; an amino group; a $C_1$ to $C_3$ alkyl group substituted by 0, 1, 2 or 3 $R^h$ groups; a $C_1$ to $C_6$ alkoxy group substituted by 0, 1, 2 or 3 $R^h$ groups; or $R^8$ and $R^9$ together form oxo group or thioxo group. Other symbols have the same meanings as described above.)

(Step 1)

The present step is a method for producing a compound (I-1) by reacting a compound (1) or a reactive derivative thereof with a compound (2).

The reactive derivative of the compound (1) means a reactive derivative of a carboxyl group, and for example, acid chloride, acyl azide, mixed acid anhydride, symmetric acid anhydride, activated amide, activated ester, and the like are cited. These reactive derivatives can be optionally chosen depending on types of carboxylic acids used.

The present reaction may be carried out according to a general amide-forming reaction by methods described in the literature (e.g., Pepuchido Gousei no Kiso to Jikken by Nobuo Izumiya, etc., Maruzen, 1983, Comprehensive Organic Synthesis, Vol. 6, Pergamon Press, 1991, etc.), equivalent methods thereto or a combination of these methods and the conventional method. Namely, the present reaction can be carried out by using a condensation agent that is well known to a person skilled in the art, or an ester activation method, a mixed acid anhydride method, an acid chloride method, a carbodiimide method and the like that are well known in the art. The reagents used in such an amide-forming reaction include, for example, thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, benzotriazol-1-yl-oxy-tris(pyrrolidinol)phosphonium hexafluorophosphate, 2-(1H-benzotriazol-1-yl)-1,1,3,3-tetramethyluronium hexafluorophosphate, 2-(5-norbornene-2,3-dicarboximido)-1,1,3,3-tetramethyluronium tetrafluoroborate, O—(N-succinimidyl)-1,1,3,3-tetramethyluronium tetrafluoroborate, bromo-tris(pyrrolidino)phosphonium hexafluorophosphate, ethyl chloroformate, isobutyl chloroformate, or 2-(7-aza-1H-benzotriazol-1-yl)-1,1,3,3-tetramethyluronium hexafluorophosphate, and the like. Above all, for example, thionyl chloride, oxalyl chloride, 1-ethyl-3-(3-dimethylaminopropyl)carbodiimide hydrochloride or 2-(7-aza-1H-benzotriazol-1-yl)-1,1,3,3-tetramethyluronium hexafluorophosphate, and the like are preferable. In the amide-forming reaction, a base and/or a condensation agent may be used along with the above-mentioned amide-forming agent.

The amount of the condensation agent that is consumed is not strictly limited, and is generally 0.1 equivalents to 100 equivalents with respect to 1 equivalent of the compound (1), and preferably 0.1 equivalents to 10 equivalents.

A base used includes, for example, tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene, 1,5-azabicyclo[4.3.0]non-5-ene, and the like; aromatic amines such as pyridine, 4-dimethylaminopyridine, picoline, lutidine, quinoline, or isoquinoline, and the like. Above all, tertiary aliphatic amine and the like are preferable, and triethylamine or N,N-diisopropylethylamine and the like are in particular preferable.

The amount of the base used varies depending on the compound used, types of solvents and other reaction conditions, however, it is generally 0.1 equivalents to 100 equivalents with respect to 1 equivalent of the compound (1), preferably 1 equivalent to 5 equivalents.

The condensation agent used includes, for example, N-hydroxybenzotriazole hydrate, N-hydroxysuccinimide, and the like.

The amount of the compound (2) used varies depending on the compound used, types of solvents and other reaction conditions, however, it is generally 1 equivalent to 10 equivalents with respect to 1 equivalent of the compound (1) or a reactive derivative thereof, and preferably 1 equivalent to 3 equivalents.

The reaction is generally carried out in an inactive solvent, and examples of the inactive solvent include tetrahydrofuran, acetonitrile, N,N-dimethylformamide, 1,4-dioxane, benzene, toluene, dichloromethane, chloroform, carbon tetrachloride, 1,2-dichloroethane, pyridine, and the like, or mixtures thereof.

The reaction time is generally 0.5 hours to 96 hours, preferably 1 hour to 24 hours.

The reaction temperature is generally 0° C. to the boiling point temperature of the solvent, and preferably room temperature to 80° C.

A base, an amide-forming reagent, and a condensation agent used in the present reaction can be used as a combination of one or more types thereof.

The compound (I-1) obtained in such a manner can be isolated and purified by an isolation and purification method that is well known to a person skilled in the art (e.g., concentration, concentration under reduced pressure, crystallization, solvent extraction, reprecipitation, chromatography, and the like; in the category of "general synthesis method", the term "isolation and purification method that is well known to a person skilled in the art" has the same meaning unless otherwise particularly specified).

Moreover, among all the compounds represented formula (I) in the present invention, compounds (I-2) and (I-3) can be produced, for example, by the following method:

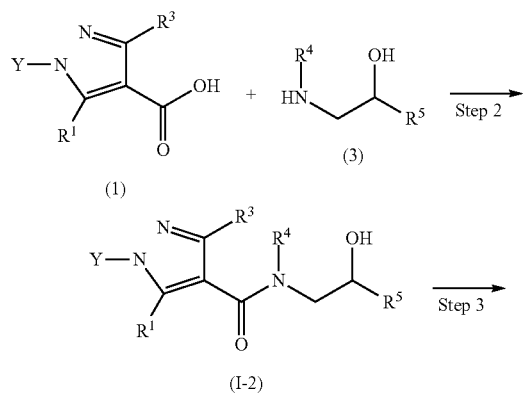

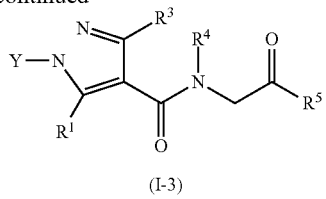

(wherein, other symbols have the same meanings as described above.)

(Step 2)

The present step is a method for producing a compound (I-2) by reacting the compound (1) or a reactive derivative thereof with a compound (3).

The reaction in the present step can be carried out by the same method as in the step 1, an equivalent method thereto, or a combination of these methods and a conventional method.

The compound (I-2) obtained in such a manner can be subjected to a next step with or without isolation and purification by an isolation and purification method that is well known to a person skilled in the art.

(Step 3)

The present step is a method for producing a compound (I-3) by subjecting the compound (I-2) to an oxidation reaction.

The present step can be carried out according to a method well known to a person skilled in the art. For example, the PCC oxidation, the Swern oxidation, the $MnO_2$ oxidation, and the Dess-Martin oxidation, and the like are cited.

For example, the Dess-Martin oxidation can be carried out by using the Dess-Martin reagent without solvent or in a solvent inert to the reaction.

The amount of the Dess-Martin reagent used is generally 1 equivalent to 10 equivalents with respect to 1 equivalent of the compound (I-2), preferably 1 equivalent to 4 equivalents.

The reaction in the present step is generally carried out in an inactive solvent. As the inactive solvent, for example, tetrahydrofuran, acetonitrile, N,N-dimethylformamide, dimethyl sulfoxide, 1,4-dioxane, benzene, toluene, dichloromethane, chloroform, carbon tetrachloride, 1,2-dichloroethane, and the like; or mixtures thereof are cited.

The reaction time is generally 0.5 hours to 96 hours, and preferably 1 hour to 24 hours.

The reaction temperature is generally −78° C. to the boiling point temperature of the solvent, and preferably −20° C. to room temperature.

The compound (I-3) obtained in such a manner can be isolated and purified by an isolation and purification method that is well known to a person skilled in the art.

Also, when the reactive substance has a carboxyl group that is not involved in the reaction in the first step, the second step and the third step, the carboxyl group is preferably protected in advance by a protecting group and then the protecting group is eliminated after completion of the reaction. Selection of such a protecting group and eliminating conditions can be conducted by referring to the method in previously mentioned "Protecting Groups in Organic Synthesis (the third edition, 1999)".

Moreover, among compounds represented by formula (I) in the present invention, a compound (I-3) can be prepared, for example, by the following method:

Also, among the compounds (1) used to prepare the compounds in the present invention, a compound (1) wherein $R^3$ is H can be prepared, for example, by the following method:

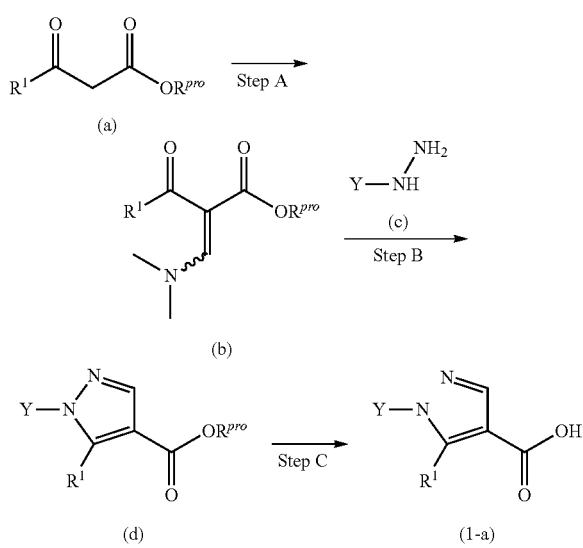

(wherein, $R^{pro}$ is a protecting group. Other symbols have the same meanings as described above.)

A compound represented by formula (a) can be synthesized according to a method well known to a person skilled in the art.

A compound represented by formula (c) can be synthesized according to a method well known to a person skilled in the art.

(Step A)

The present step is a method for producing a compound (b) by reacting a compound (a) with N,N-dimethylformamide dimethyl acetal in the presence or absence of a solvent.

Also, N,N-dimethylformamide diethyl acetal, N,N-dimethylformamide diisopropyl acetal, or the like can be used instead of N,N-dimethylformamide dimethyl acetal.

The amount of N,N-dimethylformamide dimethyl acetal used is generally 1 equivalent to 10 equivalents with respect to 1 equivalent of the compound (a).

The reaction solvent used is not in particular limited as far as it is inert to the reaction, and specifically includes, for example, methanol, ethanol, benzene, toluene, xylene, tetrahydrofuran, 1,4-dioxane, N,N-dimethylformamide, or mixtures thereof.

The reaction time is generally 0.5 hours to 96 hours, and preferably 1 hour to 24 hours.

The reaction temperature is generally 0° C. to the boiling point temperature of the solvent, and preferably room temperature to 160° C.

The compound (b) obtained in such a manner can be subjected to a next step with or without isolation and purification by an isolation and purification means well known to a person skilled in the art.

(Step B)

The present step is a method for producing a compound (d) by reacting the compound (b) with a compound having a hydrazino group represented by formula (c).

The amount of the compound (c) used is generally 0.5 equivalents to 10 equivalents with respect to 1 equivalent of the compound (b), and preferably 0.7 equivalents to 3 equivalents.

In the present step, when the compound (c) is a salt, it is necessary to use a base for neutralization. Examples of such a base include sodium carbonate, potassium carbonate, sodium bicarbonate, potassium bicarbonate, sodium acetate, potassium acetate, sodium hydroxide, potassium hydroxide, lithium hydroxide, triethylamine, N,N-diisopropylethylamine, pyridine, and the like. The amount of the base used is generally 1 equivalent to 3 equivalents with respect to 1 equivalent of the compound (c).

The reaction solvent used is not in particular limited as far as it is inert to the reaction. Specifically, examples include, methanol, ethanol, n-propanol, n-butanol, isopropanol, acetonitrile, diethyl ether, tetrahydrofuran, 1,4-dioxane, N,N-dimethylformamide, dichloromethane, chloroform, benzene, toluene, xylene or mixtures thereof.

The reaction time is generally 0.5 hours to 96 hours, and preferably 1 hour to 24 hours.

The reaction temperature is generally 0° C. to the boiling point temperature of the solvent, and preferably room temperature to 100° C.

The compound (d) obtained in such a manner can be subjected to a next step with or without isolation and purification by an isolation and purification method that is well known to a person skilled in the art.

(Step C)

The present step is a method for producing a compound (I-a) by eliminating the protecting group $R^{pro}$ of the compound (d).

The elimination of the protecting group can be carried out by a method described in previously mentioned "Protecting Groups in Organic Synthesis (the third edition, 1999)", an equivalent method thereto or a combination of these methods and the conventional method. For example, when the protecting group is a benzyl group, the benzyl group can be eliminated by a catalytic reduction method with the use of hydrogen and palladium catalytic agent and the like.

The compound (I-a) obtained in such a manner can be subjected to a next step with or without isolation and purification by an isolation and purification method that is well known to a person skilled in the art.

Moreover, among the compounds (2) used to prepare the compounds of the present invention, a compound (2-a) wherein both $R^8$ and $R^9$ are H can be synthesized, for example, by the following method:

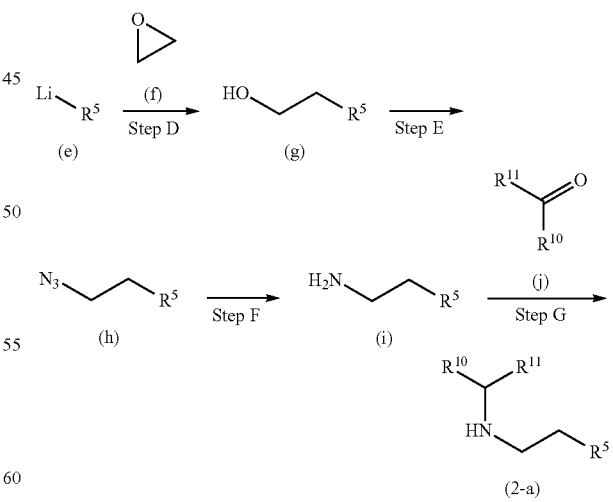

(wherein, $R^{10}$ and $R^{11}$ each independently are H, a group having one less carbon atoms than the hydrocarbon chain of $R^4$, or $R^{10}$ and $R^{11}$ are together form a lower cycloalkyl or cycloalkenyl group. Other symbols have the same meanings as described above.)

The compound represented by formula (f) can be synthesized according to a method well known to a person skilled in the art.

(Step D)

The present step is a method for producing a compound (g) by reacting an organic lithium compound (e) with ethylene oxide (f).

The amount of ethylene oxide (f) used is generally 0.1 equivalents to 10 equivalents with respect to 1 equivalent of the compound (e), and preferably 0.5 equivalents to 3 equivalents.

The reaction solvent is not in particular limited as far as it is inert to the reaction, and examples include, tetrahydrofuran, 1,4-dioxane, diethyl ether, 1,2-dimethoxyethane, n-hexane, n-heptane, dichloromethane, chloroform, carbon tetrachloride, 1,2-dichloroethane, benzene, toluene, xylene, and the like.

The reaction time is generally 0.5 hour to 48 hours, and preferably 1 hour to 24 hours.

The reaction temperature is generally −78° C. to the boiling point temperature of the solvent, and preferably −78° C. to room temperature.

The compound (g) obtained in such a manner can be subjected to a next step with or without isolation and purification by an isolation and purification method that is well known to a person skilled in the art.

(Step E)

The present step is a method for producing a compound (h) by reacting the compound (g) with diphenylphosphoryl azide.

The reaction in the present step can be carried out by the same method as in the step 16, an equivalent method thereto, or a combination of these methods and the conventional method.

The compound (h) obtained in such a manner can be subjected to a next step with or without isolation and purification by an isolation and purification method that is well known to a person skilled in the art.

(Step F)

The present step is a method for producing a compound (i) by subjecting the compound (h) to a reduction reaction of the azide group.

The present step can be carried out according to methods well known to a person skilled in the art. These methods include, for example, a reduction method using phosphine; a catalytic reduction method using H and a palladium catalyst and the like; a reduction method using sodium borohydride; and the like.

For example, the reduction method using phosphine can be carried out using triphenylphosphine and water in a solvent inert to the reaction. Specifically, examples include tetrahydrofuran, acetonitrile, N,N-dimethylformamide, 1,4-dioxane, benzene, toluene, dichloromethane, chloroform, carbon tetrachloride, 1,2-dichloroethane, water, and the like; or mixtures thereof.

The amount of triphenylphosphine used is generally 1 equivalent to 10 equivalents with respect to 1 equivalent of the compound (15), and preferably 1 to 4 equivalents.

The reaction time is generally 0.5 hours to 96 hours, and preferably 2 hours to 48 hours.

The reaction temperature is generally 0° C. to the boiling point temperature of the solvent, and preferably room temperature to the boiling point temperature of the solvent.

The compound (i) obtained in such a manner can be subjected to a next step with or without isolation and purification by an isolation and purification method that is well known to a person skilled in the art.

(Step G)

The present step is a method for producing a compound (2-a) by reacting the compound (i) with a compound (j) in the presence of a reducing agent.

The amount of the compound (i) used in the present step is generally 0.5 equivalents to 10 equivalents with respect to 1 equivalent of the compound (j), and preferably, 0.8 equivalents to 4 equivalents.

The reducing agents used include, for example, sodium borohydride, sodium triacetoxyborohydride, sodium cyanoborohydride, and the like.

The amount of the reducing agent used is generally 0.1 equivalents to 10 equivalents with respect to 1 equivalent of the compound (i), and preferably 0.3 equivalents to 5 equivalents.

The reaction solvent used is not in particular limited as far as it is inert to the reaction, and examples include methanol, ethanol, acetic acid, tetrahydrofuran, 1,4-dioxane, dichloromethane, chloroform, 1,2-dichloroethane, benzene, toluene, xylene, and the like.

The reaction time is generally 0.5 hours to 48 hours, and preferably, 1 hour to 24 hours.

The reaction temperature is generally 0° C. to the boiling point temperature of the solvent.

The compound (2-a) obtained in such a manner can be subjected to a next step with or without isolation and purification by an isolation and purification method that is well known to a person skilled in the art.

A group represented by formula:

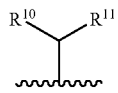

(wherein, each symbol has the same meanings as described above) corresponds to the $R^4$.

Moreover, among the compounds (2) used to prepare the compounds in the present invention, a compound (2-b) wherein either $R^8$ or $R^9$ is F and the other is H can be synthesized, for example, by the following method:

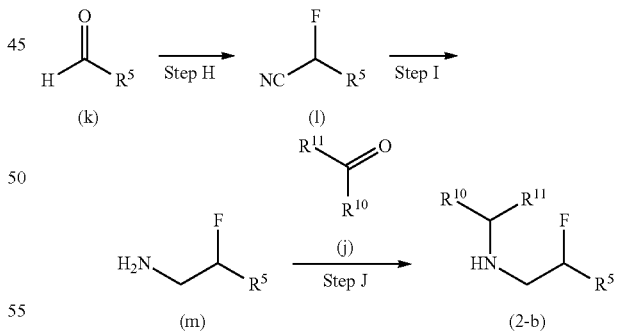

(wherein, each symbol has the same meanings as described above.)

A compound represented by formula (k) can be synthesized according to a method well known to a person skilled in the art.

(Step H)

The present step is a method for producing a compound (l) by reacting the compound (k) with trimethylsilyl cyanide in the presence of a zinc catalyst and subsequently reacting with a fluorinating agent.

The amount of trimethylsilyl cyanide used is generally 1 equivalent to 10 equivalents with respect to 1 equivalent of the compound (k), and preferably, 1 equivalent to 5 equivalents.

The zinc catalyst used includes, for example, zinc iodide, zinc bromide, and the like.

The fluorinating agent used includes, for example, (N,N-diethylamino)sulfur trifluoride, bis(2-methoxyethyl)aminosulfur trifluoride, 1,1,2,2-tetrafluoroethyl-N,N-dimethylamine, and the like.

The amount of fluorinating agent used is generally 1 equivalent to 10 equivalents with respect to 1 equivalent of the compound (k), and preferably, 1 equivalent to 5 equivalents.

The reaction solvent that used is not in particular limited as far as it is inert to the reaction, and examples include tetrahydrofuran, acetonitrile, 1,4-dioxane, diethyl ether, dichloromethane, chloroform, 1,2-dichloroethane, carbon tetrachloride, benzene, toluene, N,N-dimethylformamide, and the like.

The reaction time is generally 30 minutes to 48 hours, and preferably, 1 hour to 24 hours.

The reaction temperature is generally 0° C. to the boiling point temperature of the solvent.

The compound (1) obtained in such a manner can be subjected to a next step with or without isolation and purification by an isolation and purification method that is well known to a person skilled in the art.

(Step I)

The present step is a method for producing a compound (m) by subjecting the compound (1) to a reduction reaction of the cyano group.

The reducing agents used include, for example, lithium aluminium hydride, sodium bis(2-methoxyethoxy)aluminumhydride, a borane-tetrahydrofuran complex, and the like.

The amount of the reducing agent used is generally 1 to 10 equivalents with respect to 1 equivalent of the compound (1).

The reaction solvent that used is not in particular limited as far as it is inert to the reaction, and examples include tetrahydrofuran, 1,4-dioxane, dichloromethane, benzene, toluene, diethyl ether, and the like.

The reaction time is generally 1 hour to 24 hours.

The reaction temperature is generally 0° C. to the boiling point temperature of the solvent.

The compound (m) obtained in such a manner can be subjected to a next step with or without isolation and purification by an isolation and purification method that is well known to a person skilled in the art.

(Step J)

The present step is a method for producing a compound (2-b) by reacting the compound (m) with a compound (j) in the presence of a reducing agent.

The reaction in the present step can be carried out by the same method as in the step G, an equivalent method thereto, or a combination of these methods and the conventional method.

The compound (2-b) obtained in such a manner can be subjected to a next step with or without isolation and purification by an isolation and purification method that is well known to a person skilled in the art.

Moreover, among the compounds (3) used to prepare the compounds of the present invention, a compound (3-P) wherein either $R^8$ or $R^9$ is a hydroxyl group which is protected by a protecting group and the other is H can be synthesized, for example, by the following method:

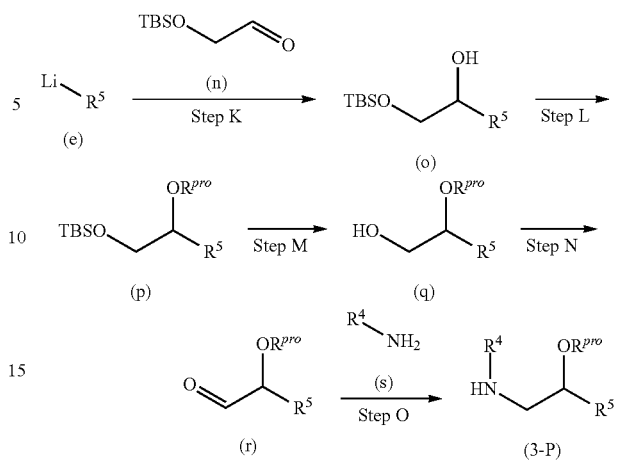

(wherein, $R^{pro}$ is a protecting group. Other symbols have the same meanings as described above.)

A compound represented by formula (n) can be synthesized according to a method well known to a person skilled in the art.

(Step K)

The present step is a method for producing a compound (o) by reacting an organic lithium compound (m) with (tert-butyldimethylsilyloxy)acetaldehyde (n).

The reaction in the present step can be carried out by the same method as in the step D, an equivalent method thereto, or a combination of these methods and the conventional method.

The compound (o) obtained in such a manner can be subjected to a next step with or without isolation and purification by an isolation and purification method that is well known to a person skilled in the art.

(Step L)

The present step is a method for introducing a protecting group to the hydroxyl group of the compound (o). The introduction of the protecting group can be carried out by a method described in the previously mentioned "Protecting Groups in Organic Synthesis (the third edition, 1999)", an equivalent method thereto, or a combination of these methods and the conventional method.

The compound (p) obtained in such a manner can be subjected to a next step with or without isolation and purification by an isolation and purification method that is well known to a person skilled in the art.

(Step M)

The present step is a method for producing a compound (q) by eliminating the tert-butyldimethylsilyl group of the compound (p).

The elimination of the protecting group can be carried out by a method described in the previously-mentioned "Protecting Groups in Organic Synthesis (the third edition, 1999)", an equivalent method thereto, or a combination of these methods and the conventional method, and for example, tetrabutylammonium fluoride can be used.

The compound (q) obtained in such a manner can be subjected to a next step with or without isolation and purification by an isolation and purification method that is well known to a person skilled in the art.

(Step N)

The present step is a method for producing a compound (r) by subjecting the compound (q) to an oxidation reaction.

The reaction in the present step can be carried out by the same method as in the step 3, an equivalent method thereto, or a combination of these methods and the conventional method.

The compound (r) obtained in such a manner can be subjected to a next step with or without isolation and purification by an isolation and purification method that is well known to a person skilled in the art.

(Step O)

The present step is a method for producing the compound (3-P) by reacting the compound (r) with a compound (s) in the presence of a reducing agent.

The reaction in the present step can be carried out by the same method as in the step G, an equivalent method thereto, or a combination of these methods and the conventional method.

The compound (3-P) obtained in such a manner can be subjected to a next step with or without isolation and purification by an isolation and purification method that is well known to a person skilled in the art.

Moreover, among the compounds (2) used to prepare the compounds in the present invention, a compound (2-c) wherein both $R^8$ and $R^9$ are F can be synthesized, for example, by the following method:

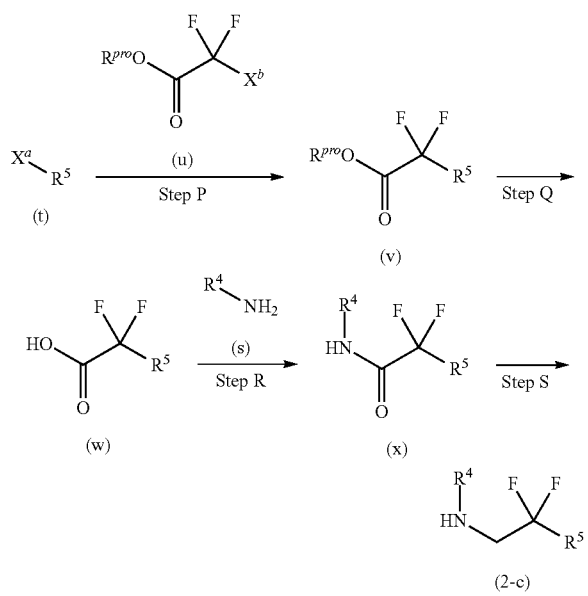

(wherein, $X^a$ and $X^b$ each independently are Br or I. Other symbols have the same meanings as described above.)

A compound represented by formula (u) can be synthesized according to a method well known to a person skilled in the art.

(Step P)

The present step is a method for producing a compound (v) by reacting the compound (t) with a compound (u) in the presence of copper to prepare.

The amount of the compound (t) used is generally 1 equivalent to 10 equivalents with respect to 1 equivalent of the compound (u), and preferably 1 equivalent to 3 equivalents.

The amount of copper used is generally 1 equivalent to 10 equivalents with respect to 1 equivalent of the compound (t), and preferably 1 equivalent to 5 equivalents.

The reaction solvent used is not in particular limited as far as it is inert to the reaction, and examples include tetrahydrofuran, acetonitrile, 1,4-dioxane, dimethyl sulfoxide, N,N-dimethylformamide, and the like.

The reaction time is generally 30 minutes to 48 hours.

The reaction temperature is generally room temperature to the boiling point temperature of the solvent.

The compound (v) obtained in such a manner can be subjected to a next step with or without isolation and purification by an isolation and purification method that is well known to a person skilled in the art.

(Step Q)

The present step is a method for producing a compound (w) by eliminating the protecting group $R^{pro}$ of the compound (v).

The reaction in the present step can be carried out by the same method as in the step C, an equivalent method thereto, or a combination of these methods and the conventional method.

The compound (w) obtained in such a manner can be subjected to a next step with or without isolation and purification by an isolation and purification means well known to a person skilled in the art.

(Step R)

The present step is a method for producing a compound (x) by reacting the compound (w) or a reactive derivative thereof with a compound (s).

The reaction in the present step can be carried out by the same method as in the step 1, an equivalent method thereto, or a combination of these methods and the conventional method.

The compound (x) obtained in such a manner can be subjected to a next step with or without isolation and purification by an isolation and purification method that is well known to a person skilled in the art.

(Step S)

The present step is a method for producing a compound (2-c) by reducing the amide group of the compound (x).

The reaction in the present step can be carried out by the same method as in the step I, an equivalent method thereto, or a combination of these methods and the conventional method.

The compound (2-c) obtained in such a manner can be subjected to a next step with or without isolation and purification by an isolation and purification method that is well known to a person skilled in the art.

Moreover, the compound represented by formula (I) in the present invention may have a tautomer and/or optical isomer in some cases depending on types of substituents. However, the present invention includes a mixture of these tautomers and isomers, and isolated ones.

Furthermore, the present invention relates to a pharmaceutically acceptable prodrug of the compound represented by formula (I). The term "pharmaceutically acceptable prodrug" means a compound producing a compound represented by formula (I) by solvolysis or conversion to $CO_2H$, $NH_2$, OH, etc. under physiological conditions. An example of the group that produces prodrug is found, for example, in Prog. Med., 5, 2157-2161 (1985), "Iyakuhin no Kaihatsu" (Hirokawa Shoten, 1990) Vol. 7, Bunshi Sekkei 163-198. In the present invention, some of the compounds within the scope of formula (I) which have the group that produces a prodrug can serve as a prodrug of the corresponding compound of formula (I) which has $CO_2H$, $NH_2$, OH, etc. For example, a compound within the scope of formula (I) which has an alkoxycarbonyl group can be converted into a corresponding carboxyl acid derivative.

The present invention also relates to a pharmaceutically acceptable salt of the compound represented by formula (I) and a pharmaceutically acceptable prodrug thereof. Such a salt includes, for example, hydrogen halides such as hydrochloric acid, hydrofluoric acid, hydrobromic acid, hydriodic acid, and the like; inorganic acids such as sulfuric acid, nitric acid, phosphoric acid, carbonic acid, and the like; lower alkyl sulfonic acids such as methanesulfonic acid, ethanesulfonic acid, and the like; arylsulfonic acids such as benzenesulfonic acid, p-toluenesulfonic acid and the like; organic acids such as formic acid, acetic acid, propionic acid, oxalic acid, malonic acid, succinic acid, fumaric acid, maleic acid, lactic acid, malic acid, tartaric acid, citric acid, and the like; and acid addition salts with amino acids including aspartic acid, glutamic acid, and the like. Moreover, depending on types of substituents, the salt in the present invention may form a salt with a base. Examples include inorganic bases including metals such as sodium, potassium, magnesium, calcium, aluminum, lithium, and the like; salts with an organic base such as methyl amine, ethylamine, ethanolamine, guanidine, lysine, ornithine, and the like; and an ammonium salt, and the like.

The various pharmaceutically acceptable salts of compound represented by formula (I) can be synthesized based on general knowledge in the technical field in the art.

The compound represented by formula (I) and the pharmaceutically acceptable salt thereof in the present invention (hereinafter, general term for these is referred to as the compound of the present invention) has an excellent RORγ inhibitory activity and can be used as a RORγ inhibitor that is clinically applicable to treat or prevent RORγ associated diseases and symptoms. Among RORγ related diseases, the compound of the present invention is useful as a therapeutic agent or preventive agent for, in particular, diseases selected from auto immune disease and inflammatory disease (e.g., multiple sclerosis, chronic rheumatoid arthritis, ankylosing spondylitis, systemic erythematodes, psoriasis, psoriatic arthritis, inflammatory bowel disease (e.g., Crohn's disease), and asthma), metabolic disease (especially, diabetes), and cancer (especially, malignant melanoma).

Moreover, the term "prevention" in the present invention means a procedure of administration of a pharmaceutical composition including the compound of the present invention or administration this to individuals who have not developed diseases or symptoms. Moreover, the term "treatment" means a procedure of administration of a pharmaceutical composition including the compound of the present invention or administration this to individuals who have already developed diseases or symptoms. Accordingly, a procedure of administration to individuals who have already developed diseases or symptoms in order to prevent aggravation or attacks is one aspect of the "treatment".

When the compound of the present invention is used as medicine, the compound of the present invention can be mixed with a pharmaceutically acceptable carrier (diluting agent, bonding agent, disintegrant, flavoring substance, odor improving agent, emulsifying agent, diluent, solubilizing agent, and the like) and can be administered in the form of a pharmaceutical composition or drug formulation (oral preparation, injections, and the like) orally or parenterally. The pharmaceutical composition can be formulated according to an ordinal method.

In the present description, parenteral administration includes subcutaneous injection, intravenous injection, intramuscular injection, intraperitoneal injection, infusion technique, and local administration (percutaneous administration, ophthalmic administration, pulmonary/bronchial administration, nasal administration, rectal administration, and the like), and the like. The dosage form of oral administration includes, for example, tablets, pills, granules, powders, solvent, suspensions, syrups, capsules, and the like.

The amount of the compound of the present invention that can be combined with a carrier can be changed depending on a specific individual who receives treatment and on specific dosage forms. In this regard, the specific dosage for the specific patient is determined depending on various factors including age, body weight, overall health conditions, gender, diet, administration time, administration method, excretion rate, and the degree of the specified disease during treatment.

The dosage amount of the compound of the present invention is determined depending on age, body weight, general health conditions, gender, diet, administration time, administration method, excretion speed, the degree of a disease in a patient who is being treated, or in view of other factors. The compound of the present invention can be administered in single or multiple times daily for adult in a range of 0.01 mg to 1000 mg, although the dosage is different depending on the conditions of the patient, body weight, types of the compound, administration route, and the like.

ABBREVIATIONS

Ac Acetyl
aq. aqueous
Bn benzyl
Boc tert-butoxycarbonyl
BuOH butanol
Bzl benzyl
cat. catalytic
conc. concentrated
DAST N,N-diethylaminosulfur trifluoride
DBU 1,8-diazabicyclo[5.4.0]undec-7-ene
DCM dichloromethane
DIAD diisopropyl azodicarboxylate
DIPEA N,N-diisopropylethylamine
DMA N,N-dimethylacetoamide
DMAP 4-(N,N-dimethylamino)pyridine
DMF N,N-dimethylformamide
DMSO dimethyl sulfoxide
DPPA diphenylphosphoryl azide
Et$_2$O dietylether
EtOAc ethyl acetate
EtOH ethanol
HATU 1-[Bis(dimethylamino)methylene]-1H-1,2,3-triazolo[4,5-b]pyridinium 3-oxid hexafluorophosphate
LDA lithium diisopropylamide
MeOH methanol
Ms methanesulfonyl (mesyl)
MTBE methyl tert-butyl ether
NBS N-Bromosuccinimide
NMO N-methylmorpholine N-oxide
quant. quantitative
sat. saturated
SEM 2-(trimethylsilyl)ethoxymethyl group
TBAF tetrabutylammonium fluoride
tert tertiary
TES triethylsilyl group
TFA trifluoroacetic acid
THF tetrahydrofuran
TLC thin layer chromatography
TMS trimethylsilyl group
TMSCN trimethylsilyl cyanide
TsOH toluenesulfonic acid

EXAMPLES

Hereinafter, the present invention will be explained based on specific examples. However, the present invention is not limited to these examples.

Unless noted otherwise, reagents, starting materials, and solvents were purchased from vendors (for example, Aldrich, Wako Junyaku, Tokyo Kasei, Fluka, Sigma, and the like) and used without further purification.

The structure of the novel compound isolated was confirmed by and/or mass spectrometry using single quadrupole instrumentation equipped with an electron spray source and other appropriate analytical methods.

As for the compounds for which spectrum (300 MHz, 400 MHz or 500 MHz, MeOH-$d_4$, DMSO-$d_6$, $CD_3CN$ or $CDCl_3$) was measured, the chemical shift (δ: ppm) and coupling constant (J: Hz) are shown. In addition, the following abbreviations represent the followings, respectively: s=singlet, d=doublet, t=triplet, q=quartet, brs=broad singlet, m=multiplet.

The compounds synthesized according to the following methods of examples were further analyzed by high performance liquid chromatography mass spectroscopy (LC/MS) analysis. As for the result of mass spectroscopy, the observed value of [M+H]+, that is, the observed value is shown as the value of the molecular mass of the compound (M) with a proton (H+).

LCMS Measurement Condition: (UPLC/MS)
LC Mass spectrometer: Waters Corporation Acquity UPLC™-SQD Column: Acquity UPLC™ BEH C18 1.7 µm 2.1 mm×50 mm
UV: PDA detection (254 nm)
CAD: CORONA™ ULTRA detector
Column temperature: 40° C.
ES voltage: 3.0 kV (capillary)
Cone voltage: 30 V
Gradient Conditions:
Solvents:
A: $H_2O$/MeCN=95/5
 0.05% TFA
B: $H_2O$/MeCN=5/95
 0.05% TFA
Flow rate: 0.6 mL/min
Gradients: 0.01 to 0.20 min, Solvent B: 2%, Solvent A: 98% 0.20 to 3.0 min, Solvent B: 2% to 100%, Solvent A: 98% to 0% 3.0 to 4.2 min, Solvent B: 100%, Solvent A: 0% 4.2 to 4.21 min, Solvent B: 100% to 2%, Solvent A: 0% to 98% 4.21 to 5.2 min, Solvent B: 2%, Solvent A: 98% 5.2 to 5.5 min, Solvent B: 2%, Solvent A: 98%, Flow rate: 0.2 mL/min LCMS Measurement Condition (LC/MS method A):
LC Mass spectrometer: Agilent Technologies Corporation 1260 INFINITY™ HPLC-6130MSD
Column: Phenomenex Gemini™ C18 A110 3 µm 4.6 mm×30 mm
UV: PDA detection (254 nm)
Column temperature: 40° C.
Capillary voltage: 3.5 kV
Frag mentor voltage: 70 V
Gradient Conditions:
Solvents: A:
$H_2O$/MeCN=95/5
 0.05% TFA
B: $H_2O$/MeCN=5/95
 0.05% TFA
Flow rate: 1.0 mL/min
Gradients: 0.01 to 0.30 min, Solvent B: 2% to 10%, Solvent A: 98% to 90% 0.30 to 1.5 min, Solvent B: 10% to 100%, Solvent A: 90% to 0% 1.5 to 3.5 min, Solvent B: 100%, Solvent A: 0% 3.5 to 3.51 min, Solvent B: 100% to 2%, Solvent A: 0% to 98% 3.51 to 4.5 min, Solvent B: 2%, Solvent A: 98%

LCMS Measurement Condition (LC/MS method B):
LC Mass spectrometer: Shimadzu Corporation LCMS-2010 EV Column: Shim-Pack™ XR-ODII 2.0 mm×75 mm
UV: PDA detection (254 nm)
Flow rate: 0.4 mL/min
Column temperature: 40° C.
Detection voltage: 1.20 kV
Gradient Conditions:
Solvents:
A: $H_2O$/MeCN=90/5
 0.1% $HCO_2H$
B: $H_2O$/MeCN=10/95
 0.1% $HCO_2H$
Flow rate: 0.4 mL/min
Gradients: 0.01 to 0.50 min, Solvent B: 10%, Solvent A: 90% 0.50 to 2.0 min, Solvent B: 10% to 95%, Solvent A: 90% to 5% 2.0 to 3.8 min, Solvent B: 95%, Solvent A: 5% 3.8 to 4.0 min, Solvent B: 95% to 10%, Solvent A: 5% to 90% 4.0 to 5.0 min, Solvent B: 10%, Solvent A: 90%

Reference Example A1

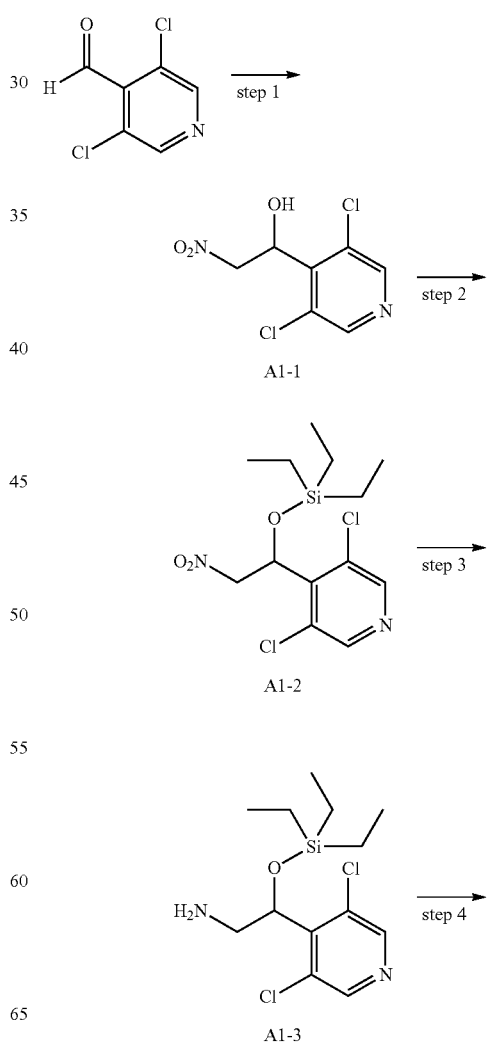

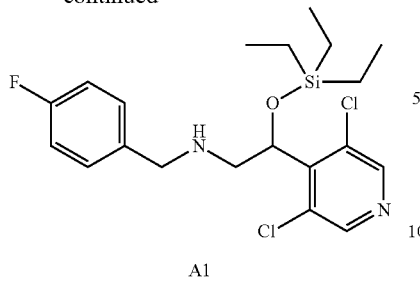

A1

Step 1: 1-(3,5-dichloropyridin-4-yl)-2-nitroethanol (A1-1)

To a solution of 3,5-dichloro-4-pyridinecarboxaldehyde (2.3 g, 13.3 mmol) in MeOH (25 mL) were added nitromethane (2.2 mL, 39.9 mmol) and sodium methoxide (861 mg, 15.9 mmol). After addition, the mixture was stirred for 1 h. The reaction mixture was quenched by adding 2 M aqueous HCl (7 mL) and extracted with EtOAc. The organic layer washed with brine×2 and dried over MgSO$_4$. After the solvent was removed, the residue was purified by column chromatography on silica gel to give compound A1-1 (2.8 g, 90%) as a white solid.

Step 2: 3,5-dichloro-4-(2-nitro-1-((triethylsilyl)oxy)ethyl)pyridine (A1-2)

To a solution of compound A1-1 (2.8 g, 11.9 mmol) in DMF (15 mL) were added imidazole (973 mg, 14.3 mmol) and triethylchlorosilane (2.2 mL, 13.1 mmol). After addition, the mixture was stirred for 1 h. The reaction mixture was quenched with water and extracted with EtOAc. The organic layer washed with brine×2 and dried over MgSO$_4$. After the solvent was removed, the residue was purified by column chromatography on silica gel to give compound A1-2 (4.1 g, 98%) as a colorless oil.

Step 3: 2-(3,5-dichloropyridin-4-yl)-2-((triethylsilyl)oxy)ethanamine (A1-3)

Compound A1-2 (4.1 g, 11.6 mmol) and Raney nickel 2800 (690 mg, in water) in MeOH (50 mL) was hydrogenated in H$_2$ atmosphere (1 atm) at room temperature for 8 h. The reaction mixture was filtered through a pad of celite and washed with EtOAc. After the solvent was removed, the residue was purified by column chromatography on silica gel to give compound A1-3 (1.9 g, 50%) as a white solid.

Step 4: 2-(3,5-dichloropyridin-4-yl)-N-(4-fluorobenzyl)-2-((triethylsilyl)oxy)ethanamine (A1)

To a solution of compound A1-3 (2.8 g, 11.9 mmol) in toluene (6 mL) and MeOH (6 mL) was added 4-fluorobenzaldehyde (360 µL, 3.4 mmol), and the mixture was stirred at 70° C. for 2 h. The reaction mixture was cooled to 0° C., and NaBH$_4$ was added gradually. The reaction mixture was allowed to warm to room temperature and stirred at room temperature for 12 h. The reaction mixture was quenched with water and extracted with EtOAc. The organic layer was washed with brine×2 and anhydrous Na$_2$SO$_4$. After the solvent was removed, the residue was purified by column chromatography on silica gel to give compound A1 (1.2 g, 88%) as a colorless oil.

Reference Example A12

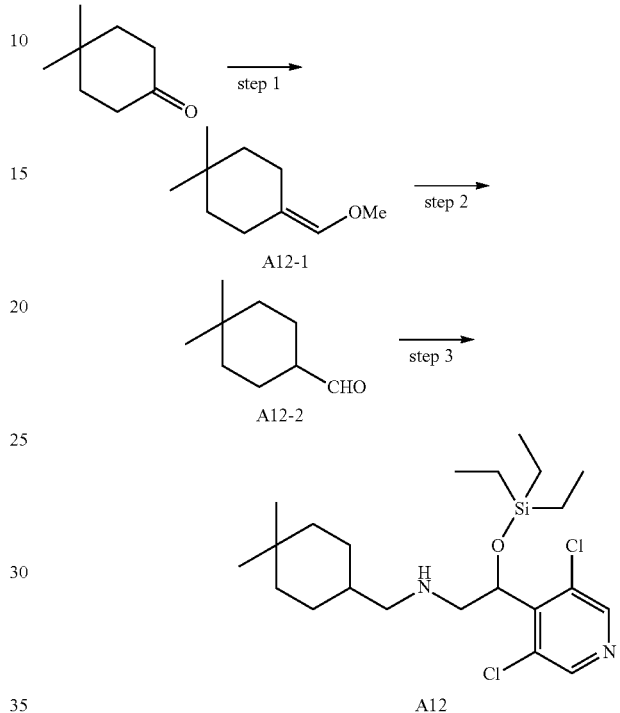

Step 1: 4-(methoxymethylene)-1,1-dimethylcyclohexane (A12-1)

n-BuLi (2.6 M in hexane, 2.3 mL, 5.94 mmol) was added dropwisely to a stirred solution of (methoxymethyl)triphenylphosphonium chloride (2.04 g, 5.94 mmol) in THF (20 mL) at −78° C. and stirred for 10 min at the same temperature and then stirred for 2.5 h at room temperature. The reaction mixture was cooled down to −78° C., a solution of 4,4-dimethylcyclohexanone (500 mg, 3.96 mmol) in THF (5 mL) was added slowly at −78° C. The reaction mixture was allowed to warm to room temperature and stirred at room temperature for overnight. The reaction mixture was quenched with sat. NaHCO$_3$ aq. (20 mL) and extracted with EtOAc. The combined organic layers were dried over anhydrous Na$_2$SO$_4$ and concentrated under reduced pressure to provide compound A12-1 (512.2 mg, crude) as pale yellow oil. The crude product was used for next step without purification.

Step 2: 4,4-dimethylcyclohexanecarbaldehyde (A12-2)

TFA (2 mL) was added to a stirred solution of compound A12-1 (512.2 mg, crude) in DCM (1 mL) at room temperature and stirred for 1.5 h at the same temperature. The reaction mixture was quenched with sat. NaHCO$_3$ aq. (10 mL) and extracted with EtOAc. The combined organic layer was dried over anhydrous Na$_2$SO$_4$, and concentrated under reduced pressure to provide crude compound A12-2 as pale yellow oil. The crude product was used for next step without purification.

Step 3: 2-(3,5-dichloropyridin-4-yl)-N-((4,4-dimethylcyclohexyl)methyl)-2-((triethylsilyl)oxy)ethanamine (A12)

Crude A12-2 (52 mg) and amine A1-3 (100 mg, 311.2 mmol) was added to a solution of MeOH (1 mL) and toluene (1 mL) and stirred at 80° C. for 4 h. The reaction mixture was cooled down to room temperature. MeOH (2 mL) was added to the reaction mixture and NaBH$_4$ (100 mg) was added to reaction mixture at room temperature. The mixture was stirred at room temperature for 1 h. The reaction mixture was quenched with sat. NaHCO$_3$ aq. (10 mL) and extracted with EtOAc (50 mL). The organic layer washed with sat. NaHCO$_3$ aq. and brine, dried over anhydrous Na$_2$SO$_4$, and concentrated under reduced pressure. The residue was purified by preparative thin layer chromatography (Merck KGaA, PLC Silicagel 60 F$_{254}$, 1 mm, 20×20 cm with concentrating zone 20×4 cm, 20% EtOAc/hexane as eluent) to provide compound A12 (58.6 mg, 42%) as pale yellow oil. $^1$H NMR (CDCl$_3$, 400 MHz): δ 8.42 (s, 2H), 5.49 (dd, J=8.8, J=4.4 Hz, 1H), 3.21 (dd, J=12.5, J=8.8 Hz, 1H), 2.77 (dd, J=12.5, J=4.4 Hz, 1H), 2.54-2.47 (m, 2H), 1.54-1.04 (m, 9H), 0.90-0.86 (m, 15H), 0.62-0.49 (m, 6H).

Reference Example A31

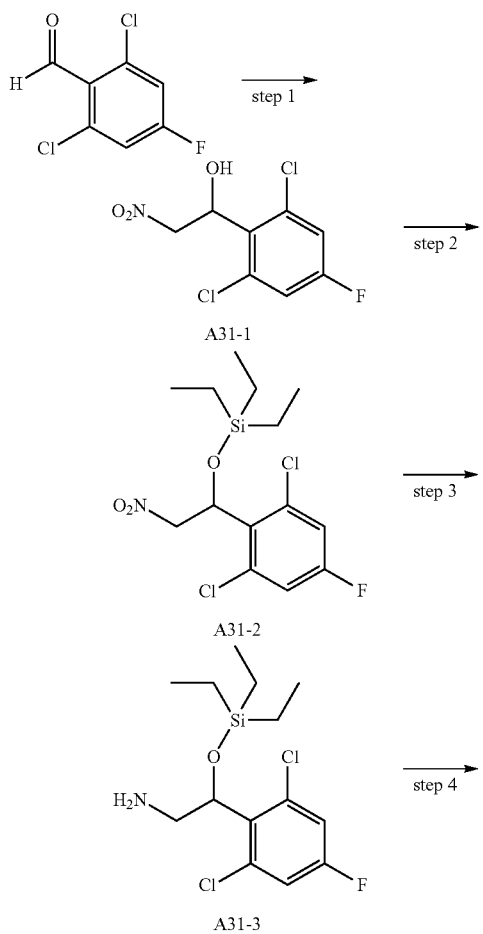

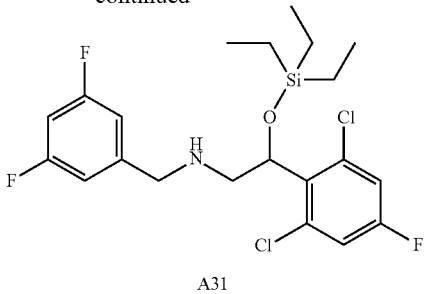

Step 1: 1-(2,6-dichloro-4-fluorophenyl)-2-nitroethanol (A31-1)

A mixture of 2,6-dichloro-4-fluorobenzaldehyde (10.0 g, 51.8 mmol), nitromethane (2 mL) and K$_2$CO$_3$ (3.57 g, 25.9 mmol) was stirred at room temperature for 2 h. The reaction mixture was quenched with water and extracted with EtOAc (2×100 mL). The combined organic layers were washed with water (2×50 mL) and brine (20 mL), dried over anhydrous Na$_2$SO$_4$, and concentrated under reduced pressure to provide compound A31-1 (26.0 g, crude) as yellow gum. The crude product was used in the next step without purification.

Step 2: (1-(2,6-dichloro-4-fluorophenyl)-2-nitroethoxy)triethylsilane (A31-2)

To a stirred solution of compound A31-1 (26.0 g, 102.3 mmol) in DMF (100 mL) was added imidazole (20.9 g, 307.0 mmol) and TES-Cl (25.7 mL, 153.5 mmol) and the mixture was stirred at room temperature for 1 h. Upon reaction completion, the mixture was quenched with water (50 mL) and extracted with EtOAc (2×100 mL). The combined organic layers were washed with brine (2×50 mL), dried over anhydrous Na$_2$SO$_4$, and concentrated under reduced pressure. The residue was purified by column chromatography (silica gel, 0-10% EtOAc/hexane as eluent) to provide compound A31-2 (32.8 g, 74%) as colorless gum. $^1$H NMR (CDCl$_3$, 400 MHz): δ 7.12 (s, 1H), 7.10 (s, 1H), 6.22 (dd, J=9.2, J=3.2 Hz, 1H), 5.22-5.11 (m, 1H), 4.42 (dd, J=12.2, J=3.6 Hz, 1H), 0.84 (t, J=8.0 Hz, 9H), 0.55-0.50 (m, 6H).

Step 3: 2-(2,6-dichloro-4-fluorophenyl)-2-((triethylsilyl)oxy)ethanamine (A31-3)

To a stirred solution of compound A31-2 (15.0 g, 40.7 mmol) in EtOH/water (60 mL, 4:1) was added Fe powder (22.7 g, 407.6 mmol) and solid NH$_4$Cl (21.8 g, 407.6 mmol). The mixture was stirred at 70° C. for 1 h. The reaction mixture was filtered through a pad of celite, washed with EtOAc (3×150 mL) and solvent was removed under reduced pressure. The residue was suspended in water (100 mL) and extracted with EtOAc (3×100 mL). The combined organic layers were washed with brine (100 mL), dried over anhydrous Na$_2$SO$_4$, and concentrated under reduced pressure. The residue was purified by column chromatography (silica gel, 5% MeOH/DCM as eluent) to provide compound A31-3 (13.0 g, 94%) as colorless oil. $^1$H NMR (CDCl$_3$, 400 MHz): δ 7.06 (s, 1H), 7.04 (s, 1H), 5.29 (dd, J=8.4, J=5.0 Hz, 1H), 3.25 (dd, J=13.2, J=8.8 Hz, 1H), 2.89 (dd, J=13.2, J=5.0 Hz, 1H), 0.88 (t, J=8.0 Hz, 9H), 0.57-0.52 (m, 6H).

Step 4: 2-(2,6-dichloro-4-fluorophenyl)-N-(3,5-difluorobenzyl)-2-((triethylsilyl)oxy)ethanamine (A31)

To a stirred solution of compound A31-3 (30.0 g, 88.7 mmol) in MeOH (200 mL) was added 3,5-difluorobenzaldehyde (12.6 g, 88.7 mmol) and the mixture was stirred at room temperature for 2 h. Upon completion of imine formation (monitored by TLC), solid NaBH₄ (4.9 g, 133.1 mmol) was added in portions at 0° C. The mixture was warmed to room temperature and stirred for 2 h. The reaction mixture was quenched with water (100 mL) and extracted with EtOAc (3×100 mL). The combined organic layers were washed with brine (2×75 mL), dried over anhydrous Na₂SO₄, and concentrated under reduced pressure. The residue was purified by column chromatography (silica gel, 10% EtOAc/hexane as eluent) to provide compound A31 (30.0 g, 70%) as colorless gum.

Reference Example A35

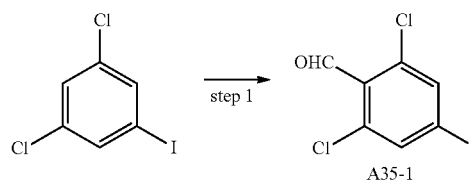

A35-1

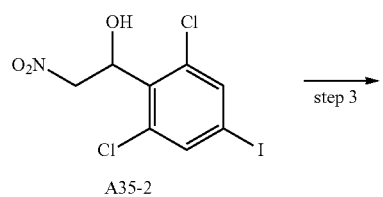

A35-2

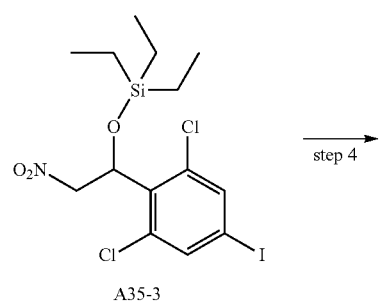

A35-3

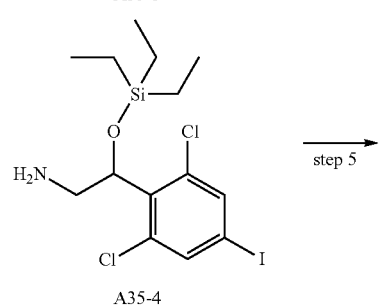

A35-4

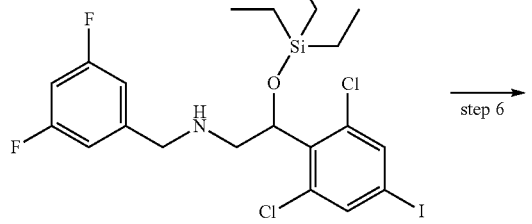

A35-5

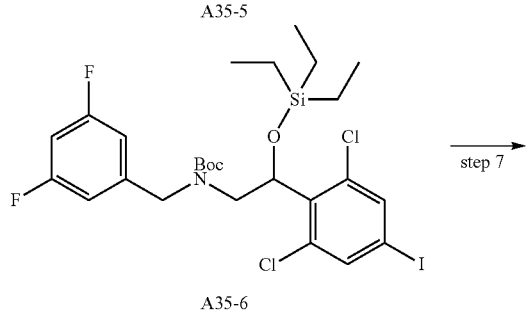

A35-6

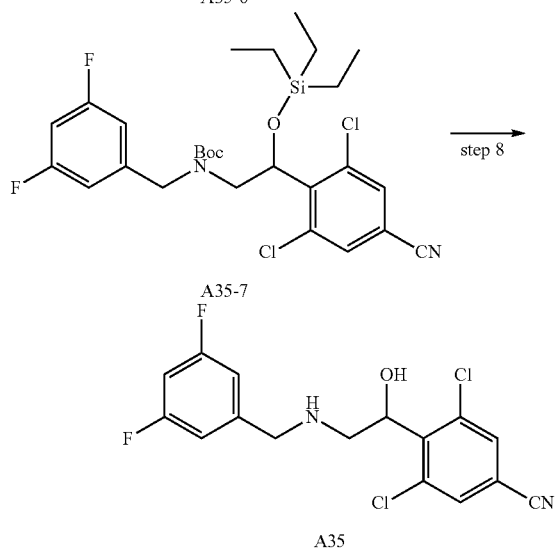

A35-7

A35

Step 1: 2,6-dichloro-4-iodobenzaldehyde (A35-1)

To a stirred solution of 1,3-dichloro-5-iodobenzene (4.0 g, 14.6 mmol) in THF (30 mL), LDA (2.0 M in THF/heptane/ethylbenzene, 9.6 mL, 16.9 mmol) was added dropwise at −78° C. and stirred for 1 h at the same temperature. A solution of DMF (1.7 mL, 22.0 mmol) in THF (5 mL) was added slowly at −78° C. and stirred for 3 h. The reaction mixture was quenched with saturated NH₄Cl (50 mL) and extracted with EtOAc (2×30 mL). The combined organic layers were washed with water (50 mL), brine (50 mL), dried over anhydrous Na₂SO₄ and concentrated under reduced pressure. The crude product was purified by column chromatography (silica gel, 20% EtOAc/hexane as eluent) to afford compound A35-1 (1.4 g, 32%) as colorless oil.

Step 2: 1-(2,6-dichloro-4-iodophenyl)-2-nitroethanol (A35-2)

Compound A35-2 (1.84 g, crude) was obtained as a colorless gum from the reaction of compound A35-1 (1.4 g, 4.8 mmol) and K$_2$CO$_3$ (0.23 g, 2.0 mmol) in CH$_3$NO$_2$ (10 mL) using a similar procedure to that described in reference example A1, step 1.

Step 3: (1-(2,6-dichloro-4-iodophenyl)-2-nitroethoxy)triethylsilane (A35-3)

Compound A35-3 (2.4 g, crude) was obtained as colorless gum from the reaction of compound A35-2 (1.84 g, 5.08 mmol), TES-Cl (1.02 mL, 6.12 mmol) and imidazole (1.03 g, 15.2 mmol) in DMF (10 mL) using a similar procedure to that described in reference example A1, step 2.

Step 4: 2-(2,6-dichloro-4-iodophenyl)-2-((triethylsilyl)oxy)ethanamine (A35-4)

Compound A35-4 (2.2 g, crude) was obtained as a brown oil from the reaction of compound A35-3 (2.4 g, 5.0 mmol), Fe (2.83 g, 50.0 mmol) and NH$_4$Cl (2.68 g, 50.0 mmol) in EtOH/water (4:1, 20 mL) using a similar procedure to that described in reference example A31, step 3.

Step 5: 2-(2,6-dichloro-4-iodophenyl)-N-((3,5-difluorophenyl)((triethylsilyl)oxy)methyl)ethanamine (A35-5)

Compound A35-5 (1.87 g, 67%) was obtained as a colorless gum from the reaction of compound A35-4 (2.2 g, 5.0 mmol), 3,5-difluorobenzaldehyde (0.55 mL, 5.0 mmol) and NaBH$_4$ (0.38 g, 10.0 mmol) in MeOH (15 mL) using a similar procedure to that described in example A31, step 4.

Step 6: tert-butyl (2-(2,6-dichloro-4-iodophenyl)-2-((triethylsilyl)oxy)ethyl)(3,5-difluorobenzyl)carbamate (A35-6)

To a stirred solution of compound A35-5 (1.87 g, 3.26 mmol) in DCM/water (4:1, 20 mL) was added NaHCO$_3$ (0.55 g, 6.5 mmol) and (Boc)$_2$O (1.07 g, 4.9 mmol) in DCM (8 mL) at 0° C. The mixture was stirred at room temperature for 2 h. The reaction mixture was quenched in water (100 mL) and extracted with DCM (2×30 mL). The combined organic layers were washed with water (50 mL), brine (50 mL), dried over anhydrous Na$_2$SO$_4$ and concentrated under reduced pressure to get compound A35-6 (2.47 g, crude) as a colorless gum.

Step 7: tert-butyl (2-(2,6-dichloro-4-cyanophenyl)-2-((triethylsilyl)oxy)ethyl)(3,5-difluorobenzyl)carbamate (A35-7)

To a solution of compound A35-6 (2.0 g, 2.9 mmol) in DMA (10 mL) in sealed tube, Zn(CN)$_2$ (0.7 g, 5.9 mmol) and Pd(PPh$_3$)$_4$ were added and stirred for 2 h at 80° C. The reaction mixture was quenched with water (50 mL) and extracted with EtOAc (2×50 mL). The combined organic layers were washed with water (50 mL), brine (50 mL), dried over anhydrous Na$_2$SO$_4$ and concentrated under reduced pressure. The crude product was purified by column chromatography (silica gel, 20% EtOAc/hexane as eluent) to afford compound A35-7 (1.1 g, 61%) as colorless oil.

Step 8: 3,5-dichloro-4-(2-((3,5-difluorobenzyl)amino)-1-hydroxyethyl)benzonitrile (A35)

To a stirred solution of compound A35-7 (0.2 g, 0.3 mmol) in EtOH (10 mL) was added 4 M HCl (5 mL) and the mixture was stirred at 80° C. for overnight. The reaction mixture was quenched with water (50 mL) and basified with 10% NaOH solution up to pH 9 and extracted with EtOAc (2×30 mL). The combined organic layers were washed with water (50 mL), brine (50 mL), dried over anhydrous Na$_2$SO$_4$ and concentrated under reduced pressure. The crude product was purified by column chromatography (silica gel, 30% EtOAc/hexane as eluent) to afford compound A35 (0.12 g, 99%) as colorless oil.

Reference Example A56

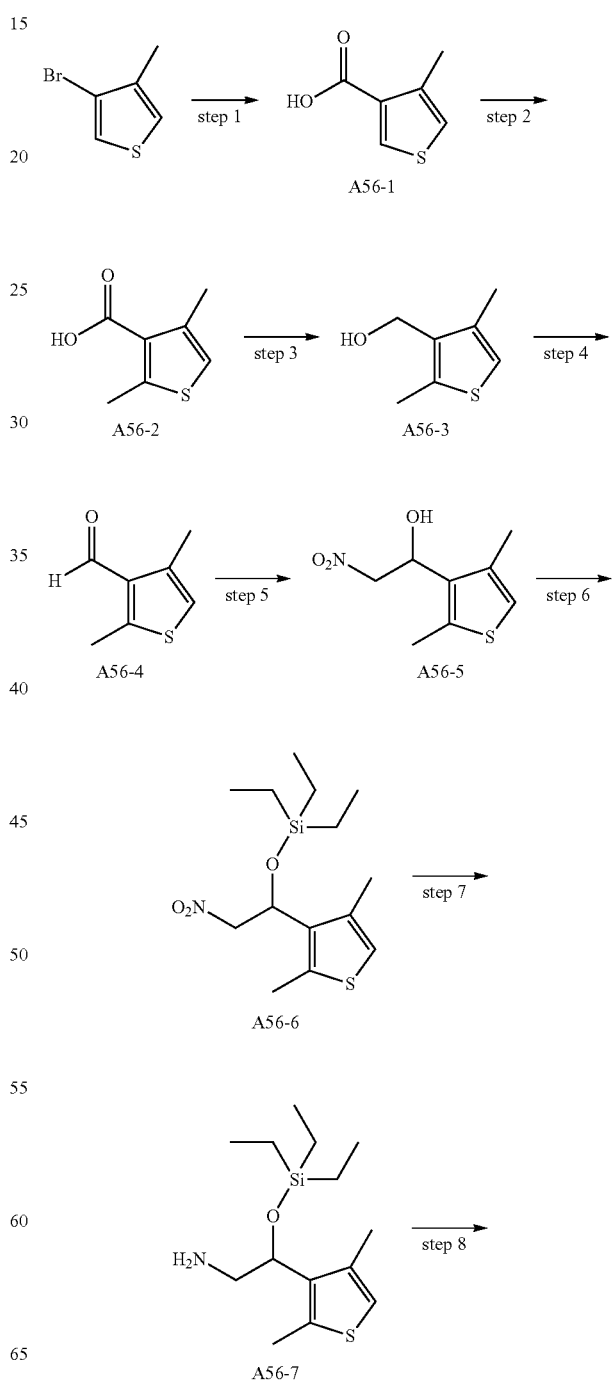

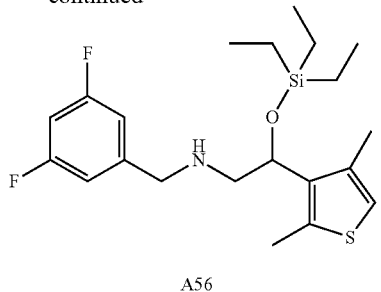

A56

Step 1: 4-methylthiophene-3-carboxylic acid (A56-1)

To a stirred solution of 3-bromo-4-methylthiophene (2.7 g, 15.6 mmol) in THF (35 mL) was added n-BuLi (1.6 M in hexane, 14.6 mL, 23.3 mmol) at −78° C. dropwise over a period of 15 min and the mixture was stirred at −78° C. for 30 min. The $CO_2$ (gaseous) was passed through the reaction mixture for 10 min and the mixture was stirred at the same temperature for 20 min. Thereafter, the reaction mixture was warmed to 0° C., quenched with aqueous 1 M NaOH (60 mL) and washed with EtOAc (2×50 mL). The aqueous layer was acidified to pH ~5 and extracted with DCM (2×50 mL). The combined organic layers were washed with water (100 mL), brine (100 mL), dried over anhydrous $Na_2SO_4$ and concentrated under reduced pressure. The residue was purified by column chromatography (silica gel, 8% MeOH/DCM as eluent) to provide compound A56-1 (1.5 g, 70%) as a white solid.

Step 2: 2,4-dimethylthiophene-3-carboxylic acid (A56-2)

To a stirred solution of compound A56-1 (390 mg, 2.7 mmol) in THF (4 mL) was added n-BuLi (1.6 M in hexane, 3.8 mL, 6.0 mmol) dropwise at −78° C. for 10 min. The mixture was stirred at −78° C. for 5 min. A solution of iodomethane (0.4 mL, 6.8 mmol) in THF (1 mL) was added dropwise, and the reaction mixture was stirred at −78° C. for 30 min. The mixture was allowed to warm to room temperature and stirred at the same temperature for 15 h. The reaction mixture was quenched with saturated aqueous $NH_4Cl$ and extracted with EtOAc (2×25 mL). The combined organic layers were washed with water (100 mL), brine (100 mL), dried over anhydrous $Na_2SO_4$ and concentrated under reduced pressure. The residue was purified by column chromatography (silica gel, 2% MeOH/DCM as eluent) to provide compound A56-2 (246 mg, 57%) as a white solid.

Step 3: (2,4-dimethylthiophen-3-yl)methanol (A56-3)

To a stirred solution of compound A56-2 (246 mg, 1.5 mmol) in THF (3 mL) was added $BH_3$.THF (1 M in THF, 5.5 mL, 5.5 mmol) dropwise at 0° C. for 15 min. The mixture was allowed to warm to room temperature and stirred at the same temperature for 15 h. The reaction mixture was quenched with saturated aqueous $NaHCO_3$ and extracted with EtOAc (2×30 mL). The combined organic layers were washed with brine (2×10 mL), dried over anhydrous $Na_2SO_4$ and concentrated under reduced pressure. The residue was purified by column chromatography (silica gel, 25% EtOAc/hexane as eluent) to provide compound A56-3 (201 mg, 90%) as a colorless gum.

Step 4: 2,4-dimethylthiophene-3-carbaldehyde (A56-4)

To a stirred solution of compound A56-3 (740 mg, 5.2 mmol) in DCM (18 mL) was added Dess-Martin periodinane (4.6 g, 10.9 mmol) at 0° C. and the mixture was stirred at room temperature for 3 h. The reaction mixture was quenched with saturated aqueous $Na_2S_2O_3$ and $NaHCO_3$, and extracted with EtOAc (2×50 mL). The combined organic layers were washed with brine (2×20 mL), dried over anhydrous $Na_2SO_4$, and concentrated under reduced pressure. The residue was purified by column chromatography (silica gel, 10% EtOAc/hexane as eluent) to provide compound A56-4 (275 mg, 38%) as a yellow solid.

Step 5: 1-(2,4-dimethylthiophen-3-yl)-2-nitroethanol (A56-5)

A mixture of compound A56-4 (133 mg, 0.95 mmol), nitromethane (2 mL) and $K_2CO_3$ (50 mg, 0.36 mmol) was stirred at room temperature for 60 h. The reaction mixture was quenched with water, and extracted with EtOAc (3×20 mL). The combined organic layers were washed with water (2×100 mL), and brine (100 mL), dried over anhydrous $Na_2SO_4$, and concentrated under reduced pressure. The residue was purified by column chromatography (silica gel, 40% EtOAc/hexane as eluent) to provide compound A56-5 (80 mg, 42%) as a yellow gum.

Step 6: (1-(2,4-dimethylthiophen-3-yl)-2-nitroethoxy)triethylsilane (A56-6)

To a stirred solution of compound A56-5 (235 mg, 1.17 mmol) in DMF (4 mL) were added imidazole (238 mg, 3.5 mmol) and TES-Cl (0.23 mL, 1.4 mmol) and the mixture was stirred at room temperature for 4 h. Upon completion, the reaction mixture was quenched with water (50 mL) and extracted with EtOAc (2×50 mL). The combined organic layers were washed with brine (2×30 mL), dried over anhydrous $Na_2SO_4$, and concentrated under reduced pressure. The residue was purified by column chromatography (silica gel, 5% EtOAc/hexane as eluent) to provide compound A56-6 (240 mg, 65%) as a colorless gum.

Step 7: 2-(2,4-dimethylthiophen-3-yl)-2-((triethylsilyl)oxy)ethanamine (A56-7)

To a stirred solution of compound A56-6 (240 mg, 0.76 mmol) in EtOH/water (10 mL, 4:1) were added powdered Fe (425 mg, 7.6 mmol) and solid $NH_4Cl$ (407 mg, 7.6 mmol). The mixture was stirred at 70° C. for 45 min. Upon completion, the reaction mixture was filtered through a pad of celite and washed with MeOH (3×15 mL). The solvent was removed under reduced pressure. The residue was suspended in EtOAc (100 mL) and washed with water (30 mL) and brine (30 mL). The organic layer was dried over anhydrous $Na_2SO_4$, and concentrated under reduced pressure. The residue was purified by column chromatography (silica gel, 5% MeOH/DCM as eluent) to provide compound A56-7 (192 mg, 88%) as a yellow gum.

Step 8: N-(3,5-difluorobenzyl)-2-(2,4-dimethylthiophen-3-yl)-2-((triethylsilyl)oxy)ethanamine (A56)

To a stirred solution of compound A56-7 (192 mg, 0.67 mmol) in MeOH (5 mL) was added 3,5-difluorobenzaldehyde (95 mg, 0.67 mmol) and the mixture was stirred at room temperature for 2 h. Upon completion of imine formation (monitored by TLC), solid NaBH$_4$ (51 mg, 1.3 mmol) was added in portions at 0° C. The mixture was warmed to room temperature and stirred at the same temperature for 4 h. The reaction mixture was quenched with water (30 mL) and extracted with EtOAc (3×30 mL). The combined organic layers were washed with brine (2×30 mL), dried over anhydrous Na$_2$SO$_4$, and concentrated under reduced pressure. The residue was purified by column chromatography (silica gel, 10% EtOAc/hexane as eluent) to provide compound A56 (200 mg, 72%) as a colorless gum. $^1$H NMR (CDCl$_3$, 300 MHz): δ 6.90-6.77 (m, 3H), 6.71-6.60 (m, 1H), 5.09 (dd, J=7.8, 4.2 Hz, 1H), 3.78 (s, 2H), 2.87 (dd, J=12.0, 7.8 Hz, 1H), 2.71 (dd, J=12.0, 4.5 Hz, 1H), 2.11 (d, J=0.6, 3H), 2.06 (s, 3H), 1.65 (brs, 1H), 0.89 (t, J=7.8 Hz, 9H), 0.62-0.50 (m, 6H).

Reference Example A57

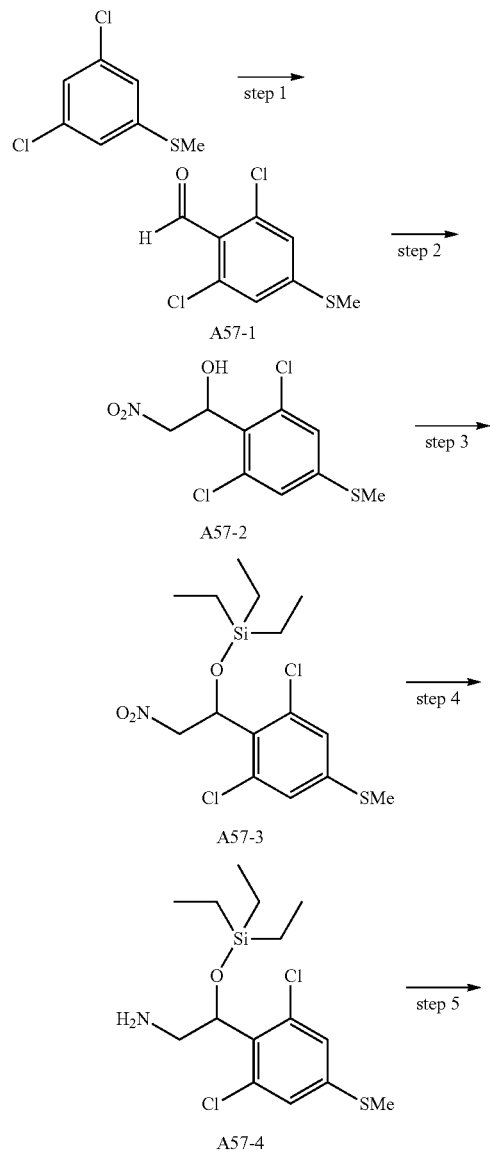

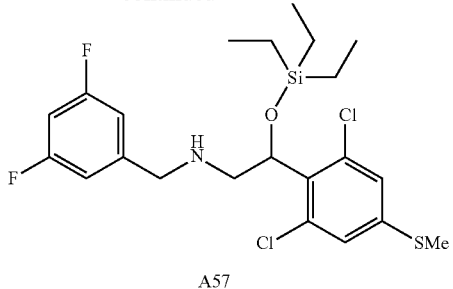

Step 1: 2,6-dichloro-4-(methylthio)benzaldehyde (A57-1)

To a stirred solution of (3,5-dichlorophenyl)(methyl)sulfane (1.0 g, 5.1 mmol) in THF (15 mL), n-BuLi (1.6 M in THF, 4.8 mL, 7.7 mmol) was added dropwise at −78° C. and stirred for 1 h at the same temperature. A solution of DMF (0.6 mL, 7.7 mmol) in THF (3 mL) was added slowly at −78° C. and stirred for 1 h. The reaction mixture was quenched with saturated NH$_4$Cl aq. (50 mL) and extracted with EtOAc (2×30 mL). The combined organic layers were washed with water (30 mL), brine (30 mL), dried over anhydrous Na$_2$SO$_4$ and concentrated under reduced pressure. The crude product was purified by column chromatography (silica gel, 20% EtOAc/hexane as eluent) to afford compound A57-1 (1.4 g, 99%) as colorless oil.

Step 2: 1-(2,6-dichloro-4-(methylthio)phenyl)-2-nitroethanol (A57-2)

Compound A57-2 (0.71 g, crude) was obtained as a colorless gum from the reaction of compound A57-1 (0.5 g, 2.44 mmol) and K$_2$CO$_3$ (0.13 g, 0.92 mmol) in CH$_3$NO$_2$ (5 mL) using a similar procedure to that described in reference example A1, step 1.

Step 3: (1-(2,6-dichloro-4-(methylthio)phenyl)-2-nitroethoxy)triethylsilane (A57-3)

Compound A57-3 (1.0 g, crude) was obtained as colorless gum from the reaction of compound A57-2 (0.71 g, 2.5 mmol), TES-Cl (0.5 mL, 3.02 mmol) and imidazole (0.51 g, 7.55 mmol) in DMF (10 mL) using a similar procedure to that described in reference example A1, step 2.

Step 4: 2-(2,6-dichloro-4-(methylthio)phenyl)-2-((triethylsilyl)oxy)ethanamine (A57-4)

Compound A57-4 (0.98 g, crude) was obtained as a brown color oil from the reaction of compound A57-3 (1.0 g, 2.53 mmol), Fe (1.42 g, 25.3 mmol) and NH$_4$Cl (1.34 g, 25.3 mmol) in EtOH/water (4:1, 20 mL) using a similar procedure to that described in reference example A31, step 3.

Step 5: 2-(2,6-dichloro-4-(methylthio)phenyl)-N-(3,5-difluorobenzyl)-2-((triethylsilyl)oxy)ethanamine (A57)

Compound A57 (0.73 g, 55%) was obtained as a colorless gum from the reaction of compound A57-4 (0.98 g, 2.69 mmol), 3,5-difluorobenzaldehyde (0.29 mL, 2.69 mmol) and NaBH$_4$ (0.2 g, 5.36 mmol) in MeOH (10 mL) using a similar procedure to that described in reference example A31, step 4.

¹H NMR (CDCl₃, 300 MHz): δ 7.10 (s, 2H), 6.87-6.61 (m, 3H), 5.53 (dd, J=8.6, 4.8 Hz, 1H), 3.82 (s, 2H), 3.23 (dd, J=12.1, 8.6 Hz, 1H), 2.78 (dd, J=12.1, 4.8 Hz, 1H), 2.49 (s, 3H), 0.90-0.85 (m, 9H), 0.58-0.50 (m, 6H).

Reference Example A58

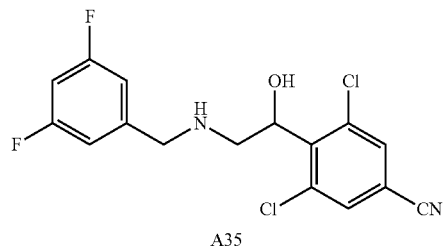

A35

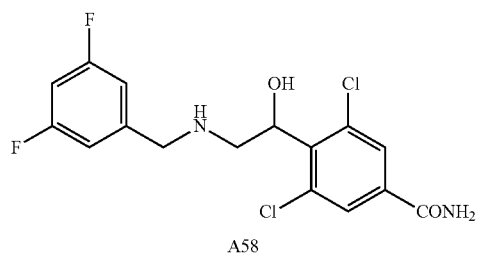

A58

3,5-Dichloro-4-(2-((3,5-difluorobenzyl)amino)-1-hydroxyethyl)benzamide (A58)

To a stirred solution of compound A35 (0.12 g, 0.29 mmol) in THF/MeOH/water (2:2:1, 5 mL) was added LiOH (4 M aq. solution, 0.44 mL, 1.76 mmol) dropwise at 0° C. The mixture was allowed to warm to room temperature while stirring continued for 4 h. The reaction mixture was acidified with HCl (1 M, 6 mL) and extracted with EtOAc (3×10 mL). The combined organic layers were washed with water (10 mL), brine (10 mL), dried over anhydrous Na₂SO₄ and concentrated under reduced pressure to provide compound A58 (60 mg, 47%) as a yellow solid. LCMS (APCI): 391 (M+H)⁺.

Reference Example A59

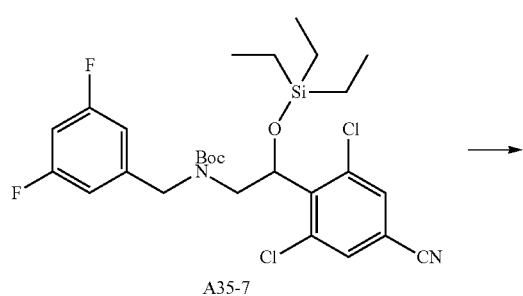

A35-7

-continued

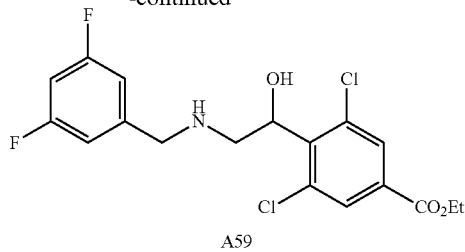

A59

Ethyl 3,5-dichloro-4-(2-((3,5-difluorobenzyl)amino)-1-hydroxyethyl)benzoate (A59)

To a stirred solution of compound A35-7 (0.2 g, 0.3 mmol) in EtOH (5 mL) was added conc. HCl (5 mL) and the mixture was stirred at reflux for overnight. The reaction mixture was quenched with water (50 mL) and basified with 10% NaOH solution up to pH 9 and extracted with EtOAc (2×30 mL). The combined organic layers were washed with water (50 mL), brine (50 mL), dried over anhydrous Na₂SO₄ and concentrated under reduced pressure. The crude product was purified by column chromatography (silica gel, 30% EtOAc/hexane as eluent) to afford compound A59 (0.1 g, 92%) as a white solid.

Reference Example A66

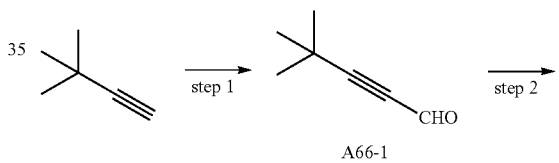

A66-1

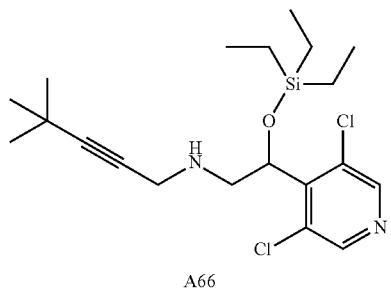

A66

Step 1: 4,4-dimethylpent-2-ynal (A66-1)

To a stirred solution of 3,3-dimethylbutan-1-yl (2.45 mL, 20 mmol) in THF (20 mL), n-BuLi (2.6 M in hexane, 8.46 mL, 22 mmol) was added at −78° C. dropwise and stirred for 1 h at the same temperature. A solution of DMF (3.85 mL, 50.0 mmol) was added slowly at −78° C. and the reaction mixture was allowed to warm to room temperature for overnight. The reaction mixture was quenched with saturated NH₄Cl (100 mL) and extracted with hexane (2×100 mL). The collected organic layers were washed with water (3×200 mL) and concentrated under reduced pressure to provide compound A66-1. The crude product was used for next step without purification.

Step 2: N-(2-(3,5-dichloropyridin-4-yl)-2-((triethylsilyl)oxy)ethyl)-4,4-dimethylpent-2-yn-1-amine (A66)

Compound A66 (76.1 mg, 36.6%) was obtained as a pale yellow oil from the reaction of compound A1-3 (160 mg, 0.5 mmol), compound A66-1 (80 mg, 0.726 mmol), NaBH$_4$ (120 mg) and MgSO$_4$ (100 mg) in MeOH (6 mL) and DCM (3 mL) using a similar procedure to that described in reference example A31, step 4. $^1$H NMR (CDCl$_3$, 400 MHz): δ 8.43 (s, 2H), 5.49 (dd, J=8.5, J=5.1 Hz, 1H), 3.48 (d, J=16.4 Hz, 1H), 3.37 (d, J=16.4 Hz, 1H), 3.32 (dd, J=12.0, J=8.5 Hz, 1H), 2.87 (dd, J=12.0, J=5.1 Hz, 1H), 1.21 (s, 9H), 0.89 (t, J=7.8 Hz, 9H), 0.61-0.50 (m, 6H).

Reference Example A75

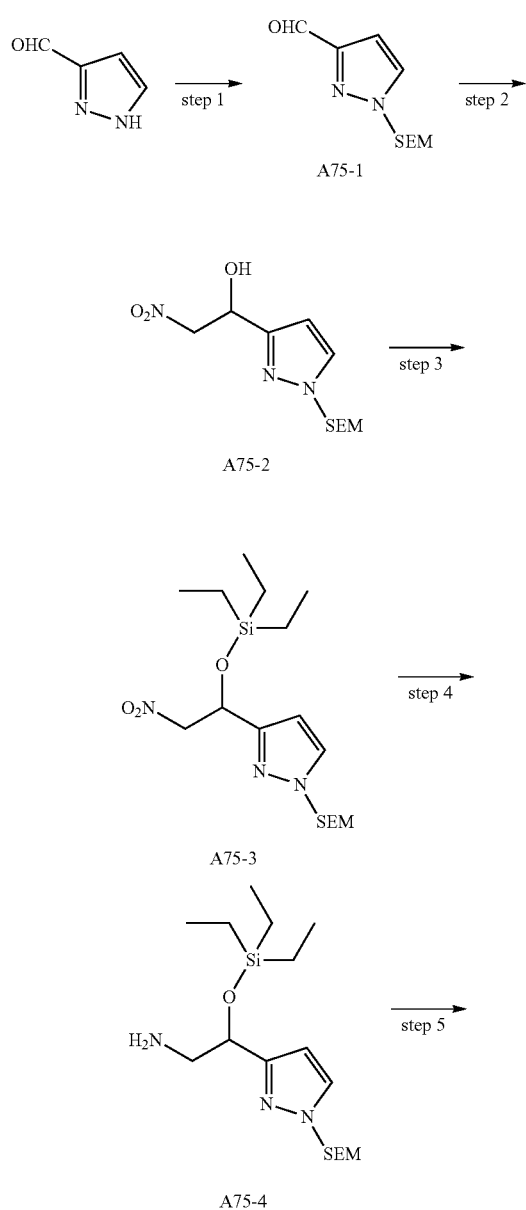

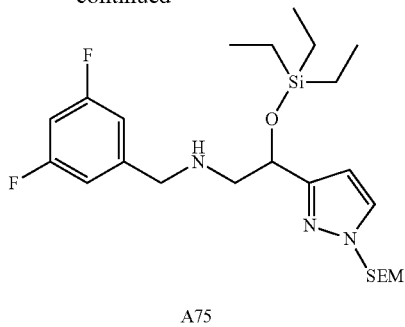

Step 1: 1-((2-(trimethylsilyl)ethoxy)methyl)-1H-pyrazole-3-carbaldehyde (A75-1)

To a stirred suspension of NaH (274 mg, 11.4 mmol) in DMF (20 mL) was added solution of 1H-pyrazole-3-carbaldehyde (1.0 g, 10.4 mmol) in DMF (10 mL) dropwise at 0° C. and the mixture was stirred at room temperature for 10 min. The reaction mixture was cooled to 0° C. and SEM-Cl (1.90 g, 11.4 mmol) was added dropwise. The mixture was warmed to room temperature and stirred at the same temperature for 16 h. The reaction mixture was quenched with water and extracted with EtOAc (3×20 mL). The combined organic layers were washed water (20 mL), dried over anhydrous Na$_2$SO$_4$ and concentrated under reduced pressure. The residue was purified by column chromatography (silica gel, 10% EtOAc/hexane as eluent) to provide compound A75-1 (350 mg, 29%) as colorless gum.

Step 2: 2-nitro-1-(1-((2-(trimethylsilyl)ethoxy)methyl)-1H-pyrazol-3-yl)ethanol (A75-2)

Compound A75-2 (428 mg, 64%) was obtained as yellow gum from the reaction of compound A75-1 (350 mg, 1.54 mmol), CH$_3$NO$_2$ (1 mL) and K$_2$CO$_3$ (85 mg, 0.616 mol) using a similar procedure to that described in reference example A1, step 2.

Step 3: 3-(2-nitro-1-((triethylsilyl)oxy)ethyl)-1-((2-(trimethylsilyl)ethoxy)methyl)-1H-pyrazole (A75-3)

Compound A75-3 (604 mg, crude) was obtained as yellow gum from the reaction of compound A75-2 (428 mg, 1.49 mmol), TES-Cl (0.280 mL, 1.78 mmol) and imidazole (303 mg, 4.47 mmol) using a similar procedure to that described in reference example A1, step 3.

Step 4: 2-((triethylsilyl)oxy)-2-(1-((2-(trimethylsilyl)ethoxy)methyl)-1H-pyrazol-3-yl)ethanamine (A75-4)

Compound A75-4 (600 mg, crude) was obtained as colorless gum from the reaction of compound A75-3 (604 mg, 1.51 mmol), Fe powder (843 mg, 15.1 mmol) and NH$_4$Cl (806 mg, 15.1 mmol) using a similar procedure to that described in reference example A31, step 3.

Step 5: N-(3,5-difluorobenzyl)-2-((triethylsilyl)oxy)-2-(1-((2-(trimethylsilyl)ethoxy)methyl)-1H-pyrazol-3-yl)ethanamine (A75)

Compound A75 (40 mg, 5%, over 3 steps) was obtained as colorless gum from the reaction of compound A75-4 (600 mg, 1.61 mmol), 3,5-difluorobenzaldehyde (206 mg, 1.45 mmol) and NaBH$_4$ (119 mg, 3.22 mmol) using a similar procedure to that described in reference example A31, step 4. $^1$H NMR (CDCl$_3$, 300 MHz): δ 7.59 (s, 0.7H), 7.48 (s, 0.3H), 6.39 (s, 1H), 5.38-5.71 (m, 2H), 4.91-5.08 (m, 1H), 3.54-3.61 (m, 2H), 2.95-3.04 (m, 2H), 0.85-0.95 (m, 9H), 0.59-0.62 (m, 6H); LCMS (APCI): 499 (M+H)$^+$.

Reference Example A84

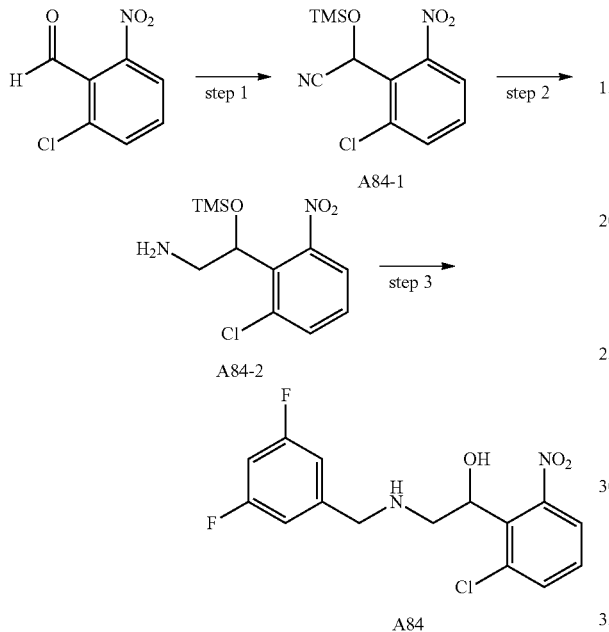

Step 1: 2-(2-chloro-6-nitrophenyl)-2-((trimethylsilyl)oxy)acetonitrile (A84-1)

To a stirred solution of 2-chloro-6-nitrobenzaldehyde (1.0 g, 5.4 mmol) in DCM (15 mL) were added TMSCN (1.0 mL, 8.1 mmol) and NMO (0.19 g, 1.6 mmol) at room temperature and stirred for 1 h. The reaction mixture was quenched with water (50 mL) and extracted with DCM (2×30 mL). The combined organic layers were washed with water (50 mL), brine (50 mL), dried over anhydrous Na$_2$SO$_4$ and concentrated under reduced pressure to get compound A84-1 (1.0 g, 67%) as a brown color oil.

Step 2: 2-(2-chloro-6-nitrophenyl)-2-((trimethylsilyl)oxy)ethanamine

To a stirred solution of compound A84-1 (0.85 g, 3.0 mmol) in THF (15 mL) was added BH$_3$.THF (1.0 M in THF, 17.9 mL, 17.88 mmol) and stirred at room temperature for 16 h. The reaction mixture was quenched with MeOH and extracted with EtOAc (2×30 mL). The combined organic layers were washed with water (50 mL), brine (50 mL), dried over anhydrous Na$_2$SO$_4$ and concentrated under reduced pressure to get compound A84-2 (0.65 g, 75%) as a brown color gum.

Step 3: 1-(2-chloro-6-nitrophenyl)-2-((3,5-difluorobenzyl)amino)ethanol (A84)

Compound A84 (0.57 g, 74%) was obtained as a yellow solid from the reaction of compound A84-2 (0.65 g, 2.24 mmol), 3,5-difluorobenzaldehyde (0.24 mL, 2.24 mmol) and NaBH$_4$ (0.17 g, 4.49 mmol) in MeOH (10 mL) using a similar procedure to that described in reference example A56, step 8. $^1$H NMR (CDCl$_3$, 300 MHz): δ 7.52-7.29 (m, 3H), 6.89-6.66 (m, 3H), 5.22 (dd, J=10.0, 3.7 Hz, 1H), 3.88 (s, 2H), 3.27-3.19 (m, 1H), 3.07 (dd, J=12.6, 3.7 Hz, 1H); LCMS (APCI): 343 (M+H)$^+$.

Reference Example A92

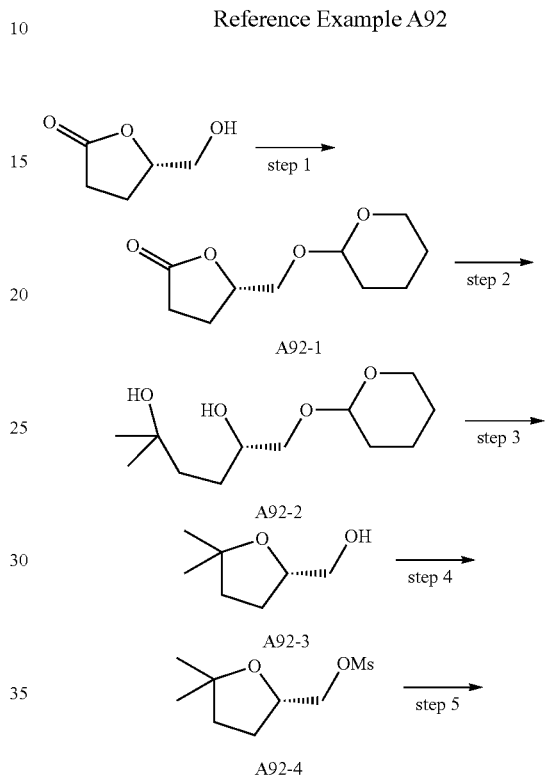

Step 1: (5S)-5-(((tetrahydro-2H-pyran-2-yl)oxy)methyl)dihydrofuran-2(3H)-one (A92-1)

To a stirred solution of (S)-5-(hydroxymethyl)dihydrofuran-2(3H)-one (4.0 g, 34.45 mmol) in DCM (20 mL) was added 3,4-dihydro-2H-pyran (3.95 mL, 41.34 mmol) followed by pyridinium p-toluenesulfonate (0.86 g, 3.44 mmol) at room temperature and the mixture was stirred for 16 h. The reaction mixture was diluted with DCM (20 mL), quenched with water (40 mL) and extracted with DCM (2×50 mL). The combined organic layers were washed with brine (2×20 mL), dried over anhydrous Na$_2$SO$_4$, and concentrated under reduced pressure. The residue was purified by column chromatography (silica gel, 50% EtOAc/hexane as eluent) to provide compound A92-1 (5.85 mg, 85%) as a colorless gum.

Step 2: (2S)-5-methyl-1-((tetrahydro-2H-pyran-2-yl)oxy)hexane-2,5-diol (A92-2)

To a stirred solution of compound A92-1 (5.85 g, 29.1 mmol) in THF (50 mL) was added methyl magnesium bromide (3.0 M in Et$_2$O, 22.4 mL, 67.2 mmol) dropwise at 0° C. for 10 min and the mixture was stirred at 0° C. for 4 h. The mixture was allowed to warm to room temperature and stirred for 15 h. The reaction mixture was quenched with saturated aqueous NH$_4$Cl and extracted with EtOAc (2×50 mL). The combined organic layers were washed with water (100 mL), brine (100 mL), dried over anhydrous Na$_2$SO$_4$ and concentrated under reduced pressure. The residue was purified by column chromatography (silica gel, 90% EtOAc/hexane as eluent) to provide compound A92-2 (6.09 g, 90%) as a colorless gum.

Step 3: (S)-(5,5-dimethyltetrahydrofuran-2-yl)methanol (A92-3)

To a stirred solution of compound A92-2 (1.03 g, 4.43 mmol) in MeOH (8 mL) was added p-toluenesulfonic acid monohydrate (421 mg, 2.2 mmol) at room temperature and the mixture was refluxed for 5 h. The reaction mixture was cooled to room temperature, quenched with water (15 mL) and extracted with DCM (2×25 mL). The combined organic layers were washed with brine (20 mL), dried over anhydrous Na$_2$SO$_4$ and concentrated under reduced pressure. The residue was purified by column chromatography (silica gel, 35% EtOAc/hexane as eluent) to provide compound A92-3 (330 mg, 57%) as a colorless gum.

Step 4: (S)-(5,5-dimethyltetrahydrofuran-2-yl)methyl methanesulfonate (A92-4)

To a stirred solution of compound A92-3 (300 mg, 2.30 mmol) in DCM (6 mL) was added Et$_3$N (0.64 mL, 4.6 mmol) followed by methanesulfonyl chloride (0.21 mL, 2.76 mmol) at 0° C. The mixture was stirred at 0° C. for 30 min. The mixture was allowed to warm to room temperature over a period of 2 h. The reaction mixture was quenched with water (10 mL) and extracted with DCM (2×20 mL). The combined organic layers were washed with water (20 mL), brine (20 mL), dried over anhydrous Na$_2$SO$_4$ and concentrated under reduced pressure. The residue was purified by column chromatography (silica gel, 35% EtOAc/hexane as eluent) to provide compound A92-4 (310 mg, 64%) as a colorless gum.

Step 5: 2-(3,5-dichloropyridin-4-yl)-N—(((S)-5,5-dimethyltetrahydrofuran-2-yl)methyl)-2-((triethylsilyl)oxy)ethanamine (A92)

A mixture of compound A92-4 (140 mg, 0.67 mmol), compound A1-3 (216 mg, 0.67 mmol), Na$_2$CO$_3$ (710 mg, 6.7 mmol) and isopropanol (4 mL) was taken in a microwave vial. The vial was capped and the mixture was subjected to microwave irradiation at 120° C. for 2 h. The reaction mixture was cooled to room temperature, quenched with water (15 mL) and extracted with DCM (2×25 mL). The combined organic layers were washed with brine (20 mL), dried over anhydrous Na$_2$SO$_4$ and concentrated under reduced pressure. The residue was purified by column chromatography (silica gel, 2% MeOH/DCM as eluent) to provide compound A92 (40 mg, 14%) as a colorless gum.

Reference Example A93

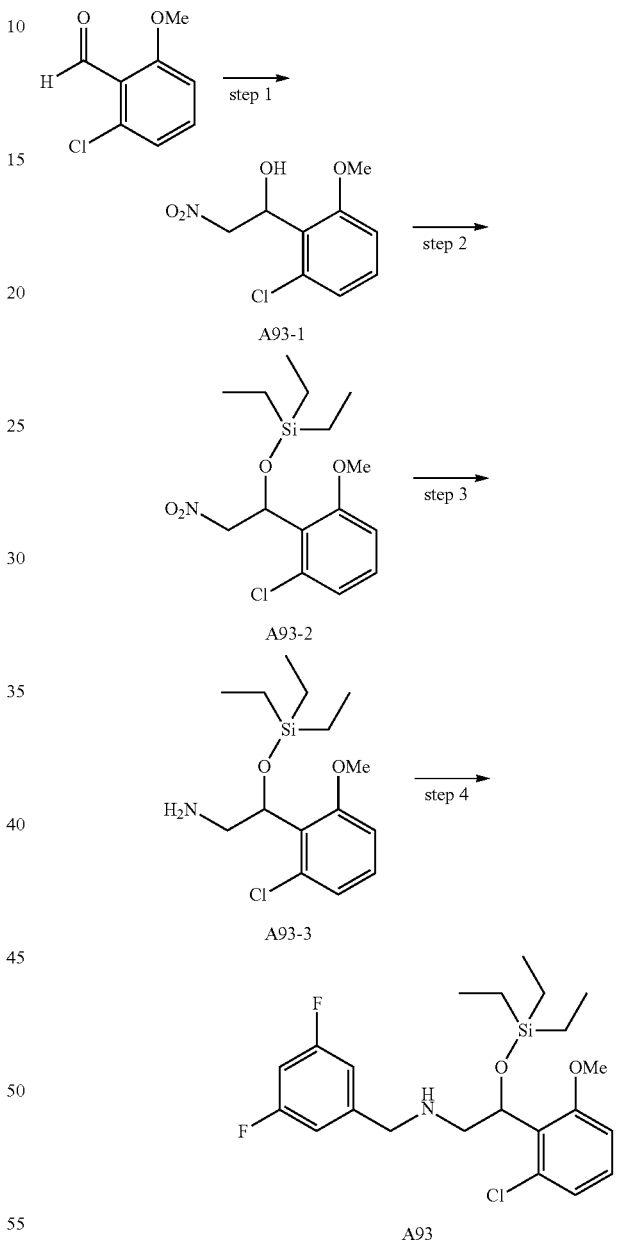

Step 1: 1-(2-chloro-6-methoxyphenyl)-2-nitroethanol (A93-1)

Compound A93-1 (1.35 g, crude) was obtained as a colorless oil from the reaction of 2-chloro-6-methoxybenzaldehyde (1.0 g, 5.88 mmol) and K$_2$CO$_3$ (0.3 g, 2.2 mmol) in CH$_3$NO$_2$ (10 mL) using a similar procedure to that described in reference example A1, step 1.

Step 2: (1-(2-chloro-6-methoxyphenyl)-2-nitroethoxy)triethylsilane (A93-2)

Compound A93-2 (2.14 g, crude) was obtained as a colorless oil from the reaction of compound A93-1 (1.35 g, 5.84 mmol), TES-Cl (1.17 mL, 7.01 mmol) and imidazole (1.19 g, 17.53 mmol) in DMF (10 mL) using a similar procedure to that described in reference example A1, step 2.

Step 3: 2-(2-chloro-6-methoxyphenyl)-2-((triethylsilyl)oxy)ethanamine (A93-3)

Compound A93-3 (1.6 g, 84%) was obtained as a colorless oil from the reaction of compound A93-2 (2.14 g, 6.2 mmol), Fe (3.48 g, 62.0 mmol) and NH$_4$Cl (3.3 g, 62.0 mmol) in EtOH/water (4:1, 20 mL) using a similar procedure to that described in reference example A1, step 3.

Step 4: 2-(2-chloro-6-methoxyphenyl)-N-(3,5-difluorobenzyl)-2-((triethylsilyl)oxy)ethanamine (A93)

Compound A93 (1.2 g, 54%) was obtained as a colorless gum from the reaction of compound A93-3 (1.6 g, 5.16 mmol), 3,5-difluorobenzaldehyde (0.56 mL, 5.16 mmol) and NaBH$_4$ (0.39 g, 10.2 mmol) in MeOH (10 mL) using a similar procedure to that described in reference example A1, step 4. $^1$H NMR (CDCl$_3$, 300 MHz): δ 7.13 (t, J=8.1 Hz, 1H), 6.95-6.60 (m, 5H), 5.58 (dd, J=8.6, 4.7 Hz, 1H), 3.83-3.77 (m, 5H), 3.28 (dd, J=12.0, 8.7 Hz, 1H), 2.78 (dd, J=12.0, 4.7 Hz, 1H), 0.87-0.82 (m, 9H), 0.60-0.46 (m, 6H); LCMS (APCI): 442 (M+H)$^+$.

Reference Example A94

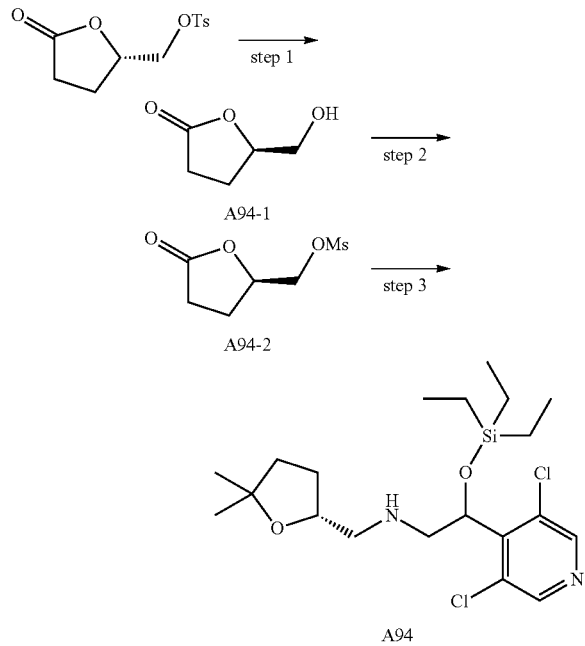

Step 1: (S)-(5-oxotetrahydrofuran-2-yl)methyl 4-methylbenzenesulfonate (A94-1)

To a stirred solution of (S)-5-(hydroxymethyl)dihydrofuran-2(3H)-one (2.0 g, 17.2 mmol) in DCM (20 mL) was added Et$_3$N (4.8 mL, 34.44 mmol) followed by p-toluenesulfonyl chloride (3.61 g, 18.94 mmol) at 0° C. The mixture was allowed to warm to room temperature and stirred at the same temperature for 15 h. The reaction mixture was quenched with water (100 mL) and extracted with DCM (2×50 mL). The combined organic layers were washed with water (50 mL), brine (50 mL), dried over anhydrous Na$_2$SO$_4$ and concentrated under reduced pressure. The residue was purified by column chromatography (silica gel, 50% EtOAc/hexane as eluent) to provide compound A94-1 (4.06 g, 87%) as a white solid.

Step 2: (R)-(5,5-dimethyltetrahydrofuran-2-yl)methanol (A94-2)

To a stirred solution of compound A94-1 (1.63 g, 6.03 mmol) in THF (20 mL) was added MeLi (3.0 M in diethoxymethane, 4.4 mL, 13.26 mmol) dropwise at −78° C. for 10 min and the mixture was stirred at −78° C. for 1 h. The mixture was allowed to warm to room temperature over a period of 4 h. The reaction mixture was quenched with saturated aqueous NaCl, diluted with water (30 mL) and extracted with EtOAc (2×25 mL). The combined organic layers were washed with water (30 mL), brine (30 mL), dried over anhydrous Na$_2$SO$_4$ and concentrated under reduced pressure. The residue was purified by column chromatography (silica gel, 35% EtOAc/hexane as eluent) to provide compound A94-2 (220 mg, 28%) as a colorless gum.

Step 3: (R)-(5,5-dimethyltetrahydrofuran-2-yl)methyl methanesulfonate (A94-3)

Compound A94-3 (351 mg, 61%) was obtained as a colorless gum from the reaction of compound A94-2 (360 mg, 2.76 mmol), Et$_3$N (0.77 mL, 5.52 mmol) and methanesulfonyl chloride (0.25 mL, 3.31 mmol) in DCM (5.0 mL) using a similar procedure to that described in reference example A92, step 4.

Step 4: 2-(3,5-dichloropyridin-4-yl)-N—(((R)-5,5-dimethyltetrahydrofuran-2-yl)methyl)-2-((triethylsilyl)oxy)ethanamine (A94)

Compound A94 (32 mg, 8%) was obtained as a colorless gum from the reaction of compound A94-3 (200 mg, 0.96 mmol), compound A1-3 (247 mg, 0.77 mmol) and Na$_2$CO$_3$ (508 mg, 4.8 mmol) in isopropanol (3.0 mL) using a similar procedure to that described in reference example A92, step 5.

Reference Example A103

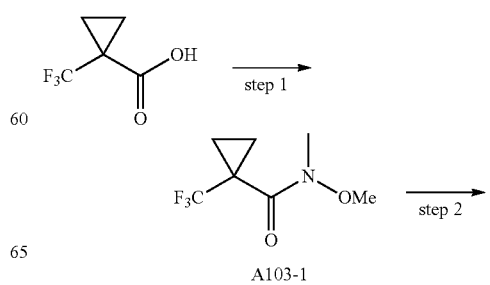

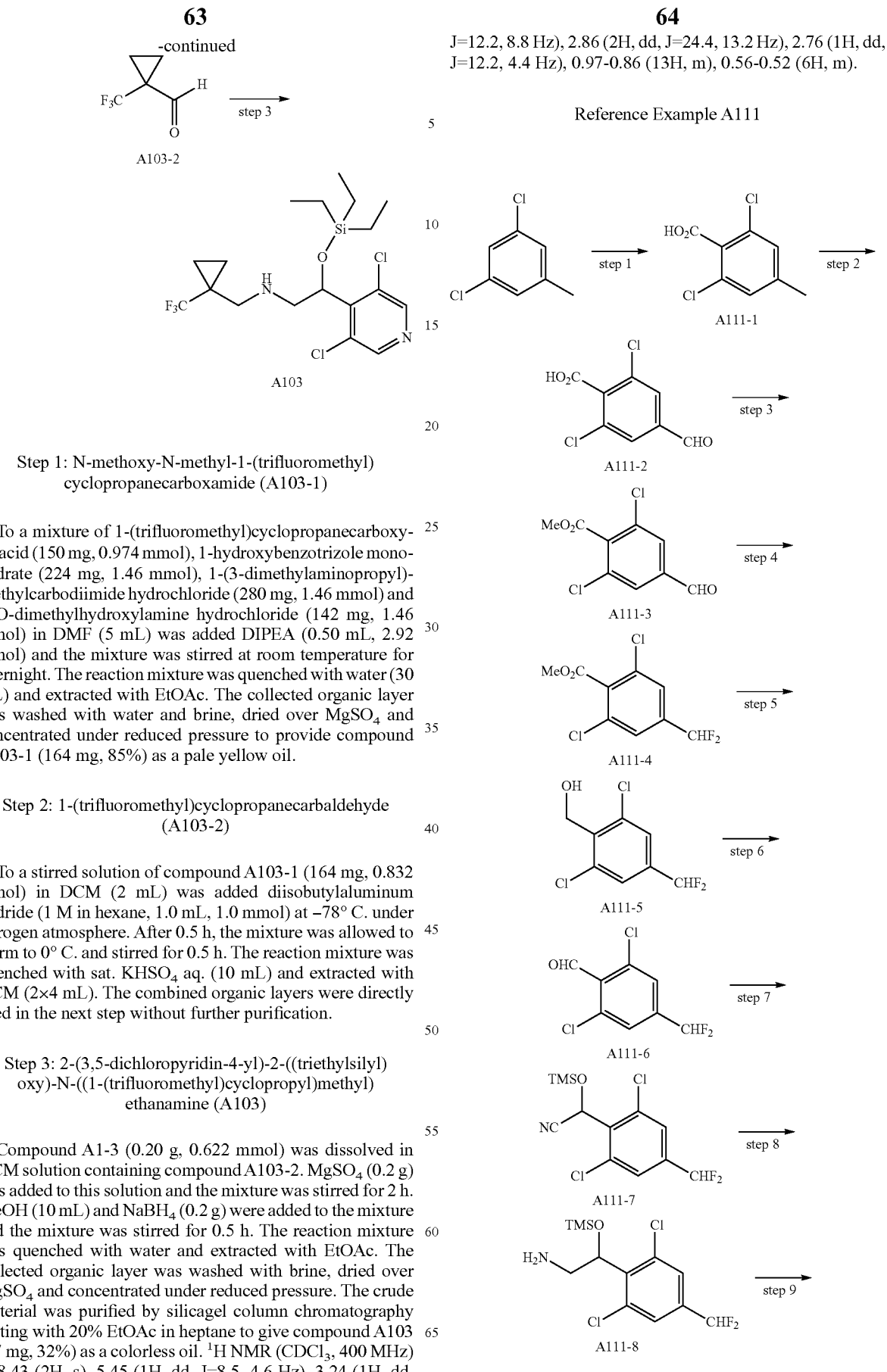

J=12.2, 8.8 Hz), 2.86 (2H, dd, J=24.4, 13.2 Hz), 2.76 (1H, dd, J=12.2, 4.4 Hz), 0.97-0.86 (13H, m), 0.56-0.52 (6H, m).

Reference Example A111

Step 1: N-methoxy-N-methyl-1-(trifluoromethyl)cyclopropanecarboxamide (A103-1)

To a mixture of 1-(trifluoromethyl)cyclopropanecarboxylic acid (150 mg, 0.974 mmol), 1-hydroxybenzotrizole monohydrate (224 mg, 1.46 mmol), 1-(3-dimethylaminopropyl)-3-ethylcarbodiimide hydrochloride (280 mg, 1.46 mmol) and N,O-dimethylhydroxylamine hydrochloride (142 mg, 1.46 mmol) in DMF (5 mL) was added DIPEA (0.50 mL, 2.92 mmol) and the mixture was stirred at room temperature for overnight. The reaction mixture was quenched with water (30 mL) and extracted with EtOAc. The collected organic layer was washed with water and brine, dried over MgSO$_4$ and concentrated under reduced pressure to provide compound A103-1 (164 mg, 85%) as a pale yellow oil.

Step 2: 1-(trifluoromethyl)cyclopropanecarbaldehyde (A103-2)

To a stirred solution of compound A103-1 (164 mg, 0.832 mmol) in DCM (2 mL) was added diisobutylaluminum hydride (1 M in hexane, 1.0 mL, 1.0 mmol) at −78° C. under nitrogen atmosphere. After 0.5 h, the mixture was allowed to warm to 0° C. and stirred for 0.5 h. The reaction mixture was quenched with sat. KHSO$_4$ aq. (10 mL) and extracted with DCM (2×4 mL). The combined organic layers were directly used in the next step without further purification.

Step 3: 2-(3,5-dichloropyridin-4-yl)-2-((triethylsilyl)oxy)-N-((1-(trifluoromethyl)cyclopropyl)methyl)ethanamine (A103)

Compound A1-3 (0.20 g, 0.622 mmol) was dissolved in DCM solution containing compound A103-2. MgSO$_4$ (0.2 g) was added to this solution and the mixture was stirred for 2 h. MeOH (10 mL) and NaBH$_4$ (0.2 g) were added to the mixture and the mixture was stirred for 0.5 h. The reaction mixture was quenched with water and extracted with EtOAc. The collected organic layer was washed with brine, dried over MgSO$_4$ and concentrated under reduced pressure. The crude material was purified by silicagel column chromatography eluting with 20% EtOAc in heptane to give compound A103 (87 mg, 32%) as a colorless oil. $^1$H NMR (CDCl$_3$, 400 MHz) δ: 8.43 (2H, s), 5.45 (1H, dd, J=8.5, 4.6 Hz), 3.24 (1H, dd,

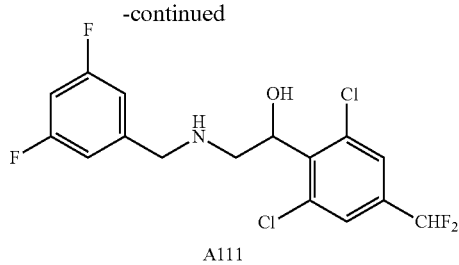

A111

Step 1: 2,6-dichloro-4-methylbenzoic acid (A111-1)

To a stirred solution of 1,3-dichloro-5-methylbenzene (2.0 g, 12.4 mmol) in THF (20 mL) was added n-BuLi (2.0 M in hexane, 9.3 mL, 18.6 mmol) at −78° C. dropwise over a period of 10 min and mixture was stirred at −78° C. for 30 min. A dry-ice was added to the reaction mixture slowly and the mixture was stirred at the same temperature for 20 min. Thereafter, the reaction mixture was slowly warmed to room temperature, quenched with 6 M HCl (10 mL) and extracted with EtOAc (2×30 mL). The combined organic layers were washed with water (50 mL), brine (50 mL), dried over anhydrous $Na_2SO_4$ and concentrated under reduced pressure to get compound A111-1 (1.1 g, 44%) as a white solid.

Step 2: 2,6-dichloro-4-formylbenzoic acid (A111-2)

To a stirred solution of compound A111-1 (1.1 g, 5.3 mmol) in DCM (20 mL) was added NBS (2.3 g, 13.4 mmol) and diphenyl oxalate (65 mg, 0.27 mmol) and placed at reflux for 40 h. The reaction mixture was brought to room temperature and evaporated the solvent. To the residue, EtOAc (10 mL) was added and the obtained solids were filtered through Buckner funnel. The filtrate was evaporated and the crude product was dissolved in EtOH (20 mL) and heated to 50° C. A solution of silver(I) nitrate (1.37 g, 8.0 mmol) in hot water (3 mL), was added to the reaction mixture dropwise and continued at the same temperature for 45 min. The reaction mixture was quenched with 1 M HCl (10 mL) and the obtained solids were filtered and washed with EtOH (30 mL). Filtrate was evaporated and remaining aqueous layer was extracted with EtOAc (2×50 mL). The combined organic layers were washed with water (50 mL), brine (50 mL), dried over anhydrous $Na_2SO_4$ and concentrated under reduced pressure to get compound A111-2 (1.6 g, crude) as a brown oil.

Step 3: methyl 2,6-dichloro-4-formylbenzoate (A111-3)

To a stirred solution of compound A111-2 (1.1 g, 5.0 mmol) in DMF (10 mL) was added $K_2CO_3$ (1.0 g, 7.5 mmol) at 0° C. followed by slow addition of MeI (0.94 mL, 15.0 mmol) and the reaction mixture was stirred at the same temperature for 30 min. Then reaction mixture was quenched with water (50 mL) and extracted with EtOAc (2×30 mL). The combined organic layers were washed with water (50 mL), brine (50 mL), dried over anhydrous $Na_2SO_4$ and concentrated under reduced pressure. The residue was purified by column chromatography (silica gel, 10% EtOAc/hexane as eluent) to provide compound A111-3 (0.59 g, 50%) as a white solid.

Step 4: methyl 2,6-dichloro-4-(difluoromethyl)benzoate (A111-4)

To a stirred solution of compound A111-3 (0.36 g, 1.5 mmol) in DCM (10 mL) was added DAST (0.37 mL, 2.8 mmol) at −78° C. dropwise followed by a drop addition of MeOH and the reaction was stirred at the same temperature for 15 min and brought to 0° C. The reaction mixture was stirred for 30 min at the same temperature and 16 h at room temperature. The reaction mixture was quenched with saturated $NaHCO_3$ (20 mL) at 0° C. and stirred for 20 min and extracted with DCM (2×30 mL). The combined organic layers were washed with water (50 mL), brine (50 mL), dried over anhydrous $Na_2SO_4$ and concentrated under reduced pressure to get compound A111-4 (0.37 g, 94%) as a colorless oil.

Step 5: (2,6-dichloro-4-(difluoromethyl)phenyl)methanol (A111-5)

To a stirred solution of compound A111-4 (1.44 g, 5.64 mmol) in THF (10 mL) was added $LiAlH_4$ (2.0 M in THF, 4.23 mL, 8.46 mmol) in THF (10 mL) at −78° C. dropwise for 15 min and brought to 0° C. The reaction mixture was stirred for 30 min at the same temperature and 16 h at room temperature. The reaction mixture was quenched with 1 M HCl (20 mL) at 0° C. and stirred for 20 min and extracted with EtOAc (2×30 mL). The combined organic layers were washed with water (50 mL), brine (50 mL), dried over anhydrous $Na_2SO_4$ and concentrated under reduced pressure to get compound A111-5 (0.59 g, 45%) as a colorless oil.

Step 6: 2,6-dichloro-4-(difluoromethyl)benzaldehyde (A111-6)

Compound A111-6 (0.38 g, 65%) was obtained as a colorless oil from the reaction of compound A111-5 (0.59 g, 2.46 mmol) and Dess-Martin periodinane (2.1 g, 4.92 mmol) in DCM (10 mL) using a similar procedure to that described in reference example A56, step 4.

Step 7: 2-(2,6-dichloro-4-(difluoromethyl)phenyl)-2-((trimethylsilyl)oxy)acetonitrile (A111-7)

To a stirred solution of compound A111-6 (0.38 g, 1.6 mmol) in DCM (15 mL) were added TMSCN (0.31 mL, 2.5 mmol) and NMO (60 mg, 0.5 mmol) at room temperature and stirred for 1 h. The reaction mixture was quenched with water (50 mL) and extracted with DCM (2×30 mL). The combined organic layers were washed with water (50 mL), brine (50 mL), dried over anhydrous $Na_2SO_4$ and concentrated under reduced pressure to get compound A111-7 (0.53 g, 97%) as a yellow solid.

Step 8 2-(2,6-dichloro-4-(difluoromethyl)phenyl)-2-((trimethylsilyl)oxy)ethanamine (A111-8)

To a stirred solution of compound A111-7 (0.53 g, 1.6 mmol) in THF (10 mL) was added $BH_3.THF$ (8.2 mL, 8.1 mmol) and stirred at room temperature for 16 h. The reaction mixture was quenched with MeOH and extracted with EtOAc (2×30 mL). The combined organic layers were washed with water (50 mL), brine (50 mL), dried over anhydrous $Na_2SO_4$ and concentrated under reduced pressure to get compound A111-8 (0.5 g, crude) as a yellow oil.

Step 9: 1-(2,6-dichloro-4-(difluoromethyl)phenyl)-2-(3,5-difluorobenzyl)amino)ethanol (A111)

Compound A111 (0.21 g, 36%) was obtained as a colorless gum from the reaction of compound A111-8 (0.5 g, 1.52 mmol), 3,5-difluorobenzaldehyde (0.16 mL, 1.52 mmol) and NaBH$_4$ (0.11 g, 3.0 mmol) in MeOH (5 mL) using a similar procedure to that described in reference example A56, step 8. $^1$H NMR (CDCl$_3$, 400 MHz): δ 7.44 (s, 2H), 6.89-6.42 (m, 4H), 5.56-5.25 (m, 1H), 3.87 (s, 2H), 3.26 (dd, J=12.8, 9.6 Hz, 1H), 2.91-2.86 (m, 1H).

Reference Example A112

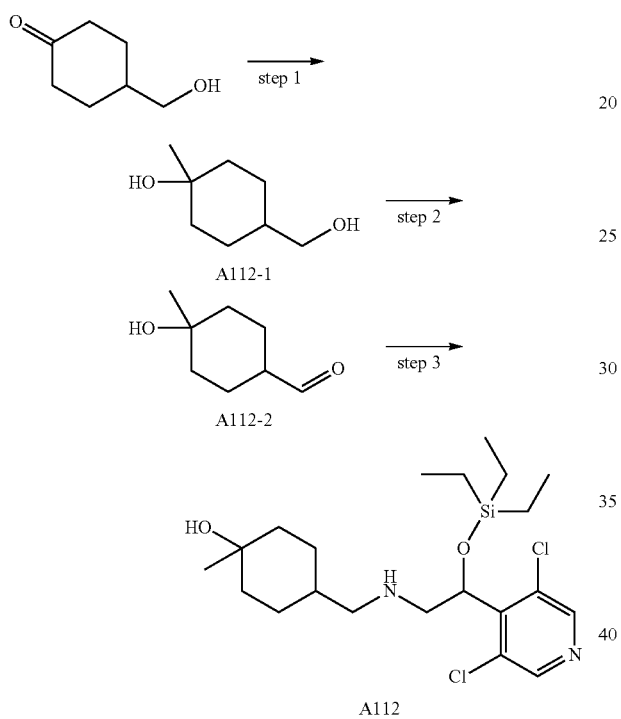

A112

Step 1: 4-(hydroxymethyl)-1-methylcyclohexanol (A112-1)

To a stirred solution of 4-(hydroxymethyl)cyclohexanone (1.0 g, 7.8 mmol) in THF (20 mL) was added methyl magnesium bromide (3.0 M in Et$_2$O, 7.8 mL, 23.4 mmol) dropwise at 0° C. for 5 min. The mixture was allowed to warm to room temperature and stirred at the same temperature for 2 h. The reaction mixture was quenched with saturated aqueous NH$_4$Cl and extracted with EtOAc (2×20 mL). The combined organic layers were washed with water (20 mL), brine (20 mL), dried over anhydrous Na$_2$SO$_4$ and concentrated under reduced pressure. The residue was purified by column chromatography (silica gel, 80% EtOAc/hexane as eluent) to provide compound A112-1 (300 mg, 27%) as a white solid.

Step 2: 4-hydroxy-4-methylcyclohexanecarbaldehyde (A112-2)

Compound A112-2 (49 mg, crude) was obtained as a yellow foam from the reaction of compound A112-1 (50 mg, 0.348 mmol) and Dess-Martin periodinane (206 mg, 0.48 mmol) in DCM (5.0 mL) using a similar procedure to that described in reference example A56, step 4.

Step 3: 4-((2-(3,5-dichloropyridin-4-yl)-2-((triethylsilyl)oxy)ethyl)amino)methyl)-1-methylcyclohexanol (A112)

To a stirred solution of compound A112-2 (49 mg, 0.34 mmol) in DCM (15 mL) was added compound A1-3 (109 mg, 0.34 mmol) followed by NaBH(OAc)$_3$ (108 mg, 0.51 mmol) at room temperature. The mixture was stirred for 4 h at room temperature. The reaction mixture was quenched with aqueous saturated NaHCO$_3$ (10 mL) and extracted with EtOAc (2×20 mL). The combined organic layer washed with water (20 mL), brine (20 mL), dried over anhydrous Na$_2$SO$_4$ and concentrated under reduced pressure. The residue was purified by column chromatography (silica gel, 5% MeOH/DCM as eluent) to provide compound A112 (58 mg, 37% over two steps) as a yellow gum.

Reference Example A118

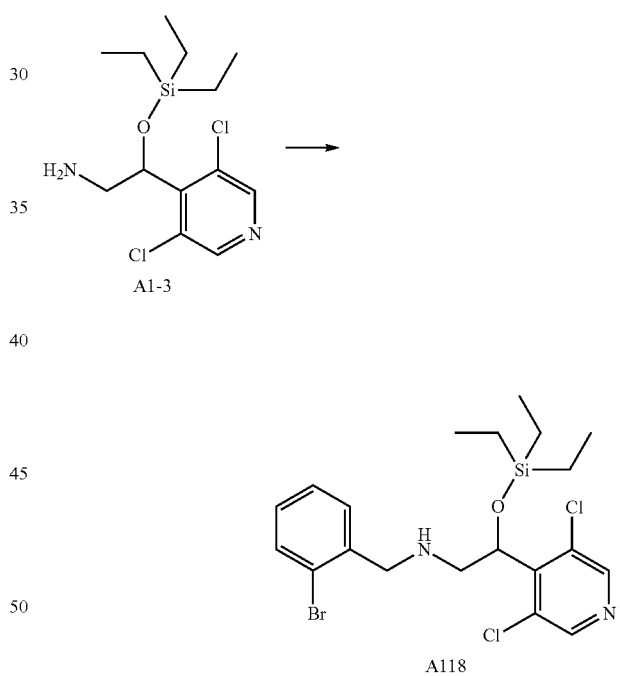

N-(2-bromobenzyl)-2-(3,5-dichloropyridin-4-yl)-2-((triethylsilyl)oxy)ethanamine (A118)

Compound A118 (1.2 g, 79%) was obtained as a colorless oil from the reaction of compound A1-3 (1.0 g, 3.16 mmol), 2-bromobenzaldehyde (576 mg, 3.11 mmol) and NaBH$_4$ (172 mg, 4.67 mmol) in MeOH (40 mL) using a similar procedure to that described in reference example A1, step 4. $^1$H NMR (CDCl$_3$, 400 MHz): δ 8.41 (s, 2H), 7.53-7.51 (m, 1H), 7.37-7.35 (m, 1H), 7.28-7.25 (m, 1H), 7.13-7.08 (m, 1H), 5.55 (dd, J=8.2, 5.2 Hz, 1H), 3.94-3.85 (m, 1H), 3.20 (dd, J=12.1, 8.4

Hz, 1H), 2.88 (d, J=4.8 Hz, 0.5H), 2.86 (dd, J=12.1, 5.1 Hz, 0.5H), 0.89-0.86 (m, 9H), 0.58-0.51 (m, 6H).

Reference Example A119

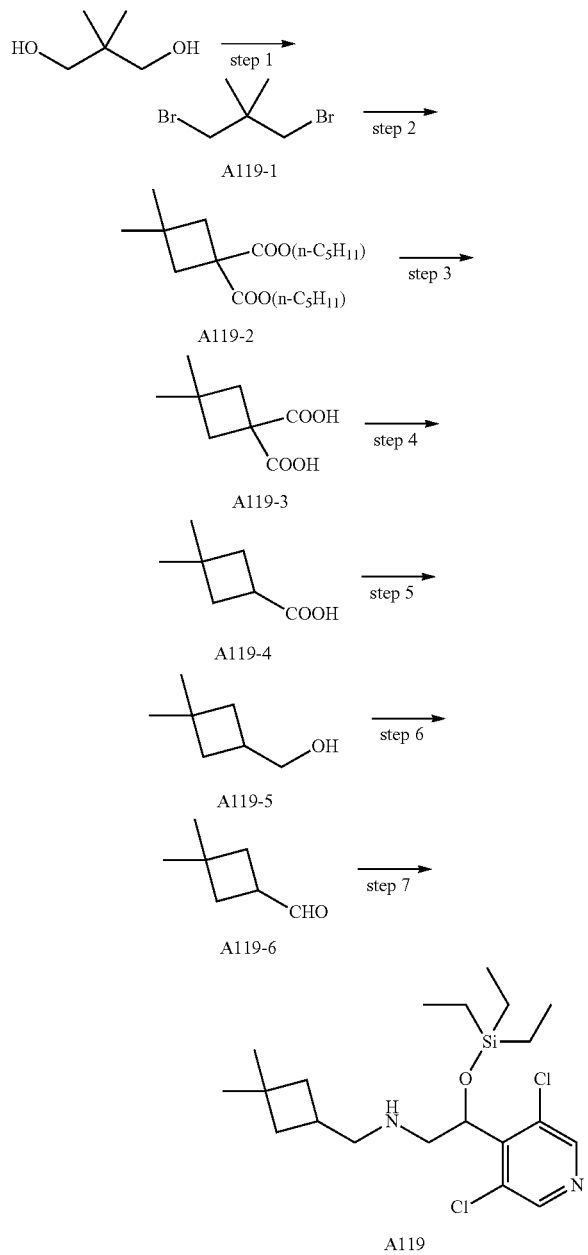

Step 1: 1,3-dibromo-2,2-dimethylpropane (A119-1)

To a stirred solution of triphenylphosphine (26.2 g, 0.1 mol) in $CH_3CN$ (50 mL) was added a solution of bromine (5.13 mL, 0.10 mol) in $CH_3CN$ (30 mL) dropwise at 0° C. 2,2-Dimethylpropane-1,3-diol (5.1 g, 0.05 mol) was added in portion to the reaction and the reaction mixture was stirred at 90° C. for 16 h. The solvent was removed under reduced pressure. The residue was suspended in MTBE (150 mL), and resulting solid was removed by filtration. The filtrate was concentrated under reduced pressure and the residue was dissolved in $CH_3CN$ and extracted with hexane (3×100 mL). The combined hexane extracts were concentrated under reduced pressure to provide compound A119-1 (6.5 g, 59%) as brown oil.

Step 2: dipentyl 3,3-dimethylcyclobutane-1,1-dicarboxylate (A119-2)

The sodium (0.98 g, 43.0 mmol) was added in portion to pentanol (25 mL) and the mixture was stirred at 50° C. to get a clear solution. The reaction mixture was heated to 70° C., and then diethyl malonate (3.50 g, 26.0 mmol) was added over a period of 5 min. The reaction mixture was heated to 130° C. and compound A119-1 (5.0 g, 21 mmol) was added dropwise over a period of 10 min. The reaction mixture was heated at 130° C. for 4 h. The solvent was removed under vacuum at 100° C. The residue was quenched with water (100 mL) and extracted with EtOAc (2×50 mL). The combined organic extracts were concentrated under reduced pressure to provide compound A119-2 (6 g, crude) as brown oil. The crude product was used for next step without purification.

Step 3: 3,3-dimethylcyclobutane-1,1-dicarboxylic acid (A119-3)

To a solution of compound A119-2 (6 g, crude) in EtOH/water (60 mL, 2:1) was added KOH solution (40% aqueous solution, 10 mL) and the reaction mixture was stirred at 100° C. for 4 h. After removing the solvent under reduced pressure, the residue was suspended in water (100 mL) and washed with MTBE. The aqueous layer was acidified to pH 1 and extracted with EtOAc (3×50 mL). The combined organic layers were washed with water (100 mL), brine (100 mL), dried over anhydrous $Na_2SO_4$ and concentrated under reduced pressure to provide compound A119-3 (2.5 g, crude) as brown semi-solid gum. The crude product was used for next step without purification.

Step 4: 3,3-dimethylcyclobutanecarboxylic acid (A119-4)

Compound A119-3 (2.5 g, crude) was heated neat at 200° C. for 2 h to provide compound A119-4 (900 mg, crude) as light brown gum.

Step 5: (3,3-dimethylcyclobutyl)methanol (A119-5)

To a stirred suspension of $LiAlH_4$ (534 mg, 14.0 mmol) in THF (20 mL) was added a solution of compound A119-4 (900 mg, 7.0 mmol) in THF (10 mL) at 0° C. and the mixture was stirred at the same temperature for 3 h. The reaction mixture was quenched with water (3 mL) and 20% aqueous NaOH (3 mL) and stirred at room temperature for 10 min. The solid was filtered over a pad of celite and the organic layer washed with water (20 mL), brine (20 mL), dried over anhydrous $Na_2SO_4$ and concentrated under reduced pressure. The residue was purified by column chromatography (silica gel, 20% EtOAc/hexane as eluent) to provide compound A119-5 (160 mg, 20%) as light yellow oil.

Step 6: 3,3-dimethylcyclobutanecarbaldehyde (A119-6)

To a stirred solution of compound A119-5 (160 mg, 1.4 mmol) in DCM (10 mL) was added Dess-Martin periodinane (1.20 g, 2.8 mmol) and the mixture was stirred at room temperature for 2 h. The reaction mixture was diluted with DCM (10 mL) and quenched with aqueous NO₂O₈ (5 mL) and NaHCO₃ solution (5 mL). The organic layer washed with water (10 mL), brine (10 mL), dried over anhydrous Na₂SO₄ and concentrated under reduced pressure to provide compound A119-6 (150 mg, quant.) as yellow oil. The crude product was used for next step without purification.

Step 7: 2-(3,5-dichloropyridin-4-yl)-N-((3,3-dimethylcyclobutyl)methyl)-2-((triethylsilyl)oxy)ethanamine (A119)

The mixture of compound A119-6 (150 mg, 1.33 mmol) and compound A1-3 (300 mg, 0.97 mmol) in MeOH (10 mL) was stirred at room temperature for 3 h. NaBH₄ (75 mg, 1.99 mmol) was added in portion and the mixture was stirred at room temperature for 3 h. The reaction mixture was quenched with water and extracted with EtOAc (2×20 mL). The combined organic layers were washed with water (100 mL), brine (100 mL), dried over anhydrous Na₂SO₄ and concentrated under reduced pressure. The residue was purified by column chromatography (silica gel, 20% EtOAc/hexane as eluent) to provide compound A119 (190 mg, 36%) as yellow gum. ¹H NMR (CDCl₃, 400 MHz): δ 8.42 (s, 2H), 5.46-5.52 (m, 1H), 3.16-3.23 (m, 1H), 2.71-2.79 (m, 1H), 2.53-2.69 (m, 2H), 1.42-1.62 (m, 5H), 1.23-1.38 (m, 6H), 0.84-0.92 (m, 9H), 0.49-0.58 (m, 6H).

Reference Example A122

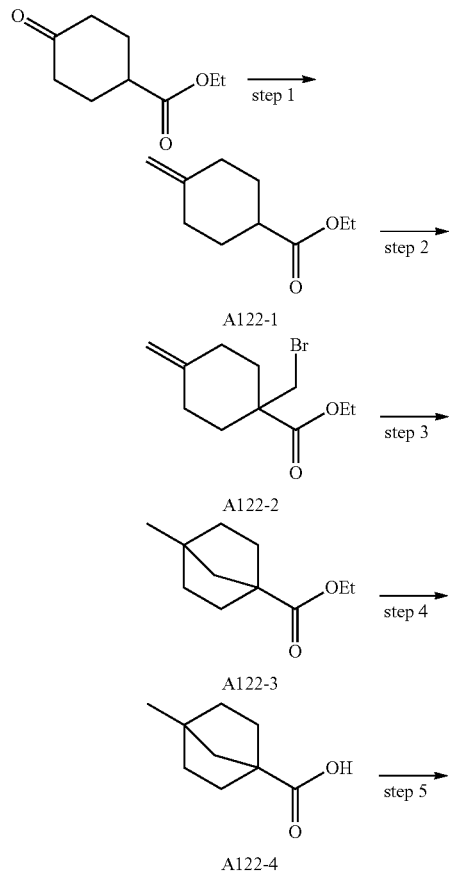

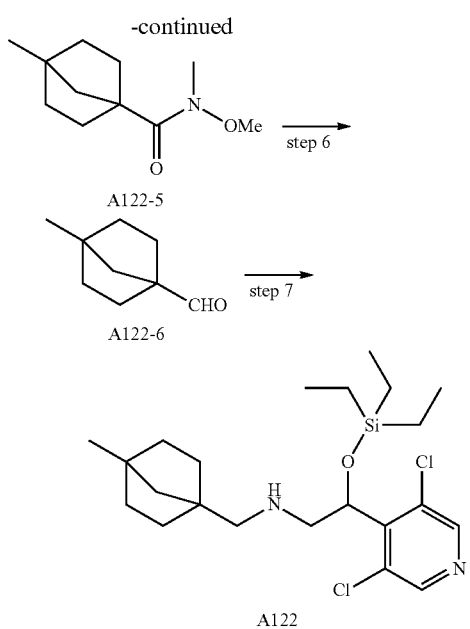

Step 1: ethyl 4-methylenecyclohexanecarboxylate (A122-1)

Lithium bis(trimethylsilyl)amide (1.0 M in THF, 15 mL, 15 mmol) was added dropwisely to a stirred solution of methyltriphenylphosphonium bromide (5.36 g, 15 mmol) in THF (50 mL) at 0° C. and stirred for 40 min at the same temperature. A solution of ethyl 4-oxocyclohexanecarboxylate (2.04 g, 12 mmol) in THF (20 mL) was added slowly at 0° C. and stirred for 2 h from 0° C. to room temperature. The reaction was quenched with saturated NH₄Cl aq. and extracted with hexane. The collected organic layer was dried over MgSO₄ and concentrated under reduced pressure. The solvent (100 mL, hexane/Et₂O=5/1) was added to the residue and stirred for 30 min. The suspension was filtrated. The filtrate was concentrated under reduced pressure. The residue was purified by silicagel chromatography (5% EtOAc/hexane as eluent) to provide compound A122-1 (1.478 g, 73%) as a colorless oil.

Step 2: ethyl 1-(bromomethyl)-4-methylenecyclohexanecarboxylate (A122-2)

n-BuLi (2.6 M in hexane, 2.5 mL, 6.6 mmoL) was added dropwisely to a solution of diisopropylamine (0.93 mL, 6.6 mmol) in THF (20 mL) at −78° C. and stirred for 30 min at the same temperature. Hexamethylphosphoramide (4 mL) was added to the reaction mixture and stirred for 20 min at the same temperature. A solution of compound A122-1 (1.01 g, 6 mmol) in THF (5 mL) was added and stirred for 1 h at the same temperature. A solution of dibromomethane (2.1 mL, 30 mmol) was added to the reaction mixture and the mixture was allowed to warm to room temperature for 1.5 h. The reaction mixture was diluted hexane (80 mL) and AcOEt (20 mL). The collected organic layer washed with water, saturated NH₄Cl aq., brine, dried over MgSO₄ and concentrated under reduced pressure. The residue was purified by silicagel chromatography (10% EtOAc/hexane as eluent) to provide compound A122-2 (1.39 g, 89%) as a pale yellow oil.

Step 3: ethyl 4-methylbicyclo[2.2.1]heptane-1-carboxylate (A122-3)

To a stirred solution of compound A122-2 (783 mg, 3 mmol) in toluene (65 mL) was added tributyltin hydride (0.888 mL, 3.3 mmol) and 2,2'-azobis(isobutyronitrile) (25 mg) in toluene (20 mL) and the mixture was stirred at 110° C. for 1 h. The reaction mixture was cooled down and concentrated under reduced pressure. DCM (20 mL) and a solution of KF (1.0 g) in water (0.31 mL) were added to the residue and the mixture was stirred for 1 h. The reaction mixture was filtrated with anhydrous $Na_2SO_4$ and concentrated under reduced pressure. The residue was purified by silicagel chromatography (10% EtOAc/hexane as eluent) to provide compound A122-3 (501 mg, 92%) as a colorless oil.

Step 4: 4-methylbicyclo[2.2.1]heptane-1-carboxylic acid (A122-4)

To a stirred solution of compound A122-3 (500 mg, 2.74 mmol) in MeOH/water (8 mL, 3:1) was added a solution of LiOH aq. (4 M, 2 mL, 8 mmol). The mixture was stirred at room temperature for 2.5 h and stirred at 50° C. for 1.5 h. The organic solvent was removed under reduced pressure. The residue was diluted with water (10 mL) and hexane (10 mL). The aqueous layer was acidified with 6 M aqueous HCl to pH 1 and extracted with DCM. The organic layers were dried over $MgSO_4$ and concentrated under reduced pressure to provide compound A122-4 (313 mg, 74%) as a pale yellow solid.

Step 5: N-methoxy-N,4-dimethylbicyclo[2.2.1]heptane-1-carboxamide (A122-5)

To a mixture of compound A122-4 (302 mg, 1.96 mmol), 1-hydroxybenzotrizole monohydrate (460 mg, 3 mmol), 1-(3-dimethylaminopropyl)-3-ethylcarbodiimide hydrochloride (466 mg, 3 mmol) and N,O-dimethylhydroxylamine hydrochloride (293 mg, 3 mmol) in DMF (10 mL) was added DIPEA (1.03 mL, 6 mmol) and the mixture was stirred at room temperature for overnight. The reaction mixture was quenched with water (30 mL) and extracted with EtOAc. The collected organic layer washed with saturated $NH_4Cl$ aq., brine, dried over $MgSO_4$ and concentrated under reduced pressure. The residue was purified by silicagel chromatography (30% EtOAc/hexane as eluent) to provide compound A122-5 (271.4 mg, 70%) as a colorless oil.

Step 6: 4-methylbicyclo[2.2.1]heptane-1-carbaldehyde (A122-6)

To a solution of compound A122-5 (271 mg, 1.37 mmol) in $Et_2O$ (5 mL) was added a suspension of $LiAlH_4$ (52 mg, 1.37 mmol) in $Et_2O$ (2 mL) at 0° C. and stirred for 45 min at the same temperature. The reaction mixture was quenched with saturated $KHSO_4$ aq. (5 mL) at 0° C. and stirred for 30 min at room temperature and extracted with $Et_2O$. The organic layer was dried with $MgSO_4$ and concentrated under reduced pressure to provide compound A122-6 (163 mg, 86%) as a colorless oil. The crude product was used for next step without purification.

Step 7: 2-(3,5-dichloropyridin-4-yl)-N-((4-methylbicyclo[2.2.1]heptan-1-yl)methyl)-2-((triethylsilyl)oxy)ethanamine (A122)

Compound A122 (177 mg, 80%) was obtained as a pale yellow oil from the reaction of compound A1-3 (160 mg, 0.50 mmol), compound A122-6 (82 mg, 0.59 mmol), $NaBH_4$ (120 mg) and $MgSO_4$ (200 mg) in MeOH (4 mL) and DCM (3 mL) using a similar procedure to that described in reference example A31, step 4. $^1H$ NMR ($CDCl_3$, 400 MHz): δ 8.42 (s, 2H), 5.50 (dd, J=8.7, J=4.6 Hz, 1H), 3.24 (dd, J=12.6, J=8.7 Hz, 1H), 2.78 (dd, J=12.6, J=4.6 Hz, 1H), 2.75 (d, J=11.7 Hz, 1H), 2.67 (d, J=11.7 Hz, 1H), 1.54-1.32 (m, 8H), 1.10-1.08 (m, 5H), 0.89 (t, J=8.0 Hz, 9H), 0.58-0.49 (m, 6H).

Reference Example A124

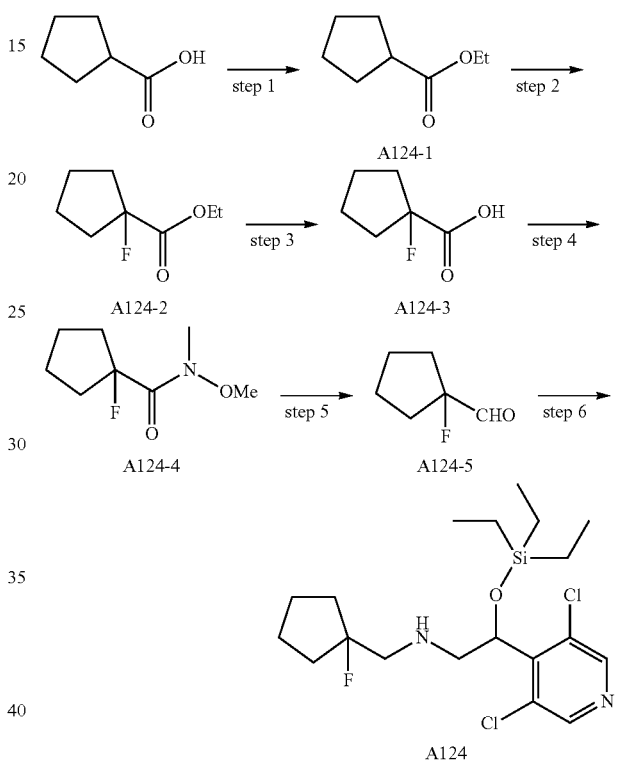

Step 1: ethyl cyclopentanecarboxylate (A124-1)

To a solution of cyclopentanecarboxylate (1.14 g, 10 mmol) in EtOH (5 mL) was added $H_2SO_4$ (0.1 mL) at room temperature. The mixture was allowed to warm to 80° C. and stirred at the same temperature for 3.5 h. The reaction mixture was cooled down to room temperature and poured into saturated $NaHCO_3$ aq. (40 mL). The mixture was stirred at room temperature for 30 min and extracted with EtOAc. The organic layer was dried over $MgSO_4$ and concentrated under reduced pressure to provide compound A124-1 (1.01 g, 71%) as a pale yellow oil. The crude product was used for next step without purification.

Step 2: ethyl 1-fluorocyclopentanecarboxylate (A124-2)

n-BuLi (2.6 M in hexane, 4.0 mL, 10.5 mmoL) was added dropwisely to a solution of diisopropylamine (1.55 mL, 11 mmol) in THF (40 mL) at −78° C. and stirred for 30 min at the same temperature. A solution of compound A124-1 (1.00 g, 7 mmol) in THF (10 mL) was added to the mixture and the mixture was stirred for 50 min at the same temperature. The reaction mixture was allowed to warm to 0° C. for 1 h. A solution of N-fluoro-N-(phenylsulfonyl)benzenesulfonamide (3.47 g, 10 mmol) in THF (10 mL) was added to the mixture and the mixture was stirred for 1 h at the same temperature. The reaction mixture was allowed to warm to room temperature for overnight. The reaction was quenched with saturated NH₄Cl aq. and extracted with EtOAc. The collected organic layer was concentrated under reduced pressure. The residue was purified by silicagel chromatography (10% EtOAc/hexane as eluent) to provide compound A124-2 (911 m g, 81%) as a yellow oil.

Step 3: 1-fluorocyclopentanecarboxylic acid (A124-3)

To a stirred solution of compound A124-2 (910 mg, 5.68 mmol) in EtOH/THF/water (7 mL, 4:2:1) was added a solution of LiOH aq. (4 M, 3 mL, 12 mmol). The mixture was stirred at room temperature for 2.5 h. The organic solvent was removed under reduced pressure. The residue was acidified with 2 M aqueous HCl to pH 1 and extracted with EtOAc. The organic layer was dried over MgSO₄ and concentrated under reduced pressure to provide compound A124-3 (709 mg, 95%) as a brown oil. The crude product was used for next step without purification.

Step 4: 1-fluoro-N-methoxy-N-methylcyclopentanecarboxamide (A124-4)

To a mixture of compound A124-3 (709 mg, 5.37 mmol), 1-hydroxybenzotrizole (986 mg, 6.44 mmol), 1-(3-dimethylaminopropyl)-3-ethylcarbodiimide hydrochloride (1.0 g, 6.44 mmol) and N,O-dimethylhydroxylamine hydrochloride (628 mg, 6.44 mmol) in DMF (10 mL) was added triethylamine (1.12 mL, 8.05 mmol) and the mixture was stirred at room temperature for overnight. The reaction mixture was quenched with 2 M aqueous HCl (30 mL) and extracted with EtOAc. The collected organic layer washed with water, brine, dried over MgSO₄ and concentrated under reduced pressure. The residue was purified by silicagel chromatography (20% EtOAc/hexane as eluent) to provide compound A124-4 (543 mg, 58%) as a yellow oil.

Step 5: 1-fluorocyclopentanecarbaldehyde (A124-5)

To a solution of compound A124-4 (140 mg, 0.8 mmol) in Et₂O (20 mL) was added LiAlH₄ (33 mg, 0.88 mmol) at 0° C. and stirred for 5 h at the same temperature. The reaction mixture was quenched with saturated KHSO₄ aq. (5 mL) at 0° C. and extracted with Et₂O. The combined organic layer was dried over MgSO₄ and concentrated under reduced pressure to provide compound A124-5. The crude product was used for next step without purification.

Step 6: 2-(3,5-dichloropyridin-4-yl)-N-((1-fluorocyclopentyl)methyl)-2-((triethylsilyl)oxy)ethanamine (A124)

Compound A124 (207 mg, 68%) was obtained from the reaction of compound A1-3 (233 mg, 0.73 mmol), compound A124-5 (93 mg, 0.8 mmol), NaBH(OAc)₃ (231 mg, 1.09 mmol), MgSO₄ (93 mg) and AcOH (0.042 mL, 0.73 mmol) in DCM (2 mL) using a similar procedure to that described in reference example A31, step 4. ¹H NMR (CDCl₃, 400 MHz): δ 8.43 (s, 2H), 5.49 (dd, J=8.5, J=4.5 Hz, 1H), 3.26 (dd, J=12.6, J=8.5 Hz, 1H), 2.87 (d, J=21.0 Hz, 2H), 2.83 (dd, J=12.6, J=4.5 Hz, 1H), 1.93-1.60 (m, 8H), 0.88 (t, J=7.8 Hz, 9H), 0.60-0.49 (m, 6H).

Reference Example A141

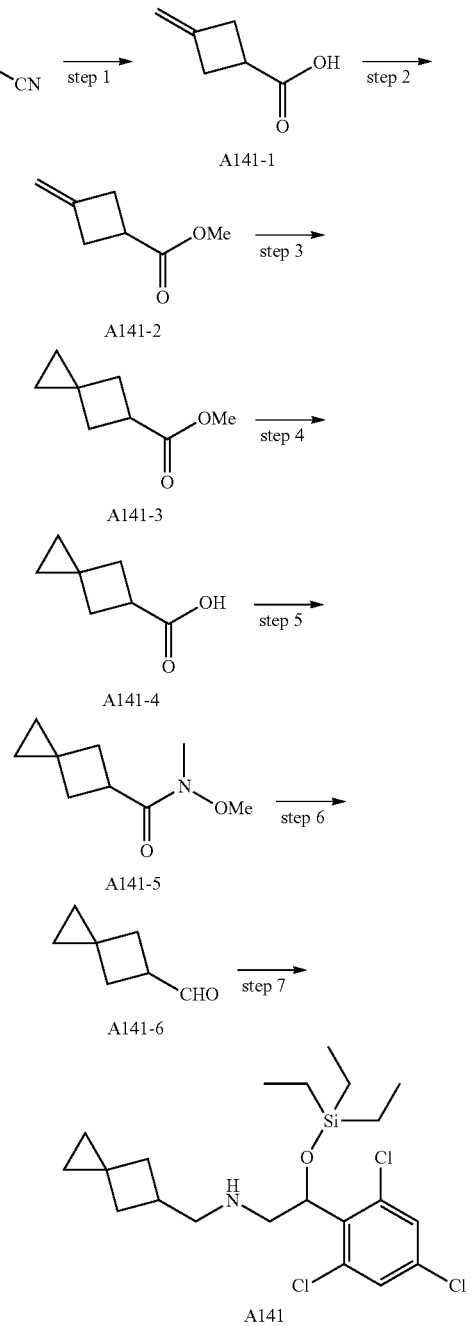

Step 1: 3-methylenecyclobutanecarboxylic acid (A141-1)

To a stirred solution of KOH (10 g, 178 mmol) in water (15 mL) and EtOH (15 mL) was added 3-methylenecyclobutanecarbonitrile (3.92 g, 42 mmol) at room temperature for 10 min. The mixture was allowed to warm to 90° C. and stirred at the same temperature for 3.5 h. The reaction mixture was concentrated under reduced pressure. The residue was dissolved in water (10 mL) at 0° C. The mixture was acidified with 6 M aqueous HCl to pH 1 and extracted with DCM. The organic layer was dried over MgSO$_4$ and concentrated under reduced pressure to provide compound A141-1 (4.65 g, 98%) as a colorless oil. The product was used for next step without further purification.

Step 2: methyl 3-methylenecyclobutanecarboxylate (A141-2)

Trimethylsilyldiazomethane (2.0 M in hexane, 25 mL, 50 mmol) was added to a stirred solution of compound A141-1 (4.64 g, 41.4 mmol) in DCM (25 mL) and MeOH (5 mL) dropwise at 0° C. for 5 min. The mixture was allowed to warm to room temperature and stirred at the same temperature for 30 min. The reaction mixture was quenched with AcOH (0.45 mL) and concentrated under reduced pressure. The residue was purified by silicagel chromatography (20% DCM/hexane as eluent) to provide compound A141-2 (3.8 g, 73%) as a colorless oil.

Step 3: methyl spiro[2.3]hexane-5-carboxylate (A141-3)

To a solution of diethylzinc (1.0 M in hexane, 46 mL, 46 mmol) in DCM (200 mL) was added a solution of TFA (3.54 mL, 46 mmol) in DCM (50 mL) dropwise at 0° C. for 30 min. A solution of diiodomethane (3.7 mL, 46 mmol) in DCM (50 mL) was added dropwise at 0° C. for 45 min. The mixture was stirred at the same temperature for 1 h. A solution of compound A141-2 (2.52 g, 20 mmol) in DCM (30 mL) was added to the reaction mixture. The mixture was allowed to warm to room temperature for overnight. The reaction mixture was quenched with saturated NH$_4$Cl aq. (200 mL) and extracted with DCM. The collected organic layer was dried over MgSO$_4$ and concentrated under reduced pressure. The residue was purified by silicagel chromatography (20% EtOAc/hexane as eluent) to provide compound A141-3 (1.77 g, 63%) as a colorless oil.

Step 4: spiro[2.3]hexane-5-carboxylic acid (A141-4)

To a stirred solution of LiOH (4 M in water, 10 mL, 40 mmol) in water (10 mL) and MeOH (20 mL) was added compound A141-3 (1.76 g, 12.6 mmol) at room temperature. The mixture was stirred at room temperature for 40 min. The reaction mixture was concentrated under reduced pressure to ca. 20 mL of solution. The solution was acidified with 6 M aqueous HCl to pH 1 and extracted with DCM. The organic layer was dried over MgSO$_4$ and concentrated under reduced pressure to provide compound A141-4 (1.51 g, 95%) as a colorless oil. The product was used for next step without further purification.

Step 5: N-methoxy-N-methylspiro[2.3]hexane-5-carboxamide (A141-5)

To a mixture of compound A141-4 (1.51 mg, 12.0 mmol), 1-hydroxybenzotrizole monohydrate (2.30 g, 15 mmol), 1-(3-dimethylaminopropyl)-3-ethylcarbodiimide hydrochloride (2.33 g, 15 mmol) and N,O-dimethylhydroxylamine hydrochloride (1.46 g, 15 mmol) in DMF (20 mL) was added DIPEA (3.43 mL, 20 mmol) and the mixture was stirred at room temperature for overnight. The reaction mixture was quenched with water and extracted with hexane and EtOAc. The collected organic layer washed with 1 M HCl aq. (100 mL), water, saturated Na$_2$CO$_3$ aq. (2×100 mL), brine, dried over MgSO$_4$ and concentrated under reduced pressure. The residue was purified by silicagel chromatography (75% EtOAc/hexane as eluent) to provide compound A141-5 (1.72 g, 84%) as a colorless oil.

Step 6: spiro[2.3]hexane-5-carbaldehyde (A141-6)

To a solution of compound A141-5 (677 mg, 4 mmol) in Et$_2$O (15 mL) was added a suspension of LiAlH$_4$ (152 mg, 4 mmol) in Et$_2$O (5 mL) at 0° C. over 5 min and stirred for 2 h at the same temperature. The reaction mixture was quenched with saturated KHSO$_4$ aq. (10 mL) at 0° C. and extracted with Et$_2$O. The combined organic layer was dried with MgSO$_4$ and concentrated under reduced pressure to provide compound A141-6 (351 mg, 80%) as a colorless oil.

The crude product was used for next step without purification.

Step 7: 2-(2,4,6-trichlorophenyl)-N-(spiro[2.3]hexan-5-ylmethyl)-2-((triethylsilyl)oxy)ethanamine (A141)

Compound A141 (123 mg, 39%) was obtained as a pale yellow oil from the reaction of 2-(2,4,6-trichlorophenyl)-2-((triethylsilyl)oxy)ethanamine (248 mg, 0.7 mmol), compound A141-6 (100 mg, 0.91 mmol), NaBH$_4$ (212 mg) and MgSO$_4$ (100 mg) in MeOH (1.4 mL) and THF (3.5 mL) using a similar procedure to that described in reference example A31, step 4. $^1$H NMR (CDCl$_3$, 400 MHz): δ 7.29 (s, 2H), 5.53 (dd, J=9.0, J=4.6 Hz, 1H), 3.26 (dd, J=12.2, J=8.8 Hz, 1H), 2.85-2.71 (m, 3H), 2.62-2.51 (m, 1H), 2.17-2.10 (m, 2H), 1.86-1.81 (m, 2H), 0.87 (t, J=7.8 Hz, 9H), 0.57-0.50 (m, 6H), 0.43-0.33 (m, 4H).

Reference Example A194

1-(2,6-dichloro-3-fluorophenyl)-2-(((1-(trifluoromethyl)cyclopropyl)methyl)amino)ethanol

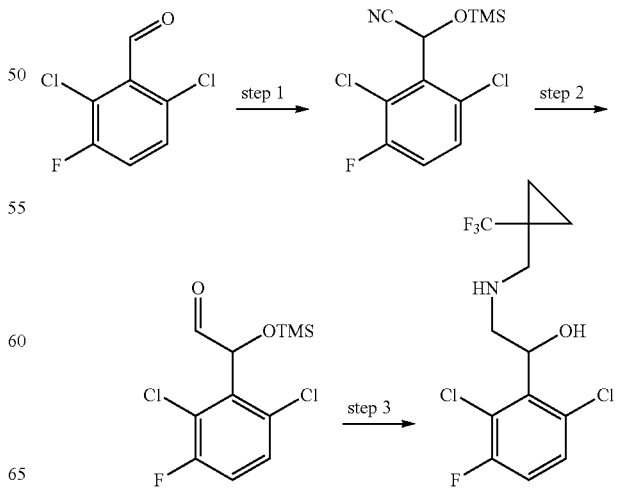

Step 1: 2-(2,6-dichloro-3-fluorophenyl)-2-((trimethylsilyl)oxy)acetonitrile

To a 200 ml RBF was charged with solution of 2,6-dichloro-3-fluorobenzaldehyde (2.29 g, 11.87 mmol), DCM (23 ml), TMSCN (1.9 ml, 14.24 mmol), and zinc iodide (0.379 g, 1.187 mmol) was added. The mixture was stirred at room temperature for 4 h. Then the mixture washed with water (2×20 ml) and brine. Organic layer was concentrated under reduced pressure. The crude material was purified by column chromatography (silica gel, eluent: 0% to 30% EtOAc/heptane) to provide 2-(2,6-dichloro-3-fluorophenyl)-2-((trimethylsilyl)oxy)acetonitrile (1.435 g, 4.91 mmol, 41.4% yield) as colorless oil. $^1$H NMR (400 MHz, CDCl$_3$) δ 7.32-7.42 (m, 1H); 7.12-7.24 (m, 1H); 6.17-6.30 (m, 1H); 0.12-0.33 (m, 9H).

Step 2: 2-(2,6-dichloro-3-fluorophenyl)-2-((trimethylsilyl)oxy)acetaldehyde

To a 100 mL three-necked RBF were added 2-(2,6-dichloro-3-fluorophenyl)-2-((trimethylsilyl)oxy)acetonitrile (0.50 g, 1.711 mmol) and DCM (9 ml). The reaction mixture was purged with nitrogen and cooled to −64° C. Under a nitrogen atmosphere, diisobutylaluminum hydride, 1.0 M solution in hexane (2.6 ml, 2.6 mmol) was added dropwise. The mixture was stirred at −64° C. After 2 h, the reaction was quenched. While maintaining temp <−65° C., MeOH (1.4 ml, 34.2 mmol) was carefully added dropwise to the reaction mixture followed by saturated Rochelle salt solution (5 mL). The mixture was allowed to reach room temperature and stirred for 30 min. Water and DCM were added and the aqueous layer was extracted with DCM. The combined organic layer washed with brine, dried over anhydrous MgSO$_4$, and concentrated to afford 2-(2,6-dichloro-3-fluorophenyl)-2-((trimethylsilyl)oxy)acetaldehyde as a colorless oil (0.517 g, crude).

Step 3: 1-(2,6-dichloro-3-fluorophenyl)-2-(((1-(trifluoromethyl)cyclopropyl)methyl)amino)ethanol To a solution of crude 2-(2,6-dichloro-3-fluorophenyl)-2-((trimethylsilyl)oxy)acetaldehyde (0.258 g, 0.874 mmol) in MeCN (9 ml) was added (1-(trifluoromethyl)cyclopropyl)methanamine (0.122 g, 0.874 mmol) followed by AcOH (0.050 ml, 0.874 mmol). The reaction mixture was stirred at room temperature for 1 h. Then NaBH(OAc)$_3$ (0.370 g, 1.748 mmol) was added. The reaction mixture was stirred at room temperature for 23 h. Then it was quenched by adding saturated aqueous NaHCO$_3$ solution and stirred for 30 min. It was extracted with DCM (2×5 mL). The combined organic layer washed with brine, dried over anhydrous MgSO$_4$, and concentrated under reduced pressure to provide a yellow oil. The yellow oil was dissolved in 2 mL of THF. Then TBAF, 1.0 M solution in THF (0.874 ml, 0.874 mmol) was added. The reaction mixture was stirred at room temperature for 15 min. It was quenched with saturated aqueous NaHCO$_3$ and extracted with DCM. The combined organic layer was dried over anhydrous MgSO$_4$ and concentrated under reduced pressure. The crude material was purified by column chromatography (silica gel, eluent: 0% to 50% EtOAc/heptane) to provide 1-(2,6-dichloro-3-fluorophenyl)-2-(((1-(trifluoromethyl)cyclopropyl)methyl)amino)ethanol (116 mg, 0.335 mmol, 38.3% yield) as a yellow oil. $^1$H NMR (400 MHz, CDCl$_3$) δ 7.25-7.31 (m, 1H), 7.06 (dd, J=8.9, 8.0 Hz, 1H), 5.45 (dd, J=9.7, 4.5 Hz, 1H), 3.45 (br. s., 1H), 3.28 (dd, J=12.6, 9.8 Hz, 1H), 2.89-2.92 (m, 3H), 0.99-1.04 (m, 2H), 0.69-0.76 (m, 2H); LCMS: 346.0 [M+H]$^+$.

Reference Example A224

2-(2,6-dichloro-4-fluorophenyl)-N-((1-methylcyclopropyl)methyl)-2-((triethylsilyl)oxy)ethanamine

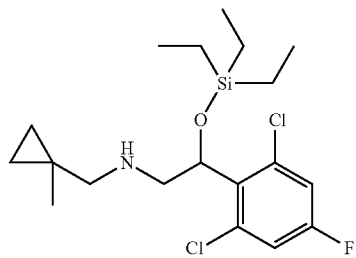 [SMILES: CC[Si](CC)(CC)OC(CNCC1(C)CC1)c1c(Cl)cc(F)cc1Cl]

A mixture of 1-methylcyclopropanecarbaldehyde (31.6 mg, 0.375 mmol) and 2-(2,6-dichloro-4-fluorophenyl)-2-((triethylsilyl)oxy)ethanamine (127 mg, 0.375 mmol) in MeOH (1.9 ml) was stirred at room temperature for 3 h. NaBH$_4$ (14.20 mg, 0.375 mmol) was added in portions and the mixture was stirred at room temperature for 40 min. The mixture was concentrated and purified by prep TLC eluted with 5% MeOH/DCM to provide 2-(2,6-dichloro-4-fluorophenyl)-N-((1-methylcyclopropyl)methyl)-2-((triethylsilyl)oxy)ethanamine (111 mg, 0.273 mmol, 72.8% yield). $^1$H NMR (500 MHz, CDCl$_3$) δ 7.29 (s, 1H), 7.06-7.10 (m, 2H), 5.56 (br. s., 1H), 3.33 (t, J=10.51 Hz, 1H), 2.81 (d, J=9.17 Hz, 1H), 2.60-2.67 (m, 1H), 2.44 (d, J=11.86 Hz, 1H), 1.46-1.59 (m, 1H), 1.13 (s, 3H), 0.85-0.96 (m, 9H), 0.50-0.63 (m, 6H), 0.36 (br. s., 2H), 0.30 (br. s., 2H); LCMS (ESI) m/z 406.0 (M+H)$^+$.

Reference Example A258

2-(2,6-dichlorophenyl)-N-((1-methylcyclopropyl)methyl)-2-((triethylsilyl)oxy)ethanamine

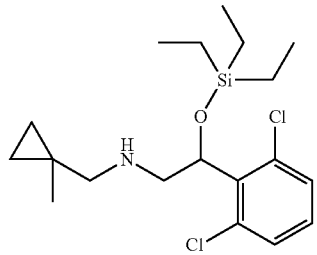 [SMILES: CC[Si](CC)(CC)OC(CNCC1(C)CC1)c1c(Cl)cccc1Cl]

To a mixture of 1-methylcyclopropanecarbaldehyde (32.8 mg, 0.390 mmol) in DCM (2.0 ml) was added 2-(2,6-dichlorophenyl)-2-((triethylsilyl)oxy)ethanamine (125 mg, 0.390 mmol) followed by NaBH(OAc)$_3$ (124 mg, 0.585 mmol). After 45 min, this was quenched with sat. aq. NaHCO$_3$. The layers were separated. The aqueous layer was extracted with DCM. The combined organic layers were concentrated then purified by prep TLC eluted with 5% MeOH/DCM to provide 2-(2,6-dichlorophenyl)-N-((1-methylcyclopropyl)methyl)-2-((triethylsilyl)oxy)ethanamine (95 mg, 0.245 mmol, 62.7% yield). 1H NMR (500 MHz, CDCl$_3$) δ 7.28-7.30 (m, 2H), 7.12-7.16 (m, 1H), 5.65 (br. s., 1H), 3.37-3.44 (m, 1H), 2.82-2.90 (m, 1H), 2.69 (br. s., 1H), 2.48 (d, J=11.86 Hz, 1H), 1.60 (br. s., 1H), 1.15 (s, 3H), 0.87-0.92 (m, 9H), 0.51-0.63 (m, 6H), 0.28-0.44 (m, 4H); LCMS (ESI) m/z 388.3 (M+H)+.

Reference Example A259

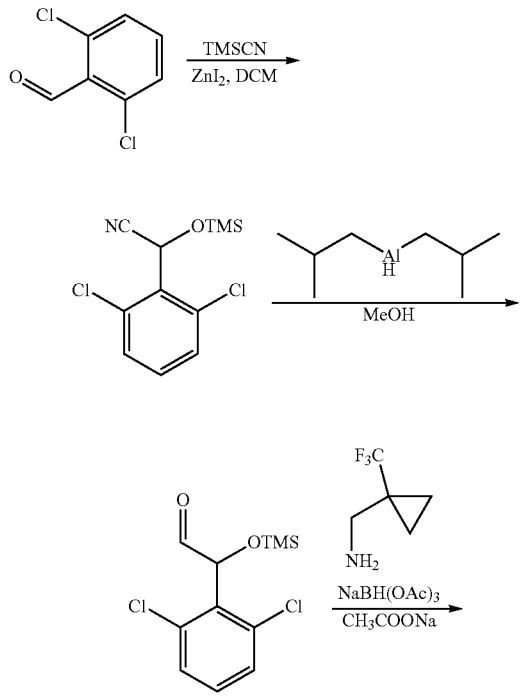

Step 1: 2-(2,6-dichlorophenyl)-2-((trimethylsilyl)oxy)acetonitrile

A 100 ml RBF was charged with solution of 2,6-dichlorobenzaldehyde (5.08 g, 29.0 mmol) and TMSCN (4.64 ml, 34.8 mmol) in DCM (60 ml). Zinc iodide (0.926 g, 2.90 mmol) was added and the mixture was stirred at ambient temperature for 3 h. Reaction mixture was diluted with DCM (200 mL). The organic layer washed with water (2×20 mL) and brine (20 mL), organic layer was filtered through celite and concentrated. The residue was purified by flash chromatography on 100 g Biotage SNAP cartridge using 0-40% EtOAc in heptane to afford 2-(2,6-dichlorophenyl)-2-((trimethylsilyl)oxy)acetonitrile (3.01 g, 38%).

Step 2: 2-(2,6-dichlorophenyl)-2-((trimethylsilyl)oxy)acetaldehyde

To a solution of 2-(2,6-dichlorophenyl)-2-((trimethylsilyl)oxy)acetonitrile (1.372 g, 5.00 mmol) in DCM (23.16 ml), diisobutylaluminum hydride 1.0 M solution in hexane (7.50 ml, 7.50 mmol) was added at −78° C. dropwise over 20 min. Reaction was carefully quenched first with MeOH (1 ml, 24.97 mmol) and then with Rochelle salt 1.5 M (5.00 ml, 7.50 mmol). The flask was removed from the bath and allowed to reach ambient temperature and extracted with EtOAc (20 ml). The organic layer was separated and washed with brine, filtered through celite pad and concentrated to obtain 2-(2,6-dichlorophenyl)-2-((trimethylsilyl)oxy)acetaldehyde (1.34 g, 97%) as a white solid.

Step 3: 2-(2,6-dichlorophenyl)-N-((1-(trifluoromethyl)cyclopropyl)methyl)-2-((trimethylsilyl)oxy)ethanamine To a solution of crude 2-(2,6-dichlorophenyl)-2-((trimethylsilyl)oxy)acetaldehyde (0.35 g, 1.263 mmol) in DCM (6.31 ml) was added (1-(trifluoromethyl)cyclopropyl)methanamine (0.176 g, 1.263 mmol) and NaBH(OAc)₃ (0.374 ml, 2.53 mmol) and stirred for 2 h at ambient temperature. The reaction was quenched with aqueous sat NH₄Cl solution and diluted with DCM (50 mL). Organic layer was passed through phase separator and concentrated to obtain 2-(2,6-dichlorophenyl)-N-((1-(trifluoromethyl)cyclopropyl)methyl)-2-((trimethylsilyl)oxy)ethanamine (0.378 g, 70%) as light yellow oil. This was used in next step without further purification.

Reference Example A260

2-(2,6-dichlorophenyl)-N-((1-methylcyclobutyl)methyl)-2-((triethylsilyl)oxy)ethanamine

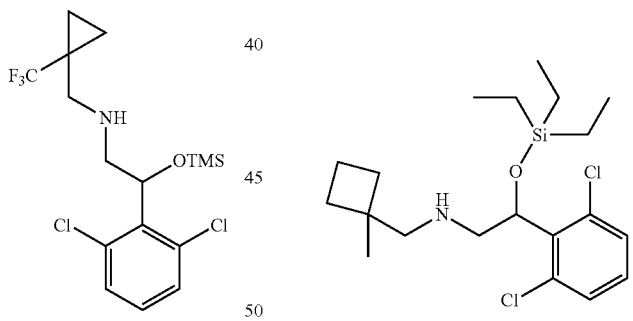

To a mixture of 1-methylcyclobutanecarbaldehyde (38.3 mg, 0.390 mmol) in DCM (2.0 ml) was added 2-(2,6-dichlorophenyl)-2-((triethylsilyl)oxy)ethanamine (125 mg, 0.390 mmol) followed by NaBH(OAc)₃ (124 mg, 0.585 mmol). After 45 min, this was quenched with sat. aq. NaHCO₃. The layers were separated. The aqueous layer was extracted with DCM. The combined organic layers were concentrated and then purified by prep TLC eluted with 5% MeOH/DCM to provide 2-(2,6-dichlorophenyl)-N-((1-methylcyclobutyl)methyl)-2-((triethylsilyl)oxy)ethanamine (89 mg, 0.221 mmol, 56.7% yield). ¹H NMR (500 MHz, CDCl₃) δ 7.18-7.22 (m, 2H), 6.98-7.10 (m, 1H), 5.57 (br. s., 1H), 3.30 (t, J=10.70 Hz, 1H), 2.74 (br. s., 1H), 2.60 (br. s., 1H), 2.51 (d, J=10.03 Hz, 1H), 1.68-1.89 (m, 4H), 1.60 (br. s., 2H), 1.47 (br. s., 1H), 1.03-1.14 (m, 3H), 0.76-0.84 (m, 9H), 0.41-0.54 (m, 6H); LCMS (ESI) m/z 402.4 (M+H)+.

Reference Example A262

2-(2,6-dichlorophenyl)-N-((5-fluorospiro[2.3]hexan-5-yl)methyl)-2-((triethylsilyl)oxy)ethanamine

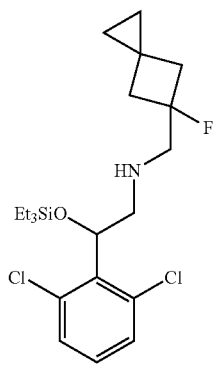

Spiro[2.3]hexane-5-carbaldehyde (300 mg, 2.72 mmol) and N-ethyl-N-isopropylpropan-2-amine (546 µl, 3.13 mmol) were combined in MeCN (5 mL) and trimethylsilyl trifluoromethanesulfonate (517 µl, 2.86 mmol) was added dropwise. The solution was stirred for 30 min and selectfluor (1061 mg, 3.00 mmol) in MeCN (5 mL) was added. The solution was stirred and sonicated for an additional 30 min. 2-(2,6-dichlorophenyl)-2-((triethylsilyl)oxy)ethanamine (785 mg, 2.451 mmol) and AcOH (187 µl, 3.27 mmol) were added. The solution was stirred for 30 min and NaBH(OAc)$_3$ (1154 mg, 5.45 mmol) was added and the solution was stirred for an additional 2 h. The solution was quenched with saturated NaHCO$_3$, the aqueous layer was extracted with ethyl acetate and the combined organic layers were washed with brine and dried over anhydrous Na$_2$SO$_4$, filtered and concentrated. The product was purified via silica gel column chromatography (40 g column) using 0-100% EtOAc in heptane to afford 2-(2,6-dichlorophenyl)-N-((5-fluorospiro[2.3]hexan-5-yl)methyl)-2-((triethylsilyl)oxy)ethanamine (300 mg, 0.694 mmol, 25.5% yield). MS m/z=432 [M+H]$^+$.

Reference Example A267

2-(2,6-dichlorophenyl)-N-(spiro[2.5]octan-6-ylmethyl)-2-((triethylsilyl)oxy)ethanamine

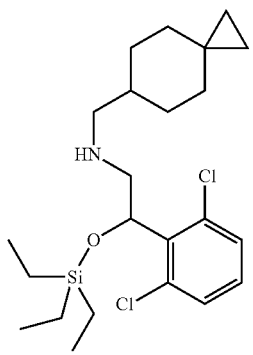 [SMILES: CC[Si](CC)(CC)OC(CNCC1CCC2(CC1)CC2)c1c(Cl)cccc1Cl]

To a solution of 2-(2,6-dichlorophenyl)-2-((triethylsilyl)oxy)ethanamine (248 mg, 0.774 mmol) in DCM (2581 µl) was added spiro[2.5]octane-6-carbaldehyde (107 mg, 0.774 mmol), AcOH (35.5 µl, 0.619 mmol) and NaBH(OAc)$_3$ (246 mg, 1.161 mmol). The slurry mixture was stirred at room temperature for overnight. The mixture was quenched with 0.5 M NaOH and mixture was stirred at rt for 30 min. Evolution of gas was observed. The layers were separated. The organic layer was dried over Na$_2$SO$_4$ and concentrated. The residue was purified by silica gel column chromatography eluting with a gradient of 0% to 100% EtOAc in hexane to give 2-(2,6-dichlorophenyl)-N-(spiro[2.5]octan-6-ylmethyl)-2-((triethylsilyl)oxy)ethanamine Reference Example A275

N-(2-(3-chloroquinolin-4-yl)-2-((triethylsilyl)oxy)ethyl)-2,2-dimethylpropan-1-amine

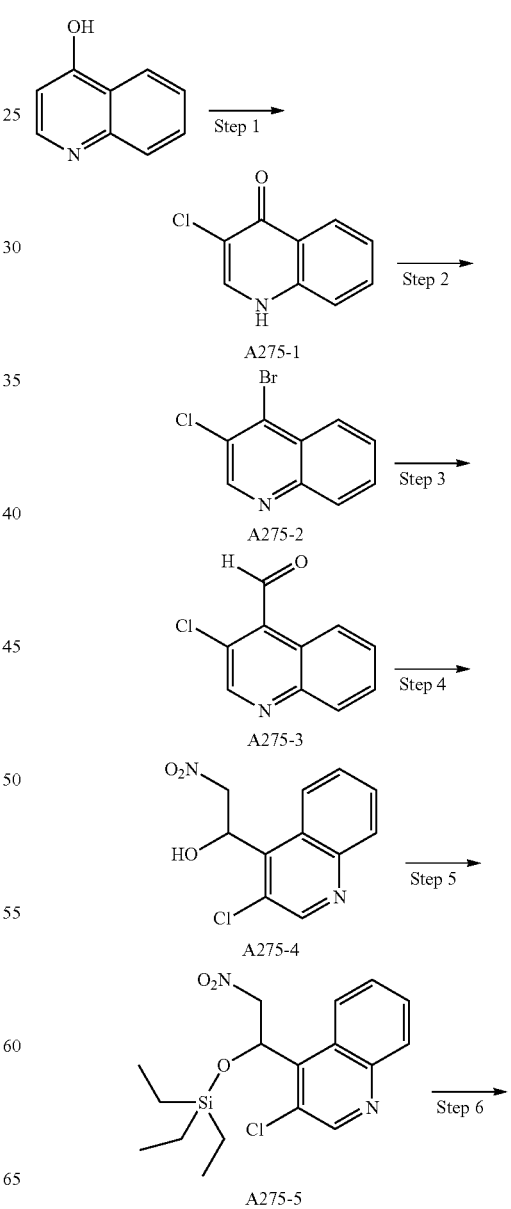

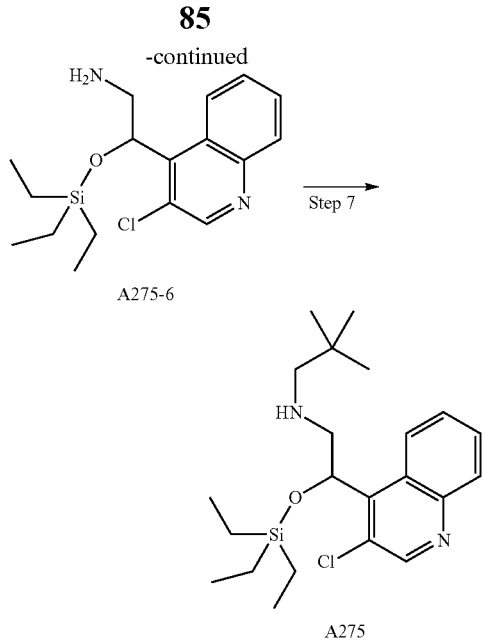

Step 1: 3-chloroquinolin-4(1H)-one (A275-1)

A mixture of 4-hydroxyquinoline (5.33 g, 36.7 mmol) in AcOH (184 mL) was treated with N-chlorosuccinimide (6.37 g, 47.7 mmol) and the yellow homogeneous mixture was stirred and heated at 60° C. After 3 h, the mixture was cooled to room temperature and concentrated in vacuo. Saturated aqueous NaHCO$_3$ solution (300 mL) was added until pH became ~8.5. The resulting solid was collected by filtration, washed with water (300 mL), and dried under high vacuum to give 3-chloroquinolin-4(1H)-one (A275-1) as a yellow solid. $^1$H NMR (400 MHz, DMSO-d$_6$) δ 12.28 (1H, br. s.), 8.40 (1H, d, J=6.5 Hz), 8.15 (1H, dd, J=8.2, 1.4 Hz), 7.65-7.73 (1H, m), 7.58-7.63 (1H, m), 7.39 (1H, ddd, J=8.1, 6.9, 1.2 Hz); LCMS (ESI) m/z 180.1 (M+H)$^+$.

Step 2: 4-bromo-3-chloroquinoline (A275-2)

To a cooled suspension of 3-chloroquinolin-4(1H)-one (A275-1) (5.15 g, 28.7 mmol) in DMF (43.4 mL) at 0° C. was added phosphorous tribromide (2.77 mL, 29.5 mmol) dropwise over 3 min and then the mixture became orange homogenous mixture. After 4 min, yellow precipitates were formed and the yellow heterogeneous mixture was further stirred at 0° C. for 15 min. After 15 min, the cooling bath was removed and the yellow heterogeneous mixture was stirred at room temperature. After 15 h, the mixture was poured into ice water (300 mL) and stirred at 0° C. for 20 min. The mixture was then neutralized by the addition of 2 M NaOH solution (50 mL) until pH was >9 (pH paper). The resulting precipitate was collected by filtration, washed the solid with water (400 mL), and dried under high vacuum to give 4-bromo-3-chloroquinoline (A275-2) as off-white solid. $^1$H NMR (400 MHz, DMSO-d$_6$) δ 8.96 (1H, s), 8.20 (1H, dd, J=8.2, 1.6 Hz), 8.12 (1H, dd, J=8.3, 0.9 Hz), 7.81-7.93 (2H, m); LCMS (ESI) m/z 242.0 [M+H (79Br)]$^+$ and 243.9 [M+H (81Br)]$^+$.

Step 3: 3-chloroquinoline-4-carbaldehyde (A275-3)

A flask was charged with 4-bromo-3-chloroquinoline (A275-2) (1.00 g, 4.12 mmol) and THF (16.5 mL) under nitrogen, and the solution was cooled to –78° C. To the cooled mixture was added n-butyllithium (2.5 M solution in hexane, 1.65 mL, 4.12 mmol) and the mixture was stirred at –78° C. for 1 hour. To the mixture was added DMF (1.60 mL, 20.6 mmol) dropwise, and the mixture was allowed to warm to room temperature. After 4 h, the mixture was quenched with saturated aqueous NH$_4$Cl (20 mL). The mixture was partitioned between water (50 mL) and EtOAc (50 mL). The aqueous layer was extracted with EtOAc (1×50 mL). The organic extract was dried over MgSO$_4$. The solution was filtered and concentrated in vacuo to give the crude material as a brown syrup. The crude material was absorbed onto a plug of silica gel and purified by chromatography through a REDISEP™ pre-packed silica gel column (80 g), eluting with a gradient of 0% to 20% EtOAc in hexane, and dried under high vacuum to give 3-chloroquinoline-4-carbaldehyde (A275-3) as brown solid. $^1$H NMR (400 MHz, DMSO-d$_6$) δ 10.74 (1H, s), 9.10 (1H, s), 8.68-8.73 (1H, m), 8.15 (1H, dd, J=8.5, 0.9 Hz), 7.79-7.92 (2H, m); LCMS (ESI) m/z 192.1 (M+H)$^+$.

Steps 4: 1-(3-chloroquinolin-4-yl)-2-nitroethanol (A275-4)

To a brown clear solution of 3-chloroquinoline-4-carbaldehyde (A275-3) (0.362 g, 1.89 mmol) in THF (1.9 mL) at room temperature was added potassium carbonate (0.078 g, 0.566 mmol) and nitromethane (1.420 mL, 26.4 mmol). The brown homogeneous mixture was stirred at room temperature. After 4 h, the reaction mixture was quenched with water (50 mL) and extracted with EtOAc (2×50 mL). The organic extract washed with saturated NaCl (1×50 mL), and dried over Na$_2$SO$_4$. The solution was filtered, concentrated in vacuo, and dried under high vacuum to give 1-(3-chloroquinolin-4-yl)-2-nitroethanol (A275-4) as a brown solid. $^1$H NMR (400 MHz, DMSO-d$_6$) δ 8.88-8.93 (1H, m), 8.73 (1H, dd, J=8.6, 0.8 Hz), 8.08 (1H, dd, J=8.4, 1.0 Hz), 7.82 (1H, ddd, J=8.4, 6.9, 1.5 Hz), 7.72 (1H, ddd, J=8.5, 6.9, 1.4 Hz), 6.91 (1H, dd, J=4.5, 1.0 Hz), 6.26 (1H, ddd, J=10.0, 4.6, 3.6 Hz), 5.03-5.12 (1H, m), 4.94-5.01 (1H, m); LC-MS (ESI) m/z 253.1 (M+H)$^+$.

Step 5: 3-chloro-4-(2-nitro-1-((triethylsilyl)oxy)ethyl)quinoline (A275-5)

To a brown clear solution of 1-(3-chloroquinolin-4-yl)-2-nitroethanol (A275-4) (0.423 g, 1.68 mmol) in DMF (4.19 mL) at room temperature was added imidazole (0.342 g, 5.03 mmol) and triethylsilyl chloride (0.341 mL, 2.01 mmol). The mixture was stirred at room temperature. After 2 h, the mixture was quenched with water (50 mL) and extracted with EtOAc (2×50 mL). The organic extract washed with 1 M LiCl (1×50 mL) and brine (1×50 mL), and dried over Na$_2$SO$_4$. The solution was filtered and concentrated in vacuo to give the crude material as a yellow syrup. The crude material was absorbed onto a plug of silica gel and purified by chromatography through a REDISEP pre-packed silica gel column (40 g), eluting with a gradient of 0% to 10% EtOAc in hexane, and dried under high vacuum to give 3-chloro-4-(2-nitro-1-((triethylsilyl)oxy)ethyl)quinoline (A275-5). $^1$H NMR (400 MHz, DMSO-d$_6$) δ 8.95 (1H, s), 8.67 (1H, d, J=7.4 Hz), 8.10 (1H, dd, J=8.4, 0.8 Hz), 7.84 (1H, td, J=7.6, 1.4 Hz), 7.71-7.79 (1H, m), 6.38 (1H, dd, J=9.8, 2.5 Hz), 5.14-5.23 (1H, m), 5.03-5.11 (1H, m), 0.65-0.74 (9H, m), 0.32-0.51 (6H, m); LCMS (ESI) m/z 367.1 (M+H)$^+$.

Step 6: 2-(3-chloroquinolin-4-yl)-2-((triethylsilyl)oxy)ethanamine (A275-6)

To a clear yellow solution of 3-chloro-4-(2-nitro-1-((triethylsilyl)oxy)ethyl)quinoline (0.511 g, 1.39 mmol) in EtOH (7.96 mL) and water (1.99 mL) at room temperature was added iron powder (0.778 g, 13.9 mmol) and ammonium chloride (0.745 g, 13.9 mmol). The dark brown mixture was stirred and heated at 60° C. After 4 h, the mixture was cooled to room temperature and filtered through a celite pad and washed the pad with MeOH (3×30 mL). The combined filtrates were concentrated in vacuo. The residue was partitioned between EtOAc (100 mL) and water (50 mL). The mixture (pH ~4.0) washed with saturated aqueous NaHCO$_3$ (1×50 mL), water (1×50 mL), and brine (1×50 mL), dried over anhydrous Na$_2$SO$_4$, concentrated in vacuo, and dried under high vacuum to give 2-(3-chloroquinolin-4-yl)-2-((triethylsilyl)oxy)ethanamine (A275-6) as a yellow syrup. $^1$H NMR (400 MHz, DMSO-d$_6$) δ 8.84 (1H, s), 8.72 (1H, d, J=8.2 Hz), 8.04 (1H, dd, J=8.4, 1.0 Hz), 7.76 (1H, ddd, J=8.4, 6.9, 1.4 Hz), 7.64 (1H, ddd, J=8.5, 7.0, 1.3 Hz), 5.52 (1H, dd, J=7.6, 5.5 Hz), 3.16 (1H, dd, J=13.0, 7.9 Hz), 2.88 (1H, dd, J=13.0, 5.4 Hz), 1.74 (1H, br. s.), 0.71-0.80 (1H, m), 0.71-0.80 (9H, m), 0.37-0.57 (6H, m); LCMS (ESI) m/z 337.1 (M+H)$^+$.

Step 7: N-(2-(3-chloroquinolin-4-yl)-2-((triethylsilyl)oxy)ethyl)-2,2-dimethylpropan-1-amine (A275)

To a yellow clear solution of 2-(3-chloroquinolin-4-yl)-2-((triethylsilyl)oxy)ethanamine (A275-6) (0.217 g, 0.644 mmol) in DCM (2.15 mL) was added trimethylacetaldehyde (0.077 mL, 0.71 mmol), AcOH (0.045 mL, 0.77 mmol), and NaBH(OAc)$_3$ (0.205 g, 0.966 mmol). The yellow homogeneous mixture was stirred at room temperature. After 2 h, the mixture was quenched with water (20 mL) and neutralized with 0.5 M NaOH (10 mL) to pH ~9.0. The reaction mixture was extracted with DCM (2×50 mL). The organic extract washed with saturated NaCl (1×50 mL) and dried over Na$_2$SO$_4$. The solution was filtered and concentrated in vacuo to give the crude material as a yellow syrup. The crude material was absorbed onto a plug of silica gel and purified by chromatography through a REDISEP™ pre-packed silica gel column (40 g), eluting with a gradient of 0% to 20% EtOAc in hexane, and dried under high vacuum to give N-(2-(3-chloroquinolin-4-yl)-2-((triethylsilyl)oxy)ethyl)-2,2-dimethylpropan-1-amine (A275) as colorless syrup. $^1$H NMR (400 MHz, DMSO-d$_6$) δ 8.84 (1H, s), 8.75 (1H, d, J=7.2 Hz), 8.04 (1H, dd, J=8.4, 1.0 Hz), 7.77 (1H, ddd, J=8.4, 6.9, 1.4 Hz), 7.61-7.68 (1H, m), 5.70 (1H, dd, J=7.7, 5.0 Hz), 3.26 (1H, dd, J=12.6, 8.1 Hz), 2.85 (1H, dd, J=12.6, 5.0 Hz), 2.23-2.39 (2H, m), 1.72 (1H, br. s.), 0.81 (9H, s), 0.72-0.79 (9H, m), 0.36-0.56 (6H, m); LCMS (ESI) m/z 407.1 (M+H)$^+$.

Reference Example A281

2-(3,5-dichloropyridin-4-yl)-N-((5-methyltetrahydrofuran-2-yl)methyl)-2-((triethylsilyl)oxy)ethanamine

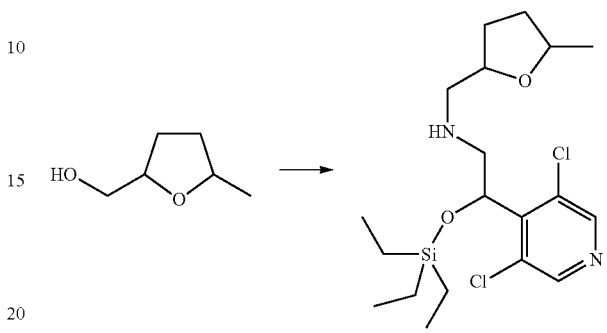

To a clear solution of 5-methyltetrahydrofuran-2-methanol in DCM was added Dess-Martin periodinane (1.2 eq.). The mixture was stirred at room temperature overnight. The crude mixture was directly added to a solution of 2-(3,5-dichloropyridin-4-yl)-2-((triethylsilyl)oxy)ethanamine (1 eq.) in DCM followed by AcOH (1.2 eq.) and NaBH(OAc)$_3$ (1.5 eq.). The reaction mixture was stirred at room temperature. After 2 h, the mixture was quenched with saturated aqueous Na$_2$S$_2$O$_3$ and saturated NaHCO$_3$. The reaction mixture was extracted with DCM. The organic extract was dried over Na$_2$SO$_4$. The solution was filtered and concentrated in vacuo to give the crude material. The crude material was absorbed onto a plug of silica gel and purified by silica gel column chromatography eluting with a gradient of 0% to 25% EtOAc in heptane to provide 2-(3,5-dichloropyridin-4-yl)-N-((5-methyltetrahydrofuran-2-yl)methyl)-2-((triethylsilyl)oxy)ethanamine (A281) as a light-yellow syrup. $^1$H NMR (300 MHz, DMSO-d$_6$) δ 8.58 (2H, s), 5.34-5.46 (1H, m), 3.71-3.90 (2H, m), 3.10 (1H, dt, J=12.5, 8.1 Hz), 2.90 (1H, td, J=12.1, 6.0 Hz), 2.52-2.67 (2H, m), 1.71-2.07 (3H, m), 1.47-1.64 (1H, m), 1.19-1.38 (1H, m), 1.11 (3H, t, J=6.3 Hz), 0.77-0.89 (9H, m), 0.40-0.62 (6H, m); LCMS (ESI) m/z 419.1 (M+H)$^+$.

Reference Example A294

N-(2-(3,5-dichloropyridin-4-yl)-2-((triethylsilyl)oxy)ethyl)-3,3,3-trifluoro-2,2-dimethylpropan-1-amine

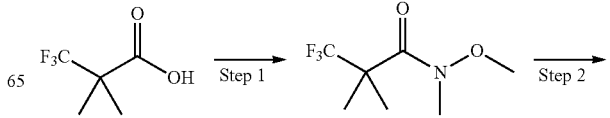

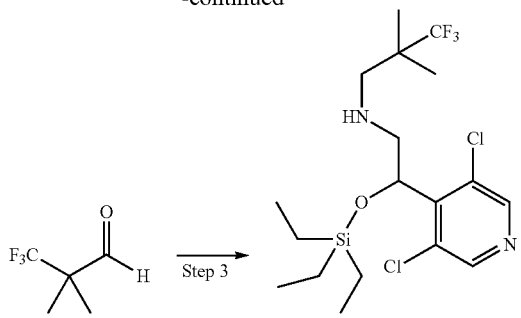

Step 1: 3,3,3-trifluoro-N-methoxy-N,2,2-trimethyl-propanamide (A294-1)

To a clear solution of 3,3,3-trifluoro-2,2-dimethylpropionic acid (5.000 g, 32.0 mmol) in MeCN (22.88 ml) was added triethylamine (9.82 ml, 70.5 mmol) followed by HATU (12.79 g, 33.6 mmol) and the mixture was stirred at room temperature. After 15 min, to the dark clear mixture was added N,O-dimethylhydroxylamine hydrochloride (3.44 g, 35.2 mmol) and the mixture was stirred at room temperature. After 18 h, the reaction mixture was diluted with EtOAc (100 mL) and washed with 1 N HCl (2×100 mL), and sat. NaCl (5×100 mL) and dried over $Na_2SO_4$. The solution was filtered and concentrated in vacuo to give the crude material as a orange solid. The orange solid was absorbed onto a plug of silica gel and purified by silica gel chromatography eluting with a gradient of 0% to 25% EtOAc in heptane to provide 3,3,3-trifluoro-N-methoxy-N,2,2-trimethylpropanamide (5.0503 g, 25.4 mmol, 79% yield) as yellow liquid. $^1$H NMR (300 MHz, $CDCl_3$) δ 3.71 (3H, s), 3.22 (3H, s), 1.51 (6H, d, J=0.7 Hz); LCMS (ESI) m/z 200.1 (M+H)$^+$.

Step 2: 3,3,3-trifluoro-2,2-dimethylpropanal

To a 250-mL of three neck round-bottomed flask equipped with goose neck for nitrogen and for thermocouple was added lithium aluminium hydride, 1 M solution in $Et_2O$ (25.3 ml, 25.3 mmol) at 0° C. To the cooled mixture was added a solution of 3,3,3-trifluoro-N-methoxy-N,2,2-trimethylpropanamide (A294-1) (5.0325 g, 25.3 mmol) in $Et_2O$ (47.7 ml) dropwise over 35 min at 0° C. After the completion of the addition, the reaction mixture was further stirred at 0° C. After 2 h, the mixture was carefully quenched at 0° C. with water (0.96 mL), NaOH (15%, 0.96 mL) and water (2.88 mL) and the mixture was vigorously stirred for 40 min. The reaction mixture was diluted with $Et_2O$ (50 mL), treated with $Na_2SO_4$ and then filtered through a Celite pad, washed with $Et_2O$ (100 mL). The filtrate was concentrated in vacuo to provide 3,3,3-trifluoro-2,2-dimethylpropanal (A294-2) (3.2304 g, 23.06 mmol, 91% yield) as yellow liquid. $^1$H NMR (400 MHz, $CDCl_3$) δ 9.69 (1H, d, J=1.4 Hz), 1.31 (6H, s).

Step 3: N-(2-(3,5-dichloropyridin-4-yl)-2-((triethylsilyl)oxy)ethyl)-3,3,3-trifluoro-2,2-dimethylpropan-1-amine (A294)

To a yellow clear mixture of 2-(3,5-dichloropyridin-4-yl)-2-((triethylsilyl)oxy)ethanamine (3.57 g, 11.11 mmol) in DCM (37.0 mL) was added 3,3,3-trifluoro-2,2-dimethylpropanal (11.11 mmol) in DCM followed by AcOH (0.770 ml, 13.33 mmol) and $NaBH(OAc)_3$ (3.53 g, 16.67 mmol). The yellow heterogeneous mixture was stirred at room temperature. After 8 h, the mixture was quenched with saturated $NaHCO_3$ (100 mL). The reaction mixture was extracted with DCM (2×100 mL). The organic extract was dried over $Na_2SO_4$. The solution was filtered and concentrated in vacuo to give the crude material as orange syrup. The crude material was absorbed onto a plug of silica gel and purified by silica gel column chromatography eluting with a gradient of 0% to 20% EtOAc in heptane to provide N-(2-(3,5-dichloropyridin-4-yl)-2-((triethylsilyl)oxy)ethyl)-3,3,3-trifluoro-2,2-dimethylpropan-1-amine (A294) (3.4393 g, 7.72 mmol, 69.5% yield) as colorless oil. $^1$H NMR (400 MHz, $CDCl_3$) δ 8.44 (2H, s), 5.48 (1H, dd, J=7.7, 4.4 Hz), 3.27 (1H, dd, J=12.3, 8.4 Hz), 2.58-2.83 (3H, m), 1.25-1.44 (1H, m), 1.10 (6H, s), 0.85-0.94 (9H, m), 0.47-0.64 (6H, m); LCMS (ESI) m/z 445.1 (M+H)$^+$.

The following secondary amines were prepared using similar procedure in reference examples described above:

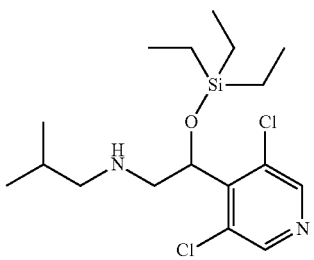

A2

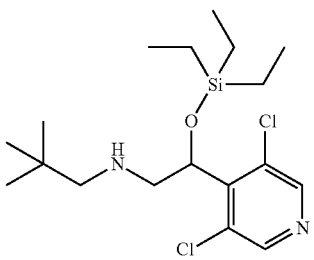

A3

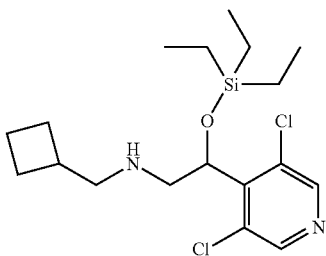

A4

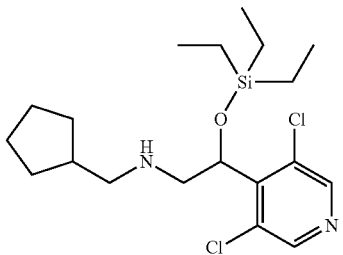

A5

A6 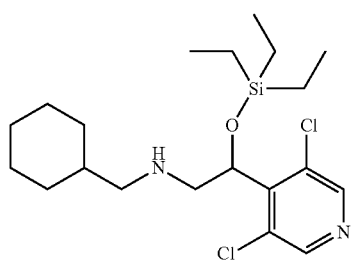
A7 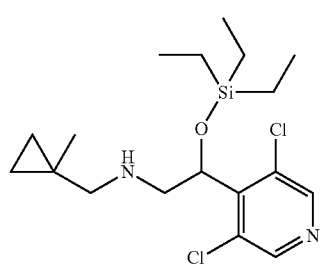
A8 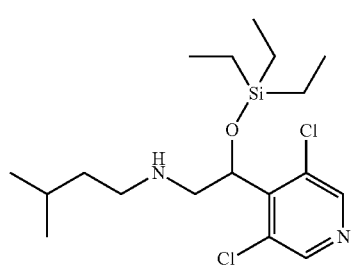
A9 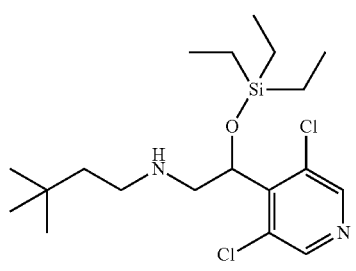
A10 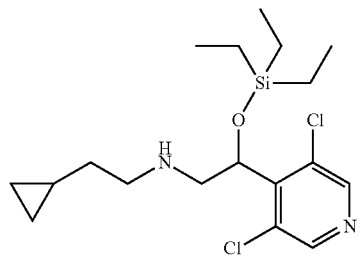
A11 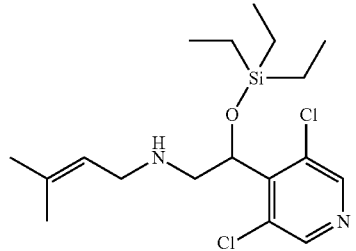
A13 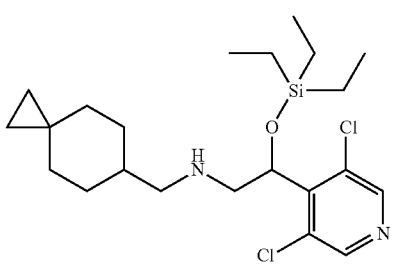
A14 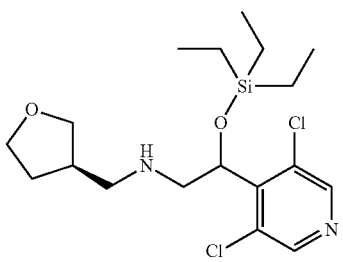
A15 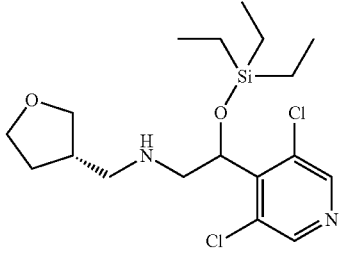
A16 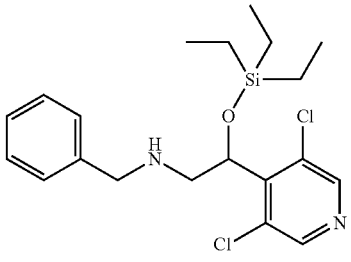
A17 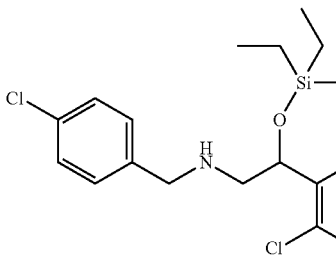
A18 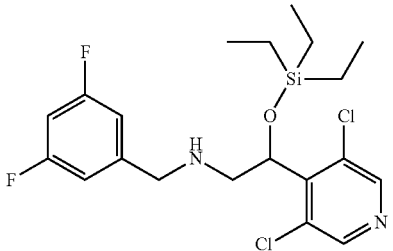

A19
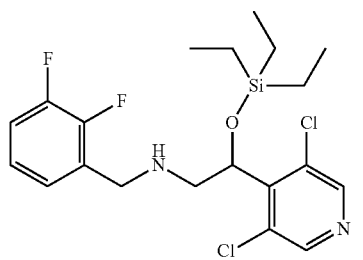
A20
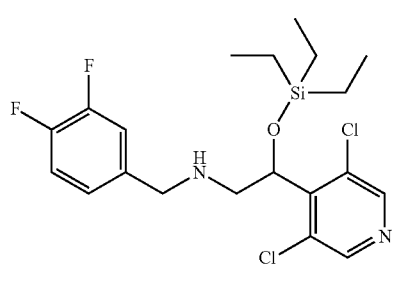
A21
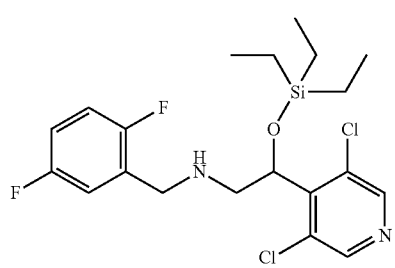
A22
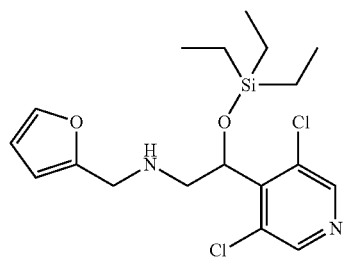
A23
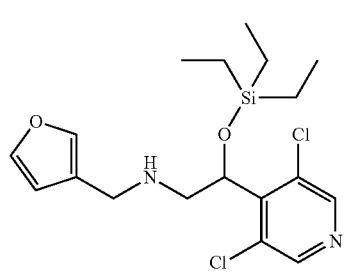
A24
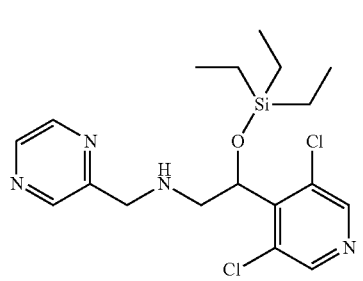
A25
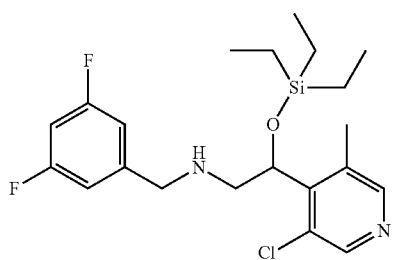
A26
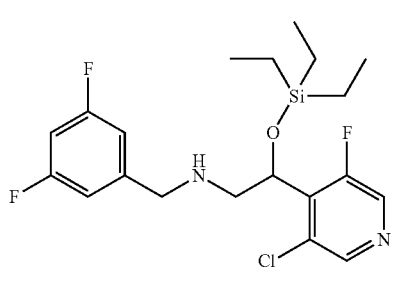
A27
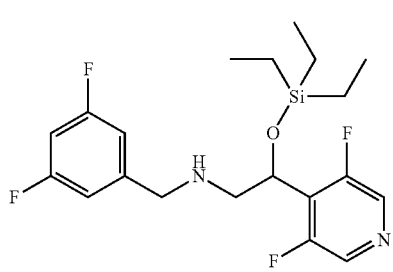
A28
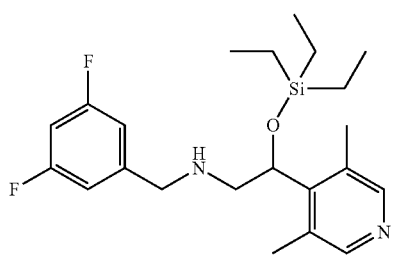
A29
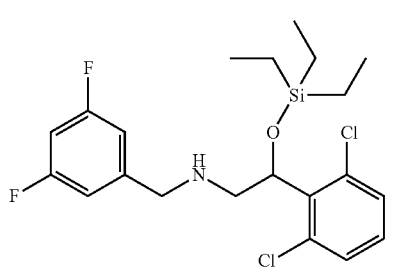
A30
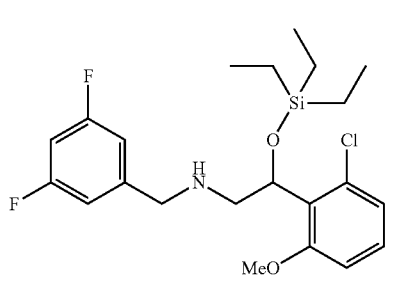

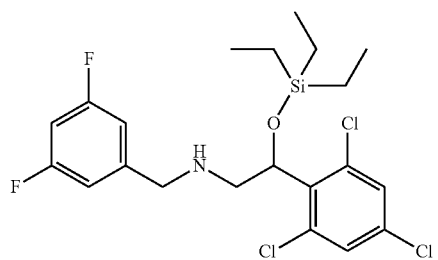
A32
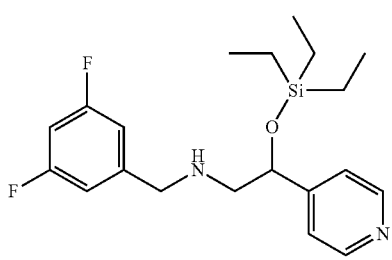
A39
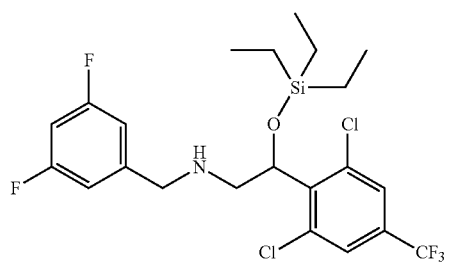
A33
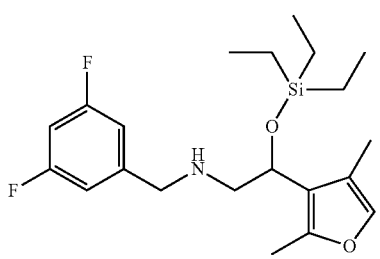
A40
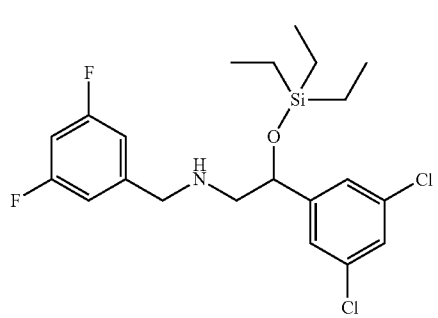
A36
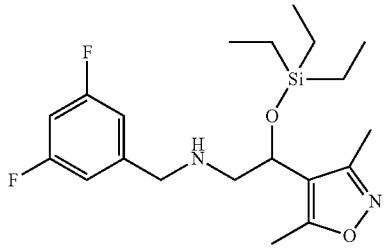
A41
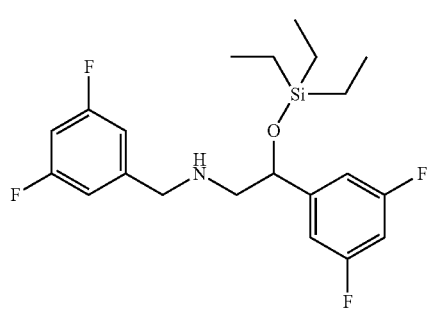
A37
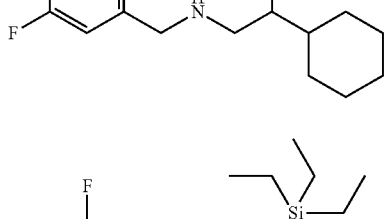
A42
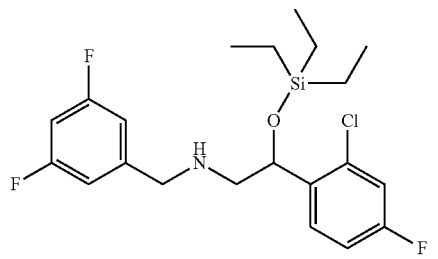
A38
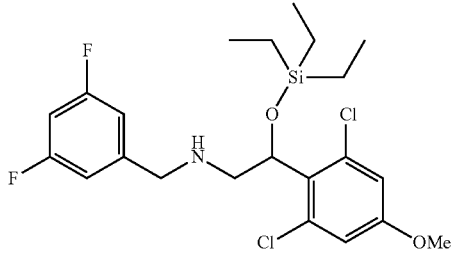
A43
A44

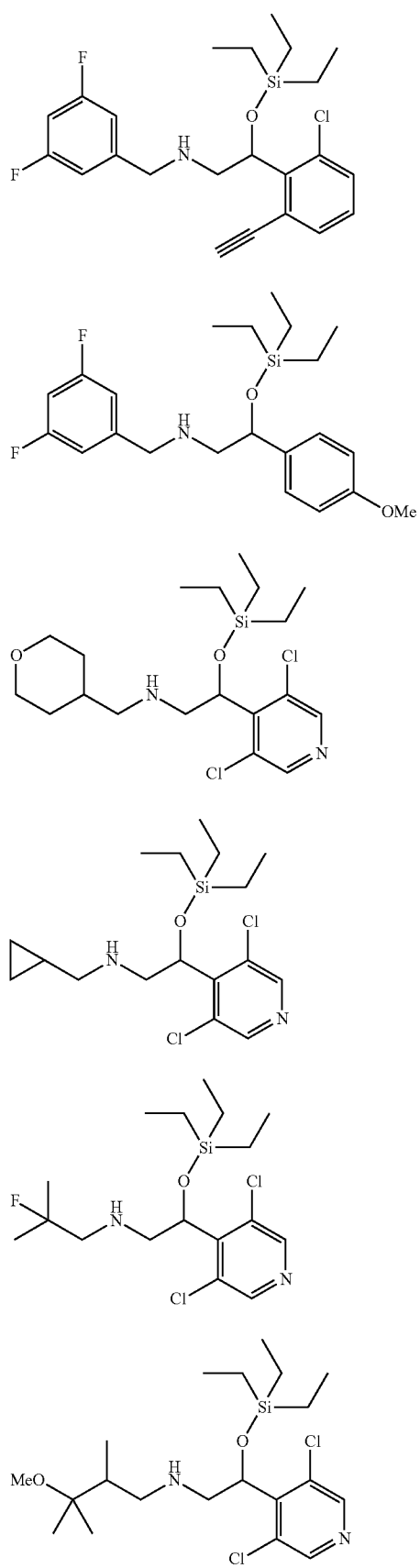
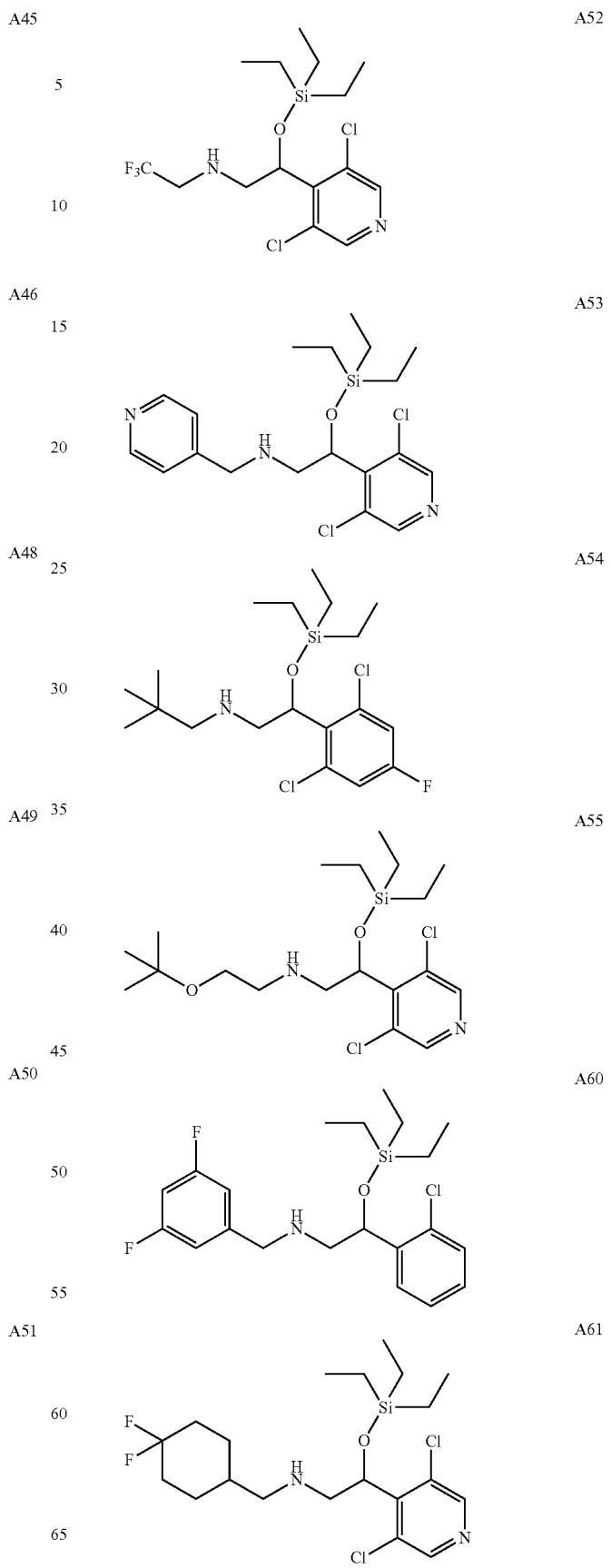

| | |
|---|---|
| 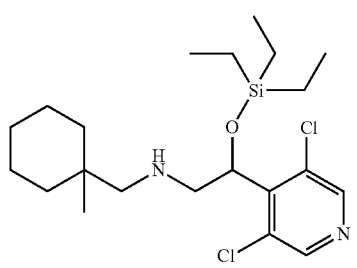 A62 | 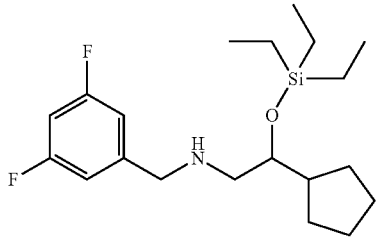 A70 |
| 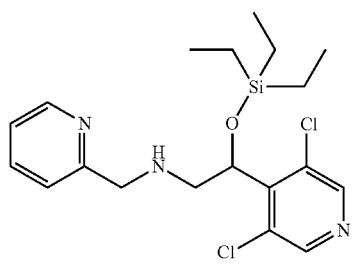 A63 | 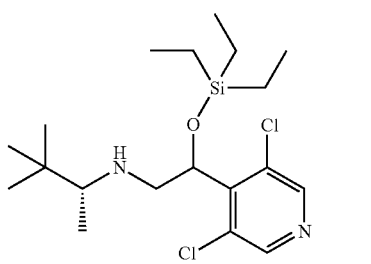 A71 |
| 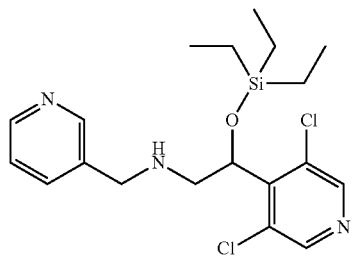 A64 | 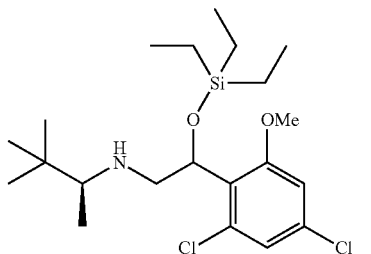 A72 |
| 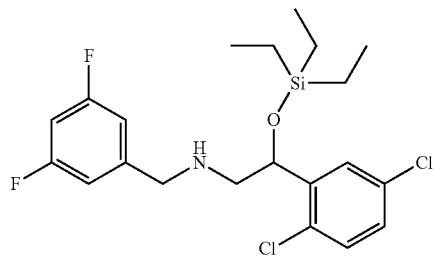 A65 | 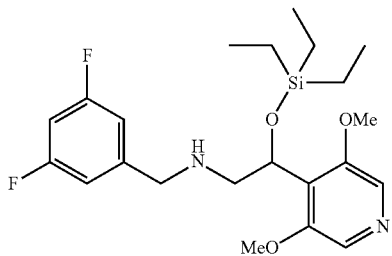 A73 |
| 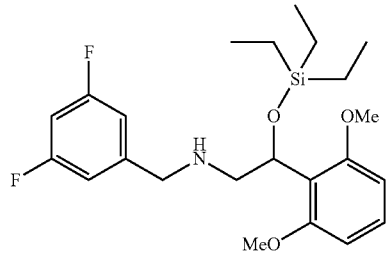 A67 | 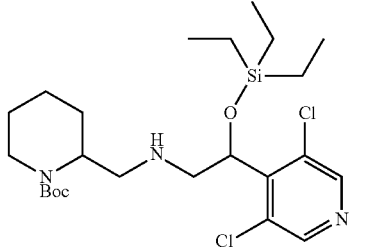 A74 |
| 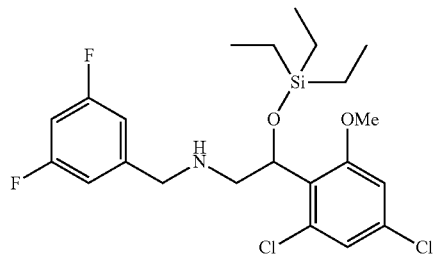 A69 | 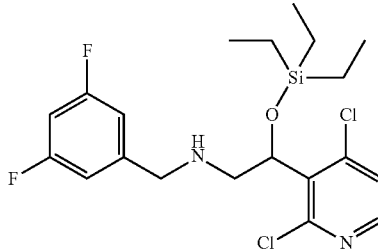 A76 |

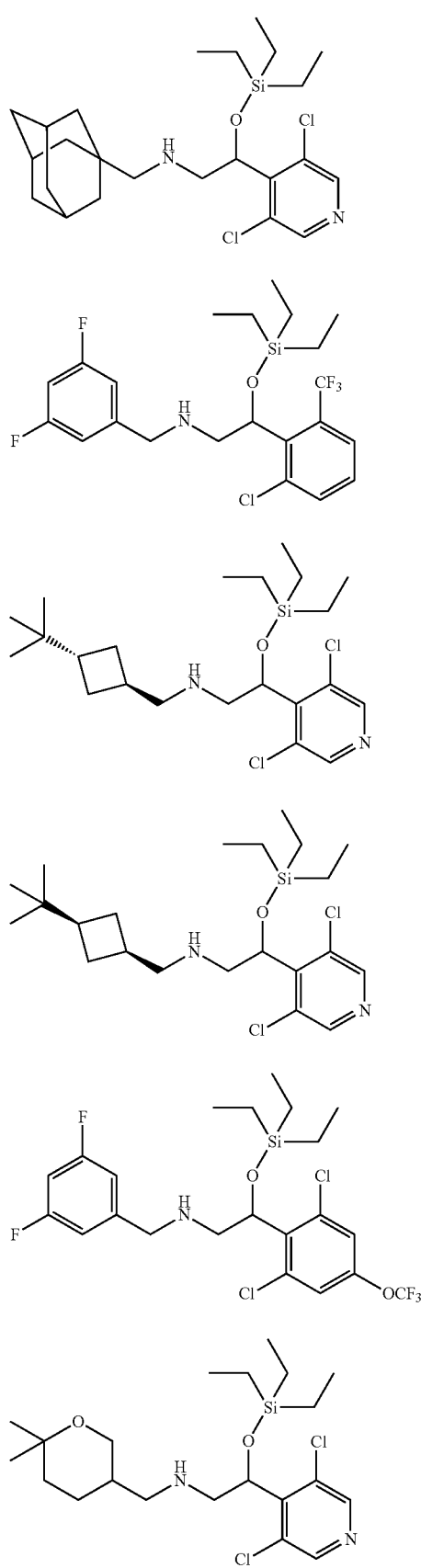
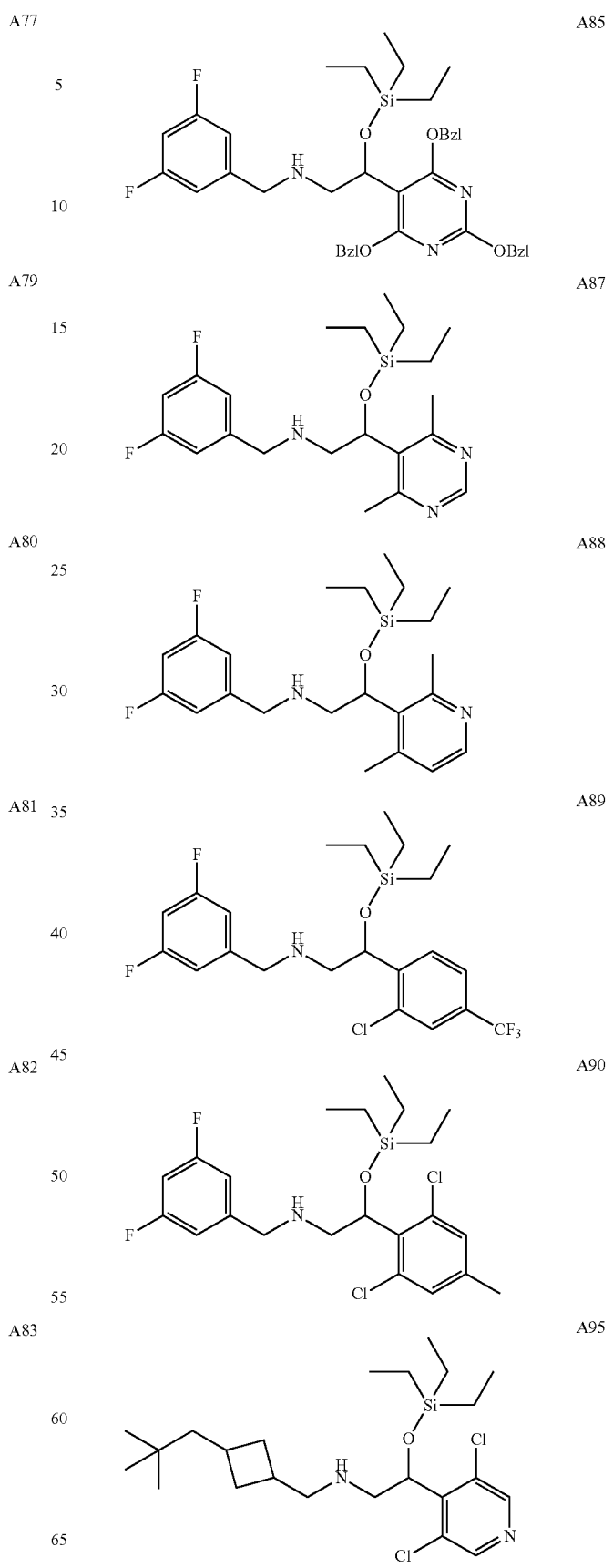

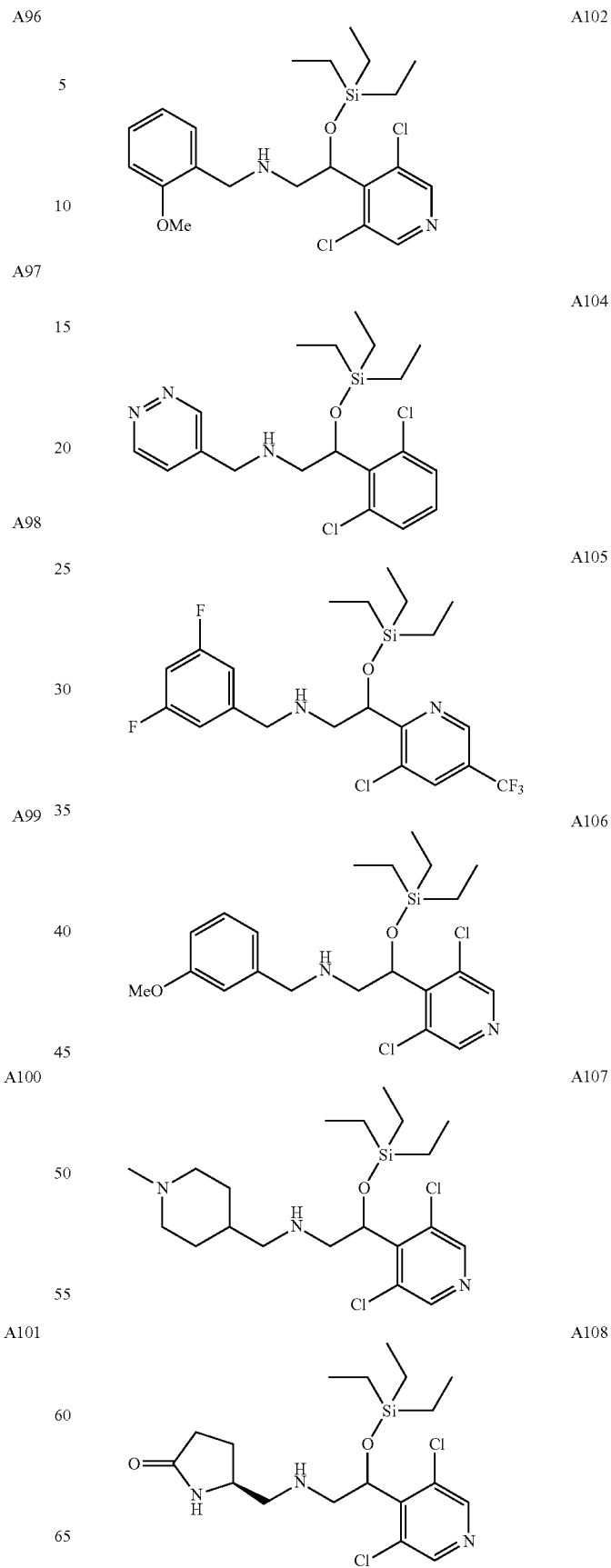

A109
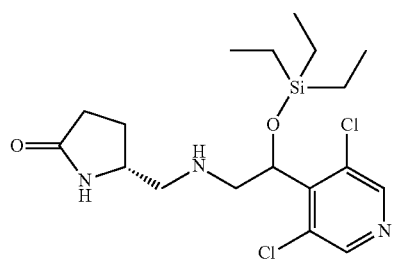
A110
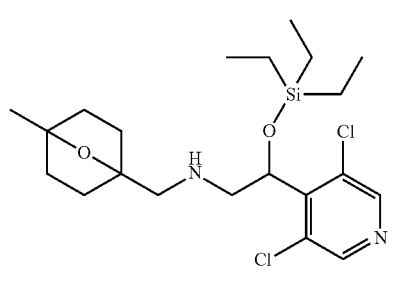
A113
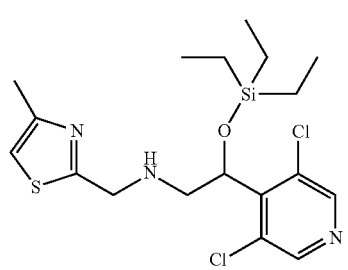
A114
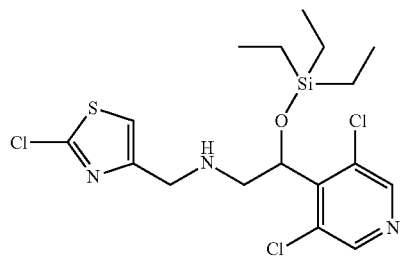
A115
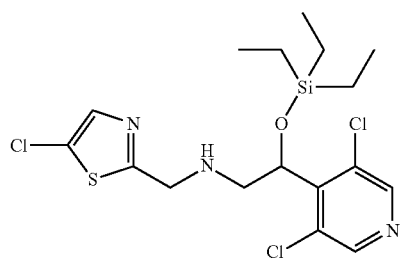
A116
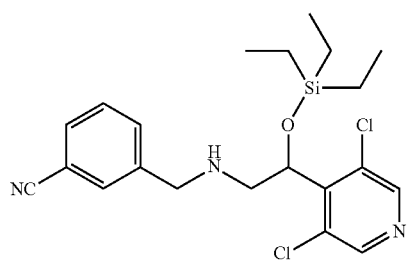
A117
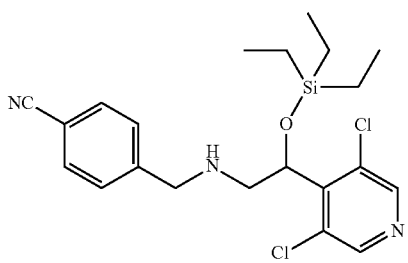
A120
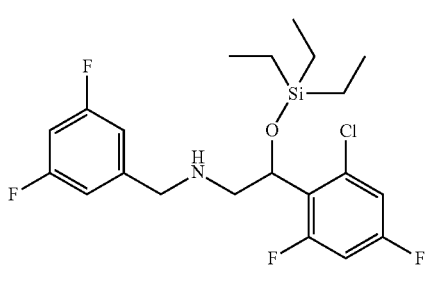
A121
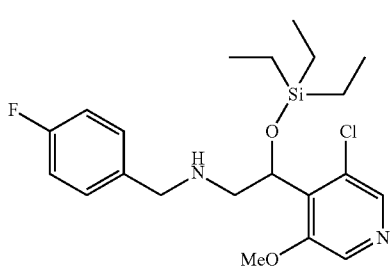
A123
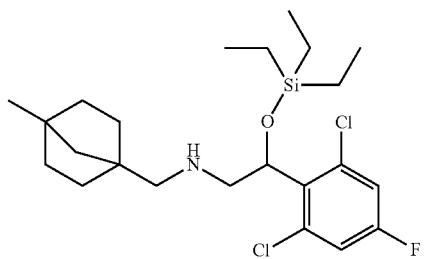
A125
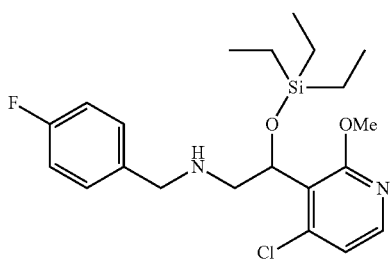
A126
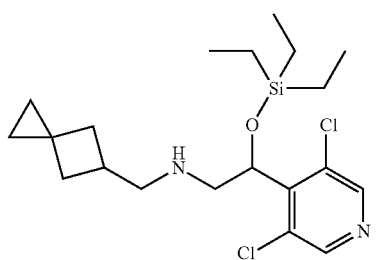

A127 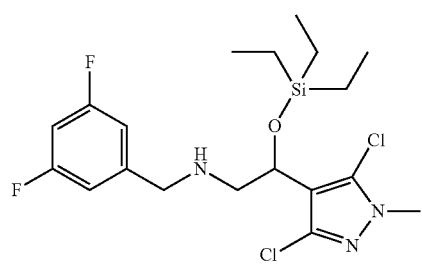
A128 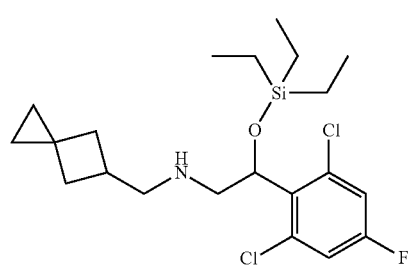
A129 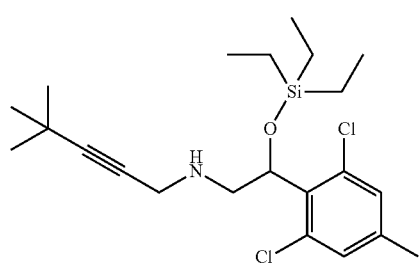
A130 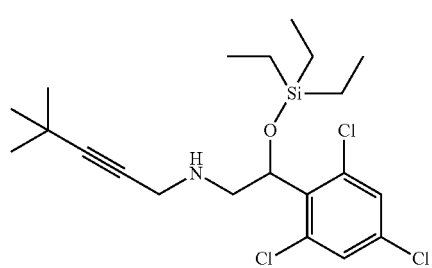
A131 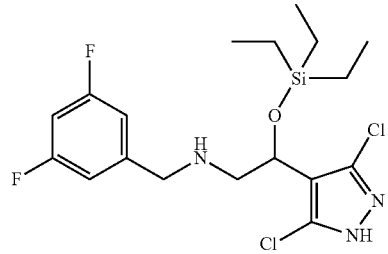
A132 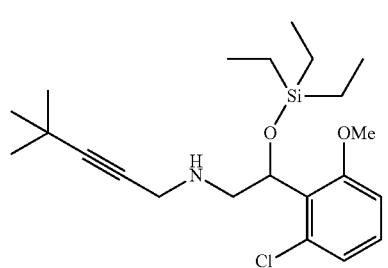
A133 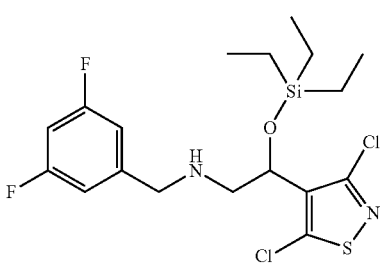
A134 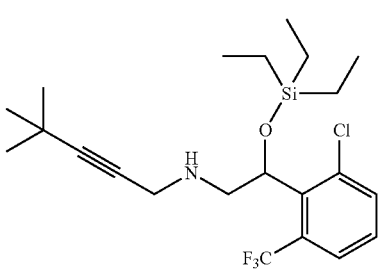
A135 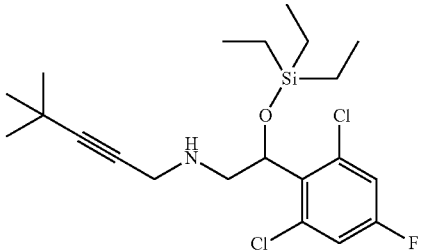
A136 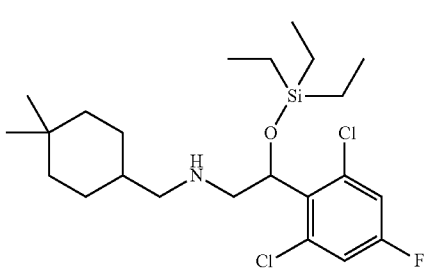
A137 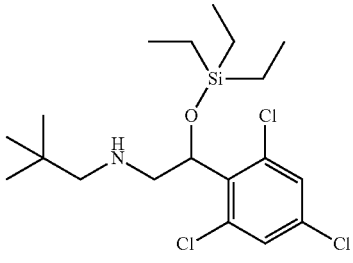
A138 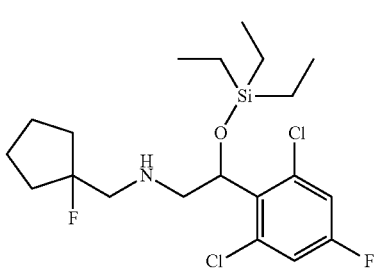

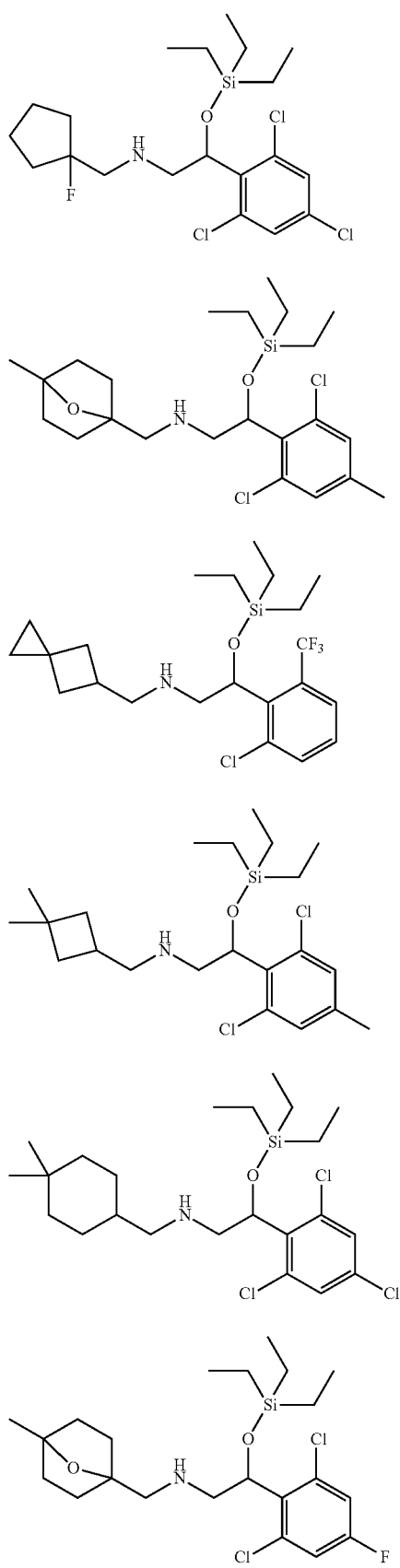
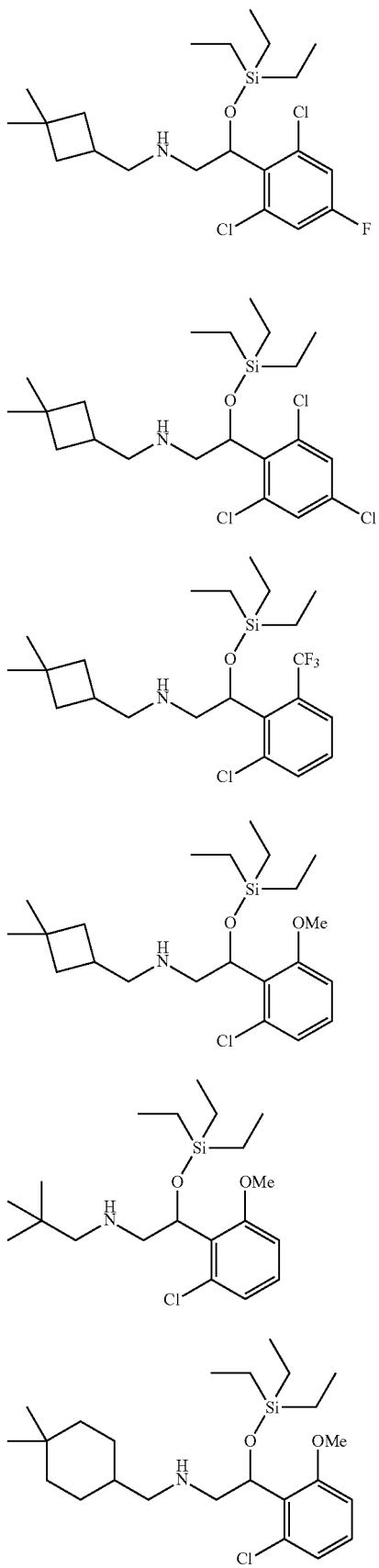

A152 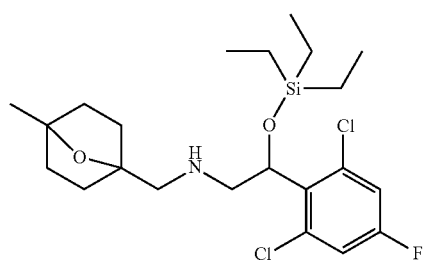
A153 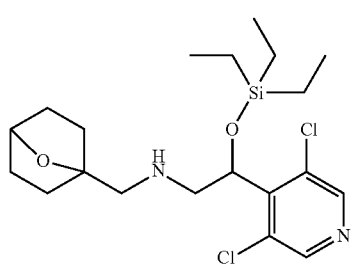
A154 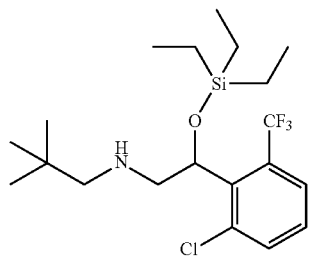
A155 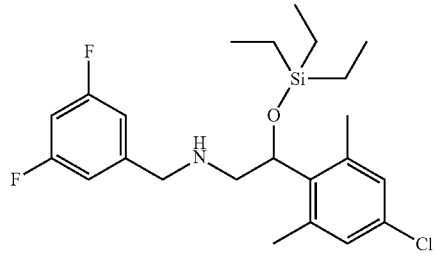
A156 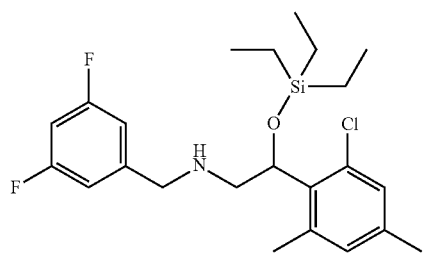
A157 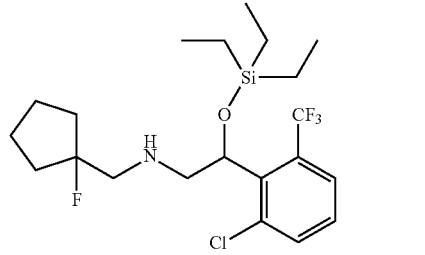
A158 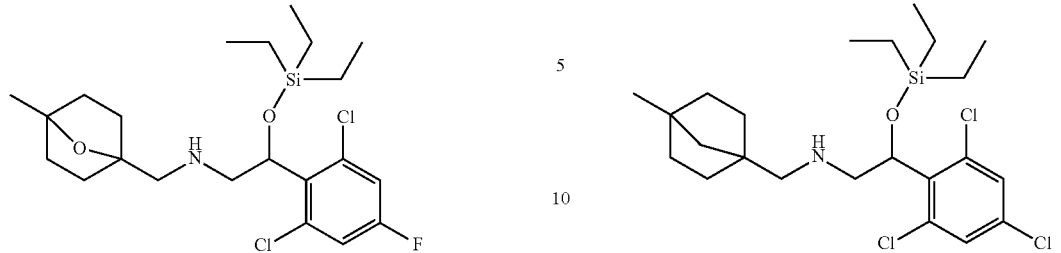
A159 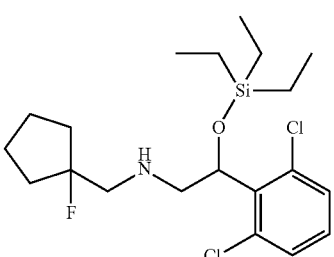
A160 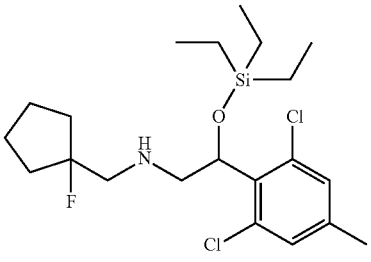
A161 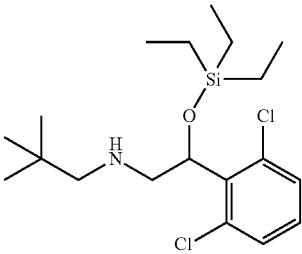
A162 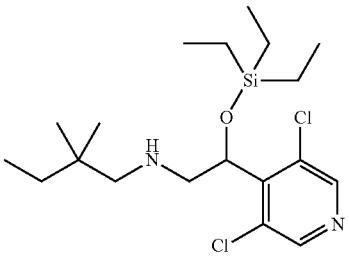
A163 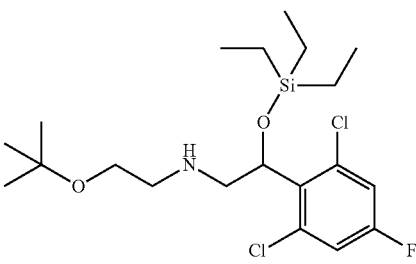

A164 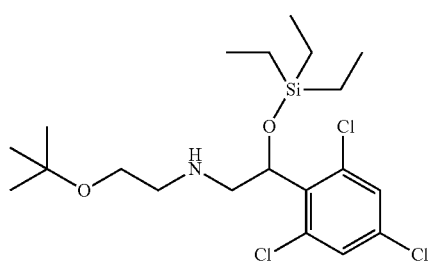
A165 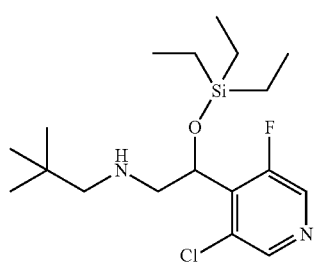
A166 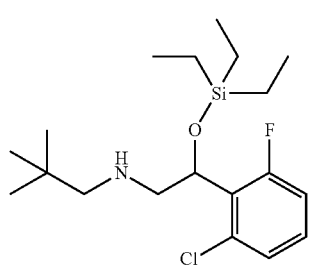
A167 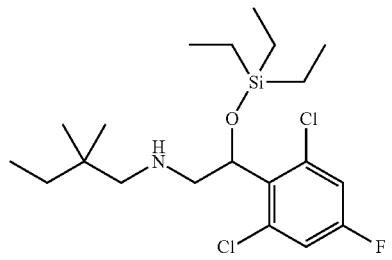
A168 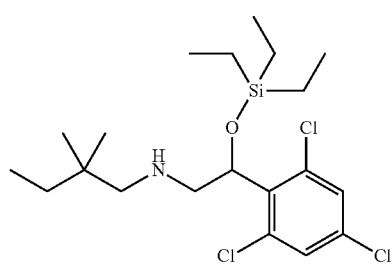
A169 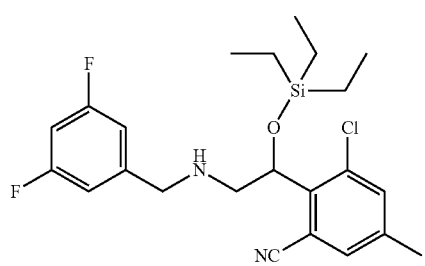
A170 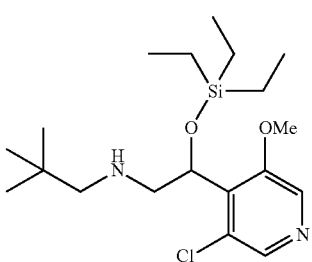
A171 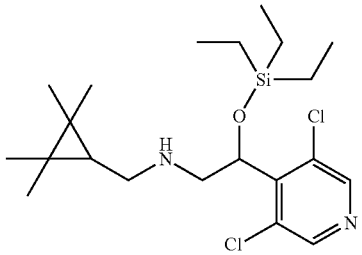
A172 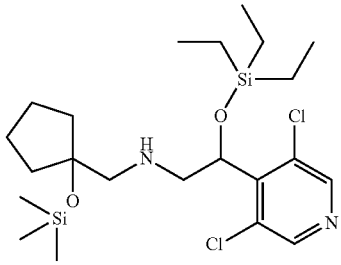
A173 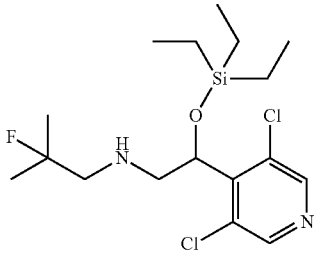
A174 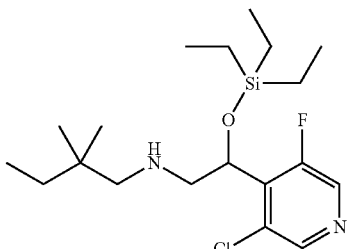
A175 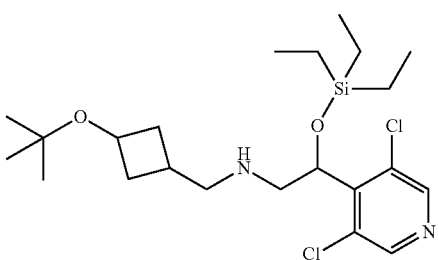

| reference example | structure |
|---|---|
| A176 | 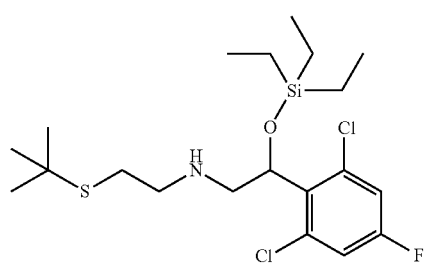 |
| A177 | 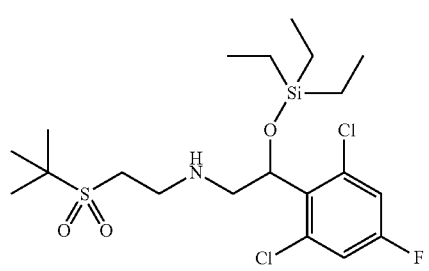 |
| A178 | 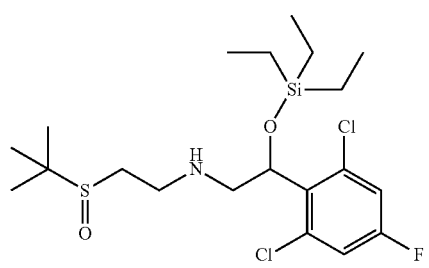 |
| A179 | 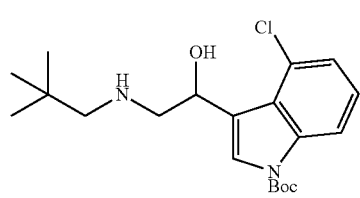 |
| A180 | 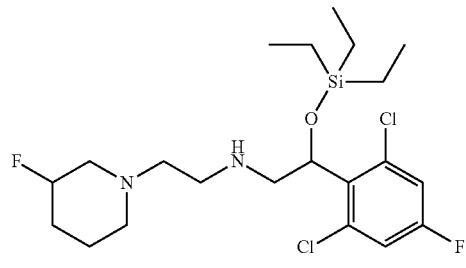 |
| A181 | 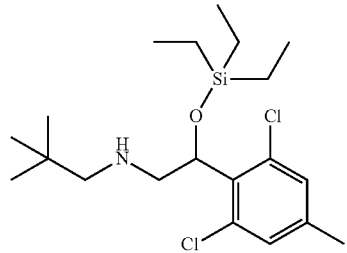 |
| A182 | 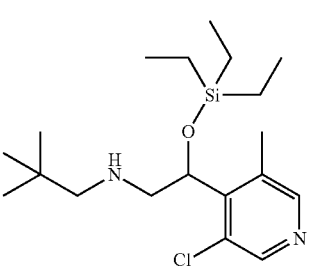 |
| A183 | 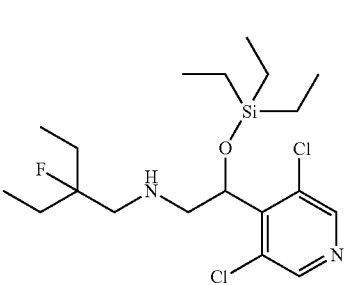 |
| A184 | 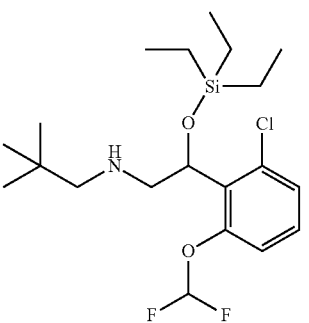 |
| reference example | structure |
|---|---|
| A185 | 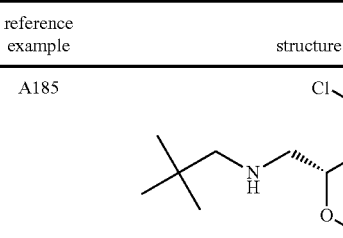 |
| A186 | 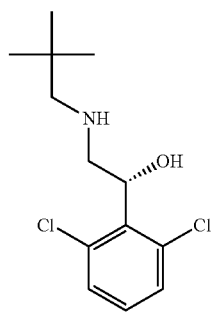 [SMILES: CC(C)(C)CNC[C@H](O)c1c(Cl)cccc1Cl] |

| reference example | structure |
|---|---|
| A187 | 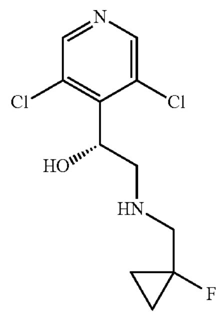 [SMILES: O[C@@H](CNCC1(F)CC1)c1c(Cl)cncc1Cl] |
| A188 | 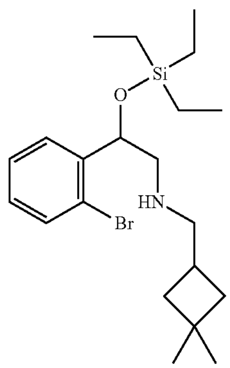 [SMILES: CC[Si](CC)(CC)OC(CNCC1CC(C)(C)C1)c1ccccc1Br] |
| A189 | 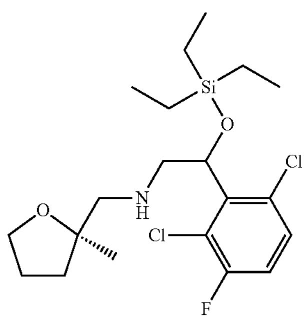 [SMILES: CC[Si](CC)(CC)OC(CNC[C@@]1(C)CCCO1)c1c(Cl)ccc(F)c1Cl] |
| A190 | 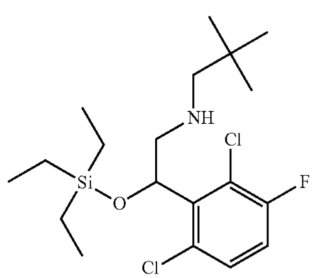 [SMILES: CC[Si](CC)(CC)OC(CNCC(C)(C)C)c1c(Cl)ccc(F)c1Cl] |
| A191 | 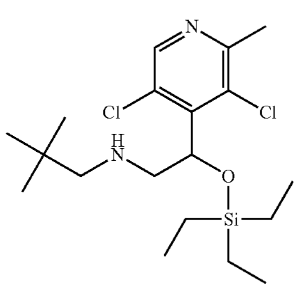 [SMILES: CC[Si](CC)(CC)OC(CNCC(C)(C)C)c1c(Cl)cnc(C)c1Cl] |
| A192 | |
| A193 | |
| A194 | |
| A195 | |
| A196 | |

-continued
| reference example | structure |
|---|---|
| A197 | 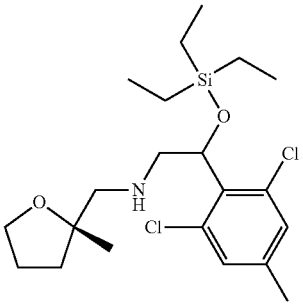 [SMILES: CC[Si](CC)(CC)OC(CNC[C@]1(C)CCCO1)c1c(Cl)cc(C)cc1Cl] |
| A198 | 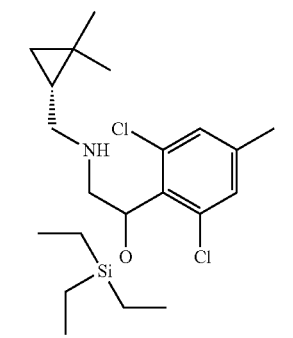 |
| A199 | 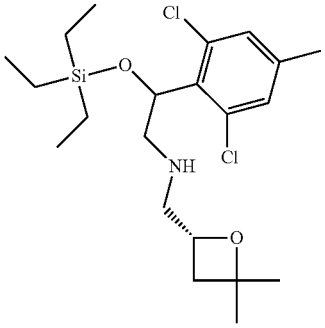 [SMILES: CC[Si](CC)(CC)OC(CNC[C@H]1CC(C)(C)O1)c1c(Cl)cc(C)cc1Cl] |
| A200 | 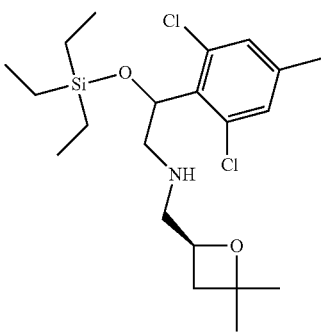 [SMILES: CC[Si](CC)(CC)OC(CNC[C@@H]1CC(C)(C)O1)c1c(Cl)cc(C)cc1Cl] |
| A201 | 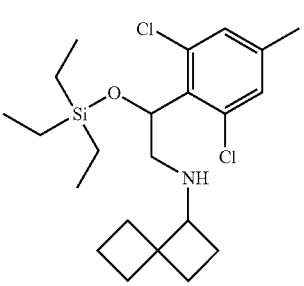 [SMILES: CC[Si](CC)(CC)OC(CNC1CCC12CCC2)c1c(Cl)cc(C)cc1Cl] |
-continued
| reference example | structure |
|---|---|
| A202 | 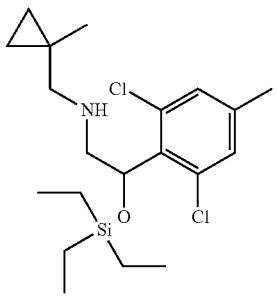 |
| A203 | 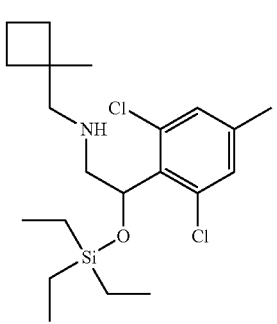 [SMILES: CC[Si](CC)(CC)OC(CNCC1(C)CCC1)c1c(Cl)cc(C)cc1Cl] |
| A204 | 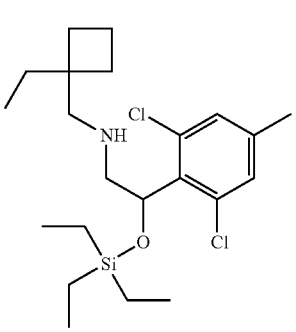 [SMILES: CCC1(CNCC(O[Si](CC)(CC)CC)c2c(Cl)cc(C)cc2Cl)CCC1] |
| A205 | 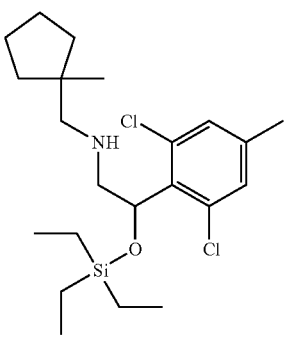 [SMILES: CC[Si](CC)(CC)OC(CNCC1(C)CCCC1)c1c(Cl)cc(C)cc1Cl] |

-continued
| reference example | structure |
|---|---|
| A206 | 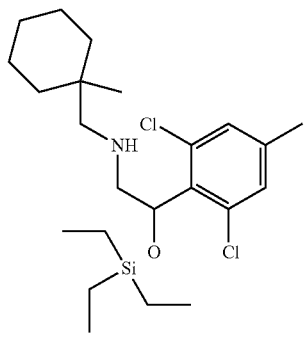 |
| A207 | 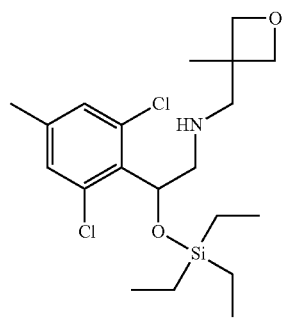 [SMILES: CC[Si](CC)(CC)OC(CNCC1(C)COC1)c1c(Cl)cc(C)cc1Cl] |
| A208 | 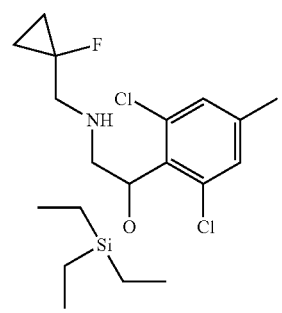 |
| A209 | 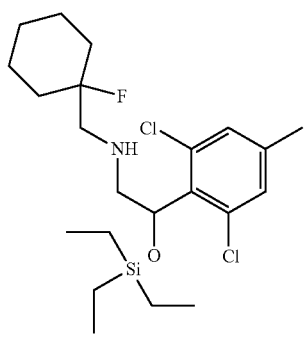 |
-continued
| reference example | structure |
|---|---|
| A210 | 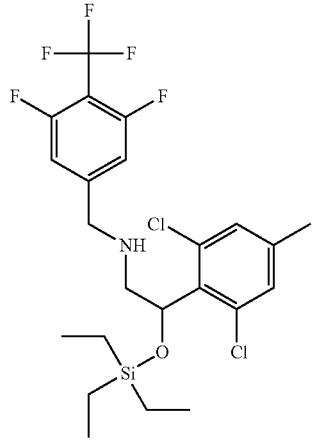 [SMILES: CC[Si](CC)(CC)OC(CNCc1cc(F)c(C(F)(F)F)c(F)c1)c1c(Cl)cc(C)cc1Cl] |
| A211 | 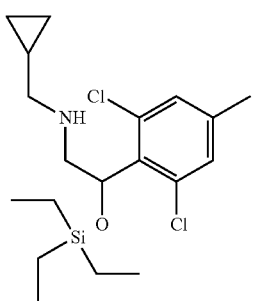 |
| A212 | 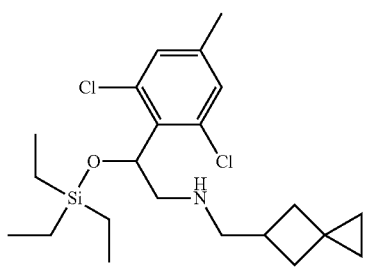 [SMILES: CC[Si](CC)(CC)OC(CNCC1CC2(CC2)C1)c1c(Cl)cc(C)cc1Cl] |
| A213 | 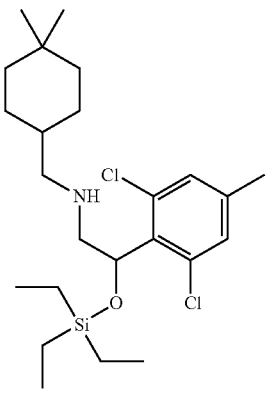 [SMILES: CC[Si](CC)(CC)OC(CNCC1CCC(C)(C)CC1)c1c(Cl)cc(C)cc1Cl] |

-continued
| reference example | structure |
|---|---|
| A214 | 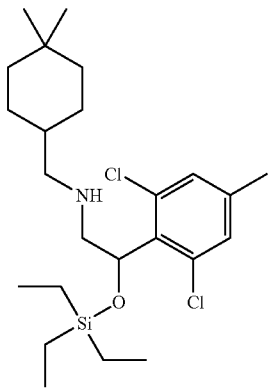 [SMILES: CC[Si](CC)(CC)OC(CNCC1CCC(C)(C)CC1)c1c(Cl)cc(C)cc1Cl] |
| A215 | 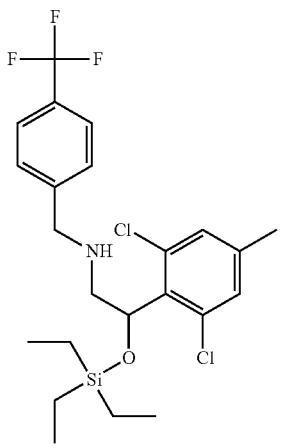 [SMILES: CC[Si](CC)(CC)OC(CNCc1ccc(C(F)(F)F)cc1)c1c(Cl)cc(C)cc1Cl] |
| A216 | 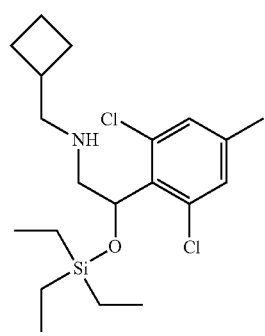 [SMILES: CC[Si](CC)(CC)OC(CNCC1CCC1)c1c(Cl)cc(C)cc1Cl] |
| A217 | 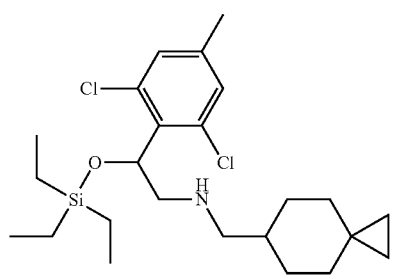 [SMILES: CC[Si](CC)(CC)OC(CNCC1CCC2(CC1)CC2)c1c(Cl)cc(C)cc1Cl] |
-continued
| reference example | structure |
|---|---|
| A218 | 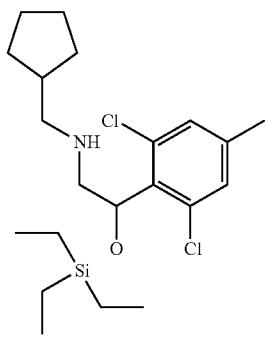 |
| A219 | 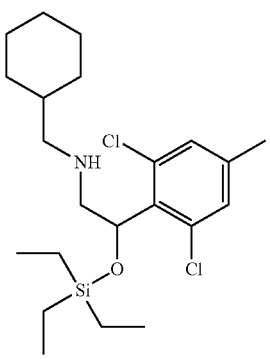 [SMILES: CC[Si](CC)(CC)OC(CNCC1CCCCC1)c1c(Cl)cc(C)cc1Cl] |
| A220 | 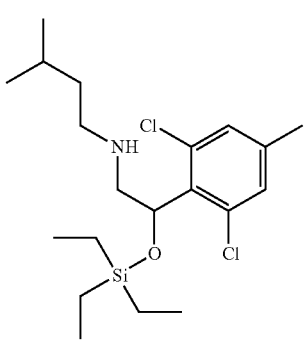 [SMILES: CC[Si](CC)(CC)OC(CNCCC(C)C)c1c(Cl)cc(C)cc1Cl] |
| A221 | 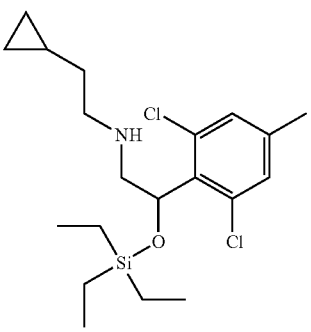 [SMILES: CC[Si](CC)(CC)OC(CNCCC1CC1)c1c(Cl)cc(C)cc1Cl] |

125
-continued
| reference example | structure |
|---|---|
| A222 | 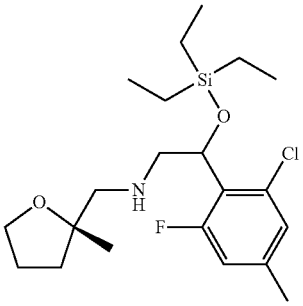 [SMILES: CC[Si](CC)(CC)OC(CNC[C@]1(C)CCCO1)c1c(F)cc(C)cc1Cl] |
| A223 | 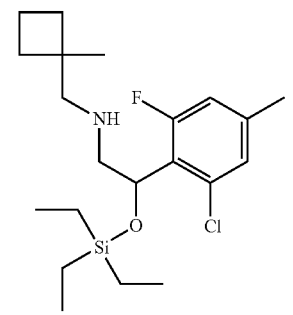 |
| A224 | 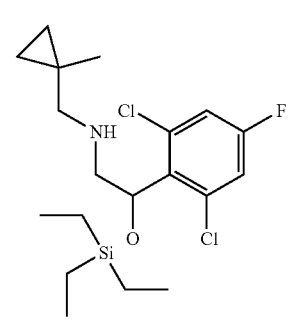 |
| A225 | 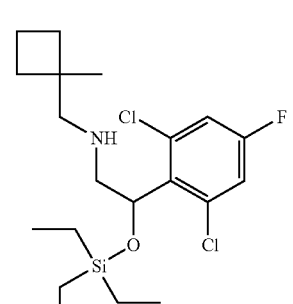 |
| A226 | 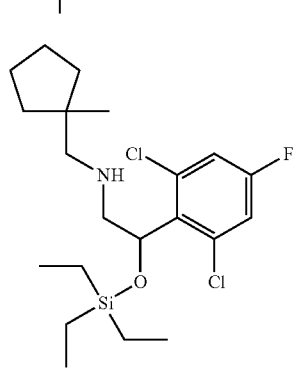 |
126
-continued
| reference example | structure |
|---|---|
| A227 | 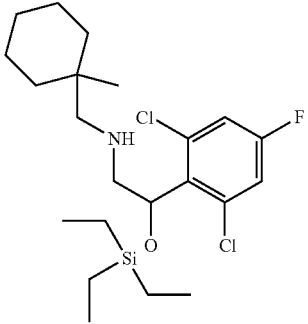 |
| A228 | 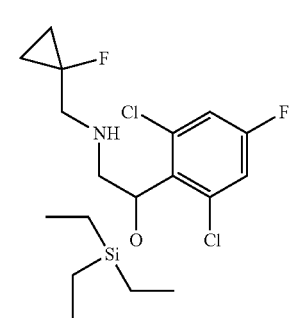 |
| A229 | 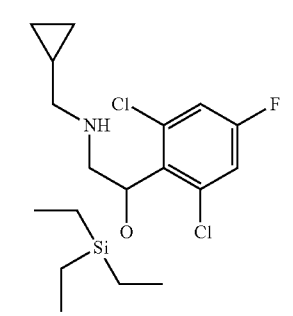 |
| A230 | 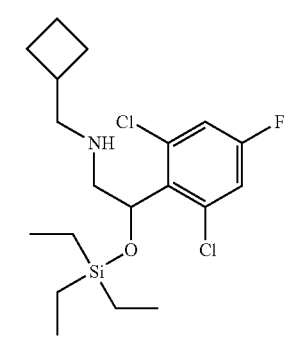 [SMILES: CC[Si](CC)(CC)OC(CNCC1CCC1)c1c(Cl)cc(F)cc1Cl] |

-continued

| reference example | structure |
|---|---|
| A231 | 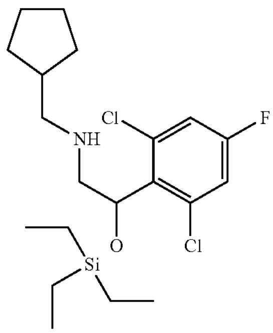 |
| A232 | 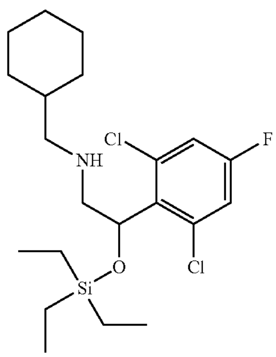 [SMILES: CC[Si](CC)(CC)OC(CNCC1CCCCC1)c1c(Cl)cc(F)cc1Cl] |
| A233 | 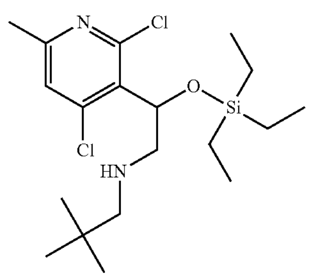 [SMILES: CC[Si](CC)(CC)OC(CNCC(C)(C)C)c1c(Cl)cc(C)nc1Cl] |
| A234 | 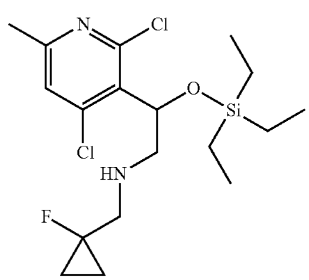 [SMILES: CC[Si](CC)(CC)OC(CNCC1(F)CC1)c1c(Cl)cc(C)nc1Cl] |
| A235 | 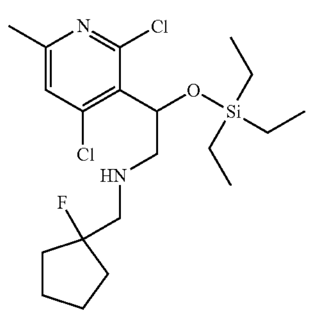 [SMILES: CC[Si](CC)(CC)OC(CNCC1(F)CCCC1)c1c(Cl)cc(C)nc1Cl] |

-continued

| reference example | structure |
|---|---|
| A236 | 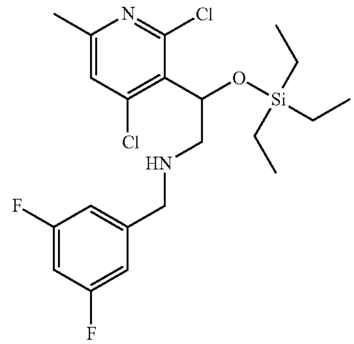 [SMILES: CC[Si](CC)(CC)OC(CNCc1cc(F)cc(F)c1)c1c(Cl)cc(C)nc1Cl] |
| A237 | 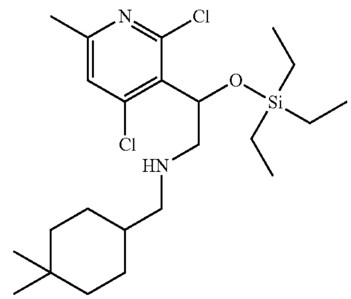 [SMILES: CC[Si](CC)(CC)OC(CNCC1CCC(C)(C)CC1)c1c(Cl)cc(C)nc1Cl] |
| A238 | 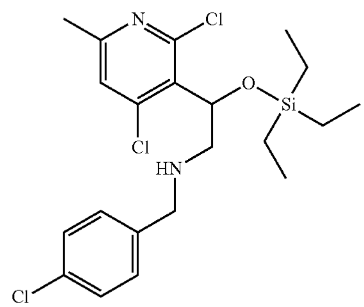 [SMILES: CC[Si](CC)(CC)OC(CNCc1ccc(Cl)cc1)c1c(Cl)cc(C)nc1Cl] |
| A239 | 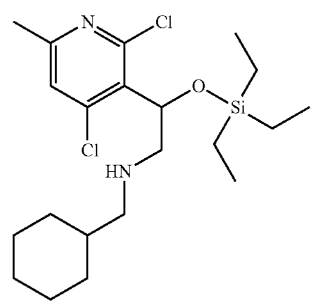 [SMILES: CC[Si](CC)(CC)OC(CNCC1CCCCC1)c1c(Cl)cc(C)nc1Cl] |
| A240 | 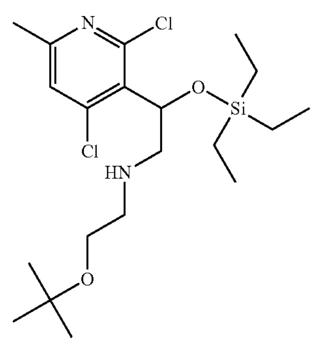 [SMILES: CC[Si](CC)(CC)OC(CNCCOC(C)(C)C)c1c(Cl)cc(C)nc1Cl] |

| reference example | structure |
|---|---|
| A241 | 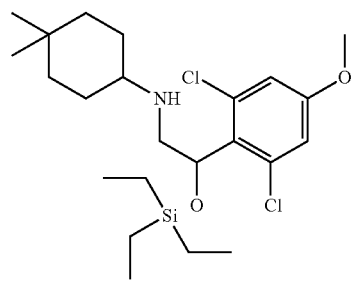 |
| A242 | 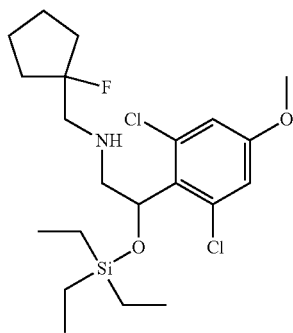 [SMILES: CC[Si](CC)(CC)OC(CNCC1(F)CCCC1)c1c(Cl)cc(OC)cc1Cl] |
| A243 | 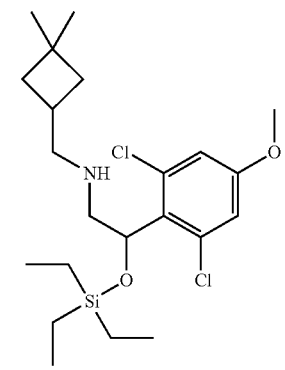 [SMILES: CC[Si](CC)(CC)OC(CNCC1CC(C)(C)C1)c1c(Cl)cc(OC)cc1Cl] |
| A244 | 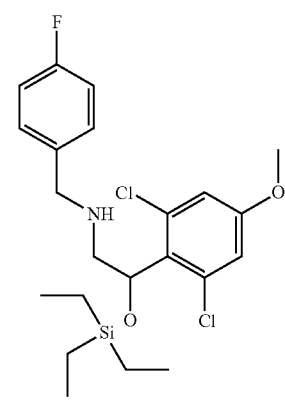 |
| reference example | structure |
|---|---|
| A245 | 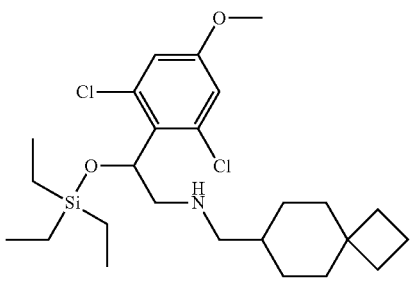 [SMILES: CC[Si](CC)(CC)OC(CNCC1CCC2(CCC2)CC1)c1c(Cl)cc(OC)cc1Cl] |
| A246 | 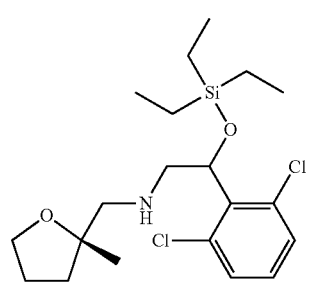 [SMILES: CC[Si](CC)(CC)OC(CNC[C@]1(C)CCCO1)c1c(Cl)cccc1Cl] |
| A247 | 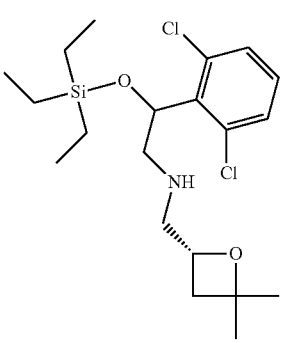 [SMILES: CC[Si](CC)(CC)OC(CNC[C@H]1CC(C)(C)O1)c1c(Cl)cccc1Cl] |
| A248 | 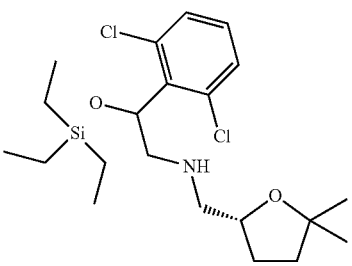 |
| A249 | 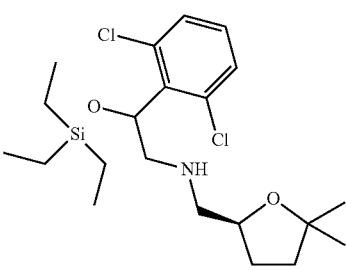 |

TABLE -continued
| reference example | structure |
|---|---|
| A250 | 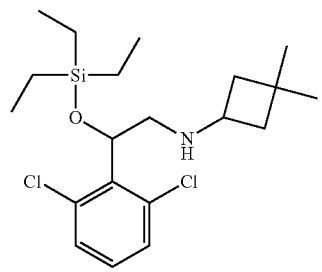 [SMILES: CC[Si](CC)(CC)OC(CNC1CC(C)(C)C1)c1c(Cl)cccc1Cl] |
| A251 | 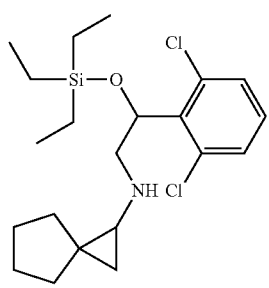 [SMILES: CC[Si](CC)(CC)OC(CNC1CC12CCCC2)c1c(Cl)cccc1Cl] |
| A252 | 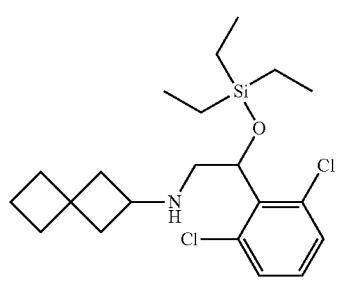 [SMILES: CC[Si](CC)(CC)OC(CNC1CC2(CCC2)C1)c1c(Cl)cccc1Cl] |
| A253 | 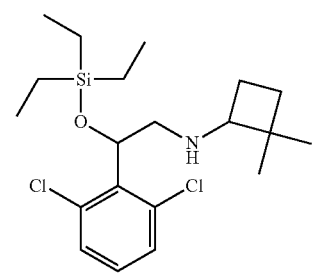 [SMILES: CC[Si](CC)(CC)OC(CNC1CCC1(C)C)c1c(Cl)cccc1Cl] |
| A254 | 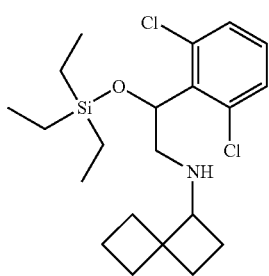 [SMILES: CC[Si](CC)(CC)OC(CNC1CCC12CCC2)c1c(Cl)cccc1Cl] |
| A255 | 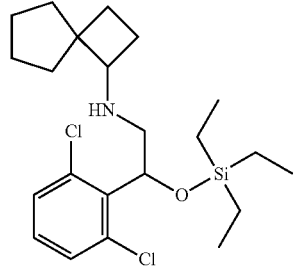 [SMILES: CC[Si](CC)(CC)OC(CNC1CCC12CCCC2)c1c(Cl)cccc1Cl] |
| A256 | 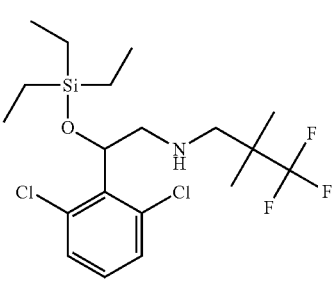 [SMILES: CC[Si](CC)(CC)OC(CNCC(C)(C)C(F)(F)F)c1c(Cl)cccc1Cl] |
| A257 | 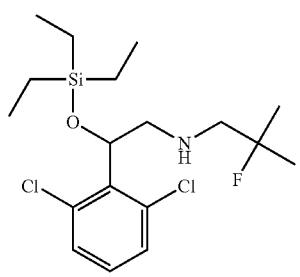 [SMILES: CC[Si](CC)(CC)OC(CNCC(C)(C)F)c1c(Cl)cccc1Cl] |
| A258 | 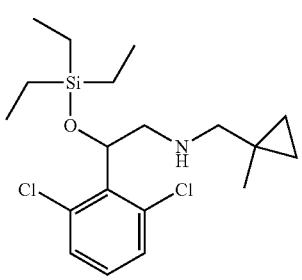 [SMILES: CC[Si](CC)(CC)OC(CNCC1(C)CC1)c1c(Cl)cccc1Cl] |
| A259 | 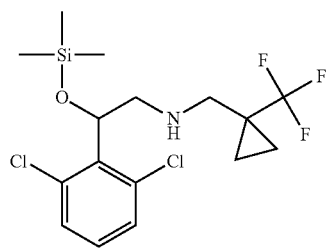 [SMILES: C[Si](C)(C)OC(CNCC1(C(F)(F)F)CC1)c1c(Cl)cccc1Cl] |

| reference example | structure |
|---|---|
| A260 | 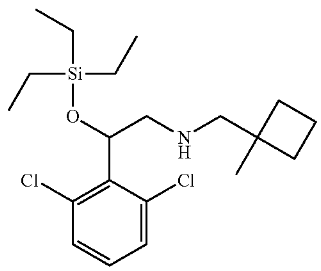 [SMILES: CC[Si](CC)(CC)OC(CNCC1(C)CCC1)c1c(Cl)cccc1Cl] |
| A261 | 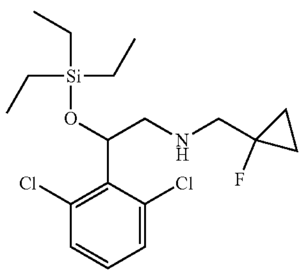 [SMILES: CC[Si](CC)(CC)OC(CNCC1(F)CC1)c1c(Cl)cccc1Cl] |
| A262 | 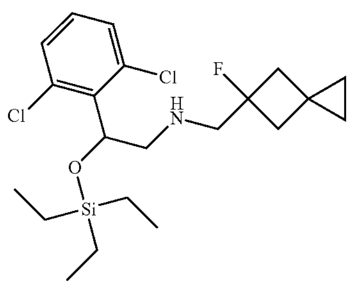 [SMILES: CC[Si](CC)(CC)OC(CNCC1(F)CC2(CC2)C1)c1c(Cl)cccc1Cl] |
| A263 | 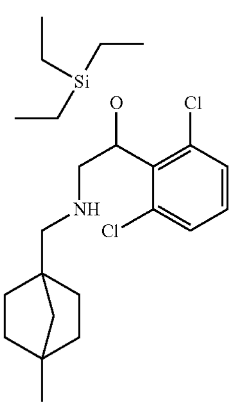 |
| A264 | 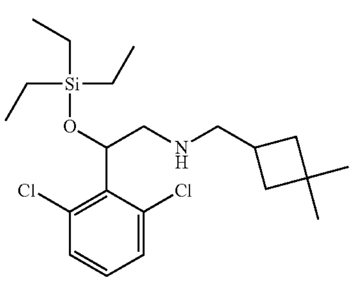 [SMILES: CC[Si](CC)(CC)OC(CNCC1CC(C)(C)C1)c1c(Cl)cccc1Cl] |

| reference example | structure |
|---|---|
| A265 | 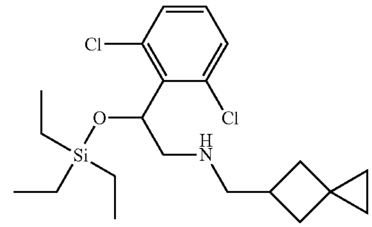 [SMILES: CC[Si](CC)(CC)OC(CNCC1CC2(CC2)C1)c1c(Cl)cccc1Cl] |
| A266 | 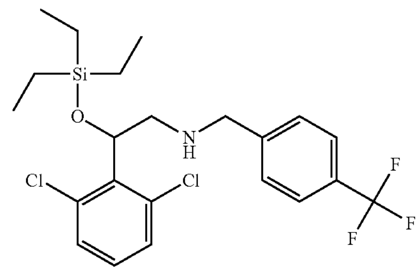 [SMILES: CC[Si](CC)(CC)OC(CNCc1ccc(C(F)(F)F)cc1)c1c(Cl)cccc1Cl] |
| A267 | 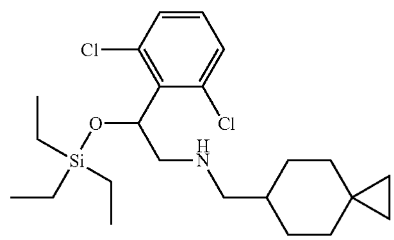 [SMILES: CC[Si](CC)(CC)OC(CNCC1CCC2(CC1)CC2)c1c(Cl)cccc1Cl] |
| A268 | 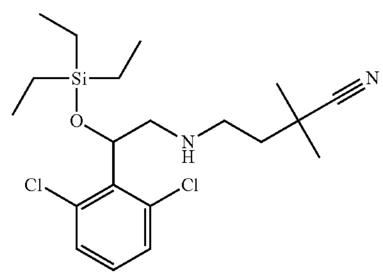 [SMILES: CC[Si](CC)(CC)OC(CNCCC(C)(C)C#N)c1c(Cl)cccc1Cl] |
| A269 | 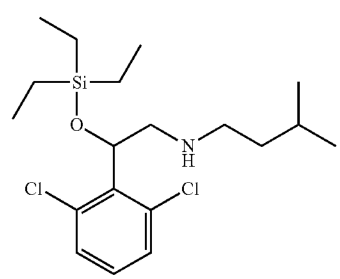 [SMILES: CC[Si](CC)(CC)OC(CNCCC(C)C)c1c(Cl)cccc1Cl] |
| A270 | 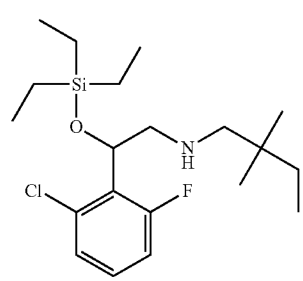 [SMILES: CCC(C)(C)CNCC(O[Si](CC)(CC)CC)c1c(F)cccc1Cl] |

| reference example | structure |
|---|---|
| A271 | 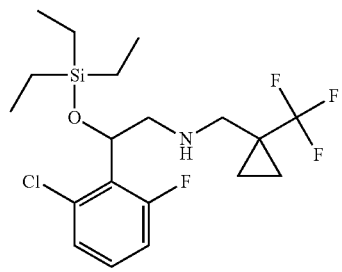 [SMILES: CC[Si](CC)(CC)OC(CNCC1(C(F)(F)F)CC1)c1c(F)cccc1Cl] |
| A272 | 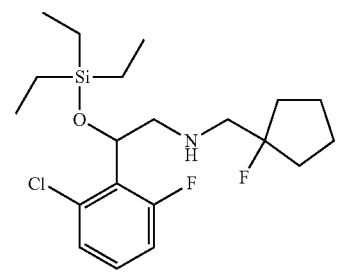 [SMILES: CC[Si](CC)(CC)OC(CNCC1(F)CCCC1)c1c(F)cccc1Cl] |
| A273 | 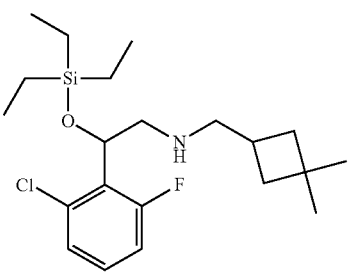 [SMILES: CC[Si](CC)(CC)OC(CNCC1CC(C)(C)C1)c1c(F)cccc1Cl] |
| A274 | 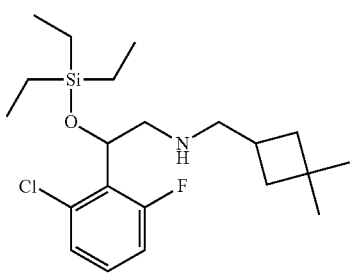 |
| A275 | 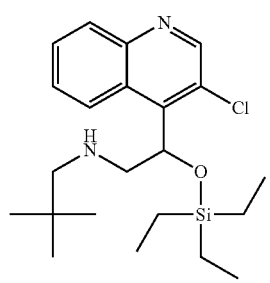 [SMILES: CC[Si](CC)(CC)OC(CNCC(C)(C)C)c1c(Cl)cnc2ccccc12] |
| reference example | structure |
|---|---|
| A276 | 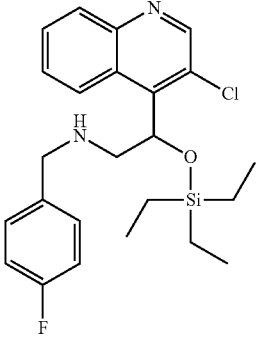 [SMILES: CC[Si](CC)(CC)OC(CNCc1ccc(F)cc1)c1c(Cl)cnc2ccccc12] |
| A277 | 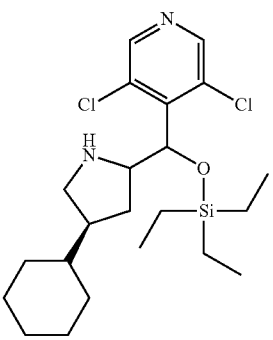 [SMILES: CC[Si](CC)(CC)OC(c1c(Cl)cncc1Cl)C1C[C@@H](C2CCCCC2)CN1] |
| A278 | 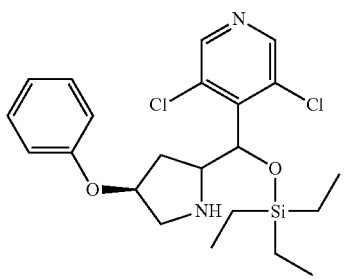 [SMILES: CC[Si](CC)(CC)OC(c1c(Cl)cncc1Cl)C1C[C@H](Oc2ccccc2)CN1] |
| A279 | 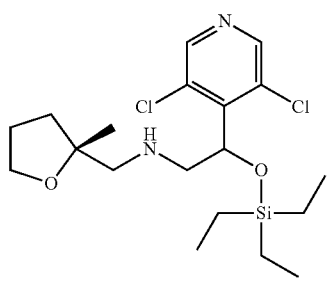 [SMILES: CC[Si](CC)(CC)OC(CNC[C@@]1(C)CCCO1)c1c(Cl)cncc1Cl] |
| A280 | 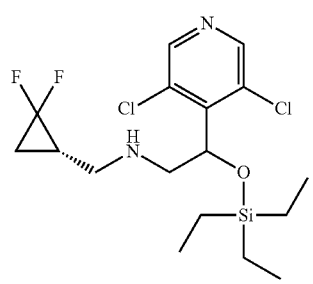 [SMILES: CC[Si](CC)(CC)OC(CNC[C@@H]1CC1(F)F)c1c(Cl)cncc1Cl] |

| reference example | structure |
|---|---|
| A281 | 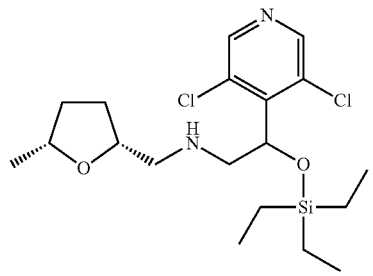 [SMILES: CC[Si](CC)(CC)OC(CNC[C@H]1CC[C@@H](C)O1)c1c(Cl)cncc1Cl] |
| A282 | 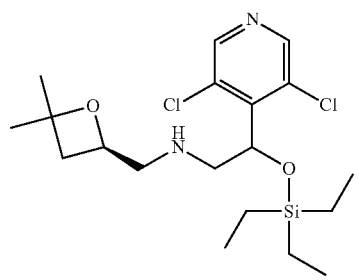 [SMILES: CC[Si](CC)(CC)OC(CNC[C@H]1CC(C)(C)O1)c1c(Cl)cncc1Cl] |
| A283 | 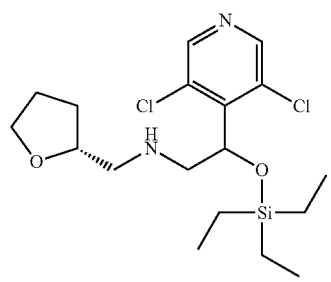 [SMILES: CC[Si](CC)(CC)OC(CNC[C@H]1CCCO1)c1c(Cl)cncc1Cl] |
| A284 | 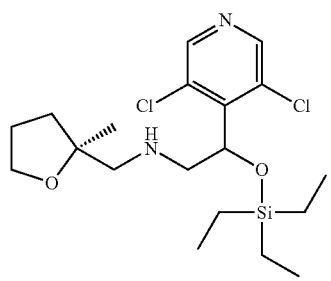 [SMILES: CC[Si](CC)(CC)OC(CNC[C@]1(C)CCCO1)c1c(Cl)cncc1Cl] |
| A285 | 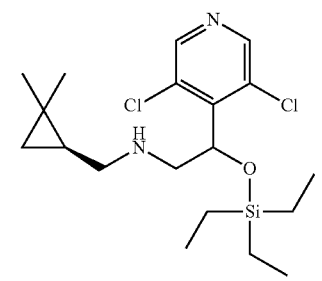 [SMILES: CC[Si](CC)(CC)OC(CNC[C@H]1CC1(C)C)c1c(Cl)cncc1Cl] |
| reference example | structure |
|---|---|
| A286 | 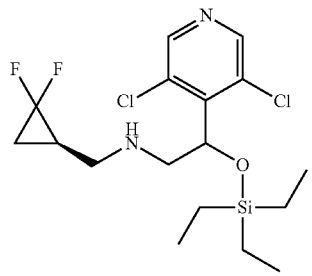 [SMILES: CC[Si](CC)(CC)OC(CNC[C@H]1CC1(F)F)c1c(Cl)cncc1Cl] |
| A287 | 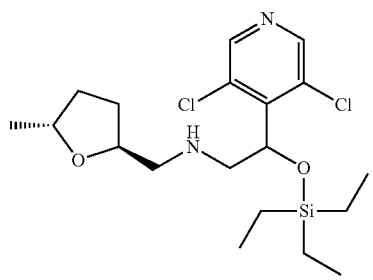 [SMILES: CC[Si](CC)(CC)OC(CNC[C@@H]1CC[C@@H](C)O1)c1c(Cl)cncc1Cl] |
| A288 | 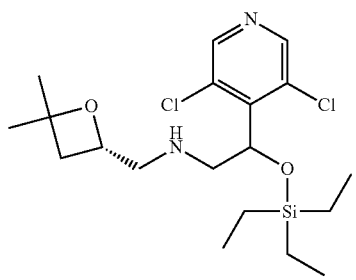 [SMILES: CC[Si](CC)(CC)OC(CNC[C@@H]1CC(C)(C)O1)c1c(Cl)cncc1Cl] |
| A289 | 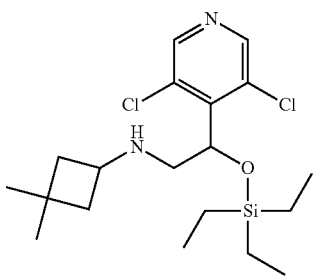 [SMILES: CC[Si](CC)(CC)OC(CNC1CC(C)(C)C1)c1c(Cl)cncc1Cl] |
| A290 | 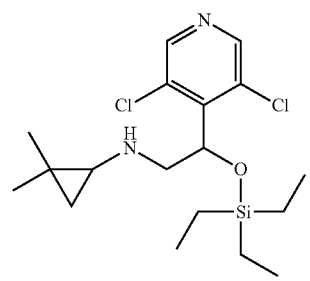 [SMILES: CC[Si](CC)(CC)OC(CNC1CC1(C)C)c1c(Cl)cncc1Cl] |

-continued

| reference example | structure |
|---|---|
| A291 | (3,5-dichloropyridin-4-yl, CH(OTES)CH2NH-spiro[3.3]heptyl) |
| A292 | (3,5-dichloropyridin-4-yl, CH(OTES)CH2NH-(3,3-dimethylcyclobutyl)) |
| A293 | (3,5-dichloropyridin-4-yl, CH(OTES)CH2NH-spiro[3.3]heptyl) |
| A294 | (3,5-dichloropyridin-4-yl, CH(OTES)CH2NHCH2C(CH3)2CF3) |
| A295 | (3,5-dichloropyridin-4-yl, CH(OTES)CH2NHCH2C(Et)2H) |

-continued

| reference example | structure |
|---|---|
| A296 | (3,5-dichloropyridin-4-yl, CH(OTES)CH2NHCH2C(CH3)2OEt) |
| A297 | (3,5-dichloropyridin-4-yl, CH(OTES)CH2NHCH2-(1-methyl-3,3-difluorocyclobutyl)) |
| A298 | (3,5-dichloropyridin-4-yl, CH(OTES)CH2NHCH2-(1-methylcyclobutyl)) |
| A299 | (3,5-dichloropyridin-4-yl, CH(OTES)CH2NHCH2-(1-(trifluoromethyl)cyclobutyl)) |
| A300 | (3,5-dichloropyridin-4-yl, CH(OTES)CH2NHCH2-(1-ethylcyclobutyl)) |

TABLE-continued
| reference example | structure |
|---|---|
| A301 | 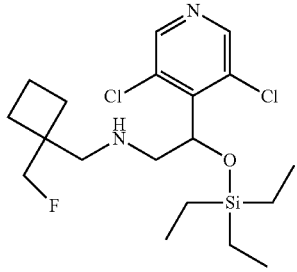 [SMILES: CC[Si](CC)(CC)OC(CNCC1(CF)CCC1)c1c(Cl)cncc1Cl] |
| A302 | 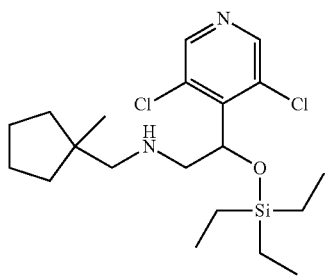 [SMILES: CC[Si](CC)(CC)OC(CNCC1(C)CCCC1)c1c(Cl)cncc1Cl] |
| A303 | 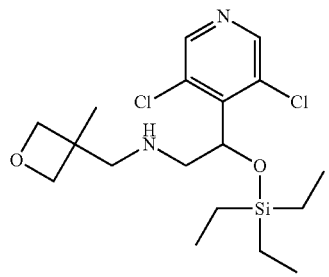 [SMILES: CC[Si](CC)(CC)OC(CNCC1(C)COC1)c1c(Cl)cncc1Cl] |
| A304 | 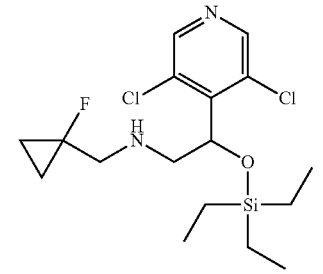 [SMILES: CC[Si](CC)(CC)OC(CNCC1(F)CC1)c1c(Cl)cncc1Cl] |
| A305 | 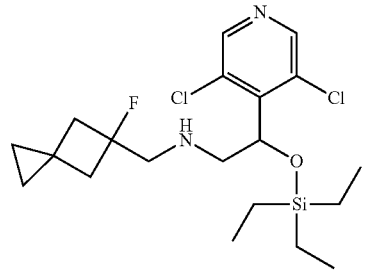 [SMILES: CC[Si](CC)(CC)OC(CNCC1(F)CC2(CC2)C1)c1c(Cl)cncc1Cl] |
| reference example | structure |
|---|---|
| A306 | |
| A307 | |
| A308 | |
| A309 | |
| A310 | 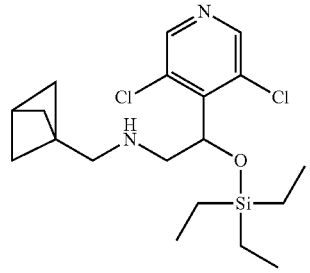 [SMILES: CC[Si](CC)(CC)OC(CNCC12CC(C1)C2)c1c(Cl)cncc1Cl] |

| reference example | structure |
|---|---|
| A311 | 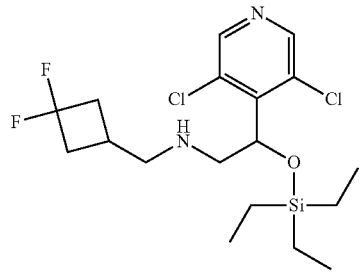 [SMILES: CC[Si](CC)(CC)OC(CNCC1CC(F)(F)C1)c1c(Cl)cncc1Cl] |
| A312 | 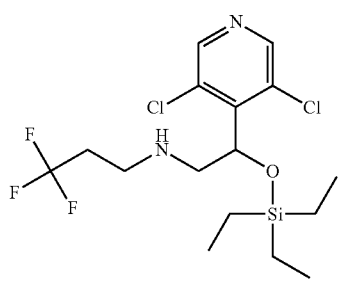 [SMILES: CC[Si](CC)(CC)OC(CNCCC(F)(F)F)c1c(Cl)cncc1Cl] |
| A313 | 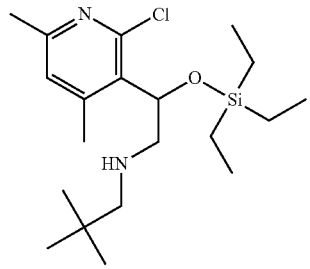 [SMILES: CC[Si](CC)(CC)OC(CNCC(C)(C)C)c1c(C)cc(C)nc1Cl] |
| A314 | 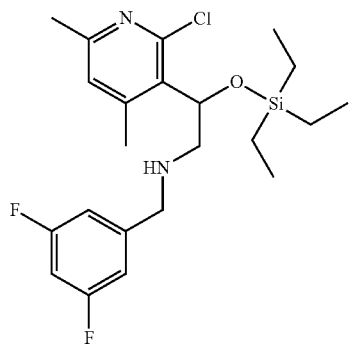 [SMILES: CC[Si](CC)(CC)OC(CNCc1cc(F)cc(F)c1)c1c(C)cc(C)nc1Cl] |
| A315 | 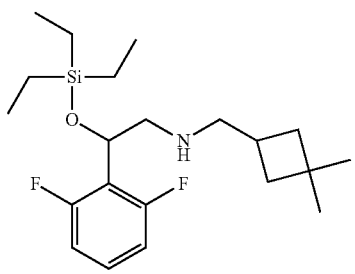 [SMILES: CC[Si](CC)(CC)OC(CNCC1CC(C)(C)C1)c1c(F)cccc1F] |
| reference example | structure |
|---|---|
| A316 | 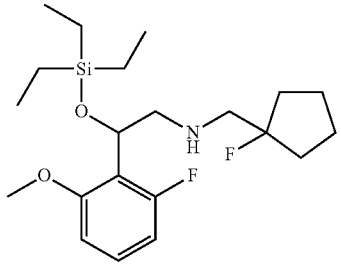 [SMILES: CC[Si](CC)(CC)OC(CNCC1(F)CCCC1)c1c(F)cccc1OC] |
| A317 | 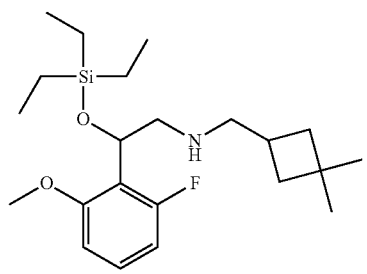 |
| A318 | 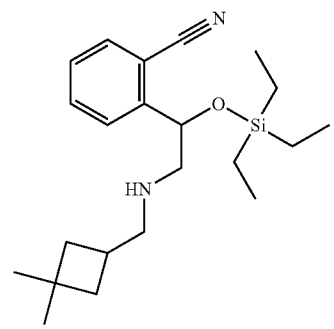 [SMILES: CC[Si](CC)(CC)OC(CNCC1CC(C)(C)C1)c1ccccc1C#N] |
Reference Example B10
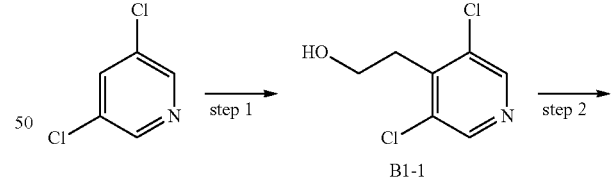
B1-1
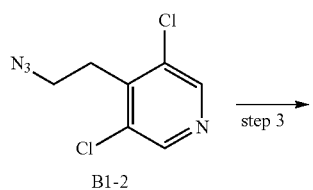
B1-2
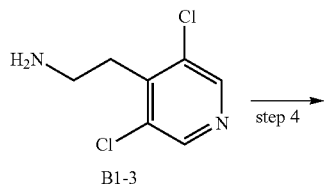
B1-3

-continued

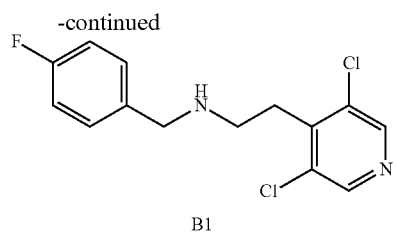

B1

Step 1: 2-(3,5-dichloropyridin-4-yl)ethanol (B1-1)

To a solution of 3,5-dichloropyridine (4.0 g, 27.0 mmol) in THF (70 mL) was added LDA (1.8 M in THF/heptane/ethylbenzene, 22.0 mL, 39.6 mmol) at −78° C. and the mixture was stirred at the same temperature for 2 h, and then ethylene oxide (1.2 M in THF, 25 ml, 30.0 mmol) was added. The reaction mixture was allowed to warm to room temperature gradually and stirred for 1 h at room temperature. The reaction mixture was quenched by adding saturated aqueous $NH_4Cl$ solution and extracted with EtOAc. The organic layer was washed with brine (2 times) and dried over $MgSO_4$. After the solvent was removed, the residue was purified by column chromatography on silica gel to give compound B1-1 (3.1 g, 60%) as a yellow solid.

Step 2: 4-(2-azidoethyl)-3,5-dichloropyridine (B1-2)

To a solution of compound B1-1 (3.1 g, 16.2 mmol) in THF (60 mL) were added DIAD (6.3 mL, 32.0 mmol), triphenylphosphine (8.52 g, 32.5 mmol) and DPPA (6.98 mL, 32.5 mmol) at 0° C. The reaction mixture was allowed to warm to room temperature gradually and stirred at room temperature for 4.5 h. The reaction mixture was quenched by adding water and extracted with EtOAc. The organic layer washed with brine (×2) and dried over $MgSO_4$. After the solvent was removed, the residue was purified by column chromatography on silica gel to give compound B1-2 (2.4 g, 68%) as a yellow oil.

Step 3: 2-(3,5-dichloropyridin-4-yl)ethanamine (B1-3)

To a solution of compound B1-2 (2.4 g, 11.1 mmol) in THF (25 mL) was added triphenylphosphine (2.9 g, 22.1 mmol) at 0° C. The mixture was stirred at room temperature for 2 h, and then water (2.5 mL) was added. The reaction mixture was allowed to warm to room temperature gradually and stirred at room temperature for 22 h. The reaction mixture was quenched by adding 2 M aqueous HCl (10 mL) and diluted with EtOAc. The aqueous layer washed with EtOAc×3, and then basified with 2 M aqueous NaOH to pH 12. The aqueous layer was extracted with EtOAc, washed with brine (×2) and dried over $MgSO_4$. Drying the solution under high vacuum yielded compound B1-3 (1.9 g, 90%) as a white solid.

Step 4: 2-(3,5-dichloropyridin-4-yl)-N-(4-fluorobenzyl)ethanamine (B1)

To a solution of compound B1-3 (2.9 g, 15.2 mmol) in MeOH (30 mL) was added 4-fluorobenzaldehyde (1.89 g, 15.2 mmol) and the mixture was stirred at room temperature for 3 h. The reaction mixture was cooled to 0° C. and $NaBH_4$ (1.16 g, 30.4 mmol) was added gradually. The reaction mixture was allowed to warm to room temperature and stirred at room temperature for 4 h. The reaction mixture was quenched with water and extracted with EtOAc. The organic layer washed with brine×2 and dried over $MgSO_4$. After the solvent was removed, the residue was purified by column chromatography on silica gel to give compound B1 (3.4 g, 75%) as a pale yellow solid.

Reference Example B2

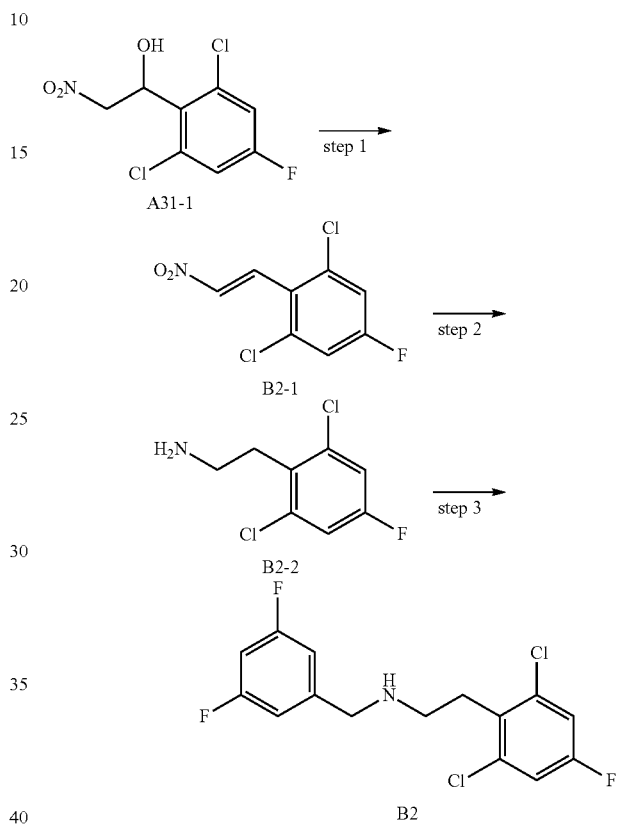

Step 1: 1,3-dichloro-5-fluoro-2-(2-nitrovinyl)benzene (B2-1)

To a stirred solution of compound A31-1 (1.3 g, 5.1 mmol) in dioxane (10 mL) was added 6 M HCl (20 mL) at room temperature and the mixture was stirred at reflux for overnight. The reaction mixture was neutralized with 10% NaOH solution and extracted with EtOAc (2×30 mL). The combined organic layers were washed with water (50 mL), brine (50 mL), dried over anhydrous $Na_2SO_4$ and concentrated under reduced pressure. The residue was purified by column chromatography (silica gel, 10% EtOAc/hexane as eluent) to provide compound B2-1 (0.22 g, 18%) as a colorless oil.

Step 2: 2-(2,6-dichloro-4-fluorophenyl)ethanamine (B2-2)

To a stirred solution of $LiBH_4$ (3.0 M, 4.2 mL, 12.5 mmol) in THF (5 mL) was added TMS-Cl (3.2 mL, 25.2 mmol) dropwise at room temperature and the mixture was stirred at room temperature for 30 min. $N_2$ gas was bubbled through the reaction mixture for 5 min to remove remaining trimethylsilane that had formed. A solution of compound B2-1 (0.22 g, 3.1 mmol) in THF (2 mL) was added dropwise to the mixture at room temperature and later refluxed for 1 h. The reaction mixture was cooled to 0° C. and quenched with MeOH (10 mL) carefully. Solvent was evaporated under reduced pressure and the residue was partitioned between 20% KOH (10 mL) and DCM (20 mL). The organic layer was dried over anhydrous $Na_2SO_4$ and concentrated under reduced pressure. The residue was purified by column chromatography (silica gel, 20% EtOAc/hexane as eluent) to give compound B2-2 (0.21 g, 99%) as a colorless oil.

Step 3: 2-(2,6-dichloro-4-fluorophenyl)-N-(3,5-difluorobenzyl)ethanamine (B2)

Compound B2 (0.21 g, 69%) was obtained as a colorless gum from the reaction of compound B2-2 (0.19 g, 0.91 mmol), 3,5-difluorobenzaldehyde (0.1 mL, 0.91 mmol) and $NaBH_4$ (70 mg, 1.8 mmol) in MeOH (5 mL) using a similar procedure to that described in reference example B1, step 4. $^1$H NMR ($CDCl_3$, 300 MHz): δ 7.13-7.05 (m, 2H), 6.87-6.59 (m, 3H), 3.83 (s, 2H), 3.12-2.80 (m, 4H).

Reference Example B3

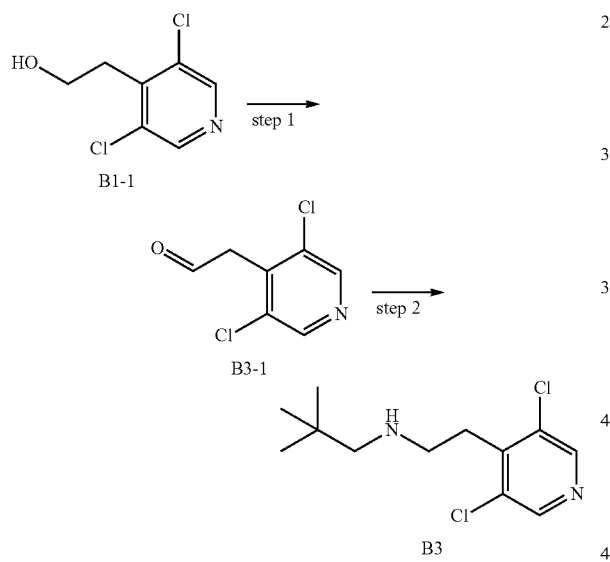

Step 1: 2-(3,5-dichloropyridin-4-yl)acetaldehyde (B3-1)

Compound B1-1 (1.0 g, 5.21 mmol) was dissolved in DCM (26.0 ml) and Dess-Martin periodinane (2.43 g, 5.73 mmol) was added. The solution was stirred for 1 h. The reaction mixture was quenched with 50 ml of 5% $Na_2S_2O_3$, the organic layer washed with saturated $NaHCO_3$ dried with anhydrous $Na_2SO_4$ and concentrated. The product was purified by silica gel column chromatography (40 g column) using 0-100% EtOAc in heptane to afford compound B3-1 (750 mg, 3.95 mmol, 76% yield). LC/MS (ESI+) m/z=189.9 $(M+H)^+$.

Step 2: N-(2-(3,5-dichloropyridin-4-yl)ethyl)-2,2-dimethylpropan-1-amine (B3)

Compound B3-1 (0.65 g, 3.42 mmol) was dissolved in DCM (17 ml) under inert atmosphere, then 2,2-dimethylpropan-1-amine (0.605 ml, 5.13 mmol) was added followed by glacial AcOH (0.198 ml, 3.42 mmol). The solution was stirred for 15 min and then $NaBH(OAc)_3$ (1.450 g, 6.84 mmol) was added. The solution was quenched with 15 ml of saturated $NaHCO_3$ and stirred for 45 min. The organic layer was separated and concentrated. The product was purified via silica gel column chromatography (40 g column) using 0-100% EtOAc in heptane to afford compound B3 (775 mg, 2.97 mmol, 87% yield). LC/MS (ESI+) m/z=261.0 $(M+H)^+$.

Reference Example B13

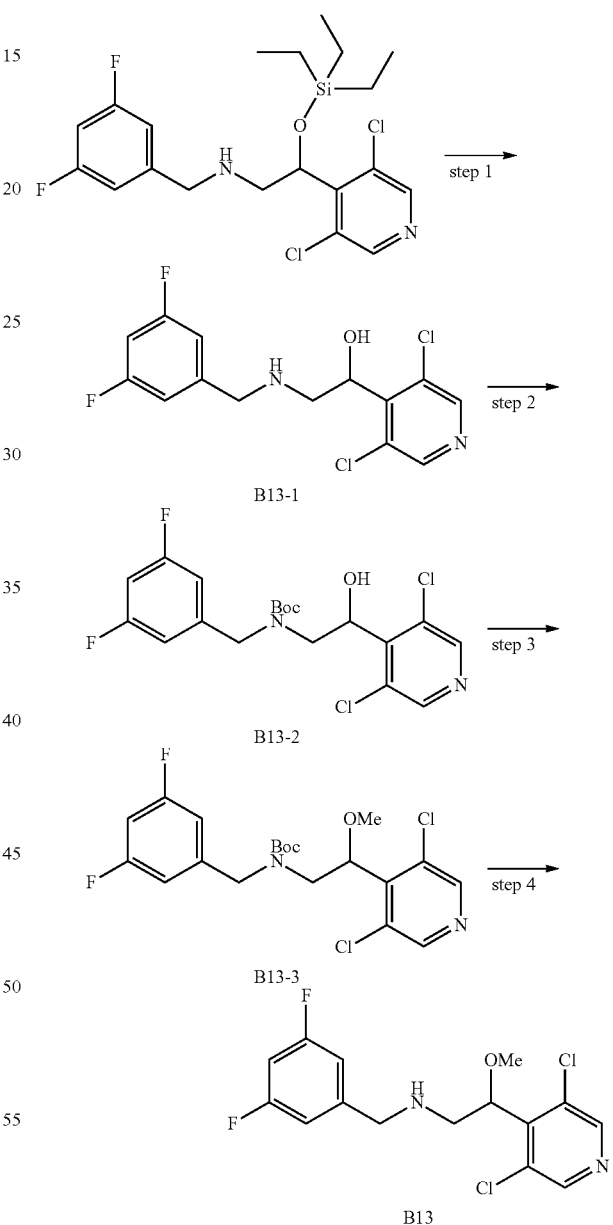

Step 1: 1-(3,5-dichloropyridin-4-yl)-2-(3,5-difluorobenzyl)amino)ethanol (B13-1)

To a stirred solution of 2-(3,5-dichloropyridin-4-yl)-N-(3,5-difluorobenzyl)-2-((triethylsilyl)oxy)ethanamine (0.2 g, 0.44 mmol) in THF (5 mL) was added TBAF (1.0 M in THF, 0.9 mL, 0.88 mmol) dropwise at 0° C., and the mixture was allowed to warm up from 0° C. to room temperature while stirred for 2 h. The reaction mixture was quenched with saturated aqueous NH₄Cl and extracted with EtOAc (2×20 mL). The combined organic layers were washed with water (20 mL), brine (20 mL) and dried over anhydrous Na₂SO₄. Solvent was evaporated under reduced pressure to provide compound B13-1 (0.2 g, crude) as brown color gum.

Step 2: tert-butyl (2-(3,5-dichloropyridin-4-yl)-2-hydroxyethyl)(3,5-difluorobenzyl)carbamate (B13-2)

To a stirred solution of compound B13-1 (0.2 g, 0.6 mmol) in DCM/water (4:1, 5 mL) were added NaHCO₃ (0.1 g, 1.2 mmol) and (Boc)₂O (0.19 g, 0.9 mmol) in DCM (2 mL) at 0° C. The mixture was stirred at room temperature for 2 h. The reaction mixture was quenched with water (50 mL) and extracted with DCM (2×30 mL). The combined organic layers were washed with water (50 mL), brine (50 mL), dried over anhydrous Na₂SO₄ and concentrated under reduced pressure. The residue was purified by column chromatography (silica gel, 20% EtOAc/hexane as eluent) to provide compound B13-2 (0.17 g, 65%) as a colorless oil.

Step 3: tert-butyl (2-(3,5-dichloropyridin-4-yl)-2-methoxyethyl)(3,5-difluorobenzyl)carbamate (B13-3)

To a stirred solution of compound B13-2 (0.1 g, 0.2 mmol) in THF (5 mL) was added NaH (14 mg, 0.5 mmol) followed by dropwise addition of MeI (44 µL, 0.7 mmol) at 0° C. The mixture was stirred at room temperature for 2 h. The reaction mixture was quenched with water (50 mL) and extracted with EtOAc (2×20 mL). The combined organic layers were washed with water (30 mL), brine (30 mL), dried over anhydrous Na₂SO₄ and concentrated under reduced pressure. The residue was purified by column chromatography (silica gel, 10% EtOAc/hexane as eluent) to provide compound B13-3 (0.11 g, 99%) as a colorless oil.

Step 4: tert-butyl 2-(3,5-dichloropyridin-4-yl)-N-(3,5-difluorobenzyl)-2-methoxyethanamine (B13)

To a stirred solution of compound B13-3 (0.28 g, 0.6 mmol) in dioxane (5 mL) was added 4 M HCl (in dioxane, 1.9 mL, 7.4 mmol) at room temperature and the mixture was stirred for overnight. Solvent was evaporated under reduced pressure to provide compound B13-3 (0.1 g, 48%) as a white solid. ¹H NMR (CDCl₃, 300 MHz): δ 8.45 (s, 2H), 6.90-6.63 (m, 3H), 5.14 (dd, J=8.9, 4.1 Hz, 1H), 3.89-3.77 (m, 2H), 3.30-3.23 (m, 4H), 2.78 (dd, J=12.6, 4.1 Hz, 1H).

Reference Example B15

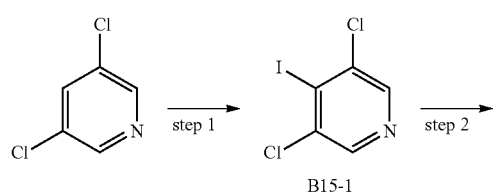

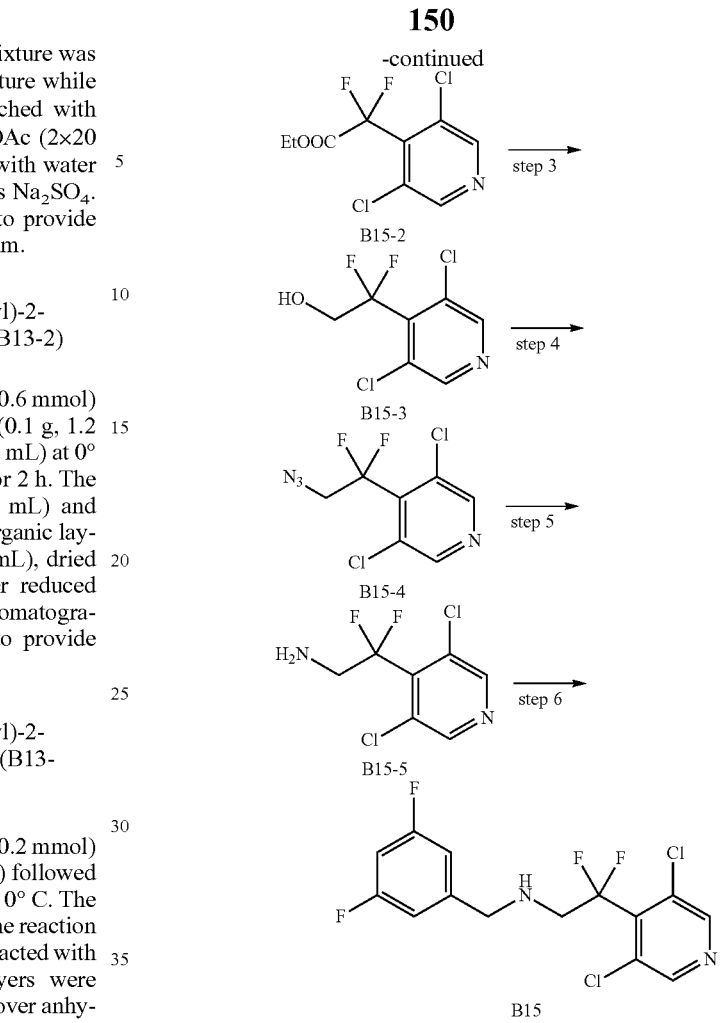

Step 1: 3,5-dichloro-4-iodopyridine (B15-1)

To a stirred solution of 3,5-dichloropyridine (3.0 g, 20.4 mmol) in THF (15 mL) was added LDA (2.0 M solution in THF/heptane/ethylbenzene, 12.14 mL, 24.4 mmol) dropwise at 0° C. and the mixture was stirred at the same temperature for 1 h. A solution of iodine (2.7 g, 21.4 mmol) in THF (10 mL) added dropwise to above mixture. Upon completion of addition, the mixture was stirred at the same temperature for 1 h. The reaction mixture was quenched with water (40 mL) and extracted with EtOAc (4×50 mL). The combined organic layers were washed with brine (50 mL), dried over anhydrous Na₂SO₄ and concentrated under reduced pressure to provide compound B15-1 (3.2 g, 57%) as a yellow gum.

Step 2: ethyl-2-(3,5-dichloropyridin-4-yl)-2,2-difluoroacetate (B15-2)

The mixture of compound B15-1 (530 mg, 0.83 mmol), ethyl 2-bromo-2,2-difluoroacetate (0.12 ml, 1.38 mmol) and Cu (800 mg, 12.5 mmol) in DMSO (10 mL) was heated to 55° C. for 16 h. The reaction mixture was cooled to room temperature and quenched with saturated NH₄Cl solution (100 mL) and extracted with EtOAc (2×50 mL). The combined organic layers were washed with water (50 mL), brine (50 mL), dried over anhydrous Na₂SO₄ and concentrated under reduced pressure. The residue was purified by column chromatography (silica gel, 30% EtOAc/hexane as eluent) to provide compound B15-2 (315 mg, 60%) as yellowish brown gum.

Step 3: 2-(3,5-dichloropyridin-4-yl)-2,2-difluoroethanol (B15-3)

To a stirred solution of compound B15-2 (315 mg, 1.16 mmol) in EtOH (10 mL) was added solid NaBH$_4$ (16.2 mg, 1.74 mmol) in portions at 0° C. The mixture was warmed to room temperature and stirred at the same temperature for 2 h. The reaction mixture was quenched with water (30 mL) and extracted with EtOAc (3×30 mL). The combined organic layers were washed with brine (2×30 mL), dried over anhydrous Na$_2$SO$_4$ and concentrated under reduced pressure. The residue was purified by column chromatography (silica gel, 55% EtOAc/hexane as eluent) to provide compound B15-3 (180 mg, 44%) as a colorless gum.

Step 4: 4-(2-azido-1,1-difluoroethyl)-3,5-dichloropyridine (B15-4)

To a stirred solution of compound B15-3 (140 mg, 0.72 mmol) in THF (5 mL) were added DIAD (0.31 mL, 1.60 mmol), DPPA (0.34 mL, 1.60 mmol) and PPh$_3$ (420 mg, 1.60 mmol) at 0° C. The mixture was warmed to room temperature and stirred at the same temperature for 16 h. The reaction mixture was quenched with water (10 mL) and extracted with EtOAc (2×20 mL). The combined organic layers were washed with brine (20 mL), dried over anhydrous Na$_2$SO$_4$, and concentrated under reduced pressure. The residue was purified by column chromatography (silica gel, 20% EtOAc/hexane as eluent) to provide compound B15-4 (80 mg, 55%) as a yellow gum.

Step 5: 2-(3,5-dichloropyridin-4-yl)-2,2-difluoroethanamine (B15-5)

To a stirred solution of compound B15-4 (80 mg, 0.31 mmol) in EtOAc (2 mL) were added (CH$_3$)$_3$P (0.47 mL, 0.47 mmol) and H$_2$O (0.5 mL). The mixture was stirred at room temperature for 16 h. The reaction mixture was diluted with EtOAc (10 mL) and washed with water (10 mL). The organic layer washed with brine (10 mL), dried over anhydrous Na$_2$SO$_4$, and concentrated under reduced pressure to provide compound B15-5 (60 mg) as a yellow gum. The crude residue was used for next step without purification.

Step 6: 2-(3,5-dichloropyridin-4-yl)-N-(3,5-difluorobenzyl)-2,2-difluoroethanamine (B15)

A mixture of compound B15-5 (113 mg, 0.49 mmol), 3,5-difluorobenzaldehyde (70 mg, 0.49 mmol) and NaBH(OAc)$_3$ (316 mg, 1.49 mmol) in DCM was stirred at room temperature for 16 h. The reaction mixture was quenched with water (20 mL) and extracted with DCM (2×25 mL). The combined organic layers were washed with water (50 mL), brine (50 mL), dried over anhydrous Na$_2$SO$_4$ and concentrated under reduced pressure. The residue was purified by column chromatography (silica gel, 20% EtOAc/hexane as eluent) to provide compound B15 (66 mg, 38%) as a white solid. $^1$H NMR (CDCl$_3$, 300 MHz): δ 8.54-8.53 (m, 2H), 6.73-6.66 (m, 3H), 3.86 (s, 2H), 3.36-3.45 (t, J=28.7 Hz, 2H); LCMS (APCI): 353 (M+H)$^+$.

Reference Example B19

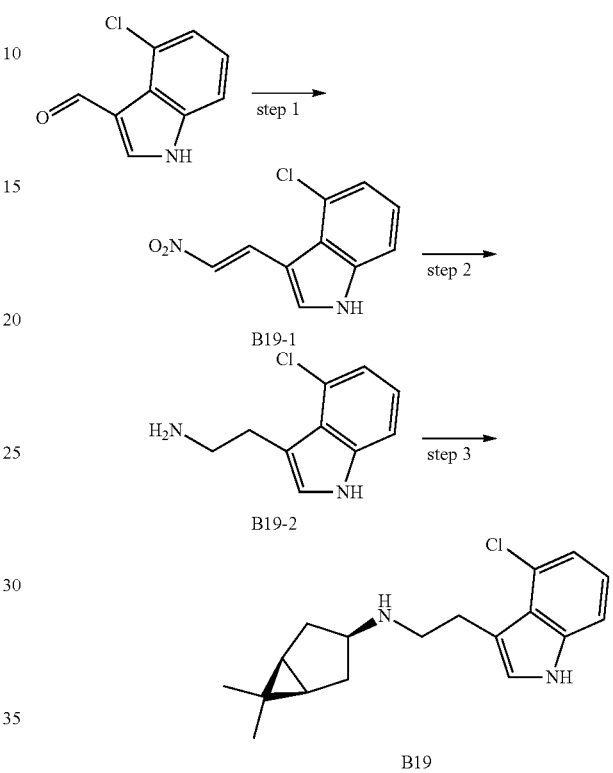

Step 1: (E)-4-chloro-3-(2-nitrovinyl)-1H-indole (B19-1)

A mixture of 4-chloroindole-3-carbaldehyde (314 mg, 1.75 mmol) and ammonium acetate (404 mg, 5.25 mmol) in nitromethane (6 mL) was stirred at 100° C. for 20 min. The reaction mixture was cooled, diluted with water and extracted with EtOAc (2×40 mL). The combined organic layers were washed with brine, dried over MgSO$_4$ and concentrated under reduced pressure. The crude material was purified by silicagel column chromatography (50-100% EtOAc/heptane) to give compound B19-1 (224 mg, 58%) as an orange solid.

Step 2: 2-(4-chloro-1H-indol-3-yl)ethanamine (B19-2)

A solution of compound B19-1 (1.46 g, 6.56 mmol) in THF (25 mL) was added to a stirred slurry of lithium aluminum hydride (995 mg, 26.2 mmol) in THF (50 mL) at room temperature. The mixture was refluxed for 2 h and allowed to cool to room temperature. The reaction was quenched by dropwise addition of water (1.3 mL), followed by 15% NaOH aq. (1.3 mL), followed again by water (3.25 mL). After stirring vigorously for 14 h the mixture was filtered through Celite and the filtrate was concentrated. The residue was dissolved with EtOAc and then extracted with 2 N HCl aq. (2×20 mL). The combined aqueous layers were basified by adding 5 N NaOH aq. and extracted with EtOAc (2×40 mL). The combined organic layers were washed with brine, dried over MgSO₄, filtered and concentrated under reduced pressure to give compound B19-2 (1.02 g, 80%) as a dark red syrup.

Step 3: (1R,3r,5S)—N-(2-(4-chloro-1H-indol-3-yl) ethyl)-6,6-dimethylbicyclo[3.1.0]hexan-3-amine (B19)

Compound B19 (22 mg, 14%) was obtained from the reaction of compound B19-2 (100 mg, 0.514 mmol), compound C22-5 (128 mg, 1.03 mmol), NaBH(OAc)₃ (326 mg, 1.54 mmol) and AcOH (0.108 mL, 2.05 mmol) in DCM (2 mL) using a similar procedure to that described in reference example A31, step 4.

¹H NMR (CDCl₃, 400 MHz) δ: 8.09 (1H, br s), 7.26-7.22 (1H, m), 7.07-7.05 (3H, m), 3.57-3.47 (1H, m), 3.13 (2H, t, J=7.3 Hz), 2.89 (2H, t, J=7.3 Hz), 2.17-2.10 (2H, m), 1.03-0.93 (10H, m).

Reference Example B50

3,5-dichloro-4-(((2R)-4-isopropylpyrrolidin-2-yl) methyl)pyridine (B50)

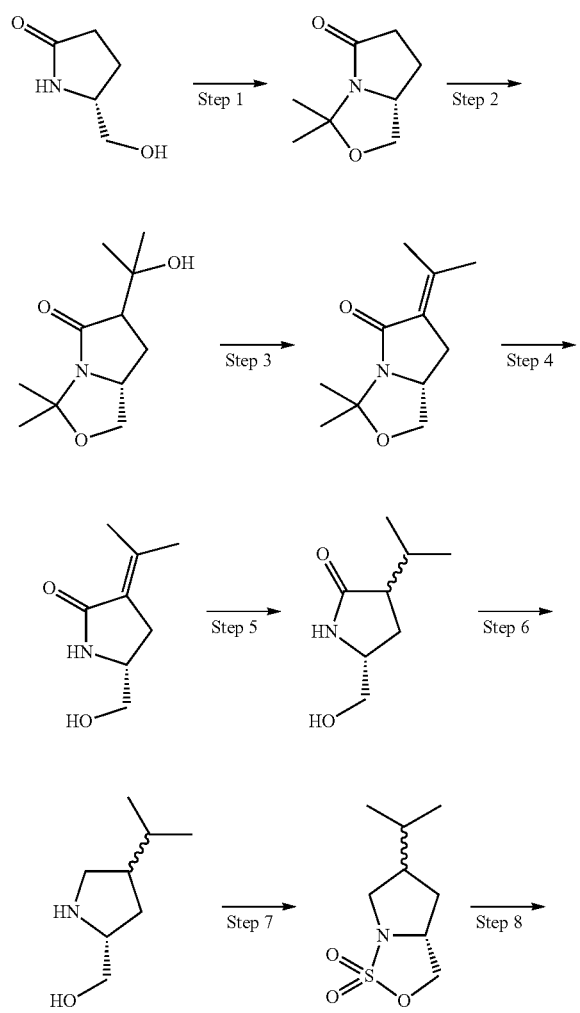

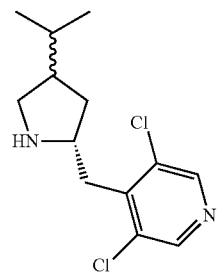

Step 1: (R)-3,3-dimethyltetrahydropyrrolo[1,2-c] oxazol-5(3H)-one

The reaction was equipped with a Dean-Stark then 2,2-dimethoxypropane (17.09 mL, 139 mmol) was added to a stirred mixture of (R)-(−)-5-(hydroxymethyl)-2-pyrrolidinone (5.353 g, 46.5 mmol) and p-toluenesulfonic acid monohydrate (0.126 g, 0.662 mmol) in toluene (100 mL). The reaction mixture was refluxed for 1.5 h and allowed to stir at room temperature overnight. Solvent was evaporated to afford (R)-3,3-dimethyltetrahydropyrrolo[1,2-c]oxazol-5 (3H)-one (7.22 g, 100% yield) as a light yellow solid. ¹H NMR (400 MHz, DMSO-d₆) δ 4.18 (tt, J=8.8, 6.2 Hz, 1H), 4.00 (dd, J=8.1, 5.8 Hz, 1H), 3.40 (t, J=8.6 Hz, 1H), 2.69 (ddd, J=16.4, 12.1, 8.6 Hz, 1H), 2.33 (dd, J=16.3, 9.1 Hz, 1H), 2.02-2.11 (m, 1H), 1.73 (tt, J=12.1, 8.9 Hz, 1H), 1.53 (s, 3H), 1.33 (s, 3H). m/z (ESI, +ve) 156 (M+H).

Step 2: (7aR)-6-(2-hydroxypropan-2-yl)-3,3-dimethyltetrahydropyrrolo[1,2-c]oxazol-5(3H)-one To a solution of (R)-3,3-dimethyltetrahydropyrrolo[1,2-c] oxazol-5(3H)-one (6.68 g, 43.0 mmol) in THF (100 mL) cooled to −78° C., was added lithium diisopropylamide, 2.0 M solution in THF/heptane/ethylbenzene (43.0 mL, 86 mmol) and stirred at −78° C. for 1 h. The resulting mixture was treated with acetone, 99.8%, extra dry, acroseal (6.32 mL, 86 mmol) at −78° C. and then allowed to warm up to room temperature for 16 h. The reaction was quenched with sat. NH₄Cl and extracted with EtOAc (2×200 mL). The combined extracts were washed with brine, dried over Na₂SO₄, filtered and concentrated to provide (7aR)-6-(2-hydroxypropan-2-yl)-3,3-dimethyltetrahydropyrrolo[1,2-c]oxazol-5 (3H)-one (6.088 g, 28.5 mmol, 66.3% yield) as a yellow oil. ¹H NMR (400 MHz, DMSO-d₆) δ 4.50 (s, 1H), 4.07-4.18 (m, 1H), 3.98 (dd, J=8.0, 5.7 Hz, 1H), 3.32-3.35 (m, 1H), 2.50-2.56 (m, 1H), 2.22 (ddd, J=13.4, 7.2, 2.0 Hz, 1H), 1.83 (ddd, J=13.3, 10.4, 7.6 Hz, 1H), 1.54 (s, 3H), 1.32 (s, 3H), 1.21 (s, 3H), 1.14 (s, 3H). m/z (ESI, +ve) 214 (M+H).

Step 3: (R)-3,3-dimethyl-6-(propan-2-ylidene)tetrahydropyrrolo[1,2-c]oxazol-5(3H)-one To a solution of (7aR)-6-(2-hydroxypropan-2-yl)-3,3-dimethyltetrahydropyrrolo[1,2-c]oxazol-5(3H)-one (5.06 g, 23.73 mmol) in DCM (50 mL) at room temperature was added methanesulfonyl chloride (2.75 mL, 35.6 mmol) followed by triethylamine (16.50 mL, 119 mmol) and then heated at 55° C. for 1 h. The resulting mixture was treated with additional methanesulfonyl chloride (2.75 mL, 35.6 mmol) and heated for another 1 h. The reaction mixture was allowed to cool to room temperature, quenched with water (50 mL) and extracted with DCM (2×100 mL). The combined extracts were washed with brine, dried over MgSO₄, filtered and concentrated to provide crude (R)-3,3-dimethyl-6-(propan-2-ylidene)tetrahydropyrrolo[1,2-c]oxazol-5(3H)-one as a brown oil, which was used in the next step without purification. m/z (ESI, +ve) 196 (M+H).

Step 4: (R)-5-(hydroxymethyl)-3-(propan-2-ylidene)pyrrolidin-2-one

To a solution of (R)-3,3-dimethyl-6-(propan-2-ylidene)tetrahydropyrrolo[1,2-c]oxazol-5(3H)-one (4.63 g, 23.73 mmol) in MeOH (50 mL) at room temperature was added p-toluenesulfonic acid monohydrate (0.451 g, 2.373 mmol) and then heated at 60° C. for 45 min. The solvent was evaporated and the crude material was absorbed onto a plug of silica gel and was purified by chromatography through a REDISEP™ pre-packed silica gel column (80 g), eluting with a gradient of 0% to 10% MeOH in DCM to give (R)-5-(hydroxymethyl)-3-(propan-2-ylidene)pyrrolidin-2-one (2.223 g, 14.32 mmol, 60.4% yield) as an yellow solid. ¹H NMR (400 MHz, CDCl₃) δ 6.60 (br. s., 1H), 3.74 (td, J=8.0, 3.9 Hz, 1H), 3.67 (dd, J=11.1, 3.6 Hz, 1H), 3.44 (dd, J=11.1, 7.3 Hz, 1H), 2.75-2.86 (m, 1H), 2.81 (dd, J=16.5, 8.7 Hz, 1H), 2.33-2.43 (m, 1H), 2.23 (s, 3H), 1.77 (s, 3H). m/z (ESI, +ve) 156 (M+H).

Step 5: (5R)-5-(hydroxymethyl)-3-isopropylpyrrolidin-2-one

A mixture of (R)-5-(hydroxymethyl)-3-(propan-2-ylidene)pyrrolidin-2-one (2.223 g, 14.32 mmol) and platinum (iv) oxide (0.325 g, 1.432 mmol) in EtOAc (40 mL)/MeOH (4 mL) at room temperature was stirred in the pressure bottle reactor under H₂ (28 psi to 2 psi) overnight. The resulting mixture was filtered through a pad of Celite, washed with EtOAc, and concentrated to give (5R)-5-(hydroxymethyl)-3-isopropylpyrrolidin-2-one (2.251 g, 14.32 mmol, 90% yield) as a light yellow solid. ¹H NMR (400 MHz, CDCl₃) δ 6.56-6.71 (m, 1H), 3.64-3.80 (m, 2H), 3.37-3.53 (m, 1H), 2.48 (td, J=9.9, 4.5 Hz, 2H), 2.14-2.27 (m, 1H), 1.97-2.13 (m, 1H), 1.50 (ddd, J=12.7, 10.7, 8.3 Hz, 1H), 0.98 (d, J=6.8 Hz, 3H), 0.86 (d, J=6.8 Hz, 3H). m/z (ESI, +ve) 158 (M+H).

Step 6: ((2R)-4-isopropylpyrrolidin-2-yl)methanol

To a solution of (5R)-5-(hydroxymethyl)-3-isopropylpyrrolidin-2-one (2.251 g, 14.32 mmol) in THF (25 mL) was added lithium aluminium hydride, 1.0 M solution in THF (20.05 mL, 20.05 mmol) at room temperature dropwise slowly. The resulting mixture was then refluxed at 75° C. for 2 h. Additional lithium aluminium hydride, 1.0 M solution in THF (20.05 mL, 20.05 mmol) was added and the mixture was refluxed overnight. After 18 h, the reaction mixture was allowed to cool to 0° C. The reaction was quenched by adding saturated aqueous solution of Rochelle's salt. The reaction mixture was stirred vigorously for 1 h and the layers were separated. The aqueous layer was extracted with EtOAc twice and the organics were combined, washed with brine, dried over MgSO₄, filtered and concentrated in vacuo to provide ((2R)-4-isopropylpyrrolidin-2-yl)methanol (1.645 g, 11.49 mmol, 80% yield) as a light yellow oil. The crude material was used in the next step without further purification. m/z (ESI, +ve) 144 (M+H).

Step 7: (3aR)-5-isopropyltetrahydro-3H-pyrrolo[1,2-c][1,2,3]oxathiazole 1,1-dioxide A solution of ((2R)-4-isopropylpyrrolidin-2-yl)methanol (1.639 g, 11.44 mmol) and triethylamine (3.18 mL, 22.89 mmol) in DCM (100 mL) was cooled to −78° C. To this mixture was added sulfuryl chloride, 1.0 M solution in DCM (13.73 mL, 13.73 mmol) dropwise. The reaction mixture was allowed to warm to room temperature overnight. The reaction mixture was concentrated onto a plug of silica gel and purified by ISCO, chromatograph through a REDISEP™ pre-packed silica gel column (40 g), eluting with a gradient of 0% to 10% MeOH (with 2 M NH₃) in DCM to give (3aR)-5-isopropyltetrahydro-3H-pyrrolo[1,2-c][1,2,3]oxathiazole 1,1-dioxide (211.9 mg, 1.032 mmol, 9% yield) as light yellow oil. m/z (ESI, +ve) 206 (M+H).

Step 8: 3,5-dichloro-4-(((2R)-4-isopropylpyrrolidin-2-yl)methyl)pyridine

To a solution of 3,5-dichloropyridine (228 mg, 1.542 mmol) in THF (2.6 mL) at −78° C. was added lithium diisopropylamide, 2.0 M heptane/THF/ethylbenzene (0.976 mL, 1.953 mmol) dropwise. After stirring for 45 min, a solution of (3aR)-5-isopropyltetrahydro-3H-pyrrolo[1,2-c][1,2,3]oxathiazole 1,1-dioxide (211 mg, 1.028 mmol) in THF (3.0 mL) was added dropwise at −78° C. The resulting mixture was allowed to warm to room temperature and then stirred for 3 h. After evaporation of the solvent, the resulting brown solid was treated with 2 N HCl (3 mL) and EtOH (3 mL) and heated at 80° C. for 2 h. The reaction mixture was concentrated to remove the EtOH. The resulting mixture was treated with ice and basified with 2 N NaOH to pH-10 and extracted with EtOAc (2×10 mL). The extracts were dried, evaporated and purified by ISCO, chromatograph through a REDISEP™ pre-packed silica gel column (12 g), eluting with a gradient of 0% to 5% MeOH (with 2 M NH₃) in DCM to give 3,5-dichloro-4-(((2R)-4-isopropylpyrrolidin-2-yl)methyl)pyridine (102 mg, 0.373 mmol, 36.3% yield) as an orange oil. ¹H NMR (400 MHz, DMSO-d₆) δ 8.56 (s, 2H), 3.35-3.51 (m, 1H), 2.84-3.08 (m, 3H), 2.35-2.44 (m, 1H), 1.80-1.93 (m, 1H), 1.55-1.69 (m, 1H), 1.31-1.49 (m, 2H), 1.02-1.17 (m, 1H), 0.85 (t, J=6.7 Hz, 6H).

m/z (ESI, +ve) 273 (M+H).

Reference Example B52

(R)-3,5-dichloro-4-((4,4-diallylpyrrolidin-2-yl)methyl)pyridine

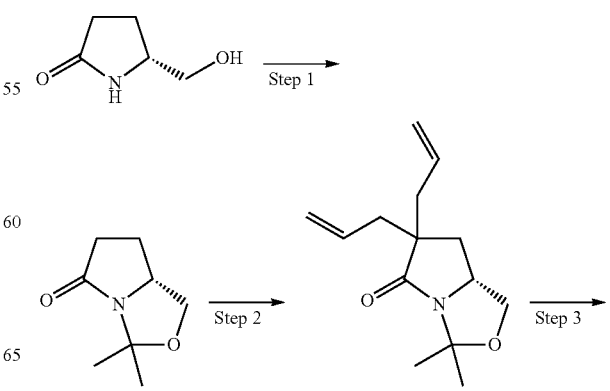

157
-continued

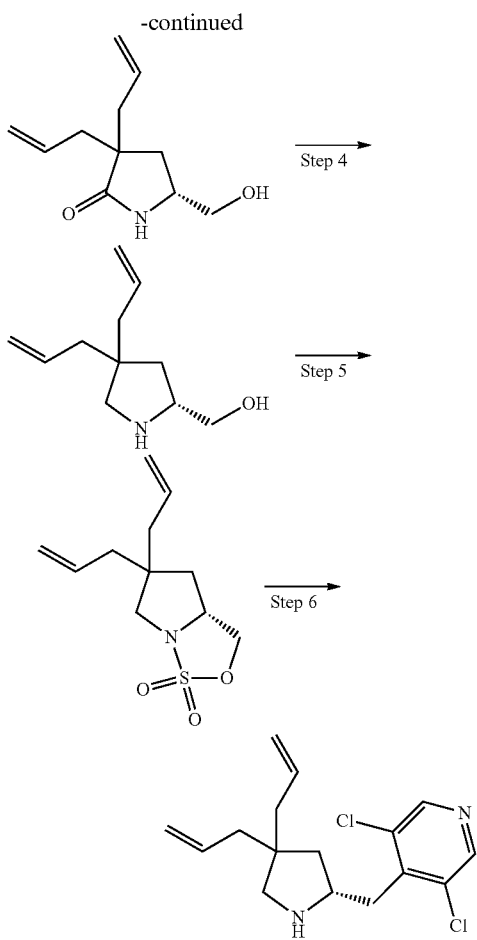

Step 1:
(R)-3,3-dimethyltetrahydropyrrolo[1,2-c]oxazol-5 (3H)-one

To a stirred suspension of (R)-(−)-5-(hydroxymethyl)-2-pyrrolidinone (2.20 g, 19.11 mmol) and p-toluenesulfonic acid (0.018 g, 0.096 mmol) in toluene (54.6 ml), 2,2-dimethoxypropane (7.02 ml, 57.3 mmol) was added and the reaction was refluxed for 2 h. The reaction was equipped with a Dean-Stark then 2,2-dimethoxypropane (7.02 ml, 57.3 mmol) was added and the reaction was refluxed overnight. Solvent was evaporated to afford (R)-3,3-dimethyltetrahydropyrrolo[1,2-c]oxazol-5(3H)-one (3.04 g, 19.59 mmol, 103% yield) as yellow oil. ¹H NMR (400 MHz, CDCl₃) δ 4.27 (tt, J=6.01, 9.00 Hz, 1H), 4.09 (dd, J=5.65, 8.24 Hz, 1H), 3.43-3.50 (m, 1H), 2.81 (ddd, J=8.53, 12.19, 16.65 Hz, 1H), 2.55 (ddd, J=1.01, 9.15, 16.64 Hz, 1H), 2.13-2.23 (m, 1H), 1.72-1.80 (m, 1H), 1.66-1.72 (m, 3H), 1.48 (s, 3H).

Step 2: (R)-6,6-diallyl-3,3-dimethyltetrahydropyrrolo[1,2-c]oxazol-5(3H)-one

To a solution of (R)-3,3-dimethyltetrahydropyrrolo[1,2-c]oxazol-5(3H)-one (2.55 g, 16.43 mmol) in THF (54.8 ml) cooled to −78° C., was added lithium diisopropylamide (14.79 ml, 29.6 mmol) solution. The solution was stirred at this temperature for 1 h before adding allyl bromide (2.133 ml, 24.65 mmol). The reaction mixture was warmed to rt (1 h) then cooled to −78° C. prior addition of lithium diisopropy-

158 lamide (14.79 ml, 29.6 mmol). The mixture was stirred at −78° C. for 1 h before adding allyl bromide (2.133 ml, 24.65 mmol). The mixture was slowly warm to rt and stirred overnight. The reaction was quenched with sat. NH₄Cl and extracted with EtOAc. The combined extracts were washed with brine, dried and concentrated. The crude material was absorbed onto a plug of silica gel and purified by chromatography through a REDISEP™ pre-packed silica gel column (80 g), eluting with a gradient of 0% to 25% EtOAc in hexane, to provide (R)-6,6-diallyl-3,3-dimethyltetrahydropyrrolo[1,2-c]oxazol-5(3H)-one (3.31 g, 14.07 mmol, 86% yield) as light-yellow oil. 1H NMR (400 MHz, CDCl₃) δ 5.66-5.90 (m, 2H), 5.06-5.19 (m, 4H), 4.01-4.11 (m, 2H), 3.29-3.38 (m, 1H), 2.32-2.48 (m, 2H), 2.20-2.29 (m, 1H), 2.12 (dd, J=8.97, 13.79 Hz, 1H), 1.86-1.98 (m, 1H), 1.73-1.84 (m, 1H), 1.65 (s, 3H), 1.46 (s, 3H).

Step 3:
(R)-3,3-diallyl-5-(hydroxymethyl)pyrrolidin-2-one

To a solution of (R)-6,6-diallyl-3,3-dimethyltetrahydropyrrolo[1,2-c]oxazol-5(3H)-one (0.75 g, 3.19 mmol) in MeOH (12 ml) was added p-toluenesulfonic acid monohydrate (0.061 g, 0.319 mmol). The resulting mixture was heated at reflux for 2 h. TLC showed complete conversion.

Solvent was evaporated and the crude material was absorbed onto a plug of silica gel and purified by chromatography through a REDISEP™ pre-packed silica gel column (12 g), eluting with a gradient of 0% to 6% MeOH in DCM, to provide (R)-3,3-diallyl-5-(hydroxymethyl)pyrrolidin-2-one (0.62 g, 3.18 mmol, 100% yield) as white oil. ¹H NMR (400 MHz, CDCl₃) δ 6.68 (br. s., 1H), 5.67-5.86 (m, 2H), 5.06-5.20 (m, 4H), 3.62-3.74 (m, 2H), 3.36-3.45 (m, 1H), 2.37 (ddd, J=6.45, 11.86, 13.15 Hz, 2H), 2.19 (ddd, J=4.79, 8.40, 13.45 Hz, 2H), 1.99 (dd, J=7.72, 13.37 Hz, 1H), 1.69 (dd, J=7.44, 13.40 Hz, 1H).

Step 4: (R)-(4,4-diallylpyrrolidin-2-yl)methanol

To a solution of (R)-3,3-diallyl-5-(hydroxymethyl)pyrrolidin-2-one (0.43 g, 2.202 mmol) in THF (5.51 ml) cooled to 0° C., lithium aluminum hydride, 1.0 M solution in THF (2.86 ml, 2.86 mmol) was added. The mixture was stirred at room temperature overnight. Extra lithium aluminum hydride, 1.0 M solution in THF (2.86 ml, 2.86 mmol) was added and it was refluxed for 6 h. More lithium aluminum hydride, 1.0 M solution in THF (2.86 ml, 2.86 mmol) was added and the mixture was refluxed overnight. The reaction mixture was cooled to 0° C. prior to addition of aq. Rochelle's salt into the mixture slowly. The resulting slurry solution was extracted with EtOAc (10 mL). The combined extracts were washed with brine, dried and concentrated to afford (R)-(4,4-diallylpyrrolidin-2-yl)methanol (0.34 g, 1.876 mmol, 85% yield) as colorless oil. ¹H NMR (400 MHz, CDCl₃) δ 5.72-5.88 (m, 2H), 5.00-5.17 (m, 4H), 3.49-3.59 (m, 1H), 3.30-3.46 (m, 2H), 2.79 (d, J=11.30 Hz, 1H), 2.67 (d, J=11.35 Hz, 1H), 2.08-2.19 (m, 4H), 1.72 (dd, J=6.97, 13.04 Hz, 1H), 1.22-1.39 (m, 1H).

Step 5: (R)-5,5-diallyltetrahydro-3H-pyrrolo[1,2-c][1,2,3]oxathiazole 1,1-dioxide A solution of triethylamine (2.460 ml, 17.65 mmol) and (R)-(4,4-diallylpyrrolidin-2-yl)methanol (1.60 g, 8.83 mmol) in DCM (44.1 ml) was cooled to −78° C. To this mixture was added sulfuryl chloride (0.859 ml, 10.59 mmol) in DCM (44 mL) dropwise in 1 h. The reaction was maintained at this temperature for 3 h, then allowed to warm to room temperature and stirred overnight. The mixture washed with aq. 1 N HCl (30 ml×2), brine (30 ml), dried, filtered and concentrated. The crude material was absorbed onto a plug of silica gel and purified by chromatography through a REDISEP™ pre-packed silica gel column (40 g), eluting with a gradient of 0% to 30% EtOAc in hexane, to provide (R)-5,5-diallyltetrahydro-3H-pyrrolo[1,2-c][1,2,3]oxathiazole 1,1-dioxide (0.66 g, 2.71 mmol, 30.7% yield) as light-yellow oil. 1H NMR (400 MHz, CDCl₃) δ 5.71-5.86 (m, 2H), 5.10-5.20 (m, 4H), 4.57 (dd, J=6.63, 8.76 Hz, 1H), 4.24-4.36 (m, 1H), 4.19 (dd, J=4.66, 8.76 Hz, 1H), 3.21-3.32 (m, 2H), 2.19-2.29 (m, 4H), 2.03-2.18 (m, 1H), 1.57-1.63 (m, 1H).

Step 6: (R)-3,5-dichloro-4-((4,4-diallylpyrrolidin-2-yl)methyl)pyridine

To a solution of 3,5-dichloropyridine (1.069 g, 7.22 mmol) in THF (12.04 ml) at −78° C. was added lithium diisopropylamide, 2.0 M heptane/THF/ethylbenzene (4.57 ml, 9.15 mmol) dropwise. After stirring for 1 h, a solution of (R)-5,5-diallyltetrahydro-3H-pyrrolo[1,2-c][1,2,3]oxathiazole 1,1-dioxide (1.172 g, 4.82 mmol) in THF (10 mL) was added dropwise at −78° C. and the mixture was allowed to warm to room temperature with stirring for 6 h. After evaporating of the solvent, the resulting beige foam was treated with hot 2 N HCl (12 ml) and EtOH (12 ml) overnight. The mixture was cooled to room temperature and basified with 1 N NaOH and extracted with EtOAc. The extracts were dried, evaporated and purified by chromatography through a REDISEP™ pre-packed silica gel column (40 g), eluting with a gradient of 1% to 6% MeOH in DCM, to provide (R)-3,5-dichloro-4-((4,4-diallylpyrrolidin-2-yl)methyl)pyridine (0.70 g, 2.249 mmol, 46.7% yield) as yellow oil. ¹H NMR (400 MHz, CDCl₃) δ 8.46 (s, 2H), 5.66-5.86 (m, 2H), 5.03-5.18 (m, 4H), 3.59-3.72 (m, 1H), 3.25 (d, J=7.15 Hz, 1H), 2.97 (d, J=11.51 Hz, 1H), 2.82 (d, J=11.51 Hz, 1H), 2.10-2.28 (m, 4H), 1.78 (dd, J=13.06, 6.95 Hz, 1H), 1.51-1.61 (m, 1H); LCMS (ESI) m/z 311.0 (M+H)⁺.

Reference Example B53

(R)-3-((3,5-dichloropyridin-4-yl)methyl)-2-azaspiro[4.4]non-7-ene

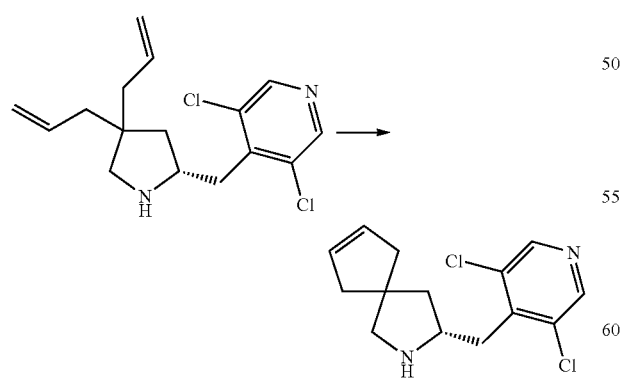

A mixture (R)-3,5-dichloro-4((4,4-diallylpyrrolidin-2-yl)methyl)pyridine (3.1 g, 9.96 mmol) and grubbs catalyst 2nd generation (1.691 g, 1.992 mmol) in DCM (996 ml). The mixture was stirred at 40° C. for 20 h. The mixture was concentrated and absorbed onto a plug of silica gel and purified by chromatography through a Biotage column (100 g), eluting with a gradient of 1% to 50% 1 M NH₃.MeOH in DCM, to provide (R)-3-((3,5-dichloropyridin-4-yl)methyl)-2-azaspiro[4.4]non-7-ene (1.0 g, 3.53 mmol, 35.5% yield) as dark-brown oil. ¹H NMR (400 MHz, CDCl₃) δ 8.45 (s, 2H), 5.61-5.72 (m, 2H), 3.69-3.82 (m, 1H), 3.25 (br. s., 2H), 3.05 (d, J=10.47 Hz, 1H), 2.89-2.97 (m, 1H), 2.47 (br. s., 2H), 2.23-2.37 (m, 2H), 1.93 (dd, J=6.84, 12.59 Hz, 1H), 1.69-1.82 (m, 1H); LCMS (ESI) m/z 283.0 (M+H)⁺.

Reference Example B54

(R)-3-((3,5-dichloropyridin-4-yl)methyl)-2-azaspiro[4.4]non-7-ene

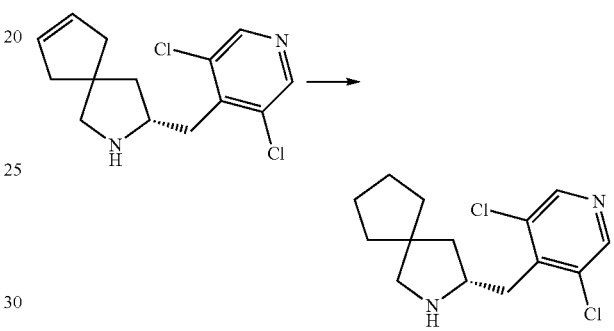

A mixture of (R)-3-((3,5-dichloropyridin-4-yl)methyl)-2-azaspiro[4.4]non-7-ene (0.090 g, 0.318 mmol) and palladium 10 wt. % on activated carbon (0.034 g, 0.032 mmol) in EtOAc (4 ml) was stirred under hydrogen balloon at room temperature for 3 h. Starting material was converted to the desired project with mono-chloro product (~4:1). The crude material was absorbed onto a plug of silica gel and purified by chromatography through a REDISEP™ pre-packed silica gel column (12 g), eluting with a gradient of 5% to 50% 1 M NH₃.MeOH in DCM, to provide (R)-3-((3,5-dichloropyridin-4-yl)methyl)-2-azaspiro[4.4]nonane (0.053 g, 0.186 mmol, 58.5% yield) as a brown oil. 1H NMR (400 MHz, CDCl₃) δ 8.42-8.50 (m, 2H), 3.63-3.83 (m, 1H), 3.28 (br. s., 2H), 3.02 (d, J=10.37 Hz, 1H), 2.87 (br. s., 1H), 1.73-1.83 (m, 1H), 1.54-1.72 (m, 9H), 1.42-1.53 (m, 1H); LCMS (ESI) m/z 285.0 (M+H)⁺.

The following secondary amines were prepared using similar procedure in reference examples described above.

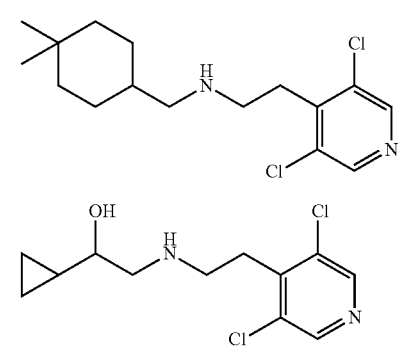

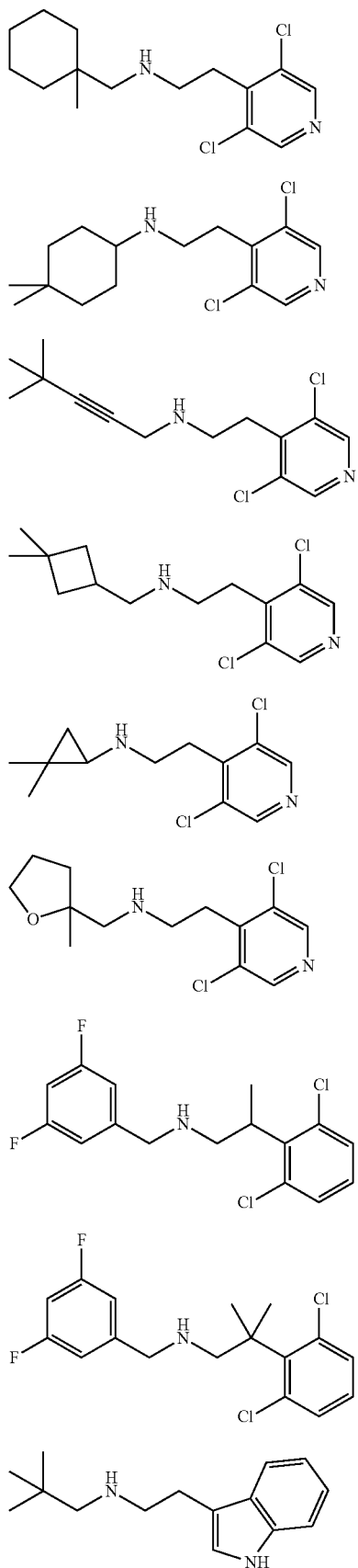
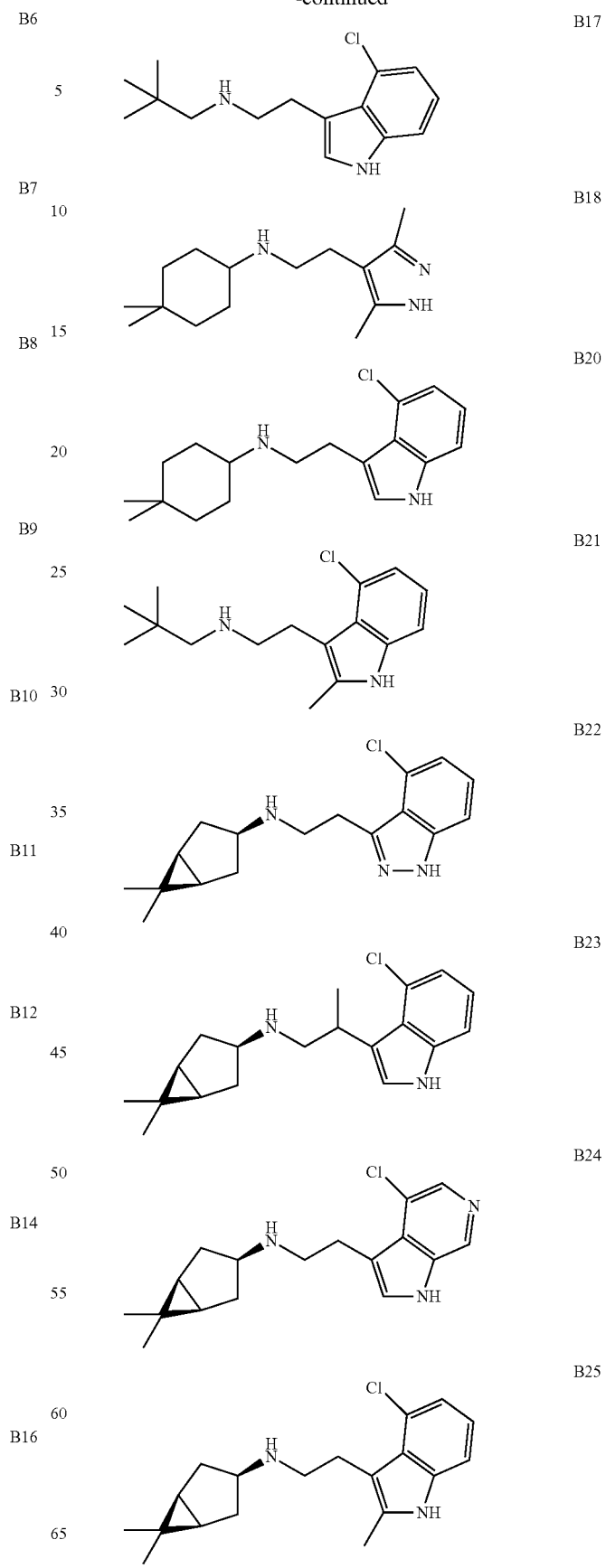

-continued
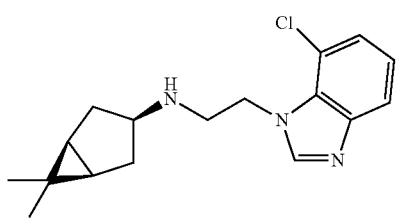
B26
| reference example | structure |
|---|---|
| B27 | 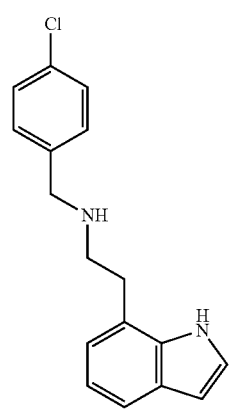 [SMILES: Clc1ccc(CNCCc2cccc3cc[nH]c23)cc1] |
| B28 | 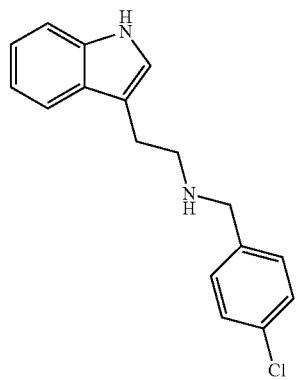 [SMILES: Clc1ccc(CNCCc2c[nH]c3ccccc23)cc1] |
| B29 | 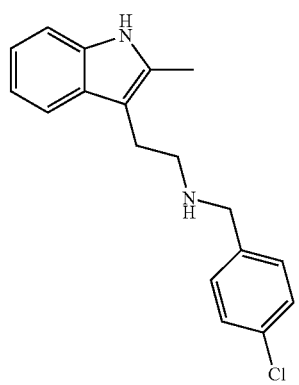 [SMILES: Cc1[nH]c2ccccc2c1CCNCc1ccc(Cl)cc1] |
-continued
| reference example | structure |
|---|---|
| B30 | 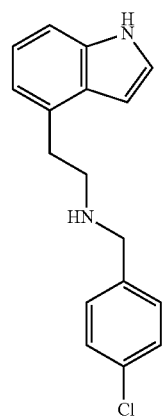 [SMILES: Clc1ccc(CNCCc2cccc3[nH]ccc23)cc1] |
| B31 | 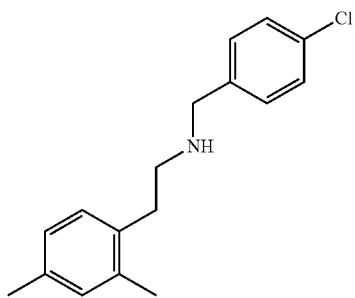 [SMILES: Cc1ccc(CCNCc2ccc(Cl)cc2)c(C)c1] |
| B32 | 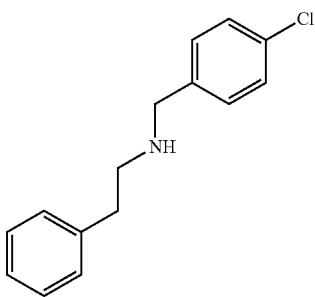 [SMILES: Clc1ccc(CNCCc2ccccc2)cc1] |
| B33 | 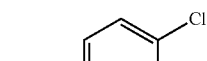 |

-continued
| reference example | structure |
|---|---|
| B34 | 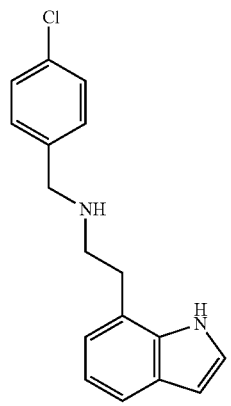 [SMILES: Clc1ccc(CNCCc2cccc3cc[nH]c23)cc1] |
| B35 | 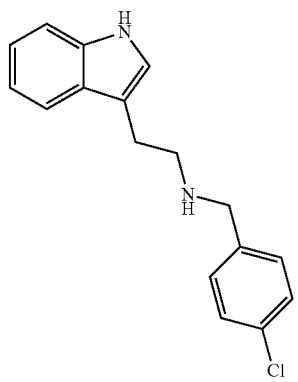 [SMILES: Clc1ccc(CNCCc2c[nH]c3ccccc23)cc1] |
| B36 | 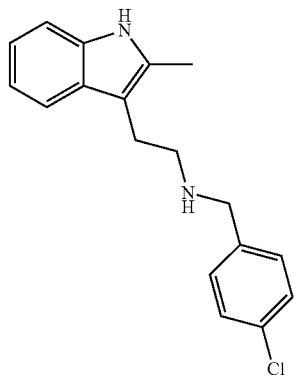 [SMILES: Cc1[nH]c2ccccc2c1CCNCc1ccc(Cl)cc1] |
| B37 | 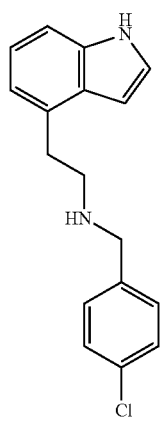 [SMILES: Clc1ccc(CNCCc2cccc3[nH]ccc23)cc1] |
-continued
| reference example | structure |
|---|---|
| B38 | 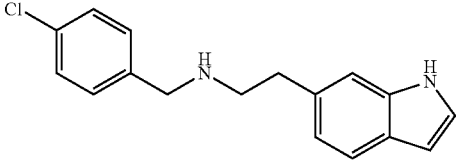 [SMILES: Clc1ccc(CNCCc2ccc3cc[nH]c3c2)cc1] |
| B39 | 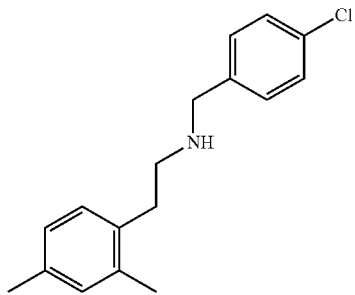 [SMILES: Cc1ccc(CCNCc2ccc(Cl)cc2)c(C)c1] |
| B40 | 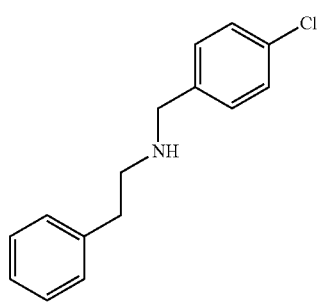 [SMILES: Clc1ccc(CNCCc2ccccc2)cc1] |
| B41 | 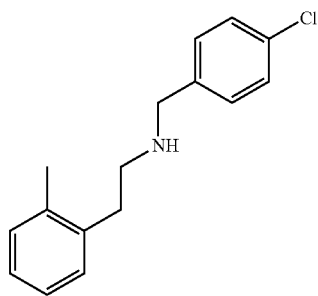 [SMILES: Cc1ccccc1CCNCc1ccc(Cl)cc1] |
| B42 | 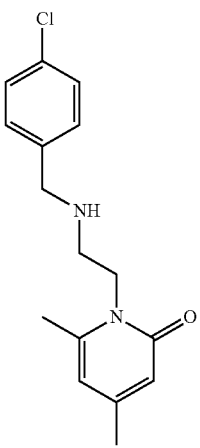 [SMILES: Cc1cc(C)n(CCNCc2ccc(Cl)cc2)c(=O)c1] |

-continued
| reference example | structure |
|---|---|
| B43 | 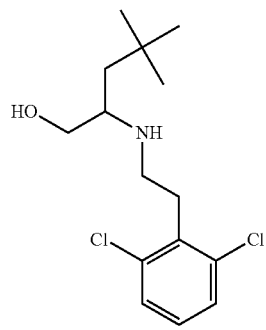 [SMILES: CC(C)(C)CC(CO)NCCc1c(Cl)cccc1Cl] |
| B44 | 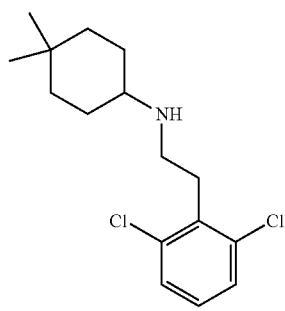 [SMILES: CC1(C)CCC(NCCc2c(Cl)cccc2Cl)CC1] |
| B45 | 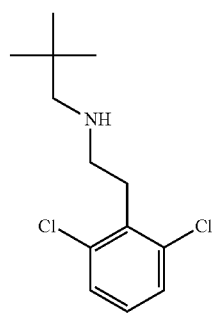 |
| B46 | 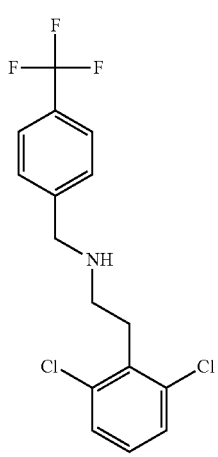 [SMILES: FC(F)(F)c1ccc(CNCCc2c(Cl)cccc2Cl)cc1] |
-continued
| reference example | structure |
|---|---|
| B47 | 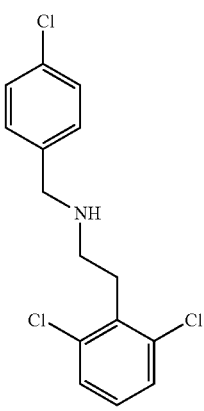 [SMILES: Clc1ccc(CNCCc2c(Cl)cccc2Cl)cc1] |
| B48 | 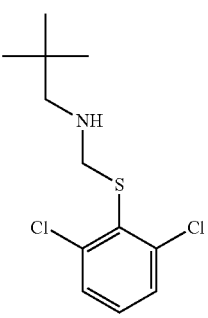 [SMILES: CC(C)(C)CNCSc1c(Cl)cccc1Cl] |
| B49 | 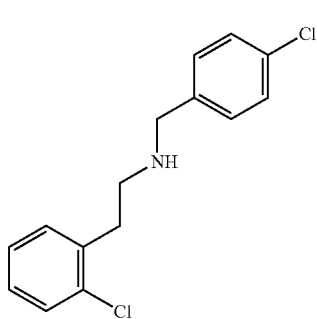 [SMILES: Clc1ccc(CNCCc2ccccc2Cl)cc1] |
| B50 | 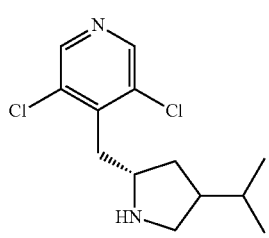 [SMILES: CC(C)C1CN[C@H](Cc2c(Cl)cncc2Cl)C1] |
| B51 | 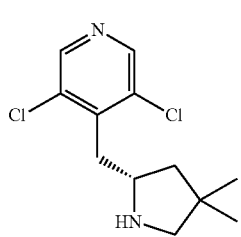 [SMILES: CC1(C)CN[C@H](Cc2c(Cl)cncc2Cl)C1] |

TABLE -continued
| reference example | structure |
|---|---|
| B52 | 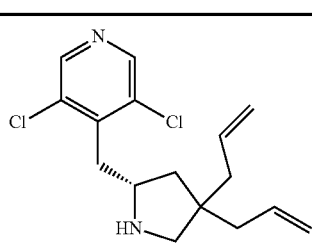 |
| B53 | 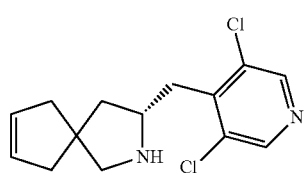 [SMILES: Clc1cncc(Cl)c1C[C@H]1CC2(CC=CC2)CN1] |
| B54 | 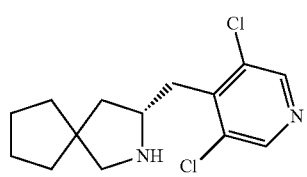 [SMILES: Clc1cncc(Cl)c1C[C@H]1CC2(CCCC2)CN1] |
| B55 | 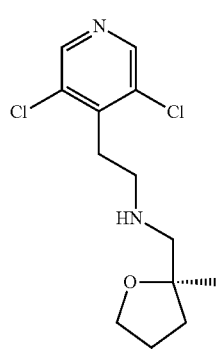 [SMILES: C[C@]1(CNCCc2c(Cl)cncc2Cl)CCCO1] |
| B56 | 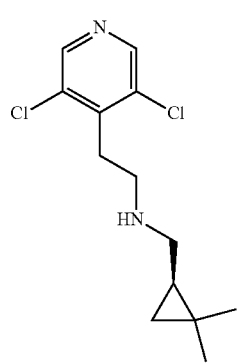 [SMILES: CC1(C)C[C@H]1CNCCc1c(Cl)cncc1Cl] |
| B57 | 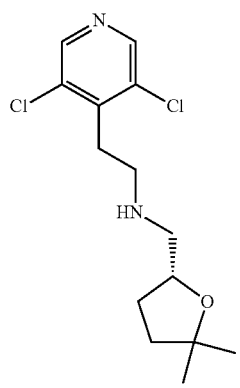 [SMILES: CC1(C)CC[C@H](CNCCc2c(Cl)cncc2Cl)O1] |
| B58 | 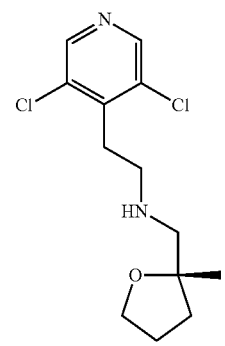 [SMILES: C[C@@]1(CNCCc2c(Cl)cncc2Cl)CCCO1] |
| B59 | 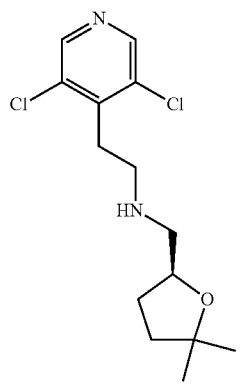 [SMILES: CC1(C)CC[C@@H](CNCCc2c(Cl)cncc2Cl)O1] |
| B60 | 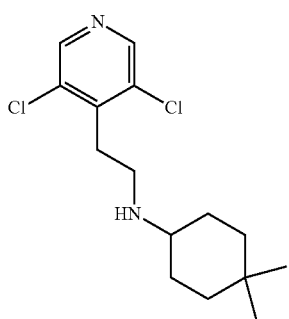 [SMILES: CC1(C)CCC(NCCc2c(Cl)cncc2Cl)CC1] |

-continued
| reference example | structure |
|---|---|
| B61 | 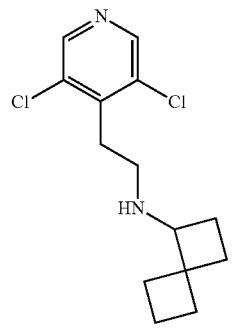 [SMILES: Clc1cncc(Cl)c1CCNC1CCC12CCC2] |
| B62 | 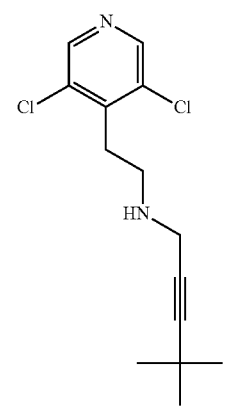 [SMILES: CC(C)(C)C#CCNCCc1c(Cl)cncc1Cl] |
| B63 | 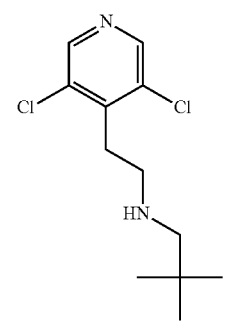 [SMILES: CC(C)(C)CNCCc1c(Cl)cncc1Cl] |
| B64 | 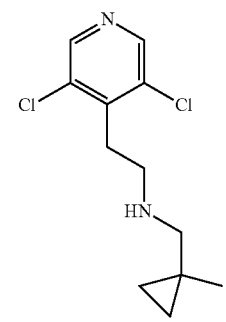 [SMILES: CC1(CNCCc2c(Cl)cncc2Cl)CC1] |
| B65 | 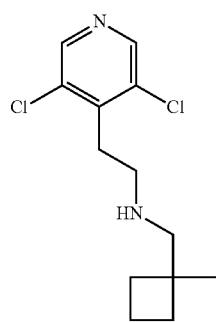 [SMILES: CC1(CNCCc2c(Cl)cncc2Cl)CCC1] |
| B66 | 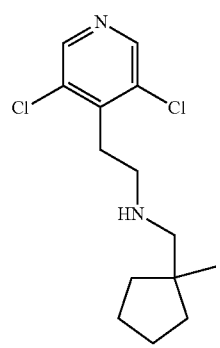 [SMILES: CC1(CNCCc2c(Cl)cncc2Cl)CCCC1] |
| B67 | 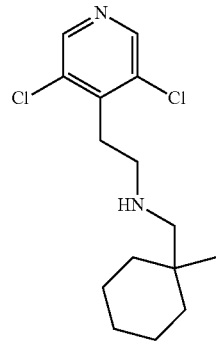 [SMILES: CC1(CNCCc2c(Cl)cncc2Cl)CCCCC1] |
| B68 | 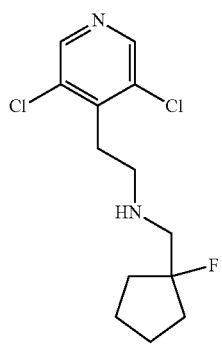 [SMILES: FC1(CNCCc2c(Cl)cncc2Cl)CCCC1] |

| reference example | structure |
|---|---|
| B69 | 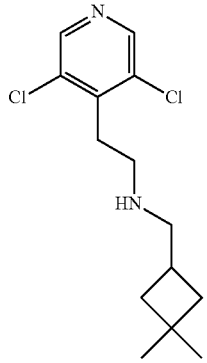 [SMILES: CC1(C)CC(CNCCc2c(Cl)cncc2Cl)C1] |
| B70 | 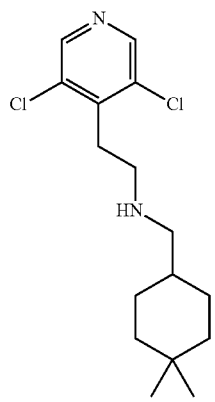 |

Reference Example C1

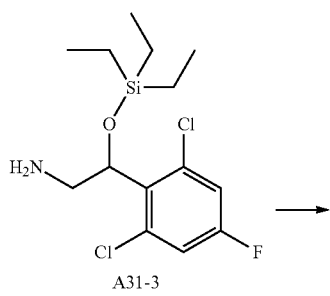

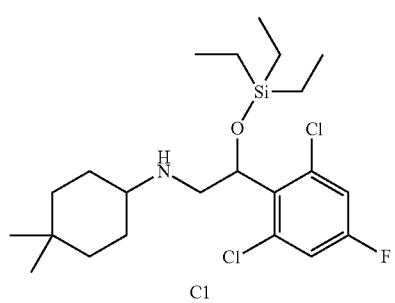

N-(2-(2,6-dichloro-4-fluorophenyl)-2-((triethylsilyl)oxy)ethyl)-4,4-dimethylcyclohexanamine (C1)

To a stirred solution of compound A31-3 (107 mg, 0.32 mmol) in DCM (2 mL) were added 4,4-dimethylcyclohexanone (40 mg, 0.32 mmol), NaBH(OAc)$_3$ (83 mg, 0.38 mmol) and AcOH (101 mg, 0.47 mmol). The resulting mixture was stirred at room temperature for 17 h, then quenched with 0.5 M NaOH aq. (10 mL) and extracted with EtOAc (2×20 mL). The combined organic layers were washed with brine (10 mL), dried over MgSO$_4$ and concentrated under reduced pressure. The residue was purified by silicagel column chromatography (eluent: 5% to 30% EtOAc/hexane) to yield compound C1 (122 mg, 86%) as colorless syrup.

Reference Example C22

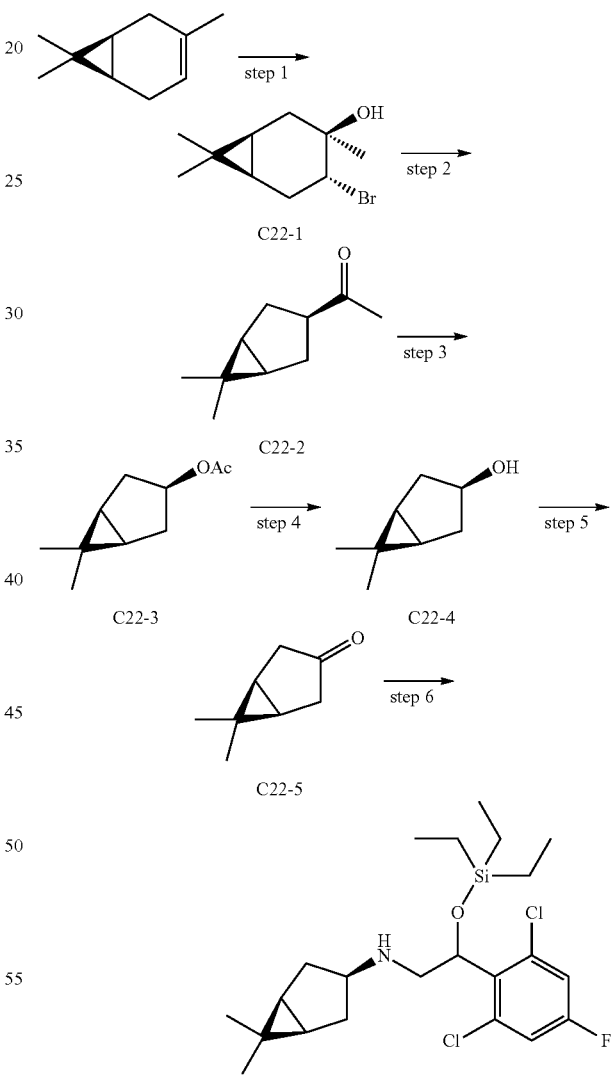

Step 1: (1S,3R,4R,6R)-4-bromo-3,7,7-trimethylbicyclo[4.1.0]heptan-3-ol (C22-1)

A suspension of (+)-3-carene (4.09 g, 30 mmol), CaCO$_3$ (3.90 g, 39 mmol) and NBS (6.94 g, 39 mmol) in water (15 mL) and 1,4-dioxane (30 mL) was stirred at room temperature for 1 h. The mixture was diluted with water (75 mL) and extracted with Et$_2$O (100 mL). The organic layer washed with water (3×50 mL), saturated Na$_2$S$_2$O$_3$ aq. (50 mL), dried over MgSO$_4$ and concentrated under reduced pressure. The residue was purified by silicagel chromatography (10% EtOAc/hexane as eluent) to provide compound C22-1 (4.53 g, 65%) as a white solid.

Step 2: 1-((1R,3r,5S)-6,6-dimethylbicyclo[3.1.0]hexan-3-yl)ethanone (C22-2)

To a solution of compound C22-1 (4.53 g, 19.4 mmol) in water (9 mL) and 1,4-dioxane (127 mL) was added silver(I) oxide (12.16 g, 52.5 mmol) and stirred at room temperature for 22 h. The mixture was filtered through a pad of celite and the filtrate was concentrated under reduced pressure. The residue was diluted with water and extracted with Et$_2$O. The organic layer washed with water, dried over MgSO$_4$ and concentrated under reduced pressure to provide compound C22-2 (2.86 g, 99%) as a pale yellow oil. The crude product was used for next step without purification.

Step 3: (1R,3r,5S)-6,6-dimethylbicyclo[3.1.0]hexan-3-yl acetate (C22-3)

To a solution of compound C22-2 (2.86 g, 18.8 mmol) in DCM (57 mL) was added m-chloroperoxybenzoic acid (6.02 g, 24.4 mmol) at 0° C. and stirred at room temperature for 15 h. The reaction mixture was quenched with 0.2 M aqueous NaOH and extracted with DCM (80 mL and 2×50 mL). The collected organic layers were washed with saturated NaHCO$_3$ aq., water and brine, dried over MgSO$_4$ and concentrated under reduced pressure. The residue was purified by silicagel chromatography (10% EtOAc/hexane as eluent) to provide compound C22-3 (2.35 g, 74%) as a colorless gum.

Step 4: (1R,3r,5S)-6,6-dimethylbicyclo[3.1.0]hexan-3-ol (C22-4)

To a solution of compound C22-3 (2.35 g, 14.0 mmol) in EtOH/water (63 mL, 2:1) was added a solution of LiOH aq. (4 M, 21 mL, 84 mmol). The mixture was stirred at room temperature for 2.5 h. The mixture was diluted with water and extracted with EtOAc (2×80 mL). The combined organic layers were washed with brine, dried over MgSO$_4$ and concentrated under reduced pressure. The residue was purified by silicagel chromatography (35% EtOAc/hexane as eluent) to provide compound C22-4 (1.54 g, 88%) as a colorless oil.

Step 5: (1R,5S)-6,6-dimethylbicyclo[3.1.0]hexan-3-one (C22-5)

Compound C22-4 (240 mg, 1.9 mmol) was dissolved in DCM (5 mL) and Dess-Martin periodinane (968 mg, 2.28 mmol) was added. The reaction mixture was stirred for 3 h. The reaction mixture was quenched with 5% Na$_2$S$_2$O$_3$ and extracted with Et$_2$O (30 mL). The organic layer washed with saturated NaHCO$_3$ aq. twice, dried over MgSO$_4$ and concentrated under reduced pressure to provide compound C22-5 (261 mg, quant.) as a colorless gum. The crude product was used for next step without purification.

Step 6: (1R,3r,5S)—N-(2-(2,6-dichloro-4-fluorophenyl)-2-((triethylsilyl)oxy)ethyl)-6,6-dimethylbicyclo[3.1.0]hexan-3-amine (C22)

Compound C22 (75 mg, 74%) was obtained from the reaction of compound A31-3 (77 mg, 0.228 mmol), compound C22-5 (31 mg, 0.250 mmol), NaBH(OAc)$_3$ (72 mg, 0.341 mmol) and AcOH (0.013 mL, 0.228 mmol) in DCM (2 mL) using a similar procedure to that described in reference example A31, step 4. $^1$H NMR (CDCl$_3$, 400 MHz): δ 7.04 (d, J=8.3 Hz, 2H), 5.48 (dd, J=9.2, J=4.5 Hz, 1H), 3.60-3.51 (m, 1H), 3.19 (dd, J=12.2, J=9.2 Hz, 1H), 2.65 (dd, J=12.2, J=4.5 Hz, 1H), 2.17-2.07 (m, 2H), 1.06-0.97 (m, 10H), 0.87 (t, J=8.0 Hz, 9H), 0.58-0.47 (m, 6H).

Reference Example C45

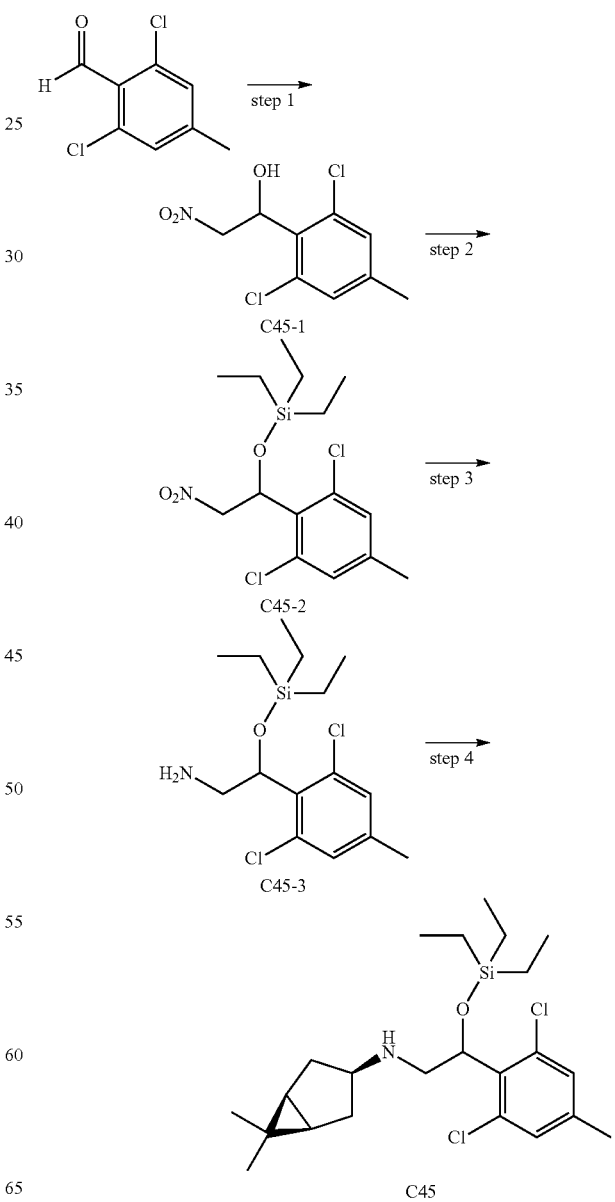

Step 1: 1-(2,6-dichloro-4-methylphenyl)-2-nitroethanol (C45-1)

Compound C45-1 (1.25 g, 96%) was obtained as a colorless gum from the reaction of 2,6-dichloro-4-methylbenzaldehyde (1.0 g, 5.3 mmol) and $K_2CO_3$ (0.28 g, 2.0 mmol) in $CH_3NO_2$ (10 mL) using a similar procedure to that described in example A1, step 2.

Step 2: (1-(2,6-dichloro-4-methylphenyl)-2-nitroethoxy)triethylsilane (C45-2)

Compound C45-2 (1.8 g, crude) was obtained as colorless gum from the reaction of compound C45-1 (1.25 g, 1.0 mmol), TES-Cl (1.0 mL, 1.2 mmol) and imidazole (1.2 g, 3.0 mmol) in DMF (10 mL) using a similar procedure to that described in reference example A1, step 3.

Step 3: 2-(2,6-dichloro-4-methylphenyl)-2-((triethylsilyl)oxy)ethanamine (C45-3)

Compound C45-3 (1.56 g, 94%) was obtained as a brown color oil from the reaction of compound C45-2 (1.8 g, 4.9 mmol), Fe (2.76 g, 49.3 mmol) and $NH_4Cl$ (2.62 g, 49.3 mmol) in EtOH/water (4:1, 20 mL) using a similar procedure to that described in reference example A31, step 3.

Step 4: (1R,3r,5S)—N-(2-(2,6-dichloro-4-methylphenyl)-2-((triethylsilyl)oxy)ethyl)-6,6-dimethylbicyclo[3.1.0]hexan-3-amine (C45)

Compound C45 (75 mg, 44%) was obtained from the reaction of C45-3 (130 mg, 0.389 mmol), ketone C22-5 (49 mg, 0.394 mmol), $NaBH(OAc)_3$ (125 mg, 0.590 mmol) and AcOH (0.023 mL, 0.402 mmol) in DCM (3 mL) using a similar procedure to that described in reference example A31, step 4. $^1H$ NMR ($CDCl_3$, 400 MHz) δ: 7.07 (2H, s), 5.49 (1H, dd, J=9.3, 4.4 Hz), 3.61-3.52 (1H, m), 3.20 (1H, dd, J=12.2, 9.3 Hz), 2.64 (1H, dd, J=12.2, 4.4 Hz), 2.27 (3H, s), 2.17-2.08 (2H, m), 1.08-0.97 (10H, m), 0.86 (9H, t, J=7.8 Hz), 0.56-0.49 (6H, m).

Reference Example C46

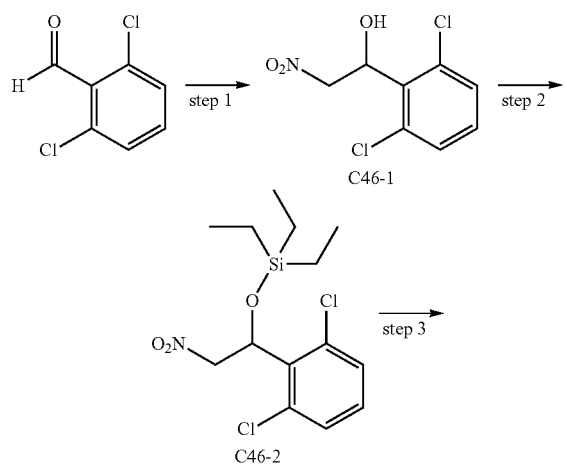

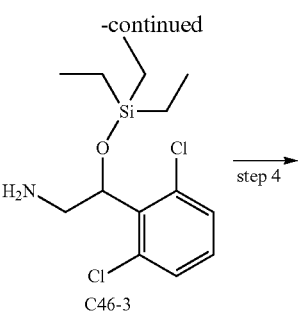

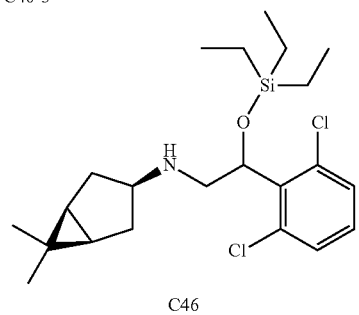

Step 1: 1-(2,6-dichlorophenyl)-2-nitroethanol (C46-1)

Compound C46-1 (0.67 g, crude) was obtained as a yellow gum from the reaction of 2,6-dichlorobenzaldehyde (0.5 g, 2.85 mmol) and $K_2CO_3$ (0.15 g, 1.08 mmol) in $CH_3NO_2$ (10 mL) using a similar procedure to that described in reference example A1, step 2.

Step 2: (1-(2,6-dichlorophenyl)-2-nitroethoxy)triethylsilane (C46-2)

Compound C46-2 (0.95 g, 52%) was obtained as a colorless oil from the reaction of compound C46-1 (0.67 g, 2.83 mmol), TES-Cl (0.57 mL, 3.4 mmol) and imidazole (0.58 g, 8.5 mmol) in DMF (10 mL) using a similar procedure to that described in reference example A1, step 3.

Step 3: 2-(2,6-dichlorophenyl)-2-((triethylsilyl)oxy)ethanamine (C46-3)

Compound C46-3 (0.86 g, crude) was obtained as a colorless oil from the reaction of compound C46-2 (0.95 g, 2.84 mmol), Fe (1.59 g, 28.4 mmol) and $NH_4Cl$ (1.51 g, 28.4 mmol) in EtOH/water (4:1, 20 mL) using a similar procedure to that described in reference example A31, step 3.

Step 4: (1R,3r,5S)—N-(2-(2,6-dichlorophenyl)-2-((triethylsilyl)oxy)ethyl)-6,6-dimethylbicyclo[3.1.0]hexan-3-amine (C46)

Compound C46 (94 mg, 78%) was obtained from the reaction of compound C46-3 (90 mg, 0.281 mmol), ketone C22-5 (42 mg, 0.337 mmol), $NaBH(OAc)_3$ (89 mg, 0.421 mmol) and AcOH (0.016 mL, 0.281 mmol) in DCM (2 mL) using a similar procedure to that described in reference example A31, step 4. $^1H$ NMR ($CDCl_3$, 400 MHz) δ: 7.30-7.26 (2H, m), 7.09 (1H, t, J=7.8 Hz), 5.53 (1H, dd, J=9.3, 4.4 Hz), 3.62-3.53

(1H, m), 3.23 (1H, dd, J=12.2, 9.3 Hz), 2.66 (1H, dd, J=12.2, 4.4 Hz), 2.17-2.10 (2H, m), 1.04-0.99 (8H, m), 0.90-0.84 (11H, m), 0.60-0.45 (6H, m).

Reference Example C80

(1R,3r,5S)—N-(2-(2,6-dichloro-3-fluorophenyl)-2-((triethylsilyl)oxy)ethyl)-6,6-dimethylbicyclo[3.1.0]hexan-3-amine

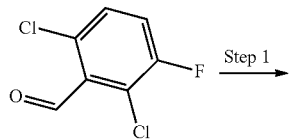

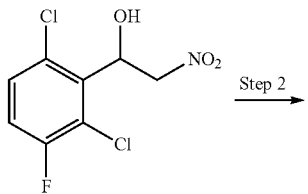

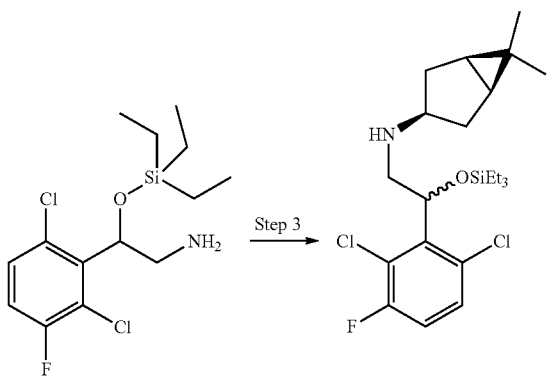

Step 1:
1-(2,6-dichloro-3-fluorophenyl)-2-nitroethanol

In a 3-necked 100 mL RBF, freshly ground potassium carbonate (0.486 g, 3.51 mmol) was added to a solution of 2,6-dichloro-3-fluorobenzaldehyde (2.26 g, 11.71 mmol) in THF (12 ml) at room temperature. Then nitromethane (8.88 ml, 164 mmol) was added. The mixture was stirred at room temperature for 2 h. The mixture was quenched with water (15 mL) and extracted with EtOAc (3×15 mL). The combined organic layer washed with brine, dried over anhydrous Na$_2$SO$_4$ and concentrated under reduced pressure to give 1-(2,6-dichloro-3-fluorophenyl)-2-nitroethanol (2.97 g, 11.69 mmol, 100% yield) as a yellow oil. $^1$H NMR (400 MHz, CDCl$_3$) δ 7.36 (dd, J=8.9, 4.8 Hz, 1H), 7.17 (dd, J=8.9, 7.8 Hz, 1H), 6.27 (m, 1H), 5.19 (dd, J=13.3, 10.1 Hz, 1H), 4.57 (dd, J=13.3, 3.4 Hz, 1H), 3.20 (br. s., 1H).

Step 2: 2-(2,6-dichloro-3-fluorophenyl)-2-((triethylsilyl)oxy)ethanamine

To a 100 mL three-necked RBF were added (1-(2,6-dichloro-3-fluorophenyl)-2-nitroethoxy)triethylsilane (3.64 g, 9.88 mmol) in EtOH (16 ml) and water (4 ml) at room temperature followed by addition of iron (5.52 g, 99 mmol) and ammonium chloride (5.29 g, 99 mmol). The flask was purged with nitrogen and was heated to 60° C. under nitrogen for 3 h. The mixture was cooled to room temperature, diluted with 40 mL of MeOH, sonicated for 10 min. Then the solution was decanted through a pad of celite. This process was repeated for three times. The filtrate was concentrated to ~30 mL and diluted with EtOAc (120 mL). The solid was filtered off and discarded. The filtrate was concentrated under reduced pressure. It was diluted with 50 mL of EtOAc, washed with water, brine, dried over anhydrous MgSO$_4$, and concentrated to give 2-(2,6-dichloro-3-fluorophenyl)-2-((triethylsilyl)oxy)ethanamine hydrochloride as an off-white solid. The HCl salt was dissolved with 50 mL of DCM. The suspension was basicified w/satd aq NaHCO$_3$ (pH=9). The organic layer was separated, washed with brine, dried over anhydrous MgSO$_4$, and concentrated to give 2-(2,6-dichloro-3-fluorophenyl)-2-((triethylsilyl)oxy)ethanamine (2.73 g, 8.07 mmol, 82% yield) as a brown oil. $^1$H NMR (400 MHz, CDCl$_3$) δ 7.23-7.29 (m, 1H), 6.99-7.06 (m, 1H), 5.35 (dd, J=8.6, 4.9 Hz, 1H), 3.29 (dd, J=13.1, 8.7 Hz, 1H), 2.92 (dd, J=13.2, 4.9 Hz, 1H), 0.83-0.93 (m, 9H), 0.46-0.61 (m, 6H); LCMS: 338.2 [M+H]$^+$.

Step 3: (1R,3r,5S)—N-(2-(2,6-dichloro-3-fluorophenyl)-2-((triethylsilyl)oxy)ethyl)-6,6-dimethylbicyclo[3.1.0]hexan-3-amine (1R,5S)-6,6-dimethylbicyclo[3.1.0]hexan-3-one (0.181 g, 1.457 mmol) and 2-(2,6-dichloro-3-fluorophenyl)-2-((triethylsilyl)oxy)ethanamine (0.493 g, 1.457 mmol) were combined in dry EtOH (7 ml) under nitrogen at room temperature and tetraisopropoxytitanium (0.86 ml, 2.91 mmol) was added. The reaction mixture was stirred at room temperature for 2 h. Then, NaBH$_4$ (0.083 g, 2.186 mmol) was added. After 2 h, the reaction solution was quenched with saturated aqueous ammonium chloride (3 mL) and then basified with saturated NaHCO$_3$. The EtOH was then removed under reduced pressure, and the solution was diluted with water EtOAc. Celite was added and the solution was vigorously mixed for 15 min. The solution was then filtered through a pad of celite. The aqueous layer was extracted with EtOAc and the combined organic layers were washed with brine and dried over anhydrous Na$_2$SO$_4$, filtered and concentrated to afford a yellow oil. The crude material was purified by column chromatography (silica gel, eluent: 0% to 10% EtOAc/heptane) to provide (1R,3r,5S)—N-(2-(2,6-dichloro-3-fluorophenyl)-2-((triethylsilyl)oxy)ethyl)-6,6-dimethylbicyclo[3.1.0]hexan-3-amine (414 mg, 0.927 mmol, 63.6% yield) as colorless oil.

$^1$H NMR (400 MHz, CDCl$_3$) δ 7.24 (dd, J=8.9, 4.9 Hz, 1H), 6.98-7.04 (m, 1H), 5.54 (br. s., 1H), 3.59 (t, J=8.8 Hz, 1H), 3.18-3.31 (m, 1H), 2.71 (d, J=12.3 Hz, 1H), 2.15 (d, J=8.1 Hz, 1H), 1.22-1.34 (m, 4H), 1.06 (d, J=5.8 Hz, 2H), 0.99 (d, J=5.0 Hz, 6H), 0.84-0.93 (m, 9H), 0.47-0.59 (m, 6H); LCMS: 446.2 [M+H]$^+$.

The following secondary amines were prepared using similar procedure in reference examples described above.

C2 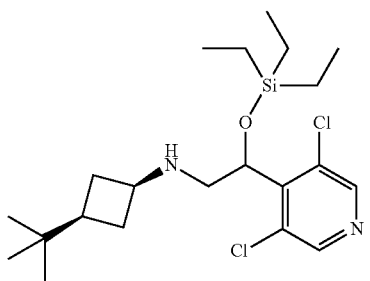
C3 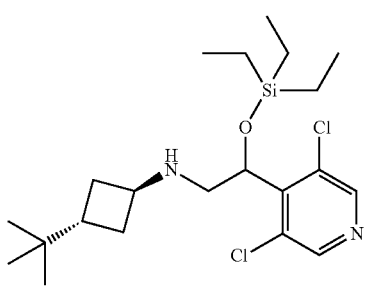
C4 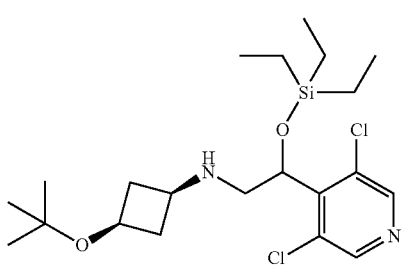
C5 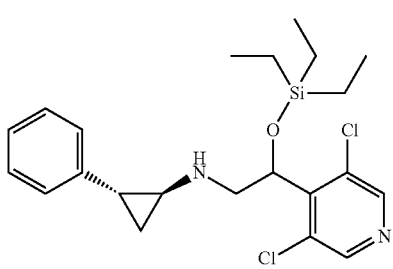
C6 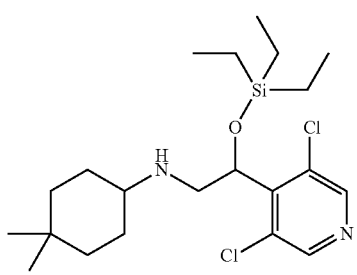
C7 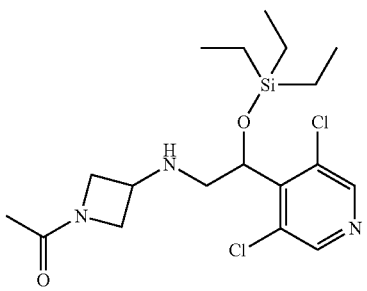
C8 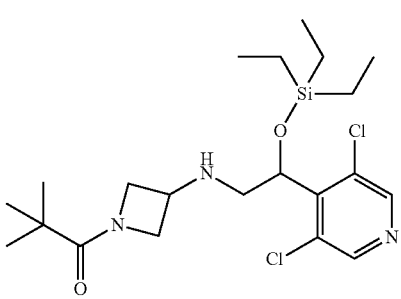
C9 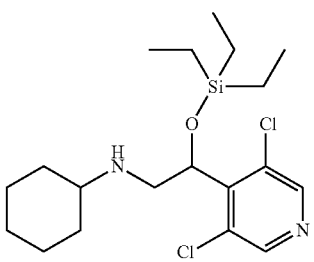
C10 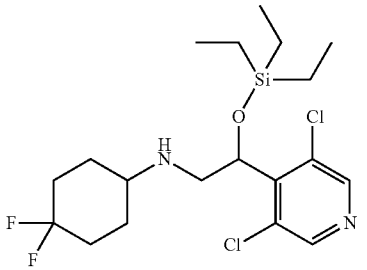
C11 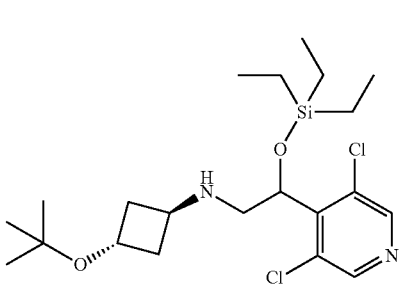

| 183 -continued | 184 -continued |
|---|---|
| C12 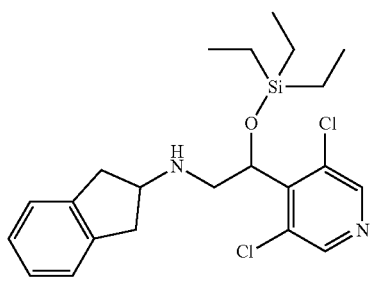 | C18 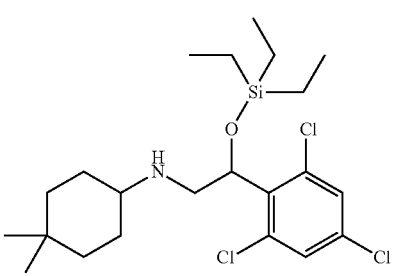 |
| C13 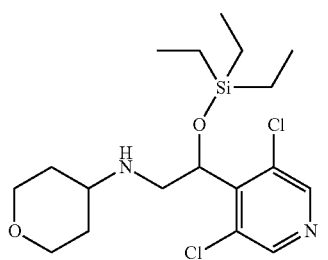 | C21 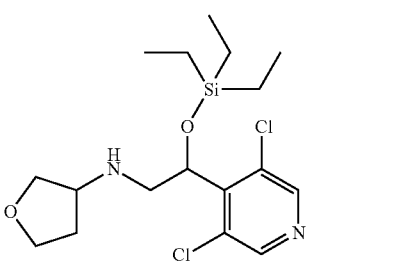 |
| C14 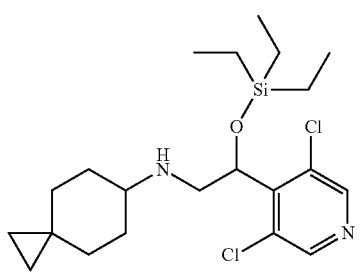 | C24 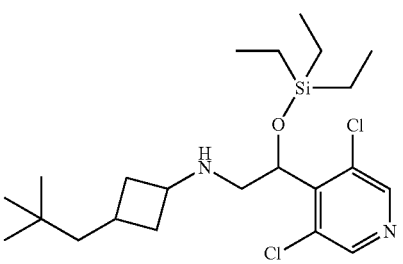 |
| C15 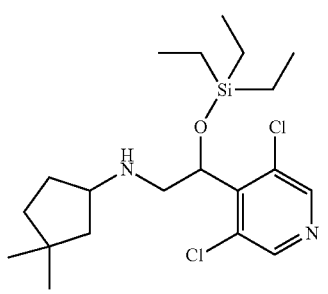 | C25 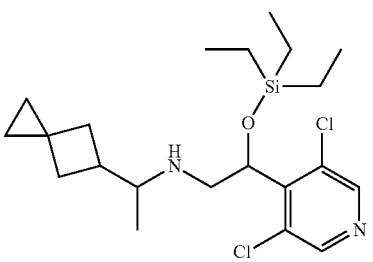 |
| C16 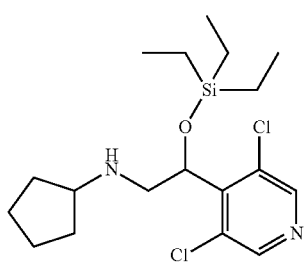 | C26 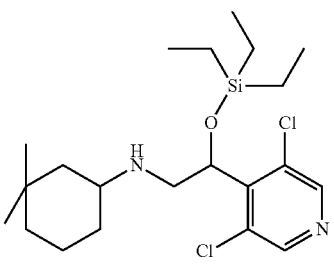 |
| C17 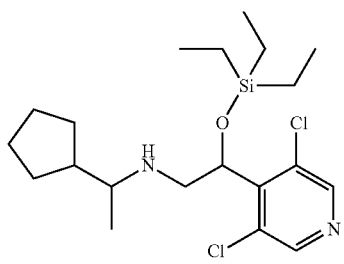 | C27 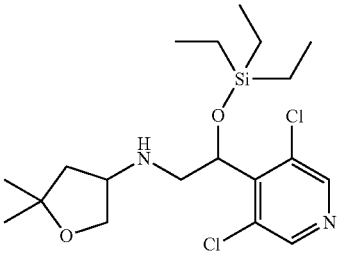 |

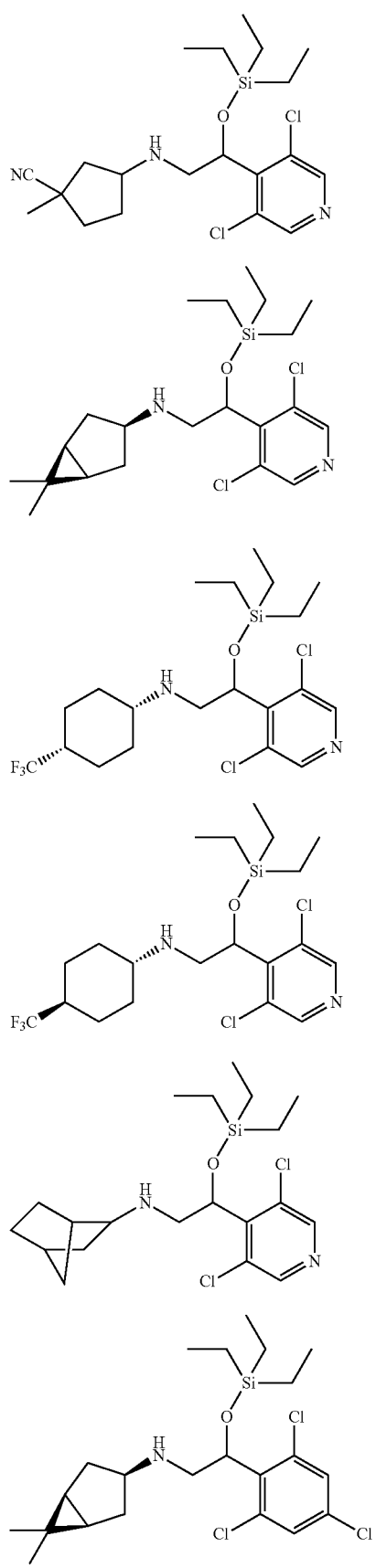
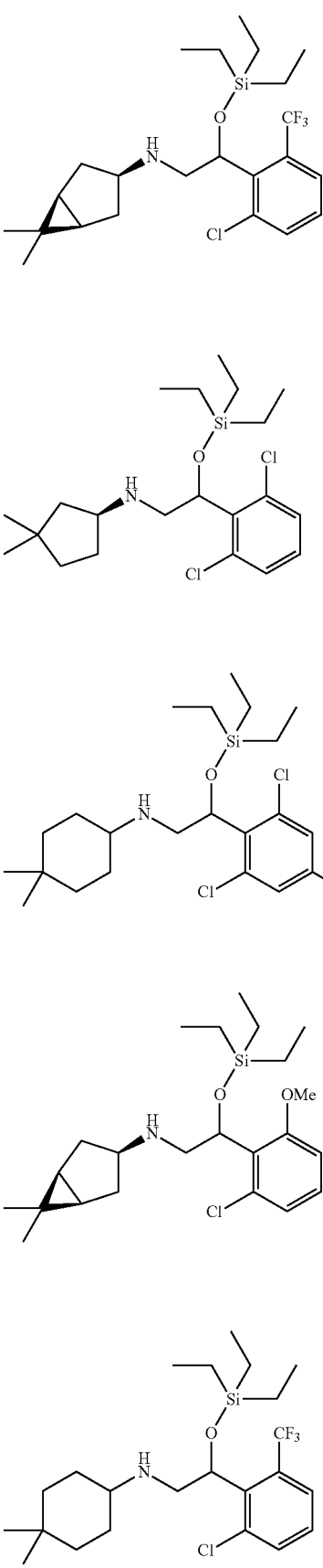

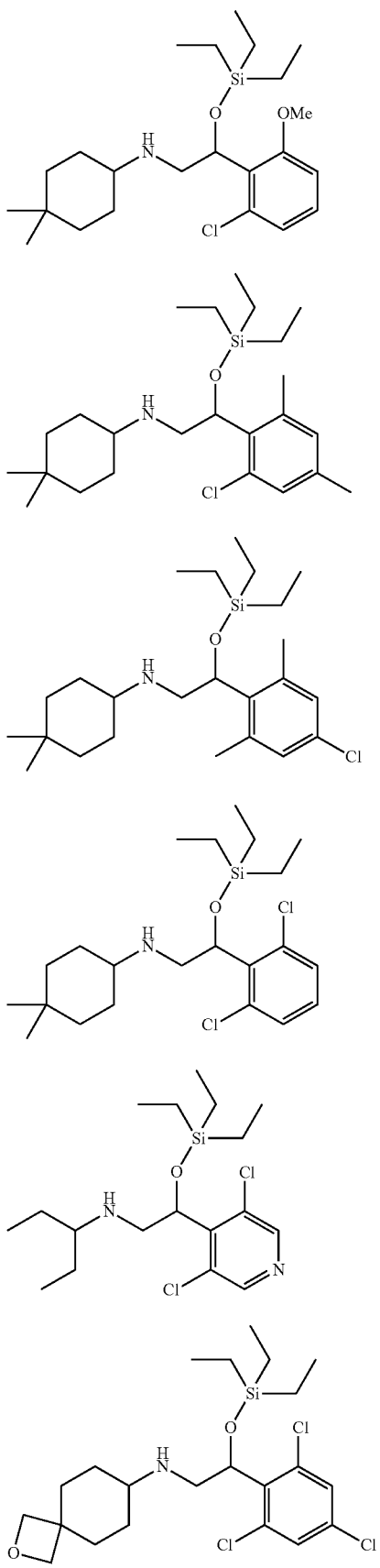
C39
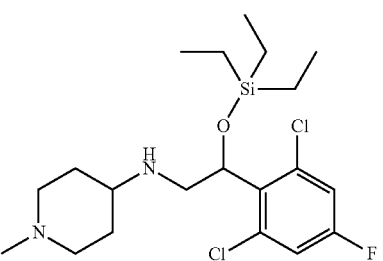
C47
C48
C49
C50
C51
C52
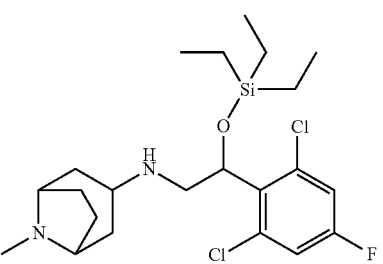
C53
C54
C55
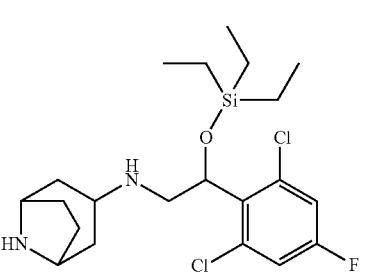
C56
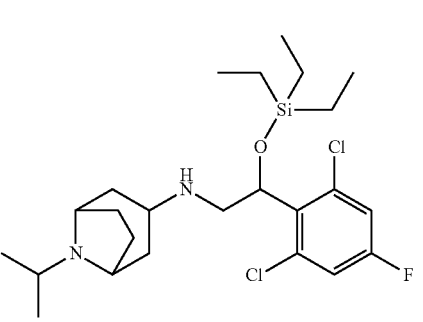

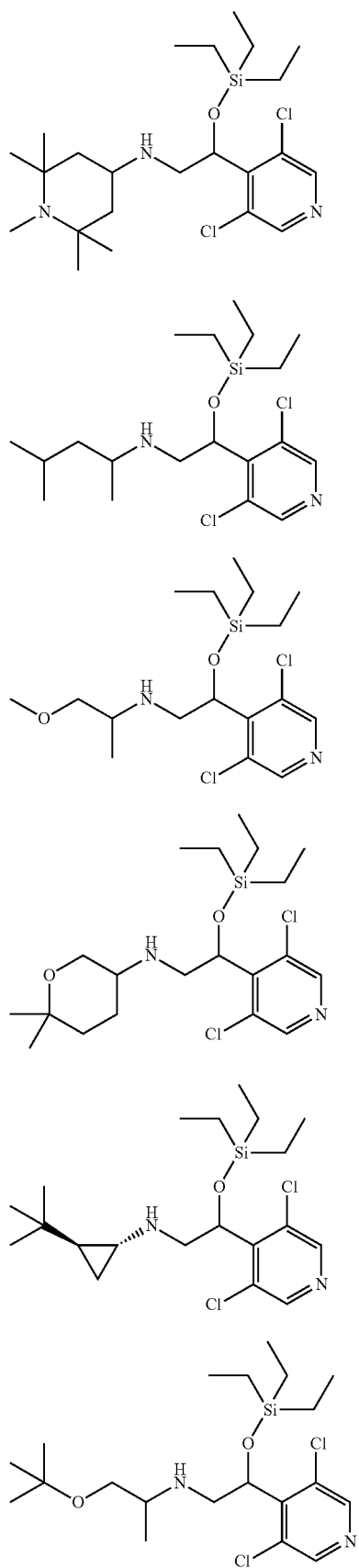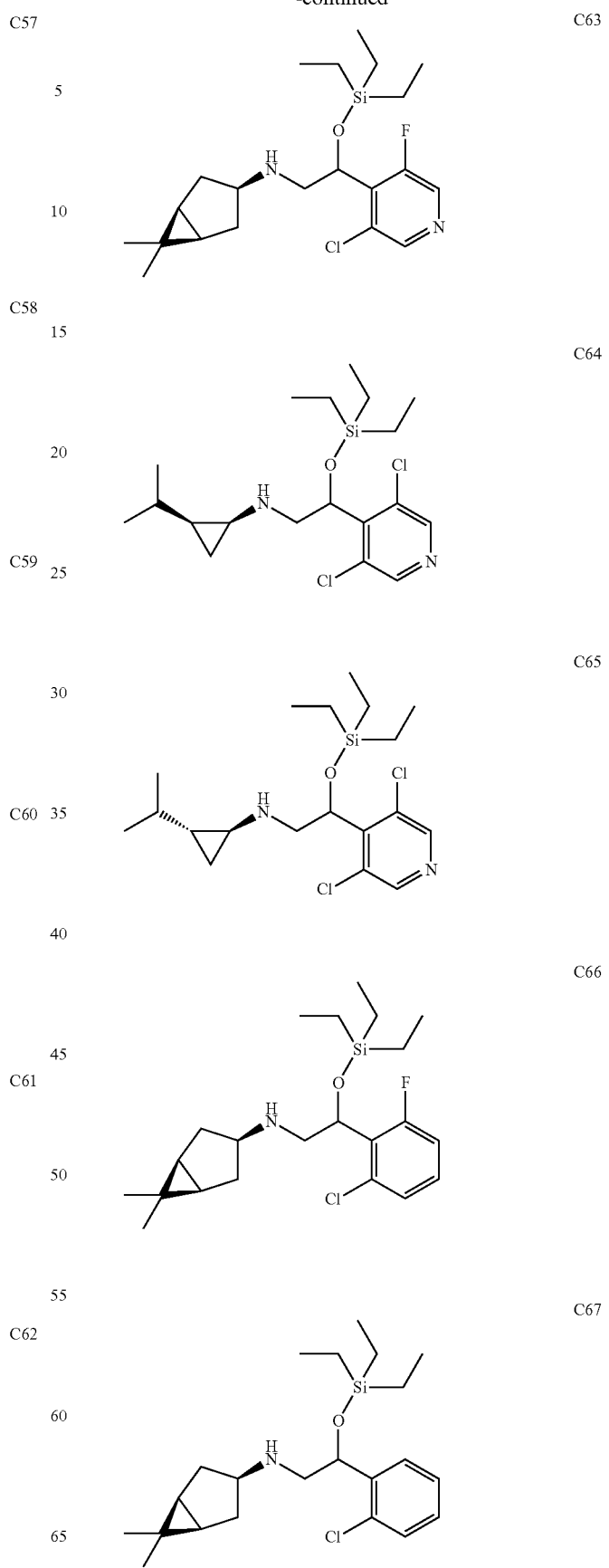

C68
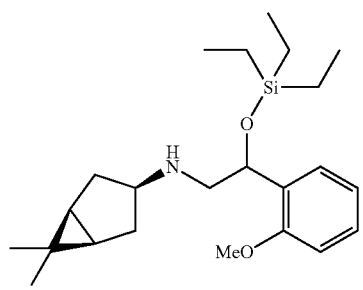
C69
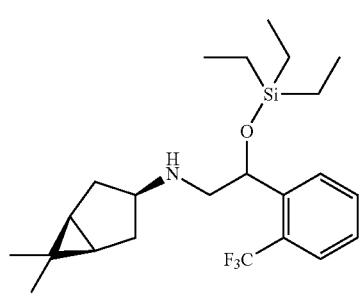
C70
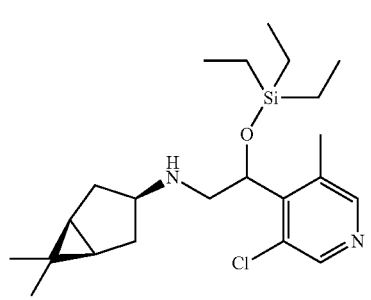
C71
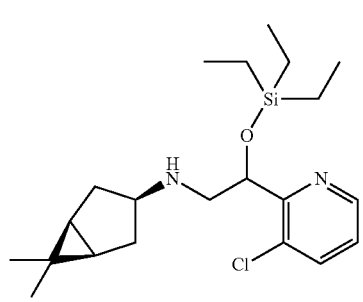
C72
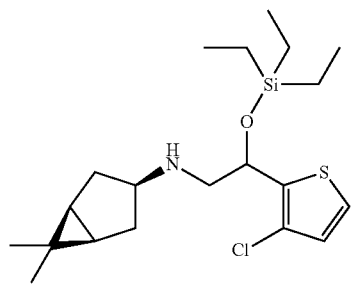
C73
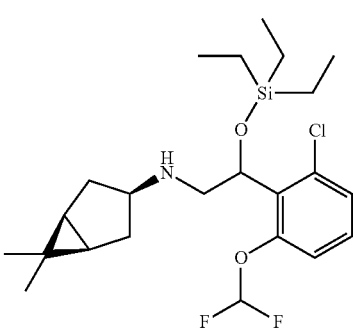
C74
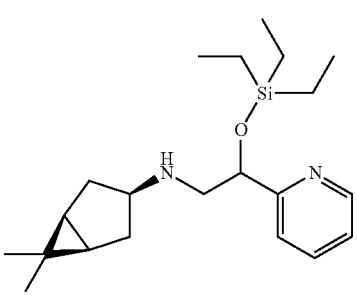
C75
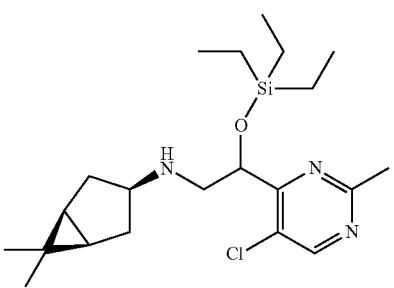
C76
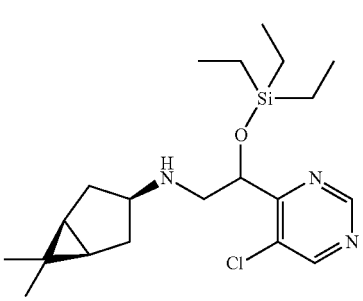
C77
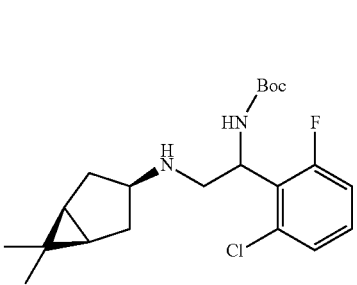

| reference example | structure |
|---|---|
| C78 | 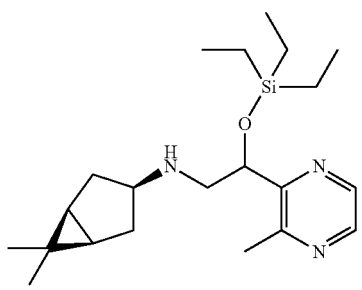 |
| C79 | 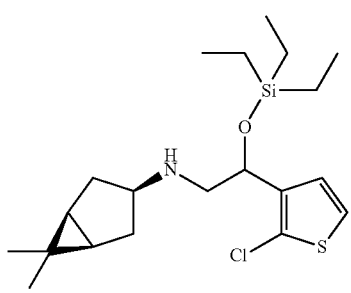 |
| reference example | structure |
|---|---|
| C80 | 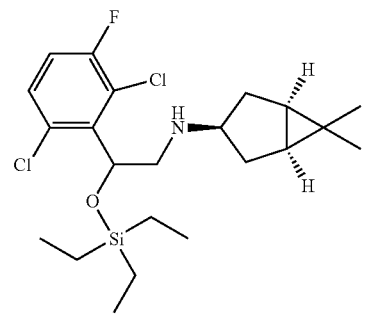 [SMILES: CC[Si](CC)(CC)OC(CN[C@H]1C[C@@H]2[C@H](C1)C2(C)C)c1c(Cl)ccc(F)c1Cl] |
| C81 | 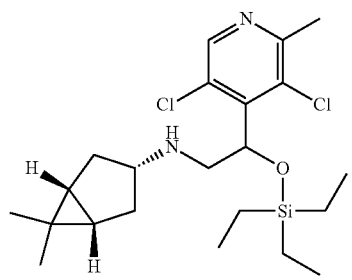 [SMILES: CC[Si](CC)(CC)OC(CN[C@H]1C[C@@H]2[C@H](C1)C2(C)C)c1c(Cl)cnc(C)c1Cl] |
| C82 | 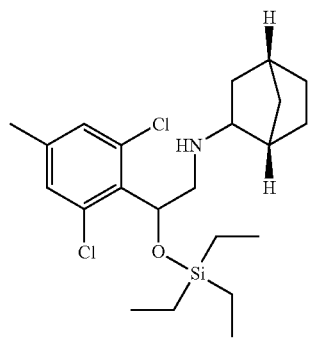 [SMILES: CC[Si](CC)(CC)OC(CNC1C[C@@H]2CC[C@H]1C2)c1c(Cl)cc(C)cc1Cl] |
| reference example | structure |
|---|---|
| C83 | 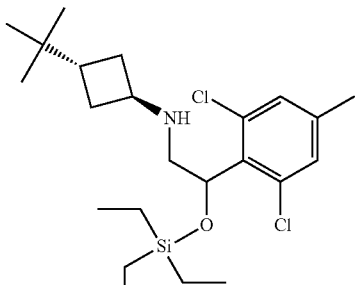 |
| C84 | 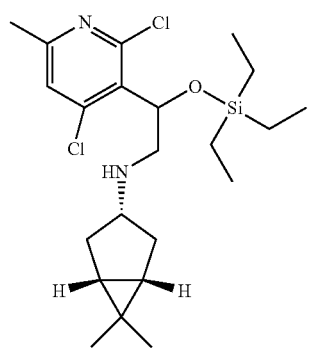 [SMILES: CC[Si](CC)(CC)OC(CN[C@H]1C[C@@H]2[C@H](C1)C2(C)C)c1c(Cl)cc(C)nc1Cl] |
| C85 | 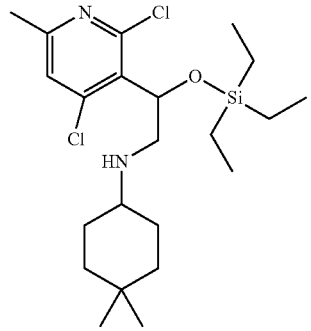 [SMILES: CC[Si](CC)(CC)OC(CNC1CCC(C)(C)CC1)c1c(Cl)cc(C)nc1Cl] |
| C86 | 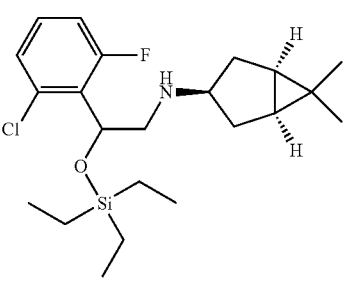 [SMILES: CC[Si](CC)(CC)OC(CN[C@H]1C[C@@H]2[C@H](C1)C2(C)C)c1c(F)cccc1Cl] |
| C87 | |

-continued

| reference example | structure |
|---|---|
| C88 | 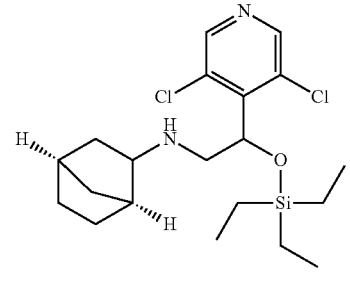 [SMILES: CC[Si](CC)(CC)OC(CNC1C[C@@H]2CC[C@H]1C2)c1c(Cl)cncc1Cl] |
| C89 | 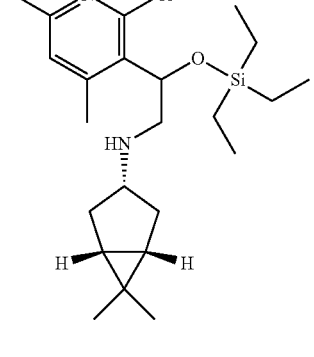 |
| C90 | 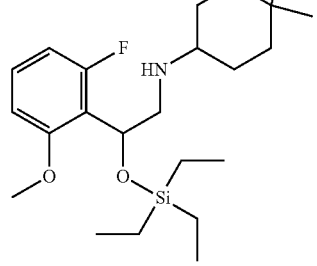 |

Reference Example D1

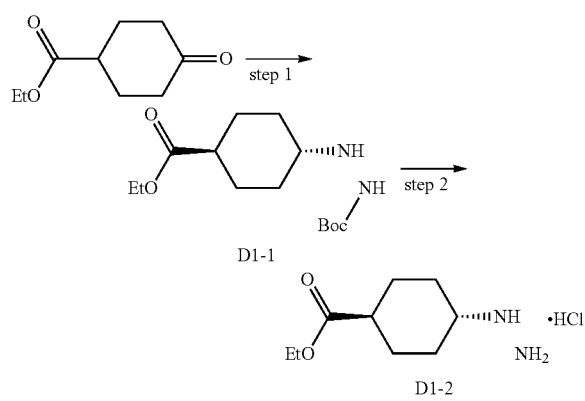

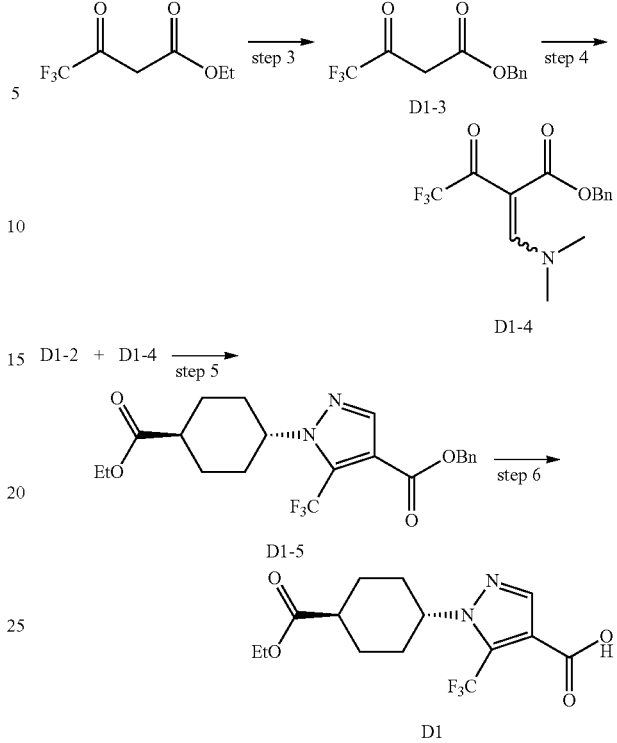

Step 1: tert-butyl 2-(trans4-(ethoxycarbonyl)cyclohexyl)hydrazinecarboxylate (D1-1)

To a solution of 4-cyclohexanonecarboxylic acid ethyl ester (5.0 g, 29.0 mmol) and tert-butyl carbazate (3.9 g, 29.4 mmol) in dichlorometane (250 mL) and AcOH (4 mL) was added $NaBH(OAc)_3$ (18.7 g, 88.0 mmol) gradually at 0° C. After addition, the mixture was stirred at the same temperature for 3 h, then allowed to warm to room temperature and stirred for 20 h. The reaction mixture was poured into saturated aqueous $Na_2CO_3$ solution and extracted with DCM. The DCM extracts were washed with brine×2 and dried over $MgSO_4$. After the solvent was removed, the residue was purified by column chromatography on silica gel to give compound D1-1 (3.0 g, 36%) as a white solid.

Step 2: ethyl trans-4-hydrazinylcyclohexanecarboxylate hydrochloride (D1-2)

To a solution of compound D1-1 in EtOH (25 mL) was added 4 M HCl (in THF, 25 mL, 100 mmol) and the mixture was stirred at room temperature for 16 h. Drying the solution under high vacuum yielded compound D1-2 (2.8 g, quant.) as a white solid.

Step 3: benzyl 4,4,4-trifluoro-3-oxobutanoate (D1-3)

To a solution of ethyl 4,4,4-trifluoro-3-oxobutanoate (17.0 g, 92.3 mmol) in toluene (80 mL) was added benzylalcohol (11.4 mL, 109.6 mmol). The mixture was stirred at 120° C. by using Dean-Stark for 5 h, and then the reaction mixture was cooled to 0° C. Drying the solution under high vacuum yielded compound D1-3 (21.2 g, quant.) as a colorless oil, which was used to the next step without further purification.

Step 4: benzyl 2-((dimethylamino)methylene)-4,4,4-trifluoro-3-oxobutanoate (D1-4)

To a solution of compound D1-3 (21.2 g, 92.3 mmol) and AcOH (10.6 mL, 184.7 mmol) in THF (100 mL) was added N,N-dimethylformamide diisopropyl acetal (38.6 mL, 184.7 mmol) dropwise over 25 min, and the mixture was stirred at room temperature for 16 h. The reaction mixture was poured into saturated aqueous NaHCO$_3$ solution and extracted with EtOAc. The organic layer was washed with brine×2 and dried over MgSO$_4$. After the solvent was removed, the residue was purified by column chromatography on silica gel to give compound D1-4 (17.1 g, 91%) as a yellow oil.

Step 5: benzyl 1-(trans-4-(ethoxycarbonyl)cyclohexyl)-5-(trifluoromethyl)-1H-pyrazole-4-carboxylate (D1-5)

To a solution of compound D1-2 (2.8 g, 10.5 mmol) in EtOH (50 mL) were added DIPEA (3.2 mL, 12.6 mmol) and compound D1-4 (3.3 g, 11.0 mmol) and the mixture was stirred at room temperature for 1.5 h. The reaction was quenched by adding brine and extracted with EtOAc. The organic layer was washed with brine (×2) and dried over MgSO$_4$. After the solvent was removed, the residue was purified by column chromatography on silica gel to give compound D1-5 (3.5 g, 78%) as a colorless oil.

Step 6: 1-(trans-4-(ethoxycarbonyl)cyclohexyl)-5-(trifluoromethyl)-1H-pyrazole-4-carboxylic acid (D1)

Compound D1-5 (3.5 g, 8.2 mmol) and 10% Pd on carbon (300 mg) in EtOAc (40 mL) was hydrogenated in H$_2$ atmosphere (1 atm) at room temperature for 25 h. The reaction mixture was filtered through a pad of celite and washed with EtOAc. Drying the solution under high vacuum yielded compound D1 (2.6 g, 95%) as a white solid.

Reference Example D2

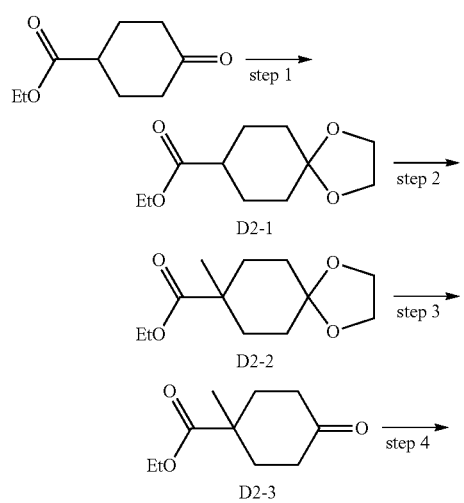

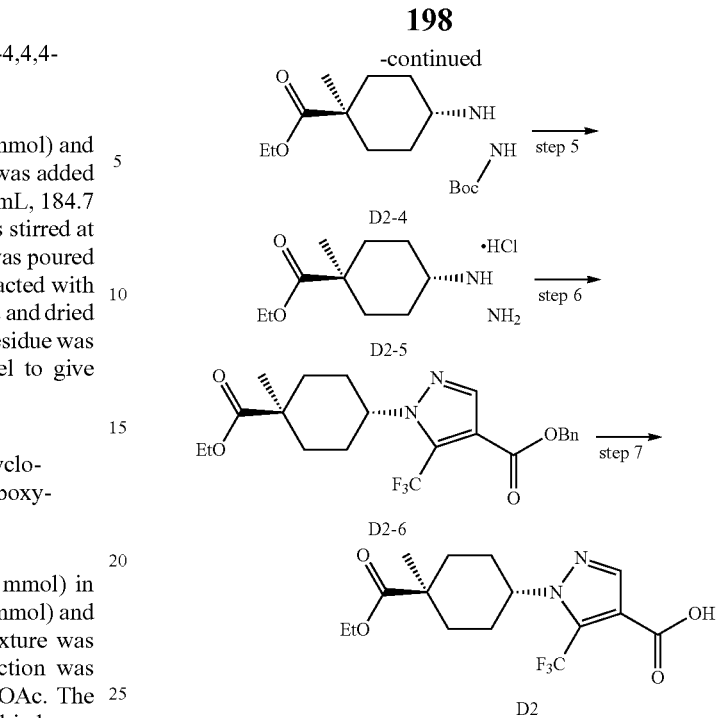

Step 1: ethyl-1,4-dioxaspiro[4.5]decane-8-carboxylate (D2-1)

The mixture of ethyl-4-oxocyclohexanecarboxylate (10 g, 58.75 mmol), ethylene glycol (4.97 ml, 88.13 mmol) and p-TsOH (cat.) in toluene (80 mL) was refluxed for 16 h in a flask equipped with Dean-Stark adapter. Upon reaction completion, the mixture was cooled to room temperature and solvent was removed under reduced pressure to provide compound D2-1 (9.6 g, crude) as brown oil. The crude product was used in the next step without purification. $^1$H NMR (CDCl$_3$, 400 MHz): δ 4.15-4.09 (m, 2H), 3.95 (s, 4H), 2.36-2.03 (m, 1H), 1.97-1.91 (m, 2H), 1.85-1.75 (m, 4H), 1.66-1.52 (m, 2H), 1.26-1.27 (m, 3H).

Step 2: ethyl-8-methyl-1,4-dioxaspiro[4.5]decane-8-carboxylate (D2-2)

To a stirred solution of compound D2-1 (5.1 g, 23.83 mmol) in THF (15 mL) was added LDA (2.0 M in THF/heptane/ethylbenzene, 17.8 mL, 35.74 mmol) dropwise at −78° C. over a period of 15 min. The mixture was stirred at −78° C. for 30 min. A solution of iodomethane (2.23 mL, 35.74 mmol) in THF (1 mL) was added to the mixture dropwise, and the whole was stirred at −78° C. for 30 min. The mixture was allowed to warm to room temperature and stirred for 16 h. The reaction mixture was quenched with saturated aqueous NH$_4$Cl and extracted with EtOAc (2×25 mL). The combined organic layers were washed with water (100 mL), brine (100 mL), dried over anhydrous Na$_2$SO$_4$ and concentrated under reduced pressure. The residue was purified by column chromatography (silica gel, 2% EtOAc/hexane as eluent) to provide compound D2-2 (2.7 g, 50%) as colorless oil. $^1$H NMR (CDCl$_3$, 400 MHz): δ 4.14 (q, J=7.2 Hz, 2H), 3.93 (s, 4H), 2.15-2.10 (m, 2H), 1.65-1.60 (m, 4H), 1.54-1.49 (m, 2H), 1.25 (t, J=7.2 Hz, 3H), 1.18 (s, 3H).

Step 3: ethyl-1-methyl-4-oxocyclohexanecarboxylate (D2-3)

To a solution of compound D2-2 (8.4 g, 36.84 mmol) in acetone (100 mL) was added HCl (3 M in water, 50 mL) dropwise at room temperature, and the whole was stirred at room temperature for 18 h. The reaction mixture was quenched with water (100 mL) and extracted with EtOAc (2×25 mL). The combined organic layers were washed with water (100 mL), brine (100 mL), dried over anhydrous $Na_2SO_4$ and concentrated under reduced pressure to provide compound D2-3 (6.3 g) as a light yellow oil. The crude product was used in the next step without purification. $^1$H NMR ($CDCl_3$, 400 MHz): δ 4.22 (q, J=7.0 Hz, 2H), 2.47-2.38 (m, 4H), 2.34-2.30 (m, 2H), 1.72-1.64 (m, 2H), 1.31-1.29 (m, 6H).

Step 4: tert-butyl-2-(trans-4-(ethoxycarbonyl)-4-methylcyclohexyl)hydrazinecarboxylate (D2-4)

To a mixture of compound D2-3 (30 g, 163.0 mmol) and tert-butylhydrazine carboxylate (21.5 g, 163.0 mmol) in isopropanol (200 mL) was added and AcOH (catalytic amount) and the mixture was stirred at room temperature for 2 h. Upon completion of imine formation (monitored by TLC), the mixture was cooled to 0° C., and solid $NaBH_3CN$ (30.7 g, 489.1 mmol) was added in portions. The pH of reaction mixture was adjusted to 5-6 using AcOH, and stirring continued for 3 h at room temperature. The mixture was quenched with water (100 mL) and extracted with EtOAc (2×200 mL). The combined organic layers were washed with water (100 mL), brine (100 mL), dried over anhydrous $Na_2SO_4$ and concentrated under reduced pressure. The residue was purified by column chromatography (silica gel, 30% EtOAc/hexane) (Note: Polar spot was the trans-isomer) to provide compound D2-4 (12.0 g, 34%) as a white solid.

Step 5: ethyl trans-4-hydrazinyl-1-methylcyclohexanecarboxylate hydrochloride (D2-5)

To a solution of compound D2-4 (36.0 g, 120.0 mmol) in EtOH (100 mL) was added HCl (4 M in 1,4-dioxane, 350 mL) dropwise at 0° C., and the whole was stirred at room temperature for 18 h. The solvent was removed under reduced pressure and residue was triturated with $Et_2O$ to get compound D2-5 (31.0 g, 95%) as white solid. The crude product was used in the next step without purification. $^1$H NMR ($CDCl_3$, 400 MHz): δ 7.24-7.00 (brs, 4H), 4.13 (q, J=7.2 Hz, 2H), 3.44 (brs, 1H), 2.08-2.05 (m, 2H), 1.97-1.90 (m, 2H), 1.81-1.80 (m, 4H), 1.30-1.26 (m, 6H).

Step 6: benzyl-1-(trans-4-(ethoxycarbonyl)-4-methylcyclohexyl)-5-(trifluoromethyl)-1H-pyrazole-4-carboxylate (D2-6)

To a solution of compound D2-5 (31.0 g, 113.9 mmol) in EtOH (150 mL) was added DIPEA (39.4 mL, 227.9 mmol) dropwise and the mixture was stirred at room temperature for 5 min. A solution of compound D1-4 (37.7 g, 125.3 mmol) in EtOH (10 mL) was added dropwise, and the whole was stirred at room temperature for 16 h. The reaction mixture was quenched with water (200 mL) and extracted with EtOAc (2×200 mL). The combined organic layer was washed with water (100 mL), brine (100 mL), dried over anhydrous $Na_2SO_4$ and concentrated under reduced pressure. The residue was purified by column chromatography (silica gel, 15% EtOAc/hexane as eluent) to provide compound D2-6 (20.0 g, 40%) as brown gum. $^1$H NMR ($CDCl_3$, 400 MHz): δ 7.94 (s, 1H), 7.40-7.35 (m, 5H), 5.30 (s, 2H), 4.36 (m, 1H), 4.15 (q, J=7.2 Hz, 2H), 2.24-2.19 (m, 2H), 1.88-1.87 (m, 6H), 1.3 (s, 3H), 1.26 (t, J=7.2 Hz, 3H).

Step 7: trans-4-(ethoxycarbonyl)-4-methylcyclohexyl)-5-(trifluoromethyl)-1H-pyrazole-4-carboxylic acid (D2)

A mixture of compound D2-6 (20.0 g, 45.6 mmol) and 5% Pd on carbon (10.0 g, 50% by weight) in MeOH (200 mL) was stirred under $H_2$ atmosphere (1 atm) for 4 h. The mixture was filtered through a pad of celite, washed with EtOAc (3×100 mL) and concentrated under reduced pressure. The residue was triturated with 10% EtOAc/hexane (2×25 mL) to provide compound D2 (13.0 g, 82%) as white solid. $^1$H NMR ($CDCl_3$, 300 MHz): δ 8.03 (s, 1H), 4.42-4.41 (m, 1H), 4.15 (q, J=7.2 Hz, 2H), 2.25-2.21 (m, 2H), 1.92-1.88 (m, 6H), 1.35 (s, 3H), 1.27 (t, J=7.0 Hz, 3H).

Reference Example D19

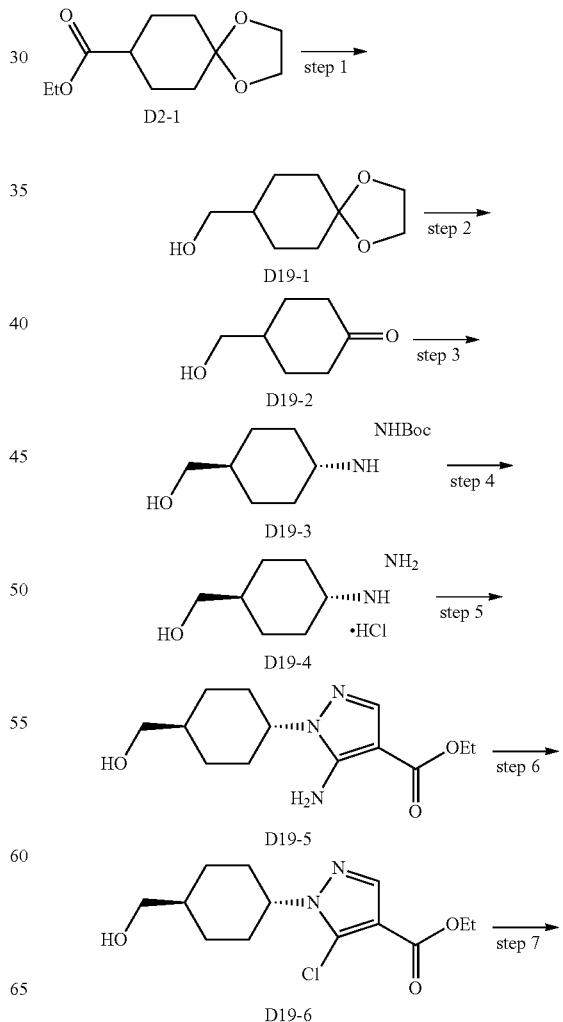

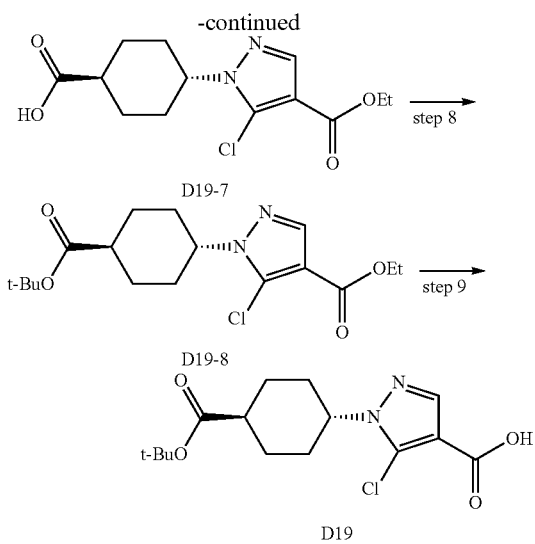

Step 1: 1,4-dioxaspiro[4.5]decan-8-ylmethanol (D19-1)

To a suspension of LiAlH$_4$ (5.69 g, 150 mmol) in THF (100 mL) was added a solution of compound D2-1 (21.4 g, 100 mmol) in THF (100 mL) dropwise at 0° C. and the reaction mixture was stirred at room temperature for 2 h. The reaction mixture was cooled to 0° C., quenched with water (7 mL) and 6 M NaOH (7 mL) and stirred at room temperature for 20 min. Na$_2$SO$_4$ (10 g) was added to the mixture, filtered over a pad of celite and washed with EtOAc (3×50 mL). The combined organic layers were washed with brine (100 mL), water (100 mL) and concentrated under reduced pressure to provide compound D19-1 (17.0 g, quant) as colorless oil. The crude product was used for next step without purification.

Step 2: 4-(hydroxymethyl)cyclohexanone (D19-2)

To a stirred solution of compound D19-1 (17.0 g, 9.88 mmol) in acetone (100 mL) was added aqueous HCl (2 M, 38 mL) and the mixture was stirred at room temperature for 18 h. The solvent was removed under reduced pressure and then diluted with water (100 mL) and extracted with EtOAc (3×100 mL). The combined organic layers were washed with water, dried over Na$_2$SO$_4$ and concentrated under reduced pressure to obtain compound D19-2 (7.5 g, 51%) as colorless gum.

Step 3: tert-butyl 2-(trans-4-(hydroxymethyl)cyclohexyl)hydrazinecarboxylate (D19-3)

A mixture of compound D19-2 (2.0 g, 15.5 mmol) and Boc-hydrzine (2.26 g, 17 mmol) in isopropanol (20 mL) was stirred at room temperature for 16 h. Na(CN)BH$_3$ (2.92 g, 45.6 mmol) and AcOH (1 mL, cat.) were added and the mixture was stirred at room temperature for 16 h. The reaction mixture was quenched with water (50 mL) and extracted with EtOAc (2×50 mL). The combined organic layers were washed with water, dried over anhydrous Na$_2$SO$_4$ and concentrated under reduced pressure. The residue was purified by column chromatography (silica gel, 50% EtOAc/hexane as eluent) to obtain compound D19-3 (820 mg, 22%) as a white semi solid.

Step 4: (trans-4-hydrazinylcyclohexyl)methanol hydrochloride (D19-4)

To a stirred mixture of compound D19-3 (1.8 g, 7.3 mmol) in dioxane (40 mL) was added HCl (20 mL, 73 mmol, 4 M in dioxane) and the mixture was stirred at room temperature for 16 h. The solvent was removed under reduced pressure, dried on high vacuum pump to provide compound D19-4 (1.7 g, crude) as an off white solid.

Step 5: ethyl-5-amino-1-(trans-4-(hydroxymethyl)cyclohexyl)-1H-pyrazole-4-carboxylate (D19-5)

To a solution of compound D19-4 (720 mg, 3.31 mmol) in EtOH (20 mL) were added ethyl-2-cyano-3-ethoxyacrylate (448 mg, 2.65 mmol) and NaOAc (571 mg, 6.96 mmol) and the mixture was stirred at 70° C. for 18 h. The solvent was removed under reduced pressure, the residue was suspended in water (20 mL) and extracted with EtOAc (3×20 mL). The combined organic layers were washed with water, dried over Na$_2$SO$_4$ and concentrated under reduced pressure. The residue was purified by reverse phase column chromatography (C18 silica gel, 30% CH$_3$CN/water as eluent) to provide compound D19-5 (320 mg, 37%) as reddish brown solid.

Step 6: ethyl-5-chloro-1-(trans-4-(hydroxymethyl)cyclohexyl)-1H-pyrazole-4-carboxylate (D19-6)

To a suspension of CuCl (103 mg, 1.04 mmol) in CH$_3$CN (5 mL) was added tert-butyl nitrite (0.134 mL, 1.125 mmol) dropwise at 0° C. A solution of compound D19-5 (200 mg, 0.749 mmol) in CH$_3$CN (4 mL) was added dropwise to above mixture at 0° C. and stirred at the same temperature for 5 min. The mixture was stirred at room temperature for 30 min and at 70° C. for 30 min. The reaction mixture was quenched with water (10 mL) and extracted with EtOAc (3×10 mL). The combined organic layers were washed with water, dried over Na$_2$SO$_4$ and concentrated under reduced pressure. The residue was purified by column chromatography (silica gel, 40% EtOAc/hexane as eluent) to provide compound D19-6 (68 mg, 31%) as a brown semi solid.

Step 7: trans-4-(5-chloro-4-(ethoxycarbonyl)-1H-pyrazol-1-yl)cyclohexanecarboxylic acid (D19-7)

To a suspension of H$_5$IO$_6$ (159 mg, 0.698 mmol) in CH$_3$CN was added CrO$_3$ (0.6 mg, 0.0061 mmol) and the mixture was stirred at room temperature for 30 min. The mixture was cooled to 0° C. and a solution of compound D19-6 (100 mg, 0.349 mmol) was added dropwise. The reaction mixture was stirred at the same temperature for 30 min. The organic solvent was removed under reduced pressure, residue was suspended in water (10 mL) and extracted with EtOAc (3×10 mL). The combined organic layers were washed with water, dried over Na$_2$SO$_4$ and concentrated under reduced pressure to provide compound D19-7 (105 mg, quant) as an off-white solid.

Step 8: ethyl-1-(trans-4-(tert-butoxycarbonyl)cyclohexyl)-5-chloro-1H-pyrazole-4-carboxylate (D19-8)

To a mixture of compound D19-7 (105 mg, 0.35 mmol) and Boc anhydride (152 mg, 0.70 mmol) in t-BuOH (5 mL) was added DMAP (13 mg, 0.105 mmol) and the mixture was stirred at 35° C. for 16 h. The reaction mixture was quenched with water (10 mL) and extracted with EtOAc (3×10 mL). The combined organic layers were washed with water, dried over $Na_2SO_4$ and concentrated under reduced pressure. The residue was purified by reverse phase column chromatography (C18 silica gel, 90% $CH_3CN$/water as eluent) to provide compound D19-8 (70 mg, 56%) as colorless gum.

Step 9: 1-(trans-4-(tert-butoxycarbonyl)cyclohexyl)-5-chloro-1H-pyrazole-4-carboxylic acid (D19)

To a stirred solution of compound D19-8 (70 mg, 0.233 mmol) in THF/MeOH (4 mL, 1:1) was added a solution of LiOH (44 mg, 1.86 mmol) in water (1 mL). The mixture was stirred at room temperature for 4 h. The organic solvent was removed under reduced pressure. The residue was diluted with water (5 mL), acidified with 20% aqueous $KHSO_4$ to pH 4 and extracted with EtOAc (3×10 mL) to provide compound D19 (62 mg, 90%) as white solid. $^1$H NMR ($CDCl_3$, 300 MHz): δ 8.01 (s, 1H), 4.29-4.37 (m, 1H), 2.25-2.43 (m, 1H), 2.10-2.19 (m, 2H), 1.99-2.09 (m, 4H), 1.52-1.65 (m, 2H), 1.45 (s, 9H).

Reference Example D20

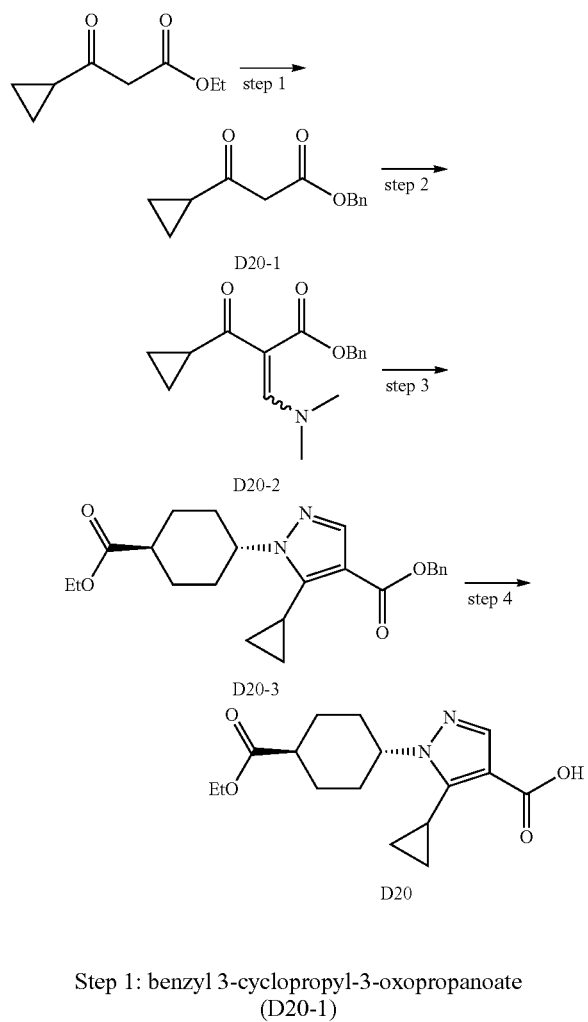

Step 1: benzyl 3-cyclopropyl-3-oxopropanoate (D20-1)

A mixture of ethyl 3-cyclopropyl-3-oxopropanoate (5.0 g, 32.0 mmol), benzyl alcohol (8.2 mL, 80.0 mmol) and LiOCl (680 mg, 6.4 mmol) in toluene (50 mL) was refluxed for 48 h in flask equipped with a Dean-stark apparatus. The reaction mixture was cooled to room temperature and solvent was removed under reduced pressure to provide compound D20-1 (5.2 g, crude) as a brown oil.

Step 2: benzyl 2-(cyclopropanecarbonyl)-3-(dimethylamino)acrylate (D20-2)

A mixture of compound D20-1 (1.0 g, 4.58 mmol) and dimethylformamide dimethylacetal (0.61 mL, 4.58 mmol) in 1,4-dioxane (25 mL) was stirred at 100° C. for 13 h. The reaction mixture was quenched with water (20 mL) and extracted with EtOAc (2×25 mL). The combined organic layers were washed with water (25 mL), brine (25 mL), dried over $Na_2SO_4$ and concentrated under reduced pressure to provide compound D20-2 (1.2 g, crude) as a yellowish brown gum.

Step 3: benzyl 5-cyclopropyl-1-(trans-4-(ethoxycarbonyl)cyclohexyl)-1H-pyrazole-4-carboxylate (D20-3)

To a solution of compound D1-2 (809 mg, 2.67 mmol) in EtOH (20 mL) was added DIPEA (0.45 mL, 2.61 mmol) dropwise. The mixture was stirred at room temperature for 5 min, thereafter, a solution of compound D20-2 (600 mg, 2.18 mmol) in EtOH (5 mL) was added dropwise and reaction mixture was stirred at room temperature for 4 h. The reaction mixture was quenched with water (200 mL) and extracted with EtOAc (2×25 mL). The combined organic layers were washed with water (25 mL), brine (25 mL), dried over anhydrous $Na_2SO_4$ and concentrated under reduced pressure. The residue was purified by column chromatography (silica gel, 20% EtOAc/hexane as eluent) to provide compound D20-3 (425 mg, impure) as yellow gum.

Step 4: 5-cyclopropyl-1-(trans-4-(ethoxycarbonyl)cyclohexyl)-1H-pyrazole-4-carboxylic acid (D20)

To a stirred solution of compound D20-3 (425 mg, 1.07 mmol) in THF/MeOH (20 mL, 1:1) was added 10% Pd on carbon (80 mg, 20% by weight) and the mixture was stirred under $H_2$ atmosphere (1 atm) for 2 h. The mixture was filtered through pad of celite and washed with EtOAc (3×50 mL). The filtrate was concentrated under reduced pressure. The residue was triturated with 10% EtOAc/hexane (2×20 mL) to provide compound D20 (200 mg, crude) as white solid.

Reference Example D22

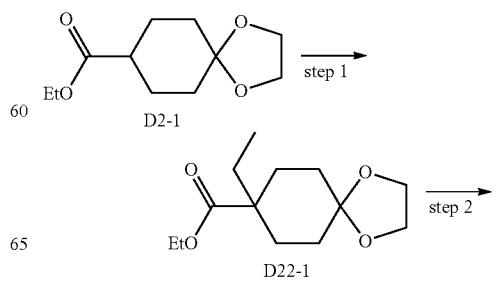

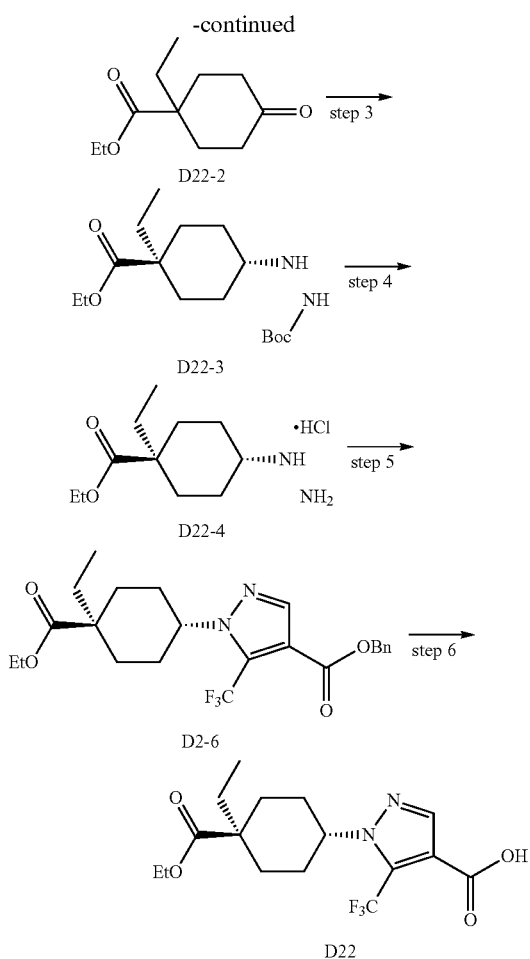

Step 1: ethyl 8-ethyl-1,4-dioxaspiro[4.5]decane-8-carboxylate (D22-1)

To a stirred solution of compound D2-1 (2.1 g, 9.80 mmol) in THF (24 mL) was added LDA (2.0 M in THF/heptane/ethylbenzene, 7.3 mL, 14.7 mmol) dropwise at −78° C. for 5 min. The mixture was stirred at −78° C. for 15 min before the addition of EtBr (1.09 mL, 14.7 mmol). The reaction mixture was stirred at −78° C. for 1 h. The mixture was allowed to warm to room temperature and stirred at the same temperature for 1 h. The reaction mixture was quenched with saturated aqueous NH$_4$Cl and extracted with EtOAc (2×25 mL). The combined organic layers were washed with water (20 mL), brine (20 mL), dried over anhydrous Na$_2$SO$_4$ and concentrated under reduced pressure. The residue was purified by column chromatography (silica gel, 20% EtOAc/hexane as eluent) to provide compound D22-1 (2.07 g, 87%) as a colorless gum.

Step 2: ethyl 1-ethyl-4-oxocyclohexanecarboxylate (D22-2)

To a stirred solution of compound D22-1 (2.07 g, 8.54 mmol) in acetone (60 mL) was added aqueous HCl (2 M solution, 40 mL) at room temperature. The mixture was stirred at the same temperature for 16 h. Acetone was removed under reduced pressure. The residue was basified with aqueous NaHCO$_3$ solution and extracted with DCM (2×30 mL). The combined organic layers were washed with water (20 mL), brine (20 mL), dried over Na$_2$SO$_4$ and concentrated under reduced pressure. The residue was purified by column chromatography (silica gel, 20% EtOAc/hexane as eluent) to give compound D22-2 (1.85 g, 99%) as a colorless gum.

Step 3: tert-butyl 2-(trans-4-(ethoxycarbonyl)-4-ethylcyclohexyl)hydrazinecarboxylate (D22-3)

Compound D22-3 (1.57 g, 53%) was obtained as a white solid from the reaction of compound D22-2 (1.87 g, 9.43 mmol), tert-butyl hydrazinecarboxylate (1.24 g, 9.4 mmol), AcOH (cat) and NaBH$_3$CN (1.78 g, 28.29 mmol) in isopropanol (20 mL) using a similar procedure to that described in reference example D2, step 4.

Step 4: ethyl trans-1-ethyl-4-hydrazinylcyclohexanecarboxylate hydrochloride (D22-4)

Compound D22-4 (1.36 g, 100%) was obtained as a white solid from the reaction of compound D22-3 (1.50 g, 4.78 mmol) and HCl (4 M in 1,4-dioxane, 8.3 mL, 33.4 mmol) using a similar procedure to that described in reference example D2, step 5.

Step 5: benzyl 1-(trans-4-(ethoxycarbonyl)-4-ethylcyclohexyl)-5-(trifluoromethyl)-1H-pyrazole-4-carboxylate (D22-5)

Compound D22-5 (820 mg, 86%) was obtained as a colorless gum from the reaction of compound D22-4 (600 mg, 2.1 mmol), compound D1-4 (669 mg, 2.2 mmol) and DIPEA (0.43 mL, 2.52 mmol) in EtOH (12 mL) using a similar procedure to that described in reference example D2, step 6.

Step 6: 1-(trans-4-(ethoxycarbonyl)-4-ethylcyclohexyl)-5-(trifluoromethyl)-1H-pyrazole-4-carboxylic acid (D22)

Compound D22 (285 mg, 98%) was obtained as a white solid from the reaction of compound D22-5 (363 mg, 0.80 mmol), 5% Pd on carbon (85 mg, 30% by weight) and H$_2$ (1 atm) in MeOH (6 mL) using a similar procedure to that described in reference example D2, step 7.

Reference Example D26

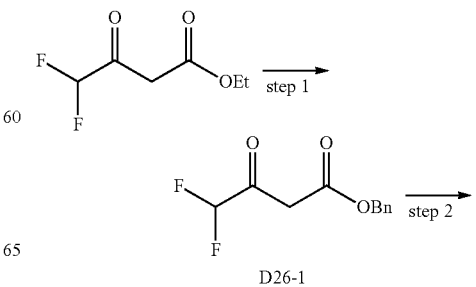

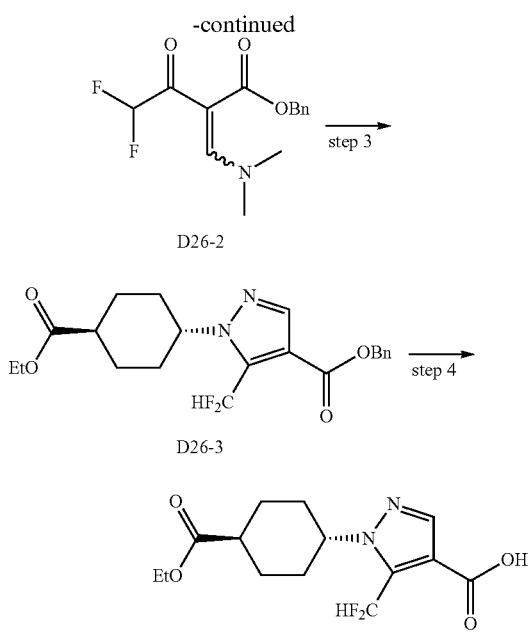

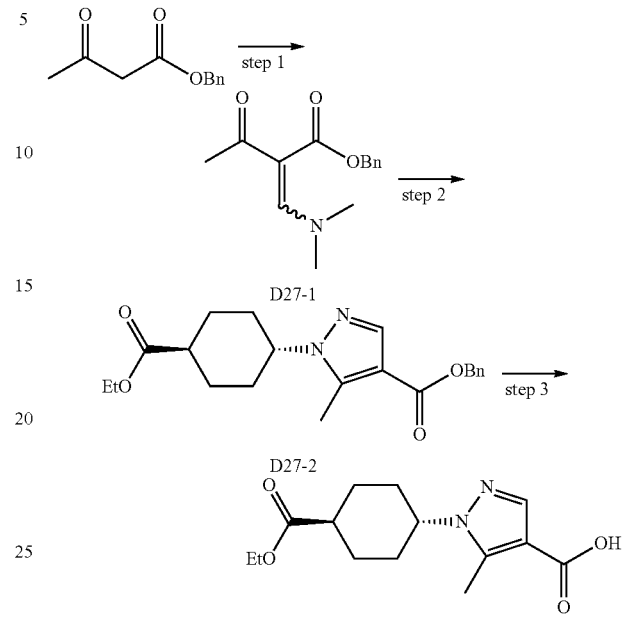

Reference Example D27

Step 1: benzyl-4,4-difluoro-3-oxobutanoate (D26-1)

Compound D26-1 (7.5 mg, crude) was obtained as a yellow oil from the reaction of ethyl-4,4-difluoro-3-oxobutanoate (5 g, 0.12 mmol) and BnOH (3.25 g, 30.0 mmol) in toluene (50 mL) using a similar procedure to that described in reference example D1, step 3.

Step 2: benzyl-2-((dimethylamino)methylene)-4,4-difluoro-3-oxobutanoate (D26-2)

Compound D26-2 (5.8 g, crude) was obtained as a yellow oil from the reaction of compound D26-1 (5.3 g, 23.2 mmol), dimethylformamide dimethylacetal (6.2 mL, 46.4 mmol) and AcOH (2.05 mL, 46.4 mmol) in THF (50 mL) using a similar procedure to that described in reference example D1, step 4.

Step 3: benzyl-5-(difluoromethyl)-trans-4-(ethoxycarbonyl)cyclohexyl)-1H-pyrazole-4-carboxylate (D26-3)

Compound D26-3 (520 mg, 16%) was obtained as a pale yellow solid from the reaction of compound D26-2 (1.50 g, 5.28 mmol), compound D1-2 (1.6 g, 5.28 mmol) and DIPEA (1.8 mL, 10.5 mmol) in EtOH (30 mL) using a similar procedure to that described in reference example D1, step 5.

Step 4: 5-(difluoromethyl)-trans-4-(ethoxycarbonyl)cyclohexyl)-1H-pyrazole-4-carboxylic acid (D26)

Compound D26 (255 mg, 63%) was obtained as a white solid from the reaction of compound D26-3 (520 mg, 1.28 mmol) and 5% Pd on carbon (70 mg, 30% by weight) in EtOH (30 mL) using a similar procedure to that described in reference example D1, step 6.

LCMS (APCI): 317 (M+H)$^+$.

Step 1: benzyl 2-((dimethylamino)methylene)-3-oxobutanoate (D27-1)

To a stirred benzyl 3-oxobutanoate (1.1 g, 5.7 mmol), dimethylformamide dimethylacetal (1 mL, 7.4 mmol) was added dropwise at room temperature. The mixture was stirred for 16 h at room temperature. The reaction mixture was concentrated under reduced pressure and the residue was azeotroped with toluene (3×10 mL) to provide compound D27-1 as a brown oil (1.4 g, quant.).

Step 2: benzyl 1-((trans-4-(ethoxycarbonyl)cyclohexyl)-5-methyl-1H-pyrazole-4-carboxylate (D27-2)

To a solution of compound D1-2 (1.12 g, 4.3 mmol) in EtOH (10 mL) was added DIPEA (1.2 mL, 6.7 mmol) dropwise. The mixture was stirred at room temperature for 5 min. A solution of compound D27-1 (0.97 g, 3.94 mmol) in EtOH (5 mL) was added dropwise and the reaction mixture was stirred at room temperature for 2 h. The reaction mixture was quenched with water (20 mL) and extracted with EtOAc (2×50 mL). The combined organic layers were washed with water (50 mL), brine (50 mL), dried over $Na_2SO_4$ and concentrated under reduced pressure. The residue was purified by column chromatography (silica gel, 20% EtOAc/hexane as eluent) to provide compound D27-2 (0.78 g, 54%) as a white solid.

Step 3: 1-((trans-4-(ethoxycarbonyl)cyclohexyl)-5-methyl-1H-pyrazole-4-carboxylic acid (D27)

To a stirred solution of compound D27-2 (0.78 g, 2.1 mmol) in MeOH (10 mL) was added 5% Pd on carbon (0.19 g, 25% by weight) and the mixture was stirred under H₂ atmosphere (1 atm) for 2 h. The mixture was filtered through a pad of celite and washed with MeOH (3×20 mL). The filtrate washed with water (50 mL), brine (50 mL), dried over anhydrous Na₂SO₄ and concentrated under reduced pressure. The residue was triturated with 5% EtOAc/hexane (20 mL) to provide compound D27 (0.5 g, 85%) as a white solid. ¹H NMR (300 MHz, DMSO-d₆): δ 1.19 (t, J=7.2 Hz), 1.56 (m, 2H), 1.88 (m, 4H), 2.00 (m, 2H), 2.35 (m, 1H), 2.50 (s, 3H), 4.07 (q, J=7.2 Hz, 2H), 4.20 (m, 1H), 7.72 (s, 1H), 12.10 (s, 1H).

Reference Example D28

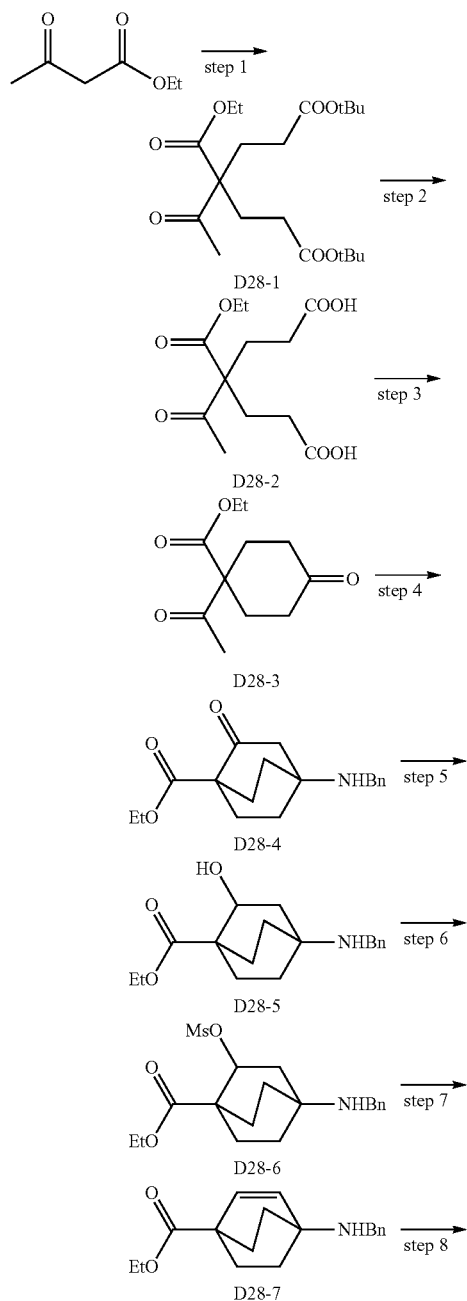

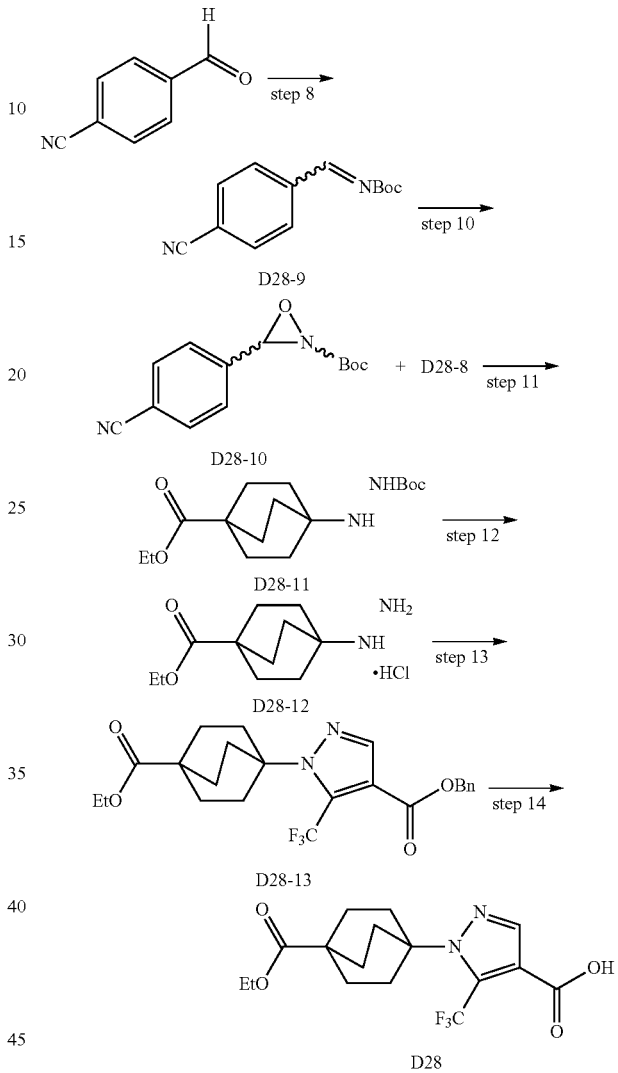

Step 1: 1,5-di-tert-butyl 3-ethyl 3-acetylpentane-1,3,5-tricarboxylate (D28-1)

To a stirred solution of ethyl 3-oxobutanoate (45 g, 345 mmol) and Triton-B (40%, weight % solution in water, 1.08 mg, 6.90 mmol) in tert-BuOH (54 mL) was added tert-butyl acrylate (100.72 g, 691 mmol) dropwise over a period of 30 min under N₂ atmosphere. The solution was stirred at room temperature for 24 h. The reaction mixture was partitioned between water (200 mL) and EtOAc (200 mL). The aqueous layer washed with EtOAc (2×50 mL). The combined organic layers were washed with water (200 mL), brine (200 mL), dried over Na₂SO₄ and concentrated under reduced pressure to provide compound D28-1 (140 g, quant) as a pale yellow oil. ¹H NMR (CDCl₃, 400 MHz): δ 4.20 (q, J=7.2 Hz 2H), 2.24-2.09 (m, 8H), 1.58 (s, 3H), 1.43 (s, 18H), 1.31 (t, J=7.2 Hz, 3H).

Step 2: 4-acetyl-4-(ethoxycarbonyl)heptanedioic acid (D28-2)

To a stirred solution of compound D28-1 (140 g, 326 mmol) in DCM (350 mL) was added TFA (350 mL) in DCM (350 mL) at 0° C. and the mixture was stirred at room temperature overnight. The solvent was removed under reduced pressure and the residue was co-evaporated with toluene (3×200 mL) to provide compound D28-2 (85 g, quant.) as an off-white solid.

Step 3: ethyl-1-acetyl-4-oxocyclohexanecarboxylate (D28-3)

To a stirred suspension of compound D28-2 (85 g, 310 mmol) in acetic anhydride (255 mL) was added pyridine (27 mL) and the mixture was stirred at 145° C. for 2 h. The solvent was removed under reduced pressure, the residue was suspended in water (200 mL) and extracted with EtOAc (3×100 mL). The combined organic layers were washed with water (100 mL), brine (100 mL), dried over $Na_2SO_4$ and concentrated under reduced pressure. The residue was purified by silica gel column chromatography (14% EtOAc/hexane as eluent) to provide compound D28-3 (11 g, 17%) as brown gum. $^1$H NMR ($CDCl_3$, 400 MHz): δ 4.28 (q, J=7.2 Hz, 2H), 2.44-2.42 (m, 6H), 2.23-2.20 (m, 5H), 1.31 (t, J=7.2 Hz, 3H).

Step 4: ethyl 4-(benzylamino)-2-oxobicyclo[2.2.2]octane-1-carboxylate (D28-4)

To a stirred mixture of compound D28-3 (25.0 g, 117 mol) and benzyl amine (38.6 mL, 353 mol) in toluene (250 mL) was added p-TsOH (0.22 g, 1.17 mmol), and the mixture was refluxed for 8 h in a flask equipped with a Dean-Stark adapter. The reaction mixture was cooled to room temperature. HCl (3 M, 250 mL) was added to the reaction mixture, and the whole was stirred for 30 min. The mixture was neutralized with aqueous solution of 6 M NaOH to pH 7. The reaction mixture was extracted with EtOAc (3×100 mL). The combined organic extracts were washed with water (100 mL), brine (100 mL), dried over $Na_2SO_4$ and concentrated under reduced pressure. The residue was purified by silica gel column chromatography (50% EtOAc/hexane as eluent) to provide compound D28-4 (30 g, 85%) as an off-white solid. $^1$H NMR ($CDCl_3$, 400 MHz): δ 7.40-7.21 (m, 5H), 6.44-6.32 (m, 2H), 4.20 (q, J=7.2 Hz, 2H), 3.74 (s, 1H), 2.45 (s, 2H), 2.30-2.20 (m, 2H), 2.10-1.95 (m, 2H), 1.89-1.75 (m, 4H), 1.27 (t, J=6.8 Hz, 3H).

Step 5: ethyl-4-(benzylamino)-2-hydroxybicyclo[2.2.2]octane-1-carboxylate (D28-5)

To a stirred solution of compound D28-4 (30.0 g, 99.0 mmol) in EtOH (300 mL) was added solid $NaBH_4$ (5.64 g, 148 mmol) in portions at 0° C. The whole was stirred at room temperature for 30 min. The mixture was quenched with water (100 mL) and extracted with EtOAc (3×200 mL). The combined organic layers were washed with water (150 mL), brine (150 mL), dried over $Na_2SO_4$ and concentrated under reduced pressure. The residue was purified by silica gel column chromatography (80% EtOAc/hexane as eluent) to provide compound D28-5 (14 g, 46%) as a white solid.

Step 6: ethyl-4-(benzylamino)-2-((methylsulfonyl)oxy)bicyclo[2.2.2]octane-1-carboxylate (D28-6)

To a stirred solution of compound D28-5 (14.0 g, 46.0 mmol) and $Et_3N$ (12.8 mL, 57.5 mmol) in THF/toluene (125 mL, 1:4) was added MsCl (4.47 mL, 57.5 mmol) at 0° C. and the mixture was stirred at room temperature for 1 h. The reaction mixture was quenched with water (100 mL) and extracted with toluene (50 mL). The organic layer was separated, dried over $Na_2SO_4$ and concentrated under reduced pressure to provide compound D28-6 (14 g, crude). The crude product was used in the next step without purification.

Step 7: ethyl-4-(benzylamino)bicyclo[2.2.2]oct-2-ene-1-carboxylate (D28-7)

To a stirred solution of compound D28-6 (17.6 g, 46.3 mol) and NaI (1.38 g, 9.25 mmol) in toluene (170 mL) were added DBU (34.65 mL, 231 mmol) and DMA (50 mL), and the whole was stirred at 120° C. for 43 h. The reaction mixture was quenched with water (100 mL) and extracted with EtOAc (2×100 mL). The combined organic layers were washed with water (50 mL), brine (50 mL), dried over anhydrous $Na_2SO_4$, and concentrated under reduced pressure. The residue was purified by column chromatography (silica gel, 50% EtOAc/hexane as eluent) to provide compound D28-7 (8 g, 61%, over two steps) as an off-white solid. $^1$H NMR ($CDCl_3$, 400 MHz): δ 7.36-7.32 (m, 5H), 6.44 (d, J=8.8 Hz, 1H), 6.32 (d, J=8.8 Hz, 1H), 4.19 (q, J=7.2 Hz, 2H), 3.86 (s, 2H), 2.04-1.97 (m, 2H), 1.65-1.50 (m, 6H), 1.28 (t, J=7.2 Hz, 3H).

Step 8: ethyl-4-aminobicyclo[2.2.2]octane-1-carboxylate (D28-8)

To a stirred solution of compound D28-7 (8.0 g, 28.0 mmol) in MeOH (80 mL) was added 10% Pd on carbon (1.6 g, 20% by weight) and the whole was stirred for 5 h under $H_2$ atmosphere (1 atm). The reaction mixture was filtered through a pad of celite and washed with MeOH (2×30 mL). The filtrate was concentrated under reduced pressure to provide compound D28-8 (5.2 g, 94%) as a colorless gum. $^1$H NMR ($CDCl_3$, 400 MHz): δ 4.00 (q, J=7.2 Hz, 2H), 1.88-1.84 (m, 4H), 1.56-1.55 (m, 8H), 1.15 (t, J=7.2 Hz, 3H).

Step 9: tert-butyl 4-cyanobenzylidenecarbamate (D28-9)

A mixture of 4-formylbenzonitrile (12.0 g, 9.16 mol) and tert-butyl(triphenylphosphoranylidene)carbamate (36.3 g, 9.61 mol) in toluene (60 mL) was refluxed for 18 h. The precipitated solid was filtered off. The filtrate was concentrated under reduced pressure to provide compound D28-9 (13 g, crude) as a colorless gum.

Step 10: tert-butyl 3-(4-cyanophenyl)-1,2-oxaziridine-2-carboxylate (D28-10, mixture of cis- and trans-isomer)

To a stirred solution of compound D28-9 (13 g, 1.67 mmol) in $CHCl_3$ (220 mL) was added a pre-cooled solution of $K_2CO_3$ (50 g) in water (400 mL) at 0° C., and the mixture was stirred vigorously. A pre-cooled solution of Oxone (80 g) in water (800 mL) was added, and the whole was stirred at 0° C. for 50 min. The reaction mixture was subjected to ten such cycles. The combined organic layer was separated, washed with water (200 mL), brine (200 mL), dried over anhydrous $Na_2SO_4$ and concentrated under reduced pressure. The residue was purified by reverse phase column chromatography (C18 silica gel, 45-50% $CH_3CN$/water as eluent) to provide compound D28-10 (1.3 g, 14% over two steps) as a white solid. ¹H NMR (CDCl₃, 400 MHz, mixture of cis- and trans-): δ 7.73-7.58 (m, 6.5H), 5.29 (s, 0.3H), 5.06 (s, 1H), 1.57 (s, 3H), 1.55 (s, 9H).

Step 11: tert-butyl 2-(4-(ethoxycarbonyl)bicyclo[2.2.2]octan-1-yl)hydrazinecarboxylate (D28-11)

A mixture of compound D28-8 (0.8 g, 4.04 mmol) and compound D28-10 (1.03 g, 4.24 mmol) in DCM (20 mL) was stirred for 3 h at 0° C. The reaction mixture was quenched with water (10 mL) and extracted with DCM (2×10 mL). The combined organic layers were washed with water (10 mL), brine (10 mL), dried over Na₂SO₄ and concentrated under reduced pressure. The residue was purified by column chromatography (silica gel, 10% EtOAc/hexane as eluent) to provide compound D28-11 (0.6 g, 50%) as a white solid.

Step 12: ethyl-4-hydrazinylbicyclo[2.2.2]octane-1-carboxylate hydrochloride (D28-12)

A mixture of compound D28-11 (0.6 g, 1.92 mmol) and 4 M HCl in dioxane (4.80 mL, 19.2 mmol) was stirred at room temperature for 18 h. The solvent was removed under reduced pressure. The residue was co-evaporated with hexane twice to provide compound D28-12 (0.58 g, crude) as a white solid.

Step 13: benzyl 1-(4-(ethoxycarbonyl)bicyclo[2.2.2]octan-1-yl)-5-(trifluoromethyl)-1H-pyrazole-4-carboxylate (D28-13)

To a stirred mixture of compound D28-12 (0.58 g, 2.04 mmol) and DIPEA (0.69 mL, 4.08 mmol) in EtOH (10 mL) was added a solution of compound D1-4 (0.64 g, 2.15 mmol) in EtOH (10 mL). The mixture was stirred at room temperature for 2 h. The reaction mixture was quenched with water (20 mL) and extracted with EtOAc (2×20 mL). The combined organic layers were washed with water (20 mL), brine (20 mL), dried over Na₂SO₄ and concentrated under reduced pressure. The residue was purified by column chromatography (silica gel, 10% EtOAc/hexane as eluent) to provide compound D28-13 (0.2 g, 21%) as a light yellow gum. ¹H NMR (CDCl₃, 400 MHz): δ 7.81-7.80 (s, 1H), 7.39-7.25 (m, 5H), 5.29 (s, 2H), 4.11 (q, J=7.2 Hz, 2H), 2.27-2.23 (m, 6H), 2.02-1.99 (m, 6H), 1.25 (t, J=7.2 Hz, 3H).

Step 14: 1-(4-(ethoxycarbonyl)bicyclo[2.2.2]octan-1-yl)-5-(trifluoromethyl)-1H-pyrazole-4-carboxylic acid (D28)

To a stirred solution of compound D28-13 (0.2 g, 0.44 mmol) in MeOH was added 10% Pd on carbon (40 mg, 30% by weight), and the whole was stirred under H₂ atmosphere (1 atm) for 5 h. The reaction mixture was filtered through a pad of celite, washed with MeOH (3×30 mL). The filtrate was concentrated under reduced pressure. The residue was triturated with hexane (2×10 mL) and the resulting solid was filtered to provide compound D28 (0.15 g, 93%) as a white solid. ¹H NMR (CDCl₃, 400 MHz): δ 7.90 (s, 1H), 4.14 (q, J=7.2 Hz, 2H), 2.30-2.26 (m, 6H), 2.04-2.00 (m, 6H), 1.25 (t, J=7.2 Hz, 3H).

Reference Example D30

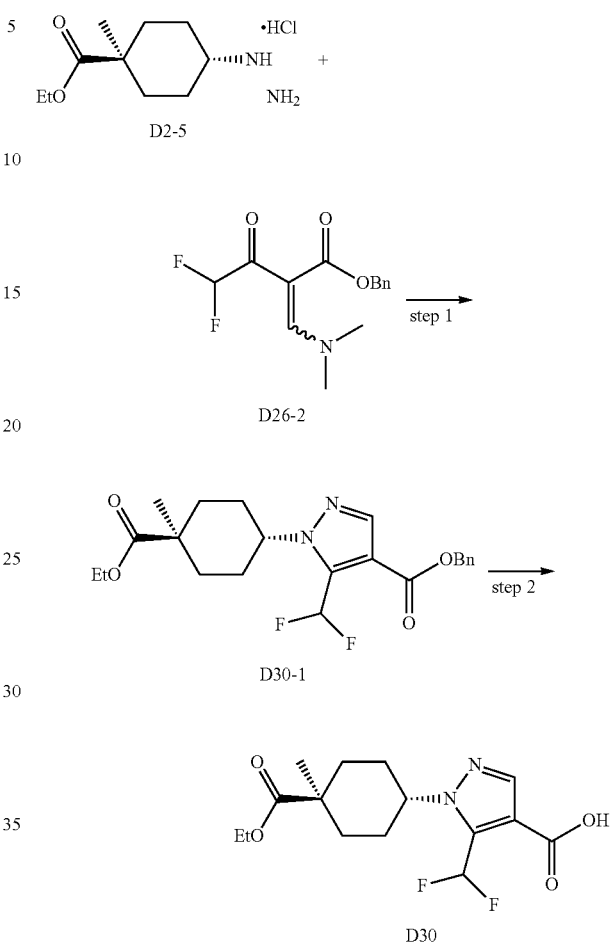

Step 1: benzyl-5-(difluoromethyl)-trans-4-(ethoxycarbonyl)-4-methylcyclohexyl)-1H-pyrazole-4-carboxylate (D30-1)

Compound D30-1 (1.91 g, 50%) was obtained as a pale yellow solid from the reaction of compound D26-2 (2.7 g, 9.55 mmol), compound D2-5 (2.6 g, 9.55 mmol) and DIPEA (3.3 mL, 19.1 mmol) in EtOH (50 mL) using a similar procedure to that described in reference example D1, step 5. ¹H NMR (CDCl₃, 400 MHz): δ 7.94 (s, 1H), 7.40-7.35 (m, 6H), 5.30 (s, 2H), 4.36 (m, 1H), 4.15 (q, J=7.2 Hz, 2H), 2.24-2.19 (m, 2H), 1.88-1.87 (m, 6H), 1.3 (s, 3H), 1.26 (t, J=7.2 Hz, 3H).

Step 2: 1-trans-4-(ethoxycarbonyl)cyclohexyl-5-(trifluoromethyl)-1H-pyrazole-4-carboxylic acid (D30)

Compound D30 (1.19 g, 79%) was obtained as a white solid from the reaction of compound D30-1 (1.91 g, 4.54 mmol) and 5% Pd on carbon (200 mg, 10% by weight) in EtOH (30 mL) using a similar procedure to that described in reference example D1, step 6. ¹H NMR (CDCl₃, 300 MHz):

δ 8.03 (s, 1H), 7.51 (t, J=51.6 Hz), 4.4-4.42 (m, 1H), 4.15 (q, J=7.2 Hz, 2H), 2.2-2.25 (m, 2H), 1.88-1.92 (m, 6H), 1.35 (s, 3H), 1.27 (t, J=7.0 Hz, 3H).

Reference Example D33

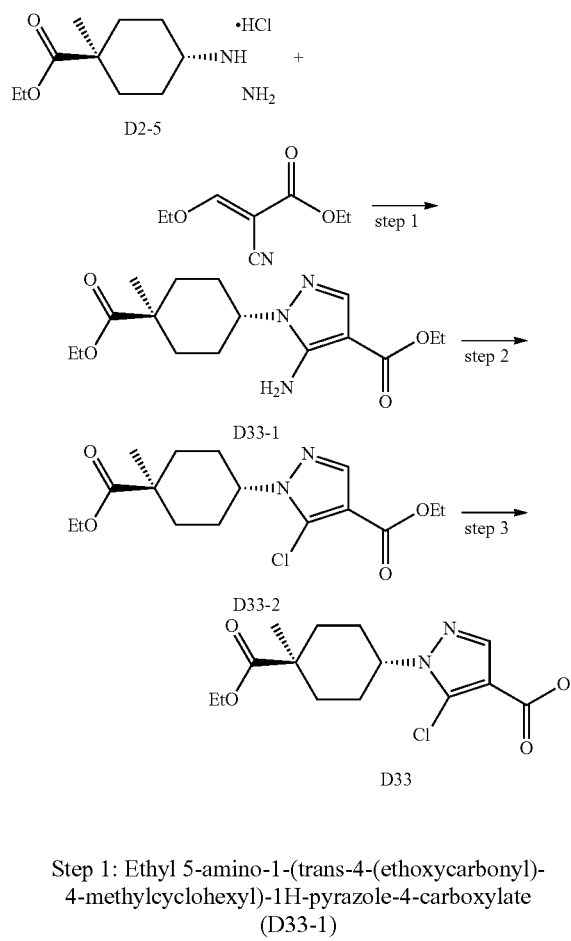

Step 1: Ethyl 5-amino-1-(trans-4-(ethoxycarbonyl)-4-methylcyclohexyl)-1H-pyrazole-4-carboxylate (D33-1)

To a solution of ethyl 2-cyano-3-ethoxyacrylate (19 g, 70 mmol) and compound D2-5 (11.96 g, 70 mmol) in EtOH (100 mL) was added sodium acetate (11.54 g, 140 mmol) and the mixture was refluxed for 6 h. The reaction mixture was quenched with water and extracted with DCM. The organic layer was washed with brine, dried over Na$_2$SO$_4$, and concentrated under reduced pressure. The residue was purified by column chromatography (silica gel, 30% EtOAc/hexane as eluent) to provide compound D33-1 (16 g, 45%) as a yellow solid.

Step 2: ethyl 5-chloro-1-(trans-4-(ethoxycarbonyl)-4-methylcyclohexyl)-1H-pyrazole-4-carboxylate (D33-2)

To a stirred mixture of copper (I) chloride (0.77 g, 7.8 mmol) in CH$_3$CN (10 mL) at 0° C. was added tert-butyl nitrite (0.92 mL, 7.8 mmol). A solution of compound D33-1 (1.26 g, 3.9 mmol) in CH$_3$CN (10 mL) was added dropwise to the mixture at the same temperature. The reaction mixture was warmed to room temperature and stirred at the same temperature for 1 h and at 60° C. for another 1 h. The reaction mixture was quenched with 6 M HCl (10 mL) at 0° C. and extracted with DCM (3×100 mL). The combined organic layers were washed with water (100 mL), brine (100 mL), dried over Na$_2$SO$_4$ and concentrated under reduced pressure. The residue was purified by column chromatography (silica gel, 30% EtOAc/hexane as eluent) to provide compound D33-2 (0.3 g, 37%) as a colourless gum.

Step 3: 5-chloro-1-(trans-4-(ethoxycarbonyl)-4-methylcyclohexyl)-1H-pyrazole-4-carboxylic acid (D33)

To a solution of compound D33-2 (0.6 g, 1.75 mmol) in EtOH (10 mL) was added 1 N NaOH solution dropwise at room temperature. The mixture was stirred for 45 min. The reaction mixture pH was adjusted to 3 and extracted with EtOAc (2×200 mL). The combined organic layers were washed with water (100 mL), brine (100 mL), dried over anhydrous Na$_2$SO$_4$ and concentrated under reduced pressure. The residue was purified by reverse phase column chromatography (C18 silica gel, 80% CH$_3$CN/water as eluent) to provide compound D33 (0.4 g, 55%) as an off-white solid.

Reference Example D41

1-((1S,3R,4S)-4-(ethoxycarbonyl)-3-methylcyclohexyl)-5-(trifluoromethyl)-1H-pyrazole-4-carboxylic acid

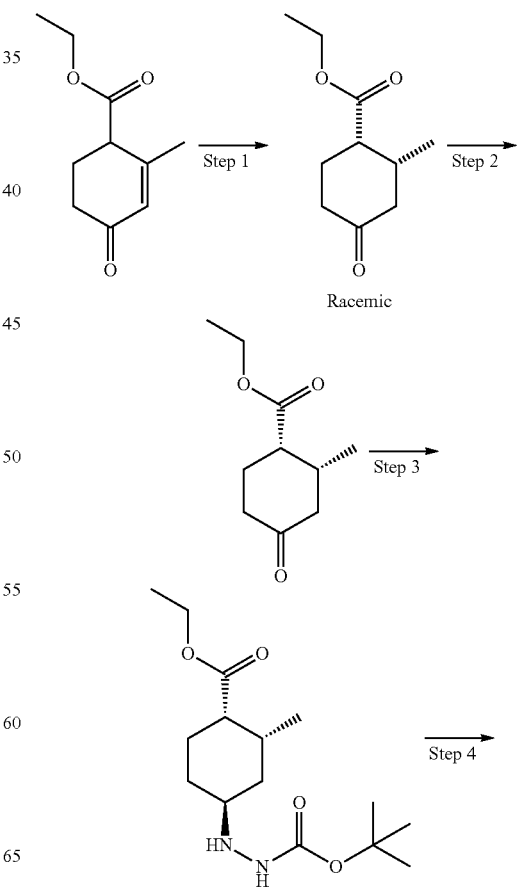

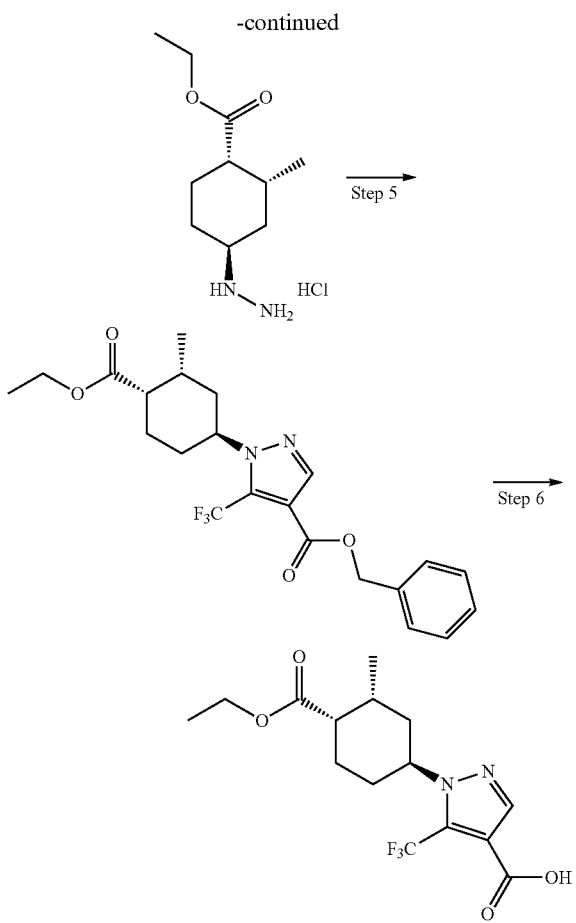

Step 1: (1S,2R)-ethyl 2-methyl-4-oxocyclohexanecarboxylate (Racemic)

To a Parr flask was added 10% palladium on carbon (wet degussa type) (4.47 g, 4.20 mmol) in EtOH (378 ml). Then ethyl 2-methyl-4-oxo-2-cyclohexene-1-carboxylate (23.65 ml, 140 mmol) and 5 N hydrochloric acid (1.679 ml, 8.40 mmol) were added into the reaction mixture. The atmosphere of the flask was degassed, and then filled with hydrogen (50 psi). The mixture was allowed to stir under hydrogenation conditions 30 min. The progress of the reaction was monitored by LC/MS and TLC (50% EtOAc/hexane; potassium permanganate stain), which suggested reaction completion. The mixture was filtered through a pad of celite and the filter cake was rinsed with EtOH. The mixture was concentrated in-vacuo. The crude material was purified by chromatography through an Interchim (15 micron) silica-gel column (220 g), eluting with a gradient of 0-50% EtOAc in hexane, to provide (1S,2R)-ethyl 2-methyl-4-oxocyclohexanecarboxylate (18.277 g, 99 mmol, 70.9% yield) (Racemic) as light-yellow oil. $^1$H NMR (400 MHz, CDCl$_3$) δ 4.19 (dtt, 2H), 2.85 (td, J=4.25, 8.31 Hz, 1H), 2.43-2.58 (m, 4H), 2.31 (ddd, J=6.06, 8.75, 14.72 Hz, 1H), 2.01-2.21 (m, 2H), 1.29 (t, J=7.14 Hz, 3H), 0.98 (d, J=6.85 Hz, 3H); LCMS (ESI) m/z 185.0 (M+H)$^+$.

Step 2: (1S,2R)-ethyl 2-methyl-4-oxocyclohexanecarboxylate (Chiral)

(1S,2R)-ethyl 2-methyl-4-oxocyclohexanecarboxylate (Racemic) was separated into chiral peak 1 and chiral peak 2 by normal phase HPLC; Varian Cardinals SD1 normal phase system (10×50 cm; 20 micron AS column) Method: 10% EtOH in Heptane Flow Rate: 400 ml/min. Detection: 220 nm, 300 nm. This purification method provided peak 1 (1S,2R)-ethyl 2-methyl-4-oxocyclohexanecarboxylate (>98% ee) as colorless oil. $^1$H NMR (400 MHz, CDCl$_3$) δ 4.19 (ddquin, 2H), 2.85 (td, J=4.25, 8.31 Hz, 1H), 2.43-2.58 (m, 4H), 2.31 (ddd, J=6.16, 8.66, 14.72 Hz, 1H), 2.01-2.21 (m, 2H), 1.24-1.32 (m, 3H), 0.98 (d, J=6.85 Hz, 3H); LCMS (ESI) m/z 185.0 (M+H)$^+$. Peak 2 (1R,2S)-ethyl 2-methyl-4-oxocyclohexanecarboxylate (>95% ee) as colorless oil. $^1$H NMR (400 MHz, CDCl$_3$) δ 4.19 (ddquin, 2H), 2.85 (td, J=4.13, 8.36 Hz, 1H), 2.43-2.58 (m, 4H), 2.31 (ddd, J=6.16, 8.66, 14.72 Hz, 1H), 2.01-2.21 (m, 2H), 1.29 (t, J=7.14 Hz, 3H), 0.98 (d, J=6.85 Hz, 3H); LCMS (ESI) m/z 185.0 (M+H)$^+$.

Step 3: tert-butyl 2-((1S,3R,4S)-4-(ethoxycarbonyl)-3-methylcyclohexyl)hydrazinecarboxylate To a 500-mL 3-neck round-bottomed flask was added (1S,2R)-ethyl 2-methyl-4-oxocyclohexanecarboxylate (10.00 g, 54.3 mmol) in chloroform (201 ml). Then AcOH, glacial (3.13 ml, 54.3 mmol), and tert-butyl carbazate (7.89 g, 59.7 mmol) was added into the reaction mixture. The flask was placed into a pre-heated bath (30° C.) and allowed to stir 10 min. Then NaBH(OAc)$_3$ (34.5 g, 163 mmol) was slowly added into the reaction mixture in small portions. The bath was removed after the addition and the overall mixture was allowed to stir under inert atmosphere 16 h. The progress of the reaction was monitored by LC/MS and TLC (30% EtOAc/DCM; Ninhydrin stain) which suggested reaction completion. The mixture was neutralized with the slow addition of sat. aq. NaHCO$_3$ into the reaction mixture. After the material was neutralized, the layers were separated and the aqueous layer was extracted with DCM (3×). The combined organic extracts were dried over Na$_2$SO$_4$, filtered and concentrated in-vacuo. The crude sample was analyzed by TLC (30% EtOAc/hexane; ninhydrin stain; Peak 1: Rf=0.46 & Peak 2: Rf=0.38) The crude material was divided into two portions and purified by chromatography through an Interchim (25 micron) silica-gel column (300 g)*(Two 300 Gram Columns were used), eluting with a gradient of 0-30% EtOAc in hexane, to provide tert-butyl 2-((1R,3R,4S)-4-(ethoxycarbonyl)-3-methylcyclohexyl)hydrazinecarboxylate (8.512 g, 28.3 mmol, 52.2% yield) (Peak 1; Cis)$^1$H NMR (400 MHz, CDCl$_3$) δ 6.03-6.28 (m, 1H), 4.07-4.16 (m, 2H), 3.59-3.90 (m, 1H), 2.76-2.97 (m, 1H), 2.55 (d, J=2.74 Hz, 1H), 2.01 (dd, J=3.03, 13.40 Hz, 1H), 1.59-1.77 (m, 3H), 1.49-1.56 (m, 2H), 1.46 (s, 10H), 1.19-1.31 (m, 3H), 1.02 (d, J=7.04 Hz, 3H); LCMS (ESI) m/z 301.1 (M+H)$^+$ and tert-butyl 2-((1S,3R,4S)-4-(ethoxycarbonyl)-3-methylcyclohexyl)hydrazinecarboxylate (5.089 g, 16.94 mmol, 31.2% yield) (Peak 2; trans) $^1$H NMR (400 MHz, DMSO-d6) δ 7.89-8.27 (m, 1H), 5.75 (s, 1H), 4.08-4.19 (m, 1H), 2.74-2.93 (m, 1H), 2.21-2.46 (m, 2H), 1.99 (s, 1H), 1.66 (d, J=3.91 Hz, 3H), 1.38 (s, 9H), 1.14-1.26 (m, 5H), 0.79 (d, J=7.04 Hz, 3H); LCMS (ESI) m/z 301.1 (M+H)$^+$.

Step 4: (1S,2R,4S)-ethyl 4-hydrazinyl-2-methylcyclohexanecarboxylate hydrochloride To a 250-mL round-bottomed flask was added tert-butyl 2-((1S,3R,4S)-4-(ethoxycarbonyl)-3-methylcyclohexyl)hydrazinecarboxylate (5.089 g, 16.94 mmol) in EtOH (56.5 ml). Then hydrogen chloride, 4.0 M solution in 1,4-dioxane (72.0 ml, 288 mmol) was added into the reaction mixture. The overall mixture was allowed to stir under inert atmosphere overnight. The progress of the reaction was monitored by TLC (30% EtOAc in hexane; ninhydrin stain), which suggested reaction completion. The mixture was concentrated in-vacuo. The residue was diluted with hexane and concentrated in-vacuo. This gave (1S,2R,4S)-ethyl 4-hydrazinyl-2-methylcyclohexanecarboxylate hydrochloride (4.60 g) as white solid. This material was carried into the next step of the synthesis, without further purification. LCMS (ESI) m/z 201.2 (M+H)$^+$.

Step 5: benzyl 1-((1S,3R,4S)-4-(ethoxycarbonyl)-3-methylcyclohexyl)-5-(trifluoromethyl)-1H-pyrazole-4-carboxylate To a 250-mL round-bottomed flask was added (1S,2R,4S)-ethyl 4-hydrazinyl-2-methylcyclohexanecarboxylate hydrochloride (4.00 g, 16.90 mmol) and DIPEA (4.43 ml, 25.3 mmol) in EtOH (84 ml). Then a solution of (Z)-benzyl 2-((dimethylamino)methylene)-4,4,4-trifluoro-3-oxobutanoate (5.09 g, 16.90 mmol) in EtOH (84 ml) was added dropwise into the reaction mixture. The overall reaction mixture was allowed to stir under inert atmosphere, while at ambient temperature overnight. The progress of the reaction was monitored by LC/MS and TLC (30% EtOAc/hexane) which showed mostly desired material LCMS (ESI) m/z 461.2 (M+Na)$^+$, without any starting material remaining. The reaction mixture was concentrated in-vacuo. The crude material was purified by chromatography through an Interchim (25 micron) silica-gel column (200 g), eluting with a gradient of 0-30% EtOAc in hexane, to provide benzyl 1-((1S,3R,4S)-4-(ethoxycarbonyl)-3-methylcyclohexyl)-5-(trifluoromethyl)-1H-pyrazole-4-carboxylate (5.631 g, 12.84 mmol, 76% yield) as light-yellow oil. $^1$H NMR (400 MHz, DMSO-d6) δ 8.14 (s, 1H), 7.32-7.45 (m, 5H), 5.30 (s, 2H), 4.55-4.65 (m, 1H), 4.02-4.15 (m, 2H), 2.65 (td, J=4.50, 11.54 Hz, 1H), 2.13 (dt, J=4.50, 12.42 Hz, 1H), 1.95-2.04 (m, 2H), 1.73 (d, J=4.89 Hz, 3H), 1.16-1.23 (m, 3H), 0.92 (d, J=7.04 Hz, 3H); LCMS (ESI) m/z 461.2 (M+Na)$^+$.

Step 6: 1-((1S,3R,4S)-4-(ethoxycarbonyl)-3-methylcyclohexyl)-5-(trifluoromethyl)-1H-pyrazole-4-carboxylic acid

*(Hydrogenation was Performed with Suitcase Apparatus)

A pressurized vial was charged with palladium 10 wt. % (dry basis) on activated carbon, wet (1.367 g, 1.284 mmol) while under a stream of N$_2$ (gas). Then a solution of benzyl 1-((1S,3R,4S)-4-(ethoxycarbonyl)-3-methylcyclohexyl)-5-(trifluoromethyl)-1H-pyrazole-4-carboxylate (5.631 g, 12.84 mmol) in a 1:1 mixture of EtOH (32.1 ml)/EtOAc (32.1 ml) was added into the vial. The reaction mixture atmosphere was purged with hydrogen gas (3×). The reaction was stirred vigorously under hydrogenation (35 psi) conditions for 2.5 h. The progress of the reaction was monitored by LC/MS, which suggested reaction completion LCMS (ESI) m/z 371.2 (M+Na)$^+$. The mixture was filtered through a plug of celite and the filtrate was concentrated in-vacuo. The residue was diluted with hexane and agitated. The precipitate was collected by filtration and the solids were rinsed with hexane. This gave 1-((1S,3R,4S)-4-(ethoxycarbonyl)-3-methylcyclohexyl)-5-(trifluoromethyl)-1H-pyrazole-4-carboxylic acid (3.810 g, 10.94 mmol, 85% yield) as white solid. $^1$H NMR (400 MHz, DMSO-d6) δ 7.91-8.21 (m, 1H), 4.47-4.69 (m, 1H), 4.01-4.16 (m, 2H), 2.56-2.70 (m, 1H), 2.12 (dt, J=4.21, 12.37 Hz, 1H), 1.93-2.06 (m, 2H), 1.71-1.90 (m, 3H), 1.19 (t, J=7.04 Hz, 3H), 0.92 (d, J=7.04 Hz, 3H); LCMS (ESI) m/z 371.2 (M+Na)$^+$.

Reference Example D43

1-((1R,3R,4R)-4-(ethoxycarbonyl)-3-methylcyclohexyl)-5-(trifluoromethyl)-1H-pyrazole-4-carboxylic acid compound with 1-((1S,3S,4S)-4-(ethoxycarbonyl)-3-methylcyclohexyl)-5-(trifluoromethyl)-1H-pyrazole-4-carboxylic acid (1:1) (D43)

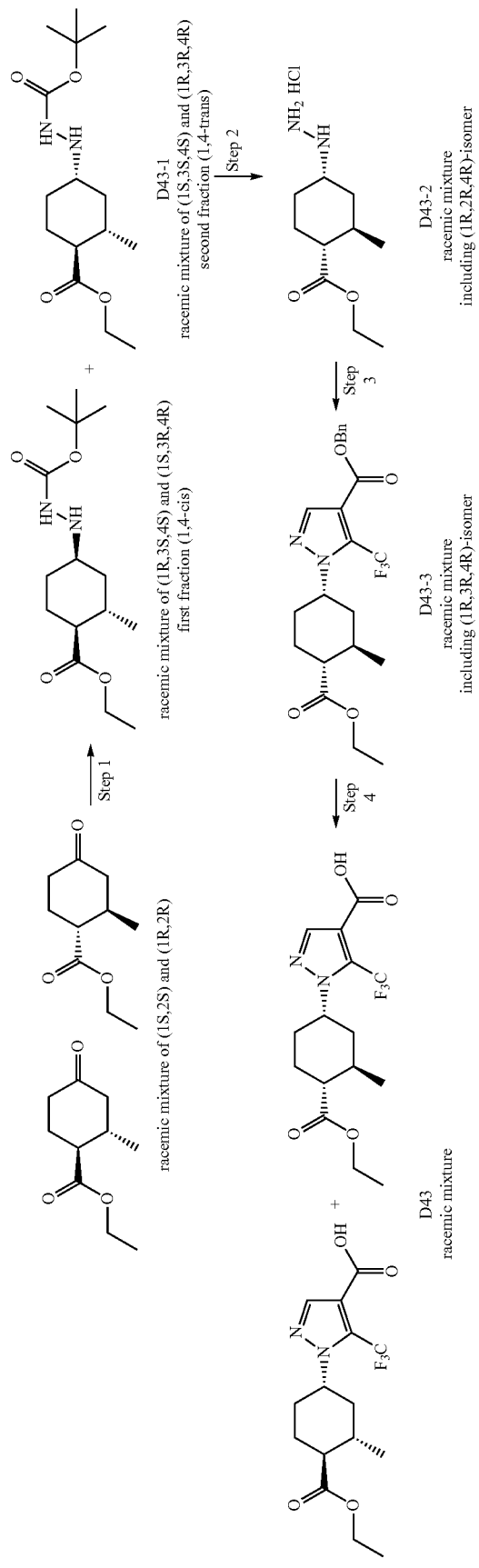

Step 1: tert-butyl 2-((1R,3R,4R)-4-(ethoxycarbonyl)-3-methylcyclohexyl)hydrazinecarboxylate compound with tert-butyl 2-((1S,3S,4S)-4-(ethoxycarbonyl)-3-methylcyclohexyl)hydrazinecarboxylate (1:1) (D43-1)

To a homogeneous racemic mixture of (1R,2R)-ethyl 2-methyl-4-oxocyclohexanecarboxylate compound with (1S,2S)-ethyl 2-methyl-4-oxocyclohexanecarboxylate (1:1) (1.600 g, 8.68 mmol) was added tert-butyl carbazate (1.263 g, 9.55 mmol), AcOH (1.038 ml, 17.98 mmol), and NaBH(OAc)$_3$ (6.00 g, 28.3 mmol). The light-yellow heterogeneous mixture was stirred at room temperature. After 24 h, LCMS (ESI) and TLC indicated that the reaction was complete, two peaks with 323.1 (M+Na).

[TLC]: (30% of EtOAc in Hexane, stained with phosphomolybdic acid in EtOH) $R_f$ of reactant=0.47, $R_f$ of 1,4-cis-desired product=0.42, $R_f$ of 1,4-trans-desired product=0.25. The reaction mixture was poured into saturated aqueous NaHCO$_3$ solution (150 mL). The reaction mixture was extracted with DCM (2×100 mL). The organic extract was dried over Na$_2$SO$_4$. The solution was filtered and concentrated in vacuo to give the crude material as a colorless oil. The crude material was absorbed onto a plug of silica gel and purified by silica gel column chromatography eluting with a gradient of 0% to 25% EtOAc in hexane to provide two fractions:

First fraction for higher spot (1,4-cis): ($R_f$=0.42 at 30% of EtOAc in Hexane) tert-butyl 2-((1R,3S,4S)-4-(ethoxycarbonyl)-3-methylcyclohexyl)hydrazinecarboxylate compound with tert-butyl 2-((1S,3R,4R)-4-(ethoxycarbonyl)-3-methylcyclohexyl)hydrazinecarboxylate (1:1) (1.4418 g, 4.80 mmol, 55.3% yield) as light-yellow syrup: $^1$H NMR (300 MHz, CDCl$_3$) δ 6.05 (1H, br. s.), 4.14 (2H, q, J=7.1 Hz), 3.25 (1H, br. s.), 1.12-2.22 (21H, m), 0.88 (3H, d, J=6.6 Hz); LCMS (ESI) m/z 301.1 (M+H)$^+$ and m/z 323.1 (M+Na)$^+$.

Second fraction for lower spot (1,4-trans): Desired product ($R_f$=0.25 at 30% of EtOAc in Hexane) tert-butyl 2-((1R,3R,4R)-4-(ethoxycarbonyl)-3-methylcyclohexyl)hydrazinecarboxylate compound with tert-butyl 2-((1S,3S,4S)-4-(ethoxycarbonyl)-3-methylcyclohexyl)hydrazinecarboxylate (1:1) (D43-1) (0.5467 g, 1.820 mmol, 20.96% yield) as off-white syrupy solid. $^1$H NMR (300 MHz, CDCl$_3$) δ 6.05 (1H, br. s.), 4.06-4.23 (2H, m), 2.81-2.99 (1H, m), 1.65-2.07 (5H, m), 1.39-1.56 (10H, m), 1.20-1.31 (4H, m), 0.99-1.16 (1H, m), 0.79-0.96 (4H, m); LCMS (ESI) m/z 323.1 (M+Na)$^+$.

[NOTE]: The second fraction was used in Step 2.

Step 2: (1R,2R,4R)-ethyl 4-hydrazinyl-2-methylcyclohexanecarboxylate compound with (1S,2S,4S)-ethyl 4-hydrazinyl-2-methylcyclohexanecarboxylate (1:1) dihydrochloride (D43-2)

To a mixture of tert-butyl 2-((1R,3R,4R)-4-(ethoxycarbonyl)-3-methylcyclohexyl)hydrazinecarboxylate compound with tert-butyl 2-((1S,3S,4S)-4-(ethoxycarbonyl)-3-methylcyclohexyl)hydrazinecarboxylate (1:1) (D42-1) (0.5245 g, 1.746 mmol) in EtOH (4.37 ml) was added hydrogen chloride, 4 M in 1,4-dioxane (4.37 ml, 17.46 mmol). The clear light-yellow mixture was stirred at room temperature. After 42 h (white heterogeneous mixture), LC-MS (ESI) showed that the reaction was complete, the desired product (m/z 201.2 (M+1)) was formed. The mixture was concentrated in vacuo to provide (1R,2R,4R)-ethyl 4-hydrazinyl-2-methylcyclohexanecarboxylate compound with (1S,2S,4S)-ethyl 4-hydrazinyl-2-methylcyclohexanecarboxylate (1:1) dihydrochloride (D43-2) as light-yellow solid. $^1$H NMR (300 MHz, DMSO-d$_6$) δ 4.07 (2H, q, J=7.0 Hz), 2.88-3.05 (1H, m), 2.04 (2H, t, J=11.6 Hz), 1.80-1.96 (2H, m), 1.52-1.73 (1H, m), 1.12-1.46 (5H, m), 0.78-1.08 (4H, m); LCMS (ESI) m/z 201.2 (M+H)$^+$.

Step 3: benzyl 1-((1R,3R,4R)-4-(ethoxycarbonyl)-3-methylcyclohexyl)-5-(trifluoromethyl)-1H-pyrazole-4-carboxylate compound with benzyl 1-((1S,3S,4S)-4-(ethoxycarbonyl)-3-methylcyclohexyl)-5-(trifluoromethyl)-1H-pyrazole-4-carboxylate (1:1) (D43-3)

To a mixture of (1R,2R,4R)-ethyl 4-hydrazinyl-2-methylcyclohexanecarboxylate compound with (1S,2S,4S)-ethyl 4-hydrazinyl-2-methylcyclohexanecarboxylate (1:1) dihydrochloride (D42-2) (0.413 g, 1.745 mmol) in EtOH (13.42 ml) was added DIPEA (0.669 ml, 3.84 mmol) followed by a solution of (Z)-benzyl 2-((dimethylamino)methylene)-4,4,4-trifluoro-3-oxobutanoate (0.526 g, 1.745 mmol) in EtOH (5 mL). The clear brown mixture was stirred at room temperature. After 15 h, LC-MS (ESI) showed that the reaction was a complete, the desired product (m/z 439.1 (M+1)) was formed. The reaction mixture was concentrated in vacuo. The residue was diluted with water (50 mL) and extracted with EtOAc (2×100 mL). The organic extract washed with satd NaCl (1×100 mL) and dried over Na$_2$SO$_4$. The solution was filtered and concentrated in vacuo to give the crude material as a brown syrup. The crude material was absorbed onto a plug of silica gel and purified by silica gel column chromatography eluting with a gradient of 0% to 10% EtOAc in hexane to give benzyl 1-((1R,3R,4R)-4-(ethoxycarbonyl)-3-methylcyclohexyl)-5-(trifluoromethyl)-1H-pyrazole-4-carboxylate compound with benzyl 1-((1S,3S,4S)-4-(ethoxycarbonyl)-3-methylcyclohexyl)-5-(trifluoromethyl)-1H-pyrazole-4-carboxylate (1:1) (D43-3) (0.4258 g, 0.971 mmol, 55.7% yield) as yellow syrup: $^1$H NMR (300 MHz, DMSO-d$_6$) δ 8.06-8.17 (1H, m), 7.29-7.50 (5H, m), 5.29 (2H, s), 4.42-4.60 (1H, m), 4.10 (2H, q, J=7.1 Hz), 1.48-2.13 (8H, m), 1.19 (3H, t, J=7.1 Hz), 0.89 (3H, d, J=6.0 Hz); LCMS (ESI) m/z 439.1 (M+H)$^+$.

Step 4: 1-((1R,3R,4R)-4-(ethoxycarbonyl)-3-methylcyclohexyl)-5-(trifluoromethyl)-1H-pyrazole-4-carboxylic acid compound with 1-((1S,3S,4S)-4-(ethoxycarbonyl)-3-methylcyclohexyl)-5-(trifluoromethyl)-1H-pyrazole-4-carboxylic acid (1:1) (D43)

A pressurized vial was charged with palladium 10 wt. % on activated carbon (0.103 g, 0.097 mmol) while under a stream of nitrogen gas. Then a solution of benzyl 1-((1R,3R,4R)-4-(ethoxycarbonyl)-3-methylcyclohexyl)-5-(trifluoromethyl)-1H-pyrazole-4-carboxylate compound with benzyl 1-((1S,3S,4S)-4-(ethoxycarbonyl)-3-methylcyclohexyl)-5-(trifluoromethyl)-1H-pyrazole-4-carboxylate (1:1) (D43-3) (0.4258 g, 0.971 mmol) in a 1:1 mixture of EtOH (2.428 ml)/EtOAc (2.428 ml) was added into the vial. The reaction atmosphere was purged with hydrogen gas (3 times). The reaction was stirred vigorously under hydrogenation (33 psi) at 21° C. After 3 h, LCMS (ESI) showed that the reaction was complete. The reaction mixture was purged with nitrogen gas for 30 min. The mixture was filtered through a pad of celite and the filter cake was rinsed with EtOAc. The filtrate was concentrated in vacuo to give 1-((1R,3R,4R)-4-(ethoxycarbonyl)-3-methylcyclohexyl)-5-(trifluoromethyl)-1H-pyrazole-4-carboxylic acid compound with 1-((1S,3S,4S)-4-(ethoxycarbonyl)-3-methylcyclohexyl)-5-(trifluoromethyl)-1H-pyrazole-4-carboxylic acid (1:1) (D43) (0.3224 g, 0.926 mmol, 95% yield) as light-yellow solid:

$^1$H NMR (300 MHz, DMSO-$d_6$) δ 13.14 (1H, br. s.), 8.01 (1H, s), 4.40-4.59 (1H, m), 4.10 (2H, q, J=7.0 Hz), 1.48-2.16 (8H, m), 1.20 (3H, t, J=7.1 Hz), 0.89 (3H, d, J=6.0 Hz); LCMS (ESI) m/z 349.1 (M+H)$^+$.

Reference Example D48

1-((3aS,5R,7aS)-3a-(methoxycarbonyl)octahydro-1H-inden-5-yl)-5-(trifluoromethyl)-1H-pyrazole-4-carboxylic acid

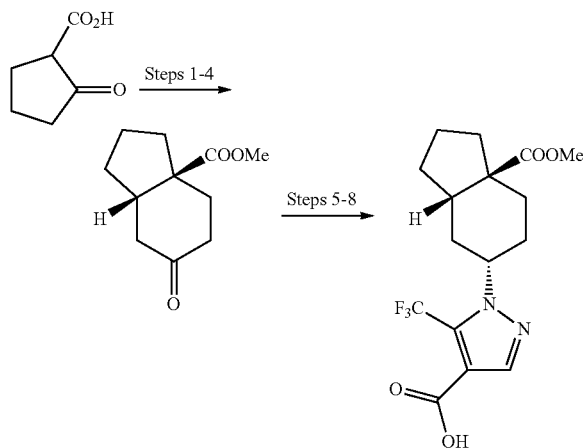

Step 1: methyl 2-oxo-1-(3-oxobutyl)cyclopentanecarboxylate

A solution of methyl 2-oxocyclopentanecarboxylate (2.000 ml, 14.07 mmol), methyl vinyl ketone (1.381 ml, 16.88 mmol) and triethylamine (2.94 ml, 21.10 mmol) in toluene (20 mL) was heated at 40° C. for 24 h. The reaction was brought to room temperature, diluted with EtOAc, washed with sat. NH$_4$Cl, dried over Na$_2$SO$_4$, filtered, concentrated and chromatographed on silica gel using 0-50% heptane/EtOAc to afford a colorless oil as methyl 2-oxo-1-(3-oxobutyl)cyclopentanecarboxylate (2.0 g, 9.42 mmol, 67.0% yield).

Step 2: methyl 5-(pyrrolidin-1-yl)-2,6,7,7a-tetrahydro-1H-indene-7a-carboxylate

A solution of methyl 2-oxo-1-(3-oxobutyl)cyclopentanecarboxylate (2.0 g, 9.42 mmol, 67.0% yield) and pyrrolidine (2.354 ml, 28.1 mmol) in dry toluene (25 mL) was heated to reflux under N$_2$ atmosphere in a Dean-Stark trap for 16 h. The reaction went to completion and concentrated. The residue was dissolved in EtOAc, washed with water, brine, dried over Na$_2$SO$_4$, filtered and concentrated to afford a greenish oil as methyl 5-(pyrrolidin-1-yl)-2,6,7,7a-tetrahydro-1H-indene-7a-carboxylate (3.3 g, 13.34 mmol, 95% yield) to be used as is.

Step 3: methyl 6-oxo-2,3,3a,4,5,6-hexahydro-1H-indene-3a-carboxylate

The crude enamine from Step 2 was dissolved in toluene (20 mL) and a solution of sodium acetate (1.360 ml, 25.3 mmol) in AcOH/water (4/4 mL) was added and the resulting mixture was heated to reflux under N$_2$ atmosphere for 2 h. The reaction went to completion, diluted with EtOAc, washed with water, sat. NH$_4$Cl, sat. NaHCO$_3$, brine, dried over Na$_2$SO$_4$, filtered, concentrated and chromatographed on silica gel using 0-30% heptane/EtOAc to afford methyl 6-oxo-2,3,3a,4,5,6-hexahydro-1H-indene-3a-carboxylate (1.32 g, 6.80 mmol, 48.3% yield) as a bright yellow oil. MS m/z=195.2 [M+H]$^+$.

Step 4: (3aS,7aR)-methyl 6-oxooctahydro-1H-indene-3a-carboxylate

To a stirred solution of methyl 6-oxo-2,3,3a,4,5,6-hexahydro-1H-indene-3a-carboxylate (1.32 g, 6.80 mmol) in EtOH (30 mL) was added palladium, 10 wt. %(dry basis) on activated carbon, wet, degussa type e101 ne/w (0.120 ml, 6.80 mmol) and the resulting mixture underwent hydrogenation using the hydrogenation kit for 3 h. The mixture was filtered through celite, concentrated and chromatographed on silica gel using 0-25% heptane/hexane to afford (3aS,7aR)-methyl 6-oxooctahydro-1H-indene-3a-carboxylate (0.278 g, 1.417 mmol, 20.84% yield) and (3aS,7aS)-methyl 6-oxooctahydro-1H-indene-3a-carboxylate (0.394 g, 2.008 mmol, 29.5% yield) as colorless oil. MS m/z=181.2 [M+H]$^+$.

Steps 5 through 8. 1-((3aS,5R,7aS)-3a-(methoxycarbonyl)octahydro-1H-inden-5-yl)-5-(trifluoromethyl)-1H-pyrazole-4-carboxylic acid was prepared from (3aS,7aR)-methyl 6-oxooctahydro-1H-indene-3a-carboxylate using similar procedures as in example D22. MS m/z=361.2 [M+H]$^+$.

Example D55 trans-1-(4-(Ethoxycarbonyl)-3,3-dimethylcyclohexyl)-5-(trifluoromethyl)-1H-pyrazole-4-carboxylic acid (racemic mixture)

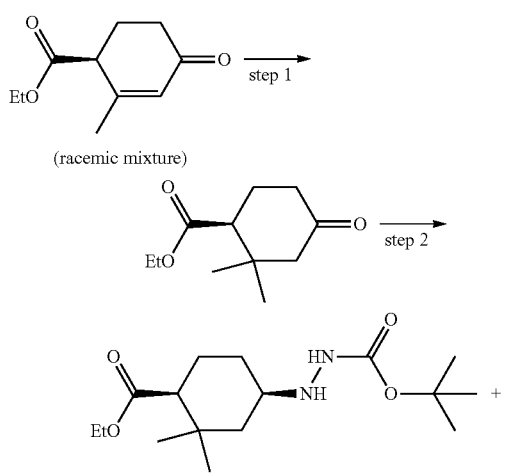

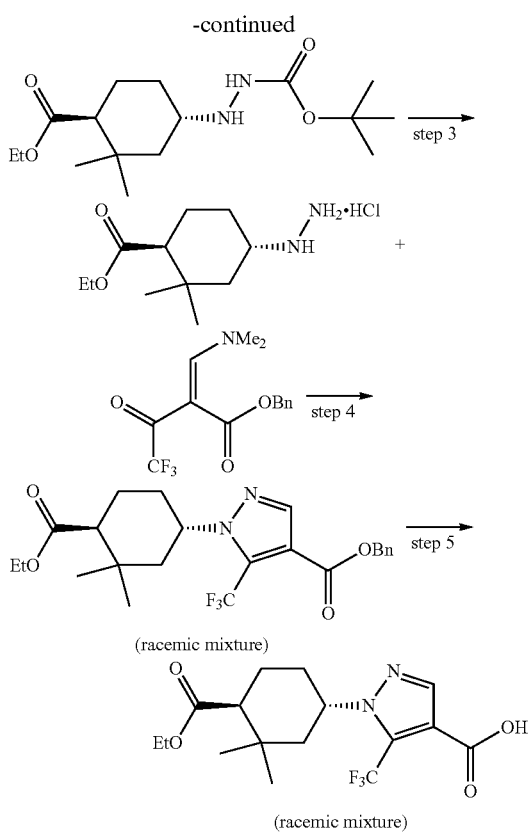

(racemic mixture)

Step 1: Ethyl 2,2-dimethyl-4-oxocyclohexanecarboxylate (racemic mixture)

Methyllithium (170 mL of a 1.6 M solution with Et$_2$O, 260 mmol) was added to a stirring mixture of copper (I) iodide (25 g, 130 mmol) and Et$_2$O (130 mL), at −40° C. under a nitrogen atmosphere. After stirring for 10 min at −40° C., ethyl 2-methyl-4-oxo-2-cyclohexene-1-carboxylate (12 g, 66 mmol) was added. After stirring for 30 min at −40° C., the reaction mixture was allowed to warm to −20° C. After stirring for 90 min at −20° C., saturated aqueous ammonium chloride and EtOAc were added sequentially, the mixture was partitioned between more saturated aqueous ammonium chloride and EtOAc, the layers were separated, the organic material washed sequentially with saturated aqueous ammonium chloride (2×) and brine, dried (Na$_2$SO$_4$), filtered, and the filtrate was concentrated. The residue was dissolved with DCM, silica gel (39 g) was added to the solution, and the volatiles were removed under reduced pressure. The residue was subjected to flash chromatography on silica gel (gradient elution; 19:1 to 9:1 hexane-EtOAc) to give ethyl 2,2-dimethyl-4-oxo-cyclohexanecarboxylate (8.9 g, 68% yield; racemic mixture) as a clear yellow oil.

Step 2: tert-Butyl trans-2-4-(ethoxycarbonyl)-3,3-dimethylcyclohexyl)hydrazinecarboxylate (racemic mixture)

NaBH(OAc)$_3$ (29 g, 140 mmol) was added to a stirring solution of ethyl 2,2-dimethyl-4-oxocyclohexanecarboxylate (8.9 g, 45 mmol, from Step 1; racemic material), tert-butyl carbazate (6.5 g, 49 mmol), glacial AcOH (7.8 mL, 140 mmol), and THF (90 mL). After stirring for 26 h, the reaction mixture was added to saturated aqueous NaHCO$_3$, the mixture was stirred for 60 min, partitioned between EtOAc and more saturated aqueous NaHCO$_3$, the layers were separated, the organic material washed sequentially with saturated aqueous NaHCO$_3$ and brine, dried (Na$_2$SO$_4$), filtered, and the filtrate was concentrated under reduced pressure. The residue was dissolved with DCM, silica gel (42 g) was added to the solution, and the volatiles were removed under reduced pressure. The residue was subjected to flash chromatography on silica gel (gradient elution; 9:1 to 4:1 hexane-EtOAc) and the isolated material containing the desired product was re-subjected to flash chromatography on silica gel (5:1 hexane-EtOAc) to give tert-butyl trans-2-4-(ethoxycarbonyl)-3,3-dimethylcyclohexyl)hydrazinecarboxylate (0.79 g, 5.6% yield; racemic mixture) as a clear colorless oil.

Step 3: Ethyl trans-4-hydrazinyl-2,2-dimethylcyclohexanecarboxylate hydrochloride (racemic mixture)

Hydrogen chloride (3.1 mL of a 4.0 M solution with 1,4-dioxane, 13 mmol) was added to a stirring solution of tert-butyl trans-2-4-(ethoxycarbonyl)-3,3-dimethylcyclohexyl)hydrazinecarboxylate (0.79 g, 2.5 mmol, from Step 2; racemic material) and EtOH (5.0 mL), and then the reaction mixture was heated at 60° C. After stirring for 3 h at 60° C., the reaction mixture was allowed to cool to room temperature and then concentrated under reduced pressure to give ethyl trans-4-hydrazinyl-2,2-dimethylcyclohexanecarboxylate hydrochloride (0.63 g, 100% yield; racemic mixture) as an off-white solid.

Step 4: Benzyl trans-1-4-(ethoxycarbonyl)-3,3-dimethylcyclohexyl)-5-(trifluoromethyl)-1H-pyrazole-4-carboxylate (racemic mixture)

A solution of (Z)-benzyl 2-((dimethylamino)methylene)-4,4,4-trifluoro-3-oxobutanoate (0.76 g, 2.5 mmol) and EtOH (2.4 mL) was added to a stirring solution of ethyl trans-4-hydrazinyl-2,2-dimethylcyclohexanecarboxylate hydrochloride (0.63 g, 2.5 mmol, from Step 3; racemic mixture), DIPEA (0.96 mL, 5.5 mmol), and EtOH (6.0 mL). After stirring for 20 h, the reaction mixture was concentrated under reduced pressure, the residue was partitioned between EtOAc and saturated aqueous NaHCO$_3$, the layers were separated, the organic material washed sequentially with saturated aqueous NaHCO$_3$ and brine, dried (Na$_2$SO$_4$), filtered, and the filtrate was concentrated under reduced pressure. The residue was dissolved with DCM, silica gel (5.0 g) was added to the solution, and the volatiles were removed under reduced pressure. The residue was subjected to flash chromatography on silica gel (19:1 hexane-EtOAc) to give benzyl trans-1-4-(ethoxycarbonyl)-3,3-dimethylcyclohexyl)-5-(trifluoromethyl)-1H-pyrazole-4-carboxylate (0.76 g, 67% yield; racemic mixture) as a clear colorless oil. $^1$H NMR (400 MHz, CDCl$_3$) δ 7.94 (s, 1H), 7.46-7.29 (m, 5H), 5.30 (s, 2H), 4.67-4.52 (m, 1H), 4.25-4.05 (m, 2H), 2.35-2.23 (m, 1H), 2.12-1.84 (m, 5H), 1.69 (dd, J=3.2, 12.8 Hz, 1H), 1.27 (t, J=7.1 Hz, 3H), 1.09 (s, 3H), 1.07 (s, 3H). LCMS (ESI): 453.0 (M+H)$^+$.

Step 5: trans-1-(4-(Ethoxycarbonyl)-3,3-dimethylcyclohexyl)-5-(trifluoromethyl)-1H-pyrazole-4-carboxylic acid (racemic mixture)

A stirring mixture of benzyl trans-1-4-(ethoxycarbonyl)-3,3-dimethylcyclohexyl)-5-(trifluoromethyl)-1H-pyrazole-4- carboxylate (0.76 g, 1.7 mmol, from Step 4; racemic mixture), palladium (0) (10 wt. % dry basis, wet) on activated carbon (0.18 g, 0.17 mmol), EtOAc (4.2 mL), and EtOH (4.2 mL) was exposed to gaseous hydrogen (33 psi). After stirring for 2 h, the reaction mixture was filtered and the filtrate was concentrated under reduced pressure to give trans-1-(4-(ethoxycarbonyl)-3,3-dimethylcyclohexyl)-5-(trifluoromethyl)-1H-pyrazole-4-carboxylic acid (0.59 g, 97% yield; racemic mixture) as a colorless solid. LCMS (ESI): 363.0 (M+H)$^+$.

Reference Example D60

1-(((+/−)-cis)-2-allylcyclohexyl)-5-(trifluoromethyl)-1H-pyrazole-4-carboxylic acid as a racemate (D60)

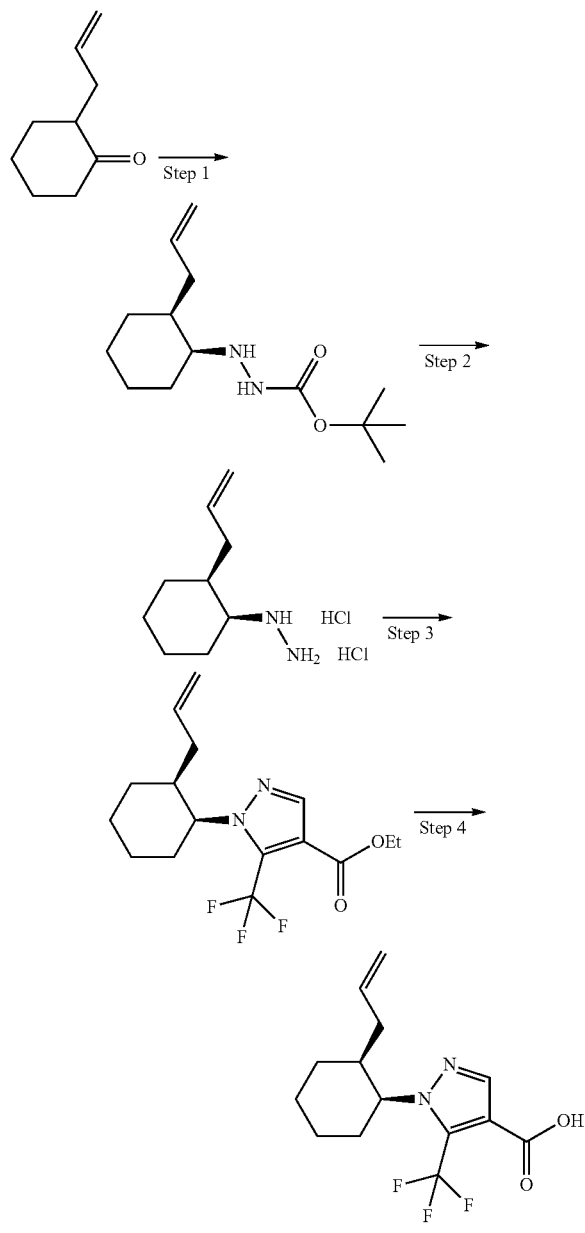

Step 1: tert-butyl 2-(((+/−)cis)-2-allylcyclohexyl)hydrazinecarboxylate as a racemate To a solution of tert-butyl carbazate (0.966 g, 7.31 mmol), 2-allylcyclohexanone (1.00 g, 7.24 mmol), and AcOH (1.00 ml, 17.47 mmol) at 0° C. was added NaBH(OAc)$_3$ (4.60 g, 21.71 mmol) and the mixture was stirred at room temperature overnight. The reaction mixture was added slowly to a saturated aqueous solution of Na$_2$CO$_3$. The layers were separated and the aqueous layer was extracted with DCM twice. The organics were pooled, washed with brine, dried over Na$_2$SO$_4$, decanted and concentrated in vacuo to provide a colorless syrup. NMR indicated ~0.16:1 mixture of isomers. The syrup was purified by silical gel column chromatography eluting with a gradient of 0% to 50% EtOAc in hexane. The first eluting peak was collected and concentrated in vacuo to provide tert-butyl 2-(((+/−)cis)-2-allylcyclohexyl)hydrazinecarboxylate as a racemate.

Step 2: (((+/−)cis)-2-allylcyclohexyl)hydrazine dihydrochloride as a racemate

4 M HCl in dioxane (11.79 ml, 47.2 mmol) was added to a solution of tert-butyl 2-(((+/−)cis)-2-allylcyclohexyl)hydrazinecarboxylate as a racemate (1.20 g, 4.72 mmol) in EtOH (11.79 ml) and the mixture was stirred at room temperature overnight. The reaction mixture was concentrated in vacuo to provide (((+/−)cis)-2-allylcyclohexyl)hydrazine dihydrochloride as a racemic, white solid.

Step 3: ethyl 1-(((+/−)cis)-2-allylcyclohexyl)-5-(trifluoromethyl)-1H-pyrazole-4-carboxylate as a racemate A solution of (Z)-ethyl 2-((dimethylamino)methylene)-4,4,4-trifluoro-3-oxobutanoate (1.073 g, 4.49 mmol) in EtOH (11 mL) was added slowly to a solution of (((+/−)cis)-2-allylcyclohexyl)hydrazine dihydrochloride as a racemate (1.07 g, 4.71 mmol) and DIPEA (1.724 ml, 9.87 mmol) in EtOH (22.43 ml) at room temperature. After 6 h, the reaction mixture was concentrated in vacuo, diluted with water and extracted with EtOAc twice. The combined organic layers were washed with brine, dried over Na$_2$SO$_4$, decanted and concentrated in vacuo to provide an orange oil. The mixture was purified by silica gel column chromatography eluting with a gradient of 0% to 35% EtOAc in hexane to provide ethyl 1-(((+/−)cis)-2-allylcyclohexyl)-5-(trifluoromethyl)-1H-pyrazole-4-carboxylate as a racemate as a pale yellow oil.

Step 4: 1-(((+/−)-cis)-2-allylcyclohexyl)-5-(trifluoromethyl)-1H-pyrazole-4-carboxylic acid as a racemate A solution of lithium hydroxide hydrate (1.265 g, 30.2 mmol) in water was added to a solution of ethyl 1-(((+/−)cis)-2-allylcyclohexyl)-5-(trifluoromethyl)-1H-pyrazole-4-carboxylate as a racemate (0.996 g, 3.02 mmol) in THF and MeOH and the mixture was stirred at room temperature overnight. The mixture was concentrated in vacuo. The resulting turbid solution was diluted with water to provide a clear solution. The pH was adjusted to 1 by adding 1 M HCl and the mixture was stirred vigorously for 30 min. The resulting precipitate was collected by vacuum filtration to provide 1-(((+/−)-cis)-2-allylcyclohexyl)-5-(trifluoromethyl)-1H-pyrazole-4-carboxylic acid as a racemate (D60) as a white solid.

Reference Example D68 (cis and trans)

1-((1r,4r)-4-(2-ethoxy-2-oxoethyl)-4-methylcyclohexyl)-5-(trifluoromethyl)-1H-pyrazole-4-carboxylic acid and 1-((1s,4s)-4-(2-ethoxy-2-oxoethyl)-4-methylcyclohexyl)-5-(trifluoromethyl)-1H-pyrazole-4-carboxylic acid

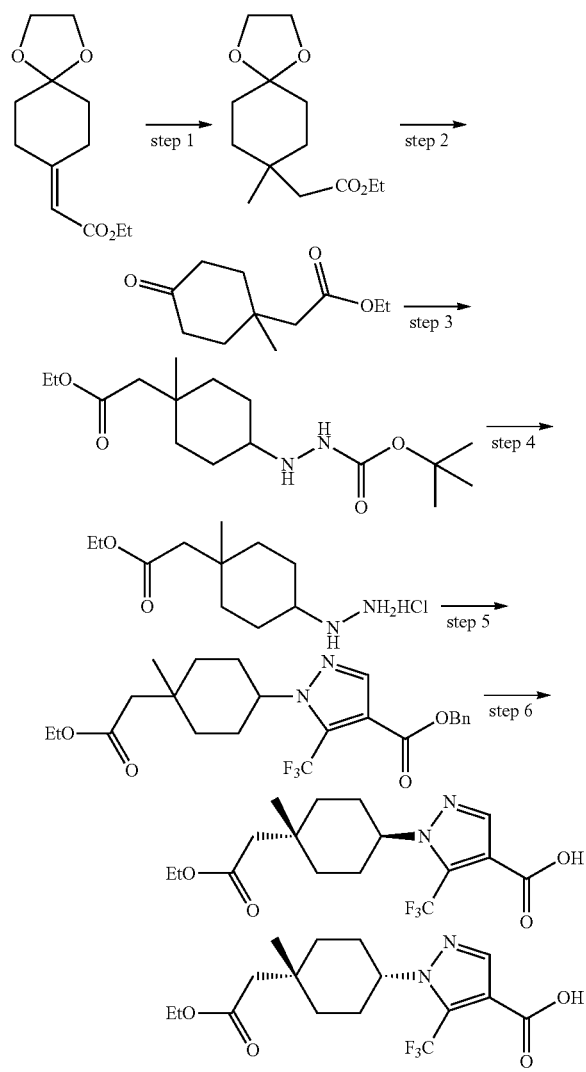

Step 1: ethyl 2-(8-methyl-1,4-dioxaspiro[4.5]decan-8-yl)acetate

To a solution of CuI (5.8 g, 30 mmol, 3.24 eq) in Et₂O (100 mL) maintained under N₂ at 0° C. was added a solution of 3.0 M MeLi (21.3 mL, 64 mmol, 6.8 eq) in dimethoxyethane dropwise. The resulting solution was stirred at 0° C. for 10 min and the ether solvent was removed from the reaction under vacuum (120 torr) at 0° C. DCM (100 mL) was then added to the residue and the reaction was cooled to −78° C.

TMSCl (4.4 mL, 35 mmol, 3.7 eq) was added followed by ethyl 2-(1,4-dioxaspiro[4.5]decan-8-ylidene)acetate (JW Pharmlab, Levittown, Pa.; 2.127 g, 9.4 mmol) in DCM (10 mL). The reaction mixture was stirred overnight and quenched with aqueous NKr' solution. The black suspension was filtered through celite and the organic layer was separated, washed, dried and purified by silica gel chromatography (EtOAc/hexane, up to 15%) on 80 g gold column to give ethyl 2-(8-methyl-1,4-dioxaspiro[4.5]decan-8-yl)acetate (1.6 g, 6.60 mmol, 70.2% yield) as a colorless liquid: ¹H NMR (500 MHz, CDCl₃) δ 1.07 (s, 3H), 1.19-1.33 (m, 3H), 1.49-1.67 (m, 8H), 2.27 (s, 2H), 3.94 (s, 4H), 4.09-4.16 (m, 2H).

Step 2: ethyl 2-(1-methyl-4-oxocyclohexyl)acetate

Water (0.5 mL) was added to a stirring solution of ethyl 2-(8-methyl-1,4-dioxaspiro[4.5]decan-8-yl)acetate (1.6 g, 6.60 mmol) and formic acid (10 mL) at room temperature. Analysis of the reaction mixture by LCMS indicated that the starting material was consumed and the desired product had formed. The reaction mixture was concentrated under reduced pressure, and the residue was partitioned between EtOAc and brine, the layers were separated, the organic material washed with brine (2×), dried (Na₂SO₄), filtered, and the filtrate was concentrated under reduced pressure to give a pale yellow liquid ethyl 2-(1-methyl-4-oxocyclohexyl)acetate (1.6 g, 8.07 mmol, 86% yield): ¹H NMR (500 MHz, CDCl₃) δ 1.22-1.31 (m, 6H), 1.77-1.91 (m, 4H), 2.39-2.43 (m, 6H), 4.12-4.23 (m, 2H).

Step 3: tert-butyl 2-(4-(2-ethoxy-2-oxoethyl)-4-methylcyclohexyl)hydrazinecarboxylate Ethyl 2-(1-methyl-4-oxocyclohexyl)acetate (1.5 g, 7.57 mmol) and tert-butyl carbazate (1.100 g, 8.32 mmol) were dissolved in chloroform (30 mL), and AcOH (1.0 mL) and NaBH(OAc)₃ (5.65 g) were added under ice-cooling. The mixture was allowed to gradually return to room temperature, and the mixture was stirred for 4 h. The reaction mixture was poured into saturated aqueous NaHCO₃ solution, and the mixture was extracted with EtOAc. The organic layer was washed with water and brine, dried over anhydrous magnesium sulfate, and concentrated under reduced pressure. The obtained residue was purified by silica gel column chromatography (hexane:EtOAc, 100%-35%) to give tert-butyl 2-(4-(2-ethoxy-2-oxoethyl)-4-methylcyclohexyl)hydrazinecarboxylate (1.72 g, 5.47 mmol, 72.3% yield) as a mixture of isomers (colorless oil). LCMS=315.4 (M+H)⁺.

Step 4: ethyl 2-(4-hydrazinyl-1-methylcyclohexyl)acetate hydrochloride tert-Butyl 2-(4-(2-ethoxy-2-oxoethyl)-4-methylcyclohexyl)hydrazinecarboxylate (1.7 g, 5.41 mmol) in EtOH (5 mL) was added HCl (4 M in 1,4-dioxane, 10 mL) dropwise at 0° C. The mixture was stirred at room temperature for 4 h and concentrated to give a white solid, used without further purification in the next step.

Step 5: benzyl 1-(4-(2-ethoxy-2-oxoethyl)-4-methylcyclohexyl)-5-(trifluoromethyl)-1H-pyrazole-4-carboxylate A solution of (Z)-benzyl 2-((dimethylamino)methylene)-4,4,4-trifluoro-3-oxobutanoate (2.018 g, 6.70 mmol) in EtOH (20 mL) was added dropwise to a solution of ethyl 2-(4-hydrazinyl-1-methylcyclohexyl)acetate hydrochloride (1.6 g, 6.38 mmol) and DIPEA (2.452 ml, 14.04 mmol) in EtOH (31.9 ml) at ambient temperature. The reaction was allowed to stir overnight. The solvent was removed and the residual oil was purified using a 40 g REDISEP™ Gold SiO$_2$ column eluting with 0-25% EtOAc/hexane using the Gold resolution method. Fractions containing the desired product were combined and concentrated in vacuo to provide benzyl 1-(4-(2-ethoxy-2-oxoethyl)-4-methylcyclohexyl)-5-(trifluoromethyl)-1H-pyrazole-4-carboxylate (2.12 g, 4.69 mmol, 73.4% yield) as a mixture of isomers (colorless syrup). LCMS=453.4 (M+H)$^+$.

Step 6: 1-((1r,4r)-4-(2-ethoxy-2-oxoethyl)-4-methylcyclohexyl)-5-(trifluoromethyl)-1H-pyrazole-4-carboxylic acid and 1-((1s,4s)-4-(2-ethoxy-2-oxoethyl)-4-methylcyclohexyl)-5-(trifluoromethyl)-1H-pyrazole-4-carboxylic acid Benzyl 1-(4-(2-ethoxy-2-oxoethyl)-4-methylcyclohexyl)-5-(trifluoromethyl)-1H-pyrazole-4-carboxylate (2.1 g, 4.64 mmol) was dissolved in EtOH (10 mL) and EtOAc (10 mL) and added to wet Pd/C (10%, 210 mg) in a pressure flask under N$_2$. The reaction mixture was equipped with a pressure gauge and one arm was connected vacuum and the other to hydrogen cylinder. The pressure was set to 20 psi and the reaction system was connected to hydrogen and open to vacuum twice. Then the valves were closed and the reaction mixture was stirred for 2 h. The pressure of the gauge was 5 psi and LCMS showed completion. Filtration through celite and removal of solvents gave an oil (1.5 g). The material was separated by prep SFC: 150×50 mm AD-H column with 18 mL/min MeOH (20 mM NH$_3$)+162 g/min CO$_2$, 10% co-solvent at 180 g/min. Temp.=29° C., Outlet pressure=100 bar, Wavelength=230 nm. Injected 0.5 mL of 1,500 mg sample dissolved in 20 mL 1:1 MeOH:DCM; c=75 mg/mL and 37.5 mg per injection. Cycle time 11 min, run time 15 min, to give Peak 1: white solid 1-((1r,4r)-4-(2-ethoxy-2-oxoethyl)-4-methylcyclohexyl)-5-(trifluoromethyl)-1H-pyrazole-4-carboxylic acid (600 mg, 1.656 mmol, 35.7% yield): $^1$H NMR (500 MHz, CD$_2$Cl$_2$) δ 1.14 (s, 3H), 1.23-1.28 (m, 3H), 1.46-1.58 (m, 2H), 1.67-1.77 (m, 2H), 1.79-1.87 (m, 2H), 2.16-2.28 (m, 4H), 4.08-4.14 (m, 2H), 4.32 (tt, J=11.7, 4.1 Hz, 1H), 6.76 (br. s, 1H), 7.94 (s, 1H). LCMS=363.3 (M+H)$^+$; Peak 2: 1-((1s,4s)-4-(2-ethoxy-2-oxoethyl)-4-methylcyclohexyl)-5-(trifluoromethyl)-1H-pyrazole-4-carboxylic acid (700 mg, 1.932 mmol, 41.6% yield): $^1$H NMR (500 MHz, CDCl$_3$) δ 1.09 (s, 3H), 1.25-1.28 (m, 3H), 1.33-1.43 (m, 2H), 1.82-1.88 (m, 4H), 2.17-2.32 (m, 2H), 2.47 (s, 2H), 4.12-4.17 (m, 2H), 4.35 (tt, J=11.7, 3.9 Hz, 1H), 6.72 (br. s, 1H), 7.98 (s, 1H). LCMS=363.4 (M+H)$^+$.

The following pyrazole carboxylic acids were prepared using similar procedure in reference examples described above.

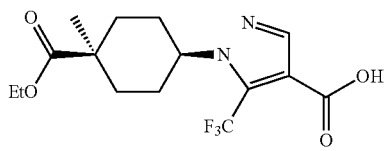

D3

-continued

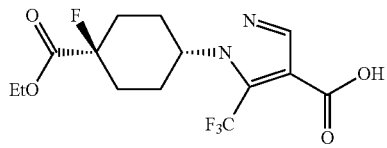

D4

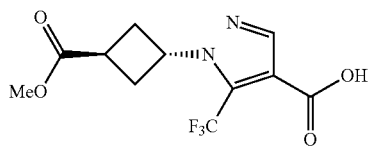

D5

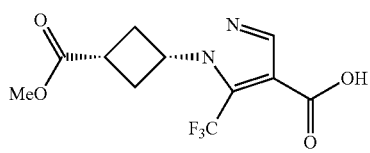

D6

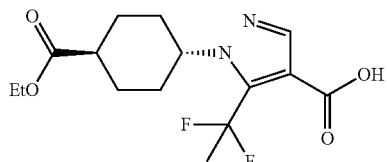

D7

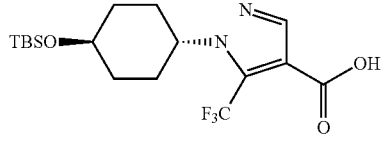

D8

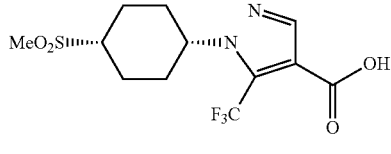

D9

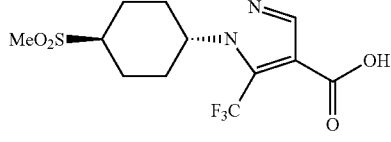

D10

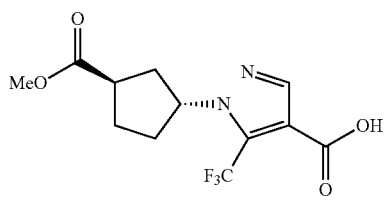

D11

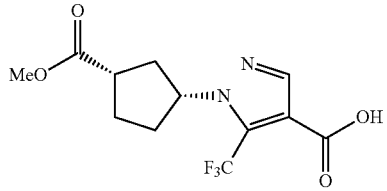

D12

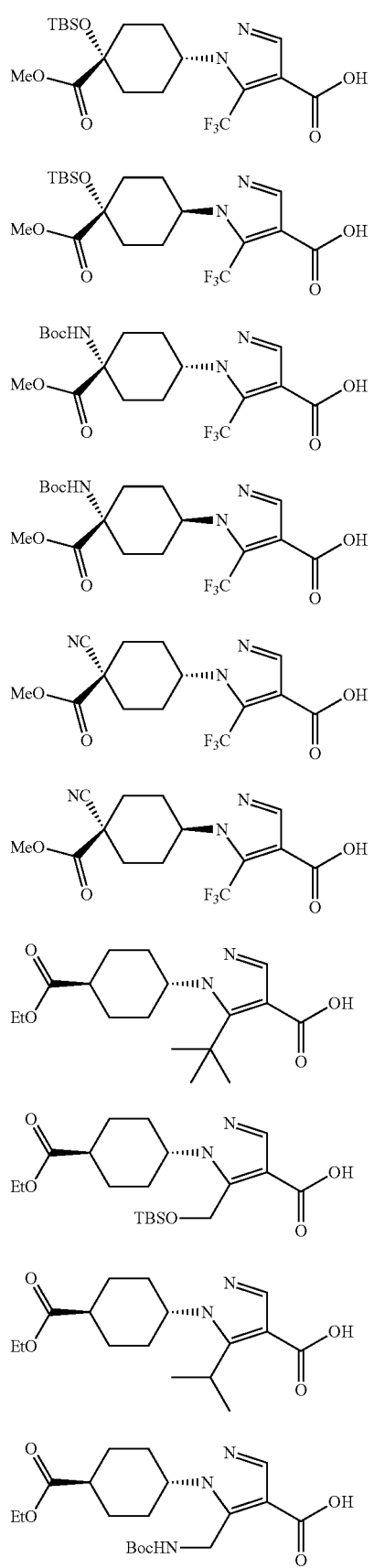
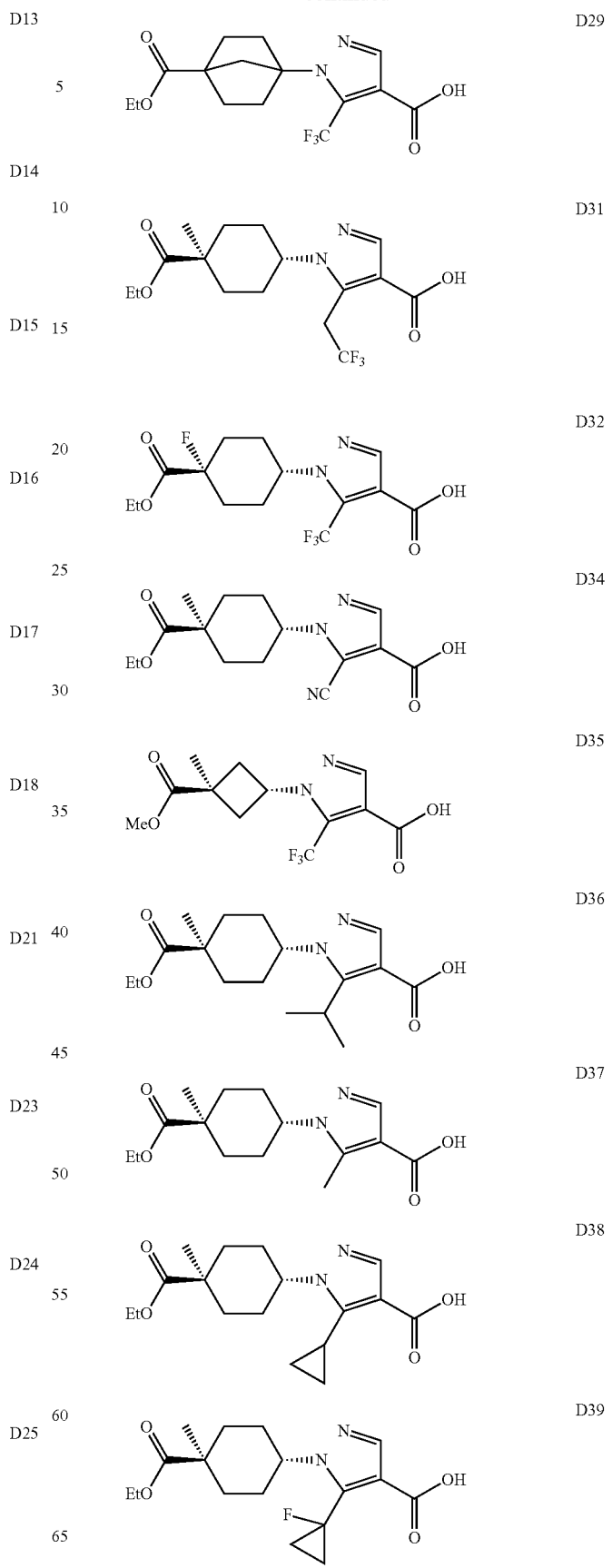

| reference example | structure |
|---|---|
| D40 | |
| D40b | |
| D41 | |
| D42 | |
| D43 | 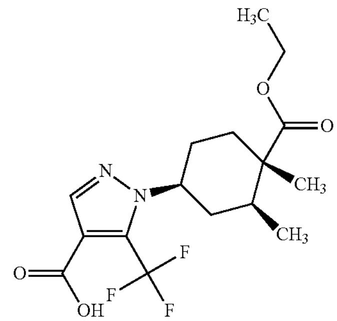 [SMILES: CCOC(=O)[C@@]1(C)CC[C@H](n2ncc(C(=O)O)c2C(F)(F)F)C[C@@H]1C] |
| D44 | 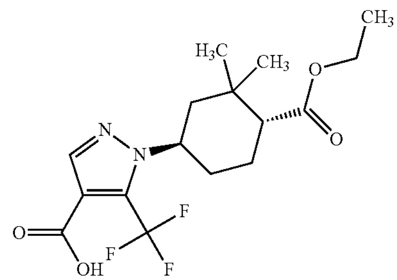 [SMILES: CCOC(=O)[C@@H]1CC[C@@H](n2ncc(C(=O)O)c2C(F)(F)F)CC1(C)C] |
| D45 | 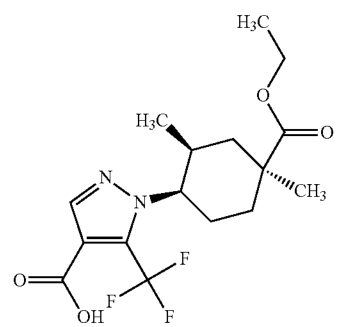 [SMILES: CCOC(=O)[C@@]1(C)CC[C@@H](n2ncc(C(=O)O)c2C(F)(F)F)[C@@H](C)C1] |
| D46 | 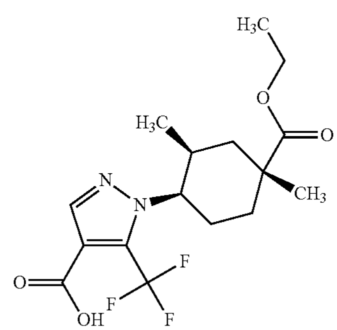 [SMILES: CCOC(=O)[C@]1(C)CC[C@@H](n2ncc(C(=O)O)c2C(F)(F)F)[C@@H](C)C1] |
| D47 | 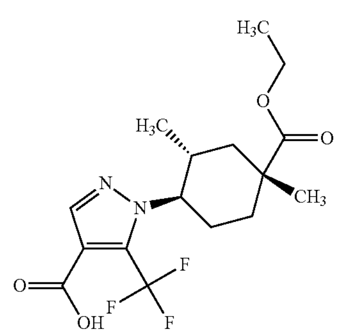 [SMILES: CCOC(=O)[C@]1(C)CC[C@@H](n2ncc(C(=O)O)c2C(F)(F)F)[C@H](C)C1] |

-continued
| reference example | structure |
|---|---|
| D48 | 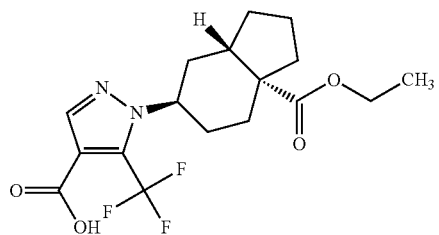 [SMILES: CCOC(=O)[C@@]12CCC[C@H]1C[C@H](n1ncc(C(=O)O)c1C(F)(F)F)CC2] |
| D49 | 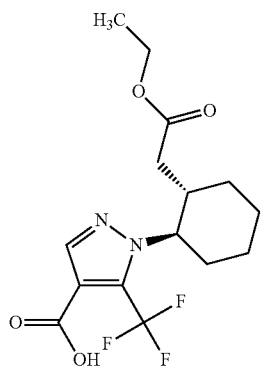 [SMILES: CCOC(=O)C[C@@H]1CCCC[C@H]1n1ncc(C(=O)O)c1C(F)(F)F] |
| D50 | 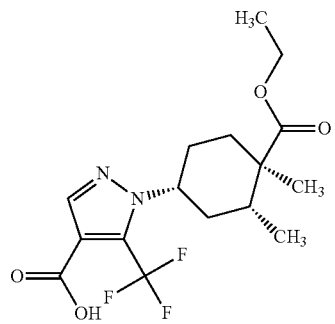 [SMILES: CCOC(=O)[C@]1(C)CC[C@@H](n2ncc(C(=O)O)c2C(F)(F)F)C[C@H]1C] |
| D51 | 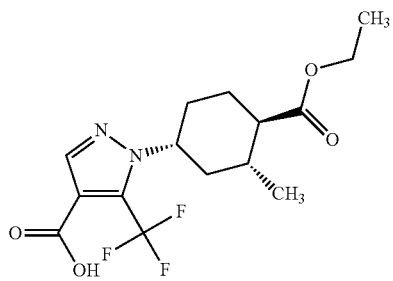 [SMILES: CCOC(=O)[C@@H]1CC[C@@H](n2ncc(C(=O)O)c2C(F)(F)F)C[C@H]1C] |
| D52 | 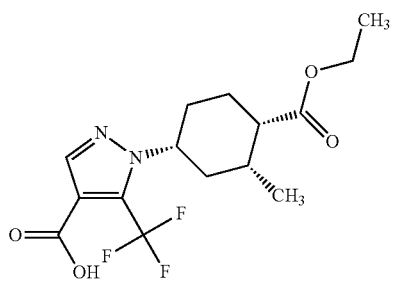 [SMILES: CCOC(=O)[C@H]1CC[C@@H](n2ncc(C(=O)O)c2C(F)(F)F)C[C@H]1C] |
-continued
| reference example | structure |
|---|---|
| D53 | 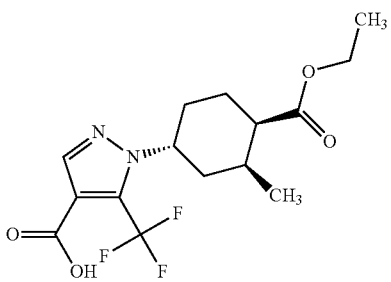 [SMILES: CCOC(=O)[C@@H]1CC[C@@H](n2ncc(C(=O)O)c2C(F)(F)F)C[C@@H]1C] |
| D54 | 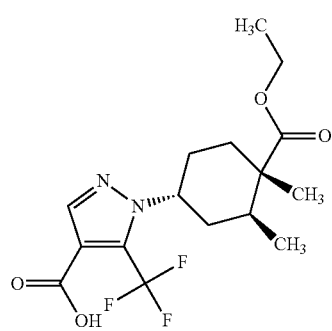 [SMILES: CCOC(=O)[C@@]1(C)CC[C@@H](n2ncc(C(=O)O)c2C(F)(F)F)C[C@@H]1C] |
| D55 | 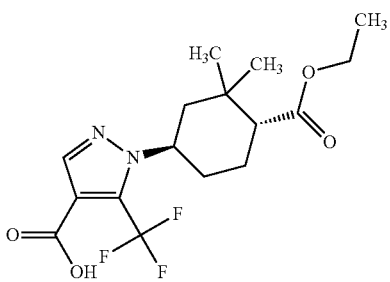 |
| D56 | 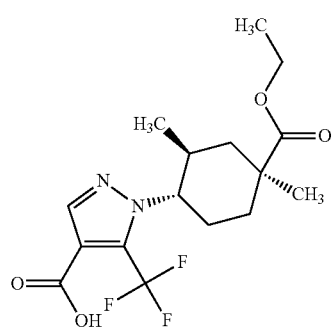 [SMILES: CCOC(=O)[C@@]1(C)CC[C@H](n2ncc(C(=O)O)c2C(F)(F)F)[C@@H](C)C1] |
| D57 | 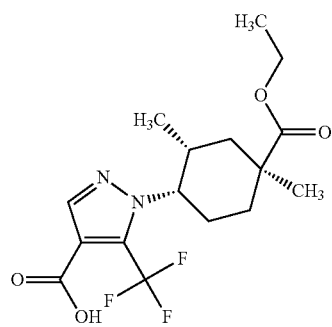 [SMILES: CCOC(=O)[C@@]1(C)CC[C@H](n2ncc(C(=O)O)c2C(F)(F)F)[C@H](C)C1] |

| reference example | structure |
|---|---|
| D58 | 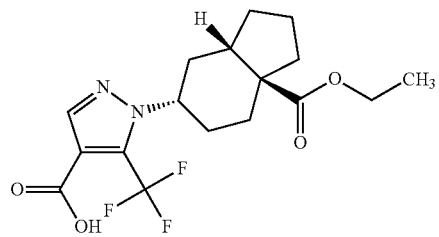 [SMILES: CCOC(=O)[C@]12CCC[C@H]1C[C@@H](n1ncc(C(=O)O)c1C(F)(F)F)CC2] |
| D59 | 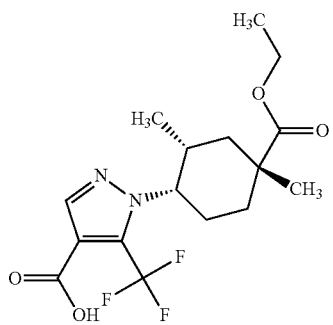 [SMILES: CCOC(=O)[C@]1(C)CC[C@H](n2ncc(C(=O)O)c2C(F)(F)F)[C@H](C)C1] |
| D60 | 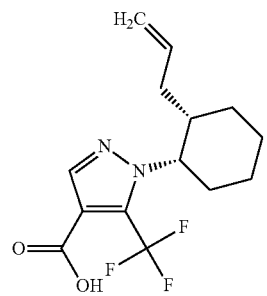 [SMILES: C=CC[C@@H]1CCCC[C@@H]1n1ncc(C(=O)O)c1C(F)(F)F] |
| D61 | 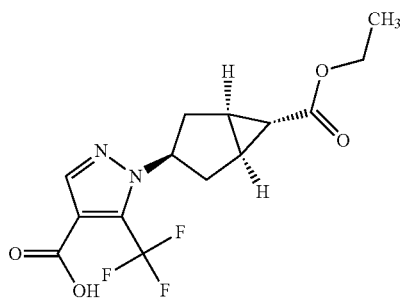 [SMILES: CCOC(=O)[C@H]1[C@@H]2C[C@H](n3ncc(C(=O)O)c3C(F)(F)F)C[C@@H]21] |
| D62 | 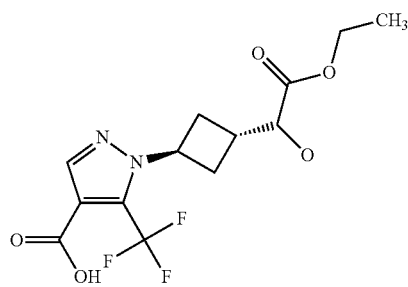 [SMILES: CCOC(=O)C(O)[C@H]1C[C@H](n2ncc(C(=O)O)c2C(F)(F)F)C1] |
| reference example | structure |
|---|---|
| D63 | 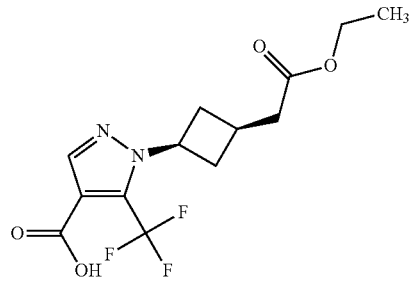 [SMILES: CCOC(=O)C[C@H]1C[C@@H](n2ncc(C(=O)O)c2C(F)(F)F)C1] |
| D64 | 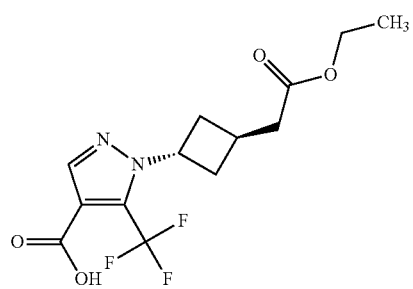 [SMILES: CCOC(=O)C[C@H]1C[C@H](n2ncc(C(=O)O)c2C(F)(F)F)C1] |
| D65 | 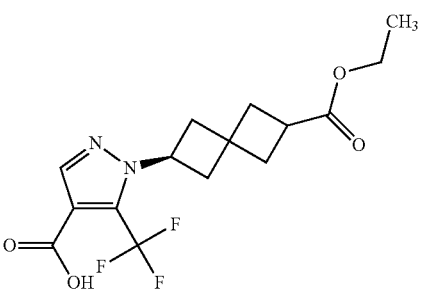 |
| D66 | 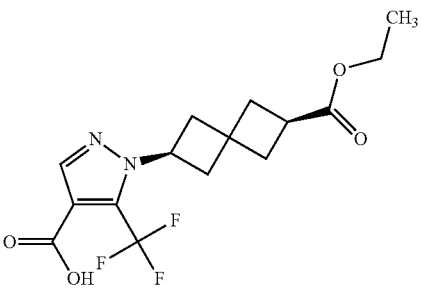 [SMILES: CCOC(=O)[C@H]1CC2(C1)C[C@H](n1ncc(C(=O)O)c1C(F)(F)F)C2] |
| D67 | 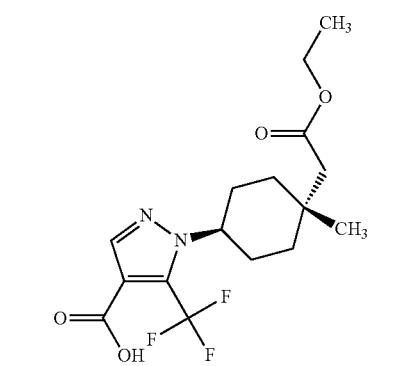 [SMILES: CCOC(=O)C[C@]1(C)CC[C@@H](n2ncc(C(=O)O)c2C(F)(F)F)CC1] |

| reference example | structure |
|---|---|
| D68 | 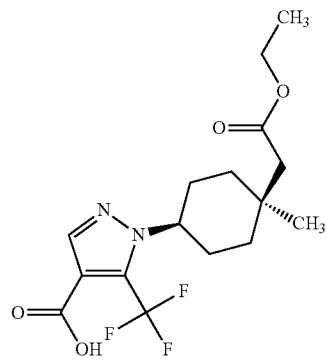 [SMILES: CCOC(=O)C[C@]1(C)CC[C@H](n2ncc(C(=O)O)c2C(F)(F)F)CC1] |
| D69 | |
| D70 | |
| D71 | |
| reference example | structure |
|---|---|
| D72 | 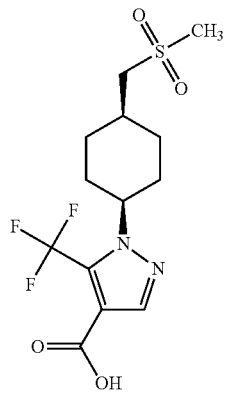 |
Example 1
trans-4-(4-((2-(3,5-dichloropyridin-4-yl)-2-oxoethyl)(4-fluorobenzyl)carbamoyl)-5-(trifluoromethyl)-1H-pyrazol-1-yl)cyclohexanecarboxylic acid
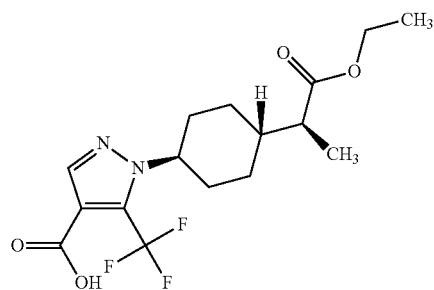 [SMILES: CCOC(=O)[C@@H](C)[C@H]1CC[C@H](n2ncc(C(=O)O)c2C(F)(F)F)CC1]

-continued

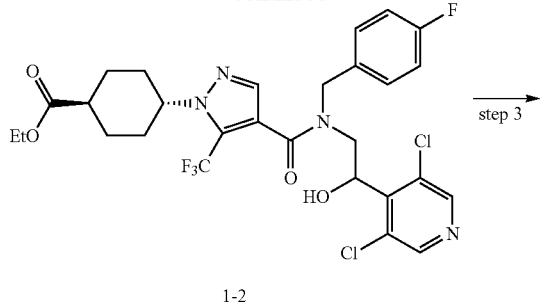

1-2

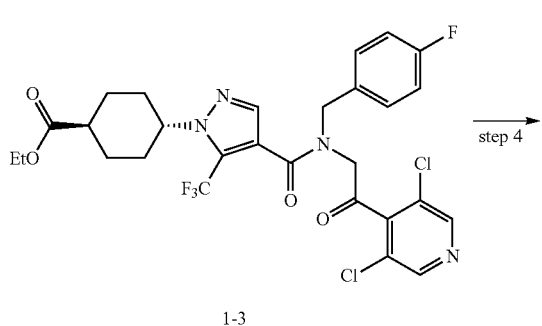

1-3

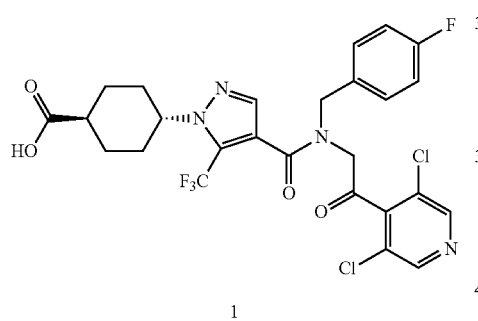

1

Step 1: ethyl trans-4-(4-((2-(3,5-dichloropyridin-4-yl)-2-(triethylsilyloxy)ethyl)(4-fluorobenzyl)carbamoyl)-5-(trifluoromethyl)-1H-pyrazol-1-yl)cyclohexanecarboxylate (1-1)

To a mixture of acid D1 (6.22 g, 18.6 mmol) and amine A1 (8.67 g, 20.4 mmol) in DMF (100 mL) were added HATU (8.48 g, 22.3 mmol) and DIPEA (4.74 mL, 27.9 mmol) and the mixture was stirred at room temperature for 5 h. The reaction mixture was quenched with water (200 mL) and extracted with EtOAc (2×100 mL). The combined organic layers were washed with water (100 mL), brine (100 mL), dried over $Na_2SO_4$ and concentrated under reduced pressure to afford compound 1-1 (15 g, crude) as a brown gum.

Step 2: ethyl trans-4-(4-((2-(3,5-dichloropyridin-4-yl)-2-hydroxyethyl)(4-fluorobenzyl)carbamoyl)-5-(trifluoromethyl)-1H-pyrazol-1-yl)cyclohexanecarboxylate (1-2)

To a stirred solution of compound 1-1 (15 g, 20.2 mmol) in THF (20 mL) was added TBAF (1.0 M in THF, 40.4 mL, 40.4 mmol) dropwise at 0° C., and the mixture was allowed to warm up from 0° C. to room temperature while stirred for 2 h. The reaction mixture was quenched with saturated aqueous $NH_4Cl$ (100 mL) and extracted with EtOAc (2×150 mL). The combined organic layers were washed with water (100 mL), brine (100 mL), dried over $Na_2SO_4$ and concentrated under reduced pressure. The residue was purified by column chromatography (silica gel, eluent: 70% EtOAc/hexane) to provide compound 1-2 (9.9 g, 84% over two steps) as a yellow-brown gum. $^1$H NMR ($CDCl_3$) rotomers present δ 8.42 and 8.38 (2H, 2×s); 7.57 and 7.53 (1H, 2×s); 7.41-7.35 and 7.14-7.09 (4H, 2×m); 5.61-5.45 (1H, m); 5.10-4.50 (3H, m); 4.25-3.90 (4H, m); 3.31-3.15 (1H, m); 2.23-2.16 (6H, m); 1.65-1.51 (2H, m); 1.28-1.23 (3H, m); LCMS: 631 $(M+H)^+$.

Step 3: ethyl trans-4-(4-((2-(3,5-dichloropyridin-4-yl)-2-oxoethyl)(4-fluorobenzyl)carbamoyl)-5-(trifluoromethyl)-1H-pyrazol-1-yl)cyclohexanecarboxylate (1-3)

To a stirred solution of compound 1-2 (9.9 g, 15.6 mmol) in DCM (120 mL) was added Dess-Martin periodinane (21.9 g, 21.9 mmol) in portions, and the mixture was stirred at room temperature for 3 h. The reaction mixture was quenched with $NaHCO_3$ (50 mL, sat. aq.) and $Na_2S_2O_3$ (50 mL, sat. aq.), then extracted with DCM (2×150 mL). The combined organic layers were washed with water (100 mL), brine (100 mL), dried over $Na_2SO_4$ and concentrated under reduced pressure. The residue was purified by column chromatography (silica gel, eluent: 10% EtOAc/hexane) to yield compound 1-3 (9.12 g, 92%) as a white solid. $^1$H NMR ($CDCl_3$) rotomers present δ 8.74 and 8.67 (2H, 2×s); 7.85 and 7.79 (1H, 2×s); 7.30-7.26 (1H, m); 7.41-7.37 and 7.22-7.15 (3H, 2×m); 4.73-4.51 (4H, m); 4.27-4.21 (1H, m); 4.07 (2H, q, J=7.2 Hz); 2.50-2.48 (1H, m); 2.06-1.93 (6H, m); 1.59-1.54 (2H, m); 1.18 (3H, t, J=6.9 Hz); LCMS: 629 $(M+H)^+$.

Step 4: trans-4-(4-((2-(3,5-dichloropyridin-4-yl)-2-oxoethyl)(4-fluorobenzyl)carbamoyl)-5-(trifluoromethyl)-1H-pyrazol-1-yl)cyclohexanecarboxylic acid (1)

To a stirred solution of compound 1-3 (9.12 g, 14.5 mmol) in a mixture of THF/water/EtOH (77 mL, 7:1:7) was added LiOH (4.0 M aq. solution, 4.45 mL, 57.9 mmol) dropwise at 0° C. The mixture was allowed to warm to room temperature while stirring continued for 4 h. The reaction mixture was acidified with HCl (1 M, 60 mL) and extracted with EtOAc (3×100 mL). The combined organic layers were washed with water (100 mL), brine (100 mL), dried over $Na_2SO_4$ and concentrated under reduced pressure to provide the compound of example 1 (8.0 g, 94%) as a white solid. $^1$H NMR ($CDCl_3$) rotomers present δ 8.53 and 8.47 (2H, 2×s); 7.69 and 7.60 (1H, 2×s); 7.31-7.28 (1H, m); 7.16-7.12 (1H, m); 7.06-7.02 (2H, m); 4.83 and 4.65 (2H, 2×s); 4.61 and 4.30 (2H, 2×s), 4.27-4.21 (1H, m); 2.78 (1H, m); 2.44-2.40 (2H, m); 2.26-2.15 (2H, m); 1.96-1.86 (2H, m); 1.74-1.67 (2H, m); LCMS (ESI): 601.2 $(M+H)^+$.

Example 2 trans-4-(4-((2-(2,6-dichloro-4-fluorophenyl)-2-oxo-ethyl)(3,5-difluorobenzyl)carbamoyl)-5-(trifluoromethyl)-1H-pyrazol-1-yl)-1-methylcyclohexanecarboxylic acid

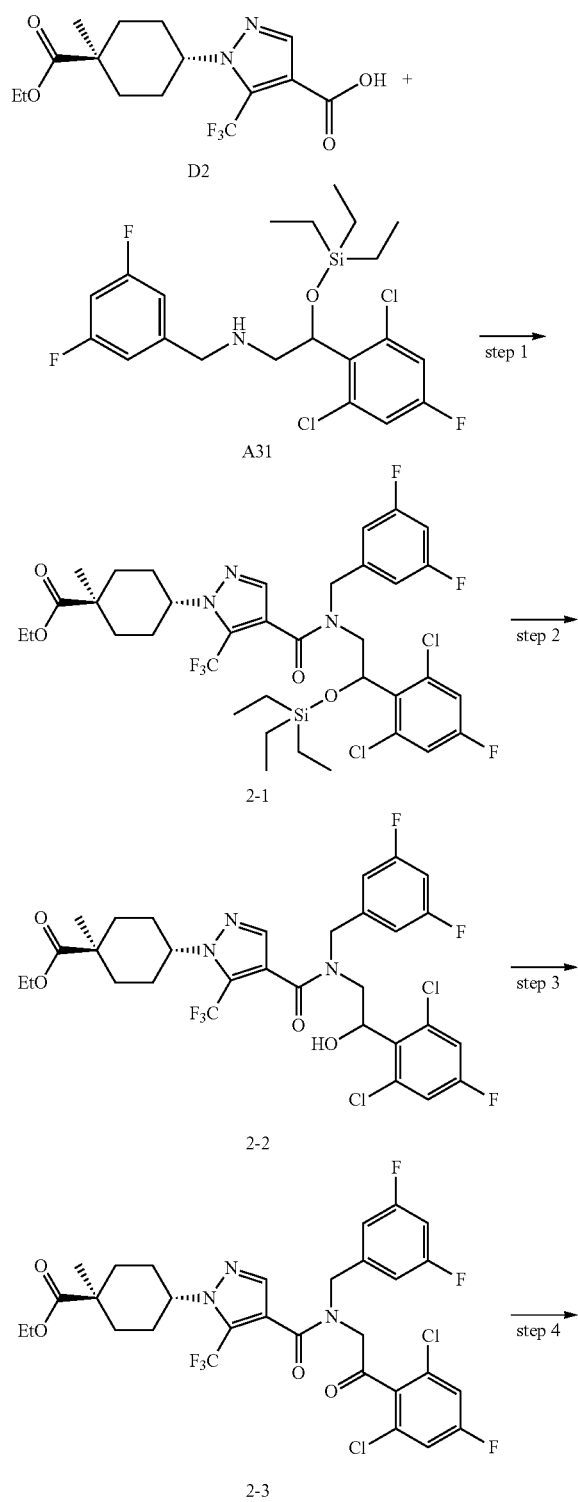

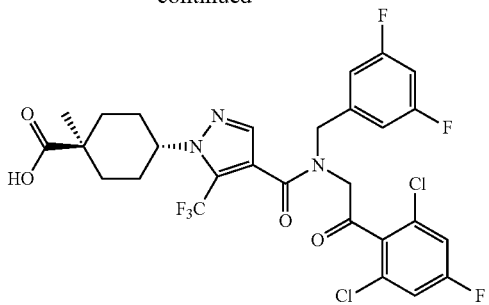

Step 1: ethyl trans-4-(4-((2-(2,6-dichloro-4-fluorophenyl)-2-((triethylsilyl)oxy)ethyl)(3,5-difluorobenzyl)carbamoyl)-5-(trifluoromethyl)-1H-pyrazol-1-yl)-1-methylcyclohexanecarboxylate (2-1)

To a solution of acid D2 (12.5 g, 35.9 mmol) and (COCl)$_2$ (4.62 mL, 39.51 mmol) in DCM (150 mL) was added DMF (catalytic amount), and the whole was stirred at room temperature for 1 h. The reaction mixture was concentrated under reduced pressure and dried under high vacuum. The residue was dissolved in DCM (10 mL) and added dropwise to a mixture of amine A31 (18.3 g, 39.5 mmol) and Et$_3$N (10.0 mL, 71.8 mmol) in DCM (150 mL) at 0° C. Upon completion of reaction (monitored by TLC), the mixture was quenched with water (50 mL) and extracted with DCM (2×100 mL). The combined organic layer washed with brine (20 mL), dried over Na$_2$SO$_4$ and concentrated under reduced pressure. The residue was purified by column chromatography (silica gel, 0-10% EtOAc/hexane as eluent) to provide compound 2-1 (27.0 g, 91%) as a colorless gum. $^1$H NMR (CDCl$_3$) rotomers present δ 7.54 and 7.47 (1H, 2xs); 7.02-6.98 (2H, m); 6.87-6.86 and 6.56-6.54 (2H, 2xm); 6.73-6.71 (1H, m); 5.90-5.88 and 5.50-5.47 (1H, 2xm); 4.99-4.29 (2H, m); 4.18-4.12 and 3.30-3.26 (4H, 2xm); 3.87-3.81 (1H, m); 2.21-2.16 (2H, m); 1.89-1.88 (6H, m); 1.35-1.24 (6H, m); 0.91-0.84 (9H, m); 0.58-0.48 (6H, m).

Step 2: ethyl trans-4-(4-((2-(2,6-dichloro-4-fluorophenyl)-2-hydroxyethyl)(3,5-difluorobenzyl)carbamoyl)-5-(trifluoromethyl)-1H-pyrazol-1-yl)-1-methylcyclohexanecarboxylate (2-2)

Compound 2-2 was prepared using a similar procedure to that described in example 1, step 2.

Step 3: ethyl trans-4-(4-((2-(2,6-dichloro-4-fluorophenyl)-2-oxoethyl)(3,5-difluorobenzyl)carbamoyl)-5-(trifluoromethyl)-1H-pyrazol-1-yl)-1-methylcyclohexanecarboxylate (2-3)

Compound 2-3 was prepared using a similar procedure to that described in example 1, step 3.

Step 4: trans-4-(4-((2-(2,6-dichloro-4-fluorophenyl)-2-oxoethyl)(3,5-difluorobenzyl)carbamoyl)-5-(trifluoromethyl)-1H-pyrazol-1-yl)-1-methylcyclohexanecarboxylic acid (2)

The compound of example 2 was prepared using a similar procedure to that described in example 1, step 4. $^1$H NMR (CDCl$_3$) rotomers present δ 8.55 and 8.49 (2H, 2×s); 7.66 and 7.62 (1H, 2×s); 6.85-6.69 (3H, m); 4.83 and 4.70 (2H, 2×s); 4.62 and 4.34 (2H, 2×s); 4.29-4.21 (1H, m); 2.25-2.17 (2H, m); 1.94-1.88 (6H, m); 1.41 and 1.40 (3H, 2×s) LCMS (ESI): 650.2 (M+H)$^+$.

Example 3 trans-4-(4-((3,5-difluorobenzyl)(2-(2,4-dimethylthiophen-3-yl)-2-oxoethyl)carbamoyl)-5-(trifluoromethyl)-1H-pyrazol-1-yl)cyclohexanecarboxylic acid

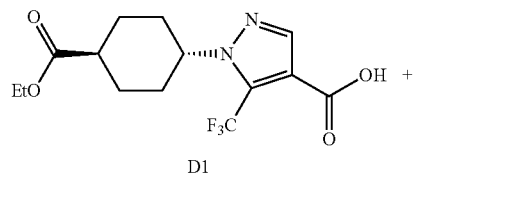

D1

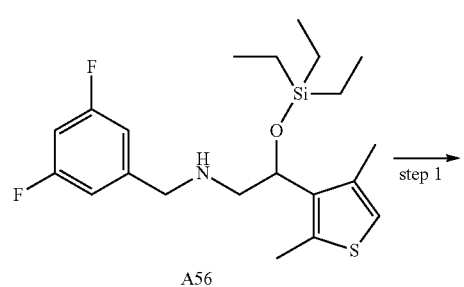

A56

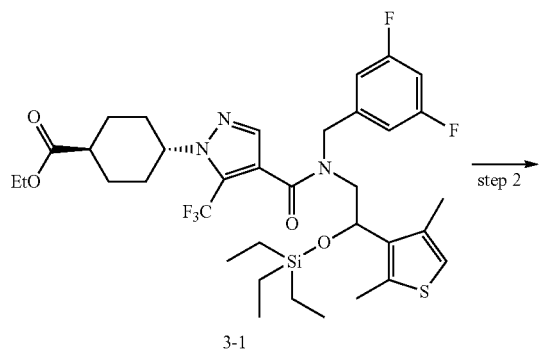

3-1

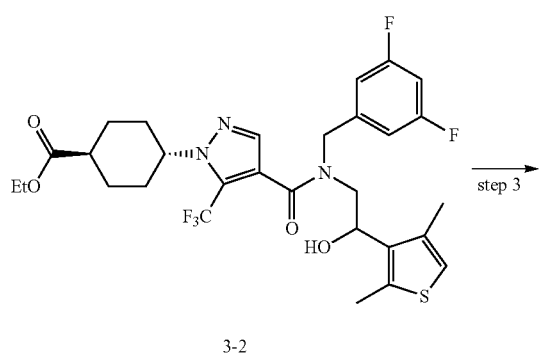

3-2

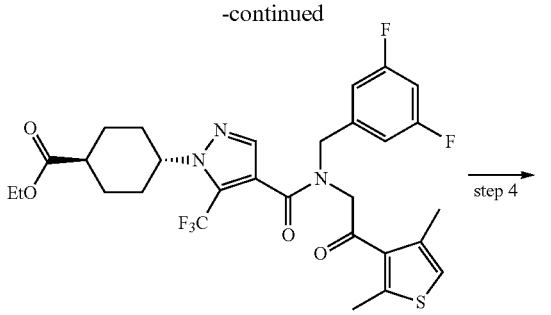

3-3

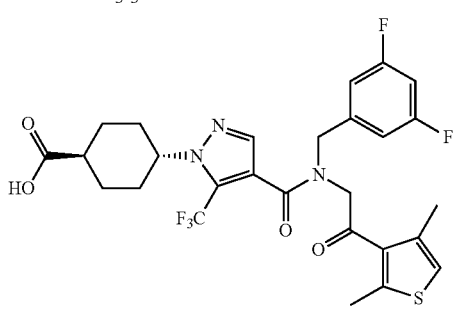

3

Step 1 and 2: ethyl trans-4-(4-((3,5-difluorobenzyl)(2-(2,4-dimethylthiophen-3-yl)-2-hydroxyethyl)carbamoyl)-5-(trifluoromethyl)-1H-pyrazol-1-yl)cyclohexanecarboxylate (3-2)

To a mixture of acid D1 (162 mg, 0.48 mmol) and amine A56 (200 mg, 0.48 mmol) in DMF (4 mL) were added DIPEA (0.12 mL, 0.72 mmol) and HATU (221 mg, 0.58 mmol) at room temperature and stirred at the same temperature for 4 h. The reaction mixture was quenched with water (50 mL) and extracted with EtOAc (2×20 mL). The combined organic layers were washed with brine (20 mL), dried over Na$_2$SO$_4$ and concentrated under reduced pressure to provide a yellow residue.

To a stirred solution of the yellow residue was added TBAF (1 M in THF, 0.96 mL, 0.96 mmol) dropwise at room temperature. The mixture was stirred at the same temperature for 1 h. The reaction mixture was quenched with saturated aqueous NaHCO$_3$ solution and extracted with EtOAc (2×20 mL). The organic layers were washed with brine (2×10 mL), dried over Na$_2$SO$_4$, and concentrated under reduced pressure. The residue was purified by column chromatography (silica gel, 10% EtOAc/hexane as eluent) to provide compound 3-2 (290 mg, 97%) as a colorless gum.

Step 3: ethyl trans-4-(4-((3,5-difluorobenzyl)(2-(2,4-dimethylthiophen-3-yl)-2-oxoethyl)carbamoyl)-5-(trifluoromethyl)-1H-pyrazol-1-yl)cyclohexanecarboxylate (3-3)

To a stirred solution of compound 3-2 (290 mg, 0.47 mmol) in DCM (8 mL) was added Dess-Martin periodinane (401 mg, 0.94 mmol) at 0° C. and the mixture was stirred at room temperature for 3 h. The reaction mixture was quenched with saturated aqueous Na$_2$S$_2$O$_3$ and NaHCO$_3$, and extracted with EtOAc (2×20 mL). The combined organic layers were washed with brine (2×10 mL), dried over Na$_2$SO$_4$, and concentrated under reduced pressure. The residue was purified by column chromatography (silica gel, 30% EtOAc/hexane as eluent) to provide compound 3-3 (220 mg, 78%) as a colorless gum.

Step 4: trans-4-(4-((3,5-difluorobenzyl)(2-(2,4-dimethylthiophen-3-yl)-2-oxoethyl)carbamoyl)-5-(trifluoromethyl)-1H-pyrazol-1-yl)cyclohexanecarboxylic acid (3)

To a solution of compound 3-3 (220 mg, 0.37 mmol) in EtOH (1 mL), THF (1 mL) and $H_2O$ (0.2 mL) was added LiOH (4 M aqueous solution, 0.55 mL, 2.2 mmol) dropwise, and the mixture was stirred at room temperature for 2 h. The reaction mixture was quenched by dropwise addition of 1 M aqueous HCl (pH was adjusted to 4.0) and extracted with EtOAc (2×20 mL). The combined organic layers were washed with brine (2×10 mL), dried over $Na_2SO_4$, and concentrated under reduced pressure. The residue was purified by reverse phase column chromatography (C18 silica gel, 56% water/$CH_3CN$ as eluent) to provide the compound of example 3 (56 mg, 26%) as a white solid. $^1$H NMR (DMSO-$d_6$) rotamers present δ 7.63 and 7.50 (1H, 2×s); 7.14 and 7.09 (1H, 2×s); 6.83-6.81 (1H, m); 6.77-6.68 (2H, m); 4.78 and 4.69 (2H, 2×s); 4.59 and 4.28 (2H, 2×s); 4.27-4.18 (1H, m); 2.49-2.38 (4H, m); 2.25-2.18 (5H, m); 2.10-1.97 (4H, m); 1.70-1.57 (2H, m); LCMS (APCI): 584 (M+H)$^+$.

Example 4 trans-4-(4-((2-(2,6-dichloro-4-(methylsulfonyl)phenyl)-2-oxoethyl)(3,5-difluorobenzyl)carbamoyl)-5-(trifluoromethyl)-1H-pyrazol-1-yl)cyclohexanecarboxylic acid

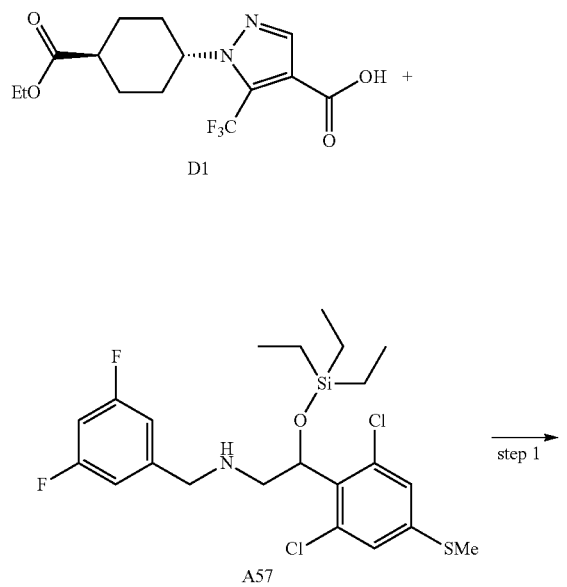

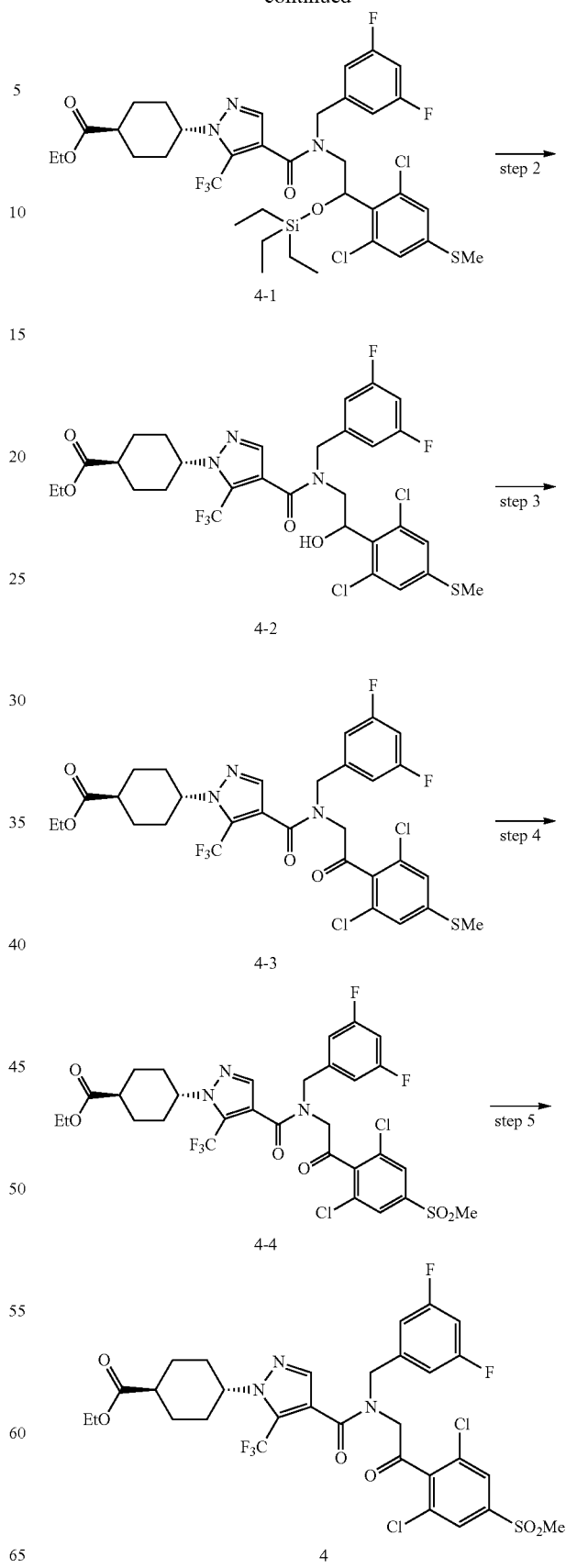

Step 1: ethyl trans-4-(4-((2-(2,6-dichloro-4-(methylthio)phenyl)-2-((triethylsilyl)oxy)ethyl)(3,5-difluorobenzyl)carbamoyl)-5-(trifluoromethyl)-1H-pyrazol-1-yl)cyclohexanecarboxylate (4-1)

Compound 4-1 (0.44 g, crude) was obtained as a brown color gum from the reaction of amine A57 (0.26 g, 0.52 mmol), acid D1 (0.17 g, 0.52 mmol), HATU (0.24 g, 0.63 mmol) and DIPEA (0.13 mL, 0.79 mmol) in DMF (5 mL) using a similar procedure to that described in example 1.

Step 2: ethyl trans-4-(4-((2-(2,6-dichloro-4-(methylthio)phenyl)-2-hydroxyethyl)(3,5-difluorobenzyl)carbamoyl)-5-(trifluoromethyl)-1H-pyrazol-1-yl)cyclohexanecarboxylate (4-2)

Compound 4-2 (0.38 g, 91%) was obtained as brown color gum from the reaction of compound 4-1 (0.44 g, 0.59 mmol) and TBAF (1.0 M in THF, 0.31 mL, 1.19 mmol) in THF (10 mL) using a similar procedure to that described in example 1.

Step 3: ethyl trans-4-(4-((2-(2,6-dichloro-4-(methylthio)phenyl)-2-oxoethyl)(3,5-difluorobenzyl)carbamoyl)-5-(trifluoromethyl)-1H-pyrazol-1-yl)cyclohexanecarboxylate (4-3)

Compound 4-3 (0.1 g, 26%) was obtained as a colorless gum from the reaction of compound 4-2 (0.38 g, 0.61 mmol) and Dess-Martin periodinane (0.52 g, 1.22 mmol) in DCM (10 mL) using a similar procedure to that described in example 1.

Step 4: ethyl trans-4-(4-((2-(2,6-dichloro-4-(methylsulfonyl)phenyl)-2-oxoethyl)(3,5-difluorobenzyl)carbamoyl)-5-(trifluoromethyl)-1H-pyrazol-1-yl)cyclohexanecarboxylate (4-4)

To a stirred solution of compound 4-3 (0.1 g, 0.1 mmol) in DCM (5 mL) was added m-CPBA (84 mg, 0.48 mmol) at room temperature. The mixture was stirred at room temperature for 2 h. The reaction mixture was quenched with water (30 mL) and extracted with DCM (2×20 mL). The combined organic layers were washed with 10% NaOH solution (20 mL), water (30 mL), brine (30 mL), dried over $Na_2SO_4$ and concentrated under reduced pressure. The residue was purified by column chromatography (silica gel, 20% EtOAc/hexane as eluent) to provide compound 4-4 (0.17 g, 65%) as a colorless oil.

Step 5: trans-4-(4-((2-(2,6-dichloro-4-(methylsulfonyl)phenyl)-2-oxoethyl)(3,5-difluorobenzyl)carbamoyl)-5-(trifluoromethyl)-1H-pyrazol-1-yl)cyclohexanecarboxylic acid (4)

The compound of example 4 (50 mg, 52%) was obtained as a white solid from the reaction of compound 4-4 (0.1 g, 0.13 mmol) and LiOH (20 mg, 0.82 mmol) in THF/MeOH/water (2:2:1, 5 mL) using a similar procedure to that described in example 1. $^1$H NMR (DMSO-$d_6$) rotamers present δ 12.21 (1H, brs); 8.10 and 8.03 (2H, 2×s); 7.88 and 7.86 (1H, 2×s); 7.20-7.14 (1H, m); 7.11-7.08 and 6.95-6.92 (2H, 2×m); 4.85 and 4.73 (2H, 2×s); 4.69 and 4.57 (2H, 2×s); 4.28-4.17 (1H, m); 3.37 and 3.32 (3H, 2×s); 2.35-2.29 (1H, m); 2.07-2.02 (2H, m); 1.98-1.90 (4H, m); 1.60-1.49 (2H, m); LCMS (APCI): 696 (M+H)$^+$.

Example 5

N-(2-(3,5-dichloropyridin-4-yl)-2-oxoethyl)-N-(3,5-difluorobenzyl)-1-(trans-4-(hydroxycarbamoyl)cyclohexyl)-5-(trifluoromethyl)-1H-pyrazole-4-carboxamide

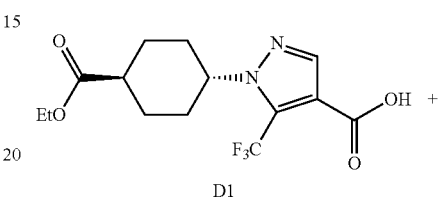

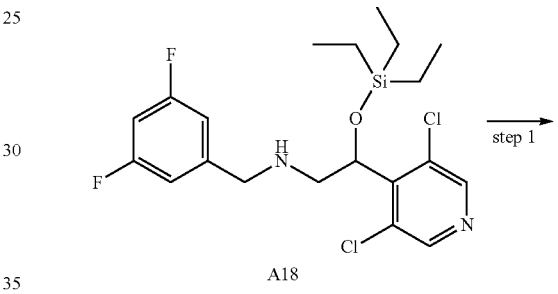

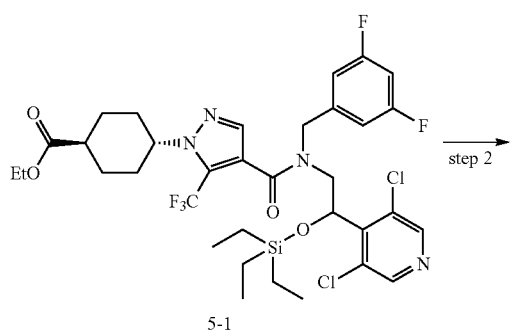

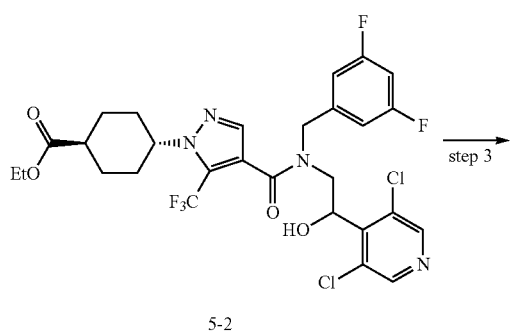

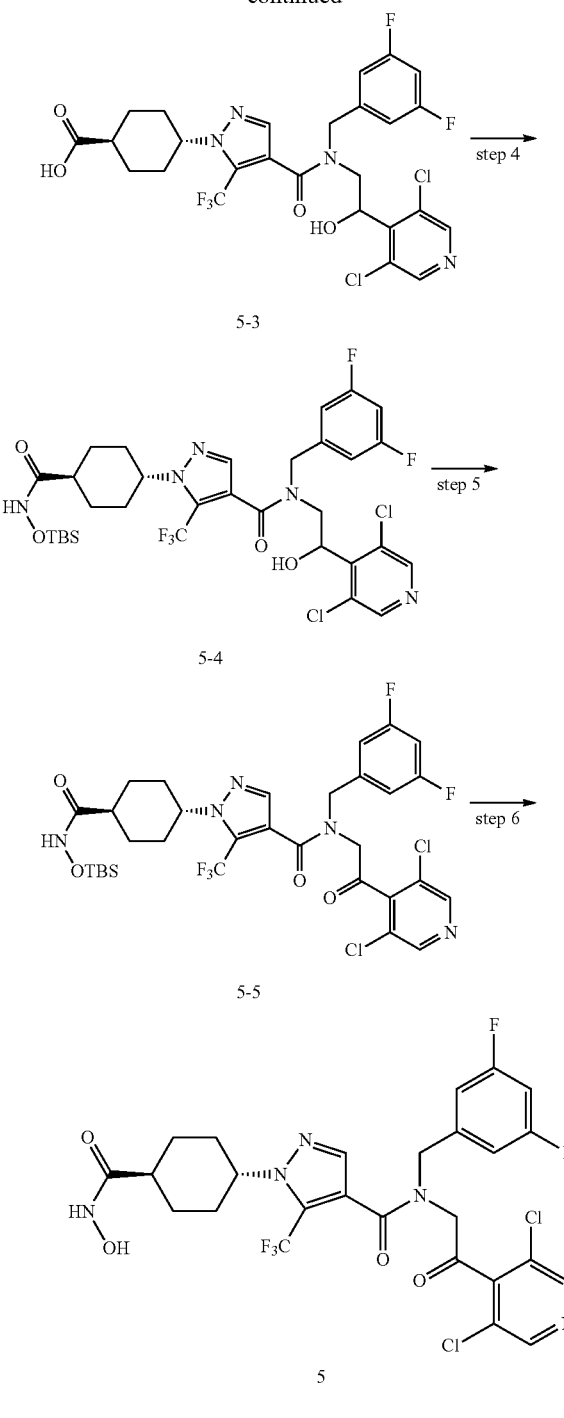

Step 1: ethyl trans-4-(4-((2-(3,5-dichloropyridin-4-yl)-2-((triethylsilyl)oxy)ethyl)(3,5-difluorobenzyl)carbamoyl)-5-(trifluoromethyl)-1H-pyrazol-1-yl)cyclohexanecarboxylate (5-1)

Compound 5-1 (633 mg, crude) was obtained as a brown gum from the reaction of acid D1, amine A18 (400 mg, 0.89 mmol), HATU (408 mg, 1.07 mmol) and DIPEA (0.23 mL, 1.34 mmol) in DMF (6.0 mL) using a similar procedure to that described in example 1.

Step 2: ethyl trans-4-(4-((2-(3,5-dichloropyridin-4-yl)-2-hydroxyethyl)(3,5-difluorobenzyl)carbamoyl)-5-(trifluoromethyl)-1H-pyrazol-1-yl)cyclohexanecarboxylate (5-2)

Compound 5-2 (410 mg, 71%) was obtained as a yellow solid from the reaction of compound 5-1 (633 mg, 0.83 mmol) and TBAF (1 M in THF, 1.65 mL, 1.65 mmol) in THF (3.0 mL) using a similar procedure to that described in example 1. LCMS: 649 (M+H)+.

Step 3: trans-4-(4-((2-(3,5-dichloropyridin-4-yl)-2-hydroxyethyl)(3,5-difluorobenzyl)carbamoyl)-5-(trifluoromethyl)-1H-pyrazol-1-yl)cyclohexanecarboxylic acid (5-3)

Compound 5-3 (185 mg, 86%) was obtained as a white solid from the reaction of compound 5-2 (224 mg, 0.34 mmol) and LiOH.H$_2$O (87 mg, 2.06 mmol) in THF (3.0 mL), EtOH (2.0 mL) and water (2.0 mL) using a similar procedure to that described in example 1.

Step 4: 1-(trans-4-(((tert-butyldimethylsilyl)oxy)carbamoyl)cyclohexyl)-N-(2-(3,5-dichloropyridin-4-yl)-2-hydroxyethyl)-N-(3,5-difluorobenzyl)-5-(trifluoromethyl)-1H-pyrazole-4-carboxamide (5-4)

Compound 5-4 (173 mg, 84%) was obtained as a white solid from the reaction of compound 5-3 (170 mg, 0.27 mmol), O-(tert-butyldimethylsilyl)hydroxylamine (41 mg, 0.27 mmol), HATU (124 mg, 0.32 mmol) and DIPEA (0.07 mL, 0.41 mmol) in DMF (3.0 mL) using a similar procedure to that described in example 1. LCMS: 750 (M+H)+.

Step 5: 1-(trans-4-(((tert-butyldimethylsilyl)oxy)carbamoyl)cyclohexyl)-N-(2-(3,5-dichloropyridin-4-yl)-2-oxoethyl)-N-(3,5-difluorobenzyl)-5-(trifluoromethyl)-1H-pyrazole-4-carboxamide (5-5)

Compound 5-5 (100 mg, 58%) was obtained as a colorless gum from the reaction of compound 5-4 (173 mg, 0.23 mmol) and Dess-Martin periodinane (117 mg, 0.27 mmol) in DCM (20.0 mL) using a similar procedure to that described in example 1. LCMS: 748 (M+H)+.

Step 6: N-(2-(3,5-dichloropyridin-4-yl)-2-oxoethyl)-N-(3,5-difluorobenzyl)-1-(trans-4-(hydroxycarbamoyl)cyclohexyl)-5-(trifluoromethyl)-1H-pyrazole-4-carboxamide (5)

To a stirred solution of compound 5-5 (100 mg, 0.13 mmol) in THF (8 mL) was added TBAF (1 M in THF, 0.20 mL, 0.20 mmol) dropwise and the mixture was stirred at room temperature for 1 h. The reaction mixture was quenched with MeOH (2 mL) and extracted with EtOAc (2×20 mL). The combined organic layers were washed with brine (2×10 mL), dried over Na$_2$SO$_4$ and concentrated under reduced pressure. The residue was purified by column chromatography (silica gel, 7% MeOH/DCM as eluent) to provide the compound of example 5 (19 mg, 22%) as a white solid. $^1$H NMR (CDCl$_3$) rotamers present δ 8.54 and 8.48 (2H, 2×s); 7.64 and 7.60 (1H, 2×s);

6.84-6.68 (3H, m); 4.82-4.25 (5H, m); 2.23-2.04 (7H, m); 1.83-1.73 (2H, m); LCMS (APCI): 634 (M+H)+.

Example 6

N-(2-(3,5-dichloropyridin-4-yl)-2-oxoethyl)-N-(3,5-difluorobenzyl)-1-(trans-4-(methoxycarbamoyl)cyclohexyl)-5-(trifluoromethyl)-1H-pyrazole-4-carboxamide

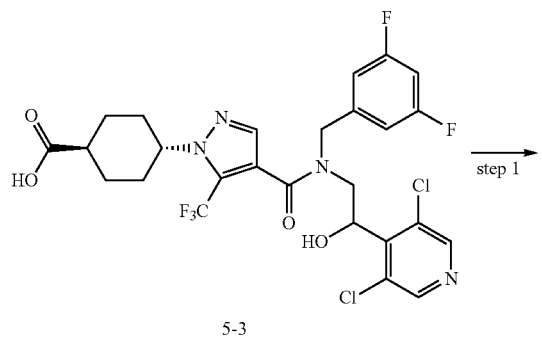

5-3

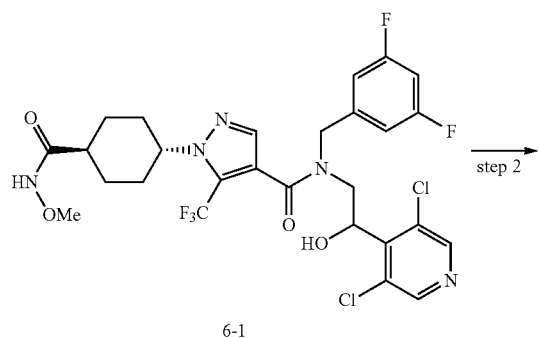

6-1

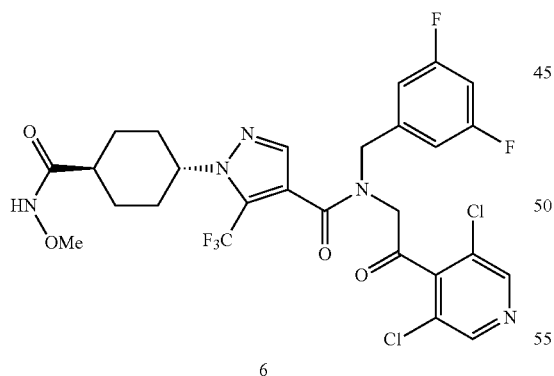

6

Step 1: N-(2-(3,5-dichloropyridin-4-yl)-2-hydroxyethyl)-N-(3,5-difluorobenzyl)-1-(trans-4-(methoxycarbamoyl)cyclohexyl)-5-(trifluoromethyl)-1H-pyrazole-4-carboxamide (6-1)

To a mixture of compound 5-3 (75 mg, 0.12 mmol) and O-methylhydroxylamine hydrochloride (10 mg, 0.12 mmol) in DMF (3 mL) were added HATU (55 mg, 0.14 mmol) and DIPEA (0.05 mL, 0.30 mmol) and mixture was stirred at room temperature for 5 h. The reaction mixture was quenched with water and extracted with EtOAc. The combined organic layers were washed with water, brine, dried over $Na_2SO_4$ and concentrated under reduced pressure to afford crude compound 6-1 (65 mg, 82%) as a white foam. LCMS: 650 (M+H)+.

Step 2: N-(2-(3,5-dichloropyridin-4-yl)-2-oxoethyl)-N-(3,5-difluorobenzyl)-1-(trans-4-(methoxycarbamoyl)cyclohexyl)-5-(trifluoromethyl)-1H-pyrazole-4-carboxamide (6)

The compound of example 6 (15 mg, 23%) was obtained as a white solid from the reaction of compound 6-1 (65 mg, 0.099 mmol) and Dess-Martin periodinane (85 mg, 0.19 mmol) in DCM (5.0 mL) using a similar procedure to that described in example 1. $^1$H NMR (CDCl$_3$) rotamers present δ 8.54 and 8.48 (2H, 2×s); 8.07 (1H, brs); 7.64 and 7.60 (1H, 2×s); 6.84-6.68 (3H, m); 4.82-4.25 (5H, m); 3.81 and 3.78 (3H, 2×s); 2.10-2.01 (7H, m); 1.84-1.75 (2H, m); LCMS (APCI): 648 (M+H)+.

Example 7 trans-4-(4-((3,5-difluorobenzyl)(2-(2-hydroxy-6-methoxyphenyl)-2-oxoethyl)carbamoyl)-5-(trifluoromethyl)-1H-pyrazol-1-yl)cyclohexanecarboxylic acid

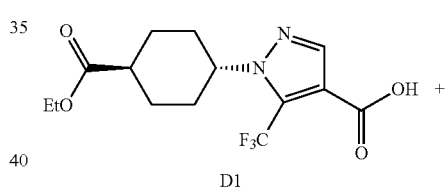

D1

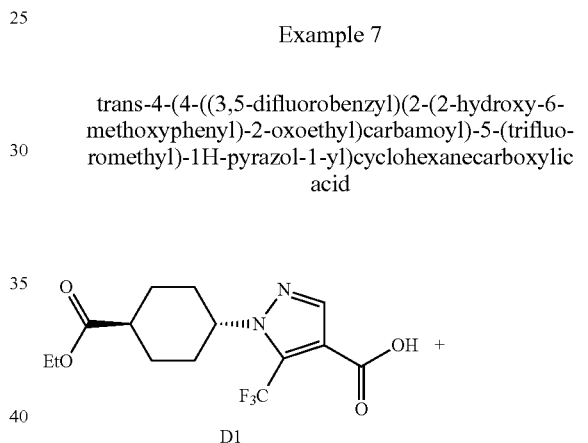

A67

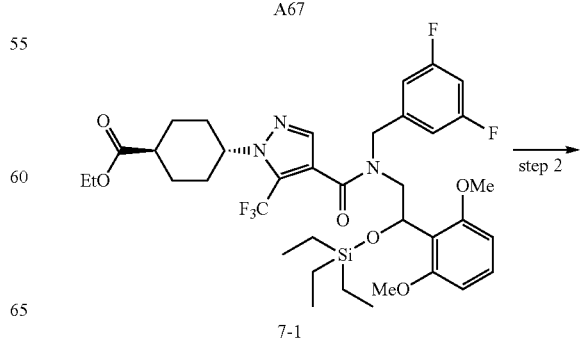

7-1

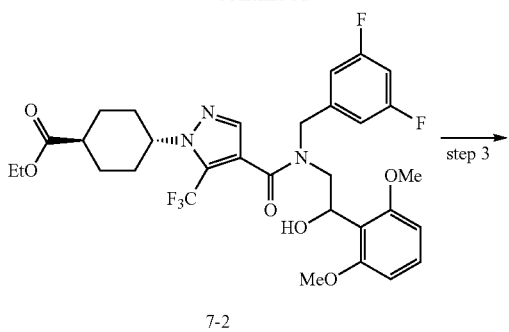

Step 2: ethyl trans-4-(4-((3,5-difluorobenzyl)(2-(2,6-dimethoxyphenyl)-2-hydroxyethyl)carbamoyl)-5-(trifluoromethyl)-1H-pyrazol-1-yl)cyclohexanecarboxylate (7-2)

Compound 7-2 (0.22 g, crude) was obtained as brown color gum from the reaction of compound 7-1 (0.23 g, 0.3 mmol) and TBAF (1.0 M in THF, 0.61 mL, 0.6 mmol) in THF (5 mL) using a similar procedure to that described in example 1.

Step 3: ethyl trans-4-(4-((3,5-difluorobenzyl)(2-(2,6-dimethoxyphenyl)-2-oxoethyl)carbamoyl)-5-(trifluoromethyl)-1H-pyrazol-1-yl)cyclohexanecarboxylate (7-3)

Compound 7-3 (0.16 g, 73%) was obtained as a colorless gum from the reaction of compound 7-2 (0.22 g, 0.34 mmol) and Dess-Martin periodinane (0.29 g, 0.69 mmol) in DCM (10 mL) using a similar procedure to that described in example 1.

Step 4: ethyl trans-4-(4-((3,5-difluorobenzyl)(2-(2-hydroxy-6-methoxyphenyl)-2-oxoethyl)carbamoyl)-5-(trifluoromethyl)-1H-pyrazol-1-yl)cyclohexanecarboxylate (7-4)

To a stirred solution of compound 7-3 (50 mg, 0.07 mmol) in DCM (5 mL) was added $BBr_3$ (1.0 M in DCM, 1.5 mL, 1.4 mmol) at room temperature and the mixture was stirred for 16 h. Solvent was evaporated under reduced pressure and the obtained residue was purified by column chromatography (silica gel, 30% EtOAc/hexane as eluent) to provide compound 7-4 (32 mg, 65%) as a brown color gum.

Step 5: trans-4-(4-((3,5-difluorobenzyl)(2-(2-hydroxy-6-methoxyphenyl)-2-oxoethyl)carbamoyl)-5-(trifluoromethyl)-1H-pyrazol-1-yl)cyclohexanecarboxylic acid (7)

The compound of example 7 (15 mg, 50%) was obtained as a white solid from the reaction of compound 7-4 (32 mg, 0.05 mmol) and LiOH (6.2 mg, 0.25 mmol) in THF/MeOH/water (2:2:1, 5 mL) using a similar procedure to that described in example 1. $^1$H NMR (DMSO-$d_6$) rotamers present δ 11.81 (1H, brs); 10.89 (1H, brs); 7.76 and 7.64 (1H, 2×s); 7.42-7.23 (1H, m); 7.18-6.86 (3H, m); 6.61-6.46 (2H, m); 4.82-4.51 (4H, m); 4.25-4.13 (1H, m); 3.84 and 3.65 (3H, 2×s); 2.28-2.21 (1H, m); 2.03-1.89 (6H, m); 1.55-1.44 (2H, m);
LCMS (APCI): 596 (M+H)$^+$.

Example 8 trans-4-(4-((3,5-difluorobenzyl)(2-oxo-2-(1H-pyrazol-3-yl)ethyl)carbamoyl)-5-(trifluoromethyl)-1H-pyrazol-1-yl)cyclohexanecarboxylic acid

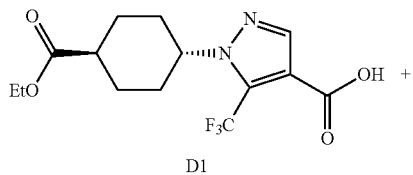

Step 1: ethyl trans-4-(4-((3,5-difluorobenzyl)(2-(2,6-dimethoxyphenyl)-2-((triethylsilyl)oxy)ethyl)carbamoyl)-5-(trifluoromethyl)-1H-pyrazol-1-yl)cyclohexanecarboxylate (7-1)

Compound 7-1 (0.23 g, crude) was obtained as a brown color gum from the reaction of amine A67 (0.13 g, 0.3 mmol), acid D1 (0.1 g, 0.3 mmol), HATU (0.13 g, 0.35 mmol) and DIPEA (76 μL, 0.44 mmol) in DMF (5 mL) using a similar procedure to that described in example 1.

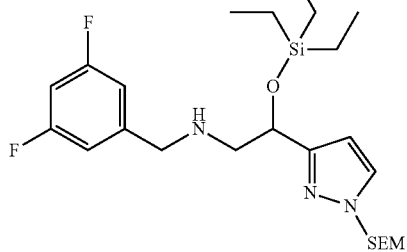

A75

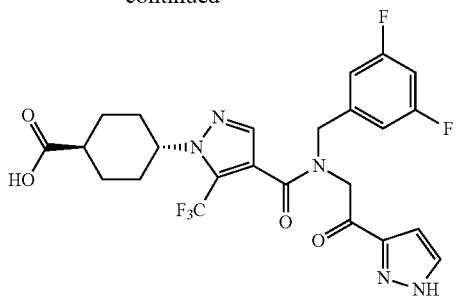

8

Step 1: ethyl trans-4-(4-((3,5-difluorobenzyl)(2-((triethylsilyl)oxy)-2-(1-((2-(trimethylsilyl)ethoxy)methyl)-1H-pyrazol-3-yl)ethyl)carbamoyl)-5-(trifluoromethyl)-1H-pyrazol-1-yl)cyclohexanecarboxylate (8-1)

Compound 8-1 (34 mg, impure) was obtained as a colorless gum from the reaction of amine A75 (40 mg, 0.080 mmol), acid D1 (26 mg, 0.080 mmol), HATU (36.4 mg, 0.096 mmol) and DIPEA (0.020 mL, 0.120 mmol) in DMF (5 mL) using a similar procedure to that described in example 1.

Step 2: ethyl trans-4-(4-((3,5-difluorobenzyl)(2-hydroxy-2-(1-((2-(trimethylsilyl)ethoxy)methyl)-1H-pyrazol-3-yl)ethyl)carbamoyl)-5-(trifluoromethyl)-1H-pyrazol-1-yl)cyclohexanecarboxylate (8-2)

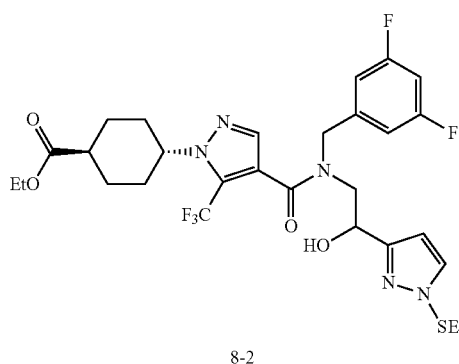

8-1

Compound 8-2 (25 mg, crude) was obtained as an colorless gum from the reaction of compound 8-1 (34 mg, 0.048 mmol) and TBAF (1 M in THF, 0.10 mL, 0.10 mmol) in THF (3 mL) using a similar procedure to that described in example 1.

Step 3: ethyl trans-4-(4-((3,5-difluorobenzyl)(2-oxo-2-(1-((2-(trimethylsilyl)ethoxy)methyl)-1H-pyrazol-3-yl)ethyl)carbamoyl)-5-(trifluoromethyl)-1H-pyrazol-1-yl)cyclohexanecarboxylate (8-3)

Compound 8-3 (40 mg, 50%) was obtained as an off-white solid from the reaction of compound 8-2 (80 mg, 0.114 mmol) and Dess-Martin periodinane (97 mg, 0.228 mmol) in DCM (5 mL) using a similar procedure to that described in example 1.

Step 4: trans-4-(4-((3,5-difluorobenzyl)(2-oxo-2-(1H-pyrazol-3-yl)ethyl)carbamoyl)-5-(trifluoromethyl)-1H-pyrazol-1-yl)cyclohexanecarboxylic acid (8)

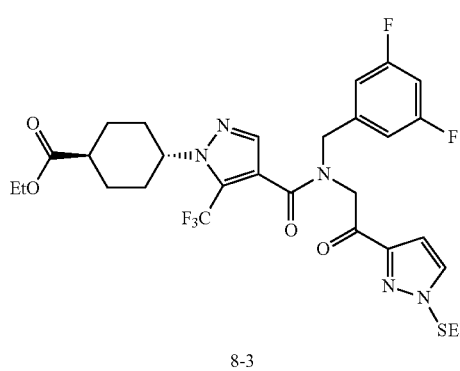

8-2

8-3

To a stirred solution of compound 8-3 (75 mg, 0.107 mmol) in 1,4-dioxane (2 mL) was added HCl (12 M, 0.5 mL). The mixture was stirred at 80° C. for 2 h. The solvent was removed under reduced pressure. The residue was dissolved in 1,4-dioxane (2 mL) and NH$_4$OH (0.5 mL) was added. The reaction mixture was stirred at room temperature for 2 h. The solvent was removed under reduced pressure and the residue was purified by reverse phase column chromatography (C18 silica gel, 70% CH$_3$CN/water as eluent) to provide the compound of example 8 (10 mg, 16%) as a white solid. $^1$H NMR (CD$_3$OD) rotamers present δ 7.74-7.50 (2H, m); 6.98-6.95 (1H, m); 6.87-6.78 (3H, m); 5.00 and 4.78 (2H, 2×s); 4.74 and 4.64 (2H, 2×s); 4.28-4.21 (1H, m); 2.36-2.28 (1H, m); 2.17-2.09 (2H, m); 2.02-1.93 (4H, m); 1.62-1.55 (2H, m); LCMS (APCI): 540 (M+H)$^+$.

Example 9

4-(4-((3,5-difluorobenzyl)(2-(2,6-dihydroxyphenyl)-2-oxoethyl)carbamoyl)-5-(trifluoromethyl)-1H-pyrazol-1-yl)cyclohexanecarboxylic acid

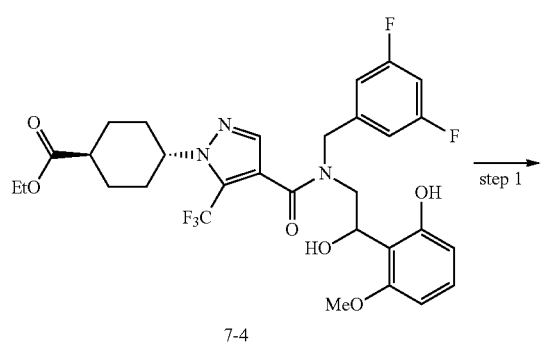

7-4

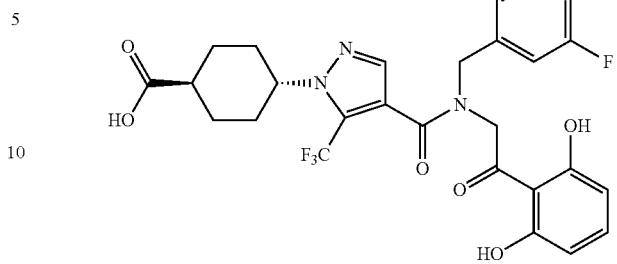

9

Step 1: ethyl trans-4-(4-((3,5-difluorobenzyl)(2-(2-hydroxy-6-methoxyphenyl)-2-oxoethyl)carbamoyl)-5-(trifluoromethyl)-1H-pyrazol-1-yl)cyclohexanecarboxylate (9-1)

To a solution of compound 7-4 (50 mg, 0.082 mmol) in dichloroethane (3 mL) was added BBr$_3$ (0.822 mL, 0.822 mmol, 1 M in DCM) dropwise, and the mixture was stirred at room temperature for 16 h. The reaction mixture was concentrated under reduced pressure to yield compound 9-1 as a brown oil (50 mg, quant.).

Step 2: 4-(4-(3,5-difluorobenzyl)(2-(2,6-dihydroxyphenyl)-2-oxoethyl)carbamoyl)-5-(trifluoromethyl)-1H-pyrazol-1-yl)cyclohexanecarboxylic acid (9)

To compound 9-1 (50 mg, 0.082 mmol) was added excess BBr$_3$ (1 M in DCM) dropwise, and the mixture was stirred at room temperature for 16 h. The reaction mixture was concentrated under reduced pressure. The residue was purified by reverse phase column chromatography (C18 silica gel, 55% water/CH$_3$CN as eluent) to provide the compound of example 9 (3 mg, 6%) as a white solid. $^1$H NMR (DMSO-d$_6$) rotamers present δ 11.91 (1H, brs); 7.79 and 7.61 (1H, 2×s); 7.28-6.88 (4H, m); 6.36-6.02 (2H, m); 4.89-4.13 (5H, m); 2.29-2.22 (1H, m); 2.05-1.83 (6H, m); 1.55-1.46 (2H, m); LCMS (ESI): 582 (M+H)$^+$.

Example 10 trans-4-(4-((2-(3,5-dichloropyridin-4-yl)-2,2-difluoroethyl)(3,5-difluorobenzyl)carbamoyl)-5-(trifluoromethyl)-1H-pyrazol-1-yl)cyclohexanecarboxylic acid

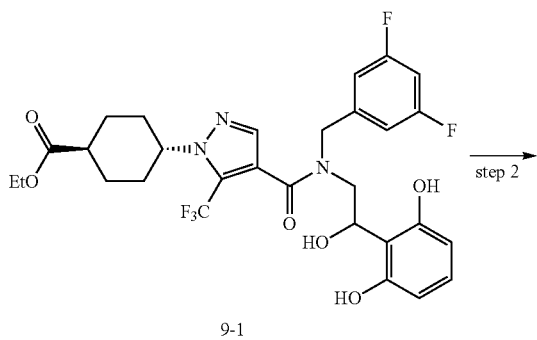

9-1

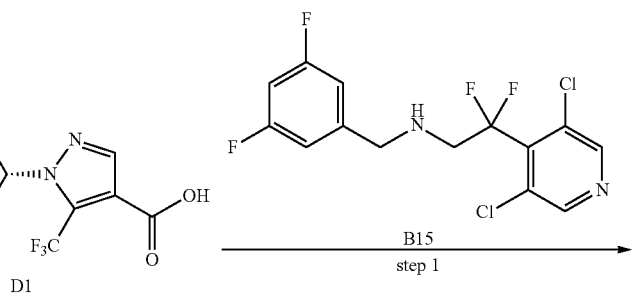

D1

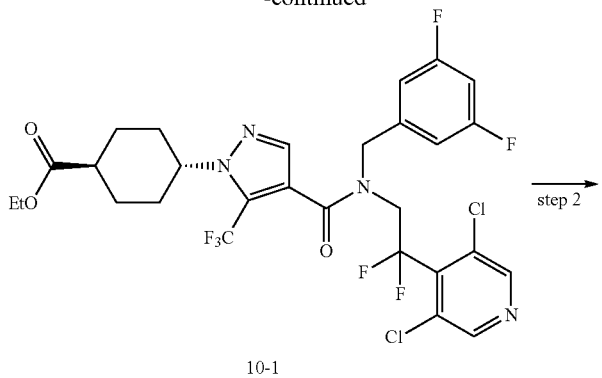

10-1

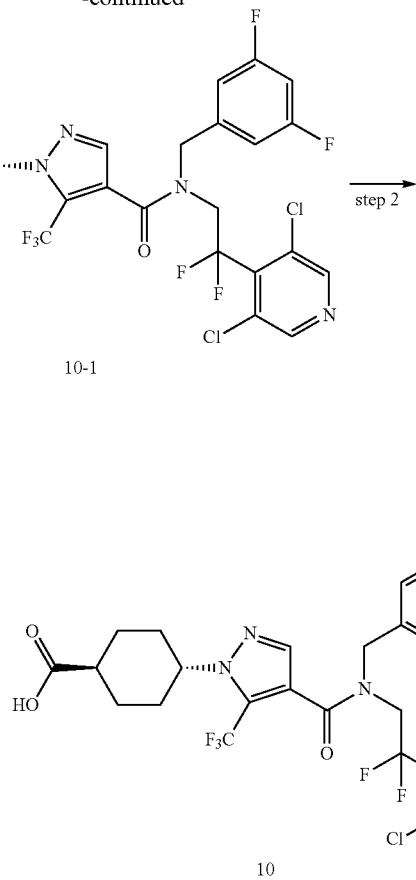

10

Step 1: ethyl trans-4-(4-((2-(3,5-dichloropyridin-4-yl)-2,2-difluoroethyl)(3,5-difluorobenzyl)carbamoyl)-5-(trifluoromethyl)-1H-pyrazol-1-yl)cyclohexanecarboxylate (10-1)

To a mixture of acid D1 (56.7 mg, 0.16 mmol) and amine B15 (60 mg, 0.016 mmol) in pyridine (4 mL) was added POCl$_3$ (0.02 mL, 0.25 mmol) dropwise at 0° C. and stirred at the same temperature for 1 h. The reaction mixture was quenched with saturated KHPO$_4$ solution (5 mL) and extracted with EtOAc (2×20 mL). The combined organic layers were washed with brine (20 mL), dried over Na$_2$SO$_4$ and concentrated under reduced pressure. The residue was purified by column chromatography (silica gel, 15% EtOAc/hexane as eluent) to provide compound 10-1 (25 mg, 22%) as a pale yellow solid.

Step 2: trans-4-(4-((2-(3,5-dichloropyridin-4-yl)-2,2-difluoroethyl)(3,5-difluorobenzyl)carbamoyl)-5-(trifluoromethyl)-1H-pyrazol-1-yl)cyclohexanecarboxylic acid (10)

The compound of example 10 (11 mg, 46%) was obtained as a white solid from the reaction of compound 10-1 (25 mg, 0.37 mmol) and LiOH (27 mg, 0.11 mmol) in EtOH (0.5 mL), THF (0.5 mL) and H$_2$O (0.2 mL) using a similar procedure to that described in example 1. $^1$H NMR (DMSO-d$_6$) rotamers present δ 8.75 and 8.69 (2H, 2×s); 7.91 and 7.74 (1H, 2×s); 7.21-6.75 (3H, m); 4.86 and 4.76 (2H, 2×s); 4.63-4.00 (3H, m); 2.34-2.23 (1H, m); 2.09-1.77 (6H, m); 1.61-1.44 (2H, m); LCMS (APCI): 641 (M+H)$^+$.

Example 11 trans-4-(4-((2-(2-amino-6-chlorophenyl)-2-oxoethyl)(3,5-difluorobenzyl)carbamoyl)-5-(trifluoromethyl)-1H-pyrazol-1-yl)cyclohexanecarboxylic acid

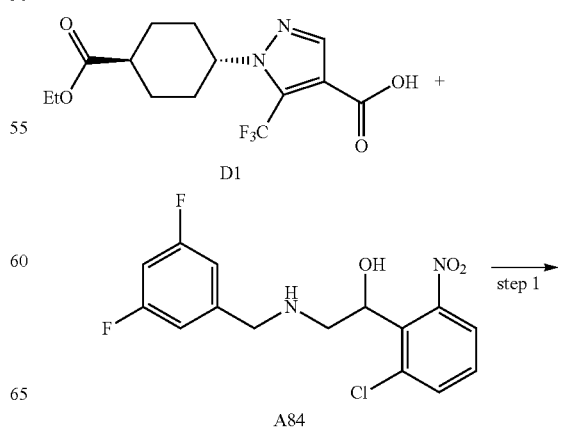

-continued

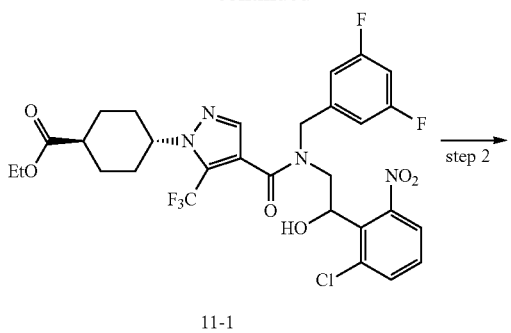

11-1

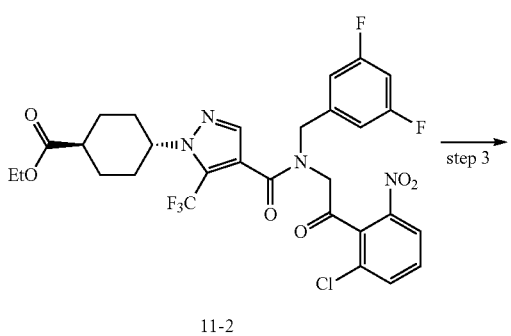

11-2

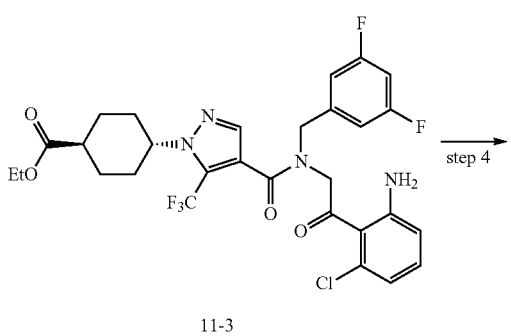

11-3

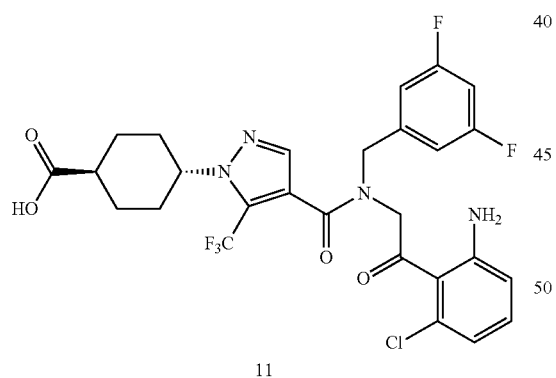

11

Step 1: ethyl trans-4-(4-((2-(2-chloro-6-nitrophenyl)-2-hydroxyethyl)(3,5-difluorobenzyl)carbamoyl)-5-(trifluoromethyl)-1H-pyrazol-1-yl)cyclohexanecarboxylate (11-1)

Compound 11-1 (0.40 g, crude) was obtained as a pale yellow color gum from the reaction of amine A84 (0.2 g, 0.58 mmol), acid D1 (0.19 g, 0.58 mmol), HATU (0.26 g, 0.7 mmol) and DIPEA (0.14 mL, 0.87 mmol) in DMF (10 mL) using a similar procedure to that described in example 1.

Step 2: ethyl trans-4-(4-((2-(2-chloro-6-nitrophenyl)-2-oxoethyl)(3,5-difluorobenzyl)carbamoyl)-5-(trifluoromethyl)-1H-pyrazol-1-yl)cyclohexanecarboxylate (11-2)

Compound 11-2 (0.28 g, 70%) was obtained as a colorless gum from the reaction of compound 11-1 (0.40 g, 0.6 mmol) and Dess-Martin periodinane (0.51 g, 1.2 mmol) in DCM (10 mL) using a similar procedure to that described in example 1.

Step 3: ethyl trans-4-(4-((2-(2-amino-6-chlorophenyl)-2-oxoethyl)(3,5-difluorobenzyl)carbamoyl)-5-(trifluoromethyl)-1H-pyrazol-1-yl)cyclohexanecarboxylate (11-3)

Compound 11-3 (70 mg, 74%) was obtained as a yellow color gum from the reaction of compound 11-2 (0.1 g, 0.15 mmol), Fe (85 mg, 1.52 mmol) and NH$_4$Cl (81 mg, 1.52 mmol) in EtOH/water (4:1, 5 mL) using a similar procedure to that described in reference example A56, step 7.

Step 4: trans-4-(4-((2-(2-amino-6-chlorophenyl)-2-oxoethyl)(3,5-difluorobenzyl)carbamoyl)-5-(trifluoromethyl)-1H-pyrazol-1-yl)cyclohexanecarboxylic acid (11)

The compound of example 11 (8 mg, 33%) was obtained as a yellow solid from the reaction of compound 11-3 (20 mg, 0.03 mmol) and LiOH (3.8 mg, 0.16 mmol) in THF/MeOH/water (2:2:1, 5 mL) using a similar procedure to that described in example 1. $^1$H NMR (DMSO-d$_6$) rotamers present δ 12.17 (1H, brs); 7.79 and 7.79 (1H, 2×s); 7.17-6.93 (4H, m); 6.70-6.54 (2H, m); 5.80 (1H, brs); 5.53 (1H, brs); 4.77-4.59 (4H, m); 4.23-4.16 (1H, m); 2.29-2.22 (1H, m); 2.06-1.88 (6H, m); 1.57-1.46 (2H, m); LCMS (APCI): 599 (M+H)$^+$.

Example 12 trans-4-(4-((3,5-difluorobenzyl)(2-oxo-2-(2,4,6-trihydroxypyrimidin-5-yl)ethyl)carbamoyl)-5-(trifluoromethyl)-1H-pyrazol-1-yl)cyclohexanecarboxylic acid

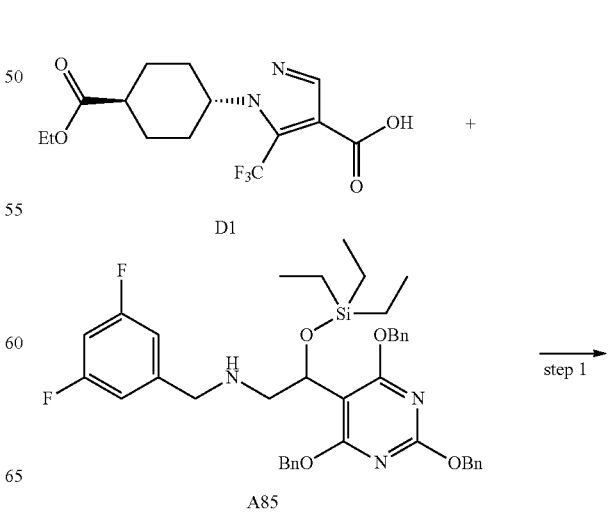

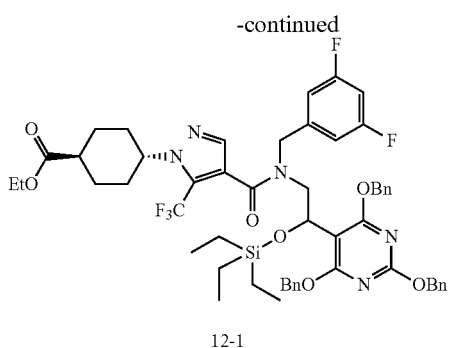

12-1

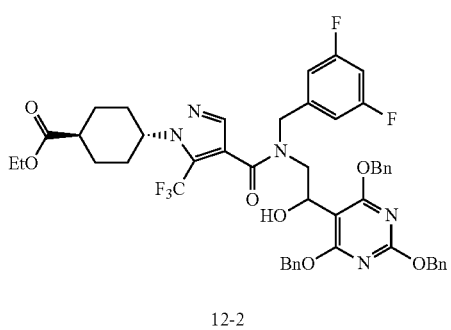

12-2

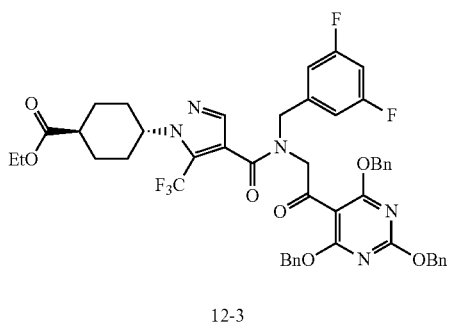

12-3

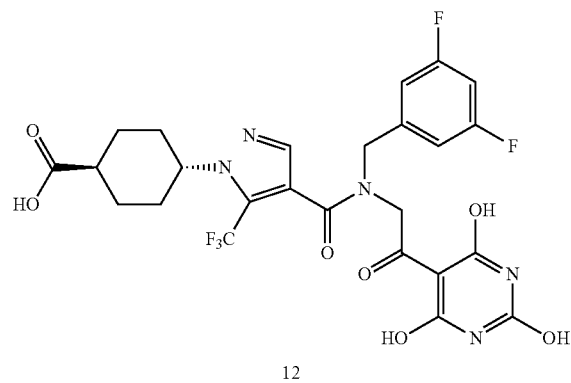 [SMILES: N=C/C(C(=O)N(CC(=O)c1c(O)nc(O)nc1O)Cc1cc(F)cc(F)c1)=C(\N[C@H]1CC[C@H](C(=O)O)CC1)C(F)(F)F]

12

Step 1: ethyl trans-4-(4-((3,5-difluorobenzyl)(2-((triethylsilyl)oxy)-2-(2,4,6-tris(benzyloxy)pyrimidin-5-yl)ethyl)carbamoyl)-5-(trifluoromethyl)-1H-pyrazol-1-yl)cyclohexanecarboxylate (12-1)

Compound 12-1 was obtained (0.45 g, crude) as a brown color gum from the reaction of amine A85 (0.3 g, 0.4 mmol), acid D1 (0.14 g, 0.4 mmol), HATU (0.19 g, 0.5 mmol) and DIPEA (0.11 mL, 0.6 mmol) in DMF (5 mL) using a similar procedure to that described in example 1.

Step 2: ethyl trans-4-(4-((3,5-difluorobenzyl)(2-hydroxy-2-(2,4,6-tris(benzyloxy)pyrimidin-5-yl)ethyl)carbamoyl)-5-(trifluoromethyl)-1H-pyrazol-1-yl)cyclohexanecarboxylate (12-2)

Compound 12-2 was obtained (0.31 g, 79%) as a brown color gum from the reaction of compound 12-1 (0.45 g, 0.4 mmol) and TBAF (1 M in THF, 0.9 mL, 0.8 mmol) in THF (10 mL) using a similar procedure to that described in example 1.

Step 3: ethyl trans-4-(4-((3,5-difluorobenzyl)(2-oxo-2-(2,4,6-tris(benzyloxy)pyrimidin-5-yl)ethyl)carbamoyl)-5-(trifluoromethyl)-1H-pyrazol-1-yl)cyclohexanecarboxylate (12-3)

Compound 12-3 was obtained (0.31 g, quant.) as a colorless gum from the reaction of compound 12-2 (0.31 g, 0.3 mmol) and Dess-Martin periodinane (0.29 g, 0.7 mmol) in DCM (10 mL) using a similar procedure to that described in example 1.

Step 4: trans-4-(4-((3,5-difluorobenzyl)(2-oxo-2-(2,4,6-trihydroxypyrimidin-5-yl)ethyl)carbamoyl)-5-(trifluoromethyl)-1H-pyrazol-1-yl)cyclohexanecarboxylic acid Example 12

To a stirred solution of compound 12-3 (0.1 g, 0.1 mmol) in dioxane (5 mL) was added 6 M HCl (5 mL) at room temperature and the mixture was stirred at 80° C. for 2 h. 10% NaOH solution was added to the reaction mixture up to pH 5 and extracted with EtOAc (2×30 mL). The combined organic layers were washed with water (50 mL), brine (50 mL), dried over $Na_2SO_4$ and concentrated under reduced pressure. The residue was purified by reverse phase column chromatography (C18 silica gel, 75% water/$CH_3CN$ as eluent) to provide the compound of example 12 (8 mg, 12%) as a white solid. $^1H$ NMR (DMSO-$d_6$) rotamers present δ 7.78 and 7.72 (1H, 2×s); 7.18-6.89 (3H, m); 4.92-4.56 (4H, m); 4.22-4.15 (1H, m); 2.33-2.25 (1H, m); 2.05-1.87 (6H, m); 1.57-1.46 (2H, m); LCMS (APCI): 600 (M+H)$^+$.

Example 13 trans-4-(4-((2-(2-acetamido-6-chlorophenyl)-2-oxoethyl)(3,5-difluorobenzyl)carbamoyl)-5-(trifluoromethyl)-1H-pyrazol-1-yl)cyclohexanecarboxylic acid

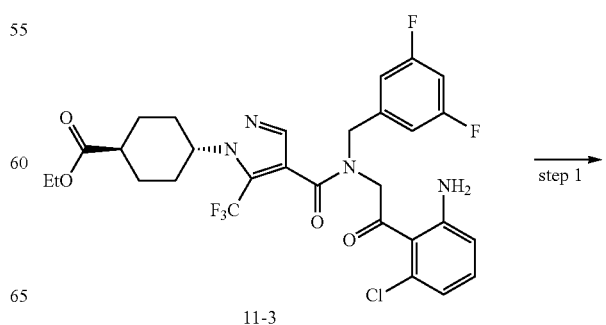

11-3

273
-continued

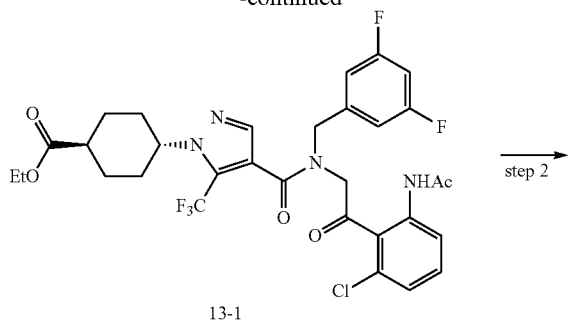

13-1

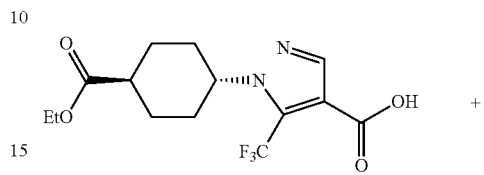

13

Step 1: ethyl trans-4-(4-((2-(2-acetamido-6-chlorophenyl)-2-oxoethyl)(3,5-difluorobenzyl)carbamoyl)-5-(trifluoromethyl)-1H-pyrazol-1-yl)cyclohexanecarboxylate (13-1)

To a stirred solution of compound 11-3 (45 mg, 0.07 mmol) in 1:1 mixture of pyridine and DCM (5 mL) was added CH₃COCl (6 μL, 0.08 mmol) at 0° C. and stirred for 2 h. The reaction mixture was quenched with water (20 mL) and extracted with DCM (2×10 mL). The combined organic layers were washed with water (50 mL), brine (50 mL), dried over Na₂SO₄ and concentrated under reduced pressure. The residue was purified by column chromatography (silica gel, 20% EtOAc/hexane as eluent) to provide compound 13-1 (50 mg, quant.) as a yellow solid.

Step 2: trans-4-(4-((2-(2-acetamido-6-chlorophenyl)-2-oxoethyl)(3,5-difluorobenzyl)carbamoyl)-5-(trifluoromethyl)-1H-pyrazol-1-yl)cyclohexanecarboxylic acid (13)

The compound of example 13 (25 mg, 52%) was obtained as a white solid from the reaction of compound 13-1 (50 mg, 0.07 mmol) and LiOH (9 mg, 0.37 mmol) in THF/MeOH/water (2:2:1, 5 mL) using a similar procedure to that described in example 1. $^1$H NMR (DMSO-d₆) rotamers present δ 10.10 and 9.74 (1H, 2×s), 7.80 and 7.78 (1H, 2×s); 7.59-6.91 (6H, m); 4.82-4.61 (4H, m); 4.26-4.15 (1H, m); 2.34-2.24 (1H, m); 2.07-1.89 (9H, m); 1.58-1.47 (2H, m); LCMS (APCI): 641 (M+H)⁺.

274

Example 14 trans-4-(4-((2-(3,5-dichloropyridin-4-yl)-2-oxoethyl)(((S)-5,5-dimethylTHF-2-yl)methyl)carbamoyl)-5-(trifluoromethyl)-1H-pyrazol-1-yl)cyclohexanecarboxylic acid

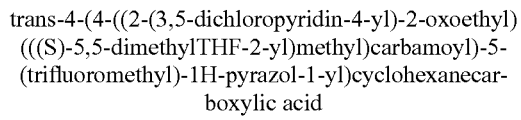

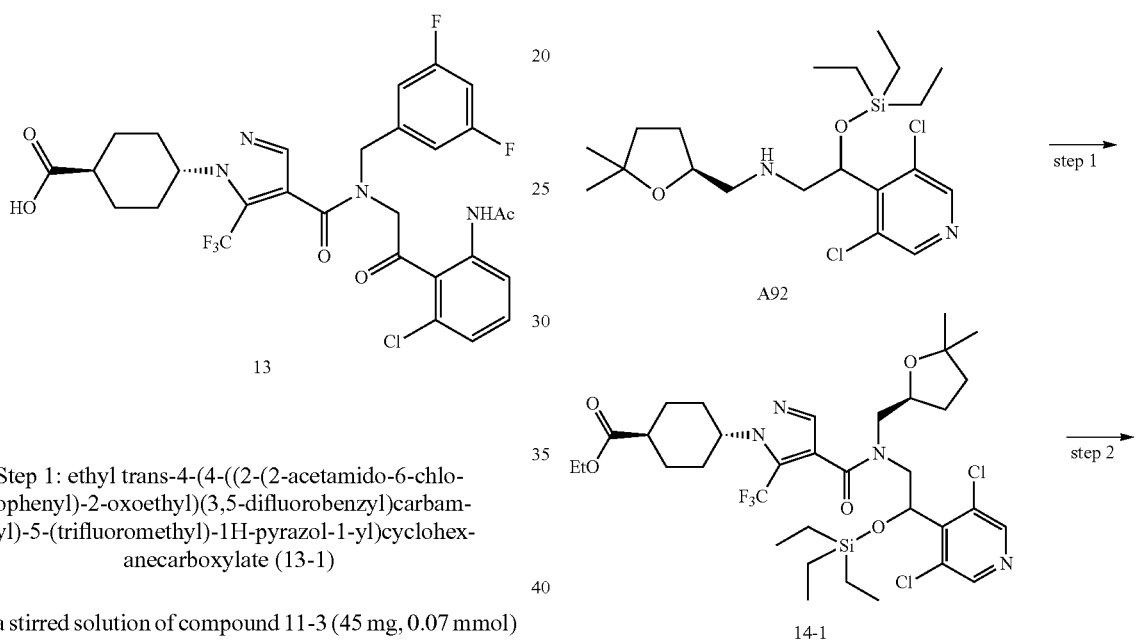

-continued

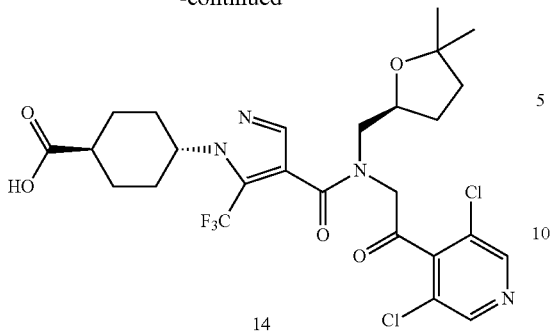

14

Step 1: ethyl trans-4-(4-((2-3,5-dichloropyridin-4-yl)-2-((triethylsilyl)oxy)ethyl)(((S)-5,5-dimethylTHF-2-yl)methyl)carbamoyl)-5-(trifluoromethyl)-1H-pyrazol-1-yl)cyclohexan ecarboxylate (14-1)

Compound 14-1 (42 mg, 61%) was obtained as a yellow foam from the reaction of acid D1 (31 mg, 0.09 mmol), amine A92 (40 mg, 0.09 mmol), HATU (42 mg, 0.11 mmol) and DIPEA (0.024 mL, 0.138 mmol) in DMF (3.0 mL) using a similar procedure to that described in example 1. LCMS (APCI): 749 (M+H)$^+$.

Step 2: ethyl trans-4-(4-((2-(3,5-dichloropyridin-4-yl)-2-hydroxyethyl)(((S)-5,5-dimethylTHF-2-yl)methyl)carbamoyl)-5-(trifluoromethyl)-1H-pyrazol-1-yl)cyclohexanecarboxylate (14-2)

Compound 14-2 (22 mg, 62%) was obtained as a colorless gum from the reaction of compound 14-1 (42 mg, 0.056 mmol) and TBAF (1 M in THF, 0.11 mL, 0.11 mmol) in THF (3.0 mL) using a similar procedure to that described in example 1.

LCMS (APCI): 635 (M+H)$^+$.

Step 3: ethyl trans-4-(4-((2-(3,5-dichloropyridin-4-yl)-2-oxoethyl)(((S)-5,5-dimethylTHF-2-yl)methyl)carbamoyl)-5-(trifluoromethyl)-1H-pyrazol-1-yl)cyclohexanecarboxylate (14-3)

Compound 14-3 (15 mg, 70%) was obtained as a colorless gum from the reaction of compound 14-2 (22 mg, 0.034 mmol) and Dess-Martin periodinane (29 mg, 0.069 mmol) in DCM (4.0 mL) using a similar procedure to that described in example 1.

LCMS (APCI): 633 (M+H)$^+$.

Step 4: trans-4-(4-((2-(3,5-dichloropyridin-4-yl)-2-oxoethyl)(((S)-5,5-dimethylTHF-2-yl)methyl)carbamoyl)-5-(trifluoromethyl)-1H-pyrazol-1-yl)cyclohexanecarboxylic acid (14)

The compound of example 14 (7.5 mg, 54%) was obtained as a white solid from the reaction of compound 14-3 (15 mg, crude) and LiOH.H$_2$O (8 mg, 0.19 mmol) in MeOH/THF/H$_2$O (4 mL, 1:1:0.5) using a similar procedure to that described in example 1. $^1$H NMR (DMSO-d$_6$) rotamers present δ 12.16 (1H, brs), 8.79 and 8.72 (2H, 2×s); 7.84 and 7.69 (1H, 2×s); 5.01-4.76 (2H, m); 4.30-3.81 (3H, m); 2.33-2.26 (1H, m); 2.06-1.45 (13H, m); 1.19-1.04 (6H, m); LCMS (APCI): 605 (M+H)$^+$.

Example 15 trans-4-(4-((2-(2-chloro-6-hydroxyphenyl)-2-oxoethyl)(3,5-difluorobenzyl)carbamoyl)-5-(trifluoromethyl)-1H-pyrazol-1-yl)cyclohexanecarboxylic acid

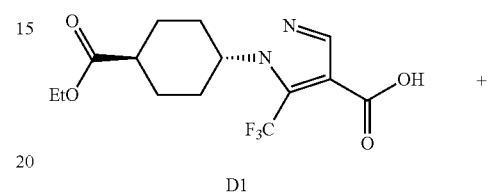

D1

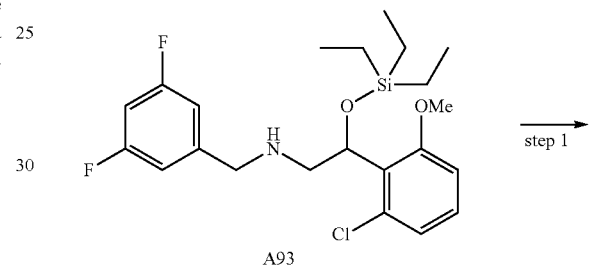

A93

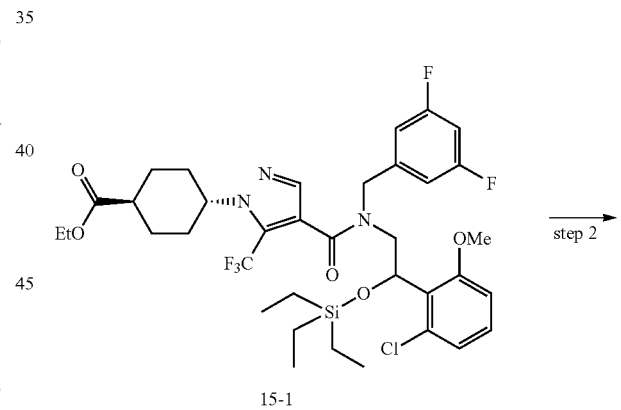

15-1

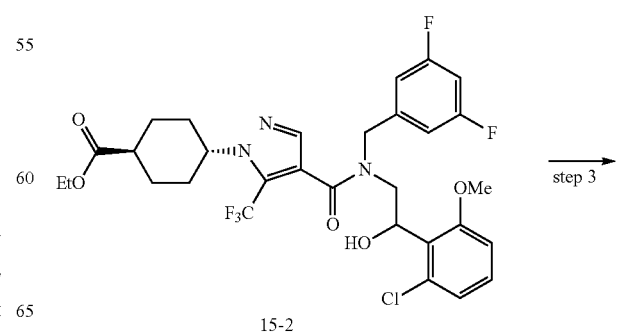

15-2

-continued

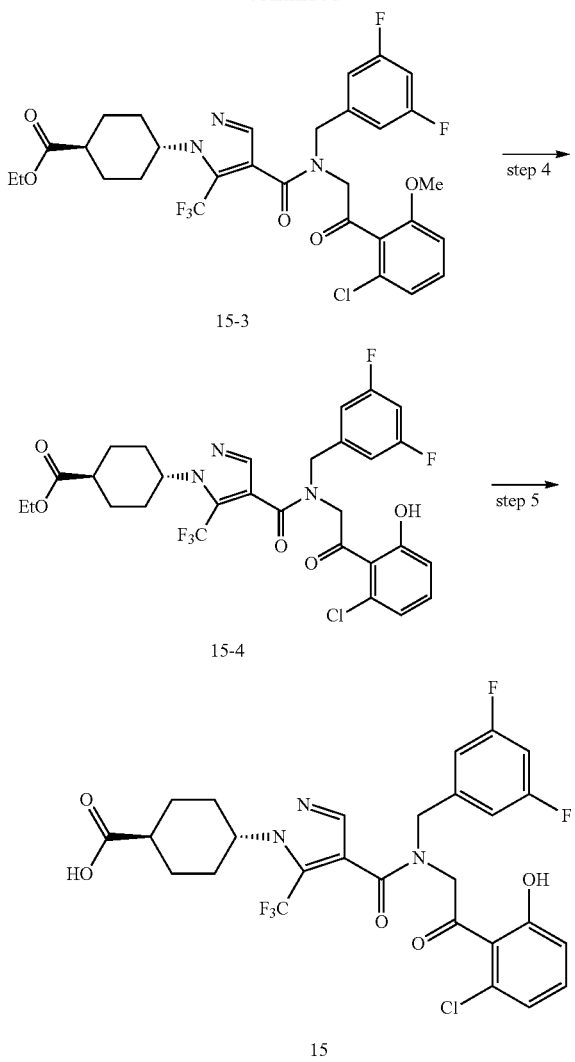

15-3

15-4

15

Step 1: ethyl trans-4-(4 #2-(2-chloro-6-methoxyphenyl)-2-((triethylsilyl)oxy)ethyl)(3,5-difluorobenzyl)carbamoyl)-5-(trifluoromethyl)-1H-pyrazol-1-yl)cyclohexanecarboxylate (15-1)

Compound 15-1 (0.41 g, crude) was obtained as a brown color gum from the reaction of amine A93 (0.23 g, 0.52 mmol), acid D1 (0.17 g, 0.52 mmol), HATU (0.23 g, 0.62 mmol) and DIPEA (0.133 mL, 0.78 mmol) in DMF (10 mL) using a similar procedure to that described in example 1.

Step 2: ethyl trans-4-(4-((2-(2-chloro-6-methoxyphenyl)-2-hydroxyethyl)(3,5-difluorobenzyl)carbamoyl)-5-(trifluoromethyl)-1H-pyrazol-1-yl)cyclohexanecarboxylate (15-2)

Compound 15-2 (0.36 g, crude) was obtained as a yellow color gum from the reaction of compound 15-1 (0.41 g, 0.54 mmol) and TBAF (1.0 M in THF, 1.1 mL, 1.08 mmol) in THF (10 mL) using a similar procedure to that described in example 1.

Step 3: ethyl trans-4-(4-((2-(2-chloro-6-methoxyphenyl)-2-oxoethyl)(3,5-difluorobenzyl)carbamoyl)-5-(trifluoromethyl)-1H-pyrazol-1-yl)cyclohexanecarboxylate (15-3)

Compound 15-3 (0.25 g, 70%) was obtained as a white solid from the reaction of compound 15-2 (0.36 g, 0.56 mmol) and Dess-Martin periodinane (0.47 g, 1.12 mmol) in DCM (10 mL) using a similar procedure to that described in example 1.

Step 4: ethyl trans-4-(4-((2-(2-chloro-6-hydroxyphenyl)-2-oxoethyl)(3,5-difluorobenzyl)carbamoyl)-5-(trifluoromethyl)-1H-pyrazol-1-yl)cyclohexanecarboxylate (15-4)

To a stirred solution of compound 15-3 (0.25 g, 0.39 mmol) in DCM (10 mL) was added $BBr_3$ (1.0 M in DCM, 3.9 mL, 3.9 mmol) at room temperature and the mixture was stirred for 16 h. Solvent was evaporated under reduced pressure and the obtained residue was purified by column chromatography (silica gel, 30% EtOAc/hexane as eluent) to provide compound 15-4 (85 mg, 35%) as a yellow oil.

Step 5: trans-4-(4-((2-(2-chloro-6-hydroxyphenyl)-2-oxoethyl)(3,5-difluorobenzyl)carbamoyl)-5-(trifluoromethyl)-1H-pyrazol-1-yl)cyclohexanecarboxylic acid (15)

The compound of example 15 (55 mg, 68%) was obtained as a white solid from the reaction of compound 15-4 (85 mg, 0.13 mmol) and LiOH (16.3 mg, 0.67 mmol) in THF/MeOH/water (2:2:1, 5 mL) using a similar procedure to that described in example 1.

$^1$H NMR (DMSO-$d_6$) rotamers present δ 7.76 and 7.74 (1H, 2×s); 7.28-6.78 (6H, m); 4.75-4.52 (4H, m); 4.26-4.15 (1H, m); 2.33-2.26 (1H, m); 2.07-1.90 (6H, m); 1.58-1.47 (2H, m); LCMS (APCI): 600 (M+H)$^+$.

Example 16 trans-4-(4-((2-(3,5-dichloropyridin-4-yl)-2-oxoethyl)(((R)-5,5-dimethylTHF-2-yl)methyl)carbamoyl)-5-(trifluoromethyl)-1H-pyrazol-1-yl)cyclohexanecarboxylic acid

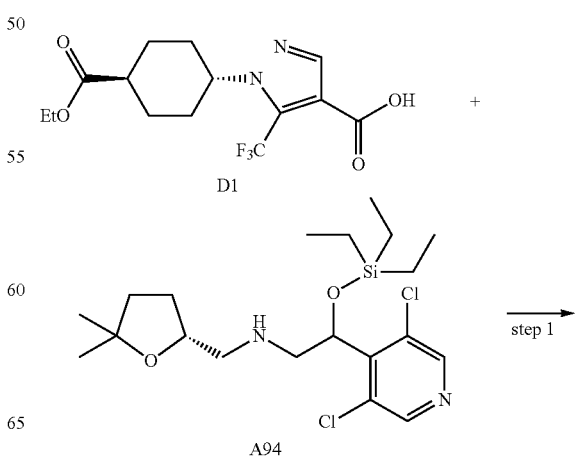

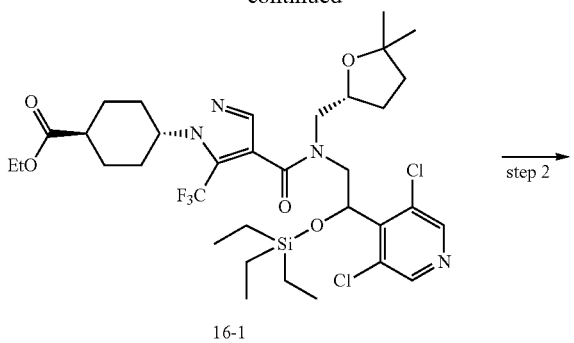

16-1

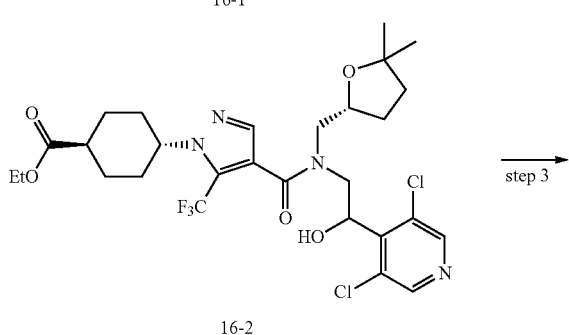

16-2

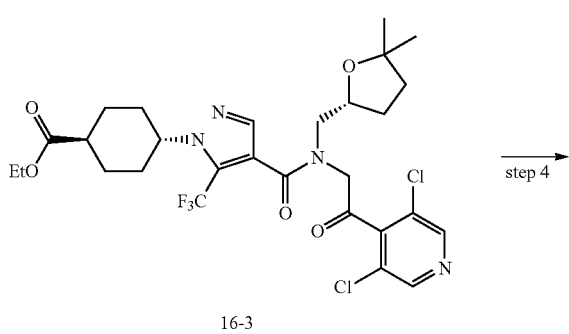

16-3

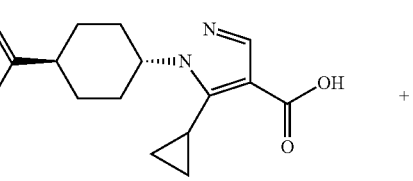

16

Step 1: ethyl trans-4-(4-((2-(3,5-dichloropyridin-4-yl)-2-(((triethylsilyl)oxy)ethyl)(((R)-5,5-dimethylTHF-2-yl)methyl)carbamoyl)-5-(trifluoromethyl)-1H-pyrazol-1-yl)cyclohexan ecarboxylate (16-1)

Compound 16-1 (29 mg, 52%) was obtained as a colorless gum from the reaction of acid D1 (25 mg, 0.074 mmol), amine A94 (32 mg, 0.074 mmol), HATU (34 mg, 0.088 mmol) and DIPEA (0.019 mL, 0.11 mmol) in DMF (3.0 mL) using a similar procedure to that described in example 1. LCMS (APCI): 749 (M+H)⁺.

Step 2: ethyl trans-4-(4-((2-(3,5-dichloropyridin-4-yl)-2-hydroxyethyl)(((R)-5,5-dimethylTHF-2-yl)methyl)carbamoyl)-5-(trifluoromethyl)-1H-pyrazol-1-yl)cyclohexanecarboxylate (16-2)

Compound 16-2 (25 mg, crude) was obtained as a colorless gum from the reaction of compound 16-1 (29 mg, 0.038 mmol) and TBAF (1 M in THF, 0.076 mL, 0.076 mmol) in THF (3.0 mL) using a similar procedure to that described in example 1. LCMS (APCI): 635 (M+H)⁺.

Step 3: ethyl trans-4-(4-((2-(3,5-dichloropyridin-4-yl)-2-oxoethyl)(((R)-5,5-dimethylTHF-2-yl)methyl)carbamoyl)-5-(trifluoromethyl)-1H-pyrazol-1-yl)cyclohexanecarboxylate (16-3)

Compound 16-3 (23 mg, crude) was obtained as a colorless gum from the reaction of compound 16-2 (25 mg, crude) and Dess-Martin periodinane (33 mg, 0.078 mmol) in DCM (4.0 mL) using a similar procedure to that described in example 1. LCMS (APCI): 633 (M+H)⁺.

Step 4: trans-4-(4-((2-(3,5-dichloropyridin-4-yl)-2-oxoethyl)(((R)-5,5-dimethylTHF-2-yl)methyl)carbamoyl)-5-(trifluoromethyl)-1H-pyrazol-1-yl)cyclohexanecarboxylic acid (16)

The compound of example 16 (8.5 mg, 39%) was obtained as a white solid from the reaction of compound 16-3 (23 mg, crude) and LiOH.H₂O (12 mg, 0.29 mmol) in MeOH/THF/H₂O (4 mL, 1:1:0.5) using a similar procedure to that described in example 1. ¹H NMR (DMSO-d₆) rotamers present δ 12.19 (1H, brs), 8.79 and 8.72 (2H, 2×s); 7.84 and 7.69 (1H, 2×s); 5.01-4.76 (2H, m); 4.27-3.80 (3H, m); 2.33-2.26 (1H, m); 2.06-1.45 (13H, m); 1.19-1.04 (6H, m); LCMS (APCI): 605 (M+H)⁺.

Example 17 trans-4-(5-cyclopropyl-4-((2-(3,5-dichloropyridin-4-yl)-2-oxoethyl)(3,5-difluorobenzyl)carbamoyl)-1H-pyrazol-1-yl)cyclohexanecarboxylic acid

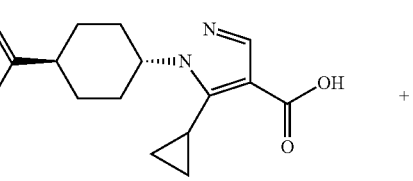

D20

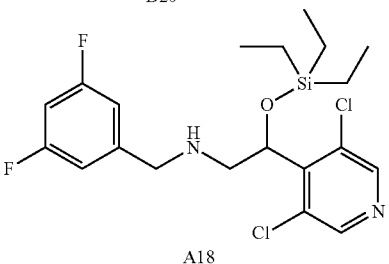

A18

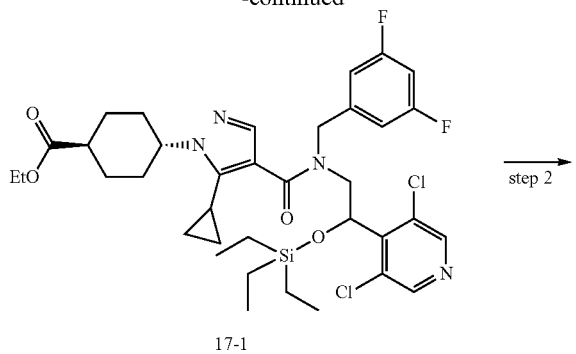

17-1

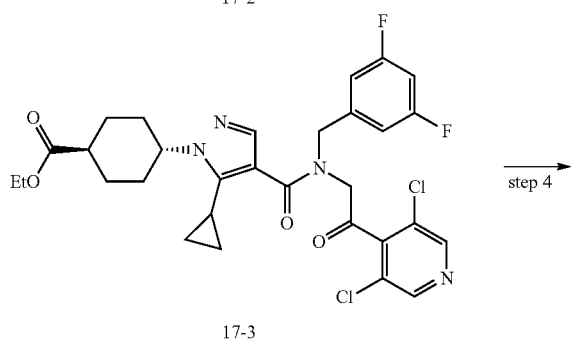

17-2

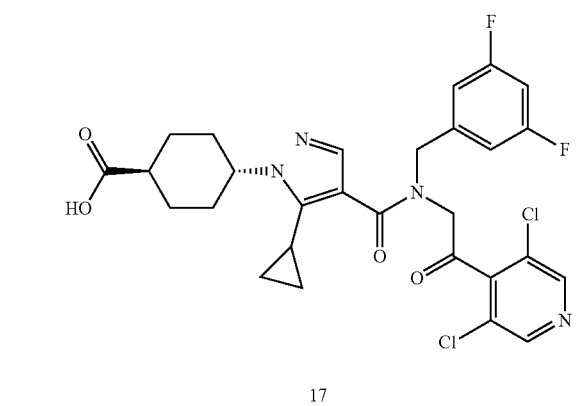 [SMILES: N=C/C(C(=O)N(CC(=O)c1c(Cl)cncc1Cl)Cc1cc(F)cc(F)c1)=C(\N[C@H]1CC[C@H](C(=O)O)CC1)C1CC1]

17-3

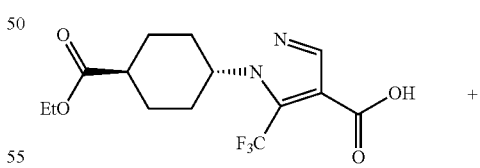

17

Step 1: ethyl trans-4-(5-cyclopropyl-4-((2-(3,5-dichloropyridin-4-yl)-2-((triethylsilyl)oxy)ethyl)(3,5-difluorobenzyl)carbamoyl)-1H-pyrazol-1-yl)cyclohexanecarboxylate (17-1)

Compound 17-1 (130 mg, crude) was obtained as a colorless gum from the reaction of acid D20 (200 mg, 0.56 mmol), amine A18 (233 mg, 0.52 mmol), HATU (296 mg, 0.78 mmol) and DIPEA (0.165 mL, 0.97 mmol) in DMF (10 mL) using a similar procedure to that described in example 1.

Step 2: ethyl trans-4-(5-cyclopropyl-4-((2-(3,5-dichloropyridin-4-yl)-2-hydroxyethyl)(3,5-difluorobenzyl)carbamoyl)-1H-pyrazol-1-yl)cyclohexanecarboxylate (17-2)

Compound 17-2 (80 mg, impure) was obtained as a colorless gum from the reaction of compound 17-1 (80 mg, 0.128 mmol) and TBAF (1 M in THF, 0.190 mL, 0.190 mmol) in THF (4 mL) using a similar procedure to that described in example 1.

Step 3: ethyl trans-4-(5-cyclopropyl-4-((2-(3,5-dichloropyridin-4-yl)-2-oxoethyl)(3,5-difluorobenzyl)carbamoyl)-1H-pyrazol-1-yl)cyclohexanecarboxylate (17-3)

Compound 17-3 (60 mg, 75%) was obtained as an off-white solid from the reaction of compound 17-2 (80 mg, 0.128 mmol) and Dess-Martin periodinane (110 mg, 0.250 mmol) in DCM (10 mL) using a similar procedure to that described in example 1.

Step 4: trans-4-(5-cyclopropyl-4-((2-(3,5-dichloropyridin-4-yl)-2-oxoethyl)(3,5-difluorobenzyl)carbamoyl)-1H-pyrazol-1-yl)cyclohexanecarboxylic acid (17)

The compound of example 17 (8 mg, 12%) was obtained as a white solid from the reaction of compound 17-3 (70 mg, 0.113 mmol) and LiOH (8.4 mg, 0.330 mmol) in EtOH/THF/water (5 mL, 2:2:1) using a similar procedure to that described in example 1. $^1$H NMR (DMSO-$d_6$) rotamers present δ 8.76 and 8.69 (2H, 2×s); 7.46 and 7.35 (1H, 2×s); 7.18-7.12 and 6.95-6.91 (3H, m); 4.76-4.62 (4H, m); 4.44-4.36 (1H, m); 2.26-2.17 (1H, m); 2.03-2.00 (2H, m); 1.87-1.83 (5H, m); 1.57-1.47 (2H, m); 0.95-0.90 (2H, m); 0.68-0.64 (2H, m); LCMS (APCI): 591 (M+H)$^+$.

Example 18 trans-4-(4-((2-(2,6-dichloro-4-(difluoromethyl)phenyl)-2-oxoethyl)(3,5-difluorobenzyl)carbamoyl)-5-(trifluoromethyl)-1H-pyrazol-1-yl)cyclohexanecarboxylic acid

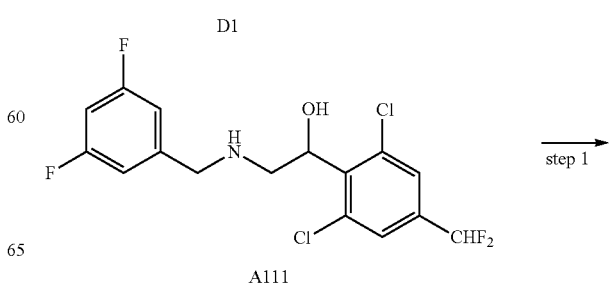

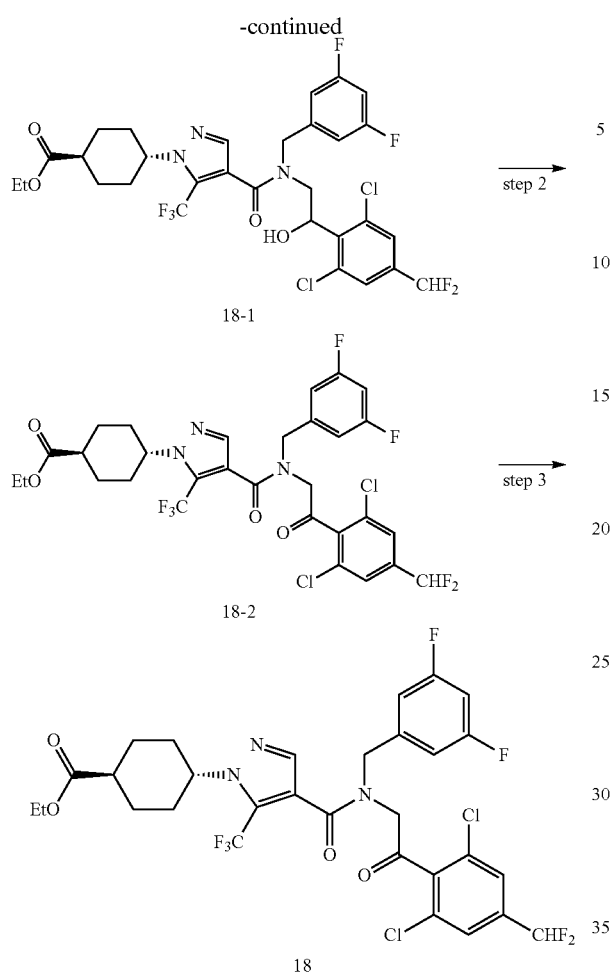

0.08 mmol) and LiOH (11 mg, 0.43 mmol) in THF/MeOH/water (2:2:1, 5 mL) using a similar procedure to that described in example 1. $^1$H NMR (DMSO-$d_6$) rotamers present δ 12.20 (1H, brs); 7.87-7.75 (3H, m); 7.21-6.88 (4H, m); 4.84 and 4.72 (2H, 2×s); 4.68 and 4.57 (2H, 2×s); 4.28-4.17 (1H, m); 2.34-2.27 (1H, m); 2.07-1.90 (6H, m); 1.59-1.49 (2H, m); LCMS (APCI): 668 (M+H)$^+$.

Example 19 trans-4-(4-((2-(3,5-dichloropyridin-4-yl)-2-oxoethyl)((4-hydroxy-4-methylcyclohexyl)methyl)carbamoyl)-5-(trifluoromethyl)-1H-pyrazol-1-yl)cyclohexanecarboxylic acid

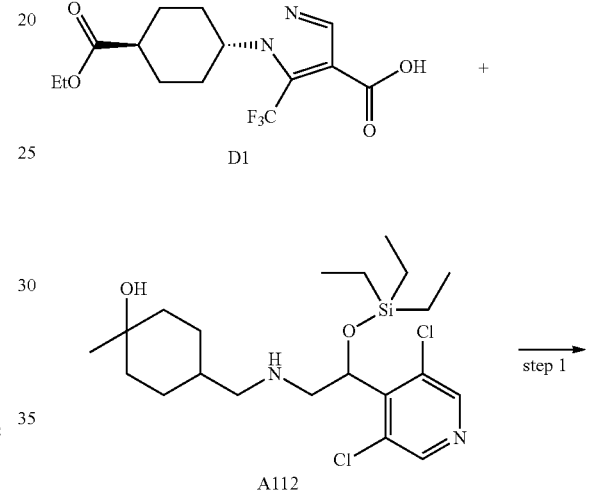

Step 1: ethyl trans-4-(4-((2-(2,6-dichloro-4-(difluoromethyl)phenyl)-2-hydroxyethyl)(3,5-difluorobenzyl)carbamoyl)-5-(trifluoromethyl)-1H-pyrazol-1-yl)cyclohexanecarboxylate (18-1)

Compound 18-1 (0.18 g, crude) was obtained as a brown color gum from the reaction of amine A111 (0.10 g, 0.26 mmol), acid D1 (87 mg, 0.26 mmol), HATU (0.12 g, 0.31 mmol) and DIPEA (67 μL, 0.39 mmol) in DMF (5 mL) using a similar procedure to that described in example 1.

Step 2: ethyl trans-4-(4-((2-(2,6-dichloro-4-(difluoromethyl)phenyl)-2-oxoethyl)(3,5-difluorobenzyl)carbamoyl)-5-(trifluoromethyl)-1H-pyrazol-1-yl)cyclohexanecarboxylate (18-2)

Compound 18-2 (0.12 g, 67%) was obtained as a colorless gum from the reaction of compound 18-1 (0.18 g, 0.26 mmol) and Dess-Martin periodinane (0.22 g, 0.52 mmol) in DCM (5 mL) using a similar procedure to that described in example 1.

Step 3: trans-4-(4-((2-(2,6-dichloro-4-(difluoromethyl)phenyl)-2-oxoethyl)(3,5-difluorobenzyl)carbamoyl)-5-(trifluoromethyl)-1H-pyrazol-1-yl)cyclohexanecarboxylic acid (18)

The compound of example 18 (15 mg, 26%) was obtained as a white solid from the reaction of compound 18-2 (60 mg,

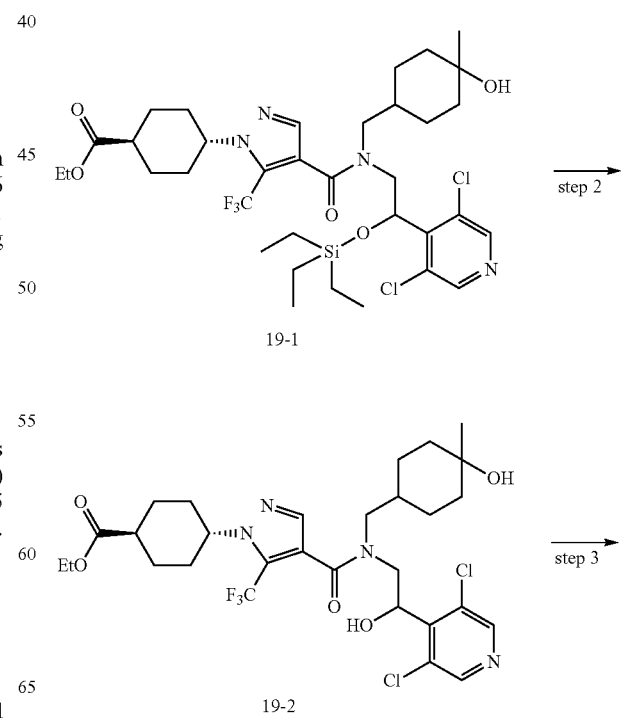

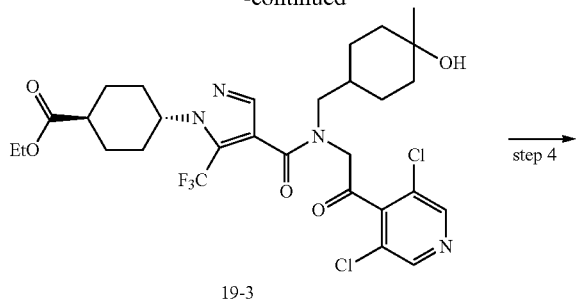

19-3

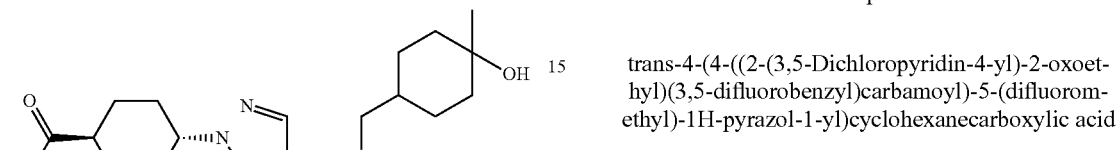

19

Step 1: ethyl trans-4-(4-((2-3,5-dichloropyridin-4-yl)-2-((triethylsilyl)oxy)ethyl)((4-hydroxy-4-methyl-cyclohexyl)methyl)carbamoyl)-5-(trifluoromethyl)-1H-pyrazol-1-yl)cyclohexanecarboxylate (19-1)

Compound 19-1 (72 mg, crude) was obtained as a colorless gum from the reaction of acid D1 (44 mg, 0.129 mmol), amine A112 (58 mg, 0.129 mmol), HATU (59 mg, 0.155 mmol) and DIPEA (0.034 mL, 0.194 mmol) in DMF (4.0 mL) using a similar procedure to that described in example 1.

Step 2: ethyl trans-4-(4-((2-3,5-dichloropyridin-4-yl)-2-hydroxyethyl)((4-hydroxy-4-methylcyclohexyl)methyl)carbamoyl)-5-(trifluoromethyl)-1H-pyrazol-1-yl)cyclohexanecarboxylate (19-2)

Compound 19-2 (46 mg, 55% over two steps) was obtained as a colorless gum from the reaction of compound 19-1 (72 mg, crude) and TBAF (1 M in THF, 0.18 mL, 0.18 mmol) in THF (4.0 mL) using a similar procedure to that described in example 1.

Step 3: ethyl trans-4-(4-((2-3,5-dichloropyridin-4-yl)-2-oxoethyl)((4-hydroxy-4-methylcyclohexyl)methyl)carbamoyl)-5-(trifluoromethyl)-1H-pyrazol-1-yl)cyclohexanecarboxylate (19-3)

Compound 19-3 (45 mg, crude) was obtained as a colorless gum from the reaction of compound 19-2 (46 mg, 0.071 mmol) and Dess-Martin periodinane (60 mg, 0.14 mmol) in DCM (5.0 mL) using a similar procedure to that described in example 1.

Step 4: trans-4-(4-((2-3,5-dichloropyridin-4-yl)-2-oxoethyl)((4-hydroxy-4-methylcyclohexyl)methyl)carbamoyl)-5-(trifluoromethyl)-1H-pyrazol-1-yl)cyclohexanecarboxylic acid (19)

The compound of example 19 (16 mg, 38%) was obtained as a white solid from the reaction of compound 19-3 (45 mg, 0.069 mmol) and LiOH.H$_2$O (18 mg, 0.41 mmol) in EtOH/THF/H$_2$O (4 mL, 1:1:0.5) using a similar procedure to that described in example 1.

$^1$H NMR (DMSO-d$_6$) rotamers present δ 12.24 (1H, brs); 8.80 and 8.73 (2H, 2×s); 7.80 and 7.70 (1H, 2×s); 4.83 and 4.67 (2H, 2×s); 4.28-4.18 (1H, m); 3.93 and 3.87 (1H, 2×s); 3.49-3.47 and 3.18-3.11 (1H, 2×m); 2.33-2.25 (1H, m); 2.06-1.90 (6H, m); 1.58-1.01 (14H, m); LCMS (APCI): 617 (M−H)$^-$.

Example 20 trans-4-(4-((2-(3,5-Dichloropyridin-4-yl)-2-oxoethyl)(3,5-difluorobenzyl)carbamoyl)-5-(difluoromethyl)-1H-pyrazol-1-yl)cyclohexanecarboxylic acid

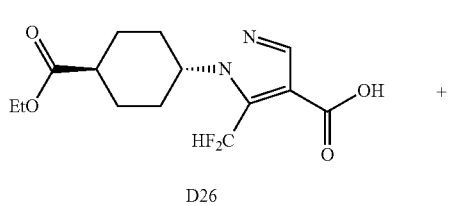

D26

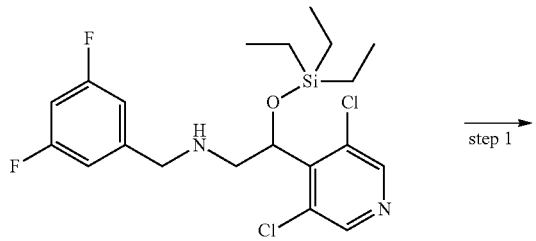

A18

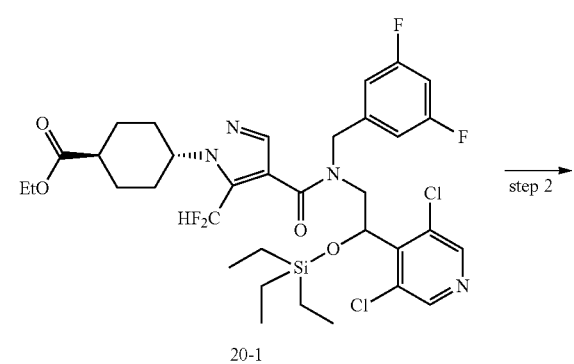

20-1

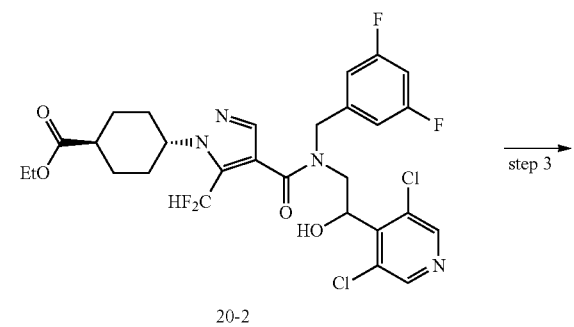

20-2

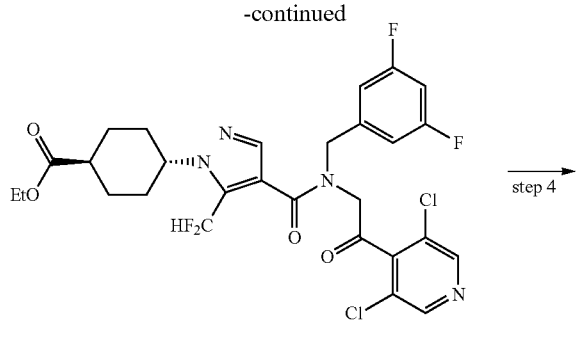

20-3

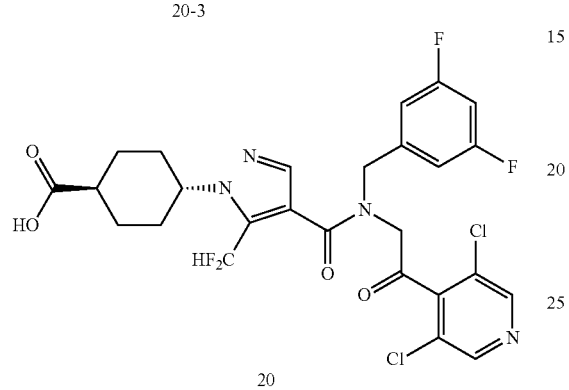

20

Step 1: ethyl trans-4-(4-((2-(3,5-dichloropyridin-4-yl)-2-((triethylsilyl)oxy)ethyl)(3,5-difluorobenzyl)carbamoyl)-5-(difluoromethyl)-1H-pyrazol-1-yl)cyclohexanecarboxylate (20-1)

Compound 20-1 (130 mg, 55%) was obtained as a white solid from the reaction of acid D26 (100 mg, 0.31 mmol), amine A18 (105 mg, 0.31 mmol), (COCl)$_2$ (0.03 mL, 0.37 mmol), Et$_3$N (0.08 mL, 0.63 mmol) and DMF (cat) in DCM using a similar procedure to that described in example 2.

Step 2: ethyl trans-4-(4-((2-(3,5-dichloropyridin-4-yl)-2-hydroxyethyl)(3,5-difluorobenzyl)carbamoyl)-5-(difluoromethyl)-1H-pyrazol-1-yl)cyclohexanecarboxylate (20-2)

Compound 20-2 (101 mg, 91%) was obtained as an off-white solid from the reaction of compound 20-1 (130 mg, 0.54 mmol) and TBAF (1.0 M solution in THF, 0.24 mL, 0.24 mmol) in THF (4 mL) using a similar procedure to that described in example 2.

Step 3: ethyl trans-4-(4-((2-(3,5-dichloropyridin-4-yl)-2-oxoethyl)(3,5-difluorobenzyl)carbamoyl)-5-(difluoromethyl)-1H-pyrazol-1-yl)cyclohexanecarboxylate (20-3)

Compound 20-3 (30 mg, 33%) was obtained as an off-white solid from the reaction of Compound 20-2 (101 mg, 0.15 mmol) and Dess-Martin periodinane (101 mg, 0.23 mmol) in DCM (8 mL) using a similar procedure to that described in example 2.

Step 4: trans-4-(4-((2-(3,5-dichloropyridin-4-yl)-2-oxoethyl)(3,5-difluorobenzyl)carbamoyl)-5-(difluoromethyl)-1H-pyrazol-1-yl)cyclohexanecarboxylic acid (20)

To a solution of compound 20-3 (106 mg, 0.17 mmol) in dioxane (6 mL) was added 6 M HCl (6 mL) and heated at 80° C. for 16 h. The reaction mixture was cooled to room temperature, added H$_2$O and extracted with EtOAc (2×50 mL). The combined organic layers were washed with brine (2×10 mL), dried over Na$_2$SO$_4$ and concentrated under reduced pressure. The residue was purified by reverse phase column chromatography (C18 silica gel, 75% CH$_3$CN/water as eluent) to provide the compound of example 20 (36 mg, 62%) as a white solid. $^1$H NMR (DMSO-d$_6$) rotamers present δ 8.76 and 8.69 (2H, 2×s); 7.77 and 7.67 (1H, 2×s); 7.45-7.00 (4H, m); 4.91-4.70 (4H, m); 4.36-4.29 (1H, m); 2.31-2.24 (1H, m); 2.06-2.02 (2H, m); 1.94-1.89 (4H, m); 1.56-1.45 (2H, m); LCMS (ESI): 599 (M+H)$^+$.

Example 21 trans-4-(4-((2-(2-amino-4-chloropyridin-3-yl)-2-oxoethyl)(3,5-difluorobenzyl)carbamoyl)-5-(trifluoromethyl)-1H-pyrazol-1-yl)cyclohexanecarboxylic acid

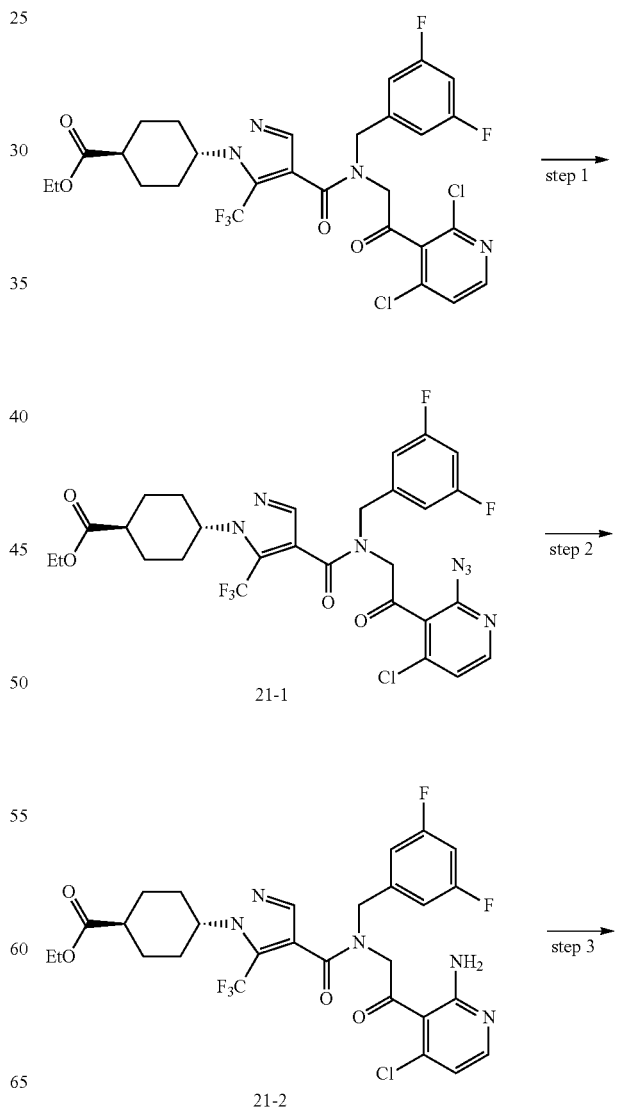

289

-continued

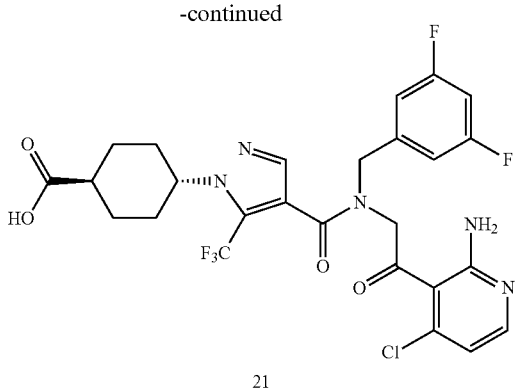

21

Step 1: ethyl trans-4-(4-((2-(2-azido-4-chloropyridin-3-yl)-2-oxoethyl)(3,5-difluorobenzyl)carbamoyl)-5-(trifluoromethyl)-1H-pyrazol-1-yl)cyclohexanecarboxylate (21-1)

To a stirred solution of ethyl trans-4-(4-((2-(2,4-dichloropyridin-3-yl)-2-oxoethyl)(3,5-difluorobenzyl)carbamoyl)-5-(trifluoromethyl)-1H-pyrazol-1-yl)cyclohexanecarboxylate (100 mg, 0.15 mmol) in DMF (5 mL) was added $NaN_3$ (50 mg, 0.7 mmol) and the mixture was stirred at room temperature for 3 h. The reaction mixture was quenched with water (20 mL) and extracted with EtOAc (2×30 mL). The combined organic layers were washed with water (50 mL) and brine (50 mL), dried over $Na_2SO_4$ and concentrated under reduced pressure. The residue was purified by column chromatography (silica gel, 30% EtOAc/hexane as eluent) to provide compound 21-1 (60 mg, 59%) as a brown oil.

Step 2: ethyl trans-4-(4-((2-(2-amino-4-chloropyridin-3-yl)-2-oxoethyl)(3,5-difluorobenzyl)carbamoyl)-5-(trifluoromethyl)-1H-pyrazol-1-yl)cyclohexanecarboxylate (21-2)

To a stirred solution of compound 21-1 (60 mg, 0.09 mmol) in THF (5 mL) was added $Me_3P$ (1.0 M in THF, 0.18 mL, 0.18 mmol) at 0° C. and mixture was stirred at room temperature for 2 h. $H_2O$ (0.06 mL) was added to the reaction mixture at 0° C. and the mixture was stirred at room temperature for 16 h. The solvent was removed under reduced pressure and the residue was purified by column chromatography (silica gel, 30% EtOAc/hexane as eluent) to provide compound 21-2 (40 mg, 69%) as a yellow oil.

Step 3: trans-4-(4-((2-(2-amino-4-chloropyridin-3-yl)-2-oxoethyl)(3,5-difluorobenzyl)carbamoyl)-5-(trifluoromethyl)-1H-pyrazol-1-yl)cyclohexanecarboxylic acid (21)

To a stirred solution of compound 21-2 (40 mg, 0.06 mmol) in THF/MeOH (4 mL, 1:1) was added a solution of LiOH (7.7 mg, 0.3 mmol) in water (1 mL). The reaction mixture was stirred at room temperature for 2 h. The reaction mixture was diluted with water (10 mL), acidified with 0.5 M HCl (to pH 5) and extracted with EtOAc (3×10 mL). The combined organic layers were washed with water (10 mL), brine (10 mL), dried over $Na_2SO_4$ and concentrated under reduced pressure. The residue was purified by reverse phase column chromatography (C18 silica gel, 70% $CH_3CN$/water as eluent) to provide the compound of example 21 (25 mg, 66%) as

290 a white solid. $^1$H NMR (DMSO-$d_6$) rotamers present δ 12.14 (1H, brs); 8.75 and 8.46 (1H, 2×s); 7.91 (2H, brs); 7.73 and 7.49 (1H, 2×s); 7.16-7.01 (2H, m); 6.89-6.85 (1H, m); 6.78 and 6.73 (1H, 2×s); 5.02 and 4.83 (2H, 2×s); 4.65 and 4.55 (2H, 2×s); 4.20-4.12 (1H, m); 2.33-2.21 (1H, m); 2.04-1.79 (6H, m); 1.56-1.43 (2H, m); LCMS (APCI): 600 (M+H)$^+$.

Example 22 trans-4-(4-((2-cyanobenzyl)(2-(3,5-dichloropyridin-4-yl)-2-oxoethyl)carbamoyl)-5-(trifluoromethyl)-1H-pyrazol-1-yl)cyclohexanecarboxylic acid

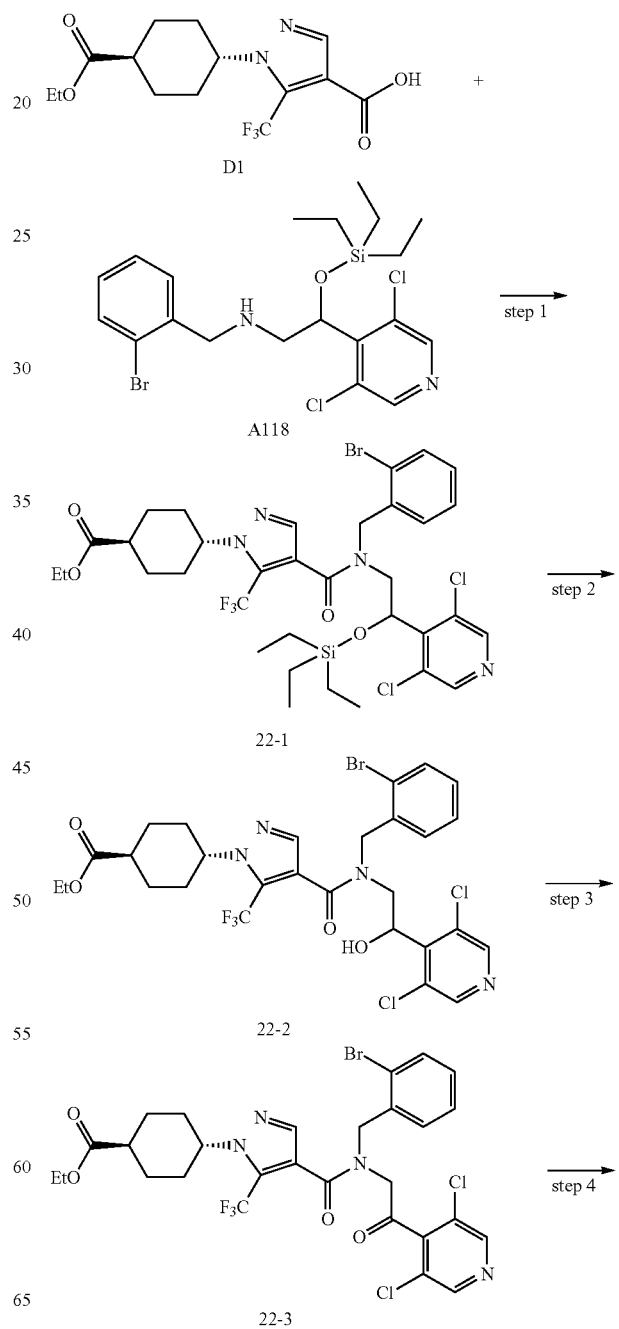

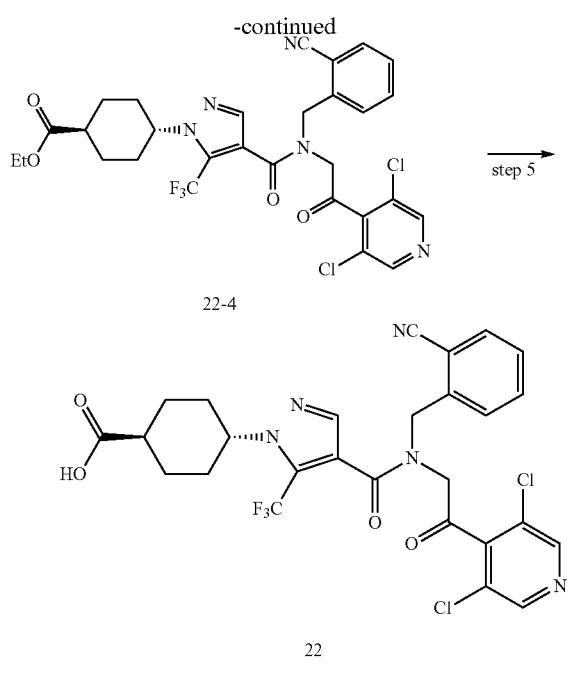

22-4

22

Step 1: ethyl trans-4-(4-((2-bromobenzyl)(2-(3,5-dichloropyridin-4-yl)-2-((triethylsilyl)oxy)ethyl)carbamoyl)-5-(trifluoromethyl)-1H-pyrazol-1-yl)cyclohexanecarboxylate (22-1)

Compound 22-1 (310 mg, crude) was obtained as a yellow oil from the reaction of amine A118 (200 mg, 0.40 mmol), acid D1 (136 mg, 0.40 mmol), HATU (232 mg, 0.61 mmol) and DIPEA (0.14 mL, 0.81 mmol) in DMF (5 mL) using a similar procedure to that described in example 1.

Step 2: ethyl trans-4-(4-((2-bromobenzyl)(2-(3,5-dichloropyridin-4-yl)-2-hydroxyethyl)carbamoyl)-5-(trifluoromethyl)-1H-pyrazol-1-yl)cyclohexanecarboxylate (22-2)

Compound 22-2 (175 mg, 73%) was obtained as an off-white solid from the reaction of compound 22-1 (310 mg, 0.38 mmol) and TBAF (1.0 M solution in THF, 0.57 mL, 0.57 mmol) in THF (4 mL) using a similar procedure to that described in example 1.

Step 3: ethyl trans-4-(4-((2-bromobenzyl)(2-(3,5-dichloropyridin-4-yl)-2-oxoethyl)carbamoyl)-5-(trifluoromethyl)-1H-pyrazol-1-yl)cyclohexanecarboxylate (22-3)

Compound 22-3 (150 mg, 86%) was obtained as an off-white solid from the reaction of compound 22-2 (175 mg, 0.25 mmol) and Dess-Martin periodinane (161 mg, 0.37 mmol) in DCM (10 mL) using a similar procedure to that described in example 1.

Step 4: ethyl trans-4-(4-((2-cyanobenzyl)(2-(3,5-dichloropyridin-4-yl)-2-oxoethyl)carbamoyl)-5-(trifluoromethyl)-1H-pyrazol-1-yl)cyclohexanecarboxylate (22-4)

A mixture of compound 22-3 (100 mg, 0.14 mmol) and $Zn(CN)_2$ (34 mg, 0.28 mmol) in DMA (8 mL) was purged with argon for 10 min. $Pd(PPh_3)_4$ (33.4 mg, 0.02 mmol) was added and the mixture was heated at 100° C. for 3 h. The reaction mixture was cooled to room temperature, quenched with water (10 mL) and extracted with EtOAc (2×20 mL). The combined organic layers were washed with water (10 mL) and brine (10 mL), dried over $Na_2SO_4$ and concentrated under reduced pressure. The residue was purified by column chromatography (silica gel, 30% EtOAc/hexane) to provide compound 22-4 (27 mg, 29%) as an off-white solid.

Step 5: trans-4-(4-((2-cyanobenzyl)(2-(3,5-dichloropyridin-4-yl)-2-oxoethyl)carbamoyl)-5-(trifluoromethyl)-1H-pyrazol-1-yl)cyclohexanecarboxylic acid (22)

The compound of example 22 (15 mg, 39%) was obtained as a white solid from the reaction of compound 22-4 (40 mg, 0.06 mmol) and LiOH (4.3 mg, 0.03 mmol) in EtOH (2 mL), THF (2 mL) and $H_2O$ (1 mL) using a similar procedure to that described in example 1. $^1H$ NMR (DMSO-$d_6$) rotamers present δ 8.56-8.50 (2H, m); 7.91 (2H, brs); 7.94 (1H, s); 7.54-7.42 and 7.17 (3H, m and s); 7.08 (1H, s); 5.62-5.58 and 4.64-4.59 (1H, 2×m); 4.33-4.17 (1H, m); 2.39-2.33 (1H, m); 2.10-1.93 (7H, m); LCMS (APCI): 608 (M+H)$^+$.

Example 23 trans-4-(4-((2-(3,5-dichloropyridin-4-yl)-2-oxoethyl)((3,3-dimethylcyclobutyl)methyl)carbamoyl)-5-(trifluoromethyl)-1H-pyrazol-1-yl)cyclohexanecarboxylic acid

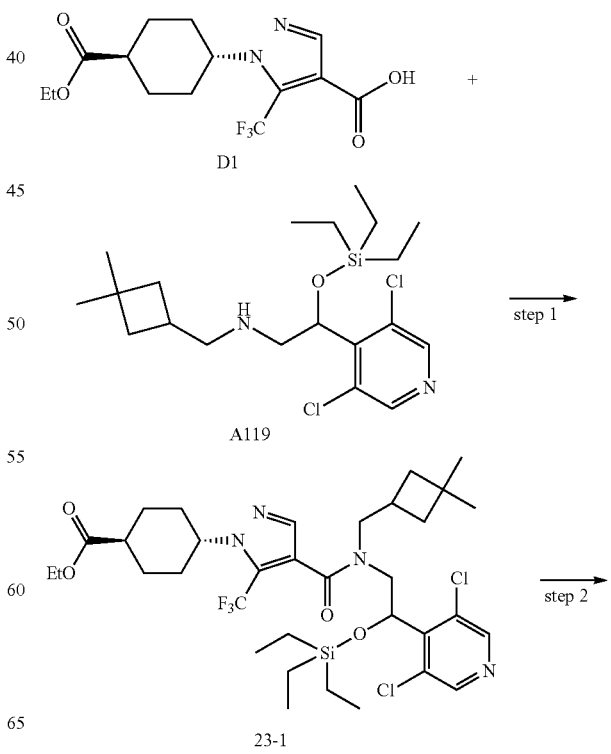

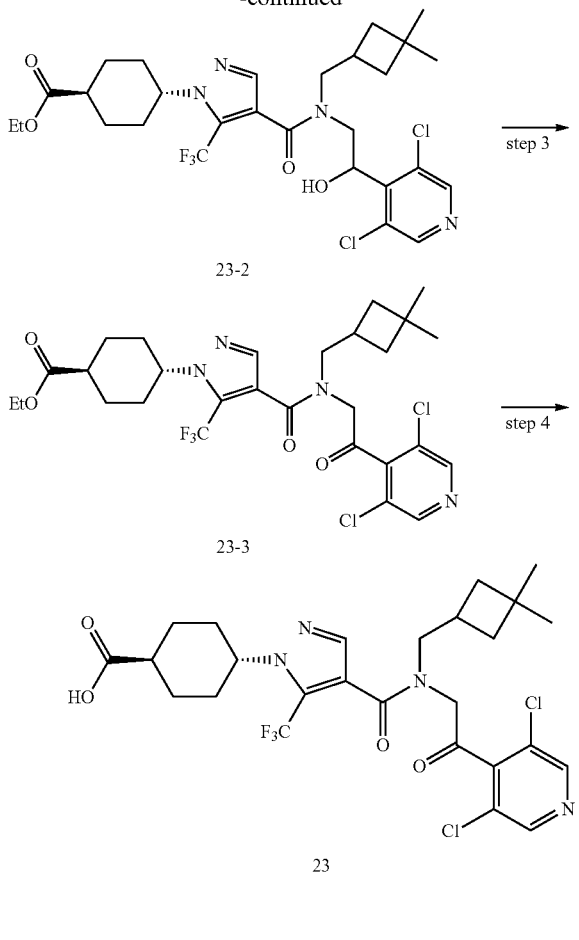

Step 1: ethyl trans-4-(4-((2-(3,5-dichloropyridin-4-yl)-2-((triethylsilyl)oxy)ethyl)((3,3-dimethyl cyclobutyl)methyl)carbamoyl)-5-(trifluoromethyl)-1H-pyrazol-1-yl)cyclohexanecarboxylate (23-1)

Compound 23-1 (180 mg, crude) was obtained as a yellow gum from the reaction of amine A119 (190 mg, 0.455 mmol), acid D1 (167 mg, 0.50 mmol), oxalyl chloride (0.086 mL, 1.0 mmol), Et₃N (0.10 ml, 0.68 mmol) and DMF (cat) in DCM (10 mL) using a similar procedure to that described in example 2.

Step 2: ethyl trans-4-(4-((2-(3,5-dichloropyridin-4-yl)-2-hydroxyethyl)((3,3-dimethylcyclobutyl)methyl)carbamoyl)-5-(trifluoromethyl)-1H-pyrazol-1-yl)cyclohexanecarboxylate (23-2)

Compound 23-2 (60 mg, 20%, over 2 steps) was obtained as a colorless gum from the reaction of compound 23-1 (180 mg, 0.245 mmol) and TBAF (0.5 mL, 0.5 mmol, 1 M in THF) in THF (3 mL) using a similar procedure to that described in example 1.

Step 3: ethyl trans-4-(4-((2-(3,5-dichloropyridin-4-yl)-2-oxoethyl)((3,3-dimethylcyclobutyl)methyl)carbamoyl)-5-(trifluoromethyl)-1H-pyrazol-1-yl)cyclohexanecarboxylate (23-3)

Compound 23-3 (60 mg, quant) was obtained as a white solid from the reaction of compound 23-2 (60 mg, 0.096 mmol) and Dess-Martin periodinane (83 mg, 0.193 mmol) in DCM (10 mL) using a similar procedure to that described in example 1.

Step 4: trans-4-(4-((2-(3,5-dichloropyridin-4-yl)-2-oxoethyl)((3,3-dimethylcyclobutyl)methyl)carbamoyl)-5-(trifluoromethyl)-1H-pyrazol-1-yl)cyclohexanecarboxylic acid (23)

The compound of example 23 (30 mg, 52%) was obtained as an off-white solid from the reaction of compound 23-3 (60 mg, 0.097 mmol) and LiOH (19 mg, 0.048 mmol) in THF/water/MeOH (5 mL, 2:2:1) using a similar procedure to that described in example 1. ¹H NMR (CD₃OD) rotamers present δ 8.65 and 8.58 (2H, 2×s); 7.74 and 7.57 (1H, 2×s); 4.81 and 4.63 (2H, 2×s); 4.36-4.24 (1H, m); 3.62 and 3.42 (2H, 2×d, J=7.5 Hz); 2.67-2.34 (2H, m); 2.21-2.02 (6H, m); 1.92-1.81 (2H, m); 1.70-1.56 (3H, m); 1.37-1.29 (1H, m); 1.15-0.93 (6H, m); LCMS (APCI): 591 (M+H)⁺.

Example 186 trans-4-(4-((2-(3,5-dichloropyridin-4-yl)-2-oxoethyl)-(2,2-dimethylpropyl)carbamoyl)-5-(trifluoromethyl)pyrazol-1-yl)-1-methylcyclohexane-1-carboxylic acid

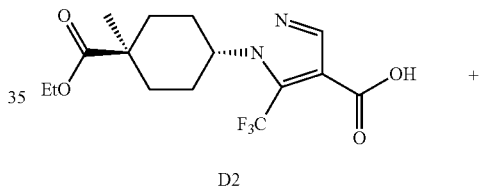

D2

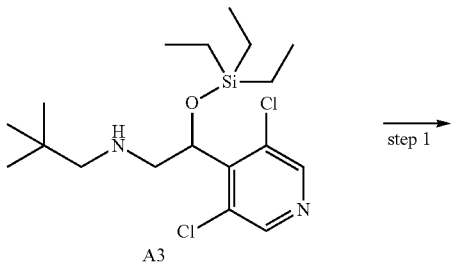

A3

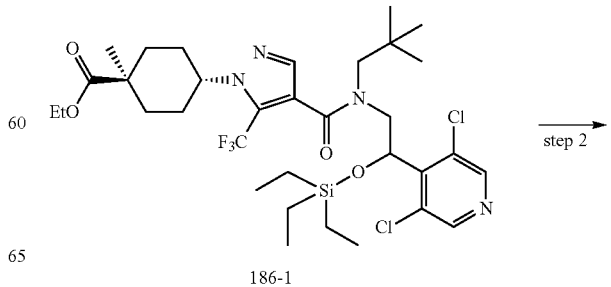

186-1

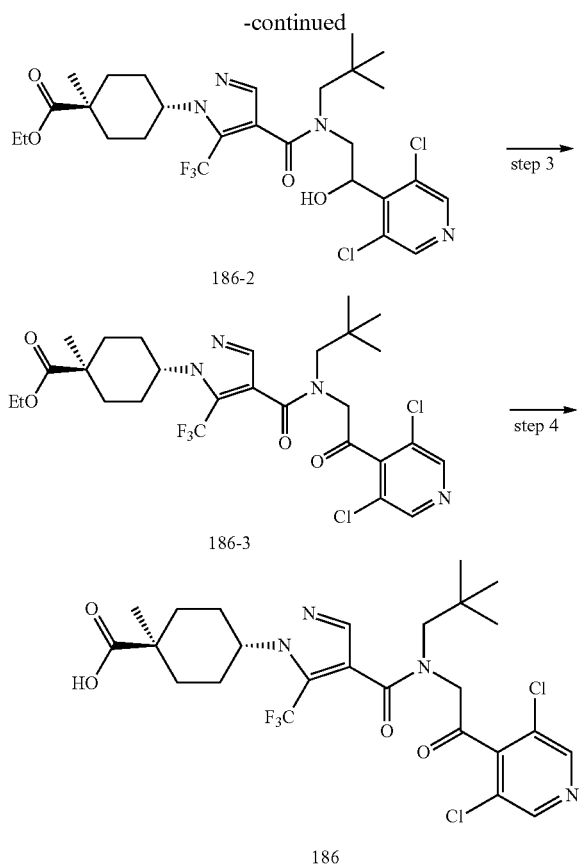

Step 1: ethyl trans-4-(4-((2-(3,5-dichloropyridin-4-yl)-2-((triethylsilyl)oxy)ethyl)(neopentyl)carbamoyl)-5-(trifluoromethyl)-1H-pyrazol-1-yl)-1-methylcyclohexanecarboxylate (186-1)

Compound 186-1 was obtained from the reaction of amine A3 (60 mg, 0.153 mmol), acid D2 (56 mg, 0.161 mmol), oxalyl chloride (0.028 mL, 0.322 mmol), 1 N NaOH (0.92 mL, 0.920 mmol) and DMF (cat) in DCM (1 mL) using a similar procedure to that described in example 2.

Step 2: ethyl trans-4-(4-((2-(3,5-dichloropyridin-4-yl)-2-hydroxyethyl)(neopentyl)carbamoyl)-5-(trifluoromethyl)-1H-pyrazol-1-yl)-1-methylcyclohexanecarboxylate (186-2)

Compound 186-2 (89 mg, 96% over 2 steps) was obtained as a colorless syrup from the reaction of compound 186-1 (crude) and TBAF (0.169 mL, 0.169 mmol, 1 M in THF) in THF (1 mL) using a similar procedure to that described in example 1.

Step 3: ethyl trans-4-(4-((2-(3,5-dichloropyridin-4-yl)-2-oxoethyl)(neopentyl)carbamoyl)-5-(trifluoromethyl)-1H-pyrazol-1-yl)-1-methylcyclohexanecarboxylate (186-3)

Compound 186-3 (69 mg, 78%) was obtained as a white solid from the reaction of compound 186-2 (89 mg, 0.147 mmol) and Dess-Martin periodinane (87 mg, 0.205 mmol) in DCM (2 mL) using a similar procedure to that described in example 1.

Step 4: trans-4-(4-((2-(3,5-Dichloropyridin-4-yl)-2-oxoethyl)-(2,2-dimethylpropyl)carbamoyl)-5-(trifluoromethyl)pyrazol-1-yl)-1-methylcyclohexane-1-carboxylic acid (186)

The compound of example 186 (51 mg, 77%) was obtained as a white solid from the reaction of compound 186-3 (69 mg, 0.114 mmol) and 4 N LiOH (0.228 mL, 0.912 mmol) in THF/water/MeOH (1 mL, 2:1:2) using a similar procedure to that described in example 1. $^1$H NMR (CDCl$_3$) rotamers present δ 8.57 and 8.50 (2H, 2×s); 7.71 and 7.57 (1H, 2×s); 4.87 and 4.53 (2H, 2×s); 4.25-4.18 (1H, m); 3.43-3.35 (2H, m); 2.25-2.15 (2H, m); 1.95-1.85 (6H, m); 1.42 and 1.40 (3H, 2×s); 1.01 and 0.85 (9H, 2×s); LCMS (ESI): 577.2 (M+H)$^+$.

Example 233

4-(4-((2-(3,5-dichloropyridin-4-yl)-2-oxoethyl)-(2,2-dimethylpropyl)carbamoyl)-5-(trifluoromethyl)pyrazol-1-yl)bicyclo[2.2.2]octane-1-carboxylic acid

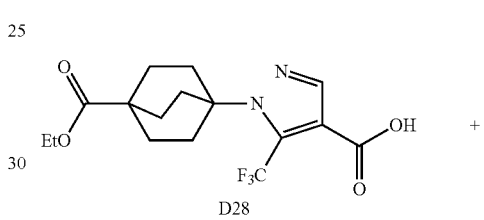

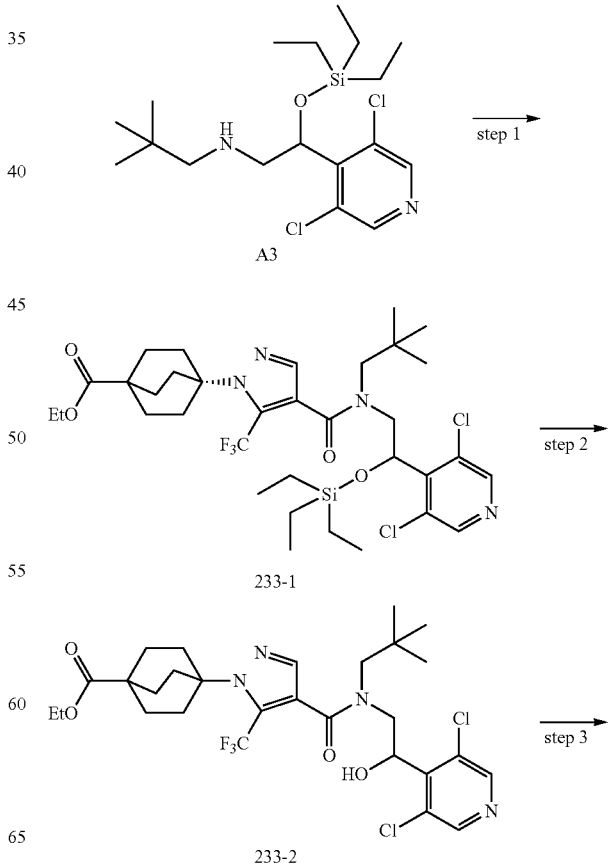

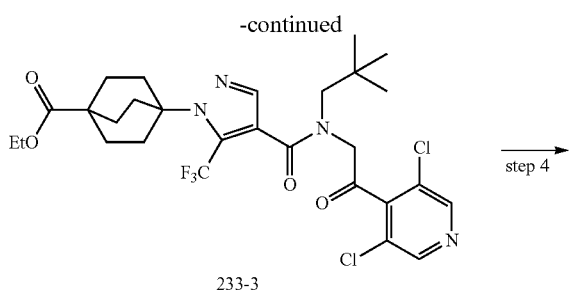

to that described in example 1. $^1$H NMR (CDCl$_3$) rotamers present δ 8.57 and 8.50 (2H, 2×s); 7.64 and 7.49 (1H, 2×s); 4.84 and 4.50 (2H, 2×s); 3.61-3.26 (2H, m); 2.32-2.22 (6H, m); 2.08-2.04 (6H, m); 1.01 and 0.85 (9H, 2×s); LCMS (ESI): 589.2 (M+H)$^+$.

Example 276 trans-4-(5-chloro-4-((2-(3,5-dichloropyridin-4-yl)-2-oxoethyl)-(2,2-dimethylpropyl)carbamoyl)pyrazol-1-yl)-1-methylcyclohexane-1-carboxylic acid Step 1: ethyl 4-(4-((2-(3,5-dichloropyridin-4-yl)-2-((triethylsilyl)oxy)ethyl)(neopentyl)carbamoyl)-5-(trifluoromethyl)-1H-pyrazol-1-yl)bicyclo[2.2.2]octane-1-carboxylate (233-1)

Compound 233-1 was obtained from the reaction of amine A3 (58 mg, 0.148 mmol), acid D28 (50 mg, 0.139 mmol), oxalyl chloride (0.024 mL, 0.278 mmol), 1 N NaOH (0.833 mL, 0.833 mmol) and DMF (cat) in DCM (1 mL) using a similar procedure to that described in example 2.

Step 2: ethyl 4-(4-((2-(3,5-dichloropyridin-4-yl)-2-hydroxyethyl)(neopentyl)carbamoyl)-5-(trifluoromethyl)-1H-pyrazol-1-yl)bicyclo[2.2.2]octane-1-carboxylate (233-2)

Compound 233-2 (67 mg, 78% over 2 steps) was obtained as a colorless syrup from the reaction of compound 233-1 (crude) and TBAF (0.148 mL, 0.148 mmol, 1 M in THF) in THF (1 mL) using a similar procedure to that described in example 1.

Step 3: ethyl 4-(4-((2-(3,5-dichloropyridin-4-yl)-2-oxoethyl)(neopentyl)carbamoyl)-5-(trifluoromethyl)-1H-pyrazol-1-yl)bicyclo[2.2.2]octane-1-carboxylate (233-3)

Compound 233-3 (56 mg, 84%) was obtained as a white solid from the reaction of compound 233-2 (67 mg, 0.108 mmol) and Dess-Martin periodinane (64 mg, 0.151 mmol) in DCM (2 mL) using a similar procedure to that described in example 1.

Step 4: 4-(4-((2-(3,5-dichloropyridin-4-yl)-2-oxoethyl)-(2,2-dimethylpropyl)carbamoyl)-5-(trifluoromethyl)pyrazol-1-yl)bicyclo[2.2.2]octane-1-carboxylic acid (233)

The compound of example 233 (27 mg, 51%) was obtained as a white solid from the reaction of compound 233-3 (56 mg, 0.091 mmol) and 4 N LiOH (0.091 mL, 0.363 mmol) in THF/water/MeOH (0.7 mL, 3:1:3) using a similar procedure -continued

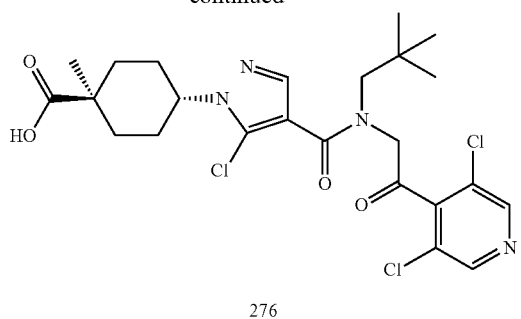

276

Step 1: ethyl trans-4-(5-chloro-4-((2-(3,5-dichloro-pyridin-4-yl)-2-((triethylsilyl)oxy)ethyl)(neopentyl)carbamoyl)-1H-pyrazol-1-yl)-1-methylcyclohexanecarboxylate (276-1)

Compound 276-1 was obtained from the reaction of amine A3 (124 mg, 0.31 mmol), acid D33 (100 mg, 0.31 mmol), oxalyl chloride (0.082 mL, 0.95 mmol), Et$_3$N (0.088 ml, 0.66 mmol) and DMF (cat) in DCM (5 mL) using a similar procedure to that described in example 2.

Step 2: ethyl trans-4-(5-chloro-4-((2-(3,5-dichloro-pyridin-4-yl)-2-hydroxyethyl)(neopentyl)carbamoyl)-1H-pyrazol-1-yl)-1-methylcyclohexanecarboxylate (276-2)

Compound 276-2 (160 mg, 88%, over 2 steps) was obtained as white solid from the reaction of compound 276-1 (crude) and TBAF (0.5 mL, 0.5 mmol, 1 M in THF) in THF (2 mL) using a similar procedure to that described in example 1.

Step 3: ethyl trans-4-(5-chloro-4-((2-(3,5-dichloro-pyridin-4-yl)-2-oxoethyl)(neopentyl)carbamoyl)-1H-pyrazol-1-yl)-1-methylcyclohexanecarboxylate (276-3)

Compound 276-3 (130 mg, 81%) was obtained as an off-white solid from the reaction of compound 276-2 (160 mg, 0.279 mmol) and Dess-Martin periodinane (233 mg, 0.56 mmol) in DCM (10 mL) using a similar procedure to that described in example 1.

Step 4: trans-4-(5-chloro-4-((2-(3,5-dichloropyridin-4-yl)-2-oxoethyl)-(2,2-dimethylpropyl)carbamoyl)pyrazol-1-yl)-1-methylcyclohexane-1-carboxylic acid (276)

The compound of example 276 (60 mg, 47%) was obtained as a white solid from the reaction of compound 276-3 (130 mg, 0.224 mmol) and LiOH (26.9 mg, 1.123 mmol) in THF/EtOH/water (11 mL, 5:5:1) using a similar procedure to that described in example 1. $^1$H NMR (DMSO-d$_6$) rotamers present δ 12.25 (1H, brs); 8.77 and 8.72 (2H, 2×s); 7.79 and 7.73 (1H, 2×s); 4.84 and 4.77 (2H, 2×s); 4.36-4.28 (1H, m); 2.02-1.72 (8H, m); 1.21 (3H, s); 0.95 and 0.74 (9H, 2×s); LCMS (APCI): 545 (M+H)$^+$.

Example 277 trans-4-(4-((2-(2,6-dichloro-4-methylphenyl)-2-oxo-ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid

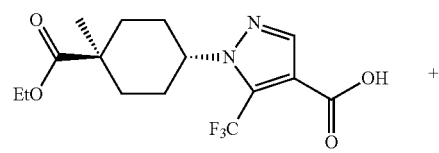

D2

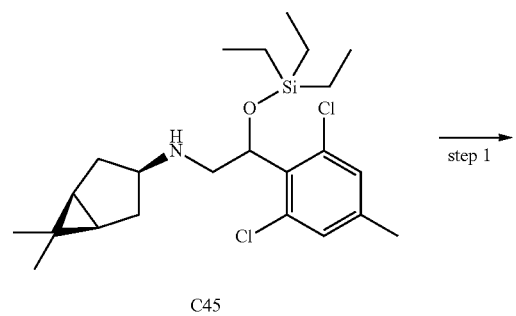

C45

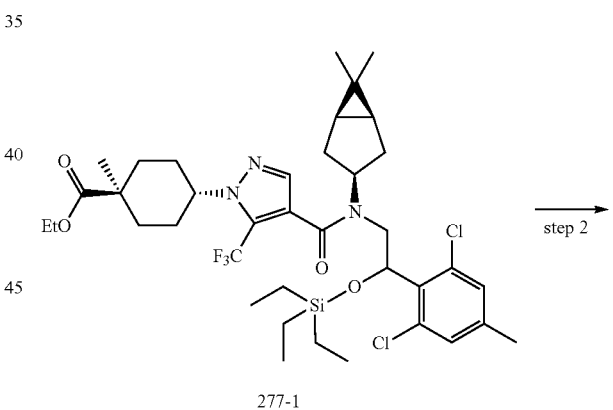

277-1

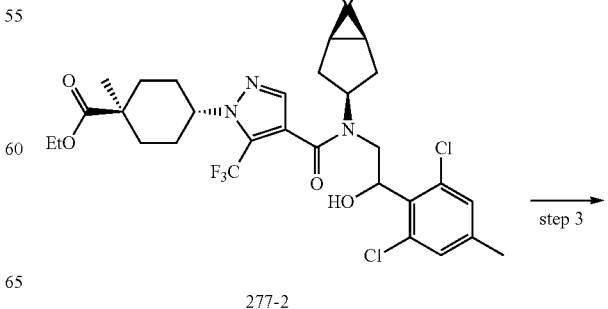

277-2

-continued

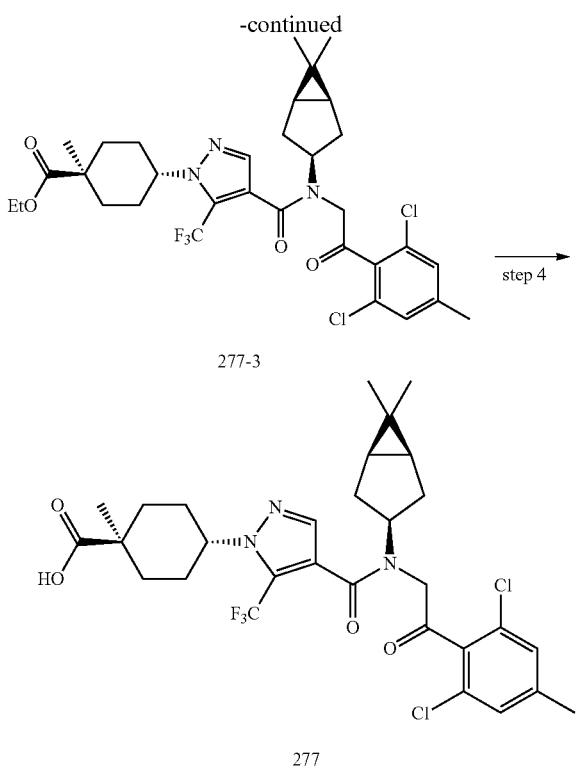

Step 1: ethyl trans-4-(4-((2-(2,6-dichloro-4-methylphenyl)-2-((triethylsilyl)oxy)ethyl)((1R,3r,5 S)-6,6-dimethylbicyclo[3.1.0]hexan-3-yl)carbamoyl)-5-(trifluoromethyl)-1H-pyrazol-1-yl)-1-methylcyclohexanecarboxylate (277-1)

Compound 277-1 was obtained from the reaction of amine C45 (74 mg, 0.167 mmol), acid D2 (55 mg, 0.158 mmol), HATU (72 mg, 0.190 mmol) and DIPEA (0.055 mL, 0.320 mmol) in DMF (2 mL) using a similar procedure to that described in example 1.

Step 2: ethyl trans-4-(4-((2-(2,6-dichloro-4-methylphenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylate (277-2)

Compound 277-2 (85 mg, 82% over 2 steps) was obtained as a yellow semi-solid from the reaction of compound 277-1 (crude) and TBAF (0.3 mL, 0.3 mmol, 1 M in THF) in THF (2 mL) using a similar procedure to that described in example 1.

Step 3: ethyl trans-4-(4-((2-(2,6-dichloro-4-methylphenyl)-2-oxoethyl)((1R,3 r,5S)-6,6-dimethylbicyclo[3.1.0]hexan-3-yl)carbamoyl)-5-(trifluoromethyl)-1H-pyrazol-1-yl)-1-methylcyclohexanecarboxylate (277-3)

Compound 277-3 (80 mg, 95%) was obtained as a pale yellow semi-solid from the reaction of compound 277-2 (85 mg, 0.129 mmol) and Dess-Martin periodinane (66 mg, 0.155 mmol) in DCM (2 mL) using a similar procedure to that described in example 1.

Step 4: trans-4-(4-((2-(2,6-dichloro-4-methylphenyl)-2-((triethylsilyl)oxy)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylate (277)

The compound of example 277 (58 mg, 75%) was obtained as a white solid from the reaction of compound 277-3 (80 mg, 0.122 mmol) and 4 N LiOH (0.31 mL, 1.22 mmol) in THF/water/MeOH (1.5 mL, 2:1:2) using a similar procedure to that described in example 1. $^1$H NMR (CDCl$_3$) rotamers present δ 7.69 and 7.54 (1H, 2×s); 7.16 and 7.08 (2H, 2×s); 5.10-5.00 and 4.36-4.14 (2H, 2×m); 4.59 and 4.39 (2H, 2×s); 2.35 and 2.31 (3H, 2×s); 2.31-1.85 (10H, m); 1.42 and 1.39 (3H, 2×s); 1.39-1.23 (2H, m); 1.09-0.95 (8H, m); LCMS (ESI): 628.3 (M+H)$^+$.

Example 278 trans-4-(4-((2-(2,6-dichlorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid

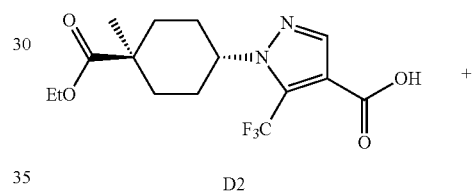

D2

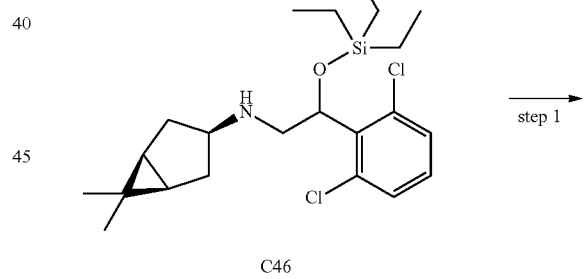

C46

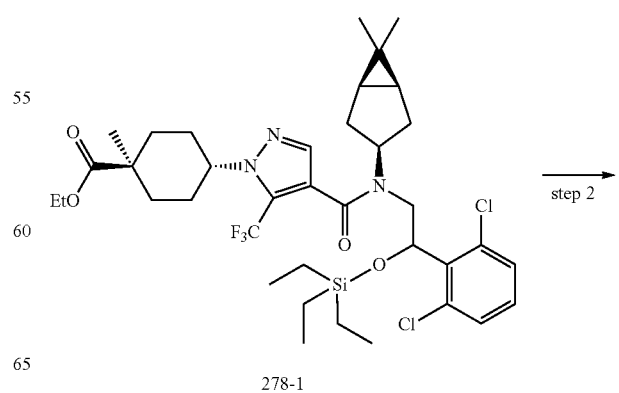

278-1

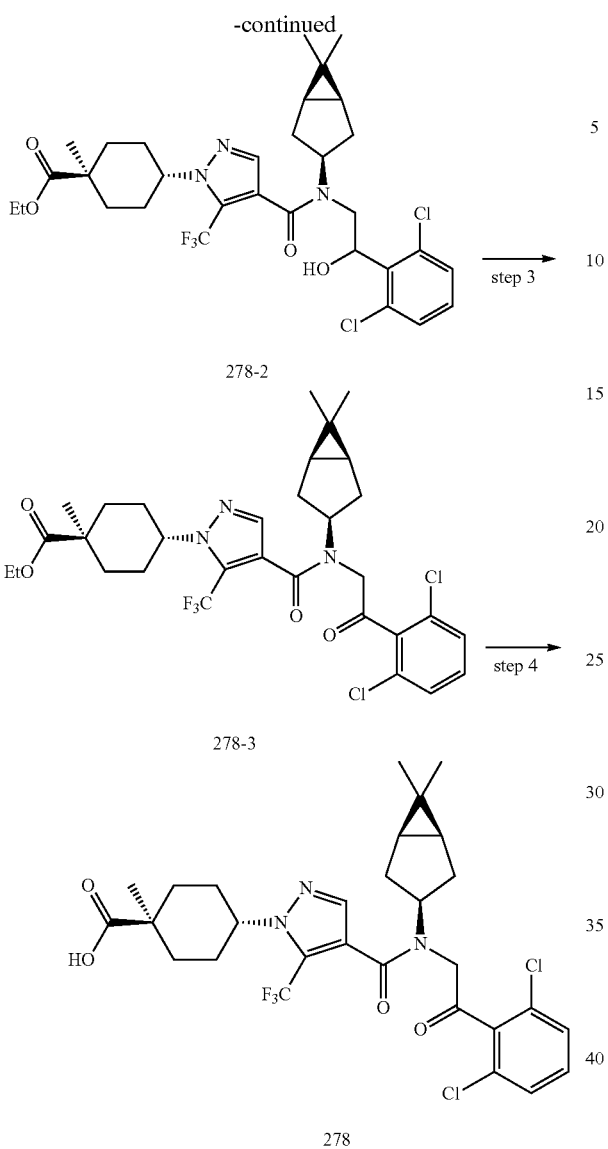

(crude) and TBAF (0.22 mL, 0.22 mmol, 1 M in THF) in THF (1 mL) using a similar procedure to that described in example 1.

Step 3: ethyl trans-4-(4-((2-(2,6-dichlorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylate (278-3)

Compound 278-3 (84 mg, 83%) was obtained as a white solid from the reaction of compound 278-2 (102 mg, 0.158 mmol) and Dess-Martin periodinane (100 mg, 0.237 mmol) in DCM (1 mL) using a similar procedure to that described in example 1.

Step 4: trans-4-(4-((2-(2,6-dichlorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid (278)

The compound of example 278 (35 mg, 44%) was obtained as a white solid from the reaction of compound 278-3 (84 mg, 0.131 mmol) and 4 N LiOH (0.33 mL, 1.31 mmol) in THF/water/MeOH (1.5 mL, 2:1:2) using a similar procedure to that described in example 1. $^1$H NMR (CDCl$_3$) rotamers present δ 7.70 and 7.55 (1H, 2×s); 7.36-7.26 (3H, m); 5.10-5.00 and 4.37-4.15 (2H, 2×m); 4.61 and 4.42 (2H, 2×s); 2.31-1.87 (10H, m); 1.42 and 1.39 (3H, 2×s); 1.39-1.23 (2H, m); 1.09-0.95 (8H, m); LCMS (ESI): 614.2 (M+H)$^+$.

Example 330 trans-4-(4-((2-3,5-dichloropyridin-4-yl)-2-oxoethyl)-((1-(trifluoromethyl)cyclopropyl)methyl)carbamoyl)-5-(trifluoromethyl)pyrazol-1-yl)-1-methylcyclohexane-1-carboxylic acid

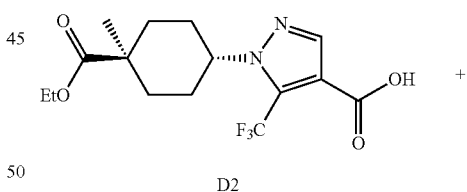

D2

Step 1: ethyl trans-4-(4-((2-(2,6-dichlorophenyl)-2-((triethylsilyl)oxy)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylate (278-1)

Compound 278-1 was obtained from the reaction of amine C46 (94 mg, 0.219 mmol), acid D2 (76 mg, 0.219 mmol), oxalyl chloride (0.038 mL, 0.438 mmol), DIPEA (0.114 mL, 0.657 mmol) and DMF (cat) in DCM (1 mL) using a similar procedure to that described in example 2.

Step 2: ethyl trans-4-(4-((2-(2,6-dichlorophenyl)-2-hydroxyethyl)((1R,3 r,5S)-6,6-dimethylbicyclo[3.1.0]hexan-3-yl)carbamoyl)-5-(trifluoromethyl)-1H-pyrazol-1-yl)-1-methylcyclohexanecarboxylate (278-2)

Compound 278-2 (102 mg, 72% over 2 steps) was obtained as a colorless oil from the reaction of compound 278-1

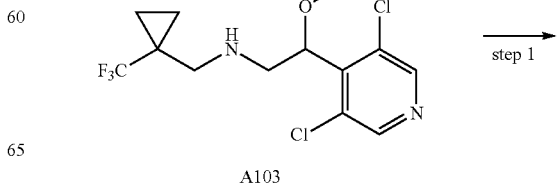

A103

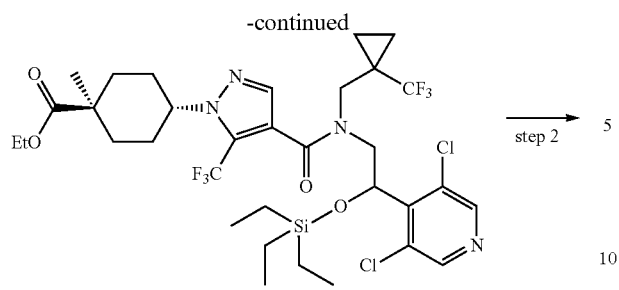

330-1

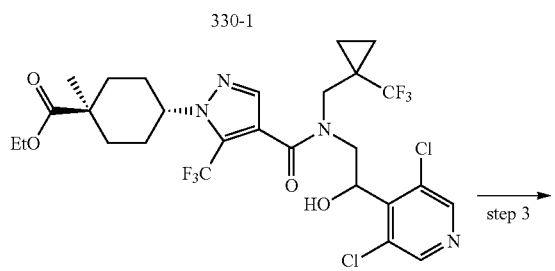

330-2

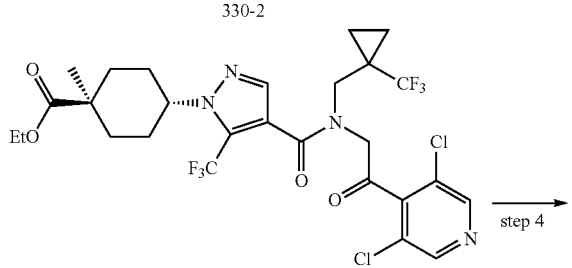

330-3

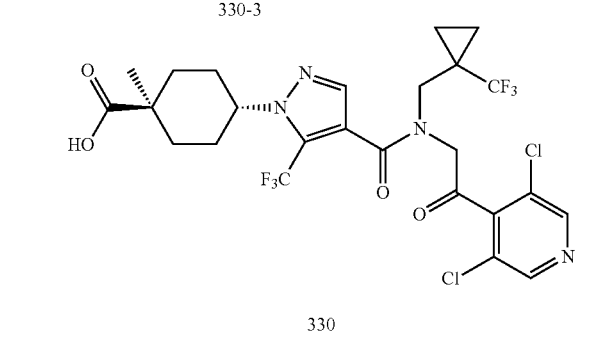

330

Step 1: ethyl trans-4-(4-((2-3,5-dichloropyridin-4-yl)-2-((triethylsilyl)oxy)ethyl)((1-(trifluoromethyl)cyclopropyl)methyl)carbamoyl)-5-(trifluoromethyl)-1H-pyrazol-1-yl)-1-methylcyclohexanecarboxylate (330-1)

Compound 330-1 was obtained from the reaction of amine A103 (44 mg, 0.098 mmol), acid D2 (34 mg, 0.098 mmol), oxalyl chloride (0.017 mL, 0.196 mmol), 1 N NaOH (0.49 mL, 0.491 mmol) and DMF (cat) in DCM (1 mL) using a similar procedure to that described in example 2.

Step 2: ethyl trans-4-(4-((2-3,5-dichloropyridin-4-yl)-2-hydroxyethyl)((1-(trifluoromethyl)cyclopropyl)methyl)carbamoyl)-5-(trifluoromethyl)-1H-pyrazol-1-yl)-1-methylcyclohexanecarboxylate (330-2)

Compound 330-2 (37 mg, 58% over 2 steps) was obtained as a colorless oil from the reaction of compound 330-1 (crude) and TBAF (0.098 mL, 0.098 mmol, 1 M in THF) in THF (1 mL) using a similar procedure to that described in example 1.

Step 3: ethyl trans-4-(4-((2-3,5-dichloropyridin-4-yl)-2-oxoethyl)((1-(trifluoromethyl)cyclopropyl)methyl)carbamoyl)-5-(trifluoromethyl)-1H-pyrazol-1-yl)-1-methylcyclohexanecarboxylate (330-3)

Compound 330-3 (31 mg, 83%) was obtained as a colorless oil from the reaction of 330-2 (37 mg, 0.056 mmol) and Dess-Martin periodinane (36 mg, 0.085 mmol) in DCM (1 mL) using a similar procedure to that described in example 1.

Step 4: trans-4-(4-((2-3,5-dichloropyridin-4-yl)-2-oxoethyl)-((1-(trifluoromethyl)cyclopropyl)methyl)carbamoyl)-5-(trifluoromethyl)pyrazol-1-yl)-1-methylcyclohexane-1-carboxylic acid (330)

The compound of example 330 (17 mg, 58%) was obtained as a white solid from the reaction of compound 330-3 (31 mg, 0.047 mmol) and 4 N LiOH (0.12 mL, 0.467 mmol) in THF/water/MeOH (0.75 mL, 2:1:2) using a similar procedure to that described in example 1. $^1$H NMR (CDCl$_3$) rotamers present δ 8.59 and 8.52 (2H, 2×s); 7.65 and 7.54 (1H, 2×s); 4.95 and 4.58 (2H, 2×s); 4.28-4.20 (1H, m); 3.84 and 3.74 (2H, 2×s); 2.26-2.16 (2H, m); 1.95-1.85 (6H, m); 1.42 and 1.41 (3H, 2×s); 1.12-1.06 (4H, m); LCMS (ESI): 629.2 (M+H)$^+$.

Example 343 trans-4-(4-((2-(4-chloro-1H-indol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methyl-cyclohexanecarboxylic acid

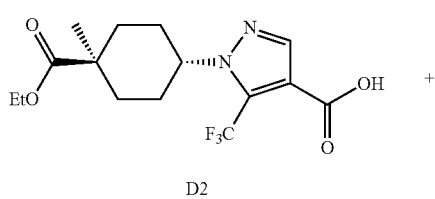

D2

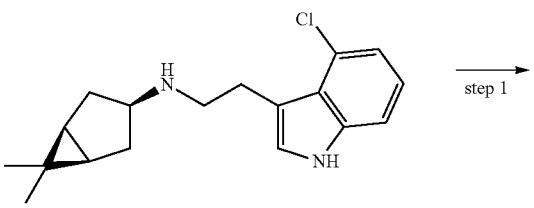

B19

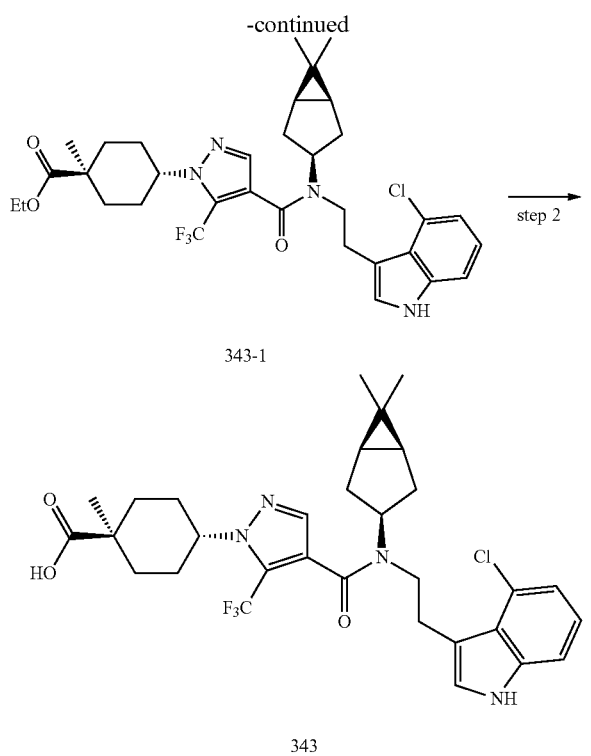

343-1

343

Step 1: ethyl trans-4-(4-((2-(4-chloro-1H-indol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylate (343-1)

Compound 343-1 (42 mg, 91%) was obtained as a yellow gum from the reaction of amine B19 (22 mg, 0.073 mmol), acid D2 (25 mg, 0.073 mmol), HATU (33 mg, 0.087 mmol) and DIPEA (0.037 mL, 0.218 mmol) in DMF (1 mL) using a similar procedure to that described in example 1.

Step 2: trans-4-(4-((2-(4-chloro-1H-indol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohex anecarboxylic acid (343)

The compound of example 343 (31 mg, 78%) was obtained as a white solid from the reaction of compound 343-1 (42 mg, 0.066 mmol) and 4 N LiOH (0.066 mL, 0.265 mmol) in THF/water/MeOH (0.5 mL, 2:1:2) using a similar procedure to that described in example 1. $^1$H NMR (CDCl$_3$) rotamers present δ 8.20 (1H, brs); 7.53-6.90 (5H, m); 4.68-4.61 and 4.29-4.02 (2H, 2×m); 3.64-3.61 and 3.53-3.49 (2H, 2×m); 3.35-3.32 and 3.04-3.00 (2H, 2×m); 2.28-1.86 (8H, m); 1.70-1.60 (2H, m); 1.41 and 1.39 (3H, 2×s); 1.28-0.85 (10H, m); LCMS (ESI): 606.0 (M+H)$^+$.

Example 361 and 362 trans-4-(4-(((2R)-2-(2,6-dichloro-4-fluorophenyl)-2-hydroxyethyl)-(4,4-dimethylcyclohexyl)carbamoyl)-5-(trifluoromethyl)pyrazol-1-yl)-1-methylcyclohexane-1-carboxylic acid or trans-4-(4-(((2S)-2-(2,6-dichloro-4-fluorophenyl)-2-hydroxyethyl)-(4,4-dimethylcyclohexyl)carbamoyl)-5-(trifluoromethyl)pyrazol-1-yl)-1-methylcyclohexane-1-carboxylic acid

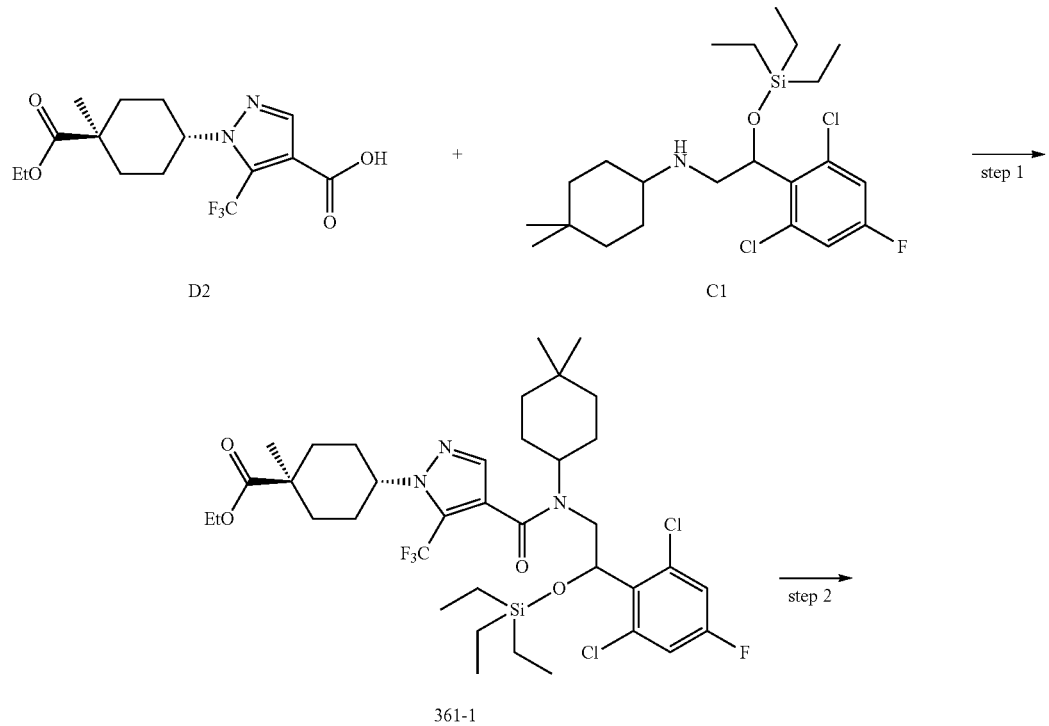

D2

C1

361-1

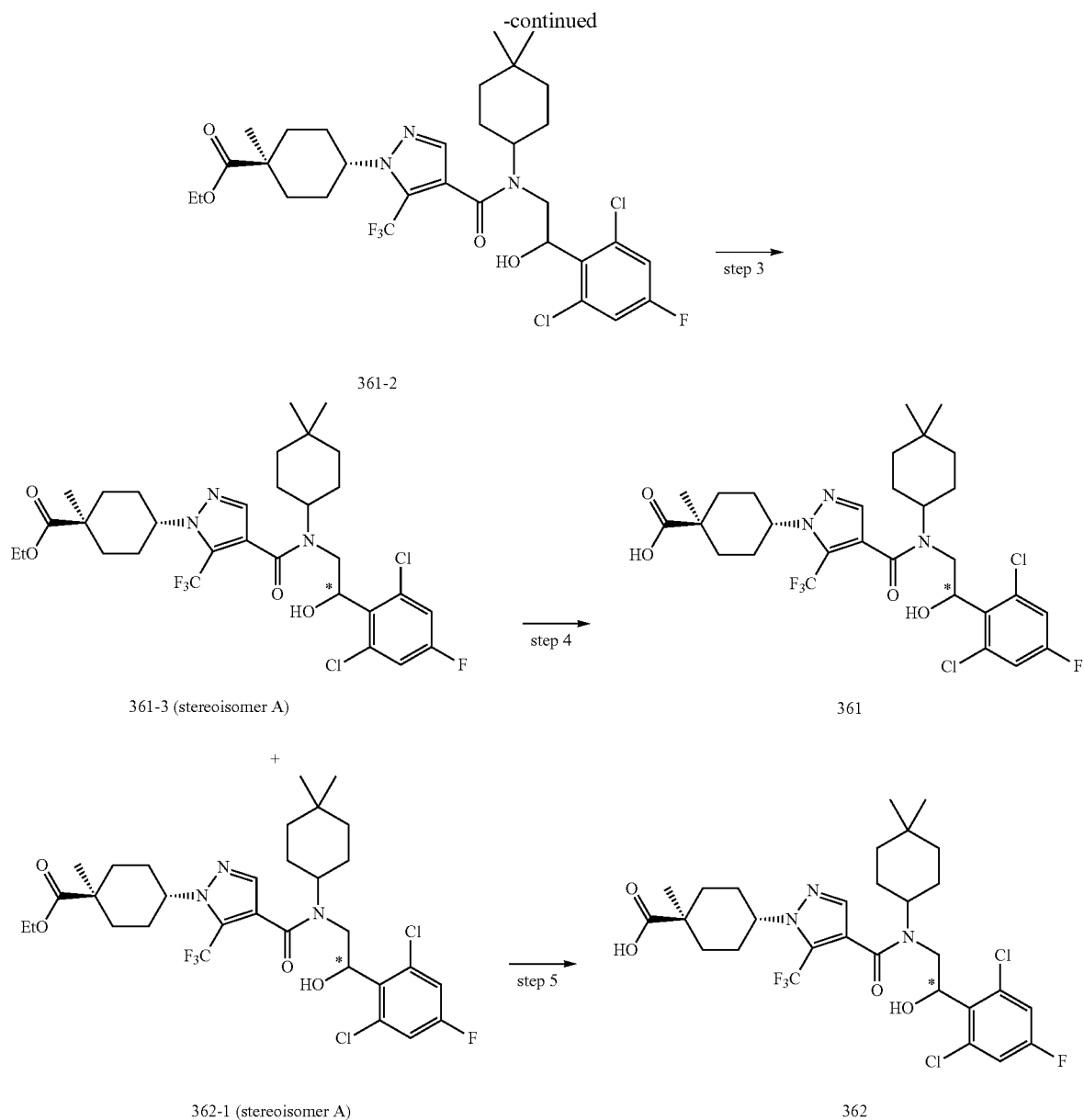

Step 1: ethyl trans-4-(4-((2-(2,6-dichloro-4-fluorophenyl)-2-((triethylsilyl)oxy)ethyl)(4,4-dimethylcyclohexyl)carbamoyl)-5-(trifluoromethyl)-1H-pyrazol-1-yl)-1-methylcyclohexanecarboxylate (361-1)

Compound 361-1 was obtained from the reaction of amine C1 (89 mg, 0.199 mmol), acid D2 (60 mg, 0.172 mmol), oxalyl chloride (0.044 mL, 0.517 mmol), DIPEA (0.090 mL, 0.517 mmol) and DMF (cat) in DCM (2 mL) using a similar procedure to that described in example 2.

Step 2: ethyl trans-4-(4-((2-(2,6-dichloro-4-methylphenyl)-2-hydroxyethyl)(4,4-dimethylcyclohexyl)carbamoyl)-5-(trifluoromethyl)-1H-pyrazol-1-yl)-1-methylcyclohexanecarboxylate (377-2)

Compound 361-2 (100 mg, 88% over 2 steps) was obtained from the reaction of 361-1 (crude) and TBAF (0.26 mL, 0.258 mmol, 1 M in THF) in THF (2 mL) using a similar procedure to that described in example 1.

Step 3: ethyl trans-4-(4-(((S)-2-(2,6-dichloro-4-methylphenyl)-2-hydroxyethyl)(4,4-dimethylcyclohexyl)carbamoyl)-5-(trifluoromethyl)-1H-pyrazol-1-yl)-1-methylcyclohexanecarboxylate and ethyl trans-4-(4-(((R)-2-(2,6-dichloro-4-methylphenyl)-2-hydroxyethyl)(4,4-dimethylcyclohexyl)carbamoyl)-5-(trifluoromethyl)-1H-pyrazol-1-yl)-1-methylcyclohexanecarboxylate (361-3 and 362-1)

Compound 361-2 (100 mg, 0.151 mmol) was purified by chiral HPLC (250×20 mm DAICEL CHIRALPAK™ IA 5 µm column with 16 mL/min n-hexane/IPA (96/4)) to give 361-3 (49 mg, 49%) as the first eluting isomer and compound 362-1 (48 mg, 48%) as the second eluting isomer.

Step 4: trans-4-(4-(((2R)-2-(2,6-dichloro-4-fluorophenyl)-2-hydroxyethyl)-(4,4-dimethylcyclohexyl)carbamoyl)-5-(trifluoromethyl)pyrazol-1-yl)-1-methylcyclohexane-1-carboxylic acid or trans-4-(4-(((2S)-2-(2,6-dichloro-4-fluorophenyl)-2-hydroxyethyl)-(4,4-dimethylcyclohexyl)carbamoyl)-5-(trifluoromethyl)pyrazol-1-yl)-1-methylcyclohexane-1-carboxylic acid (361)

The compound of example 361 (37 mg, 79%) was obtained as a white solid from the reaction of compound 361-3 (49 mg, 0.074 mmol) and 4 N LiOH (0.25 mL, 1.00 mmol) in EtOH/water (1.5 mL, 2:1) using a similar procedure to that described in example 1. LCMS (ESI): 636.3 (M+H)$^+$.

Step 5: trans-4-(4-(((2R)-2-(2,6-dichloro-4-fluorophenyl)-2-hydroxyethyl)-(4,4-dimethylcyclohexyl)carbamoyl)-5-(trifluoromethyl)pyrazol-1-yl)-1-methylcyclohexane-1-carboxylic acid or trans-4-(4-(((2S)-2-(2,6-dichloro-4-fluorophenyl)-2-hydroxyethyl)-(4,4-dimethylcyclohexyl)carbamoyl)-5-(trifluoromethyl)pyrazol-1-yl)-1-methylcyclohexane-1-carboxylic acid (362)

The compound of example 362 (39 mg, 85%) was obtained as a white solid from the reaction of compound 362-1 (48 mg, 0.073 mmol) and 4 N LiOH (0.25 mL, 1.00 mmol) in EtOH/water (1.5 mL, 2:1) using a similar procedure to that described in example 1. $^1$H NMR (CDCl$_3$) rotamers present δ 7.57 and 7.56 (1H, 2×s); 7.11 and 7.05 (2H, 2×d, J=7.8 Hz); 5.62-5.47 (1H, m); 4.86 (1H, brs); 4.70-4.64 and 4.09-4.02 (1H, 2×m); 4.30-4.20 (1H, m); 3.46-3.26 (2H, m); 2.31-2.18 (2H, m); 1.99-1.66 (8H, m); 1.47-1.26 (7H, m); 1.12-0.86 (8H, m); LCMS (ESI): 636.0 (M+H)$^+$.

Example 569 trans-4-(4-((2-(2,6-dichlorophenyl)-2-oxoethyl)(spiro[25]oct-6-ylmethyl)carbamoyl)-5-(trifluoromethyl)-1H-pyrazol-1-yl)-1-methylcyclohexanecarboxylic acid

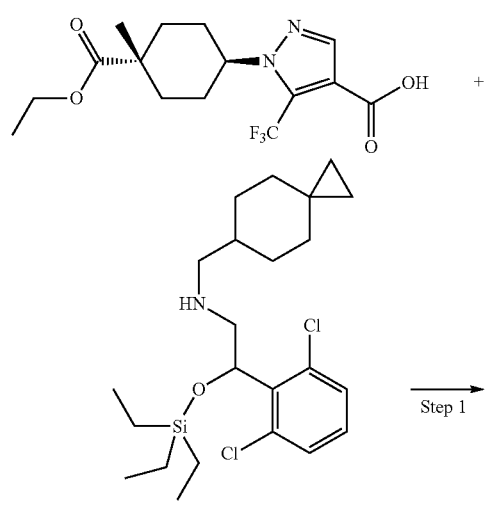

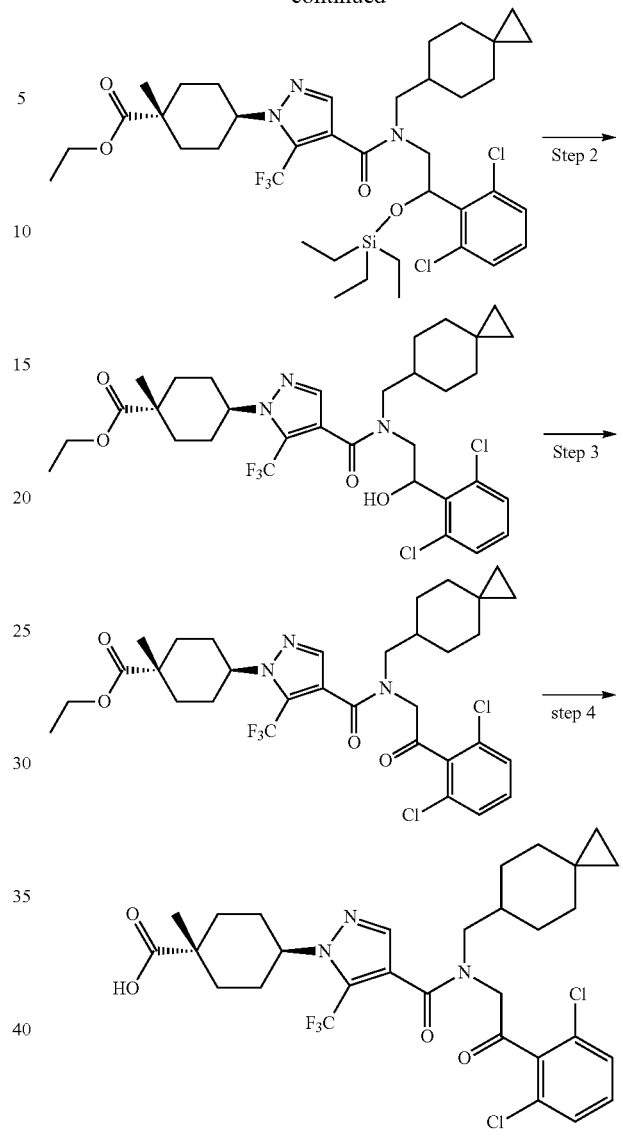

Step 1 and Step 2: ethyl trans-4-(4-((2-(2,6-dichlorophenyl)-2-hydroxyethyl)(spiro[2.5]octan-6-ylmethyl)carbamoyl)-5-(trifluoromethyl)-1H-pyrazol-1-yl)-1-methylcyclohexanecarboxylate To a solution of 1-((trans)-4-(ethoxycarbonyl)-4-methylcyclohexyl)-5-(trifluoromethyl)-1H-pyrazole-4-carboxylic acid (0.157 g, 0.452 mmol) and oxalyl chloride (0.049 ml, 0.565 mmol) in DCM (4.52 ml) was added DMF (1 drop) and the mixture was stirred at room temperature. After 1 h, the reaction mixture was concentrated in vacuo. To the residue was added a solution of 2-(2,6-dichlorophenyl)-N-(spiro[2.5]octan-6-ylmethyl)-2-((triethylsilyl)oxy)ethanamine (0.200 g, 0.452 mmol) in THF (4.5 mL) followed by DIPEA (0.158 ml, 0.904 mmol) and the mixture was stirred at room temperature. After 17 h, to the reaction mixture was added TBAF solution, 1.0 M in THF (0.904 ml, 0.904 mmol) and the mixture was stirred at room temperature. After 7 h, the reaction mixture was diluted with water (50 mL) and brine (50 mL). The reaction mixture was extracted with EtOAc (2×50 mL). The organic extract washed with satd NaCl (1×50 mL)

and dried over Na₂SO₄. The solution was filtered and concentrated in vacuo to give the crude material as a light-yellow syrup. The crude material was absorbed onto a plug of silica gel and purified by silica gel column chromatography eluting with a gradient of 0% to 50% EtOAc in heptane to provide ethyl trans-4-(4-((2-(2,6-dichlorophenyl)-2-hydroxyethyl)(spiro[2.5]octan-6-ylmethyl)carbamoyl)-5-(trifluoromethyl)-1H-pyrazol-1-yl)-1-methylcyclohexanecarboxylate (0.0815 g, 0.124 mmol, 27.4% yield) a colorless gum.

Step 3: ethyl trans-4-(4-((2-(2,6-dichlorophenyl)-2-oxoethyl)(spiro[2.5]octan-6-ylmethyl)carbamoyl)-5-(trifluoromethyl)-1H-pyrazol-1-yl)-1-methylcyclohexanecarboxylate To a solution of ethyl trans-4-(4-((2-(2,6-dichlorophenyl)-2-hydroxyethyl)(spiro[2.5]octan-6-ylmethyl)carbamoyl)-5-(trifluoromethyl)-1H-pyrazol-1-yl)-1-methylcyclohexanecarboxylate (0.0815 g, 0.124 mmol) in DCM (1.238 ml) was added Dess-Martin periodinane (0.079 g, 0.186 mmol) and the mixture was stirred at room temperature. After 6 h, the mixture was quenched with saturated aqueous Na₂S₂O₃ (50 mL) and saturated aqueous NaHCO₃ (50 mL). The reaction mixture was extracted with DCM (2×100 mL). The organic extract was dried over Na₂SO₄. The solution was filtered and concentrated in vacuo to give the crude material as a white solid. The crude material was absorbed onto a plug of silica gel and purified by silica gel column chromatography eluting with a gradient of 0% to 35% EtOAc in heptane to provide ethyl trans-4-(4-((2-(2,6-dichlorophenyl)-2-oxoethyl)(spiro[2.5]octan-6-ylmethyl)carbamoyl)-5-(trifluoromethyl)-1H-pyrazol-1-yl)-1-methylcyclohexanecarboxylate (0.0685 g, 0.104 mmol, 84% yield) as a colorless syrup.

Step 4: trans-4-(4-((2-(2,6-dichlorophenyl)-2-oxoethyl)(spiro[25]oct-6-ylmethyl)carbamoyl)-5-(trifluoromethyl)-1H-pyrazol-1-yl)-1-methylcyclohexanecarboxylic acid To a solution of ethyl trans-4-(4-((2-(2,6-dichlorophenyl)-2-oxoethyl)(spiro[2.5]octan-6-ylmethyl)carbamoyl)-5-(trifluoromethyl)-1H-pyrazol-1-yl)-1-methylcyclohexanecarboxylate (0.0685 g, 0.104 mmol) in THF (0.750 mL) was added a solution of lithium hydroxide hydrate (0.044 g, 1.043 mmol) in water (0.500 mL) and the mixture was stirred and heated at 50° C. overnight. The THF and MeOH were removed in vacuo and the turbid solution was diluted with water (3 mL) to provide a clear solution. 1 M HCl was added to adjust the pH to 1. The mixture was stirred for 30 min before collecting the precipitate by vacuum filtration to provide a white solid. The solid was purified by silica gel column chromatography eluting with a gradient of 0% to 5% MeOH in DCM to provide Example 569 (0.0457 g, 0.073 mmol, 69.7% yield) as white solid. ¹H NMR (400 MHz, CD₃OD) δ 7.40-7.79 (4H, m), 5.30-5.54 (1H, m), 4.87 (1H, s), 4.64 (1H, s), 4.22-4.36 (1H, m), 3.50 (2H, d, J=7.2 Hz), 2.12-2.30 (2H, m), 1.54-1.98 (10H, m), 1.27-1.41 (5H, m), 0.78-1.05 (3H, m), 0.07-0.37 (4H, m), (rotamers present); LCMS (ESI) m/z 628.2 (M+H)⁺.

Example 688 trans-4-(4#(2R)-2-(3,5-dichloro-4-pyridinyl)methyl)-4,4-dimethyl-1-pyrrolidinyl)carbonyl)-5-(trifluoromethyl)-1H-pyrazol-1-yl)-1-methylcyclohexanecarboxylic acid

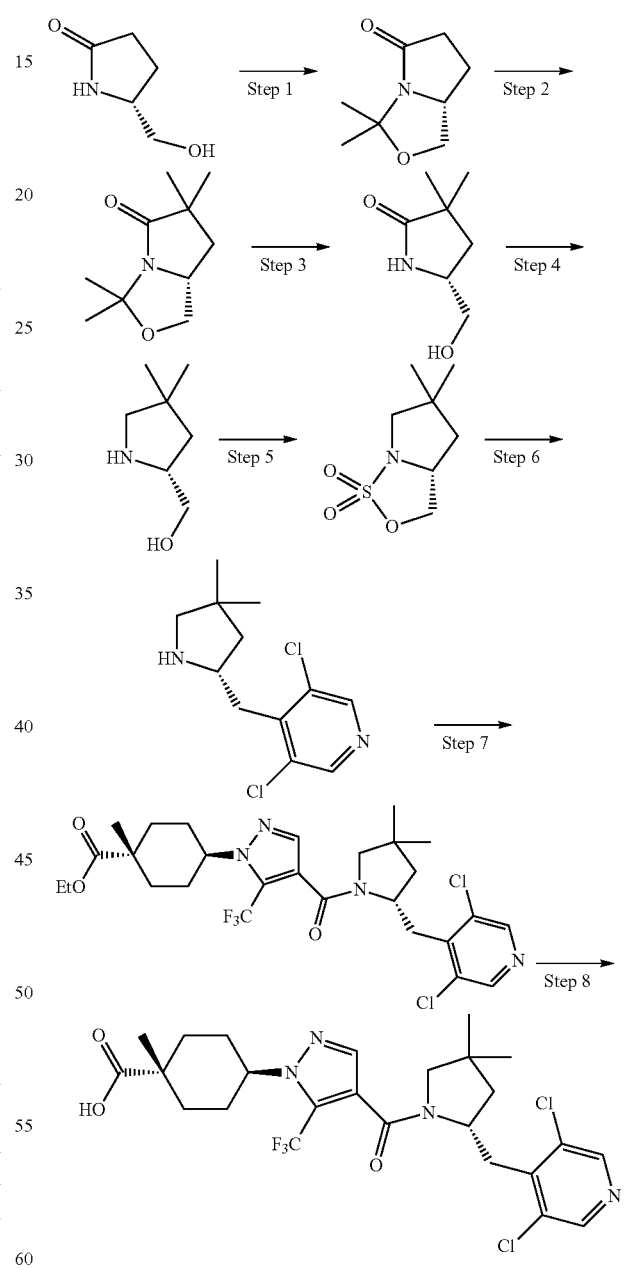

Step 1: Prepared according to WO patent: 2013004290A1. To a stirred suspension of (R)-(-)-5-(hydroxymethyl)-2-pyrrolidinone (Sigma Aldrich Chemical Company, St. Louis, Mo., 5.36 g, 46.5 mmol) and p-toluenesulfonic acid (44 mg, 0.233 mmol) in toluene (100 mL), 2,2-dimethoxypropane (17.1 mL, 140 mmol) was added and the reaction was refluxed for 1.5 h. The reaction was equipped with a Dean-Stark apparatus then additional 2,2-dimethoxypropane (17.1 mL, 140 mmol) was added and the reaction was refluxed for 36 h. The solvent was evaporated to afford (R)-3,3-dimethyltetrahydropyrrolo[1,2-c]oxazol-5(3H)-one as an orange waxy solid. MS (ESI) 156.1 [M+H]$^+$. The crude material was taken to the next step without further purification.

Step 2: Prepared according to WO patent: WO2013004290A1. To a solution of (R)-3,3-dimethyltetrahydropyrrolo[1,2-c]oxazol-5(3H)-one (3.50 g, 22.55 mmol) in THF (75 mL) cooled to −78° C., was added lithium diisopropylamide (2.0M heptane/THF/ethylbenzene, 20.30 mL, 40.6 mmol) solution. The solution was stirred at this temperature for 1 h before adding iodomethane (2.12 mL, 33.8 mmol). The reaction mixture was warmed to room temperature and stirred for 1 h, then cooled to −78° C. prior addition of lithium diisopropylamide (2.0 M heptane/THF/ethylbenzene, 20.30 mL, 40.6 mmol). The mixture was stirred at −78° C. for 1 h before adding additional iodomethane (2.12 mL, 33.8 mmol). The mixture was slowly warmed to room temperature and stirred overnight (16 h). The reaction was quenched with a saturated solution of ammonium chloride and extracted with EtOAc (2×75 mL). The combined organic extracts were washed with brine, dried over MgSO$_4$, filtered and concentrated to provide crude (R)-3,3,6,6-tetramethyltetrahydropyrrolo[1,2-c]oxazol-5(3H)-one as an orange tar. MS (ESI) 184.1 [M+H]$^+$.

Step 3: Prepared according to WO patent: 2013004290. To a solution of (R)-3,3,6,6-tetramethyltetrahydropyrrolo[1,2-c]oxazol-5(3H)-one (4.13 g, 22.54 mmol) in MeOH (90 mL) was added p-toluenesulfonic acid monohydrate (0.429 g, 2.254 mmol). The resulting mixture was heated at reflux for 2 h. The solvent was removed under reduced pressure (rotary evaporator) and the crude material was absorbed onto a plug of silica gel and purified by chromatography on an ISCO Combiflash™ RF (40 g Grace Reverlis column, using a gradient of 0-20% MeOH in DCM) affording (R)-5-(hydroxymethyl)-3,3-dimethylpyrrolidin-2-one (2.91 g, 20.31 mmol, 90% yield) as a white semi-solid. MS (ESI) 144.1 [M+H]$^+$.

Step 4: Prepared according to US patent: 20070032433A1. To a solution of (R)-5-(hydroxymethyl)-3,3-dimethylpyrrolidin-2-one (2.91 g, 20.30 mmol) in THF (50.8 mL) cooled to 0° C., lithium aluminum hydride (2.0 M solution in THF, 12.18 mL, 24.36 mmol) was added. The mixture was stirred at room temperature overnight (16 h). Additional lithium aluminum hydride (2.0 M solution in THF, 12.18 mL, 24.36 mmol) was added and the solution was refluxed for 6 h. The reaction mixture was cooled and additional lithium aluminum hydride (2.0 M solution in THF, 12.18 mL, 24.36 mmol) was added and the mixture was refluxed overnight. The reaction mixture was cooled to 0° C. in an ice bath prior to addition of water (3.67 mL) followed by 15% aqueous NaOH (3.67 mL) and water (10.9 mL). It was then stir vigorously at room temperature for 1 h and filtered on a medium porosity sintered glass frit with cotton and celite washing with EtOAc. The solution was then concentrated affording crude (R)-(4,4-dimethylpyrrolidin-2-yl)methanol (2.29 g, 17.73 mmol, 87% yield) as yellow viscous oil. MS (ESI) 130.1 [M+H]$^+$.

Step 5: A solution of triethylamine (4.94 mL, 35.4 mmol) and (R)-(4,4-dimethylpyrrolidin-2-yl)methanol (2.29 g, 17.72 mmol) in DCM (89 mL) was cooled to −78° C. To this mixture was added sulfuryl chloride (1.0 M in DCM, 21.27 mL, 21.27 mmol) over 15 seconds. The reaction was maintained at this temperature for ~3 h, allowed to warm to room temperature and stirred overnight (16 h). The mixture washed with aqueous 1 N HCl (30 mL×2), brine (40 mL), dried over MgSO$_4$, filtered and concentrated affording crude product as a brown-orange oil that crystallized upon standing. The crude material was absorbed onto a plug of silica gel and purified by chromatography on an ISCO Combiflash™ RF (40 g Grace Reverlis column, using a gradient of 0-60% EtOAc in heptane) affording (R)-5,5-dimethyltetrahydro-3H-pyrrolo[1,2-c][1,2,3]oxathiazole 1,1-dioxide (708 mg, 3.70 mmol, 21% yield) as a white crystalline solid. MS (ESI) 192.1 [M+H]$^+$.

Step 6: To a solution of 3,5-dichloropyridine (796 mg, 5.38 mmol) in THF (9.0 mL) at −78° C. was added lithium diisopropylamide (2.0 M heptane/THF/ethylbenzene, 3.41 mL, 6.82 mmol) dropwise. After stirring for 1 h at this temperature, a solution of (R)-5,5-dimethyltetrahydro-3H-pyrrolo[1,2-c][1,2,3]oxathiazole 1,1-dioxide (686 mg, 3.59 mmol) in THF (9.0 mL) was added dropwise at −78° C. and the mixture was allowed to warm to room temperature over 3 h and then stirred at room temperature for 4 h. After evaporation of the solvent, the resulting beige foam was treated with hot (80° C.) 2 N HCl (8 mL) and EtOH (8 mL) overnight. The reaction mixture was concentrated under reduced pressure (rotary evaporator) and the mixture was treated with ice and basified with 5 N NaOH (8 mL) and extracted with EtOAc (2×75 mL). The organic extracts were dried, evaporated and purified by chromatography on an ISCO Combiflash™ RF (25 g Thomson SingleStep column, using a gradient of 0-10% MeOH in DCM) affording (R)-3,5-dichloro-4-((4,4-dimethylpyrrolidin-2-yl)methyl)pyridine (748 mg, 2.89 mmol, 80% yield) as an orange oil. MS (ESI) 259.1, 261.0 [M+H]$^+$.

Step 7: 1-((1r,4r)-4-(ethoxycarbonyl)-4-methylcyclohexyl)-5-(trifluoromethyl)-1H-pyrazole-4-carboxylic acid (445 mg, 1.28 mmol) was treated with DCM (8 mL) and three drops of DMF, cooled to 0° C. in an ice bath and treated with oxalyl chloride (0.16 mL, 1.82 mmol) slowly dropwise. The reaction mixture was removed from the ice bath and allowed to stir at room temperature for 1.5 h. The volatiles were removed under reduced pressure (rotary evaporator) and the crude acid chloride was treated with DCM (10 mL), cooled in an ice bath and treated with (R)-3,5-dichloro-4-((4,4-dimethylpyrrolidin-2-yl)methyl)pyridine (315 mg, 1.22 mmol) (in DCM 5 mL) slowly dropwise followed by DIPEA (0.64 mL, 3.65 mmol). The solution was removed from the ice bath and allowed to warm to rt and stirred for 1 h. The solvent was evaporated and the crude material was absorbed onto a plug of silica gel and purified by chromatography on an ISCO Combiflash™ RF (40 g Thomson SingleStep column, using a gradient of 0-40% EtOAc in heptane) to provide (1R,4r)-ethyl 4-(4-((R)-2-((3,5-dichloropyridin-4-yl)methyl)-4,4-dimethylpyrrolidine-1-carbonyl)-5-(trifluoromethyl)-1H-pyrazol-1-yl)-1-methylcyclohexanecarboxylate (489 mg, 0.83 mmol, 68% yield) as a light yellow amorphous solid after drying in a vacuum oven over 48 hrs at 40° C. MS (ESI) 589.3/591.2 [M+H]$^+$.

Step 8: To a mixture of (1R,4r)-ethyl 4-(4-((R)-2-((3,5-dichloropyridin-4-yl)methyl)-4,4-dimethylpyrrolidine-1-carbonyl)-5-(trifluoromethyl)-1H-pyrazol-1-yl)-1-methylcyclohexanecarboxylate (464 mg, 0.787 mmol) in THF (3.9 mL) and MeOH (3.9 mL) was added lithium hydroxide monohydrate (1.0 M aqueous solution, 3.9 mL, 3.94 mmol). The mixture was stirred at room temperature overnight (16 h). The organics were removed under reduced pressure (rotary evaporator) and the aqueous solution was acidified with 1 N HCl leading to the formation of a precipitate. The mixture was extracted with EtOAc (2×40 mL). The combined extracts were washed with brine, dried over anhydrous MgSO$_4$, filtered and concentrated. The crude material was absorbed onto a plug of silica gel and purified by chromatography on an ISCO Combiflash™ RF (40 g Thomson SingleStep column, using a gradient of 0-8% MeOH in DCM) affording (1R,4r)-4-(4-((R)-2-((3,5-dichloropyridin-4-yl)methyl)-4,4-dimethylpyrrolidine-1-carbonyl)-5-(trifluoromethyl)-1H-pyrazol-1-yl)-1-methylcyclohexanecarboxylic acid (258 mg, 0.46 mmol, 59% yield) as white amorphous foam. MS (ESI) 561.0, 563.1 [M+H]$^+$.

Example 692 trans-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-1-methylcyclohexanecarboxylic acid

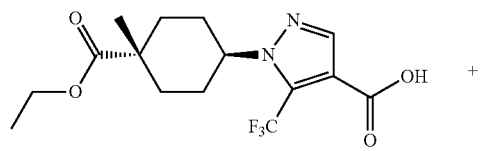

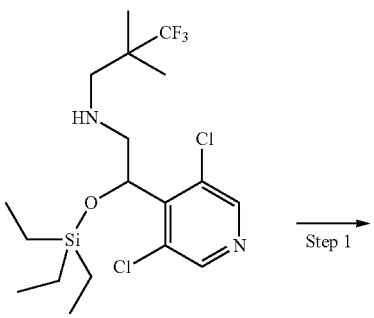

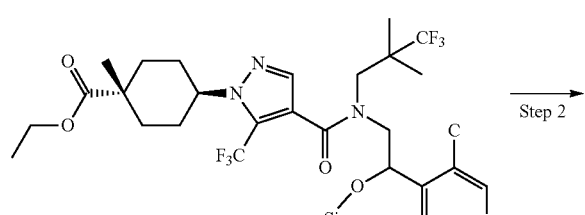

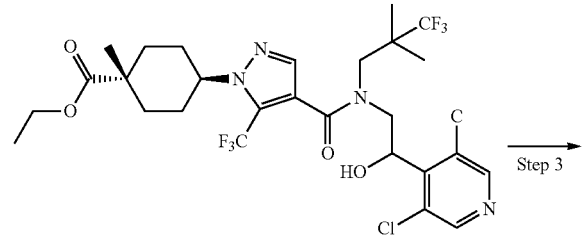

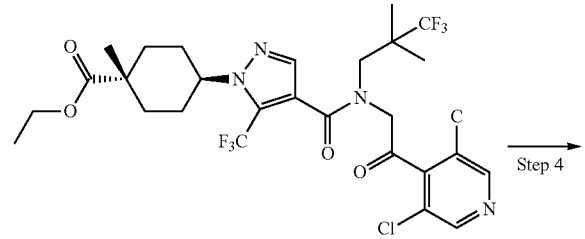

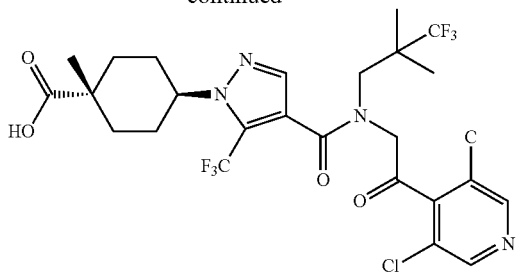

Step 1 and Step 2: ethyl trans-4-(4-((2-(3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-1-methylcyclohexane carboxylate To a slightly cloudy solution of 1-((1r,4r)-4-(ethoxycarbonyl)-4-methylcyclohexyl)-5-(trifluoromethyl)-1H-pyrazole-4-carboxylic acid (1.0102 g, 2.90 mmol) in DCM (29.0 ml) was added oxalyl chloride (0.307 ml, 3.63 mmol) followed by DMF (1 drop) and the light-yellow slightly cloudy reaction mixture was stirred at room temperature. After 3 h, the mixture was concentrated in vacuo to give ethyl trans-4-(4-(chlorocarbonyl)-5-(trifluoromethyl)-1H-pyrazol-1-yl)-1-methylcyclohexanecarboxylate as light-yellow syrup. To the residue was added a solution of N-(2-(3,5-dichloropyridin-4-yl)-2-((triethylsilyl)oxy)ethyl)-3,3,3-trifluoro-2,2-dimethylpropan-1-amine (1.292 g, 2.90 mmol) in THF (29.0 ml) followed by DIPEA (2.021 ml, 11.60 mmol) and the mixture was stirred at room temperature. After 19 h, LCMS (ESI) showed that ethyl trans-4-(4-((2-(3,5-dichloropyridin-4-yl)-2-((triethylsilyl)oxy)ethyl)(3,3,3-trifluoro-2,2-dimethylpropyl)carbamoyl)-5-(trifluoromethyl)-1H-pyrazol-1-yl)-1-methylcyclohexanecarboxylate was formed: LCMS (ESI) m/z 775.1 (M+H)$^+$.

To the reaction mixture was added TBAF solution, 1.0 M in THF (11.60 ml, 11.60 mmol) and the mixture was stirred at room temperature. After 30 min, LC-MS (ESI) showed that the reaction was complete. The reaction mixture was diluted with water (100 mL) and brine (100 mL). The reaction mixture was extracted with EtOAc (2×100 mL). The organic extract washed with satd NaCl (1×100 mL) and dried over Na$_2$SO$_4$. The solution was filtered and concentrated in vacuo to give the crude material as a light-yellow syrup. The crude material was absorbed onto a plug of silica gel and purified by silica gel column chromatography eluting with a gradient of 0% to 50% EtOAc in heptane to provide ethyl trans-4-(4-((2-3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-1-methylcyclohexane carboxylate (1.6938 g, 2.56 mmol, 88% yield) as a white gummy solid. $^1$H NMR (400 MHz, DMSO-d$_6$) δ 8.46-8.63 (2H, m), 7.71-7.83 (1H, m), 6.11 (1H, d, J=4.1 Hz), 5.19-5.33 (1H, m), 4.27 (1H, t, J=11.0 Hz), 4.09 (2H, q, J=7.2 Hz), 3.39-3.97 (4H, m), 2.02-2.19 (2H, m), 1.66-1.97 (6H, m), 1.14-1.30 (12H, m), NMR showed several peak sets due to diastereomers and rotamers; LCMS (ESI) m/z 661.1 (M+H)$^+$.

Step 3: ethyl trans-4-(4-((2-3,5-dichloropyridin-4-yl)-2-oxoethyl)(3,3,3-trifluoro-2,2-dimethylpropyl)carbamoyl)-5-(trifluoromethyl)-1H-pyrazol-1-yl)-1-methylcyclohexanecarboxylate To a clear solution of ethyl trans-4-(4-((2-3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-1-methylcyclohexane carboxylate (1.6826 g, 2.54 mmol) in DCM (25.4 ml) was added Dess-Martin periodinane (1.618 g, 3.82 mmol). The white cloudy mixture was stirred at room temperature. After 1 h, the mixture was quenched with saturated aqueous $Na_2S_2O_3$ (50 mL) and saturated aqueous $NaHCO_3$ (50 mL). The reaction mixture was extracted with DCM (2×100 mL). The organic extract was dried over $Na_2SO_4$. The solution was filtered and concentrated in vacuo to give the crude material as a white solid. The crude material was absorbed onto a plug of silica gel and purified by silica gel column chromatography eluting with a gradient of 0% to 30% EtOAc in heptane to provide ethyl trans-4-(4-((2-(3,5-dichloropyridin-4-yl)-2-oxoethyl)(3,3,3-trifluoro-2,2-dimethyl propyl)carbamoyl)-5-(trifluoromethyl)-1H-pyrazol-1-yl)-1-methylcyclohexanecarboxylate (1.5825 g, 2.400 mmol, 94% yield) as a white gummy solid. $^1$H NMR (400 MHz, $CDCl_3$) δ 8.45-8.64 (2H, m), 7.51-7.78 (1H, m), 4.52 (2H, s), 4.09-4.30 (3H, m), 3.70 (2H, br. s.), 2.12-2.32 (2H, m), 1.79-2.00 (6H, m), 1.02-1.46 (12H, m), rotamers present; LCMS (ESI) m/z 659.0 (M+H)$^+$.

Step 4: trans-4-(4-((2-(3,5-dichloro-4-pyridinyl)-2-oxoethyl)(3,3,3-trifluoro-2,2-dimethyl propyl)carbamoyl)-5-(trifluoromethyl)-1H-pyrazol-1-yl)-1-methylcyclohexanecarboxylic acid To a clear mixture of ethyl trans-4-(4-((2-(3,5-dichloropyridin-4-yl)-2-oxoethyl)(3,3,3-trifluoro-2,2-dimethylpropyl)carbamoyl)-5-(trifluoromethyl)-1H-pyrazol-1-yl)-1-methylcyclohexanecarboxylate (1.5739 g, 2.387 mmol) in THF (9.55 ml), EtOH (9.55 ml), and water (4.77 ml) was added 2 M LiOH in water (11.93 ml, 23.87 mmol). After adding 2 M LiOH solution, the white heterogeneous mixture became yellow cloudy mixture. The yellow cloudy mixture was stirred and heated at 60° C. After 15 h, the reaction mixture was concentrated in vacuo to remove THF and EtOH. The resulting aqueous solution was diluted with water (30 mL). The pH of the solution was adjusted to ~3.0 with 1 N HCl and the resulting precipitate was collected by vacuum filtration, wash with water, and freeze-dried on lyophilizer overnight to provide example 692 (1.3955 g, 2.210 mmol, 93% yield) as white solid. $^1$H NMR (400 MHz, DMSO-$d_6$) δ 12.27 (1H, br. s.), 8.58-8.83 (2H, m), 7.75-8.02 (1H, m), 4.68-5.43 (2H, m), 4.26 (1H, t, J=11.0 Hz), 3.46-3.90 (2H, m), 1.97-2.17 (2H, m), 1.69-1.92 (6H, m), 1.00-1.39 (9H, m), rotamers present; LCMS (ESI) m/z 631.0 (M+H)$^+$.

Example 713

(1r,4r)-4-(4-((2-(2,6-dichlorophenyl)-2-oxoethyl)((5-fluorospiro[2.3]hexan-5-yl)methyl)carbamoyl)-5-(trifluoromethyl)-1H-pyrazol-1-yl)-1-methylcyclohexanecarboxylic acid

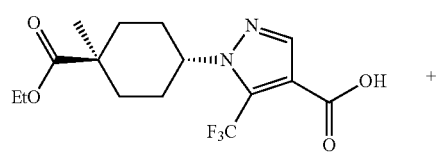

+

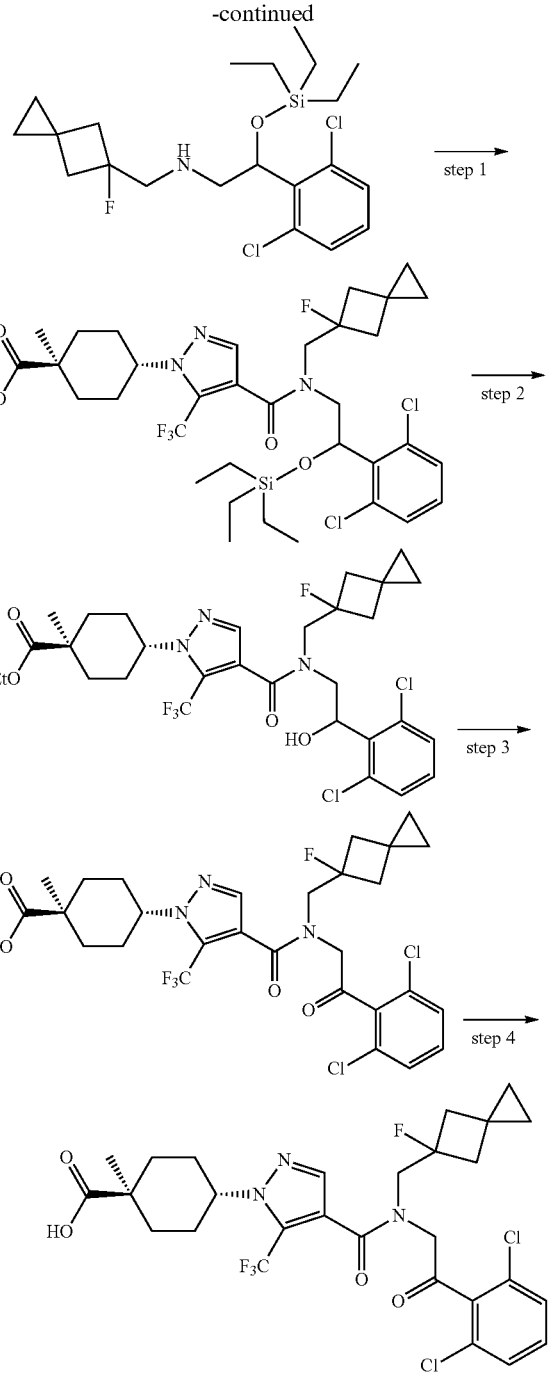

Step 1: ethyl trans-4-(4-((2-(2,6-dichloro-4-fluorophenyl)-2-(((triethylsilyl)oxy)ethyl)(3,5-difluorobenzyl)carbamoyl)-5-(trifluoromethyl)-1H-pyrazol-1-yl)-1-methylcyclohexanecarboxylate 1-((1r,4r)-4-(ethoxycarbonyl)-4-methylcyclohexyl)-5-(trifluoromethyl)-1H-pyrazole-4-carboxylic acid (3.48 g, 9.99 mmol) was dissolved in DCM (30 ml) and thionyl chloride (0.875 ml, 11.99 mmol) was added followed by 1 drop of DMF. The reaction was refluxed for 2.5 h. The solvents were removed in vacuo and the residue was placed in the freezer overnight. The solidified material was then dried under vacuo for 1 h to afford (1s,4s)-ethyl 4-(4-(chlorocarbonyl)-5-(trifluoromethyl)-1H-pyrazol-1-yl)-1-methylcyclohexane carboxylate.

2-(2,6-dichlorophenyl)-N-((5-fluorospiro[2.3]hexan-5-yl)methyl)-2-((triethylsilyl)oxy)ethanamine (150 mg, 0.347 mmol) was dissolved in 2 ml of DCM and (1s,4s)-ethyl 4-(4-(chlorocarbonyl)-5-(trifluoromethyl)-1H-pyrazol-1-yl)-1-methylcyclohexane carboxylate (127 mg, 0.347 mmol) dissolved in 2 ml of DCM was added, followed by triethylamine (242 μl, 1.734 mmol). The solution was stirred for 1 h and was concentrated to afford crude (1r,4r)-ethyl 4-(4-((2-(2,6-dichlorophenyl)-2-((triethylsilyl)oxy)ethyl)((5-fluorospiro[2.3]hexan-5-yl)methyl)carbamoyl)-5-(trifluoromethyl)-1H-pyrazol-1-yl)-1-methylcyclohexanecarboxylate (265 mg, 0.347 mmol, 100% yield).

Step 2: (1r,4r)-ethyl 4-(4-((2-(2,6-dichlorophenyl)-2-hydroxyethyl)((5-fluorospiro[2.3]hexan-5-yl)methyl)carbamoyl)-5-(trifluoromethyl)-1H-pyrazol-1-yl)-1-methylcyclohexanecarboxylate To a stirred solution of (1r,4r)-ethyl 4-(4-((2-(2,6-dichlorophenyl)-2-((triethylsilyl)oxy)ethyl)((5-fluorospiro[2.3]hexan-5-yl)methyl)carbamoyl)-5-(trifluoromethyl)-1H-pyrazol-1-yl)-1-methylcyclohexanecarboxylate (265 mg, 0.347 mmol) in 2 ml of THF was added TBAF (695 μl, 0.695 mmol), and the mixture was stirred for 1 h. The reaction mixture was quenched with saturated aqueous NH$_4$Cl and extracted with EtOAc. The combined organic layers were washed with water and brine, dried over anhydrous Na$_2$SO$_4$ and concentrated under reduced pressure to afford crude (1r,4r)-ethyl 4-(4-((2-(2,6-dichlorophenyl)-2-hydroxyethyl)((5-fluorospiro[2.3]hexan-5-yl)methyl)carbamoyl)-5-(trifluoromethyl)-1H-pyrazol-1-yl)-1-methylcyclohexanecarboxylate (225 mg, 0.347 mmol, 100% yield). MS m/z=648 [M+H]$^+$.

Step 3: (1r,4r)-ethyl 4-(4-((2-(2,6-dichlorophenyl)-2-oxoethyl)((5-fluorospiro[2.3]hexan-5-yl)methyl)carbamoyl)-5-(trifluoromethyl)-1H-pyrazol-1-yl)-1-methylcyclohexanecarboxylate (1r,4r)-ethyl 4-(4-((2-(2,6-dichlorophenyl)-2-hydroxyethyl)((5-fluorospiro[2.3]hexan-5-yl)methyl)carbamoyl)-5-(trifluoromethyl)-1H-pyrazol-1-yl)-1-methylcyclohexanecarboxylate (225 mg, 0.347 mmol) was dissolved in 10 ml of DCM and Dess-Martin periodane (184 mg, 0.434 mmol) was added. The solution was stirred for 1 h. The solution was quenched with 5% Na$_2$S$_2$O$_3$, washed with saturated NaHCO$_3$, dried with Na$_2$SO$_4$ and concentrated. The product was purified via silica gel column chromatography (40 g column) using 0-100% EtOAc in heptane to afford (1r,4r)-ethyl
4-(4-((2-(2,6-dichlorophenyl)-2-oxoethyl)((5-fluorospiro[2.3]hexan-5-yl)methyl)carbamoyl)-5-(trifluoromethyl)-1H-pyrazol-1-yl)-1-methylcyclohexanecarboxylate (140 mg, 0.217 mmol, 62.4% yield). MS m/z=646 [M+H]$^+$.

Step 4: (1r,4r)-4-(4-((2-(2,6-dichlorophenyl)-2-oxoethyl)((5-fluorospiro[2.3]hexan-5-yl)-5-(trifluoromethyl)-1H-pyrazol-1-yl)-1-methylcyclohexanecarboxylic acid (1r,4r)-ethyl 4-(4-((2-(2,6-dichlorophenyl)-2-oxoethyl)((5-fluorospiro[2.3]hexan-5-yl)methyl)carbamoyl)-5-(trifluoromethyl)-1H-pyrazol-1-yl)-1-methylcyclohexanecarboxylate (140 mg, 0.217 mmol) and lithium hydroxide (100 mg, 4.18 mmol) were combined in 5 ml of MeOH, 5 ml of THF, and 2 ml of water. The solution was heated at 50° C. for 3 h. The solution was made acidic with 6 N HCl and diluted with water. The product was extracted with EtOAc, dried with Na$_2$SO$_4$, filtered and concentrated to afford (1r,4r)-4-(4-((2-(2,6-dichlorophenyl)-2-oxoethyl)((5-fluorospiro[2.3]hexan-5-yl)methyl)carbamoyl)-5-(trifluoromethyl)-1H-pyrazol-1-yl)-1-methylcyclohexanecarboxylic acid (115 mg, 0.186 mmol, 86% yield). $^1$H NMR (400 MHz, CD$_3$OD, mixture of rotamers) δ 7.88 (s, 0.2H) 7.66 (s, 0.8H) 7.40-7.50 (m, 3H) 4.11 (m, 3H) 2.43-2.61 (m, 2H) 2.15-2.32 (m, 3H) 1.81-2.05 (m, 7H) 1.17-1.43 (m, 5H) 0.42-0.70 (m, 4H) LC/MS (ESL) m/z=618 (M+H)$^+$.

Example 716 trans-4-(4-((2-(2,6-dichloro-4-fluorophenyl)-2-oxoethyl)((1-methylcyclopropyl)methyl)carbamoyl)-5-(trifluoromethyl)-1H-pyrazol-1-yl)-1-methylcyclohexanecarboxylic acid

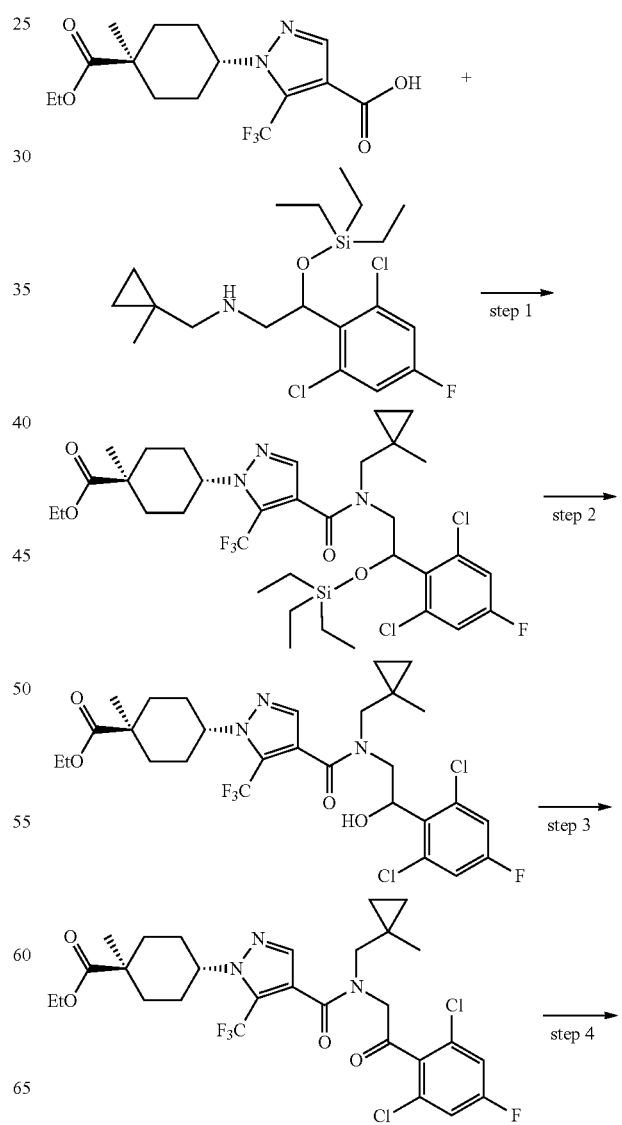

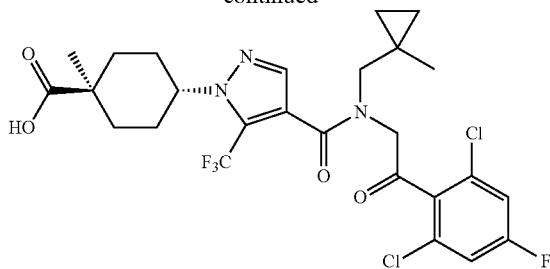

Step 1: ethyl trans-4-(4-((2-(2,6-dichloro-4-fluorophenyl)-2-((triethylsilyl)oxy)ethyl)((1-methylcyclopropyl)methyl)carbamoyl)-5-(trifluoromethyl)-1H-pyrazol-1-yl)-1-methylcyclohexanecarboxylate This compound was prepared using similar procedure described for examples 1, step 1 without chromatography purification. LCMS (ESI) m/z 735.8 (M+H)+.

Step 2: ethyl trans-4-(4-((2-(2,6-dichloro-4-fluorophenyl)-2-hydroxyethyl)((1-methylcyclopropyl)methyl)carbamoyl)-5-(trifluoromethyl)-1H-pyrazol-1-yl)-1-methylcyclohexane carboxylate This compound was prepared using similar procedure described for examples 1, step 2 without chromatography purification. LCMS (ESI) m/z 623.9 (M+H)+.

Step 3: ethyl trans-4-(4-((2-(2,6-dichloro-4-fluorophenyl)-2-oxoethyl)((1-methylcyclopropyl)methyl)carbamoyl)-5-(trifluoromethyl)-1H-pyrazol-1-yl)-1-methylcyclohexanecarboxylate This compound was prepared using similar procedure described for examples 1, step 3. $^1$H NMR (500 MHz, CDCl$_3$) rotamers present δ 7.65 and 7.58 (2×s, 1H), 7.16 and 7.15 (2×s, 1H), 7.09 and 7.08 (2×s, 1H), 4.98 (s, 1H), 4.60 (s, 1H), 4.22-4.33 (m, 1H), 4.15-4.22 (m, 2H), 3.36 (s, 1H), 2.15-2.31 (m, 2H), 1.84-1.99 (m, 6H), 1.39 and 1.37 (2×s, 3H), 1.30 (td, J=7.09, 2.32 Hz, 3H), 1.12 and 0.98 (2×s, 3H), 0.48-0.56 (m, 1H), 0.34-0.43 (m, 3H); LCMS (ESI) m/z 619.8 (M+H)+.

Step 4: trans-4-(4-((2-(2,6-dichloro-4-fluorophenyl)-2-oxoethyl)((1-methylcyclopropyl)methyl)carbamoyl)-5-(trifluoromethyl)-1H-pyrazol-1-yl)-1-methylcyclohexanecarboxylic acid This compound was obtained as a white solid using similar procedures described for example 1, step 4. $^1$H NMR (500 MHz, DMSO-d$_6$) rotamers present δ 12.29 (s, 1H), 7.52-7.82 (m, 3H), 5.17 and 4.87 (2×s, 1H), 4.69 (s, 1H), 4.18-4.32 (m, 1H), 3.52 and 3.38 (2×s, 1H), 3.32 and 3.22 (2×s, 1H), 2.00-2.16 (m, 2H), 1.73-1.91 (m, 6H), 1.24 and 1.08 (2×s, 3H), 1.05 and 0.91 (2×s, 3H), 0.44-0.57 (m, 1H), 0.23-0.38 (m, 3H); LCMS (ESI) m/z 592.1 (M+H)+.

Example 729

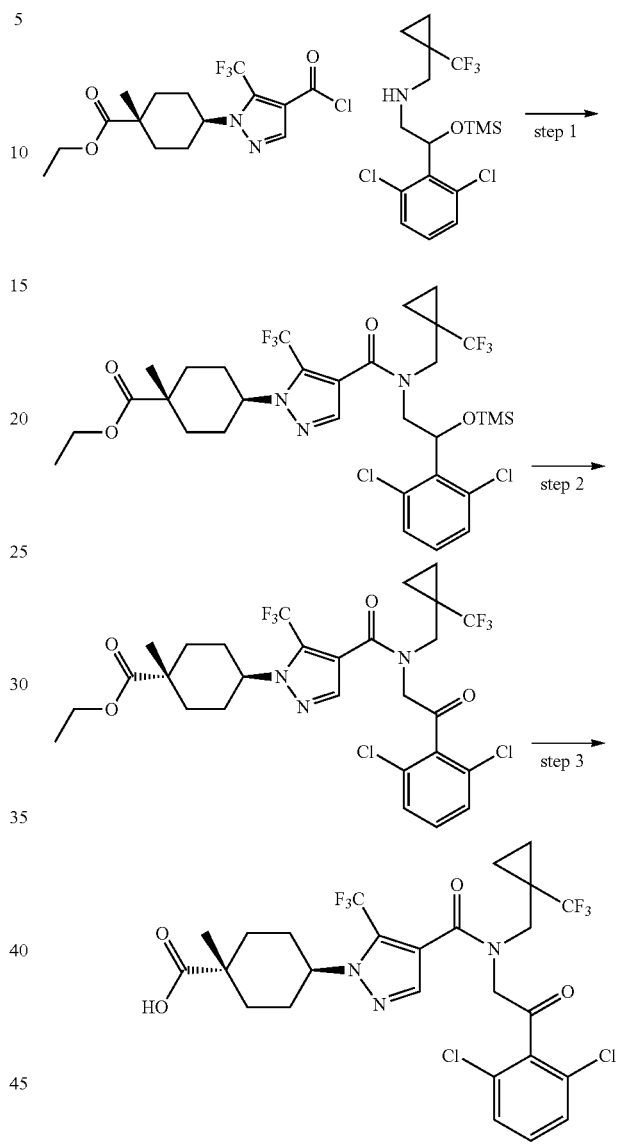

Step 1: (1r,4r)-ethyl 4-(4-((2-(2,6-dichlorophenyl)-2-((trimethylsilyl)oxy)ethyl)((1-(trifluoromethyl)cyclopropyl)methyl)carbamoyl)-5-(trifluoromethyl)-1H-pyrazol-1-yl)-1-methylcyclohexanecarboxylate To a solution of 2-(2,6-dichlorophenyl)-N-((1-(trifluoromethyl)cyclopropyl)methyl)-2-((trimethylsilyl)oxy)ethanamine (0.15 g, 0.375 mmol) in DCM (3 mL) was added ethyl 4-(4-(chlorocarbonyl)-5-(trifluoromethyl)-1H-pyrazol-1-yl)-1-methylcyclohexane carboxylate (0.137 g, 0.375 mmol) followed by triethylamine (0.104 mL, 0.749 mmol) and stirred at ambient temperature for 15 min. Reaction mixture was loaded on a 25 g column (MPLC) and eluted with Hex: EtOAc (0-50%) to obtain (1r,4r)-ethyl 4-(4-((2-(2,6-dichlorophenyl)-2-((trimethylsilyl)oxy)ethyl)((1-(trifluoromethyl)cyclopropyl)methyl)carbamoyl)-5-(trifluoromethyl)-1H- pyrazol-1-yl)-1-methylcyclohexanecarboxylate (0.177 g, 0.242 mmol, 65%) as clear oil.

Step 2: (1r,4r)-ethyl 4-(4-((2-(2,6-dichlorophenyl)-2-hydroxyethyl)((1-(trifluoromethyl)cyclopropyl)methyl)carbamoyl)-5-(trifluoromethyl)-1H-pyrazol-1-yl)-1-methylcyclohexanecarboxylate To a solution of (1r,4r)-ethyl 4-(4-((2-(2,6-dichlorophenyl)-2-((trimethylsilyl)oxy)ethyl)((1-(trifluoromethyl)cyclopropyl)methyl)carbamoyl)-5-(trifluoromethyl)-1H-pyrazol-1-yl)-1-methylcyclohexanecarboxylate (0.177 g, 0.242 mmol) in 2-Me-THF (0.808 ml) was added tetra-n-butylammonium fluoride (0.291 ml, 0.291 mmol) The mixture was stirred at ambient temperature for 1 h. The reaction mixture was quenched with saturated aqueous NH$_4$Cl (1 mL) and diluted with EtOAc (50 mL) and water (20 mL). The organic layer was concentrated under reduced pressure to afford (1r,4r)-ethyl 4-(4-((2-(2,6-dichlorophenyl)-2-hydroxyethyl)((1-(trifluoromethyl)cyclopropyl)methyl)carbamoyl)-5-(trifluoromethyl)-1H-pyrazol-1-yl)-1-methylcyclohexanecarboxylate as an off-white solid. This was dissolved in DCM (3 mL) and dess-martin periodinane (0.134 g, 0.315 mmol) was added and the reaction mixture was stirred at ambient temperature for 16 h. To this was then added Na$_2$S$_2$O$_3$ (5 mL) followed by saturated NaHCO$_3$ (2 mL) and DCM (20 mL) and stirred for 15 min. Organic layer was passed through phase separator and concentrated. The crude mixture was purified by MPLC (25 g column) and eluting with Hex:EtOAc (10-40%) to obtain (1r,4r)-ethyl 4-(4-((2-(2,6-dichlorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylate (0.13 g, 82%) as amorphous white solid.

Step 3: (1r,4r)-4-(4-((2-(2,6-dichlorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylic acid To a solution of (1r,4r)-ethyl 4-(4-((2-(2,6-dichlorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylate (0.13 g, 0.198 mmol) in 2Me-THF (0.660 ml), MeOH (0.660 ml) and water (0.660 ml) was added lithium hydroxide (0.047 g, 1.980 mmol) and stirred at 40° C. for 1 h. Reaction mixture was acidified with 2 N HCl to pH 2 and extracted with EtOAc (2×30 mL). Organic layer was dried on anhydrous Na$_2$SO$_4$ filtered and concentrated to obtain (1r,4r)-4-(4-((2-(2,6-dichlorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylic acid (0.1 g, 75%) as amorphous white solid. 1H NMR δ (DMSO-d$_6$) rotamers present 12.22 (1H, brs); 9.79 (1H, 2×s); 7.69 and 7.67 (1H, 2×s); 7.55 and 7.54 (1H, 2×s); 7.46 and 7.44 (1H, 2×s); 5.19 (1H, m); 4.30-4.20 (2H, m); 3.78 (2H, m); 2.28-2.20 (2H, m); 2.18-1.98 (3H, m); 1.88-1.47 (8H, m); 1.24 and 1.23 (3H, 2×s) LCMS (ESI): 628.0 (M+H)$^+$.

Example 759 trans-4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylic acid

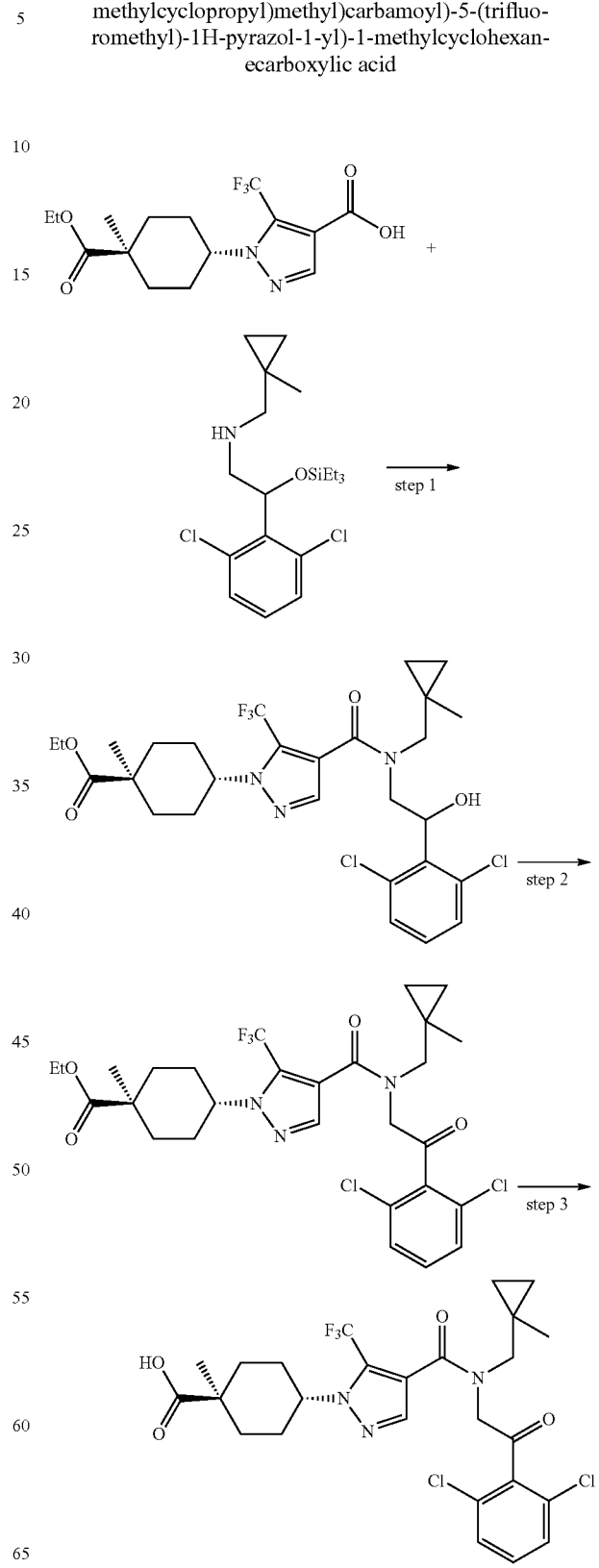

Step 1: trans-ethyl 4-(4-((2-(2,6-dichlorophenyl)-2-hydroxyethyl)((1-methylcyclopropyl)methyl)carbamoyl)-5-(trifluoromethyl)-1H-pyrazol-1-yl)-1-methylcyclohexanecarboxylate To a solution of 1-(trans-4-(ethoxycarbonyl)-4-methylcyclohexyl)-5-(trifluoromethyl)-1H-pyrazole-4-carboxylic acid (2.88 g, 8.27 mmol) in DCM thionyl chloride (0.663 ml, 9.10 mmol) was added followed by 1 drop of DMF. The flask was then equipped with reflux condenser and the mixture was then stirred for 4 h at 40° C. and then stirred overnight at rt. The solvents were removed in vacuo and the residue was dried in vacuo to afford trans-ethyl 4-(4-(chlorocarbonyl)-5-(trifluoromethyl)-1H-pyrazol-1-yl)-1-methylcyclohexane carboxylate (2.87 g, 95% yield) which was used without further purification. To a solution of 2-(2,6-dichlorophenyl)-N-((1-methylcyclopropyl)methyl)-2-((triethylsilyl)oxy)ethanamine (95 mg, 0.245 mmol) in DCM (1.2 ml) was added DIPEA (85 µl, 0.489 mmol) and trans-ethyl 4-(4-(chlorocarbonyl)-5-(trifluoromethyl)-1H-pyrazol-1-yl)-1-methylcyclohexane carboxylate (90 mg, 0.245 mmol). After 45 min, TBAF (1 M solution in THF) (905 µl, 0.905 mmol) was added. After 2 h, 1 M aq. HCl was added to the reaction mixture. Organic layer was separated, and the aqueous layer was extracted with DCM. The combined organic layers were washed with sat. aq. NaHCO$_3$, dried with Na$_2$SO$_4$ and concentrated to provide crude trans-ethyl 4-(4-((2-(2,6-dichlorophenyl)-2-hydroxyethyl)((1-methylcyclopropyl)methyl)carbamoyl)-5-(trifluoromethyl)-1H-pyrazol-1-yl)-1-methylcyclohexanecarboxylate (206 mg) which was used without purification in the next step.

Step 2: trans-ethyl 4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylate To a solution of trans-ethyl 4-(4-((2-(2,6-dichlorophenyl)-2-hydroxyethyl)((1-methylcyclopropyl)methyl)carbamoyl)-5-(trifluoromethyl)-1H-pyrazol-1-yl)-1-methylcyclohexanecarboxylate (206 mg, 0.341 mmol) in DCM (3.5 ml) was added Dess-Martin periodinane (217 mg, 0.511 mmol). After 40 min 1 M aq. Na$_2$S$_2$O$_3$ and sat. aq. NaHCO$_3$ were added. The mixture was stirred for 1 h, organic layer was separated, the aqueous layer was extracted with DCM. The combined organic layers were concentrated. The residue was purified by preparative TLC eluted with 30% EtOAc/hexane to provide trans-ethyl 4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylate (100 mg, 0.166 mmol, 48.7% yield).

Step 3: trans-4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylic acid To a mixture of trans-ethyl 4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylate (100 mg, 0.166 mmol) in MeOH (1.5 mL), THF (1.5 mL), and water (1 mL) was added lithium hydroxide monohydrate (69 mg, 1.66 mmol). The mixture was heated at 50° C. for 90 min. Most of the MeOH and THF were removed in vacuo. The mixture was brought to pH 1 with 1 M aq. HCl. The mixture was stirred for 15 min, precipitated solid was filtered, washed with water and dried in vacuo to afford trans-4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylic acid (82 mg, 0.143 mmol, 86% yield). $^1$H NMR (400 MHz, DMSO-d$_6$) mixture of rotamers and keto-enol tautomers δ 12.24 (br. s, 1H), 9.59 (s, 0.2H), 7.80 (s, 0.2H), 7.73 (s, 0.55H), 7.72 (s, 0.25H), 7.32-7.63 (m, 3H), 5.15 (s, 0.2H), 4.88 (br. s, 0.5H), 4.70 (br. s, 1.1H), 4.15-4.35 (m, 1H), 3.52 (s, 0.4H), 3.32 (s, 1.1H), 3.22 (s, 0.5H), 1.99-2.16 (m, 2H), 1.70-1.93 (m, 6H), 1.21-1.28 (m, 3H), 0.88-1.11 (m, 3H), 0.45-0.58 (m, 2H), 0.23-0.35 (m, 2H). LCMS (APCI): 574.3 (M+H)$^+$.

Example 760 trans-4-(4-((2-(2,6-dichlorophenyl)-2-oxoethyl)((1-methylcyclobutyl)methyl)carbamoyl)-5-(trifluoromethyl)-1H-pyrazol-1-yl)-1-methylcyclohexanecarboxylic acid

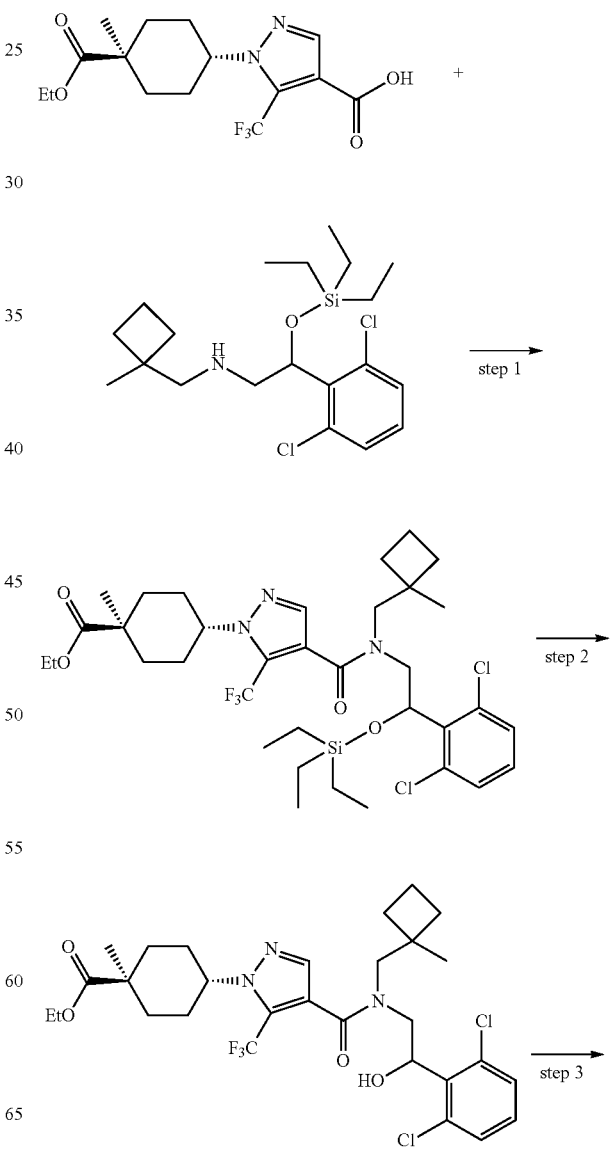

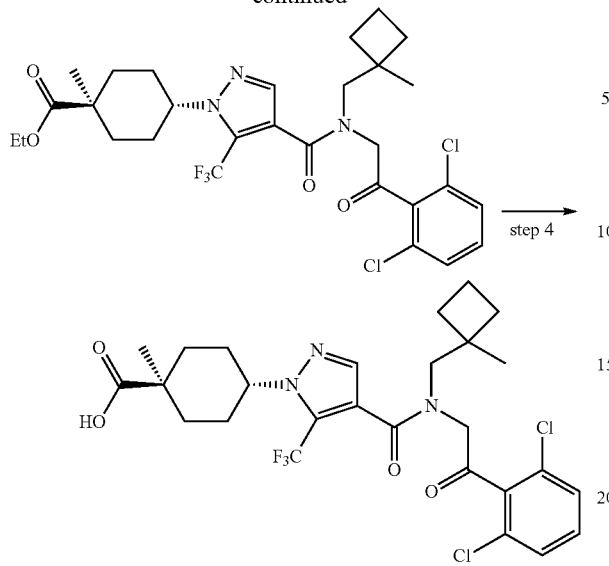

2.05 (m, 4H), 1.67-1.85 (m, 8H), 1.44-1.61 (m, 2H), 1.16 (s, 3H), 1.10 (s, 3H); LCMS (ESI) m/z 588.3 (M+H)+.

Example 785

(1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylic acid

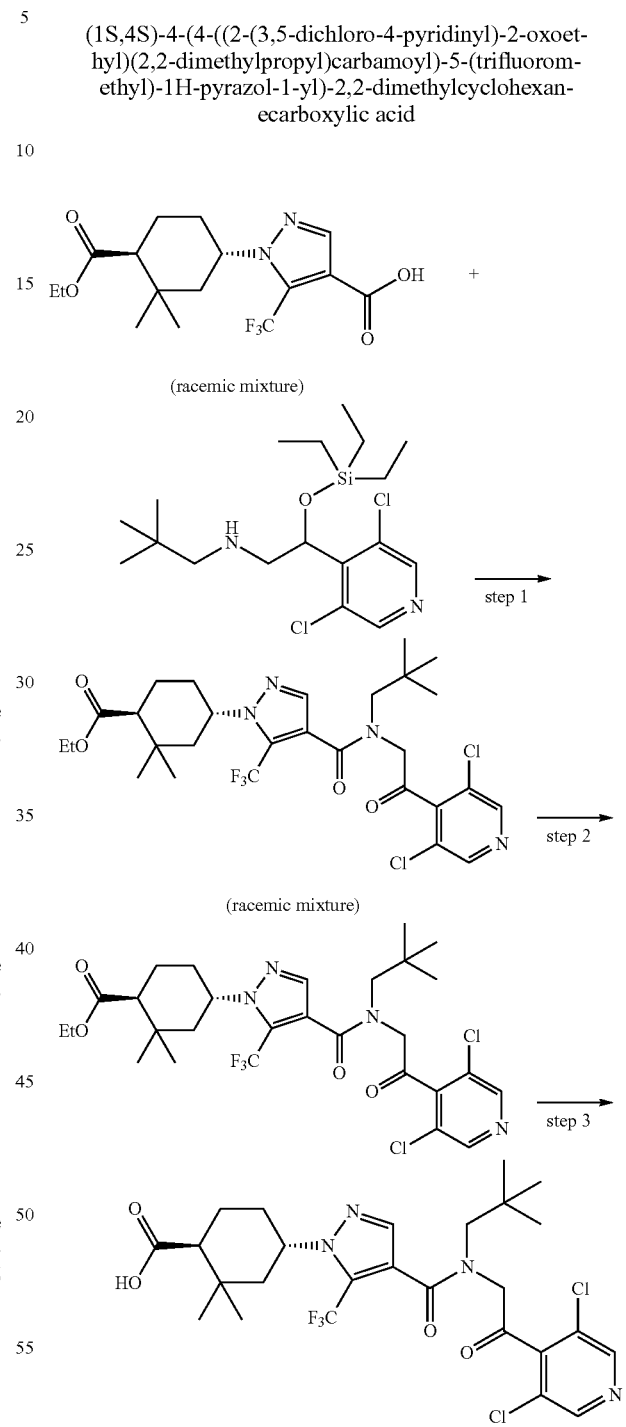

Step 1: ethyl trans-4-(4-((2-(2,6-dichlorophenyl)-2-((triethylsilyl)oxy)ethyl)((1-methylcyclobutyl)methyl)carbamoyl)-5-(trifluoromethyl)-1H-pyrazol-1-yl)-1-methylcyclohexane carboxylate This compound was prepared using similar procedure described for example 1, step 1 without chromatography purification.

Step 2: ethyl trans-4-(4-((2-(2,6-dichlorophenyl)-2-hydroxyethyl)((1-methylcyclobutyl)methyl)carbamoyl)-5-(trifluoromethyl)-1H-pyrazol-1-yl)-1-methyl-cyclohexanecarboxylate This compound was prepared using similar procedure described for example 1, step 2 without chromatography purification. LCMS (ESI) m/z 618.3 (M+H)+.

Step 3: ethyl trans-4-(4-((2-(2,6-dichlorophenyl)-2-oxoethyl)((1-methylcyclobutyl)methyl)carbamoyl)-5-(trifluoromethyl)-1H-pyrazol-1-yl)-1-methylcyclohexanecarboxylate This compound was prepared using similar procedure described for example 1, step 3. $^1$H NMR (500 MHz, DMSO-$d_6$) rotamers present δ 7.44-7.77 (m, 4H), 4.63 (2×s, 2H), 4.26 (m, 1H), 4.09 (q, J=7.13 Hz, 2H), 3.48 (br. s., 2H), 1.98-2.13 (m, 4H), 1.82-1.96 (m, 3H), 1.74-1.82 (m, 5H), 1.58-1.67 (m, 2H), 1.14-1.28 (m, 9H); LCMS (ESI) m/z 616.3 (M+H)+.

Step 4: trans-4-(4-((2-(2,6-dichlorophenyl)-2-oxoethyl)((1-methylcyclobutyl)methyl)carbamoyl)-5-(trifluoromethyl)-1H-pyrazol-1-yl)-1-methylcyclohexanecarboxylic acid This compound was obtained as a white solid using similar procedure described for example 1, step 4. $^1$H NMR (500 MHz, DMSO-$d_6$) rotamers present δ 12.18 (br. s., 1H), 9.58 (d, J=1.10 Hz, 1H), 7.66 (s, 1H), 7.27-7.48 (m, 3H), 5.05 (d, J=1.22 Hz, 1H), 4.09-4.22 (m, 1H), 3.55-3.61 (m, 1H), 1.91-

Step 1: Ethyl trans-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate (racemic mixture)

Oxalyl chloride (64 μL, 0.72 mmol) and DMF (1 drop) were added sequentially to a stirring solution of trans-1-(4-

(ethoxycarbonyl)-3,3-dimethylcyclohexyl)-5-(trifluoromethyl)-1H-pyrazole-4-carboxylic acid (0.20 g, 0.55 mmol; racemic mixture) and DCM (5.5 mL). After stirring for 2 h, the reaction mixture was concentrated under reduced pressure. The residue was dissolved with THF (4.5 mL), and then a solution of N-(2-(3,5-dichloropyridin-4-yl)-2-((triethylsilyl)oxy)ethyl)-2,2-dimethylpropan-1-amine (0.22 g, 0.55 mmol) and THF (1.0 mL) was added followed by DIPEA (0.29 mL, 1.7 mmol). After stirring for 30 min, TBAF (1.7 mL of a 1.0 M solution with THF, 1.7 mmol) was added. After stirring for 1 h, the reaction mixture was partitioned between EtOAc and saturated aqueous NaHCO₃, the layers were separated, the organic material washed sequentially with saturated aqueous NaHCO₃ (2×) and brine, dried (Na₂SO₄), filtered, and the filtrate was concentrated under reduced pressure. The residue was dissolved with DCM (5.5 mL) and the resulting solution was treated with Dess-Martin periodinane (0.26 g, 0.60 mmol). After stirring for 10 min, the reaction mixture was concentrated under reduced pressure, the residue was partitioned between THF-EtOAc (1:1 vol/vol) and saturated aqueous NaHCO₃, the layers were separated, the organic material was washed sequentially with saturated aqueous NaHCO₃ and brine, dried (Na₂SO₄), filtered, and the filtrate was concentrated under reduced pressure. The residue was dissolved with DCM, silica gel (1.0 g) was added to the solution, and the volatiles were removed under reduced pressure. The residue was subjected to flash chromatography on silica gel (gradient elution; 9:1 to 4:1 hexane-EtOAc) to give ethyl trans-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate (0.27 g, 80% overall yield; racemic mixture) as a colorless solid.

Step 2: Ethyl (1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate Ethyl trans-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate (0.22 g, from Step 1; racemic mixture) was resolved using preparative high-performance liquid chromatography (CHIRALPAK™ AD-H column from Chiral Technologies, Inc., West Chester, Pa. (250 mm×30 mm, 5 μm column) eluting with a mixture of heptane/EtOH (90:10 v/v) at a flow rate of 50 mL/min) to give two products in greater than 97% enantiomeric excess.
Peak 1: Ethyl (1R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate (0.10 g) as a colorless solid. Peak 2: Ethyl (1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate (0.098 g) as a colorless solid.

Step 3: (1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylic acid NaOH (1.6 mL of a 1.0 M aqueous solution, 1.6 mmol) was added to a stirring solution of ethyl (1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylate (0.098 g, 0.16 mmol, from Step 2), THF (1.6 mL), and EtOH (1.6 mL), and then the reaction mixture was heated at 60° C. After stirring for 40 h, the reaction mixture was allowed to cool to room temperature and then concentrated under reduced pressure. The residue was dissolved with water (10 mL), concentrated hydrochloric acid (10 drops) was added to the solution, the resulting heterogeneous mixture was filtered, the filter cake washed with water, dissolved with Et₂O, the solution was filtered, and the filtrate was concentrated under reduced pressure. The residue was dissolved with DCM, the solution was filtered, and the filtrate was concentrated under reduced pressure to give (1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylic acid (0.082 g, 88% yield) as a colorless solid.

¹H NMR (400 MHz, CDCl₃) major rotamer/tautomer (carboxylic acid proton not observed) δ 8.50 (s, 2H), 7.55 (s, 1H), 4.61-4.35 (m, 3H), 3.70-3.16 (m, 2H), 2.47-2.31 (m, 1H), 2.16-1.86 (m, 5H), 1.81-1.57 (m, 1H), 1.17 (br. s., 3H), 1.10 (br. s., 3H), 1.01 (br. s., 9H); LCMS (ESI): 591.0 (M+H)⁺.

[Example 754]: made from the racemic ethyl ester from Step 1 of example 785.

[Example 784]: made from the (1R,4R)-ethyl ester from Step 2 example 785.

[Example 807]: made in the same manner as example 754.

Example 791

(trans-4-(4-((2-(3,5-dichloro-4-pyridinyl)-2-oxoethyl)(2,2-dimethylpropyl)carbamoyl)-5-(trifluoromethyl)-1H-pyrazol-1-yl)-1-methylcyclohexyl)acetic acid

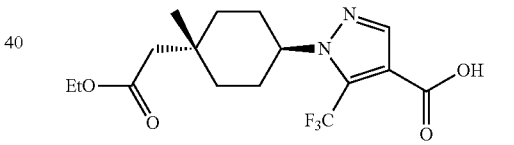

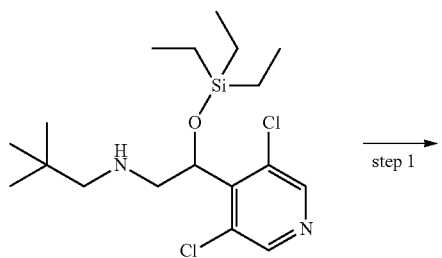

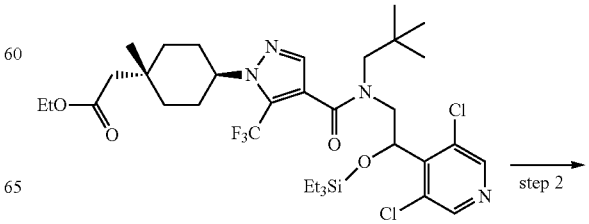

-continued

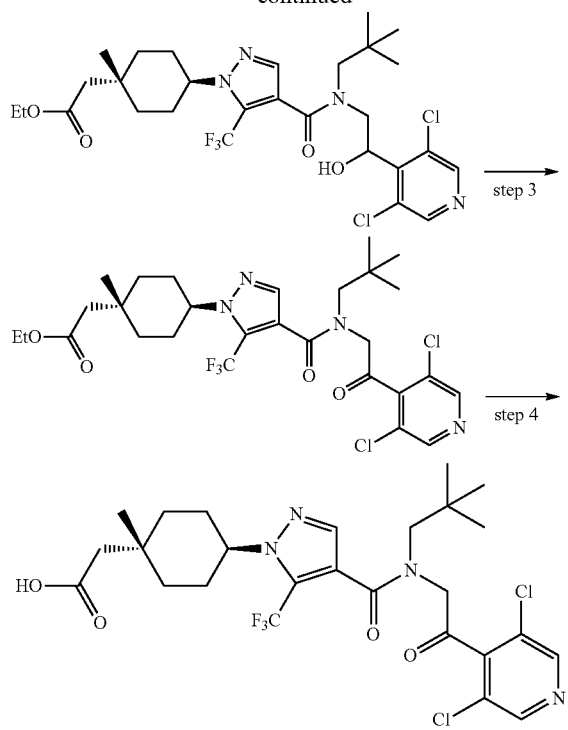

Steps 1 and 2: 2-((1r,4r)-4-(4-((2-(3,5-dichloropyridin-4-yl)-2-hydroxyethyl)(neopentyl)carbamoyl)-5-(trifluoromethyl)-1H-pyrazol-1-yl)-1-methylcyclohexyl)acetate Steps 1 and 2 were conducted in a similar manner to Example 1 to give ethyl 2-((1r,4r)-4-(4-((2-(3,5-dichloropyridin-4-yl)-2-hydroxyethyl)(neopentyl)carbamoyl)-5-(trifluoromethyl)-1H-pyrazol-1-yl)-1-methylcyclohexyl)acetate.

Step 3: ethyl 2-((1r,4r)-4-(4-((2-(3,5-dichloropyridin-4-yl)-2-oxoethyl)(neopentyl)carbamoyl)-5-(trifluoromethyl)-1H-pyrazol-1-yl)-1-methylcyclohexyl) acetate To a solution of ethyl 2-((1r,4r)-4-(4-((2-(3,5-dichloropyridin-4-yl)-2-hydroxyethyl)(neopentyl)carbamoyl)-5-(trifluoromethyl)-1H-pyrazol-1-yl)-1-methylcyclohexyl)acetate (134.7 mg, 0.217 mmol) in DCM (2 mL) was added Dess-Martin periodinane (129 mg, 0.303 mmol). The resulting mixture was stirred at ambient temperature for 30 min. The reaction mixture was quenched with NaHCO$_3$ (5 mL, sat. aq.) and Na$_2$S$_2$O$_3$ (5 mL, sat. aq.), then extracted with CH$_2$Cl$_2$ (2×15 mL). The combined organic layers were washed with water (10 mL), brine (10 mL), dried over anhydrous Na$_2$SO$_4$ and concentrated under reduced pressure. The residue was purified by column chromatography (24 g Gold, 0%-50% EtOAc/Hexane) to yield pure white solid as ethyl 2-((1r,4r)-4-(4-((2-(3,5-dichloropyridin-4-yl)-2-oxoethyl)(neopentyl) carbamoyl)-5-(trifluoromethyl)-1H-pyrazol-1-yl)-1-methylcyclohexyl)acetate (85.5 mg, 0.138 mmol, 63.7% yield). LCMS=618 (M+H)$^+$.

Step 4: (trans-4-(4-((2-(3,5-dichloro-4-pyridinyl)-2-oxoethyl)(2,2-dimethylpropyl)carbamoyl)-5-(trifluoromethyl)-1H-pyrazol-1-yl)-1-methylcyclohexyl) acetic acid To solution of ethyl 2-((1r,4r)-4-(4-((2-(3,5-dichloropyridin-4-yl)-2-oxoethyl)(neopentyl)carbamoyl)-5-(trifluoromethyl)-1H-pyrazol-1-yl)-1-methylcyclohexyl)acetate (85.5 mg, 0.138 mmol) in THF (2 mL)/EtOH (0.500 mL) was added LiOH, 1 M aqueous (0.552 mL, 0.552 mmol). The reaction mixture was stirred at ambient temperature overnight. Solvent was partially removed. The aqueous solution was acidified to pH 2. The resulting precipitate was filtered, washed with water and allowed to dry in the open air to afford pure white solid as 2-((1r,4r)-4-(4-((2-(3,5-dichloropyridin-4-yl)-2-oxoethyl)(neopentyl)carbamoyl)-5-(trifluoromethyl)-1H-pyrazol-1-yl)-1-methylcyclohexyl)acetic acid (82 mg, 0.139 mmol, 100% yield) as mixture of tautomers. $^1$H NMR (500 MHz, DMSO-d$_6$) δ 0.90-1.01 (m, 9H) 1.05-1.14 (m, 3H) 1.46-1.59 (m, 2H) 1.61-1.83 (m, 4H) 2.00-2.21 (m, 2H) 3.49 (s, 2H) 4.05-4.23 (m, 1H) 5.34 (s, 1H) 7.75 (s, 1H) 8.62 (s, 2H) 9.88 (s, 1H). LCMS=590.0 (M+H)$^+$.

Example 795

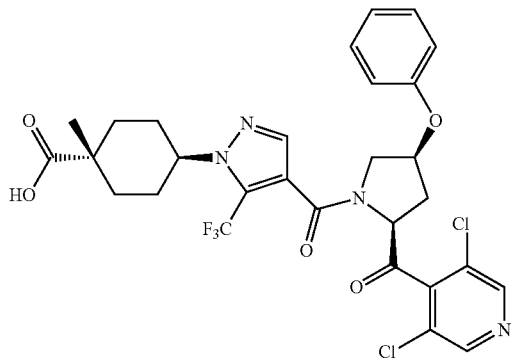 [SMILES: C[C@]1(C(=O)O)CC[C@H](n2ncc(C(=O)N3C[C@@H](Oc4ccccc4)C[C@H]3C(=O)c3c(Cl)cncc3Cl)c2C(F)(F)F)CC1]

trans-4-(4#(2S,4S)-2-(3,5-dichloro-4-pyridinyl)carbonyl)-4-phenoxy-1-pyrrolidinyl)carbonyl)-5-(trifluoromethyl)-1H-pyrazol-1-yl)-1-methylcyclohexanecarboxylic acid The title compound was prepared according to example 822 using (2S,4S)-Boc-4-phenoxy-pyrrolidine-2-carboxylic acid (Chem Impex Int'l, Wood Dale, Ill., 2.07 g, 6.74 mmol). The mixture of epimers were separated using preparatory SFC under the following conditions. Step 1: Preparative SFC: OX—H (5 um, 21 mm×25 cm), Organic modifier: 15% MeOH. F=70 ml/min, T=40° C., BPR=100 bar, 220 nm. P=151 bar. All sample (605 mg) dissolved in MeOH (10 mL) ~60 mg/ml, 0.5 ml inj.

Step 2: Preparative SFC: Reprocessing Peak 2. OX—H (5 um, 21 mm×25 cm), Organic modifier: 25% MeOH. F=70 ml/min, T=40° C., BPR=100 bar, 220 nm. P=165 bar. All sample dissolved in MeOH (10 mL), ~60 mg/ml, 1.0 mL inj.

Step 3: Preparative SFC: Recycling Peak 1 collection. OX—H (5 um, 21 mm×25 cm) Organic modifier: 25% MeOH. F=70 ml/min, T=40° C., BPR=100 bar, 220 nm. P=165 bar. All sample dissolved in MeOH (10 mL), 1.0 ml inj. MS (ESI) 639.0, 641.0 [M+H]+. Note: this epimer was the second eluting peak under the separation conditions described above.

Example 796

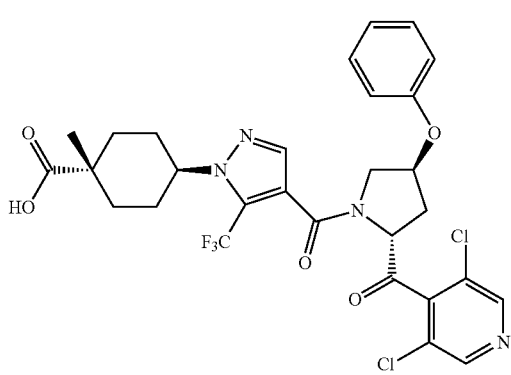 [SMILES: C[C@]1(C(=O)O)CC[C@H](n2ncc(C(=O)N3C[C@@H](Oc4ccccc4)C[C@@H]3C(=O)c3c(Cl)cncc3Cl)c2C(F)(F)F)CC1]

trans-4-(4#(2R,4S)-2#3,5-dichloro-4-pyridinyl)carbonyl)-4-phenoxy-1-pyrrolidinyl)carbonyl)-5-(trifluoromethyl)-1H-pyrazol-1-yl)-1-methylcyclohexanecarboxylic acid The title compound was isolated (107 mg, 0.17 mmol, 11% yield) as a light yellow amorphous solid following preparatory SFC separation of the mixture of epimers (at the C2 position of the pyrrolidine) from Example 712. MS (ESI) 639.0, 641.0 [M+H]+. Note: this epimer was the third eluting peak under the separation conditions described above for example 795.

Example 797

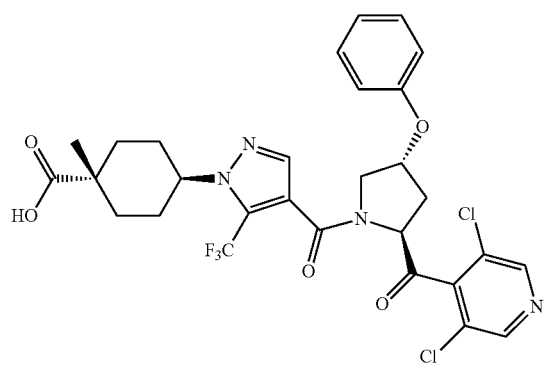 [SMILES: C[C@]1(C(=O)O)CC[C@H](n2ncc(C(=O)N3C[C@H](Oc4ccccc4)C[C@H]3C(=O)c3c(Cl)cncc3Cl)c2C(F)(F)F)CC1]

trans-4-(4#(2S,4R)-2#3,5-dichloro-4-pyridinyl)carbonyl)-4-phenoxy-1-pyrrolidinyl)carbonyl)-5-(trifluoromethyl)-1H-pyrazol-1-yl)-1-methylcyclohexanecarboxylic acid The title compound was isolated (6.7 mg, 10.48 µmol, 0.7% yield) as a light yellow amorphous solid following preparatory SFC separation of the mixture of epimers (at the C2 position of the pyrrolidine) from example 795. MS (ESI) 639.0, 641.0 [M+H]+. Note: this epimer was the first eluting peak under the separation conditions described above for example 795.

Example 798

(1r,4r)-4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylic acid

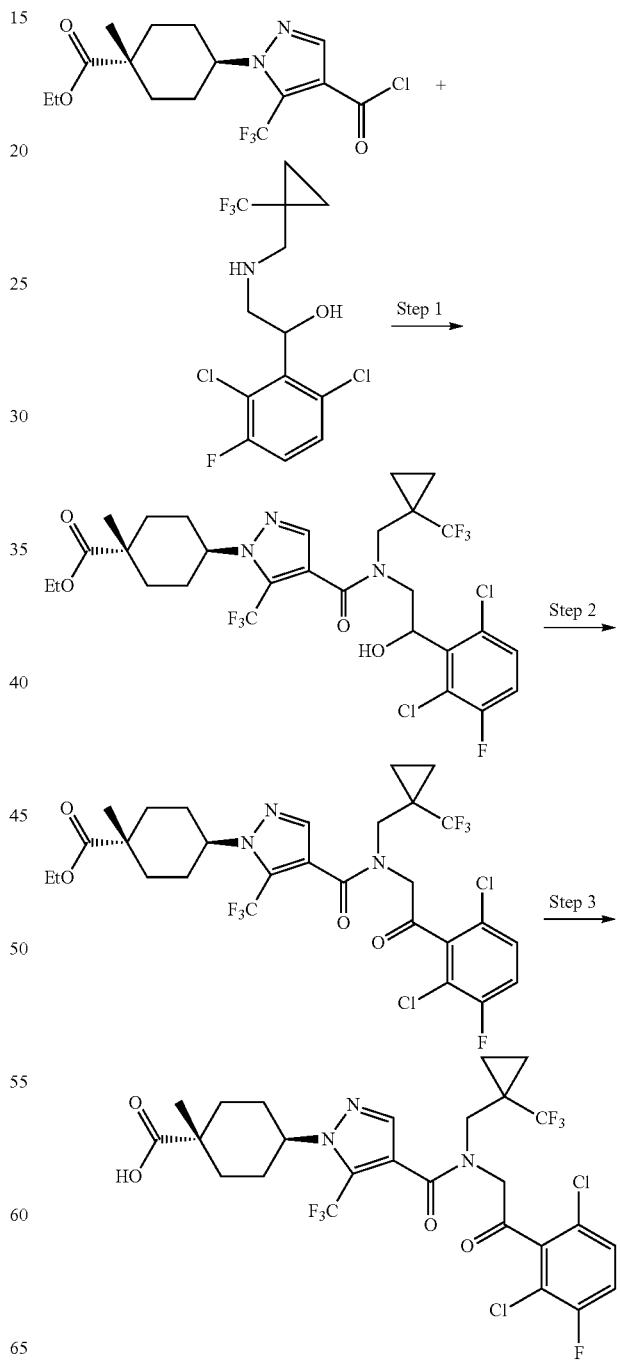

Step 1: (1r,4r)-ethyl 4-(4-((2-(2,6-dichloro-3-fluorophenyl)-2-hydroxyethyl)((1-(trifluoromethyl)cyclopropyl)methyl)carbamoyl)-5-(trifluoromethyl)-1H-pyrazol-1-yl)-1-methylcyclohexanecarboxylate To a solution of 1-(2,6-dichloro-3-fluorophenyl)-2-(((1-(trifluoromethyl)cyclopropyl)methyl)amino)ethanol (116 mg, 0.335 mmol) and (1r,4r)-ethyl 4-(4-(chlorocarbonyl)-5-(trifluoromethyl)-1H-pyrazol-1-yl)-1-methylcyclohexane carboxylate (147 mg, 0.402 mmol) in DCM (2.3 mL) was added DIPEA (117 µl, 0.670 mmol). The reaction mixture was stirred at room temperature. After 1.5 h, the reaction mixture was quenched with saturated aqueous $NaHCO_3$ and extracted with DCM. The combined organic layers were washed with water, brine, dried over anhydrous $Na_2SO_4$ and concentrated under reduced pressure to afford a light-yellow oil. The crude material was purified by column chromatography (silica gel, eluent: 10% to 70% EtOAc/heptane), to provide (1r,4r)-ethyl 4-(4-((2-(2,6-dichloro-3-fluorophenyl)-2-hydroxyethyl)((1-(trifluoromethyl)cyclopropyl)methyl)carbamoyl)-5-(trifluoromethyl)-1H-pyrazol-1-yl)-1-methylcyclohexanecarboxylate (150 mg, 0.222 mmol, 66.2% yield) as a white solid. LCMS: 675.9 $(M+H)^+$.

Step 2: (1r,4r)-ethyl 4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexane carboxylate A mixture of (1r,4r)-ethyl 4-(4-((2-(2,6-dichloro-3-fluorophenyl)-2-hydroxyethyl)((1-(trifluoromethyl)cyclopropyl)methyl)carbamoyl)-5-(trifluoromethyl)-1H-pyrazol-1-yl)-1-methylcyclohexanecarboxylate (150 mg, 0.222 mmol), TEMPO (3.46 mg, 0.022 mmol), DCM (2.2 mL) and 1 M aq $NaHCO_3$ (554 µl, 0.554 mmol) was stirred at 0° C. Then sodium hypochlorite, 5.65-6% (1.5 ml, 1.1 mmol) was added slowly. After 1 h, the reaction was quenched with saturated aqueous $Na_2S_2O_3$ at 0° C. and extracted with DCM (10 mL). The organic layer was dried over anhydrous $MgSO_4$, and concentrated under reduced pressure to afford colorless residue. The crude material was purified by column chromatography (silica gel, eluent: 0% to 40% EtOAc/heptane) to provide (1r,4r)-ethyl 4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexane carboxylate (113 mg, 0.168 mmol, 76% yield) as a white solid. $^1$H NMR (400 MHz, $CDCl_3$) δ 7.54 (s, 1H), 7.25-7.30 (m, 1H), 7.15-7.21 (m, 1H), 4.57 (s, 2H), 4.12-4.20 (m, 3H), 3.86 and 3.75 (2H, 2×s), 2.12-2.29 (m, 2H), 1.81-1.97 (m, 6H), 1.34-1.39 (m, 3H), 1.25-1.31 (m, 3H), 1.07 (d, J=6.4 Hz, 4H); LCMS: 674.1 $[M+H]^+$.

Step 3: (1r,4r)-4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylic acid To a mixture of (1r,4r)-ethyl 4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexane carboxylate (113 mg, 0.168 mmol) in MeOH (0.4 mL) and THF (0.4 mL) (1:1 ratio) was added 2 N aqueous NaOH (0.42 µl, 0.838 mmol). The reaction mixture was heated to 50° C. for 2 h. It was concentrated, cooled to 0° C. and acidified with 1 N aqueous HCl solution. The white solid was collected, washed with water and dried under reduced pressure to provide (1r,4r)-4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylic acid (86 mg, 0.133 mmol, 79% yield). $^1$H NMR (400 MHz, DMSO-$d_6$) δ 12.26 (br. s., 1H), 7.68 (s, 1H), 7.62 (d, J=6.5 Hz, 2H), 4.88 and 4.71 (2H, 2×s), 4.27 (m, 1H), 3.77 and 3.67 (2H, 2×m), 1.98-2.16 (m, 2H), 1.69-1.90 (m, 6H), 1.20-1.27 (m, 3H), 1.01 (br. s., 4H); LCMS: 645.9$[M+H]^+$.

Example 813

(1S,2S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2-methylcyclohexanecarboxylic acid

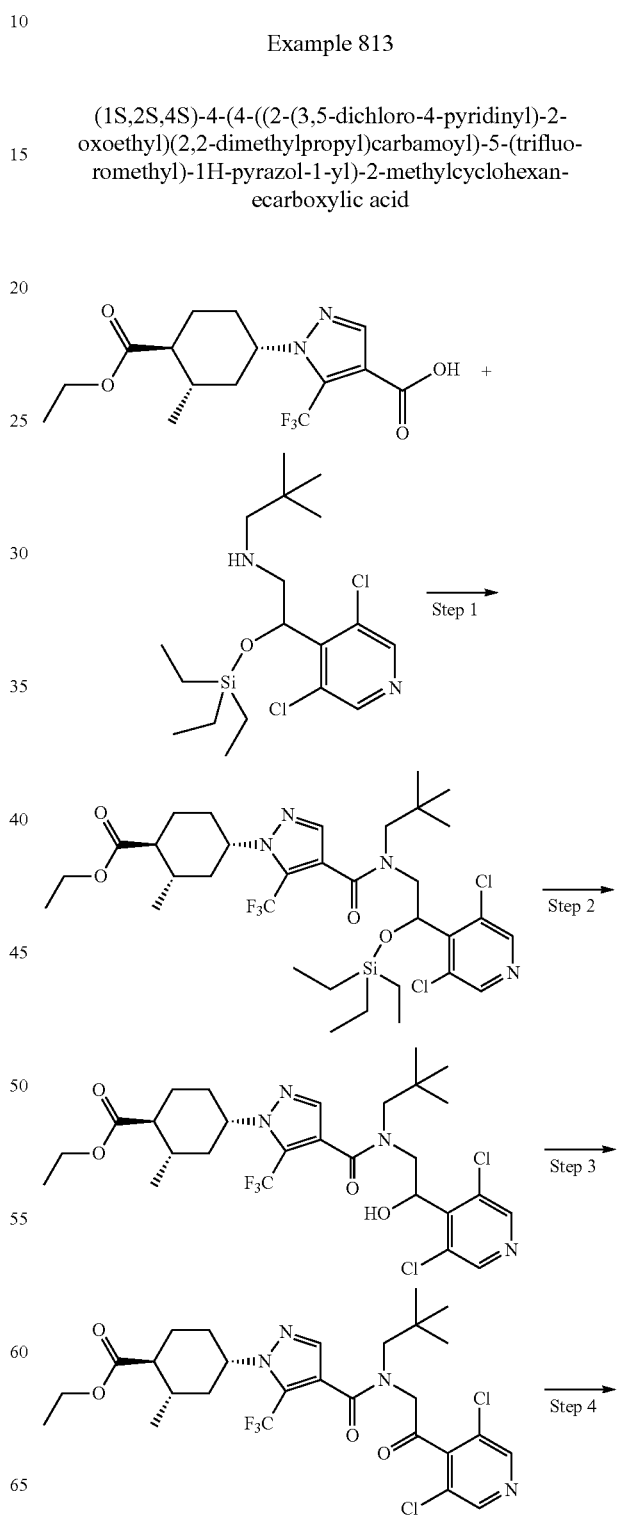

Step 1 and Step 2: (1S,2S,4S)-ethyl 4-(4-((2-3,5-dichloropyridin-4-yl)-2-hydroxyethyl)(neopentyl) carbamoyl)-5-(trifluoromethyl)-1H-pyrazol-1-yl)-2-methylcyclohexanecarboxylate with its (1R,2R,4R)-isomer

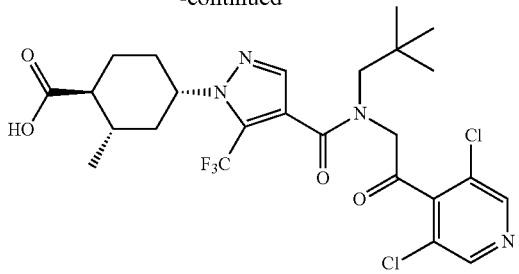

To a light-yellow clear solution of 1-((1S,3S,4S)-4-(ethoxycarbonyl)-3-methylcyclohexyl)-5-(trifluoromethyl)-1H-pyrazole-4-carboxylic acid with its (1R,3R,4R)-isomer (0.3128 g, 0.898 mmol) in DCM (8.98 ml) was added oxalyl chloride (0.095 ml, 1.123 mmol) followed by DMF (1 drop) and the light-yellow clear reaction mixture was stirred at room temperature. After 2 h. The mixture was concentrated in vacuo to give (1S,2S,4S)-ethyl 4-(4-(chlorocarbonyl)-5-(trifluoromethyl)-1H-pyrazol-1-yl)-2-methylcyclohexane carboxylate with its (1R,2R,4R)-isomer as brown syrupy solid. To the residue was added a solution of N-(2-(3,5-dichloropyridin-4-yl)-2-((triethylsilyl)oxy)ethyl)-2,2-dimethylpropan-1-amine (0.352 g, 0.898 mmol) in THF (8.98 ml) followed by DIPEA (0.626 ml, 3.59 mmol). The brown heterogeneous mixture was stirred at room temperature. After 3 h, LC-MS (ESI) showed that the intermediate (1S,2S,4S)-ethyl 4-(4-((2-(3,5-dichloropyridin-4-yl)-2-((triethylsilyl)oxy)ethyl)(neopentyl)carbamoyl)-5-(trifluoromethyl)-1H-pyrazol-1-yl)-2-methylcyclohexanecarboxylate with its (1R,2R,4R)-isomer was formed: LCMS (ESI) m/z 721.1 (M+H)$^+$.

To the reaction mixture was added TBAF solution, 1.0 M in THF (3.59 ml, 3.59 mmol). After 1 hour, the reaction mixture was diluted with water (30 mL) and brine (30 mL). The reaction mixture was extracted with EtOAc (2×50 mL). The organic extract washed with satd NaCl (1×100 mL) and dried over Na$_2$SO$_4$. The solution was filtered and concentrated in vacuo to give the crude material as a orange syrup. The crude material was absorbed onto a plug of silica gel and purified by silica gel column chromatography eluting with a gradient of 0% to 50% EtOAc in hexane to provide (1S,2S,4S)-ethyl 4-(4-((2-(3,5-dichloropyridin-4-yl)-2-hydroxyethyl)(neopentyl)carbamoyl)-5-(trifluoromethyl)-1H-pyrazol-1-yl)-2-methylcyclohexanecarboxylate with its (1R,2R,4R)-isomer (0.4742 g, 0.781 mmol, 87% yield) as off-white syrupy solid: $^1$H NMR (300 MHz, DMSO-d$_6$) δ 8.44-8.63 (2H, m), 7.57-7.71 (1H, m), 6.01 (1H, d, J=4.4 Hz), 5.28 (1H, dt, J=9.0, 4.5 Hz), 4.32 (1H, d, J=7.2 Hz), 4.11 (2H, q, J=7.1 Hz), 3.85 (1H, dd, J=14.6, 9.2 Hz), 3.53 (2H, d, J=13.0 Hz), 3.32-3.41 (1H, m), 1.49-2.16 (8H, m), 1.21 (3H, t, J=7.1 Hz), 0.63-0.98 (12H, m), (several peak sets due to diastereomers and rotamers); LCMS (ESI) m/z 607.1 (M+H)$^+$.

Step 3: (1S,2S,4S)-ethyl 4-(4-((2-(3,5-dichloropyridin-4-yl)-2-oxoethyl)(neopentyl)carbamoyl)-5-(trifluoromethyl)-1H-pyrazol-1-yl)-2-methylcyclohexanecarboxylate To a light-yellow clear solution of (1S,2S,4S)-ethyl 4-(4-((2-(3,5-dichloropyridin-4-yl)-2-hydroxyethyl)(neopentyl)carbamoyl)-5-(trifluoromethyl)-1H-pyrazol-1-yl)-2-methylcyclohexanecarboxylate with its (1R,2R,4R)-isomer (0.4702 g, 0.774 mmol) in DCM (12.90 ml) was added Dess-Martin periodinane (0.492 g, 1.161 mmol). The white cloudy mixture was stirred at room temperature. After 2 h, the mixture was quenched with saturated aqueous NaHCO$_3$ (30 mL) and saturated aqueous Na$_2$S$_2$O$_3$ (30 mL). The reaction mixture was extracted with DCM (2×50 mL). The organic extract was dried over Na$_2$SO$_4$. The solution was filtered and concentrated in vacuo to give the crude material as a colorless syrup. The crude material was absorbed onto a plug of silica gel and purified by silica gel column chromatography eluting with a gradient of 0% to 50% EtOAc in hexane to give (1S,2S,4S)-ethyl 4-(4-((2-(3,5-dichloropyridin-4-yl)-2-oxoethyl)(neopentyl)carbamoyl)-5-(trifluoro methyl)-1H-pyrazol-1-yl)-2-methylcyclohexanecarboxylate with its (1R,2R,4R)-isomer (0.437 g, 0.722 mmol, 93% yield): $^1$H NMR (400 MHz, CDCl$_3$) δ 8.46-8.61 (2H, m), 7.51-7.74 (1H, m), 4.49-4.92 (2H, m), 4.25-4.39 (1H, m), 4.18 (2H, q, J=7.1 Hz), 3.29-3.61 (2H, m), 1.63-2.18 (8H, m), 1.29 (3H, t, J=7.1 Hz), 0.81-1.06 (12H, m), rotamers present; LCMS (ESI) m/z 605.0 (M+H)$^+$.

The racemic mixture was separated by SFC to give two fractions:

The stereochemistry of each fraction was arbitrarily assigned.

First peak on SFC IA column: (1R,2R,4R)-ethyl 4-(4-((2-(3,5-dichloropyridin-4-yl)-2-oxoethyl)(neopentyl)carbamoyl)-5-(trifluoromethyl)-1H-pyrazol-1-yl)-2-methylcyclohexanecarboxylate (0.1588 g, 0.262 mmol, 33.9% yield) as white solid: $^1$H NMR (300 MHz, DMSO-d$_6$) δ 8.68-8.87 (2H, m), 7.71-7.89 (1H, m), 4.65-4.92 (2H, m), 4.33 (1H, br. s.), 4.10 (2H, q, J=7.0 Hz), 3.24-3.30 (2H, m), 1.49-2.17 (8H, m), 1.20 (3H, t, J=7.1 Hz), 0.73-1.00 (12H, m); LCMS (ESI) m/z 605.0 (M+H)$^+$.

Second peak on SFC IA column: (1S,2S,4S)-ethyl 4-(4-((2-(3,5-dichloropyridin-4-yl)-2-oxoethyl)(neopentyl)carbamoyl)-5-(trifluoro methyl)-1H-pyrazol-1-yl)-2-methylcyclohexanecarboxylate (0.1526 g, 0.252 mmol, 32.6% yield) as white solid: $^1$H NMR (300 MHz, DMSO-d$_6$) δ 8.70-8.87 (2H, m), 7.72-7.89 (1H, m), 4.64-4.93 (2H, m), 4.34 (1H, d, J=5.1 Hz), 4.10 (2H, q, J=7.0 Hz), 3.27 (2H, br. s.), 1.50-2.18 (8H, m), 1.20 (3H, t, J=7.1 Hz), 0.72-1.01 (12H, m); LCMS (ESI) m/z 605.0 (M+H)$^+$.

Step 4: (1S,2S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2-methylcyclohexanecarboxylic acid To a mixture of the racemic mixture of (1S,2S,4S)-ethyl 4-(4-((2-(3,5-dichloropyridin-4-yl)-2-oxoethyl)(neopentyl) carbamoyl)-5-(trifluoro methyl)-1H-pyrazol-1-yl)-2-methylcyclohexanecarboxylate (0.1245 g, 0.206 mmol) in THF (1.645 ml), EtOH (1.645 ml), and water (0.822 ml) was added 2 M LiOH in water (1.028 ml, 2.056 mmol). The yellow homogeneous mixture was stirred and heated at 60° C. After 17 h, the reaction mixture was concentrated in vacuo to remove THF and EtOH. The resulting aqueous solution was diluted with water (10 mL). The pH of the solution was adjusted to ~3.0 with 2 N HCl and the resulting precipitate was collected by vacuum filtration and freeze-dried on lyophilizer overnight to provide example 813 (0.0939 g, 0.163 mmol, 79% yield) as white solid. $^1$H NMR (300 MHz, DMSO-d$_6$) δ 12.19 (1H, br. s.), 8.57-9.91 (2H, m), 7.72-7.88 (1H, m), 4.65-5.39 (2H, m), 4.32 (1H, d, J=4.5 Hz), 3.22-3.53 (2H, m), 1.46-2.10 (8H, m), 0.72-1.03 (12H, m), rotamers present; LC-MS (ESI) m/z 577.1 (M+H)$^+$.

The stereochemistry was arbitrarily assigned as (1S,2S,4S).

341
Example 822
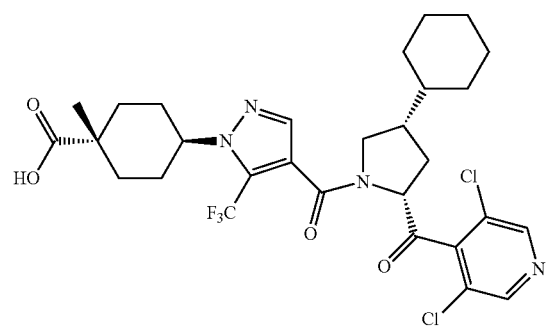 [SMILES: C[C@]1(C(=O)O)CC[C@H](n2ncc(C(=O)N3C[C@H](C4CCCCC4)C[C@@H]3C(=O)c3c(Cl)cncc3Cl)c2C(F)(F)F)CC1]
trans-4-(4-(((2R,4S)-4-cyclohexyl-2-((3,5-dichloro-4-pyridinyl)carbonyl)-1-pyrrolidinyl)carbonyl)-5-(trifluoromethyl)-1H-pyrazol-1-yl)-1-methylcyclohexanecarboxylic acid
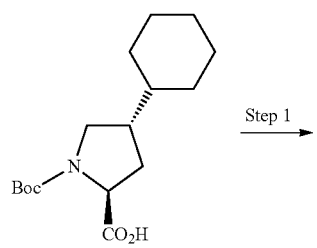
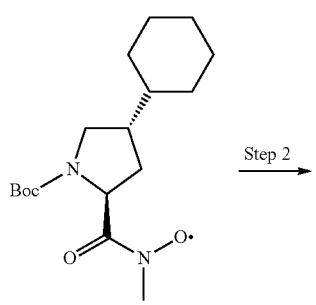
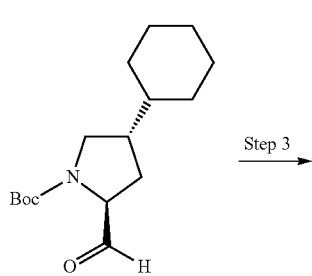
342
-continued
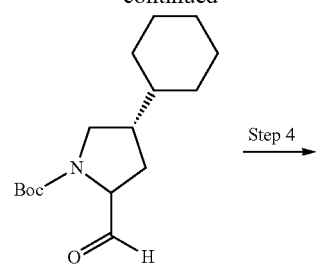
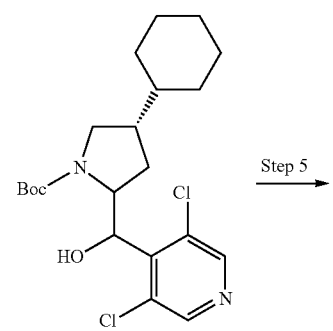
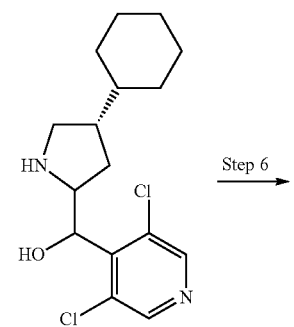
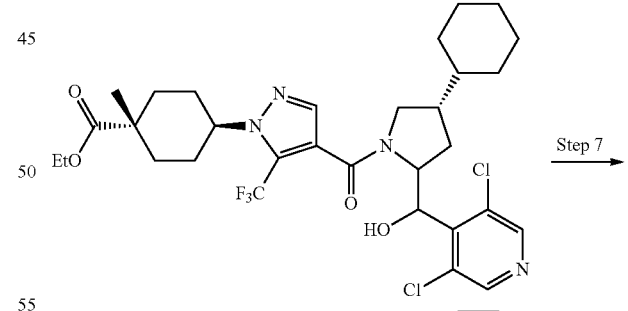
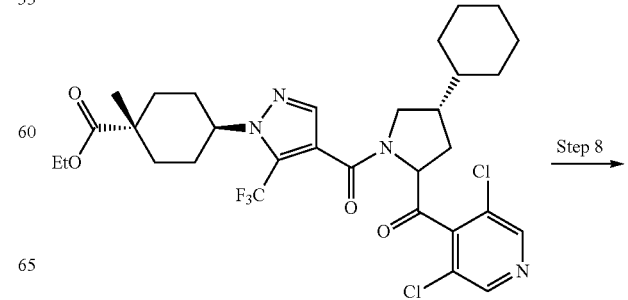

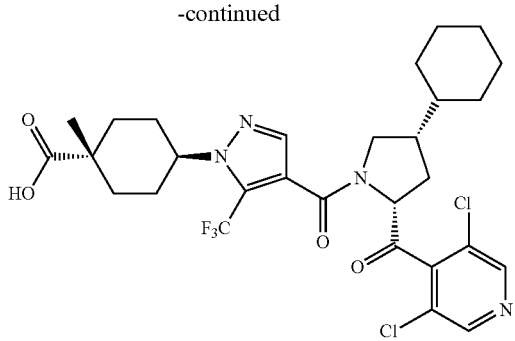

Example 822

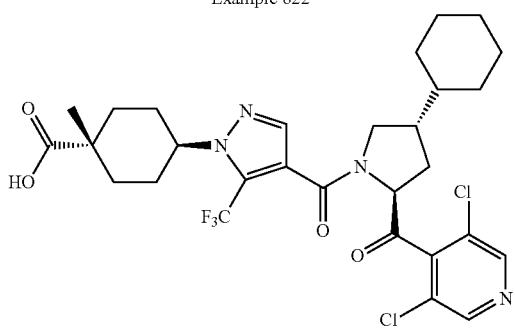

Example 823

Step 1: (2S,4S)-Boc-4-cyclohexyl-pyrrolidine-2-carboxylic acid (Chem Impex Int'l, Wood Dale, Ill., 997 mg, 3.35 mmol) was treated with DCM (25 mL) followed by 1,1'-carbonyldiimidazole (598 mg, 3.69 mmol). The solution was allowed to stir at room temperature for 1.5 h then the reaction mixture was then treated with N,O-dimethyl hydroxylamine hydrochloride (360 mg, 3.69 mmol) and allowed to stir over the weekend at room temperature. The reaction mixture was diluted with EtOAc (50 mL), washed with a saturated solution of NaHCO$_3$ (30 mL) and brine (30 mL), dried over MgSO$_4$, filtered and concentrated affording crude (2S,4S)-tert-butyl 4-cyclohexyl-2-(methoxy(methyl)carbamoyl)pyrrolidine-1-carboxylate (1.14 g, 3.35 mmol, 99% yield) as a clear, colorless viscous oil. MS (ESI) 363.2 [M+Na]$^+$. The crude material was used in the next step without further purification.

Step 2: (2S,4S)-tert-butyl 4-cyclohexyl-2-(methoxy(methyl)carbamoyl)pyrrolidine-1-carboxylate (1.14 g, 3.35 mmol) was treated with THF (20 mL), cooled to 0° C. in an ice bath and then treated with lithium aluminum hydride (1.0M solution in THF, 3.35 mL, 3.35 mmol) slowly dropwise over 3 min. The solution was then stirred at 0° C. for 45 min. The reaction mixture was quenched with a solution of sodium potassium tartrate, stirred at room temperature for 20 min, then extracted with EtOAc (3×50 mL), washed with brine and dried over MgSO$_4$, filtered and concentrated affording crude (2S,4S)-tert-butyl 4-cyclohexyl-2-formylpyrrolidine-1-carboxylate as a clear, viscous oil. MS (ESI) 304.1 [M+Na]. The crude material was used in the next step without further purification.

Step 3: (2S,4S)-tert-butyl 4-cyclohexyl-2-formylpyrrolidine-1-carboxylate (943 mg, 3.35 mmol) was treated with THF (20 mL) and DBU (1.0 mL, 6.70 mmol) and allowed to stir at room temperature overnight. The reaction mixture was concentrated to dryness on the rotovap, treated with DCM and a saturated solution of NH$_4$Cl and extracted, washed with brine, dried over MgSO$_4$, filtered and concentrated affording a mixture of crude (2S,4S)-tert-butyl 4-cyclohexyl-2-formylpyrrolidine-1-carboxylate and (2R,4S)-tert-butyl 4-cyclohexyl-2-formylpyrrolidine-1-carboxylate (470 mg, 1.67 mmol, 99% yield) as a clear, colorless viscous oil. MS (ESI) 304.1 [M+Na]$^+$.

Step 4: Lithium diisopropylamide (2.0 M solution in heptane/THF/ethylbenzene, 3.51 mL, 7.02 mmol) was added to 3,5-dichloropyridine (820 mg, 5.54 mmol) dissolved in THF (15 mL) cooled at −78° C. and stirred at this temperature for 1 h. (2S,4S)-tert-butyl 4-cyclohexyl-2-formylpyrrolidine-1-carboxylate (1.04 g, 3.70 mmol) and its epimer at C2 of the pyrrolidine in THF (11 mL) was added and the solution was removed from the cooling bath and allowed to warm to room temperature and stirred for 2 h. The solution was quenched with saturated ammonium chloride, the aqueous layer was extracted with EtOAc (2×50 mL) and the organic layer washed with brine (30 mL) and dried over anhydrous magnesium sulfate, filtered and concentrated. The crude product was purified on an ISCO Combiflash™ RF (40 g Grace Reverlis column, using a gradient of 0-80% EtOAc in heptane) affording (2S,4S)-tert-butyl 4-cyclohexyl-2-((S)-(3,5-dichloropyridin-4-yl)(hydroxy)methyl)pyrrolidine-1-carboxylate (1.20 g, 2.79 mmol, 76% yield) as a mixture of epimers. MS (ESI) 451.1, 453.1 [M+Na]$^+$.

Step 5: (2S,4S)-tert-butyl 4-cyclohexyl-2-((S)-(3,5-dichloropyridin-4-yl)(hydroxy)methyl)pyrrolidine-1-carboxylate (1.20 g, 2.79 mmol) and its epimer at C2 of the pyrrolidine was treated with DCM (10 mL) and TFA (7 mL, 91 mmol) and allowed to stir at room temperature for 1.5 h. The reaction mixture was concentrated on the rotovap and the crude residue purified on an ISCO Combiflash™ RF (40 g Grace Reveleris column, using a gradient of 0-20% 2M NH$_3$/MeOH in DCM) affording (S)-((2S,4S)-4-cyclohexylpyrrolidin-2-yl)(3,5-dichloropyridin-4-yl)methanol 2,2,2-trifluoroacetate (755 mg, 1.705 mmol, 61% yield) along with its epimer at C2 of the pyrrolidine as a light tan-colored foam. MS (ESI) 329.0, 331.1 [M+H]$^+$.

Step 6: Oxalyl chloride (0.22 mL, 2.55 mmol) was added to a solution of 1-((1r,4r)-4-(ethoxycarbonyl)-4-methylcyclohexyl)-5-(trifluoromethyl)-1H-pyrazole-4-carboxylic acid (593 mg, 1.70 mmol) in DCM (10.0 mL), followed by 2 drops of DMF while cooling in an ice bath. The solution was then removed from the ice bath and allowed to stir at room temperature for 1 h. The reaction mixture was concentrated to dryness on the rotovap and the crude residue was treated with DCM (10.0 mL) and cooled to 0° C. The stirring solution was then treated with (S)-((2S,4S)-4-cyclohexylpyrrolidin-2-yl)(3,5-dichloropyridin-4-yl)methanol 2,2,2-trifluoroacetate (755 mg, 1.70 mmol) and DIPEA (0.89 mL, 5.11 mmol) in DCM (10 mL) and allowed to warm to room temperature and stirred for 1 h. The reaction mixture was concentrated to dryness under reduced pressure (rotary evaporator) and the crude residue was purified on an ISCO Combiflash™ RF (40 g Grace Reveleris column, using a gradient of 0-100% EtOAc in heptane) affording (1S,4r)-ethyl 4-(4-((2S,4S)-4-cyclohexyl-2-((S)-(3,5-dichloropyridin-4-yl)(hydroxy)methyl)pyrrolidine-1-carbonyl)-5-(trifluoromethyl)-1H-pyrazol-1-yl)-1-methylcyclohexanecarboxylate (640 mg, 0.970 mmol, 57% yield) along with its epimer at C2 of the pyrrolidine as a light tan foam. MS (ESI) 659.2, 661.1 [M+H]$^+$.

Step 7: Dess-Martin Periodinane (823 mg, 1.94 mmol) and (1R,4r)-ethyl 4-(4-((2R,4S)-4-cyclohexyl-2-((R)-(3,5-dichloropyridin-4-yl)(hydroxy)methyl)pyrrolidine-1-carbonyl)-5-(trifluoromethyl)-1H-pyrazol-1-yl)-1-methylcyclohexanecarboxylate (640 mg, 0.97 mmol) as a mixture with its epimer at C2 of the pyrrolidine were treated with DCM (10 mL) and allowed to stir at room temperature for 3 h. The reaction was treated with a saturated solution of NaHCO$_3$ and solid sodium metabisulfite. The reaction mixture was then extracted with DCM (2×75 mL), dried over MgSO₄, filtered and concentrated affording crude product as a light orange foam. This residue was purified on an ISCO Combiflash™ RF (25 g Grace Reverlis column, using a gradient of 0-70% EtOAc in heptane) affording (1R,4r)-ethyl 4-(4-(((2R,4S)-4-cyclohexyl-2-(3,5-dichloroisonicotinoyl)pyrrolidine-1-carbonyl)-5-(trifluoromethyl)-1H-pyrazol-1-yl)-1-methylcyclohexanecarboxylate (605 mg, 95%) along with its epimer at C2 of the pyrrolidine as a light yellow foam. MS (ESI) 657.0, 659.0 [M+H]⁺.

Step 8: (1S,4r)-ethyl 4-(4-(((2S,4S)-4-cyclohexyl-2-(3,5-dichloroisonicotinoyl)pyrrolidine-1-carbonyl)-5-(trifluoromethyl)-1H-pyrazol-1-yl)-1-methylcyclohexanecarboxylate (454 mg, 0.69 mmol) and its epimer at C2 of the pyrrolidine in THF (3.5 mL) and MeOH (3.5 mL) was treated with lithium hydroxide monohydrate (1.0 M solution, 3.5 mL, 3.45 mmol). The mixture was stirred at room temperature overnight (16 h), the organics were removed under reduced pressure (rotary evaporator) and the resulting aqueous solution was acidified with 1 N HCl leading to the formation of a precipitate. The mixture was extracted with EtOAc (2×40 mL). The combined extracts were washed with brine, dried over anhydrous MgSO₄, filtered and concentrated. The crude material was absorbed onto a plug of silica gel and purified by chromatography on an ISCO Combiflash™ RF (25 g Thomson SingleStep column, using a gradient of 0-100% [10% MeOH in DCM] in DCM) affording a mixture of two products epimeric at C2 of the pyrrolidine. This material was subjected to separation on a preparatory SFC using the following conditions: OX column (SN=2121, 5 um, 21 mm×25 cm, 50/50/50 p=172), Organic modifier: 25% MeOH with 20 mM NH₃. F=70 ml/min, T=40° C., BPR=100 bar, 220 nm. P=165 bar, all sample (416 mg) dissolved in 8 mL of MeOH, ~52 mg/ml), 1.0 mL inj. affording trans-4-(4-(((2R,4S)-4-cyclohexyl-2-((3,5-dichloro-4-pyridinyl)carbonyl)-1-pyrrolidinyl)carbonyl)-5-(trifluoromethyl)-1H-pyrazol-1-yl)-1-methylcyclohexanecarboxylic acid (55.3 mg, 0.088 mmol, 13% yield) as a light yellow amorphous solid. MS (ESI) 629.1, 631.1 [M+H]⁺. Note: this epimer was the first eluting peak under the separation conditions described above.

Example 823

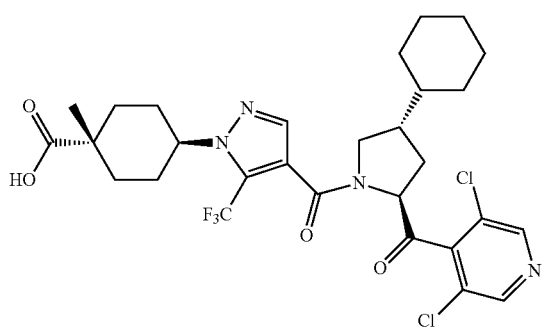 [SMILES: C[C@]1(C(=O)O)CC[C@H](n2ncc(C(=O)N3C[C@H](C4CCCCC4)C[C@H]3C(=O)c3c(Cl)cncc3Cl)c2C(F)(F)F)CC1]

trans-4-(4-(((2S,4S)-4-cyclohexyl-2-((3,5-dichloro-4-pyridinyl)carbonyl)-1-pyrrolidinyl)carbonyl)-5-(trifluoromethyl)-1H-pyrazol-1-yl)-1-methylcyclohexanecarboxylic acid The title compound was isolated (291 mg, 0.46 mmol, 67% yield) as a light yellow amorphous solid following preparatory SFC separation of the mixture of epimers (at the C2 position of the pyrrolidine) from Example 739. MS (ESI) 629.1, 631.1 [M+H]⁺. Note: this epimer was the second eluting peak under the separation conditions described above.

Example 827

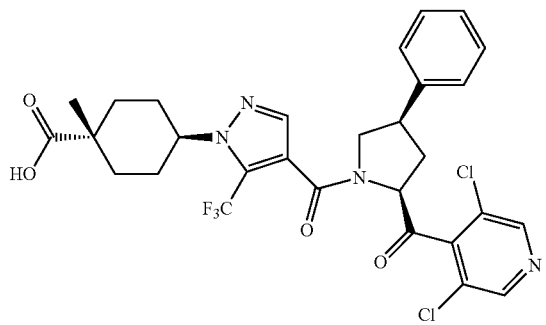 [SMILES: C[C@]1(C(=O)O)CC[C@H](n2ncc(C(=O)N3C[C@@H](c4ccccc4)C[C@H]3C(=O)c3c(Cl)cncc3Cl)c2C(F)(F)F)CC1]

trans-4-(4-(((2S,4R)-2-((3,5-dichloro-4-pyridinyl)carbonyl)-4-phenyl-1-pyrrolidinyl)carbonyl)-5-(trifluoromethyl)-1H-pyrazol-1-yl)-1-methylcyclohexanecarboxylic acid The title compound was prepared according to example 822 using (2S,4R)-1-(tert-butoxycarbonyl)-4-phenylpyrrolidine-2-carboxylic acid (Frontier Scientific, Newark, Del., 1.00 g, 3.43 mmol) and isolated (63.7 mg, 0.10 mmol, 18% yield) as a white amorphous solid. The mixture of epimers were separated using preparative SFC under the following conditions. Column: CHIRALPAK™ AZ-H (Reversed) (250×21 mm, 5 nm), Mobile Phase: 82:18 (A:B), A: Liquid CO₂, B: EtOH. Flow Rate: 70 mL/min. Column/Oven temp.: 40° C., 186-193 bar inlet pressure. SN: 403121. MS (ESI) 623.0, 625.0 [M+H]⁺. Note: this epimer was the second eluting peak under the separation conditions described above.

Example 828

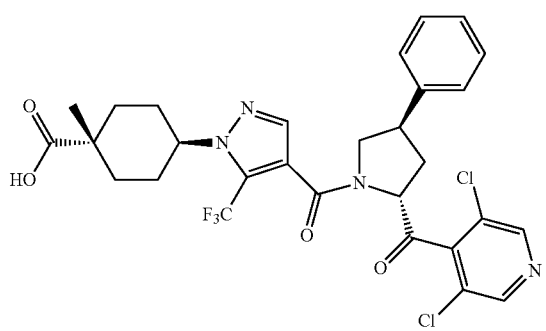 [SMILES: C[C@]1(C(=O)O)CC[C@H](n2ncc(C(=O)N3C[C@@H](c4ccccc4)C[C@@H]3C(=O)c3c(Cl)cncc3Cl)c2C(F)(F)F)CC1]

trans-4-(4-(((2R,4R)-2-(3,5-dichloro-4-pyridinyl)carbonyl)-4-phenyl-1-pyrrolidinyl)carbonyl)-5-(trifluoromethyl)-1H-pyrazol-1-yl)-1-methylcyclohexanecarboxylic acid The title compound was isolated (135 mg, 0.217 mmol, 39% yield) as a white foam following preparatory SFC separation of the mixture of epimers (at the C2 position of the pyrrolidine) from example 827. MS (ESI) 623.0, 625.0 [M+1-1]⁺. Note: this epimer was the third eluting peak under the separation conditions described above for example 827.

Example 845

(1S,2R,4S)-4-(4-((2-(2,6-dichloro-3-fluorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-2-methylcyclohexanecarboxylic acid

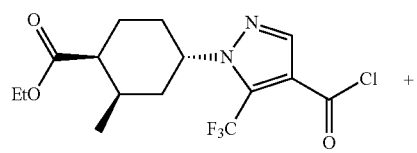
+
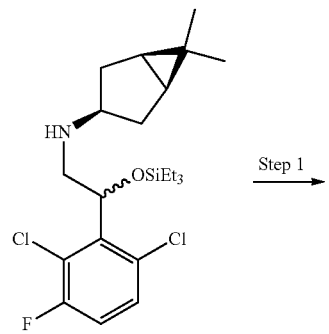
Step 1
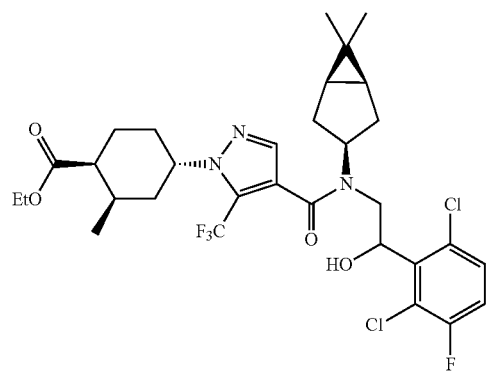
Step 2
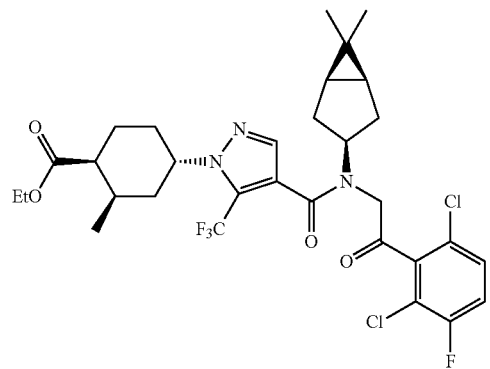
Step 3
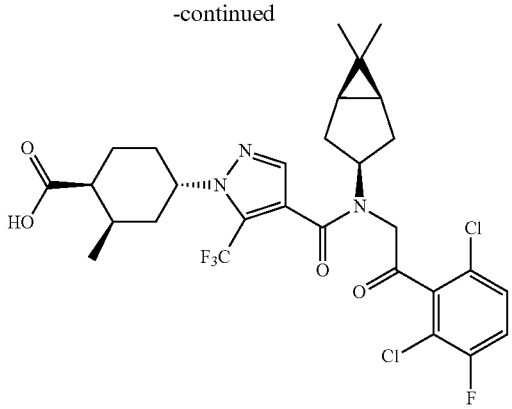

Step 1: (1S,2R,4S)-ethyl 4-(4-((2-(2,6-dichloro-3-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-2-methyl cyclohexanecarboxylate To a solution of (1R,3r,5S)—N-(2-(2,6-dichloro-3-fluorophenyl)-2-((triethylsilyl)oxy)ethyl)-6,6-dimethylbicyclo[3.1.0]hexan-3-amine (97 mg, 0.217 mmol) and (1S,2R,4S)-ethyl 4-(4-(chlorocarbonyl)-5-(trifluoromethyl)-1H-pyrazol-1-yl)-2-methylcyclohexane carboxylate (96 mg, 0.261 mmol) in DCM (0.8 mL) was added DIPEA (76 µl, 0.434 mmol). The reaction mixture was stirred at room temperature for 2 h. The reaction mixture was quenched with saturated aqueous NaHCO₃ solution and extracted with DCM (3×10 mL). The organic layer was combined, dried over anhydrous MgSO₄, filtered, and concentrated to afford product as yellow residue. The residue was dissolved with THF (0.75 mL), then added TBAF solution, 1.0 M in THF (434 µl, 0.434 mmol). The mixture was stirred at room temperature for 0.5 h. It was quenched with saturated aqueous NaHCO₃ and extracted with DCM. The combined organic layer washed with water, brine, dried over anhydrous Na₂SO₄ and concentrated under reduced pressure to afford a light-yellow oil. The crude material was purified by column chromatography (silica gel, eluent: 0% to 40% EtOAc/heptane) to provide (1S,2R,4S)-ethyl 4-(4-((2-(2,6-dichloro-3-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-2-methyl cyclohexanecarboxylate (96 mg, 0.145 mmol, 66.7% yield) as a white solid. LCMS: 662.1[M+H]⁺

Step 2: (1S,2R,4S)-ethyl 4-(4-((2-(2,6-dichloro-3-fluorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-2-methylcyclohexanecarboxylate (1S,2R,4S)-ethyl 4-(4-((2-(2,6-dichloro-3-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-2-methyl cyclohexanecarboxylate (96 mg, 0.145 mmol) was dissolved in DCM (3 mL) and Dess-Martin periodane (77 mg, 0.181 mmol) was added. It was stirred at room temperature for 3 h. The reaction mixture was quenched with 5% Na₂S₂O₃, washed with saturated NaHCO₃, dried with anhydrous Na₂SO₄ and concentrated. The crude product was purified by column chromatography (silica gel, eluent: 0-40% EtOAc/heptane) to afford (1S,2R,4S)-ethyl 4-(4-((2-(2,6- dichloro-3-fluorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-2-methylcyclohexanecarboxylate (90 mg, 0.136 mmol, 94% yield) as a viscous white oil. LCMS 660.0 [M+H]+.

Step 3: (1S,2R,4S)-4-(4-((2-(2,6-dichloro-3-fluorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-2-methylcyclohexanecarboxylic acid To a mixture of (1S,2R,4S)-ethyl 4-(4-((2-(2,6-dichloro-3-fluorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-2-methylcyclohexanecarboxylate (90 mg, 0.136 mmol) in MeOH (0.34 mL) and THF (0.34 mL) (1:1 ratio) was added 2 N aq. NaOH (0.34 mL, 0.68 mmol). The reaction mixture was heated to 50° C. for 3 h. It was concentrated, cooled to 0° C. and acidified with 1 N aqueous HCl. The white solid was collected, washed with water and dried under reduced pressure to provide (1S,2R,4S)-4-(4-((2-(2,6-dichloro-3-fluorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-2-methylcyclohexanecarboxylic acid (58 mg, 0.092 mmol, 67.3% yield). $^1$H NMR (500 MHz, DMSO-d$_6$) δ 12.18 (br. s., 1H), 7.87-7.56 (m, 2H), 7.40-7.51 (m, 1H), 4.96-5.10 (m, 1H), 4.53-4.77 (m, 1H), 4.11-4.52 (m, 2H), 2.54-2.64 (m, 1H), 1.66-2.24 (m, 10H), 1.35-1.59 (m, 2H), 1.19-1.29 (m, 1H), 0.82-1.14 (m, 15H); LCMS: 632.2 [M+H]+

Example 853 trans-4-(4-((2-(3,5-dichloro-4-pyridinyl)-2-oxoethyl)((1s,4s)-7-oxabicyclo[221]hept-1-ylmethyl)carbamoyl)-5-(trifluoromethyl)-1H-pyrazol-1-yl)-1-methylcyclohex anecarboxylic acid

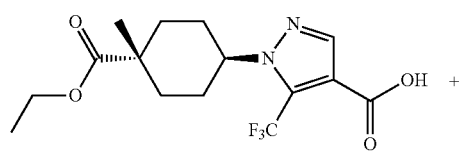

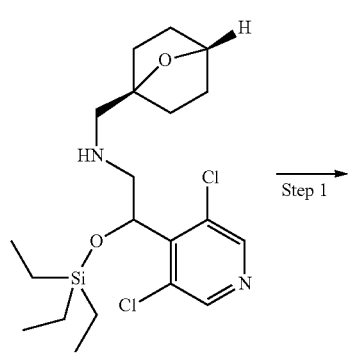

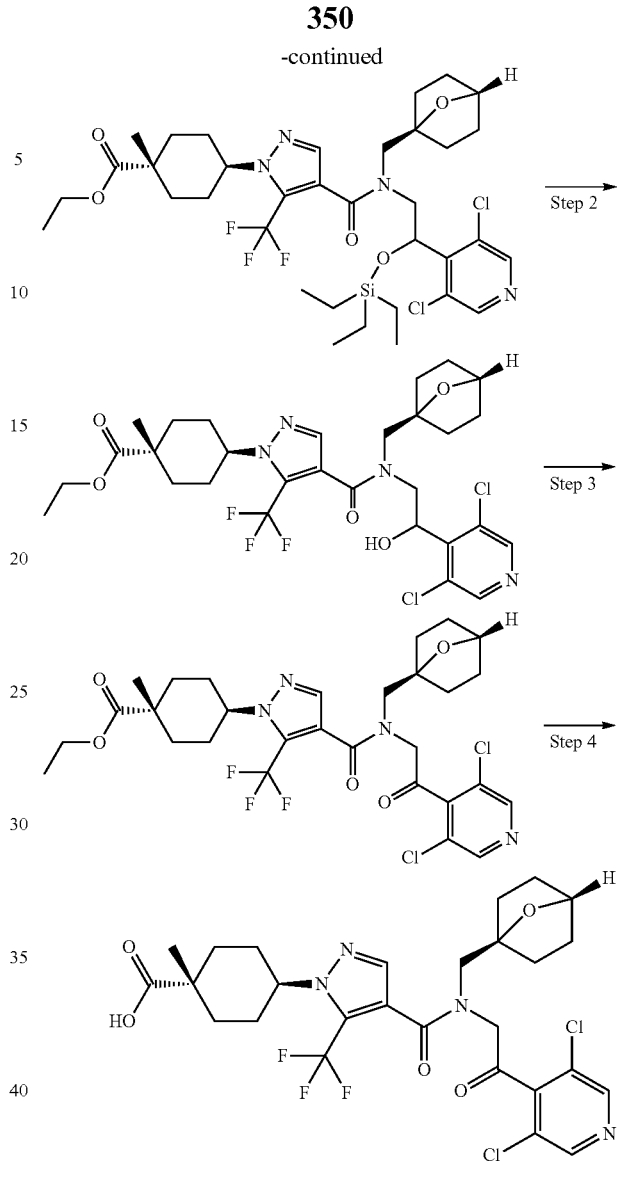

Step 1 and Step 2: ethyl trans-4-(4-(((1s,4S)-7-oxabicyclo[2.2.1]heptan-1-ylmethyl)(2-(3,5-dichloropyridin-4-yl)-2-hydroxyethyl)carbamoyl)-5-(trifluoromethyl)-1H-pyrazol-1-yl)-1-methyl cyclohexanecarboxylate To a clear solution of 1-((1r,4r)-4-(ethoxycarbonyl)-4-methylcyclohexyl)-5-(trifluoromethyl)-1H-pyrazole-4-carboxylic acid (0.121 g, 0.348 mmol) in DCM (3.48 ml) was added oxalyl chloride (0.037 ml, 0.435 mmol) followed by DMF (1 drop) and the clear reaction mixture was stirred at room temperature. After 5 h, the mixture was concentrated in vacuo to give (1r,4r)-ethyl 4-(4-(chlorocarbonyl)-5-(trifluoromethyl)-1H-pyrazol-1-yl)-1-methylcyclohexane carboxylate as light-yellow syrup. To the residue was added a solution of N-((1s,4s)-7-oxabicyclo[2.2.1]heptan-1-ylmethyl)-2-(3,5-dichloropyridin-4-yl)-2-((triethylsilyl)oxy)ethanamine (0.150 g, 0.348 mmol) in THF (3.48 ml) followed by DIPEA (0.242 ml, 1.391 mmol). The yellow heterogeneous mixture was stirred at room temperature. After 13 h, LCMS showed that the intermediate ethyl trans-4-(4-(((1s,4S)-7-oxabicyclo[2.2.1]heptan-1-ylmethyl)(2-(3,5-dichloropyridin-4-yl)-2-

((triethylsilyl)oxy)ethyl)carbamoyl)-5-(trifluoromethyl)-1H-pyrazol-1-yl)-1-methylcyclohexanecarboxylate was formed: LCMS (ESI) m/z 761.2 (M+H)+. To the reaction mixture was added TBAF solution, 1.0 M in THF (1.391 ml, 1.391 mmol). After 4 h, the reaction mixture was diluted with water (30 mL) and brine (30 mL). The reaction mixture was extracted with EtOAc (2×50 mL). The organic extract washed with satd NaCl (1×100 mL) and dried over $Na_2SO_4$.

The solution was filtered and concentrated in vacuo to give the crude material as a light-yellow syrup. The crude material was absorbed onto a plug of silica gel and purified by silica gel column chromatography eluting with a gradient of 0% to 50% EtOAc in heptane to provide ethyl trans-4-(4-(((1s,4S)-7-oxabicyclo[2.2.1]heptan-1-ylmethyl)(2-(3,5-dichloropyridin-4-yl)-2-hydroxyethyl)carbamoyl)-5-(trifluoromethyl)-1H-pyrazol-1-yl)-1-methyl cyclohexanecarboxylate (0.1083 g, 0.167 mmol, 48.1% yield) as colorless syrupy solid:
$^1$H NMR (400 MHz, DMSO-$d_6$) δ 8.43-8.59 (2H, m), 7.49-7.84 (1H, m), 5.95-6.04 (1H, m), 5.32-5.63 (1H, m), 3.51-4.54 (8H, m), 1.11-2.22 (22H, m), (diastereomers and rotamers present); LCMS (ESI) m/z 647.2 (M+H)+.

Step 3: ethyl trans-4-(4-(((1s,4S)-7-oxabicyclo[2.2.1]heptan-1-ylmethyl)(2-(3,5-dichloropyridin-4-yl)-2-oxoethyl)carbamoyl)-5-(trifluoromethyl)-1H-pyrazol-1-yl)-1-methylcyclohexanecarboxylate To a clear solution of ethyl trans-4-(4-(((1s,4S)-7-oxabicyclo[2.2.1]heptan-1-ylmethyl)(2-(3,5-dichloropyridin-4-yl)-2-hydroxyethyl)carbamoyl)-5-(trifluoromethyl)-1H-pyrazol-1-yl)-1-methyl cyclohexanecarboxylate (0.1015 g, 0.157 mmol) in DCM (2.61 ml) was added Dess-Martin periodinane (0.100 g, 0.235 mmol). The cloudy mixture was stirred at room temperature. After 2 h, the mixture was quenched with saturated aqueous $Na_2S_2O_3$ (30 mL) and saturated aqueous $NaHCO_3$ (30 mL). The reaction mixture was extracted with DCM (2×50 mL). The organic extract was dried over $Na_2SO_4$.

The solution was filtered and concentrated in vacuo to give the crude material as a light-yellow syrup. The crude material was absorbed onto a plug of silica gel and purified by silica gel column chromatography eluting with a gradient of 0% to 50% EtOAc in heptane to provide ethyl trans-4-(4-(((1s,4S)-7-oxabicyclo[2.2.1]heptan-1-ylmethyl)(2-(3,5-dichloropyridin-4-yl)-2-oxoethyl)carbamoyl)-5-(trifluoromethyl)-1H-pyrazol-1-yl)-1-methylcyclohexanecarboxylate (0.0841 g, 0.130 mmol, 83% yield) as colorless syrup. $^1$H NMR (400 MHz, $CDCl_3$) δ 8.43-8.60 (2H, m), 7.51-7.68 (1H, m), 3.71-5.12 (8H, m), 1.21-2.36 (22H, m), rotamers present; LC-MS (ESI) m/z 645.0 (M+H)+.

Step 4: trans-4-(4-((2-(3,5-dichloro-4-pyridinyl)-2-oxoethyl)((1s,4s)-7-oxabicyclo[221]hept-1-ylmethyl)carbamoyl)-5-(trifluoromethyl)-1H-pyrazol-1-yl)-1-methylcyclohex anecarboxylic acid To clear solution of ethyl trans-4-(4-(((1s,4S)-7-oxabicyclo[2.2.1]heptan-1-ylmethyl)(2-(3,5-dichloropyridin-4-yl)-2-oxoethyl)carbamoyl)-5-(trifluoromethyl)-1H-pyrazol-1-yl)-1-methylcyclohexanecarboxylate (0.0786 g, 0.122 mmol) in THF (0.974 ml), EtOH (0.974 ml), and water (0.487 ml) was added 2 M LiOH in water (0.609 ml, 1.218 mmol). The yellow homogeneous mixture was stirred and heated at 60° C. After 10 h, the reaction mixture was concentrated in vacuo to remove THF and EtOH. The resulting aqueous solution was diluted with water (10 mL). The pH of the solution was adjusted to ~3.0 with 2 N HCl and the resulting precipitate was collected by vacuum filtration, wash with water, and freeze-dried on lyophilizer overnight to provide example 853 as white solid. $^1$H NMR (400 MHz, DMSO-$d_6$) δ 12.25 (1H, br. s.), 8.57-8.84 (2H, m), 7.69-7.86 (1H, m), 4.77-5.00 (2H, m), 4.40-4.53 (1H, m), 4.25 (1H, t, J=11.3 Hz), 3.64-4.06 (2H, m), 1.10-2.20 (19H, m), rotamers present; LCMS (ESI) m/z 617.0 (M+H)+.

Example 872

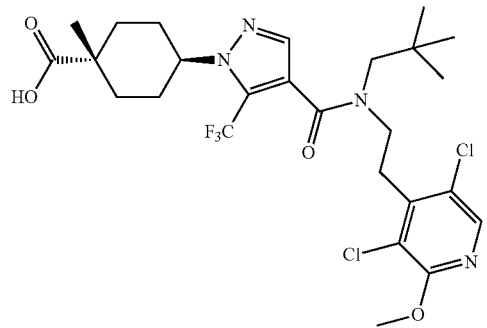 [SMILES: COc1ncc(Cl)c(CCN(CC(C)(C)C)C(=O)c2cnn([C@H]3CC[C@](C)(C(=O)O)CC3)c2C(F)(F)F)c1Cl]

trans-4-(4-((2-(3,5-dichloro-2-methoxy-4-pyridinyl)ethyl)(2,2-dimethylpropyl)carbamoyl)-5-(trifluoromethyl)-1H-pyrazol-1-yl)-1-methylcyclohexanecarboxylic acid The title compound was prepared from N-(2-(3,5-dichloro-2-methoxypyridin-4-yl)ethyl)-2,2-dimethylpropan-1-amine and 1-((1r,4r)-4-(ethoxycarbonyl)-4-methylcyclohexyl)-5-(trifluoromethyl)-1H-pyrazole-4-carboxylic acid by procedures similar to those described in example 545. MS (ESI) 593.2, 595.1 [M+H]+.

Example 879

(1S,2S,4S)-4-(4-((2-(3,5-dichloro-4-pyridinyl)-2-oxoethyl)(3,3,3-trifluoro-2,2-dim ethylpropyl)carbamoyl)-5-(trifluoromethyl)-1H-pyrazol-1-yl)-2-methylcyclohexanecarboxylic acid

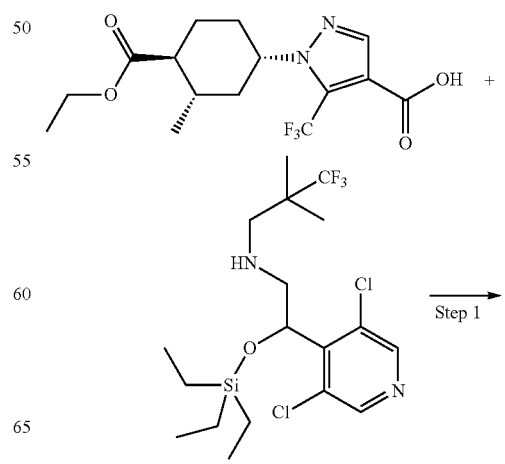

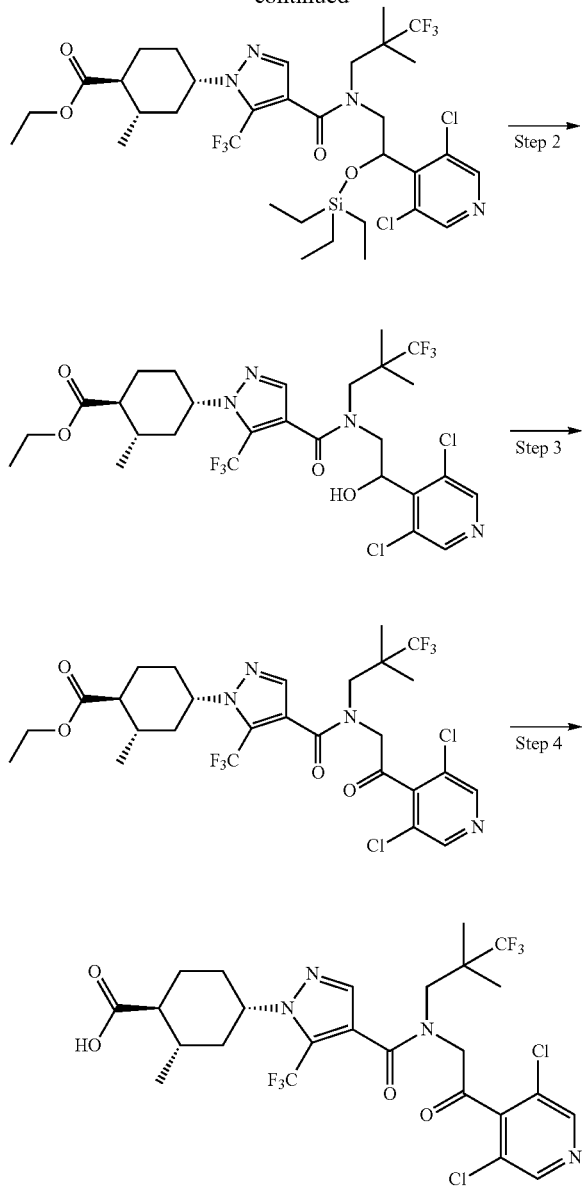

Step 1 and Step 2: (1R,2R,4R)-ethyl 4-(4-((2-3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-2-methylcyclohexanecarboxylate compound with (1S,2S,4S)-ethyl 4-(4-((2-3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-2-methylcyclohexanecarboxylate (1:1)

To a slightly cloudy mixture of 1-((1R,3R,4R)-4-(ethoxycarbonyl)-3-methylcyclohexyl)-5-(trifluoromethyl)-1H-pyrazole-4-carboxylic acid compound with 1-((1S,3S,4S)-4-(ethoxycarbonyl)-3-methylcyclohexyl)-5-(trifluoromethyl)-1H-pyrazole-4-carboxylic acid (1:1) (0.300 g, 0.431 mmol) in DCM (17.23 ml) was added oxalyl chloride (0.091 ml, 1.077 mmol) followed by DMF (1 drop) and the light-yellow slightly cloudy reaction mixture was stirred at room temperature. After 1.5 h, the mixture was concentrated in vacuo to give (1R,2R,4R)-ethyl 4-(4-(chlorocarbonyl)-5-(trifluoromethyl)-1H-pyrazol-1-yl)-2-methylcyclohexane carboxylate compound with (1S,2S,4S)-ethyl 4-(4-(chlorocarbonyl)-5-(trifluoromethyl)-1H-pyrazol-1-yl)-2-methylcyclohexane carboxylate (1:1) as light-yellow syrup.

To the yellow syrup was added a solution of N-(2-(3,5-dichloropyridin-4-yl)-2-((triethylsilyl)oxy)ethyl)-3,3,3-trifluoro-2,2-dimethylpropan-1-amine (0.384 g, 0.862 mmol) in THF (17.23 ml) followed by DIPEA (0.600 ml, 3.45 mmol). The yellow homogeneous mixture was stirred at room temperature. After 4 h, LCMS (ESI) showed that the intermediate (1S,2S,4S)-ethyl 4-(4-((2-(3,5-dichloropyridin-4-yl)-2-((triethylsilyl)oxy)ethyl)(3,3,3-trifluoro-2,2-dimethylpropyl)carbamoyl)-5-(trifluoromethyl)-1H-pyrazol-1-yl)-2-methylcyclohexanecarboxylate including its isomer (1R,2R,4R) was formed: LCMS (ESI) m/z 775.1 (M+H)+.

To the reaction mixture was added TBAF solution, 1.0 M in THF (3.45 ml, 3.45 mmol) and the yellow homogeneous mixture was stirred at room temperature. After 20 min, the reaction mixture was diluted with water (50 mL) and brine (50 mL). The reaction mixture was extracted with EtOAc (2×50 mL). The organic extract washed with satd NaCl (1×100 mL) and dried over $Na_2SO_4$. The solution was filtered and concentrated in vacuo to give the crude material as a light-yellow syrup. The crude material was absorbed onto a plug of silica gel and purified by silica gel column chromatography eluting with a gradient of 0% to 50% EtOAc in heptane to provide (1R,2R,4R)-ethyl 4-(4-((2-(3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-2-methylcyclohexanecarboxylate compound with (1S,2S,4S)-ethyl 4-(4-((2-(3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-2-methylcyclohexanecarboxylate (1:1) (0.4648 g, 0.351 mmol, 82% yield) as colorless syrup: $^1$H NMR (400 MHz, DMSO-$d_6$) δ 8.46-8.63 (2H, m), 7.70-7.82 (1H, m), 6.11 (1H, d, J=3.3 Hz), 5.20-5.32 (1H, m), 4.34 (1H, d, J=8.0 Hz), 4.06-4.16 (2H, m), 3.43-3.97 (4H, m), 1.53-2.15 (8H, m), 0.82-1.31 (12H, m), (diastereomers and rotamers); LCMS (ESI) m/z 661.1 (M+H)+.

Step 3: (1S,2S,4S)-ethyl 4-(4-((2-(3,5-dichloropyridin-4-yl)-2-oxoethyl)(3,3,3-trifluoro-2,2-dimethylpropyl)carbamoyl)-5-(trifluoromethyl)-1H-pyrazol-1-yl)-2-methylcyclohexanecarboxylate To a clear solution of (1R,2R,4R)-ethyl 4-(4-((2-(3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-2-methylcyclohexanecarboxylate compound with (1S,2S,4S)-ethyl 4-(4-((2-(3,5-dichloropyridin-4-yl)-2-hydroxyethyl)(3,3,3-trifluoro-2,2-dimethylpropyl)carbamoyl)-5-(trifluoromethyl)-1H-pyrazol-1-yl)-2-methylcyclohexanecarboxylate (1:1) (0.458 g, 0.346 mmol) in DCM (11.54 ml) was added Dess-Martin periodinane (0.441 g, 1.039 mmol). The white cloudy mixture was stirred at room temperature. After 14 h, the mixture was quenched with saturated aqueous $Na_2S_2O_3$ (50 mL) and saturated aqueous $NaHCO_3$ (50 mL). The reaction mixture was extracted with DCM (2×50 mL). The organic extract was dried over $Na_2SO_4$.

The solution was filtered and concentrated in vacuo to give the crude material as a white solid. The crude material was absorbed onto a plug of silica gel and purified by silica gel column chromatography eluting with a gradient of 0% to 50%

355

EtOAc in hexane to provide (1R,2R,4R)-ethyl 4-(4-((2-3,5-dichloropyridin-4-yl)-2-oxoethyl)(3,3,3-trifluoro-2,2-dimethylpropyl)carbamoyl)-5-(trifluoromethyl)-1H-pyrazol-1-yl)-2-methylcyclohexanecarboxylate compound with (1S,2S,4S)-ethyl 4-(4-((2-3,5-dichloropyridin-4-yl)-2-oxoethyl)(3,3,3-trifluoro-2,2-dimethylpropyl)carbamoyl)-5-(trifluoromethyl)-1H-pyrazol-1-yl)-2-methylcyclohexanecarboxylate (1:1) (0.3795 g, 0.288 mmol, 83% yield) as white solid. $^1$H NMR (400 MHz, DMSO-$d_6$) δ 8.70-8.85 (2H, m), 7.73-7.99 (1H, m), 4.69-4.93 (2H, m), 4.35 (1H, d, J=3.7 Hz), 4.10 (2H, q, J=7.0 Hz), 3.51-3.87 (2H, m), 1.51-2.15 (8H, m), 0.87-1.23 (12H, m), rotamers present; LCMS (ESI) m/z 659.0 (M+H)$^+$.

The racemic mixture was separated by SFC to give two fractions where the stereochemisty of each fraction was arbitrarily assigned.

First peak on SFC IA column: (1R,2R,4R)-ethyl 4-(4-((2-3,5-dichloropyridin-4-yl)-2-oxoethyl)(3,3,3-trifluoro-2,2-dimethylpropyl)carbamoyl)-5-(trifluoromethyl)-1H-pyrazol-1-yl)-2-methylcyclohexanecarboxylate (0.1371 g, 0.208 mmol, 43.4% yield) as white solid: $^1$H NMR (400 MHz, CDCl$_3$) δ 8.47-8.63 (2H, m), 7.51-7.77 (1H, m), 4.52 (2H, s), 4.26-4.39 (1H, m), 4.18 (2H, q, J=7.1 Hz), 3.70 (2H, br. s.), 1.62-2.17 (8H, m), 1.29 (3H, t, J=7.1 Hz), 1.24 (6H, s), 1.00 (3H, d, J=6.1 Hz), rotamers present; LCMS (ESI) m/z 659.0 (M+H)$^+$.

Second peak on SFC IA column: (1S,2S,4S)-ethyl 4-(4-((2-(3,5-dichloropyridin-4-yl)-2-oxoethyl)(3,3,3-trifluoro-2,2-dimethylpropyl)carbamoyl)-5-(trifluoromethyl)-1H-pyrazol-1-yl)-2-methylcyclohexanecarboxylate (0.1447 g, 0.219 mmol, 45.8% yield) as white powder: $^1$H NMR (400 MHz, CDCl$_3$) δ 8.44-8.64 (2H, m), 7.51-7.77 (1H, m), 4.52 (2H, s), 4.25-4.38 (1H, m), 4.18 (2H, q, J=7.1 Hz), 3.57-3.98 (2H, m), 1.63-2.14 (8H, m), 1.29 (3H, t, J=7.1 Hz), 1.24 (6H, s), 1.00 (3H, d, J=6.1 Hz), rotamers present; LCMS (ESI) m/z 659.0 (M+H)$^+$.

Step 4: (1S,2S,4S)-4-(4-((2-(3,5-dichloro-4-pyridinyl)-2-oxoethyl)(3,3,3-trifluoro-2,2-dim ethylpropyl)carbamoyl)-5-(trifluoromethyl)-1H-pyrazol-1-yl)-2-methylcyclohexanecarboxylic acid To a clear solution of (1S,2S,4S)-ethyl 4-(4-((2-(3,5-dichloropyridin-4-yl)-2-oxoethyl)(3,3,3-trifluoro-2,2-dimethylpropyl)carbamoyl)-5-(trifluoromethyl)-1H-pyrazol-1-yl)-2-methylcyclohexanecarboxylate (0.1345 g, 0.204 mmol) in THF (1.632 ml), EtOH (1.632 ml), and water (0.816 ml) was added 2 M LiOH in water (1.020 ml, 2.040 mmol). The light-yellow slightly cloudy mixture was stirred and heated at 60° C. After 4 h, the reaction mixture was concentrated in vacuo to remove THF and EtOH. The resulting aqueous solution was diluted with water (10 mL). The pH of the solution was adjusted to ~3.0 with 1 N HCl and the resulting precipitate was collected by vacuum filtration, wash with water, and freeze-dried on lyophilizer overnight to provide example 879 (0.1151 g, 0.182 mmol, 89% yield) as white solid: $^1$H NMR (400 MHz, DMSO-$d_6$) δ 12.18 (1H, br. s.), 8.59-8.86 (2H, m), 7.73-8.02 (1H, m), 4.65-5.49 (2H, m), 4.33 (1H, d, J=8.4 Hz), 3.44-3.94 (2H, m), 1.48-2.10 (8H, m), 0.85-1.36 (9H, m), rotamers present; LCMS (ESI) m/z 631.1 (M+H)$^+$. The stereochemistry was arbitrarily assigned as (1S,2S,4S).

Example 885

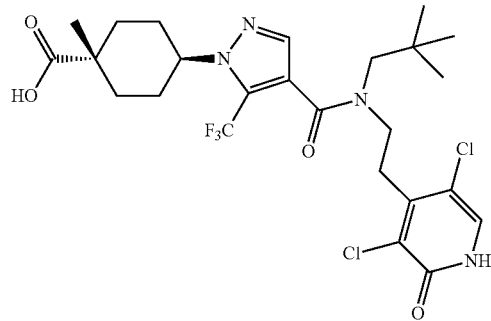 [SMILES: CC(C)(C)CN(CCc1c(Cl)c[nH]c(=O)c1Cl)C(=O)c1cnn([C@H]2CC[C@](C)(C(=O)O)CC2)c1C(F)(F)F]

trans-4-(4-((2-(3,5-dichloro-2-oxo-1,2-dihydro-4-pyridinyl)ethyl)(2,2-dimethylpropyl)carbamoyl)-5-(trifluoromethyl)-1H-pyrazol-1-yl)-1-methylcyclohexanecarboxylic acid The title compound was prepared in an analogous manner to example 886 and isolated (36.7 mg, 0.063 mmol, 54% yield) as a white amorphous solid. MS (ESI) 579.0, 581.0 [M+H]$^+$.

Example 886

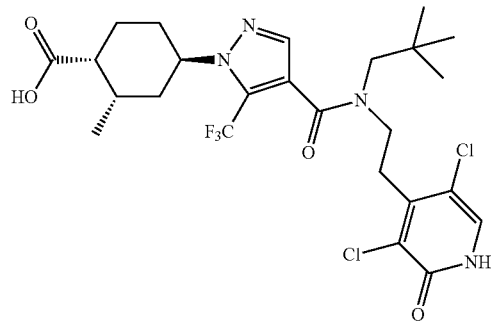 [SMILES: C[C@H]1C[C@H](n2ncc(C(=O)N(CCc3c(Cl)c[nH]c(=O)c3Cl)CC(C)(C)C)c2C(F)(F)F)CC[C@H]1C(=O)O]

(1S,2R,4S)-4-(4-((2-(3,5-dichloro-2-oxo-1,2-dihydro-4-pyridinyl)ethyl)(2,2-dimethylpropyl)carbamoyl)-5-(trifluoromethyl)-1H-pyrazol-1-yl)-2-methylcyclohexane carboxylic acid

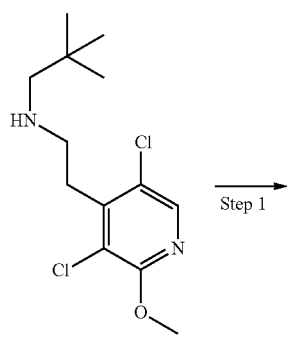

Step 1

-continued

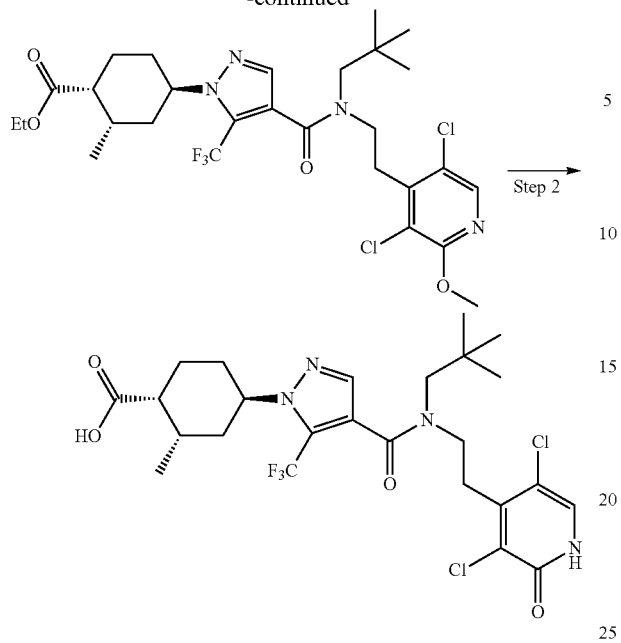

Step 1: Oxalyl chloride (2.0M in DCM, 0.52 mL, 1.03 mmol) was added to a solution of 1-((1S,3R,4S)-4-(ethoxycarbonyl)-3-methylcyclohexyl)-5-(trifluoromethyl)-1H-pyrazole-4-carboxylic acid (239 mg, 0.687 mmol) in DCM (2.0 mL) followed by 1 drop of DMF while cooling in an ice bath. The solution was removed from the ice bath and allowed to stir at room temperature for 1 h. The reaction mixture was concentrated to dryness under reduced pressure (rotary evaporator) and the crude residue was treated with DCM (2.0 mL) and cooled to 0° C. The stirring solution was then treated with N-(2-(3,5-dichloro-2-methoxypyridin-4-yl)ethyl)-2,2-dimethylpropan-1-amine (200 mg, 0.687 mmol) in DCM (2 mL) followed by the addition of DIPEA (0.36 mL, 2.06 mmol) and allowed to warm to room temperature and stirred overnight (16 h). The reaction mixture was concentrated to dryness under reduced pressure (rotary evaporator) and the crude residue was purified on an ISCO Combiflash™ RF (25 g Grace Reveleris column, using a gradient of 0-50% EtOAc in heptane) affording (1S,2R,4S)-ethyl 4-(4-((2-(3,5-dichloro-2-methoxypyridin-4-yl)ethyl)(neopentyl)carbamoyl)-5-(trifluoromethyl)-1H-pyrazol-1-yl)-2-methylcyclohexanecarboxylate (350 mg, 0.56 mmol, 82% yield) as a white crystalline solid. MS (ESI) 621.2, 623.2 [M+H]⁺.

Step 2: (1S,2R,4S)-ethyl 4-(4-((2-(3,5-dichloro-2-methoxypyridin-4-yl)ethyl)(neopentyl)carbamoyl)-5-(trifluoromethyl)-1H-pyrazol-1-yl)-2-methylcyclohexanecarboxylate (109 mg, 0.175 mmol) was treated with aqueous hydrochloric acid (5.0 N, 3.00 mL, 15.00 mmol) and hydrochloric acid (4.0 N in 1,4-dioxane, 3.00 mL, 12.00 mmol), fitted with a reflux condenser and heated to 120° C. for 3 h. The reaction mixture was concentrated to dryness under reduced pressure (rotary evaporator) and the crude residue was purified on a Gilson (Gemini™ Phenomenex; 30×150 mm, 5 u, using a gradient of 10-95% 0.1% TFA/CH₃CN in 0.1% TFA/water), concentrated in a genevac overnight affording (1S,2R,4S)-4-(4-((2-(3,5-dichloro-2-oxo-1,2-dihydropyridin-4-yl)ethyl)(neopentyl)carbamoyl)-5-(trifluoromethyl)-1H-pyrazol-1-yl)-2-methylcyclohexanecarboxylic acid (57 mg, 0.098 mmol, 56% yield) as a white amorphous solid. MS (ESI) 579.0, 581.2 [M+H]⁺.

Example 887

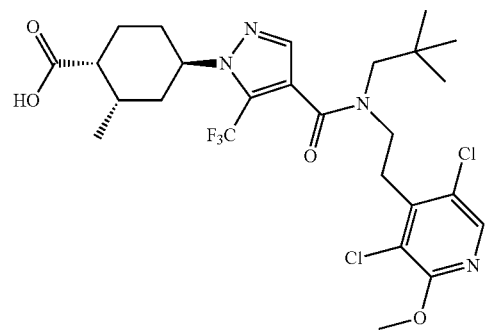 [SMILES: COc1ncc(Cl)c(CCN(CC(C)(C)C)C(=O)c2cnn([C@@H]3CC[C@@H](C(=O)O)[C@@H](C)C3)c2C(F)(F)F)c1Cl]

(1S,2R,4S)-4-(4-((2-(3,5-dichloro-2-methoxy-4-pyridinyl)ethyl)(2,2-dimethylpropyl)carbamoyl)-5-(trifluoromethyl)-1H-pyrazol-1-yl)-2-methylcyclohexanecarboxylic acid The title compound was prepared from N-(2-(3,5-dichloro-2-methoxypyridin-4-yl)ethyl)-2,2-dimethylpropan-1-amine and 1-((1S,3R,4S)-4-(ethoxycarbonyl)-3-methylcyclohexyl)-5-(trifluoromethyl)-1H-pyrazole-4-carboxylic acid by procedures similar to those described in example 872. MS (ESI) 593.2, 595.1 [M+H]⁺.

The following examples were synthesized similar procedures described above.

| example | structure | name |
|---|---|---|
| 24 | 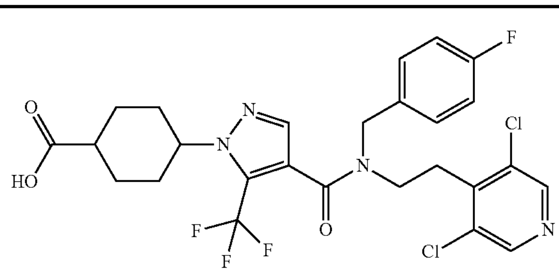 | 4-(4-((2-(3,5-dichloropyridin-4-yl)ethyl)(4-fluorobenzyl)carbamoyl)-5-(trifluoromethyl)-1H-pyrazol-1-yl)cyclohexanecarboxylic acid |

-continued

| example | structure | name |
| --- | --- | --- |
| 25 | 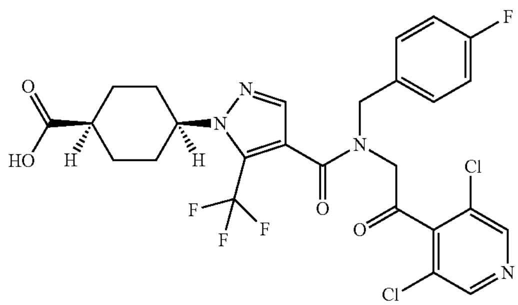 [SMILES: O=C(CN(Cc1ccc(F)cc1)C(=O)c1cnn([C@H]2CC[C@@H](C(=O)O)CC2)c1C(F)(F)F)c1c(Cl)cncc1Cl] | cis-4-(4-((2-(3,5-dichloropyridin-4-yl)-2-oxoethyl)(4-fluorobenzyl)carbamoyl)-5-(trifluoromethyl)-1H-pyrazol-1-yl)cyclohexanecarboxylic acid |
| 26 | 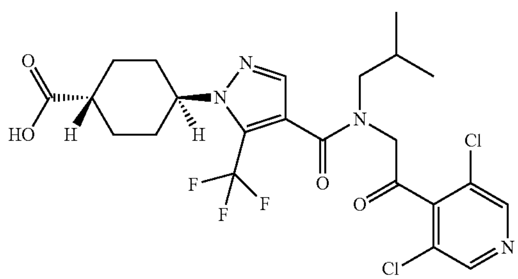 [SMILES: CC(C)CN(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)(isobutyl)carbamoyl)-5-(trifluoromethyl)-1H-pyrazol-1-yl)cyclohexanecarboxylic acid |
| 27 | 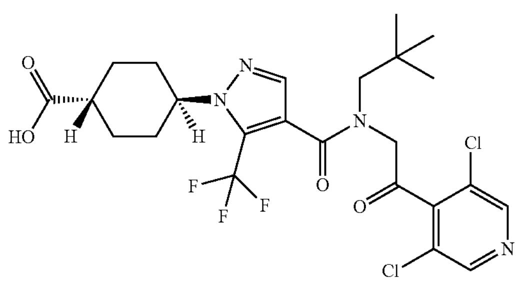 [SMILES: CC(C)(C)CN(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)(neopentyl)carbamoyl)-5-(trifluoromethyl)-1H-pyrazol-1-yl)cyclohexanecarboxylic acid |
| 28 | 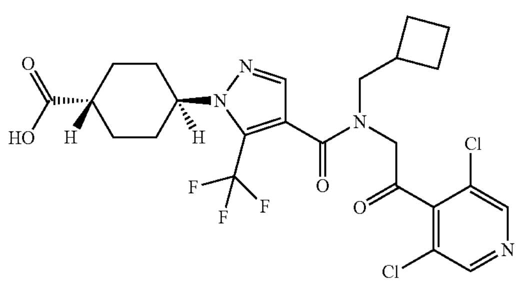 [SMILES: O=C(CN(CC1CCC1)C(=O)c1cnn([C@H]2CC[C@H](C(=O)O)CC2)c1C(F)(F)F)c1c(Cl)cncc1Cl] | trans-4-(4-((cyclobutylmethyl)(2-(3,5-dichloropyridin-4-yl)-2-oxoethyl)carbamoyl)-5-(trifluoromethyl)-1H-pyrazol-1-yl)cyclohexanecarboxylic acid |
| 29 | 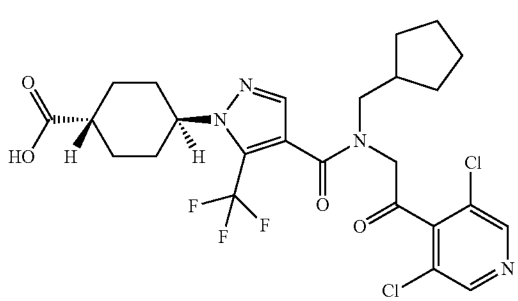 [SMILES: O=C(CN(CC1CCCC1)C(=O)c1cnn([C@H]2CC[C@H](C(=O)O)CC2)c1C(F)(F)F)c1c(Cl)cncc1Cl] | trans-4-(4-((cyclopentylmethyl)(2-(3,5-dichloropyridin-4-yl)-2-oxoethyl)carbamoyl)-5-(trifluoromethyl)-1H-pyrazol-1-yl)cyclohexanecarboxylic acid |

-continued

| example | structure | name |
|---|---|---|
| 30 | 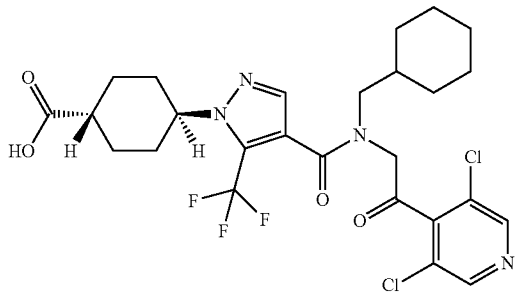 [SMILES: O=C(CN(CC1CCCCC1)C(=O)c1cnn([C@H]2CC[C@H](C(=O)O)CC2)c1C(F)(F)F)c1c(Cl)cncc1Cl] | trans-4-(4-((cyclohexylmethyl)(2-(3,5-dichloropyridin-4-yl)-2-oxoethyl)carbamoyl)-5-(trifluoromethyl)-1H-pyrazol-1-yl)cyclohexanecarboxylic acid |
| 31 | 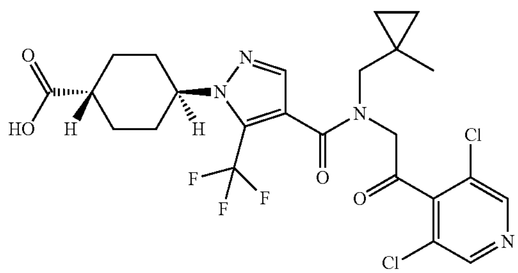 [SMILES: CC1(CN(CC(=O)c2c(Cl)cncc2Cl)C(=O)c2cnn([C@H]3CC[C@H](C(=O)O)CC3)c2C(F)(F)F)CC1] | trans-4-(4-((2-(3,5-dichloropyridin-4-yl)-2-oxoethyl)((1-methylcyclopropyl)methyl)carbamoyl)-5-(trifluoromethyl)-1H-pyrazol-1-yl)cyclohexanecarboxylic acid |
| 32 | 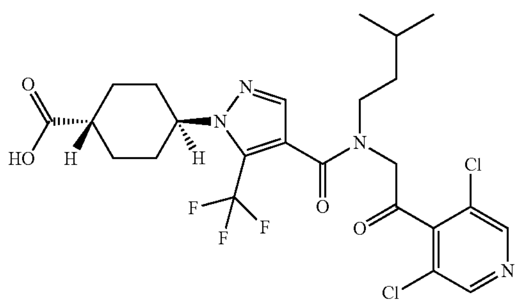 [SMILES: CC(C)CCN(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)(isopentyl)carbamoyl)-5-(trifluoromethyl)-1H-pyrazol-1-yl)cyclohexanecarboxylic acid |
| 33 | 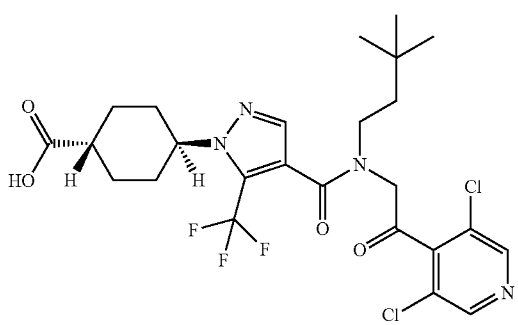 [SMILES: CC(C)(C)CCN(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)(3,3-dimethylbutyl)carbamoyl)-5-(trifluoromethyl)-1H-pyrazol-1-yl)cyclohexanecarboxylic acid |
| 34 | 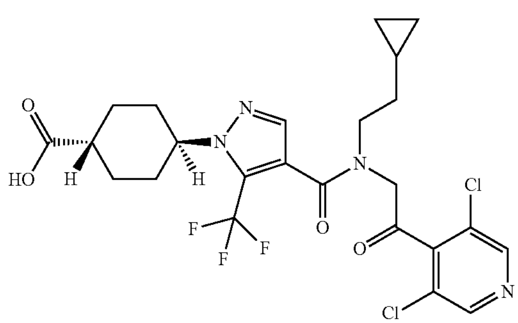 [SMILES: O=C(CN(CCC1CC1)C(=O)c1cnn([C@H]2CC[C@H](C(=O)O)CC2)c1C(F)(F)F)c1c(Cl)cncc1Cl] | trans-4-(4-((2-cyclopropylethyl)(2-(3,5-dichloropyridin-4-yl)-2-oxoethyl)carbamoyl)-5-(trifluoromethyl)-1H-pyrazol-1-yl)cyclohexanecarboxyic acid |

-continued

| example | structure | name |
|---|---|---|
| 35 | 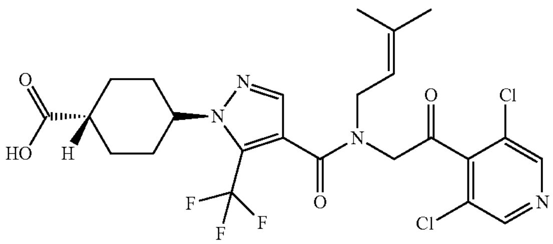 | trans-4-(4-((2-(3,5-dichloropyridin-4-yl)-2-oxoethyl)(3-methylbut-2-en-1-yl)carbamoyl)-5-(trifluoromethyl)-1H-pyrazol-1-yl)cyclohexanecarboxyic acid |
| 36 | 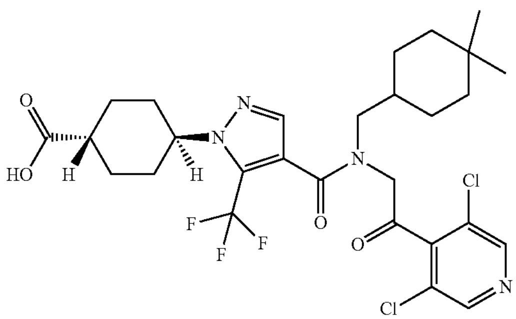 [SMILES: CC1(C)CCC(CN(CC(=O)c2c(Cl)cncc2Cl)C(=O)c2cnn([C@H]3CC[C@H](C(=O)O)CC3)c2C(F)(F)F)CC1] | trans-4-(4-((2-(3,5-dichloropyridin-4-yl)-2-oxoethyl)((4,4-dimethylcyclohexyl)methyl)carbamoyl)-5-(trifluoromethyl)-1H-pyrazol-1-yl)cyclohexanecarboxylic acid |
| 37 | 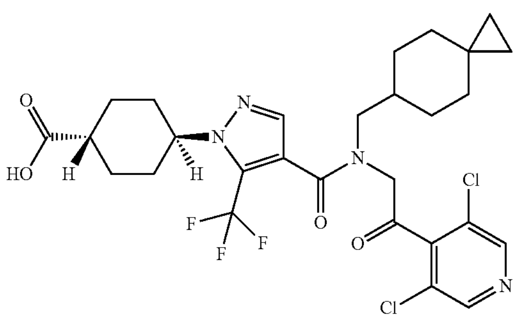 [SMILES: O=C(CN(CC1CCC2(CC1)CC2)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(spiro[2.5]octan-6-ylmethyl)carbamoyl)-5-(trifluoromethyl)-1H-pyrazol-1-yl)cyclohexanecarboxylic acid |
| 38 | 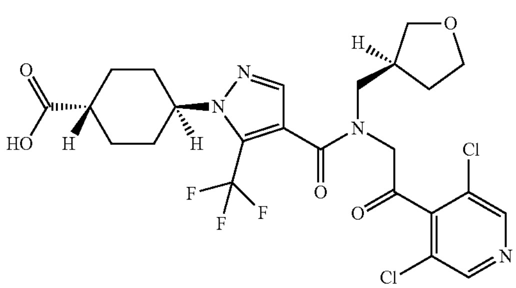 [SMILES: O=C(CN(C[C@@H]1CCOC1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(((S)-tetrahydrofuran-3-yl)methyl)carbamoyl)-5-(trifluoromethyl)-1H-pyrazol-1-yl)cyclohexanecarboxylic acid |
| 39 | 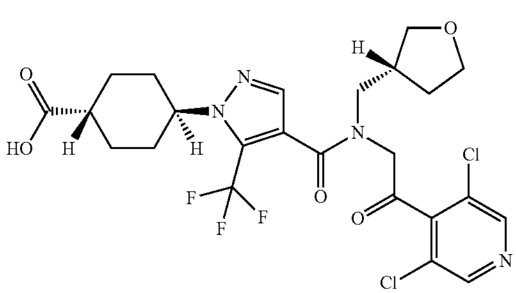 [SMILES: O=C(CN(C[C@H]1CCOC1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(((R)-tetrahydrofuran-3-yl)methyl)carbamoyl)-5-(trifluoromethyl)-1H-pyrazol-1-yl)cyclohexanecarboxylic acid |

| example | structure | name |
| --- | --- | --- |
| 40 | 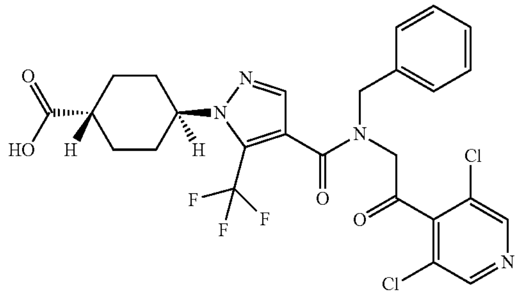 [SMILES: O=C(CN(Cc1ccccc1)C(=O)c1cnn([C@H]2CC[C@H](C(=O)O)CC2)c1C(F)(F)F)c1c(Cl)cncc1Cl] | trans-4-(4-(benzyl(2-(3,5-dichloropyridin-4-yl)-2-oxoethyl)carbamoyl)-5-(trifluoromethyl)-1H-pyrazol-1-yl)cyclohexanecarboxylic acid |
| 41 | 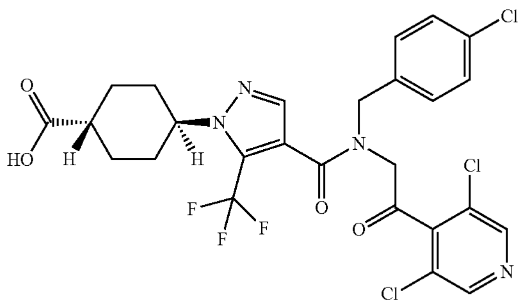 [SMILES: O=C(CN(Cc1ccc(Cl)cc1)C(=O)c1cnn([C@H]2CC[C@H](C(=O)O)CC2)c1C(F)(F)F)c1c(Cl)cncc1Cl] | trans-4-(4-((4-chlorobenzyl)(2-(3,5-dichloropyridin-4-yl)-2-oxoethyl)carbamoyl)-5-(trifluoromethyl)-1H-pyrazol-1-yl)cyclohexanecarboxylic acid |
| 42 | 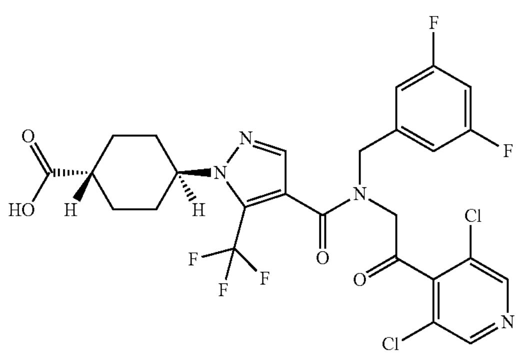 [SMILES: O=C(CN(Cc1cc(F)cc(F)c1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(3,5-difluorobenzyl)carbamoyl)-5-(trifluoromethyl)-1H-pyrazol-1-yl)cyclohexanecarboxylic acid |
| 43 | 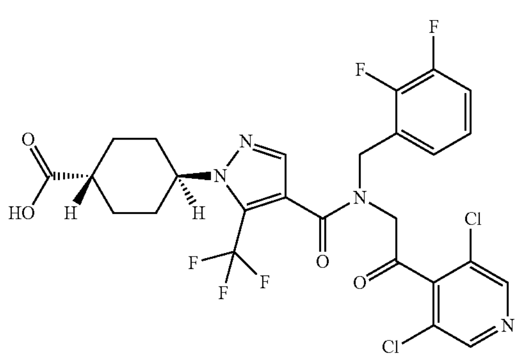 [SMILES: O=C(CN(Cc1cccc(F)c1F)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(2,3-difluorobenzyl)carbamoyl)-5-(trifluoromethyl)-1H-pyrazol-1-yl)cyclohexanecarboxylic acid |

-continued

| example | structure | name |
|---|---|---|
| 44 | 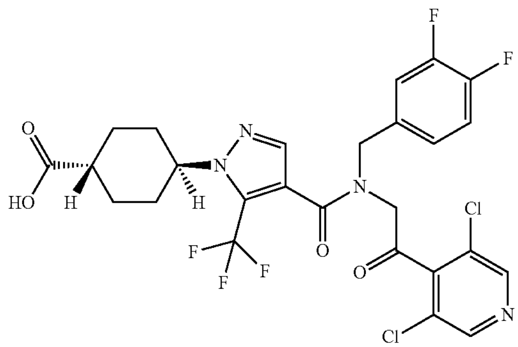 [SMILES: O=C(CN(Cc1ccc(F)c(F)c1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(3,4-difluorobenzyl)carbamoyl)-5-(trifluoromethyl)-1H-pyrazol-1-yl)cyclohexanecarboxylic acid |
| 45 | 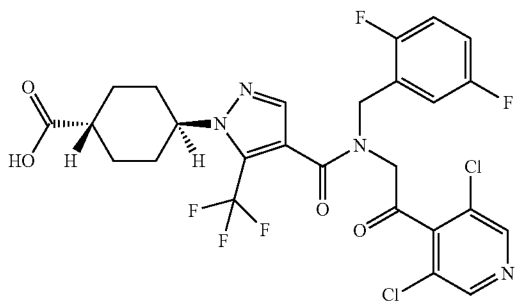 [SMILES: O=C(CN(Cc1cc(F)ccc1F)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(2,5-difluorobenzyl)carbamoyl)-5-(trifluoromethyl)-1H-pyrazol-1-yl)cyclohexanecarboxylic acid |
| 46 | 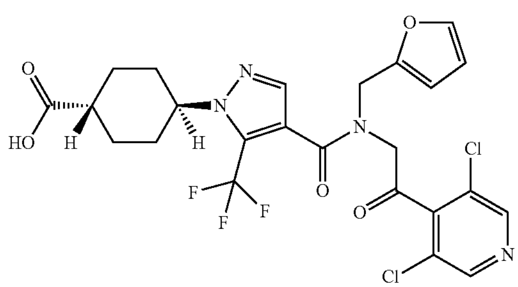 [SMILES: O=C(CN(Cc1ccco1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(furan-2-ylmethyl)carbamoyl)-5-(trifluoromethyl)-1H-pyrazol-1-yl)cyclohexanecarboxylic acid |
| 47 | 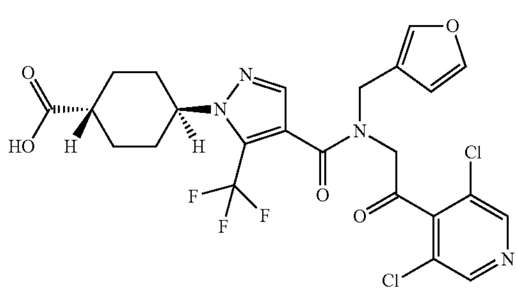 [SMILES: O=C(CN(Cc1ccoc1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(furan-3-ylmethyl)carbamoyl)-5-(trifluoromethyl)-1H-pyrazol-1-yl)cyclohexanecarboxylic acid |
| 48 | 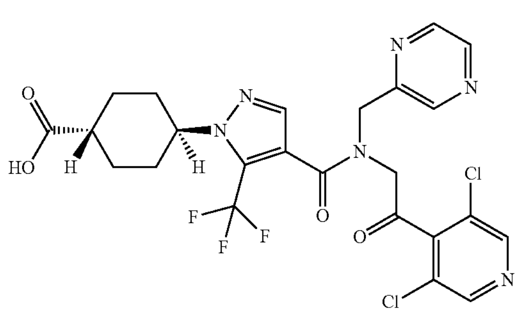 | trans-4-(4-((2-(3,5-dichloropyridin-4-yl)-2-oxoethyl)(pyrazin-2-ylmethyl)carbamoyl)-5-(trifluoromethyl)-1H-pyrazol-1-yl)cyclohexanecarboxylic acid |

| example | structure | name |
|---|---|---|
| 49 | 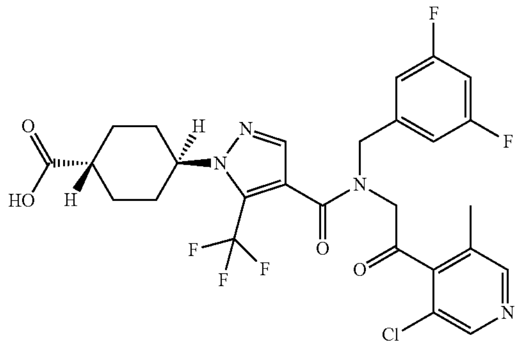 [SMILES: O=C(CN(Cc1cc(F)cc(F)c1)C(=O)c1cnn([C@H]2CC[C@H](C(=O)O)CC2)c1C(F)(F)F)c1c(F)cncc1Cl] | trans-4-(4-((2-(3-chloro-5-methylpyridin-4-yl)-2-oxoethyl)(3,5-difluorobenzyl)carbamoyl)-5-(trifluoromethyl)-1H-pyrazol-1-yl)cyclohexanecarboxylic acid |
| 50 | 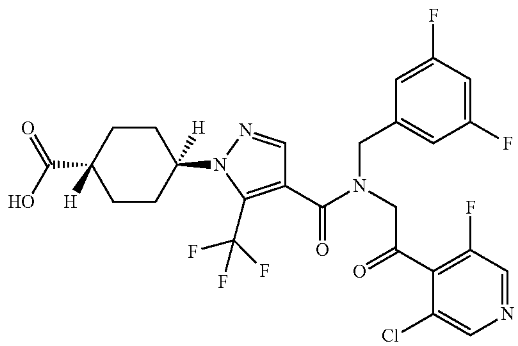 | trans-4-(4-((2-(3-chloro-5-fluoropyridin-4-yl)-2-oxoethyl)(3,5-difluorobenzyl)carbamoyl)-5-(trifluoromethyl)-1H-pyrazol-1-yl)cyclohexanecarboxylic acid |
| 51 | 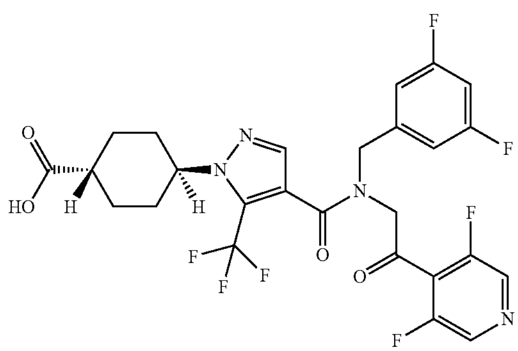 [SMILES: O=C(CN(Cc1cc(F)cc(F)c1)C(=O)c1cnn([C@H]2CC[C@H](C(=O)O)CC2)c1C(F)(F)F)c1c(F)cncc1F] | trans-4-(4-((3,5-difluorobenzyl)(2-(3,5-difluoropyridin-4-yl)-2-oxoethyl)carbamoyl)-5-(trifluoromethyl)-1H-pyrazol-1-yl)cyclohexanecarboxylic acid |
| 52 | 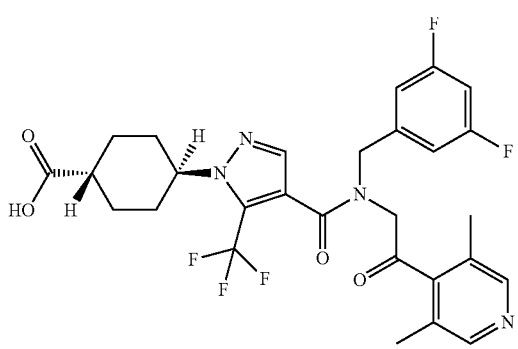 [SMILES: Cc1cncc(C)c1C(=O)CN(Cc1cc(F)cc(F)c1)C(=O)c1cnn([C@H]2CC[C@H](C(=O)O)CC2)c1C(F)(F)F] | trans-4-(4-(3,5-difluorobenzyl)(2-(3,5-dimethylpyridin-4-yl)-2-oxoethyl)carbamoyl)-5-(trifluoromethyl)-1H-pyrazol-1-yl)cyclohexanecarboxylic acid |

-continued

| example | structure | name |
|---|---|---|
| 53 | 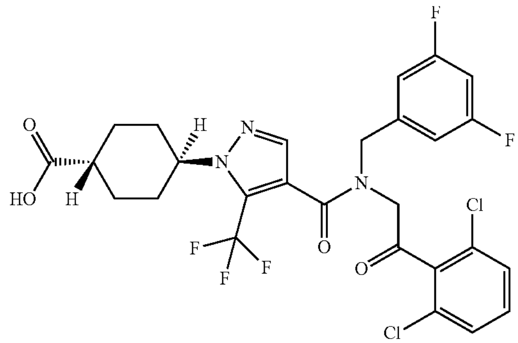 | trans-4-(4-((2-(2,6-dichlorophenyl)-2-oxoethyl)(3,5-difluorobenzyl)carbamoyl)-5-(trifluoromethyl)-1H-pyrazol-1-yl)cyclohexanecarboxylic acid |
| 54 | 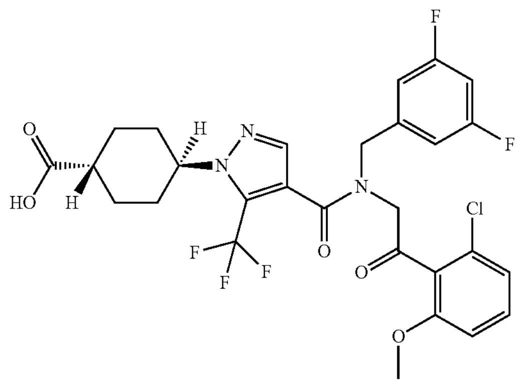 [SMILES: COc1cccc(Cl)c1C(=O)CN(Cc1cc(F)cc(F)c1)C(=O)c1cnn([C@H]2CC[C@H](C(=O)O)CC2)c1C(F)(F)F] | trans-4-(4-((2-(2-chloro-6-methoxyphenyl)-2-oxoethyl)(3,5-difluorobenzyl)carbamoyl)-5-(trifluoromethyl)-1H-pyrazol-1-yl)cyclohexanecarboxylic acid |
| 55 | 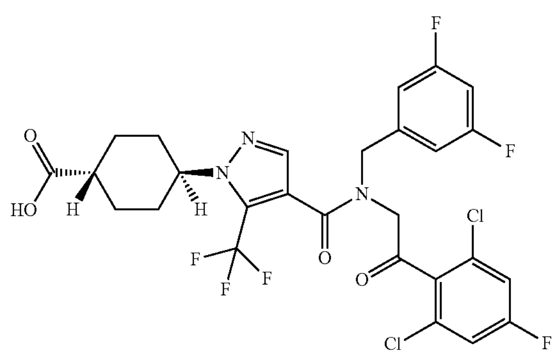 [SMILES: O=C(CN(Cc1cc(F)cc(F)c1)C(=O)c1cnn([C@H]2CC[C@H](C(=O)O)CC2)c1C(F)(F)F)c1c(Cl)cc(F)cc1Cl] | trans-4-(4-((2-(2,6-dichloro-4-fluorophenyl)-2-oxoethyl)(3,5-difluorobenzyl)carbamoyl)-5-(trifluoromethyl)-1H-pyrazol-1-yl)cyclohexanecarboxylic acid |
| 56 | 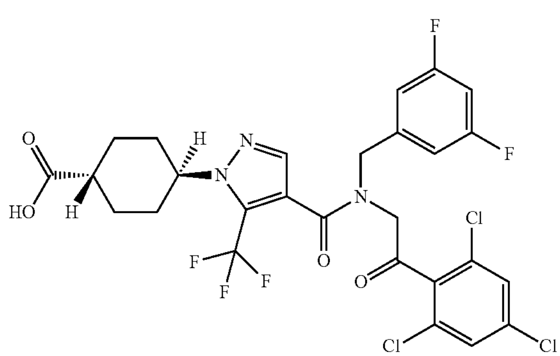 [SMILES: O=C(CN(Cc1cc(F)cc(F)c1)C(=O)c1cnn([C@H]2CC[C@H](C(=O)O)CC2)c1C(F)(F)F)c1c(Cl)cc(Cl)cc1Cl] | trans-4-(4-((3,5-difluorobenzyl)(2-oxo-2-(2,4,6-trichlorophenyl)ethyl)carbamoyl)-5-(trifluoromethyl)-1H-pyrazol-1-yl)cyclohexanecarboxylic acid |

| example | structure | name |
|---|---|---|
| 57 | 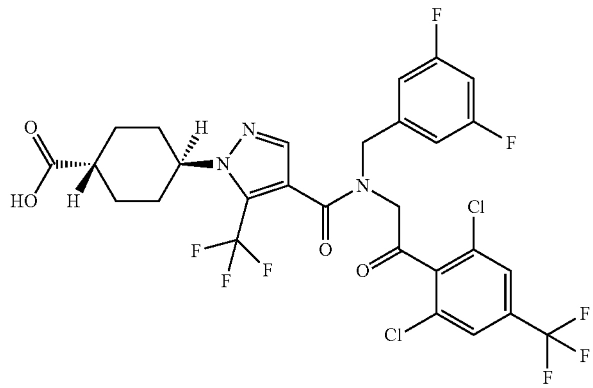 [SMILES: O=C(CN(Cc1cc(F)cc(F)c1)C(=O)c1cnn([C@H]2CC[C@H](C(=O)O)CC2)c1C(F)(F)F)c1c(Cl)cc(C(F)(F)F)cc1Cl] | trans-4-(4-((2-(2,6-dichloro-4-(trifluoromethyl)phenyl)-2-oxoethyl)(3,5-difluorobenzyl)carbamoyl)-5-(trifluoromethyl)-1H-pyrazol-1-yl)cyclohexanecarboxylic acid |
| 58 | 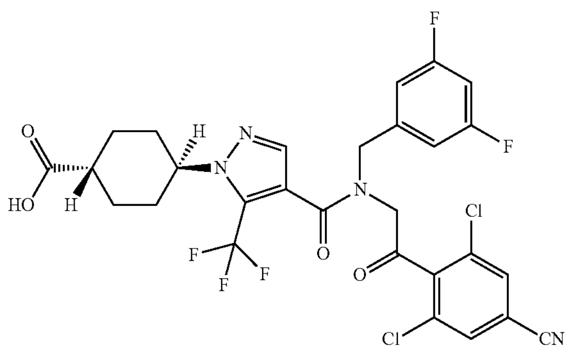 [SMILES: N#Cc1cc(Cl)c(C(=O)CN(Cc2cc(F)cc(F)c2)C(=O)c2cnn([C@H]3CC[C@H](C(=O)O)CC3)c2C(F)(F)F)c(Cl)c1] | trans-4-(4-((2-(2,6-dichloro-4-cyanophenyl)-2-oxoethyl)(3,5-difluorobenzyl)carbamoyl)-5-(trifluoromethyl)-1H-pyrazol-1-yl)cyclohexanecarboxylic acid |
| 59 | 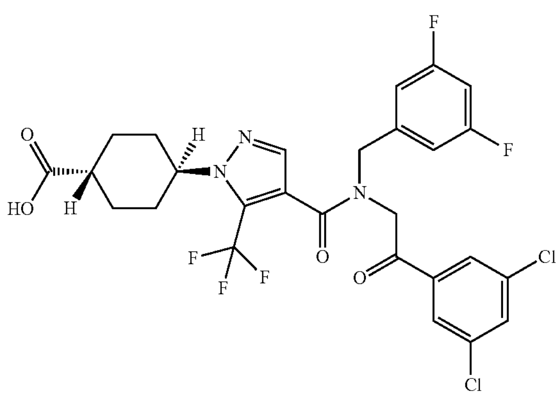 [SMILES: O=C(CN(Cc1cc(F)cc(F)c1)C(=O)c1cnn([C@H]2CC[C@H](C(=O)O)CC2)c1C(F)(F)F)c1cc(Cl)cc(Cl)c1] | trans-4-(4-((2-(3,5-dichlorophenyl)-2-oxoethyl)(3,5-difluorobenzyl)carbamoyl)-5-(trifluoromethyl)-1H-pyrazol-1-yl)cyclohexanecarboxylic acid |
| 60 | 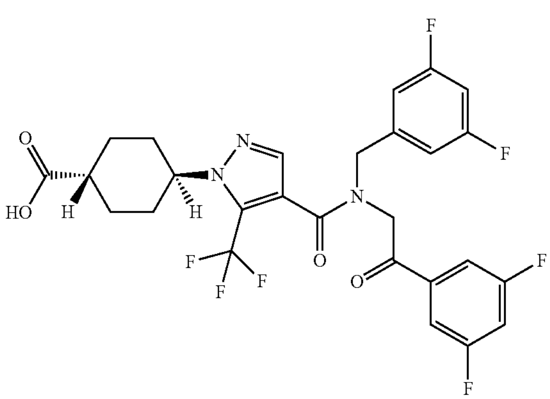 [SMILES: O=C(CN(Cc1cc(F)cc(F)c1)C(=O)c1cnn([C@H]2CC[C@H](C(=O)O)CC2)c1C(F)(F)F)c1cc(F)cc(F)c1] | trans-4-(4-((3,5-difluorobenzyl)(2-(3,5-difluorophenyl)-2-oxoethyl)carbamoyl)-5-(trifluoromethyl)-1H-pyrazol-1-yl)cyclohexanecarboxylic acid |

-continued

| example | structure | name |
|---|---|---|
| 61 | 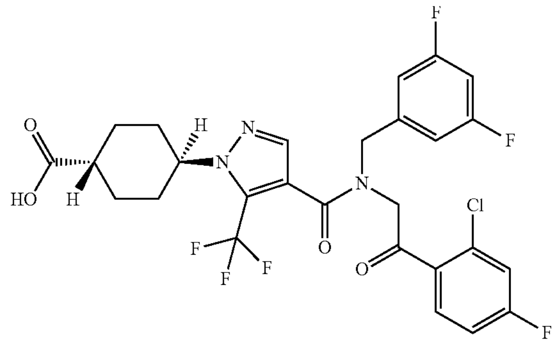 [SMILES: O=C(CN(Cc1cc(F)cc(F)c1)C(=O)c1cnn([C@H]2CC[C@H](C(=O)O)CC2)c1C(F)(F)F)c1ccc(F)cc1Cl] | trans-4-(4-((2-(2-chloro-4-fluorophenyl)-2-oxoethyl)(3,5-difluorobenzyl)carbamoyl)-5-(trifluoromethyl)-1H-pyrazol-1-yl)cyclohexanecarboxylic acid |
| 62 | 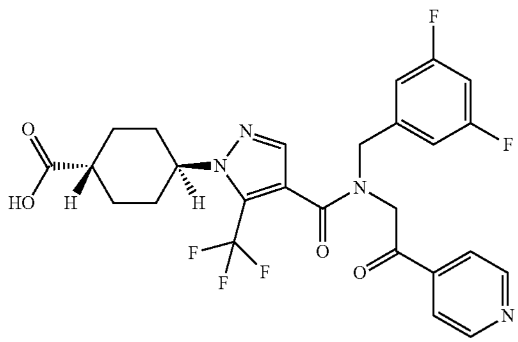 [SMILES: O=C(CN(Cc1cc(F)cc(F)c1)C(=O)c1cnn([C@H]2CC[C@H](C(=O)O)CC2)c1C(F)(F)F)c1ccncc1] | trans-4-(4-((3,5-difluorobenzyl)(2-oxo-2-(pyridin-4-yl)ethyl)carbamoyl)-5-(trifluoromethyl)-1H-pyrazol-1-yl)cyclohexanecarboxylic acid |
| 63 | 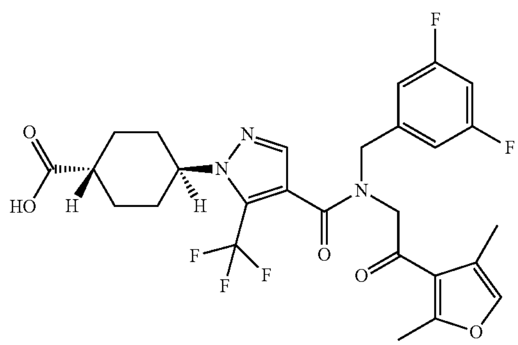 [SMILES: Cc1coc(C)c1C(=O)CN(Cc1cc(F)cc(F)c1)C(=O)c1cnn([C@H]2CC[C@H](C(=O)O)CC2)c1C(F)(F)F] | trans-4-(4-((3,5-difluorobenzyl)(2-(2,4-dimethylfuran-3-yl)-2-oxoethyl)carbamoyl)-5-(trifluoromethyl)-1H-pyrazol-1-yl)cyclohexanecarboxylic acid |
| 64 | 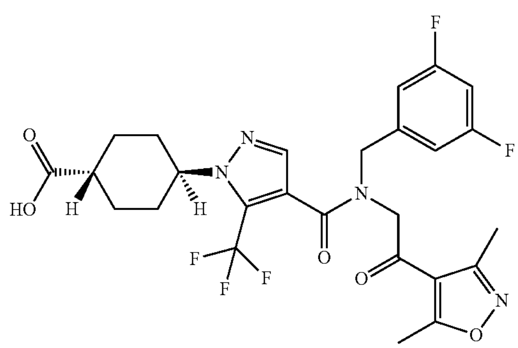 [SMILES: Cc1noc(C)c1C(=O)CN(Cc1cc(F)cc(F)c1)C(=O)c1cnn([C@H]2CC[C@H](C(=O)O)CC2)c1C(F)(F)F] | trans-4-(4-((3,5-difluorobenzyl)(2-(3,5-dimethylisoxazol-4-yl)-2-oxoethyl)carbamoyl)-5-(trifluoromethyl)-1H-pyrazol-1-yl)cyclohexanecarboxylic acid |

-continued

| example | structure | name |
|---|---|---|
| 65 | 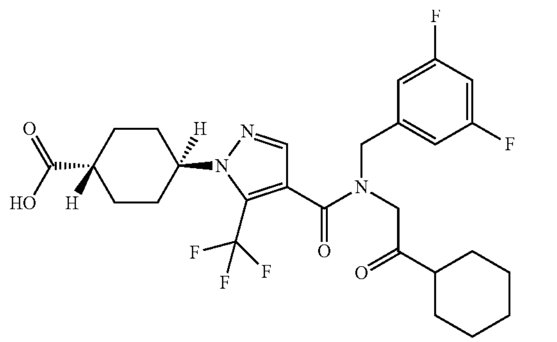 [SMILES: O=C(CN(Cc1cc(F)cc(F)c1)C(=O)c1cnn([C@H]2CC[C@H](C(=O)O)CC2)c1C(F)(F)F)C1CCCCC1] | trans-4-(4-((2-cyclohexyl-2-oxoethyl)(3,5-difluorobenzyl)carbamoyl)-5-(trifluoromethyl)-1H-pyrazol-1-yl)cyclohexanecarboxylic acid |
| 66 | 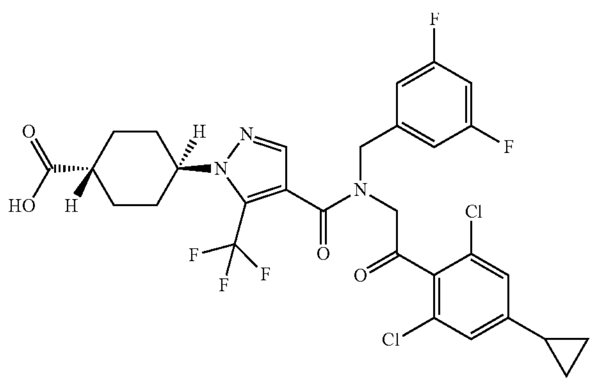 [SMILES: O=C(CN(Cc1cc(F)cc(F)c1)C(=O)c1cnn([C@H]2CC[C@H](C(=O)O)CC2)c1C(F)(F)F)c1c(Cl)cc(C2CC2)cc1Cl] | trans-4-(4-((2-(2,6-dichloro-4-cyclopropylphenyl)-oxoethyl)(3,5-difluorobenzyl)carbamoyl)-5-(trifluoromethyl)-1H-pyrazol-1-yl)cyclohexanecarboxylic acid |
| 67 | 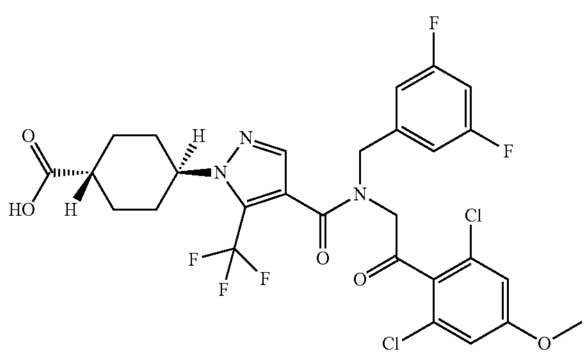 [SMILES: COc1cc(Cl)c(C(=O)CN(Cc2cc(F)cc(F)c2)C(=O)c2cnn([C@H]3CC[C@H](C(=O)O)CC3)c2C(F)(F)F)c(Cl)c1] | trans-4-(4-((2-(2,6-dichloro-4-methoxyphenyl)-2-oxoethyl)(3,5-difluorobenzyl)carbamoyl)-5-(trifluoromethyl)-1H-pyrazol-1-yl)cyclohexanecarboxylic acid |
| 68 | 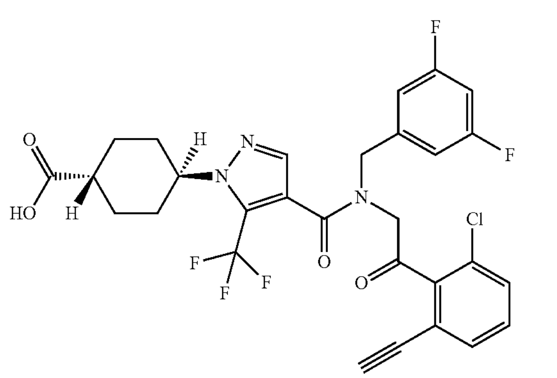 [SMILES: C#Cc1cccc(Cl)c1C(=O)CN(Cc1cc(F)cc(F)c1)C(=O)c1cnn([C@H]2CC[C@H](C(=O)O)CC2)c1C(F)(F)F] | trans-4-(4-((2-(2-chloro-6-ethynylphenyl)-2-oxoethyl)(3,5-difluorobenzyl)carbamoyl)-5-(trifluoromethyl)-1H-pyrazol-1-yl)cyclohexanecarboxylic acid |

-continued

| example | structure | name |
|---|---|---|
| 69 | 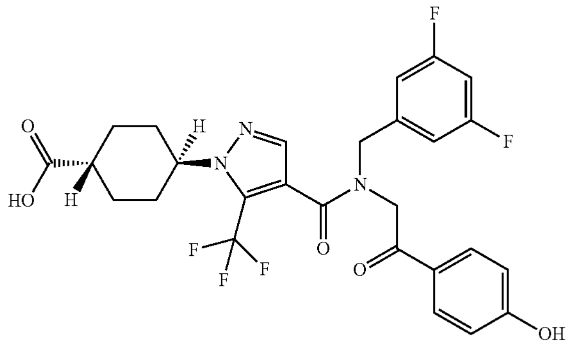 [SMILES: O=C(CN(Cc1cc(F)cc(F)c1)C(=O)c1cnn([C@H]2CC[C@H](C(=O)O)CC2)c1C(F)(F)F)c1ccc(O)cc1] | trans-4-(4-((3,5-difluorobenzyl)(2-(4-hydroxyphenyl)-2-oxoethyl)carbamoyl)-5-(trifluoromethyl)-1H-pyrazol-1-yl)cyclohexanecarboxylic acid |
| 70 | 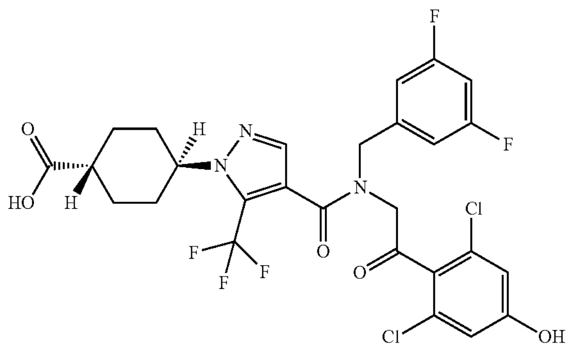 [SMILES: O=C(CN(Cc1cc(F)cc(F)c1)C(=O)c1cnn([C@H]2CC[C@H](C(=O)O)CC2)c1C(F)(F)F)c1c(Cl)cc(O)cc1Cl] | trans-4-(4-((2-(2,6-dichloro-4-hydroxyphenyl)-2-oxoethyl)(3,5-difluorobenzyl)carbarnoyl)-5-(trifluoromethyl)-1H-pyrazol-1-yl)cyclohexanecarboxylic acid |
| 71 | 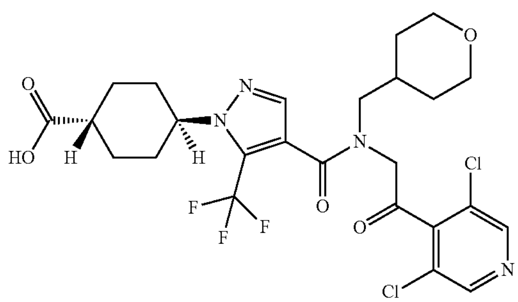 | trans-4-(4-((2-(3,5-dichloropyridin-4-yl)-2-oxoethyl)((tetrahydro-2H-pyran-4-yl)methyl)carbamoyl)-5-(trifluoromethyl)-1H-pyrazol-1-yl)cyclohexanecarboxylic acid |
| 72 | 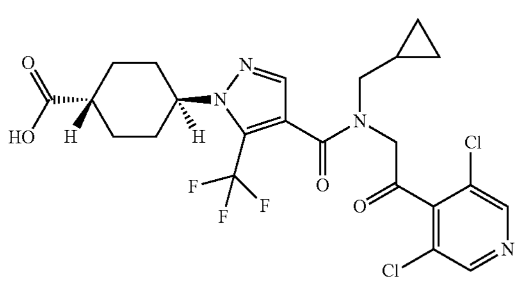 [SMILES: O=C(CN(CC1CC1)C(=O)c1cnn([C@H]2CC[C@H](C(=O)O)CC2)c1C(F)(F)F)c1c(Cl)cncc1Cl] | trans-4-(4-((cyclopropylmethyl)(2-(3,5-dichloropyridin-4-yl)-2-oxoethyl)carbamoyl)-5-(trifluoromethyl)-1H-pyrazol-1-yl)cyclohexanecarboxylic acid |
| 73 | 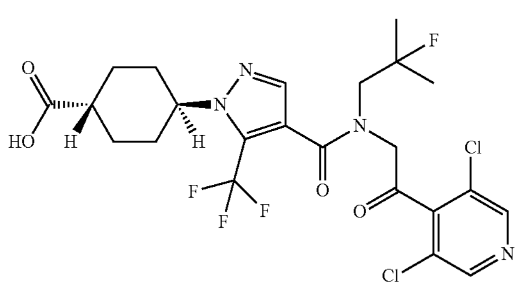 | trans-4-(4-((2-(3,5-dichloropyridin-4-yl)-2-oxoethyl)(2-fluoro-2-methylpropyl)carbamoyl)-5-(trifluoromethyl)-1H-pyrazol-1-yl)cyclohexanecarboxylic acid |

-continued

| example | structure | name |
|---|---|---|
| 74 | 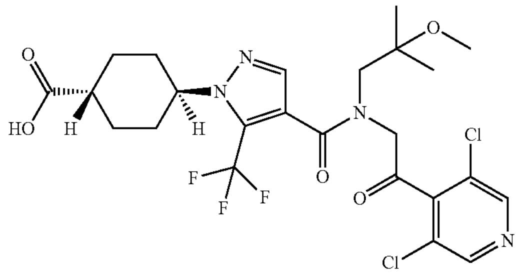 [SMILES: COC(C)(C)CN(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)(2-methoxy-2-methylpropyl)carbamoyl)-5-(trifluoromethyl)-1H-pyrazol-1-yl)cyclohexanecarboxylic acid |
| 75 | 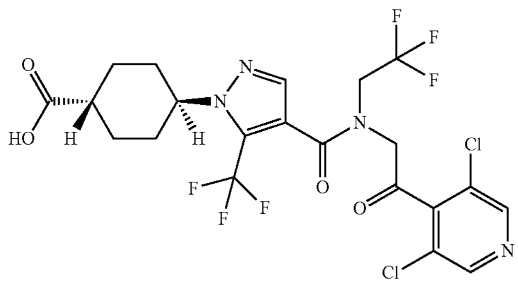 [SMILES: O=C(CN(CC(F)(F)F)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)(2,2,2-trifluoroethyl)carbamoyl)-5-(trifluoromethyl)-1H-pyrazol-1-yl)cyclohexanecarboxylic acid |
| 76 | 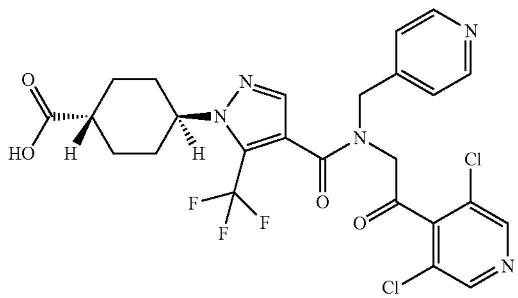 | trans-4-(4-((2-(3,5-dichloropyridin-4-yl)-2-oxoethyl)(pyridin-4-ylmethyl)carbamoyl)-5-(trifluoromethyl)-1H-pyrazol-1-yl)cyclohexanecarboxylic acid |
| 77 | 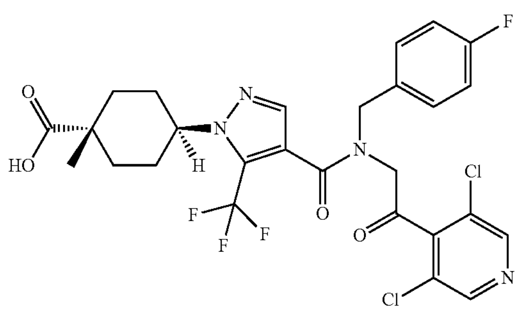 [SMILES: C[C@]1(C(=O)O)CC[C@H](n2ncc(C(=O)N(CC(=O)c3c(Cl)cncc3Cl)Cc3ccc(F)cc3)c2C(F)(F)F)CC1] | trans-4-(4-((2-(3,5-dichloropyridin-4-yl)-2-oxoethyl)(4-fluorobenzyl)carbamoyl)-5-(trifluoromethyl)-1H-pyrazol-1-yl)-1-methylcylohexanecarboxylic acid |
| 78 | 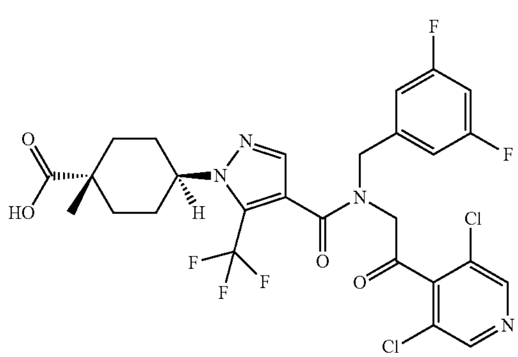 [SMILES: C[C@]1(C(=O)O)CC[C@H](n2ncc(C(=O)N(CC(=O)c3c(Cl)cncc3Cl)Cc3cc(F)cc(F)c3)c2C(F)(F)F)CC1] | trans-4-(4-((2-(3,5-dichloropyridin-4-yl)-2-oxoethyl)(3,5-difluorobenzyl)carbamoyl)-5-(trifluoromethyl)-1H-pyrazol-1-yl)-1-methylcyclohexanecarboxylic acid |

-continued

| example | structure | name |
|---|---|---|
| 79 | 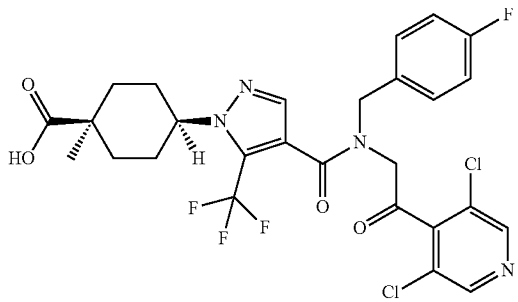 | trans-4-(4-((2-(3,5-dichloropyridin-4-yl)-2-oxoethyl)(4-fluorobenzyl)carbamoyl)-5-(trifluoromethyl)-1H-pyrazol-1-yl)-1-methylcyclohexanecarboxylic acid |
| 80 | 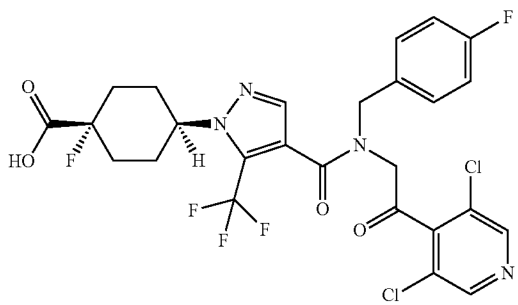 | trans-4-(4-((2-(3,5-dichloropyridin-4-yl)-2-oxoethyl)(4-fluorobenzyl)carbamoyl)-5-(trifluoromethyl)-1H-pyrazol-1-yl)-1-fluorocyclohexanecarboxylic acid |
| 81 | 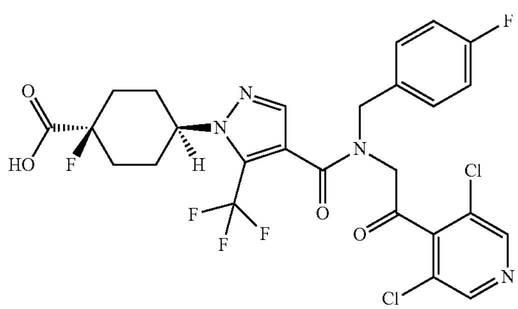 [SMILES: O=C(CN(Cc1ccc(F)cc1)C(=O)c1cnn([C@H]2CC[C@](F)(C(=O)O)CC2)c1C(F)(F)F)c1c(Cl)cncc1Cl] | cis-4-(4-((2-(3,5-dichloropyridin-4-yl)-2-oxoethyl)(4-fluorobenzyl)carbamoyl)-5-(trifluoromethyl)-1H-pyrazol-1-yl)-1-fluorocyclohexanecarboxylic acid |
| 82 | 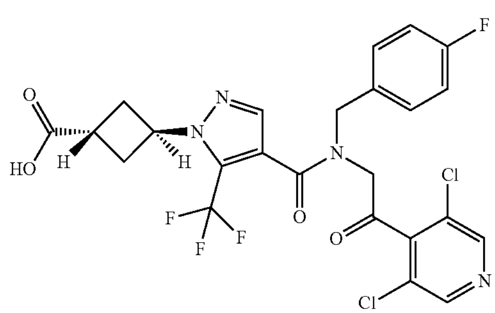 [SMILES: O=C(CN(Cc1ccc(F)cc1)C(=O)c1cnn([C@H]2C[C@H](C(=O)O)C2)c1C(F)(F)F)c1c(Cl)cncc1Cl] | trans-3-(4-((2-(3,5-dichloropyridin-4-yl)-2-oxoethyl)(4-fluorobenzyl)carbamoyl)-5-(trifluoromethyl)-1H-pyrazol-1-yl)cyclobutanecarboxylic acid |
| 83 | 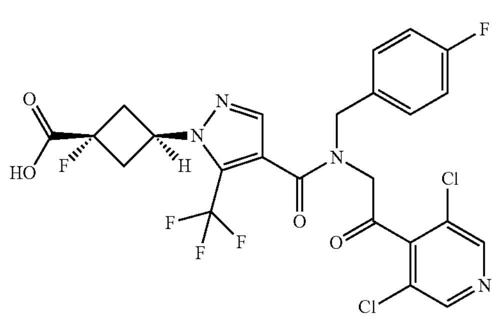 [SMILES: O=C(CN(Cc1ccc(F)cc1)C(=O)c1cnn([C@H]2C[C@@](F)(C(=O)O)C2)c1C(F)(F)F)c1c(Cl)cncc1Cl] | cis-3-(4-((2-(3,5-dichloropyridin-4-yl)-2-oxoethyl)(4-fluorobenzyl)carbamoyl)-5-(trifluoromethyl)-1H-pyrazol-1-yl)-1-fluorocyclohexanecarboxylic acid |

-continued

| example | structure | name |
|---|---|---|
| 84 | 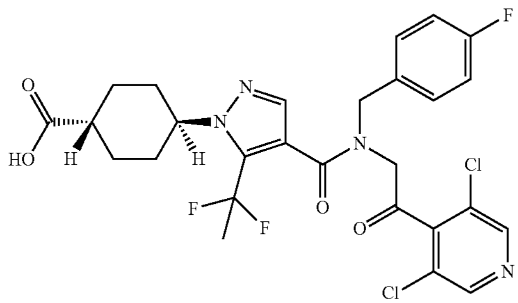 [SMILES: CC(F)(F)c1c(C(=O)N(CC(=O)c2c(Cl)cncc2Cl)Cc2ccc(F)cc2)cnn1[C@H]1CC[C@H](C(=O)O)CC1] | trans-4-(4-((2-(3,5-dichloropyridin-4-yl)-2-oxoethyl)(4-fluorobenzyl)carbamoyl)-5-(1,1-difluoroethyl)-1H-pyrazol-1-yl)cyclohexanecarboxylic acid |
| 85 | 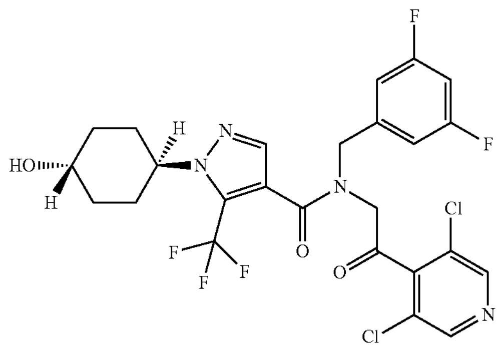 [SMILES: O=C(CN(Cc1cc(F)cc(F)c1)C(=O)c1cnn([C@H]2CC[C@H](O)CC2)c1C(F)(F)F)c1c(Cl)cncc1Cl] | N-(2-(3,5-dichloropyridin-4-yl)-2-oxoethyl)-N-(3,5-difluorobenzyl)-1-(trans-4-hydroxycyclohexyl)-5-(trifluoromethyl)-1H-pyrazole-4-carboxamide |
| 86 | 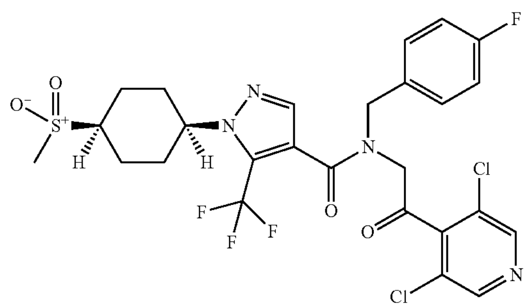 [SMILES: C[S+](=O)([O-])[C@H]1CC[C@@H](n2ncc(C(=O)N(CC(=O)c3c(Cl)cncc3Cl)Cc3ccc(F)cc3)c2C(F)(F)F)CC1] | N-(2-(3,5-dichloropyridin-4-yl)-2-oxoethyl)-N-(4-fluorobenzyl)-1-(cis-4-(methylsulfonyl)cyclohexyl)-5-(trifluoromethyl)-1H-pyrazole-4-carboxamide |
| 87 | 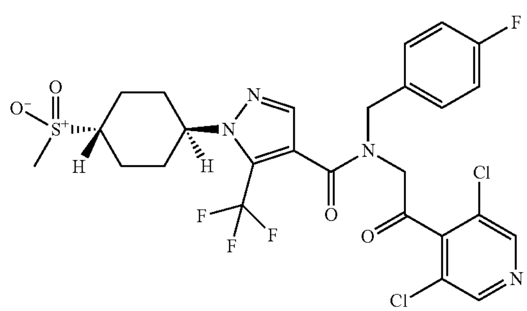 [SMILES: C[S+](=O)([O-])[C@H]1CC[C@H](n2ncc(C(=O)N(CC(=O)c3c(Cl)cncc3Cl)Cc3ccc(F)cc3)c2C(F)(F)F)CC1] | N-(2-(3,5-dichloropyridin-4-yl)-2-oxoethyl)-N-(4-fluorobenzyl)-1-(trans-4-(methylsulfonyl)cyclohexyl)-5-(trifluoromethyl)-1H-pyrazole-4-carboxamide |
| 88 | 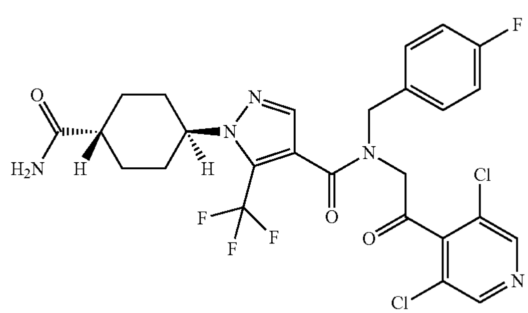 [SMILES: NC(=O)[C@H]1CC[C@H](n2ncc(C(=O)N(CC(=O)c3c(Cl)cncc3Cl)Cc3ccc(F)cc3)c2C(F)(F)F)CC1] | 1-(trans-4-carbamoylcyclohexyl)-N-(2-(3,5-dichloropyridin-4-yl)-2-oxoethyl)-N-(4-fluorobenzyl)-5-(trifluoromethyl)-1H-pyrazole-4-carboxamide |

-continued

| example | structure | name |
|---|---|---|
| 89 | 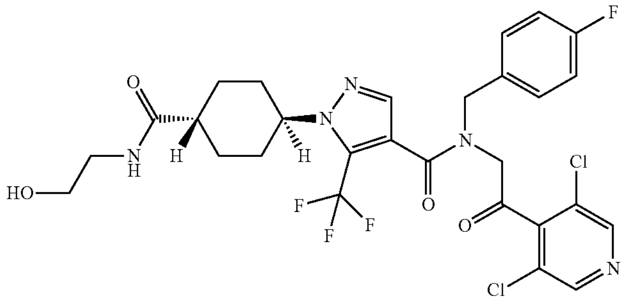 [SMILES: O=C(CN(Cc1ccc(F)cc1)C(=O)c1cnn([C@H]2CC[C@H](C(=O)NCCO)CC2)c1C(F)(F)F)c1c(Cl)cncc1Cl] | N-(2-(3,5-dichloropyridin-4-yl)-2-oxoethyl)-N-(4-fluorobenzyl)-1-(trans-4-((2-hydroxyethyl)carbamoyl)cyclohexyl)-5-(trifluoromethyl)-1H-pyrazole-4-carboxamide |
| 90 | 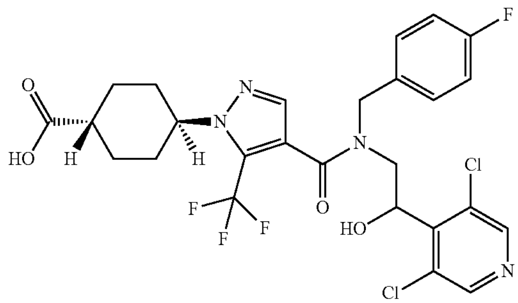 [SMILES: O=C(c1cnn([C@H]2CC[C@H](C(=O)O)CC2)c1C(F)(F)F)N(Cc1ccc(F)cc1)CC(O)c1c(Cl)cncc1Cl] | trans-4-(4-((2-(3,5-dichloropyridin-4-yl)-2-hydroxyethyl)(4-fluorobenzyl)carbamoyl)-5-(trifluoromethyl)-1H-pyrazol-1-yl)cyclohexanecarboxylic acid |
| 91 | 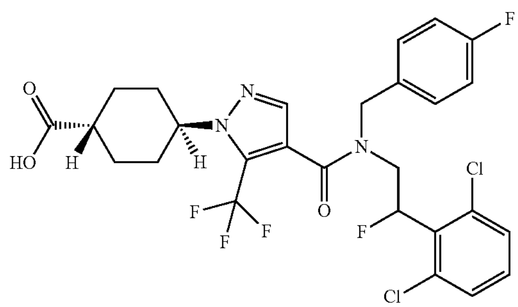 | trans-4-(4-((2-(2,6-dichlorophenyl)-2-fluoroethyl)(4-fluorobenzyl)carbamoyl)(trifluoromethyl)-1H-pyrazol-1-yl)cyclohexanecarboxylic acid |
| 92 | 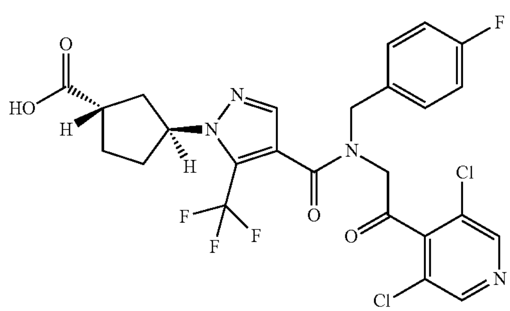 [SMILES: O=C(CN(Cc1ccc(F)cc1)C(=O)c1cnn([C@H]2CC[C@H](C(=O)O)C2)c1C(F)(F)F)c1c(Cl)cncc1Cl] | (1S,3S)-3-(4-((2-(3,5-dichloropyridin-4-yl)-2-oxoethyl)-((4-fluorophenyl)methyl)carbamoyl)-5-(trifluoromethyl)pyrazol-1-yl)cyclopentane-1-carboxylic acid |
| 93 | 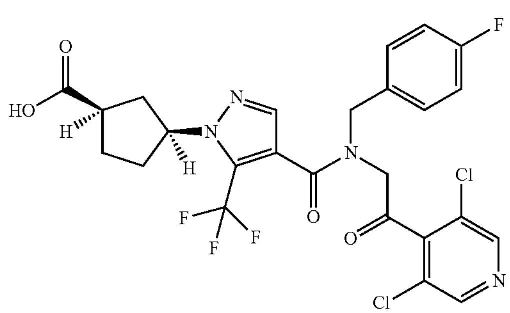 [SMILES: O=C(CN(Cc1ccc(F)cc1)C(=O)c1cnn([C@H]2CC[C@@H](C(=O)O)C2)c1C(F)(F)F)c1c(Cl)cncc1Cl] | (1S,3S)-3-(4-((2-(3,5-dichloropyridin-4-yl)-2-oxoethyl)-((4-fluorophenyl)methyl)carbamoyl)-5-(trifluoromethyl)pyrazol-1-yl)cyclopentane-1-carboxylic acid |

-continued

| example | structure | name |
|---|---|---|
| 94 | 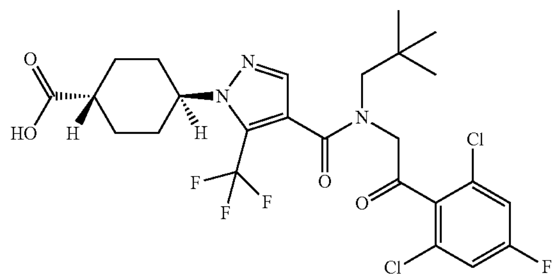 [SMILES: CC(C)(C)CN(CC(=O)c1c(Cl)cc(F)cc1Cl)C(=O)c1cnn([C@H]2CC[C@H](C(=O)O)CC2)c1C(F)(F)F] | trans-4-(4-((2-(2,6-dichloro-4-fluorophenyl)-2-oxoethyl)-(2,2-dimethylpropyl)carbamoyl)-5-(trifluoromethyl)pyrazol-1-yl)-1-methylcyclohexane-1-carboxylic acid |
| 95 | 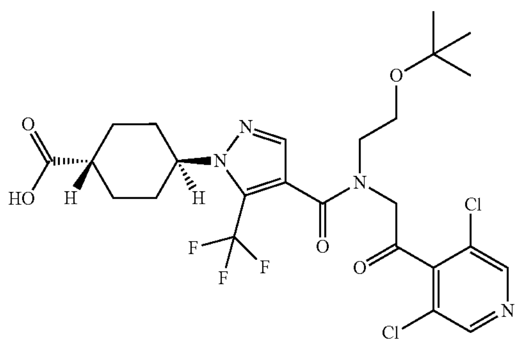 [SMILES: CC(C)(C)OCCN(CC(=O)c1c(Cl)cncc1Cl)C(=O)c1cnn([C@H]2CC[C@H](C(=O)O)CC2)c1C(F)(F)F] | trans-(4((2-(3,5-dichloropyridin-4-yl)-2-oxoethyl)-(2-((2-methylpropan-2-yl)oxy)ethyl)carbamoyl)-5-(trifluoromethyl)pyrazol-1-yl)cyclohexane-1-carboxylic acid |
| 96 | 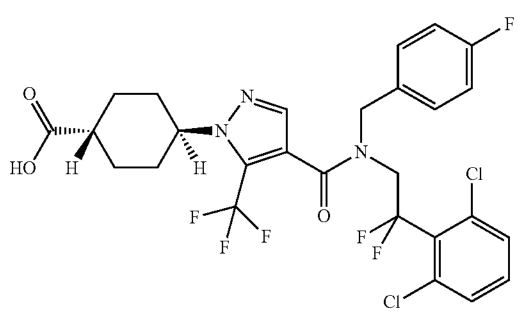 | trans-4-(4-((2-(2,6-dichlorophenyl)-2,2-difluoroethyl)-((4-fluorophenyl)methyl)carbamoyl)-5-(trifluoromethyl)pyrazol-1-yl)cyclohexane-1-carboxylic acid |
| 97 | 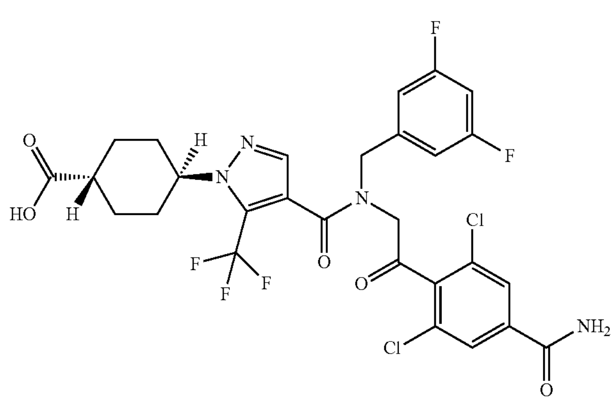 [SMILES: NC(=O)c1cc(Cl)c(C(=O)CN(Cc2cc(F)cc(F)c2)C(=O)c2cnn([C@H]3CC[C@H](C(=O)O)CC3)c2C(F)(F)F)c(Cl)c1] | trans-4-(4-((2-(4-carbamoyl-2,6-dichlorophenyl)-2-oxoethyl)-((3,5-difluorophenyl)methyl)carbamoyl)-5-(trifluoromethyl)pyrazol-1-yl)cyclohexane-1-carboxylic acid |

-continued

| example | structure | name |
|---|---|---|
| 98 | 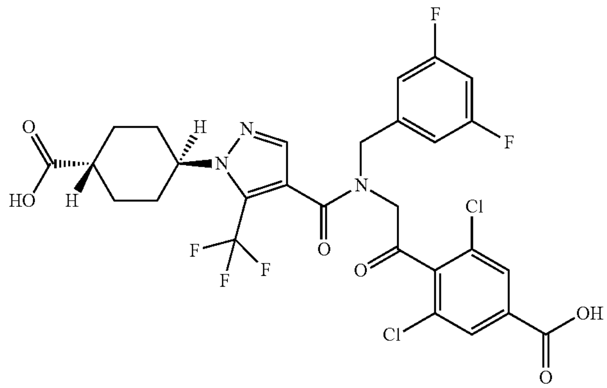 [SMILES: O=C(O)c1cc(Cl)c(C(=O)CN(Cc2cc(F)cc(F)c2)C(=O)c2cnn([C@H]3CC[C@H](C(=O)O)CC3)c2C(F)(F)F)c(Cl)c1] | trans-4-(2-((1-(4-carboxycyclohexyl)-5-(trifluoromethyl)pyrazole-4-carbonyl)-((3,5-difluorophenyl)methyl)amino)acetyl)-3,5-dichlorobenzoic acid |
| 99 | 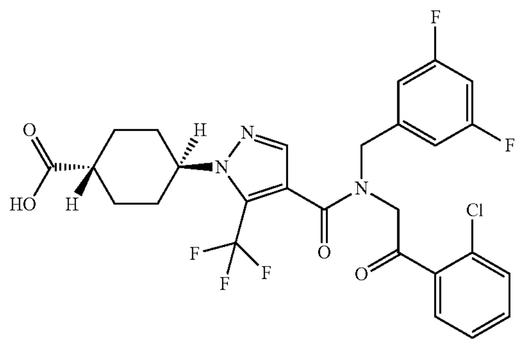 | trans-4-(4-((2-(2-chlorophenyl)-2-oxoethyl)-((3,5-difluorophenyl)methyl)carbamoyl)-5-(trifluoromethyl)pyrazol-1-yl)cyclohexane-1-carboxylic acid |
| 100 | 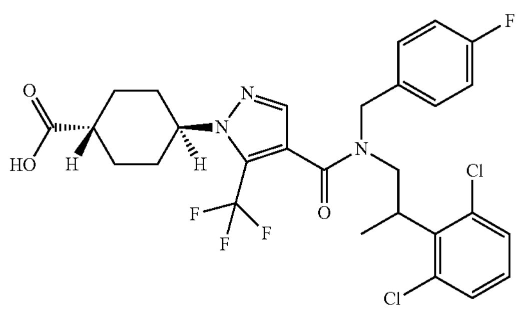 | trans-4-(4-(2-(2,6-dichlorophenyl)propyl-((4-fluorophenyl)methyl)carbamoyl)-5-(trifluoromethyl)pyrazol-1-yl)cyclohexane-1-carboxylic acid |
| 101 | 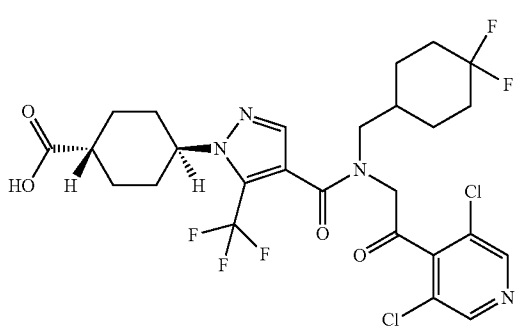 [SMILES: O=C(CN(CC1CCC(F)(F)CC1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-((4,4-difluorocylohexyl)methyl)carbamoyl)-5-(trifluoromethyl)pyrazol-1-yl)cyclohexane-1-carboxylic acid |

-continued

| example | structure | name |
|---|---|---|
| 102 | 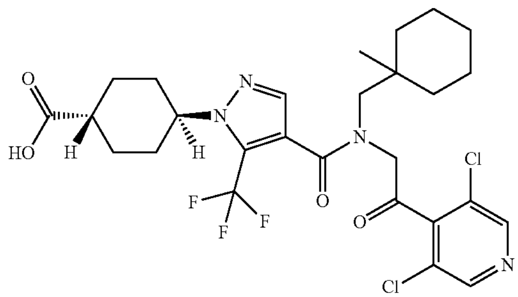 [SMILES: CC1(CN(CC(=O)c2c(Cl)cncc2Cl)C(=O)c2cnn([C@H]3CC[C@H](C(=O)O)CC3)c2C(F)(F)F)CCCCC1] | trans-4-(4-((2-(3,5-dichloropyridin-4-yl)-2-oxoethyl)-((1-methylcyclohexyl)methyl)carbamoyl)-5-(trifluoromethyl)pyrazol-1-yl)cyclohexane-1-carboxylic acid |
| 103 | 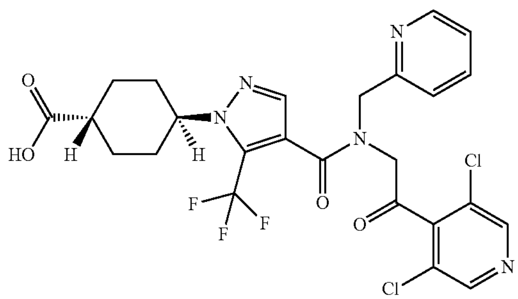 [SMILES: O=C(CN(Cc1ccccn1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-(pyridin-2-ylmethyl)carbamoyl)-5-(trifluoromethyl)pyrazol-1-yl)cyclohexane-1-carboxylic acid |
| 104 | 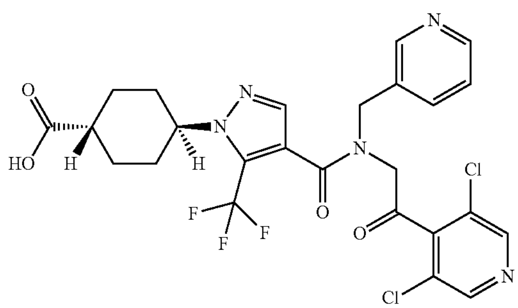 [SMILES: O=C(CN(Cc1cccnc1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-(pyridin-3-ylmethyl)carbamoyl)-5-(trifluoromethyl)pyrazol-1-yl)cyclohexane-1-carboxylic acid |
| 105 | 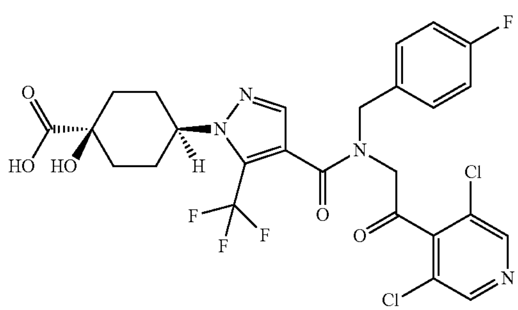 [SMILES: O=C(CN(Cc1ccc(F)cc1)C(=O)c1cnn([C@H]2CC[C@](O)(C(=O)O)CC2)c1C(F)(F)F)c1c(Cl)cncc1Cl] | cis-4-(4-((2-(3,5-dichloropyridin-4-yl)-2-oxoethyl)-((4-fluorophenyl)methyl)carbamoyl)-5-(trifluoromethyl)pyrazol-1-yl)-1-hydroxycyclohexane-1-carboxylic acid |
| 106 | 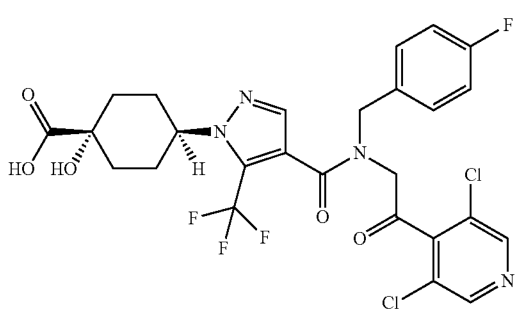 [SMILES: O=C(CN(Cc1ccc(F)cc1)C(=O)c1cnn([C@H]2CC[C@@](O)(C(=O)O)CC2)c1C(F)(F)F)c1c(Cl)cncc1Cl] | trans-4-(4-((2-(3,5-dichloropyridin-4-yl)-2-oxoethyl)-((4-fluorophenyl)methyl)carbamoyl)-5-(trifluoromethyl)pyrazol-1-yl)-1-hydroxycyclohexane-1-carboxylic acid |

| example | structure | name |
|---|---|---|
| 107 | 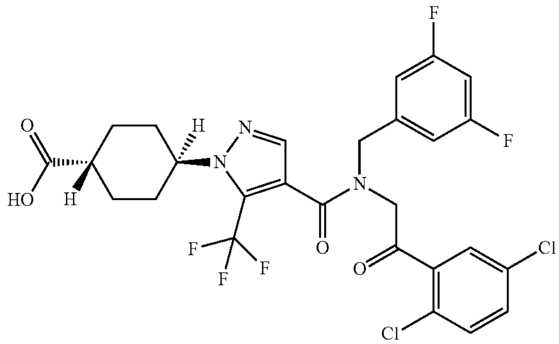 [SMILES: O=C(CN(Cc1cc(F)cc(F)c1)C(=O)c1cnn([C@H]2CC[C@H](C(=O)O)CC2)c1C(F)(F)F)c1cc(Cl)ccc1Cl] | trans-4-(4-((2-(2,5-dichlorophenyl)-2-oxoethyl)-((3,5-difluorophenyl)methyl)carbamoyl)-5-(trifluoromethyl)pyrazol-1-yl)cyclohexane-1-carboxylic acid |
| 108 | 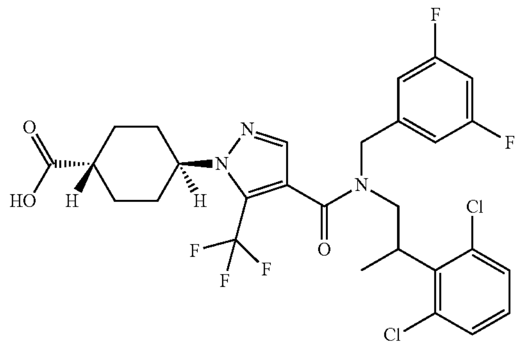 | trans-4-(4-(2-(2,6-dichlorophenyl)propyl-((3,5-difluorophenyl)methyl)carbamoyl)-5-(trifluoromethyl)pyrazol-1-yl)cyclohexane-1-carboxylic acid |
| 109 | 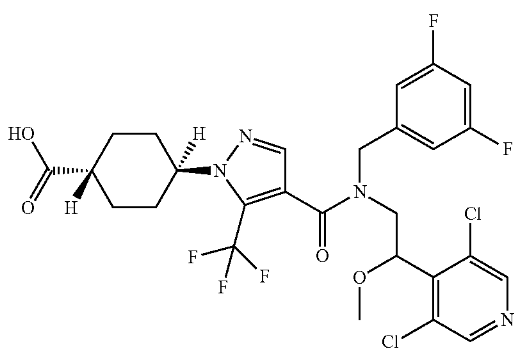 [SMILES: COC(CN(Cc1cc(F)cc(F)c1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-methoxyethyl)-((3,5-difluorophenyl)methyl)carbamoyl)-5-(trifluoromethyl)pyrazol-1-yl)cyclohexane-1-carboxylic acid |
| 110 | 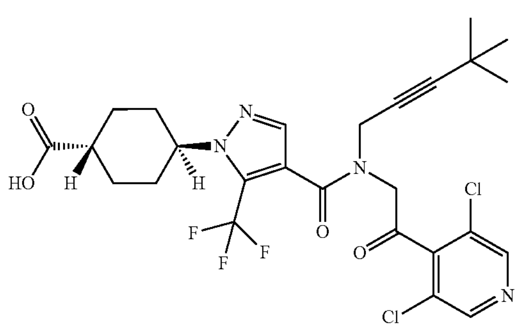 [SMILES: CC(C)(C)C#CCN(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)-(4,4-dimethylpent-2-ynyl)carbamoyl)-5-(trifluoromethyl)pyrazol-1-yl)cyclohexane-1-carboxylic acid |

-continued

| example | structure | name |
|---|---|---|
| 111 | 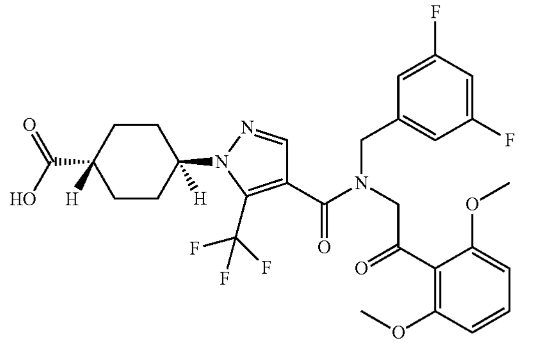 | trans-4-(4-((3,5-difluorophenyl)methyl-(2-(2,6-dimethoxyphenyl)-2-oxoethyl)carbamoyl)-5-(trifluoromethyl)pyrazol-1-yl)cyclohexane-1-carboxylic acid |
| 112 | 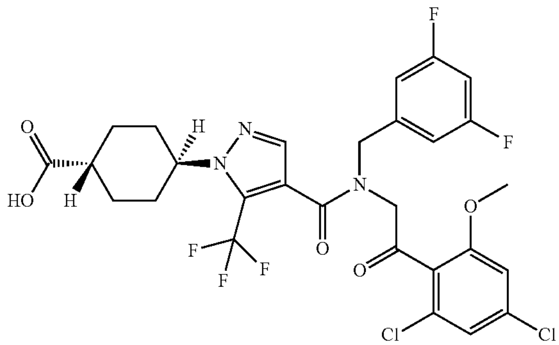 [SMILES: COc1cc(Cl)cc(Cl)c1C(=O)CN(Cc1cc(F)cc(F)c1)C(=O)c1cnn([C@H]2CC[C@H](C(=O)O)CC2)c1C(F)(F)F] | trans-4-(4-((2-(2,4-dichloro-6-methoxyphenyl)-2-oxoethyl)-((3,5-difluorophenyl)methyl) carbamoyl)-5-(trifluoromethyl)pyrazol-1-yl)cyclohexane-1-carboxylic acid |
| 113 | 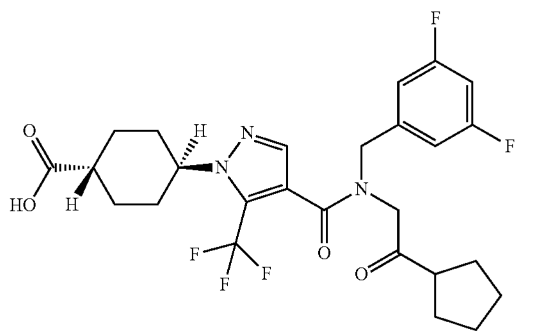 [SMILES: O=C(CN(Cc1cc(F)cc(F)c1)C(=O)c1cnn([C@H]2CC[C@H](C(=O)O)CC2)c1C(F)(F)F)C1CCCC1] | trans-4-(4-((2-cyclopentyl-2-oxoethyl)-((3,5-difluorophenyl)methyl)carbamoyl)-5-(trifluoromethyl)pyrazol-1-yl)cyclohexane-1-carboxylic acid |
| 114 | 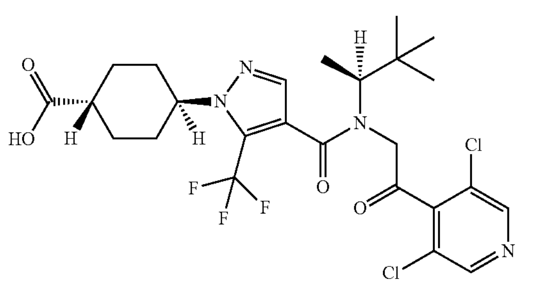 [SMILES: C[C@H](N(CC(=O)c1c(Cl)cncc1Cl)C(=O)c1cnn([C@H]2CC[C@H](C(=O)O)CC2)c1C(F)(F)F)C(C)(C)C] | trans-4-(4-((2-(3,5-dichloropyridin-4-yl)-2-oxoethyl)-((2S)-3,3-dimethylbutan-2-yl)carbamoyl)-5-(trifluoromethyl)pyrazol-1-yl)cyclohexane-1-carboxylic acid |
| 115 | 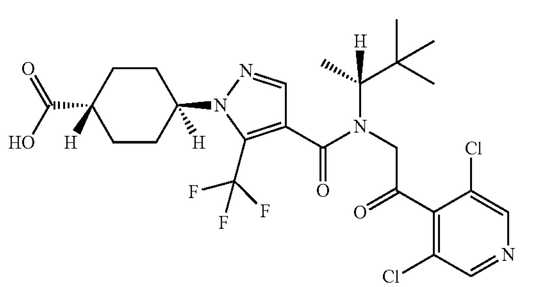 [SMILES: C[C@@H](N(CC(=O)c1c(Cl)cncc1Cl)C(=O)c1cnn([C@H]2CC[C@H](C(=O)O)CC2)c1C(F)(F)F)C(C)(C)C] | trans-4-(4-((2-(3,5-dichloropyridin-4-yl)-2-oxoethyl)-((2R)-3,3-dimethylbutan-2-yl)carbamoyl)-5-(trifluoromethyl)pyrazol-1-yl)cyclohexane-1-carboxylic acid |

-continued

| example | structure | name |
|---|---|---|
| 116 | 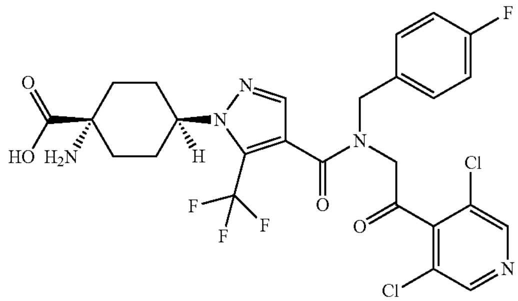 | cis-4-(4-((2-(3,5-dichloropyridin-4-yl)-2-oxoethyl)-((4-fluorophenyl)methyl)carbamoyl)-5-(trifluoromethyl)pyrazol-1-yl)-1-aminocyclohexane-1-carboxylic acid |
| 117 | 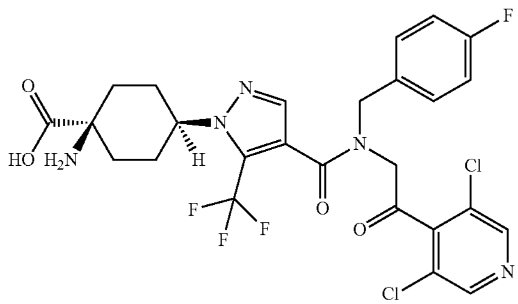 [SMILES: N[C@]1(C(=O)O)CC[C@H](n2ncc(C(=O)N(CC(=O)c3c(Cl)cncc3Cl)Cc3ccc(F)cc3)c2C(F)(F)F)CC1] | cis-4-(4-((2-(3,5-dichloropyridin-4-yl)-2-oxoethyl)-((4-fluorophenyl)methyl)carbamoyl)-5-(trifluoromethyl)pyrazol-1-yl)-1-aminocyclohexane-1-carboxylic acid |
| 118 | 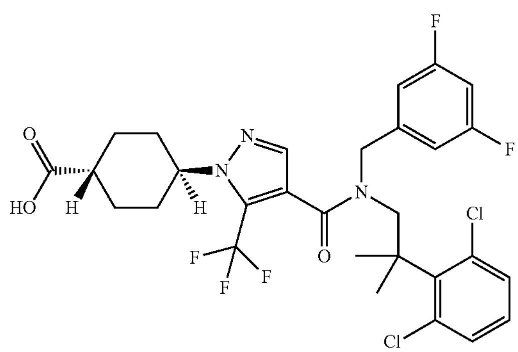 [SMILES: CC(C)(CN(Cc1cc(F)cc(F)c1)C(=O)c1cnn([C@H]2CC[C@H](C(=O)O)CC2)c1C(F)(F)F)c1c(Cl)cccc1Cl] | trans-4-(4-((2-(2,6-dichlorophenyl)-2-methylpropyl)-((3,5-difluorophenyl)methyl)carbamoyl)-5-(trifluoromethyl)pyrazol-1-yl)cyclohexane-1-carboxylic acid |
| 119 | 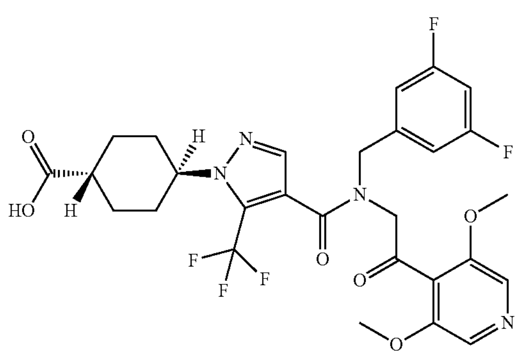 [SMILES: COc1cncc(OC)c1C(=O)CN(Cc1cc(F)cc(F)c1)C(=O)c1cnn([C@H]2CC[C@H](C(=O)O)CC2)c1C(F)(F)F] | trans-4-(4-(((3,5-difluorophenyl)methyl-(2-(3,5-dimethoxypyridin-4-yl)-2-oxoethyl)carbamoyl)-5-(trifluoromethyl)pyrazol-1-yl)cyclohexane-1-carboxylic acid |

-continued

| example | structure | name |
|---|---|---|
| 120 | 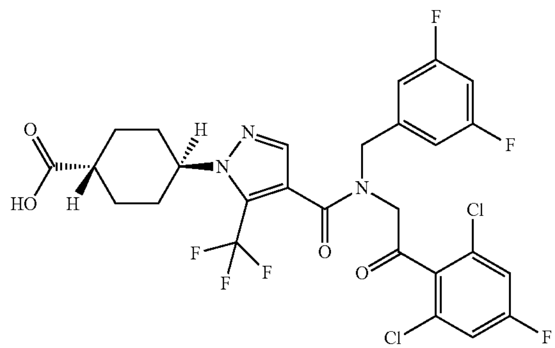 [SMILES: O=C(CN(Cc1cc(F)cc(F)c1)C(=O)c1cnn([C@H]2CC[C@H](C(=O)O)CC2)c1C(F)(F)F)c1c(Cl)cc(F)cc1Cl] | trans-4-(4-(2-(2,6-dichloro-4-fluorophenyl)ethyl-((3,5-difluorophenyl)methyl)carbamoyl)-5-(trifluoromethyl)pyrazol-1-yl)cyclohexane-1-carboxylic acid |
| 121 | 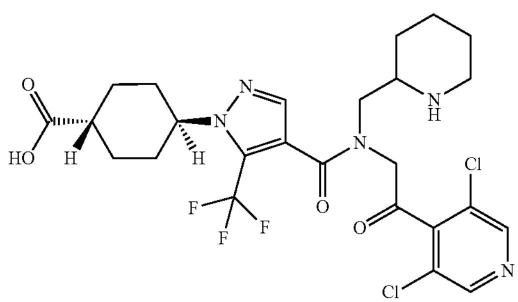 [SMILES: O=C(CN(CC1CCCCN1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-(piperidin-2-ylmethyl)carbamoyl)-5-(trifluoromethyl)pyrazol-1-yl)cyclohexane-1-carboxylic acid |
| 122 | 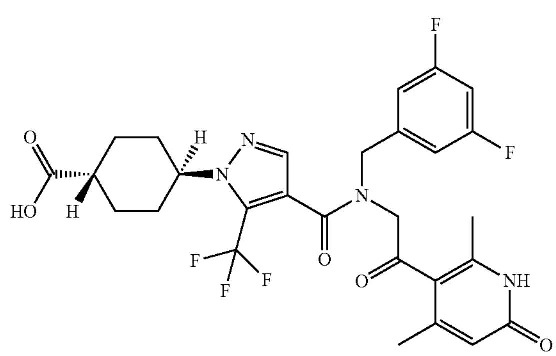 [SMILES: Cc1cc(=O)[nH]c(C)c1C(=O)CN(Cc1cc(F)cc(F)c1)C(=O)c1cnn([C@H]2CC[C@H](C(=O)O)CC2)c1C(F)(F)F] | trans-4-(4-((3,5-difluorophenyl)methyl-(2-(2,4-dimethyl-6-oxo-1H-pyridin-3-yl)-2-oxoethyl)carbamoyl)-5-(trifluoromethyl)pyrazol-1-yl)cyclohexane-1-carboxylic acid |
| 123 | 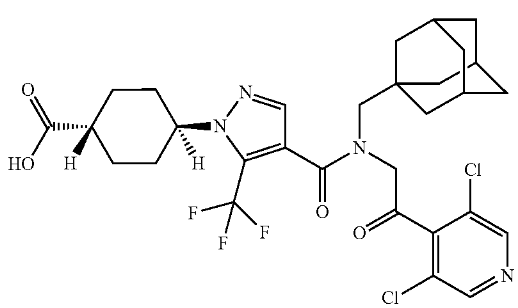 [SMILES: O=C(CN(CC12CC3CC(CC(C3)C1)C2)C(=O)c1cnn([C@H]2CC[C@H](C(=O)O)CC2)c1C(F)(F)F)c1c(Cl)cncc1Cl] | trans-4-(4-(1-adamantylmethyl-(2-(3,5-dichloropyridin-4-yl)-2-oxoethyl)carbamoyl)-5-(trifluoromethyl)pyrazol-1-yl)cyclohexane-1-carboxylic acid |

-continued

| example | structure | name |
|---|---|---|
| 124 | 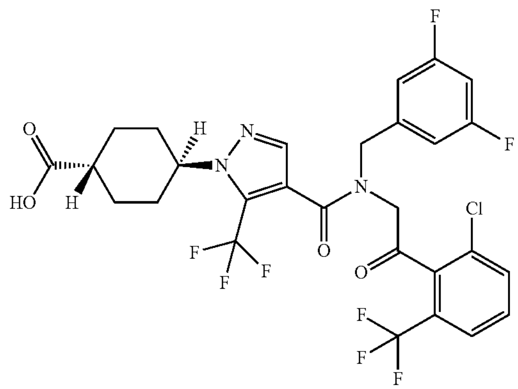 [SMILES: O=C(CN(Cc1cc(F)cc(F)c1)C(=O)c1cnn([C@H]2CC[C@H](C(=O)O)CC2)c1C(F)(F)F)c1c(Cl)cccc1C(F)(F)F] | trans-4-(4-((2-(2-chloro-6-(trifluoromethyl)phenyl)-2-oxoethyl)-((3,5-difluorophenyl)methyl)carbamoyl)-5-(trifluoromethyl)pyrazol-1-yl)cyclohexane-1-carboxylic acid |
| 125 | 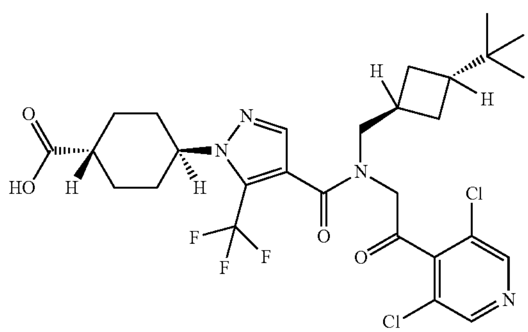 [SMILES: CC(C)(C)[C@H]1C[C@H](CN(CC(=O)c2c(Cl)cncc2Cl)C(=O)c2cnn([C@H]3CC[C@H](C(=O)O)CC3)c2C(F)(F)F)C1] | trans-4-(4-((3-tert-butylcyclobutyl)methyl-(2-(3,5-dichloropyridin-4-yl)-2-oxoethyl)carbamoyl)-5-(trifluoromethyl)pyrazol-1-yl)cyclohexane-1-carboxylic acid |
| 126 | 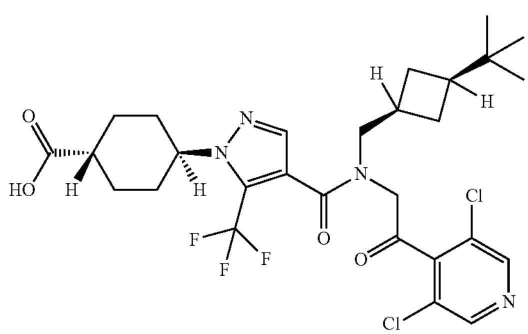 [SMILES: CC(C)(C)[C@H]1C[C@@H](CN(CC(=O)c2c(Cl)cncc2Cl)C(=O)c2cnn([C@H]3CC[C@H](C(=O)O)CC3)c2C(F)(F)F)C1] | trans-4-(4-((3-tert-butylcyclobutyl)methyl-(2-(3,5-dichloropyridin-4-yl)-2-oxoethyl)carbamoyl)-5-(trifluoromethyl)pyrazol-1-yl)cyclohexane-1-carboxylic acid |
| 127 | 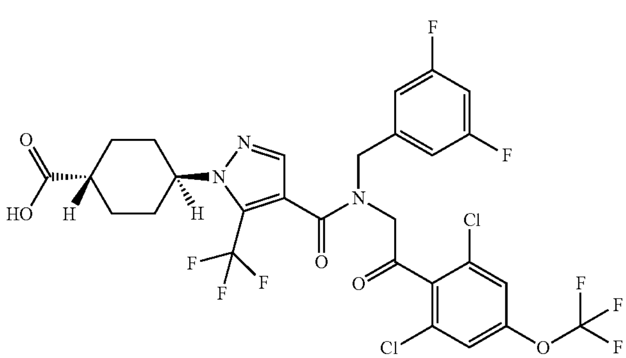 [SMILES: O=C(CN(Cc1cc(F)cc(F)c1)C(=O)c1cnn([C@H]2CC[C@H](C(=O)O)CC2)c1C(F)(F)F)c1c(Cl)cc(OC(F)(F)F)cc1Cl] | trans-4-(4-((2-(2,6-dichloro-4-(trifluoromethoxy)phenyl)-2-oxoethyl)-((3,5-difluorophenyl)methyl)carbamoyl)-5-(trifluoromethyl)pyrazol-1-yl)cyclohexane-1-carboxylic acid |

| example | structure | name |
| --- | --- | --- |
| 128 | 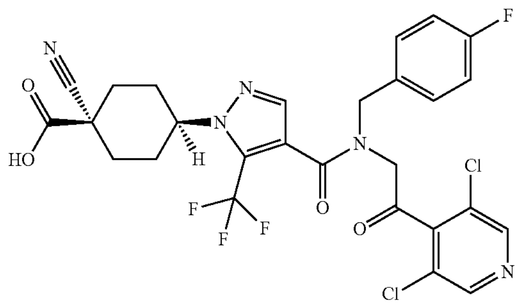 [SMILES: N#C[C@]1(C(=O)O)CC[C@@H](n2ncc(C(=O)N(CC(=O)c3c(Cl)cncc3Cl)Cc3ccc(F)cc3)c2C(F)(F)F)CC1] | trans-4-(4-((2-(3,5-dichloropyridin-4-yl)-2-oxoethyl)-((4-fluorophenyl)methyl)carbamoyl)-5-(trifluoromethyl)pyrazol-1-yl)-1-cyanocyclohexane-1-carboxylic acid |
| 129 | 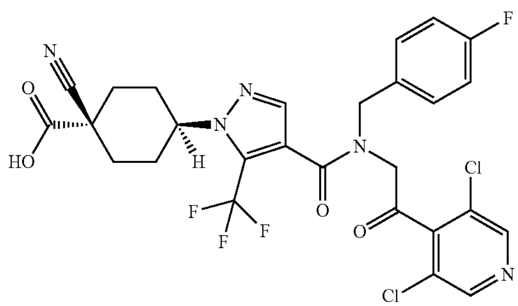 [SMILES: N#C[C@]1(C(=O)O)CC[C@H](n2ncc(C(=O)N(CC(=O)c3c(Cl)cncc3Cl)Cc3ccc(F)cc3)c2C(F)(F)F)CC1] | trans-4-(4-((2-(3,5-dichloropyridin-4-yl)-2-oxoethyl)-((4-fluorophenyl)methyl)carbamoyl)-5-(trifluoromethyl)pyrazol-1-yl)-1-cyanocyclohexane-1-carboxylic acid |
| 130 | 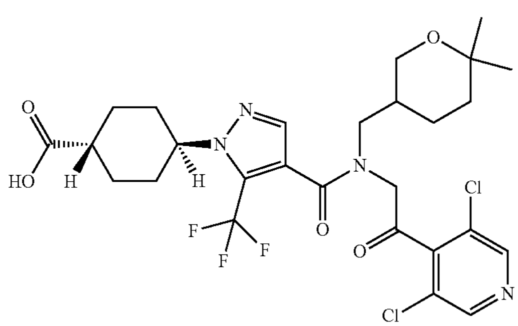 [SMILES: CC1(C)CCC(CN(CC(=O)c2c(Cl)cncc2Cl)C(=O)c2cnn([C@H]3CC[C@H](C(=O)O)CC3)c2C(F)(F)F)CO1] | trans-4-(4-((2-(3,5-dichloropyridin-4-yl)-2-oxoethyl)-((6,6-dimethyloxan-3-yl)methyl)carbamoyl)-5-(trifluoromethyl)pyrazol-1-yl)-1-cyanocyclohexane-1-carboxylic acid |
| 131 | 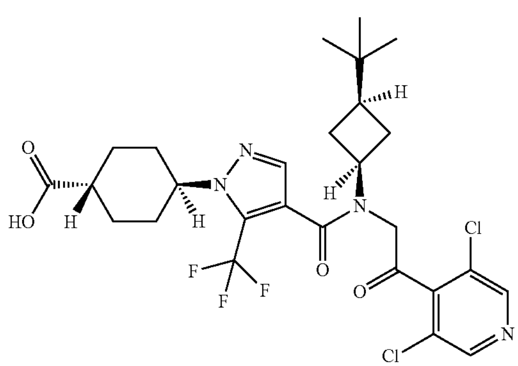 [SMILES: CC(C)(C)[C@H]1C[C@@H](N(CC(=O)c2c(Cl)cncc2Cl)C(=O)c2cnn([C@H]3CC[C@H](C(=O)O)CC3)c2C(F)(F)F)C1] | trans-4-(4-((3-tert-butylcyclobutyl)-(2-(3,5-dichloropyridin-4-yl)-2-oxoethyl)carbamoyl)-5-(trifluoromethyl)pyrazol-1-yl)cyclohexane-1-carboxylic acid |

-continued

| example | structure | name |
|---|---|---|
| 132 | 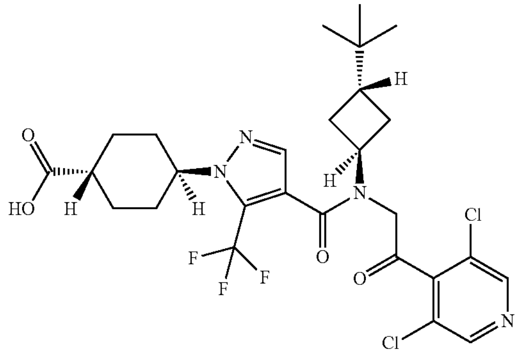 [SMILES: CC(C)(C)[C@H]1C[C@H](N(CC(=O)c2c(Cl)cncc2Cl)C(=O)c2cnn([C@H]3CC[C@H](C(=O)O)CC3)c2C(F)(F)F)C1] | trans-4-(4-((3-tert-butylcyclobutyl)-(2-(3,5-dichloropyridin-4-yl)-2-oxoethyl)carbamoyl)-5-(trifluoromethyl)pyrazol-1-yl)cyclohexane-1-carboxylic acid |
| 133 | 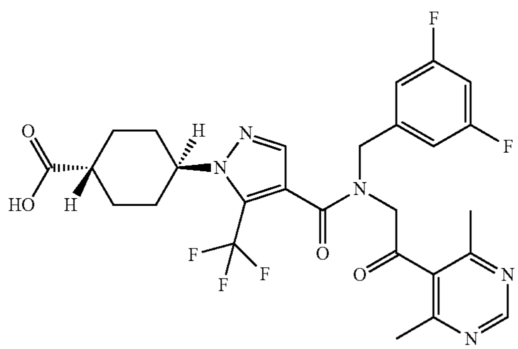 [SMILES: Cc1ncnc(C)c1C(=O)CN(Cc1cc(F)cc(F)c1)C(=O)c1cnn([C@H]2CC[C@H](C(=O)O)CC2)c1C(F)(F)F] | trans-4-(4-((3,5-difluorophenyl)methyl-(2-(4,6-dimethylpyrimidin-5-yl)-2-oxoethyl)carbamoyl)-5-(trifluoromethyl)pyrazol-1-yl)cyclohexane-1-carboxylic acid |
| 134 | 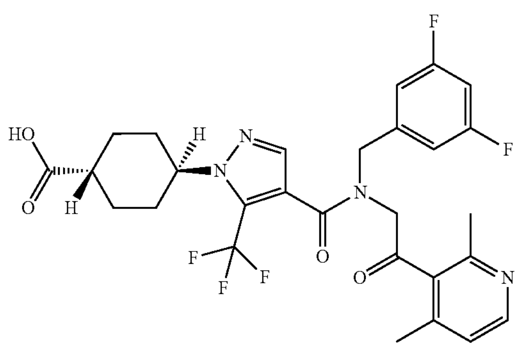 [SMILES: Cc1ccnc(C)c1C(=O)CN(Cc1cc(F)cc(F)c1)C(=O)c1cnn([C@H]2CC[C@H](C(=O)O)CC2)c1C(F)(F)F] | trans-4-(4-((3,5-difluorophenyl)methyl-(2-(2,4-dimethylpyridin-3-yl)-2-oxoethyl)carbamoyl)-5-(trifluoromethyl)pyrazol-1-yl)cyclohexane-1-carboxylic acid |
| 135 | 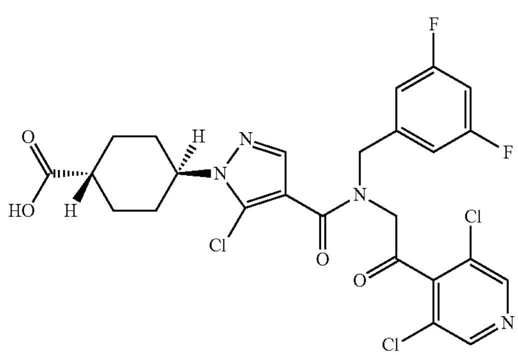 [SMILES: O=C(CN(Cc1cc(F)cc(F)c1)C(=O)c1cnn([C@H]2CC[C@H](C(=O)O)CC2)c1Cl)c1c(Cl)cncc1Cl] | trans-4-(5-chloro-4-((2-(3,5-dichloropyridin-4-yl)-2-oxoethyl)-((3,5-difluorophenyl)methyl)carbamoyl)pyrazol-1-yl)cyclohexane-1-carboxylic acid |

-continued

| example | structure | name |
|---|---|---|
| 136 | 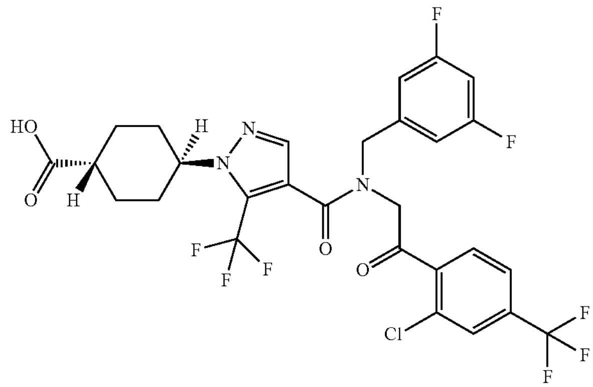 [SMILES: O=C(CN(Cc1cc(F)cc(F)c1)C(=O)c1cnn([C@H]2CC[C@H](C(=O)O)CC2)c1C(F)(F)F)c1ccc(C(F)(F)F)cc1Cl] | trans-4-(4-((2-(2-chloro-4-(trifluoromethyl)phenyl)-2-oxoethyl)-((3,5-difluorophenyl)methyl)carbamoyl)-5-(trifluoromethyl)pyrazol-1-yl)cyclohexane-1-carboxylic acid |
| 137 | 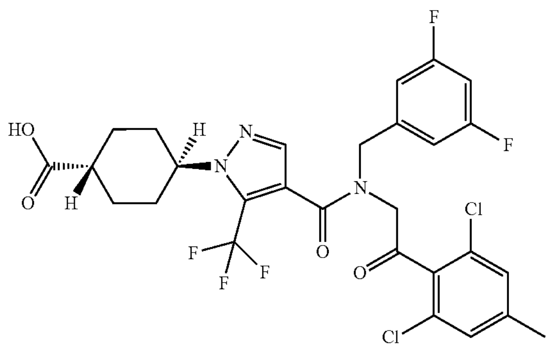 [SMILES: Cc1cc(Cl)c(C(=O)CN(Cc2cc(F)cc(F)c2)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)-((3,5-difluorophenyl)methyl)carbamoyl)-5-(trifluoromethyl)pyrazol-1-yl)cyclohexane-1-carboxylic acid |
| 138 | 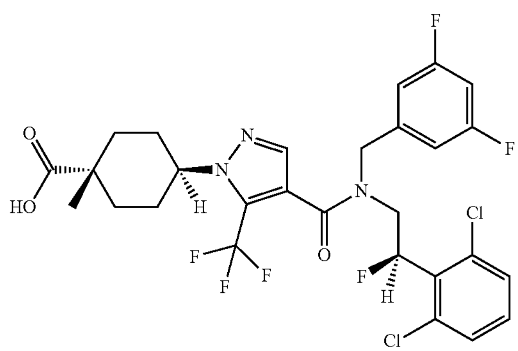 | trans-4-(4-(((2R)-2-(2,6-dichlorophenyl)-2-fluoroethyl)-((3,5-difluorophenyl)methyl)carbamoyl)-5-(trifluoromethyl)pyrazol-1-yl)-1-methylcyclohexane-1-carboxylic acid |
| 139 | 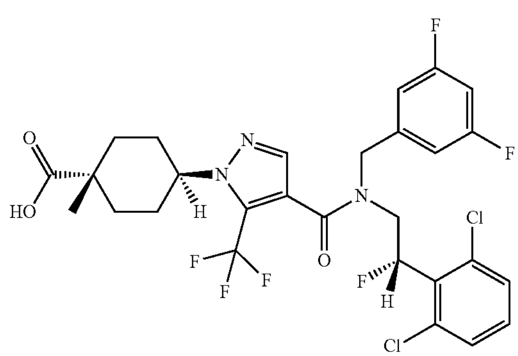 [SMILES: C[C@]1(C(=O)O)CC[C@H](n2ncc(C(=O)N(Cc3cc(F)cc(F)c3)C[C@@H](F)c3c(Cl)cccc3Cl)c2C(F)(F)F)CC1] | trans-4-(4-(((2S)-2-(2,6-dichlorophenyl)-2-fluoroethyl)-((3,5-difluorophenyl)methyl)carbamoyl)-5-(trifluoromethyl)pyrazol-1-yl)-1-methylcyclohexane-1-carboxylic acid |

-continued

| example | structure | name |
|---|---|---|
| 140 | 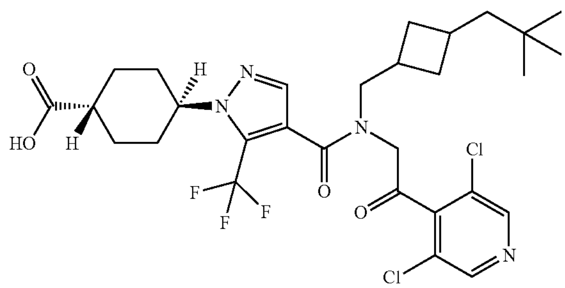 [SMILES: CC(C)(C)CC1CC(CN(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-((3-(2,2-dimethylpropyl)cyclobutyl)methyl)carbamoyl)-5-(trifluoromethyl)pyrazol-1-yl)cyclohexane-1-carboxylic acid |
| 141 | 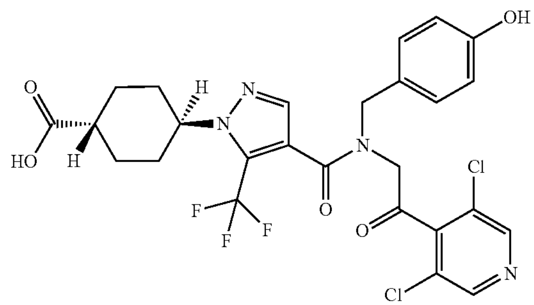 [SMILES: O=C(CN(Cc1ccc(O)cc1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-((4-hydroxyphenyl)methyl)carbamoyl)-5-(trifluoromethyl)pyrazol-1-yl)cyclohexane-1-carboxylic acid |
| 142 | 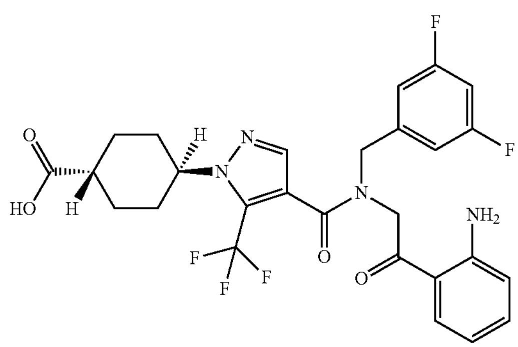 | trans-4-(4-((2-(2-aminophenyl)-2-oxoethyl)-((3,5-difluorophenyl)methyl)carbamoyl)-5-(trifluoromethyl)pyrazol-1-yl)cyclohexane-1-carboxylic acid |
| 143 | 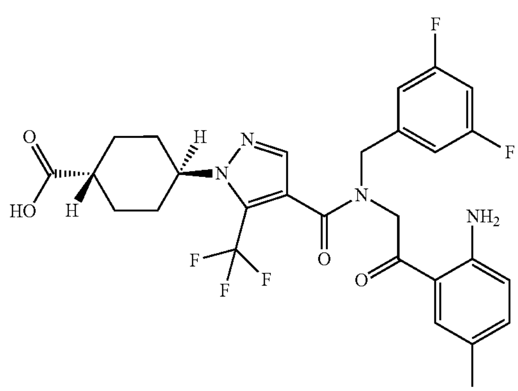 [SMILES: Cc1ccc(N)c(C(=O)CN(Cc2cc(F)cc(F)c2)C(=O)c2cnn([C@H]3CC[C@H](C(=O)O)CC3)c2C(F)(F)F)c1] | trans-4-(4-((2-(2-amino-5-methylphenyl)-2-oxoethyl)-((3,5-difluorophenyl)methyl)carbamoyl)-5-(trifluoromethyl)pyrazol-1-yl)cyclohexane-1-carboxylic acid |

| example | structure | name |
|---|---|---|
| 144 | 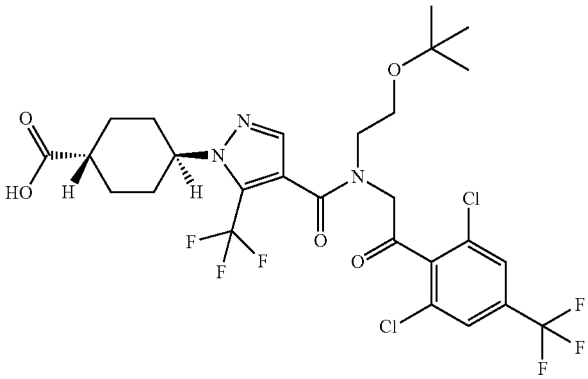 [SMILES: CC(C)(C)OCCN(CC(=O)c1c(Cl)cc(C(F)(F)F)cc1Cl)C(=O)c1cnn([C@H]2CC[C@H](C(=O)O)CC2)c1C(F)(F)F] | trans-4-(4-((2-(2,6-dichloro-4-(trifluoromethyl)phenyl)-2-oxoethyl)-(2-((2-methylpropan-2-yl)oxy)ethyl)carbamoyl)-5-(trifluoromethyl)pyrazol-1-yl)cyclohexane-1-carboxylic acid |
| 145 | 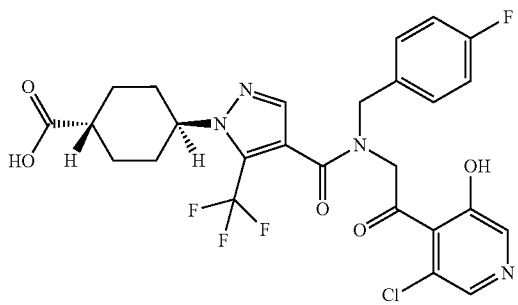 [SMILES: O=C(CN(Cc1ccc(F)cc1)C(=O)c1cnn([C@H]2CC[C@H](C(=O)O)CC2)c1C(F)(F)F)c1c(O)cncc1Cl] | trans-4-(4-((2-(3-chloro-5-hydroxypyridin-4-yl)-2-oxoethyl)-((4-fluorophenyl)methyl)carbamoyl)-5-(trifluoromethyl)pyrazol-1-yl)cyclohexane-1-carboxylic acid |
| 146 | 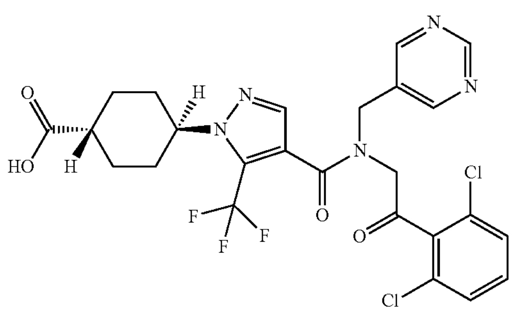 [SMILES: O=C(CN(Cc1cncnc1)C(=O)c1cnn([C@H]2CC[C@H](C(=O)O)CC2)c1C(F)(F)F)c1c(Cl)cccc1Cl] | trans-4-(4-((2-(2,6-dichlorophenyl)-2-oxoethyl)-(pyrimidin-5-ylmethyl)carbamoyl)-5-(trifluoromethyl)pyrazol-1-yl)cyclohexane-1-carboxylic acid |
| 147 | 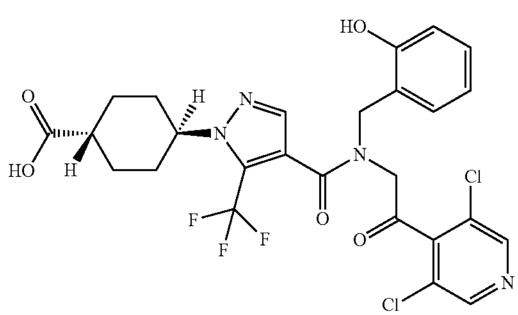 [SMILES: O=C(CN(Cc1ccccc1O)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-((2-hydroxyphenyl)methyl)carbamoyl)-5-(trifluoromethyl)pyrazol-1-yl)cyclohexane-1-carboxylic acid |

| example | structure | name |
|---|---|---|
| 148 | 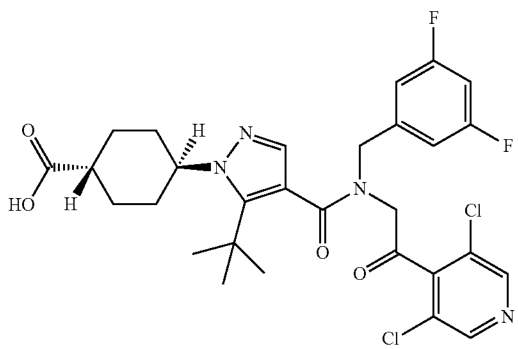 [SMILES: CC(C)(C)c1c(C(=O)N(CC(=O)c2c(Cl)cncc2Cl)Cc2cc(F)cc(F)c2)cnn1[C@H]1CC[C@H](C(=O)O)CC1] | trans-4-(5-tert-butyl-4-((2-(3,5-dichloropyridin-4-yl)-2-oxoethyl)-((3,5-difluorophenyl)methyl)carbamoyl)pyrazol-1-yl)cyclohexane-1-carboxylic acid |
| 149 | 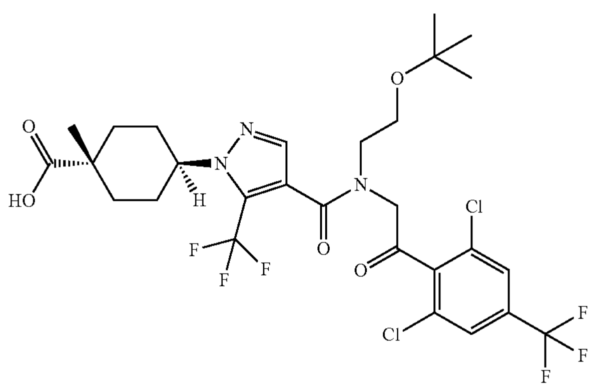 [SMILES: CC(C)(C)OCCN(CC(=O)c1c(Cl)cc(C(F)(F)F)cc1Cl)C(=O)c1cnn([C@H]2CC[C@](C)(C(=O)O)CC2)c1C(F)(F)F] | trans-4-(4-((2-(2,6-dichloro-4-(trifluoromethyl)phenyl)-2-oxoethyl)-(2-((2-methylpropan-2-yl)oxy)ethyl)carbamoyl)-5-(trifluoromethyl)pyrazol-1-yl)-1-methylcyclohexane-1-carboxylic acid |
| 150 | 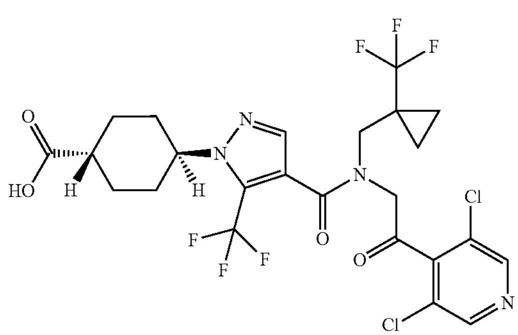 [SMILES: O=C(CN(CC1(C(F)(F)F)CC1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-((1-(trifluoromethyl)cyclopropyl)methyl)carbamoyl)-5-(trifluoromethyl)pyrazol-1-yl)cyclohexane-1-carboxylic acid |
| 151 | 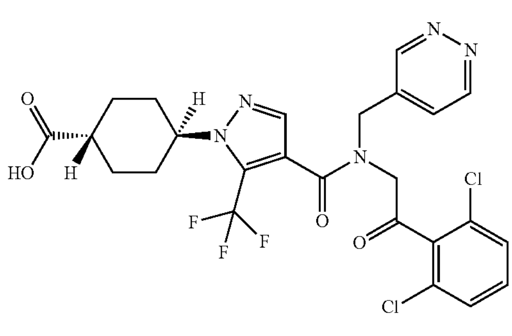 [SMILES: O=C(CN(Cc1ccnnc1)C(=O)c1cnn([C@H]2CC[C@H](C(=O)O)CC2)c1C(F)(F)F)c1c(Cl)cccc1Cl] | trans-4-(4-((2-(2,6-dichlorophenyl)-2-oxoethyl)-(pyridazin-4-ylmethyl)carbamoyl)-5-(trifluoromethyl)pyrazol-1-yl)cyclohexane-1-carboxylic acid |

| example | structure | name |
|---|---|---|
| 152 | 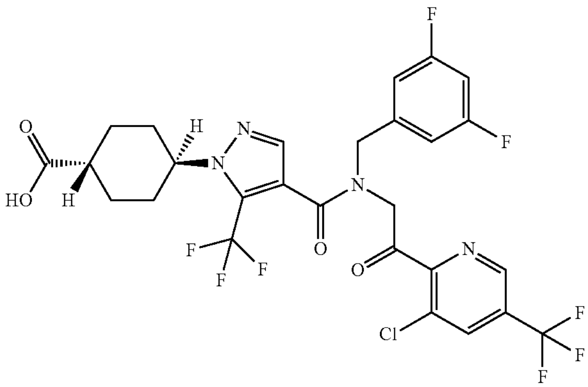 [SMILES: O=C(CN(Cc1cc(F)cc(F)c1)C(=O)c1cnn([C@H]2CC[C@H](C(=O)O)CC2)c1C(F)(F)F)c1ncc(C(F)(F)F)cc1Cl] | trans-4-(4-((2-(3-chloro-5-(trifluoromethyl)pyridin-2-yl)-2-oxoethyl)-((3,5-difluorophenyl)methyl)carbamoyl)-5-(trifluoromethyl)pyrazol-1-yl)cyclohexane-1-carboxylic acid |
| 153 | 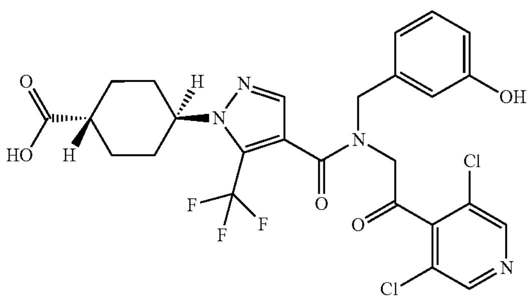 [SMILES: O=C(CN(Cc1cccc(O)c1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-((3-hydroxyphenyl)methyl)carbamoyl)-5-(trifluoromethyl)pyrazol-1-yl)cyclohexane-1-carboxylic acid |
| 154 | 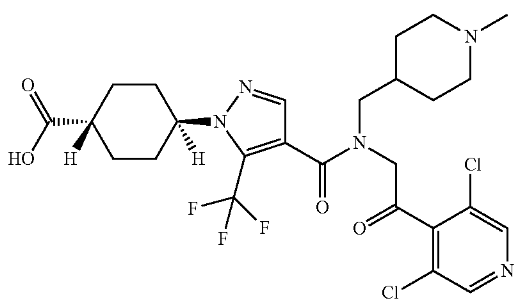 [SMILES: CN1CCC(CN(CC(=O)c2c(Cl)cncc2Cl)C(=O)c2cnn([C@H]3CC[C@H](C(=O)O)CC3)c2C(F)(F)F)CC1] | trans-4-(4-((2-(3,5-dichloropyridin-4-yl)-2-oxoethyl)-((1-methylpiperidin-4-yl)methyl)carbamoyl)-5-(trifluoromethyl)pyrazol-1-yl)cyclohexane-1-carboxylic acid |
| 155 | 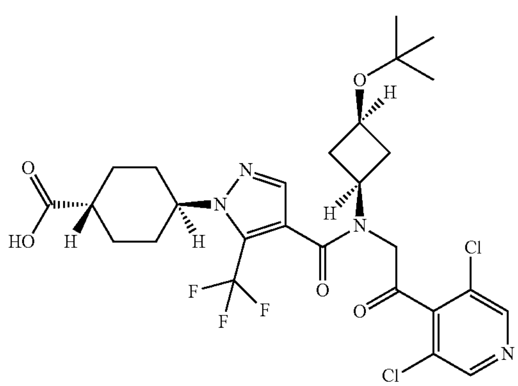 [SMILES: CC(C)(C)O[C@H]1C[C@@H](N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-(3-((2-methylpropan-2-yl)oxy)cyclobutyl)carbamoyl)-5-(trifluoromethyl)pyrazol-1-yl)cyclohexane-1-carboxylic acid |

| example | structure | name |
|---|---|---|
| 156 | 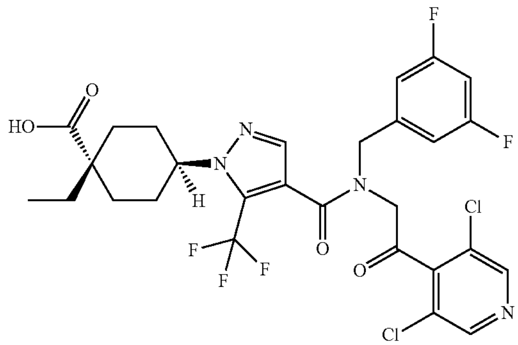 [SMILES: CC[C@]1(C(=O)O)CC[C@H](n2ncc(C(=O)N(CC(=O)c3c(Cl)cncc3Cl)Cc3cc(F)cc(F)c3)c2C(F)(F)F)CC1] | trans-4-(4-((2-(3,5-dichloropyridin-4-yl)-2-oxoethyl)-((3,5-difluorophenyl)methyl)carbamoyl)-5-(trifluoromethyl)pyrazol-1-yl)-1-ethylcyclohexane-1-carboxylic acid |
| 157 | 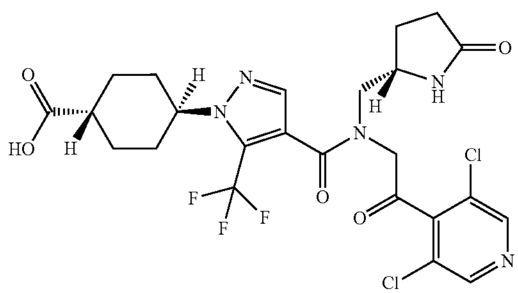 [SMILES: O=C1CC[C@@H](CN(CC(=O)c2c(Cl)cncc2Cl)C(=O)c2cnn([C@H]3CC[C@H](C(=O)O)CC3)c2C(F)(F)F)N1] | trans-4-(4-((2-(3,5-dichloropyridin-4-yl)-2-oxoethyl)-(((2S)-5-oxopyrrolidin-2-yl)methyl)carbamoyl)-5-(trifluoromethyl)pyrazol-1-yl)cyclohexane-1-carboxylic acid |
| 158 | 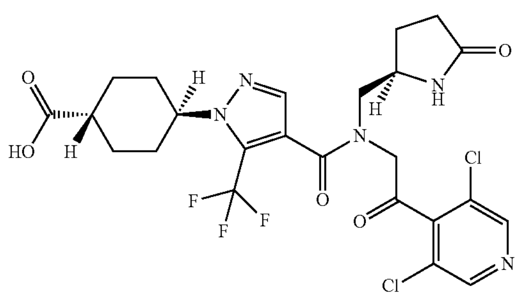 [SMILES: O=C1CC[C@H](CN(CC(=O)c2c(Cl)cncc2Cl)C(=O)c2cnn([C@H]3CC[C@H](C(=O)O)CC3)c2C(F)(F)F)N1] | trans-4-(4-((2-(3,5-dichloropyridin-4-yl)-2-oxoethyl)-(((2R)-5-oxopyrrolidin-2-yl)methyl)carbamoyl)-5-(trifluoromethyl)pyrazol-1-yl)cyclohexane-1-carboxylic acid |
| 159 | 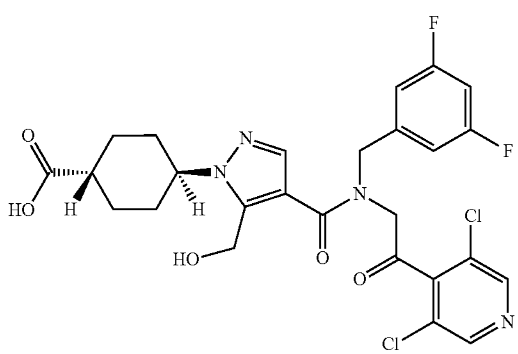 [SMILES: O=C(CN(Cc1cc(F)cc(F)c1)C(=O)c1cnn([C@H]2CC[C@H](C(=O)O)CC2)c1CO)c1c(Cl)cncc1Cl] | trans-4-(4-((2-(3,5-dichloropyridin-4-yl)-2-oxoethyl)-((3,5-difluorophenyl)methyl)carbamoyl)-5-(hydroxymethyl)pyrazol-1-yl)cyclohexane-1-carboxylic acid |
| 160 | 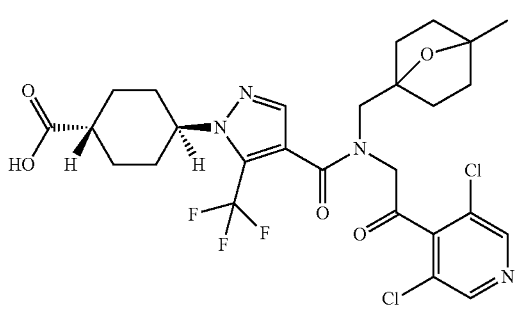 [SMILES: CC12CCC(CN(CC(=O)c3c(Cl)cncc3Cl)C(=O)c3cnn([C@H]4CC[C@H](C(=O)O)CC4)c3C(F)(F)F)(CC1)O2] | trans-4-(4-((2-(3,5-dichloropyridin-4-yl)-2-oxoethyl)-((1-methyl-7-oxabicyclo[2.2.1]heptan-4-yl)methyl)carbamoyl)-5-(trifluoromethyl)pyrazol-1-yl)cyclohexane-1-carboxylic acid |

-continued

| example | structure | name |
|---|---|---|
| 161 | 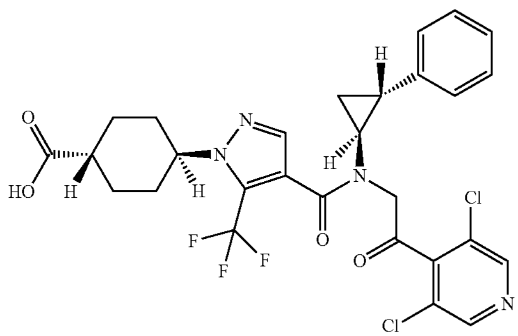 [SMILES: O=C(CN(C(=O)c1cnn([C@H]2CC[C@H](C(=O)O)CC2)c1C(F)(F)F)[C@H]1C[C@@H]1c1ccccc1)c1c(Cl)cncc1Cl] | trans-4-(4-((2-(3,5-dichloropyridin-4-yl)-2-oxoethyl)-((1S,2R)-2-phenylcyclopropyl)carbamoyl)-5-(trifluoromethyl)pyrazol-1-yl)cyclohexane-1-carboxylic acid |
| 162 | 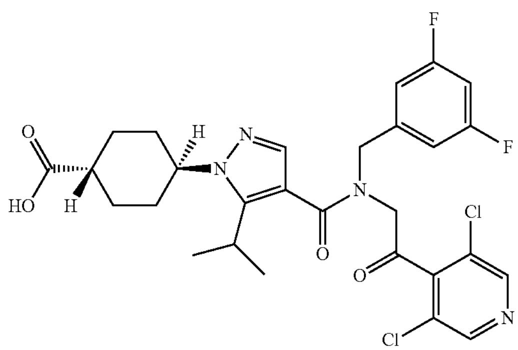 [SMILES: CC(C)c1c(C(=O)N(CC(=O)c2c(Cl)cncc2Cl)Cc2cc(F)cc(F)c2)cnn1[C@H]1CC[C@H](C(=O)O)CC1] | trans-4-(4-((2-(3,5-dichloropyridin-4-yl)-2-oxoethyl)-((3,5-difluorophenyl)methyl)carbamoyl)-5-propan-2-ylpyrazol-1-yl)cyclohexane-1-carboxylic acid |
| 163 | 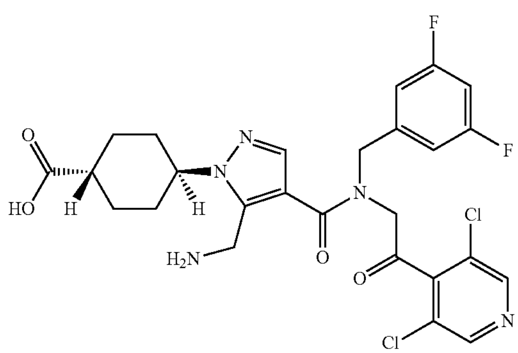 | trans-4-(5-(aminomethyl)-4-((2-(3,5-dichloropyridin-4-yl)-2-oxoethyl)-((3,5-difluorophenyl)methyl)carbamoyl)pyrazol-1-yl)cyclohexane-1-carboxylic acid |
| 164 | 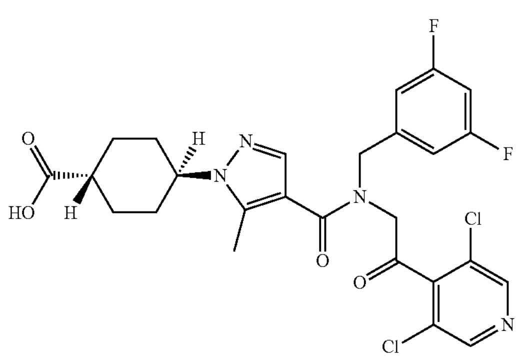 [SMILES: Cc1c(C(=O)N(CC(=O)c2c(Cl)cncc2Cl)Cc2cc(F)cc(F)c2)cnn1[C@H]1CC[C@H](C(=O)O)CC1] | trans-4-(4-((2-(3,5-dichloropyridin-4-yl)-2-oxoethyl)-((3,5-difluorophenyl)methyl)carbamoyl)-5-methylpyrazol-1-yl)cyclohexane-1-carboxylic acid |

-continued

| example | structure | name |
|---|---|---|
| 165 | 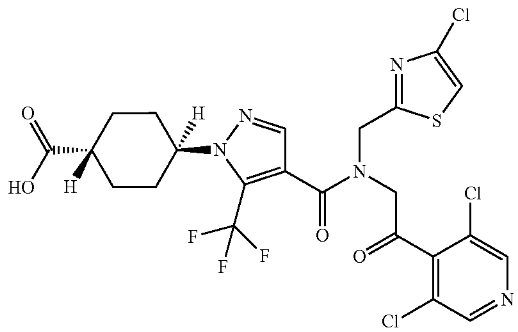 [SMILES: O=C(CN(Cc1nc(Cl)cs1)C(=O)c1cnn([C@H]2CC[C@H](C(=O)O)CC2)c1C(F)(F)F)c1c(Cl)cncc1Cl] | trans-4-(4-((4-chloro-1,3-thiazol-2-yl)methyl-(2-(3,5-dichloropyridin-4-yl)-2-oxoethyl)carbamoyl)-5-(trifluoromethyl)pyrazol-1-yl)cyclohexane-1-carboxylic acid |
| 166 | 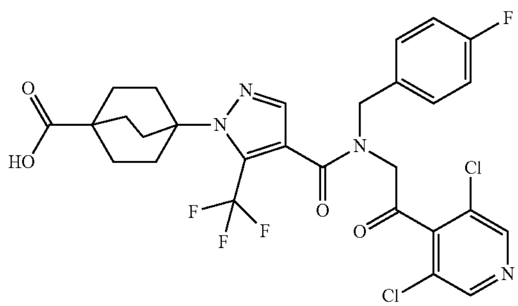 [SMILES: O=C(CN(Cc1ccc(F)cc1)C(=O)c1cnn(C23CCC(C(=O)O)(CC2)CC3)c1C(F)(F)F)c1c(Cl)cncc1Cl] | 4-(4-((2-(3,5-dichloropyridin-4-yl)-2-oxoethyl)-((4-fluorophenyl)methyl)carbamoyl)-5-(trifluoromethyl)pyrazol-1-yl)bicyclo[2.2.2]octane-1-carboxylic acid |
| 167 | 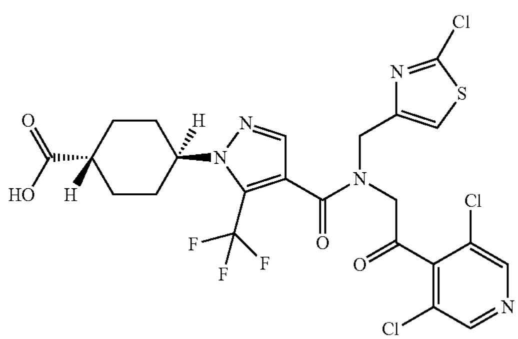 [SMILES: O=C(CN(Cc1csc(Cl)n1)C(=O)c1cnn([C@H]2CC[C@H](C(=O)O)CC2)c1C(F)(F)F)c1c(Cl)cncc1Cl] | trans-4-(4-((2-chloro-1,3-thiazol-4-yl)methyl-(2-(3,5-dichloropyridin-4-yl)-2-oxoethyl)carbamoyl)-5-(trifluoromethyl)pyrazol-1-yl)cyclohexane-1-carboxylic acid |
| 168 | 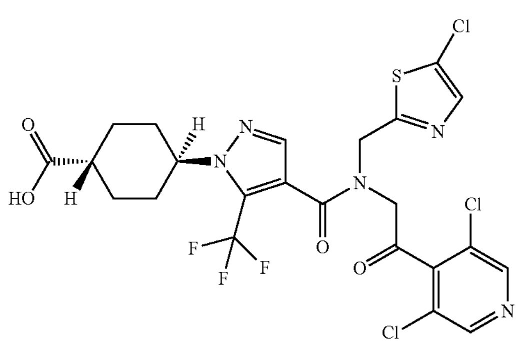 [SMILES: O=C(CN(Cc1ncc(Cl)s1)C(=O)c1cnn([C@H]2CC[C@H](C(=O)O)CC2)c1C(F)(F)F)c1c(Cl)cncc1Cl] | trans-4-(4-((5-chloro-1,3-thiazol-2-yl)methyl-(2-(3,5-dichloropyridin-4-yl)-2-oxoethyl)carbamoyl)-5-(trifluoromethyl)pyrazol-1-yl)cyclohexane-1-carboxylic acid |

-continued

| example | structure | name |
|---|---|---|
| 169 | 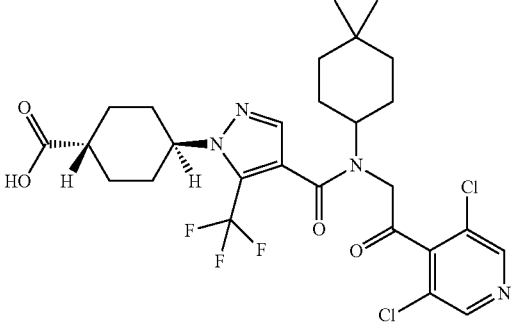 [SMILES: CC1(C)CCC(N(CC(=O)c2c(Cl)cncc2Cl)C(=O)c2cnn([C@H]3CC[C@H](C(=O)O)CC3)c2C(F)(F)F)CC1] | trans-4-(4-((2-(3,5-dichloropyridin-4-yl)-2-oxoethyl)-(4,4-dimethylcyclohexyl)carbamoyl)-5-(trifluoromethyl)pyrazol-1-yl)cyclohexane-1-carboxylic acid |
| 170 | 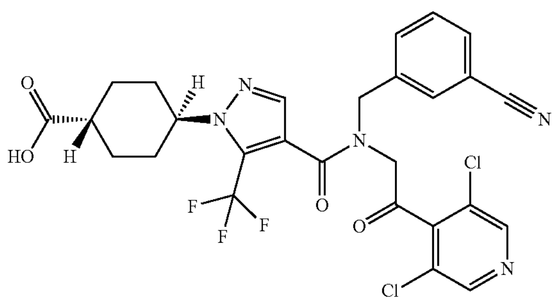 [SMILES: N#Cc1cccc(CN(CC(=O)c2c(Cl)cncc2Cl)C(=O)c2cnn([C@H]3CC[C@H](C(=O)O)CC3)c2C(F)(F)F)c1] | trans-4-(4-((3-cyanophenyl)methyl-(2-(3,5-dichloropyridin-4-yl)-2-oxoethyl)carbamoyl)-5-(trifluoromethyl)pyrazol-1-yl)cyclohexane-1-carboxylic acid |
| 171 | 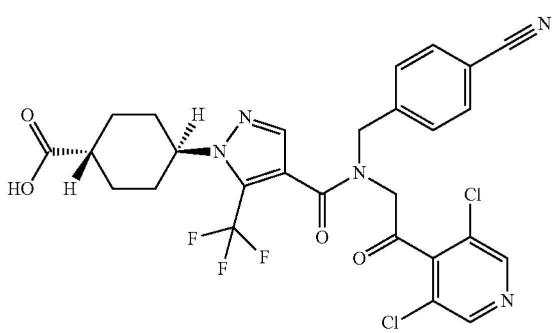 [SMILES: N#Cc1ccc(CN(CC(=O)c2c(Cl)cncc2Cl)C(=O)c2cnn([C@H]3CC[C@H](C(=O)O)CC3)c2C(F)(F)F)cc1] | trans-4-(4-((4-cyanophenyl)methyl-(2-(3,5-dichloropyridin-4-yl)-2-oxoethyl)carbamoyl)-5-(trifluoromethyl)pyrazol-1-yl)cyclohexane-1-carboxylic acid |
| 172 | 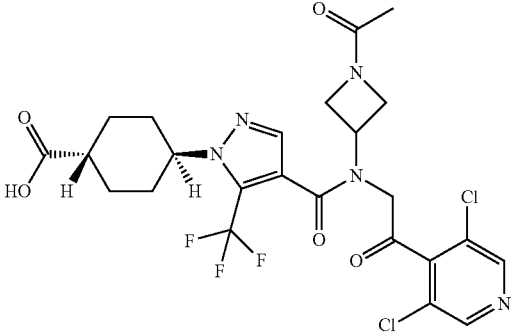 [SMILES: CC(=O)N1CC(N(CC(=O)c2c(Cl)cncc2Cl)C(=O)c2cnn([C@H]3CC[C@H](C(=O)O)CC3)c2C(F)(F)F)C1] | trans-4-(4-((1-acetylazetidin-3-yl)-(2-(3,5-dichloropyridin-4-yl)-2-oxoethyl)carbamoyl)-5-(trifluoromethyl)pyrazol-1-yl)cyclohexane-1-carboxylic acid |

-continued

| example | structure | name |
|---|---|---|
| 173 | 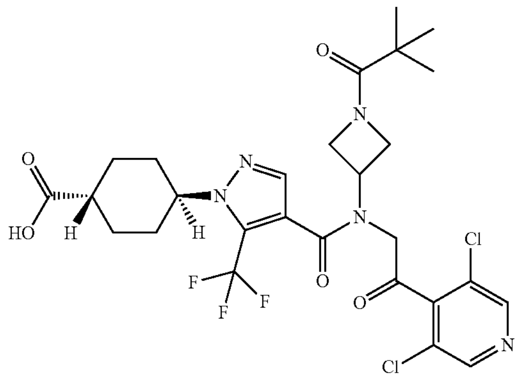 [SMILES: CC(C)(C)C(=O)N1CC(N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-(1-(2,2-dimethylpropanoyl)azetidin-3-yl)carbamoyl)-5-(trifluoromethyl)pyrazol-1-yl)cyclohexane-1-carboxylic acid |
| 174 | 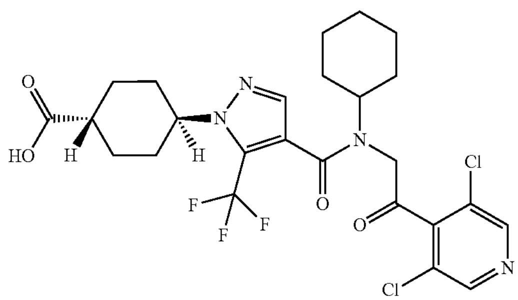 [SMILES: O=C(CN(C(=O)c1cnn([C@H]2CC[C@H](C(=O)O)CC2)c1C(F)(F)F)C1CCCCC1)c1c(Cl)cncc1Cl] | trans-4-(4-(cyclohexyl-(2-(3,5-dichloropyridin-4-yl)-2-oxoethyl)carbamoyl)-5-(trifluoromethyl)pyrazol-1-yl)cyclohexane-1-carboxylic acid |
| 175 | 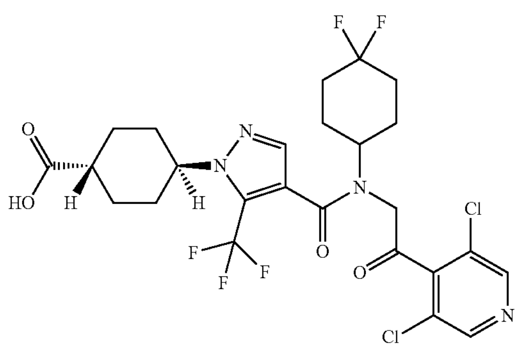 [SMILES: O=C(CN(C(=O)c1cnn([C@H]2CC[C@H](C(=O)O)CC2)c1C(F)(F)F)C1CCC(F)(F)CC1)c1c(Cl)cncc1Cl] | trans-4-(4-((2-(3,5-dichloropyridin-4-yl)-2-oxoethyl)-(4,4-difluorocyclohexyl)carbamoyl)-5-(trifluoromethyl)pyrazol-1-yl)cyclohexane-1-carboxylic acid |
| 176 | 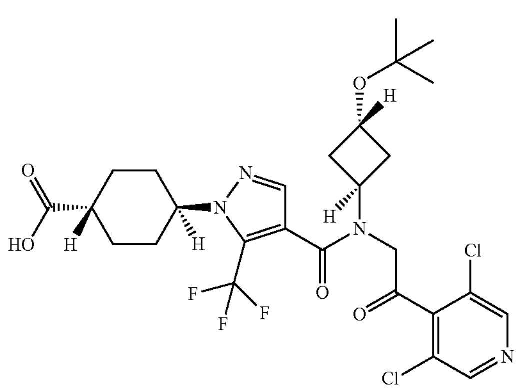 [SMILES: CC(C)(C)O[C@H]1C[C@H](N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-(3-((2-methylpropan-2-yl)oxy)cyclobutyl)carbamoyl)-5-(trifluoromethyl)pyrazol-1-yl)cyclohexane-1-carboxylic acid |

-continued

| example | structure | name |
|---|---|---|
| 177 | 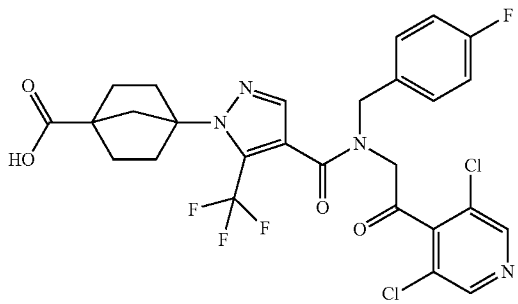 [SMILES: O=C(CN(Cc1ccc(F)cc1)C(=O)c1cnn(C23CCC(C(=O)O)(CC2)C3)c1C(F)(F)F)c1c(Cl)cncc1Cl] | 4-(4-((2-(3,5-dichloropyridin-4-yl)-2-oxoethyl)-((4-fluorophenyl)methyl)carbamoyl)-5-(trifluoromethyl)pyrazol-1-yl)bicyclo[2.2.1]heptane-1-carboxylic acid |
| 178 | 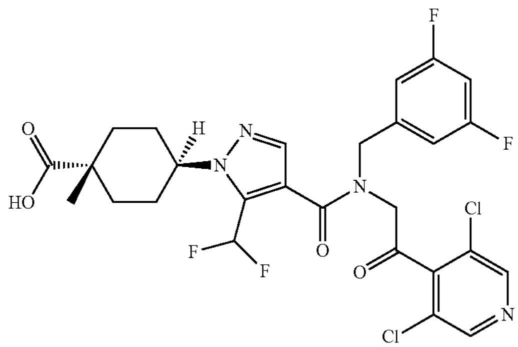 [SMILES: C[C@]1(C(=O)O)CC[C@H](n2ncc(C(=O)N(CC(=O)c3c(Cl)cncc3Cl)Cc3cc(F)cc(F)c3)c2C(F)F)CC1] | trans-4-(4-((2-(3,5-dichloropyridin-4-yl)-2-oxoethyl)-((3,5-difluorophenyl)methyl)carbamoyl)-5-(difluoromethyl)pyrazol-1-yl)-1-methylcyclohexane-1-carboxylic acid |
| 179 | 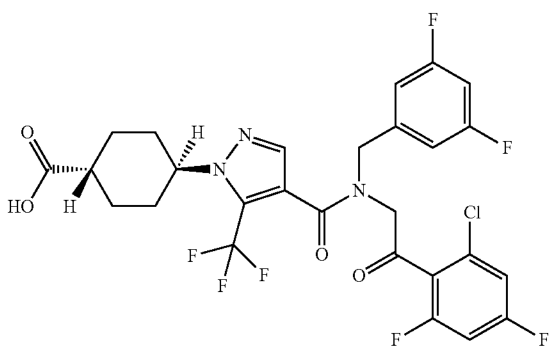 | trans-4-(4-((2-(2-chloro-4,6-difluorophenyl)-2-oxoethyl)-((3,5-difluorophenyl)methyl)carbamoyl)-5-(trifluoromethyl)pyrazol-1-yl)cyclohexane-1-carboxylic acid |
| 180 | 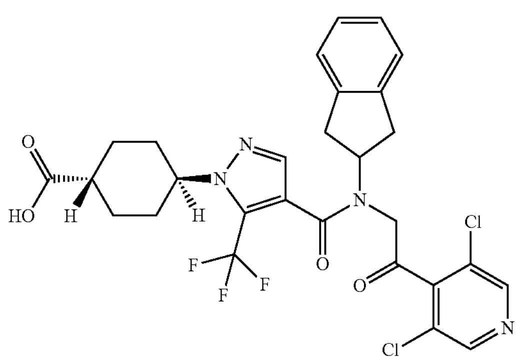 [SMILES: O=C(CN(C(=O)c1cnn([C@H]2CC[C@H](C(=O)O)CC2)c1C(F)(F)F)C1Cc2ccccc2C1)c1c(Cl)cncc1Cl] | trans-4-(4-((2-(3,5-dichloropyridin-4-yl)-2-oxoethyl)-(2,3-dihydro-1H-inden-2-yl)carbamoyl)-5-(trifluoromethyl)pyrazol-1-yl)cyclohexane-1-carboxylic acid |

| example | structure | name |
|---|---|---|
| 181 | 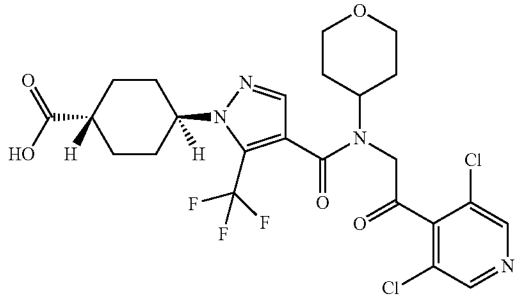 [SMILES: O=C(CN(C(=O)c1cnn([C@H]2CC[C@H](C(=O)O)CC2)c1C(F)(F)F)C1CCOCC1)c1c(Cl)cncc1Cl] | trans-4-(4-((2-(3,5-dichloropyridin-4-yl)-2-oxoethyl)-(oxan-4-yl)carbamoyl)-5-(trifluoromethyl)pyrazol-1-yl)cyclohexane-1-carboxylic acid |
| 182 | 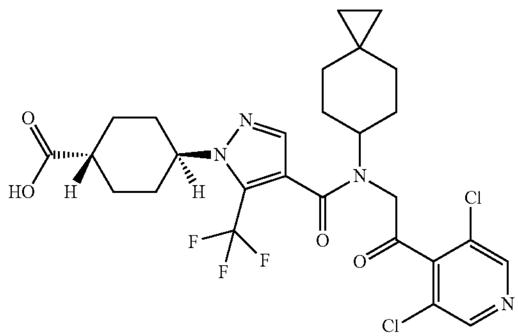 [SMILES: O=C(CN(C(=O)c1cnn([C@H]2CC[C@H](C(=O)O)CC2)c1C(F)(F)F)C1CCC2(CC1)CC2)c1c(Cl)cncc1Cl] | trans-4-(4-((2-(3,5-dichloropyridin-4-yl)-2-oxoethyl)-spiro[2,5]octan-6-ylcarbamoyl)-5-(trifluoromethyl)pyrazol-1-yl)cyclohexane-1-carboxylic acid |
| 183 | 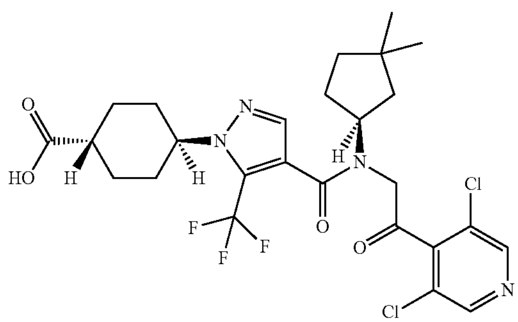 [SMILES: CC1(C)CC[C@H](N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-((1S)-3,3-dimethylcyclopentyl)carbamoyl)-5-(trifluoromethyl)pyrazol-1-yl)cyclohexane-1-carboxylic acid |
| 184 | 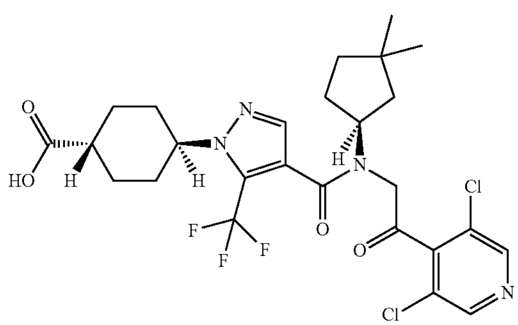 [SMILES: CC1(C)CC[C@H](N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-((1S)-3,3-dimethylcyclopentyl)carbamoyl)-5-(trifluoromethyl)pyrazol-1-yl)cyclohexane-1-carboxylic acid |
| 185 | 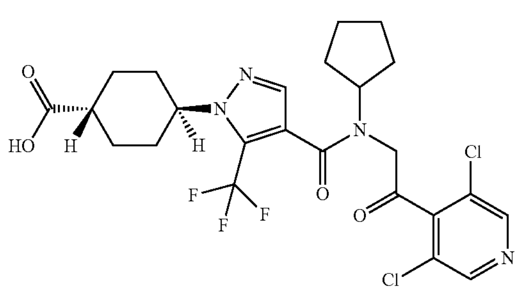 [SMILES: O=C(CN(C(=O)c1cnn([C@H]2CC[C@H](C(=O)O)CC2)c1C(F)(F)F)C1CCCC1)c1c(Cl)cncc1Cl] | trans-4-(4-(cyclopentyl-(2-(3,5-dichloropyridin-4-yl)-2-oxoethyl)carbamoyl)-5-(trifluoromethyl)pyrazol-1-yl)cyclohexane-1-carboxylic acid |

| example | structure | name |
|---|---|---|
| 187 | 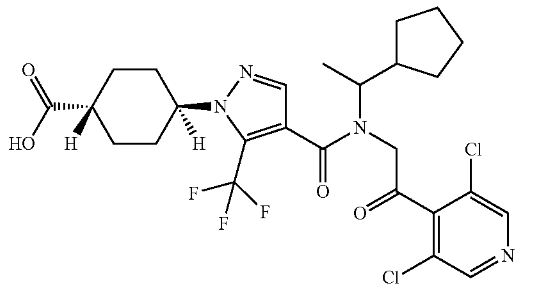 [SMILES: CC(C1CCCC1)N(CC(=O)c1c(Cl)cncc1Cl)C(=O)c1cnn([C@H]2CC[C@H](C(=O)O)CC2)c1C(F)(F)F] | trans-4-(4-(1-cyclopentylethyl-(2-(3,5-dichloropyridin-4-yl)-2-oxoethyl)carbamoyl)-5-(trifluoromethyl)pyrazol-1-yl)cyclohexane-1-carboxylic acid |
| 188 | 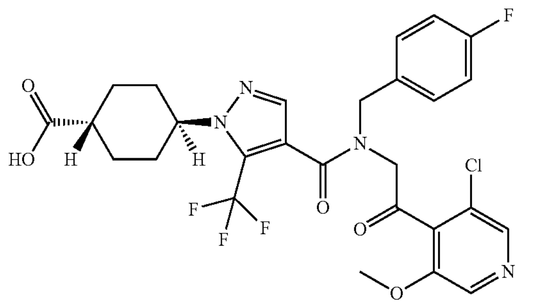 [SMILES: COc1cncc(Cl)c1C(=O)CN(Cc1ccc(F)cc1)C(=O)c1cnn([C@H]2CC[C@H](C(=O)O)CC2)c1C(F)(F)F] | trans-4-(4-((2-(3-chloro-5-methoxypyridin-4-yl)-2-oxoethyl)-((4-fluorophenyl)methyl)carbamoyl)-5-(trifluoromethyl)pyrazol-1-yl)cyclohexane-1-carboxylic acid |
| 189 | 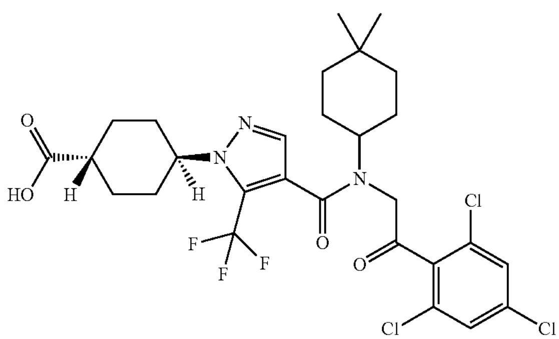 [SMILES: CC1(C)CCC(N(CC(=O)c2c(Cl)cc(Cl)cc2Cl)C(=O)c2cnn([C@H]3CC[C@H](C(=O)O)CC3)c2C(F)(F)F)CC1] | trans-4-(4-((4,4-dimethylcyclohexyl)-(2-oxo-2-(2,4,6-trichlorophenyl)ethyl)carbamoyl)-5-(trifluoromethyl)pyrazol-1-yl)cyclohexane-1-carboxylic acid |
| 190 | 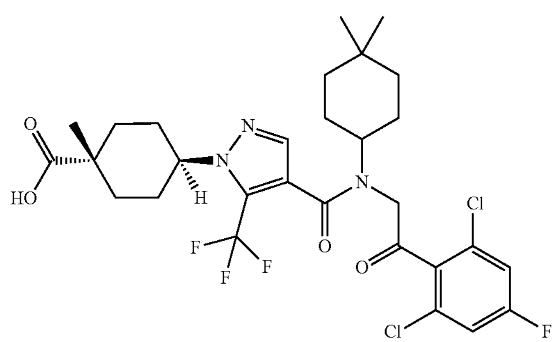 [SMILES: CC1(C)CCC(N(CC(=O)c2c(Cl)cc(F)cc2Cl)C(=O)c2cnn([C@H]3CC[C@](C)(C(=O)O)CC3)c2C(F)(F)F)CC1] | trans-4-(4-((2-(2,6-dichloro-4-fluorophenyl)-2-oxoethyl)-(4,4-dimethylcyclohexyl)carbamoyl)-5-(trifluoromethyl)pyrazol-1-yl)-1-methylcyclohexane-1-carboxylic acid |
| 191 | 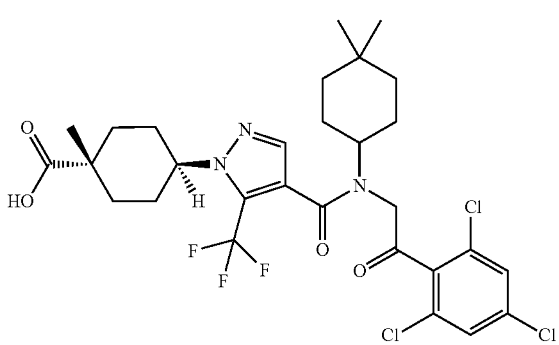 [SMILES: CC1(C)CCC(N(CC(=O)c2c(Cl)cc(Cl)cc2Cl)C(=O)c2cnn([C@H]3CC[C@](C)(C(=O)O)CC3)c2C(F)(F)F)CC1] | trans-4-(4-((4,4-dimethylcyclohexyl)-(2-oxo-2-(2,4,6-trichlorophenyl)ethyl)carbamoyl)-5-(trifluoromethyl)pyrazol-1-yl)-1-methylcyclohexane-1-carboxylic acid |

| example | structure | name |
|---|---|---|
| 192 | 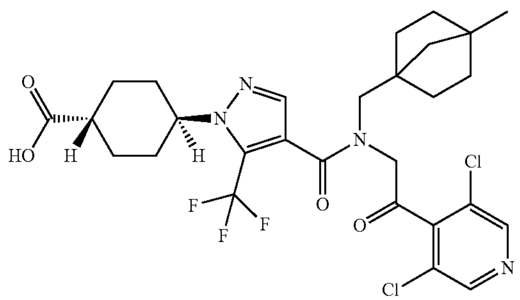 [SMILES: CC12CCC(CN(CC(=O)c3c(Cl)cncc3Cl)C(=O)c3cnn([C@H]4CC[C@H](C(=O)O)CC4)c3C(F)(F)F)(CC1)C2] | trans-4-(4-((2-(3,5-dichloropyridin-4-yl)-2-oxoethyl)-((1-methyl-4-bicyclo[2.2.1] heptanyl)methyl)carbamoyl)-5-(trifluoromethyl)pyrazol-1-yl)cyclohexane-1-carboxylic acid |
| 193 | 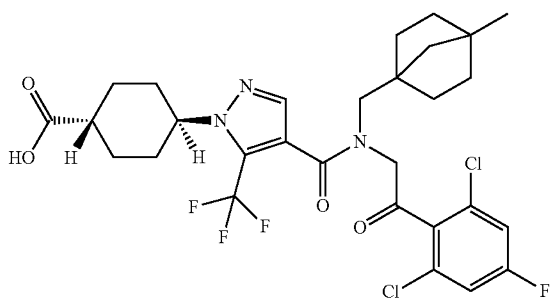 [SMILES: CC12CCC(CN(CC(=O)c3c(Cl)cc(F)cc3Cl)C(=O)c3cnn([C@H]4CC[C@H](C(=O)O)CC4)c3C(F)(F)F)(CC1)C2] | trans-4-(4-((2-(2,6-dichloro-4-fluorophenyl)-2-oxoethyl)-((1-methyl-4-bicyclo[2.2.1]heptanyl)methyl)carbamoyl)-5-(trifluoromethyl)pyrazol-1-yl)cyclohexane-1-carboxylic acid |
| 194 | 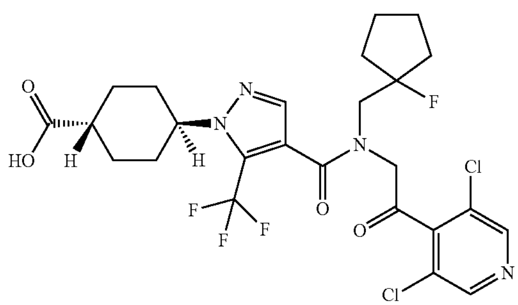 [SMILES: O=C(CN(CC1(F)CCCC1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-((1-fluorocyclopentyl)methyl)carbamoyl)-5-(trifluoromethyl)pyrazol-1-yl)cyclohexane-1-carboxylic acid |
| 195 | 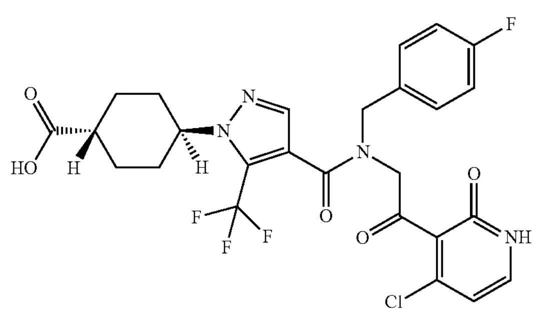 | trans-4-(4-((2-(4-chloro-2-oxo-1H-pyridin-3-yl)-2-oxoethyl)-((4-fluorophenyl)methyl)carbamoyl)-5-(trifluoromethyl)pyrazol-1-yl)cyclohexane-1-carboxylic acid |
| 196 | 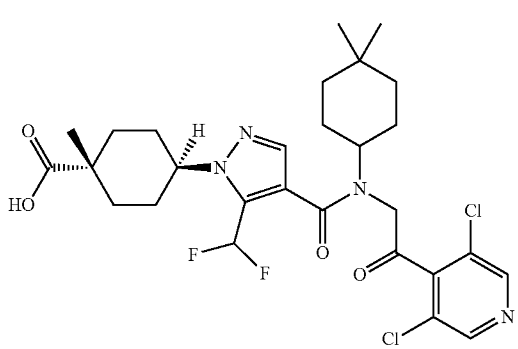 [SMILES: CC1(C)CCC(N(CC(=O)c2c(Cl)cncc2Cl)C(=O)c2cnn([C@H]3CC[C@](C)(C(=O)O)CC3)c2C(F)F)CC1] | trans-4-(4-((2-(3,5-dichloropyridin-4-yl)-2-oxoethyl)-(4,4-dimethylcyclohexyl)carbamoyl)-5-(difluoromethyl)pyrazol-1-yl)-1-methylcyclohexane-1-carboxylic acid |

-continued

| example | structure | name |
|---|---|---|
| 197 | 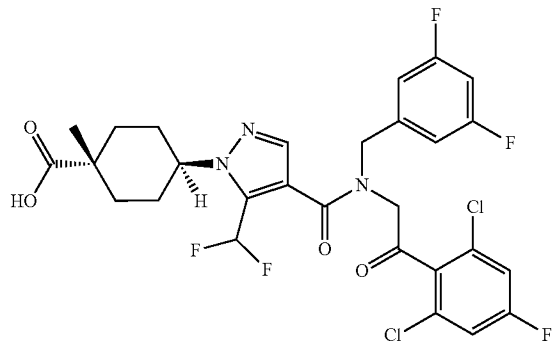 [SMILES: C[C@]1(C(=O)O)CC[C@H](n2ncc(C(=O)N(CC(=O)c3c(Cl)cc(F)cc3Cl)Cc3cc(F)cc(F)c3)c2C(F)F)CC1] | trans-4-(4-((2-(2,6-dichloro-4-fluorophenyl)-2-oxoethyl)-((3,5-difluorophenyl)methyl)carbamoyl)-5-(difluoromethyl)pyrazol-1-yl)-1-methylcyclohexane-1-carboxylic acid |
| 198 | 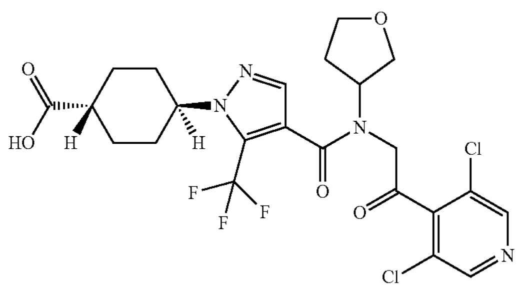 [SMILES: O=C(CN(C(=O)c1cnn([C@H]2CC[C@H](C(=O)O)CC2)c1C(F)(F)F)C1CCOC1)c1c(Cl)cncc1Cl] | trans-4-(4-((2-(3,5-dichloropyridin-4-yl)-2-oxoethyl)-(oxolan3-yl)carbamoyl)-5-(trifluoromethyl)pyrazol-1-yl)cyclohexane-1-carboxylic acid |
| 199 | 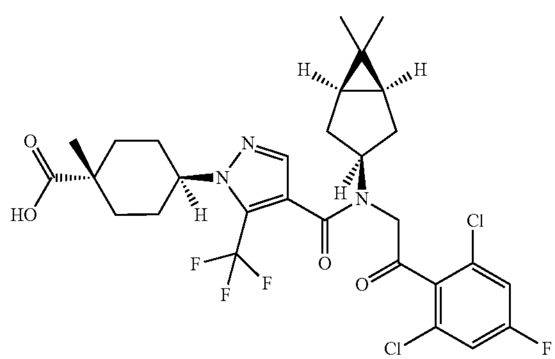 [SMILES: CC1(C)[C@@H]2C[C@H](N(CC(=O)c3c(Cl)cc(F)cc3Cl)C(=O)c3cnn([C@H]4CC[C@](C)(C(=O)O)CC4)c3C(F)(F)F)C[C@@H]21] | trans-4-(4-((2-(2,6-dichloro-4-fluorophenyl)-2-oxoethyl)-((1R,3r,5S)-6,6-dimethyl-3-bicyclo[3.1.0]hexanyl)carbamoyl)-5-(trifluoromethyl)pyrazol-1-yl)-1-methylcyclohexane-1-carboxylic acid |
| 200 | 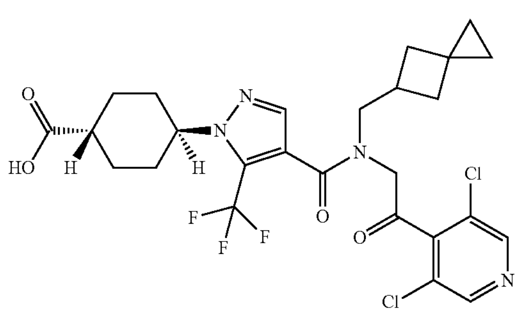 [SMILES: O=C(CN(CC1CC2(CC2)C1)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-(spiro[2.3]hexan-5-ylmethyl)carbamoyl)-5-(trifluoromethyl)pyrazol-1-yl)cyclohexane-1-carboxylic acid |

-continued

| example | structure | name |
|---|---|---|
| 201 | 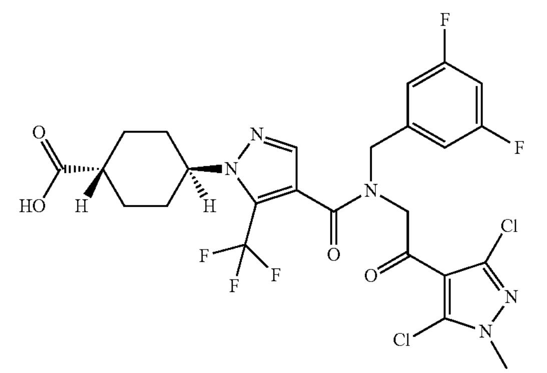 [SMILES: Cn1nc(Cl)c(C(=O)CN(Cc2cc(F)cc(F)c2)C(=O)c2cnn([C@H]3CC[C@H](C(=O)O)CC3)c2C(F)(F)F)c1Cl] | trans-4-(4-((2-(3,5-dichloro-1-methylpyrazol-4-yl)-2-oxoethyl)-((3,5-difluorophenyl)methyl)carbamoyl)-5-(trifluoromethyl)pyrazol-1-yl)cyclohexane-1-carboxylic acid |
| 202 | 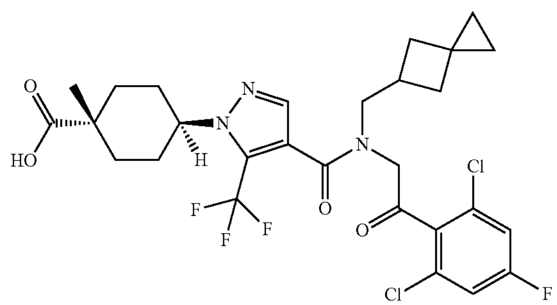 [SMILES: C[C@]1(C(=O)O)CC[C@H](n2ncc(C(=O)N(CC(=O)c3c(Cl)cc(F)cc3Cl)CC3CC4(CC4)C3)c2C(F)(F)F)CC1] | trans-4-(4-((2-(2,6-dichloro-4-fluorophenyl)-2-oxoethyl)-(spiro[2.3]hexan-5-ylmethyl)carbamoyl)-5-(trifluoromethyl)pyrazol-1-yl)-1-methylcyclohexane-1-carboxylic acid |
| 203 | 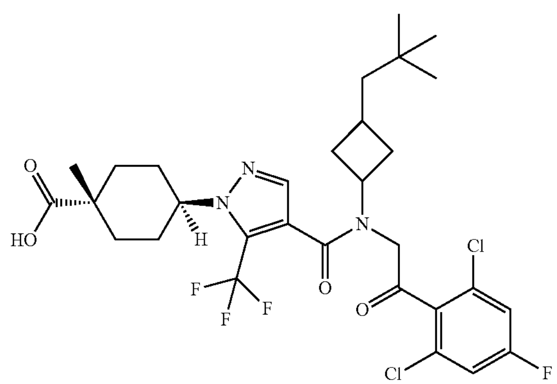 [SMILES: CC(C)(C)CC1CC(N(CC(=O)c2c(Cl)cc(F)cc2Cl)C(=O)c2cnn([C@H]3CC[C@](C)(C(=O)O)CC3)c2C(F)(F)F)C1] | trans-4-(4-((2-(2,6-dichloro-4-fluorophenyl)-2-oxoethyl)-(3-(2,2-dimethylpropyl)cyclobutyl)carbamoyl)-5-(trifluoromethyl)pyrazol-1-yl)-1-methylcyclohexane-1-carboxylic acid |
| 204 | 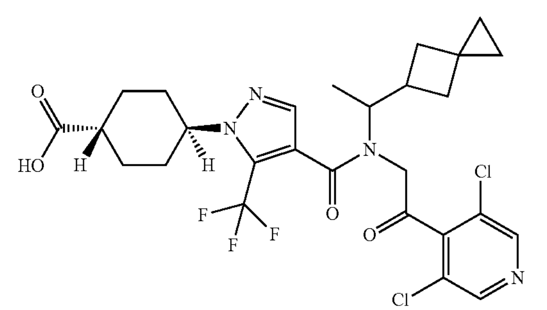 [SMILES: CC(C1CC2(CC2)C1)N(CC(=O)c1c(Cl)cncc1Cl)C(=O)c1cnn([C@H]2CC[C@H](C(=O)O)CC2)c1C(F)(F)F] | trans-4-(4-((2-(3,5-dichloropyridin-4-yl)-2-oxoethyl)-(1-spiro[2.3]hexan-5-ylethyl)carbamoyl)-5-(trifluoromethyl)pyrazol-1-yl)cyclohexane-1-carboxylic acid |

-continued

| example | structure | name |
|---|---|---|
| 205 | 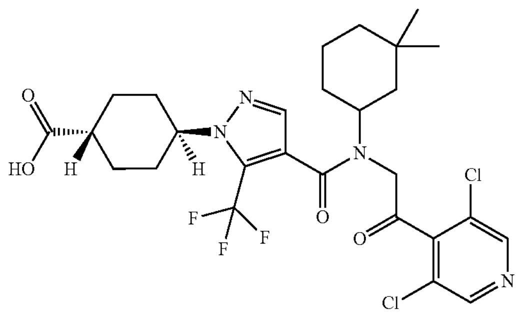 [SMILES: CC1(C)CCCC(N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-(3,3-dimethylcyclohexyl)carbamoyl)-5-(trifluoromethyl)pyrazol-1-yl)cyclohexane-1-carboxylic acid |
| 206 | 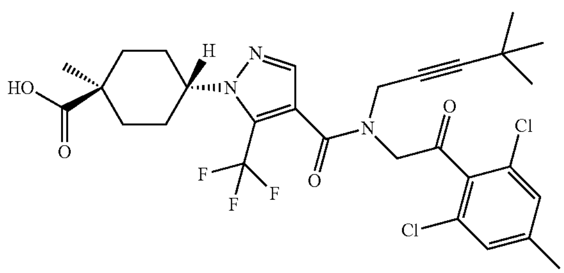 [SMILES: Cc1cc(Cl)c(C(=O)CN(CC#CC(C)(C)C)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)-(4,4-dimethylpent-2-ynyl)carbamoyl)-5-(trifluoromethyl)pyrazol-1-yl)-1-methylcyclohexane-1-carboxylic acid |
| 207 | 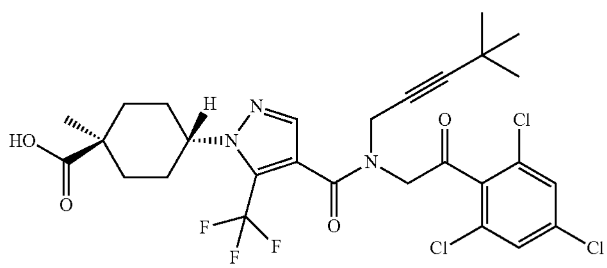 [SMILES: CC(C)(C)C#CCN(CC(=O)c1c(Cl)cc(Cl)cc1Cl)C(=O)c1cnn([C@H]2CC[C@](C)(C(=O)O)CC2)c1C(F)(F)F] | trans-4-(4-(4,4-dimethylpent-2-ynyl-(2-oxo-2-(2,4,6-trichlorophenyl)ethyl)carbamoyl)-5-(trifluoromethyl)pyrazol-1-yl)-1-methylcyclohexane-1-carboxylic acid |
| 208 | 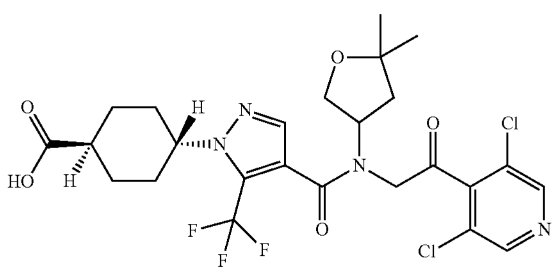 [SMILES: CC1(C)CC(N(CC(=O)c2c(Cl)cncc2Cl)C(=O)c2cnn([C@H]3CC[C@H](C(=O)O)CC3)c2C(F)(F)F)CO1] | trans-4-(4-((2-(3,5-dichloropyridin-4-yl)-2-oxoethyl)-(5,5-dimethyloxolan-3-yl)carbamoyl)-5-(trifluoromethyl)pyrazol-1-yl)cyclohexane-1-carboxylic acid |
| 209 | 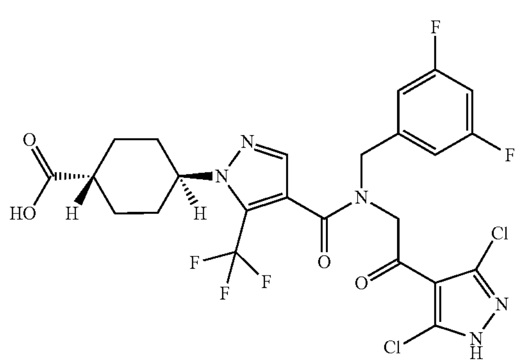 [SMILES: O=C(CN(Cc1cc(F)cc(F)c1)C(=O)c1cnn([C@H]2CC[C@H](C(=O)O)CC2)c1C(F)(F)F)c1c(Cl)n[nH]c1Cl] | trans-4-(4 ((2-(3,5-dichloro-1H-pyrazol-4-yl)-2-oxoethyl)-((3,5-difluorophenyl)methyl)carbamoyl)-5-(trifluoromethyl)pyrazol-1-yl)cyclohexane-1-carboxylic acid |

-continued

| example | structure | name |
|---|---|---|
| 210 | 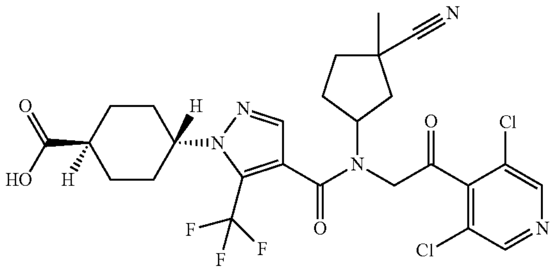 [SMILES: CC1(C#N)CCC(N(CC(=O)c2c(Cl)cncc2Cl)C(=O)c2cnn([C@H]3CC[C@H](C(=O)O)CC3)c2C(F)(F)F)C1] | trans-4-(4-((3-cyano-3-methylcyclopentyl)-(2-(3,5-dichloropyridin-4-yl)-2-oxoethyl)carbamoyl)-5-(trifluoromethyl)pyrazol-1-yl)cyclohexane-1-carboxylic acid |
| 211 | 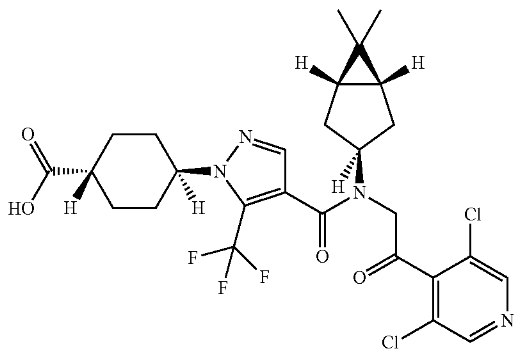 [SMILES: CC1(C)[C@@H]2C[C@H](N(CC(=O)c3c(Cl)cncc3Cl)C(=O)c3cnn([C@H]4CC[C@H](C(=O)O)CC4)c3C(F)(F)F)C[C@@H]21] | trans-4-(4-((2-(3,5-dichloropyridin-4-yl)-2-oxoethyl)-((1R,3r,5S)-6,6-dimethyl-3-bicyclo[3.1.0] hexanyl)carbamoyl)-5-(trifluoromethyl)pyrazol-1-yl)cyclohexane-1-carboxylic acid |
| 212 | 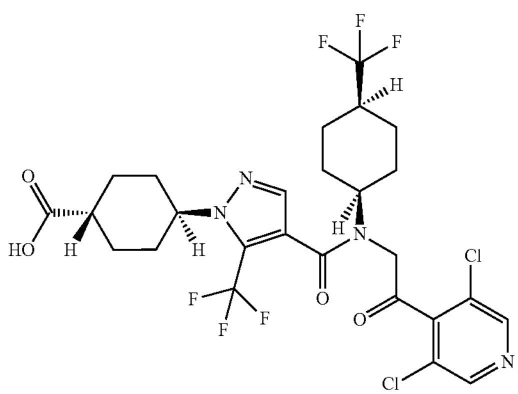 [SMILES: O=C(CN(C(=O)c1cnn([C@H]2CC[C@H](C(=O)O)CC2)c1C(F)(F)F)[C@H]1CC[C@@H](C(F)(F)F)CC1)c1c(Cl)cncc1Cl] | trans-4-(4-((2-(3,5-dichloropyridin-4-yl)-2-oxoethyl)-(4-(trifluoromethyl)cyclohexyl)carbamoyl)-5-(trifluoromethyl)pyrazol-1-yl)cyclohexane-1-carboxylic acid |
| 213 | 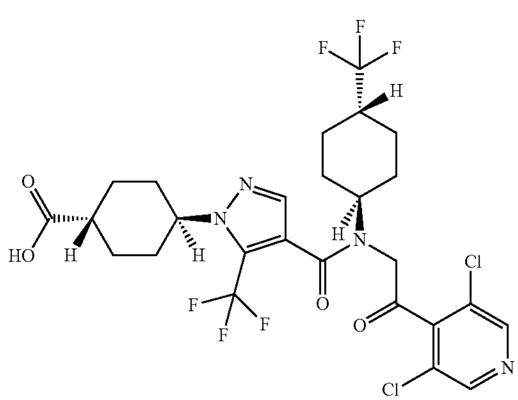 [SMILES: O=C(CN(C(=O)c1cnn([C@H]2CC[C@H](C(=O)O)CC2)c1C(F)(F)F)[C@H]1CC[C@H](C(F)(F)F)CC1)c1c(Cl)cncc1Cl] | trans-4-(4-((2-(3,5-dichloropyridin-4-yl)-2-oxoethyl)-(4-(trifluoromethyl)cyclohexyl)carbamoyl)-5-(trifluoromethyl)pyrazol-1-yl)cyclohexane-1-carboxylic acid |

| example | structure | name |
|---|---|---|
| 214 | 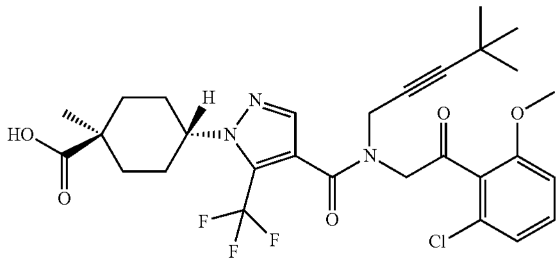 [SMILES: COc1cccc(Cl)c1C(=O)CN(CC#CC(C)(C)C)C(=O)c1cnn([C@H]2CC[C@](C)(C(=O)O)CC2)c1C(F)(F)F] | trans-4-(4-((2-(2-chloro-6-methoxyphenyl)-2-oxoethyl)-(4,4-dimethylpent-2-ynyl)carbamoyl)-5-(trifluoromethyl)pyrazol-1-yl)-1-methylcyclohexane-1-carboxylic acid |
| 215 | 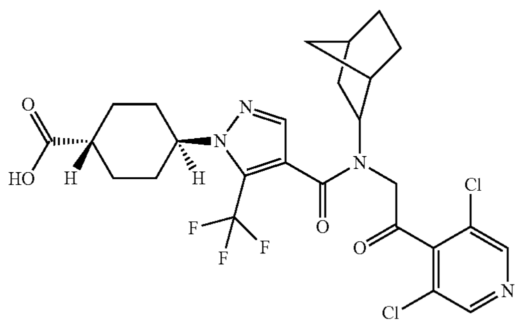 [SMILES: O=C(CN(C(=O)c1cnn([C@H]2CC[C@H](C(=O)O)CC2)c1C(F)(F)F)C1CC2CCC1C2)c1c(Cl)cncc1Cl] | trans-4-(4-(3-bicyclo[2.2.1]heptanyl-(2-(3,5-dichloropyridin-4-yl)-2-oxoethyl)carbamoyl)-5-(trifluoromethyl)pyrazol-1-yl)cyclohexane-1-carboxylic acid |
| 216 | 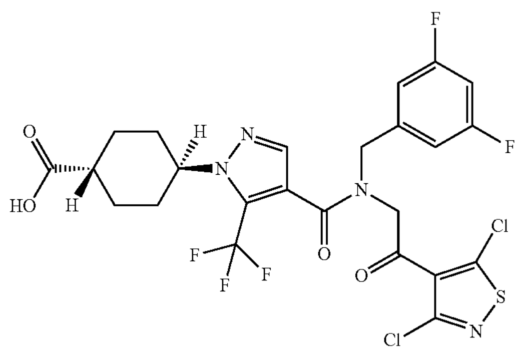 [SMILES: O=C(CN(Cc1cc(F)cc(F)c1)C(=O)c1cnn([C@H]2CC[C@H](C(=O)O)CC2)c1C(F)(F)F)c1c(Cl)nsc1Cl] | trans-4-(4-((2-(3,5-dichloro-1,2-thiazol-4-yl)-2-oxoethyl)-((3,5-difluorophenyl)methyl)carbamoyl)-5-(trifluoromethyl)pyrazol-1-yl)cyclohexane-1-carboxylic acid |
| 217 | 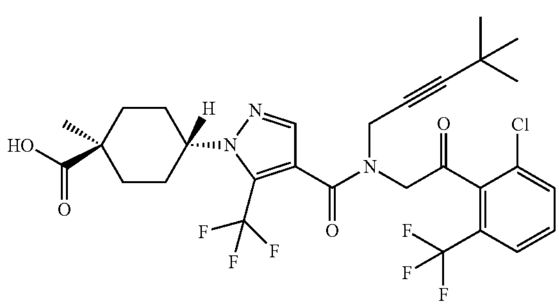 [SMILES: CC(C)(C)C#CCN(CC(=O)c1c(Cl)cccc1C(F)(F)F)C(=O)c1cnn([C@H]2CC[C@](C)(C(=O)O)CC2)c1C(F)(F)F] | trans-4-(4-((2-(2-chloro-6-(trifluoromethyl)phenyl)-2-oxoethyl)-(4,4-dimethylpent-2-ynyl)carbamoyl)-5-(trifluoromethyl)pyrazol-1-yl)-1-methylcyclohexane-1-carboxylic acid |
| 218 | 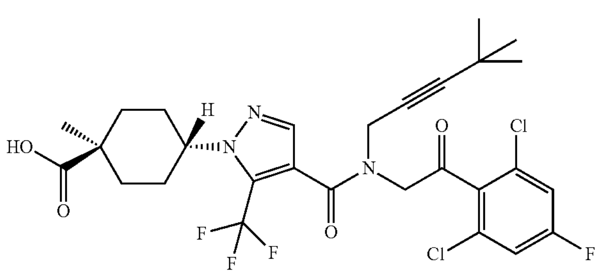 [SMILES: CC(C)(C)C#CCN(CC(=O)c1c(Cl)cc(F)cc1Cl)C(=O)c1cnn([C@H]2CC[C@](C)(C(=O)O)CC2)c1C(F)(F)F] | trans-4-(4-((2-(2,6-dichloro-4-fluorophenyl)-2-oxoethyl)-(4,4-dimethylpent-2-ynyl)carbamoyl)-5-(trifluoromethyl)pyrazol-1-yl)-1-methylcyclohexane-1-carboxylic acid |

| example | structure | name |
| --- | --- | --- |
| 219 | 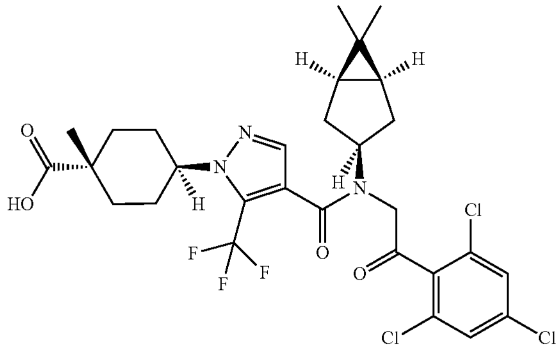 [SMILES: CC1(C)[C@@H]2C[C@H](N(CC(=O)c3c(Cl)cc(Cl)cc3Cl)C(=O)c3cnn([C@H]4CC[C@](C)(C(=O)O)CC4)c3C(F)(F)F)C[C@@H]21] | trans-4-(4-(((1R,3r,5S)-6,6-dimethyl-3-bicyclo[3.1.0]hexanyl)-(2-oxo-2-(2,4,6-trichlorophenyl)ethyl)carbamoyl)-5-(trifluoromethyl)pyrazol-1-yl)-1-methylcyclohexane-1-carboxylic acid |
| 220 | 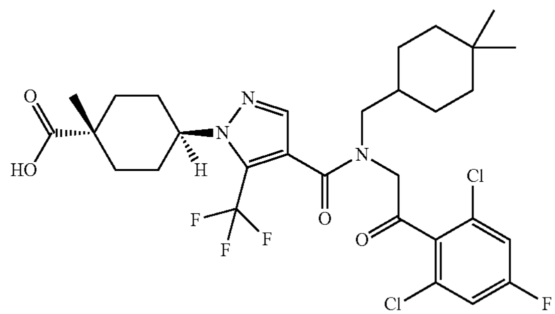 [SMILES: CC1(C)CCC(CN(CC(=O)c2c(Cl)cc(F)cc2Cl)C(=O)c2cnn([C@H]3CC[C@](C)(C(=O)O)CC3)c2C(F)(F)F)CC1] | trans-4-(4-((2-(2,6-dichloro-4-fluorophenyl)-2-oxoethyl)-((4,4-dimethylcyclohexyl)methyl)carbamoyl)-5-(trifluoromethyl)pyrazol-1-yl)-1-methylcyclohexane-1-carboxylic acid |
| 221 | 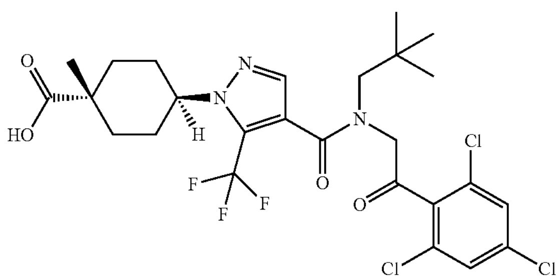 [SMILES: CC(C)(C)CN(CC(=O)c1c(Cl)cc(Cl)cc1Cl)C(=O)c1cnn([C@H]2CC[C@](C)(C(=O)O)CC2)c1C(F)(F)F] | trans-4-(4-(2,2-dimethylpropyl-(2-oxo-2-(2,4,6-trichlorophenyl)ethyl)carbamoyl)-5-(trifluoromethyl)pyrazol-1-yl)-1-methylcyclohexane-1-carboxylic acid |
| 222 | 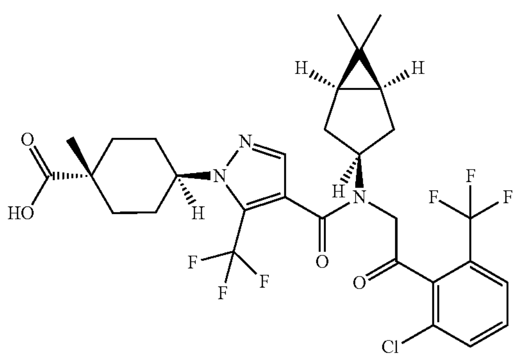 [SMILES: CC1(C)[C@@H]2C[C@H](N(CC(=O)c3c(Cl)cccc3C(F)(F)F)C(=O)c3cnn([C@H]4CC[C@](C)(C(=O)O)CC4)c3C(F)(F)F)C[C@@H]21] | trans-4-(4-((2-(2-chloro-6-(trifluoromethyl)phenyl)-2-oxoethyl)-((1R,3r,5S)-6,6-dimethyl-3-bicyclo[3.1.0] hexanyl)carbamoyl)-5-(trifluoromethyl)pyrazol-1-yl)-1-methylcyclohexane-1-carboxylic acid |
| 223 | 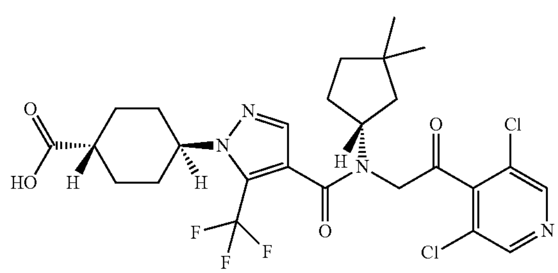 [SMILES: CC1(C)CC[C@@H](N(CC(=O)c2c(Cl)cncc2Cl)C(=O)c2cnn([C@H]3CC[C@H](C(=O)O)CC3)c2C(F)(F)F)C1] | trans-4-(4-((2-(3,5-dichloropyridin-4-yl)-2-oxoethyl)-((1R)-3,3-dimethylcyclopentyl)carbamoyl)-5-(trifluoromethyl)pyrazol-1-yl)cyclohexane-1-carboxylic acid |

| example | structure | name |
|---|---|---|
| 224 | 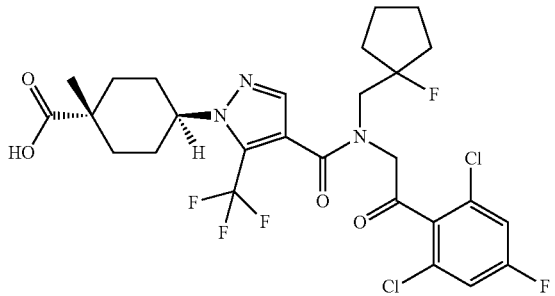 [SMILES: C[C@]1(C(=O)O)CC[C@H](n2ncc(C(=O)N(CC(=O)c3c(Cl)cc(F)cc3Cl)CC3(F)CCCC3)c2C(F)(F)F)CC1] | trans-4-(4-((2-(2,6-dichloro-4-fluorophenyl)-2-oxoethyl)-((1-fluorocyclopentyl)methyl)carbamoyl)-5-(trifluoromethyl)pyrazol-1-yl)-1-methylcyclohexane-1-carboxylic acid |
| 225 | 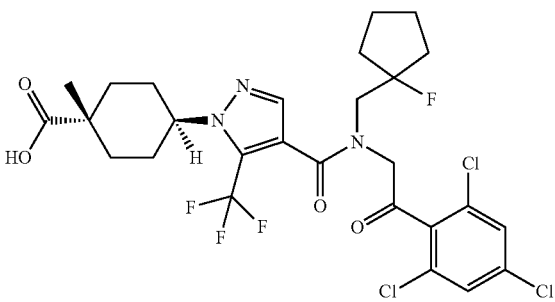 [SMILES: C[C@]1(C(=O)O)CC[C@H](n2ncc(C(=O)N(CC(=O)c3c(Cl)cc(Cl)cc3Cl)CC3(F)CCCC3)c2C(F)(F)F)CC1] | trans-4-(4-(((1-fluorocyclopentyl)methyl-(2-oxo-2-(2,4,6-trichlorophenyl)ethyl)carbamoyl)-5-(trifluoromethyl)pyrazol-1-yl)-1-methylcyclohexane-1-carboxylic acid |
| 226 | 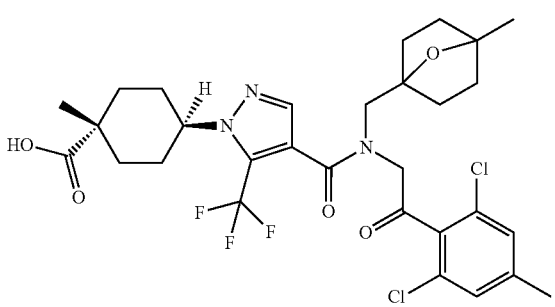 [SMILES: Cc1cc(Cl)c(C(=O)CN(CC23CCC(C)(CC2)O3)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)-((1-methyl-7-oxabicyclo[2.2.1]heptan-4-yl)methyl)carbamoyl)-5-(trifluoromethyl)pyrazol-1-yl)-1-methylcyclohexane-1-carboxylic acid |
| 227 | 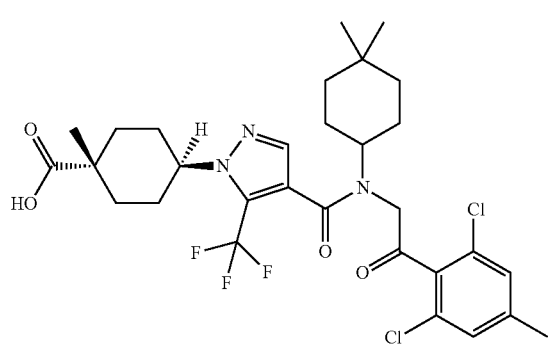 [SMILES: Cc1cc(Cl)c(C(=O)CN(C(=O)c2cnn([C@H]3CC[C@](C)(C(=O)O)CC3)c2C(F)(F)F)C2CCC(C)(C)CC2)c(Cl)c1] | trans-4-(4-((2-(2,6-dichloro-4-methylphenyl)-2-oxoethyl)-(4,4-dimethylcyclohexyl)carbamoyl)-5-(trifluoromethyl)pyrazol-1-yl)-1-methylcyclohexane-1-carboxylic acid |
| 228 | 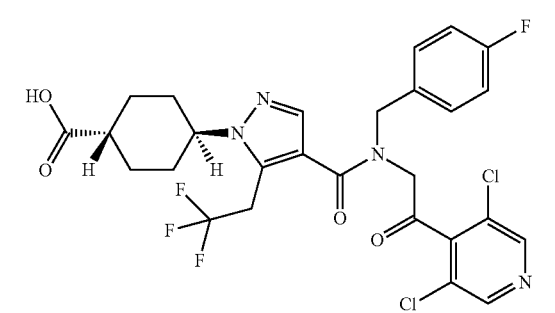 [SMILES: O=C(CN(Cc1ccc(F)cc1)C(=O)c1cnn([C@H]2CC[C@H](C(=O)O)CC2)c1CC(F)(F)F)c1c(Cl)cncc1Cl] | trans-4-(4-((2-(3,5-dichloropyridin-4-yl)-2-oxoethyl)-((4-fluorophenyl)methyl)carbamoyl)-5-(2,2,2-trifluoroethyl)pyrazol-1-yl)cyclohexane-1-carboxylic acid |

| example | structure | name |
| --- | --- | --- |
| 229 | 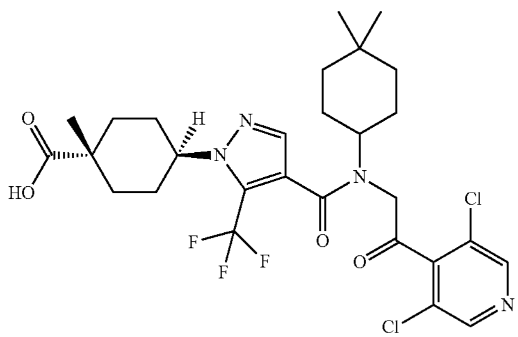 [SMILES: CC1(C)CCC(N(CC(=O)c2c(Cl)cncc2Cl)C(=O)c2cnn([C@H]3CC[C@](C)(C(=O)O)CC3)c2C(F)(F)F)CC1] | trans-4-(4-((2-(3,5-dichloropyridin-4-yl)-2-oxoethyl)-(4,4-dimethylcyclohexyl)carbamoyl)-5-(trifluoromethyl)pyrazol-1-yl)-1-methylcyclohexane-1-carboxylic acid |
| 230 | 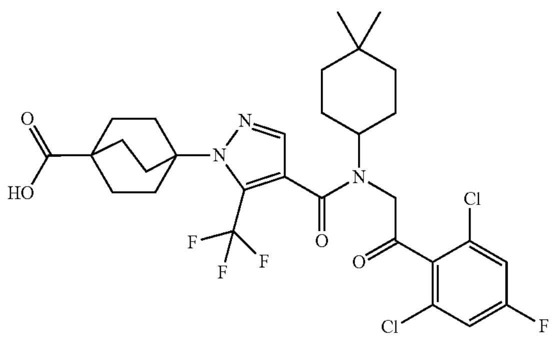 [SMILES: CC1(C)CCC(N(CC(=O)c2c(Cl)cc(F)cc2Cl)C(=O)c2cnn(C34CCC(C(=O)O)(CC3)CC4)c2C(F)(F)F)CC1] | 4-(4-((2-(2,6-dichloro-4-fluorophenyl)-2-oxoethyl)-(4,4-dimethylcyclohexyl)carbamoyl)-5-(trifluoromethyl)pyrazol-1-yl)bicyclo[2.2.2]octane-1-carboxylic acid |
| 231 | 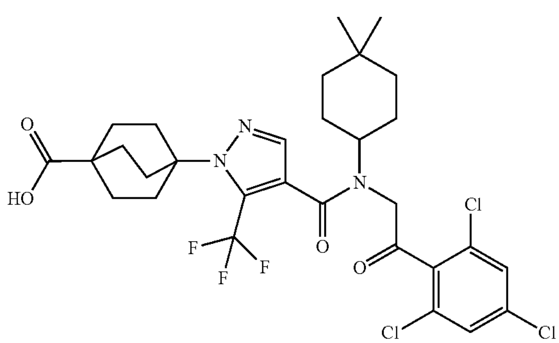 [SMILES: CC1(C)CCC(N(CC(=O)c2c(Cl)cc(Cl)cc2Cl)C(=O)c2cnn(C34CCC(C(=O)O)(CC3)CC4)c2C(F)(F)F)CC1] | 4-(4-((4,4-dimethylcyclohexyl)-(2-oxo-2-(2,4,6-trichlorophenyl)ethyl)carbamoyl)-5-(trifluoromethyl)pyrazol-1-yl)bicyclo[2.2.2]octane-1-carboxylic acid |
| 232 | 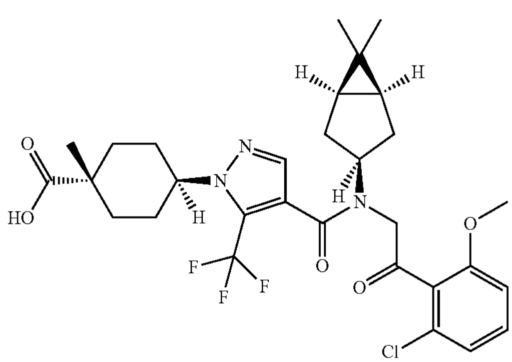 [SMILES: COc1cccc(Cl)c1C(=O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-((2-(2-chloro-6-methoxyphenyl)-2-oxoethyl)-((1R,3r,5S)-6,6-dimethyl-3-bicyclo(3.1.0)hexanyl)carbamoyl)-5-(trifluoromethyl)pyrazol-1-yl)-1-methylcyclohexane-1-carboxylic acid |

-continued

| example | structure | name |
|---|---|---|
| 234 | 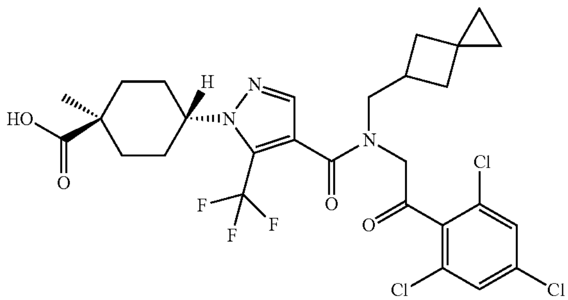 [SMILES: C[C@]1(C(=O)O)CC[C@H](n2ncc(C(=O)N(CC(=O)c3c(Cl)cc(Cl)cc3Cl)CC3CC4(CC4)C3)c2C(F)(F)F)CC1] | trans-4-(4-((2-oxo-2-(2,4,6-trichlorophenyl)ethyl)-(spiro[2.3]hexan-5-ylmethyl)carbamoyl)-5-(trifluoromethyl)pyrazol-1-yl)-1-methylcyclohexane-1-carboxylic acid |
| 235 | 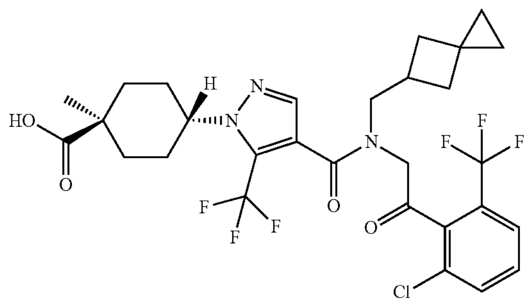 [SMILES: C[C@]1(C(=O)O)CC[C@H](n2ncc(C(=O)N(CC(=O)c3c(Cl)cccc3C(F)(F)F)CC3CC4(CC4)C3)c2C(F)(F)F)CC1] | trans-4-(4-((2-(2-chloro-6-(trifluoromethyl)phenyl)-2-oxoethyl)-(spiro[2.3]hexan-5-ylmethyl)carbamoyl)-5-(trifluoromethyl)pyrazol-1-yl)-1-methylcyclohexane-1-carboxylic acid |
| 236 | 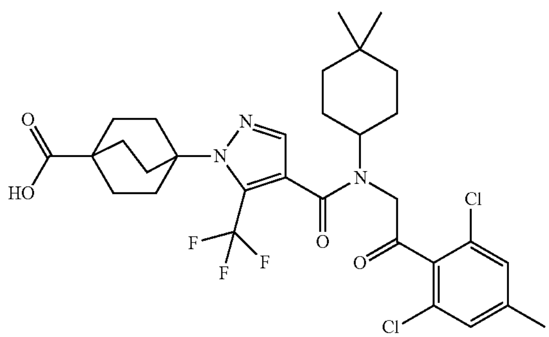 [SMILES: Cc1cc(Cl)c(C(=O)CN(C(=O)c2cnn(C34CCC(C(=O)O)(CC3)CC4)c2C(F)(F)F)C2CCC(C)(C)CC2)c(Cl)c1] | 4-(4-((2-(2,6-dichloro-4-methylphenyl)-2-oxoethyl)-(4,4-dimethylcyclohexyl)carbamoyl)-5-(trifluoromethyl)pyrazol-1-yl)bicyclo[2.2.2]octane-1-carboxylic acid |
| 237 | 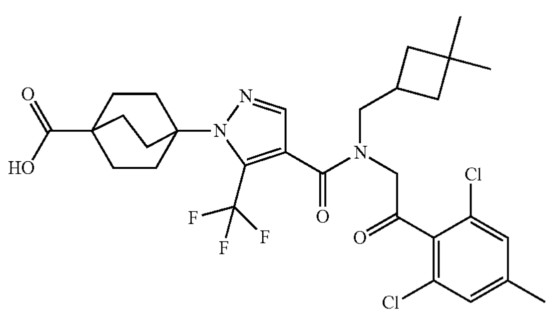 [SMILES: Cc1cc(Cl)c(C(=O)CN(CC2CC(C)(C)C2)C(=O)c2cnn(C34CCC(C(=O)O)(CC3)CC4)c2C(F)(F)F)c(Cl)c1] | 4-(4-((2-(2,6-dichloro-4-methylphenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid |
| 238 | 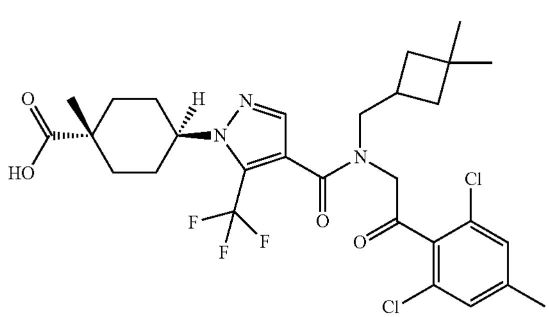 [SMILES: Cc1cc(Cl)c(C(=O)CN(CC2CC(C)(C)C2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)-((3,3-dimethylcyclobutyl)methyl)carbamoyl)-5-(trifluoromethyl)pyrazol-1-yl)-1-methylcyclohexane-1-carboxylic acid |

-continued

| example | structure | name |
|---|---|---|
| 239 | 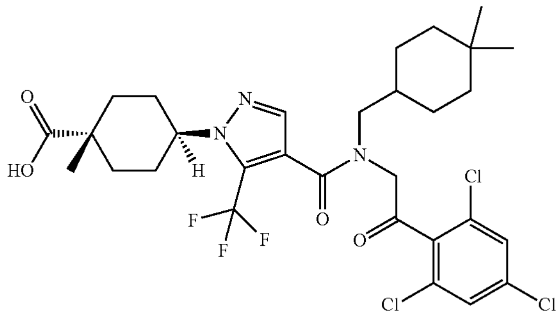 [SMILES: CC1(C)CCC(CN(CC(=O)c2c(Cl)cc(Cl)cc2Cl)C(=O)c2cnn([C@H]3CC[C@](C)(C(=O)O)CC3)c2C(F)(F)F)CC1] | trans-4-(4-(((4,4-dimethylcyclohexyl)methyl-(2-oxo-2-(2,4,6-trichlorophenyl)ethyl)carbamoyl)-5-(trifluoromethyl)pyrazol-1-yl)-1-methylcyclohexane-1-carboxylic acid |
| 240 | 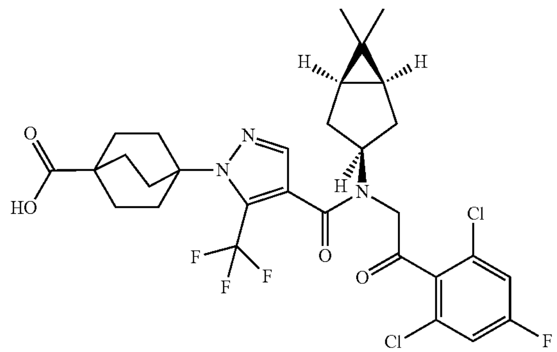 [SMILES: CC1(C)[C@@H]2C[C@H](N(CC(=O)c3c(Cl)cc(F)cc3Cl)C(=O)c3cnn(C45CCC(C(=O)O)(CC4)CC5)c3C(F)(F)F)C[C@@H]21] | 4-(4-((2-(2,6-dichloro-4-fluorophenyl)-2-oxoethyl)-((1R,3r,5S)-6,6-dimethyl-3-bicyclo[3.1.0]hexanyl)carbamoyl)-5-(trifluoromethyl)pyrazol-1-yl)bicyclo(2.2.2)octane-1-carboxylic acid |
| 241 | 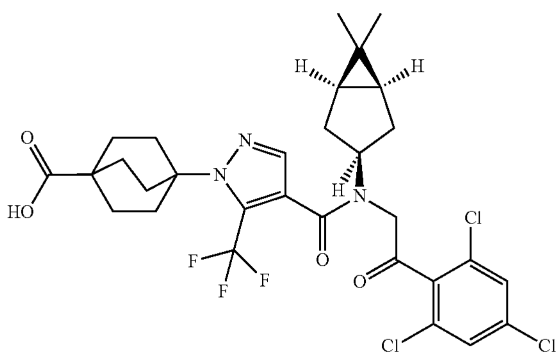 [SMILES: CC1(C)[C@@H]2C[C@H](N(CC(=O)c3c(Cl)cc(Cl)cc3Cl)C(=O)c3cnn(C45CCC(C(=O)O)(CC4)CC5)c3C(F)(F)F)C[C@@H]21] | 4-(4-(((1R,3r,5S)-6,6-dimethyl-3-bicyclo[3.1.0]hexanyl)-(2-oxo-2-(2,4,6-trichlorophenyl)ethyl)carbamoyl)-5-(trifluoromethyl)pyrazol-1-yl)bicyclo(2.2.2)octane-1-carboxylic acid |
| 242 | 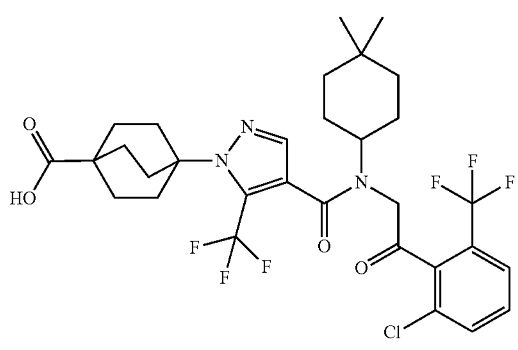 [SMILES: CC1(C)CCC(N(CC(=O)c2c(Cl)cccc2C(F)(F)F)C(=O)c2cnn(C34CCC(C(=O)O)(CC3)CC4)c2C(F)(F)F)CC1] | 4-(4-((2-(2-chloro-6-(trifluoromethyl)phenyl)-2-oxoethyl)-(4,4-dimethylcyclohexyl)carbamoyl)-5-(trifluoromethyl)pyrazol-1-yl)bicyclo[2.2.2]octane-1-carboxylic acid |

-continued

| example | structure | name |
|---|---|---|
| 243 | 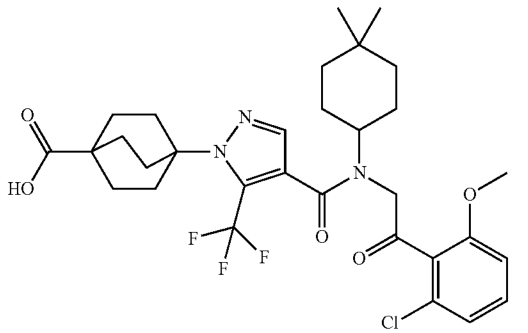 [SMILES: COc1cccc(Cl)c1C(=O)CN(C(=O)c1cnn(C23CCC(C(=O)O)(CC2)CC3)c1C(F)(F)F)C1CCC(C)(C)CC1] | 4-(4-((2-(2-chloro-6-methoxyphenyl)-2-oxoethyl)-(4,4-dimethylcyclohexyl)carbamoyl)-5-(trifluoromethyl)pyrazol-1-yl)bicyclo[2.2.2]octane-1-carboxylic acid |
| 244 | 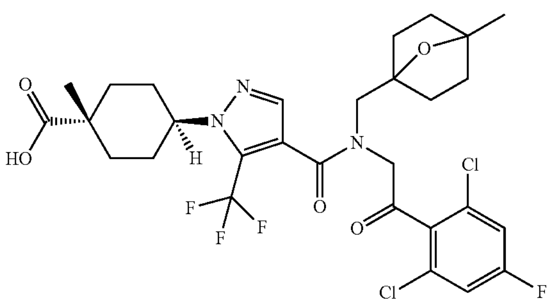 [SMILES: CC12CCC(CN(CC(=O)c3c(Cl)cc(F)cc3Cl)C(=O)c3cnn([C@H]4CC[C@](C)(C(=O)O)CC4)c3C(F)(F)F)(CC1)O2] | trans-4-(4-((2-(2,6-dichloro-4-fluorophenyl)-2-oxoethyl)-((1-methyl-7-oxabicyclo[2.2.1]heptan-4-yl)methyl)carbamoyl)-5-(trifluoromethyl)pyrazol-1-yl)-1-methylcyclohexane-1-carboxylic acid |
| 245 | 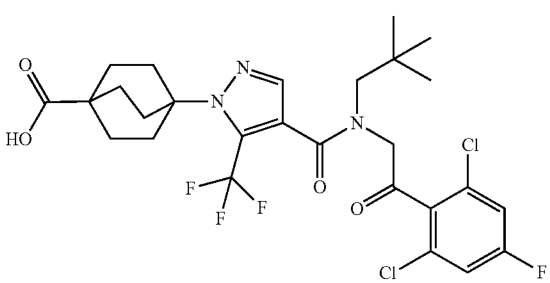 [SMILES: CC(C)(C)CN(CC(=O)c1c(Cl)cc(F)cc1Cl)C(=O)c1cnn(C23CCC(C(=O)O)(CC2)CC3)c1C(F)(F)F] | 4-(4-((2-(2,6-dichloro-4-fluorophenyl)-2-oxoethyl)-(2,2-dimethylpropyl)carbamoyl)-5-(trifluoromethyl)pyrazol-1-yl)bicyclo[2.2.2]octane-1-carboxylic acid |
| 246 | 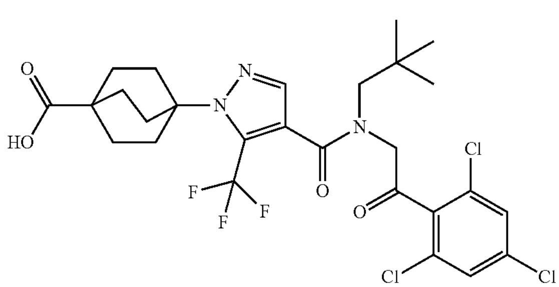 [SMILES: CC(C)(C)CN(CC(=O)c1c(Cl)cc(Cl)cc1Cl)C(=O)c1cnn(C23CCC(C(=O)O)(CC2)CC3)c1C(F)(F)F] | 4-(4-(2,2-dimethylpropyl-(2-oxo-2-(2,4,6-trichlorophenyl)ethyl)carbamoyl)-5-(trifluoromethyl)pyrazol-1-yl)bicyclo[2.2.2]octane-1-carboxylic acid |
| 247 | 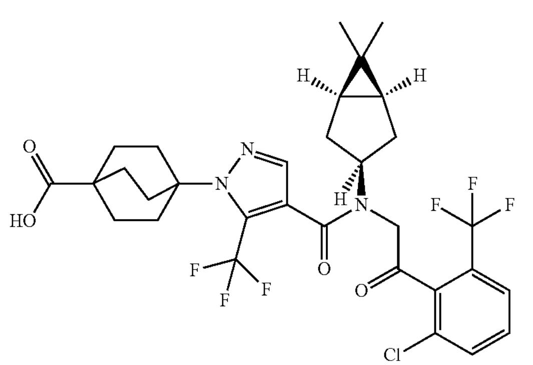 [SMILES: CC1(C)[C@@H]2C[C@H](N(CC(=O)c3c(Cl)cccc3C(F)(F)F)C(=O)c3cnn(C45CCC(C(=O)O)(CC4)CC5)c3C(F)(F)F)C[C@@H]21] | 4-(4-((2-(2-chloro-6-(trifluoromethyl)phenyl)-2-oxoethyl)-((1R,3r,5S)-6,6-dimethyl-3-bicyclo[3.1.0]hexanyl)carbamoyl)-5-(trifluoromethyl)pyrazol-1-yl)bicyclo[2.2.2]octane-1-carboxylic acid |

-continued

| example | structure | name |
|---|---|---|
| 248 | 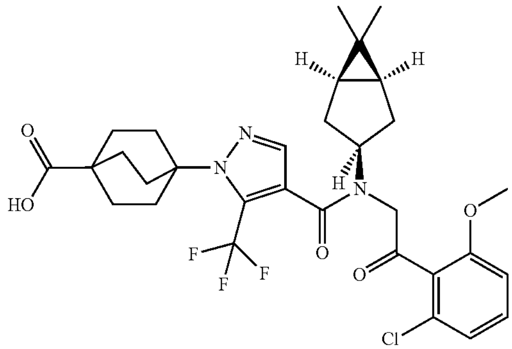 [SMILES: COc1cccc(Cl)c1C(=O)CN(C(=O)c1cnn(C23CCC(C(=O)O)(CC2)CC3)c1C(F)(F)F)[C@H]1C[C@@H]2[C@H](C1)C2(C)C] | 4-(4-((2-(2-chloro-6-methoxyphenyl)-2-oxoethyl)-((1R,3r,5S)-6,6-dimethyl-3-bicyclo[3.1.0]hexanyl)carbamoyl)-5-(trifluoromethyl)pyrazol-1-yl)bicyclo[2.2.2]octane-1-carboxylic acid |
| 249 | 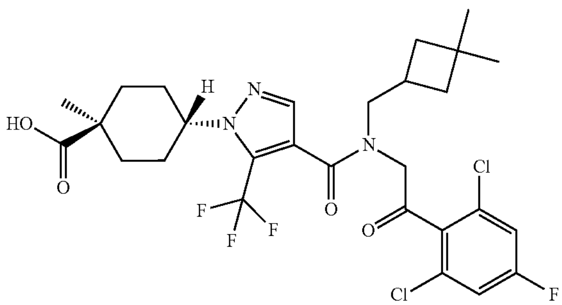 [SMILES: CC1(C)CC(CN(CC(=O)c2c(Cl)cc(F)cc2Cl)C(=O)c2cnn([C@H]3CC[C@](C)(C(=O)O)CC3)c2C(F)(F)F)C1] | trans-4-(4-((2-(2,6-dichloro-4-fluorophenyl)-2-oxoethyl)-((3,3-dimethylcyclobutyl)methyl)carbamoyl)-5-(trifluoromethyl)pyrazol-1-yl)-1-methylcyclohexane-1-carboxylic acid |
| 250 | 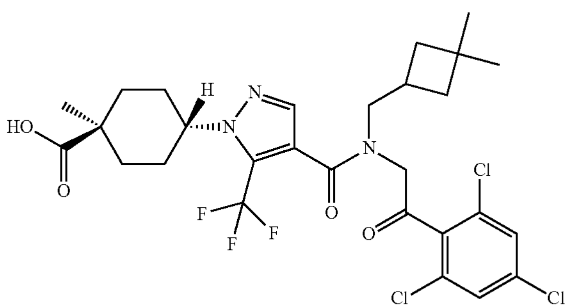 [SMILES: CC1(C)CC(CN(CC(=O)c2c(Cl)cc(Cl)cc2Cl)C(=O)c2cnn([C@H]3CC[C@](C)(C(=O)O)CC3)c2C(F)(F)F)C1] | trans-4-(4-(((3,3-dimethylcyclobutyl)methyl-(2-oxo-2-(2,4,6-trichlorophenyl)ethyl)carbamoyl)-5-(trifluoromethyl)pyrazol-1-yl)-1-methylcyclohexane-1-carboxylic acid |
| 251 | 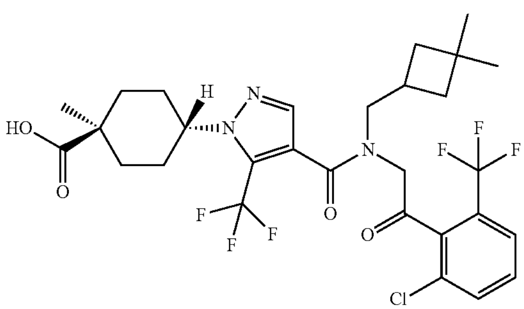 [SMILES: CC1(C)CC(CN(CC(=O)c2c(Cl)cccc2C(F)(F)F)C(=O)c2cnn([C@H]3CC[C@](C)(C(=O)O)CC3)c2C(F)(F)F)C1] | trans-4-(4-((2-(2-chloro-6-(trifluoromethyl)phenyl)-2-oxoethyl)-((3,3-dimethylcyclobutyl)methyl)carbamoyl)-5-(trifluoromethyl)pyrazol-1-yl)-1-methylcyclohexane-1-carboxylic acid |
| 252 | 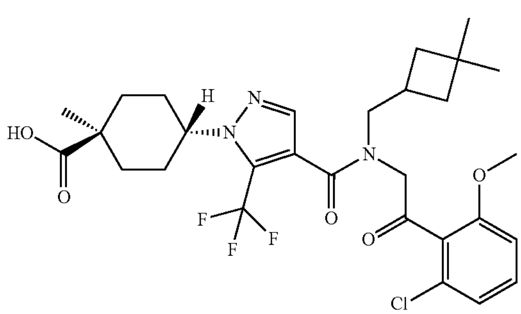 [SMILES: COc1cccc(Cl)c1C(=O)CN(CC1CC(C)(C)C1)C(=O)c1cnn([C@H]2CC[C@](C)(C(=O)O)CC2)c1C(F)(F)F] | trans-4-(4-((2-(2-chloro-6-methoxyphenyl)-2-oxoethyl)-((3,3-dimethylcyclobutyl)methyl)carbamoyl)-5-(trifluoromethyl)pyrazol-1-yl)-1-methylcyclohexane-1-carboxylic acid |

-continued

| example | structure | name |
|---|---|---|
| 253 | 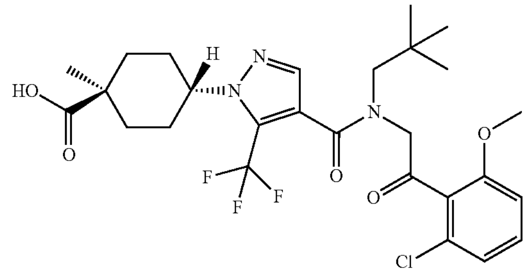 [SMILES: COc1cccc(Cl)c1C(=O)CN(CC(C)(C)C)C(=O)c1cnn([C@H]2CC[C@](C)(C(=O)O)CC2)c1C(F)(F)F] | trans-4-(4-((2-(2-chloro-6-methoxyphenyl)-2-oxoethyl)-(2,2-dimethylpropyl)carbamoyl)-5-(trifluoromethyl)pyrazol-1-yl)-1-methylcyclohexane-1-carboxylic acid |
| 254 | 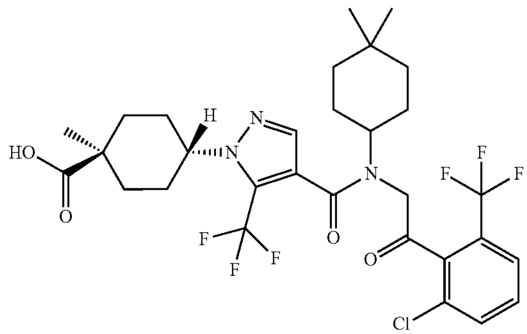 [SMILES: CC1(C)CCC(N(CC(=O)c2c(Cl)cccc2C(F)(F)F)C(=O)c2cnn([C@H]3CC[C@](C)(C(=O)O)CC3)c2C(F)(F)F)CC1] | trans-4-(4-((2-(2-chloro-6-(trifluoromethyl)phenyl)-2-oxoethyl)-(4,4-dimethylcyclohexyl)carbamoyl)-5-(trifluoromethyl)pyrazol-1-yl)-1-methylcyclohexane-1-carboxylic acid |
| 255 | 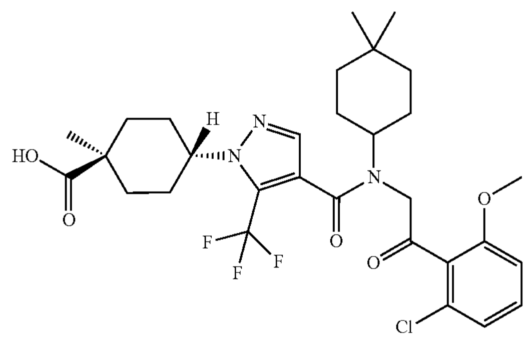 [SMILES: COc1cccc(Cl)c1C(=O)CN(C(=O)c1cnn([C@H]2CC[C@](C)(C(=O)O)CC2)c1C(F)(F)F)C1CCC(C)(C)CC1] | trans-4-(4-((2-(2-chloro-6-methoxyphenyl)-2-oxoethyl)-(4,4-dimethylcyclohexyl)carbamoyl)-5-(trifluoromethyl)pyrazol-1-yl)-1-methylcyclohexane-1-carboxylic acid |
| 256 | 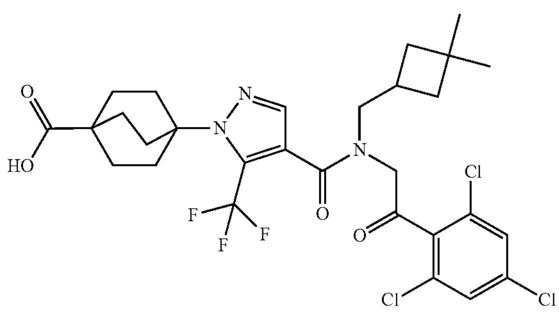 [SMILES: CC1(C)CC(CN(CC(=O)c2c(Cl)cc(Cl)cc2Cl)C(=O)c2cnn(C34CCC(C(=O)O)(CC3)CC4)c2C(F)(F)F)C1] | 4-(4-((3,3-dimethylcyclobutyl)methyl-(2-oxo-2-(2,4,6-trichlorophenyl)ethyl)carbamoyl)-5-(trifluoromethyl)pyrazol-1-yl)bicyclo[2.2.2]octane-1-carboxylic acid |
| 257 | 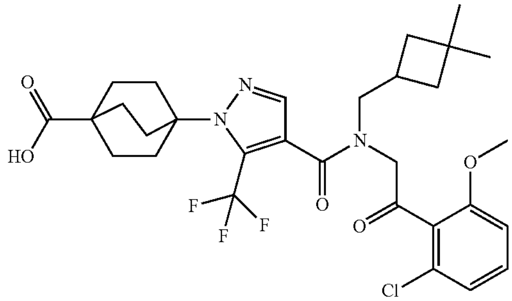 [SMILES: COc1cccc(Cl)c1C(=O)CN(CC1CC(C)(C)C1)C(=O)c1cnn(C23CCC(C(=O)O)(CC2)CC3)c1C(F)(F)F] | 4-(4-((2-(2-chloro-6-methoxyphenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid |

-continued

| example | structure | name |
|---|---|---|
| 258 | 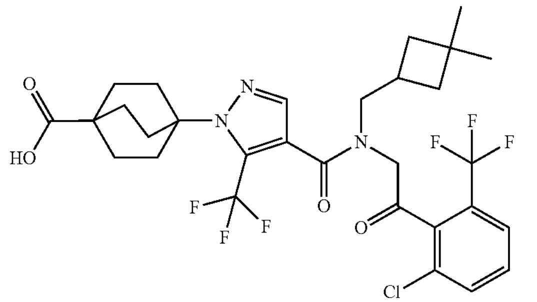 [SMILES: CC1(C)CC(CN(CC(=O)c2c(Cl)cccc2C(F)(F)F)C(=O)c2cnn(C34CCC(C(=O)O)(CC3)CC4)c2C(F)(F)F)C1] | 4-(4-((2-(2-chloro-6-(trifluoromethyl)phenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid |
| 259 | 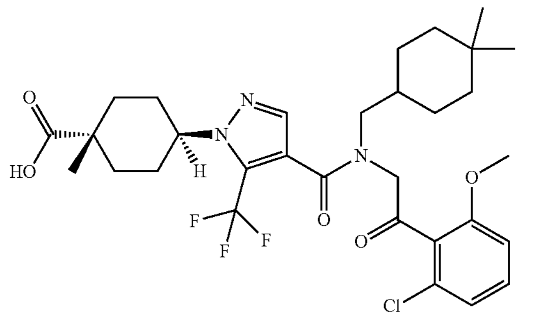 [SMILES: COc1cccc(Cl)c1C(=O)CN(CC1CCC(C)(C)CC1)C(=O)c1cnn([C@H]2CC[C@](C)(C(=O)O)CC2)c1C(F)(F)F] | trans-4-(4-((2-(2-chloro-6-methoxyphenyl)-2-oxoethyl)-((4,4-dimethylcyclohexyl)methyl)carbamoyl)-5-(trifluoromethyl)pyrazol-1-yl)-1-methylcyclohexane-1-carboxylic acid |
| 260 | 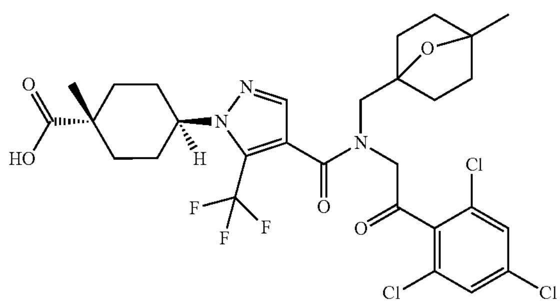 [SMILES: CC12CCC(CN(CC(=O)c3c(Cl)cc(Cl)cc3Cl)C(=O)c3cnn([C@H]4CC[C@](C)(C(=O)O)CC4)c3C(F)(F)F)(CC1)O2] | trans-4-(4-((1-methyl-7-oxabicyclo[2.2.1]heptan-4-yl)methyl-(2-oxo-2-(2,4,6-trichlorophenyl)ethyl)carbamoyl)-5-(trifluoromethyl)pyrazol-1-yl)-1-methylcyclohexane-1-carboxylic acid |
| 261 | 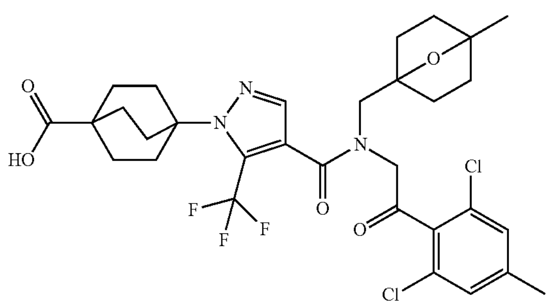 [SMILES: Cc1cc(Cl)c(C(=O)CN(CC23CCC(C)(CC2)O3)C(=O)c2cnn(C34CCC(C(=O)O)(CC3)CC4)c2C(F)(F)F)c(Cl)c1] | 4-(4-((2-(2,6-dichloro-4-methylphenyl)-2-oxoethyl)-((1-methyl-7-oxabicyclo[2.2.1]heptan-4-yl)methyl)carbamoyl)-5-(trifluoromethyl)pyrazol-1-yl)bicyclo[2.2.2]octane-1-carboxylic acid |
| 262 | 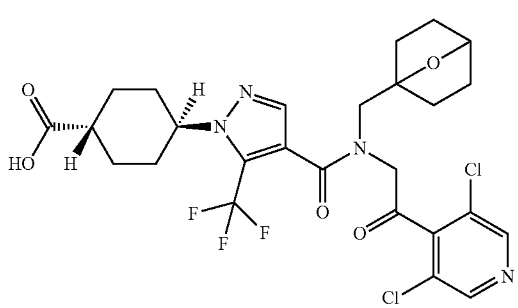 [SMILES: O=C(CN(CC12CCC(CC1)O2)C(=O)c1cnn([C@H]2CC[C@H](C(=O)O)CC2)c1C(F)(F)F)c1c(Cl)cncc1Cl] | trans-4-(4-((2-(3,5-dichloropyridin-4-yl)-2-oxoethyl)-(7-oxabicyclo[2.2.1]heptan-4-ylmethyl)carbamoyl)-5-(trifluoromethyl)pyrazol-1-yl)cyclohexane-1-carboxylic acid |

-continued

| example | structure | name |
|---|---|---|
| 263 | 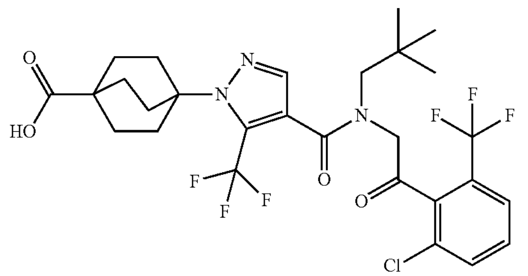 [SMILES: CC(C)(C)CN(CC(=O)c1c(Cl)cccc1C(F)(F)F)C(=O)c1cnn(C23CCC(C(=O)O)(CC2)CC3)c1C(F)(F)F] | 4-(4-((2-(2-chloro-6-(trifluoromethyl)phenyl)-2-oxoethyl)-(2,2-dimethylpropyl)carbamoyl)-5-(trifluoromethyl)pyrazol-1-yl)bicyclo[2.2.2]octane-1-carboxylic acid |
| 264 | 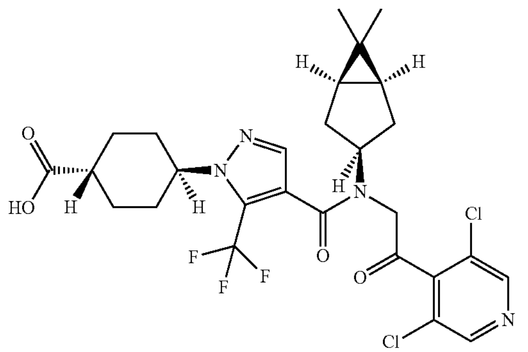 [SMILES: CC1(C)[C@@H]2C[C@H](N(CC(=O)c3c(Cl)cncc3Cl)C(=O)c3cnn([C@H]4CC[C@H](C(=O)O)CC4)c3C(F)(F)F)C[C@@H]21] | trans-4-(4-((2-(3,5-dichloropyridin-4-yl)-2-oxoethyl)-((1R,3r,5S)-6,6-dimethyl-3-bicyclo[3.1.0] hexanyl)carbamoyl)-5-(trifluoromethyl)pyrazol-1-yl)cyclohexane-1-carboxylic acid |
| 265 | 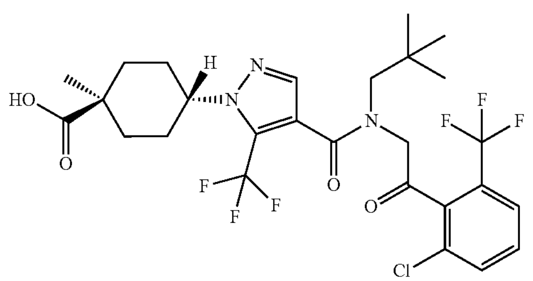 [SMILES: CC(C)(C)CN(CC(=O)c1c(Cl)cccc1C(F)(F)F)C(=O)c1cnn([C@H]2CC[C@](C)(C(=O)O)CC2)c1C(F)(F)F] | trans-4-(4-((2-(2-chloro-6-(trifluoromethyl)phenyl)-2-oxoethyl)-(2,2-dimethylpropyl(carbamoyl)-5-(trifluoromethyl)pyrazol-1-yl)-1-methylcyclohexane-1-carboxylic acid |
| 266 | 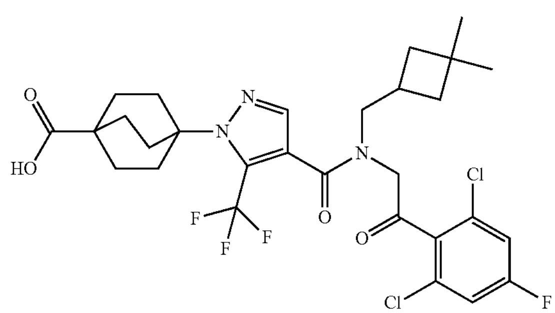 [SMILES: CC1(C)CC(CN(CC(=O)c2c(Cl)cc(F)cc2Cl)C(=O)c2cnn(C34CCC(C(=O)O)(CC3)CC4)c2C(F)(F)F)C1] | 4-(4-((2-(2,6-dichloro-4-fluorophenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid |
| 267 | 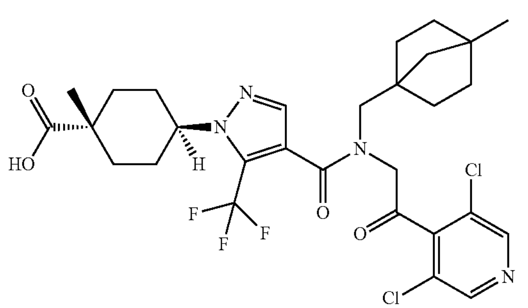 | trans-4-(4-((2-(3,5-dichloropyridin-4-yl)-2-oxoethyl)-((1-methyl-4-bicyclo[2.2.1]heptanyl)methyl)carbamoyl)-5-(trifluoromethyl)pyrazol-1-yl)-1-methylcyclohexane-1-carboxylic acid |

-continued

| example | structure | name |
|---|---|---|
| 268 | 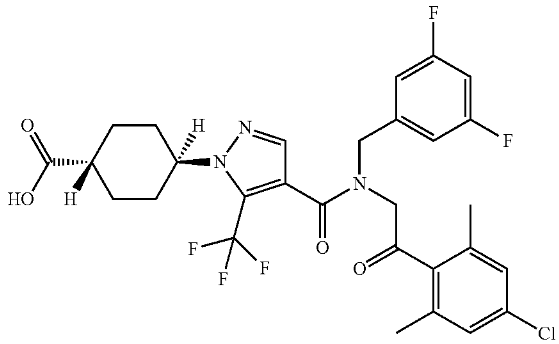 [SMILES: Cc1cc(Cl)cc(C)c1C(=O)CN(Cc1cc(F)cc(F)c1)C(=O)c1cnn([C@H]2CC[C@H](C(=O)O)CC2)c1C(F)(F)F] | trans-4-(4-((2-(4-chloro-2,6-dimethylphenyl)-2-oxoethyl)-((3,5-difluorophenyl)methyl)carbamoyl)-5-(trifluoromethyl)pyrazol-1-yl)cyclohexane-1-carboxylic acid |
| 269 | 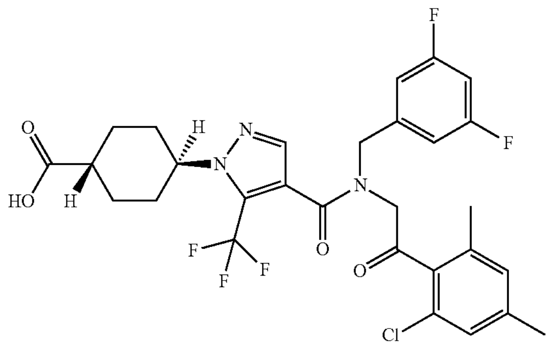 [SMILES: Cc1cc(C)c(C(=O)CN(Cc2cc(F)cc(F)c2)C(=O)c2cnn([C@H]3CC[C@H](C(=O)O)CC3)c2C(F)(F)F)c(Cl)c1] | trans-4-(4-((2-(2-chloro-4,6-dimethylphenyl)-2-oxoethyl)-((3,5-difluorophenyl)methyl)carbamoyl)-5-(trifluoromethyl)pyrazol-1-yl)cyclohexane-1-carboxylic acid |
| 270 | 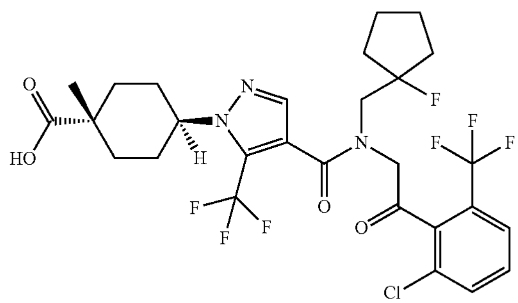 [SMILES: C[C@]1(C(=O)O)CC[C@H](n2ncc(C(=O)N(CC(=O)c3c(Cl)cccc3C(F)(F)F)CC3(F)CCCC3)c2C(F)(F)F)CC1] | trans-4-(4-((2-(2-chloro-6-(trifluoromethyl)phenyl)-2-oxoethyl)-((1-fluorocyclopentyl)methyl)carbamoyl)-5-(trifluoromethyl)pyrazol-1-yl)-1-methylcyclohexane-1-carboxylic acid |
| 271 | 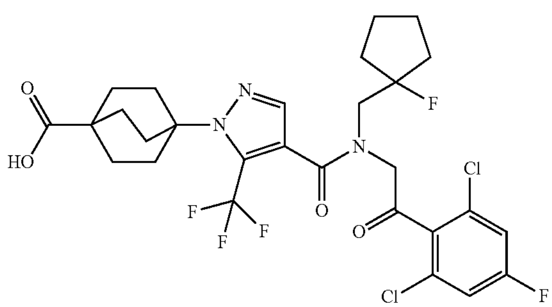 [SMILES: O=C(CN(CC1(F)CCCC1)C(=O)c1cnn(C23CCC(C(=O)O)(CC2)CC3)c1C(F)(F)F)c1c(Cl)cc(F)cc1Cl] | 4-(4-((2-(2,6-dichloro-4-fluorophenyl)-2-oxoethyl)-((1-fluorocyclopentyl)methyl)carbamoyl)-5-(trifluoromethyl)pyrazol-1-yl)bicyclo[2.2.2]octane-1-carboxylic acid |
| 272 | 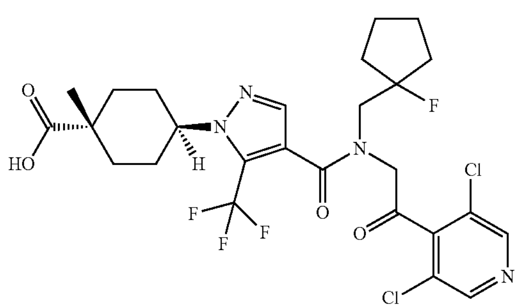 [SMILES: C[C@]1(C(=O)O)CC[C@H](n2ncc(C(=O)N(CC(=O)c3c(Cl)cncc3Cl)CC3(F)CCCC3)c2C(F)(F)F)CC1] | trans-4-(4-((2-(3,5-dichloropyridin-4-yl)-2-oxoethyl)-((1-fluorocyclopentyl)methyl)carbamoyl)-5-(trifluoromethyl)pyrazol-1-yl)-1-methylcyclohexane-1-carboxylic acid |

-continued

| example | structure | name |
|---|---|---|
| 273 | 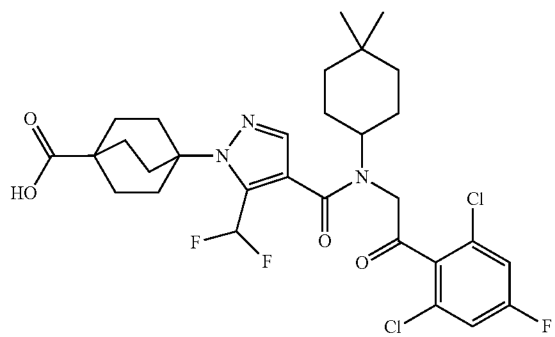 | 4-(4-((2-(2,6-dichloro-4-fluorophenyl)-2-oxoethyl)-(4,4-dimethylcyclohexyl)carbamoyl)-5-(difluoromethyl)pyrazol-1-yl)bicyclo[2.2.2]octane-1-carboxylic acid |
| 274 | 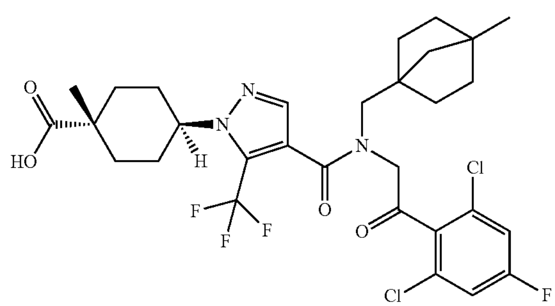 | trans-4-(4-((2-(2,6-dichloro-4-fluorophenyl)-2-oxoethyl)-((1-methyl-4-bicyclo[2.2.1]heptanyl)methyl)carbamoyl)-5-(trifluoromethyl)pyrazol-1-yl)-1-methylcyclohexane-1-carboxylic acid |
| 275 | 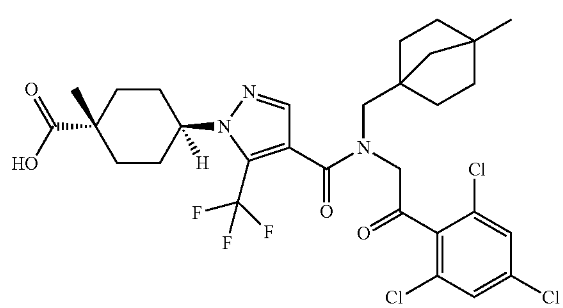 | trans-4-(4-((1-methyl-4-bicyclo[2.2.1]heptanyl)methyl-(2-oxo-2-(2,4,6-trichlorophenyl)ethyl)carbamoyl)-5-(trifluoromethyl)pyrazol-1-yl)-1-methylcyclohexane-1-carboxylic acid |
| 279 | 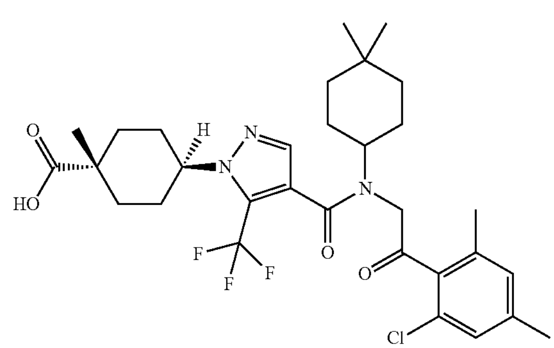 [SMILES: Cc1cc(C)c(C(=O)CN(C(=O)c2cnn([C@H]3CC[C@](C)(C(=O)O)CC3)c2C(F)(F)F)C2CCC(C)(C)CC2)c(Cl)c1] | trans-4-(4-((2-(2-chloro-4,6-dimethylphenyl)-2-oxoethyl)-(4,4-dimethylcyclohexyl)carbamoyl)-5-(trifluoromethyl)pyrazol-1-yl)-1-methylcyclohexane-1-carboxylic acid |

-continued

| example | structure | name |
|---|---|---|
| 280 | 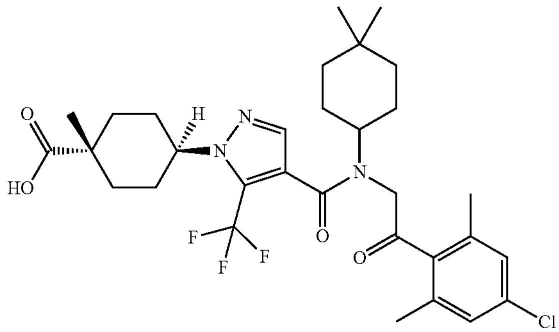 [SMILES: Cc1cc(Cl)cc(C)c1C(=O)CN(C(=O)c1cnn([C@H]2CC[C@](C)(C(=O)O)CC2)c1C(F)(F)F)C1CCC(C)(C)CC1] | trans-4-(4-((2-(4-chloro-2,6-dimethylphenyl)-2-oxoethyl)-(4,4-dimethylcyclohexyl)carbamoyl)-5-(trifluoromethyl)pyrazol-1-yl)-1-methylcyclohexane-1-carboxylic acid |
| 281 | 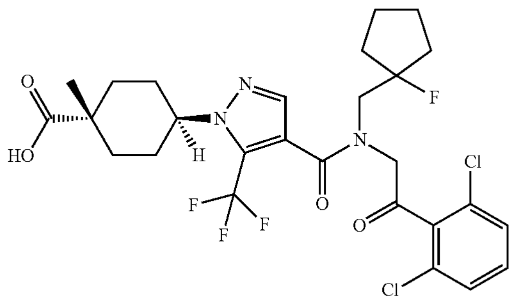 [SMILES: C[C@]1(C(=O)O)CC[C@H](n2ncc(C(=O)N(CC(=O)c3c(Cl)cccc3Cl)CC3(F)CCCC3)c2C(F)(F)F)CC1] | trans-4-(4-((2-(2,6-dichlorophenyl)-2-oxoethyl)-((1-fluorocyclopentyl)methyl)carbamoyl)-5-(trifluoromethyl) pyrazol-1-yl)-1-methylcyclohexane-1-carboxylic acid |
| 282 | 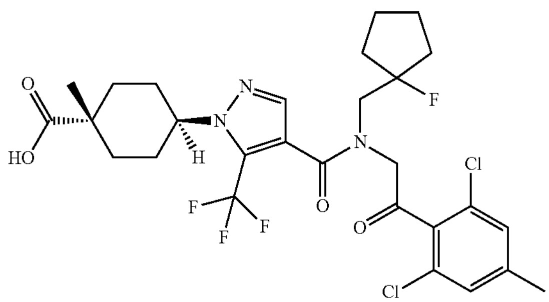 [SMILES: Cc1cc(Cl)c(C(=O)CN(CC2(F)CCCC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)-((1-fluorocyclopentyl)methyl)carbamoyl)-5-(trifluoromethyl)pyrazol-1-yl)-1-methylcyclohexane-1-carboxylic acid |
| 283 | 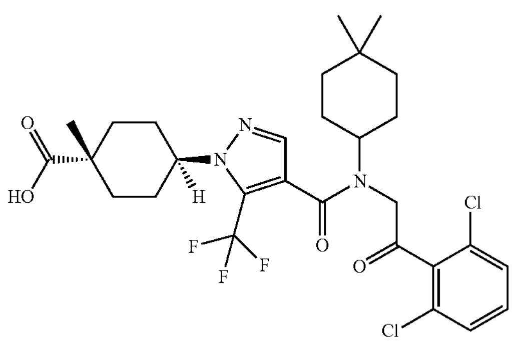 [SMILES: CC1(C)CCC(N(CC(=O)c2c(Cl)cccc2Cl)C(=O)c2cnn([C@H]3CC[C@](C)(C(=O)O)CC3)c2C(F)(F)F)CC1] | trans-4-(4-((2-(2,6-dichlorophenyl)-2-oxoethyl)-(4,4-dimethylcyclohexyl)carbamoyl)-5-(trifluoromethyl)pyrazol-1-yl)-1-methylcyclohexane-1-carboxylic acid |
| 284 | 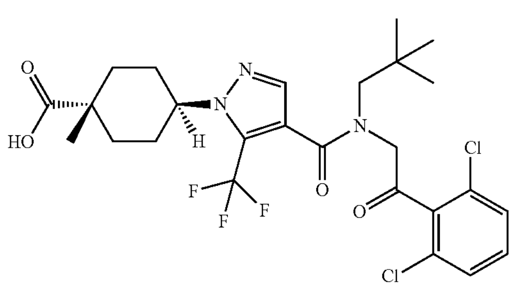 [SMILES: CC(C)(C)CN(CC(=O)c1c(Cl)cccc1Cl)C(=O)c1cnn([C@H]2CC[C@](C)(C(=O)O)CC2)c1C(F)(F)F] | trans-4-(4-((2-(2,6-dichlorophenyl)-2-oxoethyl)-(2,2-dimethylpropyl)carbamoyl)-5-(trifluoromethyl)pyrazol-1-yl)-1-methylcyclohexane-1-carboxylic acid |

-continued

| example | structure | name |
|---|---|---|
| 285 | 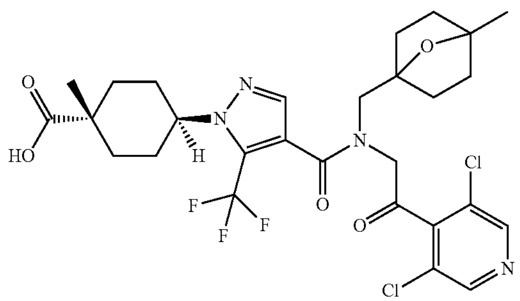 [SMILES: CC12CCC(CN(CC(=O)c3c(Cl)cncc3Cl)C(=O)c3cnn([C@H]4CC[C@](C)(C(=O)O)CC4)c3C(F)(F)F)(CC1)O2] | trans-4-(4-((2-(3,5-dichloropyridin-4-yl)-2-oxoethyl)-((1-methyl-7-oxabicyclo[2.2.1]heptan-4-yl)methyl)carbamoyl)-5-(trifluoromethyl)pyrazol-1-yl)-1-methylcyclohexane-1-carboxylic acid |
| 286 | 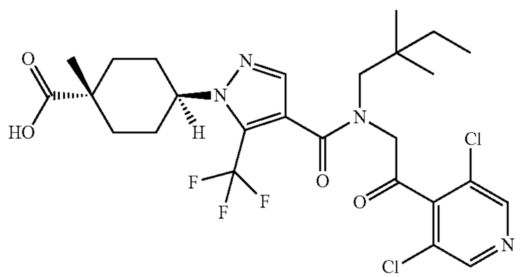 [SMILES: CCC(C)(C)CN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(2,2-dimethylbutyl)carbamoyl)-5-(trifluoromethyl)pyrazol-1-yl)-1-methylcyclohexane-1-carboxylic acid |
| 287 | 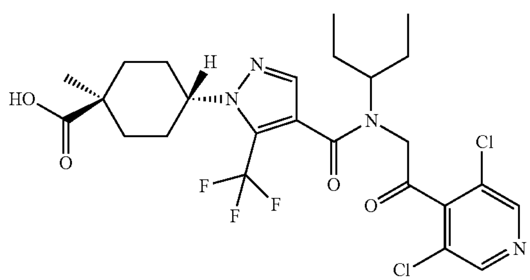 [SMILES: CCC(CC)N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-pentan-3-ylcarbamoyl)-5-(trifluoromethyl)pyrazol-1-yl)-1-methylcyclohexane-1-carboxylic acid |
| 288 | 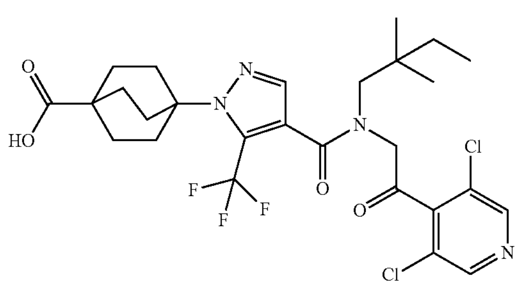 [SMILES: CCC(C)(C)CN(CC(=O)c1c(Cl)cncc1Cl)C(=O)c1cnn(C23CCC(C(=O)O)(CC2)CC3)c1C(F)(F)F] | 4-(4-((2-(3,5-dichloropyridin-4-yl)-2-oxoethyl)-(2,2-dimethylbutyl)carbamoyl)-5-(trifluoromethyl)pyrazol-1-yl)bicyclo[2.2.2]octane-1-carboxylic acid |
| 289 | 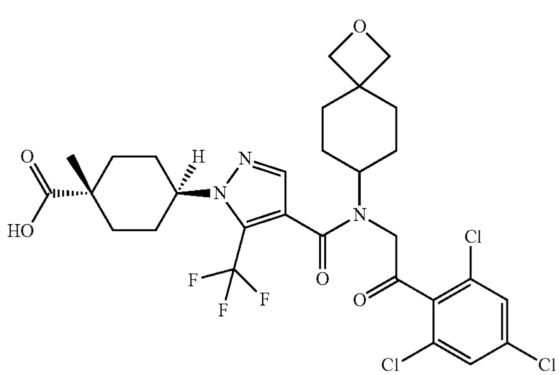 [SMILES: C[C@]1(C(=O)O)CC[C@H](n2ncc(C(=O)N(CC(=O)c3c(Cl)cc(Cl)cc3Cl)C3CCC4(CC3)COC4)c2C(F)(F)F)CC1] | trans-1-methyl-4-(4-(2-oxaspiro[3.5]nonan-7-yl-(2-oxo-2-(2,4,6-trichlorophenyl)ethyl)carbamoyl)-5-(trifluoromethyl)pyrazol-1-yl)cyclohexane-1-carboxylic acid |

-continued

| example | structure | name |
|---|---|---|
| 290 | 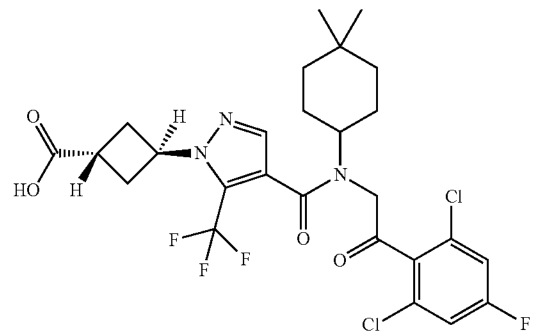 [SMILES: CC1(C)CCC(N(CC(=O)c2c(Cl)cc(F)cc2Cl)C(=O)c2cnn([C@H]3C[C@H](C(=O)O)C3)c2C(F)(F)F)CC1] | trans-3-(4-((2-(2,6-dichloro-4-fluorophenyl)-2-oxoethyl)-(4,4-dimethylcyclohexyl)carbamoyl)-5-(trifluoromethyl)pyrazol-1-yl)cyclobutane-1-carboxylic acid |
| 291 | 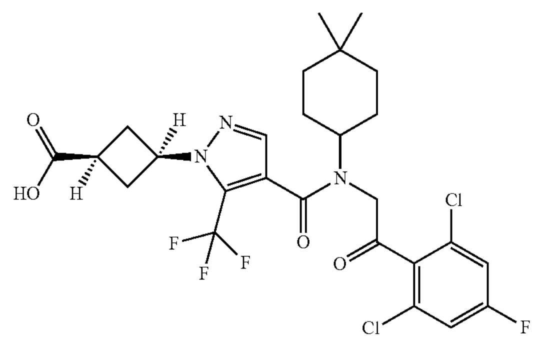 [SMILES: CC1(C)CCC(N(CC(=O)c2c(Cl)cc(F)cc2Cl)C(=O)c2cnn([C@H]3C[C@@H](C(=O)O)C3)c2C(F)(F)F)CC1] | cis-3-(4-((2-(2,6-dichloro-4-fluorophenyl)-2-oxoethyl)-(4,4-dimethylcyclohexyl)carbamoyl)-5-(trifluoromethyl)pyrazol-1-yl)cyclobutane-1-carboxylic acid |
| 292 | 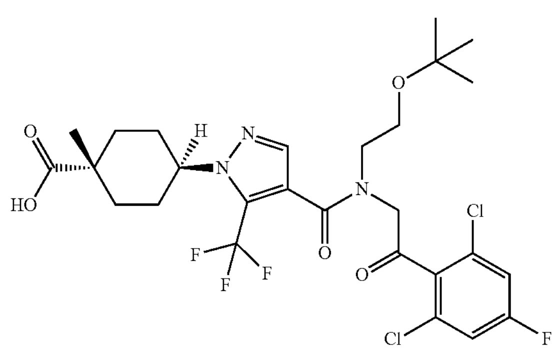 [SMILES: CC(C)(C)OCCN(CC(=O)c1c(Cl)cc(F)cc1Cl)C(=O)c1cnn([C@H]2CC[C@](C)(C(=O)O)CC2)c1C(F)(F)F] | trans-4-(4-((2-(2,6-dichloro-4-fluorophenyl)-2-oxoethyl)-(2-((2-methylpropan-2-yl)oxy)ethyl)carbamoyl)-5-(trifluoromethyl)pyrazol-1-yl)-1-methylcyclohexane-1-carboxylic acid |
| 293 | 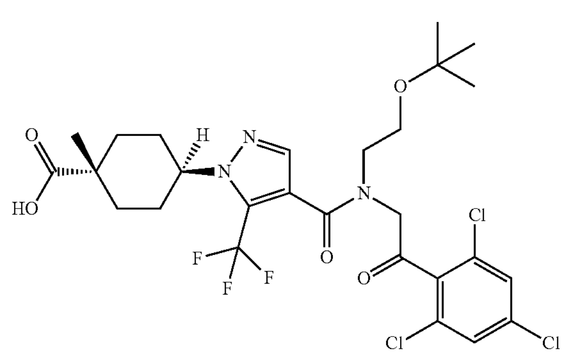 [SMILES: CC(C)(C)OCCN(CC(=O)c1c(Cl)cc(Cl)cc1Cl)C(=O)c1cnn([C@H]2CC[C@](C)(C(=O)O)CC2)c1C(F)(F)F] | trans-1-methyl-4-(4-(2-((2-methylpropan-2-yl)oxy)ethyl-(2-oxo-2-(2,4,6-trichlorophenyl)ethyl)carbamoyl)-5-(trifluoromethyl)pyrazol-1-yl)cyclohexane-1-carboxylic acid |

-continued

| example | structure | name |
|---|---|---|
| 294 | 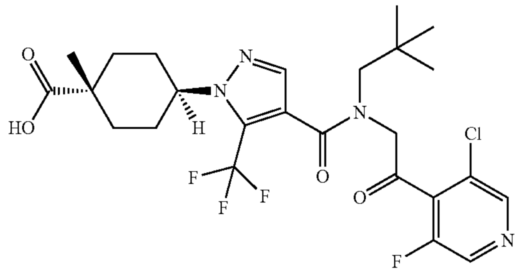 [SMILES: CC(C)(C)CN(CC(=O)c1c(F)cncc1Cl)C(=O)c1cnn([C@H]2CC[C@](C)(C(=O)O)CC2)c1C(F)(F)F] | trans-4-(4-((2-(3-chloro-5-fluoropyridin-4-yl)-2-oxoethyl)-(2,2-dimethylpropyl)carbamoyl)-5-(trifluoromethyl)pyrazol-1-yl)-1-methylcyclohexane-1-carboxylic acid |
| 295 | 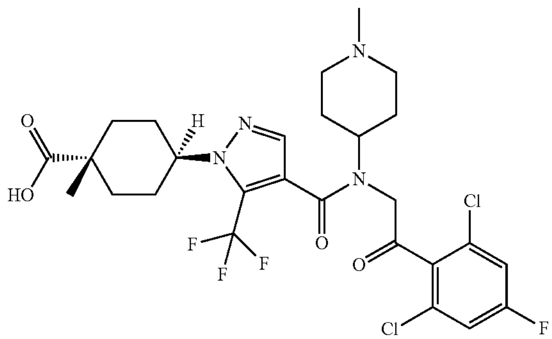 [SMILES: CN1CCC(N(CC(=O)c2c(Cl)cc(F)cc2Cl)C(=O)c2cnn([C@H]3CC[C@](C)(C(=O)O)CC3)c2C(F)(F)F)CC1] | trans-4-(4-((2-(2,6-dichloro-4-fluorophenyl)-2-oxoethyl)-(1-methylpiperidin-4-yl)carbamoyl)-5-(trifluoromethyl)pyrazol-1-yl)-1-methylcyclohexane-1-carboxylic acid |
| 296 | 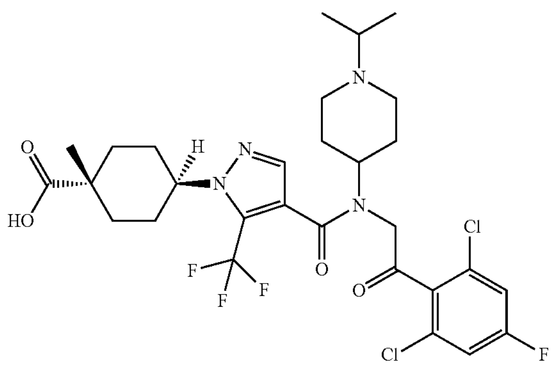 [SMILES: CC(C)N1CCC(N(CC(=O)c2c(Cl)cc(F)cc2Cl)C(=O)c2cnn([C@H]3CC[C@](C)(C(=O)O)CC3)c2C(F)(F)F)CC1] | trans-4-(4-((2-(2,6-dichloro-4-fluorophenyl)-2-oxoethyl)-(1-propan-2-ylpiperidin-4-yl)carbamoyl)-5-(trifluoromethyl)pyrazol-1-yl)-1-methylcyclohexane-1-carboxylic acid |
| 297 | 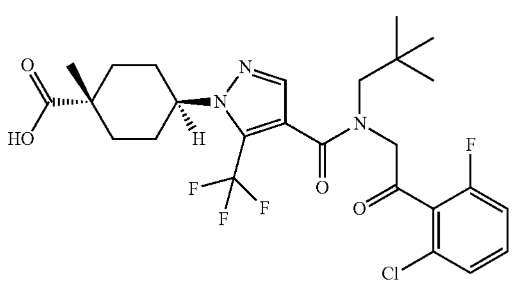 | trans-4-(4-((2-(2-chloro-6-fluorophenyl)-2-oxoethyl)-(2,2-dimethylpropyl)carbamoyl)-5-(trifluoromethyl)pyrazol-1-yl)-1-methylcyclohexane-1-carboxylic acid |
| 298 | 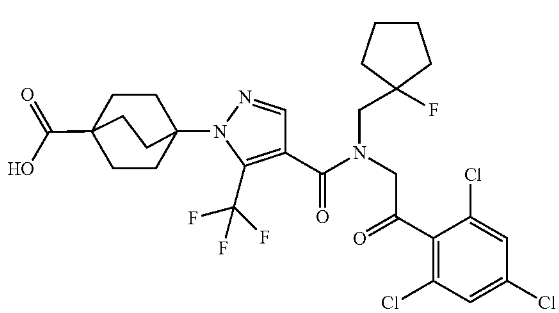 [SMILES: O=C(CN(CC1(F)CCCC1)C(=O)c1cnn(C23CCC(C(=O)O)(CC2)CC3)c1C(F)(F)F)c1c(Cl)cc(Cl)cc1Cl] | 4-(4-((1-fluorocyclopentyl)methyl-(2-oxo-2-(2,4,6-trichlorophenyl)ethyl)carbamoyl)-5-(trifluoromethyl)pyrazol-1-yl)bicyclo[2.2.2]octane-1-carboxylic acid |

-continued

| example | structure | name |
|---|---|---|
| 299 | 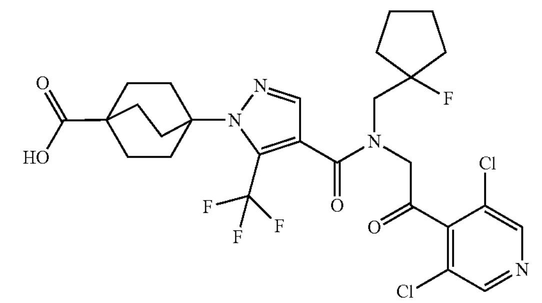 [SMILES: O=C(CN(CC1(F)CCCC1)C(=O)c1cnn(C23CCC(C(=O)O)(CC2)CC3)c1C(F)(F)F)c1c(Cl)cncc1Cl] | 4-(4-((2-(3,5-dichloropyridin-4-yl)-2-oxoethyl)-((1-fluorocyclopentyl)methyl)carbamoyl)-5-(trifluoromethyl)pyrazol-1-yl)bicyclo[2.2.2]octane-1-carboxylic acid |
| 300 | 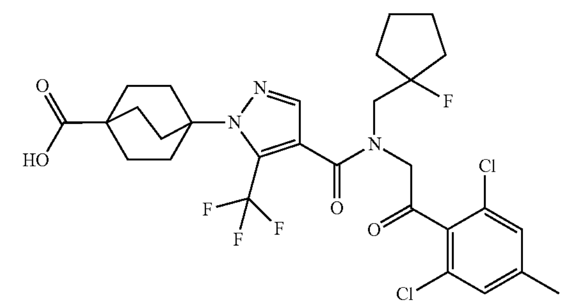 [SMILES: Cc1cc(Cl)c(C(=O)CN(CC2(F)CCCC2)C(=O)c2cnn(C34CCC(C(=O)O)(CC3)CC4)c2C(F)(F)F)c(Cl)c1] | 4-(4-((2-(2,6-dichloro-4-methylphenyl)-2-oxoethyl)-((1-fluorocyclopentyl) methyl)carbamoyl)-5-(trifluoromethyl)pyrazol-1-yl)bicyclo[2.2.2]octane-1-carboxylic acid |
| 301 | 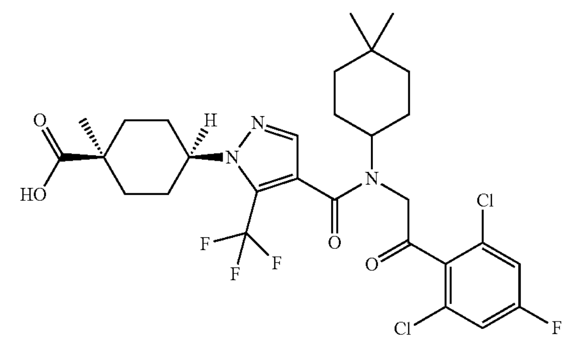 [SMILES: CC1(C)CCC(N(CC(=O)c2c(Cl)cc(F)cc2Cl)C(=O)c2cnn([C@H]3CC[C@@](C)(C(=O)O)CC3)c2C(F)(F)F)CC1] | cis-4-(4-((2-(2,6-dichloro-4-fluorophenyl)-2-oxoethyl)-(4,4-dimethylcyclohexyl)carbamoyl)-5-(trifluoromethyl)pyrazol-1-yl)-1-methylcyclohexane-1-carboxylic acid |
| 302 | 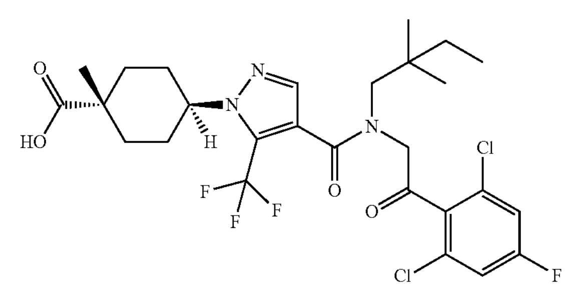 [SMILES: CCC(C)(C)CN(CC(=O)c1c(Cl)cc(F)cc1Cl)C(=O)c1cnn([C@H]2CC[C@](C)(C(=O)O)CC2)c1C(F)(F)F] | trans-4-(4-((2-(2,6-dichloro-4-fluorophenyl)-2-oxoethyl)-(2,2-dimethylbutyl)carbamoyl)-5-(trifluoromethyl)pyrazol-1-yl)-1-methylcyclohexane-1-carboxylic acid |
| 303 | 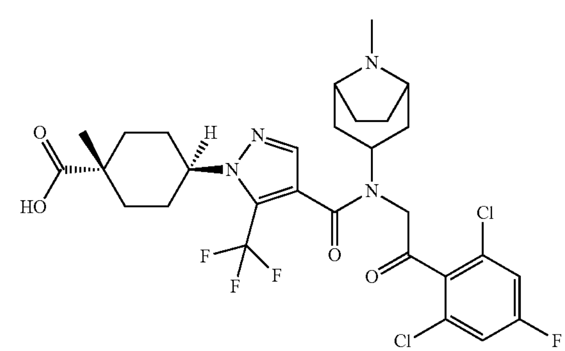 [SMILES: CN1C2CCC1CC(N(CC(=O)c1c(Cl)cc(F)cc1Cl)C(=O)c1cnn([C@H]3CC[C@](C)(C(=O)O)CC3)c1C(F)(F)F)C2] | trans-4-(4-((2-(2,6-dichloro-4-fluorophenyl)-2-oxoethyl)-(8-methyl-8-azabicyclo[3.2.1]octan-3-yl)carbamoyl)-5-(trifluoromethyl)pyrazol-1-yl)-1-methylcyclohexane-1-carboxylic acid |

-continued

| example | structure | name |
|---|---|---|
| 304 | 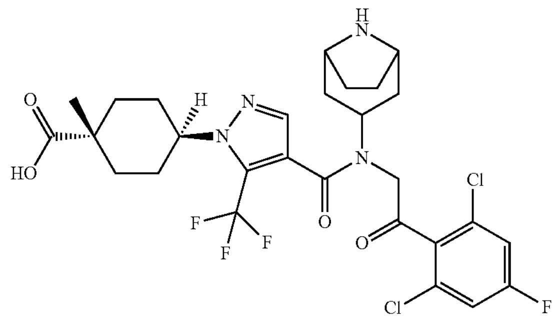 [SMILES: C[C@]1(C(=O)O)CC[C@H](n2ncc(C(=O)N(CC(=O)c3c(Cl)cc(F)cc3Cl)C3CC4CCC(C3)N4)c2C(F)(F)F)CC1] | trans-4-(4-(8-azabicyclo[3.2.1]octan-3-yl-(2-[2,6-dichloro-4-fluorophenyl]-2-oxoethyl)carbamoyl)-5-(trifluoromethyl)pyrazol-1-yl)-1-methylcyclohexane-1-carboxylic acid |
| 305 | 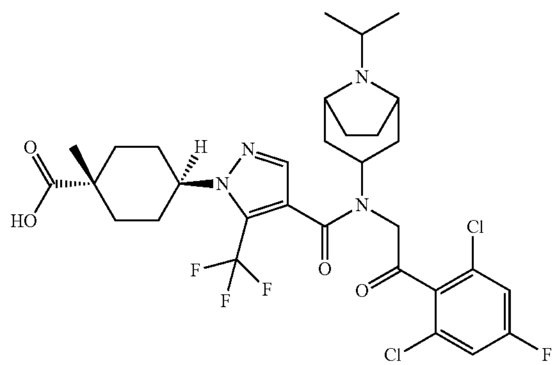 [SMILES: CC(C)N1C2CCC1CC(N(CC(=O)c1c(Cl)cc(F)cc1Cl)C(=O)c1cnn([C@H]3CC[C@](C)(C(=O)O)CC3)c1C(F)(F)F)C2] | trans-4-(4-((2-(2,6-dichloro-4-fluorophenyl)-2-oxoethyl)-(8-propan-2-yl-8-azabicyclo[3.2.1]octan-3-yl)carbamoyl)-5-(trifluoromethyl)pyrazol-1-yl)-1-methylcyclohexane-1-carboxylic acid |
| 306 | 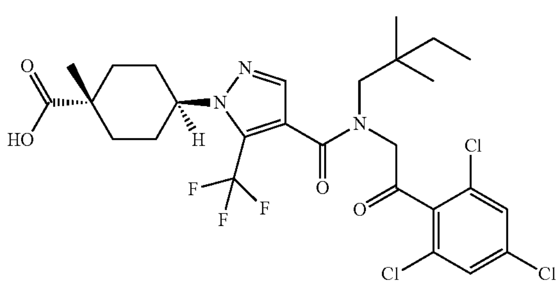 [SMILES: CCC(C)(C)CN(CC(=O)c1c(Cl)cc(Cl)cc1Cl)C(=O)c1cnn([C@H]2CC[C@](C)(C(=O)O)CC2)c1C(F)(F)F] | trans-4-(4-(2,2-dimethylbutyl-(2-oxo-2-(2,4,6-trichlorophenyl)ethyl)carbamoyl)-5-(trifluoromethyl)pyrazol-1-yl)-1-methylcyclohexane-1-carboxylic acid |
| 307 | 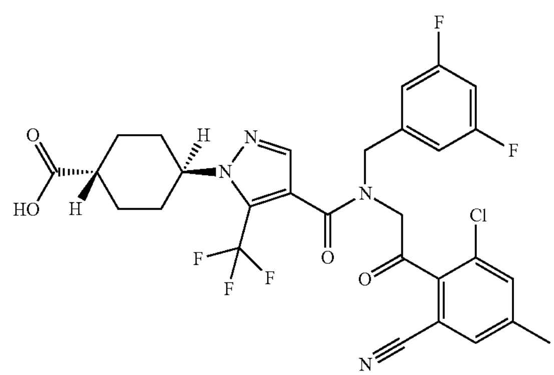 [SMILES: Cc1cc(Cl)c(C(=O)CN(Cc2cc(F)cc(F)c2)C(=O)c2cnn([C@H]3CC[C@H](C(=O)O)CC3)c2C(F)(F)F)c(C#N)c1] | trans-4-(4-((2-(2-chloro-6-cyano-4-methylphenyl)-2-oxoethyl)-((3,5-difluorophenyl)methyl)carbamoyl)-5-(trifluoromethyl)pyrazol-1-yl)cyclohexane-1-carboxylic acid |
| 308 | 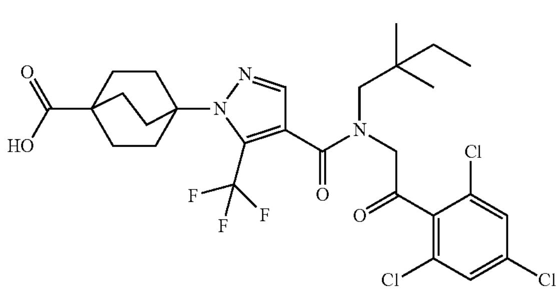 [SMILES: CCC(C)(C)CN(CC(=O)c1c(Cl)cc(Cl)cc1Cl)C(=O)c1cnn(C23CCC(C(=O)O)(CC2)CC3)c1C(F)(F)F] | 4-(4-(2,2-dimethylbutyl-(2-oxo-2-(2,4,6-trichlorophenyl)ethyl)carbamoyl)-5-(trifluoromethyl)pyrazol-1-yl)bicyclo[2.2.2]octane-1-carboxylic acid |

-continued

| example | structure | name |
|---|---|---|
| 309 | 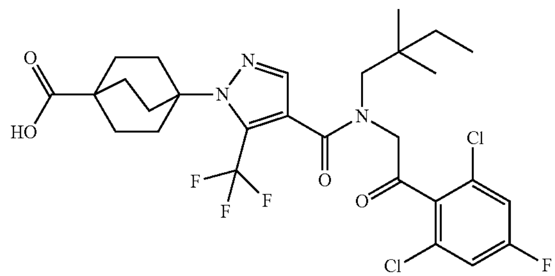 [SMILES: CCC(C)(C)CN(CC(=O)c1c(Cl)cc(F)cc1Cl)C(=O)c1cnn(C23CCC(C(=O)O)(CC2)CC3)c1C(F)(F)F] | 4-(4-((2-(2,6-dichloro-4-fluorophenyl)-2-oxoethyl)-(2,2 dimethylbutyl)carbamoyl)-5-(trifluoromethyl)pyrazol-1-yl)bicyclo [2.2.2] octane-1-carboxylic acid |
| 310 | 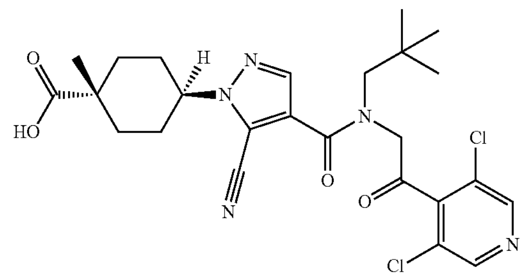 [SMILES: CC(C)(C)CN(CC(=O)c1c(Cl)cncc1Cl)C(=O)c1cnn([C@H]2CC[C@](C)(C(=O)O)CC2)c1C#N] | trans-4-(5-cyano-4-((2-(3,5-dichloropyridin-4-yl)-2-oxoethyl)-(2,2-dimethylpropyl)carbamoyl)pyrazol-1-yl)-1-methylcyclohexane-1-carboxylic acid |
| 311 | 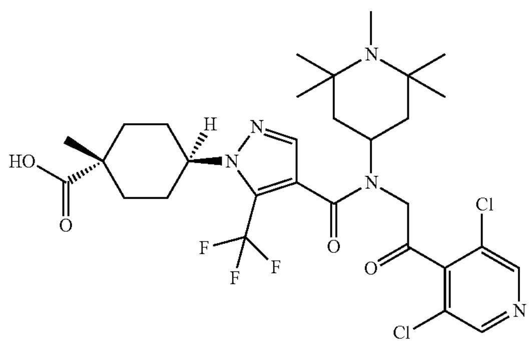 [SMILES: CN1C(C)(C)CC(N(CC(=O)c2c(Cl)cncc2Cl)C(=O)c2cnn([C@H]3CC[C@](C)(C(=O)O)CC3)c2C(F)(F)F)CC1(C)C] | trans-4-(4-((2-(3,5-dichloropyridin-4-yl)-2-oxoethyl)-(1,2,2,6,6-pentamethylpiperidin-4-yl)carbamoyl)-5-(trifluoromethyl)pyrazol-1-yl)-1-methylcyclohexane-1-carboxylic acid |
| 312 | 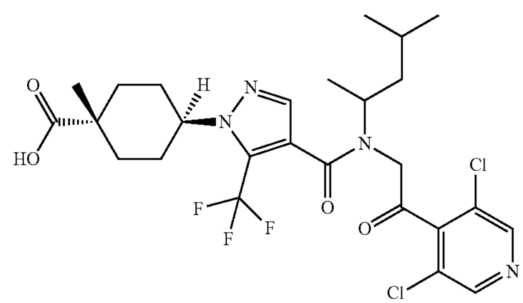 [SMILES: CC(C)CC(C)N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(4-methylpentan-2-yl)carbamoyl)-5-(trifluoromethyl)pyrazol-1-yl)-1-methylcyclohexane-1-carboxylic acid |
| 313 | 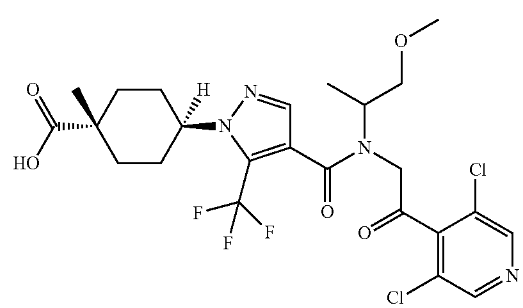 [SMILES: COCC(C)N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(1-methoxypropan-2-yl)carbamoyl)-5-(trifluoromethyl)pyrazol-1-yl)-1-methylcyclohexane-1-carboxylic acid |

| example | structure | name |
| --- | --- | --- |
| 314 | 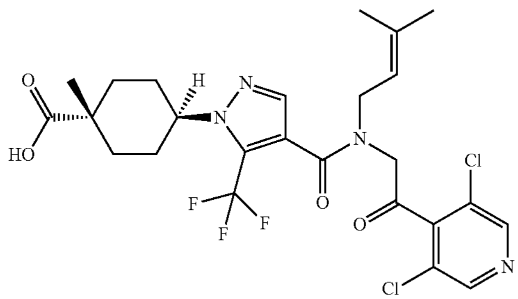 [SMILES: CC(C)=CCN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(3-methylbut-2-enyl)carbamoyl)-5-(trifluoromethyl)pyrazol-1-yl)-1-methylcyclohexane-1-carboxylic acid |
| 315 | 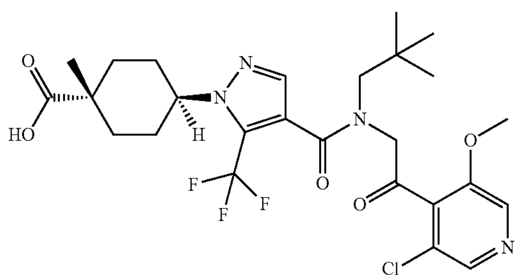 [SMILES: COc1cncc(Cl)c1C(=O)CN(CC(C)(C)C)C(=O)c1cnn([C@H]2CC[C@](C)(C(=O)O)CC2)c1C(F)(F)F] | trans-4-(4-((2-(3-chloro-5-methoxypyridin-4-yl)-2-oxoethyl)-(2,2-dimethylpropyl)carbamoyl)-5-(trifluoromethyl)pyrazol-1-yl)-1-methylcyclohexane-1-carboxylic acid |
| 316 | 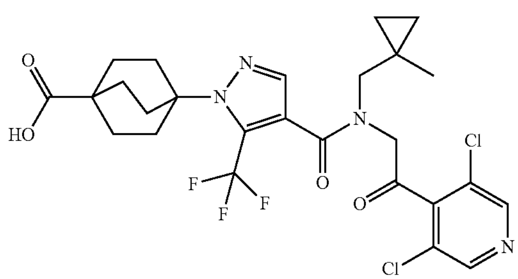 [SMILES: CC1(CN(CC(=O)c2c(Cl)cncc2Cl)C(=O)c2cnn(C34CCC(C(=O)O)(CC3)CC4)c2C(F)(F)F)CC1] | 4-(4-((2-(3,5-dichloropyridin-4-yl)-2-oxoethyl)-((1-methylcyclopropyl)methyl)carbamoyl)-5-(trifluoromethyl)pyrazol-1-yl)bicyclo[2.2.2]octane-1-carboxylic acid |
| 317 | 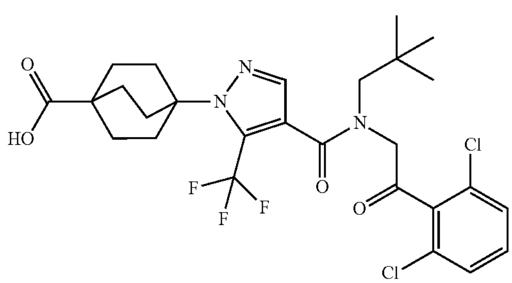 [SMILES: CC(C)(C)CN(CC(=O)c1c(Cl)cccc1Cl)C(=O)c1cnn(C23CCC(C(=O)O)(CC2)CC3)c1C(F)(F)F] | 4-(4-((2-(2,6-dichlorophenyl)-2-oxoethyl)-(2,2-dimethylpropyl)carbamoyl)-5-(trifluoromethyl)pyrazol-1-yl)bicyclo[2.2.2]octane-1-carboxylic acid |
| 318 | 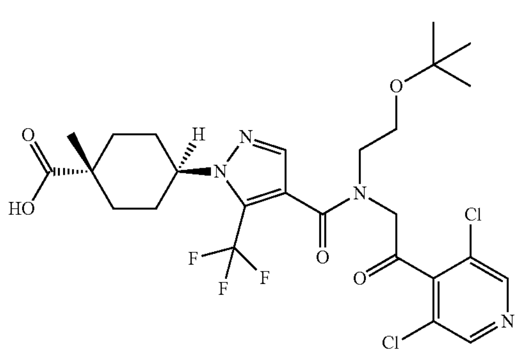 [SMILES: CC(C)(C)OCCN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(2-((2-methylpropan-2-yl)oxy)ethyl)carbamoyl)-5-(trifluoromethyl)pyrazol-1-yl)-1-methylcyclohexane-1-carboxylic acid |

-continued

| example | structure | name |
|---|---|---|
| 319 | 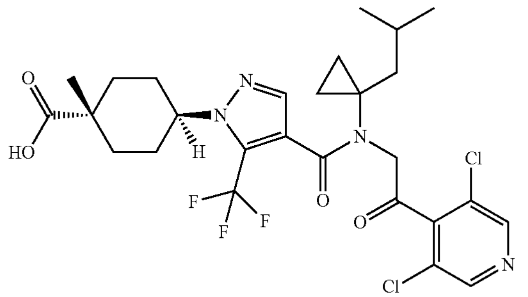 [SMILES: CC(C)CC1(N(CC(=O)c2c(Cl)cncc2Cl)C(=O)c2cnn([C@H]3CC[C@](C)(C(=O)O)CC3)c2C(F)(F)F)CC1] | trans-4-(4-((2-(3,5-dichloropyridin-4-yl)-2-oxoethyl)-(1-(2-methylpropyl)cyclopropyl)carbamoyl)-5-(trifluoromethyl) pyrazol-1-yl)-1-methylcyclohexane-1-carboxylic acid |
| 320 | 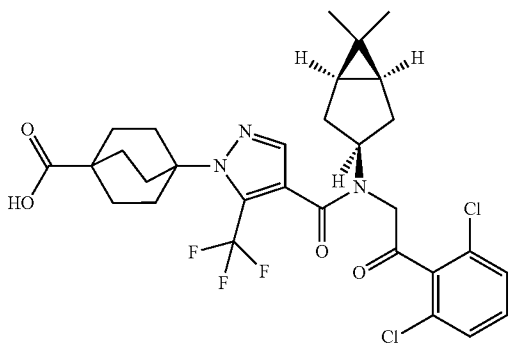 [SMILES: CC1(C)[C@@H]2C[C@H](N(CC(=O)c3c(Cl)cccc3Cl)C(=O)c3cnn(C45CCC(C(=O)O)(CC4)CC5)c3C(F)(F)F)C[C@@H]21] | 4-(4-((2-(2,6-dichlorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)bicyclo[2.2.2]octane-1-carboxylic acid |
| 321 | 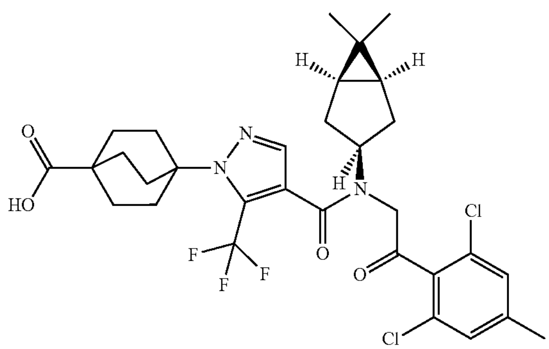 [SMILES: Cc1cc(Cl)c(C(=O)CN(C(=O)c2cnn(C34CCC(C(=O)O)(CC3)CC4)c2C(F)(F)F)[C@H]2C[C@@H]3[C@H](C2)C3(C)C)c(Cl)c1] | 4-(4-((2-(2,6-dichloro-4-methylphenyl)-2-oxoethyl)((1R,3r,5S)-6,6-dimethylbicyclo[3.1.0]hexan-3-yl)carbamoyl)-5-(trifluoromethyl)-1H-pyrazol-1-yl)bicyclo[2.2.2]octane-1-carboxylic acid |
| 322 | 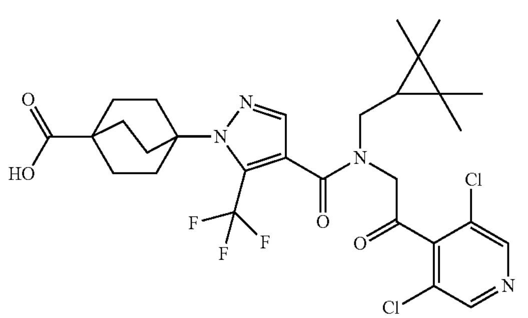 [SMILES: CC1(C)C(CN(CC(=O)c2c(Cl)cncc2Cl)C(=O)c2cnn(C34CCC(C(=O)O)(CC3)CC4)c2C(F)(F)F)C1(C)C] | 4-(4-((2-(3,5-dichloropyridin-4-yl)-2-oxoethyl)-((2,2,3,3-tetramethylcyclopropyl)methyl)carbamoyl)-5-(trifluoromethyl)pyrazol-1-yl)bicyclo[2.2.2]octane-1-carboxylic acid |

-continued

| example | structure | name |
|---|---|---|
| 323 | 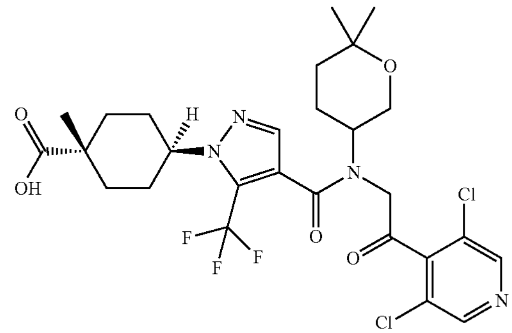 [SMILES: CC1(C)CCC(N(CC(=O)c2c(Cl)cncc2Cl)C(=O)c2cnn([C@H]3CC[C@](C)(C(=O)O)CC3)c2C(F)(F)F)CO1] | trans-4-(4-((2(3,5-dichloropyridin-4-yl)-2-oxoethyl)-(6,6-dimethyloxan-3-yl)carbamoyl)-5-(trifluorornethyl)pyrazol-1-yl)-1-methylcyclohexane-1-carboxylic acid |
| 324 | 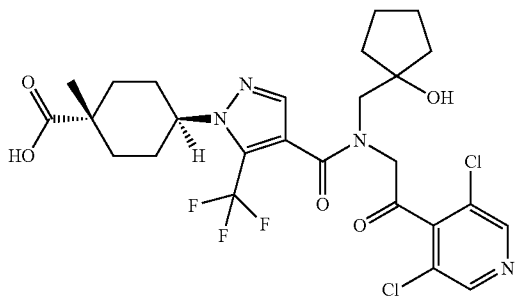 [SMILES: C[C@]1(C(=O)O)CC[C@H](n2ncc(C(=O)N(CC(=O)c3c(Cl)cncc3Cl)CC3(O)CCCC3)c2C(F)(F)F)CC1] | trans-4-(4-((2-(3,5-dichloropyridin-4-yl)-2-oxoethyl)-((1-hydroxycyclopentyl)methyl)carbamoyl)-5-(trifluoromethyl)pyrazol-1-yl)-1-methylcyclohexane-1-carboxylic acid |
| 325 | 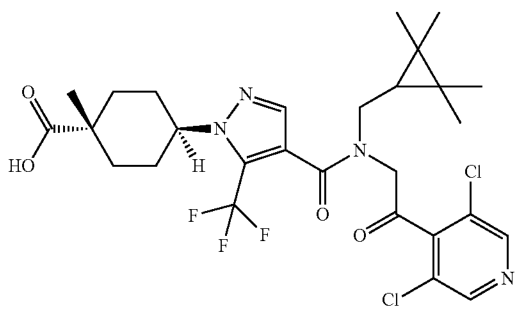 [SMILES: CC1(C)C(CN(CC(=O)c2c(Cl)cncc2Cl)C(=O)c2cnn([C@H]3CC[C@](C)(C(=O)O)CC3)c2C(F)(F)F)C1(C)C] | trans-4-(4-((2-(3,5-dichloropyridin-4-yl)-2-oxoethyl)-((2,2,3,3-tetramethylcyclopropyl)methyl)carbamoyl)-5-(trifluoromethyl)pyrazol-1-yl)-1-methylcyclohexane-1-carboxylic acid |
| 326 | 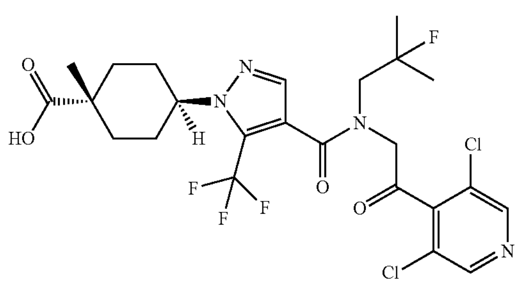 [SMILES: CC(C)(F)CN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(2-fluoro-2-methylpropyl)carbamoyl)-5-(trifluoromethyl)pyrazol-1-yl)-1-methylcyclohexane-1-carboxylic acid |
| 327 | 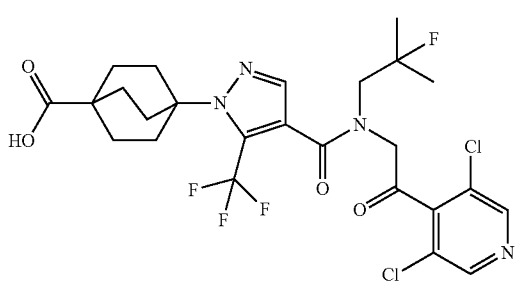 [SMILES: CC(C)(F)CN(CC(=O)c1c(Cl)cncc1Cl)C(=O)c1cnn(C23CCC(C(=O)O)(CC2)CC3)c1C(F)(F)F] | 4-(4-((2-(3,5-dichloropyridin-4-yl)-2-oxoethyl)-(2-fluoro-2-methylpropyl)carbamoyl)-5-(trifluoromethyl)pyrazol-1-yl)bicyclo[2.2.2]octane-1-carboxylic acid |

| example | structure | name |
|---|---|---|
| 328 | 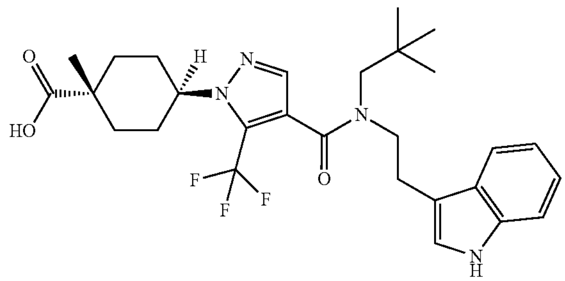 [SMILES: CC(C)(C)CN(CCc1c[nH]c2ccccc12)C(=O)c1cnn([C@H]2CC[C@](C)(C(=O)O)CC2)c1C(F)(F)F] | trans-4-(4-(2,2-dimethylpropyl-(2-(1H-indol-3-yl)ethyl)carbamoyl)-5-(trifluoromethyl)pyrazol-1-yl)-1-methylcyclohexane-1-carboxylic acid |
| 329 | 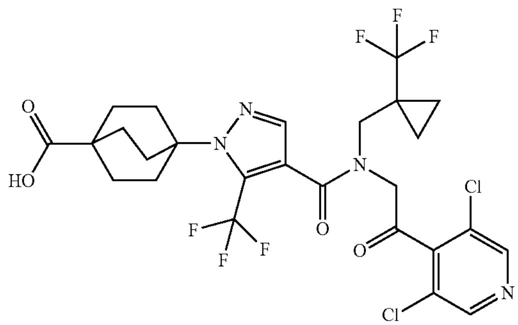 [SMILES: O=C(CN(CC1(C(F)(F)F)CC1)C(=O)c1cnn(C23CCC(C(=O)O)(CC2)CC3)c1C(F)(F)F)c1c(Cl)cncc1Cl] | 4-(4-((2-(3,5-dichloropyridin-4-yl)-2-oxoethyl)-((1-(trifluoromethyl)cyclopropyl)methyl)carbamoyl)-5-(trifluoromethyl)pyrazol-1-yl)bicyclo[2.2.2]octane-1-carboxylic acid |
| 331 | 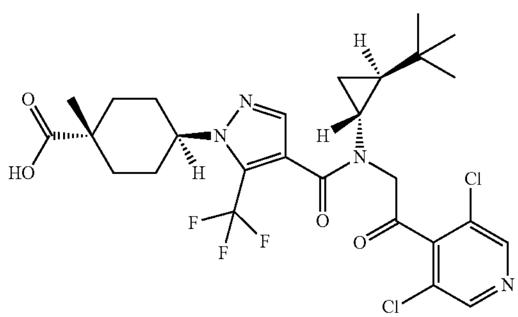 [SMILES: CC(C)(C)[C@@H]1C[C@H]1N(CC(=O)c1c(Cl)cncc1Cl)C(=O)c1cnn([C@H]2CC[C@](C)(C(=O)O)CC2)c1C(F)(F)F] | trans-4-(4-(((1R,2S)-2-tert-butylcyclopropyl)-(2-(3,5-dichloropyridin-4-yl)-2-oxoethyl)carbamoyl)-5-(trifluoromethyl)pyrazol-1-yl)-1-methylcyclohexane-1-carboxylic acid |
| 332 | 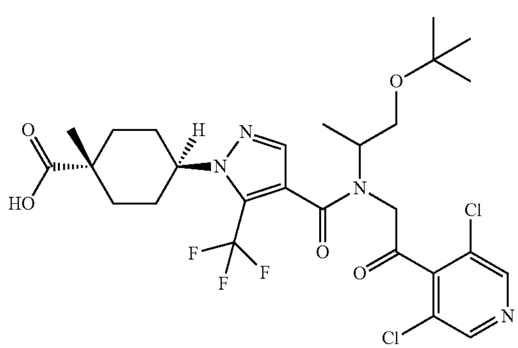 [SMILES: CC(COC(C)(C)C)N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(1-((2-methylpropan-2-yl)oxy)propan-2-yl)carbamoyl)-5-(trifluoromethyl)pyrazol-1-yl)-1-methylcyclohexane-1-carboxylic acid |

| example | structure | name |
|---|---|---|
| 333 | 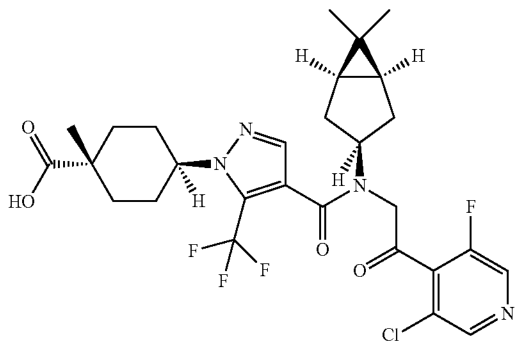 [SMILES: CC1(C)[C@@H]2C[C@H](N(CC(=O)c3c(F)cncc3Cl)C(=O)c3cnn([C@H]4CC[C@](C)(C(=O)O)CC4)c3C(F)(F)F)C[C@@H]21] | trans-4-(4-((2-(3-chloro-5-fluoropyridin-4-yl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 334 | 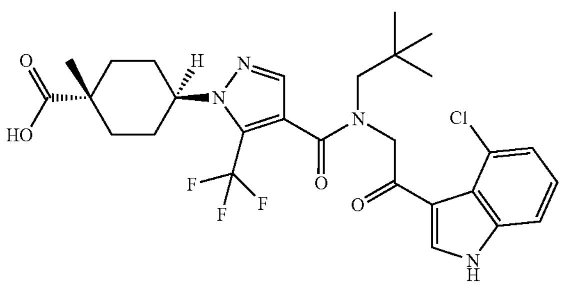 [SMILES: CC(C)(C)CN(CC(=O)c1c[nH]c2cccc(Cl)c12)C(=O)c1cnn([C@H]2CC[C@](C)(C(=O)O)CC2)c1C(F)(F)F] | trans-4-(4-(2-(4-chloro-1H-indol-3-yl)ethyl-(2,2-dimethylpropyl)carbamoyl)-5-(trifluoromethyl)pyrazol-1-yl)-1-methylcyclohexane-1-carboxylic acid |
| 335 | 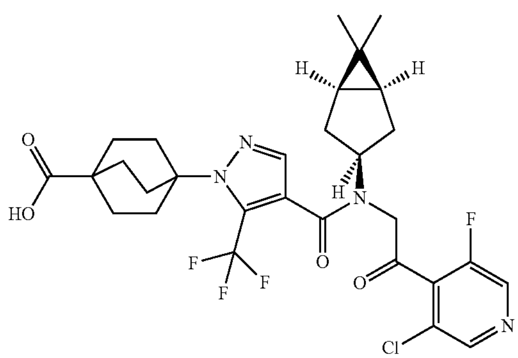 [SMILES: CC1(C)[C@@H]2C[C@H](N(CC(=O)c3c(F)cncc3Cl)C(=O)c3cnn(C45CCC(C(=O)O)(CC4)CC5)c3C(F)(F)F)C[C@@H]21] | 4-(4-((2-(3-chloro-5-fluoropyridin-4-yl)-2-oxoethyl)((1R,3r,5S)-6,6-dimethylbicyclo[3.1.0]hexan-3-yl)carbamoyl)-5-(trifluoromethyl)-1H-pyrazol-1-yl)bicyclo(2.2.2)octane-1-carboxylic acid |
| 336 | 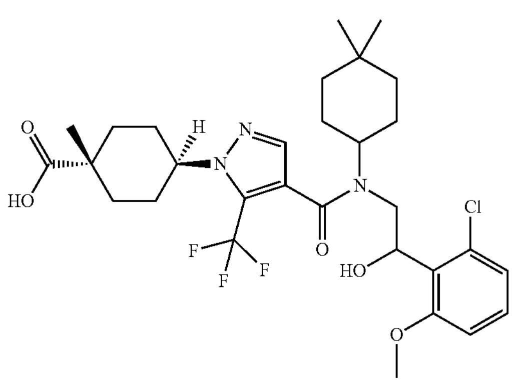 [SMILES: COc1cccc(Cl)c1C(O)CN(C(=O)c1cnn([C@H]2CC[C@](C)(C(=O)O)CC2)c1C(F)(F)F)C1CCC(C)(C)CC1] | trans-4-(4-((2-(2-chloro-6-methoxyphenyl)-2-hydroxyethyl)-(4,4-dimethylcyclohexyl)carbamoyl)-5-(trifluoromethyl)pyrazol-1-yl)-1-methylcyclohexane-1-carboxylic acid |

| example | structure | name |
| --- | --- | --- |
| 337 | 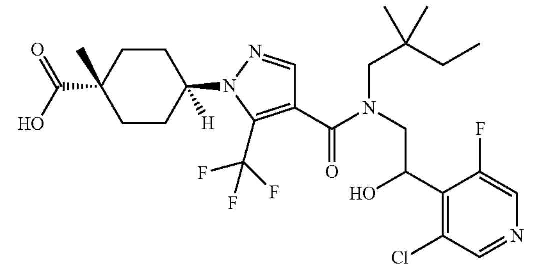 [SMILES: CCC(C)(C)CN(CC(O)c1c(F)cncc1Cl)C(=O)c1cnn([C@H]2CC[C@](C)(C(=O)O)CC2)c1C(F)(F)F] | trans-4-(4-((2-(3-chloro-5-fluoropyridin-4-yl)-2-oxoethyl)-(2,2-dimethylbutyl)carbamoyl)-5-(trifluoromethyl)pyrazol-1-yl)-1-methylcyclohexane-1-carboxylic acid |
| 338 | 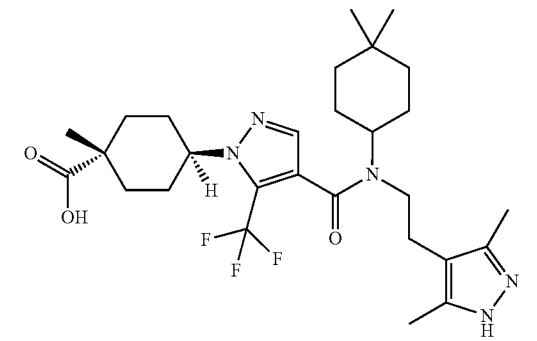 [SMILES: Cc1n[nH]c(C)c1CCN(C(=O)c1cnn([C@H]2CC[C@](C)(C(=O)O)CC2)c1C(F)(F)F)C1CCC(C)(C)CC1] | trans-4-(4-((4,4-dimethylcyclohexyl)-(2-(3,5-dimethyl-1H-pyrazol-4-yl)ethyl)carbamoyl)-5-(trifluoromethyl)pyrazol-1-yl)-1-methylcyclohexane-1-carboxylic acid |
| 339 | 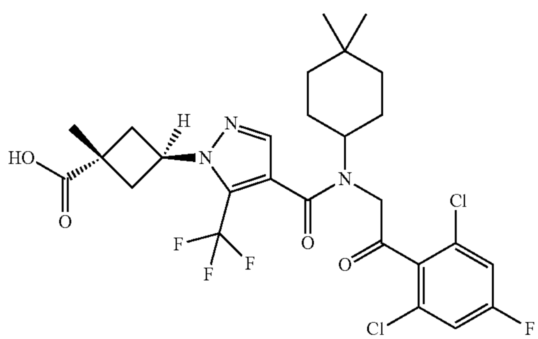 [SMILES: CC1(C)CCC(N(CC(=O)c2c(Cl)cc(F)cc2Cl)C(=O)c2cnn([C@H]3C[C@](C)(C(=O)O)C3)c2C(F)(F)F)CC1] | trans-3-(4-((2-(2,6-dichloro-4-fluorophenyl)-2-oxoethyl)-(4,4-dimethylcyclohexyl)carbamoyl)-5-(trifluoromethyl)pyrazol-1-yl)-1-methylcyclobutane-1-carboxylic acid |
| 340 | 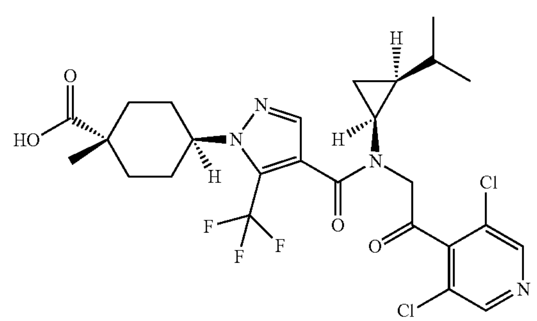 [SMILES: CC(C)[C@@H]1C[C@@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-((1S,2S)-2-propan-2-ylcyclopropyl)carbamoyl)-5-(trifluoromethyl)pyrazol-1-yl)-1-methylcyclohexane-1-carboxylic acid |
| 341 | 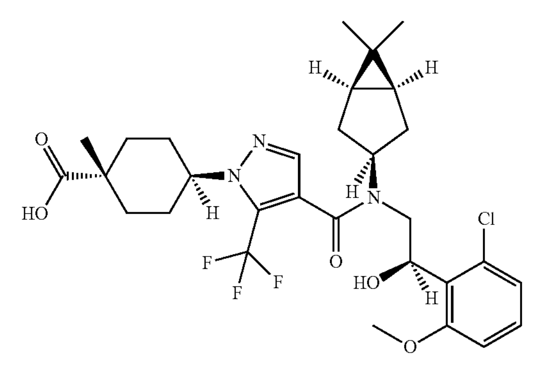 [SMILES: COc1cccc(Cl)c1[C@@H](O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-((2-(2-chloro-6-methoxyphenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

| example | structure | name |
| --- | --- | --- |
| 342 | 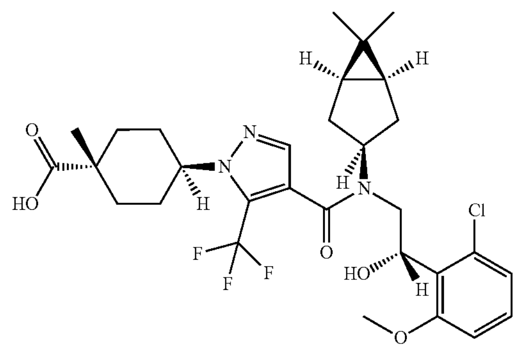 [SMILES: COc1cccc(Cl)c1[C@H](O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-((2-(2-chloro-6-methoxyphenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 344 | 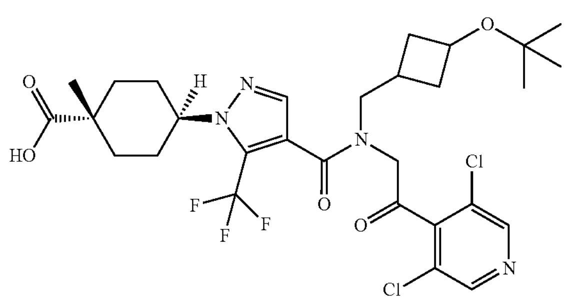 [SMILES: CC(C)(C)OC1CC(CN(CC(=O)c2c(Cl)cncc2Cl)C(=O)c2cnn([C@H]3CC[C@](C)(C(=O)O)CC3)c2C(F)(F)F)C1] | trans-4-(4-((2-(3,5-dichloropyridin-4-yl)-2-oxoethyl)-((3-((2-methylpropan-2-yl)oxy)cyclobutyl)methyl)carbamoyl)-5-(trifluoromethyl)pyrazol-1-yl)-1-methylcyclohexane-1-carboxylic acid |
| 345 | 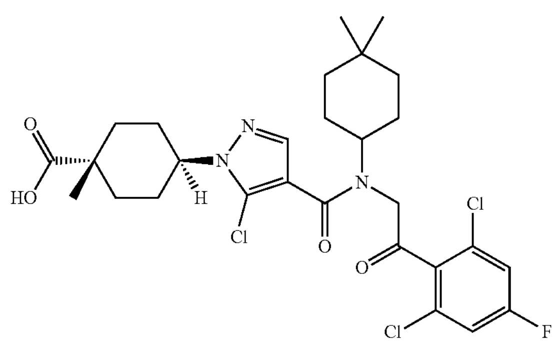 [SMILES: CC1(C)CCC(N(CC(=O)c2c(Cl)cc(F)cc2Cl)C(=O)c2cnn([C@H]3CC[C@](C)(C(=O)O)CC3)c2Cl)CC1] | trans-4-(5-chloro-4-((2-(2,6-dichloro-4-fluorophenyl)-2-oxoethyl)-(4,4-dimethylcyclohexyl)carbamoyl)pyrazol-1-yl)-1-methylcyclohexane-1-carboxylic acid |
| 346 | 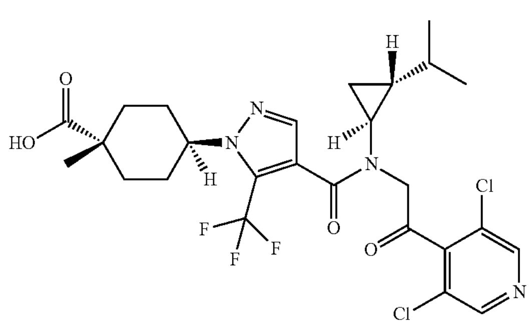 [SMILES: CC(C)[C@H]1C[C@@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-((1S,2R)-2-propan-2-ylcyclopropyl)carbamoyl)-5-(trifluoromethyl)pyrazol-1-yl)-1-methylcyclohexane-1-carboxylic acid |

| example | structure | name |
|---|---|---|
| 347 | 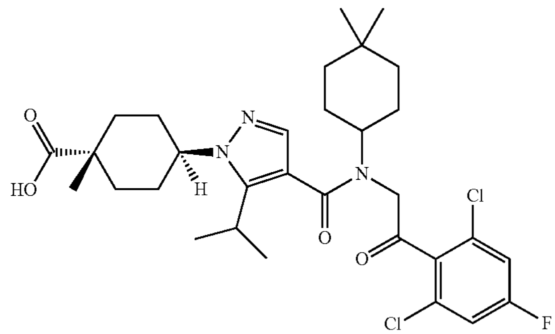 [SMILES: CC(C)c1c(C(=O)N(CC(=O)c2c(Cl)cc(F)cc2Cl)C2CCC(C)(C)CC2)cnn1[C@H]1CC[C@](C)(C(=O)O)CC1] | trans-4-(4-((2-(2,6-dichloro-4-fluorophenyl)-2-oxoethyl)-(4,4-dimethylcyclohexyl)carbamoyl)-5-propan-2-ylpyrazol-1-yl)-1-methylcyclohexane-1-carboxylic acid |
| 348 | 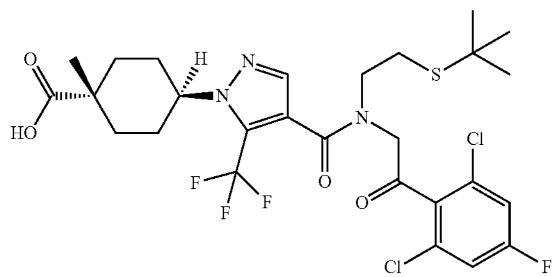 [SMILES: CC(C)(C)SCCN(CC(=O)c1c(Cl)cc(F)cc1Cl)C(=O)c1cnn([C@H]2CC[C@](C)(C(=O)O)CC2)c1C(F)(F)F] | trans-4-(4-(2-tert-butylsulfanylethyl-(2-(2,6-dichloro-4-fluorophenyl)-2-oxoethyl)carbamoyl)-5-(trifluoromethyl)pyrazol-1-yl)-1-methylcyclohexane-1-carboxylic acid |
| 349 | 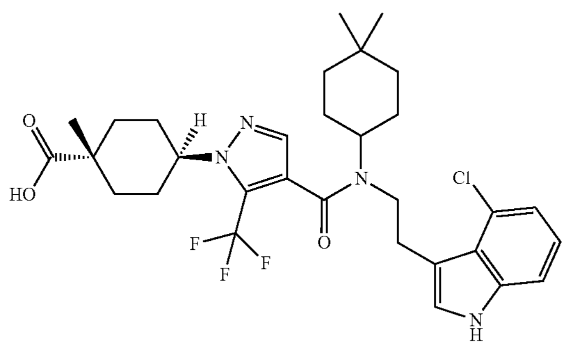 [SMILES: CC1(C)CCC(N(CCc2c[nH]c3cccc(Cl)c23)C(=O)c2cnn([C@H]3CC[C@](C)(C(=O)O)CC3)c2C(F)(F)F)CC1] | trans-4-(4-(2-(4-chloro-1H-indol-3-yl)ethyl-(4,4-dimethylcyclohexyl)carbamoyl)-5-(trifluoromethyl)pyrazol-1-yl)-1-methylcyclohexane-1-carboxylic acid |
| 350 | 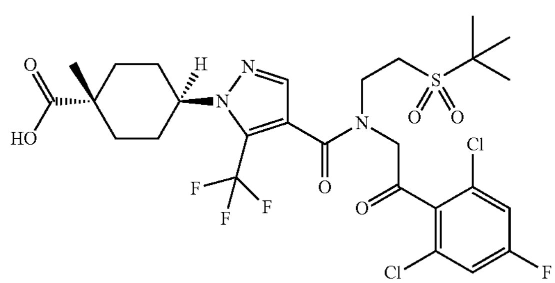 [SMILES: CC(C)(C)S(=O)(=O)CCN(CC(=O)c1c(Cl)cc(F)cc1Cl)C(=O)c1cnn([C@H]2CC[C@](C)(C(=O)O)CC2)c1C(F)(F)F] | trans-4-(4-(2-tert-butylsulfonylethyl-(2-(2,6-dichloro-4-fluorophenyl)-2-oxoethyl)carbamoyl)-5-(trifluoromethyl)pyrazol-1-yl)-1-methylcyclohexane-1-carboxylic acid |
| 351 | 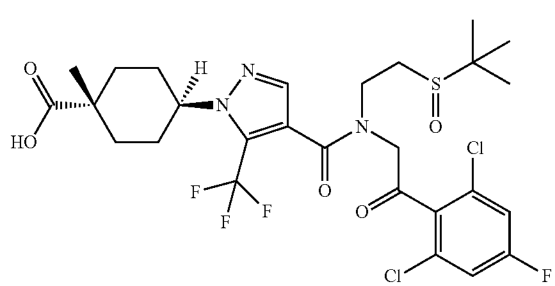 [SMILES: CC(C)(C)S(=O)CCN(CC(=O)c1c(Cl)cc(F)cc1Cl)C(=O)c1cnn([C@H]2CC[C@](C)(C(=O)O)CC2)c1C(F)(F)F] | trans-4-(4-(2-tert-butylsulfinylethyl-(2-(2, 6-dichloro-4-fluorophenyl)-2-oxoethyl)carbamoyl)-5-(trifluoromethyl)pyrazol-1-yl)-1-methylcyclohexane-1-carboxylic acid |

| example | structure | name |
|---|---|---|
| 352 | 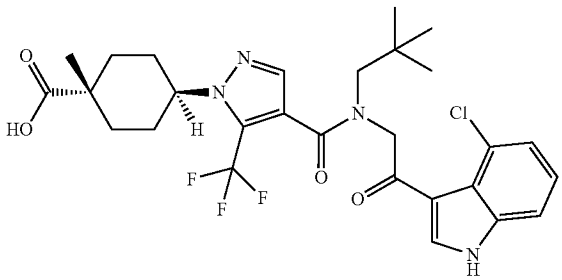 [SMILES: CC(C)(C)CN(CC(=O)c1c[nH]c2cccc(Cl)c12)C(=O)c1cnn([C@H]2CC[C@](C)(C(=O)O)CC2)c1C(F)(F)F] | trans-4-(4-((2-(4-chloro-1H-indol-3-yl)-2-oxoethyl)-(2,2-dimethylpropyl)carbamoyl)-5-(trifluoromethyl)pyrazol-1-yl)-1-methylcyclohexane-1-carboxylic acid |
| 353 | 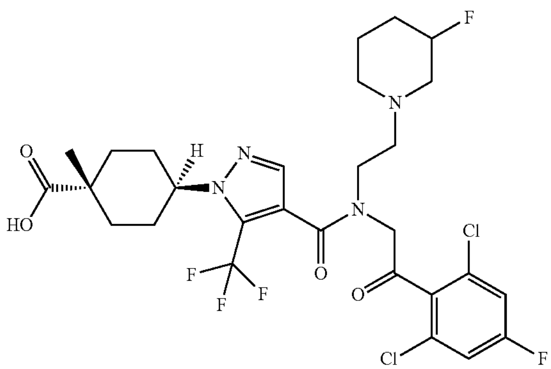 [SMILES: C[C@]1(C(=O)O)CC[C@H](n2ncc(C(=O)N(CCN3CCCC(F)C3)CC(=O)c3c(Cl)cc(F)cc3Cl)c2C(F)(F)F)CC1] | trans-4-(4-((2-(2,6-dichloro-4-fluorophenyl)-2-oxoethyl)-(2-(3-fluoropiperidin-1-yl)ethyl)carbamoyl)-5-(trifluoromethyl)pyrazol-1-yl)-1-methylcyclohexane-1-carboxylic acid |
| 354 | 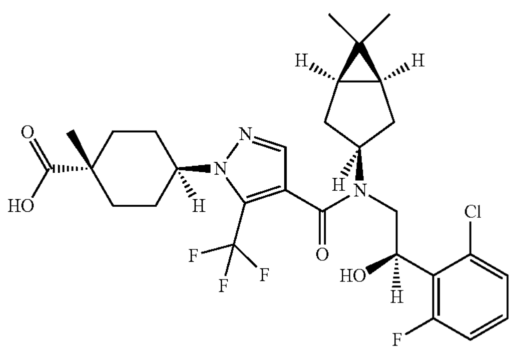 [SMILES: CC1(C)[C@@H]2C[C@H](N(C[C@H](O)c3c(F)cccc3Cl)C(=O)c3cnn([C@H]4CC[C@](C)(C(=O)O)CC4)c3C(F)(F)F)C[C@@H]21] | trans-4-(4-((2-(2-chloro-6-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 355 | 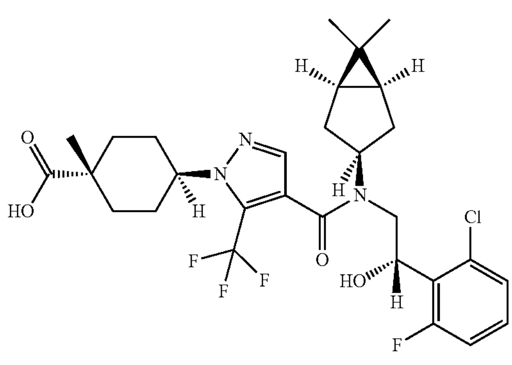 [SMILES: CC1(C)[C@@H]2C[C@H](N(C[C@@H](O)c3c(F)cccc3Cl)C(=O)c3cnn([C@H]4CC[C@](C)(C(=O)O)CC4)c3C(F)(F)F)C[C@@H]21] | trans-4-(4-((2-(2-chloro-6-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

-continued

| example | structure | name |
| --- | --- | --- |
| 356 | 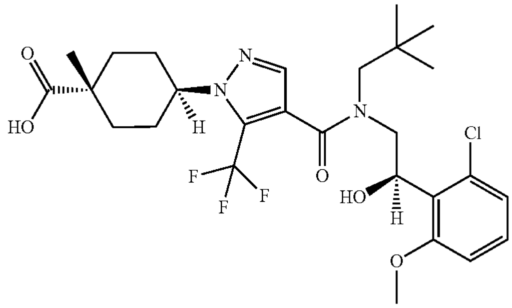 [SMILES: COc1cccc(Cl)c1[C@@H](O)CN(CC(C)(C)C)C(=O)c1cnn([C@H]2CC[C@](C)(C(=O)O)CC2)c1C(F)(F)F] | trans-4-(4-(((2R)-2-(2-chloro-6-methoxyphenyl)-2-hydroxyethyl)-(2,2-dimethylpropyl)carbamoyl)-5-(trifluoromethyl)pyrazol-1-yl)-1-methylcyclohexane-1-carboxylic acid |
| 357 | 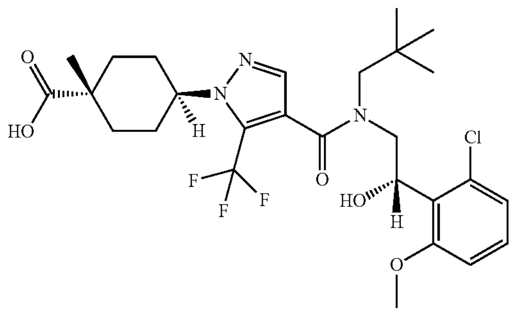 [SMILES: COc1cccc(Cl)c1[C@H](O)CN(CC(C)(C)C)C(=O)c1cnn([C@H]2CC[C@](C)(C(=O)O)CC2)c1C(F)(F)F] | trans-4-(4-(((2S)-2-(2-chloro-6-methoxyphenyl)-2-hydroxyethyl)-(2,2-dimethylpropyl)carbamoyl)-5-(trifluoromethyl)pyrazol-1-yl)-1-methylcyclohexane-1-carboxylic acid |
| 358 | 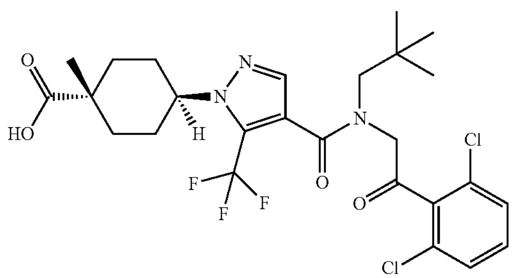 [SMILES: CC(C)(C)CN(CC(=O)c1c(Cl)cccc1Cl)C(=O)c1cnn([C@H]2CC[C@](C)(C(=O)O)CC2)c1C(F)(F)F] | trans-4-(5-chloro-4-((2-(2,6-dichlorophenyl)-2-oxoethyl)-(2,2-dimethylpropyl)carbamoyl)pyrazol-1-yl)-1-methylcyclohexane-1-carboxylic acid |
| 359 | 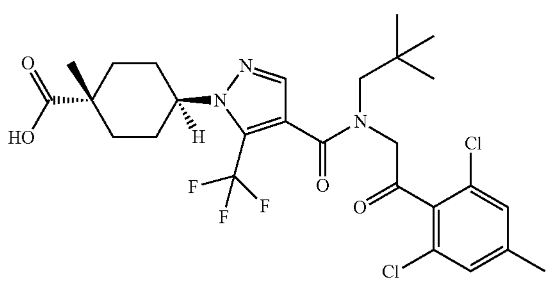 [SMILES: Cc1cc(Cl)c(C(=O)CN(CC(C)(C)C)C(=O)c2cnn([C@H]3CC[C@](C)(C(=O)O)CC3)c2C(F)(F)F)c(Cl)c1] | trans-4-(5-chloro-4-((2-(2,6-dichloro-4-methylphenyl)-2-oxoethyl)-(2,2-dimethylpropyl)carbarnoyl)pyrazol-1-yl)-1-methylcyclohexane-1-carboxylic acid |
| 360 | 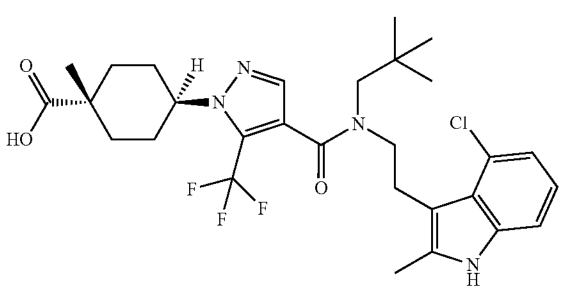 [SMILES: Cc1[nH]c2cccc(Cl)c2c1CCN(CC(C)(C)C)C(=O)c1cnn([C@H]2CC[C@](C)(C(=O)O)CC2)c1C(F)(F)F] | trans-4-(4-(2-(4-chloro-2-methyl-1H-indol-3-yl)ethyl-(2,2-dimethylpropyl)carbamoyl)-5-(trifluoromethyl)pyrazol-1-yl)-1-methylcyclohexane-1-carboxylic acid |

| example | structure | name |
| --- | --- | --- |
| 363 | 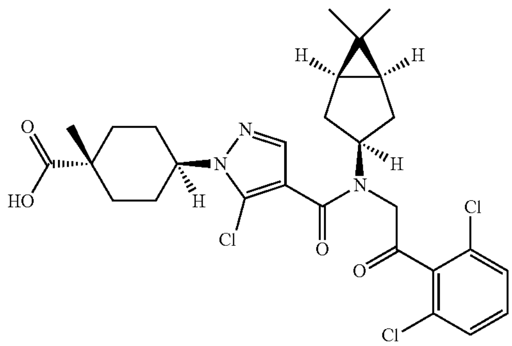 [SMILES: CC1(C)[C@@H]2C[C@H](N(CC(=O)c3c(Cl)cccc3Cl)C(=O)c3cnn([C@H]4CC[C@](C)(C(=O)O)CC4)c3Cl)C[C@@H]21] | trans-4-(5-chloro-4-((2-(2,6-dichlorophenyl)-2-oxoethyl)((1R,3r,5S)-6,6-dimethylbicyclo[3.1.0]hexan-3-yl)carbamoyl)-1H-pyrazol-yl)-1-methylcyclohexanecarboxylic acid |
| 364 | 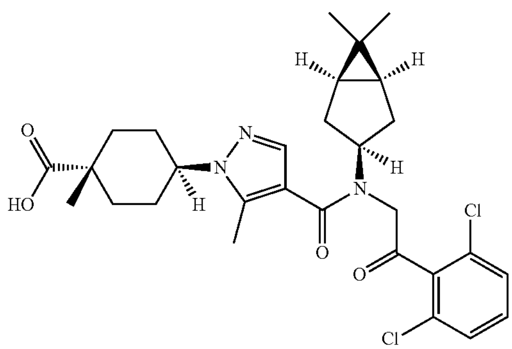 [SMILES: Cc1c(C(=O)N(CC(=O)c2c(Cl)cccc2Cl)[C@H]2C[C@@H]3[C@H](C2)C3(C)C)cnn1[C@H]1CC[C@](C)(C(=O)O)CC1] | trans-4-(4-((2-(2,6-dichlorophenyl)-2-oxoethyl)((1R,3r,5S)-6,6-dimethylbicyclo[3.1.0]hexan-3-yl)carbamoyl)-5-methyl-1H-pyrazol-1-yl)-1-methylcyclohexanecarboxylic acid |
| 365 | 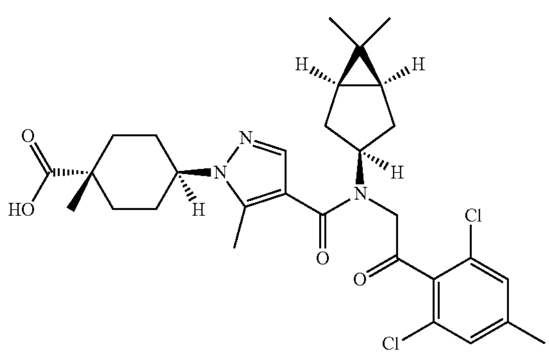 [SMILES: Cc1cc(Cl)c(C(=O)CN(C(=O)c2cnn([C@H]3CC[C@](C)(C(=O)O)CC3)c2C)[C@H]2C[C@@H]3[C@H](C2)C3(C)C)c(Cl)c1] | trans-4-(4-((2-(2,6-dichloro-4-methylphenyl)-2-oxoethyl)((1R,3r,5S)-6,6-dimethylbicyclo[3.1.0]hexan-3-yl)carbamoyl)-5-methyl-1H-pyrazol-1-yl)-1-methylcyclohexanecarboxylic acid |
| 366 | 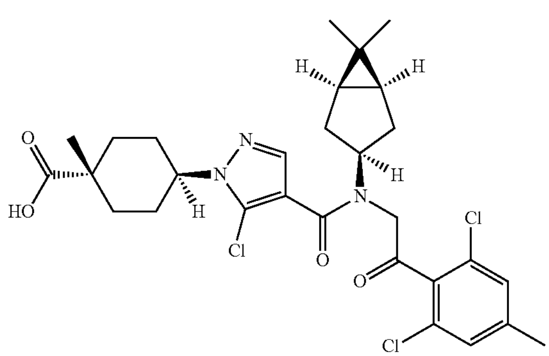 [SMILES: Cc1cc(Cl)c(C(=O)CN(C(=O)c2cnn([C@H]3CC[C@](C)(C(=O)O)CC3)c2Cl)[C@H]2C[C@@H]3[C@H](C2)C3(C)C)c(Cl)c1] | trans-4-(5-chloro-4-((2-(2,6-dichloro-4-methylphenyl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid |

| example | structure | name |
|---|---|---|
| 367 | 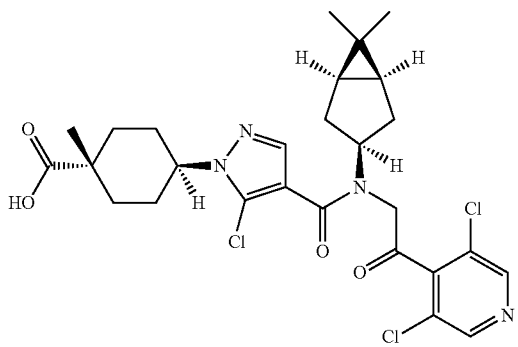 [SMILES: CC1(C)[C@@H]2C[C@H](N(CC(=O)c3c(Cl)cncc3Cl)C(=O)c3cnn([C@H]4CC[C@](C)(C(=O)O)CC4)c3Cl)C[C@@H]21] | trans-4-(5-chloro-4-((2-(3,5-dichloropyridin-4-yl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid |
| 368 | 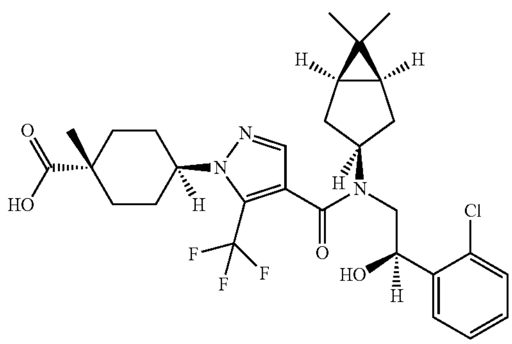 [SMILES: CC1(C)[C@@H]2C[C@H](N(C[C@H](O)c3ccccc3Cl)C(=O)c3cnn([C@H]4CC[C@](C)(C(=O)O)CC4)c3C(F)(F)F)C[C@@H]21] | trans-4-(4-((2-(2-chlorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 369 | 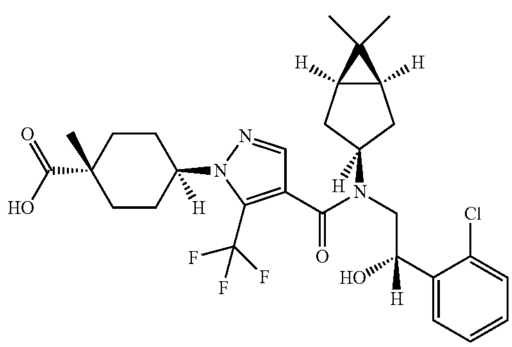 [SMILES: CC1(C)[C@@H]2C[C@H](N(C[C@@H](O)c3ccccc3Cl)C(=O)c3cnn([C@H]4CC[C@](C)(C(=O)O)CC4)c3C(F)(F)F)C[C@@H]21] | trans-4-(4-((2-(2-chlorophenyl)-2-hydroxyethyl)((1R,3r,5S)-6,6-dimethylbicyclo[3.1.0]hexan-3-yl)carbamoyl)-5-(trifluoromethyl)-1H-pyrazol-yl)-1-methylcyclohexanecarboxylic acid |
| 370 | 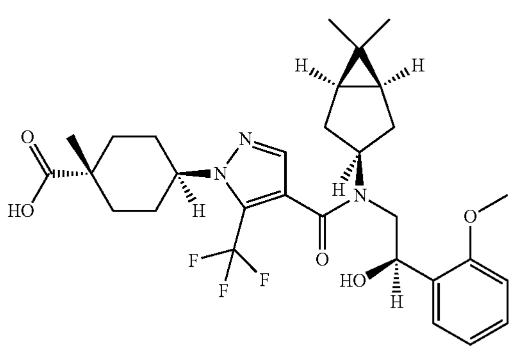 [SMILES: COc1ccccc1[C@@H](O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-(((1R,3r,5S)-6,6-dimethylbicyclo[3.1.0]hexan-3-yl)(2-hydroxy-2-(2-methoxyphenyl)ethyl)carbamoyl)-5-(trifluoromethyl)-1H-pyrazoH-yl)-1-methylcyclohexanecarboxylic acid |

-continued

| example | structure | name |
|---|---|---|
| 371 | 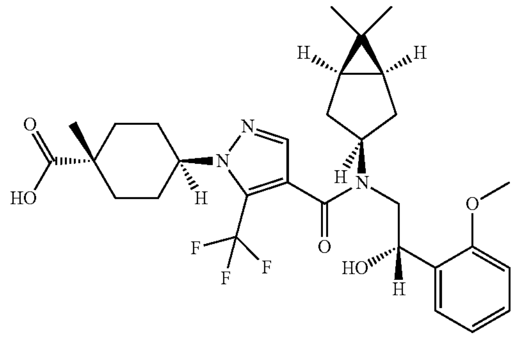 [SMILES: COc1ccccc1[C@H](O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-(((1R,3r,5S)-6,6-dimethylbicyclo[3.1.0]hexan-3-yl)(2-hydroxy-2-(2-methoxyphenyl)ethyl)carbamoyl)-5-(trifluoromethyl)-1H-pyrazol-1-yl)-1-methylcyclohexanecarboxylic acid |
| 372 | 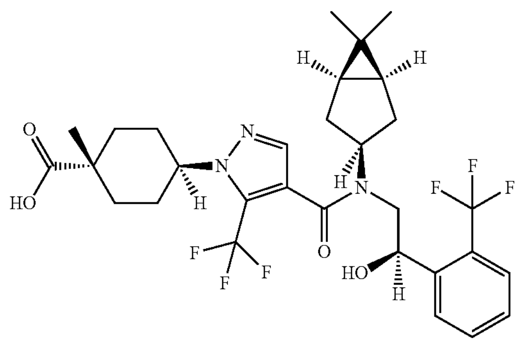 [SMILES: CC1(C)[C@@H]2C[C@H](N(C[C@H](O)c3ccccc3C(F)(F)F)C(=O)c3cnn([C@H]4CC[C@](C)(C(=O)O)CC4)c3C(F)(F)F)C[C@@H]21] | trans-4-(4-(((1R,3r,5S)-6,6-dimethylbicyclo[3.1.0]hexan-3-yl)(2-hydroxy-2-(2-(trifluoromethyl)phenyl)ethyl)carbamoyl)-5-(trifluoromethyl)-1H-pyrazol-1-yl)-1-methylcyclohexanecarboxylic acid |
| 373 | 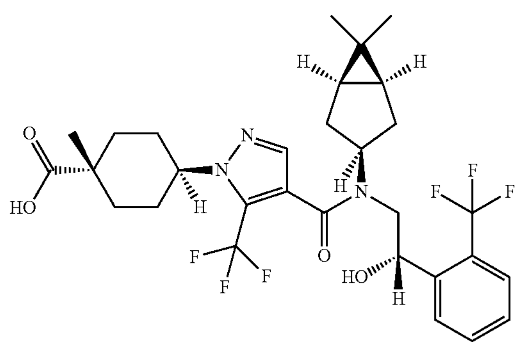 [SMILES: CC1(C)[C@@H]2C[C@H](N(C[C@@H](O)c3ccccc3C(F)(F)F)C(=O)c3cnn([C@H]4CC[C@](C)(C(=O)O)CC4)c3C(F)(F)F)C[C@@H]21] | trans-4-(4-(((1R,3r,5S)-6,6-dimethylbicyclo[3.1.0]hexan-3-yl)(2-hydroxy-2-(2-(trifluoromethyl)phenyl)ethyl)carbamoyl)-5-(trifluoromethyl)-1H-pyrazol-1-yl)-1-methylcyclohexanecarboxylic acid |
| 374 | 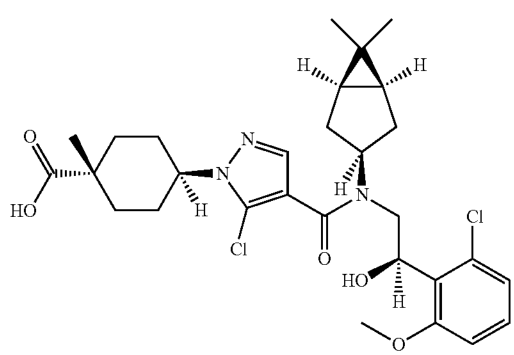 [SMILES: COc1cccc(Cl)c1[C@@H](O)CN(C(=O)c1cnn([C@H]2CC[C@](C)(C(=O)O)CC2)c1Cl)[C@H]1C[C@@H]2[C@H](C1)C2(C)C] | trans-4-(5-chloro-4-((2-(2-chloro-6-methoxyphenyl)-2-hydroxyethyl)((1R,3r,5S)-6,6-dimethylbicyclo[3.1.0]hexan-3-yl)carbamoyl)-1H-pyrazol-1-yl)-1-methylcyclohexanecarboxylic acid |

-continued

| example | structure | name |
|---|---|---|
| 375 | 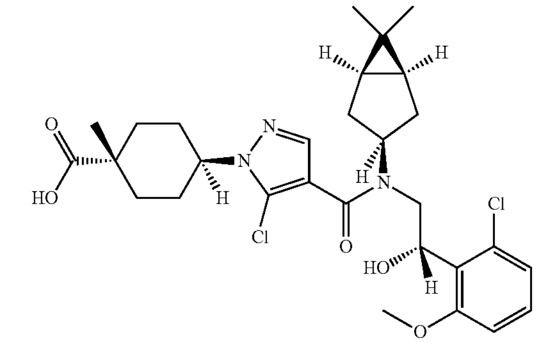 [SMILES: COc1cccc(Cl)c1[C@H](O)CN(C(=O)c1cnn([C@H]2CC[C@](C)(C(=O)O)CC2)c1Cl)[C@H]1C[C@@H]2[C@H](C1)C2(C)C] | trans-4-(5-chloro-4-((2-(2-chloro-6-methoxyphenyl)-2-hydroxyethyl)((1R,3r,5S)-6,6-dimethylbicydo[3.1.0]hexan-3-yl)carbamoyl)-1H-pyrazol-1-yl)-1-methylcyclohexanecarboxylic acid |
| 376 | 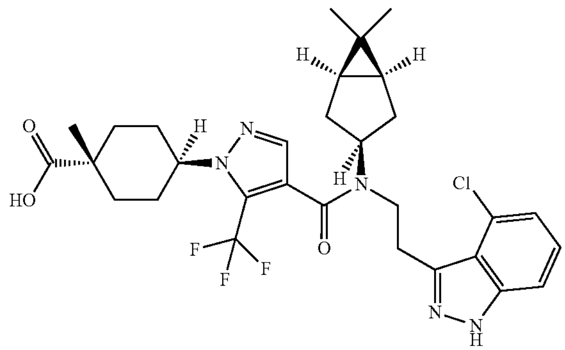 [SMILES: CC1(C)[C@@H]2C[C@H](N(CCc3n[nH]c4cccc(Cl)c34)C(=O)c3cnn([C@H]4CC[C@](C)(C(=O)O)CC4)c3C(F)(F)F)C[C@@H]21] | trans-4-(4-((2-(4-chloro-1H-indazol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 377 | 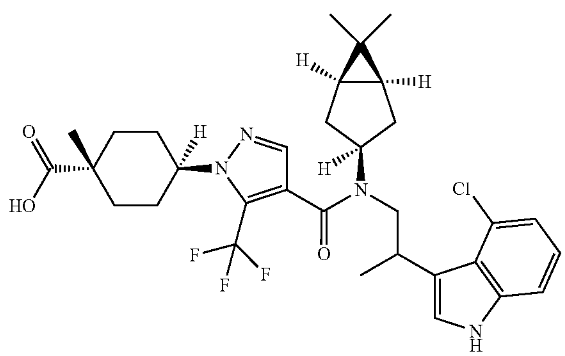 [SMILES: CC(CN(C(=O)c1cnn([C@H]2CC[C@](C)(C(=O)O)CC2)c1C(F)(F)F)[C@H]1C[C@@H]2[C@H](C1)C2(C)C)c1c[nH]c2cccc(Cl)c12] | trans-4-(4-((2-(4-chloro-1H-indol-3-yl)propyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 378 | 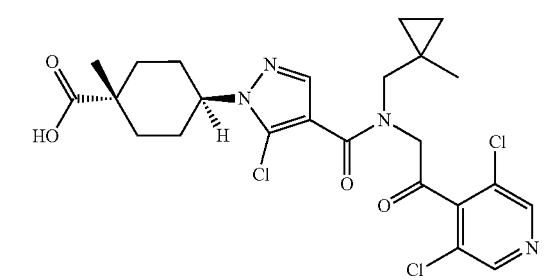 [SMILES: CC1(CN(CC(=O)c2c(Cl)cncc2Cl)C(=O)c2cnn([C@H]3CC[C@](C)(C(=O)O)CC3)c2Cl)CC1] | trans-4-(5-chloro-4-((2-(3,5-dichloropyridin-4-yl)-2-oxoethyl)-((1-methylcyclopropyl)methyl)carbamoyl)pyrazol-1-yl)-1-methylcyclohexane-1-carboxylic acid |
| 379 | 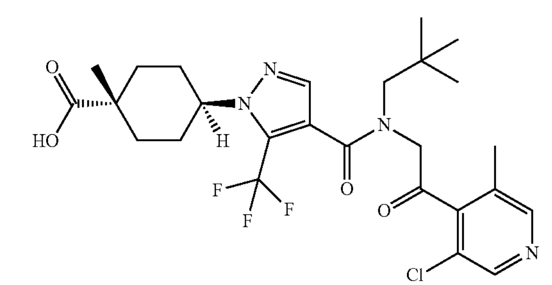 [SMILES: Cc1cncc(Cl)c1C(=O)CN(CC(C)(C)C)C(=O)c1cnn([C@H]2CC[C@](C)(C(=O)O)CC2)c1C(F)(F)F] | trans-4-(4-((2-(3-chloro-5-methylpyridin-4-yl)-2-oxoethyl)-(2,2-dimethylpropyl)carbamoyl)-5-(trifluoromethyl)pyrazol-1-yl)-1-methylcyclohexane-1-carboxylic acid |

| example | structure | name |
|---------|-----------|------|
| 380 | 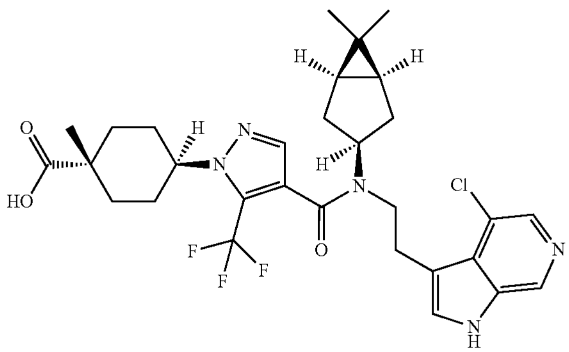 [SMILES: CC1(C)[C@@H]2C[C@H](N(CCc3c[nH]c4cncc(Cl)c34)C(=O)c3cnn([C@H]4CC[C@](C)(C(=O)O)CC4)c3C(F)(F)F)C[C@@H]21] | trans-4-(4-((2-(4-chloro-1H-pyrrolo(2,3-c)pyridin-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 381 | 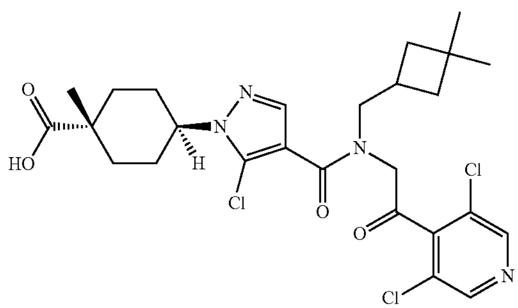 [SMILES: CC1(C)CC(CN(CC(=O)c2c(Cl)cncc2Cl)C(=O)c2cnn([C@H]3CC[C@](C)(C(=O)O)CC3)c2Cl)C1] | trans-4-(5-chloro-4-((2-(3,5-dichloropyridin-4-yl)-2-oxoethyl)-((3,3-dimethylcyclobutyl)methyl)carbamoyl)pyrazol-1-yl)-1-methylcyclohexane-1-carboxylic acid |
| 382 | 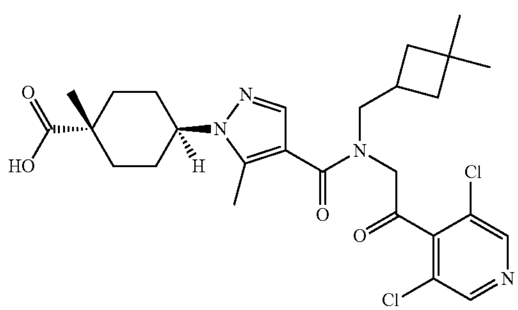 [SMILES: Cc1c(C(=O)N(CC(=O)c2c(Cl)cncc2Cl)CC2CC(C)(C)C2)cnn1[C@H]1CC[C@](C)(C(=O)O)CC1] | trans-4-(4-((2-(3,5-dichloropyridin-4-yl)-2-oxoethyl)-((3,3-dimethylcyclobutyl)methyl)carbamoyl)-5-methylpyrazol-1-yl)-1-methylcyclohexane-1-carboxylic acid |
| 383 | 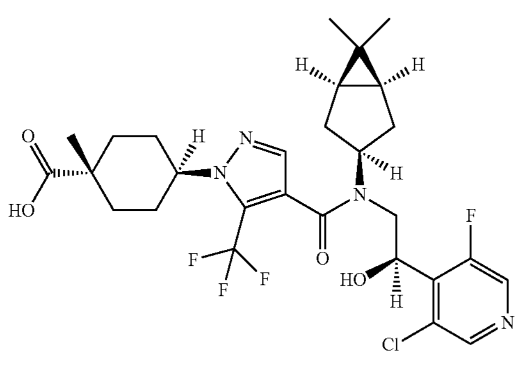 [SMILES: CC1(C)[C@@H]2C[C@H](N(C[C@H](O)c3c(F)cncc3Cl)C(=O)c3cnn([C@H]4CC[C@](C)(C(=O)O)CC4)c3C(F)(F)F)C[C@@H]21] | trans-4-(4-((2-(3-chloro-5-fluoropyridin-4-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

-continued

| example | structure | name |
|---|---|---|
| 384 | 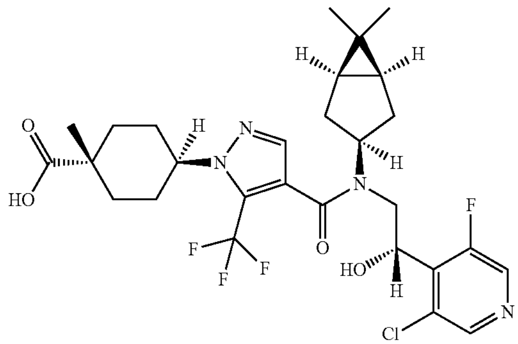 [SMILES: CC1(C)[C@@H]2C[C@H](N(C[C@@H](O)c3c(F)cncc3Cl)C(=O)c3cnn([C@H]4CC[C@](C)(C(=O)O)CC4)c3C(F)(F)F)C[C@@H]21] | trans-4-(4-((2-(3-chloro-5-fluoropyridin-4-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 385 | 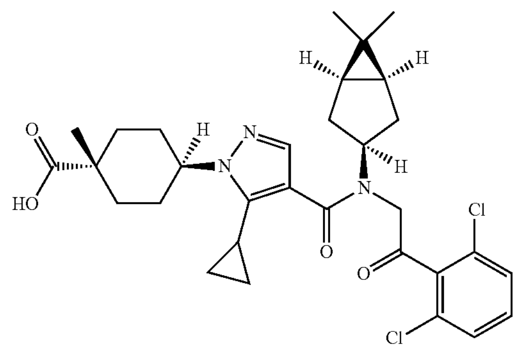 [SMILES: CC1(C)[C@@H]2C[C@H](N(CC(=O)c3c(Cl)cccc3Cl)C(=O)c3cnn([C@H]4CC[C@](C)(C(=O)O)CC4)c3C3CC3)C[C@@H]21] | trans-4-(5-cyclopropyl-4-((2-(2,6-dichlorophenyl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid |
| 386 | 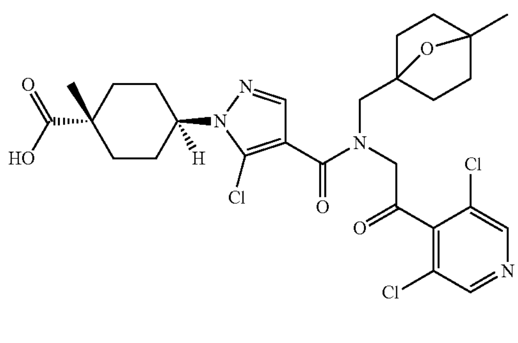 [SMILES: CC12CCC(CN(CC(=O)c3c(Cl)cncc3Cl)C(=O)c3cnn([C@H]4CC[C@](C)(C(=O)O)CC4)c3Cl)(CC1)O2] | trans-4-(5-chloro-4-((2-(3,5-dichloropyridin-4-yl)-2-oxoethyl)-((1-methyl-7-oxabicyclo[2.2.1]heptan-4-yl)methyl)carbamoyl)pyrazol-1-yl)-1-methylcyclohexane-1-carboxylic acid |
| 387 | 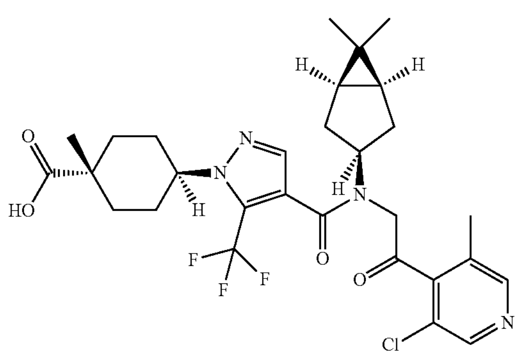 [SMILES: Cc1cncc(Cl)c1C(=O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-((2-(3-chloro-5-methylpyridin-4-yl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

| example | structure | name |
|---|---|---|
| 388 | 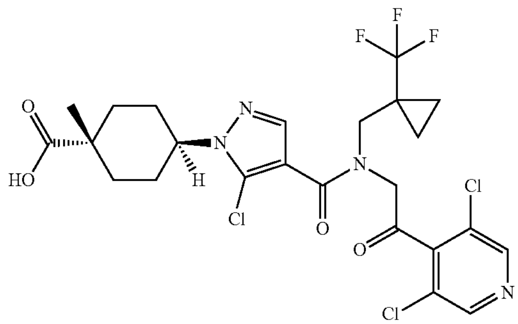 [SMILES: C[C@]1(C(=O)O)CC[C@H](n2ncc(C(=O)N(CC(=O)c3c(Cl)cncc3Cl)CC3(C(F)(F)F)CC3)c2Cl)CC1] | trans-4-(5-chloro-4-((2-(3,5-dichloropyridin-4-yl)-2-oxoethyl)-((1-(trifluoromethyl)cyclopropyl)methyl)carbamoyl)pyrazol-1-yl)-1-methylcyclohexane-1-carboxylic acid |
| 389 | 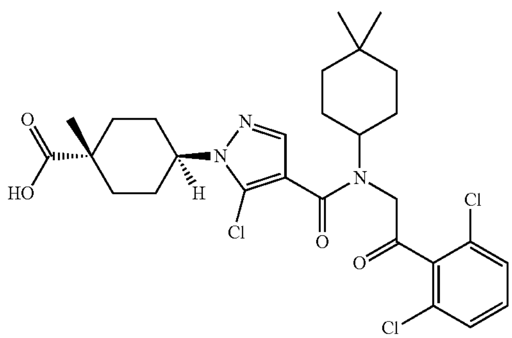 [SMILES: CC1(C)CCC(N(CC(=O)c2c(Cl)cccc2Cl)C(=O)c2cnn([C@H]3CC[C@](C)(C(=O)O)CC3)c2Cl)CC1] | trans-4-(5-chloro-4-((2-(2,6-dichlorophenyl)-2-oxoethyl)-(4,4-dimethylcyclohexyl)carbamoyl)pyrazol-1-yl)-1-methylcyclohexane-1-carboxylic acid |
| 390 | 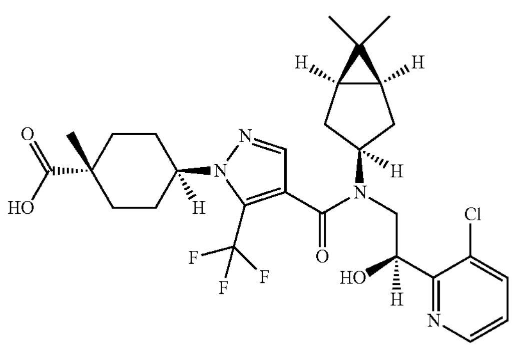 [SMILES: CC1(C)[C@@H]2C[C@H](N(C[C@H](O)c3ncccc3Cl)C(=O)c3cnn([C@H]4CC[C@](C)(C(=O)O)CC4)c3C(F)(F)F)C[C@@H]21] | trans-4-(4-((2-(3-chloropyridin-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 391 | 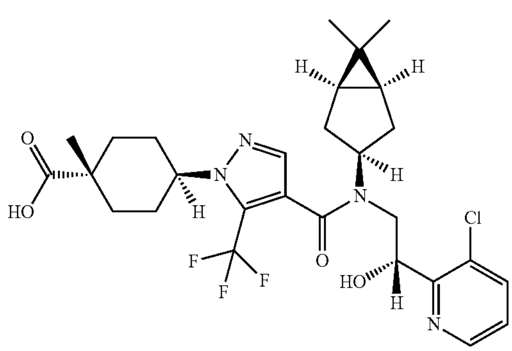 [SMILES: CC1(C)[C@@H]2C[C@H](N(C[C@@H](O)c3ncccc3Cl)C(=O)c3cnn([C@H]4CC[C@](C)(C(=O)O)CC4)c3C(F)(F)F)C[C@@H]21] | trans-4-(4-((2-(3-chloropyridin-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

| example | structure | name |
| --- | --- | --- |
| 392 | 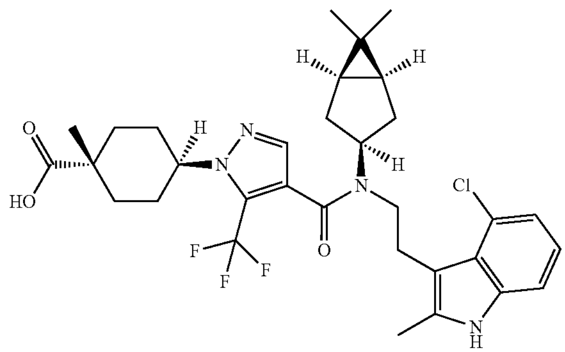 [SMILES: Cc1[nH]c2cccc(Cl)c2c1CCN(C(=O)c1cnn([C@H]2CC[C@](C)(C(=O)O)CC2)c1C(F)(F)F)[C@H]1C[C@@H]2[C@H](C1)C2(C)C] | trans-4-(4-((2-(4-chloro-2-methyl-1H-indol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 393 | 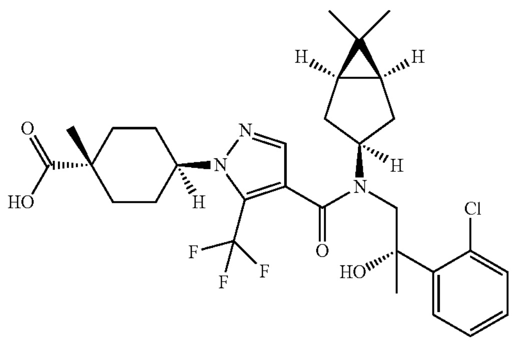 [SMILES: CC1(C)[C@@H]2C[C@H](N(C[C@@](C)(O)c3ccccc3Cl)C(=O)c3cnn([C@H]4CC[C@](C)(C(=O)O)CC4)c3C(F)(F)F)C[C@@H]21] | trans-4-(4-((2-(2-chlorophenyl)-2-hydroxypropyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 394 | 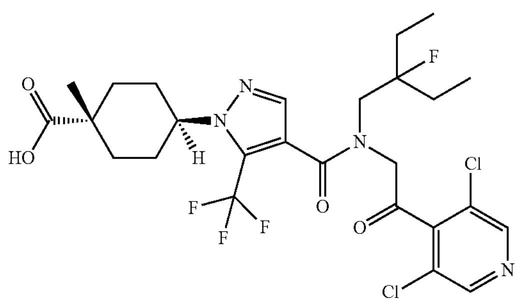 [SMILES: CCC(F)(CC)CN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloropyridin-4-yl)-2-oxoethyl)-(2-ethyl-2-fluorobutyl)carbamoyl)-5-(trifluoromethyl)pyrazol-1-yl)-1-methylcyclohexane-1-carboxylic acid |
| 395 | 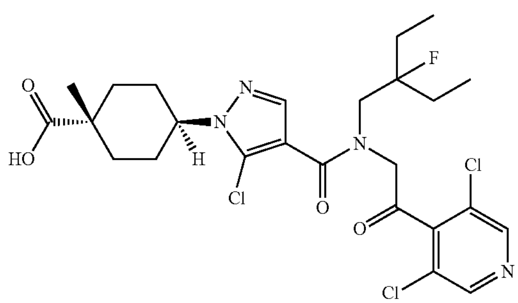 [SMILES: CCC(F)(CC)CN(CC(=O)c1c(Cl)cncc1Cl)C(=O)c1cnn([C@H]2CC[C@](C)(C(=O)O)CC2)c1Cl] | trans-4-(5-chloro-4-((2-(3,5-dichloropyridin-4-yl)-2-oxoethyl)-(2-ethyl-2-fluorobutyl)carbamoyl)pyrazol-1-yl)-1-methylcyclohexane-1-carboxylic acid |

-continued

| example | structure | name |
|---|---|---|
| 396 | 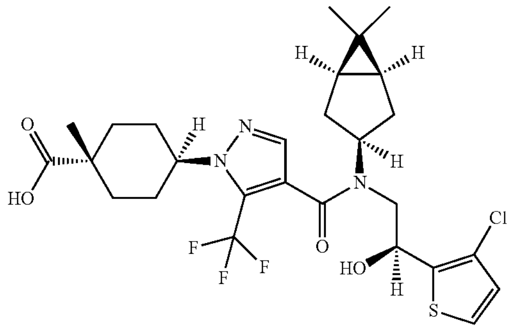 [SMILES: CC1(C)[C@@H]2C[C@H](N(C[C@H](O)c3sccc3Cl)C(=O)c3cnn([C@H]4CC[C@](C)(C(=O)O)CC4)c3C(F)(F)F)C[C@@H]21] | trans-4-(4-((2-(3-chlorothiophen-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 397 | 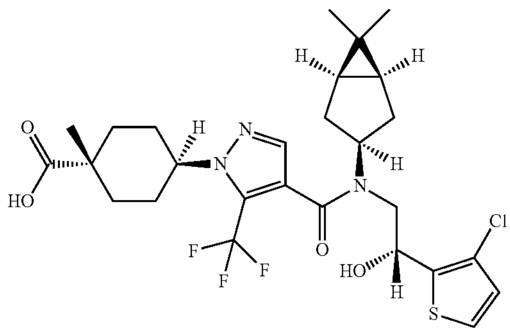 [SMILES: CC1(C)[C@@H]2C[C@H](N(C[C@@H](O)c3sccc3Cl)C(=O)c3cnn([C@H]4CC[C@](C)(C(=O)O)CC4)c3C(F)(F)F)C[C@@H]21] | trans-4-(4-((2-(3-chlorothiophen-2-yl)-2-hydroxyethyl)((1R,3r,5S)-6,6-dimethylbicyclo[3.1.0] hexan-3-yl)carbamoyl)-5-(trifluoromethyl)-1H-pyrazol-1-yl)-1-methylcyclohexanecarboxylic acid |
| 398 | 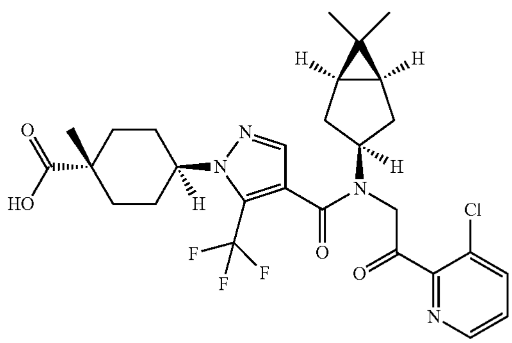 [SMILES: CC1(C)[C@@H]2C[C@H](N(CC(=O)c3ncccc3Cl)C(=O)c3cnn([C@H]4CC[C@](C)(C(=O)O)CC4)c3C(F)(F)F)C[C@@H]21] | trans-4-(4-((2-(3-chloropyridin-2-yl)-2-oxoethyl)((1R,3r,5S}-6,6-dimethylbicyclo[3.1.0]hexan-3-yl)carbamoyl)-5-(trifluoromethyl)-1H -pyrazol-1-yl)-1-methylcyclohexanecarboxylic acid |
| 399 | 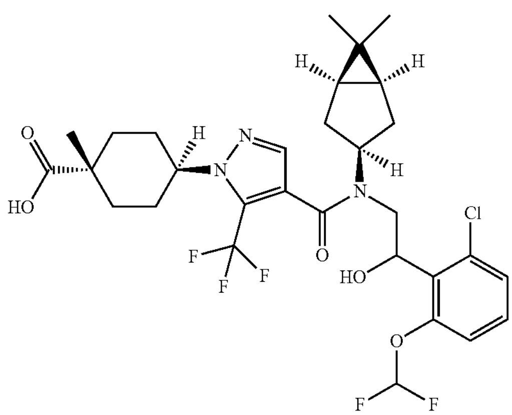 [SMILES: CC1(C)[C@@H]2C[C@H](N(CC(O)c3c(Cl)cccc3OC(F)F)C(=O)c3cnn([C@H]4CC[C@](C)(C(=O)O)CC4)c3C(F)(F)F)C[C@@H]21] | trans-4-(4-((2-(2-chloro-6-(difluoromethoxy)phenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

-continued

| example | structure | name |
|---|---|---|
| 400 | 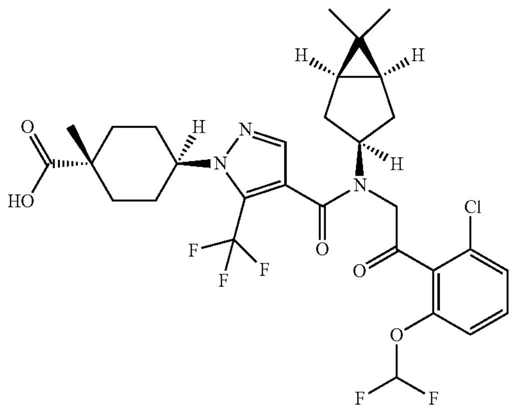 [SMILES: CC1(C)[C@@H]2C[C@H](N(CC(=O)c3c(Cl)cccc3OC(F)F)C(=O)c3cnn([C@H]4CC[C@](C)(C(=O)O)CC4)c3C(F)(F)F)C[C@@H]21] | trans-4-(4-((2-(2-chloro-6-(difluoromethoxy)phenyl)-2-oxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 401 | 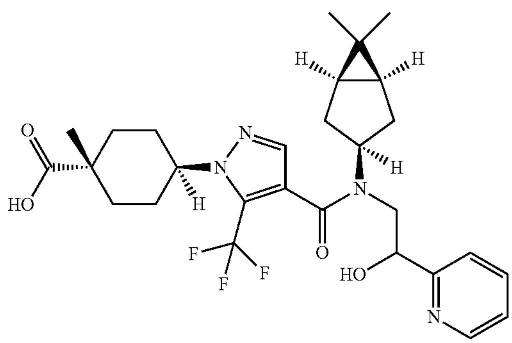 [SMILES: CC1(C)[C@@H]2C[C@H](N(CC(O)c3ccccn3)C(=O)c3cnn([C@H]4CC[C@](C)(C(=O)O)CC4)c3C(F)(F)F)C[C@@H]21] | trans-4-(4-(((1R,3r,5S)-6,6-dimethylbicyclo[3.1.0]hexan-3-yl)(2-hydroxy-2-(pyridin-2-yl)ethyl)carbamoyl)-5-(trifluoromethyl)-1H-pyrazol-1-y methylcyclohexanecarboxylic acid |
| 402 | 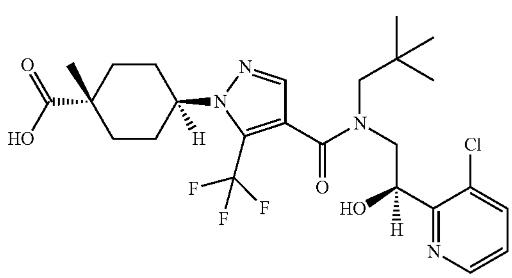 [SMILES: CC(C)(C)CN(C[C@H](O)c1ncccc1Cl)C(=O)c1cnn([C@H]2CC[C@](C)(C(=O)O)CC2)c1C(F)(F)F] | trans-4-(4-((2-(3-chloropyridin-2-yl)-2-hydroxyethyl)-(2,2-dimethylpropyl)carbamoyl)-5-(trifluoromethyl)pyrazol-1-yl)-1-methylcyclohexane-1-carboxylic acid |
| 403 | 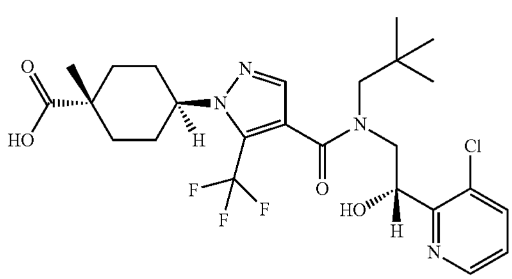 [SMILES: CC(C)(C)CN(C[C@@H](O)c1ncccc1Cl)C(=O)c1cnn([C@H]2CC[C@](C)(C(=O)O)CC2)c1C(F)(F)F] | trans-4-(4-((2-(3-chloropyridin-2-yl)-2-hydroxyethyl)-(2,2-dimethylpropyl)carbamoyl)-5-(trifluoromethyl)pyrazol-1-yl)-1-methylcyclohexane-1-carboxylic acid |

| example | structure | name |
|---|---|---|
| 404 | 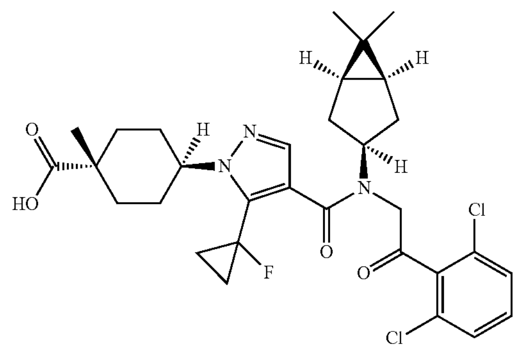 [SMILES: CC1(C)[C@@H]2C[C@H](N(CC(=O)c3c(Cl)cccc3Cl)C(=O)c3cnn([C@H]4CC[C@](C)(C(=O)O)CC4)c3C3(F)CC3)C[C@@H]21] | trans-4-(4-((2-(2,6-dichlorophenyl)-2-oxoethyl)((1R,3r,5S)-6,6-dimethylbicyclo[3.1.0]hexan-3-yl)carbamoyl)-5-(1-fluorocyclopropyl)-1H-pyrazol-1-yl)-1-methylcyclohexanecarboxylic acid |
| 405 | 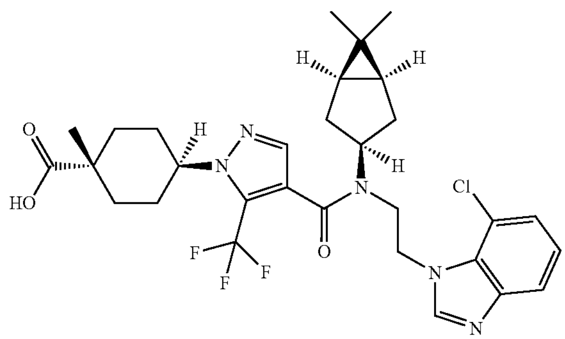 [SMILES: CC1(C)[C@@H]2C[C@H](N(CCn3cnc4cccc(Cl)c43)C(=O)c3cnn([C@H]4CC[C@](C)(C(=O)O)CC4)c3C(F)(F)F)C[C@@H]21] | trans-4-(4-((2-(7-chloro-1H-benzo(d)imidazol-1-yl)ethyl)((1R,3r,5S)-6,6-dimethylbicyclo[3.1.0] hexan-3-yl)carbamoyl)-5-(trifluoromethyl)-1H-pyrazol-1-yl)-1-methylcyclohexanecarboxylic acid |
| 406 | 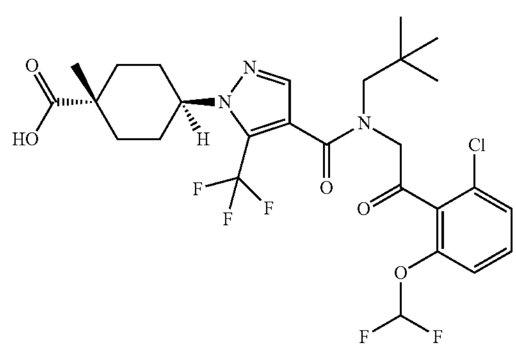 [SMILES: CC(C)(C)CN(CC(=O)c1c(Cl)cccc1OC(F)F)C(=O)c1cnn([C@H]2CC[C@](C)(C(=O)O)CC2)c1C(F)(F)F] | trans-4-(4-((2-(2-chloro-6-(difluoromethoxy)phenyl)-2-oxoethyl)-(2,2-dimethylpropyl)carbamoyl)-5-(trifluoromethyl)pyrazol-1-yl)-1-methylcyclohexane-1-carboxylic acid |
| 407 | 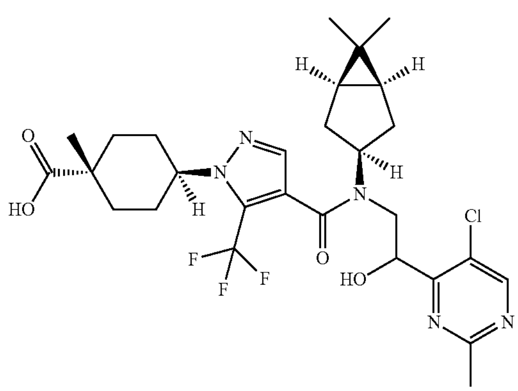 [SMILES: Cc1ncc(Cl)c(C(O)CN(C(=O)c2cnn([C@H]3CC[C@](C)(C(=O)O)CC3)c2C(F)(F)F)[C@H]2C[C@@H]3[C@H](C2)C3(C)C)n1] | trans-4-(4-((2-(5-chloro-2-methylpyrimidin-4-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |

| example | structure | name |
| --- | --- | --- |
| 408 | 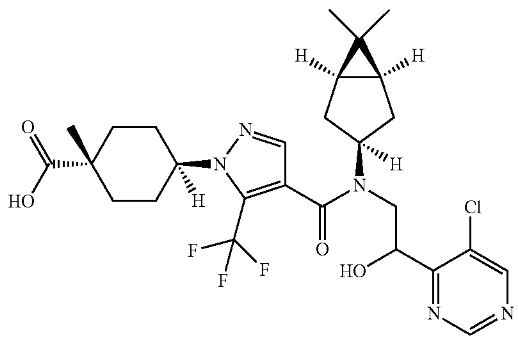 [SMILES: CC1(C)[C@@H]2C[C@H](N(CC(O)c3ncncc3Cl)C(=O)c3cnn([C@H]4CC[C@](C)(C(=O)O)CC4)c3C(F)(F)F)C[C@@H]21] | trans-4-(4-((2-(5-chloropyrimidin-4-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 409 | 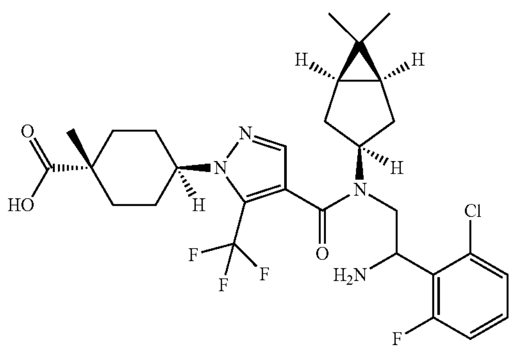 [SMILES: CC1(C)[C@@H]2C[C@H](N(CC(N)c3c(F)cccc3Cl)C(=O)c3cnn([C@H]4CC[C@](C)(C(=O)O)CC4)c3C(F)(F)F)C[C@@H]21] | trans-4-(4-((2-amino-2-(2-chloro-6-fluorophenyl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid |
| 410 | 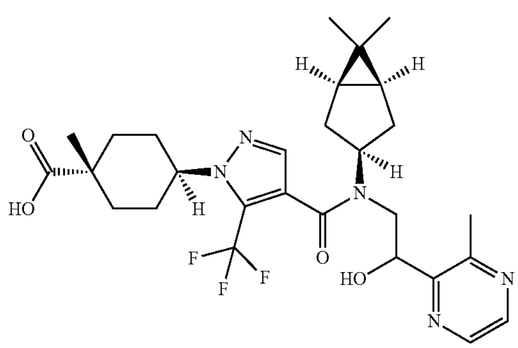 [SMILES: Cc1nccnc1C(O)CN(C(=O)c1cnn([C@H]2CC[C@](C)(C(=O)O)CC2)c1C(F)(F)F)[C@H]1C[C@@H]2[C@H](C1)C2(C)C] | trans-4-(4-(((1R,3r,5S)-6,6-dimethylbicyclo[3.1.0] hexan-3-yl)(2-hydroxy-2-(3-methylpyrazin-2-yl)ethyl)carbamoyl)-5-(trifluoromethyl)-1H-pyrazol-1-yl)-1-methylcyclohexanecarboxylic acid |
| 411 | 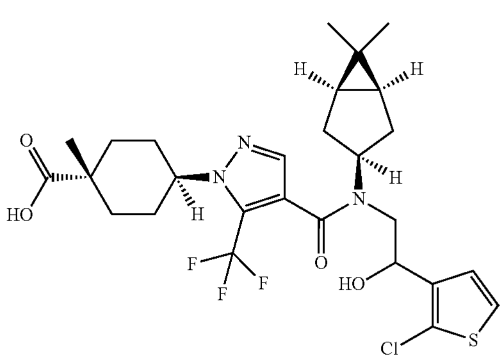 [SMILES: CC1(C)[C@@H]2C[C@H](N(CC(O)c3ccsc3Cl)C(=O)c3cnn([C@H]4CC[C@](C)(C(=O)O)CC4)c3C(F)(F)F)C[C@@H]21] | trans-4-(4-((2-(2-chlorothiophen-3-yl)-2-hydroxyethyl)((1R,3r,5S)-6,6-dimethylbicyclo[3.1.0]hexan-3-yl)carbamoyl)-5-(trifluoromethyl)-1H-pyrazol-1-y1)-1-methylcyclohexanecarboxylic acid |

-continued

| example | structure | name |
|---|---|---|
| 412 | 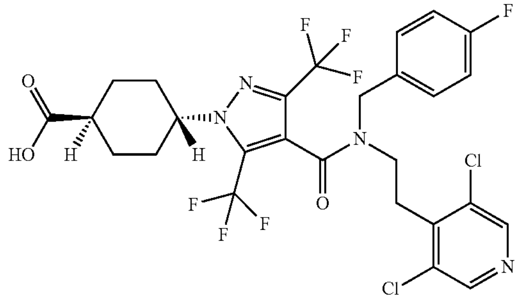 [SMILES: O=C(c1c(C(F)(F)F)nn([C@H]2CC[C@H](C(=O)O)CC2)c1C(F)(F)F)N(CCc1c(Cl)cncc1Cl)Cc1ccc(F)cc1] | trans-4-(4-(2-(3,5-dichloropyridin-4-yl)ethyl-((4-fluorophenyl)methyl)carbamoyl)-3,5-bis(trifluoromethyl)pyrazol-1-yl)cyclohexane-1-carboxylic acid |
| 500 | 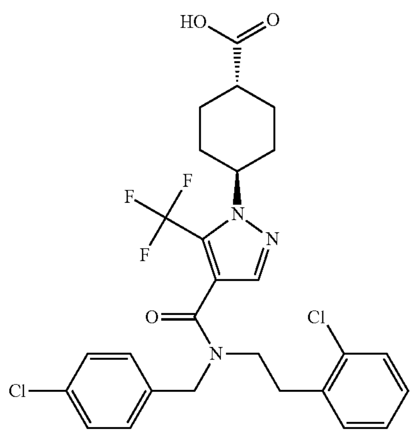 [SMILES: O=C(c1cnn([C@H]2CC[C@H](C(=O)O)CC2)c1C(F)(F)F)N(CCc1ccccc1Cl)Cc1ccc(Cl)cc1] | trans-4-(4-((4-chlorobenzyl)(2-(2-chlorophenyl)ethyl)carbamoyl)-5-(trifluoromethyl)-1H-pyrazol-1-yl)cyclohexanecarboxylic acid |
| 501 | 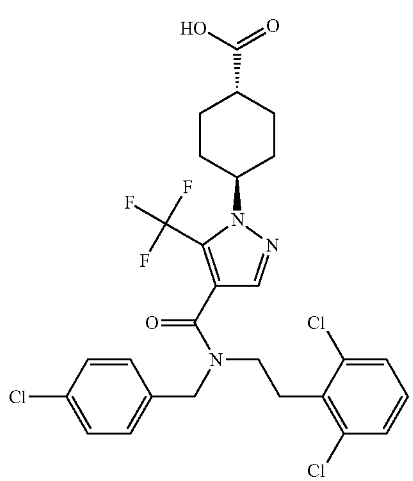 [SMILES: O=C(c1cnn([C@H]2CC[C@H](C(=O)O)CC2)c1C(F)(F)F)N(CCc1c(Cl)cccc1Cl)Cc1ccc(Cl)cc1] | trans-4-(4-((4-chlorobenzyl)(2-(2,6-dichlorophenyl)ethyl)carbamoyl)-5-(trifluoromethyl)-1H-pyrazol-1-yl)cyclohexanecarboxylic acid |

-continued

| example | structure | name |
|---|---|---|
| 502 | 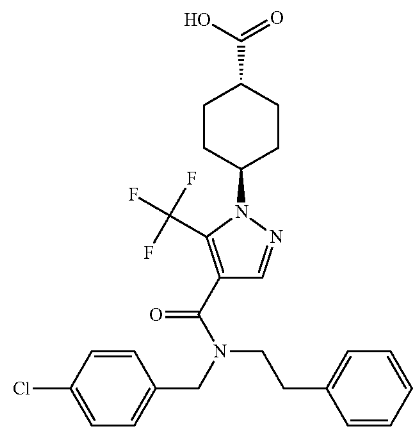 [SMILES: O=C(c1cnn([C@H]2CC[C@H](C(=O)O)CC2)c1C(F)(F)F)N(CCc1ccccc1)Cc1ccc(Cl)cc1] | trans-4-(4-((4-chlorobenzyl)(2-phenylethyl)carbamoyl)-5-(trifluoromethyl)-1H-pyrazol-1-yl)cyclohexanecarboxylic acid |
| 503 | 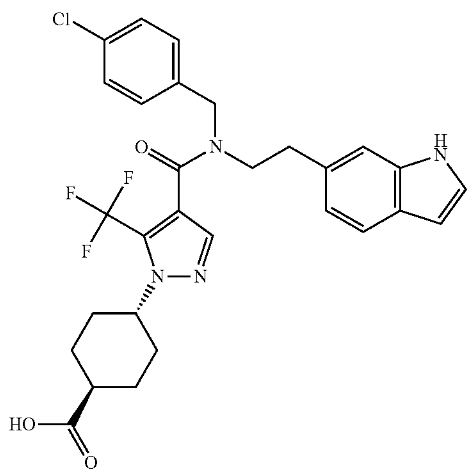 [SMILES: O=C(c1cnn([C@H]2CC[C@H](C(=O)O)CC2)c1C(F)(F)F)N(CCc1ccc2cc[nH]c2c1)Cc1ccc(Cl)cc1] | trans-4-(4-((4-chlorobenzyl)(2-(1H-indol-6-yl)ethyl)carbamoyl)-5-(trifluoromethyl)-1H-pyrazol-1-yl)cyclohexanecarboxylic acid |
| 504 | 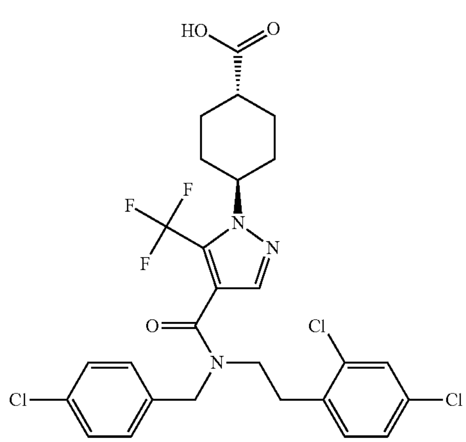 [SMILES: O=C(c1cnn([C@H]2CC[C@H](C(=O)O)CC2)c1C(F)(F)F)N(CCc1ccc(Cl)cc1Cl)Cc1ccc(Cl)cc1] | trans-4-(4-((4-chlorobenzyl)(2-(2,4-dichlorophenyl)ethyl)carbamoyl)-5-(trifluoromethyl)-1H-pyrazol-1-yl)cyclohexanecarboxylic acid |

| example | structure | name |
|---|---|---|
| 505 | 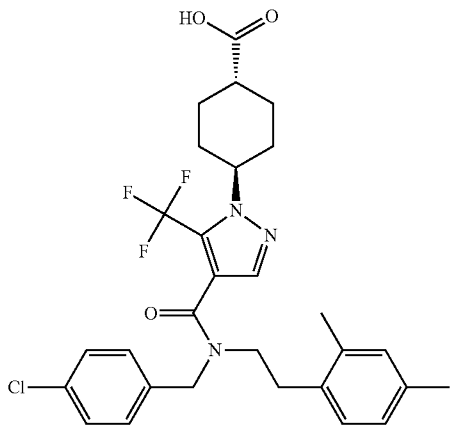 [SMILES: Cc1ccc(CCN(Cc2ccc(Cl)cc2)C(=O)c2cnn([C@H]3CC[C@H](C(=O)O)CC3)c2C(F)(F)F)c(C)c1] | trans-4-(4-((4-chlorobenzyl)(2-(2,4-dimethylphenyl)ethyl)carbamoyl)-5-(trifluoromethyl)-1H-pyrazol-1-yl)cyclohexanecarboxylic acid |
| 506 | 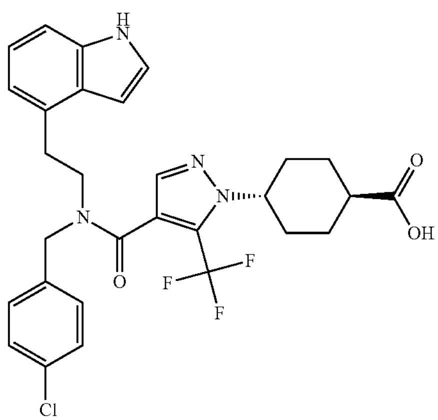 [SMILES: O=C(c1cnn([C@H]2CC[C@H](C(=O)O)CC2)c1C(F)(F)F)N(CCc1cccc2[nH]ccc12)Cc1ccc(Cl)cc1] | trans-4-(4-((4-chlorobenzyl)(2-(1H-indol-4-yl)ethyl)carbamoyl)-5-(trifluoromethyl)-1H-pyrazol-1-yl)cyclohexanecarboxylic acid |
| 507 | 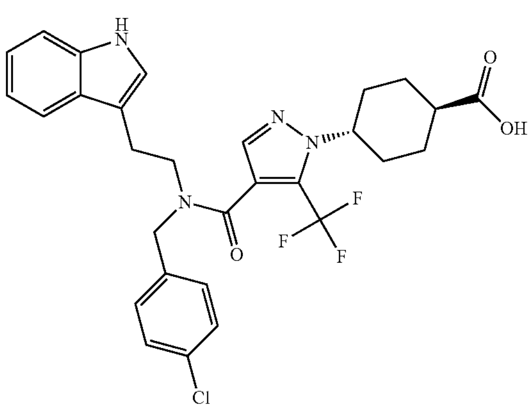 [SMILES: O=C(c1cnn([C@H]2CC[C@H](C(=O)O)CC2)c1C(F)(F)F)N(CCc1c[nH]c2ccccc12)Cc1ccc(Cl)cc1] | trans-4-(4-((4-chlorobenzyl)(2-(1H-indol-3-yl)ethyl)carbamoyl)-5-(trifluoromethyl)-1H-pyrazol-1-yl)cyclohexanecarboxylic acid |

| example | structure | name |
|---|---|---|
| 508 | 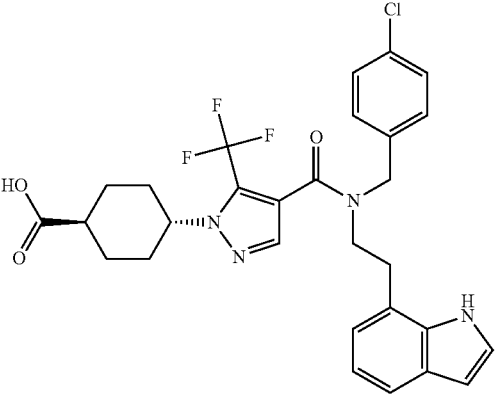 [SMILES: O=C(c1cnn([C@H]2CC[C@H](C(=O)O)CC2)c1C(F)(F)F)N(CCc1cccc2cc[nH]c12)Cc1ccc(Cl)cc1] | trans-4-(4-((4-chlorobenzyl)(2-(1H-indol-7-yl)ethyl)carbamoyl)-5-(trifluoromethyl)-1H-pyrazol-1-yl)cyclohexanecarboxylic acid |
| 509 | 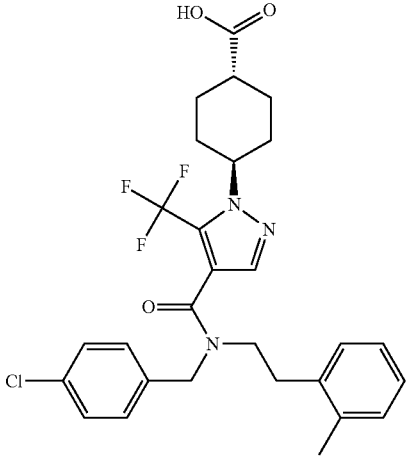 [SMILES: Cc1ccccc1CCN(Cc1ccc(Cl)cc1)C(=O)c1cnn([C@H]2CC[C@H](C(=O)O)CC2)c1C(F)(F)F] | trans-4-(4-((4-chlorobenzyl)(2-(2-methylphenyl)ethyl)carbamoyl)-5-(trifluoromethyl)-1H-pyrazol-1-yl)cyclohexanecarboxylic acid |
| 510 | 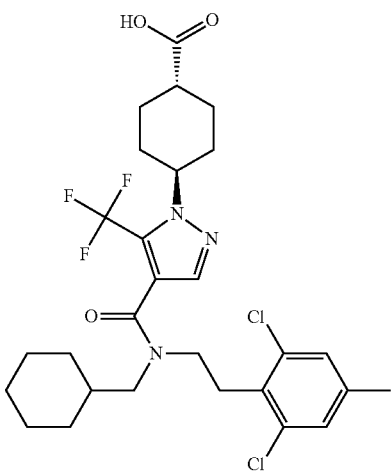 [SMILES: Cc1cc(Cl)c(CCN(CC2CCCCC2)C(=O)c2cnn([C@H]3CC[C@H](C(=O)O)CC3)c2C(F)(F)F)c(Cl)c1] | trans-4-(4-((cyclohexylmethyl)(2-(2,6-dichloro-4-methylphenyl)ethyl)carbamoyl)-5-(trifluoromethyl)-1H-pyrazol-1-yl)cyclohexanecarboxylic acid |

-continued

| example | structure | name |
|---|---|---|
| 511 | 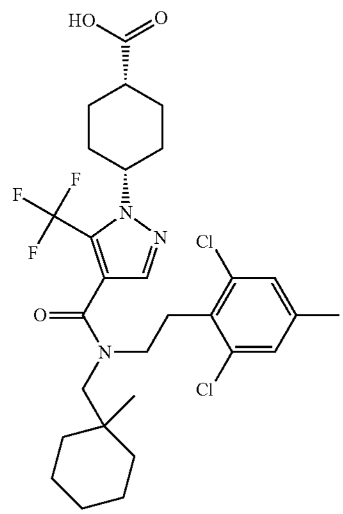 [SMILES: Cc1cc(Cl)c(CCN(CC2(C)CCCCC2)C(=O)c2cnn([C@H]3CC[C@@H](C(=O)O)CC3)c2C(F)(F)F)c(Cl)c1] | trans-4-(4-((2-(2,6-dichloro-4-methylphenyl)ethyl)((1-methylcyclohexyl)methyl)carbamoyl)-5-(trifluoromethyl)-1H-pyrazol-1-yl)cyclohexanecarboxylic acid |
| 512 | 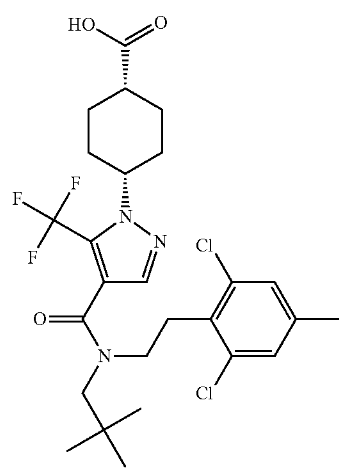 [SMILES: Cc1cc(Cl)c(CCN(CC(C)(C)C)C(=O)c2cnn([C@H]3CC[C@@H](C(=O)O)CC3)c2C(F)(F)F)c(Cl)c1] | trans-4-(4-((2-(2,6-dichloro-4-methylphenyl)ethyl)(2,2-dimethylpropyl)carbamoyl)-5-(trifluoromethyl)-1H-pyrazol-1-yl)cyclohexanecarboxylic acid |
| 513 | 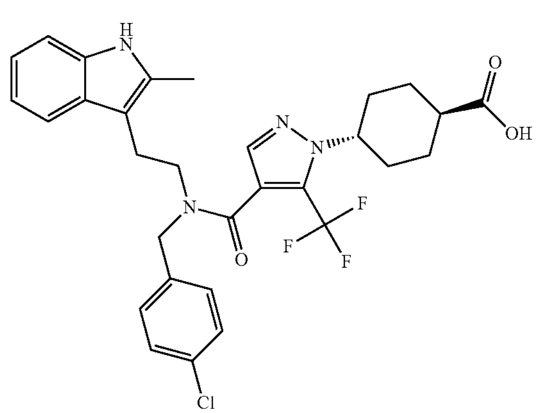 [SMILES: Cc1[nH]c2ccccc2c1CCN(Cc1ccc(Cl)cc1)C(=O)c1cnn([C@H]2CC[C@H](C(=O)O)CC2)c1C(F)(F)F] | trans-4-(4-((4-chlorobenzyl)(2-(2-methyl-1H-indol-3-yl)ethyl)carbamoyl)-5-(trifluoromethyl)-1H-pyrazol-1-yl)cyclohexanecarboxylic acid |

-continued

| example | structure | name |
| --- | --- | --- |
| 514 | 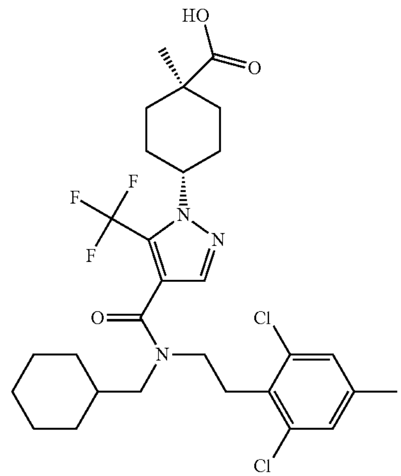 [SMILES: Cc1cc(Cl)c(CCN(CC2CCCCC2)C(=O)c2cnn([C@H]3CC[C@](C)(C(=O)O)CC3)c2C(F)(F)F)c(Cl)c1] | trans-4-(4-((cyclohexylmethyl)(2-(2,6-dichloro-4-methylphenyl)ethyl)carbamoyl)-5-(trifluoromethyl)-1H-pyrazol-1-yl)-1-methylcyclohexanecarboxylic acid |
| 515 | 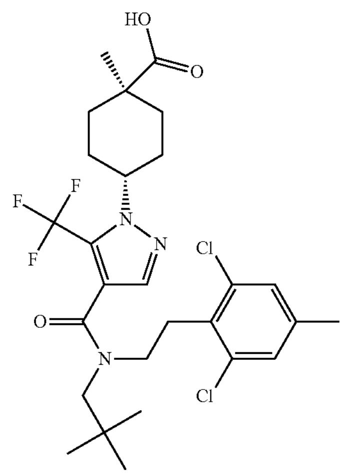 [SMILES: Cc1cc(Cl)c(CCN(CC(C)(C)C)C(=O)c2cnn([C@H]3CC[C@](C)(C(=O)O)CC3)c2C(F)(F)F)c(Cl)c1] | trans-4-(4-((2-(2,6-dichloro-4-methylphenyl)ethyl)(2,2-dimethylpropyl)carbamoyl)-5-(trifluoromethyl)-1H-pyrazol-1-yl)-1-methylcyclohexanecarboxylic acid |
| 516 | 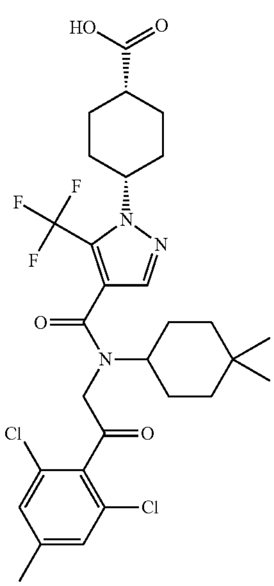 [SMILES: Cc1cc(Cl)c(C(=O)CN(C(=O)c2cnn([C@H]3CC[C@@H](C(=O)O)CC3)c2C(F)(F)F)C2CCC(C)(C)CC2)c(Cl)c1] | trans-4-(4-((2-(2,6-dichloro-4-methylphenyl)-2-oxoethyl)(4,4-dimethylcyclohexyl)carbamoyl)-5-(trifluoromethyl)-1H-pyrazol-1-yl)-1-cyclohexanecarboxylic acid |

-continued

| example | structure | name |
|---|---|---|
| 517 | 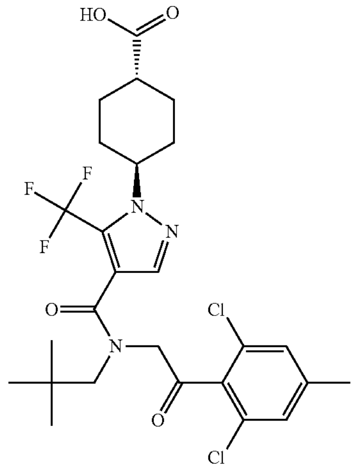 [SMILES: Cc1cc(Cl)c(C(=O)CN(CC(C)(C)C)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)(2,2-dimethylpropyl)carbamoyl)-5-(trifluoromethyl)-1H-pyrazol-1-yl)cyclohexanecarboxylic acid |
| 518 | 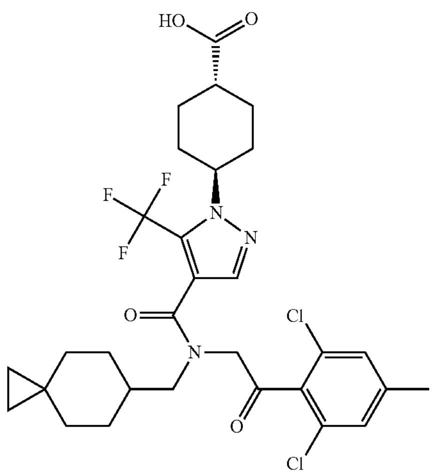 [SMILES: Cc1cc(Cl)c(C(=O)CN(CC2CCC3(CC2)CC3)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)(spiro[2.5]oct-6-ylmethyl)carbamoyl)-5-(trifluoromethyl)-1H-pyrazol-1-yl)cyclohexanecarboxylic acid |
| 519 | 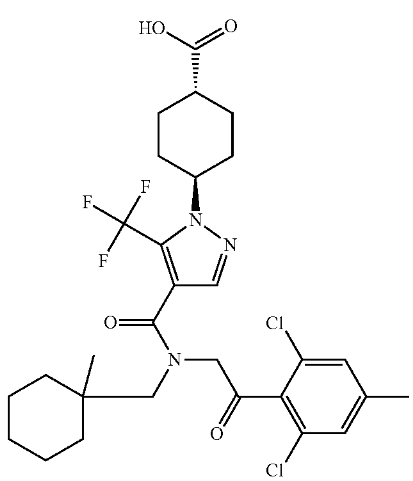 [SMILES: Cc1cc(Cl)c(C(=O)CN(CC2(C)CCCCC2)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)((1-methylcyclohexyl)methyl)carbamoyl)-5-(trifluoromethyl)-1H-pyrazol-1-yl)cyclohexanecarboxylic acid |

-continued

| example | structure | name |
|---|---|---|
| 520 | 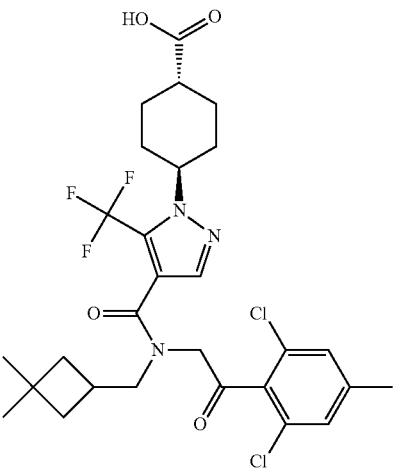 | trans-4-(4-((2-(2,6-dichloro-4-methylphenyl)-2-oxoethyl)((3,3-dimethylcyclobutyl)methyl)carbamoyl)-5-(trifluoromethyl)-1H-pyrazol-1-yl)cyclohexanecarboxylic acid |
| 521 | 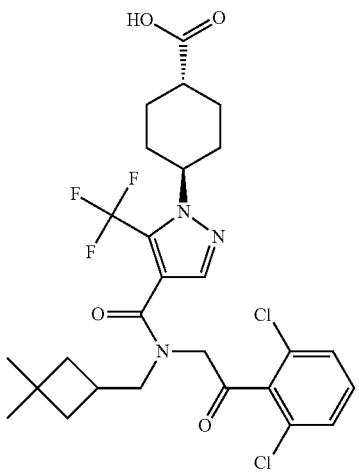 [SMILES: CC1(C)CC(CN(CC(=O)c2c(Cl)cccc2Cl)C(=O)c2cnn([C@H]3CC[C@H](C(=O)O)CC3)c2C(F)(F)F)C1] | trans-4-(4-((2-(2,6-dichlorophenyl)-2-oxoethyl)((3,3-dimethylcyclobutyl)methyl)carbamoyl)5-(trifluoromethyl)-1H-pyrazol-1-yl)cyclohexanecarboxylic acid |
| 522 | 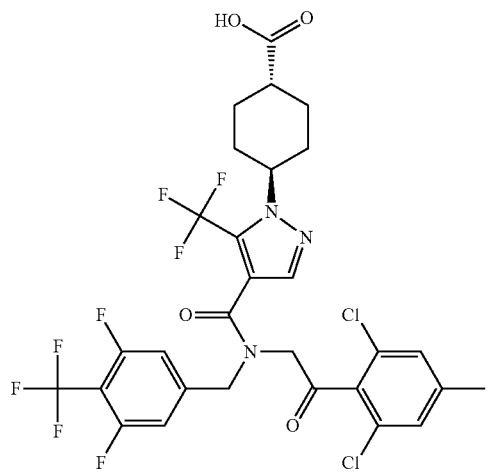 [SMILES: Cc1cc(Cl)c(C(=O)CN(Cc2cc(F)c(C(F)(F)F)c(F)c2)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)(3,5-difluoro-4-(trifluoromethyl)benzyl)carbamoyl)-5-(trifluoromethyl)-1H-pyrazol-1-yl)cyclohexanecarboxylic acid |

-continued

| example | structure | name |
|---|---|---|
| 523 | 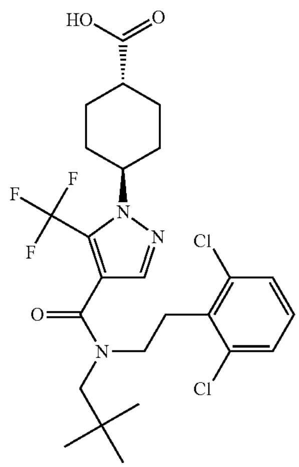 [SMILES: CC(C)(C)CN(CCc1c(Cl)cccc1Cl)C(=O)c1cnn([C@H]2CC[C@H](C(=O)O)CC2)c1C(F)(F)F] | trans-4-(4-((2-(2,6-dichlorophenyl)ethyl)(2,2-dimethylpropyl)carbamoyl)-5-(trifluoromethyl)-1H-pyrazol-1-yl)cyclohexanecarboxylic acid |
| 524 | 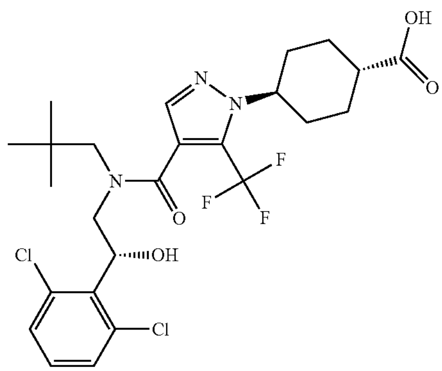 [SMILES: CC(C)(C)CN(C[C@H](O)c1c(Cl)cccc1Cl)C(=O)c1cnn([C@H]2CC[C@H](C(=O)O)CC2)c1C(F)(F)F] | trans-4-(4-(((2R)-2-(2,6-dichlorophenyl)-2-hydroxyethyl)(2,2-dimethylpropyl)carbamoyl)-5-(trifluoromethyl)-1H-pyrazol-1-yl)cyclohexanecarboxylic acid |
| 525 | 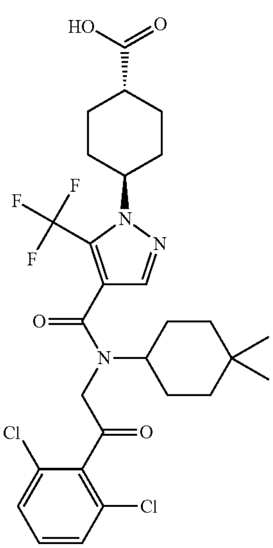 [SMILES: CC1(C)CCC(N(CC(=O)c2c(Cl)cccc2Cl)C(=O)c2cnn([C@H]3CC[C@H](C(=O)O)CC3)c2C(F)(F)F)CC1] | trans-4-(4-((2-(2,6-dichlorophenyl)-2-oxoethyl)(4,4-dimethylcyclohexyl)carbamoyl)-5-(trifluoromethyl)-1H-pyrazol-1-yl)cyclohexanecarboxylic acid |

-continued

| example | structure | name |
|---|---|---|
| 526 | 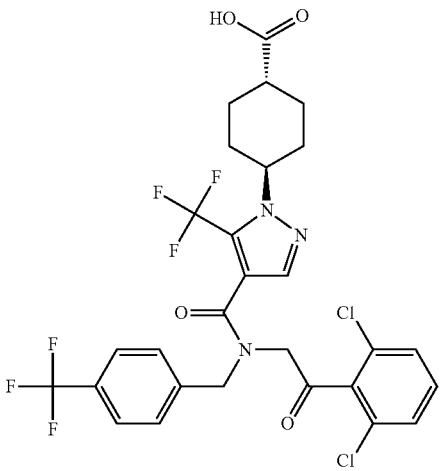 [SMILES: O=C(CN(Cc1ccc(C(F)(F)F)cc1)C(=O)c1cnn([C@H]2CC[C@H](C(=O)O)CC2)c1C(F)(F)F)c1c(Cl)cccc1Cl] | trans-4-(4-((2-(2,6-dichlorophenyl)ethyl)(4-(trifluoromethyl)benzyl)carbamoyl)-5-(trifluoromethyl)-1H-pyrazol-1-yl)cyclohexanecarboxylic acid |
| 527 | 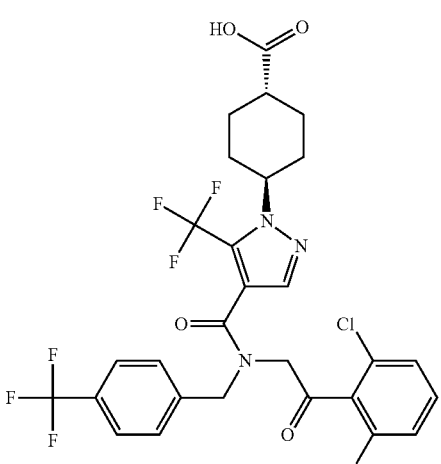 | trans-4-(4-((2-(2,6-dichlorophenyl)-2-oxoethyl)(4-(trifluoromethyl)benzyl)carbamoyl)-5-(trifluoromethyl)-1H-pyrazol-1-yl)cyclohexanecarboxylic acid |
| 528 | 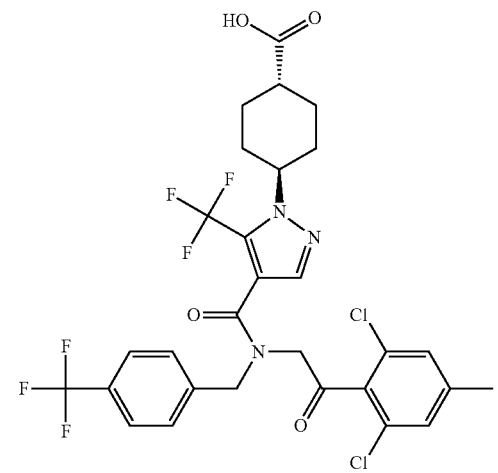 [SMILES: Cc1cc(Cl)c(C(=O)CN(Cc2ccc(C(F)(F)F)cc2)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)(4-(trifluoromethyl)benzyl)carbamoyl)-5-(trifluoromethyl)-1H-pyrazol-1-yl)cyclohexanecarboxylic acid |

-continued

| example | structure | name |
|---|---|---|
| 529 | 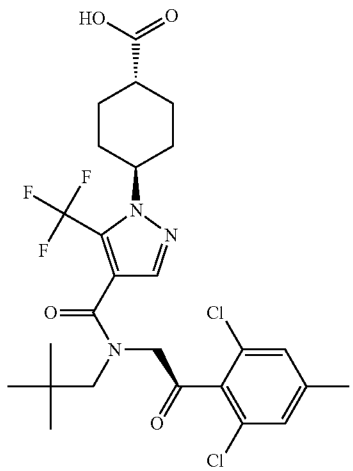 | trans-4-(4-(((2R/S)-2-(2,6-dichloro-4-methylphenyl)-2-methoxyethyl)(2,2-dimethylpropyl)carbamoyl)-5-(trifluoromethyl)-1H-pyrazol-1-yl)cyclohexanecarboxylic acid |
| 530 | 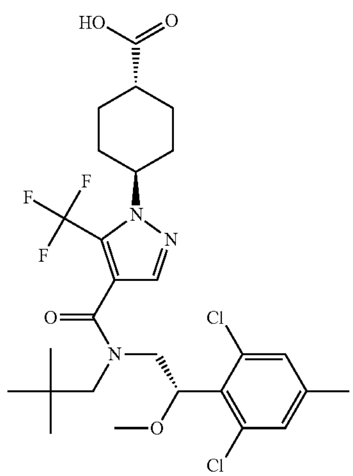 [SMILES: CO[C@H](CN(CC(C)(C)C)C(=O)c1cnn([C@H]2CC[C@H](C(=O)O)CC2)c1C(F)(F)F)c1c(Cl)cc(C)cc1Cl] | trans-4-(4-(((2S)-2-(2,6-dichloro-4-methylphenyl)-2-methoxyethyl)(2,2-dimethylpropyl)carbamoyl)-5-(trifluoromethyl)-1H-pyrazol-1-yl)cyclohexanecarboxylic acid |
| 531 | 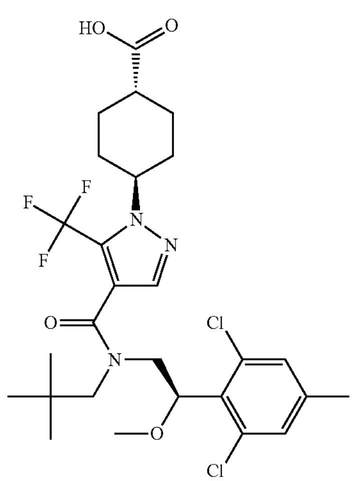 [SMILES: CO[C@@H](CN(CC(C)(C)C)C(=O)c1cnn([C@H]2CC[C@H](C(=O)O)CC2)c1C(F)(F)F)c1c(Cl)cc(C)cc1Cl] | trans-4-(4-(((2R)-2-(2,6-dichloro-4-methylphenyl)-2-methoxyethyl)(2,2-dimethylpropyl)carbamoyl)-5-(trifluoromethyl)-1H-pyrazol-1-yl)cyclohexanecarboxylic acid |

| example | structure | name |
|---|---|---|
| 532 | 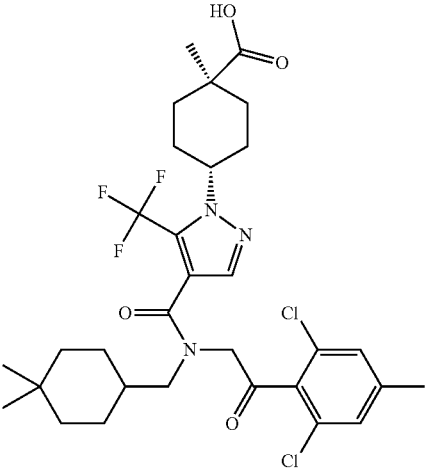 | trans-4-(4-((2-(2,6-dichloro-4-methylphenyl)-2-oxoethyl)((4,4-dimethylcyclohexyl)methyl)carbamoyl)-5-(trifluoromethyl)-1H-pyrazol-1-yl)-1-methylcyclohexanecarboxylic acid |
| 533 | 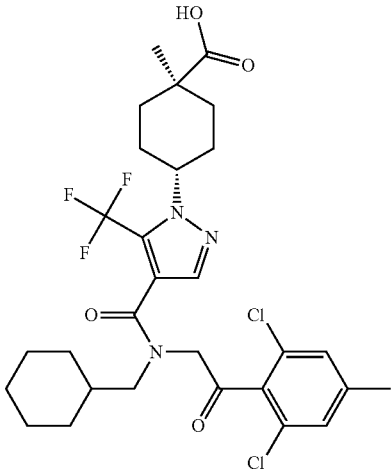 [SMILES: Cc1cc(Cl)c(C(=O)CN(CC2CCCCC2)C(=O)c2cnn([C@H]3CC[C@](C)(C(=O)O)CC3)c2C(F)(F)F)c(Cl)c1] | trans-4-(4-((cyclohexylmethyl)(2-(2,6-dichloro-4-methylphenyl)-2-oxoethyl)carbamoyl)-5-(trifluoromethyl)-1H-pyrazol-1-yl)-1-methylcyclohexanecarboxylic acid |
| 534 | 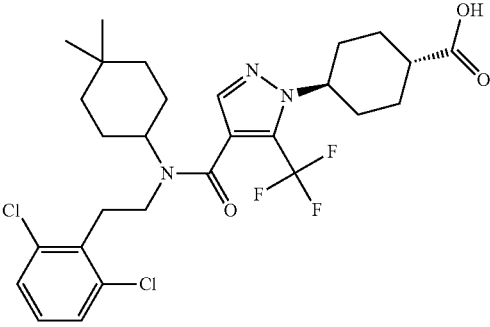 [SMILES: CC1(C)CCC(N(CCc2c(Cl)cccc2Cl)C(=O)c2cnn([C@H]3CC[C@H](C(=O)O)CC3)c2C(F)(F)F)CC1] | trans-4-(4-((2-(2,6-dichlorophenyl)ethyl)(4,4-dimethylcyclohexyl)carbamoyl)-5-(trifluoromethyl)-1H-pyrazol-1-yl)cyclohexanecarboxylic acid |

| example | structure | name |
|---|---|---|
| 535 | 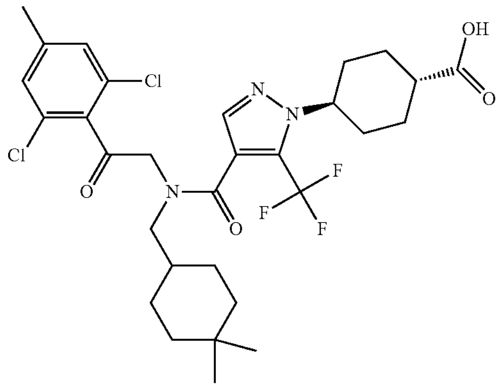 [SMILES: Cc1cc(Cl)c(C(=O)CN(CC2CCC(C)(C)CC2)C(=O)c2cnn([C@H]3CC[C@H](C(=O)O)CC3)c2C(F)(F)F)c(Cl)c1] | trans-4-(4-((2-(2,6-dichloro-4-methylphenyl)-2-oxoethyl)((4,4-dimethylcyclohexyl)methyl)carbamoyl)-5-(trifluoromethyl)-1H-pyrazol-1-yl)cyclohexanecarboxylic acid |
| 536 | 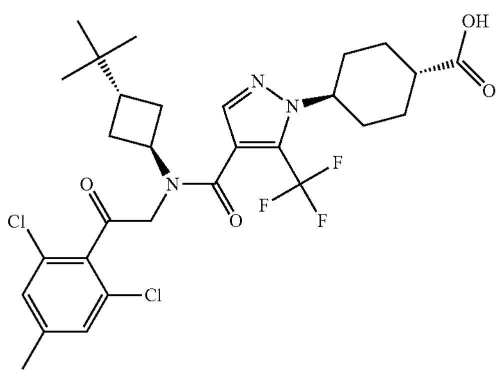 [SMILES: Cc1cc(Cl)c(C(=O)CN(C(=O)c2cnn([C@H]3CC[C@H](C(=O)O)CC3)c2C(F)(F)F)[C@H]2C[C@H](C(C)(C)C)C2)c(Cl)c1] | trans-4-(4-((2-(2,6-dichloro-4-methylphenyl)-2-oxoethyl)(trans-3-(2-methyl-2-propanyl)cyclobutyl)carbamoyl)-5-(trifluoromethyl)-1H-pyrazol-1-yl)cyclohexanecarboxylic acid |
| 537 | 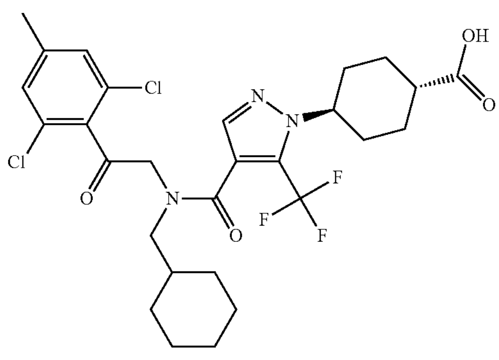 [SMILES: Cc1cc(Cl)c(C(=O)CN(CC2CCCCC2)C(=O)c2cnn([C@H]3CC[C@H](C(=O)O)CC3)c2C(F)(F)F)c(Cl)c1] | trans-4-(4-((cyclohexylmethyl)(2-(2,6-dichloro-4-methylphenyl)-2-oxoethyl)carbamoyl)-5-(trifluoromethyl)-1H-pyrazol-1-yl)cyclohexanecarboxylic acid |

-continued

| example | structure | name |
|---|---|---|
| 538 | 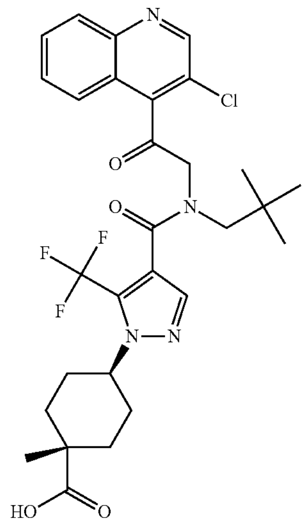 [SMILES: CC(C)(C)CN(CC(=O)c1c(Cl)cnc2ccccc12)C(=O)c1cnn([C@H]2CC[C@](C)(C(=O)O)CC2)c1C(F)(F)F] | trans-4-(4-((2-(3-chloro-4-quinolinyl)-2-oxoethyl)(2,2-dimethylpropyl)carbamoyl)-5-(trifluoromethyl)-1H-pyrazol-1-yl)-1-methylcyclohexanecarboxylic acid |
| 539 | 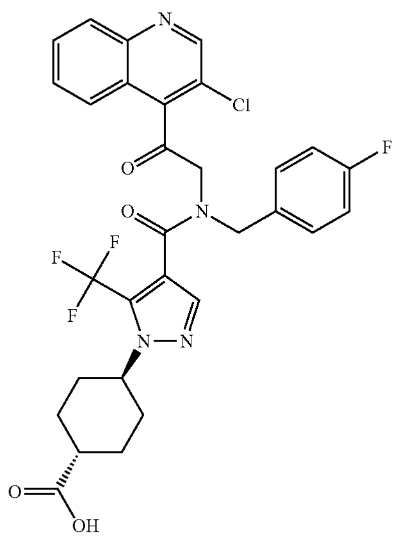 [SMILES: O=C(CN(Cc1ccc(F)cc1)C(=O)c1cnn([C@H]2CC[C@H](C(=O)O)CC2)c1C(F)(F)F)c1c(Cl)cnc2ccccc12] | trans-4-(4-((2-(3-chloro-4-quinolinyl)-2-oxoethyl)(4-fluorobenzyl)carbamoyl)-5-(trifluoromethyl)-1H-pyrazol-1-yl)cyclohexanecarboxylic acid |
| 541 | 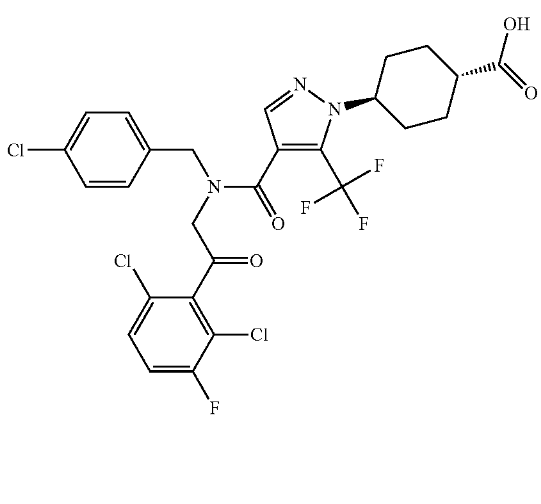 [SMILES: O=C(CN(Cc1ccc(Cl)cc1)C(=O)c1cnn([C@H]2CC[C@H](C(=O)O)CC2)c1C(F)(F)F)c1c(Cl)ccc(F)c1Cl] | trans-4-(4-((4-chlorobenzyl)(2-(2,6-dichloro-3-fluorophenyl)-2-oxoethyl)carbamoyl)-5-(trifluoromethyl)-1H-pyrazol-1-yl)cyclohexanecarboxylic acid |

| example | structure | name |
|---|---|---|
| 542 | 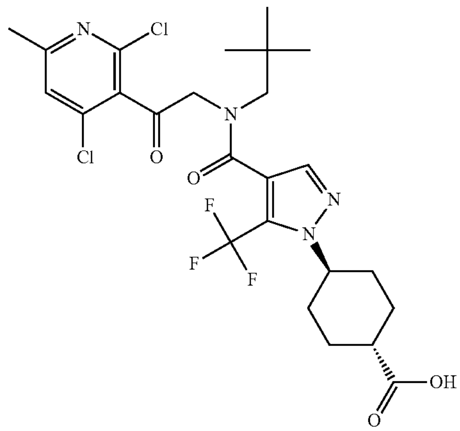 [SMILES: Cc1cc(Cl)c(C(=O)CN(CC(C)(C)C)C(=O)c2cnn([C@H]3CC[C@H](C(=O)O)CC3)c2C(F)(F)F)c(Cl)n1] | trans-4-(4-((2-(2,4-dichloro-6-methyl-3-pyridinyl)-2-oxoethyl)(2,2-dimethylpropyl)carbamoyl)-5-(trifluoromethyl)-1H-pyrazol-1-yl)cyclohexanecarboxylic acid |
| 543 | 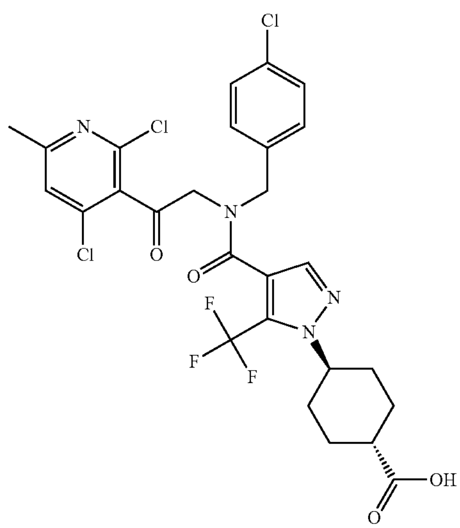 [SMILES: Cc1cc(Cl)c(C(=O)CN(Cc2ccc(Cl)cc2)C(=O)c2cnn([C@H]3CC[C@H](C(=O)O)CC3)c2C(F)(F)F)c(Cl)n1] | trans-4-(4-((4-chlorobenzyl)(2-(2,4-dichloro-6-methyl-3-pyridinyl)-2-oxoethyl)carbamoyl)-5-(trifluoromethyl)-1H-pyrazol-1-yl)cyclohexanecarboxylic acid |
| 544 | 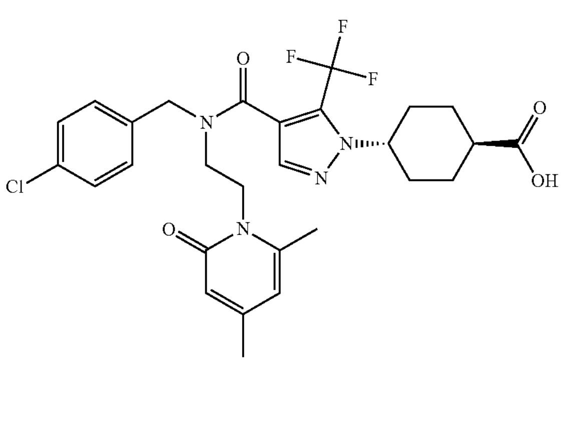 [SMILES: Cc1cc(C)n(CCN(Cc2ccc(Cl)cc2)C(=O)c2cnn([C@H]3CC[C@H](C(=O)O)CC3)c2C(F)(F)F)c(=O)c1] | trans-4-(4-((4-chlorobenzyl)(2-(4,6-dimethyl-2-oxo-1(2H)-pyridinyl)ethyl)carbamoyl)-5-(trifluoromethyl)-1H-pyrazol-1-yl)cyclohexanecarboxylic acid |

-continued

| example | structure | name |
|---|---|---|
| 545 | 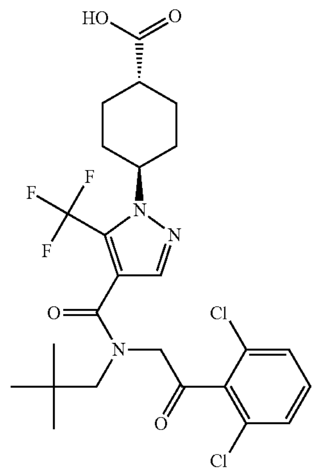 [SMILES: CC(C)(C)CN(CC(=O)c1c(Cl)cccc1Cl)C(=O)c1cnn([C@H]2CC[C@H](C(=O)O)CC2)c1C(F)(F)F] | trans-4-(4-((2-(2,6-dichlorophenyl)-2-oxoethyl)(2,2-dimethylpropyl)carbamoyl)-5-(trifluoromethyl)-1H-pyrazol-1-yl)cyclohexanecarboxylic acid |
| 546 | 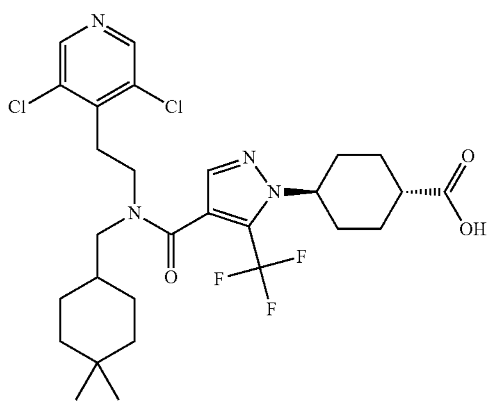 [SMILES: CC1(C)CCC(CN(CCc2c(Cl)cncc2Cl)C(=O)c2cnn([C@H]3CC[C@H](C(=O)O)CC3)c2C(F)(F)F)CC1] | trans-4-(4-((2-(3,5-dichloro-4-pyridinyl)ethyl)((4,4-dimethylcyclohexyl)methyl)carbamoyl)-5-(trifluoromethyl)-1H-pyrazol-1-yl)cyclohexanecarboxylic acid |
| 547 | 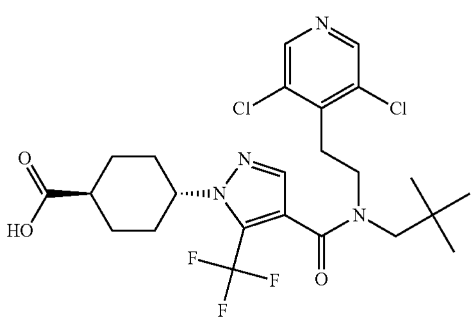 [SMILES: CC(C)(C)CN(CCc1c(Cl)cncc1Cl)C(=O)c1cnn([C@H]2CC[C@H](C(=O)O)CC2)c1C(F)(F)F] | trans-4-(4-((2-(3,5-dichloro-4-pyridinyl)ethyl)((2,2-dimethylpropyl)carbamoyl)-5-(trifluoromethyl)-1H-pyrazol-1-yl)cyclohexanecarboxylic acid |
| 548 | 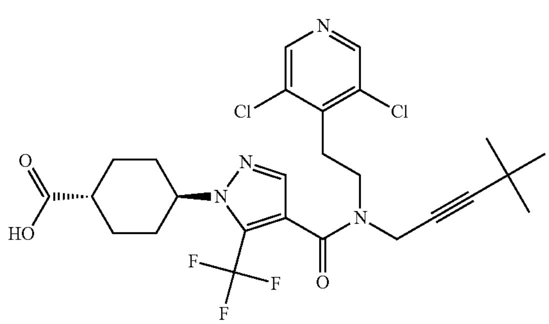 [SMILES: CC(C)(C)C#CCN(CCc1c(Cl)cncc1Cl)C(=O)c1cnn([C@H]2CC[C@H](C(=O)O)CC2)c1C(F)(F)F] | trans-4-(4-((2-(3,5-dichloro-4-pyridinyl)ethyl)(4,4-dimethyl-2-pentyn-1-yl)carbamoyl)-5-(trifluoromethyl)-1H-pyrazol-1-yl)cyclohexanecarboxylic acid |

-continued

| example | structure | name |
|---|---|---|
| 549 | 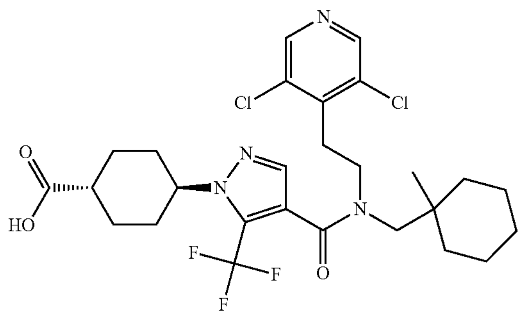 [SMILES: CC1(CN(CCc2c(Cl)cncc2Cl)C(=O)c2cnn([C@H]3CC[C@H](C(=O)O)CC3)c2C(F)(F)F)CCCCC1] | trans-4-(4-((2-(3,5-dichloro-4-pyridinyl)ethyl)((1-methylcyclohexyl)methyl)carbamoyl)-5-(trifluoromethyl)-1H-pyrazol-1-yl)cyclohexanecarboxylic acid |
| 550 | 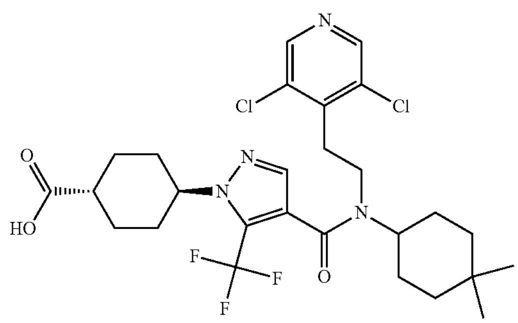 [SMILES: CC1(C)CCC(N(CCc2c(Cl)cncc2Cl)C(=O)c2cnn([C@H]3CC[C@H](C(=O)O)CC3)c2C(F)(F)F)CC1] | trans-4-(4-((2-(3,5-dichloro-4-pyridinyl)ethyl)(4,4-dimethylcyclohexyl)carbamoyl)-5-(trifluoromethyl)-1H-pyrazol-1-yl)cyclohexanecarboxylic acid |
| 552 | 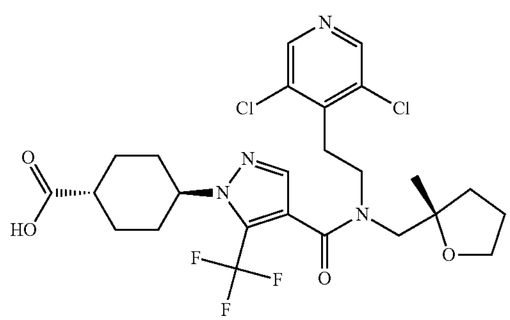 [SMILES: C[C@@]1(CN(CCc2c(Cl)cncc2Cl)C(=O)c2cnn([C@H]3CC[C@H](C(=O)O)CC3)c2C(F)(F)F)CCCO1] | trans-4-(4-((2-(3,5-dichloro-4-pyridinyl)ethyl)(((2S)-2-methyltetrahydro-2-furanyl)methyl)carbamoyl)-5-(trifluoromethyl)-1H-pyrazol-1-yl)cyclohexanecarboxylic acid |
| 553 | 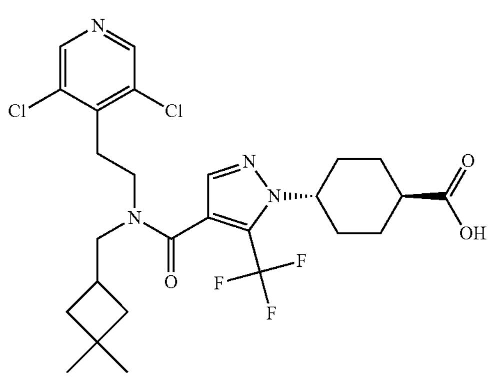 [SMILES: CC1(C)CC(CN(CCc2c(Cl)cncc2Cl)C(=O)c2cnn([C@H]3CC[C@H](C(=O)O)CC3)c2C(F)(F)F)C1] | trans-4-(4-((2-(3,5-dichloro-4-pyridinyl)ethyl)((3,3-dimethylcyclobutyl)methyl)carbamoyl)-5-(trifluoromethyl)-1H-pyrazol-1-yl)cyclohexanecarboxylic acid |

-continued

| example | structure | name |
|---|---|---|
| 554 | 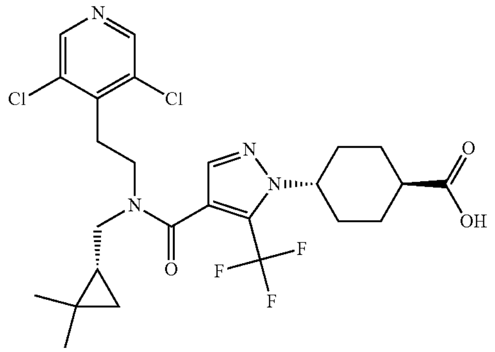 [SMILES: CC1(C)C[C@H]1CN(CCc1c(Cl)cncc1Cl)C(=O)c1cnn([C@H]2CC[C@H](C(=O)O)CC2)c1C(F)(F)F] | trans-4-(4-((2-(3,5-dichloro-4-pyridinyl)ethyl)(((1R)-2,2-dimethylcyclopropyl)methyl)carbamoyl)-5-(trifluoromethyl)-1H-pyrazol-1-yl)cyclohexanecarboxylic acid |
| 555 | 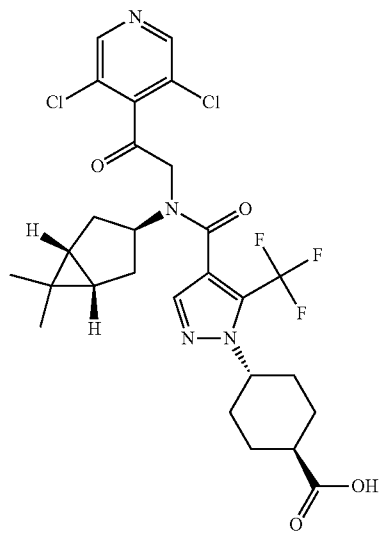 [SMILES: CC1(C)[C@@H]2C[C@@H](N(CC(=O)c3c(Cl)cncc3Cl)C(=O)c3cnn([C@H]4CC[C@H](C(=O)O)CC4)c3C(F)(F)F)C[C@@H]21] | trans-4-(4-((2-(3,5-dichloro-4-pyridinyl)-2-oxoethyl)((1R,3s,5S)-6,6-dimethylbicyclo[3.1.0]hex-3-yl)carbamoyl)-5-(trifluoromethyl)-1H-pyrazol-1-yl)cyclohexanecarboxylic acid |
| 556 | 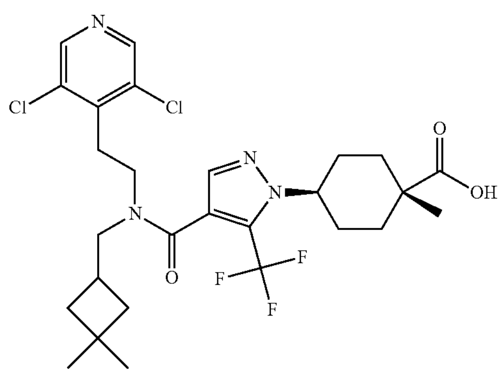 [SMILES: CC1(C)CC(CN(CCc2c(Cl)cncc2Cl)C(=O)c2cnn([C@H]3CC[C@](C)(C(=O)O)CC3)c2C(F)(F)F)C1] | trans-4-(4-((2-(3,5-dichloro-4-pyridinyl)ethyl)((3,3-dimethylcyclobutyl)methyl)carbamoyl)-5-(trifluoromethyl)-1H-pyrazol-1-yl)-1-methylcyclohexanecarboxylic acid |
| 557 | 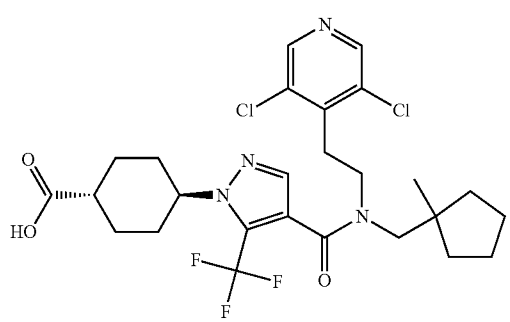 [SMILES: CC1(CN(CCc2c(Cl)cncc2Cl)C(=O)c2cnn([C@H]3CC[C@H](C(=O)O)CC3)c2C(F)(F)F)CCCC1] | trans-4-(4-((2-(3,5-dichloro-4-pyridinyl)ethyl)((1-methylcyclopentyl)methyl)carbamoyl)-5-(trifluoromethyl)-1H-pyrazol-1-yl)cyclohexanecarboxylic acid |

-continued

| example | structure | name |
|---|---|---|
| 558 | 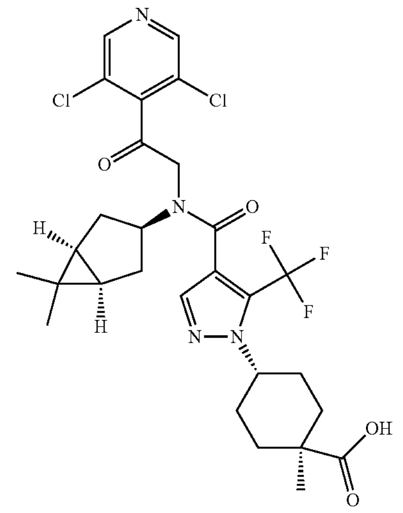 [SMILES: CC1(C)[C@@H]2C[C@H](N(CC(=O)c3c(Cl)cncc3Cl)C(=O)c3cnn([C@H]4CC[C@](C)(C(=O)O)CC4)c3C(F)(F)F)C[C@@H]21] | trans-4-(4-((2-(3,5-dichloro-4-pyridinyl)-2-oxoethyl)((1R,3r,5S)-6,6-dimethylbicyclo[3.1.0]hex-3-yl)carbamoyl)-5-(trifluoromethyl)-1H-pyrazol-1-yl)-1-methylcyclohexanecarboxylic acid |
| 559 | 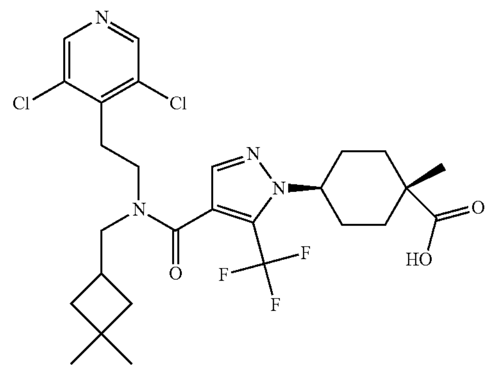 [SMILES: CC1(C)CC(CN(CCc2c(Cl)cncc2Cl)C(=O)c2cnn([C@H]3CC[C@](C)(C(=O)O)CC3)c2C(F)(F)F)C1] | trans-4-(4-((2-(3,5-dichloro-4-pyridinyl)-2-oxoethyl)((3,3-dimethylcyclobutyl)methyl)carbamoyl)-5-(trifluoromethyl)-1H-pyrazol-1-yl)-1-methylcyclohexanecarboxylic acid |
| 560 | 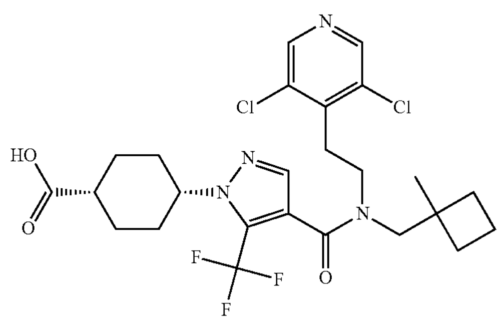 [SMILES: CC1(CN(CCc2c(Cl)cncc2Cl)C(=O)c2cnn([C@H]3CC[C@@H](C(=O)O)CC3)c2C(F)(F)F)CCC1] | cis-4-(4-((2-(3,5-dichloro-4-pyridinyl)ethyl)((1-methylcyclobutyl)methyl)carbamoyl)-5-(trifluoromethyl)-1H-pyrazol-1-yl)cyclohexanecarboxylic acid |
| 561 | 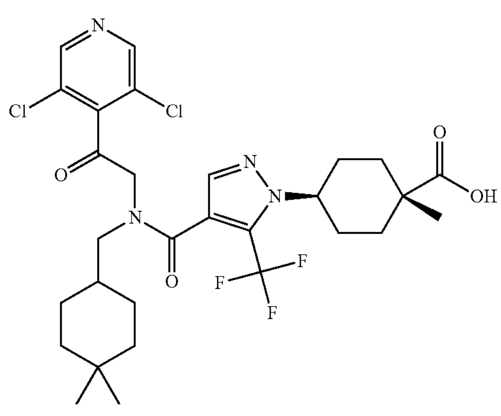 [SMILES: CC1(C)CCC(CN(CC(=O)c2c(Cl)cncc2Cl)C(=O)c2cnn([C@H]3CC[C@](C)(C(=O)O)CC3)c2C(F)(F)F)CC1] | trans-4-(4-((2-(3,5-dichloro-4-pyridinyl)-2-oxoethyl)((4,4-dimethylcyclohexyl)methyl)carbamoyl)-5-(trifluoromethyl)-1H-pyrazol-1-yl)-1-methylcyclohexanecarboxylic acid |

| example | structure | name |
|---|---|---|
| 562 | 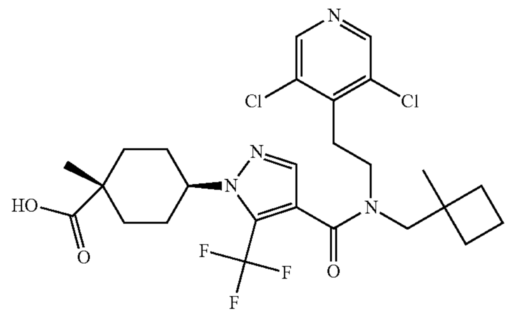 [SMILES: CC1(CN(CCc2c(Cl)cncc2Cl)C(=O)c2cnn([C@H]3CC[C@](C)(C(=O)O)CC3)c2C(F)(F)F)CCC1] | trans-4-(4-((2-(3,5-dichloro-4-pyridinyl)ethyl)((1-methylcyclobutyl)methyl)carbamoyl)-5-(trifluoromethyl)-1H-pyrazol-1-yl)-1-methylcyclohexanecarboxylic acid |
| 563 | 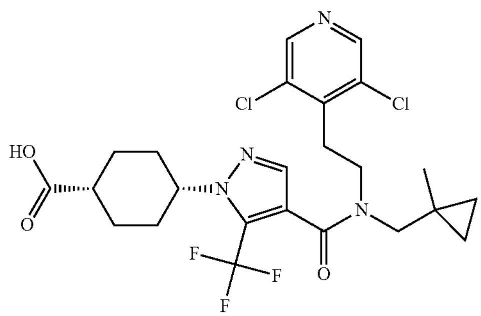 [SMILES: CC1(CN(CCc2c(Cl)cncc2Cl)C(=O)c2cnn([C@H]3CC[C@@H](C(=O)O)CC3)c2C(F)(F)F)CC1] | cis-4-(4-((2-(3,5-dichloro-4-pyridinyl)ethyl)((1-methylcyclopropyl)methyl)carbamoyl)-5-(trifluoromethyl)-1H-pyrazol-1-yl)cyclohexanecarboxylic acid |
| 564 | 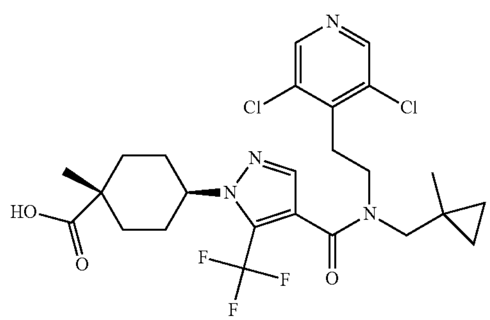 [SMILES: CC1(CN(CCc2c(Cl)cncc2Cl)C(=O)c2cnn([C@H]3CC[C@](C)(C(=O)O)CC3)c2C(F)(F)F)CC1] | trans-4-(4-((2-(3,5-dichloro-4-pyridinyl)ethyl)((1-methylcyclopropyl)methyl)carbamoyl)-5-(trifluoromethyl)-1H-pyrazol-1-yl)-1-methylcyclohexanecarboxylic acid |
| 565 | 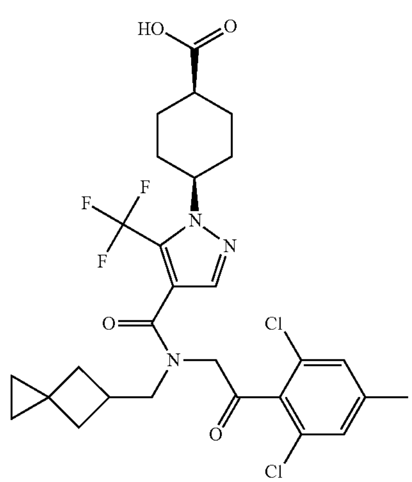 [SMILES: Cc1cc(Cl)c(C(=O)CN(CC2CC3(CC3)C2)C(=O)c2cnn([C@H]3CC[C@@H](C(=O)O)CC3)c2C(F)(F)F)c(Cl)c1] | cis-4-(4-((2-(2,6-dichloro-4-methylphenyl)-2-oxoethyl)(spiro[2.3]hex-5-ylmethyl)carbamoyl)-5-(trifluoromethyl)-1H-pyrazol-1-yl)cyclohexanecarboxylic acid |

-continued

| example | structure | name |
|---|---|---|
| 566 | 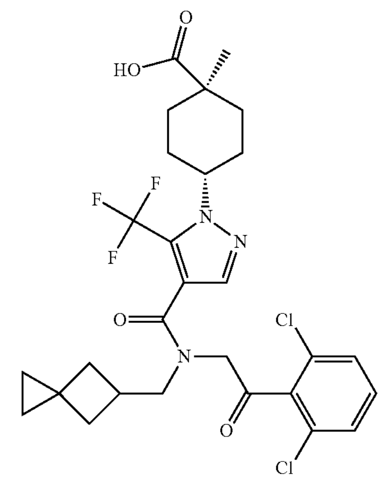 [SMILES: C[C@]1(C(=O)O)CC[C@H](n2ncc(C(=O)N(CC(=O)c3c(Cl)cccc3Cl)CC3CC4(CC4)C3)c2C(F)(F)F)CC1] | trans-4-(4-((2-(2,6-dichlorophenyl)-2-oxoethyl)(spiro[2.3]hex-5-ylmethyl)carbamoyl)-5-(trifluoromethyl)-1H-pyrazol-1-yl)-1-methylcyclohexanecarboxylic acid |
| 567 | 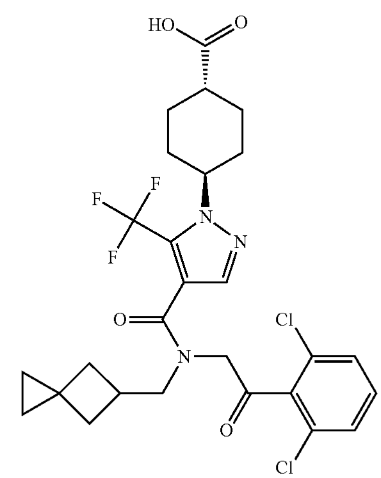 [SMILES: O=C(CN(CC1CC2(CC2)C1)C(=O)c1cnn([C@H]2CC[C@H](C(=O)O)CC2)c1C(F)(F)F)c1c(Cl)cccc1Cl] | trans-4-(4-((2-(2,6-dichlorophenyl)-2-oxoethyl)(spiro[2.3]hex-5-ylmethyl)carbamoyl)-5-(trifluoromethyl)-1H-pyrazol-1-yl)cyclohexanecarboxylic acid |
| 568 | 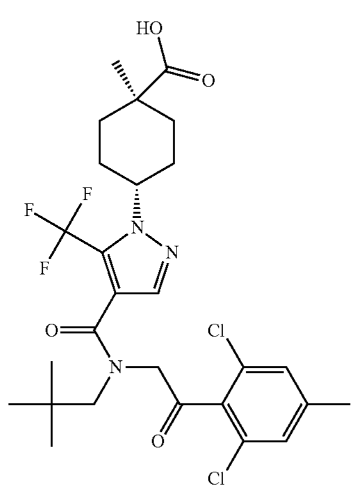 [SMILES: Cc1cc(Cl)c(C(=O)CN(CC(C)(C)C)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(2,2-dimethylpropyl)carbamoyl)-5-(trifluoromethyl)-1H-pyrazol-1-yl)-1-methylcyclohexanecarboxylic acid |

-continued

| example | structure | name |
|---|---|---|
| 569 | 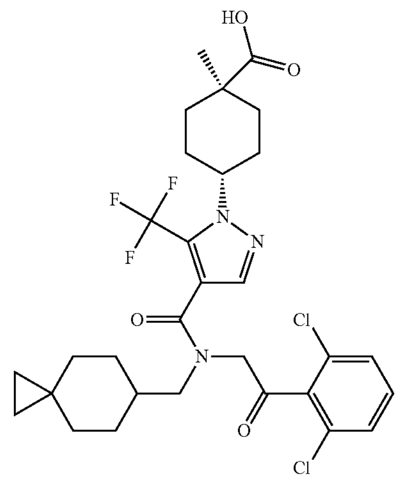 [SMILES: C[C@]1(C(=O)O)CC[C@H](n2ncc(C(=O)N(CC(=O)c3c(Cl)cccc3Cl)CC3CCC4(CC3)CC4)c2C(F)(F)F)CC1] | trans-4-(4-((2-(2,6-dichlorophenyl)-2-oxoethyl)(spiro[2.5]oct-6-ylmethyl)carbamoyl)-5-(trifluoromethyl)-1H-pyrazol-1-yl)-1-methylcyclohexanecarboxylic acid |
| 570 | 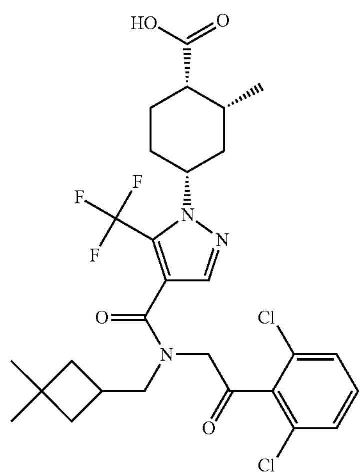 [SMILES: C[C@@H]1C[C@H](n2ncc(C(=O)N(CC(=O)c3c(Cl)cccc3Cl)CC3CC(C)(C)C3)c2C(F)(F)F)CC[C@@H]1C(=O)O] | (1S,2R,4R)-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 571 | 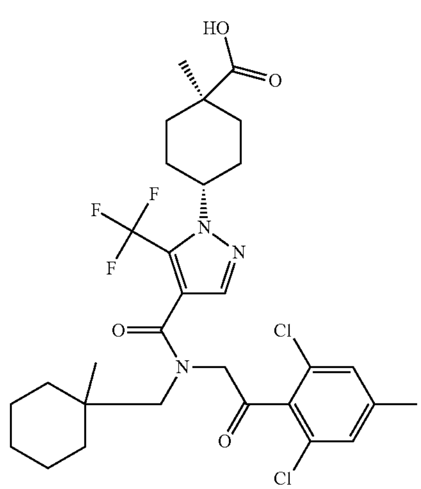 [SMILES: Cc1cc(Cl)c(C(=O)CN(CC2(C)CCCCC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)((1-methylcyclohexyl)methyl)carbamoyl)-5-(trifluoromethyl)-1H-pyrazol-1-yl)-1-methylcyclohexanecarboxylic acid |

| example | structure | name |
| --- | --- | --- |
| 572 | 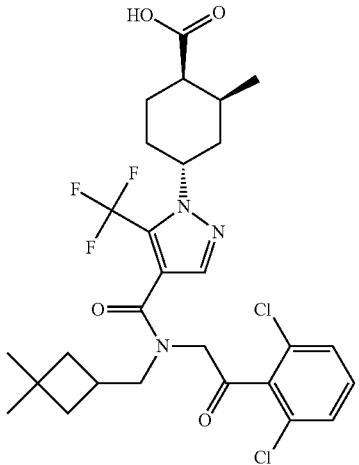 [SMILES: C[C@H]1C[C@H](n2ncc(C(=O)N(CC(=O)c3c(Cl)cccc3Cl)CC3CC(C)(C)C3)c2C(F)(F)F)CC[C@H]1C(=O)O] | (1S,2R,4S)-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 573 | 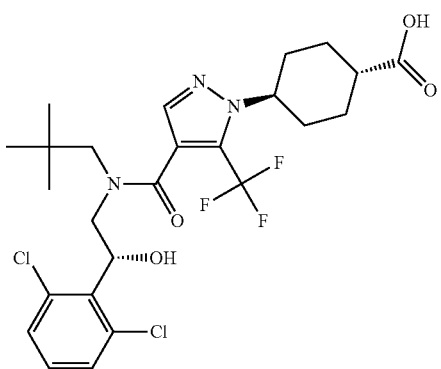 [SMILES: CC(C)(C)CN(C[C@H](O)c1c(Cl)cccc1Cl)C(=O)c1cnn([C@H]2CC[C@H](C(=O)O)CC2)c1C(F)(F)F] | trans-4-(4-(((2R)-2-(2,6-dichlorophenyl)-2-hydroxyethyl)(2,2-dimethylpropyl)carbamoyl)-5-(trifluoromethyl)-1H-pyrazol-1-yl)cyclohexanecarboxylic acid |
| 574 | 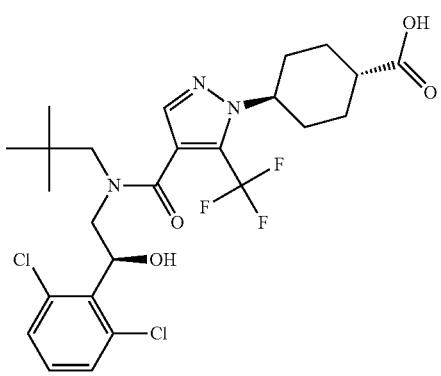 [SMILES: CC(C)(C)CN(C[C@@H](O)c1c(Cl)cccc1Cl)C(=O)c1cnn([C@H]2CC[C@H](C(=O)O)CC2)c1C(F)(F)F] | trans-4-(4-(((2S)-2-(2,6-dichlorophenyl)-2-hydroxyethyl)(2,2-dimethylpropyl)carbamoyl)-5-(trifluoromethyl)-1H-pyrazol-1-yl)cyclohexanecarboxylic acid |

| example | structure | name |
| --- | --- | --- |
| 575 | 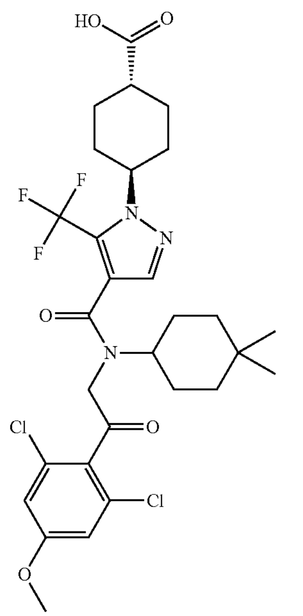 [SMILES: COc1cc(Cl)c(C(=O)CN(C(=O)c2cnn([C@H]3CC[C@H](C(=O)O)CC3)c2C(F)(F)F)C2CCC(C)(C)CC2)c(Cl)c1] | trans-4-(4-((2-(2,6-dichloro-4-methoxyphenyl)-2-oxoethyl)(4,4-dimethylcyclohexyl)carbamoyl)-5-(trifluoromethyl)-1H-pyrazol-1-yl)cyclohexanecarboxylic acid |
| 576 | 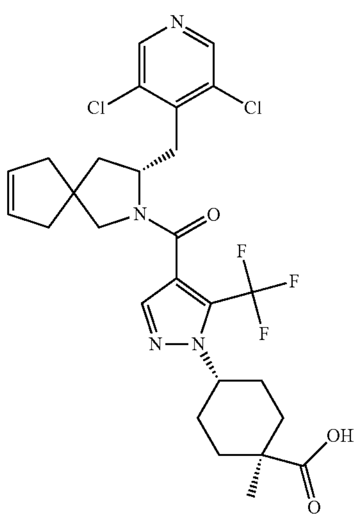 [SMILES: C[C@]1(C(=O)O)CC[C@H](n2ncc(C(=O)N3CC4(CC=CC4)C[C@@H]3Cc3c(Cl)cncc3Cl)c2C(F)(F)F)CC1] | trans-4-(4-(((3R)-3-((3,5-dichloro-4-pyridinyl)methyl)-2-azaspiro[4.4]non-7-en-2-yl)carbonyl)-5-(trifluoromethyl)-1H-pyrazol-1-yl)-1-methylcyclohexanecarboxylic acid |
| 577 | 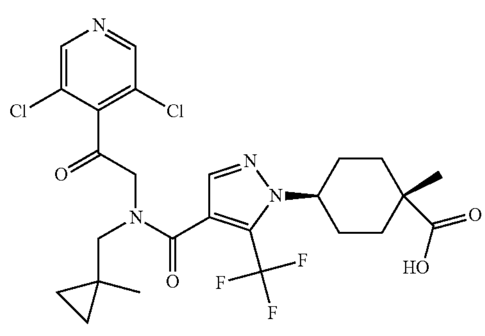 [SMILES: CC1(CN(CC(=O)c2c(Cl)cncc2Cl)C(=O)c2cnn([C@H]3CC[C@](C)(C(=O)O)CC3)c2C(F)(F)F)CC1] | trans-4-(4-((2-(3,5-dichloro-4-pyridinyl)-2-oxoethyl)((1-methylcyclopropyl)methyl)carbamoyl)-5-(trifluoromethyl)-1H-pyrazol-1-yl)-1-methylcyclohexanecarboxylic acid |

| example | structure | name |
|---|---|---|
| 578 | 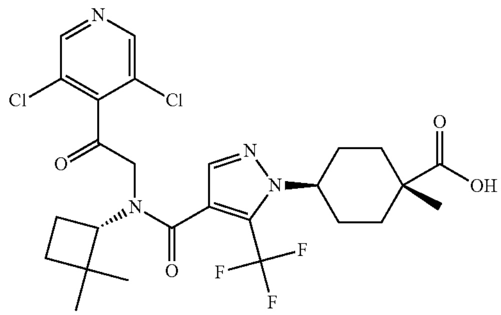 [SMILES: CC1(C)CC[C@@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)((1S)-2,2-dimethylcyclobutyl)carbamoyl)-5-(trifluoromethyl)-1H-pyrazol-1-yl)-1-methylcyclohexanecarboxylic acid |
| 579 | 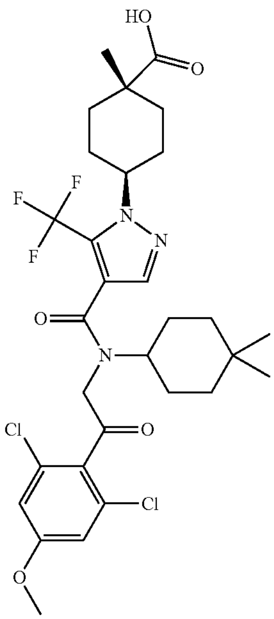 [SMILES: COc1cc(Cl)c(C(=O)CN(C(=O)c2cnn([C@H]3CC[C@](C)(C(=O)O)CC3)c2C(F)(F)F)C2CCC(C)(C)CC2)c(Cl)c1] | trans-4-(4-((2-(2,6-dichloro-4-methoxyphenyl)-2-oxoethyl)(4,4-dimethylcyclohexyl)carbamoyl)-5-(trifluoromethyl)-1H-pyrazol-1-yl)-1-methylcyclohexanecarboxylic acid |
| 580 | 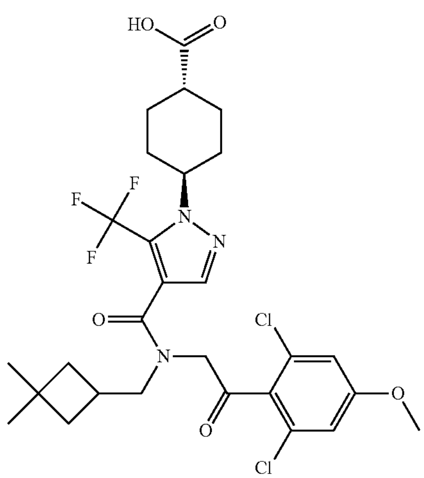 | trans-4-(4-((2-(2,6-dichloro-4-methoxyphenyl)-2-oxoethyl)((3,3-dimethylcyclobutyl)methyl)carbamoyl)-5-(trifluoromethyl)-1H-pyrazol-1-yl)cyclohexanecarboxylic acid |

| example | structure | name |
|---|---|---|
| 581 | 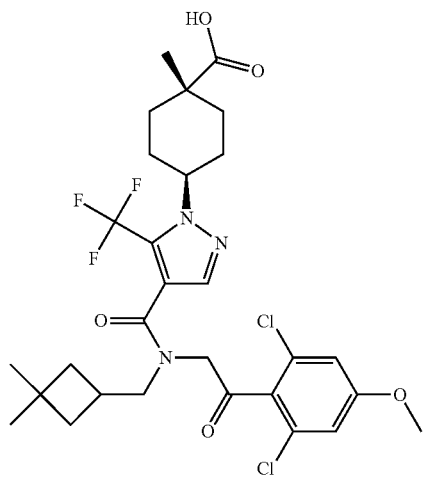 | trans-4-(4-((2-(2,6-dichloro-4-methoxyphenyl)-2-oxoethyl)((3,3-dimethylcyclohexyl)methyl)carbamoyl)-5-(trifluoromethyl)-1H-pyrazol-1-yl)-1-methylcyclohexanecarboxylic acid |
| 582 | 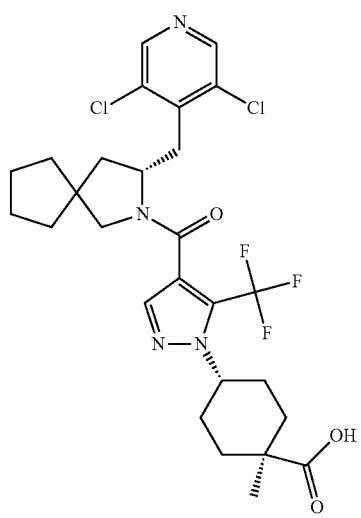 [SMILES: C[C@]1(C(=O)O)CC[C@H](n2ncc(C(=O)N3CC4(CCCC4)C[C@@H]3Cc3c(Cl)cncc3Cl)c2C(F)(F)F)CC1] | trans-4-(4-(((3R)-3-((3,5-dichloro-4-pyridinyl)methyl)-2-azaspiro[4.4]non-2-yl)carbonyl)-5-(trifluoromethyl)-1H-pyrazol-1-yl)-1-methylcyclohexanecarboxylic acid |
| 583 | 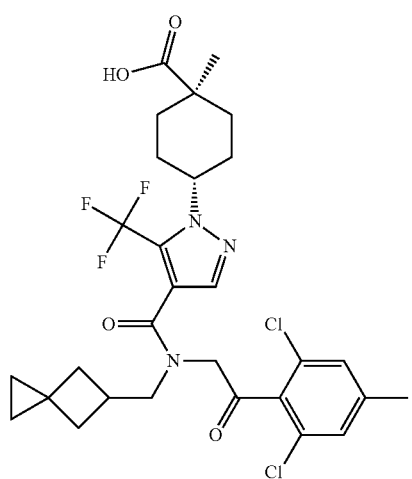 [SMILES: Cc1cc(Cl)c(C(=O)CN(CC2CC3(CC3)C2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(spiro[2.3]hex-5-ylmethyl)carbamoyl)-5-(trifluoromethyl)-1H-pyrazol-1-yl)-1-methylcyclohexanecarboxylic acid |

| example | structure | name |
| --- | --- | --- |
| 584 | 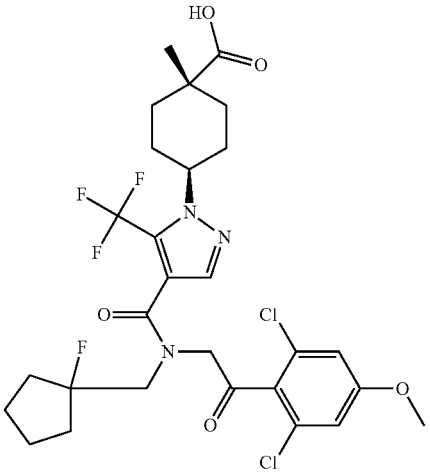 [SMILES: COc1cc(Cl)c(C(=O)CN(CC2(F)CCCC2)C(=O)c2cnn([C@H]3CC[C@](C)(C(=O)O)CC3)c2C(F)(F)F)c(Cl)c1] | trans-4-(4-((2-(2,6-dichloro-4-methoxyphenyl)-2-oxoethyl)((1-fluorocyclopentyl)methyl)carbamoyl)-5-(trifluoromethyl)-1H-pyrazol-1-yl)-1-methylcyclohexanecarboxylic acid |
| 585 | 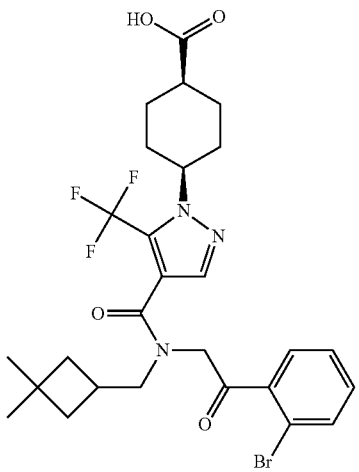 [SMILES: CC1(C)CC(CN(CC(=O)c2ccccc2Br)C(=O)c2cnn([C@H]3CC[C@@H](C(=O)O)CC3)c2C(F)(F)F)C1] | cis-4-(4-((2-(2-bromophenyl)-2-oxoethyl)((3,3-dimethylcyclobutyl)methyl)carbamoyl)-5-(trifluoromethyl)-1H-pyrazol-1-yl)cyclohexanecarboxylic acid |
| 586 | 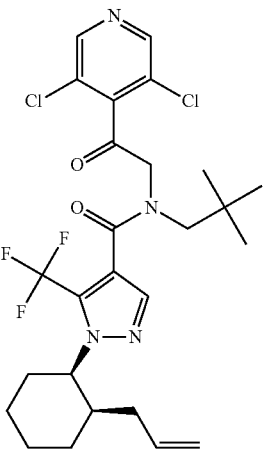 [SMILES: C=CC[C@H]1CCCC[C@H]1n1ncc(C(=O)N(CC(=O)c2c(Cl)cncc2Cl)CC(C)(C)C)c1C(F)(F)F] | N-(2-(3,5-dichloro-4-pyridinyl)-2-oxoethyl)-N-(2,2-dimethylpropyl)-1-((1S,2S)-2-(2-propen-1-yl)cyclohexyl)-5-(trifluoromethyl)-1H-pyrazole-4-carboxamide |

| example | structure | name |
|---|---|---|
| 587 | 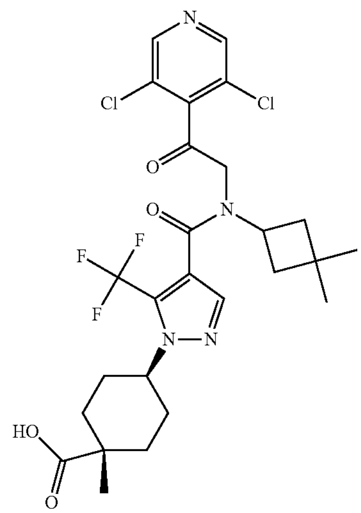 [SMILES: CC1(C)CC(N(CC(=O)c2c(Cl)cncc2Cl)C(=O)c2cnn([C@H]3CC[C@](C)(C(=O)O)CC3)c2C(F)(F)F)C1] | trans-4-(4-((2-(3,5-dichloro-4-pyridinyl)-2-oxoethyl)(3,3-dimethylcyclobutyl)carbamoyl)-5-(trifluoromethyl)-1H-pyrazol-1-yl)-1-methylcyclohexanecarboxylic acid |
| 588 | 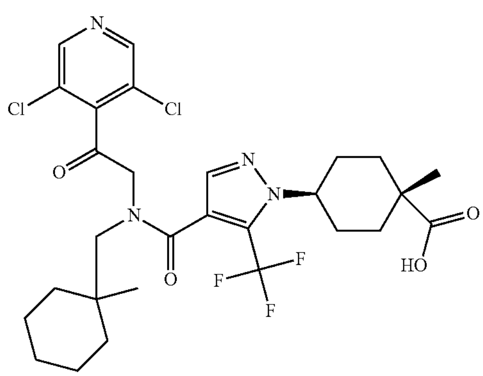 [SMILES: CC1(CN(CC(=O)c2c(Cl)cncc2Cl)C(=O)c2cnn([C@H]3CC[C@](C)(C(=O)O)CC3)c2C(F)(F)F)CCCCC1] | trans-4-(4-((2-(3,5-dichloro-4-pyridinyl)-2-oxoethyl)((1-methylcyclohexyl)methyl)carbamoyl)-5-(trifluoromethyl)-1H-pyrazol-1-yl)-1-methylcyclohexanecarboxylic acid |
| 589 | 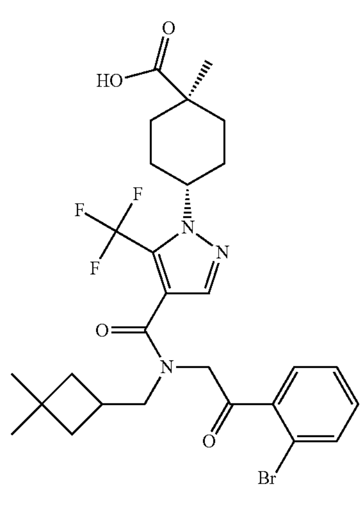 [SMILES: CC1(C)CC(CN(CC(=O)c2ccccc2Br)C(=O)c2cnn([C@H]3CC[C@](C)(C(=O)O)CC3)c2C(F)(F)F)C1] | trans-4-(4-((2-(2-bromophenyl)-2-oxoethyl)((3,3-dimethylcyclobutyl)methyl)carbamoyl)-5-(trifluoromethyl)-1H-pyrazol-1-yl)-1-methylcyclohexanecarboxylic acid |

| example | structure | name |
|---|---|---|
| 590 | 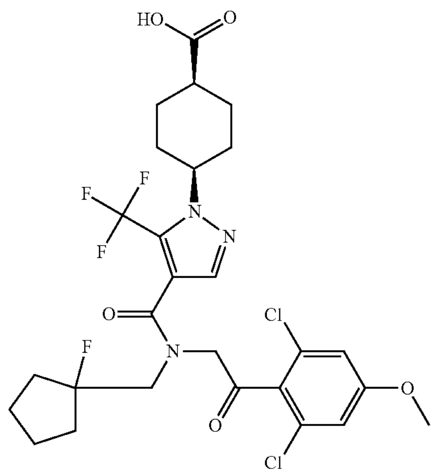 [SMILES: COc1cc(Cl)c(C(=O)CN(CC2(F)CCCC2)C(=O)c2cnn([C@H]3CC[C@@H](C(=O)O)CC3)c2C(F)(F)F)c(Cl)c1] | cis-4-(4-((2-(2,6-dichloro-4-methoxyphenyl)-2-oxoethyl)((1-fluorocyclopentyl)methyl)carbamoyl)-5-(trifluoromethyl)-1H-pyrazol-1-yl)cyclohexanecarboxylic acid |
| 591 | 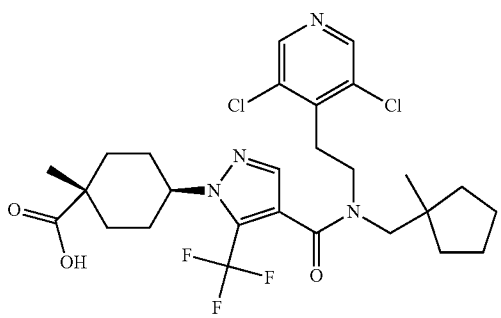 [SMILES: CC1(CN(CCc2c(Cl)cncc2Cl)C(=O)c2cnn([C@H]3CC[C@](C)(C(=O)O)CC3)c2C(F)(F)F)CCCC1] | trans-4-(4-((2-(3,5-dichloro-4-pyridinyl)ethyl)((1-methylcyclopentyl)methyl)carbamoyl)-5-(trifluoromethyl)-1H-pyrazol-1-yl)-1-methylcyclohexanecarboxylic acid |
| 592 | 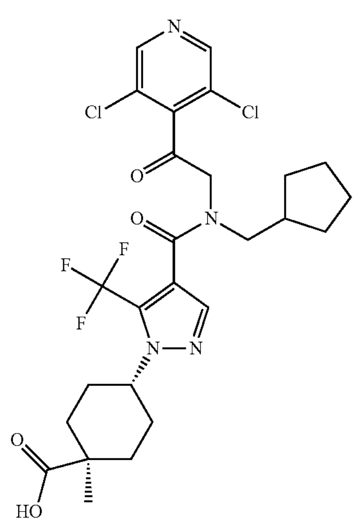 [SMILES: C[C@]1(C(=O)O)CC[C@H](n2ncc(C(=O)N(CC(=O)c3c(Cl)cncc3Cl)CC3CCCC3)c2C(F)(F)F)CC1] | trans-4-(4-((cyclopentylmethyl)(2-(3,5-dichloro-4-pyridinyl)-2-oxoethyl)carbamoyl)-5-(trifluoromethyl)-1H-pyrazol-1-yl)-1-methylcyclohexanecarboxylic acid |

-continued

| example | structure | name |
|---|---|---|
| 593 | 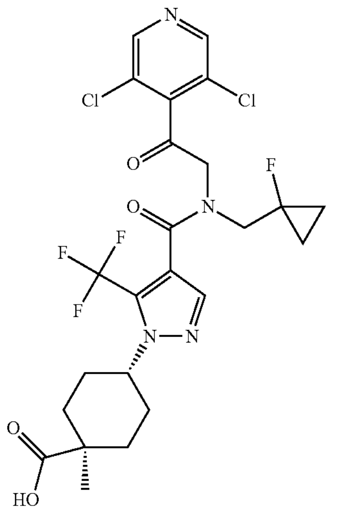 [SMILES: C[C@]1(C(=O)O)CC[C@H](n2ncc(C(=O)N(CC(=O)c3c(Cl)cncc3Cl)CC3(F)CC3)c2C(F)(F)F)CC1] | trans-4-(4-((2-(3,5-dichloro-4-pyridinyl)-2-oxoethyl)((1-fluorocyclopropyl)methyl)carbamoyl)-5-(trifluoromethyl)-1H-pyrazol-1-yl)-1-methylcyclohexanecarboxylic acid |
| 594 | 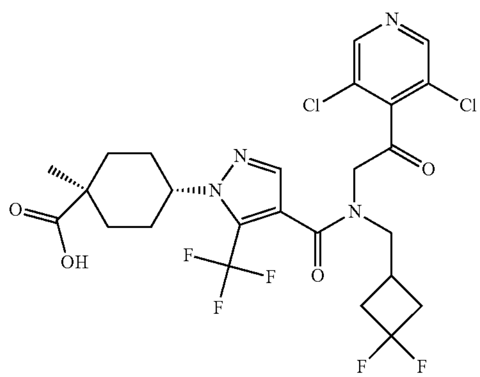 [SMILES: C[C@]1(C(=O)O)CC[C@H](n2ncc(C(=O)N(CC(=O)c3c(Cl)cncc3Cl)CC3CC(F)(F)C3)c2C(F)(F)F)CC1] | trans-4-(4-((2-(3,5-dichloro-4-pyridinyl)-2-oxoethyl)((3,3-difluorocyclobutyl)methyl)carbamoyl)-5-(trifluoromethyl)-1H-pyrazol-1-yl)-1-methylcyclohexanecarboxylic acid |
| 595 | 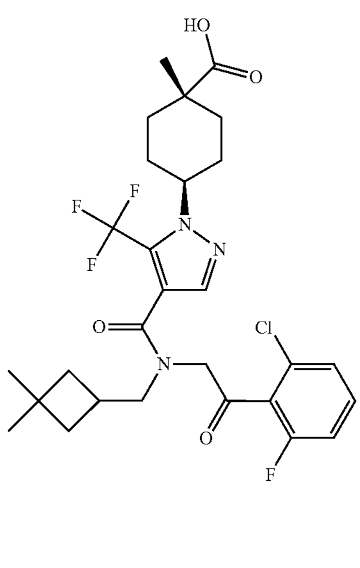 [SMILES: CC1(C)CC(CN(CC(=O)c2c(F)cccc2Cl)C(=O)c2cnn([C@H]3CC[C@](C)(C(=O)O)CC3)c2C(F)(F)F)C1] | trans-4-(4-((2-(2-chloro-6-fluorophenyl)-2-oxoethyl)((3,3-dimethylcyclobutyl)methyl)carbamoyl)-5-(trifluoromethyl)-1H-pyrazol-1-yl)-1-methylcyclohexanecarboxylic acid |

-continued

| example | structure | name |
|---|---|---|
| 596 | 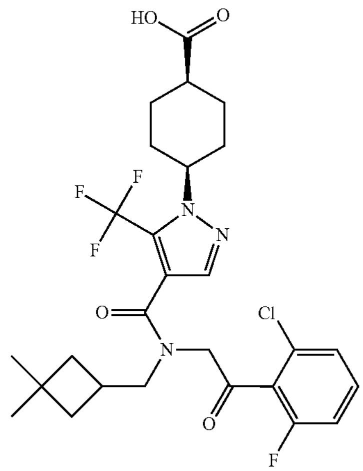 [SMILES: CC1(C)CC(CN(CC(=O)c2c(F)cccc2Cl)C(=O)c2cnn([C@H]3CC[C@@H](C(=O)O)CC3)c2C(F)(F)F)C1] | cis-4-(4-((2-(2-chloro-6-fluorophenyl)-2-oxoethyl)((3,3-dimethylcyclobutyl)methyl)carbamoyl)-5-(trifluoromethyl)-1H-pyrazol-1-yl)cyclohexanecarboxylic acid |
| 597 | 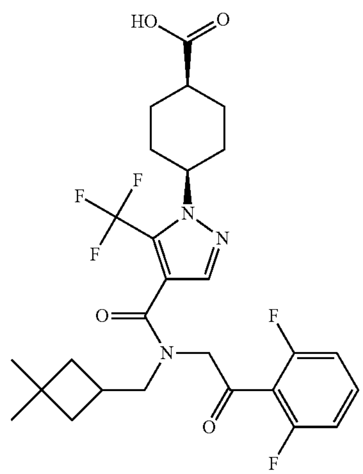 [SMILES: CC1(C)CC(CN(CC(=O)c2c(F)cccc2F)C(=O)c2cnn([C@H]3CC[C@@H](C(=O)O)CC3)c2C(F)(F)F)C1] | cis-4-(4-((2-(2,6-difluorophenyl)-2-oxoethyl)((3,3-dimethylcyclobutyl)methyl)carbamoyl)-5-(trifluoromethyl)-1H-pyrazol-1-yl)cyclohexanecarboxylic acid |
| 598 | 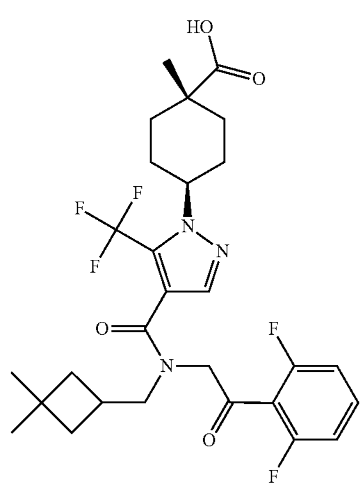 [SMILES: CC1(C)CC(CN(CC(=O)c2c(F)cccc2F)C(=O)c2cnn([C@H]3CC[C@](C)(C(=O)O)CC3)c2C(F)(F)F)C1] | trans-4-(4-((2-(2,6-difluorophenyl)-2-oxoethyl)((3,3-dimethylcyclobutyl)methyl)carbamoyl)-5-(trifluoromethyl)-1H-pyrazol-1-yl)-1-methylcyclohexanecarboxylic acid |

| example | structure | name |
| --- | --- | --- |
| 599 | 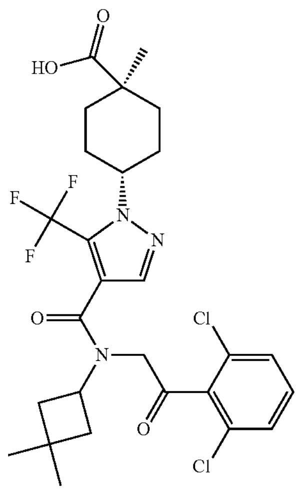 [SMILES: CC1(C)CC(N(CC(=O)c2c(Cl)cccc2Cl)C(=O)c2cnn([C@H]3CC[C@](C)(C(=O)O)CC3)c2C(F)(F)F)C1] | trans-4-(4-((2-(2,6-dichlorophenyl)-2-oxoethyl)(3,3-dimethylcyclobutyl)carbamoyl)-5-(trifluoromethyl)-1H-pyrazol-1-yl)-1-methylcyclohexanecarboxylic acid |
| 600 | 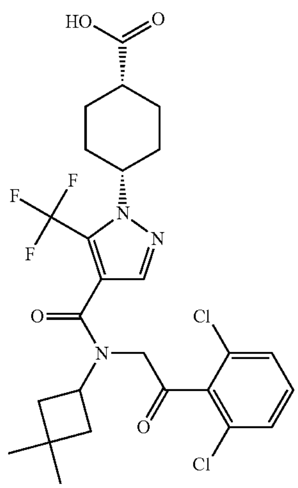 [SMILES: CC1(C)CC(N(CC(=O)c2c(Cl)cccc2Cl)C(=O)c2cnn([C@H]3CC[C@@H](C(=O)O)CC3)c2C(F)(F)F)C1] | cis-4-(4-((2-(2,6-dichlorophenyl)-2-oxoethyl)(3,3-dimethylcyclobutyl)carbamoyl)-5-(trifluoromethyl)-1H-pyrazol-1-yl)cyclohexanecarboxylic acid |
| 601 | 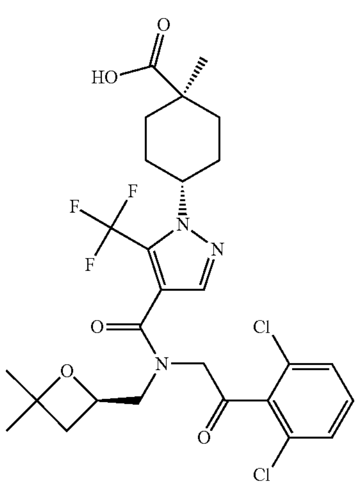 [SMILES: CC1(C)C[C@H](CN(CC(=O)c2c(Cl)cccc2Cl)C(=O)c2cnn([C@H]3CC[C@](C)(C(=O)O)CC3)c2C(F)(F)F)O1] | trans-4-(4-((2-(2,6-dichlorophenyl)-2-oxoethyl)(((2R)-4,4-dimethyl-2-oxetanyl)methyl)carbamoyl)-5-(trifluoromethyl)-1H-pyrazol-1-yl)-1-methylcyclohexanecarboxylic acid |

-continued

| example | structure | name |
| --- | --- | --- |
| 602 | 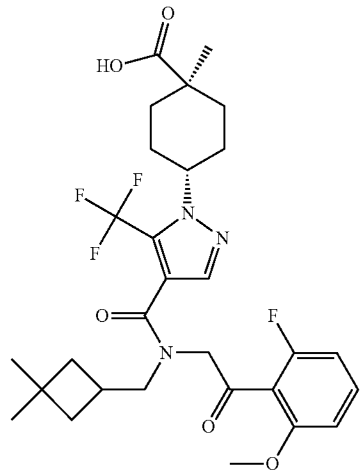 [SMILES: COc1cccc(F)c1C(=O)CN(CC1CC(C)(C)C1)C(=O)c1cnn([C@H]2CC[C@](C)(C(=O)O)CC2)c1C(F)(F)F] | trans-4-(4-(((3,3-dimethylcyclobutyl)methyl)(2-(2-fluoro-6-methoxyphenyl)-2-oxoethyl)carbamoyl)-5-(trifluoromethyl)-1H-pyrazol-1-yl)-1-methylcyclohexanecarboxylic acid |
| 603 | 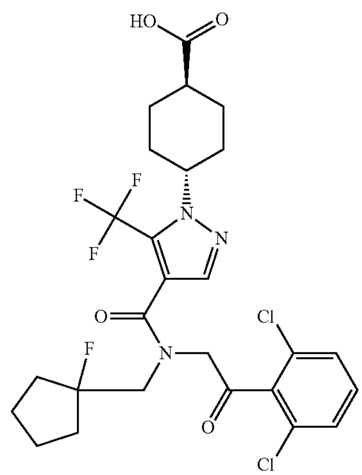 [SMILES: O=C(CN(CC1(F)CCCC1)C(=O)c1cnn([C@H]2CC[C@H](C(=O)O)CC2)c1C(F)(F)F)c1c(Cl)cccc1Cl] | cis-4-(4-((2-(2,6-dichlorophenyl)-2-oxoethyl)((1-fluorocyclopentyl)methyl)carbamoyl)-5-(trifluoromethyl)-1H-pyrazol-1-yl)cyclohexanecarboxylic acid |
| 604 | 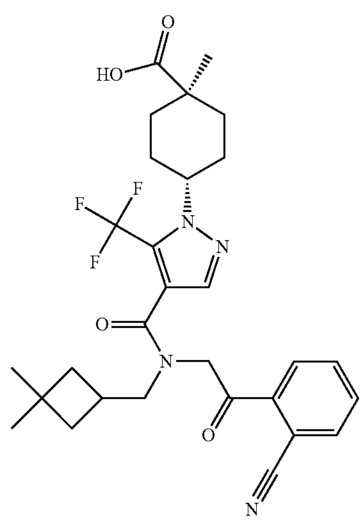 [SMILES: CC1(C)CC(CN(CC(=O)c2ccccc2C#N)C(=O)c2cnn([C@H]3CC[C@](C)(C(=O)O)CC3)c2C(F)(F)F)C1] | trans-4-(4-((2-(2-cyanophenyl)-2-oxoethyl)((3,3-dimethylcyclobutyl)methyl)carbamoyl)-5-(trifluoromethyl)-1H-pyrazol-1-yl)-1-methylcyclohexanecarboxylic acid |

| example | structure | name |
| --- | --- | --- |
| 605 | 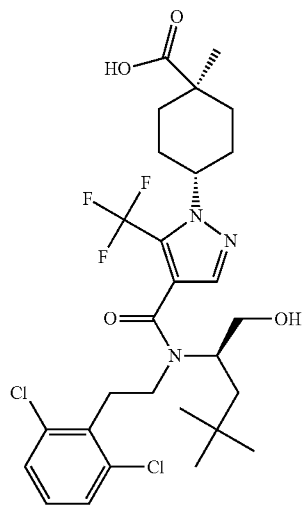 [SMILES: CC(C)(C)C[C@H](CO)N(CCc1c(Cl)cccc1Cl)C(=O)c1cnn([C@H]2CC[C@](C)(C(=O)O)CC2)c1C(F)(F)F] | trans-4-(4-((2-(2,6-dichlorophenyl)ethyl)((2R)-1-hydroxy-4,4-dimethyl-2-pentanyl)carbamoyl)-5-(trifluoromethyl)-1H-pyrazol-1-yl)-1-methylcyclohexanecarboxylic acid |
| 606 | 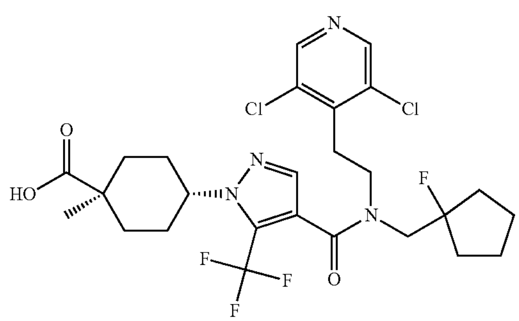 [SMILES: C[C@]1(C(=O)O)CC[C@H](n2ncc(C(=O)N(CCc3c(Cl)cncc3Cl)CC3(F)CCCC3)c2C(F)(F)F)CC1] | trans-4-(4-((2-(3,5-dichloro-4-pyridinyl)ethyl)((1-fluorocyclopentyl)methyl)carbamoyl)-5-(trifluoromethyl)-1H-pyrazol-1-yl)-1-methylcyclohexanecarboxylic acid |
| 607 | 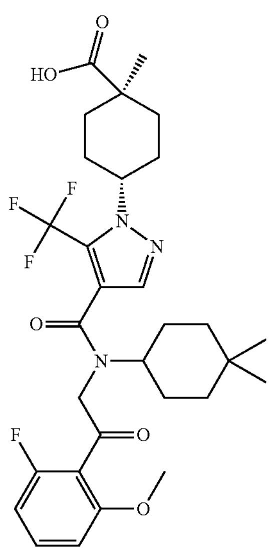 [SMILES: COc1cccc(F)c1C(=O)CN(C(=O)c1cnn([C@H]2CC[C@](C)(C(=O)O)CC2)c1C(F)(F)F)C1CCC(C)(C)CC1] | trans-4-(4-((4,4-dimethylcyclohexyl)(2-(2-fluoro-6-methoxyphenyl)-2-oxoethyl)carbamoyl)-5-(trifluoromethyl)-1H-pyrazol-1-yl)-1-methylcyclohexanecarboxylic acid |

| example | structure | name |
| --- | --- | --- |
| 608 | 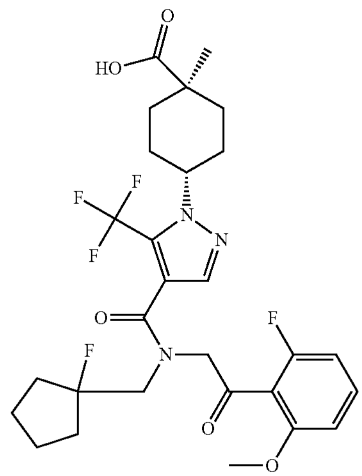 [SMILES: COc1cccc(F)c1C(=O)CN(CC1(F)CCCC1)C(=O)c1cnn([C@H]2CC[C@](C)(C(=O)O)CC2)c1C(F)(F)F] | trans-4-(4-(((1-fluorocyclopentyl)methyl)(2-(2-fluoro-6-methoxyphenyl)-2-oxoethyl)carbamoyl)-5-(trifluoromethyl)-1H-pyrazol-1-yl)-1-methylcyclohexanecarboxylic acid |
| 609 | 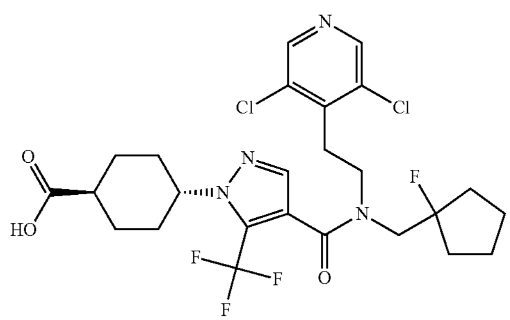 [SMILES: O=C(c1cnn([C@H]2CC[C@H](C(=O)O)CC2)c1C(F)(F)F)N(CCc1c(Cl)cncc1Cl)CC1(F)CCCC1] | cis-4-(4-((2-(3,5-dichloro-4-pyridinyl)ethyl)((1-fluorocyclopentyl)methyl)carbamoyl)-5-(trifluoromethyl)-1H-pyrazol-1-yl)cyclohexanecarboxylic acid |
| 610 | 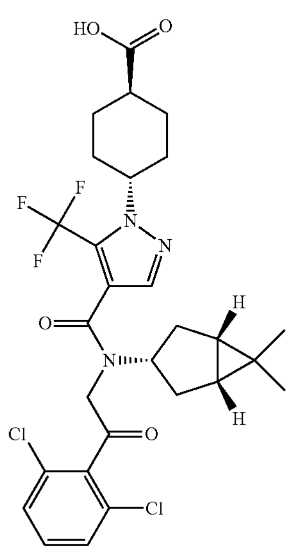 [SMILES: CC1(C)[C@@H]2C[C@H](N(CC(=O)c3c(Cl)cccc3Cl)C(=O)c3cnn([C@H]4CC[C@H](C(=O)O)CC4)c3C(F)(F)F)C[C@@H]21] | cis-4-(4-((2-(2,6-dichlorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)cyclohexanecarboxylic acid |

-continued

| example | structure | name |
|---|---|---|
| 611 | 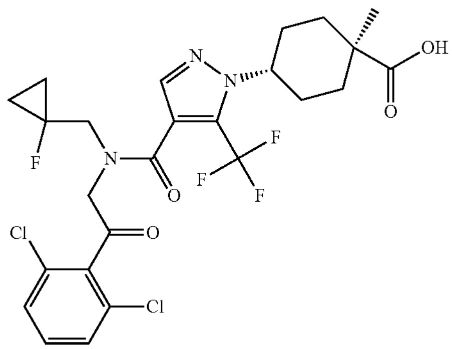 [SMILES: C[C@]1(C(=O)O)CC[C@H](n2ncc(C(=O)N(CC(=O)c3c(Cl)cccc3Cl)CC3(F)CC3)c2C(F)(F)F)CC1] | trans-4-(4-((2-(2,6-dichlorophenyl)-2-oxoethyl)((1-fluorocyclopropyl)methyl)carbamoyl)-5-(trifluoromethyl)-1H-pyrazol-1-yl)-1-methylcyclohexanecarboxylic acid |
| 612 | 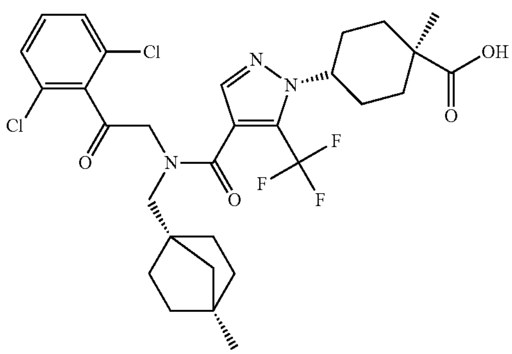 | trans-4-(4-((2-(2,6-dichlorophenyl)-2-oxoethyl)(((1r,4r)-4-methylbicyclo[2.2.1]hept-1-yl)methyl)carbamoyl)-5-(trifluoromethyl)-1H-pyrazol-1-yl)-1-methylcyclohexanecarboxylic acid |
| 613 | 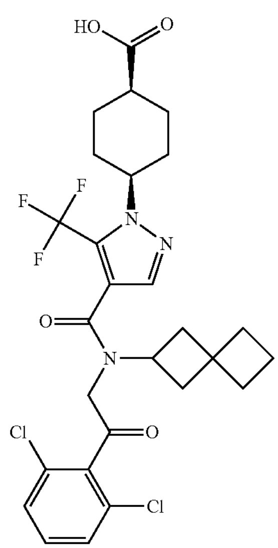 [SMILES: O=C(CN(C(=O)c1cnn([C@H]2CC[C@@H](C(=O)O)CC2)c1C(F)(F)F)C1CC2(CCC2)C1)c1c(Cl)cccc1Cl] | cis-4-(4-((2-(2,6-dichlorophenyl)-2-oxoethyl)(spiro[3.3]hept-2-yl)carbamoyl)-5-(trifluoromethyl)-1H-pyrazol-1-yl)cyclohexanecarboxylic acid |

| example | structure | name |
|---|---|---|
| 614 | 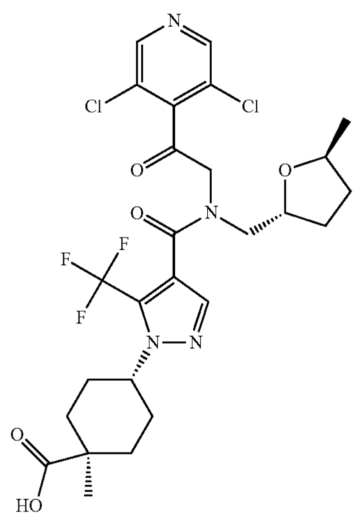 [SMILES: C[C@H]1CC[C@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2R,5R)-5-methyltetrahydro-2-furanyl)methyl)carbamoyl)-5-(trifluoromethyl)-1H-pyrazol-1-yl)-1-methylcyclohexanecarboxylic acid |
| 615 | 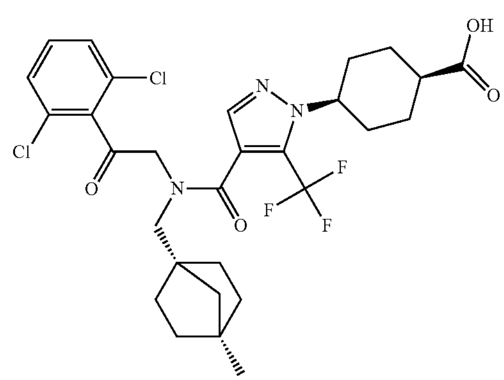 [SMILES: C[C@]12CC[C@](CN(CC(=O)c3c(Cl)cccc3Cl)C(=O)c3cnn([C@H]4CC[C@@H](C(=O)O)CC4)c3C(F)(F)F)(CC1)C2] | cis-4-(4-((2-(2,6-dichlorophenyl)-2-oxoethyl)(((1r,4r)-4-methylbicyclo[2.2.1]hept-1-yl)methyl)carbamoyl)-5-(trifluoromethyl)-1H-pyrazol-1-yl)cyclohexanecarboxylic acid |
| 616 | 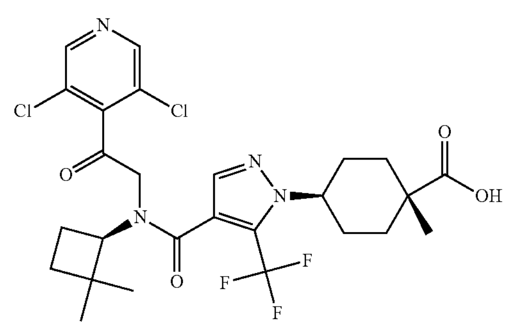 [SMILES: CC1(C)CC[C@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)((1R)-2,2-dimethylcyclobutyl)carbamoyl)-5-(trifluoromethyl)-1H-pyrazol-1-yl)-1-methylcyclohexanecarboxylic acid |
| 617 | 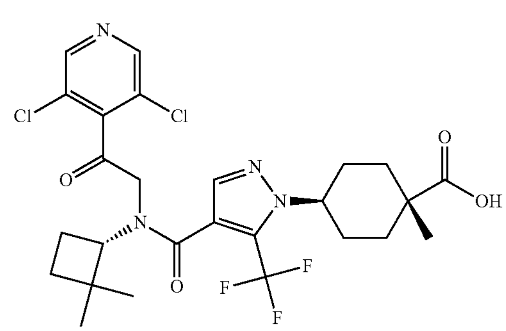 [SMILES: CC1(C)CC[C@@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)((1S)-2,2-dimethylcyclobutyl)carbamoyl)-5-(trifluoromethyl)-1H-pyrazol-1-yl)-1-methylcyclohexanecarboxylic acid |

-continued

| example | structure | name |
|---|---|---|
| 618 | 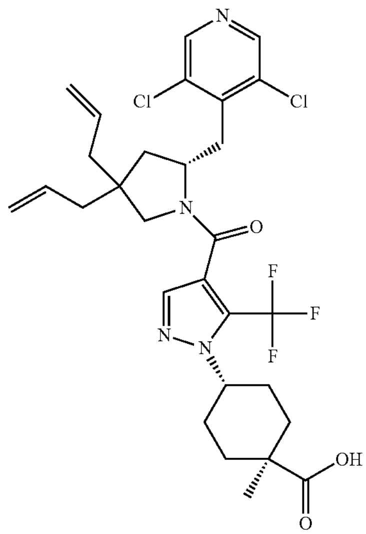 [SMILES: C=CCC1(CC=C)C[C@H](Cc2c(Cl)cncc2Cl)N(C(=O)c2cnn([C@H]3CC[C@](C)(C(=O)O)CC3)c2C(F)(F)F)C1] | trans-4-(4-(((2R)-2-((3,5-dichloro-4-pyridinyl)methyl)-4,4-di(2-propen-1-yl)-1-pyrrolidinyl)carbonyl)-5-(trifluoromethyl)-1H-pyrazol-1-yl)-1-methylcyclohexanecarboxylic acid |
| 619 | 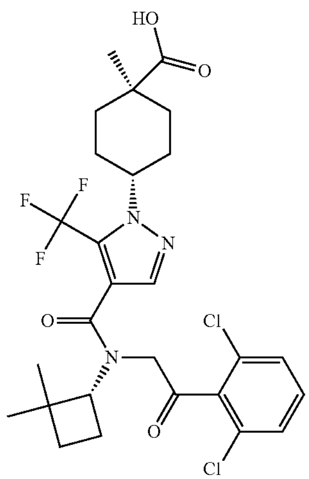 [SMILES: CC1(C)CC[C@H]1N(CC(=O)c1c(Cl)cccc1Cl)C(=O)c1cnn([C@H]2CC[C@](C)(C(=O)O)CC2)c1C(F)(F)F] | trans-4-(4-((2-(2,6-dichlorophenyl)-2-oxoethyl)((1S)-spiro[2.4]hept-1-yl)carbamoyl)-5-(trifluoromethyl)-1H-pyrazol-1-yl)-1-methylcyclohexanecarboxylic acid |
| 620 | 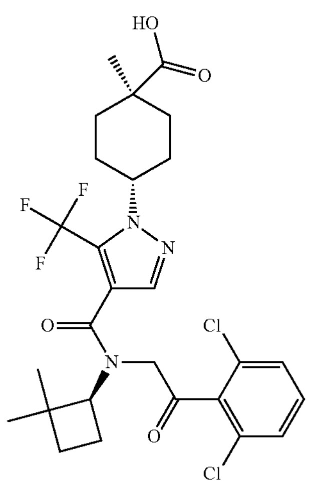 [SMILES: CC1(C)CC[C@@H]1N(CC(=O)c1c(Cl)cccc1Cl)C(=O)c1cnn([C@H]2CC[C@](C)(C(=O)O)CC2)c1C(F)(F)F] | trans-4-(4-((2-(2,6-dichlorophenyl)-2-oxoethyl)((1S)-spiro[2.4]hept-1-yl)carbamoyl)-5-(trifluoromethyl)-1H-pyrazol-1-yl)-1-methylcyclohexanecarboxylic acid |

-continued

| example | structure | name |
|---|---|---|
| 621 | 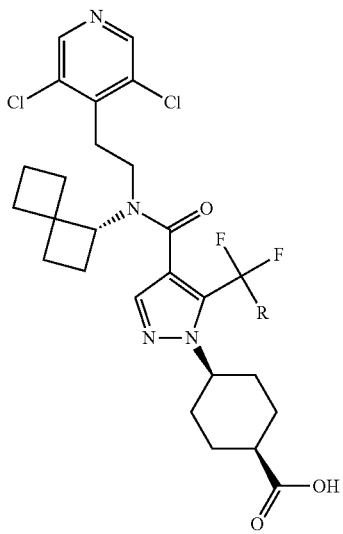 | cis-4-(4-((2-(3,5-dichloro-4-pyridinyl)ethyl)((1R)-spiro[3.3]hept-1-yl)carbamoyl)-5-(trifluoromethyl)-1H-pyrazol-1-yl)cyclohexanecarboxylic acid |
| 622 | 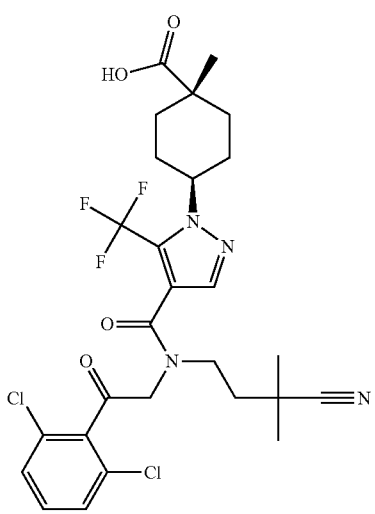 [SMILES: CC(C)(C#N)CCN(CC(=O)c1c(Cl)cccc1Cl)C(=O)c1cnn([C@H]2CC[C@](C)(C(=O)O)CC2)c1C(F)(F)F] | trans-4-(4-((3-cyano-3-methylbutyl)(2-(2,6-dichlorophenyl)-2-oxoethyl)carbamoyl)-5-(trifluoromethyl)-1H-pyrazol-1-yl)-1-methylcyclohexanecarboxylic acid |
| 623 | 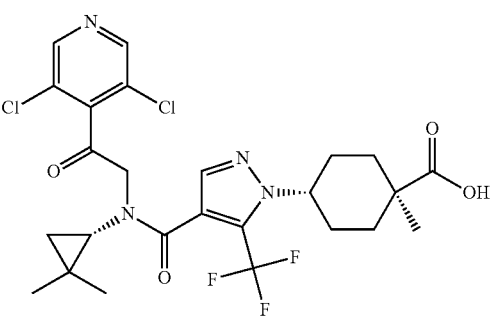 [SMILES: CC1(C)C[C@@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)((1S)-2,2-dimethylcyclopropyl)carbamoyl)-5-(trifluoromethyl)-1H-pyrazol-1-yl)-1-methylcyclohexanecarboxylic acid |

-continued

| example | structure | name |
|---|---|---|
| 624 | 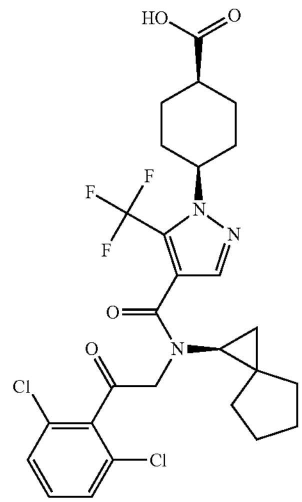 [SMILES: O=C(CN(C(=O)c1cnn([C@H]2CC[C@@H](C(=O)O)CC2)c1C(F)(F)F)[C@H]1CC12CCCC2)c1c(Cl)cccc1Cl] | cis-4-(4-((2-(2,6-dichlorophenyl)-2-oxoethyl)((1S)-spiro[2.4]hept-1-yl)carbamoyl)-5-(trifluoromethyl)-1H-pyrazol-1-yl)cyclohexanecarboxylic acid |
| 625 | 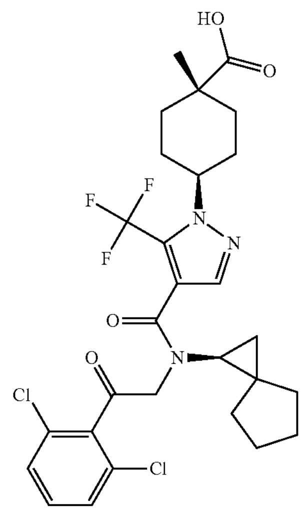 [SMILES: C[C@]1(C(=O)O)CC[C@H](n2ncc(C(=O)N(CC(=O)c3c(Cl)cccc3Cl)[C@H]3CC34CCCC4)c2C(F)(F)F)CC1] | trans-4-(4-((2-(2,6-dichlorophenyl)-2-oxoethyl)((1S)-spiro[2.4]hept-1-yl)carbamoyl)-5-(trifluoromethyl)-1H-pyrazol-1-yl)-1-methylcyclohexanecarboxylic acid |
| 626 | 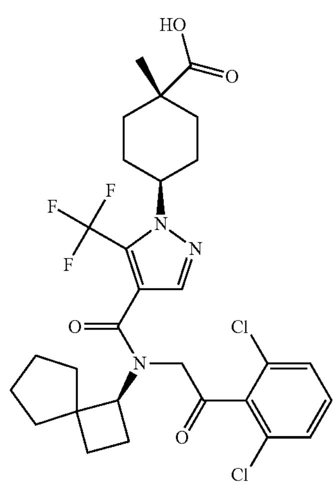 [SMILES: C[C@]1(C(=O)O)CC[C@H](n2ncc(C(=O)N(CC(=O)c3c(Cl)cccc3Cl)[C@H]3CCC34CCCC4)c2C(F)(F)F)CC1] | trans-4-(4-((2-(2,6-dichlorophenyl)-2-oxoethyl)((1S)-spiro[2.4]oct-1-yl)carbamoyl)-5-(trifluoromethyl)-1H-pyrazol-1-yl)-1-methylcyclohexanecarboxylic acid |

| example | structure | name |
| --- | --- | --- |
| 627 | 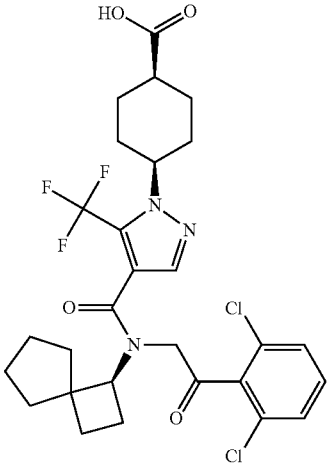 [SMILES: O=C(CN(C(=O)c1cnn([C@H]2CC[C@@H](C(=O)O)CC2)c1C(F)(F)F)[C@H]1CCC12CCCC2)c1c(Cl)cccc1Cl] | cis-4-(4-((2-(2,6-dichlorophenyl)-2-oxoethyl)(((1R)-spiro[3.4]oct-1-yl)carbamoyl)-5-(trifluoromethyl)-1H-pyrazol-1-yl)cyclohexanecarboxylic acid |
| 628 | 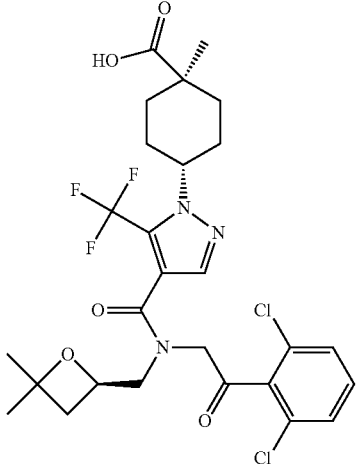 [SMILES: CC1(C)C[C@H](CN(CC(=O)c2c(Cl)cccc2Cl)C(=O)c2cnn([C@H]3CC[C@](C)(C(=O)O)CC3)c2C(F)(F)F)O1] | trans-4-(4-((2-(2,6-dichlorophenyl)-2-oxoethyl)(((2R)-4,4-dimethyl-2-oxetanyl)methyl)carbamoyl)-5-(trifluoromethyl)-1H-pyrazol-1-yl)-1-methylcyclohexanecarboxylic acid |
| 629 | 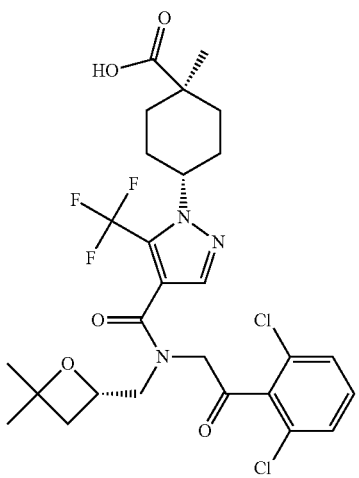 [SMILES: CC1(C)C[C@@H](CN(CC(=O)c2c(Cl)cccc2Cl)C(=O)c2cnn([C@H]3CC[C@](C)(C(=O)O)CC3)c2C(F)(F)F)O1] | trans-4-(4-((2-(2,6-dichlorophenyl)-2-oxoethyl)(((2S)-4,4-dimethyl-2-oxetanyl)methyl)carbamoyl)-5-(trifluoromethyl)-1H-pyrazol-1-yl)-1-methylcyclohexanecarboxylic acid |

| example | structure | name |
| --- | --- | --- |
| 630 | 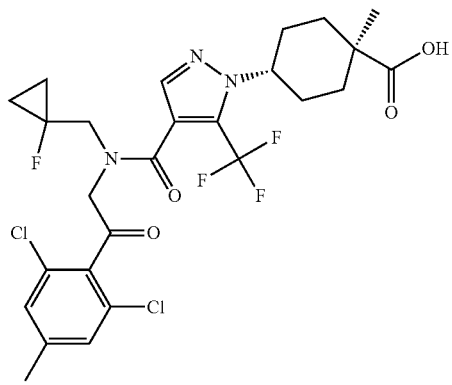 [SMILES: Cc1cc(Cl)c(C(=O)CN(CC2(F)CC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)((1-fluorocyclopropyl)methyl)carbamoyl)-5-(trifluoromethyl)-1H-pyrazol-1-yl)-1-methylcyclohexanecarboxylic acid |
| 631 | 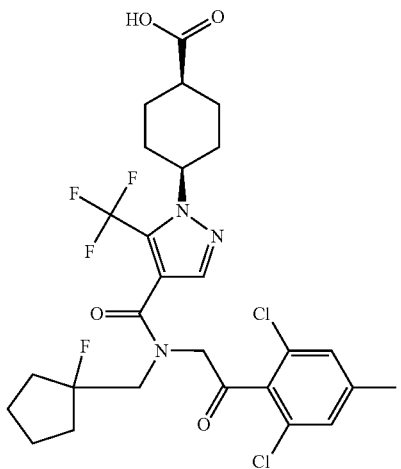 [SMILES: Cc1cc(Cl)c(C(=O)CN(CC2(F)CCCC2)C(=O)c2cnn([C@H]3CC[C@@H](C(=O)O)CC3)c2C(F)(F)F)c(Cl)c1] | cis-4-(4-((2-(2,6-dichloro-4-methylphenyl)-2-oxoethyl)((1-fluorocyclopentyl)methyl)carbamoyl)-5-(trifluoromethyl)-1H-pyrazol-1-yl)cyclohexanecarboxylic acid |
| 632 | 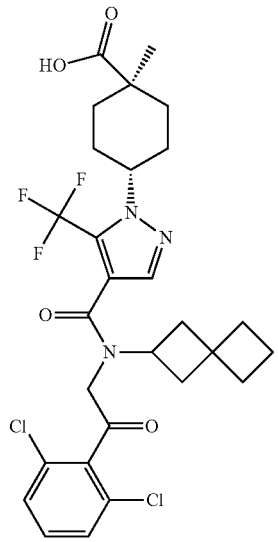 [SMILES: C[C@]1(C(=O)O)CC[C@H](n2ncc(C(=O)N(CC(=O)c3c(Cl)cccc3Cl)C3CC4(CCC4)C3)c2C(F)(F)F)CC1] | trans-4-(4-((2-(2,6-dichlorophenyl)-2-oxoethyl)(spiro[3.3]hept-2-yl)carbamoyl)-5-(trifluoromethyl)-1H-pyrazol-1-yl)-1-methylcyclohexanecarboxylic acid |

-continued

| example | structure | name |
|---|---|---|
| 633 | 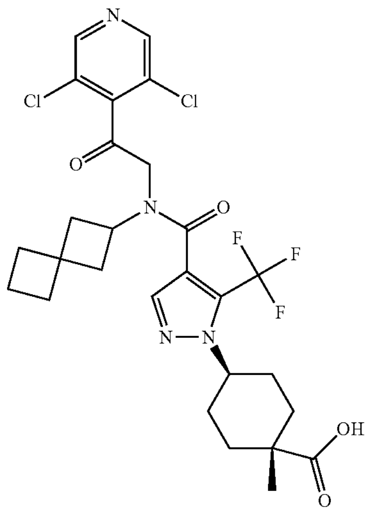 [SMILES: C[C@]1(C(=O)O)CC[C@H](n2ncc(C(=O)N(CC(=O)c3c(Cl)cncc3Cl)C3CC4(CCC4)C3)c2C(F)(F)F)CC1] | trans-4-(4-((2-(3,5-dichloro-4-pyridinyl)-2-oxoethyl)(spiro[3.3]hept-2-yl)carbamoyl)-5-(trifluoromethyl)-1H-pyrazol-1-yl)-1-methylcyclohexanecarboxylic acid |
| 634 | 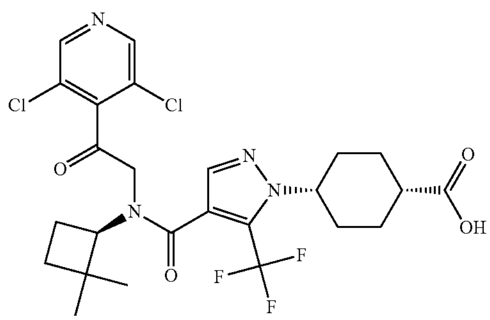 [SMILES: CC1(C)CC[C@H]1N(CC(=O)c1c(Cl)cncc1Cl)C(=O)c1cnn([C@H]2CC[C@@H](C(=O)O)CC2)c1C(F)(F)F] | cis-4-(4-((2-(3,5-dichloro-4-pyridinyl)-2-oxoethyl)((1R)-2,2-dimethylcyclobutyl)carbamoyl)-5-(trifluoromethyl)-1H-pyrazol-1-yl)cyclohexanecarboxylic acid |
| 635 | 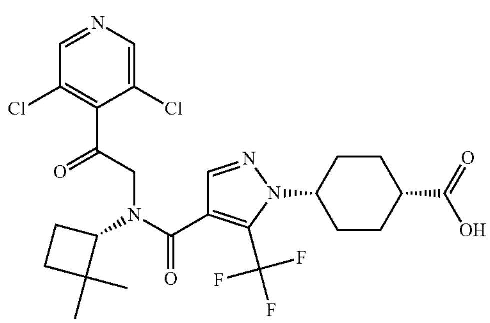 [SMILES: CC1(C)CC[C@@H]1N(CC(=O)c1c(Cl)cncc1Cl)C(=O)c1cnn([C@H]2CC[C@@H](C(=O)O)CC2)c1C(F)(F)F] | cis-4-(4-((2-(3,5-dichloro-4-pyridinyl)-2-oxoethyl)((1S)-2,2-dimethylcyclobutyl)carbamoyl)-5-(trifluoromethyl)-1H-pyrazol-1-yl)cyclohexanecarboxylic acid |
| 636 | 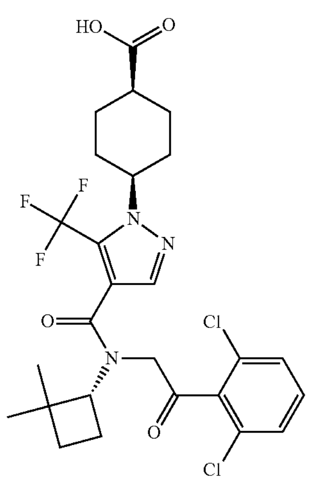 [SMILES: CC1(C)CC[C@H]1N(CC(=O)c1c(Cl)cccc1Cl)C(=O)c1cnn([C@H]2CC[C@@H](C(=O)O)CC2)c1C(F)(F)F] | cis-4-(4-((2-(2,6-dichlorophenyl)-2-oxoethyl)((1R)-2,2-dimethylcyclobutyl)carbamoyl)-5-(trifluoromethyl)-1H-pyrazol-1-yl)cyclohexanecarboxylic acid |

-continued

| example | structure | name |
|---|---|---|
| 637 | 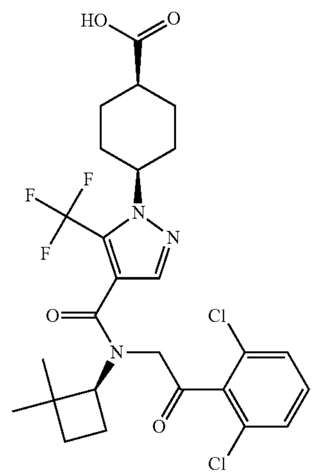 [SMILES: CC1(C)CC[C@@H]1N(CC(=O)c1c(Cl)cccc1Cl)C(=O)c1cnn([C@H]2CC[C@@H](C(=O)O)CC2)c1C(F)(F)F] | cis-4-(4-((2-(2,6-dichlorophenyl)-2-oxoethyl)((1S)-2,2-dimethylcyclobutyl)carbamoyl)-5-(trifluoromethyl)-1H-pyrazol-1-yl)cyclohexanecarboxylic acid |
| 638 | 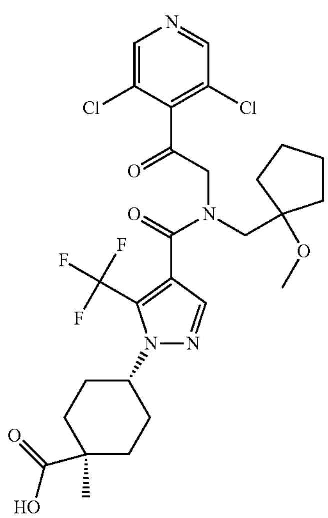 [SMILES: COC1(CN(CC(=O)c2c(Cl)cncc2Cl)C(=O)c2cnn([C@H]3CC[C@](C)(C(=O)O)CC3)c2C(F)(F)F)CCCC1] | trans-4-(4-((2-(3,5-dichloro-4-pyridinyl)-2-oxoethyl)((1-methoxycyclopentyl)methyl)carbamoyl)-5-(trifluoromethyl)-1H-pyrazol-1-yl)-1-methylcyclohexanecarboxylic acid |
| 639 | 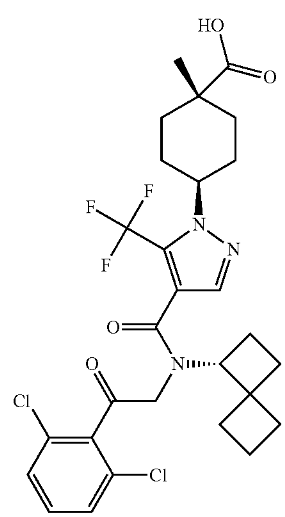 [SMILES: C[C@]1(C(=O)O)CC[C@H](n2ncc(C(=O)N(CC(=O)c3c(Cl)cccc3Cl)[C@@H]3CCC34CCC4)c2C(F)(F)F)CC1] | trans-4-(4-((2-(2,6-dichlorophenyl)-2-oxoethyl)((1R)-spiro[3.3]hept-1-yl)carbamoyl)-5-(trifluoromethyl)-1H-pyrazol-1-yl)-1-methylcyclohexanecarboxylic acid |

| example | structure | name |
| --- | --- | --- |
| 640 | 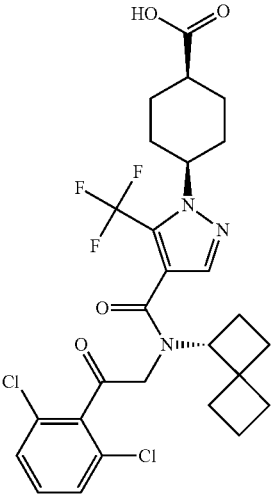 [SMILES: O=C(CN(C(=O)c1cnn([C@H]2CC[C@@H](C(=O)O)CC2)c1C(F)(F)F)[C@@H]1CCC12CCC2)c1c(Cl)cccc1Cl] | cis-4-(4-((2-(2,6-dichlorophenyl)-2-oxoethyl)((1R)-spiro[3.3]hept-1-yl)carbamoyl)-5-(trifluoromethyl)-1H-pyrazol-1-yl)cyclohexanecarboxylic acid |
| 641 | 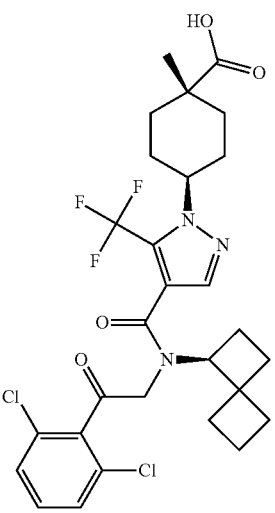 [SMILES: C[C@]1(C(=O)O)CC[C@H](n2ncc(C(=O)N(CC(=O)c3c(Cl)cccc3Cl)[C@H]3CCC34CCC4)c2C(F)(F)F)CC1] | trans-4-(4-((2-(2,6-dichlorophenyl)-2-oxoethyl)((1S)-spiro[3.3]hept-1-yl)carbamoyl)-5-(trifluoromethyl)-1H-pyrazol-1-yl)-1-methylcyclohexanecarboxylic acid |
| 642 | 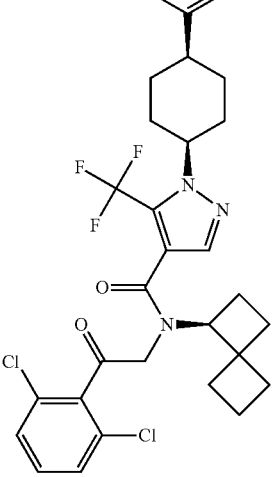 | cis-4-(4-((2-(2,6-dichlorophenyl)-2-oxoethyl)((1S)-spiro[3.3]hept-1-yl)carbamoyl)-5-(trifluoromethyl)-1H-pyrazol-1-yl)cyclohexanecarboxylic acid |

-continued

| example | structure | name |
|---|---|---|
| 643 | 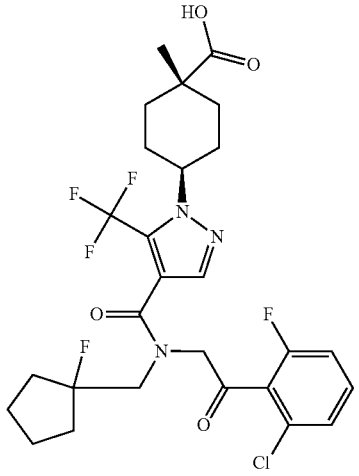 [SMILES: C[C@]1(C(=O)O)CC[C@H](n2ncc(C(=O)N(CC(=O)c3c(F)cccc3Cl)CC3(F)CCCC3)c2C(F)(F)F)CC1] | trans-4-(4-((2-(2-chloro-6-fluorophenyl)-2-oxoethyl)((1-fluorocyclopentyl)methyl)carbamoyl)-5-(trifluoromethyl)-1H-pyrazol-1-yl)-1-methylcyclohexanecarboxylic acid |
| 644 | 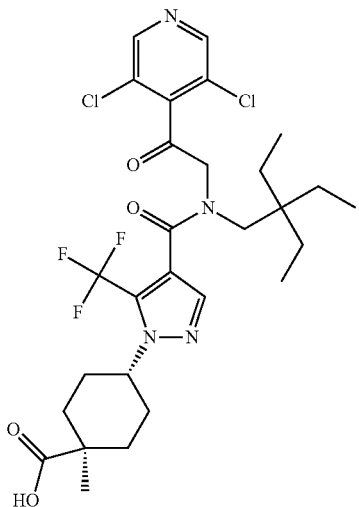 [SMILES: CCC(CC)(CC)CN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)(2,2-diethylbutyl)carbamoyl)-5-(trifluoromethyl)-1H-pyrazol-1-yl)-1-methylcyclohexanecarboxylic acid |
| 645 | 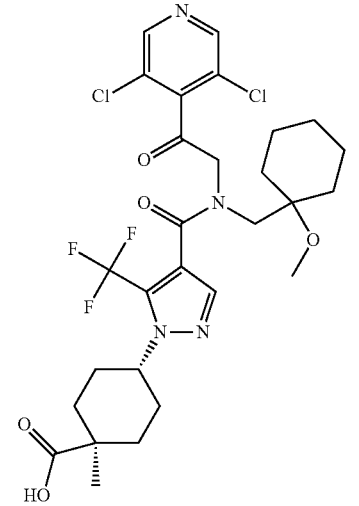 [SMILES: COC1(CN(CC(=O)c2c(Cl)cncc2Cl)C(=O)c2cnn([C@H]3CC[C@](C)(C(=O)O)CC3)c2C(F)(F)F)CCCCC1] | trans-4-(4-((2-(3,5-dichloro-4-pyridinyl)-2-oxoethyl)((1-methoxycyclohexyl)methyl)carbamoyl)-5-(trifluoromethyl)-1H-pyrazol-1-yl)1-methylcyclohexanecarboxylic acid |

-continued

| example | structure | name |
|---|---|---|
| 646 | 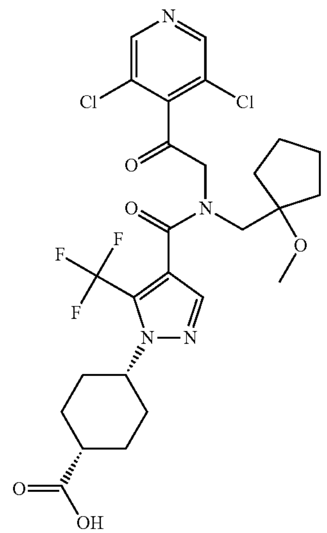 [SMILES: COC1(CN(CC(=O)c2c(Cl)cncc2Cl)C(=O)c2cnn([C@H]3CC[C@@H](C(=O)O)CC3)c2C(F)(F)F)CCCC1] | cis-4-(4-((2-(3,5-dichloro-4-pyridinyl)-2-oxoethyl)((1-methoxycyclopentyl)methyl)carbamoyl)-5-(trifluoromethyl)-1H-pyrazol-1-yl)cyclohexanecarboxylic acid |
| 647 | 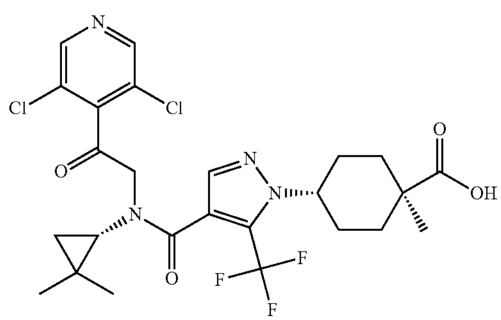 [SMILES: CC1(C)C[C@@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)((1S)-2,2-dimethylcyclopropyl)carbamoyl)-5-(trifluoromethyl)-1H-pyrazol-1-yl)-1-methylcyclohexanecarboxylic acid |
| 648 | 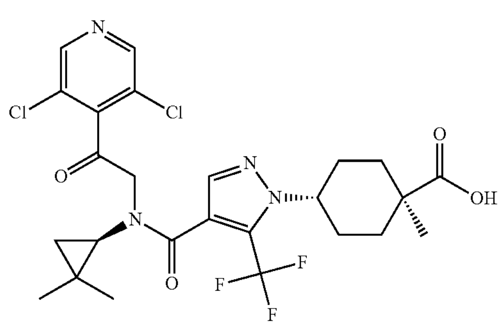 [SMILES: CC1(C)C[C@H]1N(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)((1R)-2,2-dimethylcyclopropyl)carbamoyl)-5-(trifluoromethyl)-1H-pyrazol-1-yl)-1-methylcyclohexanecarboxylic acid |

-continued

| example | structure | name |
|---|---|---|
| 649 | 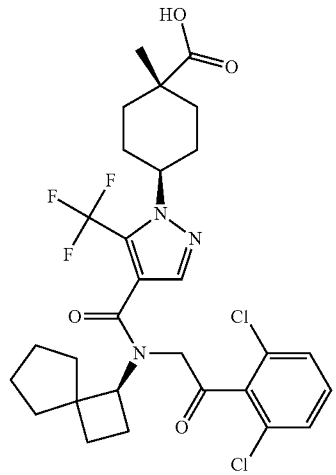 [SMILES: C[C@]1(C(=O)O)CC[C@H](n2ncc(C(=O)N(CC(=O)c3c(Cl)cccc3Cl)[C@H]3CCC34CCCC4)c2C(F)(F)F)CC1] | trans-4-(4-((2-(2,6-dichlorophenyl)-2-oxoethyl)((1S)-spiro[3.4]oct-1-yl)carbamoyl)-5-(trifluoromethyl)-1H-pyrazol-1-yl)-1-methylcyclohexanecarboxylic acid |
| 650 | 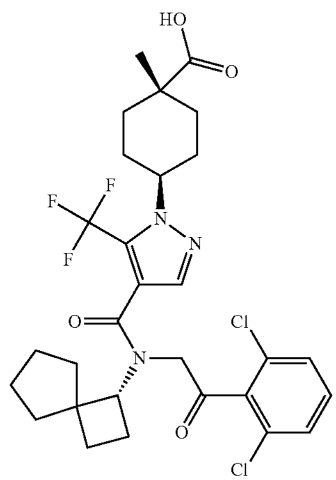 [SMILES: C[C@]1(C(=O)O)CC[C@H](n2ncc(C(=O)N(CC(=O)c3c(Cl)cccc3Cl)[C@@H]3CCC34CCCC4)c2C(F)(F)F)CC1] | trans-4-(4-((2-(2,6-dichlorophenyl)-2-oxoethyl)((1R)-spiro[3.4]oct-1-yl)carbamoyl)-5-(trifluoromethyl)-1H-pyrazol-1-yl)-1-methylcyclohexanecarboxylic acid |
| 651 | 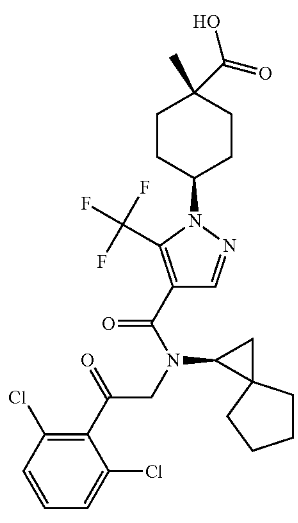 [SMILES: C[C@]1(C(=O)O)CC[C@H](n2ncc(C(=O)N(CC(=O)c3c(Cl)cccc3Cl)[C@H]3CC34CCCC4)c2C(F)(F)F)CC1] | trans-4-(4-((2-(2,6-dichlorophenyl)-2-oxoethyl)((1S)-spiro[2.4]hept-1-yl)carbamoyl)-5-(trifluoromethyl)-1H-pyrazol-1-yl)-1-methylcyclohexanecarboxylic acid |

| example | structure | name |
|---|---|---|
| 652 | 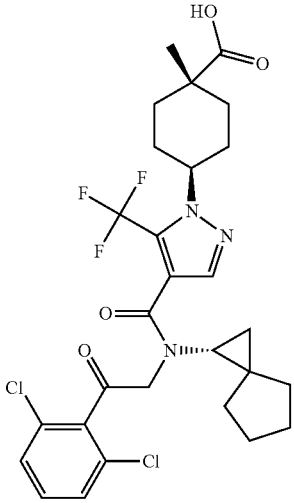 [SMILES: C[C@]1(C(=O)O)CC[C@H](n2ncc(C(=O)N(CC(=O)c3c(Cl)cccc3Cl)[C@@H]3CC34CCCC4)c2C(F)(F)F)CC1] | trans-4-(4-((2-(2,6-dichlorophenyl)-2-oxoethyl)((1R)-spiro[2.4]hept-1-yl)carbamoyl)-5-(trifluoromethyl)-1H-pyrazol-1-yl)-1-methylcyclohexanecarboxylic acid |
| 653 | 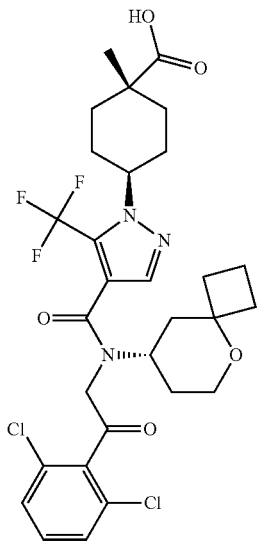 [SMILES: C[C@]1(C(=O)O)CC[C@H](n2ncc(C(=O)N(CC(=O)c3c(Cl)cccc3Cl)[C@H]3CCOC4(CCC4)C3)c2C(F)(F)F)CC1] | trans-4-(4-((2-(2,6-dichlorophenyl)-2-oxoethyl)((8S)-5-oxaspiro[3.5]non-8-yl)carbamoyl)-5-(trifluoromethyl)-1H-pyrazol-1-yl)-1-methylcyclohexanecarboxylic acid |
| 654 | 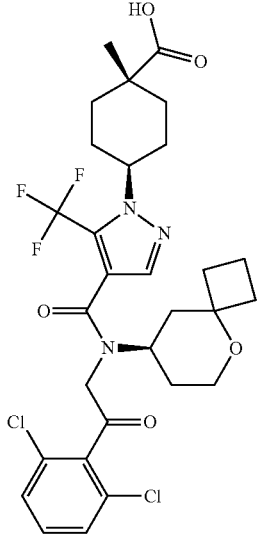 [SMILES: C[C@]1(C(=O)O)CC[C@H](n2ncc(C(=O)N(CC(=O)c3c(Cl)cccc3Cl)[C@@H]3CCOC4(CCC4)C3)c2C(F)(F)F)CC1] | trans-4-(4-((2-(2,6-dichlorophenyl)-2-oxoethyl)((8R)-5-oxaspiro[3.5]non-8-yl)carbamoyl)-5-(trifluoromethyl)-1H-pyrazol-1-yl)-1-methylcyclohexanecarboxylic acid |

-continued

| example | structure | name |
|---|---|---|
| 655 | 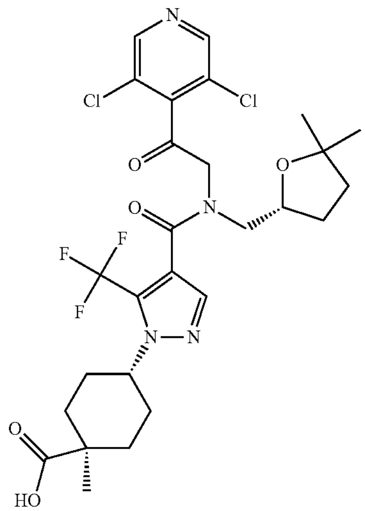 [SMILES: CC1(C)CC[C@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2R)-5,5-dimethyltetrahydro-2-furanyl)methyl)carbamoyl)-5-(trifluoromethyl)-1H-pyrazol-1-yl)-1-methylcyclohexanecarboxylic acid |
| 656 | 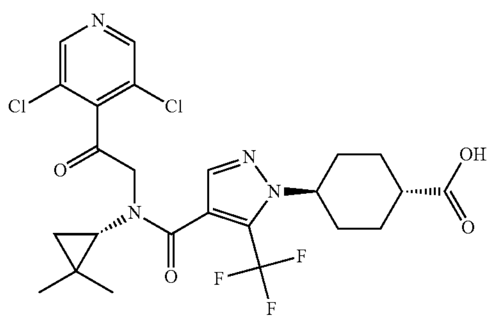 [SMILES: CC1(C)C[C@@H]1N(CC(=O)c1c(Cl)cncc1Cl)C(=O)c1cnn([C@H]2CC[C@H](C(=O)O)CC2)c1C(F)(F)F] | trans-4-(4-((2-(3,5-dichloro-4-pyridinyl)-2-oxoethyl)((1S)-2,2-dimethylcyclopropyl)carbamoyl)-5-(trifluoromethyl)-1H-pyrazol-1-yl)cyclohexanecarboxylic acid |
| 657 | 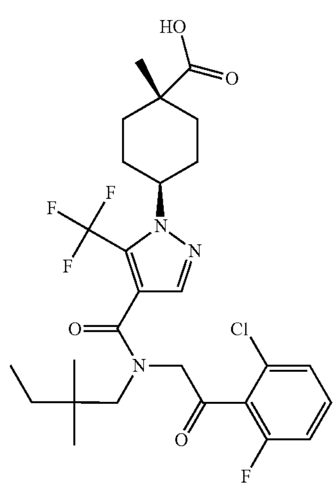 [SMILES: CCC(C)(C)CN(CC(=O)c1c(F)cccc1Cl)C(=O)c1cnn([C@H]2CC[C@](C)(C(=O)O)CC2)c1C(F)(F)F] | trans-4-(4-((2-(2-chloro-6-fluorophenyl)-2-oxoethyl)(2,2-dimethylbutyl)carbamoyl)-5-(trifluoromethyl)-1H-pyrazol-1-yl)-1-methylcyclohexanecarboxylic acid |

-continued

| example | structure | name |
|---|---|---|
| 658 | 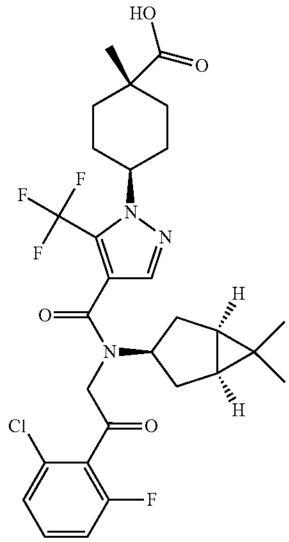 [SMILES: CC1(C)[C@@H]2C[C@H](N(CC(=O)c3c(F)cccc3Cl)C(=O)c3cnn([C@H]4CC[C@](C)(C(=O)O)CC4)c3C(F)(F)F)C[C@@H]21] | trans-4-(4-((2-(2-chloro-6-fluorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)-1-methylcyclohexanecarboxylic acid |
| 659 | 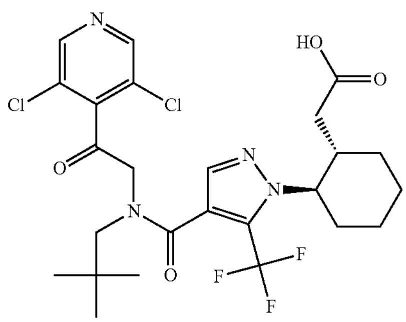 [SMILES: CC(C)(C)CN(CC(=O)c1c(Cl)cncc1Cl)C(=O)c1cnn([C@@H]2CCCC[C@H]2CC(=O)O)c1C(F)(F)F] | ((1S,2R)-2-(4-((2-(3,5-dichloro-4-pyridinyl)-2-oxoethyl)(2,2-dimethylpropyl)carbamoyl)-5-(trifluoromethyl)-1H-pyrazol-1-yl)cyclohexyl)acetic acid |
| 660 | 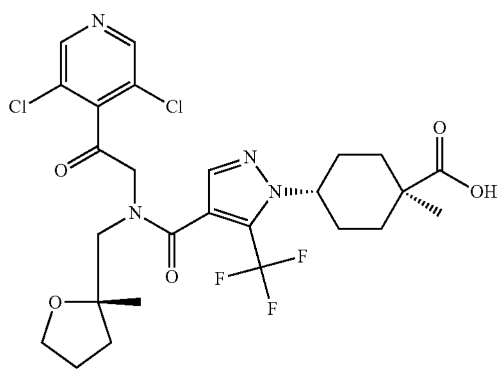 [SMILES: C[C@@]1(CN(CC(=O)c2c(Cl)cncc2Cl)C(=O)c2cnn([C@H]3CC[C@](C)(C(=O)O)CC3)c2C(F)(F)F)CCCO1] | trans-4-(4-((2-(3,5-dichloro-4-pyridinyl)-2-oxoethyl)(((2S)-2-methyltetrahydro-2-furanyl)methyl)carbamoyl)-5-(trifluoromethyl)-1H-pyrazol-1-yl)-1-methylcyclohexanecarboxylic acid |
| 661 | 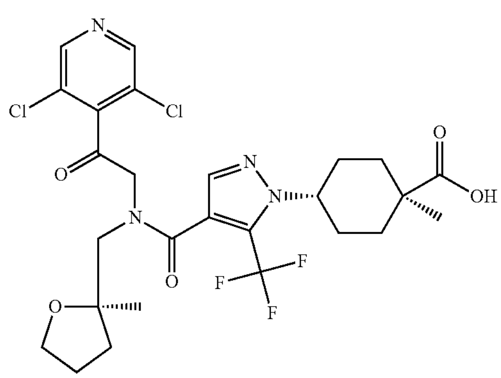 [SMILES: C[C@]1(CN(CC(=O)c2c(Cl)cncc2Cl)C(=O)c2cnn([C@H]3CC[C@](C)(C(=O)O)CC3)c2C(F)(F)F)CCCO1] | trans-4-(4-((2-(3,5-dichloro-4-pyridinyl)-2-oxoethyl)(((2R)-2-methyltetrahydro-2-furanyl)methyl)carbamoyl)-5-(trifluoromethyl)-1H-pyrazol-1-yl)-1-methylcyclohexanecarboxylic acid |

| example | structure | name |
|---|---|---|
| 662 | 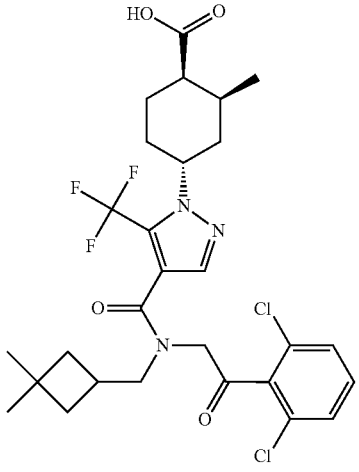 [SMILES: C[C@H]1C[C@H](n2ncc(C(=O)N(CC(=O)c3c(Cl)cccc3Cl)CC3CC(C)(C)C3)c2C(F)(F)F)CC[C@H]1C(=O)O] | (1R,2S,4R)-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 663 | 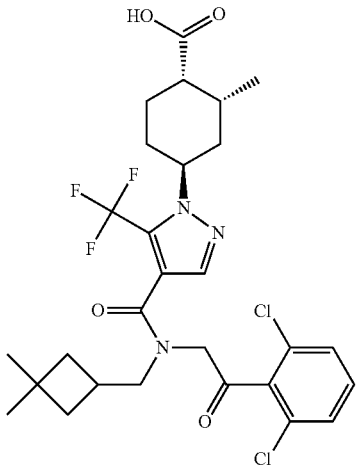 [SMILES: C[C@@H]1C[C@@H](n2ncc(C(=O)N(CC(=O)c3c(Cl)cccc3Cl)CC3CC(C)(C)C3)c2C(F)(F)F)CC[C@@H]1C(=O)O] | (1S,2R,4S)-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 664 | 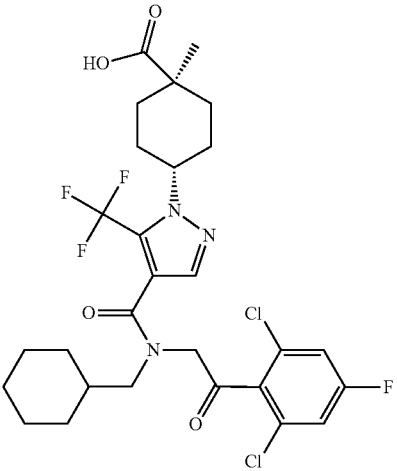 [SMILES: C[C@]1(C(=O)O)CC[C@H](n2ncc(C(=O)N(CC(=O)c3c(Cl)cc(F)cc3Cl)CC3CCCCC3)c2C(F)(F)F)CC1] | trans-4-(4-((cyclohexylmethyl)(2-(2,6-dichloro-4-fluorophenyl)-2-oxoethyl)carbamoyl)-5-(trifluoromethyl)-1H-pyrazol-1-yl)-1-methylcyclohexanecarboxylic acid |

-continued

| example | structure | name |
|---|---|---|
| 665 | 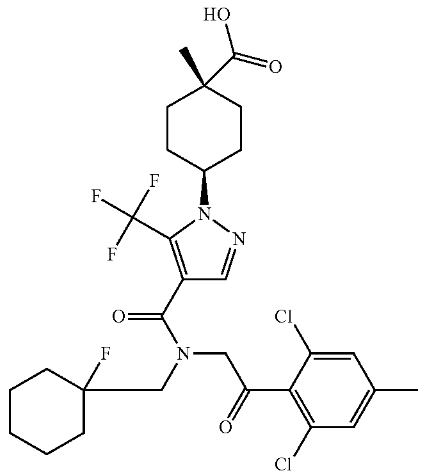 [SMILES: Cc1cc(Cl)c(C(=O)CN(CC2(F)CCCCC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)((1-fluorocyclohexyl)methyl)carbamoyl)-5-(trifluoromethyl)-1H-pyrazol-1-yl)-1-methylcyclohexanecarboxylic acid |
| 666 | 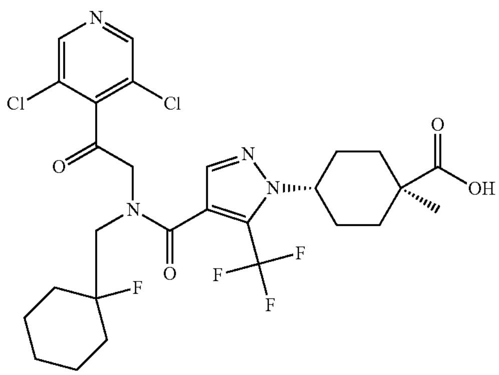 [SMILES: C[C@]1(C(=O)O)CC[C@H](n2ncc(C(=O)N(CC(=O)c3c(Cl)cncc3Cl)CC3(F)CCCCC3)c2C(F)(F)F)CC1] | trans-4-(4-((2-(3,5-dichloro-4-pyridinyl)-2-oxoethyl)((1-fluorocyclohexyl)methyl)carbamoyl)-5-(trifluoromethyl)-1H-pyrazol-1-yl)-1-methylcyclohexanecarboxylic acid |
| 667 | 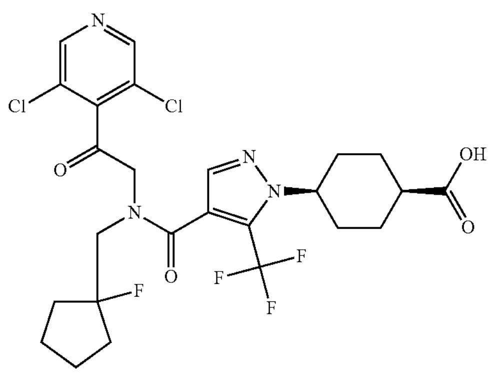 [SMILES: O=C(CN(CC1(F)CCCC1)C(=O)c1cnn([C@H]2CC[C@@H](C(=O)O)CC2)c1C(F)(F)F)c1c(Cl)cncc1Cl] | cis-4-(4-((2-(3,5-dichloro-4-pyridinyl)-2-oxoethyl)((1-fluorocyclopentyl)methyl)carbamoyl)-5-(trifluoromethyl)-1H-pyrazol-1-yl)cyclohexanecarboxylic acid |
| 668 | 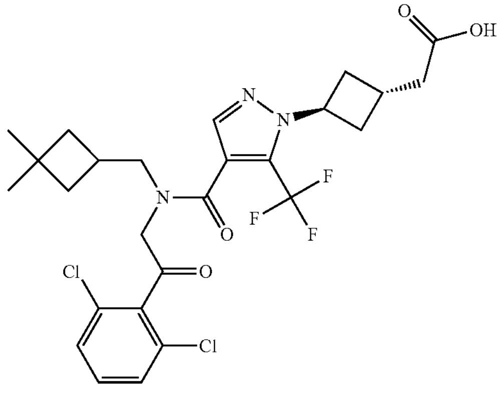 [SMILES: CC1(C)CC(CN(CC(=O)c2c(Cl)cccc2Cl)C(=O)c2cnn([C@H]3C[C@H](CC(=O)O)C3)c2C(F)(F)F)C1] | (trans-3-(4-((2-(2,6-dichlorophenyl)-2-oxoethyl)((3,3-dimethylcyclobutyl)methyl)carbamoyl)-5-(trifluoromethyl)-1H-pyrazol-1-yl)cyclobutyl)acetic acid |

-continued

| example | structure | name |
|---|---|---|
| 669 | 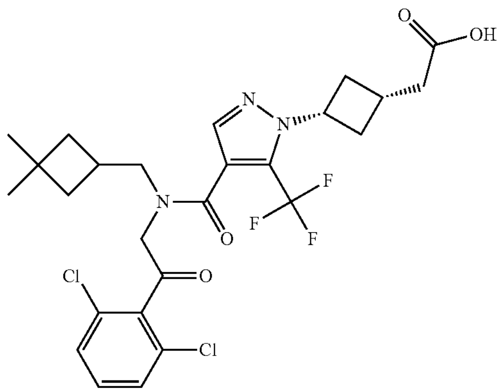 [SMILES: CC1(C)CC(CN(CC(=O)c2c(Cl)cccc2Cl)C(=O)c2cnn([C@H]3C[C@@H](CC(=O)O)C3)c2C(F)(F)F)C1] | (cis-3-(4-((2-(2,6-dichlorophenyl)-2-oxoethyl)((3,3-dimethylcyclobutyl)methyl)carbamoyl)-5-(trifluoromethyl)-1H-pyrazol-1-yl)cyclobutyl)acetic acid |
| 670 | 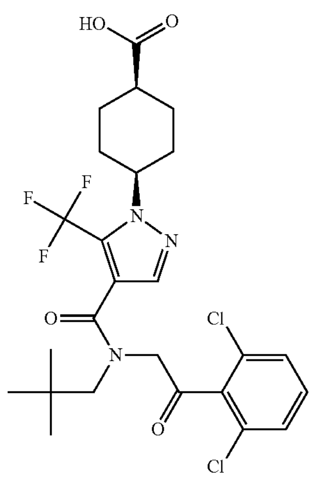 [SMILES: CC(C)(C)CN(CC(=O)c1c(Cl)cccc1Cl)C(=O)c1cnn([C@H]2CC[C@@H](C(=O)O)CC2)c1C(F)(F)F] | cis-4-(4-((2-(2,6-dichlorophenyl)-2-oxoethyl)(2,2-dimethylpropyl)carbamoyl)-5-(trifluoromethyl)-1H-pyrazol-1-yl)cyclohexanecarboxylic acid |
| 671 | 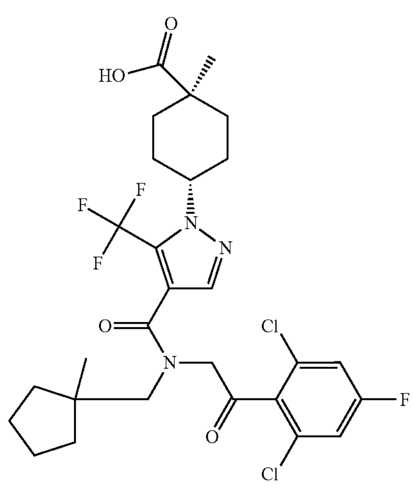 [SMILES: CC1(CN(CC(=O)c2c(Cl)cc(F)cc2Cl)C(=O)c2cnn([C@H]3CC[C@](C)(C(=O)O)CC3)c2C(F)(F)F)CCCC1] | trans-4-(4-((2-(2,6-dichloro-4-fluorophenyl)-2-oxoethyl)((1-methylcyclopentyl)methyl)carbamoyl)-5-(trifluoromethyl)-1H-pyrazol-1-yl)-1-methylcyclohexanecarboxylic acid |

| example | structure | name |
| --- | --- | --- |
| 672 | 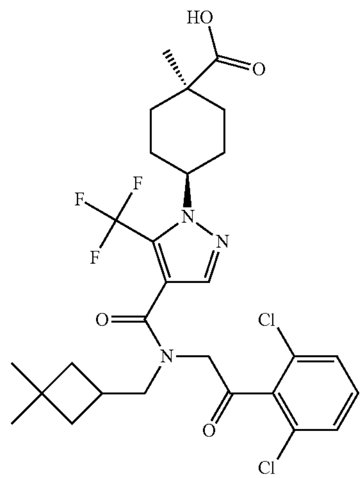 [SMILES: CC1(C)CC(CN(CC(=O)c2c(Cl)cccc2Cl)C(=O)c2cnn([C@H]3CC[C@@](C)(C(=O)O)CC3)c2C(F)(F)F)C1] | trans-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-1-methylcyclohexanecarboxylic acid |
| 673 | 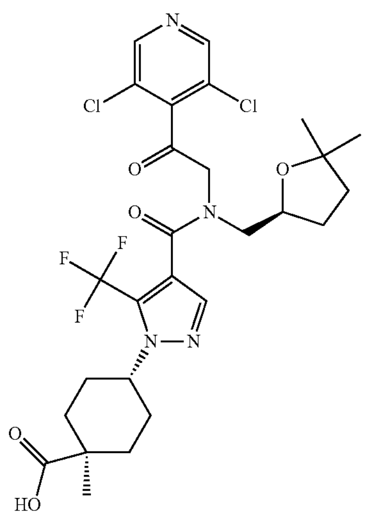 [SMILES: CC1(C)CC[C@@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2S)-5,5-dimethyltetrahydro-2-furanyl)methyl)carbamoyl)-5-(trifluoromethyl)-1H-pyrazol-1-yl)-1-methylcyclohexanecarboxylic acid |
| 674 | 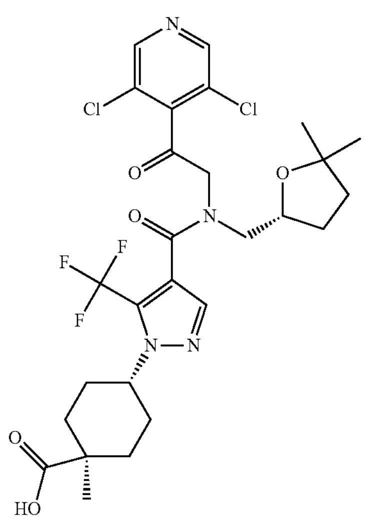 [SMILES: CC1(C)CC[C@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2S)-5,5-dimethyltetrahydro-2-furanyl)methyl)carbamoyl)-5-(trifluoromethyl)-1H-pyrazol-1-yl)-1-methylcyclohexanecarboxylic acid |

-continued

| example | structure | name |
| --- | --- | --- |
| 675 | 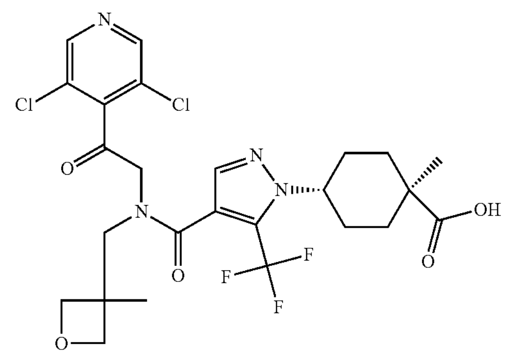 [SMILES: CC1(CN(CC(=O)c2c(Cl)cncc2Cl)C(=O)c2cnn([C@H]3CC[C@](C)(C(=O)O)CC3)c2C(F)(F)F)COC1] | trans-4-(4-((2-(3,5-dichloro-4-pyridinyl)-2-oxoethyl)((3-methyl-3-oxetanyl)methyl)carbamoyl)-5-(trifluoromethyl)-1H-pyrazol-1-yl)-1-methylcyclohexanecarboxylic acid |
| 676 | 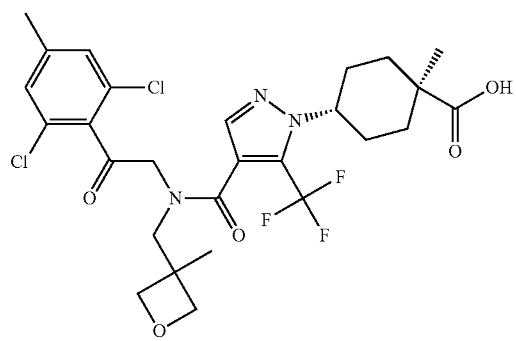 [SMILES: Cc1cc(Cl)c(C(=O)CN(CC2(C)COC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)((3-methyl-3-oxetanyl)methyl)carbamoyl)-5-(trifluoromethyl)-1H-pyrazol-1-yl)-1-methylcyclohexanecarboxylic acid |
| 677 | 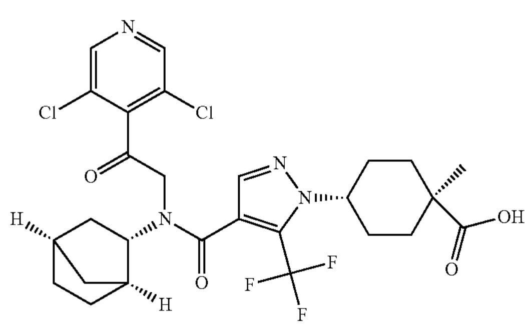 [SMILES: C[C@]1(C(=O)O)CC[C@H](n2ncc(C(=O)N(CC(=O)c3c(Cl)cncc3Cl)[C@H]3C[C@@H]4CC[C@H]3C4)c2C(F)(F)F)CC1] | trans-4-(4-(((1S,2R,4R)-bicyclo[2.2.1]hept-2-yl(2-(3,5-dichloro-4-pyridinyl)-2-oxoethyl)carbamoyl)-5-(trifluoromethyl)-1H-pyrazol-1-yl)-1-methylcyclohexanecarboxylic acid |
| 678 | 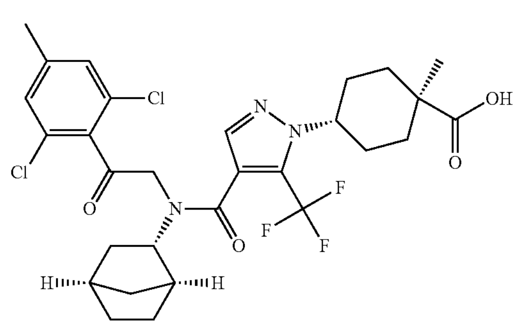 [SMILES: Cc1cc(Cl)c(C(=O)CN(C(=O)c2cnn([C@H]3CC[C@](C)(C(=O)O)CC3)c2C(F)(F)F)[C@H]2C[C@@H]3CC[C@H]2C3)c(Cl)c1] | trans-4-(4-(((1S,2S,4R)-bicyclo[2.2.1]hept-2-yl(2-(2,6-dichloro-4-methylphenyl)-2-oxoethyl)carbamoyl)-5-(trifluoromethyl)-1H-pyrazol-1-yl)-1-methylcyclohexanecarboxylic acid |

| example | structure | name |
|---|---|---|
| 679 | 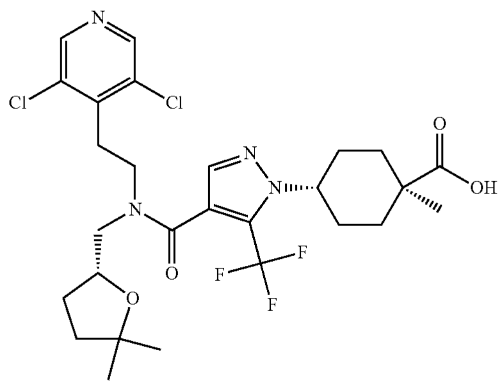 [SMILES: CC1(C)CC[C@H](CN(CCc2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)ethyl)(((2R)-5,5-dimethyltetrahydro-2-furanyl)methyl)carbamoyl)-5-(trifluoromethyl)-1H-pyrazol-1-yl)-1-methylcyclohexanecarboxylic acid |
| 680 | 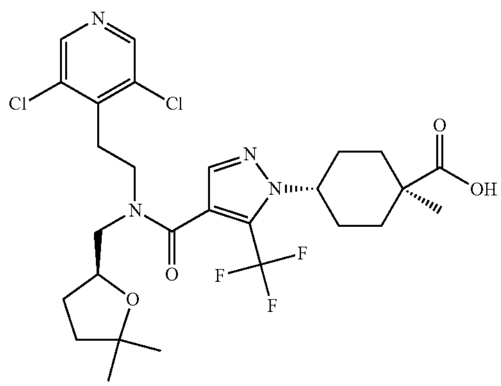 [SMILES: CC1(C)CC[C@@H](CN(CCc2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)ethyl)(((2S)-5,5-dimethyltetrahydro-2-furanyl)methyl)carbamoyl)-5-(trifluoromethyl)-1H-pyrazol-1-yl)-1-methylcyclohexanecarboxylic acid |
| 681 | 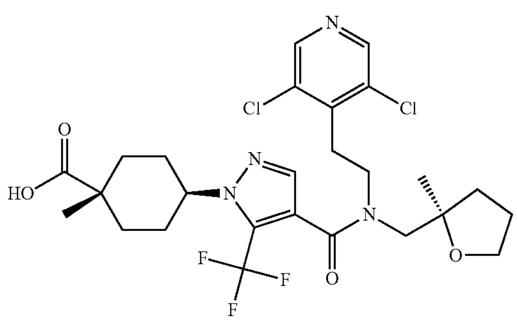 [SMILES: C[C@]1(CN(CCc2c(Cl)cncc2Cl)C(=O)c2cnn([C@H]3CC[C@](C)(C(=O)O)CC3)c2C(F)(F)F)CCCO1] | trans-4-(4-((2-(3,5-dichloro-4-pyridinyl)ethyl)(((2R)-2-methyltetrahydro-2-furanyl)methyl)carbamoyl)-5-(trifluoromethyl)-1H-pyrazol-1-yl)-1-methylcyclohexanecarboxylic acid |
| 682 | 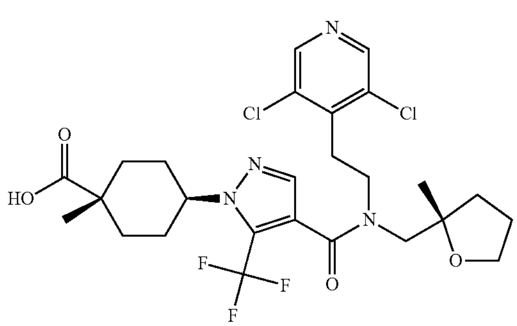 [SMILES: C[C@@]1(CN(CCc2c(Cl)cncc2Cl)C(=O)c2cnn([C@H]3CC[C@](C)(C(=O)O)CC3)c2C(F)(F)F)CCCO1] | trans-4-(4-((2-(3,5-dichloro-4-pyridinyl)ethyl)(((2S)-2-methyltetrahydro-2-furanyl)methyl)carbamoyl)-5-(trifluoromethyl)-1H-pyrazol-1-yl)-1-methylcyclohexanecarboxylic acid |

-continued

| example | structure | name |
|---|---|---|
| 683 | 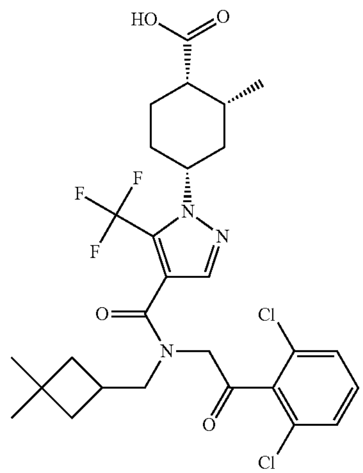 [SMILES: C[C@@H]1C[C@H](n2ncc(C(=O)N(CC(=O)c3c(Cl)cccc3Cl)CC3CC(C)(C)C3)c2C(F)(F)F)CC[C@@H]1C(=O)O] | (1S,2R,4R)-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 684 | 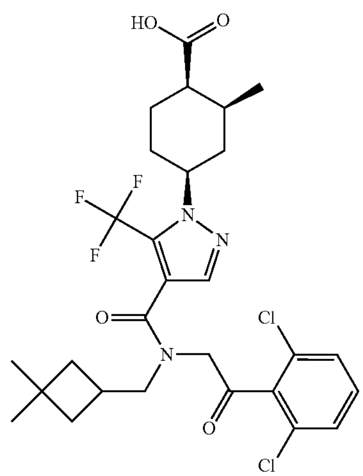 [SMILES: C[C@H]1C[C@@H](n2ncc(C(=O)N(CC(=O)c3c(Cl)cccc3Cl)CC3CC(C)(C)C3)c2C(F)(F)F)CC[C@H]1C(=O)O] | (1R,2S,4S)-4-(4-((2-(2,6-dichlorophenyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 685 | 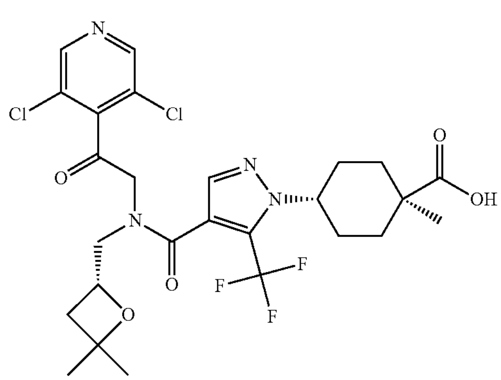 [SMILES: CC1(C)C[C@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2R)-4,4-dimethyl-2-oxetanyl)methyl)carbamoyl)-5-(trifluoromethyl)-1H-pyrazol-1-yl)-1-methylcyclohexanecarboxylic acid |

| example | structure | name |
|---|---|---|
| 686 | 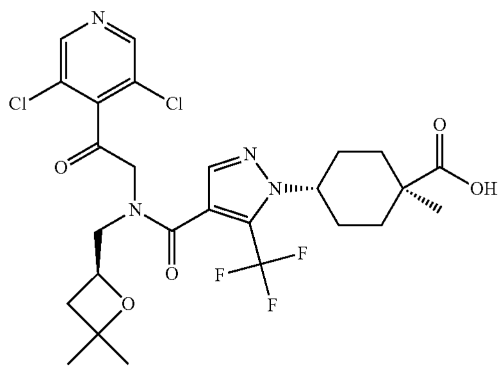 [SMILES: CC1(C)C[C@@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2S)-4,4-dimethyl-2-oxetanyl)methyl)carbamoyl)-5-(trifluoromethyl)-1H-pyrazol-1-yl)-1-methylcyclohexanecarboxylic acid |
| 687 | 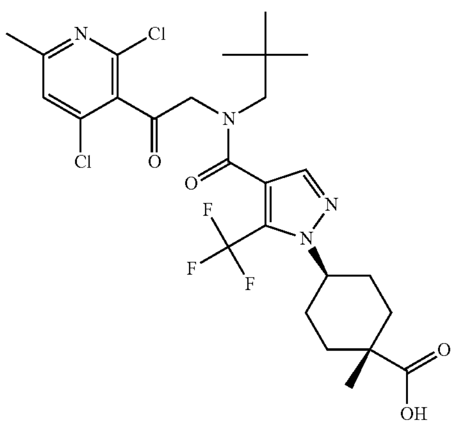 [SMILES: Cc1cc(Cl)c(C(=O)CN(CC(C)(C)C)C(=O)c2cnn([C@H]3CC[C@](C)(C(=O)O)CC3)c2C(F)(F)F)c(Cl)n1] | trans-4-(4-((2-(2,4-dichloro-6-methyl-3-pyridinyl)-2-oxoethyl)(2,2-dimethylpropyl)carbamoyl)-5-(trifluoromethyl)-1H-pyrazol-1-yl)-1-methylcyclohexanecarboxylic acid |
| 688 | 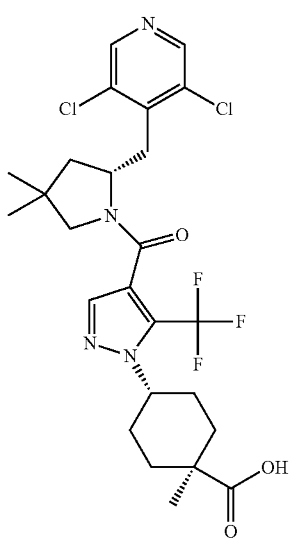 [SMILES: CC1(C)C[C@H](Cc2c(Cl)cncc2Cl)N(C(=O)c2cnn([C@H]3CC[C@](C)(C(=O)O)CC3)c2C(F)(F)F)C1] | trans-4-(4-(((2R)-2-((3,5-dichloro-4-pyridinyl)methyl)-4,4-dimethyl-1-pyrrolidinyl)carbonyl)-5-(trifluoromethyl)-1H-pyrazol-1-yl)-1-methylcyclohexanecarboxylic acid |

-continued

| example | structure | name |
|---|---|---|
| 689 | 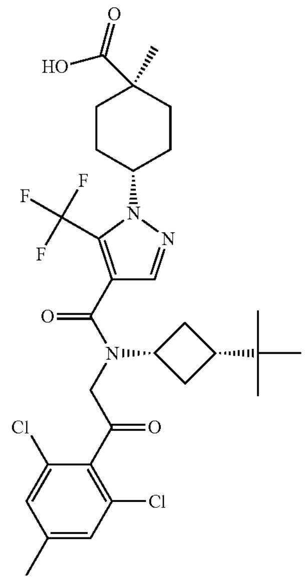 [SMILES: Cc1cc(Cl)c(C(=O)CN(C(=O)c2cnn([C@H]3CC[C@](C)(C(=O)O)CC3)c2C(F)(F)F)[C@H]2C[C@@H](C(C)(C)C)C2)c(Cl)c1] | trans-4-(4-((2-(2,6-dichloro-4-methylphenyl)-2-oxoethyl)(cis-3-(2-methyl-2-propanyl)cyclobutyl)carbamoyl)-5-(trifluoromethyl)-1H-pyrazol-1-yl)-1-methylcyclohexanecarboxylic acid |
| 690 | 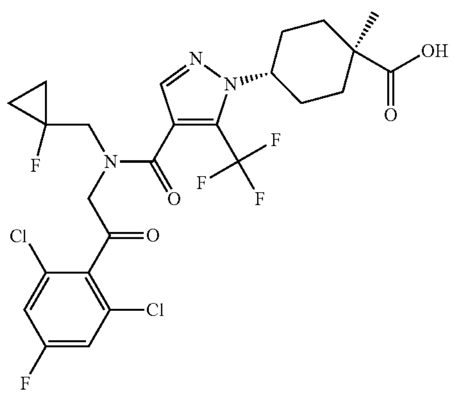 [SMILES: C[C@]1(C(=O)O)CC[C@H](n2ncc(C(=O)N(CC(=O)c3c(Cl)cc(F)cc3Cl)CC3(F)CC3)c2C(F)(F)F)CC1] | trans-4-(4-((2-(2,6-dichloro-4-fluorophenyl)-2-oxoethyl)((1-fluorocyclopropyl)methyl)carbamoyl)-5-(trifluoromethyl)-1H-pyrazol-1-yl)-1-methylcyclohexanecarboxylic acid |
| 691 | 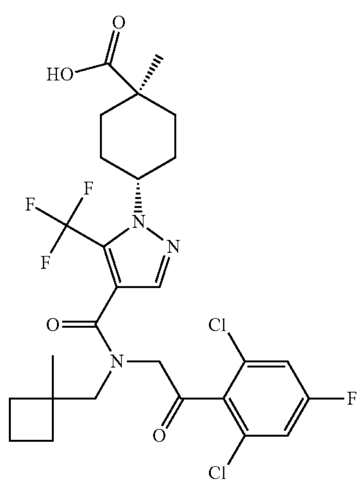 [SMILES: CC1(CN(CC(=O)c2c(Cl)cc(F)cc2Cl)C(=O)c2cnn([C@H]3CC[C@](C)(C(=O)O)CC3)c2C(F)(F)F)CCC1] | trans-4-(4-((2-(2,6-dichloro-4-fluorophenyl)-2-oxoethyl)((1-methylcyclobutyl)methyl)carbamoyl)-5-(trifluoromethyl)-1H-pyrazol-1-yl)-1-methylcyclohexanecarboxylic acid |

| example | structure | name |
| --- | --- | --- |
| 692 | 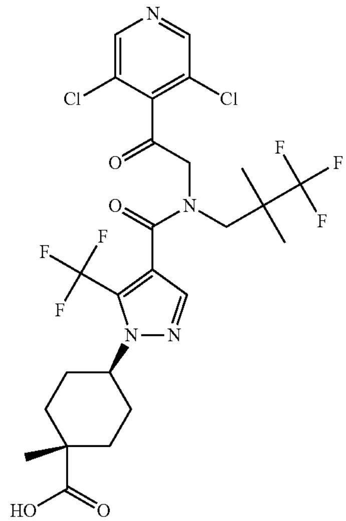 [SMILES: CC(C)(CN(CC(=O)c1c(Cl)cncc1Cl)C(=O)c1cnn([C@H]2CC[C@](C)(C(=O)O)CC2)c1C(F)(F)F)C(F)(F)F] | trans-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-1-methylcyclohexanecarboxylic acid |
| 693 | 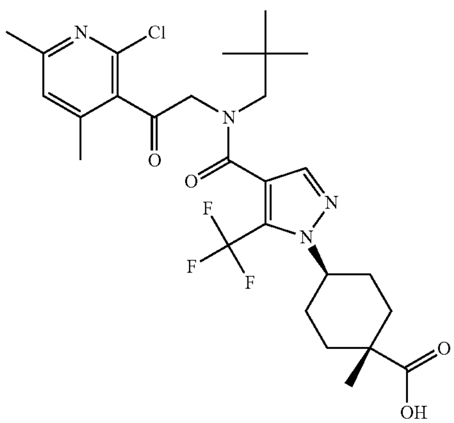 [SMILES: Cc1cc(C)c(C(=O)CN(CC(C)(C)C)C(=O)c2cnn([C@H]3CC[C@](C)(C(=O)O)CC3)c2C(F)(F)F)c(Cl)n1] | trans-4-(4-((2-(2-chloro-4,6-dimethyl-3-pyridinyl)-2-oxoethyl)(2,2-dimethylpropyl)carbamoyl)-5-(trifluoromethyl)-1H-pyrazol-1-yl)-1-methylcyclohexanecarboxylic acid |
| 694 | 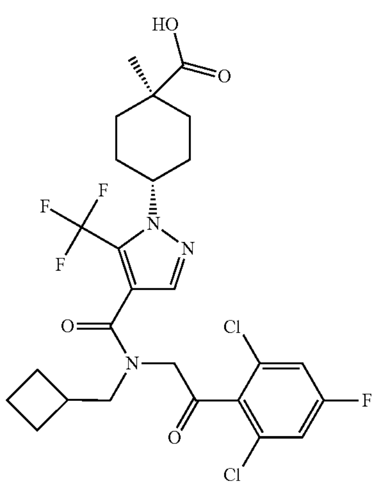 [SMILES: C[C@]1(C(=O)O)CC[C@H](n2ncc(C(=O)N(CC(=O)c3c(Cl)cc(F)cc3Cl)CC3CCC3)c2C(F)(F)F)CC1] | trans-4-(4-((cyclobutylmethyl)(2-(2,6-dichloro-4-fluorophenyl)-2-oxoethyl)carbamoyl)-5-(trifluoromethyl)-1H-pyrazol-1-yl)-1-methylcyclohexanecarboxylic acid |

| example | structure | name |
| --- | --- | --- |
| 695 | 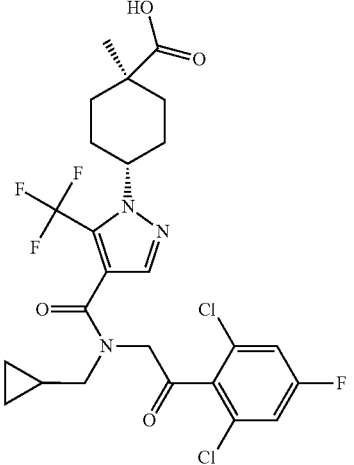 [SMILES: C[C@]1(C(=O)O)CC[C@H](n2ncc(C(=O)N(CC(=O)c3c(Cl)cc(F)cc3Cl)CC3CC3)c2C(F)(F)F)CC1] | trans-4-(4-((cyclopropylmethyl)(2-(2,6-dichloro-4-fluorophenyl)-2-oxoethyl)carbamoyl)-5-(trifluoromethyl)-1H-pyrazol-1-yl)-1-methylcyclohexanecarboxylic acid |
| 696 | 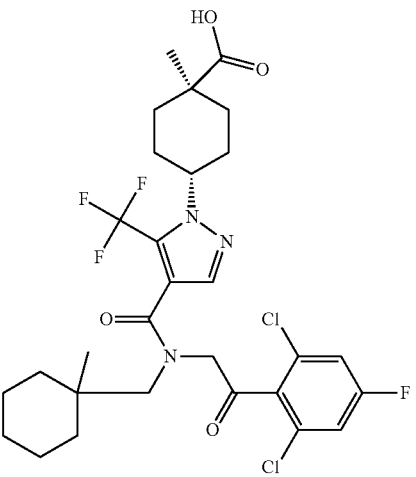 [SMILES: CC1(CN(CC(=O)c2c(Cl)cc(F)cc2Cl)C(=O)c2cnn([C@H]3CC[C@](C)(C(=O)O)CC3)c2C(F)(F)F)CCCCC1] | trans-4-(4-((2-(2,6-dichloro-4-fluorophenyl)-2-oxoethyl)((1-methylcyclohexyl)methyl)carbamoyl)-5-(trifluoromethyl)-1H-pyrazol-1-yl)-1-methylcyclohexanecarboxylic acid |
| 697 | 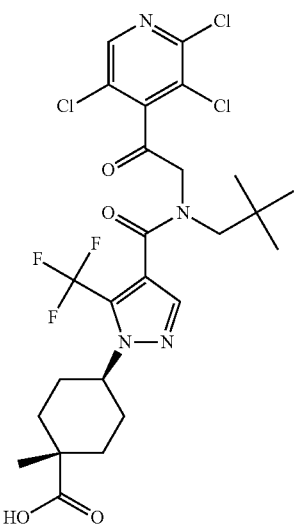 [SMILES: CC(C)(C)CN(CC(=O)c1c(Cl)cnc(Cl)c1Cl)C(=O)c1cnn([C@H]2CC[C@](C)(C(=O)O)CC2)c1C(F)(F)F] | trans-4-(4-((2,2-dimethylpropyl)(2-oxo-2-(2,3,5-trichloro-4-pyridinyl)ethyl)carbamoyl)-5-(trifluoromethyl)-1H-pyrazol-1-yl)-1-methylcyclohexanecarboxylic acid |

-continued

| example | structure | name |
|---|---|---|
| 698 | 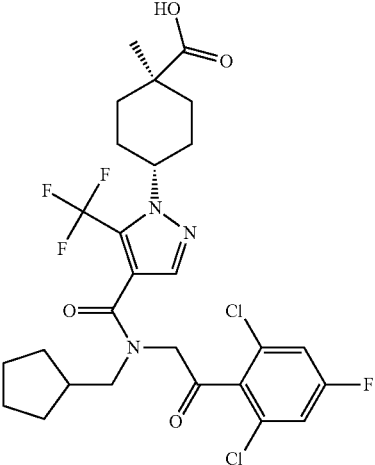 [SMILES: C[C@]1(C(=O)O)CC[C@H](n2ncc(C(=O)N(CC(=O)c3c(Cl)cc(F)cc3Cl)CC3CCCC3)c2C(F)(F)F)CC1] | trans-4-(4-((cyclopentylmethyl)(2-(2,6-dichloro-4-fluorophenyl)-2-oxoethyl)carbamoyl)-5-(trifluoromethyl)-1H-pyrazol-1-yl)-1-methylcyclohexanecarboxylic acid |
| 699 | 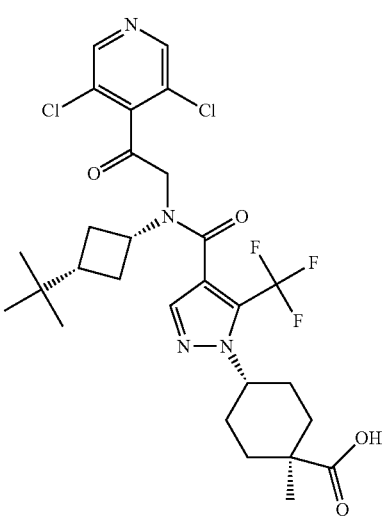 [SMILES: CC(C)(C)[C@H]1C[C@@H](N(CC(=O)c2c(Cl)cncc2Cl)C(=O)c2cnn([C@H]3CC[C@](C)(C(=O)O)CC3)c2C(F)(F)F)C1] | trans-4-(4-((2-(3,5-dichloro-4-pyridinyl)-2-oxoethyl)(cis-3-(2-methyl-2-propanyl)cyclobutyl)carbamoyl)-5-(trifluoromethyl)-1H-pyrazol-1-yl)-1-methylcyclohexanecarboxylic acid |
| 700 | 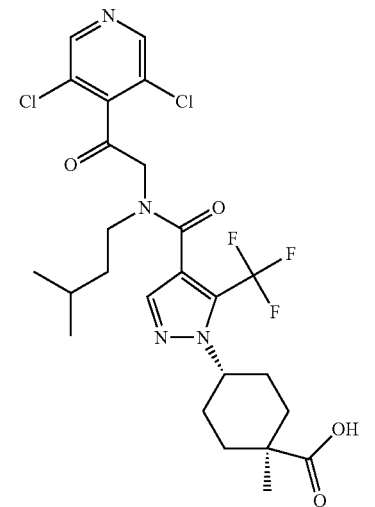 [SMILES: CC(C)CCN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)(3-methylbutyl)carbamoyl)-5-(trifluoromethyl)-1H-pyrazol-1-yl)-1-methylcyclohexanecarboxylic acid |

| example | structure | name |
| --- | --- | --- |
| 701 | 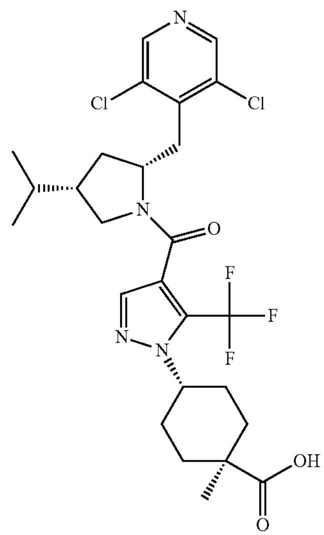 | trans-4-(4-(((2R,4R)-2-((3,5-dichloro-4-pyridinyl)methyl)-4-(2-propanyl)-1-pyrrolidinyl)carbonyl)-5-(trifluoromethyl)-1H-pyrazol-1-yl)-1-methylcyclohexanecarboxylic acid |
| 702 | 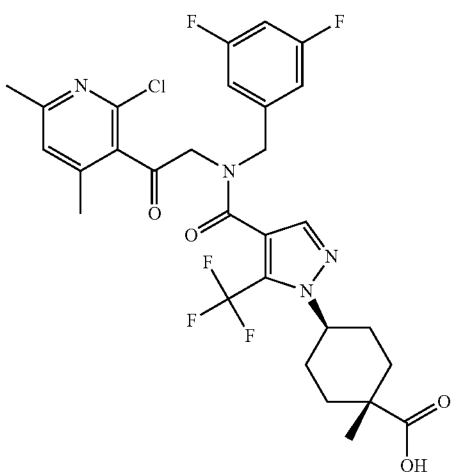 [SMILES: Cc1cc(C)c(C(=O)CN(Cc2cc(F)cc(F)c2)C(=O)c2cnn([C@H]3CC[C@](C)(C(=O)O)CC3)c2C(F)(F)F)c(Cl)n1] | trans-4-(4-((2-(2-chloro-4,6-dimethyl-3-pyridinyl)-2-oxoethyl)(3,5-difluorobenzyl)carbamoyl)-5-(trifluoromethyl)-1H-pyrazol-1-yl)-1-methylcyclohexanecarboxylic acid |
| 703 | 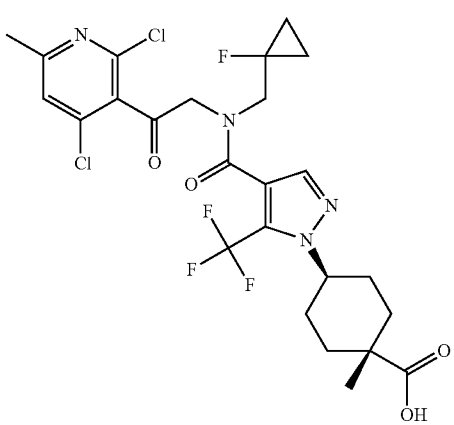 [SMILES: Cc1cc(Cl)c(C(=O)CN(CC2(F)CC2)C(=O)c2cnn([C@H]3CC[C@](C)(C(=O)O)CC3)c2C(F)(F)F)c(Cl)n1] | trans-4-(4-((2-(2,4-dichloro-6-methyl-3-pyridinyl)-2-oxoethyl)((1-fluorocyclopropyl)methyl)carbamoyl)-5-(trifluoromethyl)-1H-pyrazol-1-yl)-1-methylcyclohexanecarboxylic acid |

| example | structure | name |
|---|---|---|
| 704 | 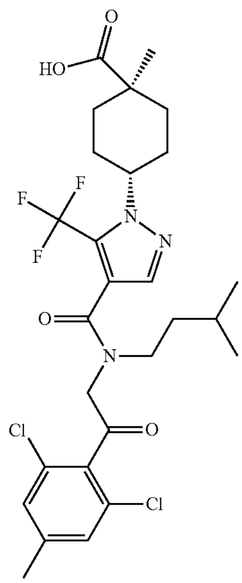 [SMILES: Cc1cc(Cl)c(C(=O)CN(CCC(C)C)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(3-methylbutyl)carbamoyl)-5-(trifluoromethyl)-1H-pyrazol-1-yl)-1-methylcyclohexanecarboxylic acid |
| 705 | 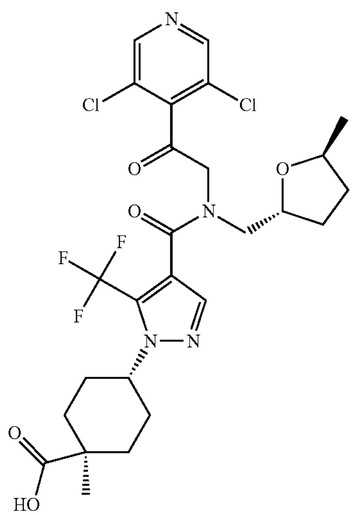 [SMILES: C[C@H]1CC[C@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2R,5S)-5-methyltetrahydro-2-furanyl)methyl)carbamoyl)-5-(trifluoromethyl)-1H-pyrazol-1-yl)-1-methylcyclohexanecarboxylic acid |
| 706 | 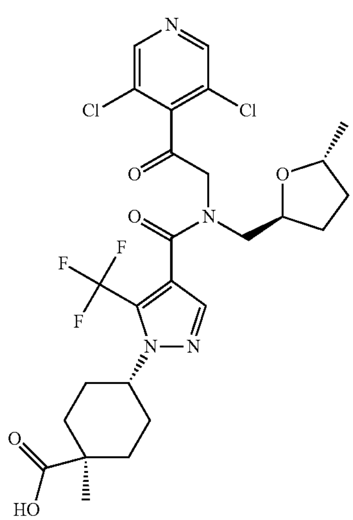 [SMILES: C[C@@H]1CC[C@@H](CN(CC(=O)c2c(Cl)cncc2Cl)C(=O)c2cnn([C@H]3CC[C@](C)(C(=O)O)CC3)c2C(F)(F)F)O1] | trans-4-(4-((2-(3,5-dichloro-4-pyridinyl)-2-oxoethyl)(((2S,5R)-5-methyltetrahydro-2-furanyl)methyl)carbamoyl)-5-(trifluoromethyl)-1H-pyrazol-1-yl)-1-methylcyclohexanecarboxylic acid |

| example | structure | name |
|---|---|---|
| 707 | 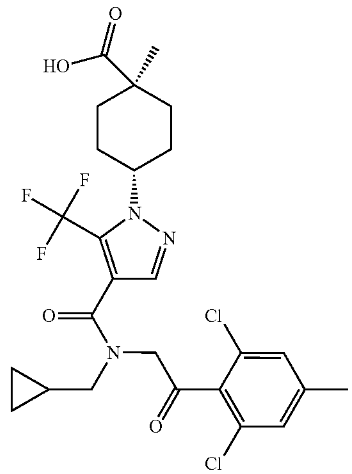 [SMILES: Cc1cc(Cl)c(C(=O)CN(CC2CC2)C(=O)c2cnn([C@H]3CC[C@](C)(C(=O)O)CC3)c2C(F)(F)F)c(Cl)c1] | trans-4-(4-((cyclopropylmethyl)(2-(2,6-dichloro-4-methylphenyl)-2-oxoethyl)carbamoyl)-5-(trifluoromethyl)-1H-pyrazol-1-yl)-1-methylcyclohexanecarboxylic acid |
| 708 | 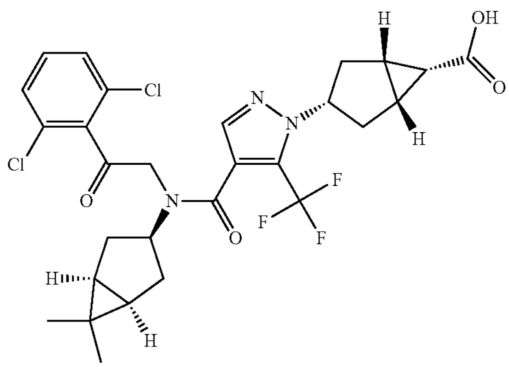 [SMILES: CC1(C)[C@@H]2C[C@H](N(CC(=O)c3c(Cl)cccc3Cl)C(=O)c3cnn([C@H]4C[C@@H]5[C@H](C4)[C@@H]5C(=O)O)c3C(F)(F)F)C[C@@H]21] | (1R,3r,5S,6s)-3-(4-((2-(2,6-dichlorophenyl)-2-oxoethyl)((1R,3r,5S)-6,6-dimethylbicyclo[3.1.0]hex-3-yl)carbamoyl)-3-(trifluoromethyl)-1H-pyrazol-1-yl)bicyclo[3.1.0]hexane-6-carboxylic acid |
| 709 | 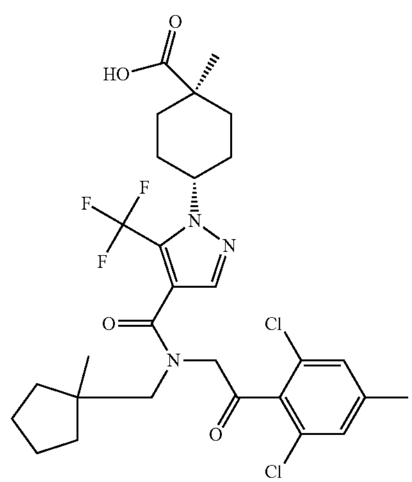 [SMILES: Cc1cc(Cl)c(C(=O)CN(CC2(C)CCCC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)((1-methylcyclopentyl)methyl)carbamoyl)-5-(trifluoromethyl)-1H-pyrazol-1-yl)-1-methylcyclohexanecarboxylic acid |

-continued

| example | structure | name |
|---|---|---|
| 710 | 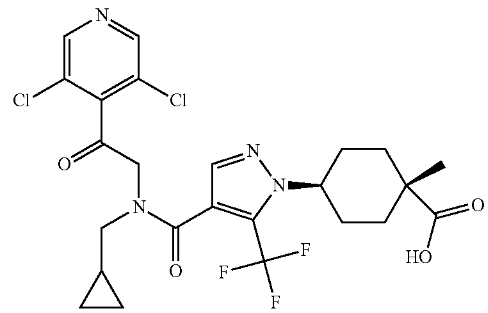 [SMILES: C[C@]1(C(=O)O)CC[C@H](n2ncc(C(=O)N(CC(=O)c3c(Cl)cncc3Cl)CC3CC3)c2C(F)(F)F)CC1] | trans-4-(4-((cyclopropylmethyl)(2-(3,5-dichloro-4-pyridinyl)-2-oxoethyl)carbamoyl)-5-(trifluoromethyl)-1H-pyrazol-1-yl)-1-methylcyclohexanecarboxylic acid |
| 711 | 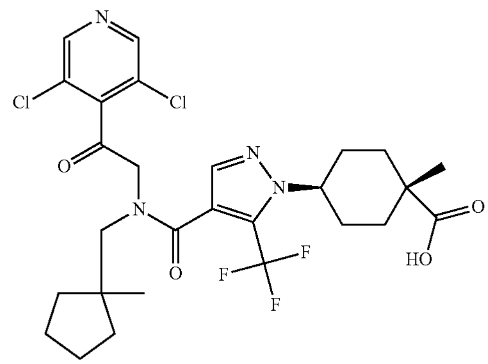 [SMILES: CC1(CN(CC(=O)c2c(Cl)cncc2Cl)C(=O)c2cnn([C@H]3CC[C@](C)(C(=O)O)CC3)c2C(F)(F)F)CCCC1] | trans-4-(4-((2-(3,5-dichloro-4-pyridinyl)-2-oxoethyl)((1-methylcyclopentyl)methyl)carbamoyl)-5-(trifluoromethyl)-1H-pyrazol-1-yl)-1-methylcyclohexanecarboxylic acid |
| 712 | 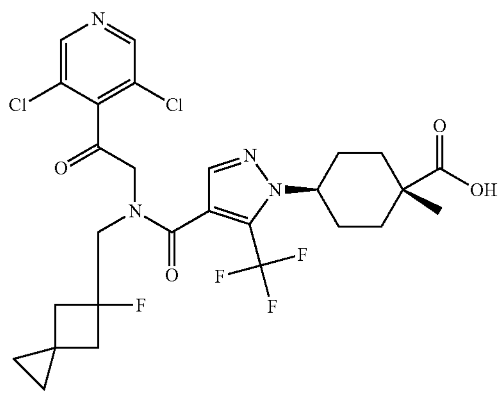 [SMILES: C[C@]1(C(=O)O)CC[C@H](n2ncc(C(=O)N(CC(=O)c3c(Cl)cncc3Cl)CC3(F)CC4(CC4)C3)c2C(F)(F)F)CC1] | trans-4-(4-((2-(3,5-dichloro-4-pyridinyl)-2-oxoethyl)((5-fluorospiro[2.3]hex-5-yl)methyl)carbamoyl)-5-(trifluoromethyl)-1H-pyrazol-1-yl)-1-methylcyclohexanecarboxylic acid |
| 713 | 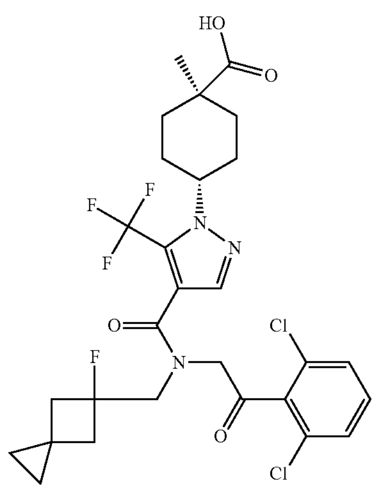 [SMILES: C[C@]1(C(=O)O)CC[C@H](n2ncc(C(=O)N(CC(=O)c3c(Cl)cccc3Cl)CC3(F)CC4(CC4)C3)c2C(F)(F)F)CC1] | trans-4-(4-((2-(2,6-dichlorophenyl)-2-oxoethyl)((5-fluorospiro[2.3]hex-5-yl)methyl)carbamoyl)-5-(trifluoromethyl)-1H-pyrazol-1-yl)-1-methylcyclohexanecarboxylic acid |

| example | structure | name |
|---|---|---|
| 714 | 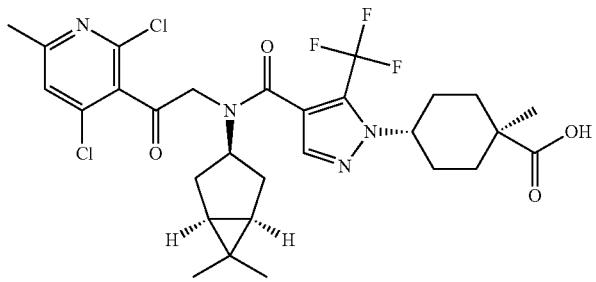 [SMILES: Cc1cc(Cl)c(C(=O)CN(C(=O)c2cnn([C@H]3CC[C@](C)(C(=O)O)CC3)c2C(F)(F)F)[C@H]2C[C@@H]3[C@H](C2)C3(C)C)c(Cl)n1] | trans-4-(4-((2-(2,4-dichloro-6-methyl-3-pyridinyl)-2-oxoethyl)((1R,3r,5S)-6,6-dimethylbicyclo[3.1.0]hex-3-yl)carbamoyl)-5-(trifluoromethyl)-1H-pyrazol-1-yl)-1-methylcyclohexanecarboxylic acid |
| 715 | 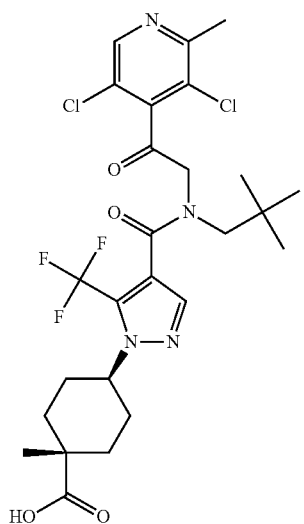 [SMILES: Cc1ncc(Cl)c(C(=O)CN(CC(C)(C)C)C(=O)c2cnn([C@H]3CC[C@](C)(C(=O)O)CC3)c2C(F)(F)F)c1Cl] | trans-4-(4-((2-(3,5-dichloro-2-methyl-4-pyridinyl)-2-oxoethyl)(2,2-dimethylpropyl)carbamoyl)-5-(trifluoromethyl)-1H-pyrazol-1-yl)-1-methylcyclohexanecarboxylic acid |
| 716 | 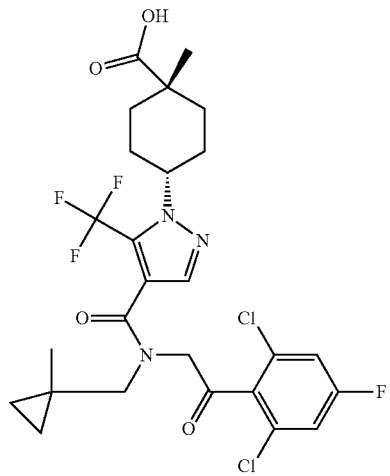 [SMILES: CC1(CN(CC(=O)c2c(Cl)cc(F)cc2Cl)C(=O)c2cnn([C@H]3CC[C@@](C)(C(=O)O)CC3)c2C(F)(F)F)CC1] | trans-4-(4-((2-(2,6-dichloro-4-fluorophenyl)-2-oxoethyl)((1-methylcyclopropyl)methyl)carbamoyl)-5-(trifluoromethyl)-1H-pyrazol-1-yl)-1-methylcyclohexanecarboxylic acid |

| example | structure | name |
|---|---|---|
| 717 | 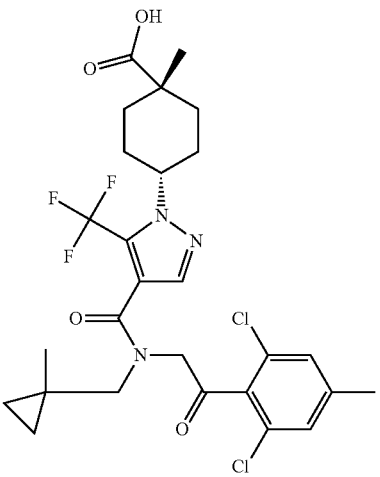 [SMILES: Cc1cc(Cl)c(C(=O)CN(CC2(C)CC2)C(=O)c2cnn([C@H]3CC[C@@](C)(C(=O)O)CC3)c2C(F)(F)F)c(Cl)c1] | trans-4-(4-((2-(2,6-dichloro-4-fluorophenyl)-2-oxoethyl)((1-methylcyclopropyl)methyl)carbamoyl)-5-(trifluoromethyl)-1H-pyrazol-1-yl)-1-methylcyclohexanecarboxylic acid |
| 718 | 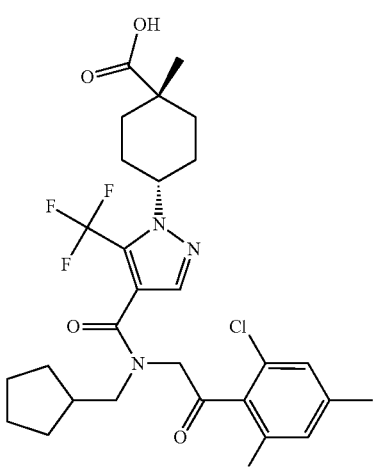 | trans-4-(4-((cyclopentylmethyl)(2-(2,6-dichloro-4-methylphenyl)-2-oxoethyl)carbamoyl)-5-(trifluoromethyl)-1H-pyrazol-1-yl)-1-methylcyclohexanecarboxylic acid |
| 719 | 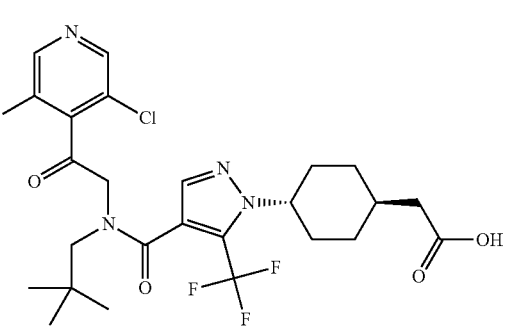 | (trans-4-(4-((2-(3,5-dichloro-4-pyridinyl)-2-oxoethyl)(2,2-dimethylpropyl)carbamoyl)-5-(trifluoromethyl)-1H-pyrazol-1-yl)cyclohexyl)acetic acid |
| 720 | 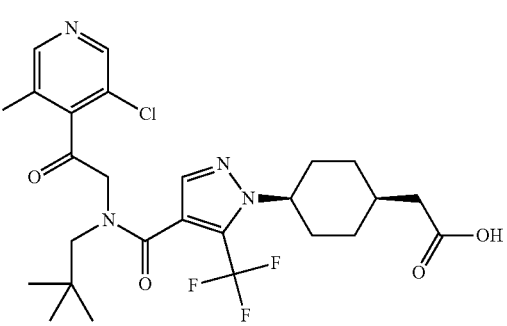 | (cis-4-(4-((2-(3,5-dichloro-4-pyridinyl)-2-oxoethyl)(2,2-dimethylpropyl)carbamoyl)-5-(trifluoromethyl)-1H-pyrazol-1-yl)cyclohexyl)acetic acid |

-continued

| example | structure | name |
| --- | --- | --- |
| 721 | 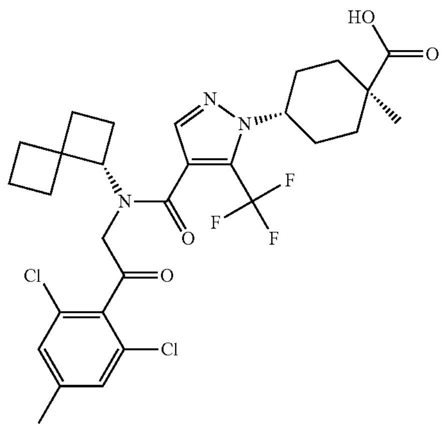 [SMILES: Cc1cc(Cl)c(C(=O)CN(C(=O)c2cnn([C@H]3CC[C@](C)(C(=O)O)CC3)c2C(F)(F)F)[C@H]2CCC23CCC3)c(Cl)c1] | trans-4-(4-((2-(2,6-dichloro-4-methylphenyl)-2-oxoethyl)((1S)-spiro[3.3]hept-1-yl)carbamoyl)-5-(trifluoromethyl)-1H-pyrazol-1-yl)-1-methylcyclohexanecarboxylic acid |
| 722 | 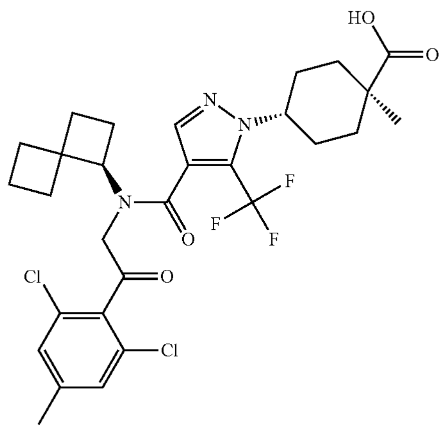 [SMILES: Cc1cc(Cl)c(C(=O)CN(C(=O)c2cnn([C@H]3CC[C@](C)(C(=O)O)CC3)c2C(F)(F)F)[C@@H]2CCC23CCC3)c(Cl)c1] | trans-4-(4-((2-(2,6-dichloro-4-methylphenyl)-2-oxoethyl)((1R)-spiro[3.3]hept-1-yl)carbamoyl)-5-(trifluoromethyl)-1H-pyrazol-1-yl)-1-methylcyclohexanecarboxylic acid |
| 723 | 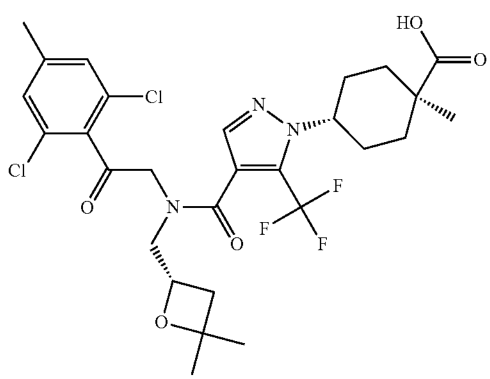 [SMILES: Cc1cc(Cl)c(C(=O)CN(C[C@@H]2CC(C)(C)O2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(((2S)-4,4-dimethyl-2-oxetanyl)methyl)carbamoyl)-5-(trifluoromethyl)-1H-pyrazol-1-yl)-1-methylcyclohexanecarboxylic acid |
| 724 | 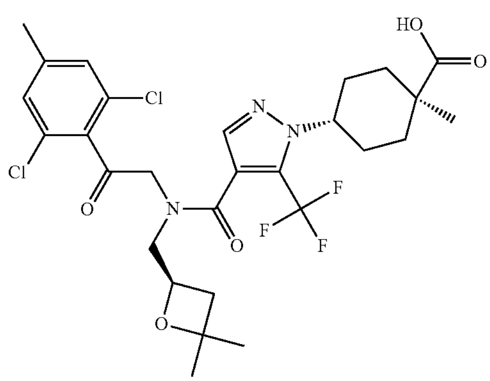 [SMILES: Cc1cc(Cl)c(C(=O)CN(C[C@H]2CC(C)(C)O2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(((2R)-4,4-dimethyl-2-oxetanyl)methyl)carbamoyl)-5-(trifluoromethyl)-1H-pyrazol-1-yl)-1-methylcyclohexanecarboxylic acid |

| example | structure | name |
| --- | --- | --- |
| 725 | 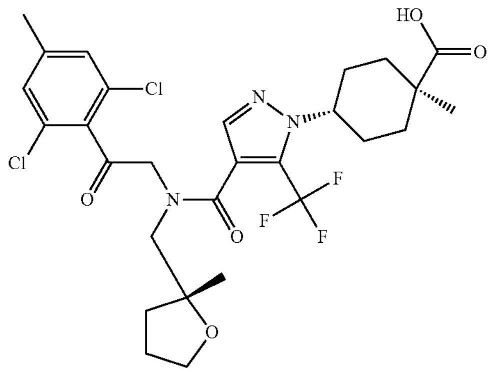 [SMILES: Cc1cc(Cl)c(C(=O)CN(C[C@@]2(C)CCCO2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(((2S)-2-methyltetrahydro-2-furanyl)methyl)carbamoyl)-5-(trifluoromethyl)-1H-pyrazol-1-yl)-1-methylcyclohexanecarboxylic acid |
| 726 | 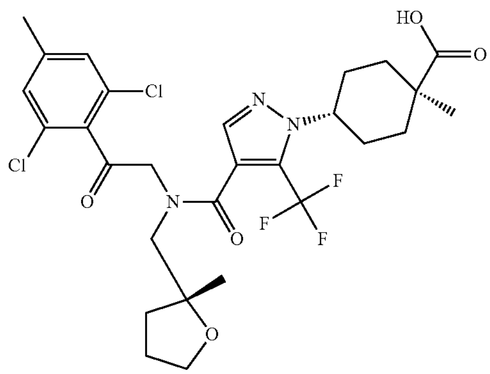 [SMILES: Cc1cc(Cl)c(C(=O)CN(C[C@@]2(C)CCCO2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(((2R)-2-methyltetrahydro-2-furanyl)methyl)carbamoyl)-5-(trifluoromethyl)-1H-pyrazol-1-yl)-1-methylcyclohexanecarboxylic acid |
| 727 | 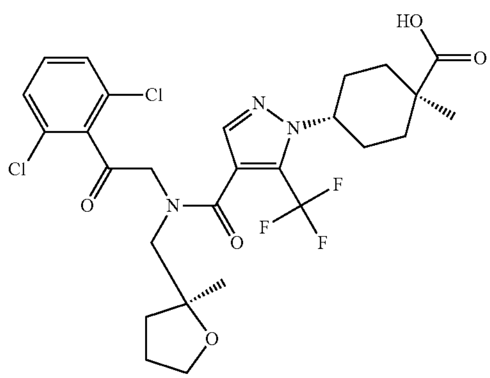 [SMILES: C[C@@]1(CN(CC(=O)c2c(Cl)cccc2Cl)C(=O)c2cnn([C@H]3CC[C@](C)(C(=O)O)CC3)c2C(F)(F)F)CCCO1] | trans-4-(4-((2-(2,6-dichlorophenyl)-2-oxoethyl)(((2S)-2-methyltetrahydro-2-furanyl)methyl)carbamoyl)-5-(trifluoromethyl)-1H-pyrazol-1-yl)-1-methylcyclohexanecarboxylic acid |
| 728 | 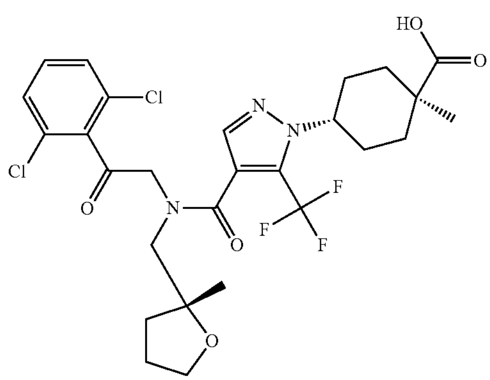 [SMILES: C[C@]1(CN(CC(=O)c2c(Cl)cccc2Cl)C(=O)c2cnn([C@H]3CC[C@](C)(C(=O)O)CC3)c2C(F)(F)F)CCCO1] | trans-4-(4-((2-(2,6-dichlorophenyl)-2-oxoethyl)(((2R)-2-methyltetrahydro-2-furanyl)methyl)carbamoyl)-5-(trifluoromethyl)-1H-pyrazol-1-yl)-1-methylcyclohexanecarboxylic acid |

| example | structure | name |
|---|---|---|
| 729 | 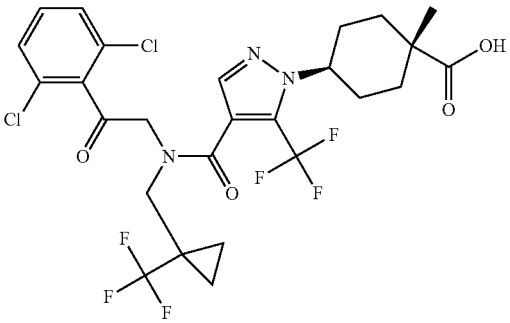 | trans-4-(4-((2-(2,6-dichlorophenyl)-2-oxoethyl)((1-(trifluoromethyl)cyclopropyl)methyl)carbamoyl)-3-(trifluoromethyl)-1H-pyrazol-1-yl)-1-methylcyclohexanecarboxylic acid |
| 730 | 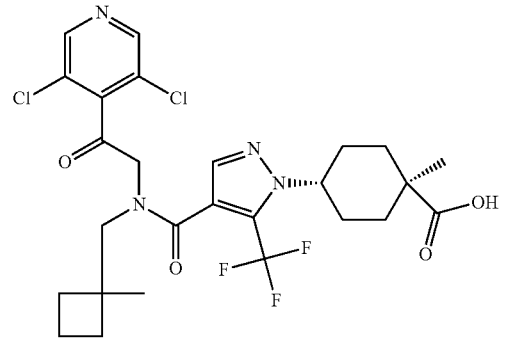 [SMILES: CC1(CN(CC(=O)c2c(Cl)cncc2Cl)C(=O)c2cnn([C@H]3CC[C@](C)(C(=O)O)CC3)c2C(F)(F)F)CCC1] | trans-4-(4-((2-(3,5-dichloro-4-pyridinyl)-2-oxoethyl)((1-methylcyclobutyl)methyl)carbamoyl)-5-(trifluoromethyl)-1H-pyrazol-1-yl)-1-methylcyclohexanecarboxylic acid |
| 731 | 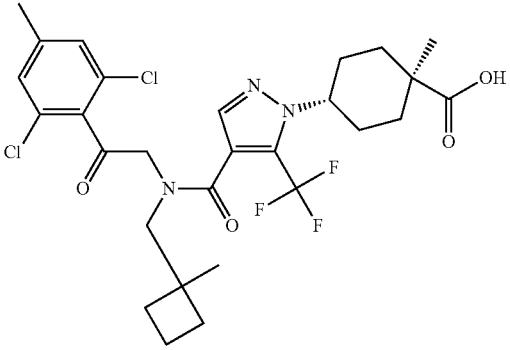 [SMILES: Cc1cc(Cl)c(C(=O)CN(CC2(C)CCC2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)((1-methylcyclobutyl)methyl)carbamoyl)-5-(trifluoromethyl)-1H-pyrazol-1-yl)-1-methylcyclohexanecarboxylic acid |
| 732 | 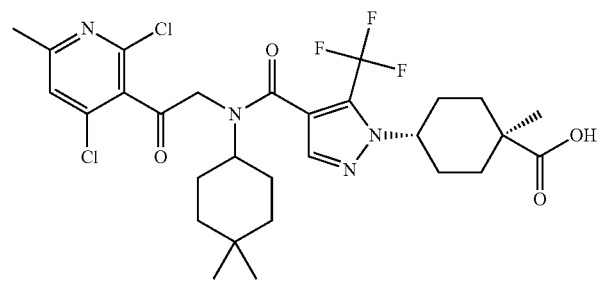 [SMILES: Cc1cc(Cl)c(C(=O)CN(C(=O)c2cnn([C@H]3CC[C@](C)(C(=O)O)CC3)c2C(F)(F)F)C2CCC(C)(C)CC2)c(Cl)n1] | trans-4-(4-((2-(2,4-dichloro-6-methyl-3-pyridinyl)-2-oxoethyl)(4,4-dimethylcyclohexyl)carbamoyl)-5-(trifluoromethyl)-1H-pyrazol-1-yl)-1-methylcyclohexanecarboxylic acid |

| example | structure | name |
| --- | --- | --- |
| 733 | 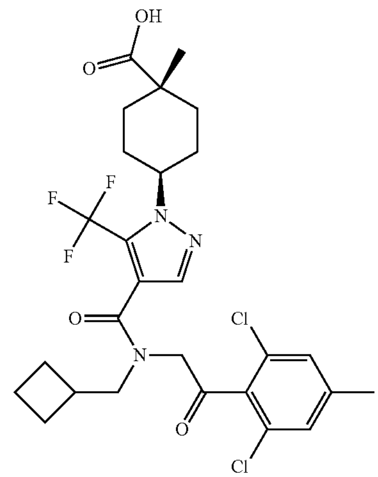 [SMILES: Cc1cc(Cl)c(C(=O)CN(CC2CCC2)C(=O)c2cnn([C@H]3CC[C@](C)(C(=O)O)CC3)c2C(F)(F)F)c(Cl)c1] | trans-4-(4-((cyclobutylmethyl)(2-(2,6-dichloro-4-methylphenyl)-2-oxoethyl)carbamoyl)-5-(trifluoromethyl)-1H-pyrazol-1-yl)-1-methylcyclohexanecarboxylic acid |
| 734 | 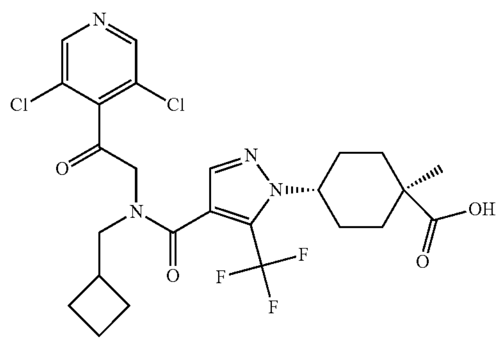 [SMILES: C[C@]1(C(=O)O)CC[C@H](n2ncc(C(=O)N(CC(=O)c3c(Cl)cncc3Cl)CC3CCC3)c2C(F)(F)F)CC1] | trans-4-(4-((cyclobutylmethyl)(2-(3,5-dichloro-4-pyridinyl)-2-oxoethyl)carbamoyl)-5-(trifluoromethyl)-1H-pyrazol-1-yl)-1-methylcyclohexanecarboxylic acid |
| 735 | 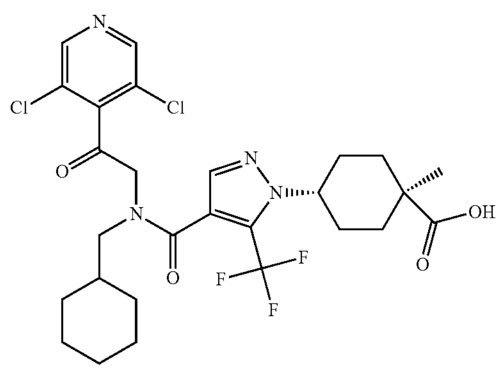 [SMILES: C[C@]1(C(=O)O)CC[C@H](n2ncc(C(=O)N(CC(=O)c3c(Cl)cncc3Cl)CC3CCCCC3)c2C(F)(F)F)CC1] | trans-4-(4-((cyclobutylmethyl)(2-(3,5-dichloro-4-pyridinyl)-2-oxoethyl)carbamoyl)-5-(trifluoromethyl)-1H-pyrazol-1-yl)-1-methylcyclohexanecarboxylic acid |
| 736 | 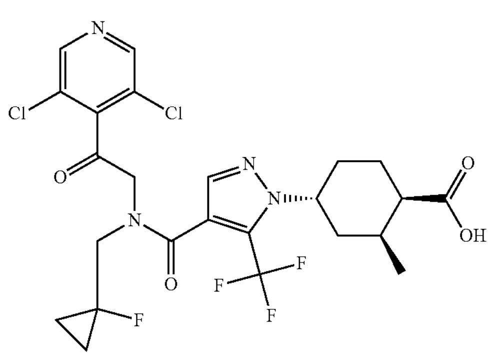 [SMILES: C[C@H]1C[C@H](n2ncc(C(=O)N(CC(=O)c3c(Cl)cncc3Cl)CC3(F)CC3)c2C(F)(F)F)CC[C@H]1C(=O)O] | (1S,2R,4S)-4-(4-((2-(3,5-dichloro-4-pyridinyl)-2-oxoethyl)((1-fluorocyclopropyl)methyl)carbamoyl)-5-(trifluoromethyl)-1H-pyrazol-1-yl)-2-methylcyclohexanecarboxylic acid |

-continued

| example | structure | name |
|---|---|---|
| 737 | 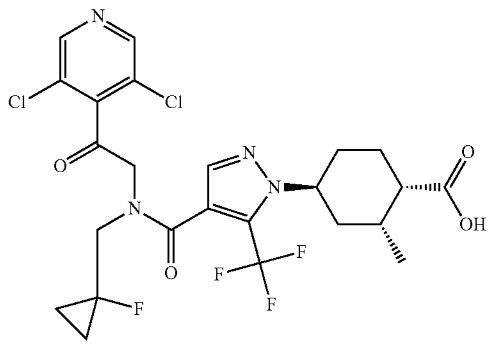 [SMILES: C[C@@H]1C[C@@H](n2ncc(C(=O)N(CC(=O)c3c(Cl)cncc3Cl)CC3(F)CC3)c2C(F)(F)F)CC[C@@H]1C(=O)O] | (1R,2S,4R)-4-(4-((2-(3,5-dichloro-4-pyridinyl)-2-oxoethyl)((1-fluorocyclopropyl)methyl)carbamoyl)-5-(trifluoromethyl)-1H-pyrazol-1-yl)-2-methylcyclohexanecarboxylic acid |
| 738 | 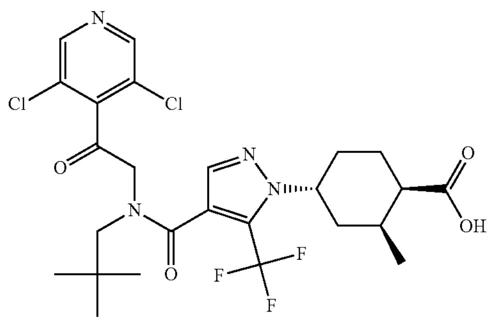 [SMILES: C[C@H]1C[C@H](n2ncc(C(=O)N(CC(=O)c3c(Cl)cncc3Cl)CC(C)(C)C)c2C(F)(F)F)CC[C@H]1C(=O)O] | (1S,2R,4S)-4-(4-((2-(3,5-dichloro-4-pyridinyl)-2-oxoethyl)((2,2-dimethylpropyl)carbamoyl)-5-(trifluoromethyl)-1H-pyrazol-1-yl)-2-methylcyclohexanecarboxylic acid |
| 739 | 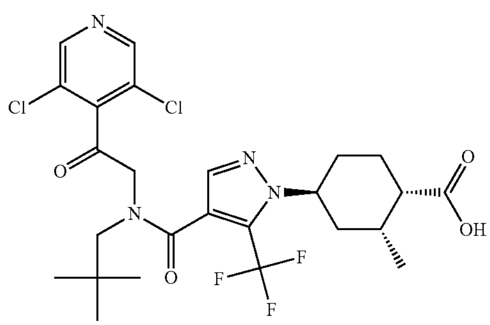 [SMILES: C[C@@H]1C[C@@H](n2ncc(C(=O)N(CC(=O)c3c(Cl)cncc3Cl)CC(C)(C)C)c2C(F)(F)F)CC[C@@H]1C(=O)O] | (1S,2S,4R)-4-(4-((2-(3,5-dichloro-4-pyridinyl)-2-oxoethyl)((2,2-dimethylpropyl)carbamoyl)-5-(trifluoromethyl)-1H-pyrazol-1-yl)-2-methylcyclohexanecarboxylic acid |
| 740 | 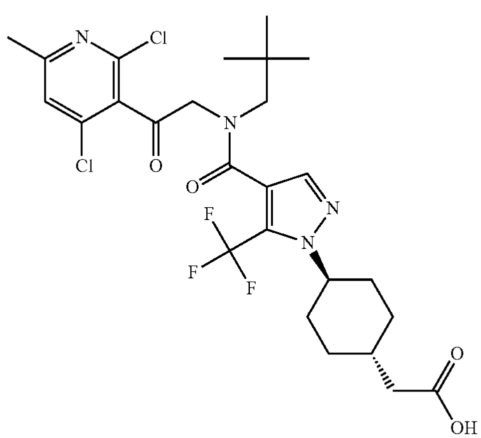 [SMILES: Cc1cc(Cl)c(C(=O)CN(CC(C)(C)C)C(=O)c2cnn([C@H]3CC[C@H](CC(=O)O)CC3)c2C(F)(F)F)c(Cl)n1] | (trans-4-(4-((2-(2,4-dichloro-6-methyl-3-pyridinyl)-2-oxoethyl)(2,2-dimethylpropyl)carbamoyl)-5-(trifluoromethyl)-1H-pyrazol-1-yl)cyclohexyl)acetic acid |

-continued

| example | structure | name |
|---|---|---|
| 741 | 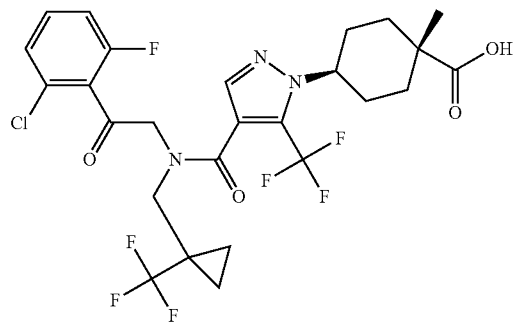 [SMILES: C[C@]1(C(=O)O)CC[C@H](n2ncc(C(=O)N(CC(=O)c3c(F)cccc3Cl)CC3(C(F)(F)F)CC3)c2C(F)(F)F)CC1] | trans-4-(4-((2-(2-chloro-6-fluorophenyl)-2-oxoethyl)((1-(trifluoromethyl)cyclopropyl)methyl)carbamoyl)-3-(trifluoromethyl)-1H-pyrazol-1-yl)-1-methylcyclohexanecarboxylic acid |
| 742 | 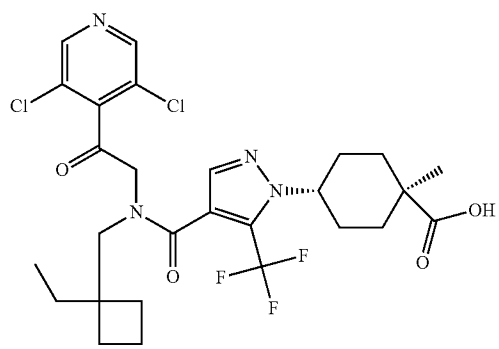 [SMILES: CCC1(CN(CC(=O)c2c(Cl)cncc2Cl)C(=O)c2cnn([C@H]3CC[C@](C)(C(=O)O)CC3)c2C(F)(F)F)CCC1] | trans-4-(4-((2-(3,5-dichloro-4-pyridinyl)-2-oxoethyl)((1-ethylcyclobutyl)methyl)carbamoyl)-5-(trifluoromethyl)-1H-pyrazol-1-yl)-1-methylcyclohexanecarboxylic acid |
| 743 | 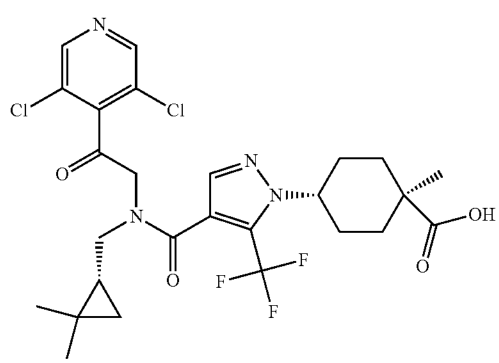 [SMILES: CC1(C)C[C@H]1CN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)(((1S)-2,2-dimethylcyclopropyl)methyl)carbamoyl)-5-(trifluoromethyl)-1H-pyrazol-1-yl)-1-methylcyclohexanecarboxylic acid |
| 744 | 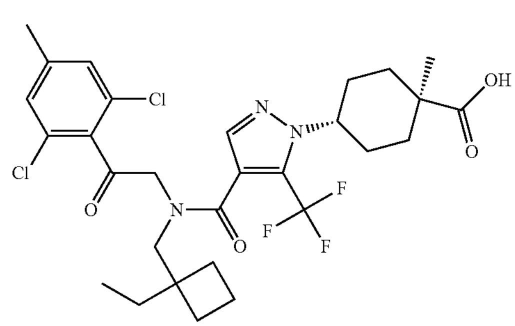 [SMILES: CCC1(CN(CC(=O)c2c(Cl)cc(C)cc2Cl)C(=O)c2cnn([C@H]3CC[C@](C)(C(=O)O)CC3)c2C(F)(F)F)CCC1] | trans-4-(4-((2-(2,6-dichloro-4-methylphenyl)-2-oxoethyl)((1-ethylcyclobutyl)methyl)carbamoyl)-5-(trifluoromethyl)-1H-pyrazol-1-yl)-1-methylcyclohexanecarboxylic acid |

| example | structure | name |
|---|---|---|
| 745 | 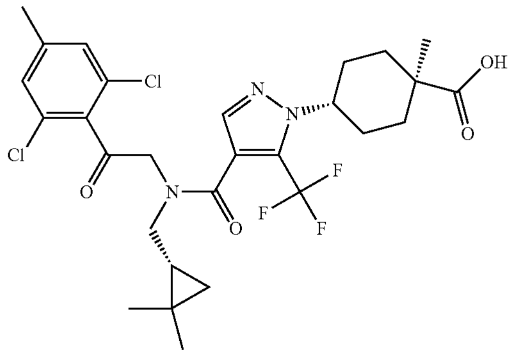 [SMILES: Cc1cc(Cl)c(C(=O)CN(C[C@@H]2CC2(C)C)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(((1R)-2,2-dimethylcyclopropyl)methyl)carbamoyl)-5-(trifluoromethyl)-1H-pyrazol-1-yl)-1-methylcyclohexanecarboxylic acid |
| 746 | 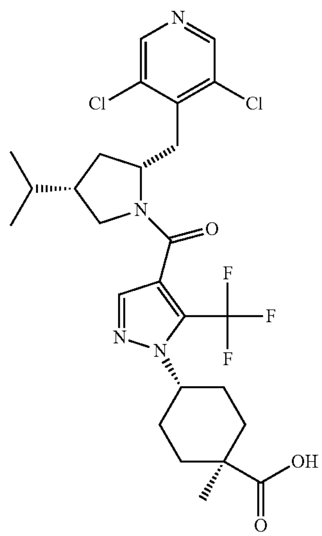 | trans-4-(4-(((2R,4S)-2-((3,5-dichloro-4-pyridinyl)methyl)-4-(2-propanyl)-1-pyrrolidinyl)carbonyl)-5-(trifluoromethyl)-1H-pyrazol-1-yl)-1-methylcyclohexanecarboxylic acid |
| 747 | 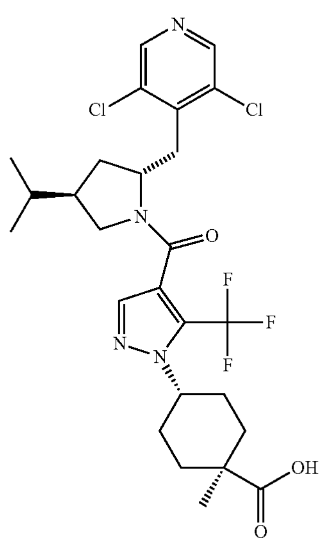 | trans-4-(4-(((2R,4R)-2-((3,5-dichloro-4-pyridinyl)methyl)-4-(2-propanyl)-1-pyrrolidinyl)carbonyl)-5-(trifluoromethyl)-1H-pyrazol-1-yl)-1-methylcyclohexanecarboxylic acid |

-continued

| example | structure | name |
|---|---|---|
| 748 | 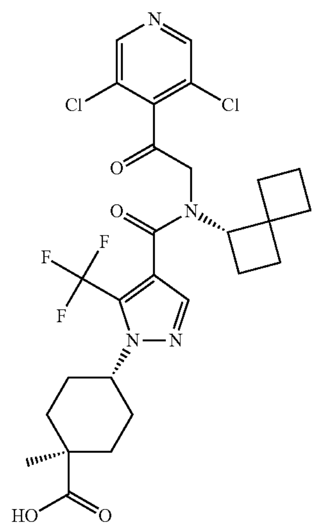 [SMILES: C[C@]1(C(=O)O)CC[C@H](n2ncc(C(=O)N(CC(=O)c3c(Cl)cncc3Cl)[C@H]3CCC34CCC4)c2C(F)(F)F)CC1] | trans-4-(4-((2-(3,5-dichloro-4-pyridinyl)-2-oxoethyl)((1S)-spiro[3.3]hept-1-yl)carbamoyl)-5-(trifluoromethyl)-1H-pyrazol-1-yl)-1-methylcyclohexanecarboxylic acid |
| 749 | 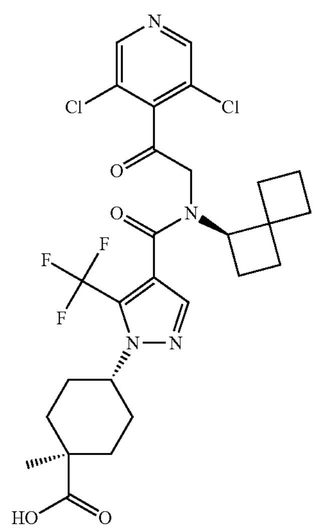 [SMILES: C[C@]1(C(=O)O)CC[C@H](n2ncc(C(=O)N(CC(=O)c3c(Cl)cncc3Cl)[C@@H]3CCC34CCC4)c2C(F)(F)F)CC1] | trans-4-(4-((2-(3,5-dichloro-4-pyridinyl)-2-oxoethyl)((1R)-spiro[3.3]hept-1-yl)carbamoyl)-5-(trifluoromethyl)-1H-pyrazol-1-yl)-1-methylcyclohexanecarboxylic acid |
| 750 | 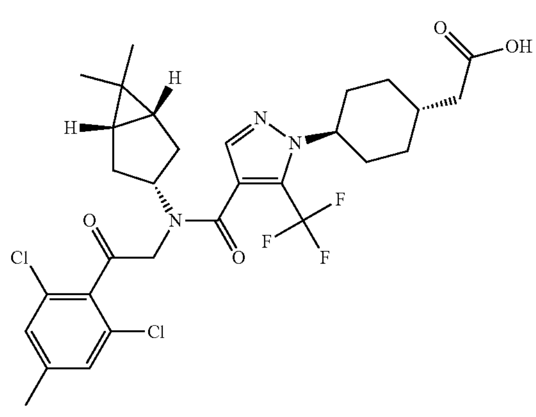 [SMILES: Cc1cc(Cl)c(C(=O)CN(C(=O)c2cnn([C@H]3CC[C@H](CC(=O)O)CC3)c2C(F)(F)F)[C@H]2C[C@@H]3[C@H](C2)C3(C)C)c(Cl)c1] | (trans-4-(4-((2-(2,6-dichloro-4-methylphenyl)-2-oxoethyl)((1R,3r,5S)-6,6-dimethylbicyclo[3.1.0]hex-3-yl)carbamoyl)-5-(trifluoromethyl)-1H-pyrazol-1-yl)cyclohexyl)acetic acid |

| example | structure | name |
|---|---|---|
| 751 | 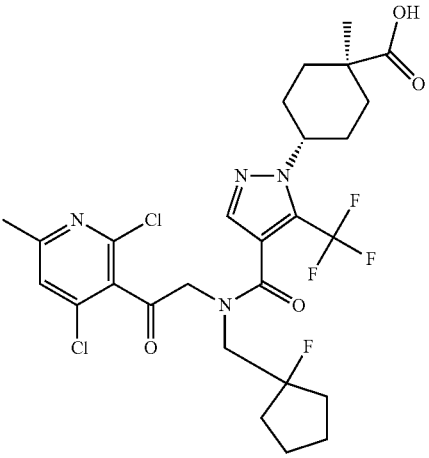 [SMILES: Cc1cc(Cl)c(C(=O)CN(CC2(F)CCCC2)C(=O)c2cnn([C@H]3CC[C@](C)(C(=O)O)CC3)c2C(F)(F)F)c(Cl)n1] | trans-4-(4-((2-(2,4-dichloro-6-methyl-3-pyridinyl)-2-oxoethyl)((1-fluorocyclopentyl)methyl)carbamoyl)-5-(trifluoromethyl)-1H-pyrazol-1-yl)-1-methylcyclohexanecarboxylic acid |
| 752 | 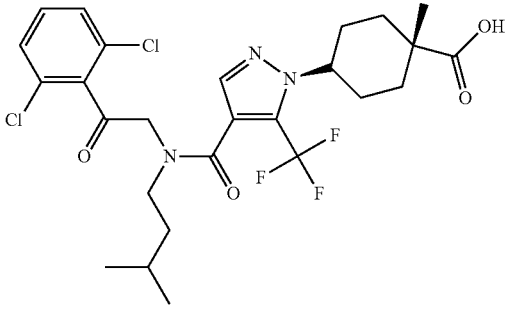 | trans-4-(4-((2-(2,6-dichlorophenyl)-2-oxoethyl)(3-methylbutyl)carbamoyl)-5-(trifluoromethyl)-1H-pyrazol-1-yl)-1-methylcyclohexanecarboxylic acid |
| 753 | 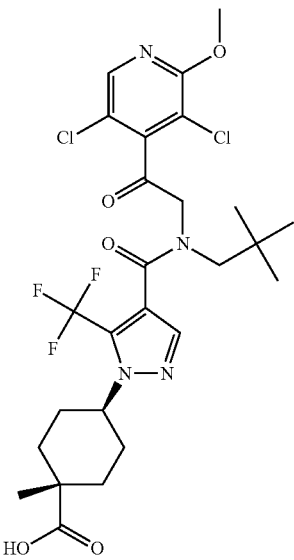 [SMILES: COc1ncc(Cl)c(C(=O)CN(CC(C)(C)C)C(=O)c2cnn([C@H]3CC[C@](C)(C(=O)O)CC3)c2C(F)(F)F)c1Cl] | trans-4-(4-((2-(3,5-dichloro-2-methoxy-4-pyridinyl)-2-oxoethyl)(2,2-dimethylpropyl)carbamoyl)-5-(trifluoromethyl)-1H-pyrazol-1-yl)-1-methylcyclohexanecarboxylic acid |

-continued

| example | structure | name |
|---|---|---|
| 754 | 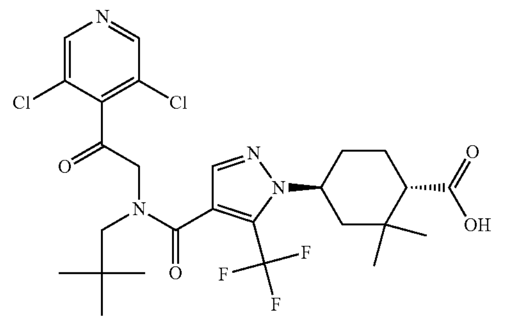 [SMILES: CC(C)(C)CN(CC(=O)c1c(Cl)cncc1Cl)C(=O)c1cnn([C@H]2CC[C@H](C(=O)O)C(C)(C)C2)c1C(F)(F)F] | (1R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylic acid |
| 755 | 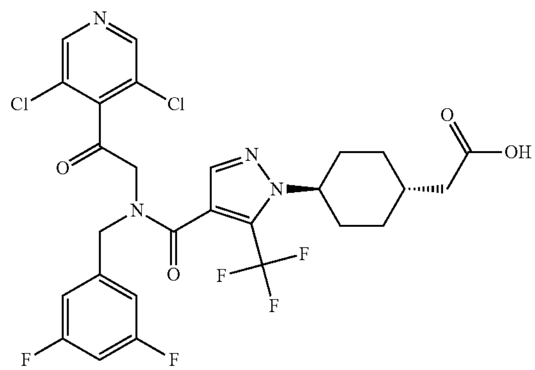 [SMILES: O=C(O)C[C@H]1CC[C@H](n2ncc(C(=O)N(CC(=O)c3c(Cl)cncc3Cl)Cc3cc(F)cc(F)c3)c2C(F)(F)F)CC1] | (trans-4-(4-((2-(3,5-dichloro-4-pyridinyl)-2-oxoethyl)(3,5-difluorobenzyl)carbamoyl)-5-(trifluoromethyl)-1H-pyrazol-1-yl)cyclohexyl)acetic acid |
| 756 | 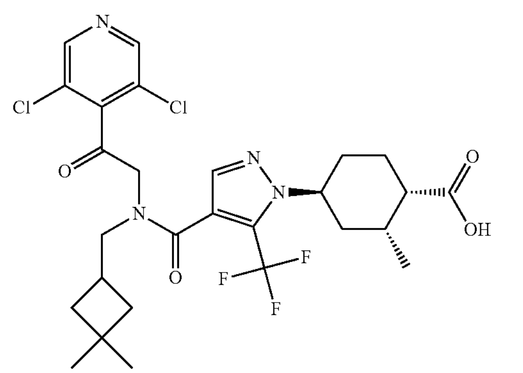 [SMILES: C[C@@H]1C[C@@H](n2ncc(C(=O)N(CC(=O)c3c(Cl)cncc3Cl)CC3CC(C)(C)C3)c2C(F)(F)F)CC[C@@H]1C(=O)O] | (1S,2R,4S)-4-(4-((2-(3,5-dichloro-4-pyridinyl)-2-oxoethyl)((3,3-dimethylcyclobutyl)methyl)carbamoyl)-5-(trifluoromethyl)-1H-pyrazol-1-yl)-2-methylcyclohexanecarboxylic acid |
| 757 | 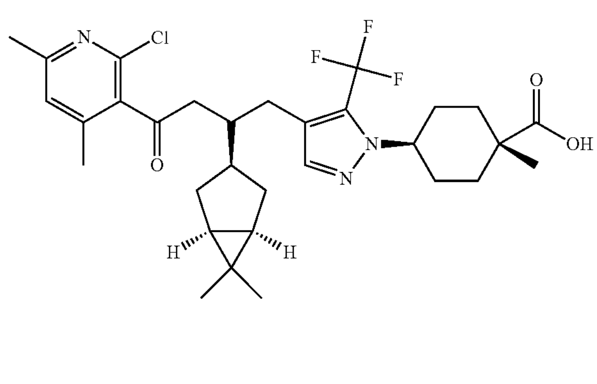 [SMILES: Cc1cc(C)c(C(=O)CC(Cc2cnn([C@H]3CC[C@](C)(C(=O)O)CC3)c2C(F)(F)F)[C@H]2C[C@@H]3[C@H](C2)C3(C)C)c(Cl)n1] | trans-4-(4-((2-(2-chloro-4,6-dimethyl-3-pyridinyl)-2-oxoethyl)((1R,3r,5S)-6,6-dimethylbicyclo[3.1.0]hex-3-yl)carbamoyl)-5-(trifluoromethyl)-1H-pyrazol-1-yl)-1-methylcyclohexanecarboxylic acid |

| example | structure | name |
|---|---|---|
| 758 | 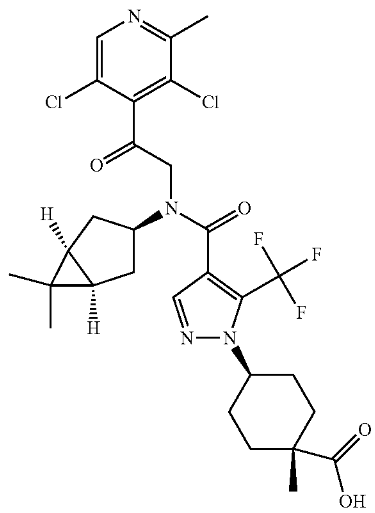 [SMILES: Cc1ncc(Cl)c(C(=O)CN(C(=O)c2cnn([C@H]3CC[C@](C)(C(=O)O)CC3)c2C(F)(F)F)[C@H]2C[C@@H]3[C@H](C2)C3(C)C)c1Cl] | trans-4-(4-((2-(3,5-dichloro-2-methyl-3-pyridinyl)-2-oxoethyl)((1R,3r,5S)-6,6-dimethylbicyclo[3.1.0]hex-3-yl)carbamoyl)-5-(trifluoromethyl)-1H-pyrazol-1-yl)-1-methylcyclohexanecarboxylic acid |
| 759 | 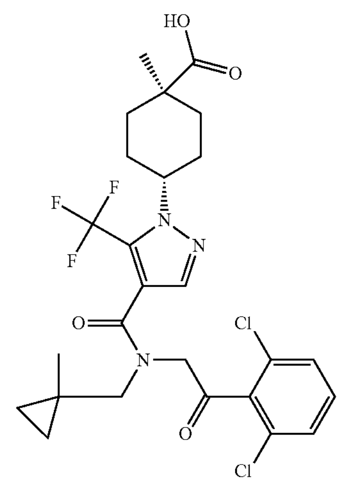 [SMILES: CC1(CN(CC(=O)c2c(Cl)cccc2Cl)C(=O)c2cnn([C@H]3CC[C@](C)(C(=O)O)CC3)c2C(F)(F)F)CC1] | trans-4-(4-((2-(2,6-dichlorophenyl)-2-oxoethyl)((1-methylcyclopropyl)methyl)carbamoyl)-5-(trifluoromethyl)-1H-pyrazol-1-yl)-1-methylcyclohexanecarboxylic acid |
| 760 | 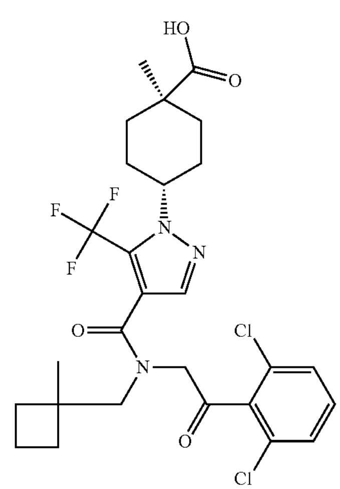 [SMILES: CC1(CN(CC(=O)c2c(Cl)cccc2Cl)C(=O)c2cnn([C@H]3CC[C@](C)(C(=O)O)CC3)c2C(F)(F)F)CCC1] | trans-4-(4-((2-(2,6-dichlorophenyl)-2-oxoethyl)((1-methylcyclobutyl)methyl)carbamoyl)-5-(trifluoromethyl)-1H-pyrazol-1-yl)-1-methylcyclohexanecarboxylic acid |

-continued

| example | structure | name |
|---|---|---|
| 761 | 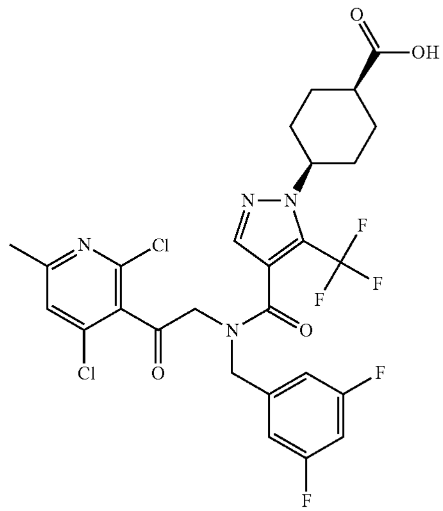 [SMILES: Cc1cc(Cl)c(C(=O)CN(Cc2cc(F)cc(F)c2)C(=O)c2cnn([C@H]3CC[C@@H](C(=O)O)CC3)c2C(F)(F)F)c(Cl)n1] | cis-4-(4-((2-(2,4-dichloro-6-methyl-3-pyridinyl)-2-oxoethyl)(3,5-difluorobenzyl)carbamoyl)-5-(trifluoromethyl)-1H-pyrazol-1-yl)cyclohexanecarboxylic acid |
| 762 | 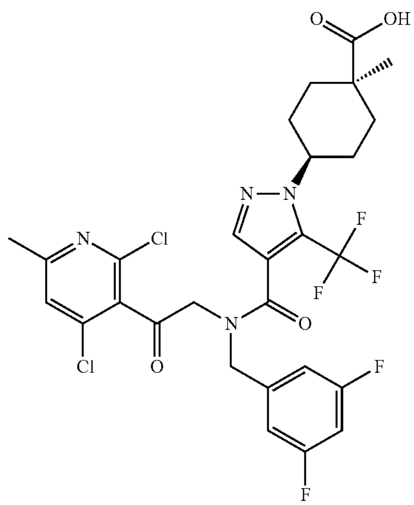 | trans-4-(4-((2-(2,4-dichloro-6-methyl-3-pyridinyl)-2-oxoethyl)(3,5-difluorobenzyl)carbamoyl)-5-(trifluoromethyl)-1H-pyrazol-1-yl)-1-methylcyclohexanecarboxylic acid |
| 763 | 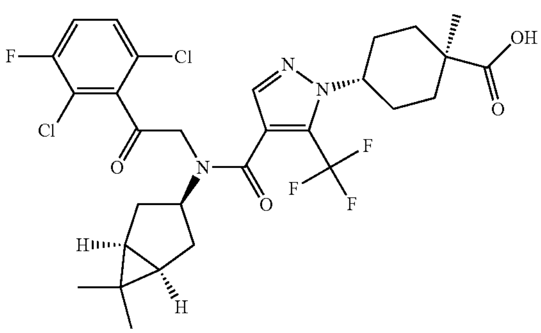 [SMILES: CC1(C)[C@@H]2C[C@H](N(CC(=O)c3c(Cl)ccc(F)c3Cl)C(=O)c3cnn([C@H]4CC[C@](C)(C(=O)O)CC4)c3C(F)(F)F)C[C@@H]21] | trans-4-(4-((2-(2,6-dichloro-3-fluorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)-1-methylcyclohexanecarboxylic acid |
| 764 | 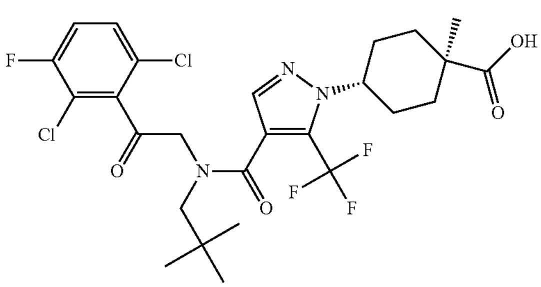 [SMILES: CC(C)(C)CN(CC(=O)c1c(Cl)ccc(F)c1Cl)C(=O)c1cnn([C@H]2CC[C@](C)(C(=O)O)CC2)c1C(F)(F)F] | trans-4-(4-((2-(2,6-dichloro-3-fluorophenyl)-2-oxoethyl)(2,2-dimethylpropyl)carbamoyl)-5-(trifluoromethyl)-1H-pyrazol-1-yl)-1-methylcyclohexanecarboxylic acid |

| example | structure | name |
| --- | --- | --- |
| 765 | 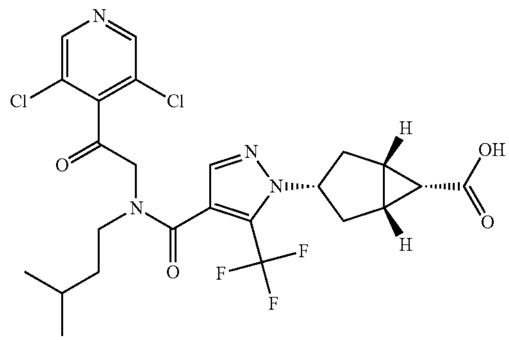 [SMILES: CC(C)CCN(CC(=O)c1c(Cl)cncc1Cl)C(=O)c1cnn([C@H]2C[C@@H]3[C@H](C2)[C@@H]3C(=O)O)c1C(F)(F)F] | (1R,3r,5S,6r)-3-(4-((2-(3,5-dichloro-4-pyridinyl)-2-oxoethyl)(3-methylbutyl)carbamoyl)-5-(trifluoromethyl)-1H-pyrazol-1-yl)bicyclo[3.1.0]hexane-6-carboxylic acid |
| 766 | 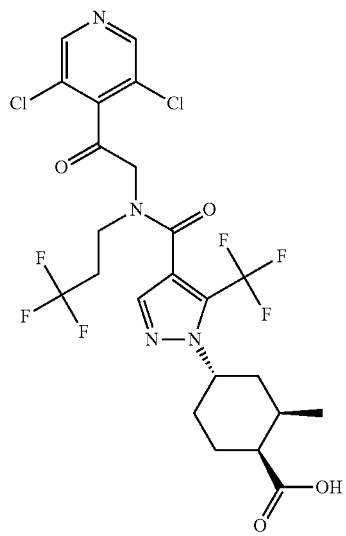 [SMILES: C[C@@H]1C[C@@H](n2ncc(C(=O)N(CCC(F)(F)F)CC(=O)c3c(Cl)cncc3Cl)c2C(F)(F)F)CC[C@@H]1C(=O)O] | (1S,2R,4S)-4-(4-((2-(3,5-dichloro-4-pyridinyl)-2-oxoethyl)(3,3,3-trifluoropropyl)carbamoyl)-5-(trifluoromethyl)-1H-pyrazol-1-yl)-2-methylcyclohexanecarboxylic acid |
| 767 | 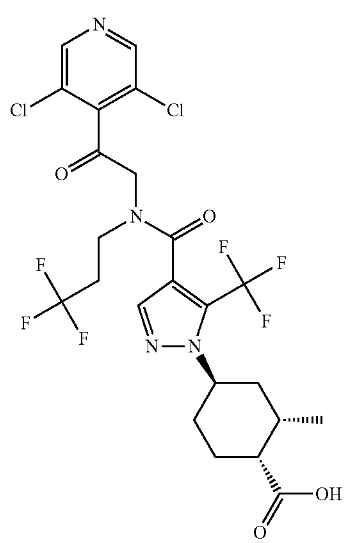 [SMILES: C[C@H]1C[C@H](n2ncc(C(=O)N(CCC(F)(F)F)CC(=O)c3c(Cl)cncc3Cl)c2C(F)(F)F)CC[C@H]1C(=O)O] | (1R,2S,4R)-4-(4-((2-(3,5-dichloro-4-pyridinyl)-2-oxoethyl)(3,3,3-trifluoropropyl)carbamoyl)-5-(trifluoromethyl)-1H-pyrazol-1-yl)-2-methylcyclohexanecarboxylic acid |

-continued

| example | structure | name |
|---|---|---|
| 768 | 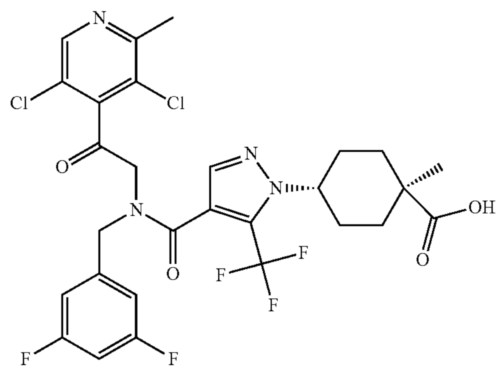 [SMILES: Cc1ncc(Cl)c(C(=O)CN(Cc2cc(F)cc(F)c2)C(=O)c2cnn([C@H]3CC[C@](C)(C(=O)O)CC3)c2C(F)(F)F)c1Cl] | trans-4-(4-((2-(3,5-dichloro-2-methyl-4-pyridinyl)-2-oxoethyl)(3,5-difluorobenzyl)carbamoyl)-5-(trifluoromethyl)-1H-pyrazol-1-yl)-1-methylcyclohexanecarboxylic acid |
| 769 | 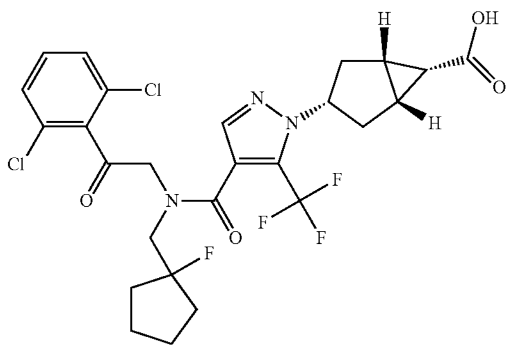 [SMILES: O=C(CN(CC1(F)CCCC1)C(=O)c1cnn([C@H]2C[C@@H]3[C@H](C2)[C@@H]3C(=O)O)c1C(F)(F)F)c1c(Cl)cccc1Cl] | (1R,3r,5S,6s)-3-(4-((2-(2,6-dichlorophenyl)-2-oxoethyl)((1-fluorocyclopentyl)methyl)carbamoyl)-5-(trifluoromethyl)-1H-pyrazol-1-yl)bicyclo[3.1.0]hexane-6-carboxylic acid |
| 770 | 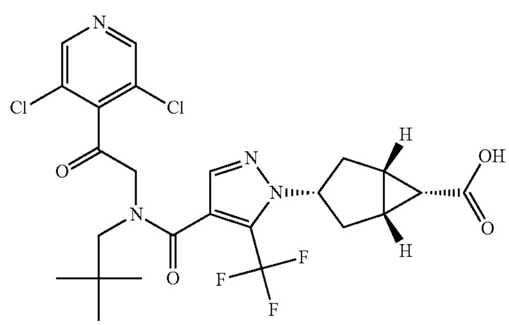 [SMILES: CC(C)(C)CN(CC(=O)c1c(Cl)cncc1Cl)C(=O)c1cnn([C@H]2C[C@@H]3[C@H](C2)[C@@H]3C(=O)O)c1C(F)(F)F] | (1R,3r,5S,6s)-3-(4-((2-(3,5-dichloro-4-pyridinyl)-2-oxoethyl)(2,2-dimethylpropyl)carbamoyl)-5-(trifluoromethyl)-1H-pyrazol-1-yl)bicyclo[3.1.0]hexane-6-carboxylic acid |
| 771 | 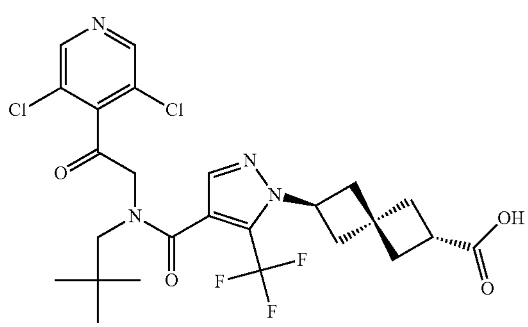 | (4r)-6-(4-((2-(3,5-dichloro-4-pyridinyl)-2-oxoethyl)(2,2-dimethylpropyl)carbamoyl)-5-(trifluoromethyl)-1H-pyrazol-1-yl)spiro[3.3]heptane-2-carboxylic acid |

-continued

| example | structure | name |
|---|---|---|
| 772 | 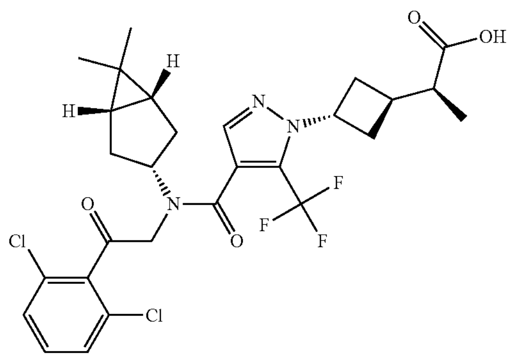 [SMILES: C[C@H](C(=O)O)[C@H]1C[C@H](n2ncc(C(=O)N(CC(=O)c3c(Cl)cccc3Cl)[C@H]3C[C@@H]4[C@H](C3)C4(C)C)c2C(F)(F)F)C1] | (S)-2-((1R,3S)-3-(4-((2-(2,6-dichlorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)cyclobutyl)propanoic acid |
| 773 | 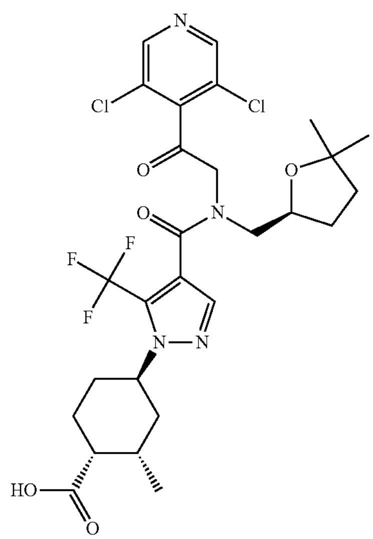 [SMILES: C[C@H]1C[C@H](n2ncc(C(=O)N(CC(=O)c3c(Cl)cncc3Cl)C[C@@H]3CCC(C)(C)O3)c2C(F)(F)F)CC[C@H]1C(=O)O] | (1S,2S,4R)-4-(4-((2-(3,5-dichloro-4-pyridinyl)-2-oxoethyl)(((2S)-5,5-dimethyltetrahydro-2-furanyl)methyl)carbamoyl)-5-(trifluoromethyl)-1H-pyrazol-1-yl)-2-methylcyclohexanecarboxylic acid |
| 774 | 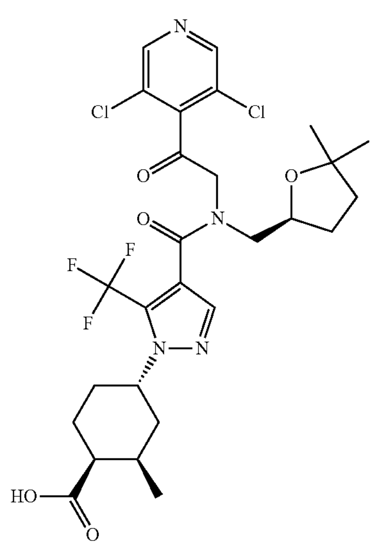 [SMILES: C[C@@H]1C[C@@H](n2ncc(C(=O)N(CC(=O)c3c(Cl)cncc3Cl)C[C@@H]3CCC(C)(C)O3)c2C(F)(F)F)CC[C@@H]1C(=O)O] | (1S,2R,4S)-4-(4-((2-(3,5-dichloro-4-pyridinyl)-2-oxoethyl)(((2S)-5,5-dimethyltetrahydro-2-furanyl)methyl)carbamoyl)-5-(trifluoromethyl)-1H-pyrazol-1-yl)-2-methylcyclohexanecarboxylic acid |

| example | structure | name |
|---|---|---|
| 775 | 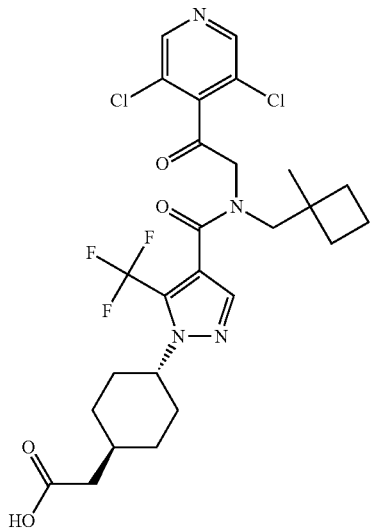 [SMILES: CC1(CN(CC(=O)c2c(Cl)cncc2Cl)C(=O)c2cnn([C@H]3CC[C@H](CC(=O)O)CC3)c2C(F)(F)F)CCC1] | (trans-4-(4-((2-(3,5-dichloro-4-pyridinyl)-2-oxoethyl)((1-methylcyclobutyl)methyl)carbamoyl)-5-(trifluoromethyl)-1H-pyrazol-1-yl)cyclohexyl)acetic acid |
| 776 | 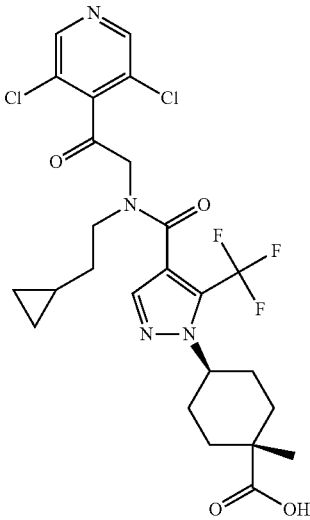 [SMILES: C[C@]1(C(=O)O)CC[C@H](n2ncc(C(=O)N(CCC3CC3)CC(=O)c3c(Cl)cncc3Cl)c2C(F)(F)F)CC1] | trans-4-(4-((2-cyclopropylethyl)(2-(3,5-dichloro-4-pyridinyl)-2-oxoethyl)carbamoyl)-5-(trifluoromethyl)-1H-pyrazol-1-yl)-1-methylcyclohexanecarboxylic acid |

| example | structure | name |
| --- | --- | --- |
| 777 | 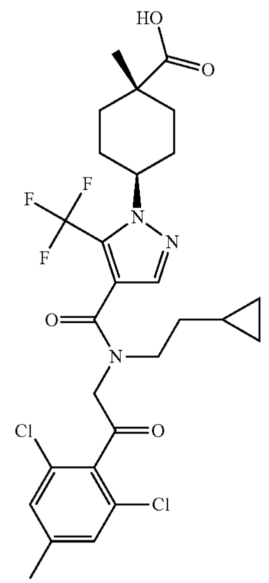 [SMILES: Cc1cc(Cl)c(C(=O)CN(CCC2CC2)C(=O)c2cnn([C@H]3CC[C@](C)(C(=O)O)CC3)c2C(F)(F)F)c(Cl)c1] | trans-4-(4-((2-cyclopropylethyl)(2-(2,6-dichloro-4-methylphenyl)-2-oxoethyl)carbamoyl)-5-(trifluoromethyl)-1H-pyrazol-1-yl)-1-methylcyclohexanecarboxylic acid |
| 778 | 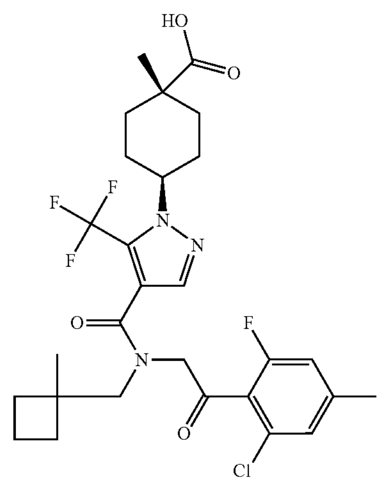 [SMILES: Cc1cc(F)c(C(=O)CN(CC2(C)CCC2)C(=O)c2cnn([C@H]3CC[C@](C)(C(=O)O)CC3)c2C(F)(F)F)c(Cl)c1] | trans-4-(4-((2-(2-chloro-6-fluoro-4-methylphenyl)-2-oxoethyl)((1-methylcyclobutyl)methyl)carbamoyl)-5-(trifluoromethyl)-1H-pyrazol-1-yl)-1-methylcyclohexanecarboxylic acid |
| 779 | 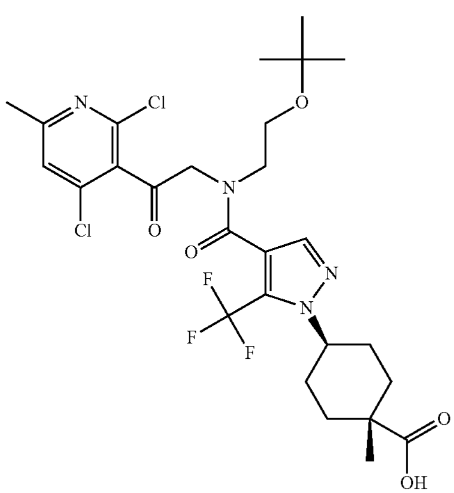 [SMILES: Cc1cc(Cl)c(C(=O)CN(CCOC(C)(C)C)C(=O)c2cnn([C@H]3CC[C@](C)(C(=O)O)CC3)c2C(F)(F)F)c(Cl)n1] | trans-4-(4-((2-(2,4-dichloro-6-methyl-3-pyridinyl)-2-oxoethyl)(2-((2-methyl-2-propanyl)oxy)ethyl)carbamoyl)-5-(trifluoromethyl)-1H-pyrazol-1-yl)-1-methylcyclohexanecarboxylic acid |

| example | structure | name |
|---|---|---|
| 780 | 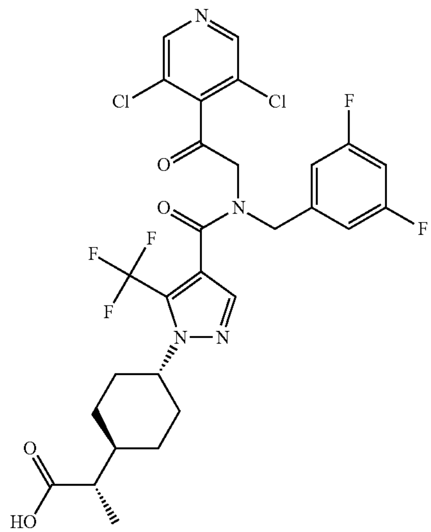 [SMILES: C[C@H](C(=O)O)[C@H]1CC[C@H](n2ncc(C(=O)N(CC(=O)c3c(Cl)cncc3Cl)Cc3cc(F)cc(F)c3)c2C(F)(F)F)CC1] | 2-(trans-4-(4-((2-(3,5-dichloro-4-pyridinyl)-2-oxoethyl)(3,5-difluorobenzyl)carbamoyl)-5-(trifluoromethyl)-1H-pyrazol-1-yl)cyclohexyl)propanoic acid |
| 781 | 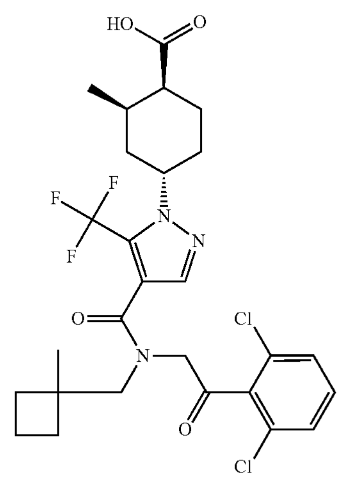 [SMILES: C[C@@H]1C[C@@H](n2ncc(C(=O)N(CC(=O)c3c(Cl)cccc3Cl)CC3(C)CCC3)c2C(F)(F)F)CC[C@@H]1C(=O)O] | (1S,2R,4S)-4-(4-((2-(2,6-dichlorophenyl)-2-oxoethyl)((1-methylcyclobutyl)methyl)carbamoyl)-5-(trifluoromethyl)-1H-pyrazol-1-yl)-2-methylcyclohexanecarboxylic acid |
| 782 | 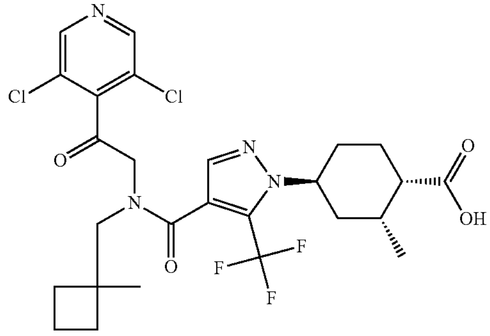 [SMILES: C[C@@H]1C[C@@H](n2ncc(C(=O)N(CC(=O)c3c(Cl)cncc3Cl)CC3(C)CCC3)c2C(F)(F)F)CC[C@@H]1C(=O)O] | (1S,2R,4S)-4-(4-((2-(3,5-dichloro-4-pyridinyl)-2-oxoethyl)((1-methylcyclobutyl)methyl)carbamoyl)-5-(trifluoromethyl)-1H-pyrazol-1-yl)-2-methylcyclohexanecarboxylic acid |

-continued

| example | structure | name |
|---|---|---|
| 783 | 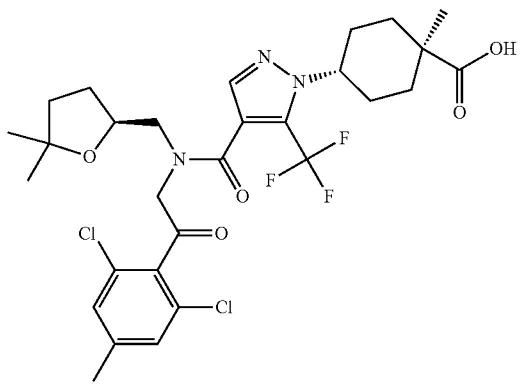 [SMILES: Cc1cc(Cl)c(C(=O)CN(C[C@@H]2CCC(C)(C)O2)C(=O)c2cnn([C@H]3CC[C@](C)(C(=O)O)CC3)c2C(F)(F)F)c(Cl)c1] | trans-4-(4-((2-(2,6-dichloro-4-methylphenyl)-2-oxoethyl)(((2S)-5,5-dimethyltetrahydro-2-furanyl)methyl)carbamoyl)-5-(trifluoromethyl)-1H-pyrazol-1-yl)-1-methylcyclohexanecarboxylic acid |
| 784 | 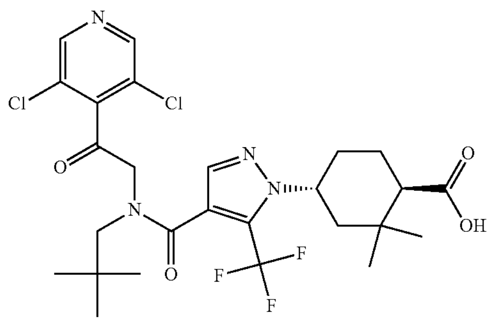 [SMILES: CC(C)(C)CN(CC(=O)c1c(Cl)cncc1Cl)C(=O)c1cnn([C@@H]2CC[C@@H](C(=O)O)C(C)(C)C2)c1C(F)(F)F] | (1R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylic acid |
| 785 | 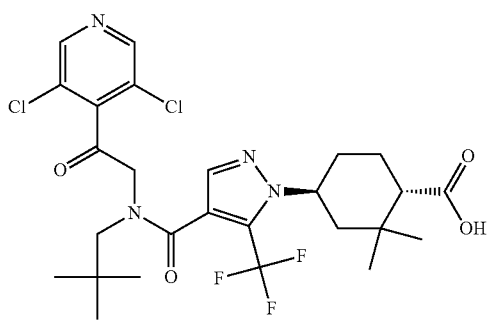 [SMILES: CC(C)(C)CN(CC(=O)c1c(Cl)cncc1Cl)C(=O)c1cnn([C@H]2CC[C@H](C(=O)O)C(C)(C)C2)c1C(F)(F)F] | (1S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2,2-dimethylcyclohexanecarboxylic acid |
| 786 | 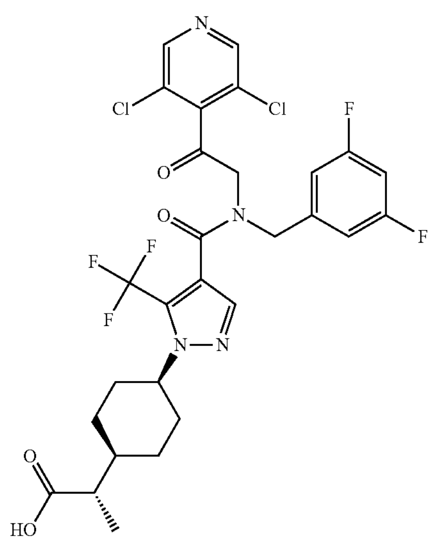 [SMILES: C[C@H](C(=O)O)[C@H]1CC[C@@H](n2ncc(C(=O)N(CC(=O)c3c(Cl)cncc3Cl)Cc3cc(F)cc(F)c3)c2C(F)(F)F)CC1] | 2-(cis-4-(4-((2-(3,5-dichloro-4-pyridinyl)-2-oxoethyl)(3,5-difluorobenzyl)carbamoyl)-5-(trifluoromethyl)-1H-pyrazol-1-yl)cyclohexyl)propanoic acid |

-continued

| example | structure | name |
|---|---|---|
| 787 | 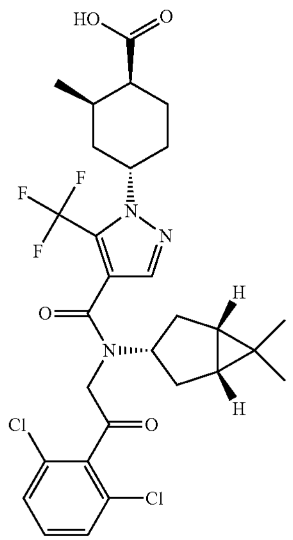 [SMILES: C[C@@H]1C[C@@H](n2ncc(C(=O)N(CC(=O)c3c(Cl)cccc3Cl)[C@H]3C[C@@H]4[C@H](C3)C4(C)C)c2C(F)(F)F)CC[C@@H]1C(=O)O] | (1S,2R,4S)-4-(4-((2-(2,6-dichlorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)-2-methylcyclohexanecarboxylic acid |
| 788 | 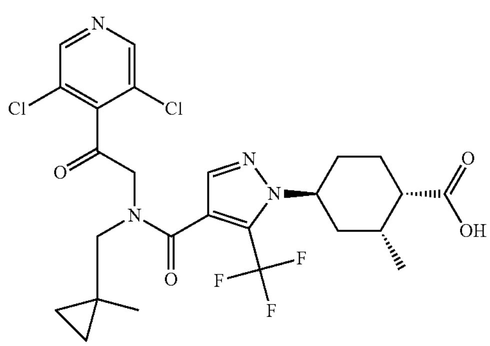 [SMILES: C[C@@H]1C[C@@H](n2ncc(C(=O)N(CC(=O)c3c(Cl)cncc3Cl)CC3(C)CC3)c2C(F)(F)F)CC[C@@H]1C(=O)O] | (1S,2R,4S)-4-(4-((2-(3,5-dichloro-4-pyridinyl)-2-oxoethyl)((1-methylcyclopropyl)methyl)carbamoyl)-5-(trifluoromethyl)-1H-pyrazol-1-yl)-2-methylcyclohexanecarboxylic acid |
| 789 | 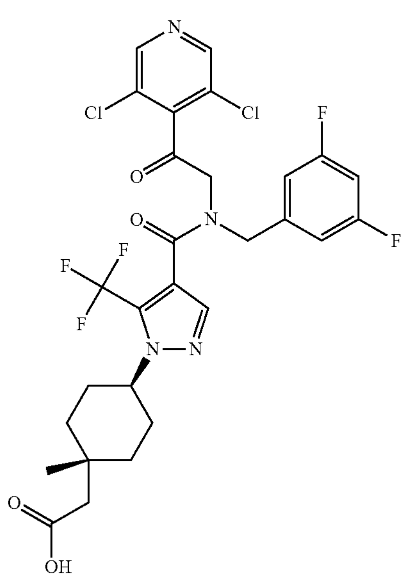 [SMILES: C[C@]1(CC(=O)O)CC[C@H](n2ncc(C(=O)N(CC(=O)c3c(Cl)cncc3Cl)Cc3cc(F)cc(F)c3)c2C(F)(F)F)CC1] | (trans-4-(4-((2-(3,5-dichloro-4-pyridinyl)-2-oxoethyl)(3,5-difluorobenzyl)carbamoyl)-5-(trifluoromethyl)-1H-pyrazol-1-yl)-1-methylcyclohexyl)acetic acid |

| example | structure | name |
|---|---|---|
| 790 | 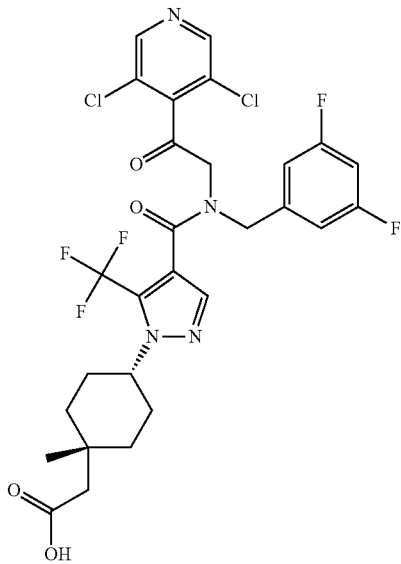 [SMILES: C[C@]1(CC(=O)O)CC[C@@H](n2ncc(C(=O)N(CC(=O)c3c(Cl)cncc3Cl)Cc3cc(F)cc(F)c3)c2C(F)(F)F)CC1] | (cis-4-(4-((2-(3,5-dichloro-4-pyridinyl)-2-oxoethyl)(3,5-difluorobenzyl)carbamoyl)-5-(trifluoromethyl)-1H-pyrazol-1-yl)-1-methylcyclohexyl)acetic acid |
| 791 | 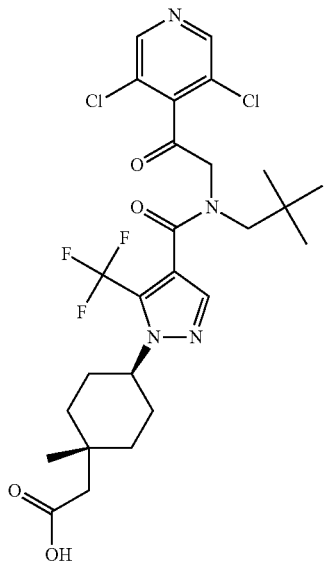 [SMILES: CC(C)(C)CN(CC(=O)c1c(Cl)cncc1Cl)C(=O)c1cnn([C@H]2CC[C@](C)(CC(=O)O)CC2)c1C(F)(F)F] | (trans-4-(4-((2-(3,5-dichloro-4-pyridinyl-2-oxoethyl)(2,2-dimethylpropyl)carbamoyl)-5-(trifluoromethyl)-1H-pyrazol-1-yl)-1-methylcyclohexyl)acetic acid |

-continued

| example | structure | name |
|---|---|---|
| 792 | 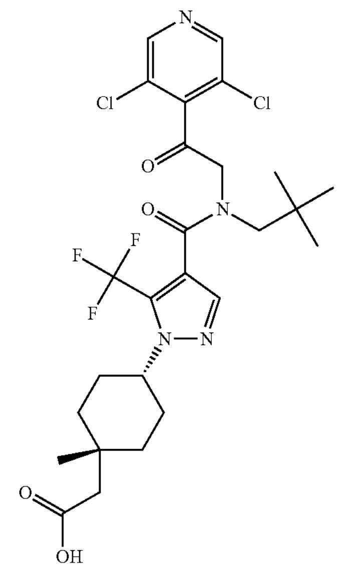 [SMILES: CC(C)(C)CN(CC(=O)c1c(Cl)cncc1Cl)C(=O)c1cnn([C@H]2CC[C@@](C)(CC(=O)O)CC2)c1C(F)(F)F] | (cis-4-(4-((2-(3,5-dichloro-4-pyridinyl)-2-oxoethyl)(2,2-dimethylpropyl)carbamoyl)-5-(trifluoromethyl)-1H-pyrazol-1-yl)-1-methylcyclohexyl)acetic acid |
| 793 | 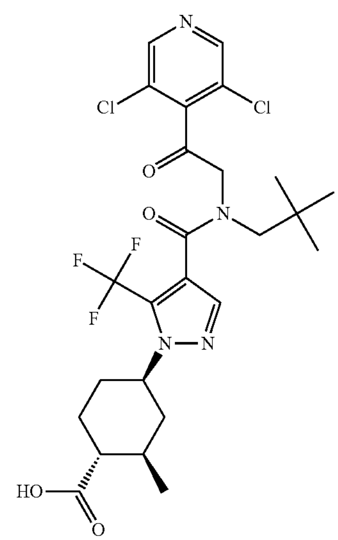 [SMILES: C[C@@H]1C[C@H](n2ncc(C(=O)N(CC(=O)c3c(Cl)cncc3Cl)CC(C)(C)C)c2C(F)(F)F)CC[C@H]1C(=O)O] | (1R,2R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2-methylcyclohexanecarboxylic acid |
| 794 | 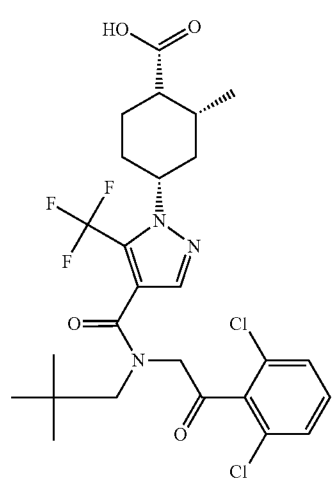 | (1S,2R,4S)-4-(4-((2-(2,6-dichlorophenyl)-2-oxoethyl)(2,2-dimethylpropyl)carbamoyl)-5-(trifluoromethyl)-1H-pyrazol-1-yl)-2-methylcyclohexanecarboxylic acid |

| example | structure | name |
|---|---|---|
| 795 | 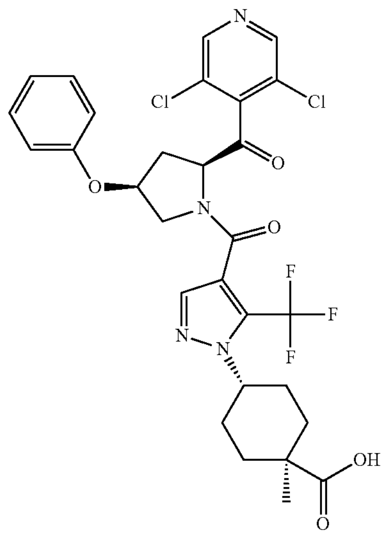 [SMILES: C[C@]1(C(=O)O)CC[C@H](n2ncc(C(=O)N3C[C@@H](Oc4ccccc4)C[C@H]3C(=O)c3c(Cl)cncc3Cl)c2C(F)(F)F)CC1] | trans-4-(4-(((2S,4S)-2-((3,5-dichloro-4-pyridinyl)carbonyl)-4-phenoxy-1-pyrrolidinyl)carbonyl)-5-(trifluoromethyl)-1H-pyrazol-1-yl)-1-methylcyclohexanecarboxylic acid |
| 796 | 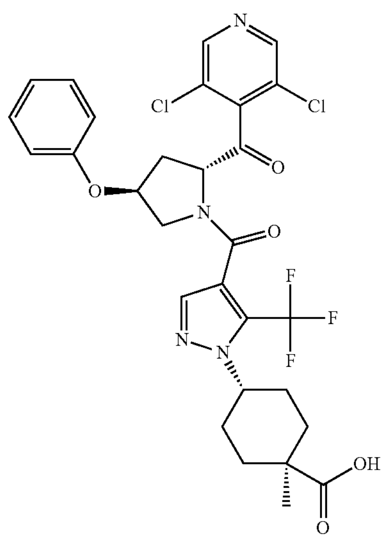 [SMILES: C[C@]1(C(=O)O)CC[C@H](n2ncc(C(=O)N3C[C@@H](Oc4ccccc4)C[C@@H]3C(=O)c3c(Cl)cncc3Cl)c2C(F)(F)F)CC1] | trans-4-(4-(((2R,4S)-2-((3,5-dichloro-4-pyridinyl)carbonyl)-4-phenoxy-1-pyrrolidinyl)carbonyl)-5-(trifluoromethyl)-1H-pyrazol-1-yl)-1-methylcyclohexanecarboxylic acid |
| 797 | 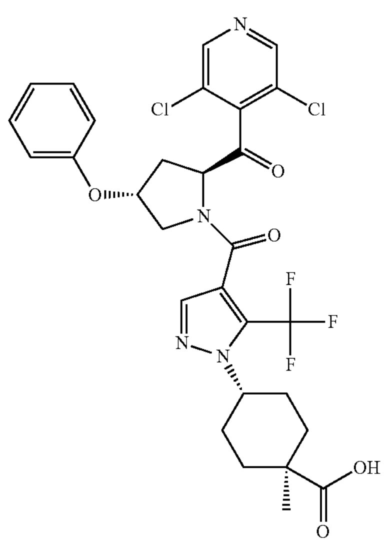 [SMILES: C[C@]1(C(=O)O)CC[C@H](n2ncc(C(=O)N3C[C@H](Oc4ccccc4)C[C@H]3C(=O)c3c(Cl)cncc3Cl)c2C(F)(F)F)CC1] | trans-4-(4-(((2S,4R)-2-((3,5-dichloro-4-pyridinyl)carbonyl)-4-phenoxy-1-pyrrolidinyl)carbonyl)-5-(trifluoromethyl)-1H-pyrazol-1-yl)-1-methylcyclohexanecarboxylic acid |

| example | structure | name |
|---|---|---|
| 798 | 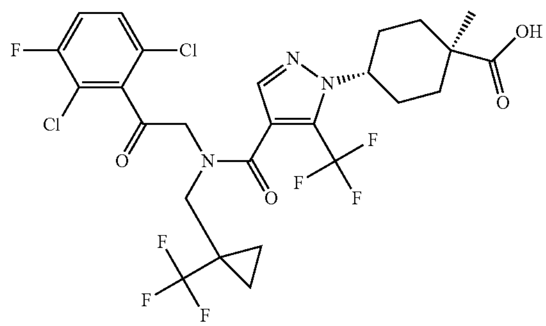 [SMILES: C[C@]1(C(=O)O)CC[C@H](n2ncc(C(=O)N(CC(=O)c3c(Cl)ccc(F)c3Cl)CC3(C(F)(F)F)CC3)c2C(F)(F)F)CC1] | trans-4-(4-((2-(2,6-dichloro-3-fluorophenyl)-2-oxoethyl)((1-(trifluoromethyl)cyclopropyl)methyl)carbamoyl)-5-(trifluoromethyl)-1H-pyrazol-1-yl)-1-methylcyclohexanecarboxylic acid |
| 799 | 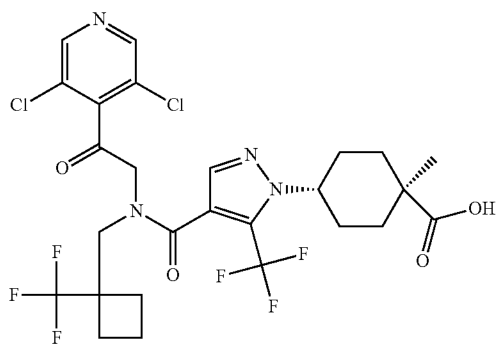 [SMILES: C[C@]1(C(=O)O)CC[C@H](n2ncc(C(=O)N(CC(=O)c3c(Cl)cncc3Cl)CC3(C(F)(F)F)CCC3)c2C(F)(F)F)CC1] | trans-4-(4-((2-(3,5-dichloro-4-pyridinyl)-2-oxoethyl)((1-(trifluoromethyl)cyclobutyl)methyl)carbamoyl)-5-(trifluoromethyl)-1H-pyrazol-1-yl)-1-methylcyclohexanecarboxylic acid |
| 800 | 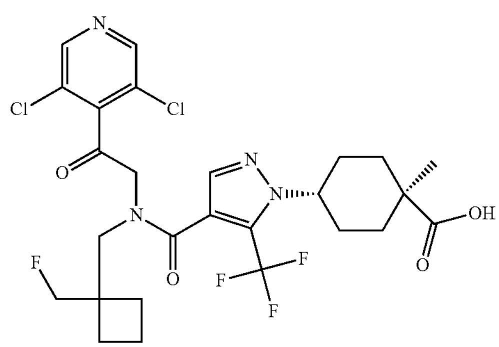 [SMILES: C[C@]1(C(=O)O)CC[C@H](n2ncc(C(=O)N(CC(=O)c3c(Cl)cncc3Cl)CC3(CF)CCC3)c2C(F)(F)F)CC1] | trans-4-(4-((2-(3,5-dichloro-4-pyridinyl)-2-oxoethyl)((1-(fluoromethyl)cyclobutyl)methyl)carbamoyl)-5-(trifluoromethyl)-1H-pyrazol-1-yl)-1-methylcyclohexanecarboxylic acid |
| 801 | 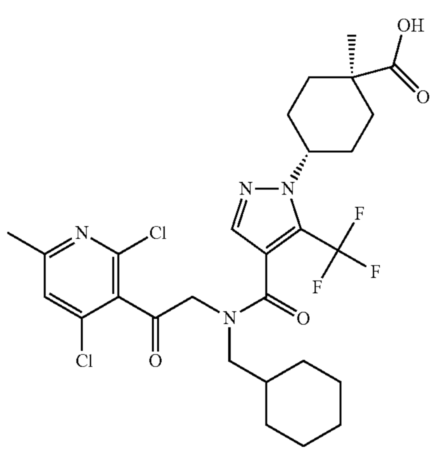 [SMILES: Cc1cc(Cl)c(C(=O)CN(CC2CCCCC2)C(=O)c2cnn([C@H]3CC[C@](C)(C(=O)O)CC3)c2C(F)(F)F)c(Cl)n1] | trans-4-(4-((cyclohexylmethyl)(2-(2,4-dichloro-6-methyl-3-pyridinyl)-2-oxoethyl)carbamoyl)-5-(trifluoromethyl)-1H-pyrazol-1-yl)-1-methylcyclohexanecarboxylic acid |

| example | structure | name |
|---|---|---|
| 802 | 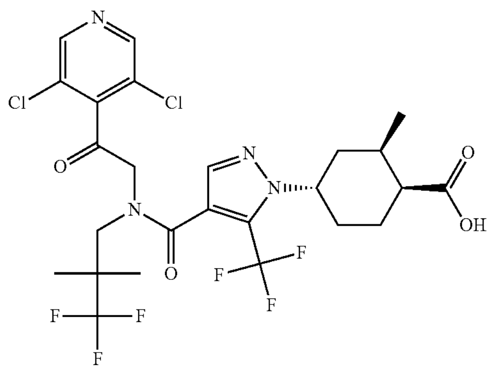 [SMILES: C[C@@H]1C[C@@H](n2ncc(C(=O)N(CC(=O)c3c(Cl)cncc3Cl)CC(C)(C)C(F)(F)F)c2C(F)(F)F)CC[C@@H]1C(=O)O] | (1S,2R,4S)-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-2-methylcyclohexanecarboxylic acid |
| 803 | 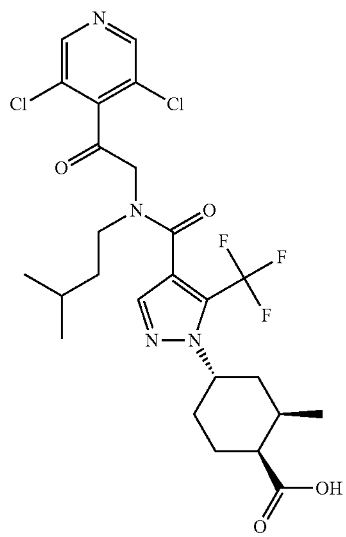 [SMILES: CC(C)CCN(CC(=O)c1c(Cl)cncc1Cl)C(=O)c1cnn([C@H]2CC[C@H](C(=O)O)[C@H](C)C2)c1C(F)(F)F] | (1S,2R,4S)-4-(4-((2-(3,5-dichloro-4-pyridinyl)-2-oxoethyl)(3-methylbutyl)carbamoyl)-5-(trifluoromethyl)-1H-pyrazol-1-yl)-2-methylcyclohexanecarboxylic acid |
| 804 | 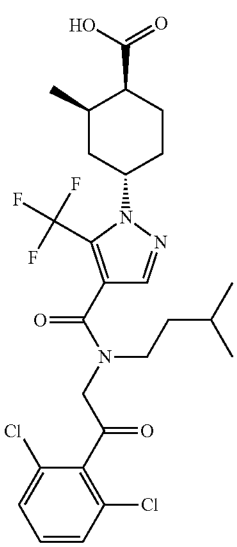 [SMILES: CC(C)CCN(CC(=O)c1c(Cl)cccc1Cl)C(=O)c1cnn([C@H]2CC[C@H](C(=O)O)[C@H](C)C2)c1C(F)(F)F] | (1S,2R,4S)-4-(4-((2-(2,6-dichlorophenyl)-2-oxoethyl)(3-methylbutyl)carbamoyl)-5-(trifluoromethyl)-1H-pyrazol-1-yl)-2-methylcyclohexanecarboxylic acid |

-continued

| example | structure | name |
|---|---|---|
| 805 | 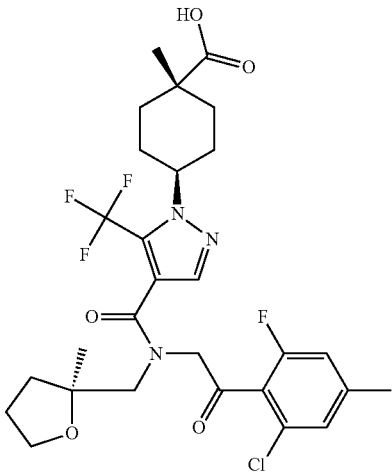 [SMILES: Cc1cc(F)c(C(=O)CN(C[C@]2(C)CCCO2)C(=O)c2cnn([C@H]3CC[C@](C)(C(=O)O)CC3)c2C(F)(F)F)c(Cl)c1] | trans-4-(4-((2-(2-chloro-6-fluoro-4-methylphenyl)-2-oxoethyl)(((2S)-2-methyltetrahydro-2-furanyl)methyl)carbamoyl)-5-(trifluoromethyl)-1H-pyrazol-1-yl)-1-methylcyclohexanecarboxylic acid |
| 806 | 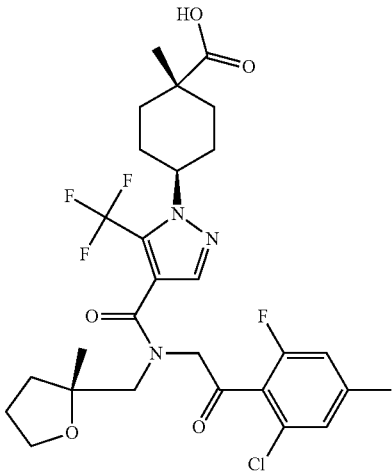 [SMILES: Cc1cc(F)c(C(=O)CN(C[C@@]2(C)CCCO2)C(=O)c2cnn([C@H]3CC[C@](C)(C(=O)O)CC3)c2C(F)(F)F)c(Cl)c1] | trans-4-(4-((2-(2-chloro-6-fluoro-4-methylphenyl)-2-oxoethyl)(((2R)-2-methyltetrahydro-2-furanyl)methyl)carbamoyl)-5-(trifluoromethyl)-1H-pyrazol-1-yl)-1-methylcyclohexanecarboxylic acid |
| 807 | 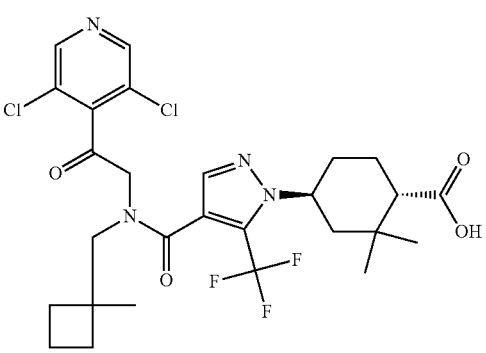 [SMILES: CC1(CN(CC(=O)c2c(Cl)cncc2Cl)C(=O)c2cnn([C@H]3CC[C@H](C(=O)O)C(C)(C)C3)c2C(F)(F)F)CCC1] | (1R,4R)-4-(4-((2-(3,5-dichloro-4-pyridinyl)-2-oxoethyl)((1-methylcyclobutyl)methyl)carbamoyl)-5-(trifluoromethyl)-1H-pyrazol-1-yl)-2,2-dimethylcyclohexanecarboxylic acid |

| example | structure | name |
|---|---|---|
| 808 | 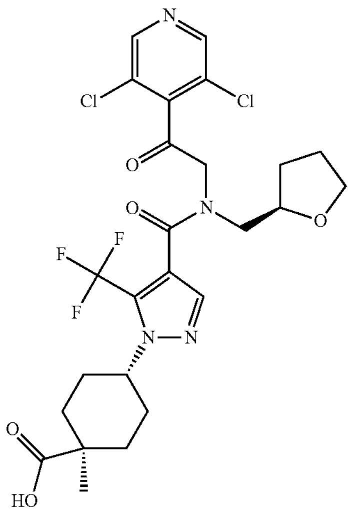 [SMILES: C[C@]1(C(=O)O)CC[C@H](n2ncc(C(=O)N(CC(=O)c3c(Cl)cncc3Cl)C[C@H]3CCCO3)c2C(F)(F)F)CC1] | trans-4-(4-((2-(3,5-dichloro-4-pyridinyl)-2-oxoethyl)((2R)-tetrahydro-2-furanylmethyl)carbamoyl)-5-(trifluoromethyl)-1H-pyrazol-1-yl)-1-methylcyclohexanecarboxylic acid |
| 809 | 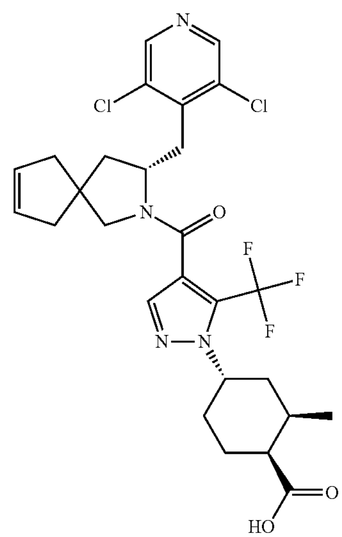 [SMILES: C[C@@H]1C[C@@H](n2ncc(C(=O)N3CC4(CC=CC4)C[C@@H]3Cc3c(Cl)cncc3Cl)c2C(F)(F)F)CC[C@@H]1C(=O)O] | (1S,2R,4S)-4-(4-(((3R)-3-((3,5-dichloro-4-pyridinyl)methyl)-2-azaspiro[4.4]non-7-e n-2-yl)carbonyl)-5-(trifluoromethyl)-1H-pyrazol-1-yl)-2-methylcyclohexanecarboxylic acid |
| 810 | 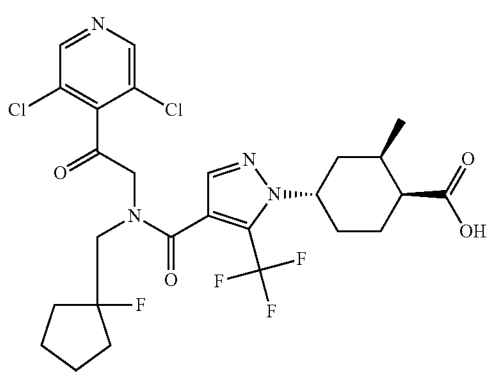 [SMILES: C[C@@H]1C[C@@H](n2ncc(C(=O)N(CC(=O)c3c(Cl)cncc3Cl)CC3(F)CCCC3)c2C(F)(F)F)CC[C@@H]1C(=O)O] | (1S,2R,4S)-4-(4-((2-(3,5-dichloro-4-pyridinyl)-2-oxoethyl)((1-fluorocyclopentyl)methyl)carbamoyl)-5-(trifluoromethyl)-1H-pyrazol-1-yl)-2-methylcyclohexanecarboxylic acid |

-continued

| example | structure | name |
|---|---|---|
| 811 | 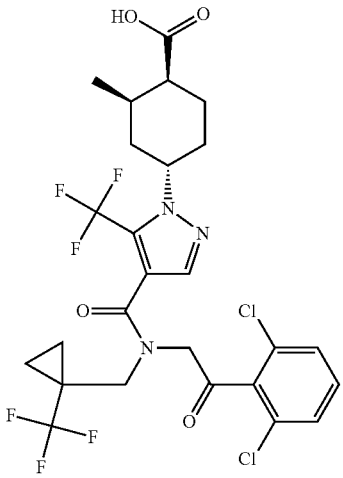 [SMILES: C[C@@H]1C[C@@H](n2ncc(C(=O)N(CC(=O)c3c(Cl)cccc3Cl)CC3(C(F)(F)F)CC3)c2C(F)(F)F)CC[C@@H]1C(=O)O] | (1S,2R,4S)-4-(4-((2-(2,6-dichlorophenyl)-2-oxoethyl)((1-(trifluoromethyl)cyclopropyl)methyl)carbamoyl)-5-(trifluoromethyl)-1H-pyrazol-1-yl)-2-methylcyclohexanecarboxylic acid |
| 812 | 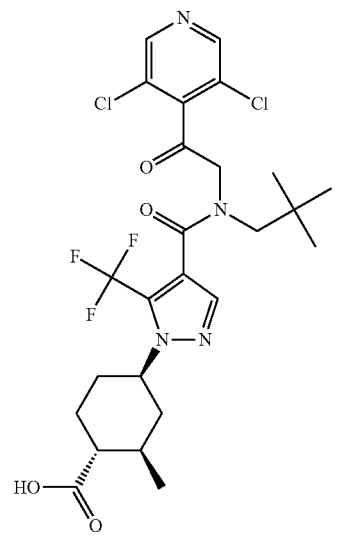 [SMILES: C[C@@H]1C[C@H](n2ncc(C(=O)N(CC(=O)c3c(Cl)cncc3Cl)CC(C)(C)C)c2C(F)(F)F)CC[C@H]1C(=O)O] | (1R,2R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2-methylcyclohexanecarboxylic acid |
| 813 | 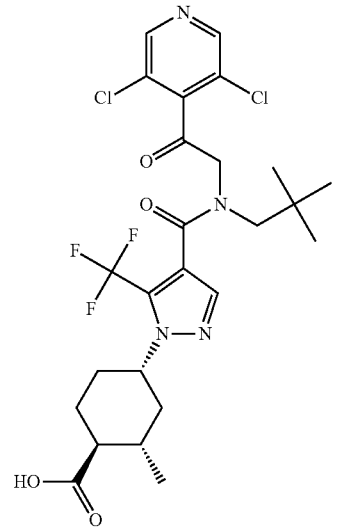 [SMILES: C[C@H]1C[C@@H](n2ncc(C(=O)N(CC(=O)c3c(Cl)cncc3Cl)CC(C)(C)C)c2C(F)(F)F)CC[C@@H]1C(=O)O] | (1S,2S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-2-methylcyclohexanecarboxylic acid |

-continued

| example | structure | name |
|---|---|---|
| 814 | 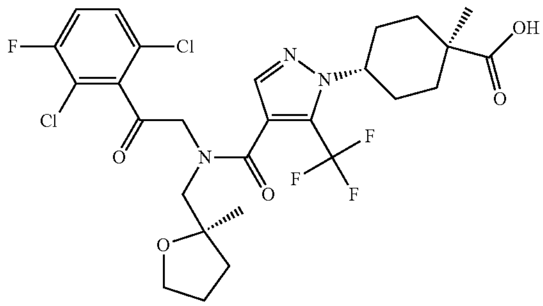 [SMILES: C[C@]1(CN(CC(=O)c2c(Cl)ccc(F)c2Cl)C(=O)c2cnn([C@H]3CC[C@](C)(C(=O)O)CC3)c2C(F)(F)F)CCCO1] | trans-4-(4-((2-(2,6-dichloro-3-fluorophenyl)-2-oxoethyl)(((2R)-2-methyltetrahydro-2-furanyl)methyl)carbamoyl)-5-(trifluoromethyl)-1H-pyrazol-1-yl)-1-methylcyclohexanecarboxylic acid |
| 815 | 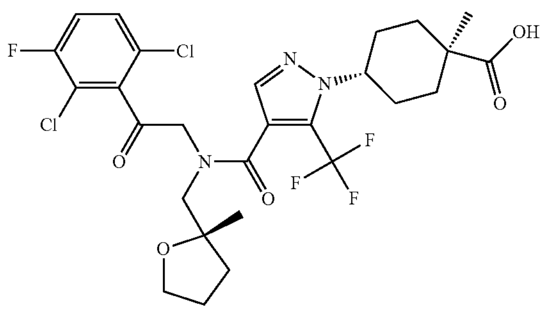 [SMILES: C[C@@]1(CN(CC(=O)c2c(Cl)ccc(F)c2Cl)C(=O)c2cnn([C@H]3CC[C@](C)(C(=O)O)CC3)c2C(F)(F)F)CCCO1] | trans-4-(4-((2-(2,6-dichloro-3-fluorophenyl)-2-oxoethyl)(((2S)-2-methyltetrahydro-2-furanyl)methyl)carbamoyl)-5-(trifluoromethyl)-1H-pyrazol-1-yl)-1-methylcyclohexanecarboxylic acid |
| 816 | 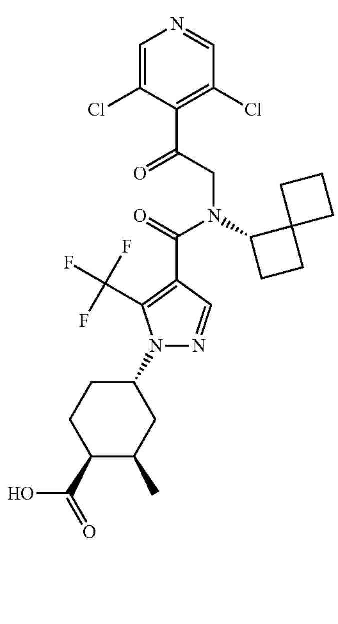 [SMILES: C[C@@H]1C[C@@H](n2ncc(C(=O)N(CC(=O)c3c(Cl)cncc3Cl)[C@H]3CCC34CCC4)c2C(F)(F)F)CC[C@@H]1C(=O)O] | (1S,2R,4S)-4-(4-((2-(3,5-dichloro-4-pyridinyl)-2-oxoethyl)((1S)-spiro[3.3]hept-1-yl)carbamoyl)-5-(trifluoromethyl)-1H-pyrazol-1-yl)-2-methylcyclohexanecarboxylic acid |

-continued

| example | structure | name |
|---|---|---|
| 817 | 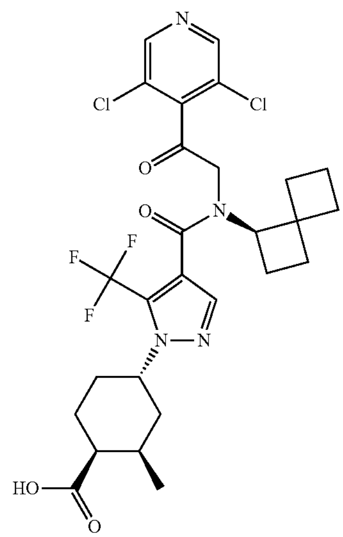 [SMILES: C[C@@H]1C[C@@H](n2ncc(C(=O)N(CC(=O)c3c(Cl)cncc3Cl)[C@@H]3CCC34CCC4)c2C(F)(F)F)CC[C@@H]1C(=O)O] | (1S,2R,4S)-4-(4-((2-(3,5-dichloro-4-pyridinyl)-2-oxoethyl)((1R)-spiro[3.3]hept-1-yl)carbamoyl)-5-(trifluoromethyl)-1H-pyrazol-1-yl)-2-methylcyclohexanecarboxylic acid |
| 818 | 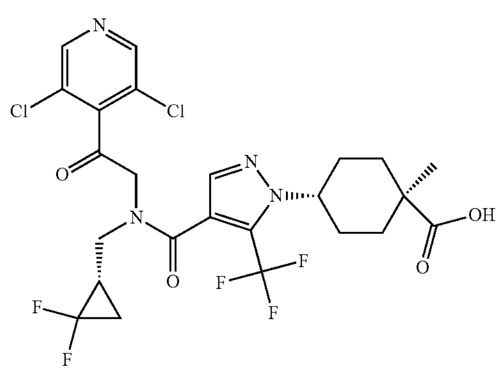 [SMILES: C[C@]1(C(=O)O)CC[C@H](n2ncc(C(=O)N(CC(=O)c3c(Cl)cncc3Cl)C[C@@H]3CC3(F)F)c2C(F)(F)F)CC1] | trans-4-(4-((2-(3,5-dichloro-4-pyridinyl)-2-oxoethyl)(((1S)-2,2-difluorocyclopropyl)methyl)carbamoyl)-5-(trifluoromethyl)-1H-pyrazol-1-yl)-1-methylcyclohexanecarboxylic acid |
| 819 | 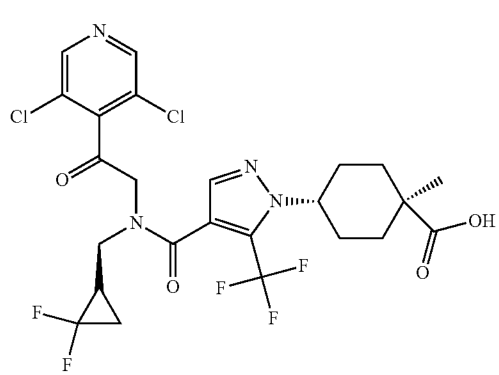 | trans-4-(4-((2-(3,5-dichloro-4-pyridinyl)-2-oxoethyl)(((1R)-2,2-difluorocyclopropyl)methyl)carbamoyl)-5-(trifluoromethyl)-1H-pyrazol-1-yl)-1-methylcyclohexanecarboxylic acid |

| example | structure | name |
|---|---|---|
| 820 | 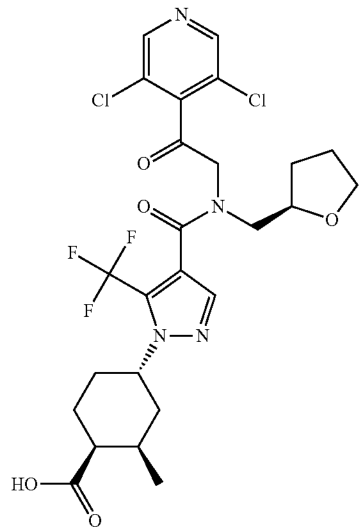 [SMILES: C[C@@H]1C[C@@H](n2ncc(C(=O)N(CC(=O)c3c(Cl)cncc3Cl)C[C@H]3CCCO3)c2C(F)(F)F)CC[C@@H]1C(=O)O] | (1S,2R,4S)-4-(4-((2-(3,5-dichloro-4-pyridinyl)-2-oxoethyl)((2R)-tetrahydro-2-furanylmethyl)carbamoyl)-5-(trifluoromethyl)-1H-pyrazol-1-yl)-2-methylcyclohexanecarboxylic acid |
| 821 | 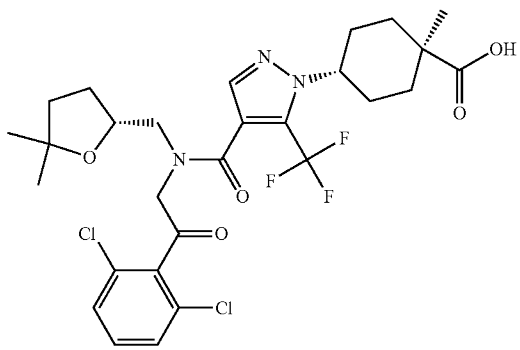 [SMILES: CC1(C)CC[C@H](CN(CC(=O)c2c(Cl)cccc2Cl)C(=O)c2cnn([C@H]3CC[C@](C)(C(=O)O)CC3)c2C(F)(F)F)O1] | trans-4-(4-((2-(2,6-dichlorophenyl)-2-oxoethyl)(((2R)-5,5-dimethyltetrahydro-2-furanyl)methyl)carbamoyl)-5-(trifluoromethyl)-1H-pyrazol-1-yl)-1-methylcyclohexanecarboxylic acid |
| 822 | 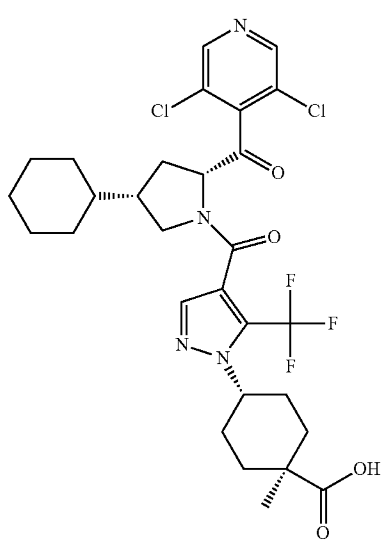 [SMILES: C[C@]1(C(=O)O)CC[C@H](n2ncc(C(=O)N3C[C@H](C4CCCCC4)C[C@@H]3C(=O)c3c(Cl)cncc3Cl)c2C(F)(F)F)CC1] | trans-4-(4-(((2R,4S)-4-cyclohexyl-2-((3,5-dichloro-4-pyridinyl)carbonyl)-1-pyrrolidinyl)carbonyl)-5-(trifluoromethyl)-1H-pyrazol-1-yl)-1-methylcyclohexanecarboxylic acid |

| example | structure | name |
|---|---|---|
| 823 | 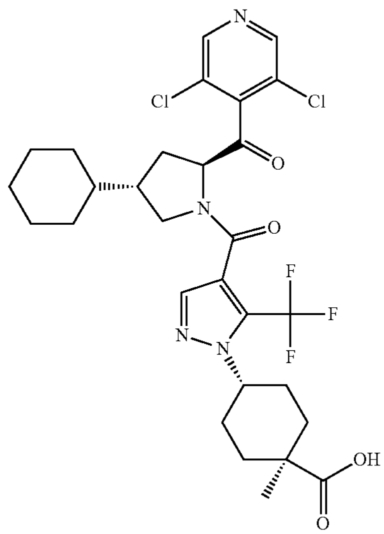 [SMILES: C[C@]1(C(=O)O)CC[C@H](n2ncc(C(=O)N3C[C@H](C4CCCCC4)C[C@H]3C(=O)c3c(Cl)cncc3Cl)c2C(F)(F)F)CC1] | trans-4-(4-(((2S,4S)-4-cyclohexyl-2-((3,5-dichloro-4-pyridinyl)carbonyl)-1-pyrrolidinyl)carbonyl)-5-(trifluoromethyl)-1H-pyrazol-1-yl)-1-methylcyclohexanecarboxylic acid |
| 824 | 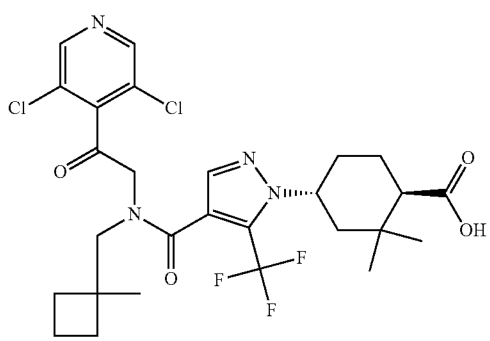 [SMILES: CC1(CN(CC(=O)c2c(Cl)cncc2Cl)C(=O)c2cnn([C@@H]3CC[C@@H](C(=O)O)C(C)(C)C3)c2C(F)(F)F)CCC1] | (1R,4R)-4-(4-((2-(3,5-dichloro-4-pyridinyl)-2-oxoethyl)((1-methylcyclobutyl)methyl)carbamoyl)-5-(trifluoromethyl)-1H-pyrazol-1-yl)-2,2-dimethylcyclohexanecarboxylic acid |
| 825 | 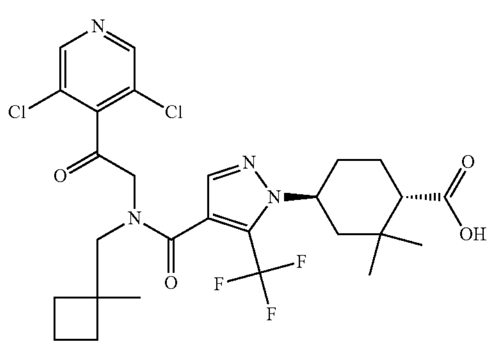 [SMILES: CC1(CN(CC(=O)c2c(Cl)cncc2Cl)C(=O)c2cnn([C@H]3CC[C@H](C(=O)O)C(C)(C)C3)c2C(F)(F)F)CCC1] | (1S,4S)-4-(4-((2-(3,5-dichloro-4-pyridinyl)-2-oxoethyl)((1-methylcyclobutyl)methyl)carbamoyl)-5-(trifluoromethyl)-1H-pyrazol-1-yl)-2,2-dimethylcyclohexanecarboxylic acid |

-continued

| example | structure | name |
|---|---|---|
| 826 | 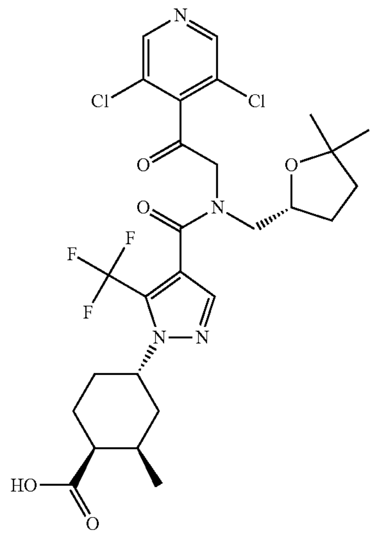 [SMILES: C[C@@H]1C[C@@H](n2ncc(C(=O)N(CC(=O)c3c(Cl)cncc3Cl)C[C@H]3CCC(C)(C)O3)c2C(F)(F)F)CC[C@@H]1C(=O)O] | (1S,2R,4S)-4-(4-((2-(3,5-dichloro-4-pyridinyl)-2-oxoethyl)(((2R)-5,5-dimethyltetrahydro-2-furanyl)methyl)carbamoyl)-5-(trifluoromethyl)-1H-pyrazol-1-yl)-2-methylcyclohexanecarboxylic acid |
| 827 | 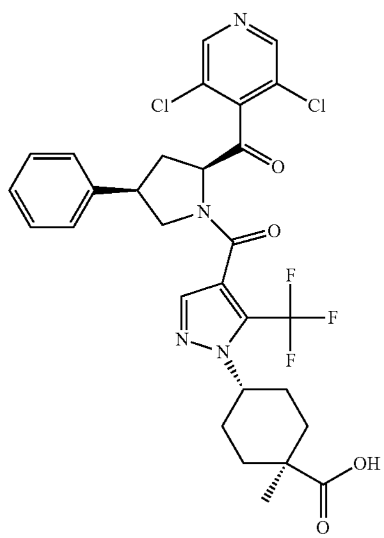 [SMILES: C[C@]1(C(=O)O)CC[C@H](n2ncc(C(=O)N3C[C@@H](c4ccccc4)C[C@H]3C(=O)c3c(Cl)cncc3Cl)c2C(F)(F)F)CC1] | trans-4-(4-(((2S,4R)-2-((3,5-dichloro-4-pyridinyl)carbonyl)-4-phenyl-1-pyrrolidinyl)carbonyl)-5-(trifluoromethyl)-1H-pyrazol-1-yl)-1-methylcyclohexanecarboxylic acid |
| 828 | 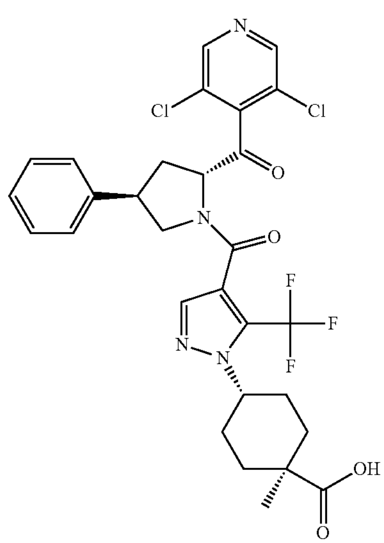 [SMILES: C[C@]1(C(=O)O)CC[C@H](n2ncc(C(=O)N3C[C@@H](c4ccccc4)C[C@@H]3C(=O)c3c(Cl)cncc3Cl)c2C(F)(F)F)CC1] | trans-4-(4-(((2R,4R)-2-((3,5-dichloro-4-pyridinyl)carbonyl)-4-phenyl-1-pyrrolidinyl)carbonyl)-5-(trifluoromethyl)-1H-pyrazol-1-yl)-1-methylcyclohexanecarboxylic acid |

| example | structure | name |
| --- | --- | --- |
| 829 | 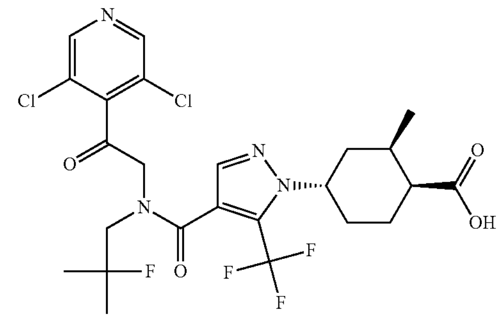 [SMILES: C[C@@H]1C[C@@H](n2ncc(C(=O)N(CC(=O)c3c(Cl)cncc3Cl)CC(C)(C)F)c2C(F)(F)F)CC[C@@H]1C(=O)O] | (1S,2R,4S)-4-(4-((2-(3,5-dichloro-4-pyridinyl)-2-oxoethyl)(2-fluoro-2-methylpropyl)carbamoyl)-5-(trifluoromethyl)-1H-pyrazol-1-yl)-2-methylcyclohexanecarboxylic acid |
| 830 | 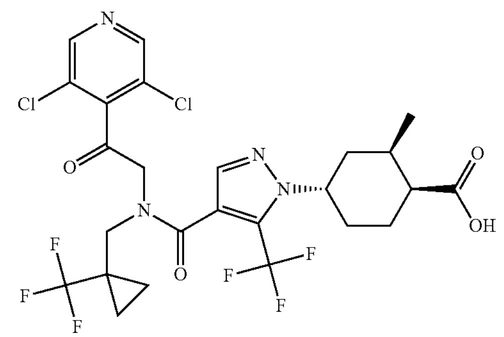 [SMILES: C[C@@H]1C[C@@H](n2ncc(C(=O)N(CC(=O)c3c(Cl)cncc3Cl)CC3(C(F)(F)F)CC3)c2C(F)(F)F)CC[C@@H]1C(=O)O] | (1S,2R,4S)-4-(4-((2-(3,5-dichloro-4-pyridinyl)-2-oxoethyl)((1-(trifluoromethyl)cyclopropyl)methyl)carbamoyl)-5-(trifluoromethyl)-1H-pyrazol-1-yl)-2-methylcyclohexanecarboxylic acid |
| 831 | 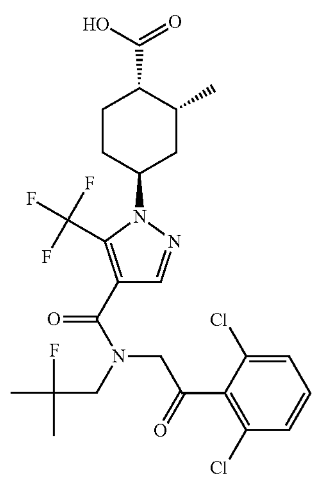 [SMILES: C[C@@H]1C[C@@H](n2ncc(C(=O)N(CC(=O)c3c(Cl)cccc3Cl)CC(C)(C)F)c2C(F)(F)F)CC[C@@H]1C(=O)O] | (1S,2R,4S)-4-(4-((2-(2,6-dichlorophenyl)-2-oxoethyl)(2-fluoro-2-methylpropyl)carbamoyl)-5-(trifluoromethyl)-1H-pyrazol-1-yl)-2-methylcyclohexanecarboxylic acid |
| 832 | 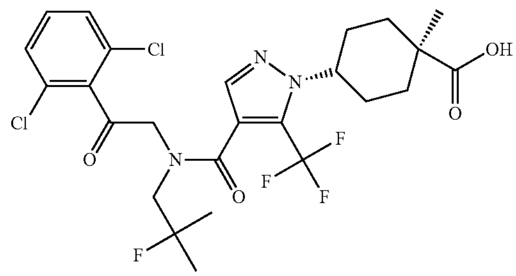 | trans-4-(4-((2-(2,6-dichlorophenyl)-2-oxoethyl)(2-fluoro-2-methylpropyl)carbamoyl)-5-(trifluoromethyl)-1H-pyrazol-1-yl)-1-methylcyclohexanecarboxylic acid |

-continued

| example | structure | name |
|---|---|---|
| 833 | 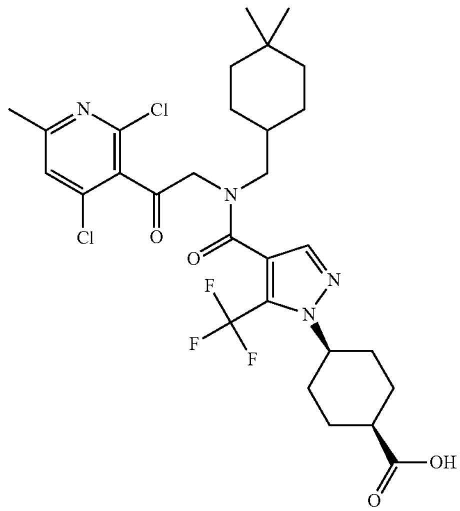 [SMILES: Cc1cc(Cl)c(C(=O)CN(CC2CCC(C)(C)CC2)C(=O)c2cnn([C@H]3CC[C@@H](C(=O)O)CC3)c2C(F)(F)F)c(Cl)n1] | cis-4-(4-((2-(2,4-dichloro-6-methyl-3-pyridinyl)-2-oxoethyl)((4,4-dimethylcyclohexyl)methyl)carbamoyl)-5-(trifluoromethyl)-1H-pyrazol-1-yl)cyclohexanecarboxylic acid |
| 834 | 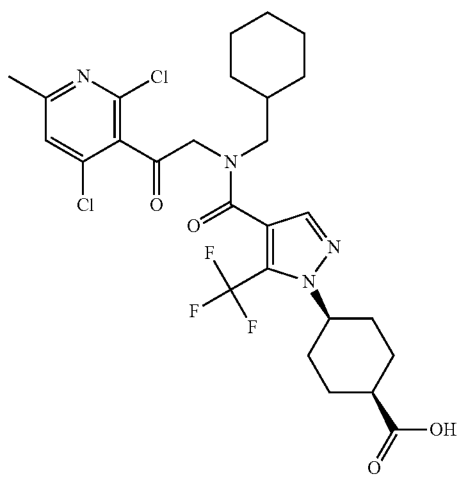 [SMILES: Cc1cc(Cl)c(C(=O)CN(CC2CCCCC2)C(=O)c2cnn([C@H]3CC[C@@H](C(=O)O)CC3)c2C(F)(F)F)c(Cl)n1] | cis-4-(4-((cyclohexylmethyl)(2-(2,4-dichloro-6-methyl-3-pyridinyl)-2-oxoethyl)carbamoyl)-5-(trifluoromethyl)-1H-pyrazol-1-yl)cyclohexanecarboxylic acid |
| 835 | 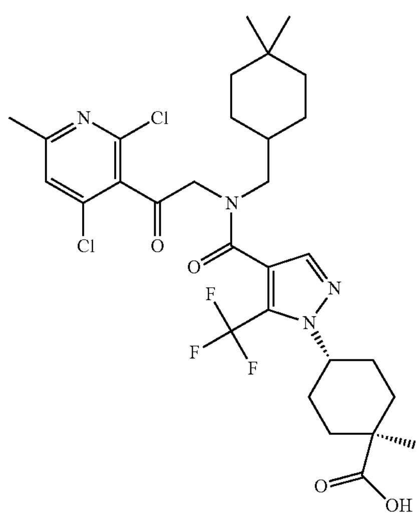 | trans-4-(4-((2-(2,4-dichloro-6-methyl-3-pyridinyl)-2-oxoethyl)((4,4-dimethylcyclohexyl)methyl)carbamoyl)-5-(trifluoromethyl)-1H-pyrazol-1-yl)-1-methylcyclohexanecarboxylic acid |

-continued

| example | structure | name |
|---|---|---|
| 836 | 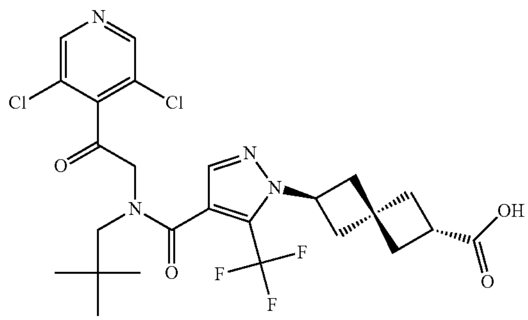 | (4R/S)-6-(4-((2-(3,5-dichloro-4-pyridinyl)-2-oxoethyl)(2,2-dimethylpropyl)carbamoyl)-5-(trifluoromethyl)-1H-pyrazol-1-yl)spiro[3.3]heptane-2-carboxylic acid |
| 837 | 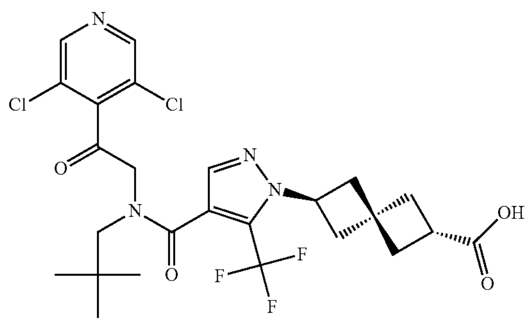 | (4R)-6-(4-((2-(3,5-dichloro-4-pyridinyl)-2-oxoethyl)(2,2-dimethylpropyl)carbamoyl)-5-(trifluoromethyl)-1H-pyrazol-1-yl)spiro[3.3]heptane-2-carboxylic acid |
| 838 | 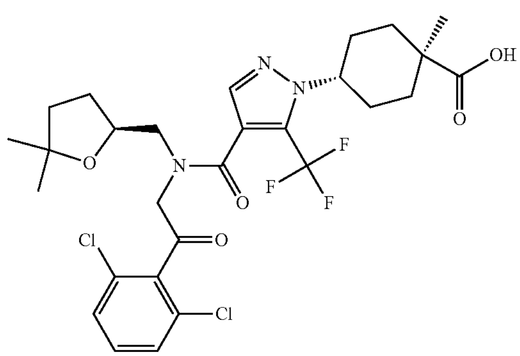 [SMILES: CC1(C)CC[C@@H](CN(CC(=O)c2c(Cl)cccc2Cl)C(=O)c2cnn([C@H]3CC[C@](C)(C(=O)O)CC3)c2C(F)(F)F)O1] | trans-4-(4-((2-(2,6-dichlorophenyl)-2-oxoethyl)(((2S)-5,5-dimethyltetrahydro-2-furanyl)methyl)carbamoyl)-5-(trifluoromethyl)-1H-pyrazol-1-yl)-1-methylcyclohexanecarboxylic acid |
| 839 | 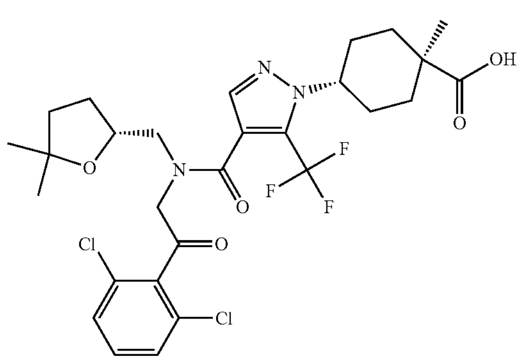 [SMILES: CC1(C)CC[C@H](CN(CC(=O)c2c(Cl)cccc2Cl)C(=O)c2cnn([C@H]3CC[C@](C)(C(=O)O)CC3)c2C(F)(F)F)O1] | trans-4-(4-((2-(2,6-dichlorophenyl)-2-oxoethyl)(((2S)-5,5-dimethyltetrahydro-2-furanyl)methyl)carbamoyl)-5-(trifluoromethyl)-1H-pyrazol-1-yl)-1-methylcyclohexanecarboxylic acid |

-continued

| example | structure | name |
|---|---|---|
| 840 | 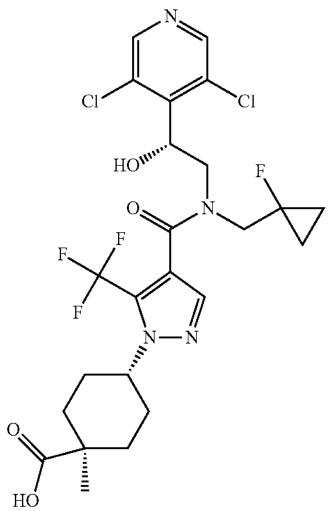 [SMILES: C[C@]1(C(=O)O)CC[C@H](n2ncc(C(=O)N(C[C@H](O)c3c(Cl)cncc3Cl)CC3(F)CC3)c2C(F)(F)F)CC1] | trans-4-(4-(((2R)-2-(3,5-dichloro-4-pyridinyl)-2-hydroxyethyl)((1-fluorocyclopropyl)methyl)carbamoyl)-5-(trifluoromethyl)-1H-pyrazol-1-yl)-1-methylcyclohexanecarboxylic acid |
| 841 | 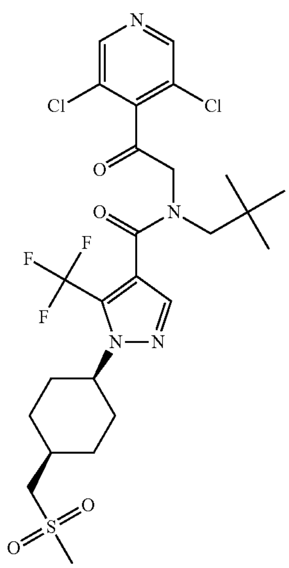 [SMILES: CC(C)(C)CN(CC(=O)c1c(Cl)cncc1Cl)C(=O)c1cnn([C@H]2CC[C@@H](CS(C)(=O)=O)CC2)c1C(F)(F)F] | N-(2-(3,5-dichloro-4-pyridinyl)-2-oxoethyl)-N-(2,2-dimethylpropyl)-1-(cis-4-((methylsulfonyl)methyl)cyclohexyl)-5-(trifluoromethyl)-1H-pyrazole-4-carboxamide |
| 842 | 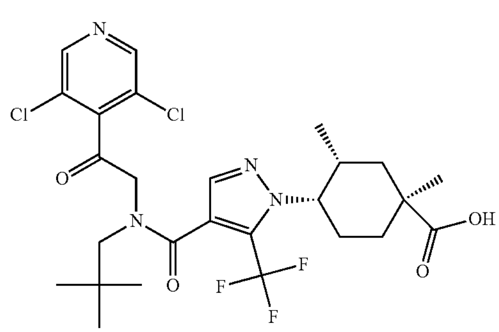 [SMILES: C[C@@H]1C[C@@](C)(C(=O)O)CC[C@@H]1n1ncc(C(=O)N(CC(=O)c2c(Cl)cncc2Cl)CC(C)(C)C)c1C(F)(F)F] | (1R,3S,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |

-continued

| example | structure | name |
|---|---|---|
| 843 | 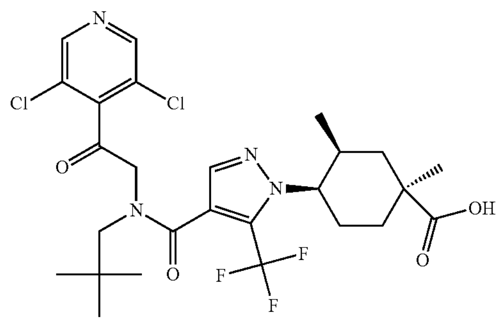 [SMILES: C[C@H]1C[C@@](C)(C(=O)O)CC[C@H]1n1ncc(C(=O)N(CC(=O)c2c(Cl)cncc2Cl)CC(C)(C)C)c1C(F)(F)F] | (1S,3S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |
| 844 | 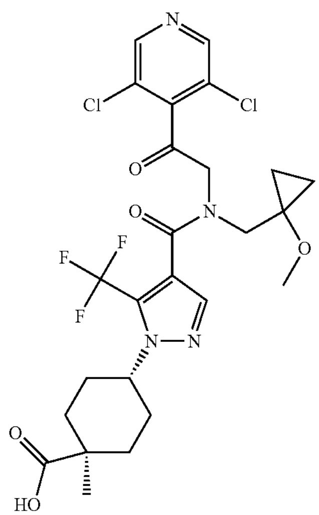 [SMILES: COC1(CN(CC(=O)c2c(Cl)cncc2Cl)C(=O)c2cnn([C@H]3CC[C@](C)(C(=O)O)CC3)c2C(F)(F)F)CC1] | trans-4-(4-((2-(3,5-dichloro-4-pyridinyl)-2-oxoethyl)((1-methoxycyclopropyl)methyl)carbamoyl)-5-(trifluoromethyl)-1H-pyrazol-1-yl)-1-methylcyclohexanecarboxylic acid |
| 845 | 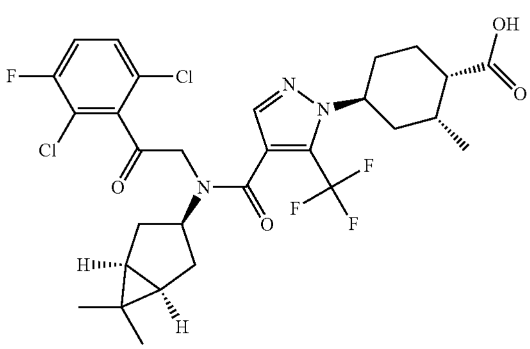 [SMILES: C[C@@H]1C[C@@H](n2ncc(C(=O)N(CC(=O)c3c(Cl)ccc(F)c3Cl)[C@H]3C[C@@H]4[C@H](C3)C4(C)C)c2C(F)(F)F)CC[C@@H]1C(=O)O] | (1S,2R,4S)-4-(4-((2-(2,6-dichloro-3-fluorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)-2-methylcyclohexanecarboxylic acid |
| 846 | 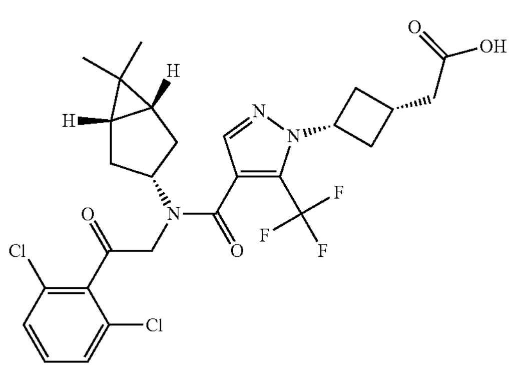 [SMILES: CC1(C)[C@@H]2C[C@H](N(CC(=O)c3c(Cl)cccc3Cl)C(=O)c3cnn([C@H]4C[C@@H](CC(=O)O)C4)c3C(F)(F)F)C[C@@H]21] | (cis-3-(4-((2-(2,6-dichlorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)cyclobutyl)acetic acid |

-continued

| example | structure | name |
|---|---|---|
| 847 | 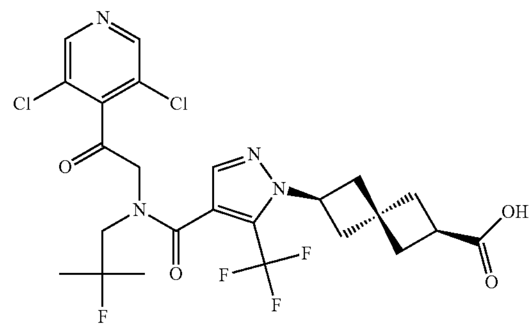 | (4s)-6-(4-((2-(3,5-dichloro-4-pyridinyl)-2-oxoethyl)(2-fluoro-2-methylpropyl)carbamoyl)-5-(trifluoromethyl)-1H-pyrazol-1-yl)spiro[3.3]heptane-2-carboxylic acid |
| 848 | 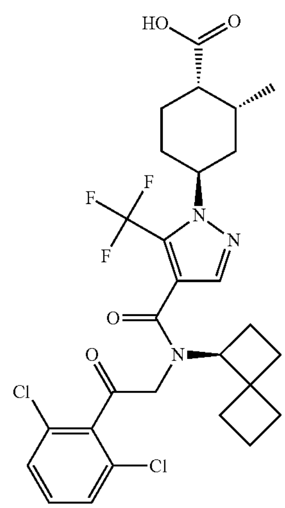 [SMILES: C[C@@H]1C[C@@H](n2ncc(C(=O)N(CC(=O)c3c(Cl)cccc3Cl)[C@H]3CCC34CCC4)c2C(F)(F)F)CC[C@@H]1C(=O)O] | (1S,2R,4S)-4-(4-((2-(2,6-dichlorophenyl)-2-oxoethyl)((1S)-spiro[3.3]hept-1-yl)carbamoyl)-5-(trifluoromethyl)-1H-pyrazol-1-yl)-2-methylcyclohexanecarboxylic acid |
| 849 | 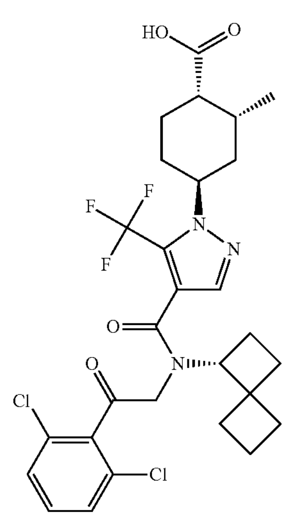 [SMILES: C[C@@H]1C[C@@H](n2ncc(C(=O)N(CC(=O)c3c(Cl)cccc3Cl)[C@@H]3CCC34CCC4)c2C(F)(F)F)CC[C@@H]1C(=O)O] | (1S,2R,4S)-4-(4-((2-(2,6-dichlorophenyl)-2-oxoethyl)((1R)-spiro[3.3]hept-1-yl)carbamoyl)-5-(trifluoromethyl)-1H-pyrazol-1-yl)-2-methylcyclohexanecarboxylic acid |

| example | structure | name |
| --- | --- | --- |
| 850 | 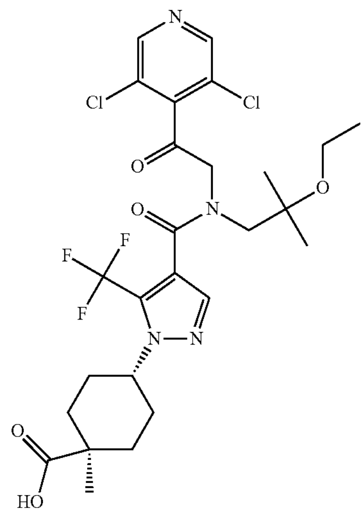 [SMILES: CCOC(C)(C)CN(CC(=O)c1c(Cl)cncc1Cl)C(=O)c1cnn([C@H]2CC[C@](C)(C(=O)O)CC2)c1C(F)(F)F] | trans-4-(4-((2-(3,5-dichloro-4-pyridinyl)-2-oxoethyl)(2-ethoxy-2-methylpropyl)carbamoyl)-5-(trifluoromethyl)-1H-pyrazol-1-yl)-1-methylcyclohexanecarboxylic acid |
| 851 | 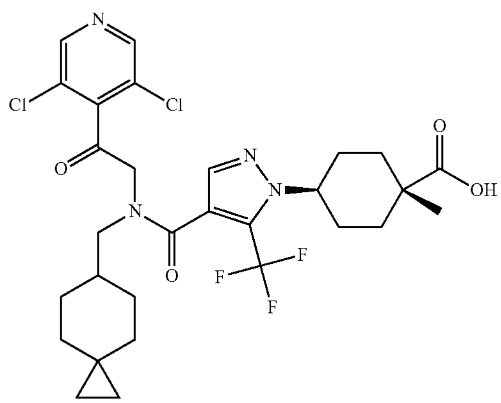 [SMILES: C[C@]1(C(=O)O)CC[C@H](n2ncc(C(=O)N(CC(=O)c3c(Cl)cncc3Cl)CC3CCC4(CC3)CC4)c2C(F)(F)F)CC1] | trans-4-(4-((2-(3,5-dichloro-4-pyridinyl)-2-oxoethyl)(spiro[2.5]oct-6-ylmethyl)carbamoyl)-5-(trifluoromethyl)-1H-pyrazol-1-yl)-1-methylcyclohexanecarboxylic acid |
| 852 | 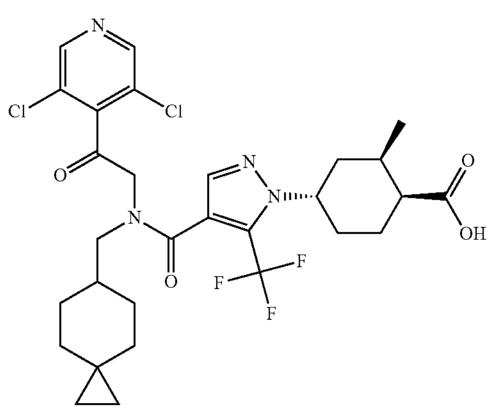 [SMILES: C[C@@H]1C[C@@H](n2ncc(C(=O)N(CC(=O)c3c(Cl)cncc3Cl)CC3CCC4(CC3)CC4)c2C(F)(F)F)CC[C@@H]1C(=O)O] | (1S,2R,4S)-4-(4-((2-(3,5-dichloro-4-pyridinyl)-2-oxoethyl)(spiro[2.5]oct-6-ylmethyl)carbamoyl)-5-(trifluoromethyl)-1H-pyrazol-1-yl)-2-methylcyclohexanecarboxylic acid |

| example | structure | name |
|---|---|---|
| 853 | 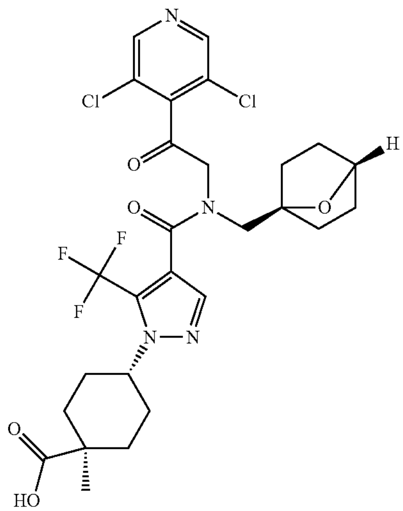 [SMILES: C[C@]1(C(=O)O)CC[C@H](n2ncc(C(=O)N(CC(=O)c3c(Cl)cncc3Cl)C[C@]34CC[C@H](CC3)O4)c2C(F)(F)F)CC1] | trans-4-(4-((2-(3,5-dichloro-4-pyridinyl)-2-oxoethyl)((1s,4s)-7-oxabicyclo[2.2.1]hept-1-ylmethyl)carbamoyl)-5-(trifluoromethyl)-1H-pyrazol-1-yl)-1-methylcyclohexanecarboxylic acid |
| 854 | 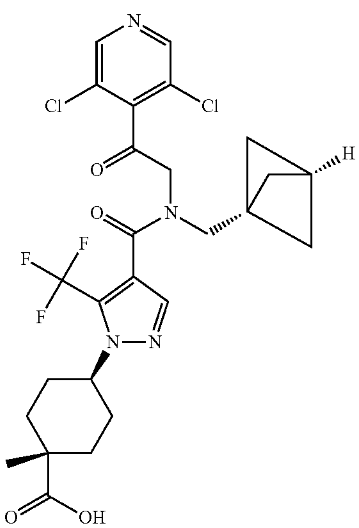 | trans-4-(4-((bicyclo[1.1.1]pent-1-ylmethyl)(2-(3,5-dichloro-4-pyridinyl)-2-oxoethyl)carbamoyl)-5-(trifluoromethyl)-1H-pyrazol-1-yl)-1-methylcyclohexanecarboxylic acid |
| 855 | 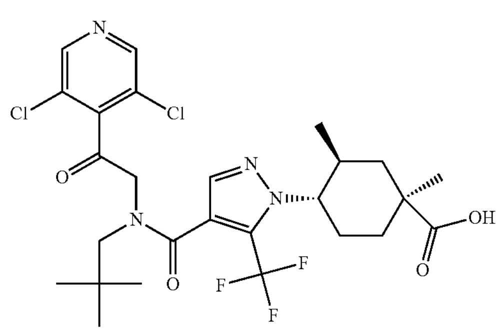 [SMILES: C[C@H]1C[C@@](C)(C(=O)O)CC[C@@H]1n1ncc(C(=O)N(CC(=O)c2c(Cl)cncc2Cl)CC(C)(C)C)c1C(F)(F)F] | (1R,3R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |

-continued

| example | structure | name |
|---|---|---|
| 856 | 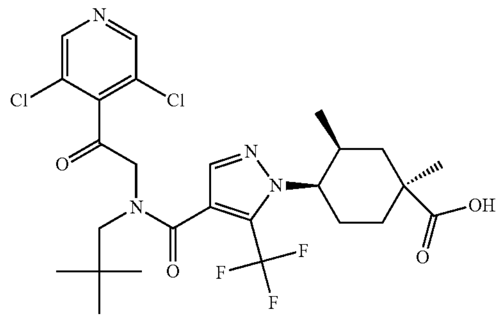 [SMILES: C[C@H]1C[C@@](C)(C(=O)O)CC[C@H]1n1ncc(C(=O)N(CC(=O)c2c(Cl)cncc2Cl)CC(C)(C)C)c1C(F)(F)F] | (1S,3S,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |
| 857 | 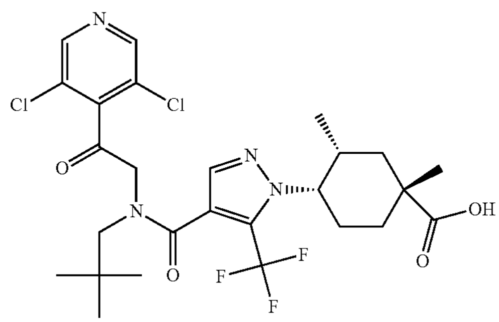 [SMILES: C[C@@H]1C[C@](C)(C(=O)O)CC[C@@H]1n1ncc(C(=O)N(CC(=O)c2c(Cl)cncc2Cl)CC(C)(C)C)c1C(F)(F)F] | (1R,3R,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |
| 858 | 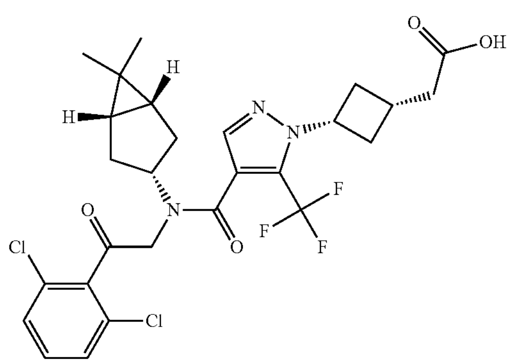 [SMILES: CC1(C)[C@@H]2C[C@H](N(CC(=O)c3c(Cl)cccc3Cl)C(=O)c3cnn([C@H]4C[C@@H](CC(=O)O)C4)c3C(F)(F)F)C[C@@H]21] | (trans-3-(4-((2-(2,6-dichlorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)cyclobutyl)acetic acid |
| 859 | 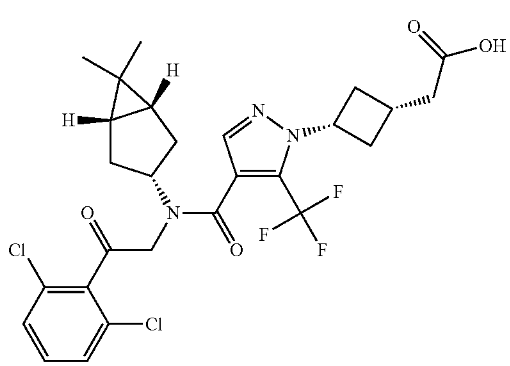 [SMILES: CC1(C)[C@@H]2C[C@H](N(CC(=O)c3c(Cl)cccc3Cl)C(=O)c3cnn([C@H]4C[C@@H](CC(=O)O)C4)c3C(F)(F)F)C[C@@H]21] | (cis-3-(4-((2-(2,6-dichlorophenyl)-2-oxoethyl)((1R,3r,5S)-6,6-dimethylbicyclo[3.1.0]hex-3-yl)carbamoyl)-5-(trifluoromethyl)-1H-pyrazol-1-yl)cyclobutyl)acetic acid |

| example | structure | name |
|---|---|---|
| 860 | 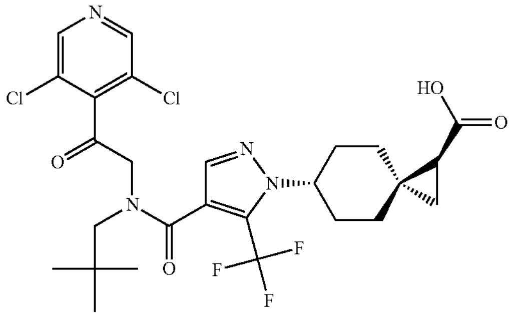 [SMILES: CC(C)(C)CN(CC(=O)c1c(Cl)cncc1Cl)C(=O)c1cnn([C@H]2CC[C@]3(CC2)C[C@@H]3C(=O)O)c1C(F)(F)F] | (1R,3r,6R)-6-(4-((2-(3,5-dichloro-4-pyridinyl)-2-oxoethyl)(2,2-dimethylpropyl)carbamoyl)-5-(trifluoromethyl)-1H-pyrazol-1-yl)spiro[2.5]octane-1-carboxylic acid |
| 861 | 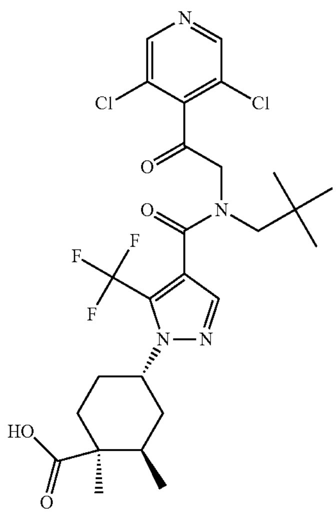 [SMILES: C[C@@H]1C[C@@H](n2ncc(C(=O)N(CC(=O)c3c(Cl)cncc3Cl)CC(C)(C)C)c2C(F)(F)F)CC[C@]1(C)C(=O)O] | (1S,2S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,2-dimethylcyclohexanecarboxylic acid |
| 862 | 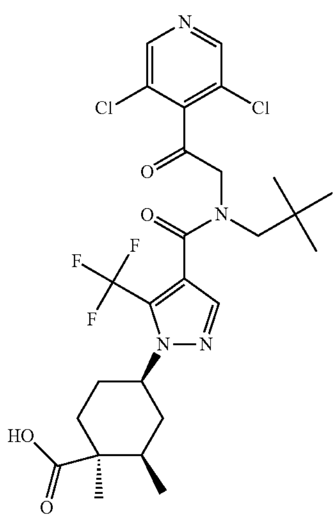 [SMILES: C[C@@H]1C[C@H](n2ncc(C(=O)N(CC(=O)c3c(Cl)cncc3Cl)CC(C)(C)C)c2C(F)(F)F)CC[C@]1(C)C(=O)O] | (1S,3S,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,2-dimethylcyclohexanecarboxylic acid |

| example | structure | name |
| --- | --- | --- |
| 863 | 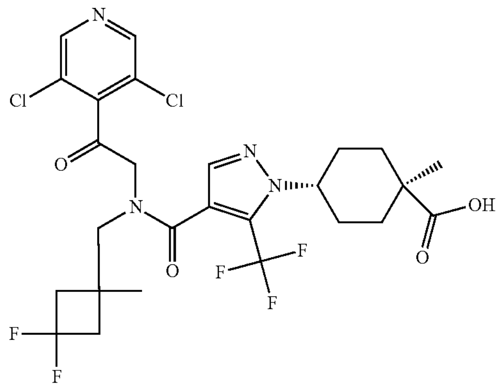 [SMILES: CC1(CN(CC(=O)c2c(Cl)cncc2Cl)C(=O)c2cnn([C@H]3CC[C@](C)(C(=O)O)CC3)c2C(F)(F)F)CC(F)(F)C1] | trans-4-(4-((2-(3,5-dichloro-4-pyridinyl)-2-oxoethyl)((3,3-difluoro-1-methylcyclobutyl)methyl)carbamoyl)-5-(trifluoromethyl)-1H-pyrazol-1-yl)-1-methylcyclohexanecarboxylic acid |
| 864 | 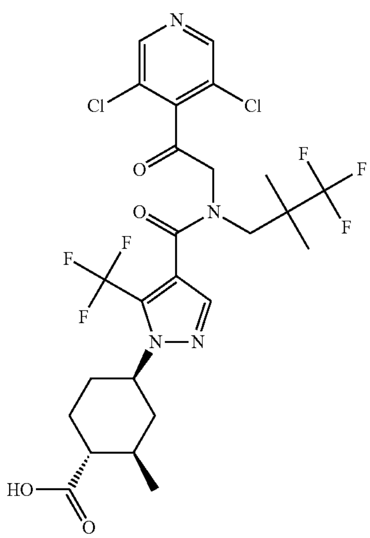 [SMILES: C[C@@H]1C[C@H](n2ncc(C(=O)N(CC(=O)c3c(Cl)cncc3Cl)CC(C)(C)C(F)(F)F)c2C(F)(F)F)CC[C@H]1C(=O)O] | (1S,2S,4S)-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-2-methylcyclohexanecarboxylic acid |
| 865 | 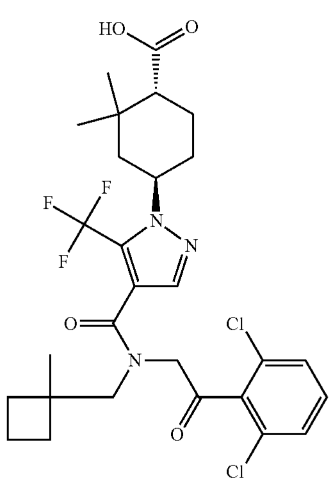 [SMILES: CC1(CN(CC(=O)c2c(Cl)cccc2Cl)C(=O)c2cnn([C@@H]3CC[C@@H](C(=O)O)C(C)(C)C3)c2C(F)(F)F)CCC1] | (1R,4R)-4-(4-((2-(2,6-dichlorophenyl)-2-oxoethyl)((1-methylcyclobutyl)methyl)carbamoyl)-5-(trifluoromethyl)-1H-pyrazol-1-yl)-2,2-dimethylcyclohexanecarboxylic acid |

| example | structure | name |
|---|---|---|
| 866 | 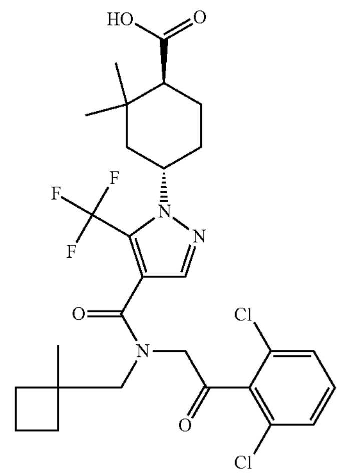 [SMILES: CC1(CN(CC(=O)c2c(Cl)cccc2Cl)C(=O)c2cnn([C@H]3CC[C@H](C(=O)O)C(C)(C)C3)c2C(F)(F)F)CCC1] | (1R,4R)-4-(4-((2-(2,6-dichlorophenyl)-2-oxoethyl)((1-methylcyclobutyl)methyl)carbamoyl)-5-(trifluoromethyl)-1H-pyrazol-1-yl)-2,2-dimethylcyclohexanecarboxylic acid |
| 867 | 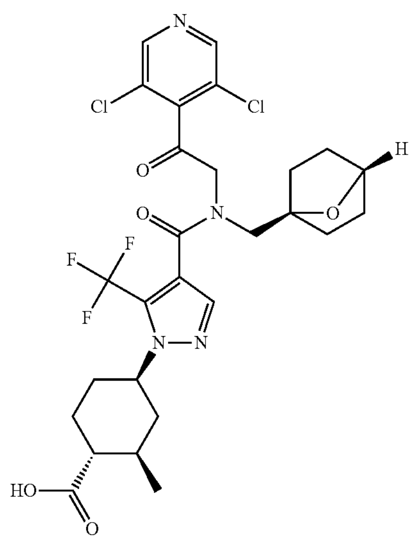 [SMILES: C[C@@H]1C[C@H](n2ncc(C(=O)N(CC(=O)c3c(Cl)cncc3Cl)C[C@]34CC[C@H](CC3)O4)c2C(F)(F)F)CC[C@H]1C(=O)O] | (1S,2S,4S)-4-(4-((2-(3,5-dichloro-4-pyridinyl)-2-oxoethyl)((1s,4s)-7-oxabicyclo[2.2.1]hept-1-ylmethyl)carbamoyl)-5-(trifluoromethyl)-1H-pyrazol-1-yl)-2-methylcyclohexanecarboxylic acid |
| 868 | 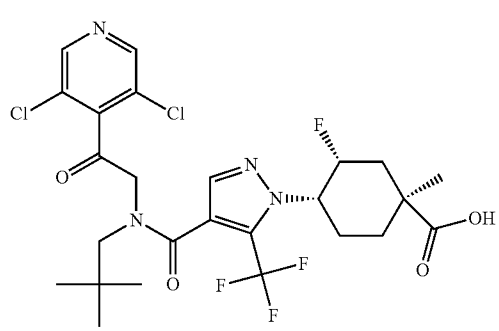 [SMILES: CC(C)(C)CN(CC(=O)c1c(Cl)cncc1Cl)C(=O)c1cnn([C@H]2CC[C@](C)(C(=O)O)C[C@H]2F)c1C(F)(F)F] | (1S,3R,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-3-fluoro-1-methylcyclohexanecarboxylic acid |

| example | structure | name |
|---|---|---|
| 869 | 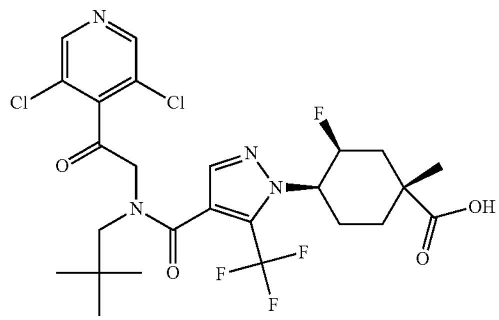 [SMILES: CC(C)(C)CN(CC(=O)c1c(Cl)cncc1Cl)C(=O)c1cnn([C@@H]2CC[C@@](C)(C(=O)O)C[C@@H]2F)c1C(F)(F)F] | (1R,3S,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-3-fluoro-1-methylcyclohexanecarboxylic acid |
| 870 | 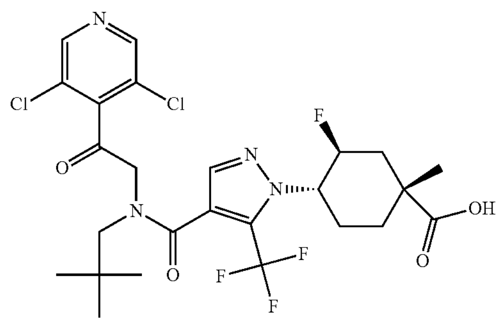 [SMILES: CC(C)(C)CN(CC(=O)c1c(Cl)cncc1Cl)C(=O)c1cnn([C@H]2CC[C@@](C)(C(=O)O)C[C@@H]2F)c1C(F)(F)F] | (1R,3S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-3-fluoro-1-methylcyclohexanecarboxylic acid |
| 871 | 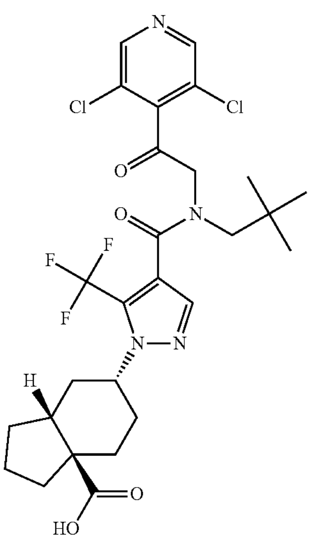 [SMILES: CC(C)(C)CN(CC(=O)c1c(Cl)cncc1Cl)C(=O)c1cnn([C@@H]2CC[C@]3(C(=O)O)CCC[C@@H]3C2)c1C(F)(F)F] | (3aR,6R,7aR)-6-(4-((2-(3,5-dichloropyridin-4-yl)-2-oxoethyl)((2,2-dimethylpropyl)carbamoyl)-5-(trifluoromethyl)-1H-pyrazol-1-yl)octahydro-1H-indene-3a-carboxylic acid |
| 872 | 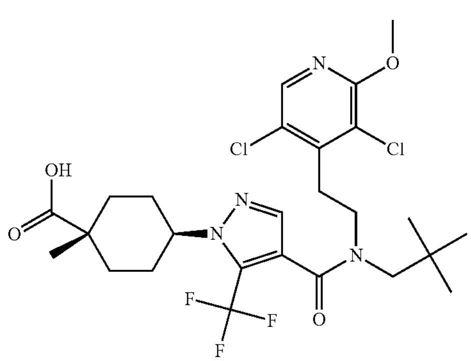 [SMILES: COc1ncc(Cl)c(CCN(CC(C)(C)C)C(=O)c2cnn([C@H]3CC[C@](C)(C(=O)O)CC3)c2C(F)(F)F)c1Cl] | trans-4-(4-((2-(3,5-dichloro-2-methoxy-4-pyridinyl)ethyl)(2,2-dimethylpropyl)carbamoyl)-5-(trifluoromethyl)-1H-pyrazol-1-yl)-1-methylcyclohexanecarboxylic acid |

-continued

| example | structure | name |
|---|---|---|
| 873 | 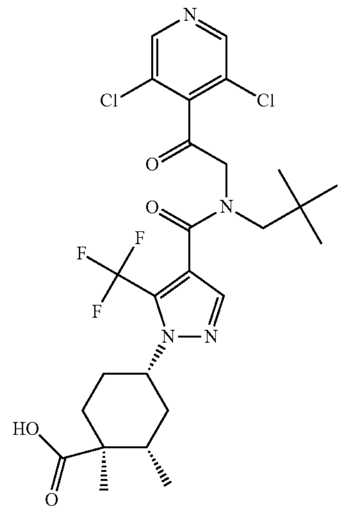 [SMILES: C[C@H]1C[C@@H](n2ncc(C(=O)N(CC(=O)c3c(Cl)cncc3Cl)CC(C)(C)C)c2C(F)(F)F)CC[C@]1(C)C(=O)O] | (1S,2S,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,2-dimethylcyclohexanecarboxylic acid |
| 874 | 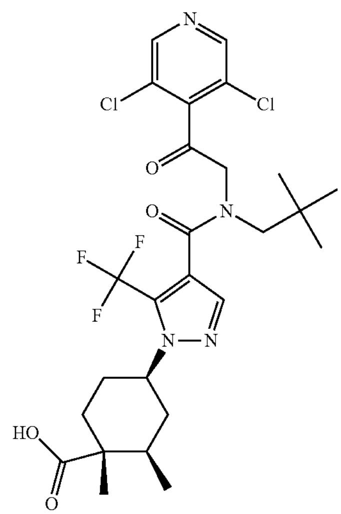 [SMILES: C[C@@H]1C[C@H](n2ncc(C(=O)N(CC(=O)c3c(Cl)cncc3Cl)CC(C)(C)C)c2C(F)(F)F)CC[C@@]1(C)C(=O)O] | (1R,2R,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,2-dimethylcyclohexanecarboxylic acid |
| 875 | 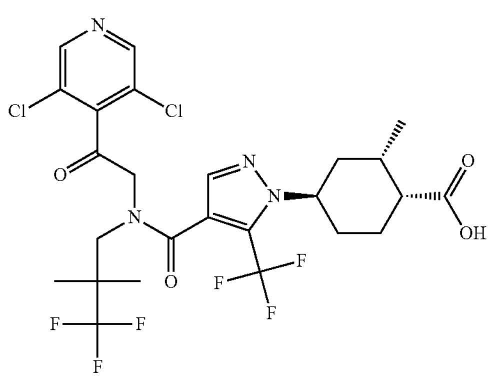 [SMILES: C[C@H]1C[C@H](n2ncc(C(=O)N(CC(=O)c3c(Cl)cncc3Cl)CC(C)(C)C(F)(F)F)c2C(F)(F)F)CC[C@H]1C(=O)O] | (1R,2S,4R)-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-2-methylcyclohexanecarboxylic acid |

| example | structure | name |
|---|---|---|
| 876 | 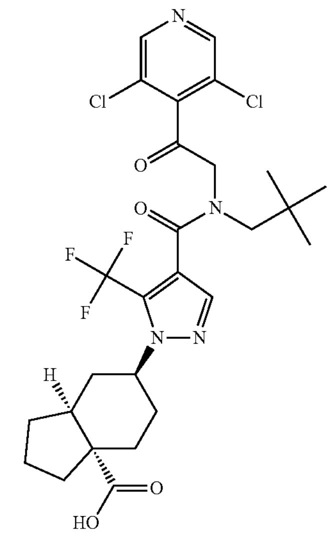 [SMILES: CC(C)(C)CN(CC(=O)c1c(Cl)cncc1Cl)C(=O)c1cnn([C@H]2CC[C@@]3(C(=O)O)CCC[C@H]3C2)c1C(F)(F)F] | (3aS,6S,7aS)-6-(4-((2-(3,5-dichloropyridin-4-yl)-2-oxoethyl)(neopentyl)carbamoyl)-5-(trifluoromethyl)-1H-pyrazol-1-yl)octahydro-1H-indene-3a-carboxylic acid |
| 877 | 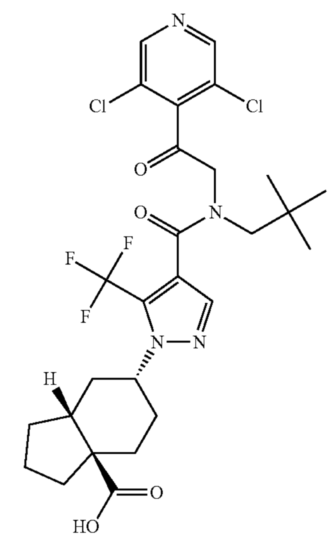 [SMILES: CC(C)(C)CN(CC(=O)c1c(Cl)cncc1Cl)C(=O)c1cnn([C@@H]2CC[C@]3(C(=O)O)CCC[C@@H]3C2)c1C(F)(F)F] | (3aR,6R,7aR)-6-(4-((2-(3,5-dichloropyridin-4-yl)-2-oxoethyl)(neopentyl)carbamoyl)-5-(trifluoromethyl)-1H-pyrazol-1-yl)octahydro-1H-indene-3a-carboxylic acid |
| 878 | 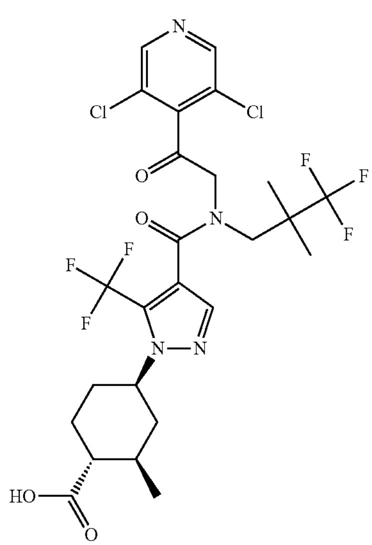 [SMILES: C[C@@H]1C[C@H](n2ncc(C(=O)N(CC(=O)c3c(Cl)cncc3Cl)CC(C)(C)C(F)(F)F)c2C(F)(F)F)CC[C@H]1C(=O)O] | (1R,2R,4R)-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-2-methylcyclohexanecarboxylic acid |

| example | structure | name |
|---|---|---|
| 879 | 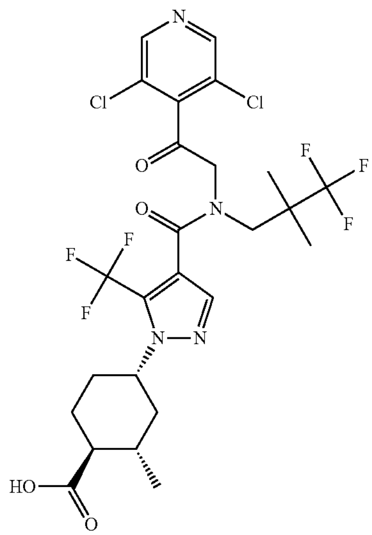 [SMILES: C[C@H]1C[C@@H](n2ncc(C(=O)N(CC(=O)c3c(Cl)cncc3Cl)CC(C)(C)C(F)(F)F)c2C(F)(F)F)CC[C@@H]1C(=O)O] | (1S,2S,4S)-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)-2-methylcyclohexanecarboxylic acid |
| 880 | 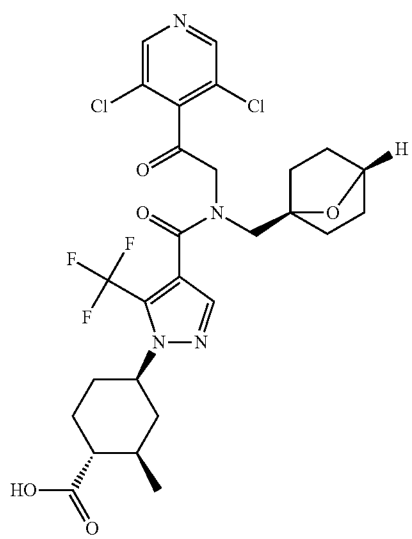 [SMILES: C[C@@H]1C[C@H](n2ncc(C(=O)N(CC(=O)c3c(Cl)cncc3Cl)C[C@]34CC[C@H](CC3)O4)c2C(F)(F)F)CC[C@H]1C(=O)O] | (1R,2R,4R)-4-(4-((2-(3,5-dichloro-4-pyridinyl)-2-oxoethyl)((1s,4s)-7-oxabicyclo[2.2.1]hept-1-ylmethyl)carbamoyl)-5-(trifluoromethyl)-1H-pyrazol-1-yl)-2-methylcyclohexanecarboxylic acid |
| 881 | 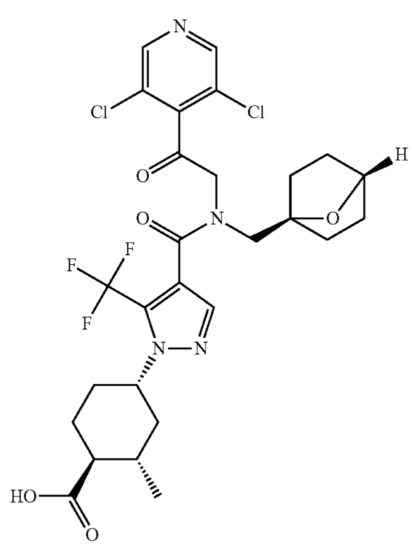 [SMILES: C[C@H]1C[C@@H](n2ncc(C(=O)N(CC(=O)c3c(Cl)cncc3Cl)C[C@]34CC[C@H](CC3)O4)c2C(F)(F)F)CC[C@@H]1C(=O)O] | (1S,2S,4S)-4-(4-((2-(3,5-dichloro-4-pyridinyl)-2-oxoethyl)((1s,4s)-7-oxabicyclo[2.2.1]hept-1-ylmethyl)carbamoyl)-5-(trifluoromethyl)-1H-pyrazol-1-yl)-2-methylcyclohexanecarboxylic acid |

-continued

| example | structure | name |
|---|---|---|
| 882 | 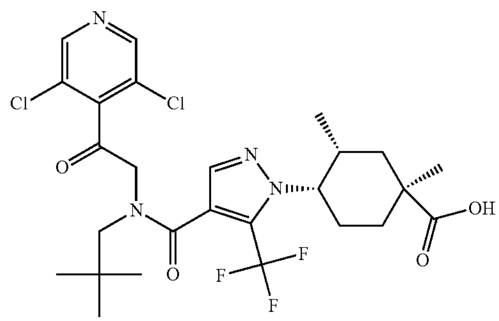 [SMILES: C[C@@H]1C[C@@](C)(C(=O)O)CC[C@@H]1n1ncc(C(=O)N(CC(=O)c2c(Cl)cncc2Cl)CC(C)(C)C)c1C(F)(F)F] | (1S,3R,4S)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |
| 883 | 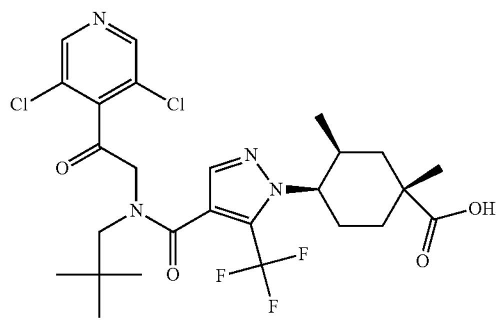 [SMILES: C[C@H]1C[C@](C)(C(=O)O)CC[C@H]1n1ncc(C(=O)N(CC(=O)c2c(Cl)cncc2Cl)CC(C)(C)C)c1C(F)(F)F] | (1R,3S,4R)-4-(4-((2-(3,5-dichloro-4-pyridinyl)-2-oxoethyl)(2,2-dimethylpropyl)carbamoyl)-5-(trifluoromethyl)-1H-pyrazol-1-yl)-1,3-dimethylcyclohexanecarboxylic acid |
| 884 | 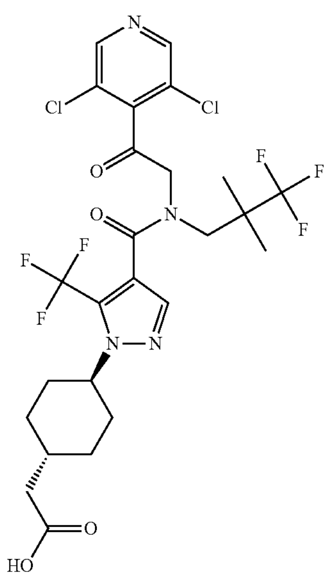 [SMILES: CC(C)(CN(CC(=O)c1c(Cl)cncc1Cl)C(=O)c1cnn([C@H]2CC[C@H](CC(=O)O)CC2)c1C(F)(F)F)C(F)(F)F] | (trans-4-(4-((2-(3,5-dichloro-4-pyridinyl)-2-oxoethyl)(3,3,3-trifluoro-2,2-dimethylpropyl)carbamoyl)-5-(trifluoromethyl)-1H-pyrazol-1-yl)cyclohexyl)acetic acid |
| 885 | 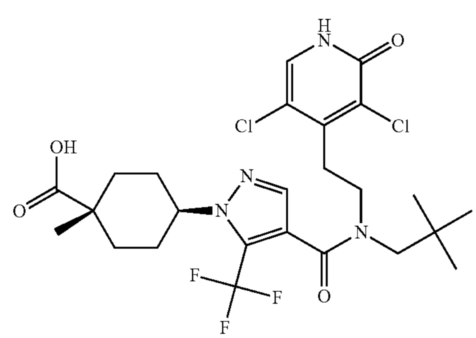 [SMILES: CC(C)(C)CN(CCc1c(Cl)c[nH]c(=O)c1Cl)C(=O)c1cnn([C@H]2CC[C@](C)(C(=O)O)CC2)c1C(F)(F)F] | trans-4-(4-((2-(3,5-dichloro-2-oxo-1,2-dihydro-4-pyridinyl)ethyl)(2,2-dimethylpropyl)carbamoyl)-5-(trifluoromethyl)-1H-pyrazol-1-yl)-1-methylcyclohexanecarboxylic acid |

| example | structure | name |
|---|---|---|
| 886 | 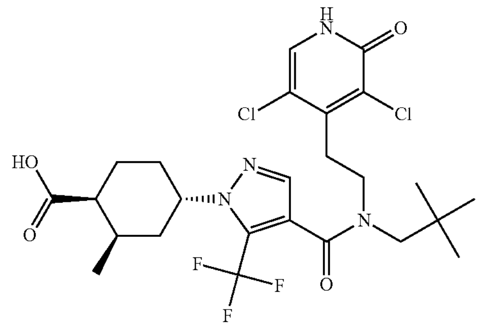 [SMILES: C[C@@H]1C[C@@H](n2ncc(C(=O)N(CCc3c(Cl)c[nH]c(=O)c3Cl)CC(C)(C)C)c2C(F)(F)F)CC[C@@H]1C(=O)O] | (1S,2R,4S)-4-(4-((2-(3,5-dichloro-2-oxo-1,2-dihydro-4-pyridinyl)ethyl)(2,2-dimethylpropyl)carbamoyl)-5-(trifluoromethyl)-1H-pyrazol-1-yl)-2-methylcyclohexanecarboxylic acid |
| 887 | 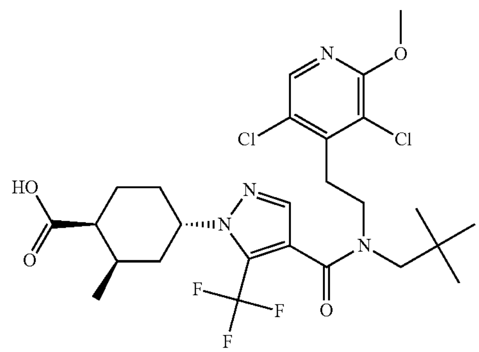 [SMILES: COc1ncc(Cl)c(CCN(CC(C)(C)C)C(=O)c2cnn([C@H]3CC[C@H](C(=O)O)[C@H](C)C3)c2C(F)(F)F)c1Cl] | (1S,2R,4S)-4-(4-((2-(3,5-dichloro-2-methoxy-4-pyridinyl)ethyl)(2,2-dimethylpropyl)carbamoyl)-5-(trifluoromethyl)-1H-pyrazol-1-yl)-2-methylcyclohexanecarboxylic acid |
| 888 | 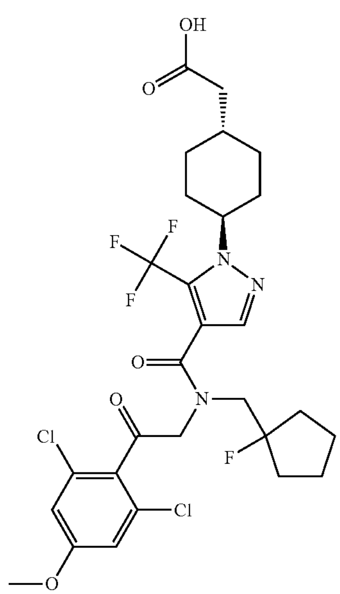 [SMILES: COc1cc(Cl)c(C(=O)CN(CC2(F)CCCC2)C(=O)c2cnn([C@H]3CC[C@H](CC(=O)O)CC3)c2C(F)(F)F)c(Cl)c1] | (trans-4-(4-((2-(2,6-dichloro-4-methoxyphenyl)-2-oxoethyl)((1-fluorocyclopentyl)methyl)carbamoyl)-5-(trifluoromethyl)-1H-pyrazol-1-yl)cyclohexyl)acetic acid |

-continued

| example | structure | name |
|---|---|---|
| 889 | 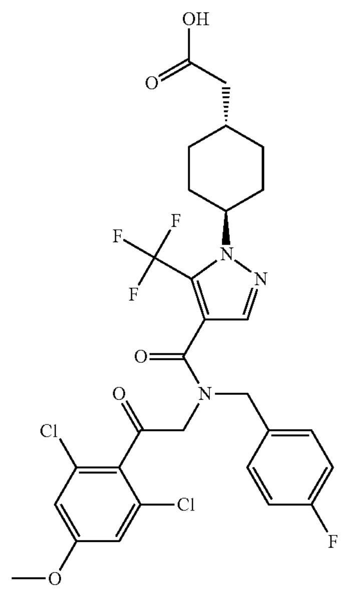 [SMILES: COc1cc(Cl)c(C(=O)CN(Cc2ccc(F)cc2)C(=O)c2cnn([C@H]3CC[C@H](CC(=O)O)CC3)c2C(F)(F)F)c(Cl)c1] | (trans-4-(4-((2-(2,6-dichloro-4-methoxyphenyl)-2-oxoethyl)(4-fluorobenzyl)carbamoyl)-5-(trifluoromethyl)-1H-pyrazol-1-yl)cyclohexyl)acetic acid |
| 890 | 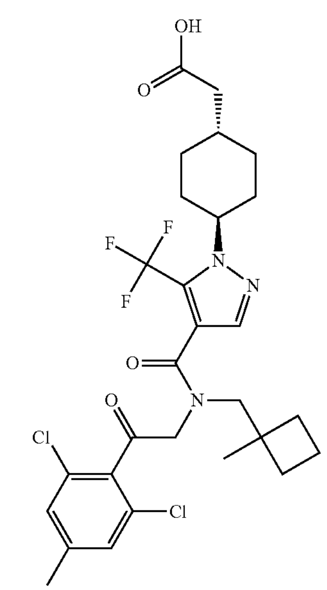 [SMILES: Cc1cc(Cl)c(C(=O)CN(CC2(C)CCC2)C(=O)c2cnn([C@H]3CC[C@H](CC(=O)O)CC3)c2C(F)(F)F)c(Cl)c1] | (trans-4-(4-((2-(2,6-dichloro-4-methylphenyl)-2-oxoethyl)((1-methylcyclobutyl)methyl)carbamoyl)-5-(trifluoromethyl)-1H-pyrazol-1-yl)cyclohexyl)acetic acid |

| example | structure | name |
|---|---|---|
| 891 | 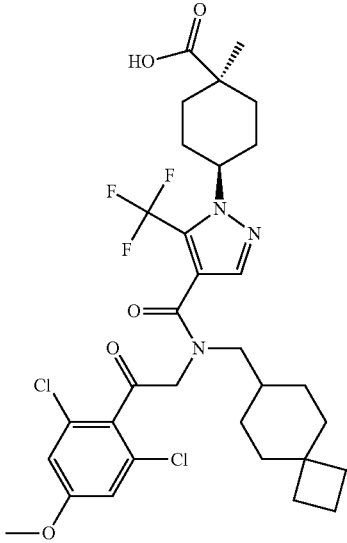 [SMILES: COc1cc(Cl)c(C(=O)CN(CC2CCC3(CCC3)CC2)C(=O)c2cnn([C@H]3CC[C@@](C)(C(=O)O)CC3)c2C(F)(F)F)c(Cl)c1] | trans-4-(4-((2-(2,6-dichloro-4-methoxyphenyl)-2-oxoethyl)(spiro[3.5]non-7-ylmethyl)carbamoyl)-5-(trifluoromethyl)-1H-pyrazol-1-yl)-1-methylcyclohexanecarboxylic acid |
| 892 | 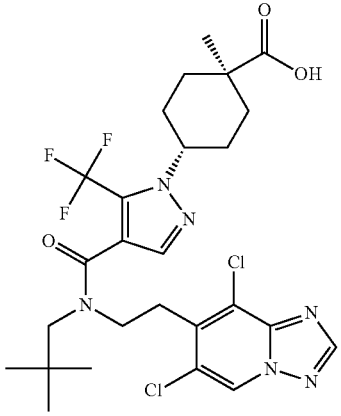 [SMILES: CC(C)(C)CN(CCc1c(Cl)cn2ncnc2c1Cl)C(=O)c1cnn([C@H]2CC[C@](C)(C(=O)O)CC2)c1C(F)(F)F] | trans-4-(4-((2-(6,8-dichloro[1,2,4]triazolo[1,5-a]pyridin-7-yl)ethyl)(2,2-dimethylpropyl)carbamoyl)-5-(trifluoromethyl)-1H-pyrazol-1-yl)-1-methylcyclohexanecarboxylic acid |
| 893 | 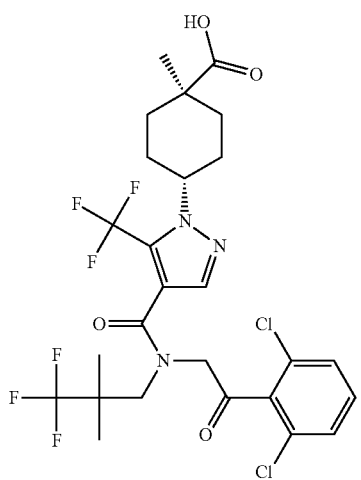 [SMILES: CC(C)(CN(CC(=O)c1c(Cl)cccc1Cl)C(=O)c1cnn([C@H]2CC[C@](C)(C(=O)O)CC2)c1C(F)(F)F)C(F)(F)F] | trans-4-(4-((2-(2,6-dichlorophenyl)-2-oxoethyl)(3,3,3-trifluoro-2,2-dimethylpropyl)carbamoyl)-5-(trifluoromethyl)-1H-pyrazol-1-yl)-1-methylcyclohexanecarboxylic acid |

The results of high performance liquid chromatography mass spectroscopy (LC/MS) analysis for the above examples were shown in the following tables.

| example | Exact Mass | Obs. Mass |
|---|---|---|
| 24 | 586.1 | 587.1 |
| 25 | 600.1 | 601.2 |
| 26 | 548.1 | 549.0 |
| 27 | 562.1 | 563.1 |
| 28 | 560.1 | 561.1 |
| 29 | 574.1 | 575.1 |
| 30 | 588.2 | 569.1 |
| 31 | 560.1 | 561.0 |
| 32 | 562.1 | 563.0 |
| 33 | 576.2 | 579.1 |
| 34 | 560.1 | 561.2 |
| 35 | 560.1 | 561.2 |
| 36 | 616.2 | 617.1 |
| 37 | 614.2 | 615.1 |
| 38 | 576.1 | 577.0 |
| 39 | 576.1 | 577.0 |
| 40 | 582.1 | 583.0 |
| 41 | 616.1 | 617.0 |
| 42 | 618.1 | 619.0 |
| 43 | 618.1 | 619.0 |
| 44 | 618.1 | 619.0 |
| 45 | 618.1 | 619.0 |
| 46 | 572.1 | 573.0 |
| 47 | 572.1 | 573.0 |
| 48 | 584.1 | 585.0 |
| 49 | 598.1 | 599 |
| 50 | 602.1 | 603 |
| 51 | 586.1 | 587 |
| 52 | 578.2 | 579 |
| 53 | 617.1 | 618 |
| 54 | 613.1 | 614 |
| 55 | 635.1 | 636 |
| 56 | 651.1 | 652 |
| 57 | 685.1 | 686 |
| 58 | 642.1 | 643 |
| 59 | 617.1 | 618 |
| 60 | 585.1 | 586 |
| 61 | 601.1 | 602 |
| 62 | 550.2 | 551 |
| 63 | 567.2 | 568 |
| 64 | 568.2 | 569 |
| 65 | 555.2 | 554 |
| 66 | 657.1 | 658 |
| 67 | 647.1 | 648 |
| 68 | 607.1 | 608 |
| 69 | 565.2 | 566 |
| 70 | 633.1 | 634 |
| 71 | 590.1 | 593.0 |
| 72 | 546.1 | 547.0 |
| 73 | 566.1 | 567.0 |
| 74 | 578.1 | 579.1 |
| 75 | 574.1 | 575.0 |
| 76 | 583.1 | 584.0 |
| 77 | 614.1 | 615.0 |
| 78 | 632.1 | 633.0 |
| 79 | 614.1 | 615.0 |
| 80 | 618.1 | 619.0 |
| 81 | 618.1 | 619.0 |
| 82 | 572.1 | 573.0 |
| 83 | 572.1 | 573.0 |
| 84 | 596.1 | 597.1 |
| 85 | 590.1 | 591 |
| 86 | 634.1 | 635.0 |
| 87 | 634.1 | 635.0 |
| 88 | 599.1 | 600.0 |
| 89 | 643.1 | 644.1 |
| 90 | 602.1 | 603.0 |
| 91 | 603.1 | 604.0 |
| 92 | 586.1 | 587.0 |
| 93 | 586.1 | 587.0 |
| 94 | 593.1 | 594.2 |
| 95 | 592.1 | 593.1 |
| 96 | 621.1 | 622.0 |
| 97 | 660.1 | 661 |
| 98 | 661.1 | 662 |
| 99 | 583.1 | 584 |
| 100 | 599.1 | 600.1 |
| 101 | 624.1 | 625.1 |
| 102 | 602.2 | 603.1 |
| 103 | 583.1 | 584.0 |
| 104 | 583.1 | 584.0 |
| 105 | 616.1 | 617.0 |
| 106 | 616.1 | 617.0 |
| 107 | 617.1 | 618 |
| 108 | 617.1 | 618 |
| 109 | 634.1 | 635 |
| 110 | 586.1 | 587.1 |
| 111 | 609.2 | 610 |
| 112 | 647.1 | 649 |
| 113 | 541.2 | 542 |
| 114 | 576.2 | 577.1 |
| 115 | 576.2 | 577.1 |
| 116 | 615.1 | 616.2 |
| 117 | 615.1 | 616.2 |
| 118 | 631.1 | 632 |
| 119 | 610.2 | 611 |
| 120 | 621.1 | 622 |
| 121 | 589.1 | 590.0 |
| 122 | 594.2 | 595 |
| 123 | 640.2 | 641.1 |
| 124 | 651.1 | 652 |
| 125 | 616.2 | 617.1 |
| 126 | 616.2 | 617.1 |
| 127 | 701.1 | 702 |
| 128 | 625.1 | 626.2 |
| 129 | 625.1 | 626.0 |
| 130 | 618.2 | 619.1 |
| 131 | 602.2 | 603.1 |
| 132 | 602.2 | 603.1 |
| 133 | 579.2 | 580 |
| 134 | 578.2 | 579 |
| 135 | 584.1 | 587 |
| 136 | 651.1 | 652 |
| 137 | 631.1 | 632 |
| 138 | 635.1 | 636.2 |
| 139 | 635.1 | 636.2 |
| 140 | 630.2 | 631 |
| 141 | 598.1 | 599 |
| 142 | 564.2 | 565 |
| 143 | 578.2 | 579 |
| 144 | 659.1 | 660.1 |
| 145 | 582.1 | 583.1 |
| 146 | 583.1 | 584 |
| 147 | 598.1 | 599 |
| 148 | 606.2 | 607 |
| 149 | 673.2 | 674.1 |
| 150 | 614.1 | 615.0 |
| 151 | 583.1 | 585 |
| 152 | 652.1 | 653 |
| 153 | 598.1 | 599 |
| 154 | 603.2 | 604.3 |
| 155 | 618.2 | 619.1 |
| 156 | 646.1 | 647 |
| 157 | 589.1 | 590 |
| 158 | 589.1 | 590 |
| 159 | 580.1 | 581.0 |
| 160 | 616.1 | 617.1 |
| 161 | 608.1 | 609.0 |
| 162 | 592.1 | 593 |
| 163 | 579.1 | 580.0 |
| 164 | 564.1 | 565 |
| 165 | 623.0 | 624 |
| 166 | 626.1 | 627.0 |
| 167 | 623.0 | 624 |
| 168 | 623.0 | 624 |
| 169 | 602.2 | 603.1 |
| 170 | 607.1 | 608 |
| 171 | 607.1 | 608 |
| 172 | 589.1 | 590.0 |
| 173 | 631.2 | 632.1 |
| 174 | 574.1 | 575.1 |

| example | Exact Mass | Obs. Mass |
|---|---|---|
| 175 | 610.1 | 611.0 |
| 176 | 618.2 | 619.1 |
| 177 | 612.1 | 613.0 |
| 178 | 614.1 | 615 |
| 179 | 619.1 | 620 |
| 180 | 608.1 | 609.0 |
| 181 | 576.1 | 577.0 |
| 182 | 600.2 | 601.1 |
| 183 | 588.2 | 589 |
| 184 | 588.2 | 589.2 |
| 185 | 560.1 | 561.2 |
| 187 | 588.2 | 589.2 |
| 188 | 596.1 | 597.1 |
| 189 | 635.1 | 636.0 |
| 190 | 633.2 | 634.3 |
| 191 | 649.1 | 650.2 |
| 192 | 614.2 | 615.3 |
| 193 | 631.2 | 632.2 |
| 194 | 592.1 | 593.2 |
| 195 | 582.1 | 583.2 |
| 196 | 598.2 | 597 |
| 197 | 631.1 | 632.2 |
| 198 | 562.1 | 563.2 |
| 199 | 631.2 | 632.3 |
| 200 | 586.1 | 587.2 |
| 201 | 621.1 | 622.2 |
| 202 | 617.1 | 618.2 |
| 203 | 647.2 | 648.3 |
| 204 | 600.2 | 601.3 |
| 205 | 602.2 | 603.3 |
| 206 | 613.2 | 614.2 |
| 207 | 633.1 | 634.2 |
| 208 | 590.1 | 591.2 |
| 209 | 607.1 | 608.2 |
| 210 | 599.1 | 600.2 |
| 211 | 600.2 | 601.3 |
| 212 | 642.1 | 643.2 |
| 213 | 642.1 | 643.2 |
| 214 | 595.2 | 596.3 |
| 215 | 586.1 | 587 |
| 216 | 624.0 | 625 |
| 217 | 633.2 | 634.3 |
| 218 | 617.1 | 618.3 |
| 219 | 647.1 | 648.2 |
| 220 | 647.2 | 648.3 |
| 221 | 609.1 | 610.2 |
| 222 | 647.2 | 648.3 |
| 223 | 588.2 | 589.3 |
| 224 | 623.1 | 624.2 |
| 225 | 639.1 | 640.2 |
| 226 | 643.2 | 645 |
| 227 | 629.2 | 630 |
| 228 | 614.1 | 615 |
| 229 | 616.2 | 617.3 |
| 230 | 645.2 | 646.3 |
| 231 | 661.1 | 662.2 |
| 232 | 609.2 | 610.3 |
| 234 | 633.1 | 634.2 |
| 235 | 633.2 | 634.3 |
| 236 | 641.2 | 642 |
| 237 | 627.2 | 628 |
| 238 | 615.2 | 616 |
| 239 | 663.2 | 664.3 |
| 240 | 643.2 | 644.3 |
| 241 | 659.1 | 660.2 |
| 242 | 661.2 | 662.3 |
| 243 | 623.2 | 624.3 |
| 244 | 647.2 | 648.3 |
| 245 | 605.1 | 606.3 |
| 246 | 621.1 | 622.2 |
| 247 | 659.2 | 660.3 |
| 248 | 621.2 | 622.3 |
| 249 | 619.2 | 620.3 |
| 250 | 635.1 | 636.2 |
| 251 | 635.2 | 636.3 |
| 252 | 597.2 | 598.3 |
| 253 | 571.2 | 572.3 |

| example | Exact Mass | Obs. Mass |
|---|---|---|
| 254 | 649.2 | 650.3 |
| 255 | 611.2 | 612.3 |
| 256 | 647.1 | 648.3 |
| 257 | 609.2 | 610.3 |
| 258 | 647.2 | 648.3 |
| 259 | 625.3 | 626.4 |
| 260 | 663.1 | 664.2 |
| 261 | 655.2 | 656 |
| 262 | 602.1 | 603 |
| 263 | 621.2 | 622.3 |
| 264 | 600.2 | 601.2 |
| 265 | 609.2 | 610.2 |
| 266 | 631.2 | 632.2 |
| 267 | 628.2 | 629.3 |
| 268 | 611.2 | 612 |
| 269 | 611.2 | 612 |
| 270 | 639.2 | 640.3 |
| 271 | 635.1 | 636.2 |
| 272 | 606.1 | 607.2 |
| 273 | 627.2 | 628.3 |
| 274 | 645.2 | 646.2 |
| 275 | 661.1 | 662.2 |
| 279 | 609.3 | 610 |
| 280 | 609.3 | 610 |
| 281 | 605.1 | 606.2 |
| 282 | 619.2 | 620.2 |
| 283 | 615.2 | 616.3 |
| 284 | 575.2 | 576.2 |
| 285 | 630.2 | 631.3 |
| 286 | 590.2 | 591.3 |
| 287 | 576.2 | 579.2 |
| 288 | 602.2 | 603.2 |
| 289 | 663.1 | 664 |
| 290 | 591.1 | 592 |
| 291 | 591.1 | 592 |
| 292 | 623.2 | 624 |
| 293 | 639.1 | 642 |
| 294 | 560.2 | 561.2 |
| 295 | 620.2 | 621 |
| 296 | 648.2 | 649 |
| 297 | 559.2 | 560.3 |
| 298 | 651.1 | 652.2 |
| 299 | 618.1 | 619.2 |
| 300 | 631.2 | 632.2 |
| 301 | 633.2 | 634 |
| 302 | 607.2 | 608.3 |
| 303 | 646.2 | 647 |
| 304 | 632.2 | 633 |
| 305 | 674.2 | 675 |
| 306 | 623.1 | 626.1 |
| 307 | 622.1 | 623 |
| 308 | 635.1 | 636.1 |
| 309 | 619.2 | 620.1 |
| 310 | 533.2 | 534.5 |
| 311 | 659.2 | 660 |
| 312 | 590.2 | 591 |
| 313 | 578.1 | 579 |
| 314 | 574.1 | 575 |
| 315 | 572.2 | 573.3 |
| 316 | 586.1 | 587.2 |
| 317 | 587.2 | 588.2 |
| 318 | 606.2 | 606.6 |
| 319 | 602.2 | 603.6 |
| 320 | 625.2 | 626.2 |
| 321 | 639.2 | 640.3 |
| 322 | 628.2 | 629.2 |
| 323 | 618.2 | 619.8 |
| 324 | 604.1 | 605.2 |
| 325 | 616.2 | 617.3 |
| 326 | 580.1 | 581.2 |
| 327 | 592.1 | 593.2 |
| 328 | 532.3 | 533.7 |
| 329 | 640.1 | 641.2 |
| 331 | 602.2 | 603 |
| 332 | 620.2 | 619 |
| 333 | 598.2 | 599.3 |
| 334 | 566.2 | 567.7 |

| example | Exact Mass | Obs. Mass |
|---|---|---|
| 335 | 610.2 | 611.3 |
| 336 | 613.3 | 614.3 |
| 337 | 574.2 | 575.2 |
| 338 | 551.3 | 552 |
| 339 | 605.1 | 606 |
| 340 | 588.2 | 589 |
| 341 | 611.2 | 612.3 |
| 342 | 611.2 | 612.9 |
| 344 | 646.2 | 645 |
| 345 | 599.2 | 600 |
| 346 | 588.2 | 589 |
| 347 | 607.2 | 606 |
| 348 | 639.1 | 640 |
| 349 | 606.3 | 608 |
| 350 | 671.1 | 672 |
| 351 | 655.1 | 656 |
| 352 | 580.2 | 581.8 |
| 353 | 652.2 | 653 |
| 354 | 599.2 | 600.3 |
| 355 | 599.2 | 600.3 |
| 356 | 573.2 | 574.3 |
| 357 | 573.2 | 574.3 |
| 358 | 541.1 | 544 |
| 359 | 555.1 | 558 |
| 360 | 580.2 | 581 |
| 363 | 579.1 | 580 |
| 364 | 559.2 | 560 |
| 365 | 573.2 | 574 |
| 366 | 593.2 | 594 |
| 367 | 580.1 | 581 |
| 368 | 581.2 | 583.0 |
| 369 | 581.2 | 582.9 |
| 370 | 577.3 | 578.9 |
| 371 | 577.3 | 579.0 |
| 372 | 615.3 | 616.9 |
| 373 | 615.3 | 617.0 |
| 374 | 577.2 | 578.9 |
| 375 | 577.2 | 578.9 |
| 376 | 605.2 | 607.0 |
| 377 | 618.3 | 620.0 |
| 378 | 540.1 | 541.2 |
| 379 | 556.2 | 557.3 |
| 380 | 605.2 | 606.3 |
| 381 | 568.1 | 569.2 |
| 382 | 548.2 | 549.3 |
| 383 | 600.2 | 601 |
| 384 | 600.2 | 601 |
| 385 | 585.2 | 586 |
| 386 | 596.1 | 597.8 |
| 387 | 594.2 | 595.9 |
| 388 | 594.1 | 595.1 |
| 389 | 581.2 | 582.3 |
| 390 | 582.2 | 583 |
| 391 | 582.2 | 583 |
| 392 | 618.3 | 619 |
| 393 | 595.2 | 596.3 |
| 394 | 608.2 | 609.3 |
| 395 | 574.1 | 575.2 |
| 396 | 587.2 | 588 |
| 397 | 587.2 | 588 |
| 398 | 580.2 | 581.3 |
| 399 | 647.2 | 648 |
| 400 | 645.2 | 646 |
| 401 | 548.3 | 549 |
| 402 | 544.2 | 545 |
| 403 | 544.2 | 545 |
| 404 | 603.2 | 604 |
| 405 | 605.2 | 606 |
| 406 | 607.2 | 608 |
| 407 | 597.2 | 598 |
| 408 | 583.2 | 584 |
| 409 | 598.2 | 599 |
| 410 | 563.3 | 564 |
| 411 | 587.2 | 588 |
| 412 | 654.1 | 655.2 |
| 500 | 567.1 | 568.1 |
| 501 | 601.1 | 602.0, 604.0 |
| 502 | 533.2 | 534.2 |
| 503 | 572.2 | 573.2 |
| 504 | 601.1 | 602.0, 604.1 |
| 505 | 561.2 | 562.2 |
| 506 | 572.2 | 573.2 |
| 507 | 572.2 | 573.1 |
| 508 | 572.2 | 573.2 |
| 509 | 547.2 | 548 |
| 510 | 587.2 | 588 |
| 511 | 601.2 | 602.2 |
| 512 | 561.2 | 562.1 |
| 513 | 586.2 | 587.2 |
| 514 | 601.2 | 602.2 |
| 515 | 575.2 | 576.2 |
| 516 | 615.2 | 616 |
| 517 | 575.2 | 575.8 |
| 518 | 627.2 | 628 |
| 519 | 615.2 | 615.7 |
| 520 | 601.2 | 601.7 |
| 521 | 587.2 | 587.8 |
| 522 | 699.1 | 699.5 |
| 523 | 547.2 | 547.7 |
| 524 | 563.2 | 564 |
| 525 | 601.2 | 601.7 |
| 526 | 635.1 | 635.6 |
| 527 | 649.1 | 649.5 |
| 528 | 663.1 | 664 |
| 529 | 591.2 | 591.7 |
| 530 | 591.2 | 592 |
| 531 | 591.2 | 591.7 |
| 532 | 643.2 | 644.2 |
| 533 | 615.2 | 616.1 |
| 534 | 587.2 | 587.7 |
| 534 | 587.2 | 587.7 |
| 535 | 629.2 | 629.8 |
| 535 | 629.2 | 629.8 |
| 536 | 615.2 | 616 |
| 536 | 615.2 | 615.7 |
| 537 | 601.2 | 601.7 |
| 537 | 601.2 | 602 |
| 538 | 592.2 | 593 |
| 539 | 616.1 | 617.2 |
| 541 | 633.1 | 634.0 |
| 542 | 576.2 | 577.1 |
| 543 | 630.1 | 629.0, 631.0 |
| 544 | 578.2 | 579 |
| 545 | 561.1 | 562 |
| 546 | 602.2 | 603.0 |
| 547 | 548.2 | 549.0 |
| 548 | 572.2 | 573 |
| 549 | 588.2 | 589 |
| 550 | 588.2 | 589.2 |
| 552 | 576.2 | 577 |
| 553 | 574.2 | 575.0 |
| 554 | 560.2 | 561 |
| 555 | 600.2 | 601.0 |
| 556 | 588.2 | 589 |
| 557 | 574.2 | 575.2 |
| 558 | 614.2 | 615.1 |
| 559 | 602.2 | 603.0, 605.0 |
| 560 | 560.2 | 561.2 |
| 561 | 630.2 | 631.0 |
| 562 | 574.2 | 575 |
| 563 | 546.1 | 547 |
| 564 | 560.2 | 561.2 |
| 565 | 599.2 | 600 |
| 566 | 599.2 | 600.1 |
| 567 | 585.1 | 586.0 |
| 568 | 589.2 | 590 |
| 569 | 627.2 | 628.2 |
| 570 | 601.2 | 604.3 |
| 571 | 629.2 | 630.2 |
| 572 | 601.2 | 602.2 |
| 573 | 563.2 | 564.2 |
| 574 | 563.2 | 564.0 |
| 575 | 631.2 | 632.2 |
| 576 | 584.2 | 585 |

| example | Exact Mass | Obs. Mass |
|---|---|---|
| 577 | 574.1 | 577 |
| 578 | 588.2 | 589.0 |
| 579 | 645.2 | 648 |
| 580 | 617.2 | 618 |
| 581 | 631.2 | 632.2 |
| 582 | 586.2 | 587.0 |
| 583 | 613.2 | 614.0 |
| 584 | 635.2 | 636.0 |
| 585 | 597.1 | 598.2 |
| 586 | 558.2 | 559.1 |
| 587 | 588.2 | 589 |
| 588 | 616.2 | 617 |
| 589 | 611.2 | 612 |
| 590 | 621.1 | 622 |
| 591 | 588.2 | 589 |
| 592 | 588.2 | 589.0 |
| 593 | 578.1 | 578.9 |
| 594 | 610.1 | 611 |
| 595 | 585.2 | 586 |
| 596 | 571.2 | 572 |
| 597 | 555.2 | 556 |
| 598 | 569.2 | 570 |
| 599 | 587.2 | 588.1 |
| 600 | 573.1 | 574 |
| 601 | 603.2 | 604 |
| 602 | 581.3 | 582 |
| 603 | 591.1 | 592.0 |
| 604 | 558.2 | 587.2 |
| 605 | 605.2027 | 606.1 |
| 606 | 592.1625 | 593 |
| 607 | 595.266 | 596.2 |
| 608 | 585.2 | 586.1 |
| 609 | 578.1 | 579 |
| 610 | 599.2 | 600.2 |
| 611 | 577.1 | 577.8 |
| 612 | 627.2 | 628.2 |
| 612 | 627.2 | 628.2 |
| 613 | 585.1 | 586.1 |
| 614 | 604.1 | 604.8 |
| 615 | 613.2 | 614 |
| 615 | 613.2 | 614.1 |
| 616 | 588.2 | 589.0 |
| 617 | 588.2 | 589.0 |
| 618 | 612.2 | 613.1 |
| 619 | 615.2 | 588.0 |
| 620 | 615.2 | 588.0 |
| 621 | 572.2 | 573.2 |
| 622 | 600.2 | 601 |
| 623 | 574.1 | 575.2 |
| 624 | 585.1 | 586.2 |
| 625 | 599.2 | 600.2 |
| 626 | 613.2 | 614 |
| 627 | 599.2 | 600 |
| 628 | 603.2 | 604.0 |
| 629 | 603.2 | 604 |
| 630 | 591.1 | 592.0 |
| 631 | 605.1 | 606 |
| 632 | 599.2 | 600.2 |
| 633 | 600.2 | 601.1 |
| 634 | 574.1 | 575 |
| 634 | 574.1 | 575 |
| 635 | 574.1 | 575.0 |
| 635 | 574.1 | 575.0 |
| 636 | 573.1 | 574.0 |
| 636 | 573.1 | 574.0 |
| 637 | 573.1403 | 574 |
| 637 | 573.1403 | 574 |
| 638 | 618.1617 | 619 |
| 639 | 599.2 | 600.2 |
| 640 | 585.1 | 586 |
| 641 | 599.2 | 600 |
| 642 | 585.1 | 586 |
| 643 | 589.2 | 590.2 |
| 644 | 618.2 | 619.2 |
| 645 | 632.2 | 632.9 |
| 646 | 604.1 | 604.8 |
| 647 | 574.1 | 575.1 |
| 648 | 574.1 | 575 |
| 649 | 613.2 | 614.2 |
| 650 | 613.2 | 614.2 |
| 651 | 599.2 | 600.2 |
| 652 | 599.2 | 600.2 |
| 653 | 629.2 | 630.2 |
| 654 | 629.2 | 630.2 |
| 655 | 618.2 | 619.0 |
| 656 | 560.1 | 561.2 |
| 657 | 573.2 | 574.2 |
| 658 | 597.2 | 598.2 |
| 659 | 576.2 | 577.1 |
| 660 | 604.1 | 605.2 |
| 661 | 604.1 | 605.2 |
| 662 | 601.2 | 602.2 |
| 663 | 601.2 | 603 |
| 664 | 619.2 | 620.2 |
| 665 | 633.2 | 634.2 |
| 666 | 620.2 | 621.2 |
| 667 | 592.1 | 593 |
| 667 | 592.1 | 593 |
| 668 | 573.1 | 574 |
| 669 | 573.1 | 573.9 |
| 670 | 561.1 | 562, 562 |
| 671 | 619.2 | 620.2 |
| 672 | 601.2 | 604 |
| 673 | 618.2 | 619.1 |
| 674 | 618.2 | 619.1 |
| 675 | 590.1 | 591 |
| 676 | 603.2 | 604 |
| 677 | 600.2 | 601.1 |
| 678 | 613.2 | 614.1 |
| 679 | 604.2 | 605.2 |
| 680 | 604.2 | 605.2 |
| 681 | 590.2 | 591.2 |
| 682 | 590.2 | 591.2 |
| 683 | 601.2 | 602.2 |
| 684 | 601.2 | 602.2 |
| 685 | 604.1 | 605.1 |
| 686 | 604.1 | 605.2 |
| 687 | 590.2 | 590.9 |
| 688 | 560.2 | 561.0, 563.1 |
| 689 | 629.2 | 630.2 |
| 690 | 595.1 | 596.0 |
| 691 | 605.1 | 606.1 |
| 692 | 630.1 | 631.0 |
| 693 | 570.2 | 570.8 |
| 694 | 591.1 | 591.8 |
| 694 | 591.1 | 591.8 |
| 695 | 577.1 | 577.8 |
| 695 | 577.1 | 577.8 |
| 696 | 633.2 | 633.8 |
| 696 | 633.2 | 633.8 |
| 697 | 610.1 | 611.2 |
| 698 | 605.1 | 605.8 |
| 698 | 605.1 | 605.8 |
| 699 | 616.2 | 617.2 |
| 700 | 576.2 | 577.2 |
| 701 | 574.2 | 574.9 |
| 702 | 626.2 | 627.3 |
| 703 | 592.1 | 592.8 |
| 704 | 589.2 | 590.2 |
| 705 | 604.1 | 605.0 |
| 706 | 604.1 | 605.0 |
| 707 | 573.1 | 574.0 |
| 708 | 597.1 | 598.2 |
| 709 | 615.2 | 616.2 |
| 710 | 560.1 | 561.0 |
| 711 | 602.2 | 603.0 |
| 712 | 618.1 | 619 |
| 712 | 618.1 | 619 |
| 713 | 617.1 | 618 |
| 713 | 617.1 | 618 |
| 714 | 628.2 | 629.2 |
| 715 | 590.2 | 591 |
| 716 | 591.1 | 592.1 |
| 716 | 591.1 | 592.1 |

| example | Exact Mass | Obs. Mass |
| --- | --- | --- |
| 717 | 587.2 | 588.1 |
| 717 | 587.2 | 588.1 |
| 718 | 601.2 | 602.2 |
| 718 | 601.2 | 602.2 |
| 719 | 576.2 | 577.3 |
| 720 | 576.2 | 577.3 |
| 721 | 613.2 | 614.2 |
| 722 | 613.2 | 614.2 |
| 723 | 617.2 | 618.2 |
| 724 | 617.2 | 618.2 |
| 725 | 617.2 | 618.2 |
| 726 | 617.2 | 618.2 |
| 727 | 603.2 | 604.2 |
| 728 | 603.2 | 604.2 |
| 729 | 627.1 | 628 |
| 730 | 588.2 | 589.1 |
| 731 | 601.2 | 602.1 |
| 732 | 630.2 | 631.3 |
| 733 | 587.2 | 588.1 |
| 733 | 587.2 | 588.1 |
| 734 | 574.1 | 575 |
| 734 | 574.1 | 575 |
| 735 | 602.2 | 603 |
| 735 | 602.2 | 603 |
| 736 | 578.1 | 580 |
| 737 | 578.1 | 580 |
| 738 | 576.2 | 578 |
| 739 | 576.2 | 578 |
| 740 | 590.2 | 591 |
| 741 | 611.1 | 612.2 |
| 742 | 602.2 | 603 |
| 743 | 588.2 | 589.2 |
| 744 | 615.2 | 616.2 |
| 745 | 601.2 | 602.1 |
| 746 | 574.2 | 574.9 |
| 747 | 574.2 | 574.9 |
| 748 | 600.2 | 601.2 |
| 749 | 600.2 | 601.2 |
| 750 | 627.2 | 628.4 |
| 751 | 620.2 | 621.3 |
| 752 | 575.2 | 612.2 |
| 753 | 606.2 | 607.3 |
| 754 | 590.2 | 591 |
| 755 | 632.1 | 633.2 |
| 756 | 602.2 | 604 |
| 757 | 608.2 | 609.3 |
| 758 | 628.2 | 629.3 |
| 759 | 573.1 | 574.3 |
| 759 | 573.1 | 574.3 |
| 760 | 587.2 | 588.3 |
| 760 | 587.2 | 588.3 |
| 761 | 632.1 | 632.2 (M − H)− |
| 762 | 646.1 | 646.2 (M − H)− |
| 763 | 631.2 | 632.2 |
| 764 | 593.1 | 594.2 |
| 765 | 560.1 | 561.2 |
| 766 | 602.1 | 604 |
| 767 | 602.1 | 604 |
| 768 | 646.1 | 647.3 |
| 769 | 589.1 | 570.2 |
| 770 | 560.1 | 561.2 |
| 771 | 574.1 | 575.2 |
| 772 | 599.2 | 600 |
| 773 | 618.2 | 619.1 |
| 774 | 618.2 | 619.1 |
| 775 | 588.2 | 587.9 |
| 776 | 574.1 | 575.2 |
| 777 | 587.2 | 588 |
| 778 | 585.2 | 586.2 |
| 779 | 620.2 | 619.8 |
| 780 | 646.1 | 645.7 |
| 781 | 587.2 | 589 |
| 782 | 588.2 | 590 |
| 783 | 631.2 | 632.0 |
| 784 | 590.2 | 591 |
| 785 | 590.2 | 591 |
| 786 | 646.1 | 646.3 |

| example | Exact Mass | Obs. Mass |
| --- | --- | --- |
| 787 | 613.2 | 614.2 |
| 788 | 574.1 | 575.2 |
| 789 | 646.1 | 646.3 |
| 790 | 646.1 | 645.5 |
| 791 | 590.2 | 590 |
| 792 | 590.2 | 590 |
| 793 | 576.2 | 577.1 |
| 794 | 575.2 | 577 |
| 795 | 638.1 | 639.0, 641.0 |
| 796 | 638.1 | 639.0, 641.0 |
| 797 | 638.1 | 639.0, 641.0 |
| 798 | 645.1 | 645.9 |
| 799 | 642.1 | 642.9 |
| 800 | 606.1 | 606.9 |
| 801 | 616.2 | 619.0 |
| 802 | 630.1 | 632 |
| 803 | 576.2 | 577.2 |
| 804 | 575.2 | 576.2 |
| 805 | 601.2 | 602.2 |
| 806 | 601.2 | 602.2 |
| 807 | 602.2 | 602.9 |
| 808 | 590.1 | 591.0 |
| 809 | 584.2 | 585.2 |
| 810 | 606.1 | 607 |
| 810 | 606.1 | 607 |
| 811 | 627.1 | 628 |
| 812 | 576.2 | 577.1 |
| 813 | 576.2 | 577.1 |
| 814 | 621.1 | 622.2 |
| 815 | 621.1 | 622.2 |
| 816 | 600.2 | 601.2 |
| 817 | 600.2 | 601.2 |
| 818 | 596.1 | 597 |
| 819 | 596.1 | 597 |
| 820 | 590.1 | 591.2 |
| 821 | 617.2 | 618.2 |
| 822 | 628.2 | 629.1, 631.1 |
| 823 | 628.2 | 629.1, 631.1 |
| 824 | 602.2 | 604 |
| 825 | 602.2 | 604 |
| 826 | 618.2 | 619.1 |
| 827 | 622.1 | 623.0, 625.0 |
| 828 | 622.1 | 623.0, 625.0 |
| 829 | 580.1 | 581.2 |
| 830 | 628.1 | 629.2, 631.2 |
| 831 | 579.1 | 580.2 |
| 832 | 579.1 | 580.2 |
| 833 | 630.2 | 631.2 |
| 834 | 602.2 | 605.2 |
| 835 | 644.2 | 647.2 |
| 836 | 574.1 | 575.2 |
| 837 | 574.1 | 575.2 |
| 838 | 617.2 | 618.2 |
| 839 | 617.2 | 618.2 |
| 840 | 580.1 | 581.2 |
| 841 | 610.1 | 611.0 |
| 842 | 590.2 | 591.2 |
| 843 | 590.2 | 591.2 |
| 844 | 590.1 | 591.0 |
| 845 | 631.2 | 632.2 |
| 846 | 585.1 | 586.2 |
| 847 | 578.1 | 579 |
| 848 | 599.2 | 600 |
| 849 | 599.2 | 600 |
| 850 | 606.2 | 607.1 |
| 851 | 628.2 | 629.2, 631.2 |
| 852 | 628.2 | 629.2, 631.2 |
| 853 | 616.1 | 617.0 |
| 854 | 586.1 | 587.2 |
| 855 | 590.2 | 591.2 |
| 856 | 590.2 | 591.2 |
| 857 | 590.2 | 591.2 |
| 858 | 585.1 | 586.2 |
| 859 | 585.1 | 586.2 |
| 860 | 588.2 | 589.2 |
| 861 | 590.2 | 591 |
| 861 | 590.2 | 591 |

| example | Exact Mass | Obs. Mass |
|---|---|---|
| 862 | 590.2 | 591 |
| 862 | 590.2 | 591 |
| 863 | 624.1 | 625 |
| 863 | 624.1 | 625 |
| 864 | 630.1 | 631.1 |
| 865 | 601.2 | 603 |
| 866 | 601.2 | 603 |
| 867 | 616.1 | 617.2 |
| 868 | 594.1 | 595.2 |
| 869 | 594.1 | 595.2 |
| 870 | 594.1 | 595.2 |
| 871 | 602.2 | 603 |
| 871 | 602.2 | 603 |
| 872 | 592.2 | 593.2, 595.1 |
| 873 | 590.2 | 591 |
| 873 | 590.2 | 591 |
| 874 | 590.2 | 591 |
| 874 | 590.2 | 591 |
| 875 | 630.1 | 632 |
| 876 | 602.2 | 603 |
| 876 | 602.2 | 603 |
| 877 | 602.2 | 603 |
| 877 | 602.2 | 603 |
| 878 | 630.1 | 631.1 |
| 879 | 630.1 | 631.1 |
| 880 | 616.1 | 617.2 |
| 881 | 616.1 | 617.2 |
| 882 | 590.2 | 591.2 |
| 883 | 590.2 | 591.2 |
| 884 | 630.1 | 631.0 |
| 885 | 578.2 | 579.0, 581.0 |
| 886 | 578.2 | 579.0, 581.2 |
| 887 | 592.2 | 593.2, 595.1 |
| 888 | 635.2 | 636 |
| 888 | 635.2 | 636 |
| 889 | 643.1 | 644 |
| 889 | 643.1 | 644 |
| 890 | 601.2 | 602 |
| 890 | 601.2 | 602 |
| 891 | 671.2 | 672 |
| 891 | 671.2 | 672 |
| 892 | 602.2 | 603.2 |
| 893 | 629.1 | 630.2 |

As for the examples, the results of spectrum were shown in the following tables.

| example | |
|---|---|
| 25 | δ (400 MHz, CDCl$_3$) rotomers present 8.53 and 8.47 (2H, 2 × s); 7.69 and 7.59 (1H, 2 × s); 7.31-7.28 (1H, m); 7.16-7.12 (1H, m); 7.06-7.02 (2H, m); 4.83 and 4.65 (2H, 2 × s); 4.61 and 4.30 (2H, 2 × s), 4.27-4.21 (1H, m); 2.78 (1H, m); 2.44-2.40 (2H, m); 2.26-2.15 (2H, m); 1.96-1.86 (2H, m); 1.74-1.67 (2H, m) |
| 26 | δ (400 MHz, CDCl$_3$) rotomers present 8.58 and 8.51 (2H, 2 × s); 7.63 and 7.55 (2H, 2 × s); 4.77 and 4.44 (2H, 2 × s); 4.28-4.19 (1H, m); 3.44 (1H, d, J = 6.8 Hz) and 3.21 (1H, d, J = 7.6 Hz); 2.52-2.42 (1H, m); 2.26-2.23 (2H, m); 2.14-2.03 (4H, m); 1.88-1.59 (1H, m); 0.99 and 0.84 (6H, 2 × d, J = 6.6 Hz) |
| 27 | δ (400 MHz, CDCl$_3$) rotomers present 8.57 and 8.50 (2H, 2 × s); 7.71 and 7.56 (2H, 2 × s); 4.87 and 4.53 (2H, 2 × s); 4.25-4.19 (1H, m); 3.43-3.34 (2H, m); 2.49-2.43 (1H, m); 2.26-2.23 (2H, m); 2.10-2.03 (4H, m); 1.70-1.59 (2H, m); 1.01 and 0.85 (9H, 2 × s) |
| 28 | δ (400 MHz, CDCl$_3$) rotomers present 8.58 and 8.50 (2H, 2 × s); 7.64 and 7.54 (2H, 2 × s); 4.71 and 4.40 (2H, 2 × s); 4.28-4.17 (1H, m); 3.66 and 3.40 (2H, 2 × d, J = 7.3 Hz); 2.71-2.42 (2H, m); 2.27-2.22 (2H, m); 2.15-1.99 (6H, m); 1.94-1.52 (6H, m) |
| 29 | δ (400 MHz, CDCl$_3$) rotomers present 8.58 and 8.51 (2H, 2 × s); 7.63 and 7.55 (1H, 2 × s); 4.79 and 4.46 (2H, 2 × s); 4.30-4.18 (1H, m); 3.57 and 3.32 (2H, 2 × d, J = 7.8 Hz); 2.50-2.42 (1H, m); 2.27-2.22 (2H, m); 2.13-2.04 (4H, m); 1.78-1.49 (9H, m); 1.31-1.27 (1H, m); 1.07-1.03 (1H, m) |
| 30 | δ (400 MHz, CDCl$_3$) rotomers present 8.58 and 8.51 (2H, 2 × s); 7.62 and 7.55 (1H, 2 × s); 4.76 and 4.44 (2H, 2 × s); 4.28-4.19 (1H, m); 3.45 and 3.22 (2H, 2 × d, J = 7.8 Hz); 2.51-2.42 (1H, m); 2.27-2.23 (2H, m); 2.14-2.03 (4H, m); 1.75-1.64 (9H, m); 1.54-1.46 (1H, m); 1.16-1.10 (1H, m); 1.07-1.01 (1H, m); 0.77-0.71 (1H, m) |
| 31 | δ (400 MHz, CDCl$_3$) rotomers present 8.58 and 8.51 (2H, 2 × s); 7.62 and 7.55 (1H, 2 × s); 4.95 and 4.60 (2H, 2 × s); 4.30-4.22 (1H, m); 3.57 and 3.34 (2H, 2 × s); 2.52-2.43 (1H, m); 2.27-2.24 (2H, m); 2.15-2.04 (4H, m); 1.72-1.62 (2H, m); 1.09 and 0.97 (3H, 2 × s); 0.51-0.32 (4H, m) |
| 32 | δ (400 MHz, CDCl$_3$) rotomers present 8.58 and 8.51 (2H, 2 × s); 7.65 and 7.55 (1H, 2 × s); 4.74 and 4.42 (2H, 2 × s); 4.30-4.17 (1H, m); 3.61 and 3.34 (2H, 2 × t, J = 7.7 Hz); 2.50-2.43 (1H, m); 2.27-2.24 (2H, m); 2.12-2.03 (4H, m); 1.72-1.38 (5H, m); 0.96 (3H, d, J = 6.6 Hz); 0.77 (3H, d, J = 6.3 Hz) |
| 33 | δ (400 MHz, CDCl$_3$) rotomers present 8.58 and 8.52 (2H, 2 × s); 7.65 and 7.54 (1H, 2 × s); 4.74 and 4.41 (2H, 2 × s); 4.30-4.20 (1H, m); 3.62-3.58 and 3.33-3.29 (2H, 2 × m); 2.50-2.43 (1H, m); 2.26-2.23 (2H, m); 2.12-2.04 (4H, m); 1.72-1.62 (2H, m); 1.56-1.51 and 1.42-1.38 (2H, 2 × m); 0.97 and 0.76 (9H, 2 × s) |
| 35 | δ (400 MHz, CDCl$_3$) rotomers present 8.56 and 8.49 (2H, 2 × s); 7.63 and 7.55 (1H, 2 × s); 5.19-5.16 and 5.10-5.06 (1H, 1 × m); 4.29-4.27 and 3.99-3.97 (2H, 2 × m); 2.50-2.43 (1H, m); 2.26-2.23 (2H, m); 2.13-2.03 (4H, m); 1.72 and 1.52 (3H, 2 × s); 1.70-1.63 (2H, m) |
| 36 | δ (400 MHz, CDCl$_3$) rotomers present 8.58 and 8.51 (2H, 2 × s); 7.63 and 7.55 (1H, 2 × s); 4.76 and 4.44 (2H, 2 × s); 4.28-4.17 (1H, m); 3.49 and 3.26 (2H, 2 × d, J = 6.8 Hz); 2.51-2.42 (1H, m); 2.27-2.23 (2H, m); 2.14-2.03 (4H, m); 1.71-0.97 (11H, m); 0.90-0.78 (6H, m) |
| 37 | δ (400 MHz, CDCl$_3$) rotomers present 8.58 and 8.51 (2H, 2 × s); 7.64 and 7.55 (1H, 2 × s); 4.77 and 4.45 (2H, 2 × s); 4.29-4.19 (1H, m); 3.51 and 3.28 (2H, 2 × d, J = 6.8 Hz); 2.51-2.43 (1H, m); 2.27-2.23 (2H, m); 2.14-2.03 (4H, m); 1.73-1.54 (7H, m); 1.27-1.18 (1H, m); 0.98-0.84 (3H, m), 0.30-0.10 (4H, m) |

| example | |
|---|---|
| 40 | δ (400 MHz, CDCl$_3$) rotamers present 8.52 and 8.45 (2H, 2 × s); 7.69 and 7.60 (1H, 2 × s); 7.37-7.29 (4H, m); 7.17-7.15 (1H, m); 4.87 and 4.66 (2H, 2 × s); 4.64 and 4.30 (2H, 2 × s); 4.30-4.21 (1H, m); 2.49-2.42 (1H, m); 2.25-2.22 (2H, m); 2.09-2.04 (4H, m); 1.71-1.64 (2H, m) |
| 41 | δ (400 MHz, CDCl$_3$) rotamers present 8.53 and 8.47 (2H, 2 × s); 7.68 and 7.60 (1H, 2 × s); 7.33 (2H, d, J = 8.3 Hz); 7.25 and 7.10 (2H, d, J = 8.3 Hz); 4.82 and 4.65 (2H, 2 × s); 4.61 and 4.29 (2H, 2 × s); 4.29-4.20 (1H, m); 2.50-2.42 (1H, m); 2.27-2.23 (2H, m); 2.11-2.03 (4H, m); 1.70-1.59 (2H, m) |
| 42 | δ (400 MHz, CDCl$_3$) rotamers present 8.55 and 8.49 (2H, 2 × s); 7.66 and 7.61 (1H, 2 × s); 6.85-6.69 (3H, m); 4.83 and 4.70 (2H, 2 × s); 4.62 and 4.34 (2H, 2 × s); 4.28-4.21 (1H, m); 2.49-2.43 (1H, m); 2.27-2.23 (2H, m); 2.10-2.04 (4H, m); 1.71-1.60 (2H, m) |
| 43 | δ (400 MHz, CDCl$_3$) rotamers present 8.54 and 8.48 (2H, 2 × s); 7.67 and 7.59 (1H, 2 × s); 7.26-7.21, 7.15-7.70 and 6.93-6.89 (3H, 3 × m); 4.92 and 4.71 (2H, 2 × s); 4.71 and 4.42 (2H, 2 × s); 4.28-4.18 (1H, m); 2.50-2.43 (1H, m); 2.26-2.23 (2H, m); 2.12-2.03 (4H, m); 1.71-1.59 (2H, m) |
| 44 | δ (400 MHz, CDCl$_3$) rotamers present 8.54 and 8.48 (2H, 2 × s); 7.67 and 7.60 (1H, 2 × s); 7.19-7.12 and 7.05-6.89 (3H, 2 × m); 4.80 and 4.67 (2H, 2 × s); 4.60 and 4.32 (2H, 2 × s); 4.27-4.19 (1H, m); 2.49-2.42 (1H, m); 2.26-2.23 (2H, m); 2.11-2.04 (4H, m); 1.70-1.63 (2H, m) |
| 45 | δ (400 MHz, CDCl$_3$) rotamers present 8.55 and 8.48 (2H, 2 × s); 7.68 and 7.60 (1H, 2 × s); 7.19-7.14, 7.06-6.95 and 6.82-6.78 (3H, 3 × m); 4.87 and 4.73 (2H, 2 × s); 4.66 and 4.42 (2H, 2 × s); 4.28-4.19 (1H, m); 2.50-2.43 (1H, m); 2.26-2.23 (2H, m); 2.13-2.03 (4H, m); 1.70-1.60 (2H, m) |
| 46 | δ (400 MHz, CDCl$_3$) rotamers present 8.56 and 8.49 (2H, 2 × s); 7.78 and 7.75 (1H, 2 × s); 7.39 (1H, m); 6.35 (1H, m); 6.33-6.32 and 6.22-6.21 (1H, 2 × m); 4.84 and 4.73 (2H, 2 × s); 4.56 and 4.44 (2H, 2 × s); 4.33-4.19 (1H, m); 2.50-2.42 (1H, m); 2.27-2.23 (2H, m); 2.14-2.03 (4H, m); 1.73-1.62 (2H, m) |
| 47 | δ (400 MHz, CDCl$_3$) rotamers present 8.55 and 8.49 (2H, 2 × s); 7.70 and 7.58 (1H, 2 × s); 7.41-7.33 (2H, m); 6.40 and 6.26 (1H, 2 × s); 4.70 (2H, s); 4.46 and 4.35 (2H, 2 × s); 4.32-4.18 (1H, m); 2.50-2.42 (1H, m); 2.27-2.23 (2H, m); 2.14-2.03 (4H, m); 1.72-1.59 (2H, m) |
| 48 | δ (400 MHz, CDCl$_3$) rotamers present 8.76-8.36 (5H, m); 7.71 and 7.60 (1H, 2 × s); 4.94 and 4.85 (2H, 2 × s); 4.74 and 4.66 (2H, 2 × s); 4.26-4.18 (1H, m); 2.49-2.42 (1H, m); 2.25-2.22 (2H, m); 2.11-2.03 (4H, m); 1.70-1.59 (2H, m) |
| 49 | δ (400 MHz, DMSO-d$_6$) rotamers present 12.16 (1H, brs); 8.56-8.51 and 8.49-8.43 (2H, 2 × m); 7.88 and 7.82 (1H, 2 × s); 7.16-6.92 (3H, m); 4.78 and 4.77 (2H, 2 × s); 4.72 and 4.60 (2H, 2 × s); 4.28-4.17 (1H, m); 2.33-2.29 (1H, m); 2.28 and 1.83 (3H, 2 × s); 2.07-2.03 (2H, m); 1.94-1.91 (4H, m); 1.60-1.49 (2H, m) |
| 50 | δ (400 MHz, DMSO-d$_6$) rotamers present 8.78 and 8.71 (1H, 2 × s); 8.69 and 8.62 (1H, 2 × s); 7.81 and 7.78 (1H, 2 × s); 7.18-6.90 (3H, m); 4.84 and 4.81 (2H, 2 × s); 4.70 and 4.59 (2H, 2 × s); 4.23-4.14 (1H, m); 2.33-2.26 (1H, m); 2.09-2.02 (2H, m); 1.99-1.90 (4H, m); 1.58-1.46 (2H, m) |
| 51 | δ (400 MHz, DMSO-d$_6$) rotamers present 12.20 (1H, brs); 8.72 and 8.66 (2H, 2 × s); 7.74 and 7.72 (1H, 2 × s); 7.18-7.10 (1H, m); 7.07 and 6.90 (2H, 2 × d, J = 6.4 Hz); 4.84 and 4.82 (2H, 2 × s); 4.71 and 4.60 (2H, 2 × s); 4.22-4.17 (1H, m); 2.33-2.27 (1H, m); 2.09-1.92 (6H, m); 1.55-1.49 (2H, m) |
| 52 | δ (400 MHz, CDCl$_3$) rotamers present 8.31 and 8.24 (2H, 2 × s); 7.67 and 7.63 (1H, 2 × s); 6.83-6.72 (3H, m); 4.84 and 4.63 (2H, 2 × s); 4.47 and 4.20 (2H, 2 × s); 4.27-4.25 (1H, m); 2.49-2.43 (1H, m); 2.27-2.23 (2H, m); 2.23 and 1.86 (6H, 2 × s); 2.11-2.06 (4H, m); 1.68-1.64 (2H, m) |
| 53 | δ (400 MHz, DMSO-d$_6$) rotamers present 12.20 (1H, brs); 7.86 and 7.84 (1H, 2 × s); 7.57-7.49 (3H, m); 7.19-7.13 (1H, m); 7.11-7.08 and 6.93-6.91 (2H, 2 × m); 4.81 and 4.72 (2H, 2 × s); 4.67 and 4.56 (2H, 2 × s); 4.27-4.19 (1H, m); 2.34-2.27 (1H, m); 2.06-2.03 (2H, m); 1.98-1.92 (4H, m); 1.58-1.50 (2H, m) |
| 54 | δ (400 MHz, DMSO-d$_6$) rotamers present 12.20 (1H, brs); 7.75 (1H, s); 7.47-7.38 (1H, m); 7.18-6.88 (5H, m); 4.71 and 4.67 (2H, 2 × s); 4.53 and 4.52 (2H, 2 × s); 4.25-4.23 (1H, m); 3.77 and 3.67 (3H, 2 × s); 2.34-2.28 (1H, m); 2.06-1.90 (6H, m); 1.59-1.49 (2H, m) |
| 55 | δ (400 MHz, DMSO-d$_6$) rotamers present 12.20 (1H, brs); 7.86 and 7.84 (1H, 2 × s); 7.68 and 7.62 (2H, 2 × d, J = 8.4 Hz); 7.19-6.91 (3H, m); 4.80 and 4.71 (2H, 2 × s); 4.65 and 4.55 (2H, 2 × s); 4.26-4.21 (1H, m); 2.35-2.28 (1H, m); 2.07-2.06 (2H, m); 1.97-1.92 (4H, m); 1.60-1.49 (2H, m) |
| 56 | δ (400 MHz, DMSO-d$_6$) rotamers present 7.86 and 7.84 (1H, 2 × s); 7.84 and 7.76 (2H, 2 × s); 7.19-6.91 (3H, m); 4.80 and 4.71 (2H, 2 × s); 4.65 and 4.56 (2H, 2 × s); 4.27-4.17 (1H, m); 2.34-2.27 (1H, m); 2.06-2.02 (2H, m); 1.97-1.91 (4H, m); 1.59-1.49 (2H, m) |
| 57 | δ (400 MHz, DMSO-d$_6$) rotamers present 12.18 (1H, brs); 8.08 and 8.02 (2H, 2 × s); 7.88 and 7.85 (1H, 2 × s); 7.19-6.92 (3H, m); 4.84 and 4.72 (2H, 2 × s); 4.68 and 4.57 (2H, 2 × s); 4.27-4.18 (1H, m); 2.35-2.27 (1H, m); 2.07-2.03 (2H, m); 1.98-1.93 (4H, m); 1.60-1.51 (2H, m) |
| 58 | δ (400 MHz, CD$_3$CN) rotamers present 7.88-7.68 (3H, m); 7.02-6.86 (3H, m); 4.79 and 4.76 (2H, 2 × s); 4.62 and 4.56 (2H, 2 × s); 4.35-4.29 (1H, m); 2.47-2.40 (1H, m); 2.17-2.12 (2H, m); 2.08-2.02 (4H, m); 1.67-1.62 (2H, m) |

-continued

| example | |
|---|---|
| 59 | δ (400 MHz, DMSO-d$_6$) rotamers present 12.20 (1H, brs); 8.04-7.87 (3H, m); 7.75 and 7.52 (1H, 2 × s); 7.17-7.10 (1H, m); 7.06-7.05 and 6.89-6.88 (2H, 2 × m); 5.08 and 4.96 (2H, 2 × s); 4.67 and 4.57 (2H, 2 × s); 4.18-4.17 (1H, m); 2.32-2.25 (1H, m); 2.04-1.98 (2H, m); 1.95-1.81 (4H, m); 1.55-1.47 (2H, m) |
| 60 | δ (400 MHz, DMSO-d$_6$) rotamers present 12.20 (1H, brs); 7.77-7.51 (4H, m); 7.17-7.07 (1H, m); 7.05 and 6.89 (2H, 2 × d, J = 1.6 Hz); 5.07 and 4.93 (2H, 2 × s); 4.68 and 4.57 (2H, 2 × s); 4.18-4.17 (1H, m); 2.29-2.25 (1H, m); 2.05-1.98 (2H, m); 1.95-1.81 (4H, m); 1.53-1.47 (2H, m) |
| 61 | δ (400 MHz, CDCl$_3$) rotamers present 7.76-7.72 and 7.38-7.34 (1H, 2 × m); 7.58 and 7.50 (1H, 2 × s); 7.18-7.02 (2H, m); 6.83-6.71 (3H, m); 4.78 and 4.71 (2H, 2 × s); 4.62 and 4.51 (2H, 2 × s); 4.25-4.22 (1H, m); 2.45-2.41 (1H, m); 2.24-2.21 (2H, m); 2.10-2.02 (4H, m); 1.66-1.62 (2H, m) |
| 62 | δ (400 MHz, DMSO-d$_6$) rotamers present 8.84 and 8.77 (2H, 2 × dd, J = 4.8, 1.6 Hz); 7.89 and 7.71 (2H, 2 × dd, J = 4.8, 1.6 Hz); 7.76 and 7.55 (1H, 2 × s); 7.15-7.10 (1H, m); 7.08-7.06 and 6.91-6.89 (2H, 2 × m); 5.08 and 4.95 (2H, 2 × s); 4.70 and 4.59 (2H, 2 × s); 4.18-4.15 (1H, m); 2.33-2.21 (1H, m); 2.04-1.79 (6H, m); 1.53-1.45 (2H, m) |
| 63 | δ (400 MHz, DMSO-d$_6$) rotamers present 12.10 (1H, brs); 7.74 and 7.61 (1H, 2 × s); 7.40 and 7.34 (1H, 2 × s); 7.16-6.88 (3H, m); 4.74 and 4.68 (2H, 2 × s); 4.55 and 4.53 (2H, 2 × s); 4.21-4.12 (1H, m); 2.56 and 2.39 (3H, 2 × s); 2.33-2.21 (1H, m); 2.14 and 1.97 (3H, 2 × s); 2.01-1.99 (2H, m); 1.93-1.85 (4H, m); 1.55-1.47 (2H, m) |
| 64 | δ (400 MHz, DMSO-d$_6$) rotamers present 12.20 (1H, brs); 7.73 and 7.62 (1H, 2 × s); 7.16-6.89 (3H, m); 4.81 and 4.67 (2H, 2 × s); 4.61 and 4.55 (2H, 2 × s); 4.20-4.11 (1H, m); 2.73 and 2.49 (3H, 2 × s); 2.39 and 2.28 (3H, 2 × s); 2.26-2.17 (1H, m); 2.02-1.99 (2H, m); 1.96-1.85 (4H, m); 1.53-1.43 (2H, m) |
| 65 | δ (400 MHz, CDCl$_3$) rotamers present 7.57 and 7.40 (1H, 2 × s); 6.78-6.65 (3H, m); 4.69 and 4.49 (2H, 2 × s); 4.27 and 3.95 (2H, 2 × s); 4.25-4.21 (1H, m); 2.47-2.37 (2H, m); 2.24-2.21 (2H, m); 2.09-2.03 (4H, m); 1.86-1.77 (2H, m); 1.68-1.60 (4H, m); 1.51-1.26 (6H, m) |
| 66 | δ (400 MHz, DMSO-d$_6$) rotamers present 7.83 and 7.82 (1H, 2 × s); 7.28 and 7.21 (2H, 2 × s); 7.18-7.12 (1H, m); 7.07 and 6.90 (2H, 2 × d, J = 1.6 Hz); 4.78 and 4.70 (2H, 2 × s); 4.61 and 4.54 (2H, 2 × s); 4.26-4.20 (1H, m); 2.28-2.21 (1H, m); 2.04-2.01 (2H, m); 1.99-1.89 (5H, m); 1.54-1.50 (2H, m); 1.04-0.96 (2H, m); 0.82-0.74 (2H, m) |
| 67 | δ (400 MHz, DMSO-d$_6$) rotamers present 12.20 (1H, brs); 7.84 and 7.82 (1H, 2 × s); 7.18-7.09 (3H, m); 7.08 and 6.91 (2H, 2 × d, J = 1.6 Hz); 4.78 and 4.70 (2H, 2 × s); 4.61 and 4.54 (2H, 2 × s); 4.26-4.20 (1H, m); 3.83 and 3.78 (3H, 2 × s); 2.33-2.27 (1H, m); 2.05-2.02 (2H, m); 1.97-1.91 (4H, m); 1.58-1.50 (2H, m) |
| 68 | δ (400 MHz, DMSO-d$_6$) rotamers present 7.98 (1H, s); 7.76-7.74 (1H, m); 7.52-7.50 (1H, m); 7.45-7.41 (1H, m); 7.12-7.05 (3H, m); 6.70 (1H, s); 5.10-4.76 (4H, m); 4.23-4.19 (1H, m); 2.27-2.21 (1H, m); 2.01-1.98 (2H, m); 1.91-1.85 (4H, m); 1.55-1.44 (2H, m) |
| 69 | δ (400 MHz, DMSO-d$_6$) rotamers present 7.92-7.90 and 7.75-7.73 (2H, 2 × m); 7.75 and 7.49 (1H, 2 × s); 7.15-7.08 (1H, m); 7.06 and 6.89 (2H, 2 × d, J = 1.6 Hz); 6.88-6.86 and 6.81-6.78 (2H, 2 × m); 4.96 and 4.76 (2H, 2 × s); 4.66 and 4.55 (2H, 2 × s); 4.17-4.14 (1H, m); 2.29-2.23 (1H, m); 2.04-1.96 (2H, m); 1.91-1.83 (4H, m); 1.53-1.45 (2H, m) |
| 70 | δ (400 MHz, DMSO-d$_6$) rotamers present 7.82 (1H, s); 7.18-7.12 (1H, m); 7.07 and 6.90 (2H, 2 × d, J = 1.6 Hz); 6.85 and 6.75 (2H, 2 × s); 4.75 and 4.68 (2H, 2 × s); 4.58 and 4.53 (2H, 2 × s); 4.25-4.19 (1H, m); 2.30-2.26 (1H, m); 2.07-2.02 (2H, m); 1.96-1.90 (4H, m); 1.58-1.48 (2H, m) |
| 71 | δ (400 MHz, CDCl$_3$) rotamers present 8.59 and 8.52 (2H, 2 × s); 7.64 and 7.55 (1H, 2 × s); 4.76 and 4.45 (2H, 2 × s); 4.28-4.19 (1H, m); 4.02-3.93 (2H, m); 3.50-3.28 (4H, m); 2.26-2.23 (2H, m); 2.13-2.03 (5H, m); 1.76-1.59 (5H, m); 1.46-1.36 (1H, m); 1.16-1.06 (1H, m) |
| 72 | δ (400 MHz, CDCl$_3$) rotamers present 8.58 and 8.51 (2H, 2 × s); 7.64 and 7.56 (1H, 2 × s); 4.91 and 4.57 (2H, 2 × s); 4.31-4.18 (1H, m); 3.54 and 3.26 (2H, d, J = 6.9 Hz); 2.50-2.43 (1H, m); 2.27-2.23 (2H, m); 2.14-2.04 (4H, m); 1.72-1.60 (2H, m); 1.09-1.01 and 0.91-0.85 (1H, 2 × m); 0.61-0.56 (2H, m); 0.36-0.32 (1H, m); 0.15-0.10 (1H, m) |
| 73 | δ (400 MHz, CDCl$_3$) rotamers present 8.57 and 8.50 (2H, 2 × s); 7.66 and 7.56 (1H, 2 × s); 5.00 and 4.68 (2H, 2 × s); 4.27-4.19 (1H, m); 3.83-3.57 (2H, m); 2.50-2.42 (1H, m); 2.27-2.23 (2H, m); 2.13-2.04 (4H, m); 1.71-1.60 (2H, m); 1.43 and 1.28 (6H, d, J = 21.6 Hz) |
| 74 | δ (400 MHz, CDCl$_3$) rotamers present 8.56 and 8.48 (2H, 2 × s); 7.66 and 7.54 (1H, 2 × s); 5.12 and 4.82 (2H, 2 × s); 4.27-4.18 (1H, m); 3.46 and 3.13 (2H, 2 × s); 3.17 (3H, s); 2.49-2.43 (1H, m); 2.26-2.23 (2H, m); 2.12-2.03 (4H, m); 1.70-1.59 (2H, m); 1.22 and 1.04 (6H, 2 × s) |
| 75 | δ (400 MHz, CDCl$_3$) rotamers present 8.60 and 8.53 (2H, 2 × s); 7.66 and 7.57 (1H, 2 × s); 4.94 and 4.62 (2H, 2 × s); 4.30-4.22 (2H, m); 4.04-3.98 (1H, m); 2.51-2.43 (1H, m); 2.27-2.24 (2H, m); 2.14-2.05 (4H, m); 1.71-1.62 (2H, m) |
| 76 | δ (400 MHz, CDCl$_3$) rotamers present 8.62 (2J, d, J = 5.2 Hz); 8.54 and 8.48 (2H, 2 × s); 7.65 and 7.62 (1H, 2 × s); 7.25 and 7.13 (2H, 2 × d, J = 5.2 Hz); 4.86 and 4.70 (2H, 2 × s); 4.66 and 4.34 (2H, 2 × s); 4.27-4.22 (1H, m); 2.49-2.42 (1H, m); 2.27-2.24 (2H, m); 2.10-2.05 (4H, m); 1.71-1.61 (2H, m) |

| example | |
|---|---|
| 77 | δ (400 MHz, CDCl$_3$) rotamers present 8.53 and 8.47 (2H, 2 × s); 7.70 and 7.61 (1H, 2 × s); 7.31-7.25 (1H, m); 7.16-7.13 (1H, m); 7.07-7.03 (2H, m); 4.83 and 4.65 (2H, 2 × s); 4.62 and 4.30 (2H, 2 × s); 4.30-4.19 (1H, m); 2.26-2.16 (2H, m); 1.94-1.86 (6H, m); 1.40 (3H, s) |
| 78 | δ (400 MHz, CDCl$_3$) rotamers present 8.55 and 8.49 (2H, 2 × s); 7.66 and 7.62 (1H, 2 × s); 6.85-6.69 (3H, m); 4.83 and 4.70 (2H, 2 × s); 4.62 and 4.34 (2H, 2 × s); 4.29-4.21 (1H, m); 2.25-2.17 (2H, m); 1.94-1.88 (6H, m); 1.41 and 1.40 (3H, 2 × s) |
| 79 | δ (400 MHz, CDCl$_3$) rotamers present 8.53 and 8.47 (2H, 2 × s); 7.68 and 7.59 (1H, 2 × s); 7.31-7.26 (1H, m); 7.15-7.12 (1H, m); 7.06-7.02 (2H, m); 4.83 and 4.65 (2H, 2 × s); 4.61 and 4.30 (2H, 2 × s); 4.25-4.17 (1H, m); 2.43-2.40 (2H, m); 2.19-2.11 (2H, m); 1.97-1.88 (2H, m); 1.41-1.34 (2H, m); 1.31 (3H, s) |
| 80 | δ (400 MHz, CDCl$_3$) rotamers present 8.53 and 8.48 (2H, 2 × s); 7.73 and 7.64 (1H, 2 × s); 7.31-7.27 (1H, m); 7.17-7.13 (1H, m); 7.07-7.03 (2H, m); 4.83 and 4.65 (2H, 2 × s); 4.62 and 4.30 (2H, 2 × s); 4.58-4.51 (1H, m); 2.67-2.56 (2H, m); 2.25-2.14 (4H, m); 2.02-1.93 (2H, m) |
| 81 | δ (400 MHz, CDCl$_3$) rotamers present 8.54 and 8.48 (2H, 2 × s); 7.72 and 7.63 (1H, 2 × s); 7.31-7.27 (1H, m); 7.17-7.13 (1H, m); 7.07-7.03 (2H, m); 4.83 and 4.65 (2H, 2 × s); 4.62 and 4.30 (2H, 2 × s); 4.41-4.34 (1H, m); 2.46-2.38 (2H, m); 2.33-2.27 (2H, m); 2.18-1.94 (4H, m) |
| 82 | δ (400 MHz, CDCl$_3$) rotamers present 8.53 and 8.47 (2H, 2 × s); 7.74 and 7.66 (1H, 2 × s); 7.30-7.27 (1H, m); 7.16-7.13 (1H, m); 7.07-7.02 (2H, m); 5.26-5.14 (1H, m); 4.83 and 4.64 (2H, 2 × s); 4.61 and 4.29 (2H, 2 × s); 3.34-3.27 (1H, m); 3.10-2.98 (2H, m); 2.86-2.77 (2H, m) |
| 83 | δ (400 MHz, CDCl$_3$) rotamers present 8.53 and 8.47 (2H, 2 × s); 7.74 and 7.65 (1H, 2 × s); 7.30-7.26 (1H, m); 7.16-7.12 (1H, m); 7.07-7.02 (2H, m); 4.90-4.82 (1H, m); 4.82 and 4.64 (2H, 2 × s); 4.61 and 4.30 (2H, 2 × s); 3.12-3.04 (3H, m); 2.82-2.76 (2H, m) |
| 84 | δ (400 MHz, CDCl$_3$) rotamers present 8.53 and 8.47 (2H, 2 × s); 7.58 and 7.48 (1H, 2 × s); 7.31-7.28 (1H, m); 7.19-7.15 (1H, m); 7.07-7.02 (2H, m); 4.82 and 4.66 (2H, 2 × s); 4.64 and 4.40 (2H, 2 × s); 4.36-4.30 (1H, m); 2.50-2.42 (1H, m); 2.24-2.03 (9H, m), 1.71-1.59 (2H, m) |
| 85 | δ (400 MHz, DMSO-d$_6$) rotamers present 8.77 and 8.70 (2H, 2 × s); 7.87 and 7.83 (1H, 2 × s); 7.20-7.14 (1H, m); 7.10 and 6.92 (2H, 2 × d, J = 1.6 Hz); 4.86 and 4.72 (2H, 2 × s); 4.72 and 4.57 (2H, 2 × s); 4.51-4.49 (1H, m); 4.26-4.21 (1H, m); 3.87 (1H, brs); 2.32-2.29 (2H, m); 1.81-1.78 (2H, m); 1.60-1.58 (4H, m) |
| 86 | δ (400 MHz, CDCl$_3$) rotamers present 8.53 and 8.48 (2H, 2 × s); 7.69 and 7.60 (1H, 2 × s); 7.31-7.26 (1H, m); 7.16-7.13 (1H, m); 7.07-7.02 (2H, m); 4.83 and 4.65 (2H, 2 × s); 4.61 and 4.29 (2H, 2 × s); 4.60-4.52 (1H, m); 3.04-2.97 (1H, m); 2.91 and 2.90 (3H, 2 × s); 2.54-2.34 (4H, m); 2.13-2.06 (2H, m); 2.01-1.91 (2H, m) |
| 87 | δ (400 MHz, CDCl$_3$) rotamers present 8.53 and 8.47 (2H, 2 × s); 7.70 and 7.61 (1H, 2 × s); 7.30-7.26 (1H, m); 7.16-7.12 (1H, m); 7.07-7.03 (2H, m); 4.82 and 4.65 (2H, 2 × s); 4.60 and 4.29 (2H, 2 × s); 4.33-4.23 (1H, m); 3.01-2.93 (1H, m); 2.90 (3H, s); 2.44-2.41 (2H, m); 2.26-2.09 (4H, m); 1.87-1.76 (2H, m) |
| 88 | δ (400 MHz, CDCl$_3$) rotamers present 8.53 and 8.47 (2H, 2 × s); 7.69 and 7.60 (1H, 2 × s); 7.30-7.26 (1H, m); 7.16-7.12 (1H, m); 7.07-7.02 (2H, m); 5.45 and 5.29 (2H, 2 × s); 4.83 and 4.64 (2H, 2 × s); 4.61 and 4.29 (2H, 2 × s); 4.29-4.21 (1H, m); 2.30-2.24 (1H, m); 2.14-2.03 (6H, m); 1.77-1.67 (2H, m) |
| 89 | δ (400 MHz, CDCl$_3$) rotamers present 8.52 and 8.47 (2H, 2 × s); 7.68 and 7.59 (1H, 2 × s); 7.30-7.26 (1H, m); 7.16-7.12 (1H, m); 7.06-7.02 (2H, m); 5.93 (1H, t, J = 5.9 Hz); 4.82 and 4.64 (2H, 2 × s); 4.60 and 4.29 (2H, 2 × s); 4.29-4.23 (1H, m); 3.77-3.73 (2H, m); 2.30-2.17 (2H, m); 2.10-2.03 (6H, m); 1.78-1.71 (2H, m) |
| 90 | δ (400 MHz, CDCl$_3$) rotamers present 8.43 and 8.39 (2H, 2 × s); 7.59 and 7.55 (1H, 2 × s); 7.38-7.35 and 7.16-7.12 (2H, 2 × m); 7.07-7.02 (2H, m); 5.60-5.45 (1H, m); 5.08-5.04, 4.75-4.71 and 3.98-3.88 (1H, 3 × m); 4.60-4.54 (2H, m); 4.29-4.21 (1H, m); 3.32-3.20 (1H, m); 2.48-2.42 (1H, m); 2.25-2.22 (2H, m); 2.10-2.04 (4H, m); 1.70-1.60 (2H, m) |
| 91 | δ (400 MHz, CDCl$_3$) rotamers present 7.58 and 7.52 (1H, 2 × s); 7.38-7.31 (2H, m); 7.26-7.17 (2H, m); 7.12-7.00 (3H, m); 6.53 and 6.13 (1H, 2 × ddd, J = 47.5, 9.8, 3.2 Hz); 5.40, 4.80, 4.63 and 4.58 (2H, 4 × d J = 15.1 Hz); 4.25-3.92 and 3.34-3.22 (3H, 2 × m); 2.49-2.43 (1H, m); 2.26-2.22 (2H, m); 1.70-1.59 (2H, m) |
| 92 | δ (400 MHz, CDCl$_3$) rotamers present 8.53 and 8.47 (2H, 2 × s); 7.67 and 7.59 (1H, 2 × s); 7.30-7.26 (1H, m); 7.16-7.13 (1H, m); 7.07-7.02 (2H, m); 5.05-4.93 (1H, m); 4.83 and 4.64 (2H, 2 × s); 4.61 and 4.29 (2H, 2 × s), 3.35-3.27 (1H, m); 2.50-2.25 (4H, m); 2.23-2.09 (1H, m); 2.04-1.95 (1H, m) |
| 93 | δ (400 MHz, CDCl$_3$) rotamers present 8.53 and 8.48 (2H, 2 × s); 7.71 and 7.62 (1H, 2 × s); 7.31-7.26 (1H, m); 7.16-7.13 (1H, m); 7.07-7.02 (2H, m); 4.94-4.78 (2H, m); 4.65 (1H, s); 4.61 and 4.30 (2H, 2 × s); 3.08-3.00 (1H, m); 2.58-2.50 (2H, m); 2.26-2.12 (4H, m) |
| 94 | δ (400 MHz, CDCl$_3$) rotamers present 7.73 and 7.57 (1H, 2 × s); 7.13 and 7.06 (2H, 2 × d, J = 7.8 Hz); 4.88 and 4.51 (2H, 2 × s); 4.24-4.16 (1H, m); 3.52-3.32 (2H, m); 2.25-2.15 (2H, m); 1.94-1.84 (6H, m); 1.42 and 1.40 (3H, 2 × s); 1.01 and 0.83 (9H, 2 × s) |
| 95 | δ (400 MHz, CDCl$_3$) rotamers present 8.57 and 8.50 (2H, 2 × s); 7.68 and 7.54 (1H, 2 × s); 4.94 and 4.74 (2H, 2 × s); 4.28-4.19 (1H, m); 3.77-3.74 (1H, m); 3.63 (1H, t, J = 4.9 Hz); 3.53 (1H, t, J = 5.4 Hz); 3.41 (1H, t, J = 5.4 Hz); 2.50-2.42 (1H, m); 2.26-2.23 (2H, m); 2.13-2.03 (4H, m); 1.72-1.60 (2H, m); 1.16 and 1.15 (9H, 2 × s) |

| example | |
|---|---|
| 96 | δ (400 MHz, CDCl$_3$) rotamers present 7.39-7.22 (5H, m); 7.10-7.01 (3H, m); 5.03 and 4.74 (2H, 2 × s); 4.32 and 3.85 (2H, 2 × t, J = 13.6 Hz); 4.20-4.16 (1H, m); 2.49-2.42 (1H, m); 2.25-2.23 (2H, m); 2.09-2.04 (4H, m); 1.69-1.59 (2H, m) |
| 97 | δ (400 MHz, DMSO-d$_6$) rotamers present 8.23-8.17 (1H, m); 7.98 and 7.91 (2H, 2 × s); 7.87 and 7.84 (1H, 2 × s); 7.77-7.75 (1H, m); 7.19-7.13 (1H, m); 7.12-7.08 and 6.93-6.91 (2H, m); 4.84 and 4.72 (2H, 2 × s); 4.68 and 4.57 (2H, 2 × s); 4.26-4.17 (1H, m); 2.34-2.25 (1H, m); 2.07-2.01 (2H, m); 1.99-1.90 (4H, m); 1.59-1.49 (2H, m) |
| 98 | δ (400 MHz, DMSO-d$_6$) rotamers present 12.16 (1H, brs); 7.95-7.85 (3H, m); 7.19-7.13 (1H, m); 7.12-7.08 and 6.94-6.91 (2H, m); 4.84 and 4.72 (2H, 2 × s); 4.69 and 4.57 (2H, 2 × s); 4.28-4.17 (1H, m); 2.37-2.28 (1H, m); 2.07-2.02 (2H, m); 1.98-1.90 (4H, m); 1.60-1.49 (2H, m) |
| 99 | δ (400 MHz, DMSO-d$_6$) rotamers present 12.17 (1H, brs); 7.81-7.41 (5H, m); 7.17-6.88 (3H, m); 4.88 and 4.83 (2H, 2 × s); 4.72 and 4.60 (2H, 2 × s); 4.25-4.12 (1H, m); 2.30-2.23 (1H, m); 2.05-2.00 (2H, m); 1.97-1.88 (4H, m); 1.56-1.46 (2H, m) |
| 100 | δ (400 MHz, CDCl$_3$) rotamers present 7.39-7.30 (3H, m); 7.14-6.97 (5H, m); 4.89-3.46 (6H, m); 2.49-2.40 (1H, m); 2.26-2.20 (2H, m); 2.12-2.03 (4H, m); 1.70-1.60 (2H, m); 1.46 and 1.28 (3H, 2 × d, J = 7.3 Hz) |
| 101 | δ (400 MHz, CDCl$_3$) rotamers present 8.59 and 8.52 (2H, 2 × s); 7.63 and 7.55 (1H, 2 × s); 4.74 and 4.44 (2H, 2 × s); 4.28-4.17 (1H, m); 3.49 and 3.30 (2H, 2 × d, J = 6.7 Hz); 2.50-2.43 (1H, m); 2.26-2.23 (2H, m); 2.13-1.35 (15H, m) |
| 102 | δ (400 MHz, CDCl$_3$) rotamers present 8.57 and 8.50 (2H, 2 × s); 7.72 and 7.56 (1H, 2 × s); 4.86 and 4.54 (2H, 2 × s); 4.27-4.17 (1H, m); 3.45-3.35 (2H, m); 2.50-2.42 (1H, m); 2.26-2.23 (2H, m); 2.11-2.02 (4H, m); 1.70-1.12 (12H, m); 0.99 and 0.83 (3H, 2 × s) |
| 103 | δ (400 MHz, CDCl$_3$) rotamers present 8.58-8.47 (3H, m); 7.76-7.47 (2H, m); 7.26-7.11 (2H, m); 4.94 and 4.82 (2H, 2 × s); 4.71 and 4.65 (2H, 2 × s); 4.27-4.18 (1H, m); 2.48-2.42 (1H, m); 2.25-2.22 (2H, m); 2.09-2.05 (4H, m); 1.71-1.57 (2H, m) |
| 104 | δ (400 MHz, CDCl$_3$) rotamers present 8.63-8.44 (2H, m); 8.54 and 8.49 (2H, 2 × s); 7.97-7.93 (1H, m); 7.71 and 7.61 (1H, 2 × s); 7.52-7.34 (1H, m); 4.89 and 4.68 (2H, 2 × s); 4.68 and 4.39 (2H, 2 × s); 4.28-4.18 (1H, m); 2.49-2.43 (1H, m); 2.26-2.23 (2H, m); 2.12-2.03 (4H, m); 1.71-1.60 (2H, m) |
| 105 | δ (400 MHz, CDCl$_3$) rotamers present 8.53 and 8.47 (2H, 2 × s); 7.71 and 7.62 (1H, 2 × s); 7.31-7.26 (1H, m); 7.16-7.13 (1H, m); 7.07-7.02 (2H, m); 4.83 and 4.65 (2H, 2 × s); 4.62 and 4.30 (2H, 2 × s); 4.36-4.28 (1H, m); 2.50-2.46 (2H, m); 2.10-1.88 (6H, m) |
| 106 | δ (400 MHz, CDCl$_3$) rotamers present 8.53 and 8.47 (2H, 2 × s); 7.92 and 7.80 (1H, 2 × s); 7.31-7.26 (1H, m); 7.17-7.14 (1H, m); 7.07-7.03 (2H, m); 4.84 and 4.65 (2H, 2 × s); 4.62 and 4.31 (2H, 2 × s); 4.49-4.39 (1H, m); 2.43-2.31 (4H, m); 2.11-2.03 (2H, m); 1.84-1.75 (2H, m) |
| 107 | δ (400 MHz, DMSO-d$_6$) rotamers present 12.14 (1H, brs); 7.90-7.53 (4H, m); 7.17-6.86 (3H, m); 4.90 and 4.86 (2H, 2 × s); 4.72 and 4.60 (2H, 2 × s); 4.26-4.12 (1H, m); 2.34-2.26 (1H, m); 2.05-2.01 (2H, m); 1.98-1.89 (4H, m); 1.58-1.46 (2H, m) |
| 108 | δ (400 MHz, DMSO-d$_6$) rotamers present 12.15 (1H, brs); 7.58-6.70 (7H, m); 4.88-3.62 (6H, m); 2.35-2.29 (1H, m); 2.09-1.86 (6H, m); 1.59-1.45 (2H, m); 1.40 and 1.22 (3H, 2 × d, J = 7.0 Hz) |
| 109 | δ (400 MHz, DMSO-d$_6$) rotamers present 8.62 and 8.53 (2H, 2 × s); 7.81 and 7.68 (1H, 2 × s); 7.21-6.81 (3H, m); 5.32-3.40 (6H, m); 3.18 and 2.93 (3H, 2 × s); 2.34-2.26 (1H, m); 2.08-1.90 (6H, m); 1.60-1.47 (2H, m) |
| 110 | δ (400 MHz, CDCl$_3$) rotamers present 8.58 and 8.52 (2H, 2 × s); 7.73 and 7.56 (1H, 2 × s); 4.89 and 4.63 (2H, 2 × s); 4.49 and 4.14 (2H, 2 × s); 4.32-4.20 (1H, m); 2.50-2.43 (1H, m); 2.27-2.24 (2H, m); 2.14-2.04 (4H, m); 1.72-1.62 (2H, m); 1.20 (9H, s) |
| 111 | δ (400 MHz, DMSO-d$_6$) rotamers present 7.73 and 7.63 (1H, 2 × s); 7.39-7.30 (1H, m); 7.19-6.85 (3H, m); 6.71 and 6.64 (2H, 2 × d, J = 8.4 Hz); 4.64-4.38 (4H, m); 4.27-4.15 (1H, m); 3.70 and 3.62 (6H, 2 × s); 2.35-2.23 (1H, m); 2.09-1.90 (6H, m); 1.58-1.47 (2H, m) |
| 112 | δ (400 MHz, CD$_3$OD) rotamers present 7.71 and 7.62 (1H, 2 × s); 7.12-6.80 (5H, m); 4.76-4.47 (4H, m); 4.34-4.26 (1H, m); 3.82 and 3.74 (3H, 2 × s); 2.42-2.35 (1H, m); 2.19-2.03 (6H, m); 1.67-1.56 (2H, m) |
| 113 | δ (400 MHz, CDCl$_3$) rotamers present 7.57 and 7.41 (1H, 2 × s); 6.79-6.65 (3H, m); 4.70 and 4.50 (2H, 2 × s); 4.28-3.95 (3H, m); 2.92-2.84 and 2.66-2.58 (1H, 2 × m); 2.47-2.40 (1H, m); 2.24-2.21 (2H, m); 2.09-2.03 (4H, m); 1.85-1.42 (10H, m) |
| 114 | δ (400 MHz, CDCl$_3$) rotamers present 8.57 and 8.49 (2H, 2 × s); 7.68 and 7.54 (1H, 2 × s); 5.02 and 4.62 (1H, 2 × d, J = 19.0 Hz); 4.48 and 4.33 (1H, 2 × d, J = 19.0 Hz); 4.31-4.19 (1H, m); 3.80 (1H, q, J = 7.0 Hz); 2.51-2.42 (1H, m); 2.27-2.24 (2H, m); 2.12-2.04 (4H, m); 1.72-1.62 (2H, m); 1.30 and 1.22 (3H, 2 × d, J = 7.0 Hz); 0.99 and 0.88 (9H, 2 × s) |
| 115 | δ (400 MHz, CDCl$_3$) rotamers present 8.57 and 8.49 (2H, 2 × s); 7.68 and 7.54 (1H, 2 × s); 5.02 and 4.62 (1H, 2 × d, J = 19.0 Hz); 4.48 and 4.33 (1H, 2 × d, J = 19.0 Hz); 4.31-4.20 (1H, m); 3.80 (1H, q, J = 7.0 Hz); 2.50-2.43 (1H, m); 2.27-2.23 (2H, m); 2.12-2.04 (4H, m); 1.69-1.63 (2H, m); 1.30 and 1.22 (3H, 2 × d, J = 7.0 Hz); 0.99 and 0.88 (9H, 2 × s) |
| 116 | δ (400 MHz, DMSO-d$_6$) rotamers present 8.74 and 8.67 (2H, 2 × s); 7.83 and 7.77 (1H, 2 × s); 7.40-7.11 (4H, m); 6.80 (2H, brs); 4.73 and 4.67 (2H, 2 × s); 4.59 and 4.50 (2H, 2 × s); 4.15-4.09 (1H, m); 2.56-2.49 (2H, m); 2.14-2.11 (2H, m); 1.76-1.72 (2H, m); 1.48-1.42 (2H, m) |

| example | |
|---|---|
| 117 | δ (400 MHz, DMSO-d$_6$) rotamers present 8.74 and 8.67 (2H, 2 × s); 7.87 and 7.81 (1H, 2 × s); 7.65 (2H, brs); 7.40-7.13 (4H, m); 4.72 and 4.68 (2H, 2 × s); 4.59 and 4.51 (2H, 2 × s); 4.27-4.21 (1H, m); 2.18-2.07 (4H, m); 1.81-1.78 (4H, m) |
| 118 | δ (400 MHz, CD$_3$OD) rotamers present 7.59 (1H, s); 7.38 and 7.33 (2H, 2 × d, J = 8.0 Hz); 7.17 (1H, t, J = 8.0 Hz); 6.83-6.78 (1H, m); 6.49 and 6.35 (2H, 2 × d, J = 6.0 Hz); 4.57 and 4.34 (2H, 2 × s); 4.25 and 4.10 (2H, 2 × s); 4.25-4.17 (1H, m); 2.17-1.84 (9H, m); 1.65-1.54 (4H, m); 1.30-1.28 (2H, m) |
| 119 | δ (400 MHz, CDCl$_3$) rotamers present 8.07 and 8.02 (2H, 2 × s); 7.63 and 7.53 (1H, 2 × s); 6.85-6.67 (3H, m); 4.81-4.21 (5H, m); 3.89 and 3.83 (6H, 2 × s); 2.48-2.42 (1H, m); 2.25-2.22 (2H, m); 2.11-2.06 (4H, m); 1.71-1.60 (2H, m) |
| 120 | δ (400 MHz, DMSO-d$_6$) rotamers present 7.81 and 7.79 (1H, 2 × s); 7.50 and 7.44 (2H, 2 × d, J = 8.6 Hz); 7.21-6.83 (3H, m); 4.80 and 4.52 (2H, 2 × s); 4.27-4.15 (1H, m); 3.62-2.89 (4H, m); 2.34-2.24 (1H, m); 2.07-1.88 (6H, m); 1.60-1.49 (2H, m) |
| 121 | δ (400 MHz, DMSO-d$_6$) rotamers present 9.33-8.95 (2H, m); 8.81-8.64 (2H, m); 8.11 and 7.91 (1H, 2 × s); 5.32-4.59 (4H, m); 4.26-4.18 (1H, m); 3.67-3.25 (3H, m); 2.87-2.79 (1H, m); 2.34-2.28 (1H, m); 2.05-1.43 (13H, m) |
| 122 | δ (400 MHz, DMSO-d$_6$) rotamers present 11.61 (1H, brs); 7.79 and 7.75 (1H, 2 × s); 7.16-7.07 (2H, m); 6.89 (1H, d, J = 6.4 Hz); 6.04 and 5.97 (1H, 2 × s); 4.67 and 4.62 (2H, 2 × s); 4.59 and 4.58 (2H, 2 × s); 4.24-4.13 (1H, m); 2.26-2.18 (1H, m); 2.20 and 2.03 (3H, 2 × s); 2.03-2.00 (2H, m); 1.90-1.88 (4H, m); 1.71 and 1.61 (3H, 2 × s); 1.56-1.47 (2H, m) |
| 123 | δ (400 MHz, CDCl$_3$) rotamers present 8.57 and 8.50 (2H, 2 × s); 7.70 and 7.56 (1H, 2 × s); 4.84 and 4.50 (2H, 2 × s); 4.29-4.19 (1H, m); 3.40-3.12 (2H, m); 2.49-2.42 (1H, m); 2.26-2.23 (2H, m); 2.13-1.94 (6H, m); 1.74-1.36 (15H, m) |
| 124 | δ (400 MHz, DMSO-d$_6$) rotamers present 7.93-7.68 (4H, m); 7.18-6.90 (3H, m); 4.88-4.14 (5H, m); 2.34-2.26 (1H, m); 2.09-1.88 (6H, m); 1.59-1.49 (2H, m) |
| 125 | δ (400 MHz, CDCl$_3$) rotamers present 8.57-8.50 (2H, m); 7.65-7.53 (1H, m); 4.72-4.42 (2H, m); 4.30-4.18 (1H, m); 3.78-3.32 (2H, m); 2.51-1.19 (15H, m); 0.82-0.69 (9H, m) |
| 126 | δ (400 MHz, CDCl$_3$) rotamers present 8.57-8.50 (2H, m); 7.66-7.53 (1H, m); 4.73-4.42 (2H, m); 4.30-4.19 (1H, m); 3.78-3.32 (2H, m); 2.48-1.19 (15H, m); 0.82-0.69 (9H, m) |
| 127 | δ (400 MHz, DMSO-d$_6$) rotamers present 12.16 (1H, brs); 7.86-7.74 (3H, m); 7.19-6.91 (3H, m); 4.82-4.56 (4H, m); 4.28-4.17 (1H, m); 2.35-2.27 (1H, m); 2.07-1.92 (6H, m); 1.60-1.49 (2H, m) |
| 129 | δ (400 MHz, CDCl$_3$) rotamers present 8.54 and 8.48 (2H, 2 × s); 7.73 and 7.63 (1H, 2 × s); 7.31-7.26 (1H, m); 7.14-7.03 (3H, m); 4.83 and 4.65 (2H, 2 × s); 4.62 and 4.31 (2H, 2 × s); 4.31-4.23 (1H, m); 2.60-2.41 (4H, m); 2.17-2.01 (4H, m) |
| 130 | δ (400 MHz, CDCl$_3$) rotamers present 8.58 and 8.51 (2H, 2 × s); 7.66 and 7.54 (1H, 2 × s); 4.83-4.45 (2H, m); 4.29-4.17 (1H, m); 3.73-3.21 (4H, m); 2.50-2.41 (1H, m); 2.26-2.22 (2H, m); 2.13-1.94 (4H, m); 1.74-1.34 (7H, m); 1.23-1.06 (6H, m) |
| 131 | δ (400 MHz, CDCl$_3$) rotamers present 8.60-8.50 (2H, m); 7.65-7.54 (1H, m); 4.80-4.46 (2H, m); 4.31-3.99 (2H, m); 2.51-2.43 (1H, m); 2.27-1.93 (9H, m); 1.81-1.56 (4H, m); 0.89-0.76 (9H, m) |
| 132 | δ (400 MHz, CDCl$_3$) rotamers present 8.60-8.50 (2H, m); 7.65-7.54 (1H, m); 4.86-4.46 (2H, m); 4.31-3.98 (2H, m); 2.50-2.44 (1H, m); 2.27-1.99 (9H, m); 1.82-1.62 (4H, m); 0.89-0.76 (9H, m) |
| 133 | δ (400 MHz, CDCl$_3$) rotamers present 8.98 and 8.93 (1H, 2 × s); 7.66 and 7.63 (1H, 2 × s); 6.84-6.74 (3H, m); 4.84-4.23 (5H, m); 2.45 and 2.04 (6H, 2 × s); 2.28-2.02 (7H, m); 1.71-1.60 (2H, m) |
| 134 | δ (400 MHz, DMSO-d$_6$) rotamers present 8.37 and 8.31 (1H, 2 × d, J = 5.1 Hz); 7.89 and 7.81 (1H, 2 × s); 7.18-6.92 (4H, m); 4.75-4.61 (4H, m); 4.27-4.14 (1H, m); 2.37 and 2.22 (3H, 2 × s); 2.33-2.25 (1H, m); 2.06-1.87 (6H, m); 1.89 and 1.73 (3H, 2 × s); 1.58-1.46 (2H, m) |
| 135 | δ (400 MHz, CDCl$_3$) rotamers present 8.52 (2H, s); 7.62 (1H, s); 6.86-6.74 (3H, m); 4.79 (2H, s); 4.67 and 4.49 (2H, 2 × s); 4.35-4.30 (1H, m); 2.47-2.41 (1H, m); 2.26-2.23 (2H, m); 2.07-1.93 (4H, m); 1.72-1.62 (2H, m) |
| 136 | δ (400 MHz, DMSO-d$_6$) rotamers present 8.02-7.72 (4H, m); 7.17-6.87 (3H, m); 4.88-4.62 (4H, m); 4.26-4.12 (1H, m); 2.33-2.24 (1H, m); 2.05-1.89 (6H, m); 1.57-1.47 (2H, m) |
| 137 | δ (400 MHz, DMSO-d$_6$) rotamers present 7.85 and 7.83 (1H, 2 × s); 7.42 and 7.25 (2H, 2 × d, J = 0.7 Hz); 7.18-6.90 (3H, m); 4.79-4.55 (4H, m); 4.27-4.16 (1H, m); 2.34-2.28 (4H, m); 2.07-1.90 (6H, m); 1.59-1.48 (2H, m) |
| 138 | δ (400 MHz, CDCl$_3$) rotamers present 7.57 and 7.55 (1H, 2 × s); 7.35-7.18 (3H, m); 6.92 and 6.65 (2H, 2 × d, J = 5.7 Hz); 6.78-6.72 (1H, m); 6.61-6.46 and 6.19-6.04 (1H, 2 × m); 5.01-4.62 (2H, m); 4.27-4.15 (2H, m); 4.02-3.93 and 3.39-3.26 (1H, 2 × m); 2.28-2.18 (2H, m); 1.96-1.90 (6H, m); 1.42 and 1.39 (3H, 2 × s) |
| 139 | δ (400 MHz, CDCl$_3$) rotamers present 7.57 and 7.55 (1H, 2 × s); 7.35-7.18 (3H, m); 6.92 and 6.65 (2H, 2 × d, J = 6.1 Hz); 6.78-6.72 (1H, m); 6.61-6.46 and 6.19-6.04 (1H, 2 × m); 5.01-4.62 (2H, m); 4.27-4.15 (2H, m); 4.02-3.93 and 3.39-3.26 (1H, 2 × m); 2.26-2.19 (2H, m); 1.96-1.90 (6H, m); 1.42 and 1.39 (3H, 2 × s) |
| 141 | δ (400 MHz, DMSO-d$_6$) rotamers present 9.45 (1H, brs); 8.74 and 8.68 (2H, 2 × s); 7.86 and 7.74 (1H, 2 × s); 7.13 and 6.98 (2H, 2 × d, J = 8.5 Hz); 6.75-6.69 (2H, m); 4.66 and 4.58 (2H, 2 × s); 4.50 and 4.39 (2H, 2 × s); 4.27-4.19 (1H, m); 2.34-2.27 (1H, m); 2.07-1.90 (6H, m); 1.59-1.48 (2H, m) |

| example | |
|---|---|
| 142 | δ (400 MHz, DMSO-d$_6$) rotamers present 12.16 (1H, brs); 7.82-7.79 and 7.52-7.50 (1H, 2 × m); 7.75 and 7.50 (1H, 2 × s); 7.30-6.87 (6H, m); 6.80-6.74 (1H, m); 6.57-6.52 and 6.45-6.41 (1H, 2 × m); 4.98 and 4.76 (2H, 2 × s); 4.66 and 4.55 (2H, 2 × s); 4.21-4.12 (1H, 2 × m); 2.33-2.19 (1H, m); 2.05-1.77 (6H, m); 1.56-1.42 (2H, m) |
| 143 | δ (400 MHz, DMSO-d$_6$) rotamers present 12.16 (1H, brs); 7.75 and 7.48 (1H, 2 × s); 7.62 and 7.32 (1H, 2 × s); 7.16-6.86 (6H, m); 6.73-6.67 (1H, m); 4.97 and 4.75 (2H, 2 × s); 4.65 and 4.55 (2H, 2 × s); 4.22-4.11 (1H, m); 2.33-2.22 (1H, m); 2.19 and 2.09 (3H, 2 × s); 2.05-1.78 (6H, m); 1.56-1.42 (2H, m) |
| 144 | δ (400 MHz, CDCl$_3$) rotamers present 7.69-7.52 (3H, m); 4.97 and 4.73 (2H, 2 × s); 4.28-4.18 (1H, m); 3.94-3.40 (4H, m); 2.49-2.43 (1H, m); 2.25-2.22 (2H, m); 2.13-2.03 (4H, m); 1.70-1.62 (2H, m); 1.31-1.14 (9H, m) |
| 145 | δ (400 MHz, CDCl$_3$) rotamers present 8.36 (1H, s); 8.18 (1H, s); 7.63 (1H, s), 7.26-7.06 (4H, m); 4.76-4.54 (4H, m); 4.30-4.25 (1H, m); 2.49-2.42 (1H, m); 2.26-2.23 (2H, m); 2.12-2.05 (4H, m); 1.68-1.58 (2H, m) |
| 146 | δ (400 MHz, DMSO-d$_6$) rotamers present 9.11 and 9.08 (1H, 2 × s); 8.82 and 8.60 (2H, 2 × s); 7.94 and 7.88 (1H, 2 × s); 7.59-7.46 (3H, m); 4.87 and 4.78 (2H, 2 × s); 4.74 and 4.61 (2H, 2 × s); 4.26-4.19 (1H, m); 2.35-2.27 (1H, m); 2.07-1.88 (6H, m); 1.59-1.48 (2H, m) |
| 147 | δ (400 MHz, DMSO-d$_6$) rotamers present 12.17 (1H, brs); 9.68 (1H, brs); 8.74 and 8.68 (2H, 2 × s); 7.76 and 7.75 (1H, 2 × s); 7.20-7.08 and 6.92-6.71 (4H, m); 4.73-4.45 (4H, m); 4.27-4.19 (1H, m); 2.34-2.26 (1H, m); 2.07-1.90 (6H, m); 1.59-1.49 (2H, m) |
| 148 | δ (400 MHz, DMSO-d$_6$) rotamers present 12.11 (1H, brs); 8.75 and 8.70 (2H, 2 × s); 7.36 and 7.26 (1H, 2 × s); 7.20-7.14 (1H, m); 7.08-7.06 and 6.98-6.95 (2H, 2 × m); 5.00-4.50 (4H, m); 4.37-4.31 (1H, m); 2.31-2.24 (1H, m); 2.03-1.91 (4H, m); 1.87-1.78 (2H, m); 1.63-1.53 (2H, m); 1.38 and 1.33 (9H, 2 × s) |
| 149 | δ (400 MHz, CDCl$_3$) rotamers present 7.69-7.52 (3H, m); 4.97 and 4.74 (2H, 2 × s); 4.29-4.19 (1H, m); 3.94-3.37 (4H, m); 2.25-2.15 (2H, m); 1.95-1.86 (6H, m); 1.41 and 1.40 (3H, 2 × s); 1.16 and 1.14 (9H, 2 × s) |
| 150 | δ (400 MHz, CDCl$_3$) rotamers present 8.59 and 8.52 (2H, 2 × s); 7.64 and 7.52 (1H, 2 × s); 4.94 and 4.57 (2H, 2 × s); 4.28-4.19 (1H, m); 3.84 and 3.73 (2H, 2 × s); 2.49-2.43 (1H, m); 2.26-2.23 (2H, m); 2.14-2.03 (4H, m); 1.73-1.60 (2H, m); 1.10-1.06 (4H, m) |
| 151 | δ (400 MHz, DMSO-d$_6$) rotamers present 12.12 (1H, brs); 9.26-9.25 and 9.05-9.04 (1H, 2 × m); 9.21-9.20 and 9.16-9.15 (1H, 2 × m); 7.92 and 7.85 (1H, 2 × s); 7.66-7.46 (4H, m); 4.85 and 4.78 (2H, 2 × s); 4.75 and 4.63 (2H, 2 × s); 4.28-4.17 (1H, m); 2.33-2.26 (1H, m); 2.06-2.02 (2H, m); 1.97-1.90 (4H, m); 1.59-1.48 (2H, m) |
| 152 | δ (400 MHz, DMSO-d$_6$) rotamers present 12.18 (1H, brs); 9.09-8.98 (1H, m); 8.68-8.63 (1H, m); 7.75 and 7.70 (1H, 2 × s); 7.18-7.10 (1H, m); 7.08-7.06 (1H, m); 6.94-6.91 (1H, m); 5.02 and 4.96 (2H, 2 × s); 4.73 and 4.60 (2H, 2 × s); 4.24-4.13 (1H, m); 2.33-2.22 (1H, m); 2.05-1.99 (2H, m); 1.94-1.86 (4H, m); 1.56-1.45 (2H, m) |
| 153 | δ (400 MHz, DMSO-d$_6$) rotamers present 12.07 (1H, brs); 9.50 (1H, brs); 8.74 and 8.68 (2H, 2 × s); 7.82 and 7.75 (1H, 2 × s); 7.17-7.10 (1H, m); 6.79-6.58 (3H, m); 4.70 and 4.61 (2H, 2 × s); 4.53 and 4.43 (2H, 2 × s); 4.28-4.21 (1H, m); 2.35-2.26 (1H, m); 2.07-2.03 (2H, m); 1.98-1.91 (4H, m); 1.60-1.48 (2H, m) |
| 155 | δ (400 MHz, CDCl$_3$) rotamers present 8.59 and 8.50 (2H, 2 × s); 7.65 and 7.54 (1H, 2 × s); 4.83 and 4.54 (2H, 2 × s); 4.54-4.46 and 3.75-3.68 (1H, 2 × m); 4.30-4.21 (1H, m); 3.96-3.87 (1H, m); 2.74-2.72 and 2.51-2.40 (3H, m); 2.27-2.24 (2H, m); 2.14-2.00 (6H, m); 1.72-1.61 (2H, m); 1.18 and 1.12 (9H, 2 × s) |
| 156 | δ (400 MHz, DMSO-d$_6$) rotamers present 12.40 (1H, brs); 8.77 and 8.70 (2H, 2 × s); 7.84 and 7.80 (1H, 2 × s); 7.19-7.08 and 6.92-6.90 (3H, m); 4.85-4.56 (4H, m); 4.27-4.14 (1H, m); 2.20-2.17 (2H, m); 2.04-1.95 (2H, m); 1.78-1.75 (2H, m); 1.48-1.43 (2H, m); 1.33-1.24 (2H, m); 0.80 (3H, t, J = 7.5 Hz) |
| 157 | δ (400 MHz, DMSO-d$_6$) rotamers present 12.15 (1H, brs); 8.81 and 8.74 (2H, 2 × s); 7.85-7.74 (2H, m); 4.95-4.76 (2H, m); 4.26-4.19 (1H, m); 3.88-3.25 (3H, m); 2.34-1.73 (11H, m); 1.59-1.49 (2H, m) |
| 158 | δ (400 MHz, DMSO-d$_6$) rotamers present 12.17 (1H, brs); 8.81 and 8.74 (2H, 2 × s); 7.85-7.74 (2H, m); 4.93-4.76 (2H, m); 4.26-4.19 (1H, m); 3.86-3.25 (3H, m); 2.35-1.73 (11H, m); 1.59-1.49 (2H, m) |
| 159 | δ (400 MHz, CDCl$_3$) rotamers present 8.55 and 8.52 (2H, 2 × s); 7.56 and 7.43 (1H, 2 × s); 6.86-6.77 (3H, m); 4.91-4.67 (6H, m); 4.32-4.23 (1H, m); 2.48-2.42 (1H, m); 2.25-2.22 (2H, m); 2.07-1.99 (4H, m); 1.72-1.61 (2H, m) |
| 160 | δ (400 MHz, CDCl$_3$) rotamers present 8.55 and 8.48 (2H, 2 × s); 7.64 and 7.56 (1H, 2 × s); 5.09 and 4.80 (2H, 2 × s); 4.28-4.18 (1H, m); 3.96 and 3.75 (2H, 2 × s); 2.50-2.42 (1H, m); 2.26-2.23 (2H, m); 2.13-2.03 (4H, m); 1.69-1.42 (10H, m); 1.40 and 1.39 (3H, 2 × s) |
| 161 | δ (400 MHz, CDCl$_3$) rotamers present 8.58 and 8.48 (2H, 2 × s); 7.67 and 7.59 (1H, 2 × s); 7.19-7.13 (3H, m); 6.73 (2H, d, J = 6.8 Hz); 4.93 and 4.72 (2H, 2 × d, J = 18.8 Hz); 4.12-4.04 (1H, m); 3.50 (1H, brs); 3.18-3.14 (1H, m); 2.43-2.37 (1H, m); 2.21-2.07 (4H, m); 1.92-1.52 (4H, m); 1.35-1.30 (1H, m); 1.14-1.09 (1H, m) |
| 162 | δ (400 MHz, CDCl$_3$) rotamers present 8.50 (2H, brs); 7.43 (1H, s); 6.90-6.72 (3H, m); 4.79-4.72 (2H, m); 4.68 and 4.59 (2H, 2 × s); 4.15-4.08 (1H, m); 3.35-3.25 (1H, m); 2.50-2.43 (1H, m); 2.25-2.22 (1H, m); 2.10-1.90 (6H, m); 1.40-1.38 (6H, m) |
| 164 | δ (400 MHz, DMSO-d$_6$) rotamers present 12.17 (1H, brs); 8.71 (2H, s); 7.57-6.99 (4H, m); 5.00-4.68 (4H, m); 4.20-4.12 (1H, m); 2.38-2.21 (4H, m); 2.02-1.95 (2H, m); 1.86-1.80 (4H, m); 1.59-1.48 (2H, m) |

| example | |
|---|---|
| 165 | δ (400 MHz, DMSO-d$_6$) rotamers present 12.16 (1H, brs); 9.12 (1H, s); 8.78 and 8.72 (2H, 2 × s); 7.86 and 7.77 (1H, 2 × s); 4.97 and 4.84 (2H, 2 × s); 4.77 and 4.74 (2H, 2 × s); 4.25-4.18 (1H, m); 2.28-2.22 (1H, m); 2.05-1.90 (6H, m); 1.57-1.48 (2H, m) |
| 166 | δ (400 MHz, CDCl$_3$) rotamers present 8.52 and 8.47 (2H, 2 × s); 7.63 and 7.54 (1H, 2 × s); 7.30-7.26 (1H, m); 7.16-7.13 (1H, m); 7.07-7.00 (2H, m); 4.82 and 4.63 (2H, 2 × s); 4.57 and 4.26 (2H, 2 × s); 2.31-2.22 (6H, m); 2.07-2.04 (6H, m) |
| 167 | δ (400 MHz, DMSO-d$_6$) rotamers present 12.19 (1H, brs); 8.77 and 8.71 (2H, 2 × s); 7.88 and 7.80 (1H, 2 × s); 7.62 and 7.54 (1H, 2 × s); 4.80-4.52 (4H, m); 4.28-4.20 (1H, m); 2.34-2.28 (1H, m); 2.07-1.92 (6H, m); 1.59-1.49 (2H, m) |
| 168 | δ (400 MHz, DMSO-d$_6$) rotamers present 12.25 (1H, brs); 8.78 and 8.71 (2H, 2 × s); 7.81-7.77 (2H, m); 5.03-4.81 (4H, m); 4.26-4.19 (1H, m); 2.32-2.24 (1H, m); 2.06-1.93 (6H, m); 1.57-1.48 (2H, m) |
| 169 | δ (400 MHz, CDCl$_3$) rotamers present 8.58 and 8.50 (2H, 2 × s); 7.65 and 7.55 (1H, 2 × s); 4.66-4.18 (4H, m); 2.51-2.42 (1H, m); 2.27-2.24 (2H, m); 2.15-2.03 (4H, m); 1.73-1.42 (9H, m); 1.14-1.07 (1H, m); 0.94-0.87 (6H, m) |
| 170 | δ (400 MHz, DMSO-d$_6$) rotamers present 12.10 (1H, brs); 8.76 and 8.69 (2H, 2 × s); 7.87-7.52 (5H, m); 4.84 and 4.75 (2H, 2 × s); 4.72 and 4.60 (2H, 2 × s); 4.28-4.17 (1H, m); 2.36-2.26 (1H, m); 2.07-2.02 (2H, m); 1.98-1.91 (4H, m); 1.60-1.49 (2H, m) |
| 171 | δ (400 MHz, DMSO-d$_6$) rotamers present 12.14 (1H, brs); 8.75 and 8.69 (2H, 2 × s); 7.87-7.80 (3H, m); 7.56 and 7.41 (2H, 2 × d, J = 8.3 Hz); 4.80 and 4.78 (2H, 2 × s); 4.69 and 4.63 (2H, 2 × s); 4.28-4.18 (1H, m); 2.36-2.26 (1H, m); 2.07-2.02 (2H, m); 1.98-1.90 (4H, m); 1.60-1.49 (2H, m) |
| 172 | δ (400 MHz, CDCl$_3$) rotamers present 8.61 and 8.53 (2H, 2 × s); 7.66 and 7.57 (1H, 2 × s); 5.03-4.93 (1H, m); 4.80-4.72 (1H, m); 4.63-3.99 (6H, m); 2.51-2.43 (1H, m); 2.28-2.24 (2H, m); 2.14-2.04 (4H, m); 1.91 and 1.87 (3H, 2 × s); 1.72-1.59 (2H, m) |
| 173 | δ (400 MHz, CDCl$_3$) rotamers present 8.61 and 8.52 (2H, 2 × s); 7.65 and 7.57 (1H, 2 × s); 5.00-4.19 (8H, m); 2.50-2.43 (1H, m); 2.27-2.24 (2H, m); 2.14-2.04 (4H, m); 1.72-1.61 (2H, m); 1.23-1.17 (9H, m) |
| 174 | δ (400 MHz, CDCl$_3$) rotamers present 8.58 and 8.50 (2H, 2 × s); 7.65 and 7.55 (1H, 2 × s); 4.62 and 4.42 (2H, 2 × s); 4.31-4.18 (1H, m); 3.55-3.50 (1H, m); 2.52-2.41 (1H, m); 2.27-2.23 (2H, m); 2.15-2.03 (4H, m); 1.88-1.30 (10H, m); 1.19-0.97 (2H, m) |
| 175 | δ (400 MHz, CDCl$_3$) rotamers present 8.59 and 8.51 (2H, 2 × s); 7.67 and 7.56 (1H, 2 × s); 4.86-4.78 and 3.74-3.66 (1H, 2 × m); 4.63 and 4.43 (2H, 2 × s); 4.32-4.17 (1H, m); 2.53-2.42 (1H, m); 2.28-1.59 (16H, m) |
| 177 | δ (400 MHz, CDCl$_3$) rotamers present 8.53 and 8.47 (2H, 2 × s); 7.64 and 7.55 (1H, 2 × s); 7.32-7.26 (1H, m); 7.17-7.13 (1H, m); 7.07-7.02 (2H, m); 4.83 and 4.64 (2H, 2 × s); 4.60 and 4.29 (2H, 2 × s); 2.57 and 2.53 (2H, 2 × s); 2.33-2.25 (4H, m); 2.21-1.99 (2H, m); 1.95-1.88 (2H, m) |
| 178 | δ (400 MHz, CDCl$_3$) rotamers present 8.56-8.51 (2H, m); 7.56-7.46 (1H, m); 7.12-6.76 (4H, m); 4.82-4.78 (2H, m); 4.67-4.57 (2H, m); 4.53-4.38 (1H, m); 2.41-2.38 (2H, m); 2.18-2.08 (2H, m); 1.99-1.93 (2H, m); 1.43-1.36 (2H, m); 1.30 (3H, s) |
| 179 | δ (400 MHz, DMSO-d$_6$) rotamers present 12.16 (1H, brs); 7.79 and 7.78 (1H, 2 × s); 7.56-7.45 (2H, m); 7.18-6.88 (3H, m); 4.78 and 4.73 (2H, 2 × s); 4.69 and 4.56 (2H, 2 × s); 4.26-4.14 (1H, m); 2.33-2.26 (1H, m); 2.09-1.90 (6H, m); 1.58-1.46 (2H, m) |
| 180 | δ (400 MHz, CDCl$_3$) rotamers present 8.50 and 8.42 (2H, 2 × s); 7.72 and 7.58 (1H, 2 × s); 7.23-7.15 (4H, m); 5.62-5.54 and 4.80-4.72 (1H, 2 × m); 4.58 and 4.42 (2H, 2 × s); 4.31-4.23 (1H, m); 3.42-3.02 (m, 4H); 2.50-2.43 (1H, m); 2.26-2.23 (2H, m); 2.14-2.03 (4H, m); 1.71-1.61 (2H, m) |
| 181 | δ (400 MHz, CDCl$_3$) rotamers present 8.59 and 8.51 (2H, 2 × s); 7.66 and 7.56 (1H, 2 × s); 4.99-4.91 and 3.84-3.76 (1H, 2 × m); 4.65 and 4.45 (2H, 2 × s); 4.33-4.17 (1H, m); 4.08-3.98 (2H, m); 3.59-3.53 and 3.28-3.22 (2H, 2 × m); 2.52-2.41 (1H, m); 2.28-2.22 (2H, m); 2.16-2.03 (4H, m); 1.82-1.59 (6H, m) |
| 182 | δ (400 MHz, CDCl$_3$) rotamers present 8.58 and 8.50 (2H, 2 × s); 7.66 and 7.56 (1H, 2 × s); 4.76-4.67 and 3.62-3.56 (1H, 2 × m); 4.67 and 4.46 (2H, 2 × s); 4.31-4.19 (1H, m); 2.51-2.42 (1H, m); 2.27-2.23 (2H, m); 2.17-1.96 (4H, m); 1.83-1.55 (8H, m); 0.94-0.86 (2H, m); 0.38-0.29 (2H, m); 0.19-0.15 (2H, m) |
| 183 | δ (400 MHz, CDCl$_3$) rotamers present 8.58 and 8.50 (2H, 2 × s); 7.66 and 7.55 (1H, 2 × s); 5.23-5.14 and 4.31-4.18 (2H, 2 × s); 4.65-4.42 (2H, m); 2.51-2.43 (1H, m); 2.27-2.24 (2H, m); 2.14-2.03 (4H, m); 1.97-1.32 (8H, m); 1.08-0.87 (6H, m) |
| 185 | δ (400 MHz, CDCl$_3$) rotamers present 8.58 and 8.50 (2H, 2 × s); 7.66 and 7.56 (1H, 2 × s); 5.01-4.95 and 4.17-4.09 (1H, 2 × m); 4.58 and 4.42 (2H, 2 × s); 4.30-4.17 (1H, m); 2.51-2.42 (1H, m); 2.27-2.23 (2H, m); 2.14-1.50 (14H, m) |
| 187 | δ (400 MHz, CDCl$_3$) rotamers present 8.58 and 8.50 (2H, 2 × s); 7.65 and 7.56 (1H, 2 × s); 4.95-4.17 and 3.57-3.50 (4H, m); 2.51-2.43 (1H, m); 2.27-2.24 (2H, m); 2.15-2.03 (4H, m); 1.94-0.98 (14H, m) |
| 189 | δ (400 MHz, CDCl$_3$) rotamers present 7.65 and 7.55 (1H, 2 × s); 7.39 and 7.31 (2H, 2 × s); 4.66 and 4.42 (2H, 2 × s); 4.61-4.52 and 3.49-3.43 (1H, 2 × m); 4.31-4.14 (1H, m); 2.51-2.42 (1H, m); 2.27-2.22 (2H, m); 2.15-2.02 (4H, m); 1.72-1.40 (9H, m); 1.13-1.05 (1H, m); 0.94-0.87 (6H, m) |
| 190 | δ (400 MHz, CDCl$_3$) rotamers present 7.67 and 7.56 (1H, 2 × s); 7.14 and 7.06 (2H, 2 × d, J = 8.1 Hz); 4.67 and 4.43 (2H, 2 × s); 4.61-4.53 and 3.52-3.44 (1H, 2 × m); 4.30-4.15 (1H, m); 2.29-2.14 (2H, m); 1.99-1.85 (6H, m); 1.65-1.39 (10H, m); 1.13-1.06 (1H, m); 0.94-0.87 (6H, m) |

-continued

| example | |
|---|---|
| 191 | δ (400 MHz, CDCl$_3$) rotamers present 7.66 and 7.56 (1H, 2 × s); 7.39 and 7.31 (2H, 2 × s); 4.66 and 4.43 (2H, 2 × s); 4.61-4.53 and 3.52-3.44 (1H, 2 × m); 4.30-4.15 (1H, m); 2.29-2.14 (2H, m); 1.99-1.86 (6H, m); 1.65-1.40 (10H, m); 1.13-1.02 (1H, m); 0.94-0.87 (6H, m) |
| 192 | δ (400 MHz, CDCl$_3$) rotamers present 8.57 and 8.50 (2H, 2 × s); 7.66 and 7.55 (1H, 2 × s); 4.81 and 4.47 (2H, 2 × s); 4.28-4.17 (1H, m); 3.71-3.59 (2H, m); 2.50-2.42 (1H, m); 2.26-2.23 (2H, m); 2.12-2.03 (4H, m); 1.72-1.06 (15H, m) |
| 193 | δ (400 MHz, CDCl$_3$) rotamers present 7.68 and 7.52 (1H, 2 × s); 7.14-7.05 (2H, m); 4.82 and 4.45 (2H, 2 × s); 4.27-4.17 (1H, m); 3.70-3.57 (2H, m); 2.46-2.42 (1H, m); 2.25-2.22 (2H, m); 2.12-2.02 (4H, m); 1.78-1.05 (15H, m) |
| 194 | δ (400 MHz, CDCl$_3$) rotamers present 8.57 and 8.49 (2H, 2 × s); 7.67 and 7.56 (1H, 2 × s); 5.00 and 4.69 (2H, 2 × s); 4.29-4.19 (1H, m); 3.98-3.70 (2H, m); 2.50-2.42 (1H, m); 2.27-2.23 (2H, m); 2.13-2.03 (4H, m); 1.94-1.52 (10H, m) |
| 195 | δ (400 MHz, CDCl$_3$) 12.80 (1H, brs); 7.52 (1H, s); 7.33 (1H, d, J = 7.1 Hz); 7.26-7.23 (2H, m); 7.03-7.00 (2H, m); 6.46 (1H, d, J = 7.1 Hz); 4.79 (2H, s); 4.43 (2H, s); 4.26-4.19 (1H, m); 2.39-2.32 (1H, m); 2.23-2.19 (2H, m); 2.14-2.09 (4H, m); 1.60-1.53 (2H, m) |
| 196 | δ (400 MHz, DMSO-d$_6$) 8.80 and 8.73 (2H, 2 × s); 7.72 and 7.59 (1H, 2 × s); 7.37-7.04 (1H, m); 4.78 (2H, s); 4.39-4.24 and 3.72-3.64 (2H, m); 2.21-2.15 (2H, m); 2.04-1.91 (2H, m); 1.83-1.23 (11H, m); 1.15-1.10 (4H, m); 0.91-0.84 (6H, m) |
| 197 | δ (400 MHz, CDCl$_3$) rotamers present 7.57-6.77 (7H, m); 4.82-4.38 (5H, m); 2.41-2.37 (2H, m); 2.17-2.09 (2H, m); 1.98-1.91 (2H, m); 1.43-1.35 (2H, m); 1.30 (3H, s) |
| 198 | δ (400 MHz, CDCl$_3$) rotamers present 8.58 and 8.50 (2H, 2 × s); 7.67 and 7.55 (1H, 2 × s); 5.38-5.33 and 4.52-4.47 (1H, 2 × m); 4.73 and 4.58 (2H, 2 × s); 4.31-4.17 (1H, m); 4.10-4.03 (1H, m); 3.91-3.84 (1H, m); 3.79-3.52 (2H, m); 2.51-2.43 (1H, m); 2.28-1.91 (6H, m); 1.73-1.59 (4H, m) |
| 199 | δ (400 MHz, CDCl$_3$) rotamers present 7.68 and 7.53 (1H, 2 × s); 7.12 and 7.05 (2H, 2 × d, J = 8.0 Hz); 5.09-4.99 and 4.58-4.15 (4H, m); 2.31-1.89 (10H, m); 1.42 and 1.39 (3H, 2 × s); 1.30-1.24 (2H, m); 1.07-0.96 (8H, m) |
| 200 | δ (400 MHz, CDCl$_3$) rotamers present 8.58 and 8.51 (2H, 2 × s); 7.67 and 7.54 (1H, 2 × s); 4.73 and 4.43 (2H, 2 × s); 4.32-4.16 (1H, m); 3.79 and 3.59 (2H, 2 × d, J = 7.7 Hz); 2.85-2.77 and 2.64-2.57 (1H, 2 × m); 2.51-2.42 (1H, m); 2.28-2.23 (2H, m); 2.19-1.97 (7H, m); 1.73-1.59 (3H, m); 0.42-0.17 (4H, m) |
| 201 | δ (400 MHz, CDCl$_3$) rotamers present 7.63 and 7.44 (1H, 2 × s); 6.82-6.69 (3H, m); 4.78 and 4.75 (2H, 2 × s); 4.57 and 4.41 (2H, 2 × s); 4.28-4.19 (1H, m); 3.85 and 3.83 (3H, 2 × s); 2.49-2.38 (1H, m); 2.24-2.21 (2H, m); 2.09-1.97 (4H, m); 1.69-1.59 (2H, m) |
| 202 | δ (400 MHz, CDCl$_3$) rotamers present 7.69 and 7.55 (1H, 2 × s); 7.14-7.06 (2H, m); 4.75 and 4.41 (2H, 2 × s); 4.30-4.16 (1H, m); 3.79 and 3.58 (2H, 2 × d, J = 7.6 Hz); 2.86-2.78 and 2.65-2.57 (1H, 2 × m); 2.54-2.12 (4H, m); 2.05-1.84 (7H, m); 1.66-1.58 (1H, m); 1.42 and 1.40 (3H, 2 × s); 0.42-0.16 (4H, m) |
| 204 | δ (400 MHz, CDCl$_3$) rotamers present 8.58 and 8.50 (2H, 2 × s); 7.70-7.55 (1H, 2 × s); 5.01-4.94 and 3.96-3.88 (1H, 2 × m); 4.78-4.73 and 4.39-4.15 (3H, m); 2.55-2.40 (2H, m); 2.28-2.23 (2H, m); 2.16-1.94 (7H, m); 1.82-1.78 and 1.71-1.67 (3H, m); 1.18-1.15 (3H, m); 0.43-0.22 (4H, m) |
| 205 | δ (400 MHz, CDCl$_3$) rotamers present 8.58 and 8.50 (2H, 2 × s); 7.65 and 7.55 (1H, 2 × s); 4.88-4.81 and 3.76-3.69 (1H, 2 × m); 4.65-4.40 (2H, m); 4.30-4.20 (1H, m); 2.51-2.44 (1H, m); 2.27-2.24 (2H, m); 2.13-2.04 (4H, m); 1.87-0.65 (16H, m) |
| 206 | δ (400 MHz, CDCl$_3$) rotamers present 7.74 and 7.58 (1H, 2 × s); 7.17 and 7.10 (2H, 2 × s); 4.91 and 4.60 (2H, 2 × s); 4.48 and 4.13 (2H, 2 × s); 4.31-4.18 (1H, m); 2.37 and 2.33 (3H, 2 × s); 2.28-2.17 (2H, m); 1.97-1.83 (6H, m); 1.41 and 1.40 (3H, 2 × s); 1.20 and 1.19 (9H, 2 × s) |
| 207 | δ (400 MHz, CDCl$_3$) rotamers present 7.73 and 7.57 (1H, 2 × s); 7.39 and 7.32 (2H, 2 × s); 4.90 and 4.60 (2H, 2 × s); 4.48 and 4.13 (2H, 2 × s); 4.31-4.18 (1H, m); 2.28-2.15 (2H, m); 1.98-1.86 (6H, m); 1.41 and 1.39 (3H, 2 × s); 1.20 and 1.19 (9H, 2 × s) |
| 208 | δ (400 MHz, CDCl$_3$) rotamers present 8.58 and 8.50 (2H, 2 × s); 7.65 and 7.54 (1H, 2 × s); 4.70-4.47 (3H, m); 4.31-4.18 (1H, m); 4.07-3.76 (2H, m); 2.51-2.45 (1H, m); 2.28-2.05 (7H, m); 1.75-1.62 (3H, m); 1.36-1.13 (6H, m) |
| 210 | δ (400 MHz, CDCl$_3$) rotamers present 8.59 and 8.51 (2H, 2 × s); 7.65 and 7.55 (1H, 2 × s); 4.77-4.19 (4H, m); 2.48-1.89 (13H, m); 1.75-1.39 (5H, m) (cis-, trans-mixture in AreaB) |
| 211 | δ (400 MHz, CDCl$_3$) rotamers present 8.59 and 8.51 (2H, 2 × s); 7.63 and 7.53 (1H, 2 × s); 5.13-5.05 and 4.19-4.11 (1H, 2 × m); 4.60 and 4.43 (2H, 2 × s); 4.29-4.21 (1H, m); 2.50-2.43 (1H, m); 2.26-2.23 (2H, m); 2.11-2.02 (4H, m); 1.87-1.84 (4H, m); 1.72-1.59 (2H, m); 1.25-1.19 (2H, m); 0.98-0.68 (6H, m) |
| 212 | δ (400 MHz, CDCl$_3$) rotamers present 8.58 and 8.49 (2H, 2 × s); 7.66 and 7.55 (1H, 2 × s); 4.81-4.75 and 3.65-3.56 (1H, 2 × m); 4.63 and 4.42 (2H, 2 × s); 4.31-4.16 (1H, m); 2.51-2.03 (8H, m); 1.84-1.43 (10H, m) |
| 213 | δ (400 MHz, CDCl$_3$) rotamers present 8.59 and 8.51 (2H, 2 × s); 7.65 and 7.55 (1H, 2 × s); 4.60 and 4.41 (2H, 2 × s); 4.60-4.54 and 3.62-3.55 (1H, 2 × m); 4.32-4.16 (1H, m); 2.52-2.42 (1H, m); 2.28-2.24 (2H, m); 2.18-1.91 (6H, m); 1.73-1.21 (9H, m) |
| 214 | δ (400 MHz, CDCl$_3$) rotamers present 7.70 and 7.55 (1H, 2 × s); 7.34-7.23 (1H, m); 7.03-6.79 (2H, m); 4.86 and 4.54 (2H, 2 × s); 4.45 and 4.10 (2H, 2 × s); 4.27-4.23 (1H, m); 3.87 and 3.75 (3H, 2 × s); 2.27-2.17 (2H, m); 1.98-1.87 (6H, m); 1.41-1.40 (3H, m); 1.19 (9H, s) |

| example | |
|---|---|
| 215 | δ (400 MHz, DMSO-d$_6$) 12.22 (1H, brs); 8.79-8.60 (2H, m); 7.85-7..69 (1H, m); 5.19-4.78 (2H, m); 4.50-4.39 and 4.09-4.02 (1H, 2 × m); 4.27-4.18 (1H, m); 2.67-2.57 (1H, m); 2.33-2.26 (1H, m); 2.23-2.19 (1H, m); 2.07-1.90 (6H, m); 1.59-1.16 (10H, m) |
| 216 | δ (400 MHz, CDCl$_3$) rotamers present 7.61 and 7.50 (1H, 2 × s); 6.84-6.71 (3H, m); 4.80 and 4.73 (2H, 2 × s); 4.60 and 4.48 (2H, 2 × s); 4.29-4.19 (1H, m); 2.49-2.42 (1H, m); 2.25-2.22 (2H, m); 2.10-2.02 (4H, m); 1.70-1.59 (2H, m) |
| 217 | δ (400 MHz, CDCl$_3$) rotamers present 7.75-7.49 (4H, m); 4.98 and 4.66 (2H, 2 × s); 4.47 and 4.13 (2H, 2 × s); 4.31-4.20 (1H, m); 2.29-2.18 (2H, m); 1.99-1.89 (6H, m); 1.42 and 1.41 (3H, 2 × s); 1.20 and 1.19 (9H, 2 × s) |
| 218 | δ (400 MHz, CDCl$_3$) rotamers present 7.74 and 7.58 (1H, 2 × s); 7.14 and 7.07 (2H, 2 × d, J = 8.0 Hz); 4.90 and 4.61 (2H, 2 × s); 4.48 and 4.14 (2H, 2 × s); 4.31-4.19 (1H, m); 2.28-2.16 (2H, m); 1.99-1.86 (6H, m); 1.41 and 1.40 (3H, 2 × s); 1.20 and 1.20 (9H, 2 × s) |
| 219 | δ (400 MHz, CDCl$_3$) rotamers present 7.68 and 7.53 (1H, 2 × s); 7.38 and 7.30 (2H, 2 × s); 5.08-4.98 and 4.36-4.14 (2H, m); 4.57 and 4.38 (2H, 2 × s); 2.31-1.84 (10H, m); 1.42 and 1.39 (3H, 2 × s); 1.35-1.24 (2H, m); 1.10-0.95 (8H, m) |
| 220 | δ (400 MHz, CDCl$_3$) rotamers present 7.65 and 7.56 (1H, 2 × s); 7.13 and 7.07 (2H, 2 × d, J = 8.1 Hz); 4.77 and 4.42 (2H, 2 × s); 4.29-4.17 (1H, m); 3.50-3.47 and 3.26-3.25 (2H, 2 × m); 2.28-2.14 (2H, m); 1.96-1.85 (6H, m); 1.57-1.05 (11H, m); 0.96-0.78 (7H, m) |
| 221 | δ (400 MHz, CDCl$_3$) rotamers present 7.73 and 7.57 (1H, 2 × s); 7.38 and 7.31 (2H, 2 × s); 4.87 and 4.50 (2H, 2 × s); 4.25-4.15 (1H, m); 3.49-3.31 (2H, m); 2.25-2.14 (2H, m); 1.94-1.83 (6H, m); 1.41 and 1.40 (3H, 2 × s); 1.00 and 0.83 (9H, 2 × s) |
| 222 | δ (400 MHz, CDCl$_3$) rotamers present 7.69-7.49 (4H, m); 4.61-4.15 (4H, m); 2.31-2.17 (2H, m); 1.99-1.87 (8H, m); 1.42 and 1.40 (3H, 2 × s); 1.30-1.19 (2H, m); 1.07-0.95 (8H, m) |
| 224 | δ (400 MHz, CDCl$_3$) rotamers present 7.69 and 7.57 (1H, 2 × s); 7.12 and 7.05 (2H, 2 × d, J = 8.0 Hz); 5.01 and 4.67 (2H, 2 × s); 4.25-4.17 (1H, m); 4.07-3.70 (2H, m); 2.25-2.15 (2H, m); 1.94-1.71 (14H, m); 1.41 and 1.40 (3H, 2 × s) |
| 225 | δ (400 MHz, CDCl$_3$) rotamers present 7.68 and 7.56 (1H, 2 × s); 7.37 and 7.30 (2H, 2 × s); 5.01 and 4.66 (2H, 2 × s); 4.25-4.17 (1H, m); 4.01-3.88 and 3.77-3.70 (2H, m); 2.25-2.15 (2H, m); 1.94-1.71 (14H, m); 1.41 and 1.40 (3H, 2 × s) |
| 226 | δ (400 MHz, CD$_3$CN) rotamers present 7.55 and 7.46 (1H, 2 × s); 7.20 and 7.12 (2H, 2 × s); 4.91 and 4.67 (2H, 2 × s); 4.22-4.16 (1H, m); 3.80 and 3.62 (2H, 2 × s); 2.26 and 2.21 (3H, 2 × s); 1.82-1.33 (16H, m); 1.27 and 1.25 (3H, 2 × s); 1.23 and 1.21 (3H, 2 × s) |
| 227 | δ (400 MHz, CD$_3$OD) rotamers present 7.76 and 7.59 (1H, 2 × s); 7.33 and 7.25 (2H, 2 × s); 4.75 and 4.63 (2H, 2 × s); 4.43-4.28 (1H, m); 4.30-4.23 and 3.52-3.47 (1H, 2 × m); 2.38 and 2.33 (3H, 2 × s); 2.30-2.15 (2H, m); 1.98-1.38 (13H, m); 1.36 and 1.34 (3H, 2 × s); 1.16-1.05 (1H, m); 0.95-0.86 (6H, m) |
| 228 | δ (400 MHz, DMSO-d$_6$) rotamers present 12.07 (1H, brs); 8.72 and 8.61 (2H, 2 × s); 7.66 and 7.63 (1H, 2 × s); 7.38-7.17 (4H, m); 4.73-4.67 (4H, m); 4.43-4.36 (1H, m); 4.26-4.08 (2H, m); 2.33-2.25 (1H, m); 2.03-1.76 (6H, m); 1.61-1.51 (2H, m) |
| 229 | δ (400 MHz, CDCl$_3$) rotamers present 8.59 and 8.50 (2H, 2 × s); 7.66 and 7.56 (1H, 2 × s); 4.66 and 4.45 (2H, 2 × s); 4.64-4.56 and 3.54-3.46 (1H, 2 × m); 4.31-4.17 (1H, m); 2.29-2.16 (2H, m); 1.99-1.86 (6H, m); 1.63-1.27 (10H, m); 1.15-1.07 (1H, m); 0.95-0.88 (6H, m) |
| 230 | δ (400 MHz, CDCl$_3$) rotamers present 7.59 and 7.50 (1H, 2 × s); 7.14 and 7.06 (2H, 2 × d, J = 8.0 Hz); 4.65 and 4.40 (2H, 2 × s); 4.61-4.53 and 3.46-3.38 (1H, 2 × m); 2.33-2.18 (6H, m); 2.09-2.03 (6H, m); 1.64-1.39 (7H, m); 1.12-1.02 (1H, m); 0.93-0.86 (6H, m) |
| 231 | δ (400 MHz, CDCl$_3$) rotamers present 7.59 and 7.50 (1H, 2 × s); 7.39 and 7.31 (2H, 2 × s); 4.64 and 4.39 (2H, 2 × s); 4.61-4.53 and 3.46-3.38 (1H, 2 × m); 2.33-2.21 (6H, m); 2.09-2.02 (6H, m); 1.63-1.39 (7H, m); 1.12-1.04 (1H, m); 0.93-0.86 (6H, m) |
| 234 | δ (400 MHz, CDCl$_3$) rotamers present 7.68 and 7.55 (1H, 2 × s); 7.38 and 7.32 (2H, 2 × s); 4.74 and 4.41 (2H, 2 × s); 4.30-4.16 (1H, m); 3.78 and 3.58 (2H, 2 × d, J = 7.8 Hz); 2.85-2.78 and 2.64-2.57 (1H, 2 × m); 2.28-2.12 (4H, m); 2.02-1.85 (7H, m); 1.66-1.61 (1H, m); 1.42 and 1.39 (3H, 2 × s); 0.43-0.16 (4H, m) |
| 235 | δ (400 MHz, CDCl$_3$) rotamers present 7.71-7.48 (4H, m); 4.84 and 4.49 (2H, 2 × s); 4.31-4.17 (1H, m); 3.83-3.59 (2H, m); 2.86-2.78 and 2.62-2.55 (1H, 2 × m); 2.28-2.10 (4H, m); 2.01-1.87 (7H, m); 1.64-1.59 (1H, m); 1.42 and 1.41 (3H, 2 × s); 0.43-0.16 (4H, m) |
| 236 | δ (400 MHz, DMSO-d$_6$) rotamers present 12.30 (1H, brs); 7.77 and 7.54 (1H, 2 × s); 7.45 and 7.38 (2H, 2 × s); 4.68 and 4.58 (2H, 2 × s); 4.32-4.26 (1H, m); 2.36 and 2.30 (3H, 2 × s); 2.21-2.18 (2H, m); 2.14-2.10 (4H, m); 1.94-1.88 (6H, m); 1.72-1.59 (2H, m); 1.47-1.24 (m, 5H); 1.00-0.92 (1H, m); 0.98-0.80 (6H, m) |
| 237 | δ (400 MHz, DMSO-d$_6$) rotamers present 12.25 (1H, brs); 7.76 and 7.54 (1H, 2 × s); 7.44 and 7.38 (2H, 2 × s); 4.70 and 4.50 (2H, 2 × s); 3.50-3.25 (2H, m); 2.59-2.53 and 2.45-2.37 (1H, 2 × m); 2.35 and 2.31 (3H, 2 × s); 2.21-2.10 (4H, m); 1.94-1.88 (6H, m); 1.82-1.70 (2H, m); 1.59-1.54 and 1.27-1.22 (2H, 2 × m); 1.10-0.87 (6H, m) |
| 238 | δ (400 MHz, DMSO-d$_6$) rotamers present 7.66 and 7.55 (1H, 2 × s); 7.16 and 7.09 (2H, 2 × s); 4.74 and 4.38 (2H, 2 × s); 4.31-4.15 (1H, m); 3.65 and 3.40 (2H, 2 × d, J = 7.1 Hz); 2.66-2.13 (6H, m); 1.97-1.78 (8H, m); 1.65-1.58 and 1.36-1.29 (2H, m); 1.42 and 1.40 (3H, 2 × s); 1.14-0.93 (6H, m) |

| example | |
|---|---|
| 239 | δ (400 MHz, CDCl₃) rotamers present 7.65 and 7.56 (1H, 2 × s); 7.38 and 7.31 (2H, 2 × s); 4.77 and 4.41 (2H, 2 × s); 4.30-4.16 (1H, m); 3.48 and 3.25 (2H, 2 × d, J = 7.0 Hz); 2.28-2.14 (2H, m); 1.96-1.84 (6H, m); 1.57-1.05 (11H, m); 0.96-0.78 (7H, m) |
| 240 | δ (400 MHz, CDCl₃) rotamers present 7.61 and 7.46 (1H, 2 × s); 7.12 and 7.05 (2H, 2 × d, J = 7.6 Hz); 5.09-4.99 and 4.31-4.21 (1H, 2 × m); 4.57 and 4.35 (2H, 2 × s); 2.34-2.21 (6H, m); 2.09-2.03 (6H, m); 1.94-1.87 and 1.40-1.33 (2H, m); 1.29-1.22 (2H, m); 1.09-0.95 (8H, m) |
| 241 | δ (400 MHz, CDCl₃) rotamers present 7.60 and 7.46 (1H, 2 × s); 7.37 and 7.30 (2H, 2 × s); 5.08-4.99 and 4.30-4.21 (1H, 2 × m); 4.56 and 4.35 (2H, 2 × s); 2.33-2.20 (6H, m); 2.09-2.02 (6H, m); 1.93-1.86 and 1.39-1.33 (2H, m); 1.28-1.21 (2H, m); 1.10-0.95 (8H, m) |
| 242 | δ (400 MHz, CDCl₃) rotamers present 7.68-7.47 (4H, m); 4.71 and 4.48 (2H, 2 × s); 4.31-4.22 and 3.46-3.39 (1H, 2 × m); 2.33-2.24 (6H, m); 2.11-2.03 (6H, m); 1.87-1.77 (1H, m); 1.67-1.34 (6H, m); 1.11-1.03 (1H, m); 0.93-0.86 (6H, m) |
| 243 | δ (400 MHz, CDCl₃) rotamers present 7.61 and 7.52 (1H, 2 × s); 7.32-7.23 (1H, m); 7.04-6.80 (2H, m); 4.64 and 4.33 (2H, 2 × s); 4.63-4.56 and 3.43-3.35 (1H, 2 × m); 3.86 and 3.76 (3H, 2 × s); 2.33-2.22 (6H, m); 2.09-2.02 (6H, m); 1.62-1.38 (7H, m); 1.11-1.04 (1H, m); 0.94-0.86 (6H, m) |
| 244 | δ (400 MHz, CDCl₃) rotamers present 7.66 and 7.57 (1H, 2 × s); 7.11 and 7.04 (2H, 2 × d, J = 8.1 Hz); 5.09 and 4.77 (2H, 2 × s); 4.29-4.18 (1H, m); 3.96-3.76 (2H, m); 2.21-2.14 (2H, m); 1.96-1.84 (6H, m); 1.68-1.39 (14H, m) |
| 245 | δ (400 MHz, CDCl₃) rotamers present 7.66 and 7.49 (1H, 2 × s); 7.13 and 7.06 (2H, 2 × d, J = 8.1 Hz); 4.86 and 4.48 (2H, 2 × s); 3.79-3.25 (2H, m); 2.31-2.21 (6H, m); 2.07-2.03 (6H, m); 1.01 and 0.84 (9H, 2 × s) |
| 246 | δ (400 MHz, CDCl₃) rotamers present 7.66 and 7.49 (1H, 2 × s); 7.38 and 7.31 (2H, 2 × s); 4.86 and 4.48 (2H, 2 × s); 3.75-3.25 (2H, m); 2.32-2.21 (6H, m); 2.07-2.03 (6H, m); 1.00 and 0.84 (9H, 2 × s) |
| 247 | δ (400 MHz, CDCl₃) rotamers present 7.66-7.47 (4H, m); 4.60 and 4.42 (2H, 2 × s); 4.31-4.18 (1H, m); 2.34-2.22 (6H, m); 2.09-2.02 (6H, m); 1.92-1.83 (2H, m); 1.29-0.95 (10H, m) |
| 248 | δ (400 MHz, CDCl₃) rotamers present 7.62 and 7.47 (1H, 2 × s); 7.31-7.23 (1H, m); 7.03-6.78 (2H, m); 5.19-5.09 and 4.28-4.19 (1H, 2 × m); 4.56 and 4.30 (2H, 2 × s); 3.84 and 3.73 (3H, 2 × s); 2.33-2.21 (6H, m); 2.09-2.01 (7H, m); 1.91-1.84 (1H, m); 1.33-1.24 (2H, m); 1.10-0.93 (8H, m) |
| 249 | δ (400 MHz, CDCl₃) rotamers present 7.66 and 7.54 (1H, 2 × s); 7.13 and 7.07 (2H, 2 × d, J = 8.0 Hz); 4.72 and 4.39 (2H, 2 × s); 4.29-4.16 (1H, m); 3.64 and 3.40 (2H, 2 × d, J = 7.6 Hz); 2.63-2.55 and 2.44-2.36 (1H, 2 × m); 2.25-2.14 (2H, m); 1.95-1.80 (8H, m); 1.64-1.58 and 1.35-1.30 (2H, 2 × m); 1.42 and 1.39 (3H, 2 × s); 1.14-0.93 (6H, m) |
| 250 | δ (400 MHz, CDCl₃) rotamers present 7.65 and 7.54 (1H, 2 × s); 7.38 and 7.31 (2H, 2 × s); 4.71 and 4.38 (2H, 2 × s); 4.29-4.17 (1H, m); 3.64 and 3.40 (2H, 2 × d, J = 7.6 Hz); 2.62-2.54 and 2.43-2.35 (1H, 2 × m); 2.28-1.79 (10H, m); 1.63-1.58 and 1.34-1.29 (2H, 2 × m); 1.41 and 1.39 (3H, 2 × s); 1.14-0.93 (6H, m) |
| 251 | δ (400 MHz, CDCl₃) rotamers present 7.68-7.48 (4H, m); 4.82 and 4.46 (2H, 2 × s); 4.27-4.17 (1H, m); 3.66-3.39 (2H, m); 2.63-2.55 and 2.41-2.33 (1H, 2 × m); 2.29-2.17 (2H, m); 1.95-1.76 (8H, m); 1.63-1.58 and 1.33-1.27 (2H, 2 × m); 1.42 and 1.41 (3H, 2 × s); 1.14-0.93 (6H, m) |
| 252 | δ (400 MHz, CDCl₃) rotamers present 7.62 and 7.53 (1H, 2 × s); 7.33-7.26 (1H, m); 7.03-6.79 (2H, m); 4.71 and 4.35 (2H, 2 × s); 4.29-4.18 (1H, m); 3.86 and 3.76 (3H, 2 × s); 3.64 and 3.37 (2H, 2 × d, J = 7.3 Hz); 2.63-2.55 and 2.44-2.36 (1H, 2 × m); 2.26-2.14 (2H, m); 1.94-1.79 (8H, m); 1.63-1.58 and 1.35-1.30 (2H, 2 × m); 1.41 and 1.39 (3H, 2 × s); 1.14-0.94 (6H, m) |
| 253 | δ (400 MHz, CDCl₃) rotamers present 7.70 and 7.55 (1H, 2 × s); 7.33-7.25 (1H, m); 7.03-6.78 (2H, m); 4.86 and 4.46 (2H, 2 × s); 4.24-4.18 (1H, m); 3.85 and 3.75 (3H, 2 × s); 3.42 and 3.33 (2H, 2 × s); 2.26-2.18 (2H, m); 1.93-1.87 (6H, m); 1.41 and 1.39 (3H, 2 × s); 1.01 and 0.83 (9H, 2 × s) |
| 254 | δ (400 MHz, CDCl₃) rotamers present 7.68-7.47 (4H, m); 4.73 and 4.51 (2H, 2 × s); 4.27-4.17 and 3.52-3.44 (2H, 2 × m); 2.26-2.21 (2H, m); 1.98-1.78 (7H, m); 1.68-1.40 (9H, m); 1.12-1.04 (1H, m); 0.94-0.86 (6H, m) |
| 255 | δ (400 MHz, CDCl₃) rotamers present 7.68 and 7.58 (1H, 2 × s); 7.32-7.25 (1H, m); 7.04-6.80 (2H, m); 4.66 and 4.36 (2H, 2 × s); 4.62-4.58 and 3.48-3.42 (1H, 2 × m); 4.29-4.15 (1H, m); 3.87 and 3.77 (3H, 2 × s); 2.28-2.16 (2H, m); 1.98-1.86 (6H, m); 1.66-1.39 (10H, m); 1.13-1.05 (1H, m); 0.94-0.87 (6H, m) |
| 256 | δ (400 MHz, CDCl₃) rotamers present 7.57 and 7.47 (1H, 2 × s); 7.38 and 7.31 (2H, 2 × s); 4.70 and 4.35 (2H, 2 × s); 3.62-3.34 (2H, m); 2.62-2.54 and 2.43-2.35 (1H, 2 × m); 2.32-2.21 (6H, m); 2.08-2.02 (6H, m); 1.89-1.79 (2H, m); 1.63-1.58 and 1.35-1.30 (2H, 2 × m); 1.14-0.94 (6H, m) |
| 257 | δ (400 MHz, CDCl₃) rotamers present 7.54 and 7.45 (1H, 2 × s); 7.32-7.26 (1H, m); 7.03-6.78 (2H, m); 4.70 and 4.32 (2H, 2 × s); 3.86 and 3.75 (3H, 2 × s); 3.63-3.32 (2H, m); 2.63-2.55 and 2.44-2.36 (1H, 2 × m); 2.32-2.22 (6H, m); 2.08-2.02 (6H, m); 1.90-1.79 (2H, m); 1.63-1.58 and 1.36-1.31 (2H, 2 × m); 1.14-0.95 (6H, m) |
| 258 | δ (400 MHz, CDCl₃) rotamers present 7.67-7.48 (4H, m); 4.81 and 4.44 (2H, 2 × s); 3.93-3.13 (2H, m); 2.63-2.23 (7H, m); 2.09-2.03 (6H, m); 1.88-1.76 (2H, m); 1.63-1.58 and 1.33-1.28 (2H, 2 × m); 1.14-0.94 (6H, m) |
| 259 | δ (400 MHz, CDCl₃) rotamers present 7.61 and 7.55 (1H, 2 × s); 7.33-7.26 (1H, m); 7.03-6.78 (2H, m); 4.76 and 4.38 (2H, 2 × s); 4.28-4.18 (1H, m); 3.86 and 3.75 (3H, 2 × s); 3.48 and 3.23 (2H, 2 × d, J = 7.1 Hz); 2.27-2.16 (2H, m); 1.95-1.87 (6H, m); 1.67-1.05 (11H, m); 0.96-0.78 (7H, m) |

| example | |
|---|---|
| 260 | δ (400 MHz, CDCl₃) rotamers present 7.65 and 7.57 (1H, 2 × s); 7.36 and 7.29 (2H, 2 × s); 5.08 and 4.76 (2H, 2 × s); 4.29-4.17 (1H, m); 3.96 and 3.75 (2H, 2 × s); 2.25-2.14 (2H, m); 1.95-1.84 (6H, m); 1.68-1.39 (14H, m) |
| 261 | δ (400 MHz, DMSO-d₆) rotamers present 12.20 (1H, brs); 7.71 and 7.61 (1H, 2 × s); 7.42 and 7.37 (2H, 2 × s); 4.92 and 4.70 (2H, 2 × s); 3.83 and 3.61 (2H, 2 × s); 2.35 and 2.30 (3H, 2 × s); 2.21-2.12 (6H, m); 1.93-1.89 (6H, m); 1.69-1.50 (6H, m); 1.45-1.38 (2H, m); 1.34 and 1.31 (3H, 2 × s) |
| 262 | δ (400 MHz, DMSO-d₆) rotamers present 11.97 (1H, brs); 8.77 and 8.70 (2H, 2 × s); 7.81 and 7.71 (1H, 2 × s); 4.95 and 4.82 (2H, 2 × s); 4.48-4.42 (1H, m); 4.27-4.19 (1H, m); 3.87 and 3.71 (2H, 2 × s); 2.34-2.26 (1H, m); 2.07-1.90 (6H, m); 1.67-1.30 (10H, m) |
| 264 | δ (400 MHz, CDCl₃) rotamers present 8.57 and 8.49 (2H, 2 × s); 7.66 and 7.52 (1H, 2 × s); 5.14-5.04 and 4.37-4.16 (2H, m); 4.57 and 4.40 (2H, 2 × s); 2.52-2.44 (1H, m); 2.28-2.25 (2H, m); 2.17-2.02 (4H, m); 1.96-1.89 (1H, m); 1.73-1.62 (2H, m,); 1.36-0.96 (11H, m) |
| 265 | δ (400 MHz, CDCl₃) rotamers present 7.78 and 7.48 (4H, m); 4.97 and 4.60 (2H, 2 × s); 4.24-4.18 (1H, m); 3.72-3.12 (2H, m); 2.27-2.19 (2H, m); 1.94-1.88 (6H, m); 1.41 and 1.25 (3H, 2 × s); 1.00 and 0.82 (9H, 2 × s) |
| 266 | δ (400 MHz, CDCl₃) rotamers present 7.58 and 7.47 (1H, 2 × s); 7.13 and 7.06 (2H, 2 × d, J = 8.0 Hz); 4.71 and 4.36 (2H, 2 × s); 3.70-3.35 (2H, m); 2.63-2.55 and 2.43-2.35 (1H, 2 × m); 2.32-2.21 (6H, m); 2.08-2.02 (6H, m); 1.89-1.79 (2H, m); 1.63-1.58 and 1.36-1.30 (2H, 2 × m); 1.14-0.94 (6H, m) |
| 267 | δ (400 MHz, CDCl₃) rotamers present 8.57 and 8.50 (2H, 2 × s); 7.67 and 7.56 (1H, 2 × s); 4.81 and 4.47 (2H, 2 × s); 4.29-4.18 (1H, m); 3.72 and 3.59 (2H, 2 × s); 2.28-2.15 (2H, m); 1.95-1.85 (6H, m); 1.67-1.06 (16H, m) |
| 268 | δ (400 MHz, DMSO-d₆) rotamers present 12.23 (1H, brs); 7.90 and 7.81 (1H, 2 × s); 7.19-7.09 (4H, m); 6.93-6.91 (1H, m); 4.72-4.59 (4H, m); 4.27-4.13 (1H, m); 2.33-2.29 (1H, m); 2.19 (3H, s); 2.05-2.02 (2H, m); 1.96-1.90 (4H, m); 1.70 (3H, s); 1.58-1.46 (2H, m) |
| 269 | δ (300 MHz, DMSO-d₆) rotamers present 12.15 (1H, brs); 7.85 and 7.81 (1H, 2 × s); 7.17-6.91 (5H, m); 4.71-4.58 (4H, m); 4.28-4.13 (1H, m); 2.34-2.23 (4H, m); 2.22 and 1.77 (3H, 2 × s); 2.08-1.90 (6H, m); 1.60-1.47 (2H, m) |
| 270 | δ (400 MHz, CDCl₃) rotamers present 7.65-7.47 (4H, m); 5.11 and 4.75 (2H, 2 × s); 4.25-4.19 (1H, m); 4.02-3.70 (2H, m); 2.28-2.18 (2H, m); 1.95-1.73 (14H, m); 1.41 (3H, s) |
| 272 | δ (400 MHz, CDCl₃) rotamers present 8.57 and 8.49 (2H, 2 × s); 7.67 and 7.56 (1H, 2 × s); 5.00 and 4.69 (2H, 2 × s); 4.26-4.19 (1H, m); 3.98-3.92 (2H, m); 2.28-2.16 (2H, m); 1.95-1.74 (14H, m); 1.41 (3H, s) |
| 275 | δ (400 MHz, CDCl₃) rotamers present 7.68 and 7.56 (1H, 2 × s); 7.38 and 7.31 (2H, 2 × s); 4.82 and 4.44 (2H, 2 × s); 4.29-4.17 (1H, m); 3.71 and 3.58 (2H, m); 2.24-2.14 (2H, m); 1.96-1.84 (6H, m); 1.66-1.05 (16H, s) |
| 279 | δ (300 MHz, DMSO-d₆) rotamers present 12.22 (1H, brs); 7.85 and 7.68 (1H, 2 × s); 7.22 and 7.15 (1H, 2 × s); 7.11 and 7.05 (1H, 2 × s); 4.61 and 4.59 (2H, 2 × s); 4.32-4.17 and 3.39-3.30 (2H, 2 × m); 2.30-1.98 (7H, m); 1.90-1.58 (9H, m); 1.50-1.31 (4H, m); 1.25 and 1.22 (3H, 2 × s); 1.04-0.82 (8H, m) |
| 280 | δ (400 MHz, CD₃OD) rotamers present 7.76 and 7.62 (1H, 2 × s); 7.13 and 7.07 (2H, 2 × s); 4.61 and 4.54 (2H, 2 × s); 4.35-4.27 and 3.57-3.45 (2H, 2 × m); 2.36-2.20 (7H, m); 1.95-1.81 (7H, m); 1.77-1.07 (11H, m); 0.95-0.86 (6H, m) |
| 281 | δ (400 MHz, CDCl₃) rotamers present 7.70 and 7.58 (1H, 2 × s); 7.36-7.23 (3H, m); 5.05 and 4.69 (2H, 2 × s); 4.25-4.18 (1H, m); 4.00-3.95 (2H, m); 2.26-2.16 (2H, m); 1.94-1.73 (14H, m); 1.40 (3H, s) |
| 282 | δ (400 MHz, CDCl₃) rotamers present 7.69 and 7.58 (1H, 2 × s); 7.15 and 7.07 (2H, 2 × s); 5.02 and 4.66 (2H, 2 × s); 4.25-4.17 (1H, m); 3.98-3.70 (2H, m); 2.35 and 2.32 (3H, 2 × s); 2.25-2.15 (2H, m); 1.94-1.73 (14H, m); 1.41 and 1.40 (3H, 2 × s) |
| 283 | δ (400 MHz, CDCl₃) rotamers present 7.68 and 7.58 (1H, 2 × s); 7.38-7.23 (3H, m); 4.70 and 4.46 (2H, 2 × s); 4.61-4.53 and 3.52-3.44 (1H, 2 × m); 4.30-4.15 (1H, m); 2.29-2.16 (2H, m); 1.98-1.86 (6H, m); 1.68-1.40 (10H, m); 1.13-1.06 (1H, m); 0.94-0.87 (6H, m) |
| 284 | δ (400 MHz, CDCl₃) rotamers present 7.75 and 7.59 (1H, 2 × s); 7.36-7.23 (3H, m); 4.92 and 4.53 (2H, 2 × s); 4.24-4.16 (1H, m); 3.44-3.36 (2H, m); 2.25-2.15 (2H, m); 1.94-1.85 (6H, m); 1.42 and 1.40 (3H, 2 × s); 1.01 and 0.84 (9H, 2 × s) |
| 287 | δ (400 MHz, CDCl₃) rotamers present 8.58 and 8.50 (2H, 2 × s); 7.65 and 7.57 (1H, 2 × s); 4.64-4.57 and 3.55-3.48 (1H, 2 × m); 4.54 and 4.35 (2H, 2 × s); 4.30-4.21 (1H, m); 2.28-2.18 (2H, m); 1.97-1.87 (6H, m); 1.62-1.49 (4H, m); 1.42 and 1.40 (3H, 2 × s); 0.99 and 0.90 (6H, 2 × t, J = 7.5 Hz) |
| 288 | δ (400 MHz, DMSO-d₆) rotamers present 12.24 (1H, brs); 8.78 and 8.72 (2H, 2 × s); 7.65 and 7.62 (1H, 2 × s); 4.82 and 4.66 (2H, 2 × s); 3.49-3.22 (2H, m); 2.15-2.11 (6H, m); 1.93-1.89 (6H, m); 1.30-1.24 (2H, m); 0.89-0.72 (9H, m) |
| 289 | δ (400 MHz, CDCl₃) rotamers present 7.66 and 7.55 (1H, 2 × s); 7.39 and 7.31 (2H, 2 × s); 4.57-4.52 (1.5H, m); 4.39-4.15 (6H, m); 3.53-3.48 (0.5H, m); 2.27-2.13 (4H, m); 1.95-1.75 (8H, m); 1.65-1.58 (1H, m); 1.45-1.28 (6H, m) |
| 290 | δ (400 MHz, DMSO-d₆) rotamers present 12.47 (1H, brs); 7.91 and 7.76 (1H, 2 × s); 7.72 and 7.65 (2H, 2 × d, J = 8.6 Hz); 5.14-4.98 (1H, m); 4.73 and 4.65 (2H, 2 × s); 4.34-4.28 and 3.43-3.38 (1H, 2 × m); 3.17-3.09 (1H, m); 2.92-2.75 (2H, m); 2.71-2.59 (2H, m); 1.71-1.61 (2H, m); 1.48-1.24 (5H, m); 1.06-1.00 (1H, m); 0.91-0.81 (6H, m) |

| example | |
|---|---|
| 291 | δ (400 MHz, DMSO-$d_6$) rotamers present 12.38 (1H, brs); 7.89 and 7.75 (1H, 2 × s); 7.72 and 7.66 (2H, 2 × d, J = 8.6 Hz); 4.98-4.85 (1H, m); 4.72 and 4.64 (2H, 2 × s); 4.35-4.28 and 3.43-3.37 (1H, 2 × m); 3.02-2.96 (1H, m); 2.81-2.59 (4H, m); 1.70-1.60 (2H, m); 1.48-1.27 (5H, m); 1.07-1.00 (1H, m); 0.91-0.82 (6H, m) |
| 292 | δ (400 MHz, $CD_3OD$) rotamers present 7.81 and 7.59 (1H, 2 × s); 7.40 and 7.34 (2H, 2 × d, J = 8.6 Hz); 4.96 and 4.78 (2H, 2 × s); 4.35-4.25 (1H, m); 3.72-3.63 and 3.51-3.46 (4H, 2 × m); 2.31-2.13 (2H, m); 1.93-1.84 (6H, m); 1.35 and 1.33 (3H, 2 × s); 1.19 and 1.16 (9H, 2 × s) |
| 293 | δ (400 MHz, $CD_3OD$) rotamers present 7.81 and 7.59 (1H, 2 × s); 7.61 and 7.55 (2H, 2 × s); 4.96 and 4.78 (2H, 2 × s); 4.36-4.26 (1H, m); 3.72-3.63 and 3.52-3.45 (4H, 2 × m); 2.35-2.13 (2H, m); 1.94-1.85 (6H, m); 1.36 and 1.34 (3H, 2 × s); 1.19 and 1.16 (9H, 2 × s) |
| 294 | δ (400 MHz, $CDCl_3$) rotamers present 8.54-8.44 (2H, m); 7.61 and 7.51 (1H, 2 × s); 4.71 and 4.54 (2H, 2 × s); 4.27-4.19 (1H, m); 3.40-3.33 (2H, m); 2.27-2.17 (2H, m); 1.94-1.87 (6H, m); 1.41 and 1.40 (3H, 2 × s); 1.01 and 0.86 (9H, 2 × s) |
| 295 | δ (400 MHz, $CD_3OD$) rotamers present 7.81 and 7.63 (1H, 2 × s); 7.41 and 7.34 (2H, 2 × d, J = 6.3 Hz); 4.79-3.93 (4H, m); 3.31-3.12 (2H, m); 2.99-2.94 (1H, m); 2.80-2.68 (4H, m); 2.46-2.37 (2H, m); 2.28-2.15 (2H, m); 1.95-1.72 (8H, m); 1.32 and 1.30 (3H, 2 × s) |
| 296 | δ (400 MHz, DMSO-$d_6$) rotamers present 7.88-7.69 (3H, m); 4.69-4.19 (4H, m); 3.12-2.73 (4H, m); 2.13-2.02 (3H, m); 1.91-1.65 (10H, m); 1.25 and 1.22 (3H, 2 × s); 1.05-0.90 (6H, m) |
| 297 | δ (400 MHz, $CDCl_3$) rotamers present 7.64 and 7.52 (1H, 2 × s); 7.39-6.99 (3H, m); 4.78 and 4.53 (2H, 2 × s); 4.25-4.18 (1H, m); 3.41-3.33 (2H, m); 2.26-2.16 (2H, m); 1.94-1.87 (6H, m); 1.41 and 1.40 (3H, 2 × s); 1.01 and 0.85 (9H, 2 × s) |
| 298 | δ (400 MHz, $CDCl_3$) rotamers present 7.61 and 7.49 (1H, 2 × s); 7.37 and 7.30 (2H, 2 × s); 4.99 and 4.64 (2H, 2 × s); 3.94-3.66 (2H, m); 2.31-2.22 (6H, m); 2.07-2.03 (6H, m); 1.93-1.73 (8H, m) |
| 299 | δ (400 MHz, $CDCl_3$) rotamers present 8.56 and 8.49 (2H, 2 × s); 7.60 and 7.49 (1H, 2 × s); 4.99 and 4.67 (2H, 2 × s); 3.94-3.66 (2H, m); 2.31-2.23 (6H, m); 2.08-2.04 (6H, m); 1.99-1.74 (8H, m) |
| 300 | δ (400 MHz, $CDCl_3$) rotamers present 7.62 and 7.50 (1H, 2 × s); 7.15 and 7.07 (2H, 2 × s); 5.01 and 4.64 (2H, 2 × s); 3.95-3.67 (2H, m); 2.35 and 2.32 (3H, 2 × s); 2.26-2.22 (6H, m); 2.07-2.03 (6H, m); 1.94-1.73 (8H, m) |
| 301 | δ (400 MHz, DMSO-$d_6$) rotamers present 12.40 (1H, brs); 7.80 and 7.63 (1H, 2 × s); 7.71 and 7.67 (2H, 2 × d, J = 8.6 Hz); 4.72 and 4.65 (2H, 2 × s); 4.34-4.17 (2H, m); 2.20-2.14 (6H, m); 2.03-1.62 (6H, m); 1.48-1.24 (7H, m); 1.14 and 1.12 (3H, 2 × s); 1.02-0.95 (1H, m); 0.90-0.81 (6H, m) |
| 302 | δ (400 MHz, DMSO-$d_6$) rotamers present 12.26 (1H, brs); 7.88 and 7.75 (1H, 2 × s); 7.70 and 7.65 (2H, 2 × d, J = 8.5 Hz); 4.81 and 4.63 (2H, 2 × s); 4.25-4.20 (1H, m); 3.82-3.75 and 3.38-3.23 (2H, 2 × m); 2.09-1.98 (2H, m); 1.87-1.72 (6H, m); 1.30-1.15 (5H, m); 0.87-0.70 (9H, m) |
| 303 | δ (400 MHz, DMSO-$d_6$) rotamers present 12.26 (1H, brs); 9.41 and 9.14 (1H, 2 × brs); 7.89 and 7.76 (1H, 2 × s); 7.75 and 7.69 (2H, 2 × d, J = 8.6 Hz); 4.80-4.73 (2.5H, m); 4.36-4.31 (0.5H, m); 4.26-4.20 (1H, m); 3.90-3.88 and 3.81-3.78 (2H, 2 × m); 2.63 and 2.56 (3H, 2 × d, J = 4.5 Hz); 2.49-2.42 (2H, m); 2.29-2.27 (2H, m); 2.14-1.63 (12H, m); 1.25 and 1.23 (3H, 2 × s) |
| 304 | δ (400 MHz, $CD_3OD$) rotamers present 7.82 and 7.62 (1H, 2 × s); 7.43 and 7.37 (2H, 2 × d, J = 8.0 Hz); 4.79 and 4.70 (2H, 2 × s); 4.45-4.36 (1H, m); 4.30-4.25 (1H, m); 4.11-4.02 (2H, m); 2.64-2.48 (2H, m); 2.26-2.06 (8H, m); 1.99-1.74 (7H, m); 1.36 and 1.34 (3H, 2 × s) |
| 305 | δ (400 MHz, $CD_3OD$) rotamers present 7.66 and 7.63 (1H, 2 × s); 7.37 and 7.29 (2H, 2 × d, J = 8.2 Hz); 4.77 and 4.72 (2H, 2 × s); 4.29-4.17 (4H, m); 3.26-3.20 (1H, m); 2.79-2.71 (2H, m); 2.33-2.15 (8H, m); 1.95-1.82 (6H, m); 1.47-1.34 (9H, m) |
| 306 | δ (400 MHz, DMSO-$d_6$) rotamers present 7.94-7.72 (3H, m); 4.80 and 4.63 (2H, 2 × s); 4.16-4.09 (1H, m); 3.48-3.20 (2H, m); 2.07-1.96 (2H, m); 1.80-1.63 (6H, m); 1.29-1.22 (2H, m); 1.12 (3H, s); 0.87-0.69 (9H, m) |
| 307 | δ (400 MHz, DMSO-$d_6$) 12.11 (1H, brs); 8.32 (2H, s); 7.49 (1H, s); 7.37 (1H, s); 7.18-7.13 (2H, m); 7.10-7.03 (2H, m); 5.13 (1H, d, J = 15.7 Hz); 4.30 (1H, d, J = 15.7 Hz); 4.16-4.08 (1H, m); 2.28 (3H, s); 2.24-2.18 (1H, m); 2.00-1.82 (4H, m); 1.75-1.69 (2H, m); 1.52-1.40 (2H, m) |
| 308 | δ (400 MHz, DMSO-$d_6$) rotamers present 7.84 and 7.79 (2H, 2 × s); 7.64 and 7.61 (1H, 2 × s); 4.79 and 4.59 (2H, 2 × s); 3.50-3.32 (2H, m); 2.19-2.10 (6H, m); 1.92-1.88 (6H, m); 1.29-1.22 (2H, m); 0.88-0.71 (9H, m) |
| 309 | δ (400 MHz, DMSO-$d_6$) rotamers present 7.80-7.61 (3H, m); 4.79 and 4.59 (2H, 2 × s); 3.50-3.22 (2H, m); 2.18-2.10 (6H, m); 1.91-1.88 (6H, m); 1.29-1.23 (2H, m); 0.87-0.71 (9H, m) |
| 310 | δ (400 MHz, DMSO-$d_6$) rotamers present 12.30 (1H, brs); 8.78 and 8.73 (2H, 2 × s); 8.13 and 8.04 (1H, 2 × s); 4.86 (2H, s); 4.50-4.43 (1H, m); 3.41-3.28 (2H, m); 2.04-1.95 (2H, m); 1.88-1.83 (4H, m); 1.74-1.71 (2H, m); 1.20 and 1.14 (3H, 2 × s); 0.94 and 0.76 (9H, 2 × s) |
| 312 | δ (400 MHz, $CD_3OD$) rotamers present 8.65 and 8.58 (2H, 2 × s); 7.79 and 7.61 (1H, 2 × s); 4.95-4.88 and 3.99-3.91 (1H, 2 × m); 4.80-4.63 (2H, m); 4.37-4.25 (1H, m); 2.33-2.14 (2H, m); 1.93-1.85 (7H, m); 1.68-1.40 (2H, m); 1.36 and 1.34 (3H, 2 × s); 1.32-1.27 (1H, m); 1.23 and 1.21 (3H, 2 × s); 0.99-0.93 (3H, m); 0.75 and 0.73 (3H, 2 × s) |

| example | |
|---|---|
| 313 | δ (400 MHz, DMSO-d$_6$) rotamers present 12.21 (1H, brs); 8.80 and 8.72 (2H, 2 × s); 7.81 and 7.70 (1H, 2 × s); 4.88-4.57 (2.5H, m); 4.31-4.21 (1H, m); 3.96-3.91 (0.5H, m); 3.54-3.22 (2H, m); 3.25 and 3.16 (3H, 2 × s); 2.15-2.01 (2H, m); 1.88-1.76 (6H, m); 1.24 and 1.23 (3H, 2 × s); 1.16 and 1.08 (3H, 2 × d, J = 6.8 Hz) |
| 314 | δ (400 MHz, DMSO-d$_6$) rotamers present 12.27 (1H, brs); 8.79 and 8.72 (2H, 2 × s); 7.85 and 7.75 (1H, 2 × s); 5.17-5.11 (1H, m); 4.75 and 4.60 (2H, 2 × s); 4.30-4.22 (1H, m); 4.11 and 3.86 (2H, 2 × d, J = 6.7 Hz); 2.14-2.01 (2H, m); 1.88-1.74 (6H, m); 1.70 and 1.66 (3H, 2 × s); 1.64 and 1.37 (3H, 2 × s); 1.24 and 1.23 (3H, 2 × s) |
| 315 | δ (400 MHz, CDCl$_3$) rotamers present 8.33-8.23 (2H, m); 7.68 and 7.53 (1H, 2 × s); 4.80 and 4.47 (2H, 2 × s); 4.24-4.19 (1H, m); 3.98 and 3.88 (3H, 2 × s); 3.41-3.31 (2H, m); 2.27-2.16 (2H, m); 1.94-1.86 (6H, m); 1.41 and 1.40 (3H, 2 × s); 1.01 and 0.85 (9H, 2 × s) |
| 316 | δ (400 MHz, CDCl$_3$) rotamers present 8.58 and 8.51 (2H, 2 × s); 7.54 and 7.48 (1H, 2 × s); 4.94 and 4.58 (2H, 2 × s); 3.55-3.30 (2H, m); 2.33-2.23 (6H, m); 2.09-2.05 (6H, m); 1.09 and 0.98 (3H, 2 × s); 0.49-0.34 (4H, m) |
| 317 | δ (400 MHz, CDCl$_3$) rotamers present 7.68 and 7.51 (2H, 2 × s); 7.37-7.25 (3H, m); 4.91 and 4.51 (2H, 2 × s); 3.49-3.33 (2H, m); 2.32-2.22 (6H, m); 2.07-2.03 (6H, m); 1.01 and 0.84 (9H, 2 × s) |
| 318 | δ (400 MHz, CDCl$_3$) rotamers present 7.71 and 7.60 (1H, 2 × s); 7.37-7.27 (2H, m); 4.96 and 4.72 (2H, 2 × s); 4.29-4.18 (1H, m); 3.77-3.40 (4H, m); 2.25-2.17 (2H, m); 1.93-1.87 (6H, m); 1.41 and 1.40 (3H, 2 × s); 1.16 and 1.15 (9H, 2 × s) |
| 319 | δ (400 MHz, CDCl$_3$) rotamers present 8.58 and 8.50 (2H, 2 × s); 7.71 and 7.52 (1H, 2 × s); 5.19-5.15 and 4.53-4.15 (3H, m); 2.28-2.14 (2H, m); 1.95-1.55 (8H, m); 1.42-0.55 (14H, m) |
| 320 | δ (400 MHz, CDCl$_3$) rotamers present 7.62 and 7.48 (1H, 2 × s); 7.36-7.26 (3H, m); 5.10-5.00 and 4.31-4.22 (1H, 2 × m); 4.60 and 4.38 (2H, 2 × s); 2.34-2.21 (6H, m); 2.09-1.88 (8H, m); 1.43-1.23 (2H, m); 1.08-0.95 (8H, m) |
| 321 | δ (400 MHz, CDCl$_3$) rotamers present 7.62 and 7.47 (1H, 2 × s); 7.16 and 7.08 (2H, 2 × s); 5.11-5.01 and 4.30-4.21 (1H, 2 × m); 4.57 and 4.35 (2H, 2 × s); 2.35-2.21 (9H, m); 2.09-2.02 (7H, m); 1.93-1.85 (1H, m); 1.40-1.23 (2H, m); 1.10-0.95 (8H, m) |
| 322 | δ (400 MHz, CDCl$_3$) rotamers present 8.58 and 8.51 (2H, 2 × s); 7.55 and 7.48 (1H, 2 × s); 4.74 and 4.45 (2H, 2 × s); 3.68 (1H, brs); 3.32 (1H, d, J = 5.9 Hz); 2.31-2.23 (6H, m); 2.08-2.05 (6H, m); 1.09 (3H, s); 1.05 (3H, s); 1.03 (3H, s); 0.80 (3H, s); 0.55-0.51 and 0.31-0.28 (1H, m) |
| 325 | δ (400 MHz, CDCl$_3$) rotamers present 8.58 and 8.51 (2H, 2 × s); 7.64 and 7.55 (1H, 2 × s); 4.76 and 4.48 (2H, 2 × s); 4.29-4.18 (1H, m); 3.68 and 3.37 (2H, 2 × d, J = 6.5 Hz); 2.31-2.16 (2H, m); 1.95-1.86 (6H, m); 1.42 and 1.41 (3H, 2 × s); 1.09 (3H, s); 1.06 (3H, s); 1.04 (3H, s); 0.80 (3H, s); 0.53 and 0.31 (1H, 2 × t, J = 6.5 Hz) |
| 326 | δ (400 MHz, CDCl$_3$) rotamers present 8.57 and 8.50 (2H, 2 × s); 7.67 and 7.57 (1H, 2 × s); 5.00 and 4.68 (2H, 2 × s); 4.26-4.20 (1H, m); 3.83-3.58 (2H, m); 2.26-2.16 (2H, m); 1.95-1.86 (6H, m); 1.46-1.23 (9H, m) |
| 327 | δ (400 MHz, CDCl$_3$) rotamers present 8.57 and 8.50 (2H, 2 × s); 7.59 and 7.50 (1H, 2 × s); 4.99 and 4.66 (2H, 2 × s); 3.80-3.54 (2H, m); 2.32-2.23 (6H, m); 2.08-2.04 (6H, m); 1.46-1.26 (6H, m) |
| 329 | δ (400 MHz, CDCl$_3$) rotamers present 8.59 and 8.52 (2H, 2 × s); 7.56 and 7.46 (1H, 2 × s); 4.94 and 4.55 (2H, 2 × s); 3.84 and 3.70 (2H, 2 × s); 2.33-2.22 (6H, m); 2.08-2.04 (6H, m); 1.10-1.06 (4H, m) |
| 331 | δ (400 MHz, CDCl$_3$) rotamers present 8.57 and 8.50 (2H, 2 × s); 7.75 and 7.55 (1H, 2 × s); 4.78 and 4.45 (2H, 2 × s); 4.29-4.24 (1H, m); 2.83-2.79 (1H, m); 2.28-2.20 (2H, m); 1.95-1.90 (6H, m); 1.42 (3H, s); 1.04-0.99 (1H, m); 0.95 and 0.70 (9H, 2 × s); 0.64-0.55 (2H, m) |
| 332 | δ (400 MHz, DMSO-d$_6$) rotamers present 12.27 (1H, brs); 8.80 and 8.73 (2H, 2 × s); 7.81 and 7.66 (1H, 2 × s); 4.89-4.57 (2.5H, m); 4.30-4.21 (1H, m); 3.87-3.82 (0.5H, m); 3.50-3.18 (2H, m); 2.13-2.04 (2H, m); 1.88-1.75 (6H, m); 1.24-1.07 (15H, m) |
| 333 | δ (400 MHz, CDCl$_3$) rotamers present 8.54-8.44 (2H, m); 7.64 and 7.49 (1H, 2 × s); 5.26-5.20 and 4.34-4.17 (2H, 2 × m); 4.52 and 4.36 (2H, 2 × s); 2.31-1.88 (10H, m); 1.42 and 1.40 (3H, 2 × s); 1.27-1.12 (2H, m); 1.04-0.97 (8H, m) |
| 337 | δ (400 MHz, CDCl$_3$) rotamers present 8.54-8.44 (2H, m); 7.62 and 7.50 (1H, 2 × s); 4.71 and 4.53 (2H, 2 × s); 4.26-4.19 (1H, m); 3.41 and 3.34 (2H, 2 × s); 2.26-2.16 (2H, m); 1.94-1.86 (6H, m); 1.40-1.14 (5H, m); 0.95-0.68 (9H, m) |
| 338 | δ (400 MHz, DMSO-d$_6$) rotamers present 12.11 (2H, brs); 7.89 and 7.80 (1H, 2 × s); 4.29-4.23 (1H, m); 4.17-4.09 (1H, m); 3.26-3.16 (1H, m); 3.04-3.00 (1H, m); 2.57-2.53 (1H, m); 2.36-2.32 (1H, m); 2.15 (3H, s); 2.13-2.05 (2H, m); 1.88-1.64 (11H, m); 1.58-1.55 (1H, m); 1.48-1.30 (4H, m); 1.24 (3H, s); 1.00-0.82 (7H, m) |
| 339 | δ (400 MHz, CD$_3$OD) rotamers present 7.79 and 7.64 (1H, 2 × s); 7.40 and 7.34 (2H, 2 × d, J = 8.5 Hz); 5.15-5.00 (1H, m); 4.77 and 4.64 (2H, 2 × s); 4.44-4.36 and 3.55-3.47 (1H, 2 × m); 2.99-2.87 (2H, m); 2.73-2.58 (2H, m); 1.83-1.70 (2H, m); 1.63-1.37 (8H, m); 1.15-1.08 (1H, m); 0.94-0.86 (6H, m) |
| 340 | δ (400 MHz, DMSO-d$_6$) rotamers present 12.27 (1H, brs); 8.81 and 8.73 (2H, 2 × s); 7.95 and 7.73 (1H, 2 × s); 4.88-4.56 (2H, m); 4.31-4.20 (1H, m); 2.71-2.60 (1H, m); 2.15-2.05 (2H, m); 1.90-1.75 (6H, m); 1.24 and 1.22 (3H, 2 × s); 1.08-1.07 (1H, m); 0.92-0.76 (2H, m); 0.67-0.59 (6H, m); 0.52-0.48 (1H, m) |
| 341 | δ (400 MHz, DMSO-d$_6$) rotamers present 12.24 (1H, brs); 7.69 and 7.52 (1H, 2 × s); 7.26-6.90 (3H, m); 5.47-4.96 (2H, m); 4.34-3.96 (2H, m); 3.79-3.50 (4H, m); 2.09-0.88 (23H, m) |

-continued

| example | |
|---|---|
| 342 | δ (400 MHz, DMSO-$d_6$) rotamers present 12.24 (1H, brs); 7.69 and 7.52 (1H, 2 × s); 7.26-6.90 (3H, m); 5.47-4.96 (2H, m); 4.34-3.96 (2H, m); 3.79-3.50 (4H, m); 2.09-0.88 (23H, m) |
| 345 | δ (400 MHz, DMSO-$d_6$) rotamers present 12.25 (1H, brs); 7.77 and 7.65 (3H, m); 4.70 (2H, s); 4.39-4.24 and 3.70-3.62 (2H, 2 × m); 2.03-1.64 (10H, m); 1.51-1.09 (10H, m); 0.91-0.85 (6H, m) |
| 346 | δ (400 MHz, DMSO-$d_6$) rotamers present 12.19 (1H, brs); 8.81 and 8.74 (2H, 2 × s); 8.09 and 7.73 (1H, 2 × s); 4.96-4.56 (2H, m); 4.31-4.23 (1H, m); 3.22-3.04 (1H, m); 2.17-2.03 (2H, m); 1.88-1.73 (6H, m); 1.24 and 1.22 (3H, 2 × s); 1.19-1.07 (1H, m); 0.99-0.48 (9H, m) |
| 348 | δ (400 MHz, DMSO-$d_6$) rotamers present 12.29 (1H, brs); 7.96 and 7.73 (1H, 2 × s); 7.73 and 7.68 (2H, 2 × d, J = 8.6 Hz); 4.86 and 4.74 (2H, 2 × s); 4.32-4.21 (1H, m); 3.57-3.53 and 3.39-3.35 (2H, 2 × m); 2.76-2.72 and 2.63-2.59 (2H, 2 × m); 2.13-1.99 (2H, m); 1.88-1.72 (6H, m); 1.30 and 1.09 (9H, 2 × s); 1.23 and 1.22 (3H, 2 × s) |
| 350 | δ (400 MHz, DMSO-$d_6$) rotamers present 12.28 (1H, brs); 8.02 and 7.73 (1H, 2 × s); 7.74 and 7.68 (2H, 2 × d, J = 8.8 Hz); 4.93 and 4.79 (2H, 2 × s); 4.32-4.22 (1H, m); 3.89-3.85 and 3.70-3.66 (2H, 2 × m); 3.42-3.38 and 3.35-3.31 (2H, 2 × m); 2.11-2.00 (2H, m); 1.88-1.73 (6H, m); 1.33-1.22 (12H, m) |
| 351 | δ (400 MHz, DMSO-$d_6$) rotamers present 12.28 (1H, brs); 7.95 and 7.74 (1H, 2 × s); 7.73 and 7.67 (2H, 2 × d, J = 8.6 Hz); 4.91-4.70 (2H, m); 4.31-4.21 (1H, m); 3.91-3.64 (2H, m); 2.98-2.64 (2H, m); 2.11-1.99 (2H, m); 1.87-1.72 (6H, m); 1.23 and 1.22 (3H, 2 × s); 1.17 and 1.10 (9H, 2 × s) |
| 352 | δ (400 MHz, DMSO-$d_6$) rotamers present 12.28-12.23 (1H, m); 8.56 and 8.23 (1H, 2 × d, J = 2.0 Hz); 7.85 and 7.50 (1H, 2 × s); 7.46-7.40 and 7.26-7.13 (3H, 2 × m); 4.83 and 4.65 (2H, 2 × s); 4.27-4.07 (1H, m); 3.41-3.28 (2H, m); 2.11-1.63 (8H, m); 1.23 and 1.13 (3H, 2 × s); 0.96 and 0.77 (9H, 2 × s) |
| 358 | δ (300 MHz, DMSO-$d_6$) rotamers present 12.24 (1H, brs); 7.80 and 7.73 (1H, 2 × s); 7.58-7.51 (3H, m); 4.84 and 4.72 (2H, 2 × s); 4.34-4.27 (1H, m); 1.98-1.72 (8H, m); 1.21 (3H, s); 0.95 and 0.74 (9H, 2 × s) |
| 359 | δ (300 MHz, DMSO-$d_6$) rotamers present 12.30 (1H, brs); 7.79 and 7.72 (1H, 2 × s); 7.43 and 7.38 (2H, 2 × s); 4.82 and 4.68 (2H, 2 × s); 4.36-4.27 (1H, m); 2.31 (3H, s); 2.02-1.72 (8H, m); 1.21 (3H, s); 0.95 and 0.74 (9H, 2 × s) |
| 360 | δ (400 MHz, DMSO-$d_6$) rotamers present 12.42 (1H, brs); 11.20 and 11.13 (1H, 2 × s); 7.77 and 7.63 (1H, 2 × s); 7.24-7.17 (1H, m); 6.96-6.85 (2H, m); 4.25-4.20 (1H, m); 3.64-3.42 (4H, m); 3.11-3.07 and 2.91-2.87 (2H, 2 × m); 2.10-1.99 (5H, m); 1.87-1.75 (6H, m); 1.24 (3H, s); 0.95 and 0.74 (9H, 2 × s) |
| 363 | δ (400 MHz, DMSO-$d_6$) rotamers present 12.23 (1H, brs); 7.83-7.29 (4H, m); 4.90-4.34 (4H, m); 1.93-1.76 (10H, m); 1.45-1.41 (2H, m); 1.22 (3H, s); 1.05-0.95 (8H, m) |
| 364 | δ (400 MHz, DMSO-$d_6$) rotamers present 12.20 (1H, brs); 7.55-7.28 (4H, m); 4.62-4.55 (3H, m); 4.25-4.15 (1H, m); 2.33-2.30 (3H, m); 2.09-1.81 (6H, m); 1.73-1.71 (4H, m); 1.32-1.27 (2H, m); 1.22 (3H, s); 1.05-0.90 (8H, m) |
| 365 | δ (300 MHz, DMSO-$d_6$) rotamers present 12.19 (1H, brs); 7.51-7.33 (3H, m); 4.64-4.57 (3H, m); 4.16-4.05 (1H, m); 2.35-2.26 (5H, m); 2.02-1.81 (6H, m); 1.74-1.71 (4H, m); 1.38-1.31 (2H, m); 1.22 (3H, s); 1.04-0.90 (8H, m) |
| 366 | δ (400 MHz, DMSO-$d_6$) rotamers present 12.23 (1H, brs); 7.80-7.41 (3H, m); 4.59-4.34 (4H, m); 2.33 (3H, s); 2.07-1.76 (10H, m); 1.31-1.21 (5H, m); 1.05-0.94 (8H, m) |
| 367 | δ (400 MHz, DMSO-$d_6$) rotamers present 12.23 (1H, brs); 8.77 and 8.61 (2H, 2 × s); 7.83 and 7.68 (1H, 2 × s); 4.65-4.36 (4H, m); 1.97-1.78 (10H, m); 1.30-1.21 (5H, m); 1.05-0.95 (8H, m) |
| 378 | δ (400 MHz, $CDCl_3$) rotamers present 8.57 and 8.51 (2H, 2 × s); 7.69 and 7.62 (1H, 2 × s); 4.96 and 4.72 (2H, 2 × s); 4.35-4.27 (1H, m); 3.57 and 3.48 (2H, 2 × s); 2.18-2.12 (2H, m); 1.95-1.84 (6H, m); 1.40 (3H, s); 1.13 and 0.96 (3H, 2 × s); 0.49-0.39 (4H, m) |
| 379 | δ (400 MHz, $CDCl_3$) rotamers present 8.48-8.35 (2H, m); 7.70 and 7.58 (1H, 2 × s); 4.76 and 4.51 (2H, 2 × s); 4.28-4.19 (1H, m); 3.43-3.35 (2H, m); 2.40 and 1.90 (3H, 2 × s); 2.28-2.16 (2H, m); 1.95-1.85 (6H, m); 1.41 and 1.40 (3H, 2 × s); 1.01 and 0.86 (9H, 2 × s) |
| 381 | δ (400 MHz, $CDCl_3$) rotamers present 8.56 and 8.53 (2H, 2 × s); 7.68 and 7.59 (1H, 2 × s); 4.70 and 4.54 (2H, 2 × s); 4.32-4.27 (1H, m); 3.63-3.56 (2H, m); 2.59-2.45 (1H, m); 2.17-2.11 (2H, m); 1.94-1.88 (8H, m); 1.39-0.96 (11H, m) |
| 382 | δ (400 MHz, $CDCl_3$) 8.55 (2H, s); 7.56 (1H, s); 4.68 (2H, s); 4.06-3.99 (1H, m); 3.61 (2H, d, J = 6.8 Hz); 2.57-2.40 (4H, m); 2.22-2.16 (2H, m); 1.94-1.82 (8H, m); 1.40-1.00 (11H, m) |
| 383 | δ (300 MHz, $CD_3OD$) rotamers present 8.43-8.33 (2H, m); 7.65 and 7.52 (2H, 2 × s); 5.63-5.59 and 5.23-5.21 (1H, 2 × m); 4.54-4.12 (2H, m); 3.90-3.73 and 3.48-3.44 (2H, 2 × m); 2.29-1.56 (12H, m); 1.35 (3H, s); 1.26-0.93 (8H, m) |
| 387 | δ (400 MHz, $CDCl_3$) 8.53 (1H, s); 8.46 (1H, s); 7.67 (1H, s); 4.51 (2H, s); 4.38-4.26 (2H, m); 2.49 (3H, s); 2.32-2.21 (2H, m); 2.01-1.94 (8H, m); 1.42 (3H, s); 1.30-1.24 (2H, m); 1.06-0.97 (8H, m) |
| 388 | δ (400 MHz, $CDCl_3$) rotamers present 8.58 and 8.52 (2H, 2 × s); 7.70 and 7.60 (1H, 2 × s); 4.93 and 4.70 (2H, 2 × s); 4.33-4.25 (1H, m); 3.86 (2H, s); 2.18-2.08 (2H, m); 1.94-1.82 (6H, m); 1.39 (3H, s); 1.09-1.05 (4H, m) |

| example | |
|---|---|
| 389 | δ (400 MHz, CDCl₃) rotamers present 7.71 and 7.61 (1H, 2 × s); 7.37-7.27 (3H, m); 4.72 and 4.57 (2H, 2 × s); 4.57-4.49 and 3.87-3.81 (1H, 2 × m); 4.38-4.21 (1H, m); 2.20-2.11 (2H, m); 1.94-1.83 (6H, m); 1.70-1.40 (10H, m); 1.27-1.23 (1H, m); 0.94-0.90 (6H, m) |
| 390 | δ (300 MHz, DMSO-d₆) rotamers present 12.19 (1H, brs); 8.56-8.46 (1H, m); 7.91-7.85 (1H, m); 7.74 and 7.63 (1H, 2 × s); 7.40-7.35 (1H, m); 5.53-5.44 and 4.98-4.93 (2H, 2 × m); 4.29-3.98 (2H, m); 3.61-3.49 (1H, m); 2.13-1.73 (10H, m); 1.56-1.37 (1H, m); 1.23-0.82 (12H, m) |
| 392 | δ (300 MHz, DMSO-d₆) rotamers present 12.24 (1H, brs); 11.19 and 11.14 (1H, 2 × s); 7.83 and 7.66 (1H, 2 × s); 7.24-7.16 (1H, m); 6.95-6.83 (2H, m); 4.47-4.00 (2H, m); 3.41-2.85 (4H, m); 2.50 and 2.41 (3H, 2 × s); 2.12-1.66 (11H, m); 1.31-1.10 (6H, m); 0.99-0.88 (6H, m) |
| 393 | δ (400 MHz, CDCl₃) 8.06 (1H, d, J = 7.3 Hz); 7.52 (1H, s); 7.35-7.20 (3H, m); 5.91 (1H, s); 4.30-4.23 (1H, m); 4.16-4.06 (1H, m); 3.99 (1H, d, J = 14.4 Hz); 3.89 (1H, d, J = 14.4 Hz); 2.28-2.17 (2H, m); 1.96-1.22 (14H, m); 1.10-0.83 (10H, m) |
| 394 | δ (400 MHz, CDCl₃) rotamers present 8.57 and 8.49 (2H, 2 × s); 7.69 and 7.57 (1H, 2 × s); 5.00 and 4.69 (2H, 2 × s); 4.25-4.20 (1H, m); 3.85-3.61 (2H, m); 2.26-2.16 (2H, m); 1.95-1.86 (6H, m); 1.76-1.41 (7H, m); 0.96 and 0.74 (6H, 2 × t, J = 7.6 Hz) |
| 395 | δ (400 MHz, CDCl₃) rotamers present 8.56 and 8.50 (2H, 2 × s); 7.71 and 7.64 (1H, 2 × s); 5.01 and 4.79 (2H, 2 × s); 4.30-4.25 (1H, m); 3.86-3.72 (2H, m); 2.18-2.08 (2H, m); 1.95-1.83 (6H, m); 1.78-1.39 (7H, m); 0.96 and 0.74 (6H, 2 × t, J = 7.3 Hz) |
| 396 | δ (400 MHz, DMSO-d₆) rotamers present 12.26 (1H, brs); 7.75 and 7.60 (1H, 2 × s); 7.60 and 7.54 (1H, 2 × d, J = 5.1 Hz); 6.99 and 6.93 (1H, 2 × d, J = 5.1 Hz); 6.31 and 6.08 (1H, 2 × s); 5.40-5.36 and 4.82-4.80 (1H, 2 × m); 4.30-4.01 (2H, m); 3.39-3.18 (2H, m); 2.07-1.70 (10H, m); 1.53-1.44 (1H, m); 1.28-0.84 (12H, m) |
| 398 | δ (400 MHz, CDCl₃) rotamers present 8.55 and 8.46 (1H, 2 × d, J = 3.2 Hz); 7.84-7.79 (1H, m); 7.66 and 7.50 (1H, 2 × s); 7.43-7.40 (1H, m); 4.92 and 4.71 (2H, 2 × s); 4.32-4.18 (2H, m); 2.28-1.87 (9H, m); 1.46-1.16 (6H, m); 1.06-0.94 (8H, m) |
| 401 | δ (300 MHz, DMSO-d₆) rotamers present 12.27 (1H, brs); 8.54-8.52 and 8.41-8.39 (1H, 2 × m); 7.83-7.23 (4H, m); 5.75-5.60 (1H, m); 5.00-4.96 and 4.64-4.59 (1H, 2 × m); 4.30-3.99 (2H, m); 3.64-3.31 (2H, m); 2.11-2.02 (2H, m); 1.88-1.74 (8H, m); 1.53-1.37 (1H, m); 1.23-0.82 (12H, m) |
| 402 | δ (400 MHz, CD₃OD) rotamers present 8.55 and 8.48 (1H, 2 × dd, J = 4.6, 1.5 Hz); 7.87 and 7.79 (1H, 2 × dd, J = 8.1, 1.5 Hz); 7.68 and 7.65 (1H, 2 × s); 7.36 and 7.33 (1H, 2 × dd, J = 8.1, 4.6 Hz); 5.64-5.61 and 5.17-5.14 (1H, 2 × m); 4.32-4.27 (1H, m); 4.07-3.33 (4H, m); 2.30-2.17 (2H, m); 1.91-1.89 (6H, m); 1.35 and 1.34 (3H, 2 × s); 1.01 and 0.81 (9H, 2 × s) |
| 404 | δ (400 MHz, DMSO-d₆) 12.27 (1H, brs); 7.66-7.37 (4H, m); 4.76-4.37 (4H, m); 2.10-1.74 (10H, m); 1.51-1.45 (3H, m); 1.34-0.91 (14H, m) |
| 406 | δ (400 MHz, CD₃OD) rotamers present 7.77 and 7.60 (1H, 2 × s); 7.53-7.21 (3H, m); 7.15-6.75 (1H, m); 4.83 and 4.63 (2H, 2 × s); 4.31-4.26 (1H, m); 3.41-3.36 (2H, m); 2.26-2.14 (2H, m); 1.95-1.84 (6H, m); 1.35 and 1.34 (3H, 2 × s); 1.01 and 0.85 (9H, 2 × s) |
| 500 | δ (500 MHz, DMSO-d₆) 12.19 (1H, br. s.), 7.75 (0.3H, s), 7.58 (0.7H, s), 7.34-7.48 (4H, m), 7.13-7.33 (4H, m), 4.78 (1.4H, s), 4.42 (0.6H, s), 4.15-4.28 (1H, m), 3.29-3.60 (2H, m), 2.94-3.00 (0.6H, m), 2.78-2.83 (1.4H, m), 2.25-2.39 (1H, m), 1.89-2.10 (6H, m), 1.46-1.60 (2H, m) |
| 501 | δ (400 MHz, DMSO-d₆) 12.18 (1H, br. s.), 7.79 (0.3H, s), 7.74 (0.7H, s), 7.34-7.47 (5H, m), 7.15-7.30 (2H, m), 4.78 (1.6H, s), 4.47 (0.4H, s), 4.14-4.29 (1H, m), 3.24-3.56 (2H, m), 3.15-3.20 (0.4H, m), 2.91-2.99 (1.6H, m), 2.25-2.38 (1H, m), 1.88-2.10 (6H, m), 1.45-1.63 (2H, m) |
| 502 | δ (500 MHz, DMSO-d₆) 12.17 (1H, br. s.), 7.68 (0.3H, s), 7.53 (0.7H, s), 7.42-7.45 (1H, m), 7.36-7.40 (2H, m), 7.28-7.32 (1H, m), 7.17-7.26 (3H, m), 7.14 (0.7H, d, J = 8.3 Hz), 6.93 (1.3H, d, J = 7.1 Hz), 4.72 (1.3H, s), 4.38 (0.7H, s), 4.13-4.26 (1H, m), 3.55 (0.7H, dd, J = 8.6, 6.8), 3.27 (1.3H, t, J = 7.6 Hz), 2.81-2.86 (0.7H, m), 2.72 (1.3H, t, J = 7.7 Hz), 2.24-2.37 (1H, m), 1.86-2.09 (6H, m), 1.46-1.591 (2H, m) |
| 503 | δ (400 MHz, DMSO-d₆) 12.18 (1H, br. s.), 10.97 (1H, br. s.), 7.68 (0.4H, s), 7.57 (0.6H, s), 7.36-7.47 (4.4H, m), 7.25-7.28 (1H, m), 7.21 (0.4H, br. s), 7.11-7.15 (0.6H, m), 6.98 (0.6H, s), 6.85 (0.4H, dd, J = 8.0, 1.4 Hz), 6.52 (0.6H, dd, J = 8.0, 1.4 Hz), 6.32-6.38 (1H, m), 4.74 (1.2H, s), 4.36 (0.8H, s), 4.13-4.29 (1H, m), 3.53-3.60 (0.8H, m), 3.23-3.37 (1.2H, m), 2.74-2.93 (2H, m), 2.25-2.38 (1H, m), 1.38-2.10 (6H, m), 1.45-1.61 (2H, m) |
| 504 | δ (500 MHz, DMSO-d₆) 12.18 (1H, br. s.), 7.74 (0.3H, s), 7.66 (0.7H, s), 7.56 (0.3H, d, J = 1.2 Hz), 7.47 (0.7H, d, J = 2.2 Hz), 7.44 (1.4H, dt, J = 2.4, 8.6 Hz), 7.33-7.42 (3.6H, m), 7.25 (0.7H, d, J = 8.3 Hz), 7.14 (0.3H, d, J = 8.3 Hz), 4.77 (1.3H, s), 4.43 (0.7H, s), 4.13-4.26 (1H, m), 3.57 (0.7H, t, J = 7.5 Hz), 3.27-3.35 (1.3H, m), 2.95 (0.7H, t, J = 7.8 Hz), 2.81 (1.3H, t, J = 7.8 Hz), 2.25-2.38 (1H, m), 1.87-2.09 (6H, m), 1.46-1.59 (2H, m) |
| 505 | δ (500 MHz, DMSO-d₆) 12.18 (1H, br. s.), 7.74 (0.3H, s), 7.68 (0.7H, s), 7.37-7.46 (3H, m), 7.17 (0.7H, d, J = 8.3 Hz), 6.85-7.01 (2.6H, m), 6.77 (0.7H, d, J = 8.3 Hz), 4.77 (1.4H, s), 4.43 (0.6H, s), 4.14-4.28 (1H, m), 3.40-3.45 (0.6H, m), 3.12-3.19 (1.4H, m), 2.74-2.79 (0.6H, m), 2.58-2.64 (1.4H, m), 2.25-2.37 (1H, m), 2.19-2.22 (1.8H, m), 2.18 (2.1H, s), 1.89-2.09 (6H, m), 1.79 (2.1H, s), 1.47-1.60 (2H, m) |

| example | |
|---|---|
| 506 | δ (500 MHz, DMSO-d$_6$) 12.18 (1H, s), 11.05 (1H, s), 7.70 (0.3H, s), 7.66 (0.7H, s), 7.19-7.47 (5.4H, m), 7.13 (0.6H, d, J = 8.3 Hz), 6.98-7.02 (0.3H, m), 6.92-6.96 (0.7H, m), 6.80 (0.3H, d, J = 7.1 Hz), 6.61 (0.7H, d, J = 7.1 Hz), 6.48-6.50 (0.3H, m), 5.78-5.80 (0.7H, m), 4.79 (1.4H, s), 4.38 (0.6H, s), 4.15-4.27 (1H, m), 3.58-3.63 (0.6H, m), 3.29-3.63 (1.4H, m), 3.06 (0.6H, dd, J = 8.8, 6.8 Hz), 2.88-2.94 (1.4H, m), 2.25-2.38 (1H, m), 1.89-2.11 (6H, m), 1.46-1.59 (2H, m) |
| 507 | δ (500 MHz, DMSO-d$_6$) 12.18 (1H, br. s.), 10.82 (1H, br. s.), 7.75 (0.7H, s), 7.70 (0.3H, s), 7.48 (0.3H, d, J = 7.8 Hz), 7.36-7.40 (3.3H, m), 7.33 (0.3H, d, J = 8.1 Hz), 7.29 0.7H, d, J = 8.1 Hz), 7.13-7.17 (1H, m), 6.94-7.08 (2H, m), 6.89 (0.7H, d, J = 8.3 Hz), 6.84 (0.7H, t, J = 7.6), 4.77 (1.4H, s), 4.42 (0.6H, s), 4.16-4.28 (1H, m), 3.59 (0.6H, t, J = 8.1 Hz), 3.28-3.34 (1.4H, m), 2.95 (0.6H, t, J = 7.8 Hz), 2.82 (1.4H, t, J = 8.1 Hz), 2.25-2.37 (1H, m), 1.88-2.10 (6H, m), 1.47-1.59 (2H, m) |
| 508 | δ (500 MHz, DMSO-d$_6$) 12.16 (1H, br. S.), 11.07 (0.4H, s), 10.96 (0.6H, s), 7.61 (0.4H, s), 7.28-7.44 (5.4H, m), 7.09 (0.6H, s), 6.86-7.02 (2H, m), 6.59 (0.6H, d, J = 7.1 Hz), 6.45 (0.4H, dd, J = 2.8, 1.8 Hz), 6.42 (0.6H, dd, J = 2.8, 1.8 Hz), 4.73 (1.2H, s), 4.32 (0.8H, s), 4.12-4.21 (1H, m), 3.65 (0.8H, t, J = 7.3 Hz), 3.30-3.40 (1.2H, m), 3.14 (0.8H, t, J = 7.3 Hz), 3.05 (1.2H, t, J = 7.1 Hz), 2.25-2.34 (1H, m), 2.00-2.07 (2H, m), 1.85-1.97 (4H, m), 1.46-1.58 (2H, m) |
| 509 | δ (500 MHz, DMSO-d$_6$) 12.17 (1H, s), 7.74 (0.3H, s), 7.64 (0.7H, s), 7.36-7.47 (3.3H, m), 7.15-7.19 (0.7H, m), 7.03-7.15 (3.3H, m), 6.89-6.92 (0.7H, m), 4.78 (1.4H, s), 4.44 (0.6H, s), 4.15-4.28 (1H, m), 3.43-3.49 (0.6H, m), 3.17-3.23 (1.4H, m), 2.79-2.84 (0.6H, m), 2.62-2.69 (1.4H, m), 2.28-2.37 (1H, m), 2.25 (1H, s), 1.89-2.092 (6H, m), 1.83 (2H, s), 1.48-1.60 (2H, m) |
| 510 | δ (500 MHz, DMSO-d$_6$) 12.21 (1H, br. s.), 7.74 (0.2H, s), 7.70 (0.8H, s), 7.32 (0.4H, s), 7.24 (1.6H, s), 4.17-4.27 (1H, m), 3.52-3.57 (0.4H, m), 3.24-3.41 (3.2H, m), 3.12 (0.4H, d, J = 7.1 Hz), 3.04 (0.4H, d, J = 6.8 Hz), 2.91 (1.6H, t, J = 8.1 Hz), 2.21-2.38 (4H, m), 1.90-2.10 (6H, m), 1.45-1.82 (8H, m), 0.90-1.25 (5H, m) |
| 511 | δ (500 MHz, DMSO-d$_6$) 12.20 (1H, br. s.), 7.79-7.83 (1H, m), 7.24 (2H, s), 4.20-4.28 (1H, m), 3.36-3.47 (2H, m), 2.89 (2H, t, J = 7.8 Hz), 2.27-2.37 (1H, m), 2.23 (3H, s), 1.89-2.10 (7H, m), 1.21-1.61 (13H, m), 0.93 (3H, s) |
| 512 | δ (500 MHz, DMSO-d$_6$) 12.17 (1H, br. s.), 7.78 (1H, s), 7.24 (2H, s), 4.20-4.28 (1H, m), 3.29-3.42 (4H, m), 2.88 (2H, t, J = 8.1 Hz), 2.29-2.32 (1H, m), 2.23 (3H, s), 1.90-2.10 (6H, m), 1.55 (2H, qd, J = 12.6, 4.2 Hz), 0.95 (9H, s) |
| 513 | δ (500 MHz, DMSO-d$_6$) 12.18 (1H, br. s.), 10.69-10.74 (1H, m), 7.79 (0.75H, s), 7.63 (0.25H, s), 7.36-7.47 (4H, m), 7.15-7.23 (1.25H, m), 6.88-6.99 (1.25H, m), 6.77-6.84 (1.5H, m), 4.82 (1.5H, s), 4.44 (0.5H, s), 4.15-4.28 (1H, m), 3.32-3.47 (0.5H, m), 3.13-3.19 (1.5H, m), 2.83-2.88 (0.5H, m), 2.66-2.71 (1.5H, m), 2.30-2.38 (1H, m), 2.28 (0.75, s), 1.89-2.10 (8.25H, m), 1.48-1.61 (2H, m) |
| 514 | δ (500 MHz, DMSO-d$_6$) 12.26 (1H, br. s.), 7.75 (0.2H, s), 7.73 (0.8H, s), 7.32 (0.4H, s), 7.24 (1.6H, s), 4.21-4.28 (1H, m), 3.52-3.57 (0.4H, m), 3.37 (1.6H, d, J = 7.3 Hz), 3.25-3.33 (1.6H, m), 3.10-3.15 (0.4H, m), 3.04 (0.4H, d, J = 6.8 Hz), 2.87-2.94 (1.6H, m), 2.28 (0.6H, s), 2.23 (2.4H, s), 2.03-2.13 (2H, m), 1.46-1.90 (12H, m), 0.91-1.27 (8H, m) |
| 515 | δ (500 MHz, DMSO-d$_6$) 12.26 (1H, br. s.), 7.81 (1H, s), 7.24 (2H, s), 4.23-4.30 (1H, m), 3.29-3.40 (2H, m), 2.89 (2H, t, J = 8.1 Hz), 2.23 (3H, s), 2.04-2.15 (3H, m), 1.74-1.90 (7H, m), 1.25 (3H, s), 0.95 (9H, s) |
| 516 | δ (400 MHz, CDCl$_3$) 7.68 (0.4H, s), 7.55 (0.6H, s), 7.18 (0.8H, s), 7.09 (1.2H, s), 4.70 (1H, br. s.), 4.49-4.64 (1H, m), 4.35-4.49 (1H, m), 4.07-4.35 (1H, m), 3.36-3.58 (1H, m), 2.39-2.53 (1H, m), 2.18-2.39 (4H, m), 1.98-2.18 (4H, m), 1.53-1.75 (6H, m), 1.37-1.53 (3H, m), 1.01-1.15 (1H, m), 0.83-0.97 (6H, m) |
| 517 | δ (400 MHz, CDCl$_3$) 7.57-7.62 (1H, m), 7.09-7.16 (2H, m), 5.48 (0.6H, s) 4.51 (1.4H, s) 4.18-4.24 (1H, m), 4.44-4.58 (1H, m), 2.39-2.54 (1H, m), 2.33 (6H, s), 1.98-2.17 (4H, m), 1.50-1.81 (2H, m), 0.90-1.09 (9H, m) |
| 518 | δ (400 MHz, CDCl$_3$) 7.66 (0.3H, s), 7.57 (0.7H, s), 7.17 (0.7H, s), 7.08 (1.4H, s), 4.81 (0.7H, s), 4.43 (1.4H, s), 4.12-4.33 (1H, m), 3.50-3.53 (1.3H, m), 3.19-3.34 (0.7H, m), 2.42-2.49 (1H, m), 2.31-2.39 (3H, m), 2.19-2.29 (2H, m), 2.04-2.14 (4H, m.), 1.53-1.81 (7H, m), 1.18-1.35 (2H, m), 0.70-1.04 (2H, m), 0.08-0.35 (4H, m) |
| 519 | δ (400 MHz, CDCl$_3$) 7.54-7.64 (1H, m), 7.19-7.08 (2H, m), 4.52 (2H, s), 4.12-4.30 (1H, m), 3.50 (2H, s), 2.46-2.50 (1H, m), 2.20-2.37 (5H, m), 1.97-2.14 (4H, m), 1.12-1.75 (12H, m), 0.85-1.07 (3H, m) |
| 520 | δ (400 MHz, CDCl$_3$) 7.64-7.67 (0.3H, m), 7.55 (0.7H, s), 7.15-7.19 (0.7H, m), 7.10 (1.3H, s), 4.70-4.79 (0.8H, m), 4.39 (1.2H, s), 4.12-4.32 (1H, m), 3.60-3.70 (1.3H, m), 3.37-3.44 (0.7H, m), 2.60 (0.3H, dt, J = 16.5, 8.4 Hz), 2.40-2.51 (1.7H, m), 2.29-2.39 (3H, m), 2.19-2.29 (2H, m), 1.99-2.17 (4H, m), 1.77-1.93 (2H, m), 1.55-1.74 (4H, m), 1.14-1.11 (6H, m) |
| 521 | δ (400 MHz, CDCl$_3$) 7.66 (0.3H, s), 7.55 (0.7H, s), 7.28-7.39 (3H, m), 4.72-4.82 (0.8H, m), 4.42 (1.2H, s), 4.15-4.32 (1H, m), 3.61-3.74 (1.2H, m), 3.33-3.43 (0.8H, m), 2.54-2.68 (0.6H, m), 2.33-2.54 (1.4H, m), 2.19-2.31 (2H, m), 1.98-2.19 (4H, m), 1.76-1.95 (2H, m), 1.54-1.71 (4H, m), 1.26-1.18 (6H, m) |
| 522 | δ (400 MHz, CDCl$_3$) 7.67-7.63 (1H, m), 7.16-7.09 (2H, m), 7.02-6.86 (2H, m), 4.84 (2H, s), 4.35 (2H, s), 4.16-4.30 (1H, m), 2.40-2.52 (1H, m), 2.37-2.23 (5H, m), 2.11-2.05 (4H, m.), 1.53-1.74 (2H, m) |
| 523 | δ (400 MHz, DMSO-d$_6$) 12.16 (br. s., 1H) 7.75 (s, 1H) 7.35-7.44 (m, 2H) 7.21-7.30 (m, 1H) 4.25 (d, J = 6.06 Hz, 1H) 3.35-3.44 (m, 4H) 2.86-3.00 (m, 2H) 2.24-2.41 (m, 1H) 1.87-2.12 (m, 6H) 1.44-1.65 (m, 2H) 0.95 (s, 9H) |

| example | |
|---|---|
| 524 | δ (400 MHz, CDCl₃) 7.72-7.77 (0.2H, m), 7.58 (0.8H, s), 7.22-7.38 (3H, m), 4.93 (0.4H, br. s.), 4.54 (1.6H, s), 4.25-4.17 (1H, m), 3.30-3.59 (1H, m), 2.37-2.56 (1H, m), 2.25 (2H, d, J = 13.5 Hz), 1.94-2.16 (3H, m), 1.52-1.76 (4H, m), 1.02 (8H, s), 0.84 (1H, s) |
| 525 | δ (400 MHz, CDCl₃) 7.68 (1H, s), 7.54-7.60 (1H, m), 7.28 (3H, s), 4.66-4.81 (1H, m), 4.51-4.64 (1H, m), 4.47 (1H, s), 4.17-4.34 (1H, m), 3.36-3.57 (1H, m), 2.36-2.58 (1H, m), 2.08-2.33 (4H, m), 1.53-1.80 (6H, m), 1.36-1.50 (3H, m), 1.03-1.17 (1H, m), 0.78-0.99 (6H, m) |
| 526 | δ (400 MHz, DMSO-d₆) 12.18 (br. s., 1H) 7.56-7.81 (m, 5H) 7.36 (s, 2H) 7.20-7.30 (m, 1H) 4.88 (s, 1.6H) 4.60 (s, 0.4H) 4.08-4.33 (m, 1H) 3.50-3.66 (m, 0.4H) 3.34-3.30 (m, 1.6H) 3.14-3.25 (m, 0.4H) 2.87-3.04 (m, 1.6H) 2.22-2.41 (m, 1H) 1.64-2.13 (m, 4H) 1.40-1.63 (m, 2H) 1.20-1.31 (m, 2H) |
| 527 | δ (400 MHz, CDCl₃) 7.55-7.74 (m, 2H) 7.45 (d, J = 8.22 Hz, 1H) 7.18-7.34 (m, 5H) 4.93 (br. s., 1H) 4.72 (d, J = 2.74 Hz, 1H) 4.32-4.21 (m, 2H) 2.46 (t, J = 12.13 Hz, 1H) 2.24 (d, J = 13.11 Hz, 2H) 2.06-2.13 (m, 5H) 1.53-1.78 (m, 2H) |
| 528 | δ (400 MHz, CDCl₃) 7.57-7.72 (3H, m), 7.48-7.55 (0.5H, m), 7.44 (0.9H, d, J = 8.1 Hz), 7.27-7.32 (1H, m), 7.10-7.17 (0.7H, m), 7.06 (0.9H, s), 4.87-5.08 (1H, m), 4.71 (1H, s), 4.13-4.34 (2H, m), 2.19-2.54 (5H, m), 1.99-2.15 (4H, m), 1.53-1.73 (4H, m) |
| 529 | δ (400 MHz, CDCl₃) 7.49 (0.2H, s), 7.44 (0.8H, s), 7.16 (0.4H, s), 7.00-7.11 (1.6H, m), 5.14-5.18 (0.2H, m), 5.04-5.07 (0.8H, m), 4.01-4.29 (1H, m), 3.71-3.76 (1H, m), 3.35-3.55 (1H, m), 3.14 (3H, s), 2.39-2.55 (1H, m), 2.20-2.34 (6H, m), 2.00-2.14 (4H, m), 1.57-1.75 (3H, m), 1.02 (8H, s), 0.81 (1H, s) |
| 530 | δ (400 MHz, CDCl₃) 7.39-7.53 (1H, m), 6.97-7.19 (2H, m), 5.42-5.53 (.1H, m), 4.94-5.11 (0.9H, m), 4.16-4.31 (1H, m), 4.03-4.15 (1H, m), 3.64-3.81 (1H, m), 3.18-3.54 (2H, m), 3.13 (3H, s), 2.37-2.52 (1H, m), 2.27 (5H, s), 2.00-2.13 (4H, m), 1.46-1.77 (2H, m), 1.01 (8H, s), 0.80 (1H, s) |
| 531 | δ (400 MHz, CDCl₃) 7.48 (0.2H, s), 7.15 (0.8H, s), 7.04 (2H, br. s.), 5.45-5.52 (0.2H, m), 5.04 (0.8H, dd, J = 9.6, 4.1 Hz), 4.15-4.29 (1H, m), 4.08 (1H, dd, J = 14.5, 9.4 Hz), 3.74 (1H, d, J = 12.1 Hz), 3.19-3.48 (2H, m), 3.12 (3H, s), 2.01-2.51 (10H, m), 1.54-1.73 (2H, m), 1.00 (8H, s), 0.79 (1H, s) |
| 532 | δ (400 MHz, CDCl₃) 7.66 (s, 0.4H), 7.57 (s, 0.6H), 7.17 (s, 0.8H). 7.10 (s, 1.2H), 4.80 (s, 0.8H), 4.42 (s, 1.2H), 4.14-4.33 (m, 1H), 3.47-3.55 (m, 1.2H), 3.24-3.29 (m, 0.8H), 2.14-2.40 (m, 5H), 1.85-2.00 (m, 5H), 1.05-1.73 (m, 13H), 0.76-1.00 (m, 6H) |
| 533 | δ (400 MHz, DMSO-d₆) 7.81 (0.3H, s), 7.70 (0.7H, s), 7.45 (0.6H, s), 7.38 (1.4H, s), 4.77 (0.6H, s), 4.37 (1.4H, s), 4.17-4.32 (1H, m), 2.36 (0.9H, s), 2.30 (2.1H, s), 1.98-2.17 (2H, m), 1.46-1.90 (12H, m) |
| 534 | δ (400 MHz, DMSO-d₆) 0.81-1.01 (m, 7H), 1.28-1.42 (m, 2H), 1.43-1.63 (m, 4H), 1.69-1.64 (m, 1H), 1.88-2.11 (m, 6H), 2.27-2.38 (m, 1H), 2.50-2.57 (m, 1H), 2.90-2.98 (m, 1H), 3.18-3.15 (m, 3H), 3.44-3.51 (m, 1H), 4.15-4.29 (m, 2H), 7.24-7.83 (m, 1H), 7.41 (d, J = 7.8 Hz, 1.3H), 7.49 (d, J = 7.8 Hz, 0.7H), 7.79 (s, 0.3H), 7.86 (s, 0.7H), 12.19 (br. s, 1H) |
| 535 | δ (400 MHz, DMSO-d₆) 7.82 (s, 0.2H), 7.69 (s, 0.8H), 7.47 (s, 0.4H). 7.40 (s, 1.6H), 4.78 (s, 0.4H), 4.59 (s, 1.6H), 4.17-4.29 (m, 1H), 3.14-3.39 (m, 2H), 2.26-2.41 (m, 4H), 1.87-2.11 (m, 6H), 1.33-1.66 (m, 7H), 0.97-1.29 (m, 6H), 0.67-0.95 (m, 6H) |
| 536 | δ (400 MHz, DMSO-d₆) 0.67-0.87 (m, 9H), 1.45-1.63 (m, 2H), 1.73-2.14 (m, 8H), 2.15-2.38 (m, 5H), 3.87-3.99 (m, 0.5H), 4.06-4.44 (m, 2.5H), 4.58-4.88 (m, 3H), 7.39 (d, J = 3.9 Hz, 1H), 7.47 (d, J = 3.9 Hz, 1H), 7.70 (s, 0.5H), 7.78 (s, 0.25H), 7.80 (s, 0.25H), 12.24 (br. S, 1H) |
| 537 | δ (400 MHz, DMSO-d₆) 12.17 (1H, s), 7.80 (0.3H, s), 7.68 (0.7H, s), 7.45 (0.6H, s), 7.38 (1.4H, s), 4.77 (0.6H, s), 4.37 (1.4H, s), 4.16-4.32 (1H, m), 3.07-3.37 (1H, m), 2.43-2.69 (1H, m), 2.24-2.38 (4H, m), 1.85-2.11 (6H, m), 1.45-1.76 (7H, m), 0.85-1.27 (5H, m |
| 538 | δ (400 MHz, DMSO-d₆) 12.26 (1H, s), 8.88-9.04 (1H, m), 7.10-8.22 (5H, m), 4.81-4.92 (2H, m), 4.29 (1H, d, J = 3.5 Hz), 3.36 (2H, s), 2.05-2.20 (2H, m), 1.70-1.93 (6H, m), 1.22-1.29 (3H, m), 0.78-1.03 (9H, m) |
| 539 | δ (400 MHz, DMSO-d₆) 12.19 (1H, br. s.), 8.81-9.01 (1H, m), 8.12 (1H, dd, J = 16.7, 8.3 Hz), 6.78-8.02 (8H, m), 4.56-4.87 (4H, m), 4.18-4.33 (1H, m), 2.25-2.41 (1H, m), 1.88-2.14 (6H, m), 1.45-1.66 (2H, m) |
| 541 | δ (400 MHz, CD₃OD) 1.62-1.70 (2H, m), 2.04-2.24 (6H, m), 2.39-2.47 (1H, m), 4.29-4.35 (1H, m), 4.57 (2H, s), 4.62-4.69 (2H, m), 7.24 (1H, d, J = 8.04 Hz), 7.35-7.45 (5H, m), 7.71 (1H, s) |
| 542 | δ (400 MHz, CD₃OD) 1.02-1.08 (9H, m), 1.57-1.69 (2H, m), 2.01-2.23 (6H, m), 2.41 (1H, tt, J = 12.23, 3.52 Hz), 2.50-2.56 (3H, m), 4.26-4.35 (1H, m), 4.72 (2H, s), 7.44 (1H, s), 7.61-7.64 (1H, m) |
| 543 | δ (500 MHz, CDCl₃) 7.61 (s, 1H), 7.53 (s, 1), 7.24-7.27 (m, 2H), 7.17-7.20 (m, 2H), 7.11 (s, 1H), 7.01-7.05 (m, 2H), 4.75 (br, s, 2H), 4.60 (s, 1H), 4.54 (s, 1H), 4.12-4.25 (m, 4H), 2.17-2.47 (m, 5H), 1.63-2.02 (m, 3H), 1.56-1.58 (m, 2H) |
| 544 | δ (400 MHz, DMSO-d₆) 1.89-2.06 (12H, m), 2.27-2.33 (1H, m), 2.27-2.32 (1H, m), 2.36 (1H, s), 3.29-3.34 (1H, m), 3.57 (1H, t, J = 7.04 Hz), 3.91-3.95 (1H, m), 4.09-4.14 (1H, m), 4.46 (1H, s), 4.72 (1H, s), 5.89 (1H, s), 5.97 (1H, d, J = 5.67 Hz), 6.06 (1H, s), 7.10 (1H, d, J = 7.49 Hz), 7.34-7.44 (4H, m), 7.73 (1H, s) |
| 739 | δ (400 MHz, DMSO-d₆) 12.06-12.33 (m, 1H), 8.72 (s, 2H), 7.75 (s, 1H), 4.71 (s, 2H), 4.40 (br. s., 1H), 3.28 (s, 2H), 2.13 (d, J = 4.11 Hz, 1H), 1.97 (br. s., 1H), 1.91 (br. s., 1H), 1.69-1.86 (m, 3H), 0.88-1.01 (m, 13H), 0.77 (s, 1H) |

Example 900

ROR gamma Reporter Gene Assay

Luciferase reporter gene assay was used to assess inhibition of RORγ transcriptional activity.

ROR gamma expression vector was prepared by inserting the ligand binding domain of human ROR gamma (amino acid 247-497 of Genbank Accession NO. NM_001001523) adjacent to the yeast GAL4 transcription factor DNA binding domain in the expression vector pM (Clontech). The resulting expression vector pM-ROR gamma was used in transfection experiments together with the pGL4 luciferase reporter plasmid (Promega) containing five copies of the UAS GAL4 recognition site and pRL-CMV plasmids (Promega) containing the constitutive CMV promoter and the renilla luciferase.

For preparing transfection reagent/DNA mixture, 1 μg pM-ROR gamma, 1 μg pGL4 5×UAS, 625 pg pRL-CMV and 6.25 μL FuGENE™ HD transfection reagent (Promega) were mixed in 0.25 mL OPTI-MEM™ (Life technologies) at room temperature. At the same time, Negative control DNA mixture was prepared by using 1 μg pM empty vector instead of pM-ROR gamma plasmid. After a fifteen minute incubation, 0.25 mL of transfection reagent/DNA mixture was added to 1,000,000 of HEK293T cells (ATCC) in 5 mL of OPTI-MEM™ containing 10% Charcoal Stripped Fetal Bovine Serum.

Transfected cells were seeded onto 384 well plate (10 μL/well) and the 7.5 nL of test compounds were added to the wells in 8 concentrations ranging from 3.5 nM to 10.5 μM. The compounds were dissolved in 100% DMSO and the final concentration of DMSO in the assay was 0.075%.

After 24 h of incubation at 37° C., 5% $CO_2$ in a cell culture incubator, the Dual-Glo™ Luciferase Assay System was used to detect activity according to the manufacturer's instructions (Promega, Cat. No.: E2920).

Data was plotted and pIC50 values were calculated using the XLfit program (ID Business Solutions Ltd.). The results are shown in the following tables.

| example | result | example | result | example | result | example | result |
|---|---|---|---|---|---|---|---|
| 1 | 7.62 | 41 | 7.53 | 81 | 7.03 | 121 | <5.00 |
| 2 | 8.12 | 42 | 7.35 | 82 | 7.09 | 122 | <5.00 |
| 3 | <5.00 | 43 | 7.47 | 83 | 5.78 | 123 | 8.31 |
| 4 | 6.42 | 44 | 7.83 | 84 | 6.97 | 124 | 7.75 |
| 5 | 6.68 | 45 | 7.23 | 85 | 5.83 | 125 | 6.49 |
| 6 | 7.06 | 46 | 6.40 | 86 | 6.79 | 126 | 6.04 |
| 7 | 5.34 | 47 | 6.99 | 87 | 6.85 | 127 | 5.69 |
| 8 | <5.00 | 48 | <5.00 | 88 | 7.06 | 128 | 5.06 |
| 9 | <5.00 | 49 | 7.39 | 89 | 5.86 | 129 | 5.06 |
| 10 | 7.59 | 50 | 7.15 | 90 | 6.30 | 130 | 6.76 |
| 11 | 7.42 | 51 | 5.39 | 91 | 8.36 | 131 | 7.08 |
| 12 | 5.43 | 52 | 6.61 | 92 | 6.81 | 132 | 7.18 |
| 13 | 7.03 | 53 | 7.79 | 93 | 6.24 | 133 | 5.46 |
| 14 | 7.12 | 54 | 7.15 | 94 | 8.08 | 134 | 6.61 |
| 15 | 7.02 | 55 | 8.05 | 95 | 6.82 | 135 | 5.51 |
| 16 | 6.93 | 56 | 7.81 | 96 | 7.54 | 136 | 7.08 |
| 17 | 7.61 | 57 | 7.42 | 97 | 6.55 | 137 | 8.32 |
| 18 | 7.93 | 58 | 6.87 | 98 | <5.00 | 138 | 8.14 |
| 19 | <5.00 | 59 | 5.23 | 99 | 6.98 | 139 | 7.76 |
| 20 | 7.15 | 60 | <5.00 | 100 | 6.63 | 140 | 6.70 |
| 21 | <5.00 | 61 | 6.70 | 101 | 7.06 | 141 | 6.27 |
| 22 | <5.00 | 62 | <5.00 | 102 | 7.13 | 142 | 5.18 |
| 23 | 7.62 | 63 | 5.47 | 103 | 5.72 | 143 | 5.65 |
| 24 | 6.78 | 64 | <5.00 | 104 | 5.69 | 144 | 7.06 |
| 25 | 6.58 | 65 | <5.00 | 105 | 6.69 | 145 | 5.46 |
| 26 | 6.55 | 66 | 7.08 | 106 | 6.42 | 146 | 6.83 |
| 27 | 7.25 | 67 | 7.25 | 107 | 5.55 | 147 | 6.46 |
| 28 | 6.71 | 68 | 5.88 | 108 | 6.49 | 148 | 6.32 |
| 29 | 7.12 | 69 | <5.00 | 109 | 6.20 | 149 | 7.22 |
| 30 | 7.33 | 70 | <5.00 | 110 | 6.79 | 150 | 7.27 |
| 31 | 7.11 | 71 | 5.68 | 111 | 6.45 | 151 | 5.09 |
| 32 | 7.09 | 72 | 5.88 | 112 | 7.21 | 152 | 5.55 |
| 33 | 6.95 | 73 | 6.19 | 113 | 5.34 | 153 | 6.68 |
| 34 | 5.87 | 74 | 6.58 | 114 | 5.64 | 154 | <5.00 |
| 35 | 6.95 | 75 | 6.50 | 115 | 6.80 | 155 | 5.29 |
| 36 | 6.93 | 76 | 5.77 | 116 | <5.00 | 156 | 5.99 |
| 37 | 7.73 | 77 | 7.47 | 117 | 5.45 | 157 | <5.00 |
| 38 | 5.81 | 78 | 8.00 | 118 | 5.76 | 158 | <5.00 |
| 39 | <5.00 | 79 | 6.68 | 119 | 5.82 | 159 | <5.00 |
| 40 | 7.25 | 80 | 6.18 | 120 | 7.73 | 160 | 7.61 |
| 161 | 5.66 | 201 | <5.00 | 241 | 8.29 | 281 | 8.37 |
| 162 | 5.99 | 202 | 8.10 | 242 | 7.50 | 282 | 8.47 |
| 163 | <5.00 | 203 | 6.04 | 243 | 7.26 | 283 | 8.04 |
| 164 | 5.93 | 204 | 7.22 | 244 | 8.16 | 284 | 7.95 |
| 165 | 5.93 | 205 | 6.86 | 245 | 8.05 | 285 | — |
| 166 | 7.81 | 206 | 7.00 | 246 | 7.94 | 286 | 8.04 |
| 167 | 6.48 | 207 | 7.20 | 247 | 7.49 | 287 | 5.92 |
| 168 | 6.83 | 208 | 6.52 | 248 | 7.67 | 288 | 7.93 |
| 169 | 7.39 | 209 | <5.00 | 249 | >8.46 | 289 | 7.03 |
| 170 | 6.75 | 210 | 5.99 | 250 | >8.46 | 290 | 6.72 |
| 171 | 6.78 | 211 | 7.65 | 251 | 8.22 | 291 | 5.99 |
| 172 | <5.00 | 212 | 7.70 | 252 | 8.00 | 292 | 7.32 |
| 173 | <5.00 | 213 | 6.95 | 253 | 7.34 | 293 | 7.48 |
| 174 | 6.18 | 214 | 6.49 | 254 | 7.73 | 294 | 7.31 |
| 175 | 6.22 | 215 | 7.49 | 255 | 7.26 | 295 | 5.25 |
| 176 | 5.59 | 216 | <5.98 | 256 | 8.22 | 296 | <4.98 |
| 177 | 6.85 | 217 | 6.66 | 257 | 7.70 | 297 | 7.18 |
| 178 | 5.36 | 218 | 6.47 | 258 | 8.18 | 298 | 7.89 |
| 179 | 7.28 | 219 | 8.31 | 259 | 6.93 | 299 | 7.68 |
| 180 | 6.95 | 220 | 6.98 | 260 | 8.22 | 300 | 7.62 |
| 181 | <5.00 | 221 | 8.53 | 261 | 8.34 | 301 | 6.73 |
| 182 | 7.18 | 222 | 8.38 | 262 | 7.39 | 302 | 7.83 |
| 183 | 6.76 | 223 | 7.30 | 263 | 8.23 | 303 | <5.46 |
| 184 | 6.79 | 224 | 8.57 | 264 | 8.09 | 304 | <4.98 |
| 185 | 5.74 | 225 | 8.53 | 265 | 7.74 | 305 | <4.98 |
| 186 | 7.57 | 226 | 8.47 | 266 | 8.27 | 306 | 8.08 |
| 187 | 6.65 | 227 | 8.40 | 267 | 7.87 | 307 | 5.08 |
| 188 | 6.56 | 228 | 6.71 | 268 | 6.97 | 308 | 7.78 |
| 189 | 7.52 | 229 | 7.89 | 269 | 8.09 | 309 | 7.95 |
| 190 | 8.08 | 230 | 8.18 | 270 | 7.79 | 310 | <4.98 |
| 191 | 8.05 | 231 | 7.97 | 271 | 8.29 | 311 | <4.98 |
| 192 | 7.93 | 232 | 7.77 | 272 | 7.95 | 312 | 7.28 |
| 193 | 8.19 | 233 | 7.80 | 273 | 7.85 | 313 | 5.81 |
| 194 | 7.85 | 234 | 8.00 | 274 | 8.08 | 314 | 7.38 |
| 195 | <5.00 | 235 | 7.88 | 275 | >8.46 | 315 | 7.26 |
| 196 | 5.46 | 236 | 7.98 | 276 | 6.91 | 316 | 8.04 |
| 197 | 6.29 | 237 | >8.46 | 277 | 8.14 | 317 | 8.00 |
| 198 | <5.00 | 238 | 8.36 | 278 | 7.93 | 318 | 7.70 |
| 199 | 8.30 | 239 | >8.46 | 279 | 7.42 | 319 | 6.85 |
| 200 | 7.80 | 240 | 8.26 | 280 | 6.61 | 320 | 8.01 |
| 321 | 7.93 | 361 | 5.92 | 401 | 5.55 | | |
| 322 | 8.09 | 362 | 7.24 | 402 | 4.98 | | |
| 323 | 6.42 | 363 | 7.88 | 403 | 5.76 | | |
| 324 | 6.42 | 364 | 7.34 | 404 | 7.65 | | |
| 325 | 7.97 | 365 | 7.51 | 405 | 4.98 | | |
| 326 | 6.99 | 366 | 7.82 | 406 | 7.30 | | |
| 327 | 7.01 | 367 | 7.52 | 407 | 6.32 | | |
| 328 | 5.53 | 368 | 6.72 | 408 | 6.48 | | |
| 329 | 7.83 | 369 | 5.91 | 409 | 6.11 | | |
| 330 | 7.62 | 370 | 6.27 | 410 | 5.67 | | |
| 331 | 6.99 | 371 | 5.27 | 411 | 6.65 | | |
| 332 | 6.29 | 372 | 6.48 | 412 | 5.95 | | |
| 333 | 7.77 | 373 | 5.47 | | | | |
| 334 | 7.25 | 374 | 6.18 | | | | |
| 335 | 7.91 | 375 | 6.97 | | | | |
| 336 | 6.84 | 376 | 6.51 | | | | |
| 337 | 7.20 | 377 | 6.36 | | | | |
| 338 | 6.26 | 378 | 7.13 | | | | |
| 339 | 7.08 | 379 | 7.10 | | | | |
| 340 | 6.91 | 380 | 7.08 | | | | |
| 341 | 6.12 | 381 | 7.00 | | | | |
| 342 | 7.34 | 382 | 6.59 | | | | |
| 343 | 7.50 | 383 | 7.40 | | | | |
| 344 | 5.80 | 384 | 6.46 | | | | |
| 345 | 7.58 | 385 | 7.73 | | | | |
| 346 | 6.96 | 386 | 6.85 | | | | |

-continued

| example | result | example | result |
|---|---|---|---|
| 347 | 6.06 | 387 | 7.16 |
| 348 | 6.81 | 388 | 7.14 |
| 349 | 7.10 | 389 | 7.53 |
| 350 | 5.94 | 390 | 6.48 |
| 351 | 5.14 | 391 | 6.85 |
| 352 | 5.39 | 392 | 7.54 |
| 353 | 6.75 | 393 | 5.34 |
| 354 | 6.29 | 394 | 7.69 |
| 355 | 7.66 | 395 | 7.04 |
| 356 | 6.99 | 396 | 6.05 |
| 357 | 5.00 | 397 | 7.21 |
| 358 | 7.21 | 398 | 6.17 |
| 359 | 7.58 | 399 | 7.06 |
| 360 | 6.75 | 400 | 7.54 |

Example 901

ROR Gamma Coactivator Peptide Recruitment Alphascreen™ Assay

Alphascreen™ is a bead-based amplified homogenous luminescent proximity assay that can be used for measuring the effect of compounds on protein-protein interactions. When biological interactions bring donor and acceptor beads into close proximity, reactive oxygen, generated upon laser excitation of the donor beads, initiates a luminescence/fluorescence cascade in the acceptor beads that leads to a highly amplified signal that can be measured as light in the 520-620 nm range. When the acceptor and donor beads are not in proximity, the reactive oxygen decays and only a very low background signal is generated.

An in vitro assay to assess inhibition of RORγ binding to the coactivator GRIP1 was established using Alphascreen™ technology. The interaction between nuclear receptors (NR) and coactivator proteins is a key step in signal transduction from the receptor to the transcriptional machinery and can be measured in vitro using only the ligand binding domain of the nuclear receptor and a peptide containing a coactivator protein LXXLL nuclear receptor binding motif For the RORγ construct used in the coactivator recruitment assay, nucleotides corresponding to the ligand binding domain (LBD) of wild type human RORγ (amino acids 262-518 of Genbank Accession No. NM_005060.3) were cloned into the pET24 expression vector (Novagen), downstream of in-frame N-terminal 6xHis and Flag tag sequences. Recombinant 6xHis:Flag-tagged human RORγ-LBD protein was expressed in *E. coli* (BL-21) and purified by affinity chromatography on a nickel Sepharose column, followed by anion exchange chromatography.

A 4x assay mixture of 6xHis:Flag-tagged human RORγ-LBD with the agonist ligand 7-β-hydroxycholesterol was prepared in assay buffer (50 mM HEPES pH 7.4, BSA 0.05%, 150 mM NaCl, 5 mM MgCl2, 1 mM DTT, 0.01% Tween-20). For control wells a 4x mixture of 6xHis:Flag-tagged human ROR gamma LBD alone was also prepared.

A 4x stock of biotinylated coactivator peptide containing the LXXLL motif from GRIP1 (Biotin-PKKKQNALL-RYLLDKDDTKDI) was prepared in assay buffer.

A 4xdetection mixture of nickel chelate Alphascreen™ acceptor beads (PerkinElmer) and streptavidin Alphascreen™ donor beads (PerkinElmer) was prepared in assay buffer.

Compounds to be tested were arranged in a pre-dose 384-well mother plate serially diluted 1 in 2 over 22 columns, in 100% DMSO, at 40x the final test concentration, from a high concentration of 4 mM. DMSO with no compound was placed in control columns. The compounds were robotically dispensed directly into assay plates containing assay buffer to a 4x final test concentration.

Following compound addition, the 6xHis:Flag-tagged human RORγ-LBD plus 7-β-hydroxycholesterol assay mixture, biotinylated coactivator peptide and detection mixture were added. Final assay conditions were 5 nM 6xHis:Flag-tagged human RORγ-LBD, 30 nM 7-β-hydroxycholesterol, 50 nM biotinylated coactivator peptide, 2.5 ug/ml nickel acceptor beads and 10 ug/ml streptavidin donor beads. The final concentration of DMSO in the assay was 2.5%.

After overnight incubation at room temperature plates were read on and Envision™ plate reader (PerkinElmer).

Data was plotted and pIC50 values were calculated using the Genedata Screener™ data analysis suite (Genedata). The results are shown in the following tables.

| example | result | example | result | example | result | example | result |
|---|---|---|---|---|---|---|---|
| 500 | 7.82 | 539 | 7.05 | 579 | 8.37 | 618 | 7.98 |
| 501 | 8.42 | 541 | 8.50 | 580 | 8.30 | 619 | 8.11 |
| 502 | 6.56 | 542 | 7.10 | 581 | 8.46 | 620 | 7.41 |
| 503 | 6.45 | 543 | 8.48 | 582 | 7.64 | 621 | 6.52 |
| 504 | 8.16 | 544 | 5.44 | 583 | 8.62 | 622 | 6.64 |
| 505 | 8.23 | 545 | 8.31 | 584 | 8.24 | 623 | 7.07 |
| 506 | 7.16 | 546 | 7.95 | 585 | 7.16 | 624 | 6.99 |
| 507 | 7.49 | 547 | 7.71 | 586 | 6.48 | 625 | 8.13 |
| 508 | 6.12 | 548 | 7.93 | 587 | 7.17 | 626 | 8.55 |
| 509 | 7.94 | 549 | 8.76 | 588 | 8.48 | 627 | 7.19 |
| 510 | 8.75 | 550 | 7.67 | 589 | 7.37 | 628 | 7.57 |
| 511 | 8.73 | 552 | 6.48 | 590 | 6.76 | 629 | 7.34 |
| 512 | 8.14 | 553 | 8.56 | 591 | 8.68 | 630 | 8.40 |
| 513 | 7.48 | 554 | 8.15 | 592 | 8.17 | 631 | 8.00 |
| 514 | 8.72 | 555 | — | 593 | 7.48 | 632 | 8.40 |
| 515 | 8.33 | 556 | 8.62 | 594 | 7.13 | 633 | 8.09 |
| 516 | 8.22 | 557 | 8.55 | 595 | 8.25 | 634 | 6.06 |
| 517 | 7.60 | 558 | 8.61 | 596 | 6.82 | 635 | 6.49 |
| 518 | 8.58 | 559 | 8.15 | 597 | 5.62 | 636 | 6.88 |
| 519 | 8.29 | 560 | 6.53 | 598 | 6.94 | 637 | 6.14 |
| 520 | 8.60 | 561 | — | 599 | 7.86 | 638 | 7.81 |
| 521 | 8.73 | 562 | 8.43 | 600 | 6.10 | 639 | 7.24 |
| 522 | 8.68 | 563 | 6.69 | 601 | 7.37 | 640 | 6.11 |
| 523 | 8.06 | 564 | 8.38 | 602 | 6.76 | 641 | 8.67 |
| 524 | 7.11 | 565 | 7.74 | 603 | 7.31 | 642 | 7.62 |
| 525 | 8.23 | 566 | 8.51 | 604 | 5.18 | 643 | 8.37 |
| 526 | 8.23 | 567 | 8.62 | 605 | 6.82 | 644 | 8.40 |
| 527 | 8.08 | 568 | 8.47 | 606 | 8.35 | 645 | 7.86 |
| 528 | 8.38 | 569 | 5.17 | 607 | 6.98 | 646 | 6.53 |
| 529 | 7.20 | 570 | 7.73 | 608 | 6.91 | 647 | 6.44 |
| 530 | 7.29 | 571 | 8.90 | 609 | 7.02 | 648 | 7.49 |
| 531 | 5.97 | 572 | 8.33 | 610 | 7.91 | 649 | 8.74 |
| 532 | 8.13 | 573 | 7.10 | 611 | 8.22 | 650 | 8.10 |
| 533 | 8.83 | 574 | 5.59 | 612 | 7.40 | 651 | 7.27 |
| 534 | 8.10 | 575 | 7.77 | 613 | 6.96 | 652 | 8.36 |
| 535 | 8.88 | 576 | 7.46 | 614 | 7.27 | 653 | 7.15 |
| 536 | 8.02 | 577 | 7.93 | 615 | 7.31 | 654 | 6.45 |
| 537 | 8.65 | 578 | 7.00 | 616 | 7.47 | 655 | 7.57 |
| 538 | 6.95 | | | 617 | 6.93 | 656 | 6.73 |
| 657 | 8.65 | 696 | 8.79 | 735 | 8.56 | 774 | 7.66 |
| 658 | 8.71 | 697 | 7.89 | 736 | 6.96 | 775 | 8.52 |
| 659 | 6.48 | 698 | 8.68 | 737 | 7.85 | 776 | 7.66 |
| 660 | 7.59 | 699 | 7.40 | 738 | 7.87 | 777 | 8.37 |
| 661 | 7.69 | 700 | 7.88 | 739 | 8.24 | 778 | 8.35 |
| 662 | 8.15 | 701 | 8.03 | 740 | 7.84 | 779 | 7.74 |
| 663 | 8.71 | 702 | 8.10 | 741 | 8.83 | 780 | 8.12 |
| 664 | 8.84 | 703 | 7.15 | 742 | 8.58 | 781 | 8.81 |
| 665 | 8.86 | 704 | 8.61 | 743 | 8.65 | 782 | 8.40 |
| 666 | 8.34 | 705 | 7.23 | 744 | 9.23 | 783 | 8.41 |
| 667 | 6.52 | 706 | 7.49 | 745 | 9.00 | 784 | 7.46 |
| 668 | 8.46 | 707 | 8.21 | 746 | 7.49 | 785 | 8.40 |
| 669 | 8.39 | 708 | 7.97 | 747 | 8.40 | 786 | 7.46 |
| 670 | 7.66 | 709 | 9.05 | 748 | 8.47 | 787 | 8.68 |
| 671 | 9.06 | 710 | 7.56 | 749 | 7.22 | 788 | 7.76 |
| 672 | 8.69 | 711 | 8.69 | 750 | 8.80 | 789 | 8.68 |

-continued

| example | result | example | result | example | result | example | result |
|---|---|---|---|---|---|---|---|
| 673 | 7.44 | 712 | 7.89 | 751 | 8.03 | 790 | 7.46 |
| 674 | 7.75 | 713 | 8.39 | 752 | 8.32 | 791 | 8.28 |
| 675 | 6.63 | 714 | 8.45 | 753 | 7.60 | 792 | 6.99 |
| 676 | 7.29 | 715 | 7.98 | 754 | 8.16 | 793 | 7.60 |
| 677 | 8.25 | 716 | 8.57 | 755 | 8.63 | 794 | 8.53 |
| 678 | 8.97 | 717 | 8.68 | 756 | 8.59 | 795 | — |
| 679 | 7.92 | 718 | 8.76 | 757 | 8.10 | 796 | 4.74 |
| 680 | 7.32 | 719 | 8.22 | 758 | 8.45 | 797 | — |
| 681 | 8.02 | 720 | 7.13 | 759 | 8.43 | 798 | 8.50 |
| 682 | 7.30 | 721 | 9.08 | 760 | 8.62 | 799 | 8.41 |
| 683 | 8.05 | 722 | 8.02 | 761 | 8.10 | 800 | 8.52 |
| 684 | 7.86 | 723 | 8.00 | 762 | 8.27 | 801 | 8.07 |
| 685 | 7.01 | 724 | 8.22 | 763 | 8.79 | 802 | 8.52 |
| 686 | 7.04 | 725 | 8.35 | 764 | 8.36 | 803 | 7.20 |
| 687 | 7.83 | 726 | 8.56 | 765 | 6.61 | 804 | 7.27 |
| 688 | 6.96 | 727 | 7.93 | 766 | 7.49 | 805 | 7.95 |
| 689 | 8.38 | 728 | 8.32 | 767 | 6.43 | 806 | 6.99 |
| 690 | 8.17 | 729 | 8.62 | 768 | 8.40 | 807 | 7.34 |
| 691 | 8.78 | 730 | 8.45 | 769 | 7.73 | 808 | 6.73 |
| 692 | 8.49 | 731 | 9.03 | 770 | 7.37 | 809 | 7.75 |
| 693 | 7.36 | 732 | 8.04 | 771 | 8.20 | 810 | 8.51 |
| 694 | 8.40 | 733 | 8.60 | 772 | 8.43 | 811 | 8.75 |
| 695 | 8.00 | 734 | 8.00 | 773 | 7.09 | 812 | 8.03 |
| 813 | 8.22 | 852 | 6.05 | 891 | 7.81 | | |
| 814 | 8.04 | 853 | 7.77 | 892 | 6.52 | | |
| 815 | 7.89 | 854 | 8.33 | 893 | 8.65 | | |
| 816 | 8.35 | 855 | 8.24 | | | | |
| 817 | 7.19 | 856 | 7.17 | | | | |
| 818 | 8.14 | 857 | 7.47 | | | | |
| 819 | 7.30 | 858 | 8.70 | | | | |
| 820 | 7.00 | 859 | 8.22 | | | | |
| 821 | 8.01 | 860 | 7.94 | | | | |
| 822 | 5.23 | 861 | 8.32 | | | | |
| 823 | 5.04 | 862 | 7.42 | | | | |
| 824 | 7.54 | 863 | 8.19 | | | | |
| 825 | 8.86 | 864 | 8.53 | | | | |
| 826 | 7.73 | 865 | 8.11 | | | | |
| 827 | — | 866 | 8.65 | | | | |
| 828 | — | 867 | 7.61 | | | | |
| 829 | 8.02 | 868 | 8.34 | | | | |
| 830 | 8.57 | 869 | 7.86 | | | | |
| 831 | 8.58 | 870 | 6.24 | | | | |
| 832 | 8.41 | 871 | 8.30 | | | | |
| 833 | 8.23 | 872 | 7.01 | | | | |
| 834 | 8.00 | 873 | 8.28 | | | | |
| 835 | 6.60 | 874 | 8.11 | | | | |
| 836 | 7.51 | 875 | 7.93 | | | | |
| 837 | 8.43 | 876 | 8.21 | | | | |
| 838 | 7.86 | 877 | 8.21 | | | | |
| 839 | 8.14 | 878 | 8.41 | | | | |
| 840 | 6.62 | 879 | 8.53 | | | | |
| 841 | 6.71 | 880 | 7.79 | | | | |
| 842 | 6.51 | 881 | 7.61 | | | | |
| 843 | 8.23 | 882 | 6.19 | | | | |
| 844 | 7.52 | 883 | 6.15 | | | | |
| 845 | 8.84 | 884 | 8.74 | | | | |
| 846 | 8.62 | 885 | 6.13 | | | | |
| 847 | 7.66 | 886 | 6.33 | | | | |
| 848 | 8.88 | 887 | 7.79 | | | | |
| 849 | 8.06 | 888 | 8.49 | | | | |
| 850 | 7.89 | 889 | 8.69 | | | | |
| 851 | — | 890 | 9.15 | | | | |

The invention claimed is:

1. A compound represented by formula (I) or a pharmaceutically acceptable salt thereof:

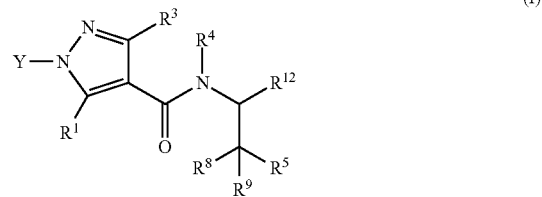

(I)

wherein:

$R^1$ is selected from F, Cl, Br, a $C_1$ to $C_6$ alkyl group substituted by 0, 1, 2 or 3 $R^a$ groups and a $C_3$ to $C_8$ cycloalkyl group substituted by 0, 1, 2 or 3 $R^a$ groups;

Y is selected from a $C_4$ to $C_6$ cycloalkyl group, a $C_6$ to $C_9$ bicycloalkyl group and a $C_6$ to $C_9$ spiroalkyl group, all of which are substituted by a $R^2$ group, 0 or 1 $R^6$ group and 0, 1, 2 or 3 $R^7$ groups;

$R^2$ is selected from —OH, —$CO_2H$, —$SO_3H$, —$CONH_2$, —$SO_2NH_2$, a ($C_1$ to $C_6$ alkoxy)carbonyl group substituted by 0, 1, 2 or 3 $R^c$ groups, a ($C_1$ to $C_6$ alkyl)aminocarbonyl group substituted by 0, 1, 2 or 3 $R^c$ groups, a $C_1$ to $C_6$ alkylsulfonyl group substituted by 0, 1, 2 or 3 $R^c$ groups, a $C_1$ to $C_6$ alkylaminosulfonyl group substituted by 0, 1, 2 or 3 $R^c$ groups, a (hydroxycarbonyl)($C_1$ to $C_3$ alkyl) group substituted by 0, 1, 2 or 3 $R^c$ groups, a ($C_1$ to $C_6$ alkoxy)carbonyl($C_1$ to $C_3$ alkyl) group substituted by 0, 1, 2 or 3 $R^c$ groups, a ($C_1$ to $C_6$ alkyl)sulfonyl($C_1$ to $C_3$ alkyl) group substituted by 0, 1, 2 or 3 $R^c$ groups and a ($C_2$ to $C_6$ alkenyl)($C_1$ to $C_3$ alkyl) group substituted by 0, 1, 2 or 3 $R^c$ groups;

$R^6$ and $R^7$ are independently selected from H, F, —OH, —$NH_2$, —CN, a $C_1$ to $C_6$ alkyl group substituted by 0, 1, 2 or 3 $R^b$ groups and a $C_1$ to $C_6$ alkoxy group substituted by 0, 1, 2 or 3 $R^b$ groups;

$R^3$ is selected from H, F, Cl, —$CH_3$ and —$CF_3$;

$R^4$ is selected from a $C_1$ to $C_6$ alkyl group substituted by 0, 1, 2, 3, 4 or 5 $R^e$ groups, a ($C_2$ to $C_6$ alkenyl)($C_1$ to $C_3$ alkyl) group substituted by 0, 1, 2, 3, 4 or 5 $R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or 5 $R^g$ groups and a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_6$ to $C_9$ spiroheteroalkyl group substituted by 0, 1, 2, 3, 4 or 5 $R^g$ groups, a $C_5$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups, a $C_6$ to $C_9$ heterobicycloalkyl group substituted by 0, 1, 2, 3, 4 or 5 $R^g$ groups, and a ($C_6$ to $C_9$ heterobicycloalkyl)($C_1$ to $C_3$ alkyl) group substituted by 0, 1, 2, 3, 4 or 5 $R^g$ groups;

$R^5$ is selected from a $C_6$ to $C_{10}$ aryl group substituted by 0, 1, 2, 3, 4 or 5 $R^i$ groups, a 5- to 10-membered heteroaryl group substituted by 0, 1, 2, 3, or 4 $R^i$ groups, a $C_3$ to $C_8$ cycloalkyl group substituted by 0, 1, 2, 3, 4 or 5$R^j$ groups, a $C_3$ to $C_8$ cycloalkenyl group substituted by 0, 1, 2, 3, 4 or 5$R^j$ groups and a 3- to 8-membered heterocycloalkyl group substituted by 0, 1, 2, 3, 4 or 5 $R^j$ groups;

$R^8$ and $R^9$ are independently selected from H, F, —OH, —$NH_2$, a $C_1$ to $C_3$ alkyl group substituted by 0, 1, 2 or 3 $R^h$ groups, and a $C_1$ to $C_6$ alkoxy group substituted by 0, 1, 2 or 3 $R^h$ groups; or $R^8$ and $R^9$ together form an oxo group or a thioxo group;

$R^{12}$ is H; or $R^4$ and $R^{12}$ together are —$CR^mR^m$—$CR^{13}R^{14}$—$CR^mR^m$— or —$CR^{13}R^{14}$—$CR^mR^m$—$CR^mR^m$— to form a pyrrolidine ring;

$R^{13}$ is selected from H, a C1 to $C_6$ alkyl group substituted by 0, 1, 2, 3, 4 or 5 $R^e$ groups, a $C_6$ to $C_{10}$ aryl group substituted by 0, 1, 2, 3, 4 or 5 $R^f$ groups, a $C_6$ to $C_{10}$ aryloxy group substituted by 0, 1, 2, 3, 4 or 5 $R^f$ groups, a ($C_2$ to $C_6$ alkenyl)($C_1$ to $C_3$ alkyl) group substituted by 0, 1, 2, 3, 4 or 5 $R^e$ groups, a ($C_2$ to $C_6$ alkynyl)($C_1$ to $C_3$ alkyl) group substituted by 0, 1, 2, 3, 4 or 5 $R^e$ groups, a ($C_1$ to $C_6$ alkoxy)($C_2$ to $C_4$ alkyl) group substituted by 0, 1, 2, 3, 4 or 5 $R^e$ groups, a ($C_6$ to $C_{10}$ aryl)($C_1$ to $C_3$ alkyl) group substituted by 0, 1, 2, 3, 4 or 5 $R^f$ groups, a (5- to 10-membered heteroaryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a $C_3$ to $C_8$ cycloalkenyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a ($C_3$ to $C_8$ cycloalkenyl)($C_1$ to $C_3$ alkyl) group substituted by 0, 1, 2, 3, 4 or 5 $R^g$ groups, a 3- to 8-membered heterocycloalkyl group substituted by 0, 1, 2, 3, 4 or 5 $R^g$ groups and a (3- to 8-membered heterocycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_6$ to $C_9$ spiroheteroalkyl group substituted by 0, 1, 2, 3, 4 or 5 $R^g$ groups, a $C_6$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups, a $C_6$ to $C_9$ heterobicycloalkyl group substituted by 0, 1, 2, 3, 4 or 5 $R^g$ groups, and a ($C_6$ to $C_9$ heterobicycloalkyl)($C_1$ to $C_3$ alkyl) group substituted by 0, 1, 2, 3, 4 or 5 $R^g$ groups;

$R^{14}$ is independently selected from H and a $C_1$ to $C_6$ alkyl group substituted by 0, 1, 2, 3, 4 or 5 $R^e$ groups; or $R^{13}$ and $R^{14}$ together form a $C_3$ to $C_8$ cycloalkane ring substituted by 0, 1, 2, 3, 4 or 5 $R^g$ groups, $C_3$ to $C_8$ cycloalkene ring substituted by 0, 1, 2, 3, 4 or 5 $R^g$ groups, or a 3- to 8-membered heterocycloalkane ring substituted by 0, 1, 2, 3, 4 or 5 $R^g$ groups;

$R^m$ is independently selected from H, F, Cl, —$CH_3$ and —$CF_3$;

$R^g$ and $R^j$ are, independently selected from F, Cl, a $C_1$ to $C_6$ alkyl group, —OH, —CN, —$NH_2$, —$NO_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$, a $C_1$ to $C_6$ alkylene group substituted by 0, 1, 2 or 3 $R^l$ groups, a $C_2$ to $C_6$ alkenylene group substituted by 0, 1, 2 or 3 $R^l$ groups and an oxo group;

$R^f$ and $R^i$ are independently selected from F, Cl, Br, —OH, —CN, —$NO_2$, —$CO_2H$, a $C_1$ to $C_6$ alkyl group substituted by 0, 1, 2 or 3 $R^k$ groups, a $C_2$ to $C_6$ alkenyl group substituted by 0, 1, 2 or 3 $R^k$ groups, a $C_2$ to $C_6$ alkynyl group substituted by 0, 1, 2 or 3 $R^k$ groups, a $C_3$ to $C_8$ cycloalkyl group substituted by 0, 1, 2 or 3 $R^k$ groups, a $C_1$ to $C_6$ alkoxy group substituted by 0, 1, 2 or 3 $R^k$ groups, a $C_3$ to $C_8$ cycloalkyloxy group substituted by 0, 1, 2 or 3 $R^k$ groups, —SH, a $C_1$ to $C_6$ alkylthio group substituted by 0, 1, 2 or 3 $R^k$ groups, a $C_3$ to $C_8$ cycloalkylthio group substituted by 0, 1, 2 or 3 $R^k$ groups, a ($C_1$ to $C_6$ alkyl)carbonyl group substituted by 0, 1, 2 or 3 $R^k$ groups, a ($C_1$ to $C_6$ alkoxy)carbonyl group substituted by 0, 1, 2 or 3 $R^k$ groups, a ($C_1$ to $C_6$ alkyl)aminocarbonyl group substituted by 0, 1, 2 or 3 $R^k$ groups, a 3- to 8-membered heterocycloalkyl group substituted by 0, 1, 2 or 3 $R^k$ groups, a $C_1$ to $C_6$ alkylsulfonyl group substituted by 0, 1, 2 or 3 $R^k$ groups, —$NH_2$, a mono($C_1$ to $C_6$ alkyl)amino group substituted by 0, 1, 2 or 3 $R^k$ groups and a di($C_1$ to $C_6$ alkyl)amino group substituted by 0, 1, 2 or 3 $R^k$ groups; and $R^a$, $R^b$, $R^c$, $R^e$, $R^h$, $R^k$ and $R^l$ are independently selected from F, a $C_1$ to $C_4$ alkyl group, —OH, —CN, —$NO_2$, —$NH_2$, —$CO_2H$, a $C_1$ to $C_6$ alkoxy group, a mono($C_1$ to $C_6$ alkyl)amino group, a di($C_1$ to $C_6$ alkyl)amino group, —$CF_3$ and an oxo group.

2. The compound according to claim 1 or pharmaceutically acceptable salt thereof, wherein Y is selected from formula (II-a), formula (II-b), formula (II-c) and formula (II-d):

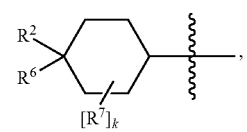

(II-a)

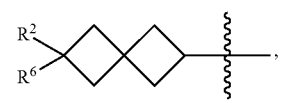

(II-b)

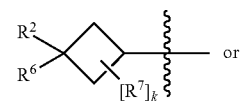

(II-c)

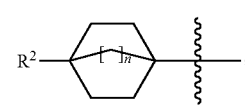

(II-d)

wherein:
k is 0, 1 or 2;
and n is 1, 2 or 3.

3. The compound according to claim 2 or pharmaceutically acceptable salt thereof, wherein Y is a group represented by formula (II-a):

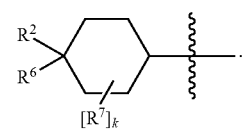

(II-a)

4. The compound according to claim 2 or pharmaceutically acceptable salt thereof, wherein Y is a group represented by formula (II-d):

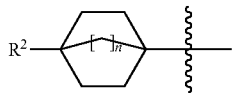

(II-d)

and n is 2.

5. The compound according to claim 1 or pharmaceutically acceptable salt thereof, wherein $R^3$ is H.

6. The compound according to claim 5 or pharmaceutically acceptable salt thereof, wherein $R^2$ is —$CO_2H$ or a hydroxycarbonylmethyl group substituted by 0, 1 or 2 $R^e$ groups.

7. The compound according to claim 6 or pharmaceutically acceptable salt thereof, wherein $R^{12}$ is H.

8. The compound according to claim 1 or pharmaceutically acceptable salt thereof, wherein $R^8$ and $R^9$ together form an oxo group or both $R^8$ and $R^9$ are H.

9. The compound according to claim 1 or pharmaceutically acceptable salt thereof, wherein $R^1$ is —$CF_3$, —$CF_2H$ or Cl.

10. The compound according to claim 1 or pharmaceutically acceptable salt thereof, wherein $R^5$ is a $C_6$ to $C_{10}$ aryl group substituted by 0, 1, 2, 3, 4 or 5 $R^i$ groups or a 5- to 10-membered heteroaryl group substituted by 0, 1, 2, 3, or 4 $R^i$ groups.

11. The compound according to claim 1 or pharmaceutically acceptable salt thereof, wherein $R^4$ is a $C_1$ to $C_6$ alkyl group substituted by 0, 1, 2 or 3 $R^e$ groups, a ($C_6$ to $C_{10}$ aryl)($C_1$ to $C_3$ alkyl) group substituted by 0, 1, 2, 3, 4 or 5 $R^f$ groups, a $C_3$ to $C_8$ cycloalkyl group substituted by 0, 1, 2, 3, 4 or 5 $R^g$ groups, a ($C_3$ to $C_8$ cycloalkyl)($C_1$ to $C_3$ alkyl) group substituted by 0, 1, 2, 3, 4 or 5 $R^g$ groups, a $C_6$ to $C_9$ spiroalkyl group substituted by 0, 1, 2, 3, 4 or 5 $R^g$ groups, a ($C_6$ to $C_9$ spiroalkyl)($C_1$ to $C_3$ alkyl) group substituted by 0, 1, 2, 3, 4 or 5 $R^g$ groups, a $C_5$ to $C_9$ bicycloalkyl group substituted by 0, 1, 2, 3, 4 or 5 $R^g$ groups, a ($C_5$ to $C_9$ bicycloalkyl)($C_1$ to $C_3$ alkyl) group substituted by 0, 1, 2, 3, 4 or 5 $R^g$ groups or a ($C_6$ to $C_9$ heterobicycloalkyl)($C_1$ to $C_3$ alkyl) group substituted by 0, 1, 2, 3, 4 or 5 $R^g$ groups.

12. A compound selected from:
(1R,3S)-3-(4-((2-(3,5-dichloropyridin-4-yl)-2-oxoethyl)-((4-fluorophenyl)methyl)carbamoyl)-5-(trifluoromethyl)pyrazol-1-yl)cyclopentane-1-carboxylic acid;
(1S,3S)-3-(4-((2-(3,5-dichloropyridin-4-yl)-2-oxoethyl)-((4-fluorophenyl)methyl)carbamoyl)-5-(trifluoromethyl)pyrazol-1-yl)cyclopentane-1-carboxylic acid;
1-(trans-4-carbamoylcyclohexyl)-N-(2-(3,5-dichloropyridin-4-yl)-2-oxoethyl)-N-(4-fluorobenzyl)-5-(trifluoromethyl)-1H-pyrazole-4-carboxamide;
4-(4-(((1R,3r,5S)-6,6-dimethyl-3-bicyclo[3.1.0]hexanyl)-(2-oxo-2-(2,4,6-trichlorophenyl)ethyl)carbamoyl)-5-(trifluoromethyl)pyrazol-1-yl)bicyclo(2.2.2)octane-1-carboxylic acid;
4-(4-((1-fluorocyclopentyl)methyl-(2-oxo-2-(2,4,6-trichlorophenyl)ethyl)carbamoyl)-5-(trifluoromethyl)pyrazol-1-yl)bicyclo[2.2.2]octane-1-carboxylic acid;
4-(4-((2-(2,6-dichloro-4-fluorophenyl)-2-oxoethyl)-((1-fluorocyclopentyl)methyl)carbamoyl)-5-(trifluoromethyl)pyrazol-1-yl)bicyclo[2.2.2]octane-1-carboxylic acid;
4-(4-((2-(2,6-dichloro-4-fluorophenyl)-2-oxoethyl)-((1R,3r,5S)-6,6-dimethyl-3-bicyclo[3.1.0]hexanyl)carbamoyl)-5-(trifluoromethyl)pyrazol-1-yl)bicyclo(2.2.2)octane-1-carboxylic acid;
4-(4-((2-(2,6-dichloro-4-fluorophenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid;
4-(4-((2-(2,6-dichloro-4-fluorophenyl)-2-oxoethyl)-(2,2-dimethylbutyl)carbamoyl)-5-(trifluoromethyl)pyrazol-1-yl)bicyclo[2.2.2]octane-1-carboxylic acid;
4-(4-((2-(2,6-dichloro-4-fluorophenyl)-2-oxoethyl)-(2,2-dimethylpropyl)carbamoyl)-5-(trifluoromethyl)pyrazol-1-yl)bicyclo[2.2.2]octane-1-carboxylic acid;
4-(4-((2-(2,6-dichloro-4-fluorophenyl)-2-oxoethyl)-(4,4-dimethylcyclohexyl)carbamoyl)-5-(trifluoromethyl)pyrazol-1-yl)bicyclo[2.2.2]octane-1-carboxylic acid;
4-(4-((2-(2,6-dichloro-4-fluorophenyl)-2-oxoethyl)-(4,4-dimethylcyclohexyl)carbamoyl)-5-(difluoromethyl)pyrazol-1-yl)bicyclo[2.2.2]octane-1-carboxylic acid;
4-(4-((2-(2,6-dichloro-4-methylphenyl)-2-oxoethyl)-((1-fluorocyclopentyl)methyl)carbamoyl)-5-(trifluoromethyl)pyrazol-1-yl)bicyclo[2.2.2]octane-1-carboxylic acid;
4-(4-((2-(2,6-dichloro-4-methylphenyl)-2-oxoethyl)-((1-methyl-7-oxabicyclo[2.2.1]heptan-4-yl)methyl)carbamoyl)-5-(trifluoromethyl)pyrazol-1-yl)bicyclo[2.2.2]octane-1-carboxylic acid;
4-(4-((2-(2,6-dichloro-4-methylphenyl)-2-oxoethyl)((1R,3r,5S)-6,6-dimethylbicyclo[3.1.0]hexan-3-yl)carbamoyl)-5-(trifluoromethyl)-1H-pyrazol-1-yl)bicyclo[2.2.2]octane-1-carboxylic acid;
4-(4-((2-(2,6-dichloro-4-methylphenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid;
4-(4-((2-(2,6-dichloro-4-methylphenyl)-2-oxoethyl)-(4,4-dimethylcyclohexyl)carbamoyl)-5-(trifluoromethyl)pyrazol-1-yl)bicyclo[2.2.2]octane-1-carboxylic acid;
4-(4-((2-(2,6-dichlorophenyl)-2-oxoethyl)((1R,3r,5S)-6,6-dimethylbicyclo[3.1.0]hexan-3-yl)carbamoyl)-5-(trifluoromethyl)-1H-pyrazol-1-yl)bicyclo[2.2.2]octane-1-carboxylic acid;
4-(4-((2-(2,6-dichlorophenyl)-2-oxoethyl)-(2,2-dimethylpropyl)carbamoyl)-5-(trifluoromethyl)pyrazol-1-yl)bicyclo[2.2.2]octane-1-carboxylic acid;
4-(4-((2-(2-chloro-6-(trifluoromethyl)phenyl)-2-oxoethyl)-((1R,3r,5S)-6,6-dimethyl-3-bicyclo[3.1.0]hexanyl)carbamoyl)-5-(trifluoromethyl)pyrazol-1-yl)bicyclo[2.2.2]octane-1-carboxylic acid;
4-(4-((2-(2-chloro-6-(trifluoromethyl)phenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid;
4-(4-((2-(2-chloro-6-(trifluoromethyl)phenyl)-2-oxoethyl)-(2,2-dimethylpropyl)carbamoyl)-5-(trifluoromethyl)pyrazol-1-yl)bicyclo[2.2.2]octane-1-carboxylic acid;
4-(4-((2-(2-chloro-6-(trifluoromethyl)phenyl)-2-oxoethyl)-(4,4-dimethylcyclohexyl)carbamoyl)-5-(trifluoromethyl)pyrazol-1-yl)bicyclo[2.2.2]octane-1-carboxylic acid;
4-(4-((2-(2-chloro-6-methoxyphenyl)-2-oxoethyl)-((1R,3r,5S)-6,6-dimethyl-3-bicyclo[3.1.0]hexanyl)carbamoyl)-5-(trifluoromethyl)pyrazol-1-yl)bicyclo[2.2.2]octane-1-carboxylic acid;
4-(4-((2-(2-chloro-6-methoxyphenyl)-2-oxoethyl)-((3,3-dimethylcyclobutyl)methyl)carbamoyl)-5-(trifluoromethyl)pyrazol-1-yl)bicyclo[2.2.2]octane-1-carboxylic acid;

4-(4-((2-(2-chloro-6-methoxyphenyl)-2-oxoethyl)-(4,4-dimethylcyclohexyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-((1-(trifluoromethyl)cyclopropyl)methyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-((1-fluorocyclopentyl)methyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-((1-methylcyclopropyl)methyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-((2,2,3,3-tetramethylcyclopropyl)methyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-((4-fluorophenyl)methyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-((4-fluorophenyl)methyl)carbamoyl)-5-(trifluoromethyl)pyrazol-1-yl)bicyclo[2.2.1]heptane-1-carboxylic acid;

4-(4-((2-(3,5-dichloropyridin-4-yl)-2-oxoethyl)-(2,2-dimethylbutyl)carbamoyl)-5-(trifluoromethyl)pyrazol-1-yl)bicyclo[2.2.2]octane-1-carboxylic acid;

4-(4-((2-(3,5-dichloropyridin-4-yl)-2-oxoethyl)-(2-fluoro-2-methylpropyl)carbamoyl)-5-(trifluoromethyl)pyrazol-1-yl)bicyclo[2.2.2]octane-1-carboxylic acid;

4-(4-((2-(3,5-dichloropyridin-4-yl)ethyl)(4-fluorobenzyl)carbamoyl)-5-(trifluoromethyl)-1H-pyrazol-1-yl)cyclohexanecarboxylic acid;

4-(4-((2-(3-chloro-5-fluoropyridin-4-yl)-2-oxoethyl)((1R,3r,5S)-6,6-dimethylbicyclo[3.1.0]hexan-3-yl)carbamoyl)-5-(trifluoromethyl)-1H-pyrazol-1-yl)bicyclo(2.2.2)octane-1-carboxylic acid;

4-(4-((3,3-dimethylcyclobutyl)methyl-(2-oxo-2-(2,4,6-trichlorophenyl)ethyl)carbamoyl)-5-(trifluoromethyl)pyrazol-1-yl)bicyclo[2.2.2]octane-1-carboxylic acid;

4-(4-((4,4-dimethylcyclohexyl)-(2-oxo-2-(2,4,6-trichlorophenyl)ethyl)carbamoyl)-5-(trifluoromethyl)pyrazol-1-yl)bicyclo[2.2.2]octane-1-carboxylic acid;

4-(4-(2,2-dimethylbutyl-(2-oxo-2-(2,4,6-trichlorophenyl)ethyl)carbamoyl)-5-(trifluoromethyl)pyrazol-1-yl)bicyclo[2.2.2]octane-1-carboxylic acid;

4-(4-(2,2-dimethylpropyl-(2-oxo-2-(2,4,6-trichlorophenyl)ethyl)carbamoyl)-5-(trifluoromethyl)pyrazol-1-yl)bicyclo[2.2.2]octane-1-carboxylic acid;

cis-3-(4-(2-(2,6-dichloro-4-fluorophenyl)-2-oxoethyl)-(4,4-dimethylcyclohexyl)carbamoyl)-5-(trifluoromethyl)pyrazol-1-yl)cyclobutane-1-carboxylic acid;

cis-3-(4-((2-(3,5-dichloropyridin-4-yl)-2-oxoethyl)(4-fluorobenzyl)carbamoyl)-5-(trifluoromethyl)-1H-pyrazol-1-yl)cyclobutanecarboxylic acid;

cis-4-(4-(2-(2,6-dichloro-4-fluorophenyl)-2-oxoethyl)-(4,4-dimethylcyclohexyl)carbamoyl)-5-(trifluoromethyl)pyrazol-1-yl)-1-methylcyclohexane-1-carboxylic acid;

cis-4-(4-((2-(3,5-dichloropyridin-4-yl)-2-oxoethyl)-((4-fluorophenyl)methyl)carbamoyl)-5-(trifluoromethyl)pyrazol-1-yl)-1-hydroxycyclohexane-1-carboxylic acid;

cis-4-(4-((2-(3,5-dichloropyridin-4-yl)-2-oxoethyl)-((4-fluorophenyl)methyl)carbamoyl)-5-(trifluoromethyl)pyrazol-1-yl)-1-aminocyclohexane-1-carboxylic acid;

cis-4-(4-((2-(3,5-dichloropyridin-4-yl)-2-oxoethyl)-((4-fluorophenyl)methyl)carbamoyl)-5-(trifluoromethyl)pyrazol-1-yl)-1-aminocyclohexane-1-carboxylic acid;

cis-4-(4-((2-(3,5-dichloropyridin-4-yl)-2-oxoethyl)(4-fluorobenzyl)carbamoyl)-5-(trifluoromethyl)-1H-pyrazol-1-yl)cyclohexanecarboxylic acid;

cis-4-(4-((2-(3,5-dichloropyridin-4-yl)-2-oxoethyl)(4-fluorobenzyl)carbamoyl)-5-(trifluoromethyl)-1H-pyrazol-1-yl)-1-fluorocyclohexane-1-carboxylic acid;

N-(2-(3,5-dichloropyridin-4-yl)-2-oxoethyl)-N-((3,5-difluorophenyl)methyl)-1-(trans-4-(hydroxycarbamoyl)cyclohexyl)-5-(trifluoromethyl)pyrazole-4-carboxamide;

N-(2-(3,5-dichloropyridin-4-yl)-2-oxoethyl)-N-((3,5-difluorophenyl)methyl)-1-(trans-4-(methoxycarbamoyl)cyclohexyl)-5-(trifluoromethyl)pyrazole-4-carboxamide;

N-(2-(3,5-dichloropyridin-4-yl)-2-oxoethyl)-N-(3,5-difluorobenzyl)-1-(trans-4-hydroxycyclohexyl)-5-(trifluoromethyl)-1H-pyrazole-4-carboxamide;

N-(2-(3,5-dichloropyridin-4-yl)-2-oxoethyl)-N-(4-fluorobenzyl)-1-(cis-4-(methylsulfonyl)cyclohexyl)-5-(trifluoromethyl)-1H-pyrazole-4-carboxamide;

N-(2-(3,5-dichloropyridin-4-yl)-2-oxoethyl)-N-(4-fluorobenzyl)-1-(trans-4-(methylsulfonyl)cyclohexyl)-5-(trifluoromethyl)-1H-pyrazole-4-carboxamide;

N-(2-(3,5-dichloropyridin-4-yl)-2-oxoethyl)-N-(4-fluorobenzyl)-1-(trans-4-((2-hydroxyethyl)carbamoyl)cyclohexyl)-5-(trifluoromethyl)-1H-pyrazole-4-carboxamide;

trans-1-methyl-4-(4-(2-((2-methylpropan-2-yl)oxy)ethyl-(2-oxo-2-(2,4,6-trichlorophenyl)ethyl)carbamoyl)-5-(trifluoromethyl)pyrazol-1-yl)cyclohexane-1-carboxylic acid;

trans-1-methyl-4-(4-(2-oxaspiro[3.5]nonan-7-yl-(2-oxo-2-(2,4,6-trichlorophenyl)ethyl)carbamoyl)-5-(trifluoromethyl)pyrazol-1-yl)cyclohexane-1-carboxylic acid;

trans-3-(4-((2-(2,6-dichloro-4-fluorophenyl)-2-oxoethyl)-(4,4-dimethylcyclohexyl)carbamoyl)-5-(trifluoromethyl)pyrazol-1-yl)cyclobutane-1-carboxylic acid;

trans-3-(4-((2-(2,6-dichloro-4-fluorophenyl)-2-oxoethyl)-(4,4-dimethylcyclohexyl)carbamoyl)-5-(trifluoromethyl)pyrazol-1-yl)-1-methylcyclobutane-1-carboxylic acid;

trans-3-(4-((2-(3,5-dichloropyridin-4-yl)-2-oxoethyl)(4-fluorobenzyl)carbamoyl)-5-(trifluoromethyl)-1H-pyrazol-1-yl)cyclobutanecarboxylic acid;

trans-4-(2-((1-(4-carboxycyclohexyl)-5-(trifluoromethyl)pyrazole-4-carbonyl)-((3,5-difluorophenyl)methyl)amino)acetyl)-3,5-dichlorobenzoic acid;

trans-4-(4-(((1R,2S)-2-tert-butylcyclopropyl)-(2-(3,5-dichloropyridin-4-yl)-2-oxoethyl)carbamoyl)-5-(trifluoromethyl)pyrazol-1-yl)-1-methylcyclohexane-1-carboxylic acid;

trans-4-(4-(((1R,3r,5S)-6,6-dimethyl-3-bicyclo[3.1.0]hexanyl)-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-(((1R,3r,5S)-6,6-dimethylbicyclo[3.1.0]hexan-3-yl)(2-hydroxy-2-(2-methoxyphenyl)ethyl)carbamoyl)-5-(trifluoromethyl)-1H-pyrazol-1-yl)-1-methylcyclohexanecarboxylic acid;

trans-4-(4-(((1R,3r,5S)-6,6-dimethylbicyclo[3.1.0]hexan-3-yl)(2-hydroxy-2-(2-methoxyphenyl)ethyl)carbamoyl)-5-(trifluoromethyl)-1H-pyrazol-1-yl)-1-methylcyclohexanecarboxylic acid;

trans-4-(4-((((1R,3r,5S)-6,6-dimethylbicyclo[3.1.0]hexan-3-yl)(2-hydroxy-2-(2-(trifluoromethyl)phenyl)ethyl)carbamoyl)-5-(trifluoromethyl)-1H-pyrazol-1-yl)-1-methylcyclohexanecarboxylic acid;

trans-4-(4-((((1R,3r,5S)-6,6-dimethylbicyclo[3.1.0]hexan-3-yl)(2-hydroxy-2-(2-(trifluoromethyl)phenyl)ethyl)carbamoyl)-5-(trifluoromethyl)-1H-pyrazol-1-yl)-1-methylcyclohexanecarboxylic acid;

trans-4-(4-((((1R,3r,5S)-6,6-dimethylbicyclo[3.1.0]hexan-3-yl)(2-hydroxy-2-(pyridin-2-yl)ethyl)carbamoyl)-5-(trifluoromethyl)-1H-pyrazol-1-yl)-1-methylcyclohexanecarboxylic acid;

trans-4-(4-((((1R,3r,5S)-6,6-dimethylbicyclo[3.1.0]hexan-3-yl)(2-hydroxy-2-(3-methylpyrazin-2-yl)ethyl)carbamoyl)-5-(trifluoromethyl)-1H-pyrazol-1-yl)-1-methylcyclohexanecarboxylic acid;

trans-4-(4-(((2R)-2-(2,6-dichlorophenyl)-2-fluoroethyl)-((3,5-difluorophenyl)methyl)carbamoyl)-5-(trifluoromethyl)pyrazol-1-yl)-1-methylcyclohexane-1-carboxylic acid;

trans-4-(4-(((2R)-2-(2-chloro-6-methoxyphenyl)-2-hydroxyethyl)-(2,2-dimethylpropyl)carbamoyl)-5-(trifluoromethyl)pyrazol-1-yl)-1-methylcyclohexane-1-carboxylic acid;

trans-4-(4-(((2S)-2-(2,6-dichlorophenyl)-2-fluoroethyl)-((3,5-difluorophenyl)methyl)carbamoyl)-5-(trifluoromethyl)pyrazol-1-yl)-1-methylcyclohexane-1-carboxylic acid;

trans-4-(4-(((2S)-2-(2-chloro-6-methoxyphenyl)-2-hydroxyethyl)-(2,2-dimethylpropyl)carbamoyl)-5-(trifluoromethyl)pyrazol-1-yl)-1-methylcyclohexane-1-carboxylic acid;

trans-4-(4-(((1-acetylazetidin-3-yl)-(2-(3,5-dichloropyridin-4-yl)-2-oxoethyl)carbamoyl)-5-(trifluoromethyl)pyrazol-1-yl)cyclohexane-1-carboxylic acid;

trans-4-(4-(((1-fluorocyclopentyl)methyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-(((1-methyl-4-bicyclo[2.2.1]heptanyl)methyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-(((1-methyl-7-oxabicyclo[2.2.1]heptan-4-yl)methyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-((2-(2,4-dichloro-6-methoxyphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2,5-dichlorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2,6-dichloro-4-(difluoromethyl)phenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2,6-dichloro-4-(trifluoromethoxy)phenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2,6-dichloro-4-(trifluoromethyl)phenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichloro-4-(trifluoromethyl)phenyl)-2-oxoethyl)-(2-((2-methylpropan-2-yl)oxy)ethyl)carbamoyl)-5-(trifluoromethyl)pyrazol-1-yl)cyclohexane-1-carboxylic acid;

trans-4-(4-((2-(2,6-dichloro-4-(trifluoromethyl)phenyl)-2-oxoethyl)-(2-((2-methylpropan-2-yl)oxy)ethyl)carbamoyl)-5-(trifluoromethyl)pyrazol-1-yl)-1-methylcyclohexane-1-carboxylic acid;

trans-4-(4-((2-(2,6-dichloro-4-cyanophenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichloro-4-cyclopropylphenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichloro-4-fluorophenyl)-2-oxoethyl)-((1-fluorocyclopentyl)methyl)carbamoyl)-5-(trifluoromethyl)pyrazol-1-yl)-1-methylcyclohexane-1-carboxylic acid;

trans-4-(4((2-(2,6-dichloro-4-fluorophenyl)-2-oxoethyl)-((1-methyl-4-bicyclo[2.2.1]heptanyl)methyl)carbamoyl)-5-(trifluoromethyl)pyrazol-1-yl)cyclohexane-1-carboxylic acid;

trans-4-(4-((2-(2,6-dichloro-4-fluorophenyl)-2-oxoethyl)-((1-methyl-7-oxabicyclo[2.2.1]heptan-4-yl)methyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-((1-methyl-4-bicyclo[2.2.1]heptanyl)methyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-((1R,3r,5S)-6,6-dimethyl-3-bicyclo[3.1.0]hexanyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-((3,3-dimethylcyclobutyl)methyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-((3,5-difluorophenyl)methyl)carbamoyl)-5-(difluoromethyl)pyrazol-1-yl)-1-methylcyclohexane-1-carboxylic acid;

trans-4-(4-((2-(2,6-dichloro-4-fluorophenyl)-2-oxoethyl)-((4,4-dimethylcyclohexyl)methyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(1-methylpiperidin-4-yl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(1-propan-2-ylpiperidin-4-yl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(2-((2-methylpropan-2-yl)oxy)ethyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(2-(3-fluoropiperidin-1-yl)ethyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(2,2-dimethylbutyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(3-(2,2-dimethylpropyl)cyclobutyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)(3,5-difluorobenzyl)carbamoyl)-5-(trifluoromethyl)-1H-pyrazol-1-yl)-1-methylcyclohexanecarboxylic acid;

trans-4-(4-((2-(2,6-dichloro-4-fluorophenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichloro-4-fluorophenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(4,4-dimethylpent-2-ynyl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(4,4-dimethylcyclohexyl)carbamoyl)-5-propan-2-ylpyrazol-1-yl)-1-methylcyclohexane-1-carboxylic acid;

trans-4-(4-((2-(2,6-dichloro-4-fluorophenyl)-2-oxoethyl)-(8-methyl-8-azabicyclo[3.2.1]octan-3-yl)carbamoyl)-5-(trifluoromethyl)pyrazol-1-yl)-1-methylcyclohexane-1-carboxylic acid;

trans-4-(4-((2-(2,6-dichloro-4-fluorophenyl)-2-oxoethyl)-(8-propan-2-yl-8-azabicyclo[3.2.1]octan-3-yl)carbamoyl)-5-(trifluoromethyl)pyrazol-1yl)-1-methylcyclohexane-1-carboxylic acid;

trans-4-(4-((2-(2,6-dichloro-4-fluorophenyl)-2-oxoethyl)-(spiro[2.3]hexan-5-ylmethyl)carbamoyl)-5-(trifluoromethyl)pyrazol-1-yl)-1-methylcyclohexane-1-carboxylic acid;

trans-4-(4-((2-(2,6-dichloro-4-hydroxyphenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichloro-4-methoxyphenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichloro-4-methylphenyl)-2-oxoethyl)-((1-fluorocyclopentyl)methyl)carbamoyl)-5-(trifluoromethyl)pyrazol-1-yl)-1-methylcyclohexane-1-carboxylic acid;

trans-4-(4-((2-(2,6-dichloro-4-methylphenyl)-2-oxoethyl)-((1-methyl-7-oxabicyclo[2.2.1]heptan-4-yl)methyl)carbamoyl)-5-(trifluoromethyl)pyrazol-1-yl)-1-methylcyclohexane-1-carboxylic acid;

trans-4-(4-((2-(2,6-dichloro-4-methylphenyl)-2-oxoethyl)((1R,3r,5S)-6,6-dimethylbicyclo[3.1.0]hexan-3-yl)carbamoyl)-5-methyl-1H-pyrazol-1-yl)-1-methylcyclohexanecarboxylic acid;

trans-4-(4-((2-(2,6-dichloro-4-methylphenyl)-2-oxoethyl)-((3,3-dimethylcyclobutyl)methyl)carbamoyl)-5-(trifluoromethyl)pyrazol-1-yl)-1-methylcyclohexane-1-carboxylic acid;

trans-4-(4-((2-(2,6-dichloro-4-methylphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2,6-dichloro-4-methylphenyl)-2-oxoethyl)-(4,4-dimethylpent-2-ynyl)carbamoyl)-5-(trifluoromethyl)pyrazol-1-yl)-1-methylcyclohexane-1-carboxylic acid;

trans-4-(4-((2-(2,6-dichloro-4-methylphenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(2,6-dichlorophenyl)-2,2-difluoroethyl)-((4-fluorophenyl)methyl)carbamoyl)-5-(trifluoromethyl)pyrazol-1-yl)cyclohexane-1-carboxylic acid;

trans-4-(4-((2-(2,6-dichlorophenyl)-2-fluoroethyl)(4-fluorobenzyl)carbamoyl)-5-(trifluoromethyl)-1H-pyrazol-1-yl)cyclohexanecarboxylic acid;

trans-4-(4-((2-(2,6-dichlorophenyl)-2-methylpropyl)-((3,5-difluorophenyl)methyl)carbamoyl)-5-(trifluoromethyl)pyrazol-1-yl)cyclohexane-1-carboxylic acid;

trans-4-(4-((2-(2,6-dichlorophenyl)-2-oxoethyl)-((1-fluorocyclopentyl)methyl)carbamoyl)-5-(trifluoromethyl)pyrazol-1-yl)-1-methylcyclohexane-1-carboxylic acid;

trans-4-(4-((2-(2,6-dichlorophenyl)-2-oxoethyl)((1R,3r,5S)-6,6-dimethylbicyclo[3.1.0]hexan-3-yl)carbamoyl)-5-methyl-1H-pyrazol-1-yl)-1-methylcyclohexanecarboxylic acid;

trans-4-(4-((2-(2,6-dichlorophenyl)-2-oxoethyl)((1R,3r,5S)-6,6-dimethylbicyclo[3.1.0]hexan-3-yl)carbamoyl)-5-(1-fluorocyclopropyl)-1H-pyrazol-1-yl)-1-methylcyclohexanecarboxylic acid;

trans-4-(4-((2-(2,6-dichlorophenyl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(2,6-dichlorophenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2,6-dichlorophenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(2,6-dichlorophenyl)-2-oxoethyl)-(pyridazin-4-ylmethyl)carbamoyl)-5-(trifluoromethyl)pyrazol-1-yl)cyclohexane-1-carboxylic acid;

trans-4-(4-((2-(2,6-dichlorophenyl)-2-oxoethyl)-(pyrimidin-5-ylmethyl)carbamoyl)-5-(trifluoromethyl)pyrazol-1-yl)cyclohexane-1-carboxylic acid;

trans-4-(4-((2-(2-acetamido-6-chlorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-amino-4-chloropyridin-3-yl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-amino-5-methylphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-amino-6-chlorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-aminophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-4-(trifluoromethyl)phenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-4,6-difluorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-4,6-dimethylphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-4,6-dimethylphenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(2-chloro-4-fluorophenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2-chloro-6-(difluoromethoxy)phenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chloro-6-(difluoromethoxy)phenyl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(2-chloro-6-(difluoromethoxy)phenyl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chloro-6-(trifluoromethyl)phenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-6-(trifluoromethyl)phenyl)-2-oxoethyl)-(4,4-dimethylpent-2-ynyl)carbamoyl)-5-(trifluoromethyl)pyrazol-1-yl)-1-methylcyclohexane-1-carboxylic acid;

trans-4-(4-((2-(2-chloro-6-(trifluoromethyl)phenyl)-2-oxoethyl)-((1R,3r,5S)-6,6-dimethyl-3-bicyclo[3.1.0]hexanyl)carbamoyl)-5-(trifluoromethyl)pyrazol-1-yl)-1-methylcyclohexane-1-carboxylic acid;

trans-4-(4-((2-(2-chloro-6-(trifluoromethyl)phenyl)-2-oxoethyl)-(spiro[2.3]hexan-5-ylmethyl)carbamoyl)-5-(trifluoromethyl)pyrazol-1-yl)-1-methylcyclohexane-1-carboxylic acid;

trans-4-(4-((2-(2-chloro-6-(trifluoromethyl)phenyl)-2-oxoethyl)-((3,3-dimethylcyclobutyl)methyl)carbamoyl)-5-(trifluoromethyl)pyrazol-1-yl)-1-methylcyclohexane-1-carboxylic acid;

trans-4-(4-((2-(2-chloro-6-(trifluoromethyl)phenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(2-chloro-6-(trifluoromethyl)phenyl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(2-chloro-6-(trifluoromethyl)phenyl)-2-oxoethyl)-((1-fluorocyclopentyl)methyl)carbamoyl)-5-(trifluoromethyl)pyrazol-1-yl)-1-methylcyclohexane-1-carboxylic acid;

trans-4-(4-((2-(2-chloro-6-cyano-4-methylphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-6-ethynylphenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2-chloro-6-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chloro-6-fluorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chloro-6-fluorophenyl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(2-chloro-6-hydroxyphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chloro-6-methoxyphenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chloro-6-methoxyphenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chloro-6-methoxyphenyl)-2-hydroxyethyl)-(4,4-dimethylcyclohexyl)carbamoyl)-5-(trifluoromethyl)pyrazol-1-yl)-1-methylcyclohexane-1-carboxylic acid;

trans-4-(4-((2-(2-chloro-6-methoxyphenyl)-2-oxoethyl)-((1R,3r,5S)-6,6-dimethyl-3-bicyclo(3.1.0)hexanyl)carbamoyl)-5-(trifluoromethyl)pyrazol-1-yl)-1-methylcyclohexane-1-carboxylic acid;

trans-4-(4-((2-(2-chloro-6-methoxyphenyl)-2-oxoethyl)-((3,3-dimethylcyclobutyl)methyl)carbamoyl)-5-(trifluoromethyl)-1-methylcyclohexane-1-carboxylic acid;

trans-4-(4-((2-(2-chloro-6-methoxyphenyl)-2-oxoethyl)-((4,4-dimethylcyclohexyl)methyl)carbamoyl)-5-(trifluoromethyl)pyrazol-1-yl)-1-methylcyclohexane-1-carboxylic acid;

trans-4-(4-((2-(2-chloro-6-methoxyphenyl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(2-chloro-6-methoxyphenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(2-chloro-6-methoxyphenyl)-2-oxoethyl)-(4,4-dimethylpent-2-ynyl)carbamoyl)-5-(trifluoromethyl)pyrazol-1-yl)-1-methylcyclohexane-1-carboxylic acid;

trans-4-(4-((2-(2-chloro-6-methoxyphenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(2-chlorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chlorophenyl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chlorophenyl)-2-hydroxypropyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(2-chlorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(2-chlorothiophen-3-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3,5-dichloro-1,2-thiazol-4-yl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(3,5-dichloro-1H-pyrazol-4-yl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(3,5-dichloro-1-methylpyrazol-4-yl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(3,5-dichlorophenyl)-2-oxoethyl)(3,5-difluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2,2-difluoroethyl)-((3,5-difluorophenyl)methyl)carbamoyl)-5-(trifluoromethyl)pyrazol-1-yl)cyclohexane-1-carboxylic acid;

trans-4-(4-((2-(3,5-dichloropyridin-4-yl)-2-hydroxyethyl)(4-fluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2-methoxyethyl)-((3,5-difluorophenyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(((2R)-5,5-dimethyloxolan-2-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(((2R)-5-oxopyrrolidin-2-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(((2S)-5,5-dimethyloxolan-2-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(((2S)-5-oxopyrrolidin-2-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(((R)-tetrahydrofuran-3-yl)methyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(((S)-tetrahydrofuran-3-yl)methyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-((1-(trifluoromethyl)cyclopropyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1-fluorocyclopentyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1-fluorocyclopentyl)methyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((1-hydroxycyclopentyl)methyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((1-methyl-7-oxabicyclo[2.2.1]heptan-4-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1-methyl-4-bicyclo[2.2.1]heptanyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1-methyl-4-bicyclo[2.2.1]heptanyl)methyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((1-methyl-7-oxabicyclo[2.2.1]heptan-4-yl)methyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((1-methylcyclohexyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)((1-methylcyclopropyl)methyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-((1-methylpiperidin-4-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1R)-3,3-dimethylcyclopentyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1R,3r,5S)-6,6-dimethyl-3-bicyclo[3.1.0]hexanyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1R,3r,5S)-6,6-dimethyl-3-bicyclo[3.1.0]hexanyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1S)-3,3-dimethylcyclopentyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1S)-3,3-dimethylcyclopentyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1S,2R)-2-phenylcyclopropyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((1S,2R)-2-propan-2-ylcyclopropyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((1S,2S)-2-propan-2-ylcyclopropyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((2,2,3,3-tetramethylcyclopropyl)methyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((2-hydroxyphenyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((2R)-3,3-dimethylbutan-2-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((2S)-3,3-dimethylbutan-2-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((3-((2-methylpropan-2-yl)oxy)cyclobutyl)methyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-((3-(2,2-dimethylpropyl)cyclobutyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((3,3-dimethylcyclobutyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((3,3-dimethylcyclobutyl)methyl)carbamoyl)-5-methylpyrazol-1-yl)-1-methylcyclohexane-1-carboxylic acid;

trans-4-(4-((2-(3,5-dichloropyridin-4-yl)-2-oxoethyl)-((3,5-difluorophenyl)methyl)carbamoyl)-5-(difluoromethyl)pyrazol-1-yl)cyclohexane-1-carboxylic acid;

trans-4-(4-((2-(3,5-dichloropyridin-4-yl)-2-oxoethyl)-((3,5-difluorophenyl)methyl)carbamoyl)-5-(trifluoromethyl)pyrazol-1-yl)-1-ethylcyclohexane-1-carboxylic acid;

trans-4-(4-((2-(3,5-dichloropyridin-4-yl)-2-oxoethyl)-((3,5-difluorophenyl)methyl)carbamoyl)-5-(hydroxymethyl)pyrazol-1-yl)cyclohexane-1-carboxylic acid;

trans-4-(4-((2-(3,5-dichloropyridin-4-yl)-2-oxoethyl)-((3,5-difluorophenyl)methyl)carbamoyl)-5-propan-2-ylpyrazol-1-yl)cyclohexane-1-carboxylic acid;

trans-4-(4-((2-(3,5-dichloropyridin-4-yl)-2-oxoethyl)-((3,5-difluorophenyl)methyl)carbamoyl)-5-methylpyrazol-1-yl)cyclohexane-1-carboxylic acid;

trans-4-(4-((2-(3,5-dichloropyridin-4-yl)-2-oxoethyl)-((3,5-difluorophenyl)methyl)carbamoyl)-5-(difluoromethyl)pyrazol-1-yl)-1-methylcyclohexane-1-carboxylic acid;

trans-4-(4-((2-(3,5-dichloropyridin-4-yl)-2-oxoethyl)-((3-hydroxyphenyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((4,4-difluorocyclohexyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)((4,4-dimethylcyclohexyl)methyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-((4-fluorophenyl)methyl)carbamoyl)-5-(trifluoromethyl)pyrazol-1-yl)-1-hydroxycyclohexane-1-carboxylic acid;

trans-4-(4-((2-(3,5-dichloropyridin-4-yl)-2-oxoethyl)-((4-fluorophenyl)methyl)carbamoyl)-5-(trifluoromethyl)pyrazol-1-yl)-1-cyanocyclohexane-1-carboxylic acid;

trans-4-(4-((2-(3,5-dichloropyridin-4-yl)-2-oxoethyl)-((4-fluorophenyl)methyl)carbamoyl)-5-(trifluoromethyl)pyrazol-1-yl)-1-cyanocyclohexane-1-carboxylic acid;

trans-4-(4-((2-(3,5-dichloropyridin-4-yl)-2-oxoethyl)-((4-fluorophenyl)methyl)carbamoyl)-5-(2,2,2-trifluoroethyl)pyrazol-1-yl)cyclohexane-1-carboxylic acid;

trans-4-(4-((2-(3,5-dichloropyridin-4-yl)-2-oxoethyl)-((4-hydroxy-4-methylcyclohexyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((4-hydroxyphenyl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-((6,6-dimethyloxan-3-yl)methyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)((tetrahydro-2H-pyran-4-yl)methyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(1-((2-methylpropan-2-yl)oxy)propan-2-yl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-(1-(2,2-dimethylpropanoyl)azetidin-3-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(1-(2-methylpropyl)cyclopropyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-(1,2,2,6,6-pentamethylpiperidin-4-yl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-(1-methoxypropan-2-yl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-(1-spiro[2.3]hexan-5-ylethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(2-((2-methylpropan-2-yl)oxy)ethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(2-((2-methylpropan-2-yl)oxy)ethyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)(2,2,2-trifluoroethyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(2,2-dimethylbutyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)(2,3-difluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(2,3-dihydro-1H-inden-2-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(2,5-difluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(2-ethyl-2-fluorobutyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)(2-fluoro-2-methylpropyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(2-fluoro-2-methylpropyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)(2-methoxy-2-methylpropyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(3-((2-methylpropan-2-yl)oxy)cyclobutyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(3-((2-methylpropan-2-yl)oxy)cyclobutyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(3,3-dimethylcyclohexyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(3,3-dimethylbutyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(3,4-difluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(3,5-difluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(3,5-difluorobenzyl)carbamoyl)-5-(trifluoromethyl)-1H-pyrazol-1-yl)-1-methylcyclohexanecarboxylic acid;

trans-4-(4-((2-(3,5-dichloropyridin-4-yl)-2-oxoethyl)-(3-methylbut-2-enyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)(3-methylbut-2-en-1-yl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(4-(trifluoromethyl)cyclohexyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(4-(trifluoromethyl)cyclohexyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(4,4-difluorocyclohexyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(4,4-dimethylpent-2-ynyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(4,4-dimethylcyclohexyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(4,4-dimethylcyclohexyl)carbamoyl)-5-(difluoromethyl)pyrazol-1-yl)-1-methylcyclohexane-1-carboxylic acid;

trans-4-(4-((2-(3,5-dichloropyridin-4-yl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)(4-fluorobenzyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(4-fluorobenzyl)carbamoyl)-5-(trifluoromethyl)-1H-pyrazol-1-yl)-1-methylcyclohexanecarboxylic acid;

trans-4-(4-((2-(3,5-dichloropyridin-4-yl)-2-oxoethyl)(4-fluorobenzyl)carbamoyl)-5-(trifluoromethyl)-1H-pyrazol-1-yl)-1-methylcyclohexanecarboxylic acid;

trans-4-(4-((2-(3,5-dichloropyridin-4-yl)-2-oxoethyl)(4-fluorobenzyl)carbamoyl)-5-(trifluoromethyl)-1H-pyrazol-1-yl)-1-fluorocyclohexanecarboxylic acid;

trans-4-(4-((2-(3,5-dichloropyridin-4-yl)-2-oxoethyl)(4-fluorobenzyl)carbamoyl)-5-(1,1-difluoroethyl)-1H-pyrazol-1-yl)cyclohexanecarboxylic acid;

trans-4-(4-((2-(3,5-dichloropyridin-4-yl)-2-oxoethyl)-(4-methylpentan-2-yl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-(5,5-dimethyloxolan-3-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(6,6-dimethyloxan-3-yl)carbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-(7-oxabicyclo[2.2.1]heptan-4-ylmethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(furan-2-ylmethyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(furan-3-ylmethyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(isobutyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(isopentyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)(neopentyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(oxan-4-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(oxolan-3-yl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(piperidin-2-ylmethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(pyrazin-2-ylmethyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(pyridin-2-ylmethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)-(pyridin-3-ylmethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(pyridin-4-ylmethyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-(spiro[2.3]hexan-5-ylmethyl)carbamoyl)-5-(trifluoromethyl)pyrazol-1-yl)cyclohexane-1-carboxylic acid;

trans-4-(4-((2-(3,5-dichloropyridin-4-yl)-2-oxoethyl)(spiro[2.5]octan-6-ylmethyl)carbamoyl)-5-(trifluoromethyl)-1H-pyrazol-1-yl)cyclohexanecarboxylic acid;

trans-4-(4-((2-(3,5-dichloropyridin-4-yl)-2-oxoethyl)-pentan-3-ylcarbamoyl)-5-(trifluoromethyl)pyrazol-1-yl)-1-methylcyclohexane-1-carboxylic acid;

trans-4-(4-((2-(3,5-dichloropyridin-4-yl)-2-oxoethyl)-spiro[2.5]octan-6-ylcarbamoyl)-5-(trifluoromethyl)pyrazol-1-yl)cyclohexane-1-carboxylic acid;

trans-4-(4-((2-(3-chloro-5-(trifluoromethyl)pyridin-2-yl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(3-chloro-5-fluoropyridin-4-yl)-2-hydroxyethyl) ((1R,3r,5S)-6,6-dimethylbicyclo[3.1.0]

hexan-3-yl)carbamoyl)-5-(trifluoromethyl)-1H-pyrazol-1-yl)-1-methylcyclohexanecarboxylic acid;

trans-4-(4-((2-(3-chloro-5-fluoropyridin-4-yl)-2-hydroxyethyl) ((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chloro-5-fluoropyridin-4-yl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chloro-5-fluoropyridin-4-yl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(3-chloro-5-fluoropyridin-4-yl)-2-oxoethyl)-(2,2-dimethylbutyl)carbamoyl)-5-(trifluoromethyl)pyrazol-1-yl)-1-methylcyclohexane-1-carboxylic acid;

trans-4-(4-((2-(3-chloro-5-fluoropyridin-4-yl)-2-oxoethyl)(3,5-difluorobenzyl)carbamoyl)-5-(trifluoromethyl)-1H-pyrazol-1-yl)cyclohexanecarboxylic acid;

trans-4-(4-((2-(3-chloro-5-hydroxypyridin-4-yl)-2-oxoethyl)-((4-fluorophenyl)methyl)carbamoyl)-5-(trifluoromethyl)pyrazol-1-yl)cyclohexane-1-carboxylic acid;

trans-4-(4-((2-(3-chloro-5-methoxypyridin-4-yl)-2-oxoethyl)-((4-fluorophenyl)methyl)carbamoyl)-5-(trifluoromethyl)pyrazol-1-yl)cyclohexane-1-carboxylic acid;

trans-4-(4-((2-(3-chloro-5-methoxypyridin-4-yl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(3-chloro-5-methylpyridin-4-yl)-2-oxoethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chloro-5-methylpyridin-4-yl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(3-chloro-5-methylpyridin-4-yl)-2-oxoethyl)(3,5-difluorobenzyl)carbamoyl)-5-(trifluoromethyl)-1H-pyrazol-1-yl)cyclohexanecarboxylic acid;

trans-4-(4-((2-(3-chloropyridin-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chloropyridin-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chloropyridin-2-yl)-2-hydroxyethyl)-(2,2-dimethylpropyl)carbamoyl)-5-(trifluoromethyl)pyrazol-1-yl)-1-methylcyclohexane-1-carboxylic acid;

trans-4-(4-((2-(3-chloropyridin-2-yl)-2-hydroxyethyl)-(2,2-dimethylpropyl)carbamoyl)-5-(trifluoromethyl)pyrazol-1-yl)-1-methylcyclohexane-1-carboxylic acid;

trans-4-(4-((2-(3-chloropyridin-2-yl)-2-oxoethyl) ((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chlorothiophen-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(3-chlorothiophen-2-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(4-carbamoyl-2,6-dichlorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(4-chloro-1H-indazol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(4-chloro-1H-indol-3-yl)-2-oxoethyl)-(2,2-dimethylpropyl)carbamoyl)-5-(trifluoromethyl)pyrazol-1-yl)-1-methylcyclohexane-1-carboxylic acid;

trans-4-(4-((2-(4-chloro-1H-indol-3-yl)propyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(4-chloro-1H-pyrrolo(2,3-c)pyridin-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(4-chloro-2,6-dimethylphenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(4-chloro-2,6-dimethylphenyl)-2-oxoethyl)-(4,4-dimethylcyclohexyl)carbamoyl)-5-(trifluoromethyl)pyrazol-1-yl)-1-methylcyclohexane-1-carboxylic acid;

trans-4-(4-((2-(4-chloro-2-methyl-1H-indol-3-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(4-chloro-2-oxo-1H-pyridin-3-yl)-2-oxoethyl)-((4-fluorophenyl)methyl)carbamoyl)-5-(trifluoromethyl)pyrazol-1-yl)cyclohexane-1-carboxylic acid;

trans-4-(4-((2-(4-methylsulfoyl-2,6-dichlorophenyl)-2-oxoethyl)-((3,5-difluorophenyl)methyl)carbamoyl)-5-(trifluoromethyl)pyrazol-1-yl)cyclohexane-1-carboxylic acid;

trans-4-(4-((2-(5-chloro-2-methylpyrimidin-4-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(5-chloropyrimidin-4-yl)-2-hydroxyethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-(7-chloro-1H-benzo(d)imidazol-1-yl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-amino-2-(2-chloro-6-fluorophenyl)ethyl)((1R,3r,5S)-6,6-dimethylbicyclo[3.1.0]hexan-3-yl)carbamoyl)-5-(trifluoromethyl)-1H-pyrazol-1-yl)-1-methylcyclohexanecarboxylic acid;

trans-4-(4-((2-chloro-1,3-thiazol-4-yl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((2-cyanophenyl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((2-cyclohexyl-2-oxoethyl)(3,5-difluorobenzyl)carbamoyl)-5-(trifluoromethyl)-1H-pyrazol-1-yl)cyclohexanecarboxylic acid;

trans-4-(4-((2-cyclopentyl-2-oxoethyl)-((3,5-difluorophenyl)methyl)carbamoyl)-5-(trifluoromethyl)pyrazol-1-yl)cyclohexane-1-carboxylic acid;

trans-4-(4-((2-cyclopropylethyl)(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-((2-oxo-2-(2,4,6-trichlorophenyl)ethyl)-(spiro[2.3]hexan-5-ylmethyl)carbamoyl)-5-(trifluoromethyl)pyrazol-1-yl)-1-methylcyclohexane-1-carboxylic acid;

trans-4-(4-((3,3-dimethylcyclobutyl)methyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-((3,5-difluorobenzyl)(2-(2,4-dimethylfuran-3-yl)-2-oxoethyl)carbamoyl)-5-(trifluoromethyl)-1H-pyrazol-1-yl)cyclohexanecarboxylic acid;

trans-4-(4-((3,5-difluorobenzyl)(2-(3,5-difluorophenyl)-2-oxoethyl)carbamoyl)-5-(trifluoromethyl)-1H-pyrazol-1-yl)cyclohexanecarboxylic acid;

trans-4-(4-((3,5-difluorobenzyl)(2-(3,5-difluoropyridin-4-yl)-2-oxoethyl)carbamoyl)-5-(trifluoromethyl)-1H-pyrazol-1-yl)cyclohexanecarboxylic acid;

trans-4-(4-((3,5-difluorobenzyl)(2-(3,5-dimethylisoxazol-4-yl)-2-oxoethyl)carbamoyl)-5-(trifluoromethyl)-1H-pyrazol-1-yl)cyclohexanecarboxylic acid;

trans-4-(4-((3,5-difluorobenzyl)(2-(3,5-dimethylpyridin-4-yl)-2-oxoethyl)carbamoyl)-5-(trifluoromethyl)-1H-pyrazol-1-yl)cyclohexanecarboxylic acid;

trans-4-(4-((3,5-difluorobenzyl)(2-(4-hydroxyphenyl)-2-oxoethyl)carbamoyl)-5-(trifluoromethyl)-1H-pyrazol-1-yl)cyclohexanecarboxylic acid;

trans-4-(4-((3,5-difluorobenzyl)(2-oxo-2-(2,4,6-trichlorophenyl)ethyl)carbamoyl)-5-(trifluoromethyl)-1H-pyrazol-1-yl)cyclohexanecarboxylic acid;

trans-4-(4-((3,5-difluorobenzyl)(2-oxo-2-(pyridin-4-yl)ethyl)carbamoyl)-5-(trifluoromethyl)-1H-pyrazol-1-yl)cyclohexanecarboxylic acid;

trans-4-(4-((3,5-difluorophenyl)methyl-(2-(2,4-dimethyl-6-oxo-1H-pyridin-3-yl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(2,4-dimethylpyridin-3-yl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(2,4-dimethylthiophen-3-yl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(2,6-dihydroxyphenyl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(2,6-dimethoxyphenyl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(2-hydroxy-6-methoxyphenyl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(3,5-dimethoxypyridin-4-yl)-2-oxoethyl)carbamoyl)-5-(trifluoromethyl)pyrazol-1-yl)cyclohexane-1-carboxylic acid;

trans-4-(4-((3,5-difluorophenyl)methyl-(2-(4,6-dimethylpyrimidin-5-yl)-2-oxoethyl)carbamoyl)-5-(trifluoromethyl)pyrazol-1-yl)cyclohexane-1-carboxylic acid;

trans-4-(4-((3,5-difluorophenyl)methyl-(2-oxo-2-(1H-pyrazol-3-yl)ethyl)carbamoyl)-5-(trifluoromethyl)pyrazol-1-yl)cyclohexane-1-carboxylic acid;

trans-4-(4-((3,5-difluorophenyl)methyl-(2-oxo-2-(2,4,6-trihydroxypyrimidin-5-yl)ethyl)carbamoyl)-5-(trifluoromethyl)pyrazol-1-yl)cyclohexane-1-carboxylic acid;

trans-4-(4-((3-cyano-3-methylcyclopentyl)-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((3-cyanophenyl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((3-tert-butylcyclobutyl)-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((3-tert-butylcyclobutyl)-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((3-tert-butylcyclobutyl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((3-tert-butylcyclobutyl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((4,4-dimethylcyclohexyl)-(2-(3,5-dimethyl-1H-pyrazol-4-yl)ethyl)carbamoyl)-5-(trifluoromethyl)pyrazol-1-yl)-1-methylcyclohexane-1-carboxylic acid;

trans-4-(4-((4,4-dimethylcyclohexyl)-(2-oxo-2-(2,4,6-trichlorophenyl)ethyl)carbamoyl)-5-(trifluoromethyl)pyrazol-1-yl)cyclohexane-1-carboxylic acid;

trans-4-(4-((4,4-dimethylcyclohexyl)-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-((4,4-dimethylcyclohexyl)methyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-((4-chloro-1,3-thiazol-2-yl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((4-chlorobenzyl)(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-((4-cyanophenyl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((5-chloro-1,3-thiazol-2-yl)methyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-((cyclobutylmethyl)(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-((cyclohexylmethyl)(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-((cyclopentylmethyl)(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-((cyclopropylmethyl)(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-(1-adamantylmethyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-(1-cyclopentylethyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-(2-(2,6-dichloro-4-fluorophenyl)ethyl-((3,5-difluorophenyl)methyl)carbamoyl)-5-(trifluoromethyl)pyrazol-1-yl)cyclohexane-1-carboxylic acid;

trans-4-(4-(2-(2,6-dichlorophenyl)propyl-((3,5-difluorophenyl)methyl)carbamoyl)-5-(trifluoromethyl)pyrazol-1-yl)cyclohexane-1-carboxylic acid;

trans-4-(4-(2-(2,6-dichlorophenyl)propyl-((4-fluorophenyl)methyl)carbamoyl)-5-(trifluoromethyl)pyrazol-1-yl)cyclohexane-1-carboxylic acid;

trans-4-(4-(2-(3,5-dichloropyridin-4-yl)ethyl-((4-fluorophenyl)methyl)carbamoyl)-3,5-bis(trifluoromethyl)pyrazol-1-yl)cyclohexane-1-carboxylic acid;

trans-4-(4-(2-(4-chloro-1H-indol-3-yl)ethyl-(2,2-dimethylpropyl)carbamoyl)-5-(trifluoromethyl)pyrazol-1-yl)-1-methylcyclohexane-1-carboxylic acid;

trans-4-(4-(2-(4-chloro-1H-indol-3-yl)ethyl-(4,4-dimethylcyclohexyl)carbamoyl)-5-(trifluoromethyl)pyrazol-1-yl)-1-methylcyclohexane-1-carboxylic acid;

trans-4-(4-(2-(4-chloro-2-methyl-1H-indol-3-yl)ethyl-(2,2-dimethylpropyl)carbamoyl)-5-(trifluoromethyl)pyrazol-1-yl)-1-methylcyclohexane-1-carboxylic acid;

trans-4-(4-(2,2-dimethylbutyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-(2,2-dimethylpropyl-(2-(1H-indol-3-yl)ethyl)carbamoyl)-5-(trifluoromethyl)pyrazol-1-yl)-1-methylcyclohexane-1-carboxylic acid;

trans-4-(4-(2,2-dimethylpropyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-(2-tert-butylsulfanylethyl-(2-(2,6-dichloro-4-fluorophenyl)-2-oxoethyl)carbamoyl)-5-(trifluoromethyl)pyrazol-1-yl)-1-methylcyclohexane-1-carboxylic acid;

trans-4-(4-(2-tert-butylsulfinylethyl-(2-(2,6-dichloro-4-fluorophenyl)-2-oxoethyl)carbamoyl)-5-(trifluoromethyl)pyrazol-1-yl)-1-methylcyclohexane-1-carboxylic acid;

trans-4-(4-(2-tert-butylsulfonylethyl-(2-(2,6-dichloro-4-fluorophenyl)-2-oxoethyl)carbamoyl)-5-(trifluoromethyl)pyrazol-1-yl)-1-methylcyclohexane-1-carboxylic acid;

trans-4-(4-(3-bicyclo[2.2.1]heptanyl-(2-(3,5-dichloropyridin-4-yl)-2-oxoethyl)carbamoyl)-5-(trifluoromethyl)pyrazol-1-yl)cyclohexane-1-carboxylic acid;

trans-4-(4-(4,4-dimethylpent-2-ynyl-(2-oxo-2-(2,4,6-trichlorophenyl)ethyl)carbamoyl)-5-(trifluoromethyl)pyrazol-1-yl)-1-methylcyclohexane-1-carboxylic acid;

trans-4-(4-(8-azabicyclo[3.2.1]octan-3-yl-(2-(2,6-dichloro-4-fluorophenyl)-2-oxoethyl)carbamoyl)-5-(trifluoromethyl)pyrazol-1-yl)-1-methylcyclohexane-1-carboxylic acid;

trans-4-(4-(benzyl(2-(3,5-dichloropyridin-4-yl)-2-oxoethyl)carbamoyl)-5-(trifluoromethyl)-1H-pyrazol-1-yl)cyclohexanecarboxylic acid;

trans-4-(4-(cyclohexyl-(2-(3,5-dichloropyridin-4-yl)-2-oxoethyl)carbamoyl)-5-(trifluoromethyl)pyrazol-1-yl)cyclohexanecarboxylic acid;

trans-4-(4-(cyclopentyl-(2-(3,5-dichloropyridin-4-yl)-2-oxoethyl)carbamoyl)-5-(trifluoromethyl)pyrazol-1-yl)cyclohexane-1-carboxylic acid;

trans-4-(5-(aminomethyl)-4-((2-(3,5-dichloropyridin-4-yl)-2-oxoethyl)-((3,5-difluorophenyl)methyl)carbamoyl)pyrazol-1-yl)cyclohexane-1-carboxylic acid;

trans-4-(5-chloro-4-((2-(2,6-dichloro-4-fluorophenyl)-2-oxoethyl)-(4,4-dimethylcyclohexyl)carbamoyl)pyrazol-1-yl)-1-methylcyclohexane-1-carboxylic acid;

trans-4-(5-chloro-4-((2-(2,6-dichloro-4-methylphenyl)-2-oxoethyl)-(2,2-dimethylpropyl)carbamoyl)pyrazol-1-yl)-1-methylcyclohexane-1-carboxylic acid;

trans-4-(5-chloro-4-((2-(2,6-dichloro-4-methylphenyl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid;

trans-4-(5-chloro-4-((2-(2,6-dichlorophenyl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid;

trans-4-(5-chloro-4-((2-(2,6-dichlorophenyl)-2-oxoethyl)-(2,2-dimethylpropyl)carbamoyl)pyrazol-1-yl)-1-methylcyclohexane-1-carboxylic acid;

trans-4-(5-chloro-4-((2-(2,6-dichlorophenyl)-2-oxoethyl)-(4,4-dimethylcyclohexyl)carbamoyl)pyrazol-1-yl)-1-methylcyclohexane-1-carboxylic acid;

trans-4-(5-chloro-4-((2-(2-chloro-6-methoxyphenyl)-2-hydroxyethyl)((1R,3r,5S)-6,6-dimethylbicyclo[3.1.0]hexan-3-yl)carbamoyl)-1H-pyrazol-1-yl)-1-methylcyclohexanecarboxylic acid;

trans-4-(5-chloro-4-((2-(2-chloro-6-methoxyphenyl)-2-hydroxyethyl)((1R,3r,5S)-6,6-dimethylbicyclo[3.1.0]hexan-3-yl)carbamoyl)-1H-pyrazol-1-yl)-1-methylcyclohexanecarboxylic acid;

trans-4-(5-chloro-4-((2-(3,5-dichloropyridin-4-yl)-2-oxoethyl)-((3,5-difluorophenyl)methyl)carbamoyl)pyrazol-1-yl)cyclohexane-1-carboxylic acid;

trans-4-(5-chloro-4-((2-(3,5-dichloropyridin-4-yl)-2-oxoethyl)-((1-methylcyclopropyl)methyl)carbamoyl)pyrazol-1-yl)-1-methylcyclohexane-1-carboxylic acid;

trans-4-(5-chloro-4-((2-(3,5-dichloropyridin-4-yl)-2-oxoethyl)-((3,3-dimethylcyclobutyl)methyl)carbamoyl)pyrazol-1-yl)-1-methylcyclohexane-1-carboxylic acid;

trans-4-(5-chloro-4-((2-(3,5-dichloropyridin-4-yl)-2-oxoethyl)-((1-methyl-7-oxabicyclo[2.2.1]heptan-4-yl)methyl)carbamoyl)pyrazol-1-yl)-1-methylcyclohexane-1-carboxylic acid;

trans-4-(5-chloro-4-((2-(3,5-dichloropyridin-4-yl)-2-oxoethyl)-((1-(trifluoromethyl)cyclopropyl)methyl)carbamoyl)pyrazol-1-yl)-1-methylcyclohexane-1-carboxylic acid;

trans-4-(5-chloro-4-((2-(3,5-dichloropyridin-4-yl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid;

trans-4-(5-chloro-4-((2-(3,5-dichloropyridin-4-yl)-2-oxoethyl)-(2-ethyl-2-fluorobutyl)carbamoyl)pyrazol-1-yl)-1-methylcyclohexane-1-carboxylic acid;

trans-4-(5-cyano-4-((2-(3,5-dichloropyridin-4-yl)-2-oxoethyl)-(2,2-dimethylpropyl)carbamoyl)pyrazol-1-yl)-1-methylcyclohexane-1-carboxylic acid;

trans-4-(5-cyclopropyl-4-((2-(2,6-dichlorophenyl)-2-oxoethyl)((1R,3r,5S)-6,6-dimethylbicyclo[3.1.0]hexan-3-yl)carbamoyl)-1H-pyrazol-1-yl)-1-methylcyclohexanecarboxylic acid;

trans-4-(5-cyclopropyl-4-((2-(3,5-dichloropyridin-4-yl)-2-oxoethyl)-((3,5-difluorophenyl)methyl)carbamoyl)pyrazol-1-yl)cyclohexane-1-carboxylic acid;

trans-4-(5-tert-butyl-4-((2-(3,5-dichloropyridin-4-yl)-2-oxoethyl)-((3,5-difluorophenyl)methyl)carbamoyl)pyrazol-1-yl)cyclohexane-1-carboxylic acid;

trans-4-(4-((2-(3,5-dichloropyridin-4-yl)-2-oxoethyl)-(2, 2-dimethylpropyl)carbamoyl)-5-(trifluoromethyl)pyrazol-1-yl)-1-methylcyclohexane-1-carboxylic acid; and trans-4-(4-((2-(3,5-dichloro-4-pyridinyl)-2-oxoethyl)(3,3, 3-trifluoro-2,2-dimethylpropyl)carbamoyl)-5-(trifluoromethyl)-1H-pyrazol-1-yl)-1-methylcyclohexanecarboxylic acid.

13. The method of treating a disease using a compound according to claim 1 or pharmaceutically acceptable salt thereof, wherein the disease is multiple sclerosis, chronic rheumatoid arthritis, ankylosing spondylitis, systemic erythematodes, psoriasis, psoriatic arthritis, inflammatory bowel disease or asthma.

14. A pharmaceutical composition comprising a compound according to claim 1 or pharmaceutically acceptable salt thereof.

\* \* \* \* \*